US009637496B2

(12) United States Patent
Coate et al.

(10) Patent No.: US 9,637,496 B2
(45) Date of Patent: May 2, 2017

(54) SUBSTITUTED 7-AZABICYCLES AND THEIR USE AS OREXIN RECEPTOR MODULATORS

(71) Applicant: Janssen Pharmaceutica NV, Beerse (BE)

(72) Inventors: Heather R. Coate, San Diego, CA (US); Curt A. Dvorak, Poway, CA (US); Anne E. Fitzgerald, San Diego, CA (US); Terry P. Lebold, San Diego, CA (US); Cathy Preville, La Jolla, CA (US); Brock T. Shireman, Poway, CA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 14/774,554

(22) PCT Filed: Mar. 12, 2014

(86) PCT No.: PCT/US2014/024322
§ 371 (c)(1),
(2) Date: Sep. 10, 2015

(87) PCT Pub. No.: WO2014/159591
PCT Pub. Date: Oct. 2, 2014

(65) Prior Publication Data
US 2016/0046640 A1  Feb. 18, 2016

Related U.S. Application Data

(60) Provisional application No. 61/780,428, filed on Mar. 13, 2013.

(51) Int. Cl.
| | | |
|---|---|---|
| *C07D 487/08* | (2006.01) | |
| *C07D 519/00* | (2006.01) | |
| *C07D 513/04* | (2006.01) | |
| *C07D 471/04* | (2006.01) | |
| *A61K 31/5377* | (2006.01) | |
| *A61K 31/506* | (2006.01) | |
| *A61K 31/444* | (2006.01) | |

(Continued)

(52) U.S. Cl.
CPC .......... *C07D 487/08* (2013.01); *A61K 31/423* (2013.01); *A61K 31/444* (2013.01); *A61K 31/4439* (2013.01); *A61K 31/4709* (2013.01); *A61K 31/4725* (2013.01); *A61K 31/496* (2013.01); *A61K 31/497* (2013.01); *A61K 31/498* (2013.01); *A61K 31/4985* (2013.01); *A61K 31/501* (2013.01); *A61K 31/506* (2013.01); *A61K 31/5377* (2013.01); *C07D 471/04* (2013.01); *C07D 513/04* (2013.01); *C07D 519/00* (2013.01)

(58) Field of Classification Search
None
See application file for complete search history.

(56) References Cited

U.S. PATENT DOCUMENTS 3,674,793 A  7/1972  Bailey
8,957,074 B2  2/2015  Brain
(Continued)

FOREIGN PATENT DOCUMENTS

WO  WO 02/094790 A1  11/2002
WO  WO 2004/069816 A1  8/2004
(Continued)

OTHER PUBLICATIONS

Ammoun et al, "Distinct Recognition of OX1 and OX2 Receptors by Orexin Peptides", Journal of Pharmacology and Experimental Therapeutics, Jan. 2003, 305(2):507-514.
Arendt et al, "Depressive Behavior and Activation of the Orexin/Hypocretin System", Behavioral Neuroscience, Feb. 2013, 127(1):86-94.
Borgland et al, "Orexin A in the VTA Is Critical for the Induction of Synaptic Plasticity and Behavioral Sensitization to Cocaine", Neuron, Feb. 2006, 49:589-601.
Brundin et al, "Reduced orexin levels in the cerebrospinal fluid of suicidal patients with major depressive disorder", European Neuropsychopharmacology, Jan. 2007, 17:573-579.
Carroll et al, "Synthesis and Muscarinic Receptor Activity of Ester Derivatives of 2-Substituted 2-Azabicyclo[2.2.1]heptan-5-ol and -6-01", Journal of Medicinal Chemistry, Jun. 1992, 35(12):2184-2191.
Chemelli et al, "Narcolepsy in orexin Knockout Mice: Molecular Genetics of Sleep Regulation", Cell, Aug. 1999, 98:437-451.
Chen et al, "Pressor effects of orexins injected intracisternally and to rostral ventrolateral medulla of anesthetized rats", American Journal of Physiology—Regulatory Integrative comparative Physiology, Mar. 2000, 278:R692-R697.

(Continued)

Primary Examiner — Timothy R Rozof
(74) Attorney, Agent, or Firm — Baker & Hostetler LLP

(57) ABSTRACT

The present invention is directed to compounds of Formula I: wherein ring A is phenyl, naphthalenyl, pyridyl, quinolinyl, isoquinolinyl, imidazopyridyl, furanyl, thiazolyl, isoxazolyl, pyrazolyl, imidazothiazolyl, benzimidazolyl, or indazolyl; $R_1$ is H, alkyl, alkoxy, hydroxyalkylene, OH, halo, phenyl, triazolyl, oxazolyl, isoxazoyl, pyridyl, pyrimidinyl, pyrazinyl, pyridazyl, piperazinyl, pyrazolyl, oxadiazolyl, pyrrolidinyl, thiophenyl, morpholinyl, or dialkylamino; $R_2$ is H, alkyl, alkoxy, hydroxyalkylene, or halo; Z is NH, N-alkyl, or O; $R_5$ is pyridyl, pyrimidinyl, pyrazinyl, pyridazyl, quinazolinyl, quinoxalinyl, pyrazolyl, benzoxazolyl, imidazopyrazinyl, triazolopyrazinyl, optionally substituted with a one or two substituents independently selected from the group consisting of alkyl, alkoxy, or halo; and n is 0 or 1, Methods of making the compounds of Formula 1 are also described. The invention also relates to pharmaceutical compositions comprising compounds of Formula I. Methods of using the compounds of the invention are also within the scope of the invention.

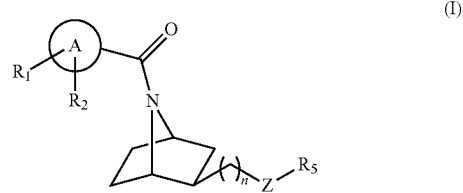

(I)

110 Claims, 2 Drawing Sheets

(51) Int. Cl.
    *A61K 31/4439*     (2006.01)
    *A61K 31/497*     (2006.01)
    *A61K 31/498*     (2006.01)
    *A61K 31/4709*     (2006.01)
    *A61K 31/501*     (2006.01)
    *A61K 31/4725*     (2006.01)
    *A61K 31/496*     (2006.01)
    *A61K 31/4985*     (2006.01)
    *A61K 31/423*     (2006.01)

(56) References Cited

U.S. PATENT DOCUMENTS

| | | |
|---|---|---|
| 8,969,352 B2 | 3/2015 | Gelin |
| 9,062,078 B2 | 6/2015 | Coate et al. |
| 9,309,252 B2 | 4/2016 | Brain |
| 2002/0148272 A1 | 10/2002 | Jroski |
| 2009/0005363 A1 | 1/2009 | Glatthar |
| 2009/0163485 A1 | 6/2009 | Knust et al. |
| 2011/0144150 A1 | 6/2011 | Lampe et al. |
| 2011/0172227 A1 | 7/2011 | Conn et al. |
| 2012/0202783 A1 | 8/2012 | Branstetter et al. |
| 2012/0208812 A1 | 8/2012 | Chai et al. |
| 2014/0275118 A1 | 9/2014 | Gelin |
| 2015/0174129 A1 | 6/2015 | Gelin |
| 2015/0218102 A1 | 8/2015 | Bogdan |
| 2015/0328224 A1 | 11/2015 | Coate et al. |
| 2016/0052939 A1 | 2/2016 | Gelin |
| 2016/0075696 A1 | 3/2016 | Shireman et al. |

FOREIGN PATENT DOCUMENTS

| | | |
|---|---|---|
| WO | WO 2004/074292 A1 | 9/2004 |
| WO | WO 2008/031550 A2 | 3/2008 |
| WO | WO 2008/065626 A2 | 6/2008 |
| WO | WO 2008/081399 A2 | 7/2008 |
| WO | WO 2008/150364 A1 | 12/2008 |
| WO | WO 2009/012275 A1 | 1/2009 |
| WO | WO 2009/012277 A1 | 1/2009 |
| WO | WO 2009/104155 A1 | 8/2009 |
| WO | WO 2009/133522 A1 | 11/2009 |
| WO | WO 2010/009195 A1 | 1/2010 |
| WO | WO 2010/048012 A1 | 4/2010 |
| WO | WO 2010/048016 A1 | 4/2010 |
| WO | WO 2010/063663 A1 | 6/2010 |
| WO | WO 2010/114958 A1 | 10/2010 |
| WO | WO 2010/122151 A1 | 10/2010 |
| WO | WO 2011/050198 A1 | 4/2011 |
| WO | WO 2011/050200 A1 | 4/2011 |
| WO | WO 2011/050202 A1 | 4/2011 |
| WO | WO 2011/053688 A1 | 5/2011 |
| WO | WO 2011/066137 A1 | 6/2011 |
| WO | WO 2011/159657 A1 | 12/2011 |
| WO | WO 2012/089606 A1 | 7/2012 |
| WO | WO 2012/145581 A1 | 10/2012 |
| WO | WO 2013/059222 A1 | 4/2013 |
| WO | WO 2014/066196 A1 | 5/2014 |
| WO | WO 2014/075392 | 5/2014 |
| WO | WO 2014/165070 A1 | 10/2014 |

OTHER PUBLICATIONS

Chiu, "An improved procedure for the synthesis of chiral2-azabicyclo[2.2.1]heptane", Synthetic Communications, 1996, 26(3):577-584.
De Lecea, Chapter 3, "Hypocretins and the neurobiology of sleep-wake mechanisms", Progress in Brain Research, 2012, vol. 198, A. Shekhar (Ed.), pp. 15-24.
Fortuyn et al, "Anxiety and mood disorders in narcolepsy: a case-control study", General Hospital Psychiatry, Jan.-Feb. 2010, 32:49-56.
Hara et al, "Genetic Ablation of Orexin Neurons in Mice Results in Narcolepsy, Hypophagia, and Obesity", Neuron, May 2001, 30:345-354.

Harris et al, "A role for lateral hypothalamic orexin neurons in reward seeking", Nature Sep. 2005, 437:556-559.
Harris et al, "Lateral hypothalamic orexin neurons are critically involved in learning to associate an environment with morphine reward", Behavioural Brain Research, Nov. 2007, 183:43-51.
Hiebabecky et al, "Synthesis of novel azanorbornylpurine derivatives", Tetrahedron, Jan. 2012, 68:1286-1298.
Hollander et al, "Insular hypocretin transmission regulates nicotine reward", Proceedings of the National Academy of Sciences USA, Dec. 2008, 105(49):19480-19485.
International Patent Application No. PCT/US2014/024293: International Search Report dated May 22, 2014, 2 pages.
Johnson et al, "A key role for orexin in panic anxiety", Nature Medicine, Sep. 2010, 16(1):111-116.
Johnson et al, "Activation of the Orexin I Receptor is a Critical Component of C02-Medidated Anxiety and Hypertension but not Bradycardia", Neuropsychopharmacology, Mar. 2012, 37:1911-1922.
Johnson et al, Chapter 9, "Orexin, stress, and anxiety/panic states", Progress in Brain Research, 2012, vol. 198, A. Shekhar (Ed.), pp. 133-161.
Kapferer et al, "Electrophilic Bromination of N-Acylated Cyclohex-3-en-1-amines: Synthesis of 7-Azanorbornanes", Helvetica Chimica Acta, Nov. 2004, 87(11):2764-2789.
Kirchgessner et al, "Orexin Synthesis and Response in the Gut", Neuron, Dec. 1999, 24:941-951.
Kukkonen, "Physiology of the orexinergic/hypocretinergic system: a revisit in 2012", American Journal of Physiology—Cell Physiology, Jan. 2013, 304:C2-C32.
Langmead et al, "Characterisation of the binding of [3H]-SB-674042, a novel non peptide antagonist, to the human orexin-1 receptor", British Journal of Pharmacology, Oct. 2004, 141:340-346.
Larsen et al, "Aza Diels-Aider Reactions in Aqueous Solution: Cyclocondensation of Dienes with Simple Iminium Salts Generated under Mannich Conditions", Journal American Chemistry Society, Mar. 1985, 107:1769-1771.
Lawrence et al, "The orexin system regulates alcohol-seeking in rats", British Journal of Pharmacology, Jul. 2006, 148:752-759.
Leroy, "Preparation of 3-Bromopropiolic Esters: Methyl and tert-Butyl 3- Bromopropiolates (2-Propynoic acid, 3-bromo-, methyl and 1,1-dimethylethyl esters)", Organic Syntheses, Shinkai et al (Eds.), 1997, 74:212-216.
Lin et al, "The Sleep Disorder Canine Narcolepsy Is Caused by a Mutation in the Hypocretin (Orexin) Receptor 2 Gene", Cell, Aug. 1999, 98:365-376.
Mahler et al, Chapter 7, "Multiple roles for orexin/hypocretin in addiction", Progress in Brain Research (2012) vol. 198, A. Shekhar (Ed.), pp. 79-121.
Malherbe et al, "Biochemical and behavioural characterization of EMPA, a novel high affinity, selective antagonist for the OX2 receptor", British Journal of Pharmacology, Nov. 2009, 156:1326-1341.
Marcus et al, "Differential Expression of Orexin Receptors 1 and 2 in the Rat Brain", Journal of Comparative Neurology, Jun. 2001, 435:6-25.
Mignot et al, "Complex HLA-DR and -DQ Interactions Confer Risk of Narcolepsy-Cataplexy in Three Ethnic Groups", American Journal Human Genetics, Feb. 2001, 68:686-699.
Mignot et al, "Narcolepsy and the HLA System", New England Journal of Medicine, Mar. 2001, 344(9):692.
Nakamura et al, "Orexin-induced hyperlocomotion and stereotypy are mediated by the dopaminergic system", Brain Research, Jun. 2000, 873:181-187.
Narita et al, "Direct Involvement of Orexinergic Systems in the Activation of the Mesolimbic Dopamine Pathway and Related Behaviors Induced by Morphine", Journal of Neuroscience, Jan. 2006, 26(2):398-405.
Peyron et al, "A mutation in a case of early onset narcolepsy and a generalized absence of hypocretin peptides in human narcoleptic brains", Nature Medicine, Sep. 2000, 6(9):991-997.

(56) References Cited

OTHER PUBLICATIONS

Peyron et al, "Neurons Containing Hypocretin (Orexin) Project to Multiple Neuronal Systems", Journal of Neuroscience, Dec. 1998, 18(23):9996-10015.
Piper et al, "The novel brain neuropeptide, orexin-A, modulates the sleep-wake cycle of rats", European Journal of Neuroscience, Feb. 2000, 12:726-730.
Sakurai et al, "Orexins and Orexin Receptors: A Family of Hypothalamic Neuropeptides and G Protein-Coupled Receptors that Regulate Feeding Behavior", Cell, Feb. 1998, 92:573-585.
Salomon et al, "Diurnal Variation of Cerebrospinal Fluid Hypocretin-1-(0rexin-A) Levels in Control and Depressed Subjects", Biological Psychiatry, Jul. 2003, 54:96-104.
Samson et al, "Cardiovascular Regulatory Actions of the Hypocretins in Brain", Brain Research, Jun. 1999, 831:248-253.
Sharf et al, "Orexin Mediates the Expression of Precipitated Morphine Withdrawal and Concurrent Activation of the Nucleus Accumbens Shell", Biological Psychiatry, Jan. 2008, 64:175-183.
Shirasaka et al, "Sympathetic and cardiovascular actions of orexins in conscious rats", American Journal of Physiology (Regulatory Integrative Camp. Physiol. 46), Dec. 1999, 277: R1780-R1785.
Shoblock et al, "Selective blockade of the orexin-2 receptor attenuates ethanol self-administration, place preference, and reinstatement", Psychopharmacology, Sep.-Oct. 2011, 215:191-203.
Singh et al, "Efficient Synthesis of (+)-N-BOC-exo-2-(methoxycarbonyl)-7-Azabicyclo [2.2.1]heptane, A Versatile Intermediate for the Synthesis of Epibatidine and Epiboxidine", Tetrahedron Letters, Sep. 1997, 38(39):6829-6830.
Strawn et al, "Low cerebrospinal fluid and plasma orexin-A (hypocretin-1) concentrations in combat-related posttraumatic stress disorder", Psychoneuroendocrinology, Aug. 2010, 35:1001-1007.
Takahashi et al, "Stimulation of Gastric Acid Secretion by Centrally Administered Orexin-A in Conscious Rats", Biochemical and Biophysical Research Communications, Jan. 1999, 254:623-627.
Trivedi et al, "Distribution of orexin receptor mRNA in the rat brain", FEBS Letters, Oct. 1998, 438:71-75.
Van Den Pol, "Hypothalamic Hypocretin (Orexin): Robust Innervation of the Spinal Cord", Journal of Neuroscience, Apr. 1999, 19(8):3171-3182.
Walker et al, "Design, synthesis, structure-activity relationship, and in vivo activity of azabicyclic aryl amides as α7 nicotinic acetylcholine receptor agonists", Bioorganic & Medicinal Chemistry, Sep. 2006, 14:8219-8248.
Yamanaka et al, "Orexins Activate Histaminergic Neurons via the Orexin 2 Receptor", Biochemical and Biophysical Research Communications, Feb. 2002, 290:1237-1245.
Aissaoui et al., "N-Glycine-sulfonamides as potent dual orexin 1/orexin 2 receptor antagonists", Bioorganic & Medicinal Chemistry Letters, Nov. 2008, 18, 5729-5733.
Baxter et al., "The First Large-Scale Synthesis of MK-4305: A Dual Orexin Receptor Antagonist for the Treatment of Sleep Disorder", Organic Process Research & Development, Mar. 2011, 15, 367-375.
Bergman et al., "Proline bis-amides as potent dual orexin receptor antagonists", Bioorganic & Medicinal Chemistry Letters, Feb. 2008, 18, 1425-1430.
Betschart et al., "Identification of a Novel Series of Orexin Receptor Antagonists with a Distinct Effect on Sleep Architecture for the Treatment of Insomnia", Journal of Medicinal Chemistry, Oct. 2013, 56, 7590-7607.
Bettica et al., "Phase I studies on the safety, tolerability, pharmacokinetics and pharmacodynamics of SB-649868, a novel dual orexin receptor antagonist", Journal of Psychopharmacology, Aug. 2012, 26(8), 1058-1070.
Bettica et al., "The Orexin Antagonist SB-649868 Promotes and Maintains Sleep in Men with Primary Insomnia", Sleep, Aug. 2012, 35(8), 1097-1104.
Brisbare-Roch et al., "Promotion of sleep by targeting the orexin system in rats, dogs and humans", Nature Medicine, Feb. 2007, 13(2), 150-155.

Coleman et al., "Design and synthesis of conformationally constrained N,N-disubstituted 1,4-diazepanes as potent orexin receptor antagonists", Bioorganic & Medicinal Chemistry Letters, Apr. 2010, 20, 2311-2315.
Coleman et al., "Discovery of [(2R,5R)-5-{[(5-Fluoropyridin-2-yl)oxy]methyl}-2methylpiperidin-1-yl][5-methyl-2-(pyrimidin-2-yl)phenyl]methanone (MK-6096): A Dual Orexin Receptor Antagonist with Potent Sleep-Promoting Properties", Chem Med Chem, Mar. 2012, 7, 415-424.
Coleman et al., "Discovery of 3,9-diazabicyclo[4.2.1]nonanes as potent dual orexin receptor antagonists with sleep-promoting activity in the rat", Bioorganic & Medicinal Chemistry Letters, Jul. 2010, 20, 4201-4205.
Cox et al., "Conformational analysis of N,N-disubstituted-1,4-diazepane orexin receptor antagonists and implications for receptor binding", Bioorganic & Medicinal Chemistry Letters, Jun. 2009, 19, 2997-3001.
Cox et al., "Discovery of the Dual Orexin Receptor Antagonist [(7R)-4-(5-Chloro-1,3-benzoxazol-2-yl)-7-methyl-1,4-diazepan-1-yl][5-methyl-2-(2H-1,2,3-triazol-2-yl)phenyl]methanone (MK-4305) for the Treatment of Insomnia", Journal of Medicinal Chemistry, Jul. 2010, 53, 5320-5332.
De Lecea et al., "The hypocretins: Hypothalamus-specific peptides with neuroexcitatory activity", Proc. Natl. Acad. Sci., Jan. 1998, 95, 322-327.
DiFabio et al., "Discovery process and pharmacological characterization of a novel dual orexin 1 and orexin 2 receptor antagonist useful for treatment of sleep disorders", Bioorganic & Medicinal Chemistry Letters, Sep. 2011, 21, 5562-5567.
Dugovic et al., "Blockade of Orexin-1 Receptors Attenuates Orexin-2 Receptor Antagonism-Induced Sleep Promotion in the Rat", The Journal of Pharmacology and Experimental Therapeutics, Jul. 2009, 330(1), 142-151.
Dugovic et al., "Orexin-1 receptor blockade dysregulates REM sleep in the presence of orexin-2 receptor antagonism", Frontiers in Neuroscience, Feb. 2014, vol. 8, Article 29, 1-8.
Fujimoto et al., "Discovery of potent, selective, orally active benzoxazepine-based Orexin-2 receptor antagonists", Bioorganic & Medicinal Chemistry Letters, Nov. 2011, 21, 6414-6416.
Fujimoto et al., "Discovery of spiropiperidine-based potent and selective Orexin-2 receptor antagonists", Nov. 2011, 21, 6409-6413.
Gatfield et al., "Orexin Receptor Antagonists: A New Concept in CNS Disorders?", Chem Med Chem, Aug. 2010, 5, 1197-1214.
Girardin et al., "Convergent Kilogram-Scale Synthesis of Dual Orexin Receptor Antagonist", Organic Process Research & Development, Jan. 2013, 17, 61-68.
Gotter et al., "International Union of Basic and Clinical Pharmacology. LXXXVI. Orexin Receptor Function, Nomenclature and Pharmacology", Pharmacological Reviews, Jul. 2012, 64(3), 389-420.
Gotter et al., "Orexin receptors as therapeutic drug targets", Progress in Brain Research, 2012, 198, 163-188.
Gozzi et al., "Functional Magnetic Resonance Imaging Reveals Different Neural Substrates for the Effects of Orexin-1 and Orexin-2 Receptor Antagonists", PLoS One, Jan. 2011, 6(1), e16406, 12 pages.
Hirose et al., "N-Acyl 6,7-Dimethoxy-1,2,3,4-tetrahydroisoquinoline: The First Orexin-2 Receptor Selective Nonpeptidic Antagonist", Bioorganic & Medicinal Chemistry Letters, Dec. 2003, 13, 4497-4499.
Jiang et al., "Disubstituted piperidines as potent orexin (hypocretin) receptor antagonists", Bioorganic & Medicinal Chemistry Letters, Jun. 2012, 22, 3890-3894.
King, "Bioisosteres, Conformational Restriction, and Pro-drugs—Case History: An Example of a Conformational Restriction Approach", Med. Chem.: Principle and Practice, 1994, 206-208.
Kuduk et al., "Synthesis and evaluation of carbon-linked analogs of dual orexin receptor antagonist filorexant", Bioorganic & Medicinal Chemistry Letters, Apr. 2014, 24, 1784-1789.
Lebold et al., "Selective orexin receptor antagonists", Bioorganic & Medicinal Chemistry Letters, Sep. 2013, 23, 4761-4769.

(56) References Cited

OTHER PUBLICATIONS

Mang et al., "The Dual Orexin Receptor Antagonist Almorexant Induces Sleep and Decreases Orexin-Induced Locomotion by Blocking Orexin 2 Receptors", Sleep, Dec. 2012, 35(12), 1625-1635.
McAtee et al., "Novel substituted 4-phenyl-[1,3]dioxanes: potent and selective orexin receptor 2 (OX2R) antagonists", Bioorganic & Medicinal Chemistry Letters, Aug. 2004, 14, 4225-4229.
McElhinny Jr. et al., "Hydrolytic instability of the important orexin 1 receptor antagonist SB-334867: Possible confounding effects on in vivo and in vitro studies", Bioorganic & Medicinal Chemistry Letters, Nov. 2012, 22, 6661-6664.
Mercer et al., "Discovery of 2,5-diarylnicotinamides as selective orexin-2 receptor antagonists (2-SORAs)", Bioorganic & Medicinal Chemistry Letters, Dec. 2013, 23, 6620-6624.
Micheli et al., "2-Methyl-3-furanyl-4H-1,2,4-triazol-3-ylthioamides: A new class of selective orexin 2 antagonists", Bioorganic & Medicinal Chemistry Letters, Nov. 2010, 20, 6405-6407.
Michelson et al., "Safety and efficacy of suvorexant during 1-year treatment of insomnia with subsequent abrupt treatment discontinuation: a phase 3 randomised, double-blind, placebo-controlled trial", The Lancet, May 2014, 13, 461-471.
Nambu et al., "Distribution of orexin neurons in the adult rat brain", Brain Research, May 1999, 827, 243-260.
Oi et al., "Synthesis and Evaluation of Novel Radioligands for Positron Emission Tomography Imaging of the Orexin-2 Receptor", Journal of Medicinal Chemistry, Jul. 2013, 56, 6371-6385.
Perrey et al., "Diaryl urea analogues of SB-334867 as orexin-1 receptor antagonists", Bioorganic & Medicinal Chemistry Letters, May 2011, 21, 2980-2985.
Perrey et al., "Substituted Tetrahydroisoquinolines as Selective Antagonists for the Orexin 1 Receptor", Journal of Medicinal Chemistry, Sep. 2013, 56, 6901-6916.
Porter et al., "1,3-Biarylureas as Selective Non-peptide Antagonists of the Orexin-1 Receptor", Bioorganic & Medicinal Chemistry Letters, Jul. 2001, 11, 1907-1910.
Renzulli et al., "Disposition and Metabolism of [$^{14}$C]SB-649868, an Orexin 1 and 2 Receptor Antagonist, in Humans", Drug Metabolism and Disposition, 2011, 39(2), 215-227.
Roecker et al., "Discovery of 5"-Chloro-N-[(5,6-dimethoxypyridin-2-yl)methyl]-2,2':5', 3"-terpyridine-3'-carboxamide (MK-1064): A Selective Orexin 2 Receptor Antagonist (2-SORA) for the Treatment of Insomnia", Chem Med Chem, Feb. 2014, 9, 311-322.
Sakurai, "The neural circuit of orexin (hypocretin): maintaining sleep and wakefulness", Nature Reviews, Mar. 2007, 8, 171-181.
Sifferlen et al., "Discovery of substituted lactams as novel dual orexin receptor antagonists. Synthesis, preliminary structure-activity relationship studies and efforts towards improved metabolic stability and pharmacokinetic properties. Part 1", Bioorganic & Medicinal Chemistry Letters, 24, Feb. 2014, 1201-1208.
Sifferlen et al., "Novel pyrazolo-tetrahydropyridines as potent orexin receptor antagonists", Bioorganic & Medicinal Chemistry Letters, Mar. 2010, 20, 1539-1542.
Sifferlen et al., "Structure-activity relationship studies and sleep-promoting activity of novel 1-chloro-5,6,7,8-tetrahydroimidazo[1,5-a]pyrazine derivatives as dual orexin receptor antagonists. Part 2", Bioorganic & Medicinal Chemistry Letters, Jul. 2013, 23, 3857-3863.
Sifferlen et al., "Synthesis, structure-activity relationship studies, and identification of novel 5,6,7,8-tetrahydroimidazo[1,5-a]pyrazine derivatives as dual orexin receptor antagonists. Part 1", Bioorganic & Medicinal Chemistry Letters, Apr. 2013, 23, 2212-2216.
Smart et al., "SB-334867-A: the first selective orexin-1 receptor antagonist", British Journal of Pharmacology, Mar. 2001, 132, 1179-1182.
Stasi et al., "Discovery, synthesis, selectivity modulation and DMPK characterization of 5-azaspiro[2.4]heptanes as potent orexin receptor antagonists", Bioorganic & Medicinal Chemistry Letters, May 2013, 23, 2653-2658.
Steiner et al. "Discovery and Characterization of ACT-335827, an Orally Available, Brain Penetrant Orexin Receptor Type 1 Selective Antagonist", Chem Med Chem, Jun. 2013, 8, 898-903.
Steiner et al., "The brain orexin system and almorexant in fear-conditioned startle reactions in the rat", Psychopharmacology, Oct. 2012, 223, 465-475.
Whitman et al., "Discovery of a Potent, CNS-Penetrant Orexin Receptor Antagonist Based on an N,N-Disubstituted-1, 4-diazepane Scaffold that Promotes Sleep in Rats", Chem Med Chem, Jul. 2009, 4, 1069-1074.
Winrow et al., "Discovery and development of orexin receptor antagonists as therapeutics for insomnia", British Journal of Pharmacology, Jan. 2014, 171, 283-293.

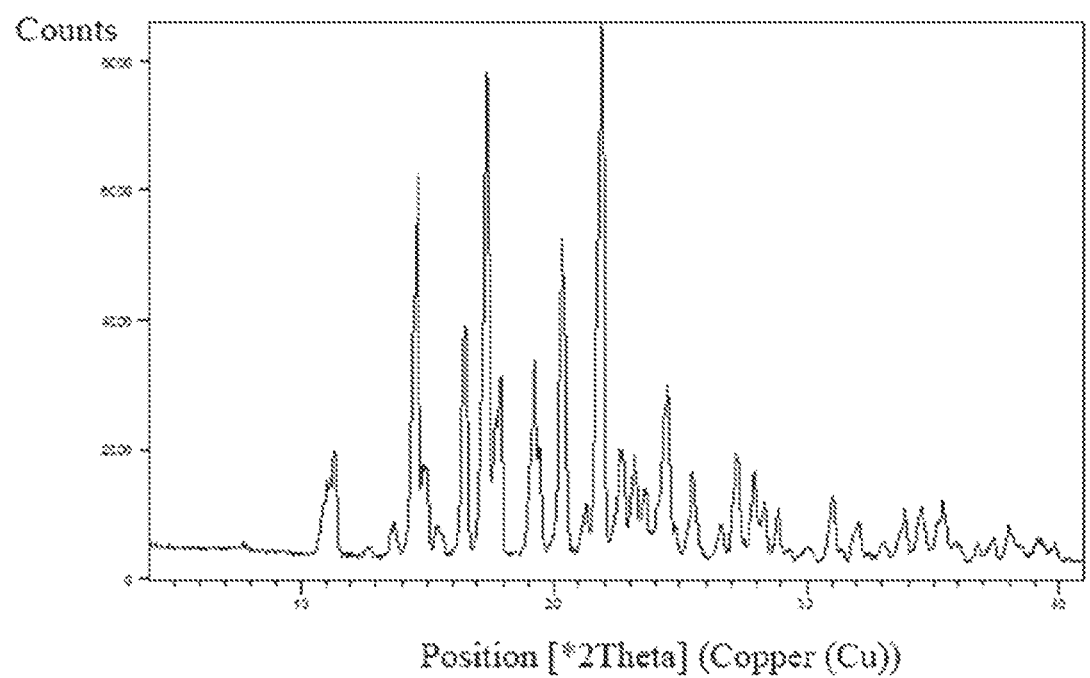

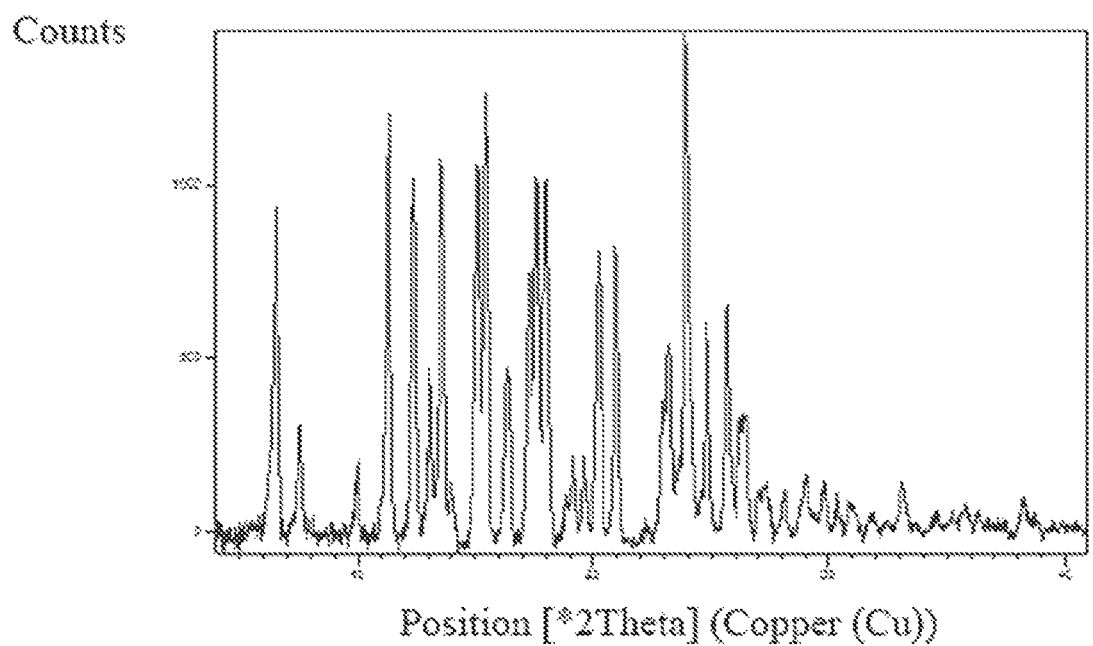

SUBSTITUTED 7-AZABICYCLES AND THEIR USE AS OREXIN RECEPTOR MODULATORS

CROSS-REFERENCE TO RELATED APPLICATIONS

This application is the National Stage of International Application No. PCT/US2014/024322, filed Mar. 12, 2014, which claims the benefit of U.S. Provisional Application No. 61/780,428, filed Mar. 13, 2013, which is incorporated herein by reference in its entirety.

TECHNICAL FIELD

The present invention is directed to substituted 7-azabicyclic compounds, pharmaceutical compositions comprising them, methods of making them, and methods of using them for the modulation of the orexin receptor for the treatment of disease states, disorders, and conditions mediated by orexin receptor activity.

BACKGROUND

Orexin/hypocretin signaling is mediated by two receptors and two peptide agonists. The peptides (orexin-A and orexin-B) are cleavage products of the same gene, pre-pro orexin. In the central nervous system, neurons producing pre-pro orexin are found solely in the perifornical nucleus, the dorsal hypothalamus, and the lateral hypothalamus (Peyron et al., 1998, *J. Neurosci.* 18: 9996-10015). Orexigenic cells in these regions project to many areas of the brain, extending rostrally to the olfactory bulbs and caudally to the spinal cord (Van den Pol, 1999, *J. Neurosci.* 19: 3171-3182).

The orexins bind to two high affinity receptors, referred to as orexin-1 and orexin-2 receptors. Orexin-1 and orexin-2 receptors are G-protein-coupled, seven transmembrane receptors that share over 64% amino acid sequence identity with one another. Both receptors are generally excitatory, the common cellular response to orexin-induced receptor activation being increases in intracellular calcium. Homology between the species orthologs is high and there are no known pharmacological differences. Orexin-A and -B are usually considered equal ligands for orexin-2 receptor but orexin-B is thought to be 5- to 100-fold weaker ligand than orexin-A at the orexin-1 receptor (Sakurai et al., 1998, *Cell* 92: 573-585; Ammoun et al., 2003, *J. Pharmacol. Exp. Ther.* 305: 507-514).

Many regions of the brain have fairly selective expression of the orexin-1 or orexin-2 receptors (Marcus et al., 2001, *J. Comp Neurology* 435, 6-25; Trivedi et al., 1998, *FEBS Letters*, 4, 71-75). Orexin-1 receptors are selective for the limbic system (bed nucleus of the stria terminalis and amygdala), cingulate cortex and noradrenergic neurons in the locus coeruleus. Conversely, the orexin-2 receptor is almost the exclusive orexin receptor in the histaminergic neurons in the tuberomammilary nucleus which play a critical role in wake promotion; in paraventricular neurons and the parabrachial nucleus. In other brain regions like the dorsal raphe, the ventral tegmental area or the prefontal cortex both receptors are coexpressed.

The broad CNS distribution of cells producing orexin, as well as cells expressing the orexin receptors, suggests involvement of orexin in a number of physiological functions, including feeding and metabolism, regulation of wakefulness and sleep, sympathetic activation and stress response (de Lecea, 2012, *Progress in Brain Research*, 19, 15-24; Kukkonen, 2013, *Am J. Physiol. Cell Physiol.*, 304, C2-C32). Orexin also plays a key role regulating motivation and reward associated with food intake and with drugs of abuse (Mahler et al., 2012, *Progress in Brain Research*, 198, 79-121).

Several lines of evidence indicate that the orexin system is an important modulator of arousal. Rodents administered orexin intracerebroventricularly spend more time awake (Piper et al., 2000, *J. Neurosci.* 12: 726-730. Orexin-mediated effects on arousal have been linked to orexin neuronal projections to histaminergic neurons in the tuberomammillary nucleus (Yamanaka et al., 2002, *Biochem. Biophys. Res. Comm.* 290: 1237-1245). Rodents whose pre-pro orexin gene has been knocked out, or whose orexigenic neurons have been killed, display altered sleep/wake cycles similar to narcolepsy (Chemelli et al., 1999, *Cell* 98: 437-451; Hara et al., 2001, *Neuron* 30: 345-354). Dog models of narcolepsy have been shown to have mutant or non-functional orexin-2 receptors (Lin et al., 1999, *Cell* 98: 365-376). Orexin signaling as a target for sleep-promoting therapies was further validated clinically by findings of attenuated orexin levels and loss of orexinergic neurons in human narcoleptic patients (Mignot et al., 2001, *Am. J. Hum. Genet.* 68: 686-699; Minot & Thorsby, 2001, *New England J. Med.* 344: 692) or, in rare cases, to mutations in the orexin-2 gene (Peyron et al., 2000, *Nature Med.* 6: 991-997). Disorders of the sleep-wake cycle are therefore likely targets for orexin-2 receptor modulator activity. Examples of sleep-wake disorders that may be treated by agonists or other modulators that up-regulate orexin-2 receptor-mediated processes include narcolepsy, jet lag (sleepiness) and sleep disorders secondary to neurological disorders such as depression. Examples of disorders that may be treated by antagonists or other modulators that down-regulate orexin-2 receptor-mediated processes include insomnia, restless leg syndrome, jet lag (wakefulness) and sleep disorders secondary to neurological disorders such as mania, schizophrenia, pain syndromes and the like.

Evidence has accumulated to demonstrate a clear involvement of orexin signaling in reward pathways associated with drug dependence (Mahler et al., 2012, *Progress in Brain Research*, 198, 79-121). Orexinergic neurons send projections to the ventral tegmental area and other brain regions involved in reward processing. Orexin ligands mediate reward behavior, and antagonizing these effects with a selective orexin-1 receptor antagonist in various preclinical model of addiction has suggested that these actions are mediated through orexin-1 receptor. Specifically, a selective orexin-1 antagonist attenuates morphine conditioned place preference and reinstatement (Harris et al., 2005, *Nature*, 437, 556-5599; Narita et al., 2006, *J Neurosci.*, 26, 398-405; Harris et al., 2007, *Behav Brain Res*, 183, 43-51), stress-induced cocaine reinstatement, cocaine-induced behavioral and synaptic plasticity (Borgland et al., 2006, *Neuron*, 49, 589-601), and intake and cue and stress-induced reinstatement of ethanol (Lawrence et al., 2006, *Br J Pharmacol*, 148, 752-759), in addition to attenuating precipitated morphine withdrawal (Sharf et al., 2008, *Biol Psychiatry*, 64, 175-183) and nicotine self-administration (Hollander et al., 2008, *Proc Natl Acad Sci USA*., 105, 19480-19485). Another recent study has also suggested a role for OX2R (Shoblock et al., 2011. *Psychopharmacology*, 215, 191-203).

Orexin's role in more complex emotional behavior is also emerging (Johnson et al., 2012, *Progress in Brain Research*, 198, 133-161). Changes in orexin levels in patients with panic and posttraumatic stress disorders have been noted as have changes in the prevalence of anxiety behaviors in narcoleptic patients (Johnson et al., 2010, *Nature Medicine*, 16, 111-115; Fortuyn et al., 2010. *General Hospital Psychiatry*, 32, 49-56; Strawn et al., 2010, *Psychoneuroendocrinology*, 35, 1001-1007). Lactate infusion or acute hypercapnia, which causes panic in humans, and are used as an animal model of panic, activates orexin neurons in the perifornical hypothalamus. This activation correlates with anxiety in the social interaction test or open field test. Blocking orexin signaling with either siRNA or selective orexin-1 receptor antagonists attenuates panic-like responses to lactate (Johnson et al., 2010, *Nature Medicine*, 16, 111-115; Johnson et al., 2012, *Neuropsychopharmacology*, 37, 1911, 1922).

Cerebral spinal fluid (CSF) levels of orexin are lower in depressed or suicidal patients, and the level of orexin inversely correlates with illness severity (Brundin et al., 2007, European *Neuropsychopharmacology*, 17, 573-579; Salomon et al., 2003, *Biol Psychiatry*, 54, 96-104). A positive correlation between orexin-1 receptor mRNA in the amygdala and depressive behavior in the forced swim test in mice has been reported (Arendt, 2013, *Behavioral Neuroscience*, 127, 86-94).

The orexin system also interacts with brain dopamine systems. Intracerebroventricular injections of orexin in mice increase locomotor activity, grooming and stereotypy; these behavioral effects are reversed by administration of D2 dopamine receptor antagonists (Nakamura et al., 2000, *Brain Res*. 873: 181-187). Therefore, orexin receptor modulators may be useful to treat various neurological disorders; e.g., agonists or up-regulators to treat catatonia, antagonists or down-regulators to treat Parkinson's disease, Tourette's syndrome, anxiety, delerium and dementias.

Orexins and their receptors have been found in both the myenteric and submucosal plexus of the enteric nervous system, where orexins have been shown to increase motility in vitro (Kirchgessner & Liu, 1999, *Neuron* 24: 941-951) and to stimulate gastric acid secretion in vitro (Takahashi et al., 1999, *Biochem. Biophys. Res. Comm.* 54: 623-627). Orexin effects on the gut may be driven by a projection via the vagus nerve (van den Pol, 1999, supra), as vagotomy or atropine prevent the effect of an intracerebroventricular injection of orexin on gastric acid secretion (Takahashi et al., 1999, supra). Orexin receptor antagonists or other down-regulators of orexin receptor-mediated systems are therefore potential treatments for ulcers, irritable bowel syndrome, diarrhea and gastroesophageal reflux.

Body weight may also be affected by orexin-mediated regulation of appetite and metabolism. Some effects of orexin on metabolism and appetite may be mediated in the gut, where, as mentioned, orexins alter gastric motility and gastric acid secretion. Orexin antagonists therefore are likely to be useful in treatment of overweight or obesity and conditions related to overweight or obesity, such as insulin resistance/type II diabetes, hyperlipidemia, gallstones, angina, hypertension, breathlessness, tachycardia, infertility, sleep apnea, back and joint pain, varicose veins and osteoarthritis. Conversely, orexin agonists are likely to be useful in treatment of underweight and related conditions such as hypotension, bradycardia, ammenorrhea and related infertility, and eating disorders such as anorexia and bulimia.

Intracerebroventricularly administered orexins have been shown to increase mean arterial pressure and heart rate in freely moving (awake) animals (Samson et al., 1999, *Brain Res*. 831: 248-253; Shirasaka et al., 1999, *Am. J. Physiol*. 277: R1780-R1785) and in urethane-anesthetized animals (Chen et al., 2000, *Am. J. Physiol*. 278: R692-R697), with similar results. Orexin receptor agonists may therefore be candidates for treatment of hypotension, bradycardia and heart failure related thereto, while orexin receptor antagonists may be useful for treatment of hypertension, tachycardia and other arrhythmias, angina pectoris and acute heart failure.

From the foregoing discussion, it can be seen that the identification of orexin receptor modulators, will be of great advantage in the development of therapeutic agents for the treatment of a wide variety of disorders that are mediated through these receptor systems.

SUMMARY

The present invention is directed to compounds of Formula I:

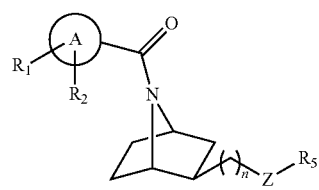

wherein ring A is phenyl, naphthalenyl, pyridyl, quinolinyl, isoquinolinyl, imidazopyridyl, furanyl, thiazolyl, isoxazolyl, pyrazolyl, imidazothiazolyl, benzimidazolyl, or indazolyl; $R_1$ is H, alkyl, alkoxy, hydroxyalkylene, OH, halo, phenyl, triazolyl, oxazolyl, isoxazolyl, pyridyl, pyrimidinyl, pyrazinyl, pyridazinyl, piperazinyl, pyrazolyl, oxadiazolyl, pyrrolidinyl, thiophenyl, morpholinyl, or dialkylamino, wherein phenyl, triazolyl, oxazolyl, isoxazolyl, pyridyl, pyrimidinyl, pyrazinyl, pyridazinyl, piperazinyl, pyrazolyl, oxadiazolyl, pyrrolidinyl, thiophenyl, or morpholinyl is optionally substituted with up to two substituents selected from halo and alkyl; $R_2$ is H, alkyl, alkoxy, hydroxyalkylene, or halo; Z is NH, N-alkyl, or O; $R_5$ is pyridyl, pyrimidinyl, pyrazinyl, pyridazinyl, quinazolinyl, quinoxalinyl, pyrazolyl, thiazolyl, thiadiazolyl, benzoxazolyl, imidazopyrazinyl, triazolopyrazinyl, optionally substituted with one or two substituents independently selected from the group consisting of alkyl, cyano, alkyl carboxylate, alkoxy, and halo; and n is 0 or 1. Enantiomers and diastereomers of the compounds of Formula I are also described, as well as the pharmaceutically acceptable salts.

Methods of making the compounds of Formula I are also described. The invention also relates to pharmaceutical compositions comprising therapeutically effective amounts of compounds of Formula I. Methods of using the compounds of the invention are also within the scope of the invention.

BRIEF DESCRIPTION OF DRAWINGS

FIG. 1 depicts a Powder X-Ray Diffraction (PXRD) pattern for one embodiment of the invention, Example 238, Form 1.

FIG. 2 depicts a Powder X-Ray Diffraction (PXRD) pattern for one embodiment of the invention, Example 238, Form 2.

DETAILED DESCRIPTION OF ILLUSTRATIVE EMBODIMENTS

The invention may be more fully appreciated by reference to the following description, including the following glossary of terms and the concluding examples.

The term "alkyl" refers to a straight- or branched-chain alkyl group having from 1 to 12 carbon atoms in the chain. In some embodiments, an alkyl group is a $C_1$-$C_6$ alkyl group. In some embodiments, an alkyl group is a $C_1$-$C_4$ alkyl group. Examples of alkyl groups include methyl (Me) ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. Alkyl groups of the invention can be optionally substituted with, for example, one or more halogen atoms. One exemplary substitutent is fluoro. Certain substituted alkyl groups of the invention include trihalogenated alkyl groups such as trifluoromethyl groups.

Alkyl groups of the invention can also refer to "cycloalkyl" moieties. Cycloalkyl refers to monocyclic, non-aromatic hydrocarbon groups having from 3 to 7 carbon atoms. Examples of cycloalkyl groups include, for example, cyclopropyl, cyclobutyl, cyclopentyl, cyclohexyl, 1-methylcyclopropyl, 2-methylcyclopentyl, and the like.

The term "alkoxy" includes a straight chain or branched alkyl group with a terminal oxygen linking the alkyl group to the rest of the molecule. In some embodiments, an alkoxy group is a $C_1$-$C_6$ alkoxy group. In some embodiments, an alkoxy group is a $C_1$-$C_4$ alkoxy group. Alkoxy includes methoxy, ethoxy, propoxy, isopropoxy, butoxy, t-butoxy, pentoxy and so on. Alkoxy groups of the inventions can be optionally substituted with, for example, one or more halogen atoms (haloalkoxy). One exemplary substitutent is fluoro. Preferred substituted alkoxy groups of the invention are substituted with one, two, or three halogen atoms, for example, —OCHCF$_2$.

The term "alkyl carboxylate" refers to the group —(C=O)O-alkyl, where alkyl is as defined above.

The term "amino" represents NH$_2$. The term "dialkylamino" represents the moiety wherein each H of the amino group is replaced by an alkyl group. These alkyl groups ca be the same or different. Preferred alkyl groups are the $C_{1-6}$alkyl groups. Examples of dialkyl amino groups include dimethylamino, diethylamino, diisopropylamino, and the like. Other examples include methylethylamino, methylisopropylamino, and the like.

The term "aryl ring" represents" a mono- or bi-cyclic aromatic, hydrocarbon ring structure. Aryl rings can have 6 or 10 carbon atoms in the ring.

The term "benzimidazolyl" represents the following moiety:

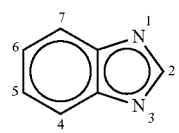

The benzimidazolyl moiety can be attached through any one of the 1-, 2-, 3-, 4-, 5-, 6-, or 7-position atoms and is optionally substituted with alkyl or halo or alkoxy groups.

The term "benzoxazolyl" represents the following moiety:

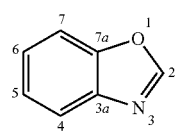

The benoxazolyl moiety can be attached through any one of the 2-, 4-, 5-, 6-, or 7-position carbon atoms and is optionally substituted with alkyl or halo or alkoxy groups.

The term "furanyl" represents the following moiety:

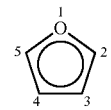

The furanyl moiety can be attached through any one of the 2-, 3-, 4-, or 5-position carbon atoms.

The term "halogen" represents chlorine, fluorine, bromine, or iodine. The term "halo" represents chloro, fluoro, bromo, or iodo.

The term "heteroaryl ring" represents a mono- or bicyclic aromatic ring structure including carbon atoms as well as up to four heteroatoms selected from nitrogen, oxygen, and sulfur. Heteroaryl rings can include a total of 5, 6, 9, or 10 ring atoms.

The term "hydroxyalkylene" represents an alkyl group, terminally substituted with OH. Examples of hydroxyalkylene moieties include —CH$_2$—OH, —CH$_2$CH$_2$—OH, —CH$_2$CH$_2$CH$_2$—OH, and the like.

The term "imidazopyridyl" represents the following moiety:

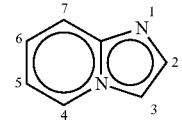

The imidazopyridyl moiety can be attached through any one of the 2-, 3-, 4-, 5-, 6-, or 7-position carbon atoms and is optionally substituted with alkyl or halo or alkoxy groups.

The term "imidazopyrazinyl" represents the following moiety:

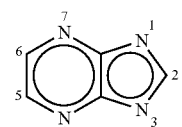

The imidazopyrazinyl moiety can be attached through any one of the 2-, 5-, or 6-position carbon atoms.

The term "imidazothiazolyl" represents the following moiety:

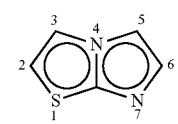

The imidazothiazolyl moiety can be attached through any one of the 2-, 3-, 5-, or 6-position carbon atoms.

The term "indazolyl" represents the following moiety:

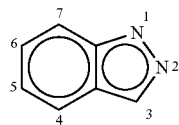

The indazolyl moiety can be attached through any one of the 1-, 3-, 4-, 5-, 6-, or 7-position atoms and is optionally substituted with alkyl or halo or alkoxy groups.

The term "isoquinolinyl" represents the following moiety:

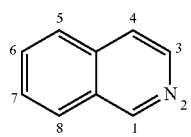

The isoquinolinyl moiety can be attached through any one of the 1-, 3-, 4-, 5-, 6-, 7-, or 8-position carbon atoms and is optionally substituted with alkyl or halo or alkoxy groups.

The term "isoxazolyl" represents the following moiety:

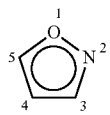

The isoxazolyl moiety can be attached through any one of the 3-, 4-, or 5-position carbon atoms. Isoxazolyl groups of the invention can be optionally substituted with, for example, one or two alkyl groups, for example, one or two methyl groups.

The term "naphthalenyl" represents the following moiety:

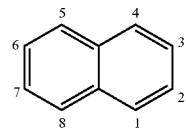

The naphthalenyl moiety can be attached through any one of the 1-, 2-, 3-, 4-, 5-, 6-, 7-, or 8-position carbon atoms and is optionally substituted with alkyl or halo or alkoxy groups.

The term "morpholinyl" represents the following moiety:

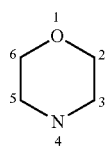

The 4-position nitrogen atom may be substituted with H or alkyl, for example methyl. The 4-position nitrogen can also be protected with a nitrogen protecting group such as a butyl-oxycarbonyl (-Boc). The morpholinyl moiety can be attached through any one of the 2-, 3-, 4-, 5-, or 6-position atoms. The morpholinyl ring is optionally substituted with halo or alkyl groups.

The term "oxazolyl" represents the following moiety:

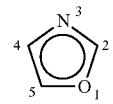

The oxazolyl moiety can be attached through any one of the carbon atoms. Oxazolyl groups of the invention can be optionally substituted with, for example, one or two alkyl groups, for example, one or two methyl groups.

The term "oxadiazolyl" represents a 1,2,3-oxadiazole, 1,2,4-oxadiazole, 1,2,5-oxadiazole, or 1,3,4-oxadiazole moiety:

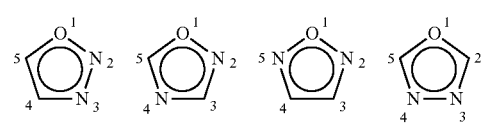

The oxadiazolyl moieties can be attached through any one of the carbon or nitrogen atoms. Within the scope of the invention, "oxadiazolyl" groups can be substituted with an alkyl group, preferably a methyl group.

The term "thiazolyl" represents the following moiety:

The thiazolyl moiety can be attached through any one of the carbon atoms. Thiazolyl groups of the invention can be optionally substituted with, for example, one or two alkyl groups, for example, one or two methyl groups.

The term "thiadiazolyl" represents a 1,2,3-thiadiazole, 1,2,4-thiadiazole, 1,2,5-thiadiazole, or 1,3,4-thiadiazole moiety:

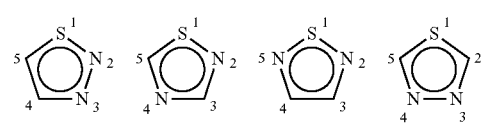

The thiadiazolyl moieties can be attached through any one of the carbon or nitrogen atoms. Within the scope of the invention, "thiadiazolyl" groups can be substituted with an alkyl group, preferably a methyl group.

The term "phenyl" represents the following moiety:

Phenyl groups of the inventions can be optionally substituted with, for example, one or more halogen atoms (halophenyl) or alkyl or alkoxy groups. Exemplary substitutents are fluoro, bromo, and chloro. Preferred substituted phenyl groups of the invention are substituted with one, two, or three halogen atoms.

The term "pyridyl" represents the following moiety:

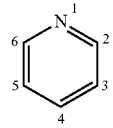

The pyridyl moiety can be attached through any one of the 2-, 3-, 4-, 5-, or 6-position carbon atoms. Pyridyl groups of the invention can be optionally substituted with, for example, one or more halo or alkyl groups, for example, one or two methyl groups.

The term "piperazinyl" represents the following moiety:

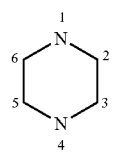

The piperazinyl moiety can be attached through any one of the 1-, 2-, 3-, 4-, 5-, or 6-position atoms. Any one of the nitrogen atoms of the piperazinyl moiety can be substituted with H or alkyl, for example, methyl.

The term "pyrimidinyl" represents the following moiety:

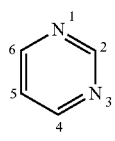

The pyrimidinyl moiety can be attached through any one of the 2-, 4-, 5-, or 6-position carbon atoms. Within the scope of the invention. "pyrimidinyl" groups of the invention can be substituted with halogen or alkyl, for example fluoro or methyl or trifluoromethyl.

The term "pyrazinyl" represents the following moiety:

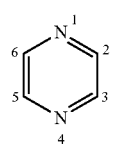

The pyrazinyl moiety can be attached through any one of the 2-, 3-, 5-, or 6-position carbon atoms and may be optionally substituted with alkyl, alkoxy or halo.

The term "pyridazinyl" represents the following moiety:

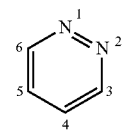

The pyridazinyl moiety can be attached through any one of the 3-, 4-, 5-, or 6-position carbon atoms and may be substituted with alkyl, alkoxy or halo groups.

The term "pyrazolyl" represents the following moiety:

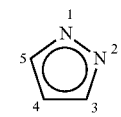

The pyrazolyl moiety can be attached through any one of the 1-, 2-, 3-, 4-, or 5-position carbon atoms. Pyrazolyl groups of the invention can be optionally substituted with, for example, one or two alkyl groups, for example, one or two methyl groups.

The term "pyrrolidinyl" represents the following moiety:

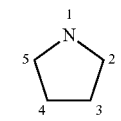

The pyrrolidinyl moiety can be attached through any one of the 1-, 2-, 3-, 4-, or 5-position atoms. When the pyrrolidinyl moiety is not attached through the 1-position nitrogen, the nitrogen can be substituted with H or alkyl, for example methyl.

The term "quinolinyl" represents the following moiety:

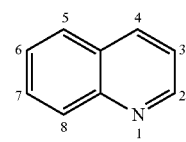

The quinolinyl moiety can be attached through any one of the 2-, 3-, 4-, 5-, 6-, 7-, or 8-position carbon atoms and may be optionally substituted with alkyl, halo or alkoxy groups.

The term "quinoxalinyl" represents the following moiety:

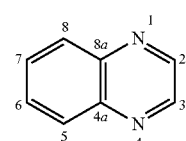

The quinoxalinyl moiety can be attached through any one of the 2-, 3-, 5-, 6-, 7-, or 8-position carbon atoms and may be optionally substituted with alkyl, halo or alkoxy groups.

The term "quinazolinyl" represents the following moiety:

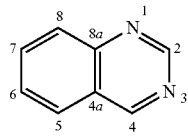

The quinoxalinyl moiety can be attached through any one of the 2-, 4-, 5-, 6-, 7-, or 8-position carbon atoms and may be optionally substituted with alkyl, halo or alkoxy groups.

The term "thiazolyl" represents the following moiety:

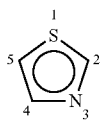

The thiazolyl moiety can be attached through any one of the 2-, 4-, or 5-position carbon atoms.

The term "thiophenyl" represents the following moiety:

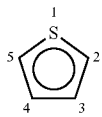

The thiophenyl moiety can be attached through any one of the 2-, 3-, 4-, or 5-position carbon atoms.

The term "triazolopyrazinyl" represents the following moiety:

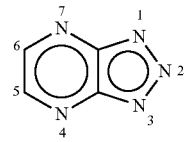

The triazolopyrazinyl moiety can be attached through any one of the 1-, 3-, 4-, 5-, 6-, or 7-position atoms.

The term "triazolyl" represents a 1,2,3-triazole or a 1,2,4-triazole moiety:

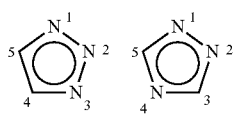

The triazolyl moieties can be attached through any one of their atoms.

"Pharmaceutically acceptable" means approved or approval by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable salt" refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like.

"Pharmaceutically acceptable vehicle" refers to a diluent, adjuvant, excipient or carrier with which a compound of the invention is administered. A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of a agent and that is compatible therewith. Examples of excipients include calcium carbonate, calcium phosphate, various sugars and types of starch, cellulose derivatives, gelatin, vegetable oils, and polyethylene glycols.

"Subject" includes humans. The terms "human," "patient," and "subject" are used interchangeably herein.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

In treatment methods according to the invention, a therapeutically effective amount of a pharmaceutical agent according to the invention is administered to a subject suffering from or diagnosed as having such a disease, disorder, or condition. A "therapeutically effective amount" means an amount or dose sufficient to generally bring about the desired therapeutic or prophylactic benefit in patients in need of such treatment for the designated disease, disorder, or condition. Effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day. "Compounds of the present invention," and equivalent expressions, are meant to embrace compounds of the Formula (I) as described herein, which expression includes the pharmaceutically acceptable salts, and the solvates, e.g., hydrates, where the context so permits. Similarly, reference to intermediates, whether or not they themselves are claimed, is meant to embrace their salts, and solvates, where the context so permits.

As used herein, the term "isotopic variant" refers to a compound that contains unnatural proportions of isotopes at one or more of the atoms that constitute such compound. For example, an "isotopic variant" of a compound can be radiolabeled, that is, contain one or more non-radioactive or radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. Radiolabeled compounds of the invention can be used in diagnostic methods such as Single-photon emission computed tomography (SPECT). The radioactive isotopes tritium, i.e. $^3$H, and carbon-14, i.e. $^{14}$C, are particularly useful for their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy.

All isotopic variants of the compounds of the invention, radioactive or not, are intended to be encompassed within the scope of the invention. In one aspect, provided herein are deuterated analogs of compounds of Formula I as described in the Examples section. In one embodiment, deuterated analogs of compounds of Formula I comprise deuterium atoms attached to one or more positions on the 7-azabicyclic ring, such as bridgehead carbons, or non-bridgehead carbons of the 7-azabicyclic ring, and preferably comprise one or more deuterium atoms attached to non-bridgehead carbons of the 7-azabicyclic ring. Also contemplated within the scope of embodiments described herein are compounds in which a single proton in compounds of Formula I is replaced with a deuterium, or 2 protons in compounds of Formula I are replaced with deuterium, or more than 2 protons in compounds of Formula I are replaced with deuterium. Deuteration of a compound of Formula I may also be effected on one or more substituents (such as e.g., ring A, $R^1$, $R^2$, or $R^5$) present on the 7-azabicyclic ring. Deuterated analogs of compounds of Formula IA are also contemplated within the scope of embodiments provided herein.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers."

Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

"Tautomers" refer to compounds that are interchangeable forms of a particular compound structure, and that vary in the displacement of hydrogen atoms and electrons. Thus, two structures may be in equilibrium through the movement of a electrons and an atom (usually H). For example, enols and ketones are tautomers because they are rapidly interconverted by treatment with either acid or base. Another example of tautomerism is the aci- and nitro-forms of phenyl nitromethane, that are likewise formed by treatment with acid or base.

Tautomeric forms may be relevant to the attainment of the optimal chemical reactivity and biological activity of a compound of interest.

Compounds of the invention may also exist as "rotamers," that is, conformational isomers that occur when the rotation leading to different conformations is hindered, resulting a rotational energy barrier to be overcome to convert from one conformational isomer to another.

The compounds of this invention may possess one or more asymmetric centers, such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

The present invention is directed to compounds of Formula I:

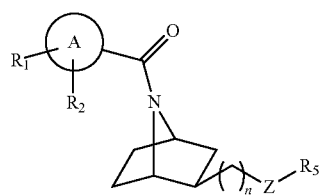

wherein
ring A is phenyl, naphthalenyl, pyridyl, quinolinyl, isoquinolinyl, imidazopyridyl, furanyl, thiazolyl, isoxazolyl, pyrazolyl, imidazothiazolyl, benzimidazolyl, or indazolyl;

$R_1$ is H, alkyl, alkoxy, hydroxyalkylene, OH, halo, phenyl, triazolyl, oxazolyl, isoxazolyl, pyridyl, pyrimidinyl, pyrazinyl, pyridazinyl, piperazinyl, pyrazolyl, oxadiazolyl, pyrrolidinyl, thiophenyl, morpholinyl, or dialkylamino, wherein phenyl, triazolyl, oxazolyl, isoxazolyl, pyridyl, pyrimidinyl, pyrazinyl, pyridazinyl, piperazinyl, pyrazolyl, oxadiazolyl, pyrrolidinyl, thiophenyl, or morpholinyl is optionally substituted with up to two substituents selected from halo and alkyl;

$R_2$ is H, alkyl, alkoxy, hydroxyalkylene, or halo;

Z is NH, N-alkyl, or O;

$R_5$ is pyridyl, pyrimidinyl, pyrazinyl, pyridazinyl, quinazolinyl, quinoxalinyl, pyrazolyl, thiazolyl, thiadiazolyl, benzoxazolyl, imidazopyrazinyl, or triazolopyrazinyl, optionally substituted with one or two substituents independently selected from the group consisting of alkyl, cyano, alkyl carboxylate, alkoxy, and halo; and n is 0 or 1.

In one aspect the invention is directed to compounds of Formula I:

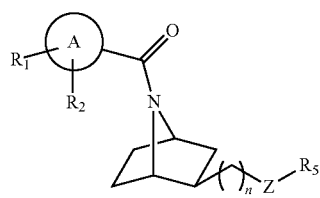

wherein
ring A is phenyl, naphthalenyl, pyridyl, quinolinyl, isoquinolinyl, imidazopyridyl, furanyl, thiazolyl, isoxazolyl, pyrazolyl, imidazothiazolyl, benzimidazolyl, or indazolyl;

$R_1$ is H, alkyl, alkoxy, hydroxyalkylene, OH, halo, phenyl, triazolyl, oxazolyl, isoxazolyl, pyridyl, pyrimidinyl, pyrazinyl, pyridazinyl, piperazinyl, pyrazolyl, oxadiazolyl, pyrrolidinyl, thiophenyl, morpholinyl, or dialkylamino;

$R_2$ is H, alkyl, alkoxy, hydroxyalkylene, or halo;

Z is NH, N-alkyl, or O;

$R_5$ is pyridyl, pyrimidinyl, pyrazinyl, pyridazinyl, quinazolinyl, quinoxalinyl, pyrazolyl, benzoxazolyl, imidazopyrazinyl, or triazolopyrazinyl, optionally substituted with a one or two substituents independently selected from the group consisting of alkyl, alkoxy, or halo; and n is 0 or 1.

Enantiomers and diastereomers of the compounds of Formula I are also within the scope of the invention. Also within the scope of the invention are the pharmaceutically acceptable salts of the compounds of Formula I, as well as the pharmaceutically acceptable salts of the enantiomers and diastereomers of the compounds of Formula I. Also contemplated within the scope of the embodiments provided herein are isotopic variants of compounds of Formula I, such as, by way of example, deuterated compounds of Formula I.

In preferred embodiments of the invention, Z is NH. In other embodiments, Z is N-alkyl, preferably N—$C_{1-6}$-alkyl, preferably N—$CH_3$.

In alternative embodiments, Z is O.

In preferred embodiments of the invention, ring A is a heteroaryl ring. Preferably, ring A is furanyl, which can be attached to the compounds of Formula I through any available atom, preferably the 2-position carbon atom. In other embodiments, ring A is thiazolyl, which can be attached to the compounds of Formula I through any available atom, preferably the 4-position carbon atom.

In still other embodiments, ring A is isoxazolyl, which can be attached to the compounds of Formula I through any available atom, preferably the 4-position carbon atom.

In yet other embodiments, ring A is pyrazolyl, which can be attached to the compounds of Formula I through any through any available atom, preferably the 3- or 4-position carbon atoms.

Also preferred are embodiments wherein ring A is imidazothiazolyl, which can be attached to the compounds of Formula I through any available atom, preferably the 5-position carbon atom.

In certain embodiments of the invention, ring A is benzimidazolyl, which can be attached to the compounds of Formula I through any available atom, preferably the 2-position carbon atom.

In other embodiments of the invention, ring A is indazolyl, which can be attached to the compounds of Formula I through any available atom, preferably the 3-position carbon atom.

In yet other embodiments, ring A is imidazopyridyl, which can be attached to the compounds of Formula I through any available atom, preferably the 4-, or 7-position carbon atom In still other embodiments, ring A is quinolinyl, which can be attached to the compounds of Formula I through any available carbon atom, preferably the 5- or 8-position carbon atom.

In other embodiments, ring A is isoquinolinyl, which can be attached to the compounds of Formula I through any available carbon atom, preferably the 4-position carbon atom.

In certain embodiments, ring A is pyridyl, which can be attached to the compounds of Formula I through any available carbon atom, preferably the 2-, 3-, or 4-position carbon atom.

In some preferred embodiments, ring A can be an aryl ring. In certain embodiments, ring A is phenyl. In other embodiments, ring A is naphthalenyl, which can be attached to the compounds of Formula I through any available carbon atom, preferably the 1-position carbon atom.

In preferred embodiments of the invention, $R_1$ is H. In other embodiments, $R_1$ is alkyl, preferably a $C_{1-6}$alkyl, for example, methyl.

In still other embodiments, $R_1$ is alkoxy, preferably a $C_{1-6}$alkoxy such as methoxy or ethoxy. Alternatively, $R_1$ is a substituted alkoxy, preferably substituted with one or more halo such as F, Cl, or Br. One preferred haloalkoxy is difluoromethoxy.

In other embodiments, $R_1$ is hydroxyalkylene, for example, hydroxy$C_{1-6}$alkylene such as —$CH_2$—OH or —$CH_2CH_2$—OH. In yet other embodiments, $R_1$ is OH.

In other preferred embodiments, $R_1$ is halo, that is, any one of F, Cl, Br, or I, with F, Cl, or Br being particularly preferred.

In still other embodiments, $R_1$ is phenyl. In some embodiments, $R_1$ is phenyl optionally substituted with up to two substituents selected from halo and alkyl. In some embodiments, the phenyl can be substituted with at least one halo, for example, phenyl substituted with at least one of F, Cl, or Br.

In certain embodiments, $R_1$ is triazolyl, with 1,2,3-triazolyl being preferred. The triazolyl can be attached through any available atom. In preferred embodiments, the 1,2,3-triazolyl is attached through the 2-position nitrogen atom. In other embodiments, the 1,2,3-triazolyl is attached through the 1-position nitrogen atom. In some embodiments, $R_1$ is triazolyl optionally substituted with up to two substituents selected from halo and alkyl.

In yet other embodiments, $R_1$ is oxazolyl, which can be attached through any available atom, preferably attached through the 2-position carbon. In some embodiments, $R_1$ is oxazolyl optionally substituted with up to two substituents selected from halo and alkyl. In some embodiments, the oxazolyl can be substituted with alkyl, for example, a $C_{1-6}$alkyl such as methyl.

In other embodiments, $R_1$ is isoxazolyl, which can be attached through any available atom. In some embodiments, $R_1$ is isoxazolyl optionally substituted with up to two substituents selected from halo and alkyl. In some embodiments, the isoxazolyl can be substituted with alkyl, for example, a $C_{1-6}$alkyl such as methyl.

In still other embodiments, $R_1$ is pyridyl, which can be attached through any available carbon atom. In some embodiments, $R_1$, is pyridyl optionally substituted with up to two substituents selected from halo and alkyl. In some embodiments, the pyridyl can be substituted with at least one alkyl, for example, $C_1$ 6 alkyl such as methyl.

In certain embodiments, $R_1$ is pyrimidinyl, which can be attached through any available carbon atom. In other embodiments, $R_1$ is pyrazinyl, which can be attached through any available carbon atom. In yet other embodiments, $R_1$ is pyridazinyl, which can be attached through any available carbon atom. In some of such embodiments, $R_1$ is pyrimidinyl, or pyrazinyl, or pyridazinyl, each optionally substituted with up to two substituents selected from halo and alkyl.

In other embodiments, $R_1$ is piperazinyl which can be attached through any available atom. In some embodiments, $R_1$ is piperazinyl optionally substituted with up to two substituents selected from halo and alkyl. In some embodiments, one or both nitrogen atoms of the piperazinyl may be substituted with H or alkyl, for example, $C_{1-6}$alkyl such as methyl.

In still other embodiments, $R_1$ is morpholinyl, which can be attached through any available atom. In some embodiments, $R_1$ is morpholinyl optionally substituted with up to two substituents selected from halo and alkyl. In some embodiments, the nitrogen of the morpholinyl may be substituted with H or alkyl, for example, $C_{1-6}$alkyl such as methyl.

In yet other embodiments, $R_1$ is pyrrolidinyl, which can be attached through any available atom. In some embodiments, $R_1$ is pyrrolidinyl optionally substituted with up to two substituents selected from halo and alkyl. In some embodiments, the nitrogen of the pyrrolidinyl may be substituted with H or alkyl, for example, $C_{1-6}$alkyl such as methyl.

In other embodiments, $R_1$ is dialkylamino, for example, dimethylamino, diethylamino, or methylethylamino.

In other embodiments, $R_1$ is pyrazolyl, which can be attached through any available atom. In some embodiments, $R_1$ is pyrazolyl optionally substituted with up to two substituents selected from halo and alkyl. In some embodiments, the pyrazolyl can be substituted with one or two alkyl, for example, $C_{1-6}$alkyl such as methyl.

In yet other embodiments, $R_1$ is oxadiazolyl, which can be a 1,2,3-oxadiazolyl, 1,2,4-oxadiazolyl, 1,2,5-oxadiazolyl, or 1,3,4-oxadiazolyl. Preferably, the oxadiazolyl is 1,2,4-oxadiazolyl. The oxadiazolyl can be attached through any available atom. In some embodiments, $R_1$ is oxadiazolyl optionally substituted with up to two substituents selected from halo and alkyl. In some embodiments, the oxadiazolyl can be substituted with alkyl, for example, $C_{1-6}$alkyl such as methyl.

In still other embodiments, $R_1$ is thiophenyl, which can be attached through any available carbon atom. In some embodiments, $R_1$ is thiophenyl optionally substituted with up to two substituents selected from halo and alkyl.

In preferred embodiments of the invention, $R_2$ is H. In other embodiments, $R_2$ is alkyl, for example, $C_{1-6}$alkyl such as methyl or ethyl. In yet other embodiments, $R_2$ is alkoxy, for example, $C_{1-6}$alkoxy such as methoxy or ethoxy. In other embodiments, $R_2$ is hydroxylalkene, for example, —$CH_2$—OH or $CH_2CH_2$—OH. In still other embodiments, $R_2$ is halo, preferably, any one of F, Cl, or Br.

In some embodiments of Formula I, ring A is aryl, preferably phenyl, $R_1$ is a ring selected from phenyl, triazolyl, oxazolyl, isoxazolyl, pyridyl, pyrimidinyl, pyrazinyl, pyridazinyl, piperazinyl, pyrazolyl, oxadiazolyl, pyrrolidinyl, thiophenyl, and morpholinyl; preferably triazolyl, pyridyl or pyrimidinyl; $R_2$ is H, alkyl, alkoxy, hydroxyalkylene, or halo; preferably halo; Z is NH or O, preferably NH, $R_5$ is a heteroaryl, preferably pyridyl or pyrazinyl; and n is 0.

In some of such embodiments, $R_1$ is a ring at the ortho position on ring A relative to the carbonyl group in Formula I, and $R_2$ is at the ortho, meta or para position on ring A relative to the carbonyl group in Formula I, preferably $R_2$ is at the meta position adjacent to $R_1$. In some other such embodiments, $R_1$ is a ring at the ortho position on ring A relative to the carbonyl group in Formula I, and $R_2$ is at the ortho, meta or para position on ring A relative to the carbonyl group in Formula I, preferably $R_2$ is at the meta position not adjacent to $R_1$. $R_1$ and $R_5$ may be optionally substituted as described above.

In some embodiments of Formula I, ring A is heteroaryl, preferably pyridinyl, $R_1$ is a ring selected from phenyl, triazolyl, oxazolyl, isoxazolyl, pyridyl, pyrimidinyl, pyrazinyl, pyridazinyl, piperazinyl, pyrazolyl, oxadiazolyl, pyrrolidinyl, thiophenyl, and morpholinyl; preferably triazolyl, pyridyl or pyrimidinyl; $R_2$ is H, alkyl, alkoxy, hydroxyalkylene, or halo; preferably halo; Z is NH or O, preferably NH, $R_5$ is a heteroaryl, preferably pyridyl or pyrazinyl; and n is 0. In some of such embodiments, $R_1$ is a ring at the ortho position on ring A relative to the carbonyl group in Formula I, and $R_2$ is at the ortho, meta or para position on ring A relative to the carbonyl group in Formula I, preferably $R_2$ is at the meta position adjacent to $R_1$. In some other such embodiments, $R_1$ is a ring at the ortho position on ring A relative to the carbonyl group in Formula I, and $R_2$ is at the ortho, meta or para position on ring A relative to the carbonyl group in Formula I, preferably $R_2$ is at the meta position not adjacent to $R_1$. $R_1$ and $R_5$ may be optionally substituted as described above.

In one aspect, the invention is directed to compounds of Formula IA:

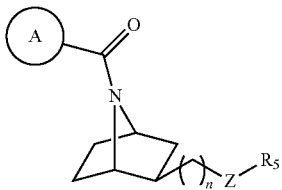

wherein
ring A is

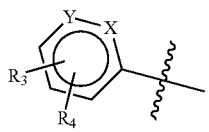

wherein
X is $CR_6$, N, or $NR_6$;
Y is $CR_7$, N, or $NR_7$;
$R_6$ is H, alkyl, alkoxy, OH, halo, triazolyl, oxazolyl, oxadiazolyl, pyridyl, pyrimidinyl, pyrazinyl, pyridazinyl, pyrazolyl, or thiophenyl, wherein triazolyl, oxazolyl, oxadiazolyl, pyridyl, pyrimidinyl, pyrazinyl, pyridazinyl, pyrazolyl, or thiophenyl is optionally substituted with up to two substituents selected from halo and alkyl;
$R_7$ is H, alkyl, alkoxy, or halo;
$R_3$ is H, alkyl, alkoxy, hydroxyalkylene, OH, halo, phenyl, triazolyl, oxazolyl, isoxazolyl, pyridyl, pyrimidinyl, pyrazinyl, pyridazinyl, piperazinyl, pyrazolyl, oxadiazolyl, pyrrolidinyl, thiophenyl, morpholinyl, or dialkylamino, wherein phenyl, triazolyl, oxazolyl, isoxazolyl, pyridyl, pyrimidinyl, pyrazinyl, pyridazinyl, piperazinyl, pyrazolyl, oxadiazolyl, pyrrolidinyl, thiophenyl, or morpholinyl is optionally substituted with up to two substituents selected from halo and alkyl;
$R_4$ is H, alkyl, alkoxy, or halo;
or
  $R_6$ and $R_7$, together with the atoms to which they are attached, form a 5- or 6-membered heteroaryl ring optionally substituted with alkyl; or
  $R_3$ and $R_4$, together with the atoms to which they are attached, form a 6-membered aryl or 6-membered heteroaryl ring; or
  $R_7$ and $R_4$, together with the atoms to which they are attached, form a 6-membered aryl or 6-membered heteroaryl ring;
Z is NH, N-alkyl, or O;
$R_5$ is pyridyl, pyrimidinyl, pyrazinyl, pyridazinyl, quinazolinyl, quinoxalinyl, pyrazolyl, thiazolyl, thiadiazolyl, benzoxazolyl, imidazopyrazinyl, or triazolopyrazinyl, optionally substituted with a one or two substituents independently selected from the group consisting of alkyl, cyano, alkyl carboxylate, alkoxy, or halo; and
n is 0 or 1.

Enantiomers and diastereomers of the compounds of Formula IA are also within the scope of the invention. Also within the scope of the invention are the pharmaceutically acceptable salts of the compounds of Formula IA, as well as the pharmaceutically acceptable salts of the enantiomers and diastereomers of the compounds of Formula IA. Also contemplated within the scope of the embodiments provided herein are isotopic variants of compounds of Formula IA, such as, by way of example, deuterated compounds of Formula IA.

In certain of these embodiments, X is $CR_6$ and Y is $CR_7$.
In other of these embodiments, X is $CR_6$ and Y is N.
In still other of these embodiments, X is N and Y is $CR_7$.
In those embodiments wherein X is $CR_6$, for example those embodiments wherein X is $CR_6$ and Y is $CR_7$ or X is $CR_6$ and Y is N, $R_6$ is H. Alternatively, $R_6$ is alkyl, for example, $C_{1-6}$alkyl such as methyl or ethyl.
In other of these embodiments, $R_6$ is alkoxy, for example, $C_{1-6}$alkoxy such as methoxy or ethoxy.
In still other of these embodiments, $R_6$ is OH.
In yet other of these embodiments, $R_6$ is halo, preferably, any one of F, Cl, or Br.
In those embodiments wherein X is $CR_6$, for example those embodiments wherein X is $CR_6$ and Y is $CR_7$ or X is $CR_6$ and Y is N, $R_6$ is triazolyl with 1,2,3-triazolyl being preferred. The triazolyl can be attached through any available atom. In preferred embodiments, the 1,2,3-triazolyl is attached through the 2-position nitrogen atom. In other embodiments, the 1,2,3-triazolyl is attached through the 1-position nitrogen atom.
In those embodiments wherein X is $CR_6$, for example those embodiments wherein X is $CR_6$ and Y is $CR_7$ or X is $CR_6$ and Y is N, $R_6$ is oxazolyl, which can be attached through any available atom. In some embodiments, the oxazolyl can be substituted with alkyl, for example, $C_{1-6}$alkyl such as methyl.
In those embodiments wherein X is $CR_6$, for example those embodiments wherein X is $CR_6$ and Y is $CR_7$ or X is $CR_6$ and Y is N, $R_6$ is oxadiazolyl, which can be a 1,2,3-oxadiazolyl, 1,2,4-oxadiazolyl, 1,2,5-oxadiazolyl, or 1,3,4-oxadiazolyl. Preferably, the oxadiazolyl is 1,2,4-oxadiazolyl. The oxadiazolyl can be attached through any available atom. In some embodiments, the oxadiazolyl can be substituted with alkyl, for example, $C_{1-6}$alkyl such as methyl.
In those embodiments wherein X is $CR_6$, for example those embodiments wherein X is $CR_6$ and Y is $CR_7$ or X is $CR_6$ and Y is N, $R_5$ is pyrazolyl, which can be attached through any available atom. In some embodiments, the pyrazolyl can be substituted with one or two alkyl, for example, $C_{1-6}$alkyl such as methyl.
In those embodiments wherein X is $CR_6$, for example those embodiments wherein X is $CR_6$ and Y is $CR_7$ or X is $CR_6$ and Y is N, $R_6$ is thiophenyl, which can be attached through any available atom.
In those embodiments wherein X is $CR_6$, for example those embodiments wherein X is $CR_6$ and Y is $CR_7$ or X is $CR_6$ and Y is N, $R_6$ is pyridyl, which can be attached through any available atom. In some embodiments, the pyridyl can be substituted with one or more alkyl, for example, $C_{1-6}$alkyl such as methyl. One exemplary substituted pyridyl is methyl-pyridyl.
In those embodiments wherein X is $CR_6$, for example those embodiments wherein X is $CR_6$ and Y is $CR_7$ or X is $CR_6$ and Y is N, $R_6$ is pyrimidinyl, which can be attached through any available atom. In other embodiments, $R_6$ is pyrazinyl, which can be attached through any available atom. In still other embodiments, $R_6$ is pyridazinyl, which can be attached through any available atom.
In preferred embodiments wherein Y is $CR_7$, for example, those embodiments wherein X is $CR_6$ and Y is $CR_7$ or X is N and Y is CRY, $R_7$ is H. In other embodiments, $R_7$ is alkyl, for example, $C_{1-6}$alkyl such as methyl or ethyl.

In those embodiments wherein Y is $CR_6$, for example, those embodiments wherein X is $CR_6$ and Y is $CR_7$ or X is N and Y is $CR_7$, $R_7$ is alkoxy, for example, $C_{1-6}$alkoxy such as methoxy or ethoxy. In other embodiments, the alkoxy is substituted with, for example, one or more halo. One preferred substituted alkoxy is difluoromethoxy.

In those embodiments wherein Y is $CR_7$, for example, those embodiments wherein X is $CR_6$ and Y is $CR_7$ or X is N and Y is $CR_7$, $R_7$ is halo, preferably one of F, Cl, or Br.

In some embodiments, X is $NR_6$ and Y is $CR_7$.

In other embodiments, X is $CR_6$ and Y is $NR_7$.

In other embodiments, X is $CR_6$ and Y is $CR_7$.

In those embodiments wherein X is $NR_6$ and Y is $CR_7$ or X is $CR_6$ and Y is $NR_7$, $R_6$ and $R_7$, together with the atoms to which they are attached, form a 5-membered heteroaryl ring. These 5-membered rings can optionally substituted with alkyl, for example $C_{1-6}$alkyl such as methyl.

In those embodiments wherein X is $NR_6$ and Y is $CR_7$ or X is $CR_6$ and Y is $NR_7$, $R_6$ and $R_7$, together with the atoms to which they are attached, form a 6-membered heteroaryl ring. These 5-membered rings can optionally substituted with alkyl, for example $C_{1-6}$alkyl such as methyl.

In those embodiments wherein Y is $CR_7$ or $NR_7$, $R_7$ and $R_4$, together with the atoms to which they are attached, form a 6-membered aryl ring. Alternatively, $R_7$ and $R_4$, together with the atoms to which they are attached, form a 6-membered heteroaryl ring.

In preferred embodiments, $R_3$ is H. In other embodiments, $R_3$ is alkyl, for example, $C_{1-6}$alkyl such as methyl or ethyl.

In other embodiments, $R_3$ is alkoxy, for example, $C_{1-6}$alkoxy such as methoxy or ethoxy. In some embodiments, the alkoxy is substituted with, for example, one or more halo. One preferred substituted alkoxy is difluoromethoxy.

In some embodiments, $R_3$ is hydroxyalkylene, for example, hydroxy$C_{1-6}$alkylene such as —$CH_2$—OH and —$CH_2CH_2$—OH. In yet other embodiments, $R_3$ is OH.

In other preferred embodiments, $R_3$ is halo, preferably any one of F, Cl, or Br.

In still other embodiments, $R_3$ is phenyl. In some embodiments, the phenyl can be substituted with one or more halo, for example, phenyl substituted with at least one of F, Cl, or Br.

In certain embodiments, $R_3$ is triazolyl, with 1,2,3-triazolyl being preferred. The triazolyl can be attached through any available atom. In preferred embodiments, the 1,2,3-triazolyl is attached through the 2-position nitrogen atom. In other embodiments, the 1,2,3-triazolyl is attached through the 1-position nitrogen atom.

In yet other embodiments, $R_3$ is oxazolyl, which can be attached through any available atom, preferably attached through the 2-position carbon. In some embodiments, the oxazolyl can be substituted with alkyl, for example, a $C_{1-6}$alkyl such as methyl.

In other embodiments, $R_3$ is isoxazolyl, which can be attached through any available atom. In some embodiments, the isoxazolyl can be substituted with alkyl, for example, a $C_{1-6}$alkyl such as methyl.

In other embodiments, $R_3$ is oxadiazolyl, which can be a 1,2,3-oxadiazolyl, 1,2,4-oxadiazolyl, 1,2,5-oxadiazolyl, or 1,3,4-oxadiazolyl. Preferably, the oxadiazolyl is 1,2,4-oxadiazolyl. The oxadiazolyl can be attached through any available atom. In some embodiments, the oxadiazolyl can be substituted with alkyl, for example, $C_{1-6}$alkyl such as methyl.

In still other embodiments, $R_3$ is pyridyl, which can be attached through any available carbon atom. In some embodiments, the pyridyl can be substituted with one or more alkyl, for example, $C_{1-6}$alkyl such as methyl.

In other embodiments, $R_3$ is pyrazolyl, which can be attached through any available atom. In some embodiments, the pyrazolyl can be substituted with one or two alkyl, for example, $C_{1-6}$alkyl such as methyl.

In certain embodiments, $R_3$ is pyrimidinyl, which can be attached through any available carbon atom. In other embodiments, $R_3$ is pyrazinyl, which can be attached through any available carbon atom. In yet other embodiments, $R_3$ is pyridazinyl, which can be attached through any available carbon atom.

In other embodiments, $R_3$ is piperazinyl which can be attached through any available atom. In some embodiments, one or both nitrogen atoms of the piperazinyl may be substituted with H or alkyl, for example, $C_{1-6}$alkyl such as methyl.

In still other embodiments, $R_3$ is morpholinyl, which can be attached through any available atom. In some embodiments, the nitrogen atom of the morpholinyl may be substituted with H or alkyl, for example, $C_{1-6}$alkyl such as methyl.

In yet other embodiments, $R_3$ is pyrrolidinyl, which can be attached through any available atom. In some embodiments, the nitrogen atom of the pyrrolidinyl may be substituted with H or alkyl, for example, $C_{1-6}$alkyl such as methyl.

In other embodiments, $R_3$ is dialkylamino, for example, dimethylamino, diethylamino, or methylethylamino.

In other embodiments, $R_3$ is pyrazolyl, which can be attached through any available atom. In some embodiments, the pyrazolyl can be substituted with one or two alkyl, for example, $C_{1-6}$alkyl such as methyl.

In still other embodiments, $R_3$ is thiophenyl, which can be attached through any available carbon atom.

In preferred embodiments of the invention, $R_4$ is H. In other embodiments, $R_4$ is alkyl, for example, $C_{1-6}$alkyl such as methyl or ethyl. In still other embodiments, $R_4$ is alkoxy, for example, $C_{1-6}$alkoxy such as methoxy or ethoxy. In yet other embodiments, $R_4$ is halo, preferably, any one of F, Cl, or Br.

In some embodiments, $R_3$ and $R_4$, together with the atoms to which they are attached, form a 6-membered aryl ring.

In other embodiments, $R_3$ and $R_4$, together with the atoms to which they are attached, form a 6-membered heteroarylaryl ring.

In preferred embodiments of the invention, $R_5$ is a heteroaryl ring. In some of such embodiments, $R_5$ is a heteroaryl optionally substituted with a one or two substituents independently selected from the group consisting of alkyl, cyano, alkyl carboxylate, alkoxy, and halo. According to some embodiments of the invention, $R_5$ is pyridyl, which can be attached through any available atom, optionally substituted with a one or two substituents independently selected from the group consisting of alkyl, alkoxy, or halo. In some embodiments, alkyl is trihaloalkyl, for example trifluoromethyl.

According to some embodiments of the invention, $R_5$ is pyrimidinyl, which can be attached through any available atom, optionally substituted with a one or two substituents independently selected from the group consisting of alkyl, alkoxy, or halo. In some embodiments, alkyl is trihaloalkyl, for example trifluoromethyl. In other embodiments, alkyl is dihaloalkyl, e.g., difluoromethyl or monohaloalkyl, e.g., monofluoromethyl.

According to some embodiments of the invention, $R_5$ is pyrazinyl, which can be attached through any available atom, optionally substituted with a one or two substituents independently selected from the group consisting of alkyl, alkoxy, or halo. In some embodiments, alkyl is trihaloalkyl, for example trifluoromethyl. In other embodiments, alkyl is dihaloalkyl. e.g., difluoromethyl or monohaloalkyl, e.g., monofluoromethyl.

According to some embodiments of the invention, $R_5$ is pyridazinyl, which can be attached through any available atom, optionally substituted with a one or two substituents independently selected from the group consisting of alkyl, alkoxy, or halo. In some embodiments, alkyl is trihaloalkyl, for example trifluoromethyl. In other embodiments, alkyl is dihaloalkyl, e.g., difluoromethyl or monohaloalkyl, e.g., monofluoromethyl.

According to some embodiments of the invention, $R_5$ is quinazolinyl, which can be attached through any available atom, optionally substituted with a one or two substituents independently selected from the group consisting of alkyl, alkoxy, or halo. In some embodiments, alkyl is trihaloalkyl, for example trifluoromethyl. In other embodiments, alkyl is dihaloalkyl, e.g., difluoromethyl or monohaloalkyl, e.g., monofluoromethyl.

According to some embodiments of the invention, $R_5$ is quinoxalinyl, which can be attached through any available atom, optionally substituted with a one or two substituents independently selected from the group consisting of alkyl, alkoxy, or halo. In some embodiments, alkyl is trihaloalkyl, for example trifluoromethyl. In other embodiments, alkyl is dihaloalkyl, e.g., difluoromethyl or monohaloalkyl, e.g., monofluoromethyl.

According to some embodiments of the invention, $R_5$ is pyrazolyl, which can be attached through any available atom, optionally substituted with a one or two substituents independently selected from the group consisting of alkyl, alkoxy, or halo. In some embodiments, alkyl is trihaloalkyl, for example trifluoromethyl. In some embodiments, the pyrazolyl is methyl-pyrazolyl substituted with trifluoromethyl. In other embodiments, alkyl is dihaloalkyl, e.g., difluoromethyl or monohaloalkyl. e.g., monofluoromethyl.

According to some embodiments of the invention, $R_5$ is benzoxazolyl, which can be attached through any available atom, optionally substituted with a one or two substituents independently selected from the group consisting of alkyl, alkoxy, or halo. In some embodiments, alkyl is trihaloalkyl, for example trifluoromethyl. In other embodiments, alkyl is dihaloalkyl, e.g., difluoromethyl or monohaloalkyl, e.g., monofluoromethyl.

According to some embodiments of the invention, $R_5$ is imidazopyrazinyl, which can be attached through any available atom, optionally substituted with a one or two substituents independently selected from the group consisting of alkyl, alkoxy, or halo. In some embodiments, alkyl is trihaloalkyl, for example trifluoromethyl. In other embodiments, alkyl is dihaloalkyl. e.g., difluoromethyl or monohaloalkyl, e.g., monofluoromethyl.

According to some embodiments of the invention, $R_5$ is triazolopyrazinyl, which can be attached through any available atom, optionally substituted with a one or two substituents independently selected from the group consisting of alkyl, alkoxy, or halo. In some embodiments, alkyl is trihaloalkyl, for example trifluoromethyl. In other embodiments, alkyl is dihaloalkyl, e.g., difluoromethyl or monohaloalkyl, e.g., monofluoromethyl.

According to some embodiments of the invention, $R_5$ is thiazolyl which can be attached through any available atom, optionally substituted with a one or two substituents independently selected from the group consisting of alkyl, alkoxy, or halo. In some embodiments, alkyl is trihaloalkyl, for example trifluoromethyl. In other embodiments, alkyl is dihaloalkyl, e.g., difluoromethyl or monohaloalkyl, e.g., monofluoromethyl.

According to some embodiments of the invention, $R_5$ is thiadiazolyl which can be attached through any available atom, optionally substituted with a one or two substituents independently selected from the group consisting of alkyl, alkoxy, or halo. In some embodiments, alkyl is trihaloalkyl, for example trifluoromethyl. In other embodiments, alkyl is dihaloalkyl. e.g., difluoromethyl or monohaloalkyl. e.g., monofluoromethyl.

In some embodiments of the invention n is 0. In other embodiments, n is 1.

The invention relates to methods of using the compounds described herein to treat subjects diagnosed with or suffering from a disease, disorder, or condition mediated by orexin receptor activity. These methods are accomplished by administering to the subject a compound of the invention. In some embodiments, the compounds described herein are selective for orexin-1 receptor activity. In some embodiments, the compounds described herein are selective for orexin-1 receptor activity over orexin-2 receptor activity.

Diseases, disorders, and conditions mediated by orexin receptor activity include disorders of the sleep-wake cycle, insomnia, restless legs syndrome, jet-lag, disturbed sleep, sleep disorders secondary to neurological disorders, mania, depression, manic depression, schizophrenia, pain syndromes, fibromyalgia, neuropathic pain, catatonia, Parkinson's disease, Tourette's syndrome, anxiety, delirium, dementia, overweight, obesity, or conditions related to overweight or obesity, insulin resistance, type II diabetes, hyperlipidemia, gallstones, angina, hypertension, breathlessness, tachycardia, infertility, sleep apnea, back and joint pain, varicose veins, osteoarthritis, hypertension, tachycardia, arrhythmias, angina pectoris, acute heart failure, ulcers, irritable bowel syndrome, diarrhea gastroesophageal reflux, mood disorders, post-traumatic stress disorder, panic disorders, attention deficit disorders, cognitive deficiencies, or substance abuse.

Compounds of the invention are particularly suited for the treatment of mood disorders, post-traumatic stress disorder, panic disorders, attention deficit disorders, cognitive deficiencies, or substance abuse.

In one aspect, compounds of the invention are particularly suited for the treatment of mood disorders. Non-limiting examples of mood disorders include anxiety-related mood disorders, depression, panic-related mood disorders, stress related mood disorders and the like. In another aspect, compounds of the invention are suitable for the treatment of post-traumatic stress disorder, panic disorders, attention deficit disorders, cognitive deficiencies, or substance abuse (e.g., morphine abuse, cocaine abuse, alcohol abuse and the like). It will be understood that certain disorders such as, for example, depression and/or schizophrenia and/or substance abuse and/or cognitive impairments also have elements of anxiety and/or panic and/or stress associated with them and the treatment of such conditions and/or combinations of conditions are also contemplated within the scope of embodiments presented herein. In some embodiments, advantageously, compounds of the invention treat a mood disorder (e.g., anxiety) with reduced concomitant sedation and/or with reduced effect on sleep (e.g. attenuated arousal effects). In one embodiment, compounds of the invention are particularly suited for the treatment of anxious depression.

In another embodiment, compounds of the invention are particularly suited for the treatment of panic, schizophrenia, and substance abuse.

Sleep disorders include, but are not limited to, sleep-wake transition disorders, insomnia, restless legs syndrome, jet-lag, disturbed sleep, and sleep disorders secondary to neurological disorders (e.g., manias, depressions, manic depression, schizophrenia, and pain syndromes (e.g., fibromyalgia, neuropathic).

Metabolic disorders include, but are not limited to, overweight or obesity and conditions related to overweight or obesity, such as insulin resistance, type II diabetes, hyperlipidemia, gallstones, angina, hypertension, breathlessness, tachycardia, infertility, sleep apnea, back and joint pain, varicose veins and osteoarthritis.

Neurological disorders include, but are not limited to, Parkinson's disease, Alzheimer's disease, Tourette's Syndrome, catatonia, anxiety, delirium and dementias.

In treatment methods according to the invention, a therapeutically effective amount of a pharmaceutical agent according to the invention is administered to a subject suffering from or diagnosed as having such a disease, disorder, or condition. A "therapeutically effective amount" means an amount or dose sufficient to generally bring about the desired therapeutic or prophylactic benefit in patients in need of such treatment for the designated disease, disorder, or condition. Effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the compounds of the invention may be used in combination with additional active ingredients in the treatment of the above conditions. The additional active ingredients may be coadministered separately with a compound of the invention or included with such an agent in a pharmaceutical composition according to the invention. In an exemplary embodiment, additional active ingredients are those that are known or discovered to be effective in the treatment of conditions, disorders, or diseases mediated by orexin activity, such as another orexin modulator or a compound active against another target associated with the particular condition, disorder, or disease. The combination may serve to increase efficacy (e.g., by including in the combination a compound potentiating the potency or effectiveness of an active agent according to the invention), decrease one or more side effects, or decrease the required dose of the active agent according to the invention.

The compounds of the invention are used, alone or in combination with one or more additional active ingredients, to formulate pharmaceutical compositions of the invention. A pharmaceutical composition of the invention comprises: (a) an effective amount of at least one compound in accordance with the invention; and (b) a pharmaceutically acceptable excipient.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the compounds may be formulated to yield a dosage of, e.g., from about 0.05 to about 100 mg/kg daily, or from about 0.05 to about 35 mg/kg daily, or from about 0.1 to about 10 mg/kg daily. For example, a total daily dosage of about 5 mg to 5 g daily may be accomplished by dosing once, twice, three, or four times per day.

Oral tablets may include a compound according to the invention mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, compounds of the invention may be mixed with a solid, semi-solid, or liquid diluent. Soft gelatin capsules may be prepared by mixing the compound of the invention with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, the compositions may be formulated for rectal administration as a suppository. For parenteral use, including intravenous, intramuscular, intraperitoneal, or subcutaneous routes, the compounds of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 .mu.g/kg/minute of compound, admixed with a pharmaceutical carrier over a period ranging from several minutes to several days.

For topical administration, the compounds may be mixed with a pharmaceutical carrier at a concentration of about 0.1% to about 10% of drug to vehicle. Another mode of administering the compounds of the invention may utilize a patch formulation to affect transdermal delivery.

Compounds of the invention may alternatively be administered in methods of this invention by inhalation, via the nasal or oral routes, e.g., in a spray formulation also containing a suitable carrier.

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

The synthesis of exemplary intermediates of structure i.e., formula $(R^1R^{2A})CO_2H$, is shown in Schemes 1-6 below, and also in the Examples section below (Intermediates A-1 to A-71).

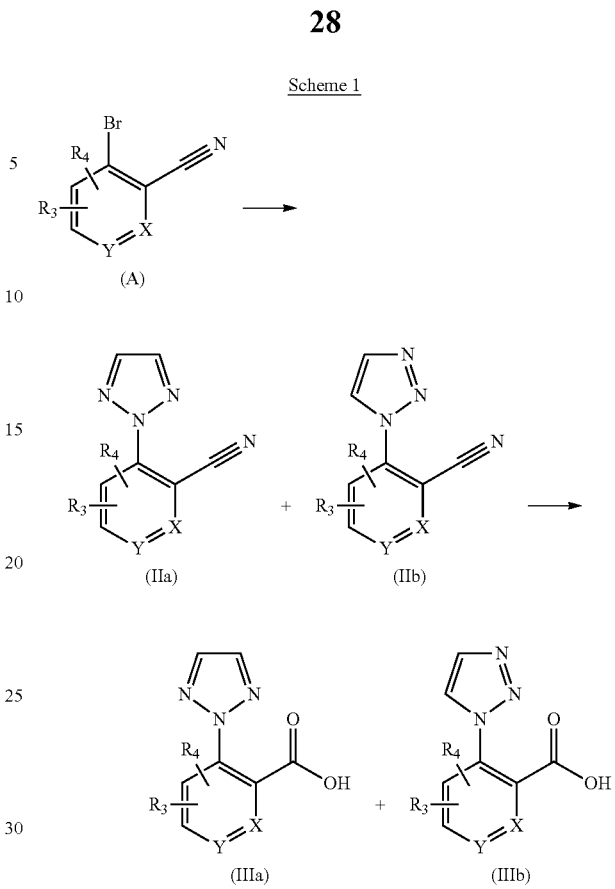

Intermediate compounds of formula (IIIa) and (IIIb) can be prepared as outlined in Scheme 1 from commercially available or synthetically accessible compounds of formula (A) where $R_3$, $R_4$, are defined in formula (IA) as above, or $R_3$ is H, $R_4$ is analogous to $R_2$ in Formula I as above, and X and Y are independently selected from C and N. Compounds of formula (IIa) and (IIb), are obtained by reacting a compound of formula (A), with commercially available 1,2,3-triazole, in the presence $K_2CO_3$ in DMF or dioxane, at temperatures ranging from about 60° C. to about 100° C. Compounds of formula (IIIa) and (IIIb) are obtained by reacting compounds of formula (II) in the presence of a base such as NaOH in a solvent such as EtOH at temperatures ranging from 80° C. to 100° C. One skilled in the art will recognize that 1,2,3-triazole can exist in two tautomeric forms defined as 2H-[1,2,3]triazole and 1H-[1,2,3]triazole thus accounting for the formation of (IIIa) and (IIIb).

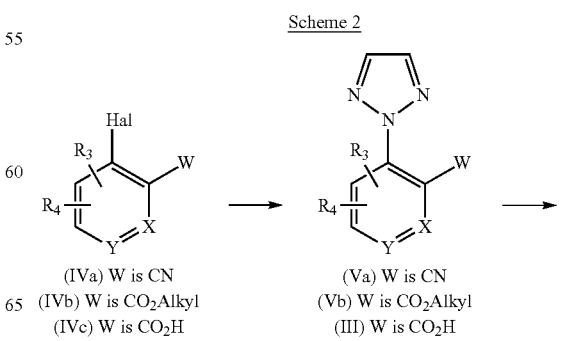

(IVa) W is CN
(IVb) W is CO$_2$Alkyl
(IVc) W is CO$_2$H (Va) W is CN
(Vb) W is CO$_2$Alkyl
(III) W is CO$_2$H

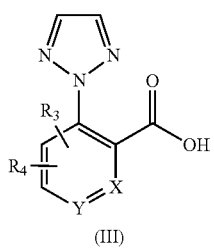

Intermediate compounds of formula (III) can be prepared as outlined in Scheme 2 from commercially available or synthetically accessible compounds of formula (IV$_{a-c}$). Compounds of formula (III), (Va) and (Vb) are obtained by reacting compounds of formula (IVa), (IVb) and (IVc) where Hal is —Br, or —I; W is CO$_2$H, CO$_2$Alkyl, or CN and R$_3$ and R$_4$ are —H, halo. —C$_{1-4}$alkyl, —C$_{1-4}$alkoxy and R$_3$ and R$_4$ together with the atoms to which they are attached form a 6-membered aryl or 6 membered heteroaryl ring, or R$_3$ is H, R$_4$ is analogous to R$_2$ in Formula I as above, and X and Y are independently selected from C and N, with commercially available 1,2,3-triazole, in the presence of, for example, copper(I)iodide, Cs$_2$CO$_3$ and trans-N,N'-dimethyl-1,2-cyclohexanediamine in, for example, DMF or dioxane, at temperatures ranging from about 60° C. to about 120° C. Compounds of formula (IVc) can be converted to the corresponding esters (Vb) by treatment with, for example, alkyl iodide in the presence of a base such as K$_2$CO$_3$ in a solvent such as DMF. Compounds of formula (III) are obtained by reacting a compound of formula (Va) and (Vb) in the presence of a base such as NaOH in a solvent such as EtOH at temperatures ranging from about 80° C. to about 100° C. One skilled in the art will recognize that 1,2,3-triazole can exist in two tautomeric forms defined as 2H-[1,2,3]triazole and 1H-[1,2,3]triazole thus compounds of formula (Va), (Vb), and (III) can also exist as the N1 linked variant (structure not shown). It will be understood that the heterocycle in (Va) and (Vb) is not limited to triazole and may be any other suitable heterocycle.

Scheme 3

(VI)

(VII)

(VIII)

(IX)

Intermediate compounds of formula (IX) are prepared as outlined in Scheme 3 from commercially available or synthetically accessible compounds of formula (VI) where R$_3$, R$_4$, are defined as in formula IA above, or R$_3$ is H, R$_4$ is analogous to R$_2$ in Formula I as above, and X and Y are independently selected from C and N, G is SnBu$_3$ or 4,4,5,5 tetramethyl-1,dioxaboralane and Hal is Cl, or Br, preferably Br in this case. Compounds of formula (VIII) are obtained by reacting a compound of formula (VI) with commercially available (VII) in the presence of a catalyst such as 1,1'-Bis (di-tert-butylphosphino)ferrocene palladium dichloride and a base such as Na$_2$CO$_3$ in a solvent such as 2-MeTHF or THF at temperatures ranging from about 60° C. to about 90° C. Compounds of formula (IX) are obtained by reacting a compound of formula (VIII) in the presence of a base such as NaOH in a solvent such as MeOH at temperatures ranging from about 80° C. to about 100° C. or acids such as H$_2$SO$_4$ in solvents such as H$_2$O at temperatures ranging from about 80 to about 100° C. It will be understood that the heterocycle in (VII) is not limited to pyrimidine and may be any other suitable heterocycle.

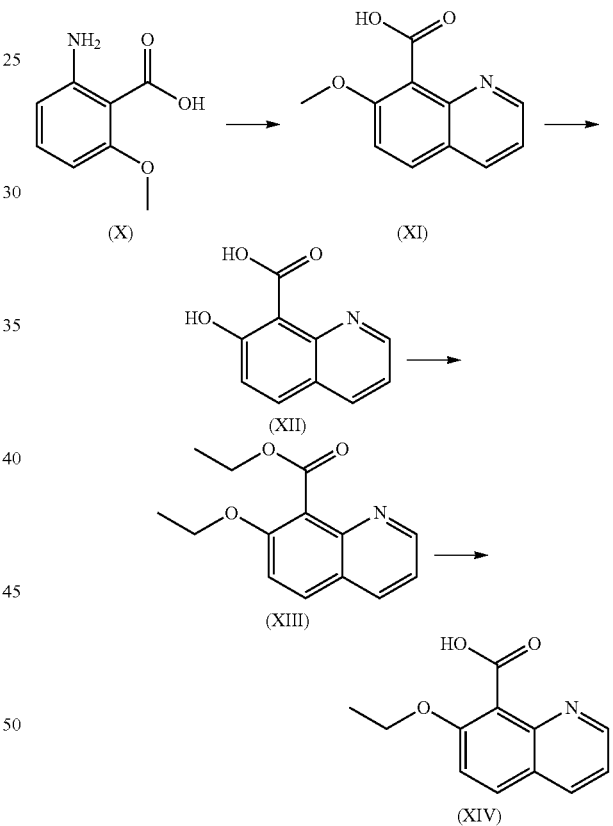

Scheme 4

Intermediate compound (XIV) is prepared as outlined in Scheme 4 from commercially available compound (X). Compounds (XI) is obtained by reacting compound (X) with commercially available acrolein in a solvent such as 1,4 dioxane at temperatures of about 200° C. in a microwave reactor. Compound (XII) can be prepared from compound (XI) by treatment with an acid such as HBr in a solvent such as toluene at a temperature of about 90° C. Compound (XIII) can be obtained by treatment of compound (XII) with commercially available iodoethane and a base such as K$_2$CO$_3$ in a solvent such as DMF at temperatures ranging from about 45° C. to about 65° C. Compound (XIV) is obtained by treating compound (XIII) with a base such as NaOH in a solvent such as MeOH at temperatures ranging from about 80° C. to about 100° C.

Scheme 5

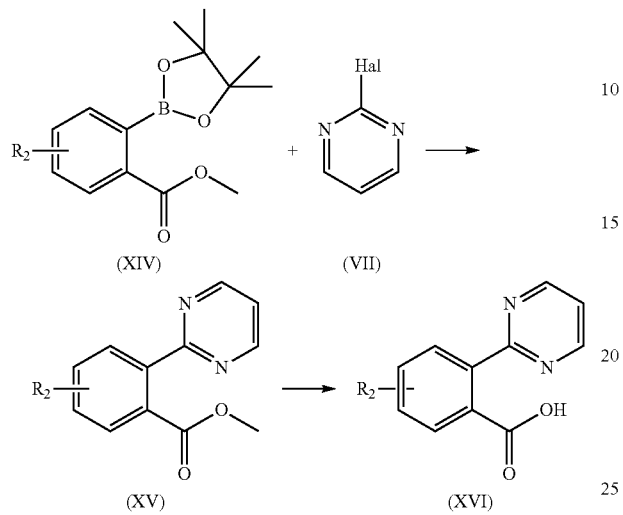

Intermediate compounds of formula (XVI) are prepared as outlined in Scheme 5 from commercially available or synthetically accessible compounds of formula (XIV) where $R_2$ is —H, —$C_{1-4}$alkyl, or —$C_{1-4}$alkoxy; or $R_2$ is —H, halo, —$C_{1-4}$alkyl, or —$C_{1-4}$alkoxy. Compounds of formula (XV) are obtained by reacting a compound of formula (XIV) with commercially available (VII) in the presence of a catalyst such as Pd(dppf)Cl$_2$ and a base such as Na$_2$CO$_3$ in a solvent such as 2-MeTHF at temperatures ranging from 75° C. to 150° C. Compounds of formula (XVI) are obtained by reacting a compound of formula (XV) in the presence of a base such as NaOH in a solvent such as MeOH at temperatures ranging from about 80° C. to about 100° C.

Scheme 6

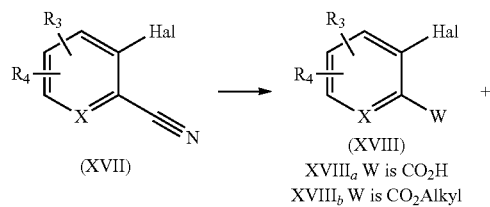

XVIII$_a$ W is CO$_2$H
XVIII$_b$ W is CO$_2$Alkyl

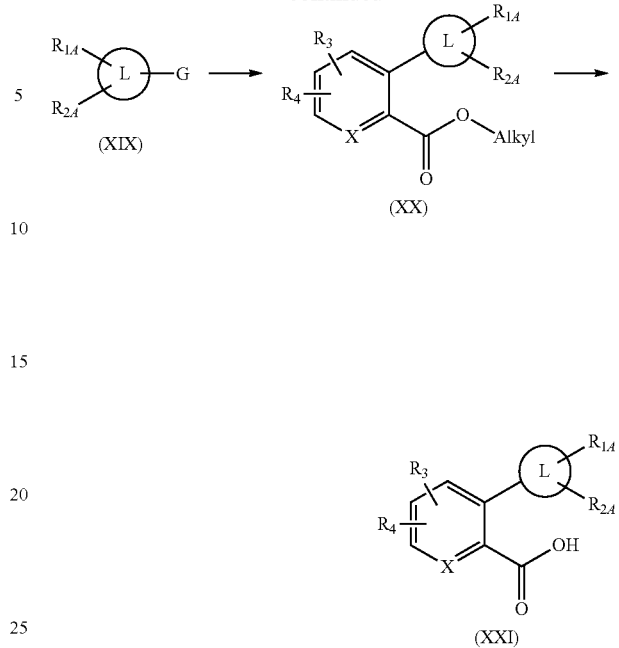

Intermediate compounds of formula (XXI) can be prepared as outlined in Scheme 6 from commercially available or synthetically accessible compounds of formula (XVII) where Hal is Br or I; and where $R_3$ is H, $R_4$ is analogous to $R_2$ in Formula I as above, and X and Y are independently selected from C and N. Compounds of formula (XVIIIa) can be converted to the corresponding ester (XVIIIb) by treatment with thionyl chloride in a solvent such as MeOH. Compounds of the formula (XX) are obtained by reacting compounds of formula (XVIIIb) with commercially available compounds of the formula XIX where L is a heterocyle such as pyrazole, pyridyl, or oxazole; G is SnBu$_3$ or 4,4,5,5 tetramethyl-1,dioxaboralane and $R_{1A}$ and $R_{2A}$ are —H, -alkyl, or -alkoxy; or $R_{1A}$ and $R_{2A}$ are —H, halo, —$C_{1-4}$ alkyl, or —$C_{1-4}$alkoxy, in the presence of a catalyst such as Pd(Ph$_3$P)$_4$ and a base such as Na$_2$CO$_3$ in a mixture of solvents such as DME and H$_2$O at temperatures ranging from 100° C. to 150° C. Compounds of formula (XXI) are obtained by reacting a compound of formula (XX) in the presence of a base such as NaOH in a solvent such as MeOH at temperatures ranging from about 80° C. to about 100° C.

Scheme 7

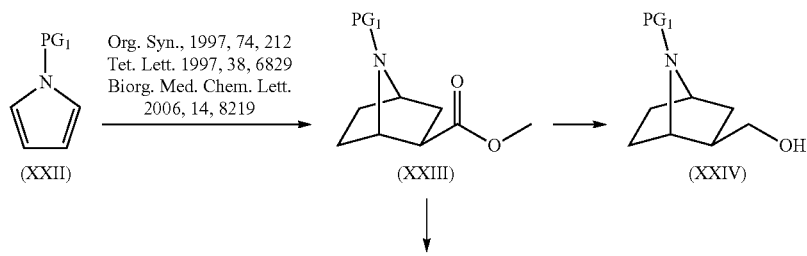

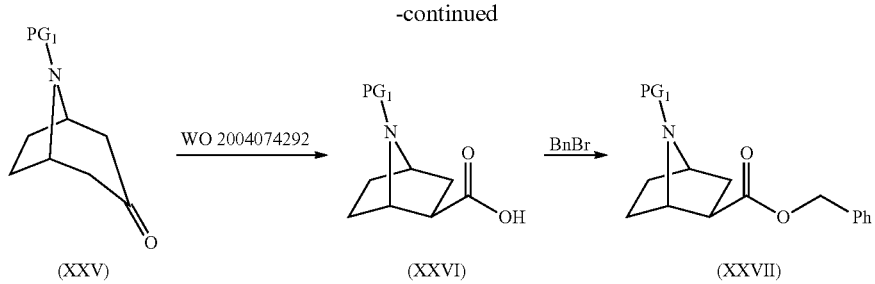

Intermediate compounds of formula (XXIV) and (XXVII) are readily prepared as outlined in Scheme 7 from commercially available or synthetically accessible compounds of formula (XXII) or (XXV). Compounds of formula (XXIII) can be obtained from compounds of formula (XXII) as described in the references listed in Scheme 7. Compounds of formula (XXIV) can be obtained from compounds of formula (XXIII) by treatment with reducing agents such as Dibal-H, LiAlH$_4$ or LiBH$_4$ in solvents such as THF or diethyl ether at temperatures ranging from about 0° C. to about 70° C. Compounds of formula (XXVI) can be obtained from compounds of formula (XXIII) by treatment with bases such as aqueous sodium hydroxide, potassium hydroxide and lithium hydroxide in solvents such as water, methanol or THF. Compounds of formula (XXVI) can also be obtained from compounds of formula (XXV) using procedures described in WO 2004074292.

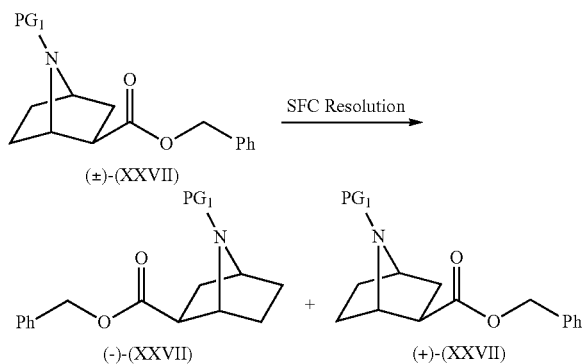

Referring to Scheme 8, where PG$_1$ is a Boc protecting group, compounds of formula (±)-(XXVII) were resolved into individual enantiomers of formula (+)-(XXVII) and (−)-(XXVII) using SFC chromatography on a chiral SFC (CHIRALPAK IC 5 μM 250×20 mm) column using 80% CO$_2$/20% iPrOH as the mobile phase.

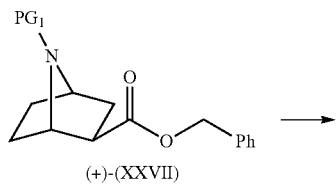

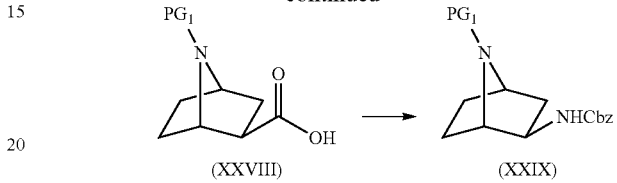

Referring to Scheme 9, where PG$_1$ is a Boc protecting group, compounds of formula (XXVIII) are prepared compounds of formula (+)-(XXIX). Compounds of formula (XXVIII) are readily prepared from compounds of formula (+)-(XXVII) by treatment with metal catalyst such as PtO$_2$, Pd/C, or Pd(OH)$_2$ in solvents such as AcOH, MeOH or EtOH under an atmosphere of hydrogen. Compounds of formula (XXIX) are readily prepared from compounds of formula (XXVIII) by reaction with DPPA and TEA in a solvent such as toluene at temperatures ranging from about 0° C. to about 100° C., preferably about 65° C. for a period of about 1 to 8 hours. BnOH is then added to afford a compound of formula (XXIX).

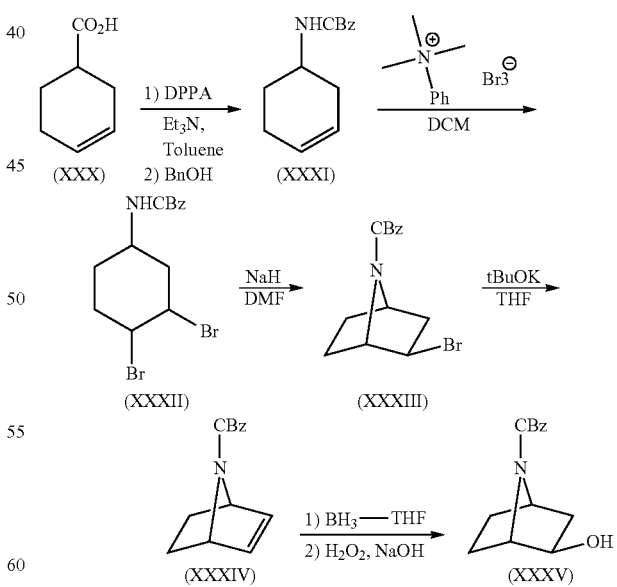

According to Scheme 10, compound (XXXI) is obtained by reaction of compound (XXX) with, for example, DPPA and TEA in a solvent such as toluene at temperatures ranging from about 0° C. to about 100° C., preferably about 65° C. for a period of about 1 to 8 hours, preferably about 4 h.

Benzyl alcohol (BnOH) is then added to afford a compound of formula (XXXI). Compound (XXXII) is obtained from compound (XXXI) by reaction with trimethylphenyl ammonium tribromide at temperatures ranging from about 0° C. to about 23° C., preferably about 0° C. for a period of from 2 to 6 hours, preferably about 4 hours. Compound (XXIII) is obtained from compound (XXXII) by treatment with a base, preferably NaH in a solvent such as DMF. Compound (XXXIV) is obtained from compound (XXXIII) by elimination of HBr with tBuOK in a solvent such as THF for a period ranging from 2 to 24 hours. Compound (XXXV) is obtained from compound (XXXIV) by hydroboration oxidation by treating the compound (XXXIV) with borane in a solvent such as THF at temperatures ranging from about 0° C. to about 23° C., preferably at about 23° C., for 2 to 12 hours, preferably about 2 hours followed by reaction with, for example, hydrogen peroxide in the presence of a base such as sodium hydroxide. Also contemplated within the scope of embodiments presented here are other nitrogen protecting groups which are known to one skilled in the art.

Scheme 10-A

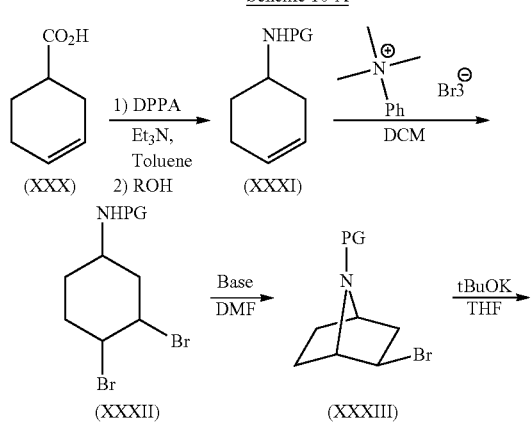

-continued

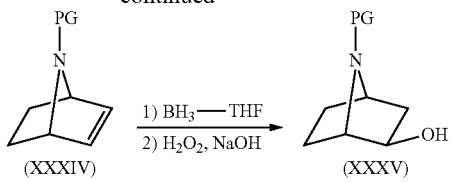

Certain variations of Scheme 10 are described in Scheme 10-A above. It will be understood that the protecting group in compound (XXXI) may be varied as shown in Scheme 10-A, for example, by adding any other suitable alcohol. An alcohol such as BnOH or preferably tBuOH is added to afford a compound of formula (XXXI). Additionally, the protecting group in a compound of formula (XXXI) can be exchanged utilizing standard methods, for example, from BOC to TFA. It will be further understood that the base utilized for the conversion of compound (XXXII) to (XXXIII) may be varied as shown in Scheme 10-A. Compound (XXIII) is obtained from compound (XXXII) by treatment with a base, such as NaH or preferably $K_2CO_3$ is a solvent such as DMF or preferably toluene at temperatures ranging from about 0° C. to about 100° C. with or without a protecting group present. Further, the choice of the protecting group and/or base and/or solvents and/or reaction temperatures will vary depending on the reaction substrate and all such variations are contemplated within the scope of embodiments provided herein.

Scheme 11

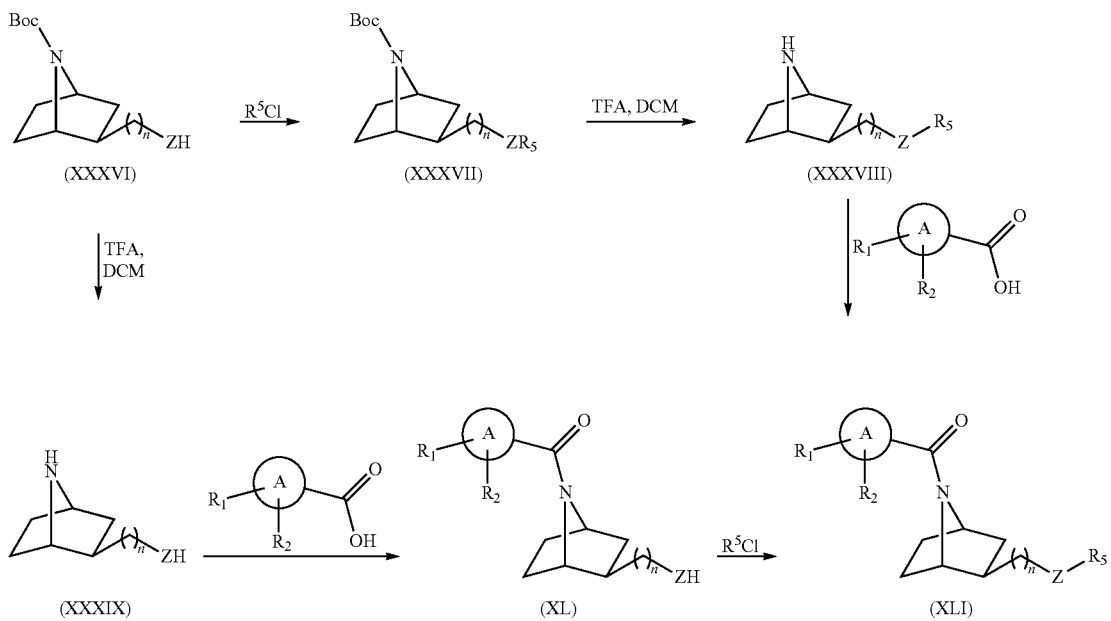

Referring to Scheme 11, one skilled in the art would recognize that compounds of formula (XLI) may be obtained from compounds of formula (XXXVI) by converging pathways. In one sequence, a compound of formula (XXXVII) is obtained by treating a compound of formula (XXXVI) with $R^5Cl$, where $R^5$ is optionally substituted pyridyl, pyrimidyl, pyrazinyl, pyridazinyl, quinazolinyl, quinoxalinyl, pyrazolyl, benzoxazolyl, imidazopyrazinyl, triazolopyrazinyl. Commercially available or synthetically accessible suitably substituted heteroaryl compounds of formula $R^5Cl$ are reacted with compounds of formula (XXXVI), in the presence of a suitably selected tertiary organic or inorganic base such as NaH, $Cs_2CO_3$, $K_2CO_3$, TEA, $iPr_2NEt$ and the like; in a solvent such as DMF, dichloromethane, THF, and the like; at a temperature between room temperature and the reflux temperature of the solvent. In a preferred embodiment the base is NaH and the solvent is DMF. Removal of the tert-butylcarbamate (Boc) in compounds of formula (XXXVII) is accomplished by using methods known to one skilled in the art, such as, HCl, TFA, or p-toluenesulfonic acid, in a solvent such as $CH_3OH$, dioxane, or $CH_2Cl_2$. In a preferred embodiment, a compound of formula (XXXVII) is treated with TFA in DCM or HCl to afford a compound of formula (XXXVIII). A compound of formula (XLI) is obtained by treating a compound of formula (XXXVIII) with $(R^1R^{2A})CO_2H$, where $R^1$ is H, alkyl, alkoxy, hydroxyalkylene, OH, halo, phenyl, triazolyl, oxazolyl, isoxazolyl, pyridyl, pyrimidyl, pyrazinyl, pyridazinyl, piperazinyl, pyrazolyl, oxadiazolyl, pyrrolidinyl, thiophenyl, morpholinyl, or dialkylamino and $R_2$ is H, alkyl, alkoxy, or halo. Commercially available or synthetically accessible suitably substituted carbocylic acid compounds of formula $(R^1R^{2A})CO_2H$ are combined with compounds of formula (XXXVIII) using under amide coupling methods known to one skilled in the art, such as, CDI, EDCI, HATU, or T3P in a solvent such as THF, DCM, or DMF In a preferred embodiment, a compound of formula (XXXVIII) and $(R^1R^{2A})CO_2H$ are treated with EDCI in the presence of HOBT in DMF at ambient temperature to afford a compound of formula (XLI). One skilled in the art would recognize that compounds of formula (XLI) may also be obtained from compounds of formula (XL). Removal of the tert-butylcarbamate (Boc) in compounds of formula (XXXVI) is accomplished by using methods known to one skilled in the art, such as, HCl, TFA, or p-toluenesulfonic acid, in a solvent such as $CH_3OH$, dioxane, or $CH_2Cl_2$. In a preferred embodiment, a compound of formula (XXXVI) is treated with TFA in DCM or HCl to afford a compound of formula (XXXIX). A compound of formula (XL) is obtained by treating a compound of formula (XXXIX) with $(R^1R^{2A})CO_2H$. Commercially available or synthetically accessible suitably substituted carbocylic acid compounds of formula $(R^1R^{2A})CO_2H$ are combined with compounds of formula (XXXIX) under amide coupling methods known to one skilled in the art, such as, CDI, EDCI, HATU, or T3P in a solvent such as THF, DCM, or DMF In a preferred embodiment, a compound of formula (XXXIX) and $(R^1R^{2A})CO_2H$ are treated with EDCI in the presence of HOBT in DMF at ambient temperature to afford a compound of formula (XL). A compound of formula (XLI) is obtained by treating a compound of formula (XL) with $R^5Cl$. Commercially available or synthetically accessible suitably substituted heteroaryl compounds of formula $R^5Cl$ are reacted with compounds of formula (XL), in the presence of a suitably selected tertiary organic or inorganic base such as NaH, $Cs_2CO_3$, $K_2CO_3$, TEA, $iPr_2NEt$ and the like; in a solvent such as DMF, dichloromethane, THF, and the like; at a temperature between room temperature and the reflux temperature of the solvent. In a preferred embodiment the base is NaH and the solvent is DMF to provide compounds of formula (XLI).

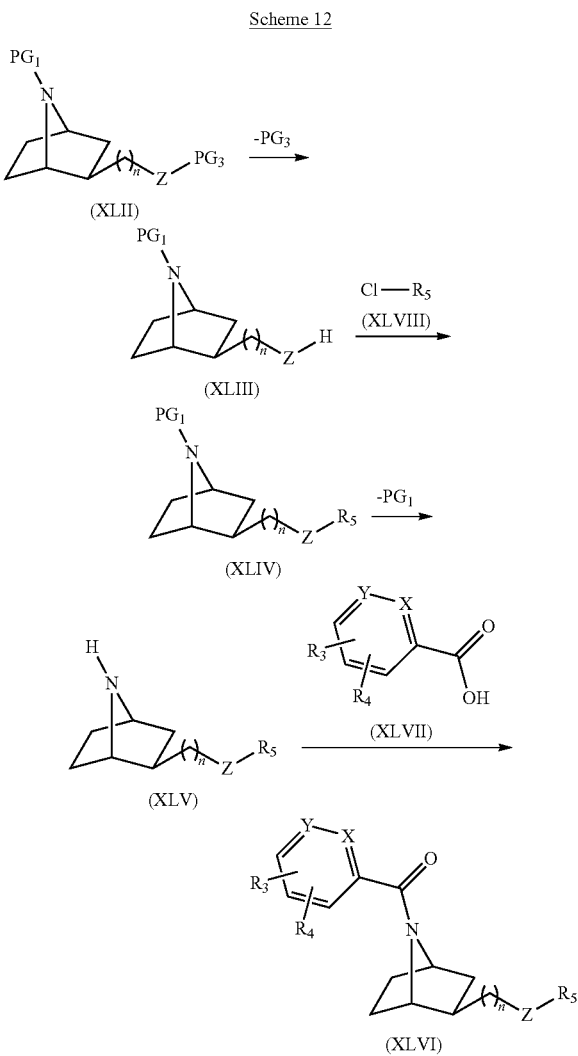

Scheme 12

Where n is 0 and Z is NH

Referring to Scheme 12, compounds of formula (XLVI) were synthesized from compounds of formula (XLII) where $PG_1$ is Boc, $PG_3$ is Cbz, Z is O or NH and n is 0 or 1. $PG_3$ was removed when compound of formula (XLII) was treated with, for example, a Pd catalyst such as 10 wt % Pd/C wet Degussa under an atmosphere of $H_2$ in a solvent such as EtOH to give compound of formula (XLIII). Compounds of formula (XLIV) were obtained from compounds of formula (XLIII) using compounds of formula (XLVIII) in a suitable solvent such as DMSO or DMF in the presence of a base such as $K_2CO_3$ at a temperature of about 70° C. Compounds of formula (XLIV) could also be obtained when compounds of formula (XLIII) and (XLVIII) were treated with a Pd catalyst such as $Pd(OAc)_2$, a ligand such as racemic BINAP, a base such as sodium tert-butoxide in a solvent such as toluene at a temperature of about 70° C. Compound of formula (XLV) were obtained from compounds of formula (XLIV) when treated with an acid such as HCl in a suitable solvent such as EtOAc or DCM at room temperature.

Compound of formula (XLVI) were obtained from compounds of formula (XLV) using compounds of formula (XLVII) in a suitable solvent such as DMF or DCM in the presence of a peptide coupling reagent such as HATU or T3P, a base such as DIPEA at a temperature ranging from room temperature to about 45° C.

Scheme 13

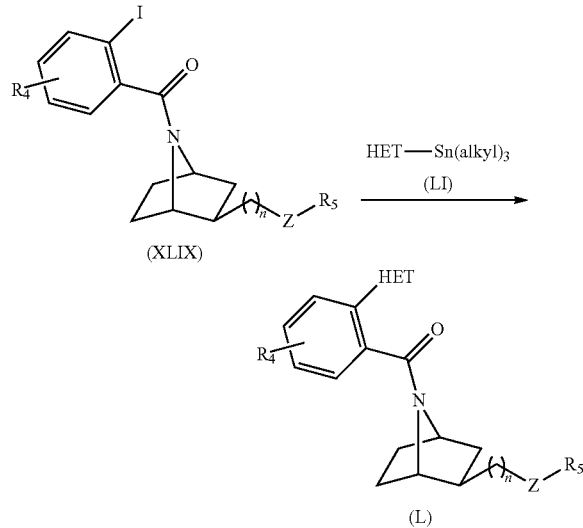

Referring to Scheme 13, compounds of formula (L), where $R_4$ is analogous to $R_2$ of Formula I above, were obtained from compound of formula (XLIX) using compounds of formula (LI) in a solvent such as DME in the presence of a Pd catalyst such as Pd(PPh3)4, an additive or catalyst such as copper iodide at a temperature ranging from about 120° C. to about 150° C.

In one group of embodiments, provided herein is a compound of Formula I of Examples 1-482 with structures and names as set forth in the Examples section below. In another group of embodiments, provided herein is a compound of Formula I of Examples 1-367 with structures and names as set forth in the Examples section below. In yet another embodiment, provided herein is a compound of Formula I of Examples 368-482 with structures and names as set forth in the Examples section below. In an additional embodiment, provided herein is a compound of Formula IA of Examples 483-495 with structures and names as set forth in the Examples section below. In one group of embodiments, provided herein is a compound of Formula I having structures and names as set forth in Table 2 below.

EXAMPLES

Abbreviations

| Term | Acronym |
|---|---|
| Acetic Acid | HOAc |
| Acetonitrile | ACN |
| Apparent | app |
| Aqueous | aq |
| Atmosphere | atm |
| 2-(1H-9-Azobenzotriazole-1-yl)-1,1,3,3-tetramethylaminium hexafluorophosphate | HATU |

-continued

| Term | Acronym |
|---|---|
| O-(Benzotriazol-1-yl)-N,N,N',N'-tetramethyluronium hexafluorophosphate | HBTU |
| 1-Ethyl-3-(3-dimethylaminopropyl)carbodiimide | EDCI |
| Hydroxybenzotriazole | HOBt |
| Benzyl | Bn |
| 2,2'-bis(diphenylphosphino)-1,1'-binaphthalene | BINAP |
| [1,1'-Bis(di-tert-butylphosphino)ferrocene]dichloropalladium(II) | PdCl$_2$(dtbpf) |
| Broad | br |
| tert-Butylcarbamoyl | Boc/Boc |
| Dichloromethane | DCM |
| Diisopropylethylamine | DIPEA |
| 1,2-Dimethoxyethane | DME |
| N,N-Dimethylformamide | DMF |
| Dimethylsulfoxide | DMSO |
| Doublet | d |
| Electrospray ionization | ESI |
| Enantiomeric excess | ee |
| Ethanol | EtOH |
| Ethyl Acetate | EtOAc, or EA |
| Grams | g |
| Hertz | Hz |
| High-pressure liquid chromatography | HPLC |
| Hours | h |
| Liquid chromatography and mass spectrometry | LCMS |
| Mass spectrometry | MS |
| Mass to charge ratio | m/z |
| Methanol | MeOH |
| Microliter | μL |
| Milligrams | mg |
| Milliliter | mL |
| Millimoles | mmol |
| Minute | min |
| Molar | M |
| Multiplet | m |
| Normal | N |
| Nuclear magnetic resonance | NMR |
| Palladium on carbon | Pd/C |
| Palladium hydroxide on carbon | Pd(OH)$_2$/C |
| Parts per million | ppm |
| Phenyl | Ph |
| Propylphosphonic anhydride | T3P |
| Retention time | $R_t$ |
| Room temperature | rt |
| Quartet | q |
| Singlet | s |
| Supercritical Fluid Chromatography | SFC |
| Temperature | T |
| Thin layer chromatography | TLC |
| Times | X |
| Triethylamine | TEA |
| Trifluoroacetic acid | TFA |
| Triplet | t |
| Diphenylphosphoryl azide | DPPA |
| Diisopropyl azodicarboxylate | DIAD |

Chemistry:

In obtaining the compounds described in the examples below and the corresponding analytical data, the following experimental and analytical protocols were followed unless otherwise indicated.

Unless otherwise stated, reaction mixtures were magnetically stirred at room temperature (rt) under a nitrogen atmosphere. Where solutions were "dried," they were generally dried over a drying agent such as Na$_2$SO$_4$ or MgSO$_4$, filtered and concentrated. Where mixtures, solutions, and extracts were "concentrated", they were typically concentrated on a rotary evaporator under reduced pressure. Reactions under microwave irradiation conditions were carried out in a Biotage Initiator or CEM Discover instrument.

Melting point determinations were performed in open capillary tubes on a FP62 or MP50 apparatus (Mettler-Toledo). Melting points were measured with a temperature gradient of 10° C./minute. Maximum temperature was 300° C. The melting point was read from a digital display.

Normal-phase flash column chromatography (FCC) was performed on silica gel ($SiO_2$) using prepackaged cartridges, eluting with the indicated solvents.

Where compounds were purified by "Prep HPLC" the method employed was either:

Preparative reverse-phase high performance liquid chromatography (HPLC) was performed on a Gilson HPLC with an Xterra Prep $RP_{18}$ (5 µm, 30×100 mm, or 50×150 mm) column, and a gradient of 10 to 99% acetonitrile/water (20 mM $NH_4OH$) over 12 to 18 min, and a flow rate of 30 mL/min.

or

Preparative reverse-phase high performance liquid chromatography (HPLC) was performed on a Agilent 1100 Series HPLC with an XBridge C18 column (5 µm, 30×100 mm), mobile phase of 5% ACN in 20 mM NH4OH (hold for 2 min) then ramp 5-99% ACN over 15 min. hold at 99% ACN for 5 min. and a flow rate of 40 mL/min.

or

Preparative reverse-phase high performance liquid chromatography (HPLC) was performed on a Agilent 1100 Series HPLC with an XBridge C18 column (5 µm, 50×100 mm), mobile phase of 5% ACN in 20 mM NH4OH (hold for 2 min) then ramp 5-99% ACN over 15 min, hold at 99% ACN for 5 min. and a flow rate of 80 mL/min.

or

Preparative reverse-phase high performance liquid chromatography (HPLC) was performed on a Gilson HPLC with an Xterra Prep $RP_{18}$ (5 µm, 30×100 mm, or 50×150 mm) column, and a gradient of 10 to 99% acetonitrile/water (20 mM $NH_4OH$) over 12 to 18 min, and a flow rate of 30 mL/min.

Where compounds were purified by "Agilent Prep Method X" the method employed was either:

Preparative reverse-phase high performance liquid chromatography (HPLC) was performed on a Agilent 1100 Series HPLC with an XBridge C18 OBD column (5 µm, 30×100 mm), mobile phase of 5% ACN in 20 mM $NH_4OH$ was held for 2 min, then a gradient of 5-99% ACN over 15 min, then held at 99% ACN for 5 min, with a flow rate of 40 mL/min.

or

Preparative reverse-phase high performance liquid chromatography (HPLC) was performed on a Agilent 1100 Series HPLC with an XBridge C18 OBD column (5 µm, 50×100 mm), mobile phase of 5% ACN in 20 mM $NH_4OH$ was held for 2 min, then a gradient of 5-99% ACN over 15 min, then held at 99% ACN for 5 min, with a flow rate of 80 mL/min.

Analytical chromatography data was acquired using an Agilent 1100 HPLC, with an Inertsil ODS-3 3 mm 4.6×50 mm column, purchased from GL Sciences (Part #1010L050W046). Samples were run using a gradient profile of 10-99% acetonitrile (ACN) in water, each containing 0.05% trifluoroacetic acid (TFA) over 1.6 minutes, then holding at 99% acetonitrile for 0.3 minutes. Flow rate was 5 mL/min and column temperature was set to 50° C. (Method A).

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. The format of the 1H NMR data below is: chemical shift in ppm downfield of the tetramethylsilane reference (multiplicity, coupling constant J in Hz, integration). Definitions for multiplicity are as follows: s=singlet, d=doublet, t=triplet, q=quartet, m=multiplet, br=broad. For compounds that are present as a mixture of rotamers the ratio is represented so that the total is 1, e.g. 0.80:0.20. Alternatively, 1H NMR data may be reported for only the major rotamer as indicated, or the data may be reported for one or more rotamers such that the total is less than 1. It will be understood that for compounds comprising an exchangeable proton, said proton may or may not be visible on an NMR spectrum depending on the choice of solvent used for running the NMR spectrum and the concentration of the compound in the solution.

Chemical names were generated using ChemDraw Ultra 12.0 (CambridgeSoft Corp., Cambridge, Mass.) or ACD/Name Version 10.01 (Advanced Chemistry).

Where compounds were purified by "SFC Chromatography" the method employed was either:

on preparative APS 1010 system with autoprep otion from Berger instrument, consisted of two varian SD-1 pumps (walnut creek, CA, USA), one of which was extensively modified to pump $CO_2$, a special pump head heat exchanger, a julabo FT 401 chiller (labortechnik GmbH, Sellback, Germany), a model SCM 2500 phase separator (berger instruments) with selection valve and set of collection vessels in a Bodan robot. A model Knauer 2500 UV detector with high pressure flow cell (berlin, germany). Samples were applied using a six-port injection valve (Valco, Houston, Tex., USA)) with a 5 ml sample loop and a model YP-300 syringue pump (cavro, san Jose, Calif.).

or

On a SFC-PICLAB-PREP 200 (PIC SOLUTION, Avignon, France). Modifier was pump with a model K1800 Knauer (Berlin, germany), with 100 ml Pump Head. The $CO_2$ was pump with 2 lewa pumps (Leonberg Germany). Cooling of the pump head and the CO2 line was achieved by a coil alimented by a Huber chiller (Offenburg/Germany). Sample injections were made using 6 switching valves (Valco, Houston, Tex., USA) and a 5 ml sample loop. The system is managed by a PLC automation system.

Examples 301, 307, 313, 319, 321-367, 396, 464-482, and 483-495 are suitable for preparation using methods analogous to the methods described in the synthetic schemes and in the Examples section.

INTERMEDIATES

| Intermediate | Name | Structure | Reference |
| --- | --- | --- | --- |
| A-1 | 2-(2H-1,2,3-triazol-2-yl)benzoic acid | 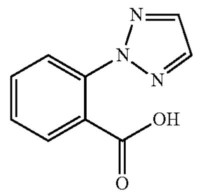 [SMILES: O=C(O)c1ccccc1-n1nccn1] | Prepared according to WO 2011/050198 Intermediate 2. |
| A-2 | 3-fluoro-2-(pyrimidin-2-yl)benzoic acid | 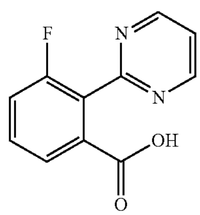 | Prepared according to WO 2011/050198 Intermediate 50. |
| A-3 | 6-methyl-2-(2H-1,2,3-triazol-2-yl)nicotinic acid | 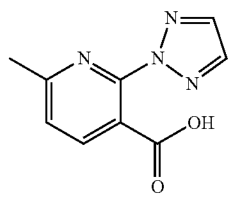 | Prepared according to WO 2011/050198 Intemediate 70 |
| A-4 | 6-methyl-2-(1H-1,2,3-triazol-1-yl)nicotinic acid | 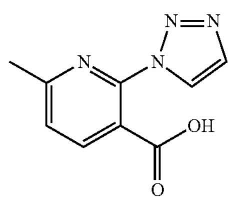 | Prepared according to WO 2011/050198 Intemediate 71 |
| A-5 | 4-methoxy-2-(2H-1,2,3-triazol-2-yl)benzoic acid | 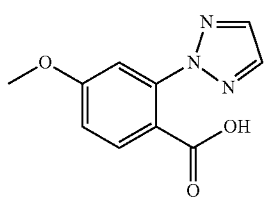 [SMILES: COc1ccc(C(=O)O)c(-n2nccn2)c1] | Prepared according to WO 2011/050198 Intemediate 54 |
| A-6 | 2-fluoro-6-(pyrimidin-2-yl)benzoic acid | 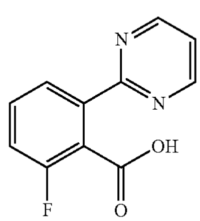 [SMILES: O=C(O)c1c(F)cccc1-c1ncccn1] | Prepared according to WO 2011/050198 Intermediate 14. |
| A-7 | 5-fluoro-2-(pyrimidin-2-yl)benzoic acid. | 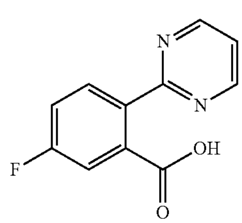 [SMILES: O=C(O)c1cc(F)ccc1-c1ncccn1] | Prepared according to WO 2011/050198 Intermediate 13. |

-continued

| Intermediate | Name | Structure | Reference |
|---|---|---|---|
| A-8 | 3-ethoxy-6-methylpicolinic acid | 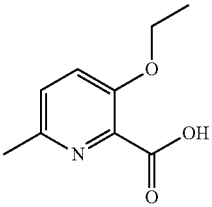 | WO 2010/063663 Description 39 |
| A-9 | 6-methyl-3-(pyrimidin-2-yl)picolinic acid | 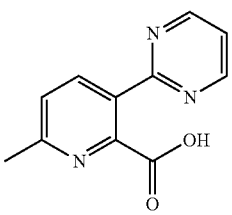 [SMILES: Cc1ccc(-c2ncccn2)c(C(=O)O)n1] | WO 2010/063663 Description 69 |
| A-10 | 5-fluoro-2-(2H-1,2,3-triazol-2-yl)benzoic acid | 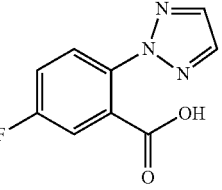 | Prepared according to WO 2011/050198 Intermediate 1. |
| A-11 | 2-fluoro-6-(2H-1,2,3-triazol-2-yl)benzoic acid | 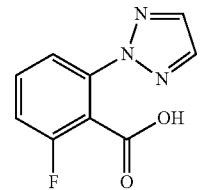 | Prepared according to WO 2011/050198 Intermediate 12. |
| A-12 | 4-fluoro-2-(2H-1,2,3-triazol-2-yl)benzoic acid | 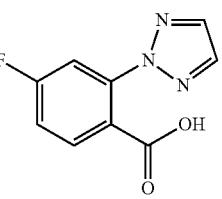 | Prepared according to WO 2011/050198 Intermediate 4. |
| A-13 | 2-methoxy-6-(2H-1,2,3-triazol-2-yl)benzoic acid | 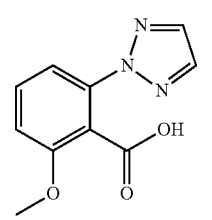 [SMILES: COc1cccc(-n2nccn2)c1C(=O)O] | Prepared analogous to Intermediate A-X using 2-bromo-6-(2H-1,2,3-triazol-2-yl)benzoic acid |
| A-14 | 2-methyl-6-(2H-1,2,3-triazol-2-yl)benzoic acid | 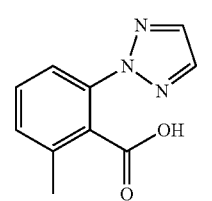 | Prepared according to WO 2011/050198 Intermediate 82. |

| Intermediate | Name | Structure | Reference |
|---|---|---|---|
| A-15 | 4-methoxy-2-(pyrimidin-2-yl)benzoic acid | 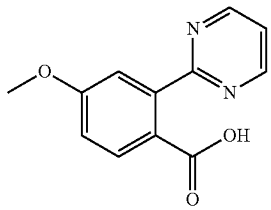 [SMILES: COc1ccc(C(=O)O)c(-c2ncccn2)c1] | Prepared according to WO 2011/050198 Intermediate 88. |
| A-16 | 3-fluoro-2-(2H-1,2,3-triazol-2-yl)benzoic acid | 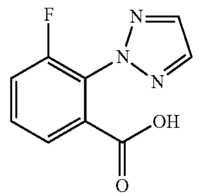 [SMILES: O=C(O)c1cccc(F)c1-n1nccn1] | Prepared according to WO 2011/050198 Intermediate 5. |
| A-17 | 3-fluoro-2-(3-methyl-1,2,4-oxadiazol-5-yl)benzoic acid | 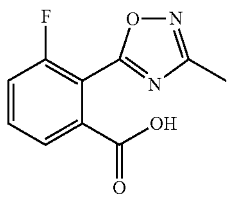 [SMILES: Cc1noc(-c2c(F)cccc2C(=O)O)n1] | Prepared according to WO 2011/050198 Intermediate 63. |
| A-18 | 5-methoxy-2-(2H-1,2,3-triazol-2-yl)benzoic acid | 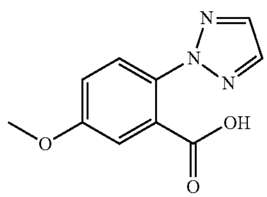 [SMILES: COc1ccc(-n2nccn2)c(C(=O)O)c1] | Prepared according to WO 2011/050198 Intermediate 10 |

Synthesis of 3-fluoro-2-(pyrimidin-2-yl)benzonitrile

Intermediate in the Synthesis of Intermediate A-2

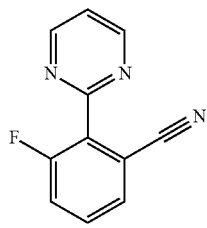 [SMILES: N#Cc1cccc(F)c1-c1ncccn1]

To a solution of 3-fluoro-2-(4,4,5,5-tetramethyl-1,3,2-dioxaborolan-2-yl)benzonitrile (4.98 g, 19.1 mmol) and 2-bromopyrimidine (3.85 g, 23 mmol) in THF (96 mL) was added $Na_2CO_3$ (6 g, 57.4 mmol) followed by water (43 mL). The reaction mixture was degassed with $N_2$ for 10 minutes. $PdCl_2$(dtbpf) (374 g, 0.57 mmol) was added and the reaction mixture was stirred at 80° C. for 5 h. The solution was cooled to room temperature and a mixture of EtOAc and water was added. The aqueous was extracted twice with EtOAc and the combined organic layers were dried over MgSO4, filtered and evaporated. The title compound was precipitated by dissolving the residue in a minimum amount of EtOAc and then adding hexanes. The solid was filtered, washed with hexanes and dried to afford the title compound (2.46 g, 64%). MS (ESI) mass calcd. for $C_{11}H_6FN_3$, 199.1; m/z found 200.1 [M+H]$^+$. $^1$H NMR (400 MHz, Chloroform-d) δ 9.02-8.91 (m, 2H), 7.65 (dt, J=7.7, 1.0 Hz, 1H), 7.60-7.52 (m, 1H), 7.51-7.43 (m, 1H), 7.41 (t, J=4.9 Hz, 1H).

Intermediate A-19

5-methyl-3-(2H-1,2,3-triazol-2-yl)picolinic acid

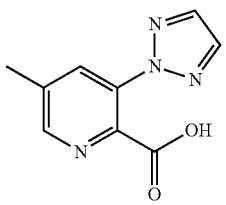

Step A:
5-methyl-3-(2H-1,2,3-triazol-2-yl)picolinonitrile

To 3-bromo-5-methylpicolinonitrile (1.5 g, 7.6 mmol) in DMF (19 mL) was added $K_2CO_3$ (1.2 g, 8.4 mmol) and 2H-1,2,3-triazole (440 μL, 7.6 mmol). The mixture was heated to 100° C. for 16 h. cooled to rt and extracted with EtOAc (2×). The combined organics were dried (Na$_2$SO$_4$) and concentrated. Purification via silica gel chromatography (5-60% EtOAc in hexanes) gave the title compound (490 g, 35%) $^1$H NMR (500 MHz, CDCl$_3$) 8.58-8.53 (m, 1H), 8.29-8.24 (m, 1H), 7.98 (s, 2H), 2.54 (s, 3H) and 5-methyl-3-(1H-1,2,3-triazol-1-yl)picolinonitrile (387 mg, 27%).

Step B: 5-methyl-3-(2H-1,2,3-triazol-2-yl)picolinate

To a solution of the title compound of Step A (489 g, 2.6 mmol) in EtOH (7 mL) was added 4 N NaOH (660 μL, 2.6 mmol). The mixture was heated at 100° C. for 24 h. The reaction mixture was concentrated in vacuo to a white solid which was used without further purification in subsequent steps. MS (ESI) mass calcd. for C$_9$H$_8$N$_4$O$_2$, 204.1; m/z found 205.0 [M+H]$^+$.

Intermediate A-20

5-methyl-3-(1H-1,2,3-triazol-1-yl)picolinic acid

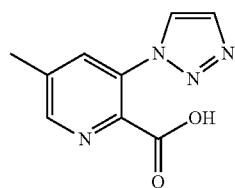

Step A:
5-methyl-3-(H-1,2,3-triazol-1-yl)picolinonitrile

The title compound was prepared in Intermediate A-19 Step A. $^1$H NMR (500 MHz, CDCl$_3$) 8.65 (dd, J=1.8, 0.9 Hz, 1H), 8.41 (d, J=1.2 Hz, 1H), 8.18-8.15 (m, 1H), 7.95 (d, J=1.2 Hz, 1H), 2.58 (s, 3H).

Step B: 5-methyl-3-(1H-1,2,3-triazol-1-yl)picolinic acid

Prepared analogous to Intermediate A-19 substituting 5-methyl-3-(2H-1,2,3-triazol-2-yl)picolinonitrile with the title compound of Step A. MS (ESI) mass calcd. for C$_9$H$_8$N$_4$O$_2$, 204.1; m/z found 205.0 [M+H]$^+$.

Intermediate A-21

6-methyl-3-(2H-1,2,3-triazol-2-yl)picolinic acid

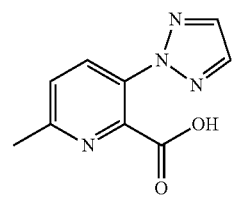

Step A:
6-methyl-3-(2H-1,2,3-triazol-2-yl)picolinonitrile

To 3-bromo-6-methylpicolinonitrile (2.2 g, 11 mmol) in DMF (28 mL) was added K$_2$CO$_3$ (1.7 g, 12 mmol) and 2H-1,2,3-triazole (650 μL, 11 mmol). The mixture was heated to 100° C. for 36 h, cooled to rt and extracted with EtOAc. The combined organics were dried (Na$_2$SO$_4$) and concentrated. Purification via silica gel chromatography (10-100% EtOAc in hexanes) gave the title compound (1 g, 48%).

Step B: 6-methyl-3-(2H-1,2,3-triazol-2-yl)picolinic acid

To a solution of the title compound of Step A (730 g, 4 mmol) in EtOH (10 mL) was added 4 N NaOH (1 mL, 4 mmol). The mixture was heated at 100° C. for 24 h. The reaction mixture was concentrated in vacuo to a white solid which was used without further purification in subsequent steps.

Intermediate A-22

3-ethoxyisoquinoline-4-carboxylic acid

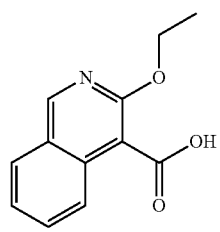 [SMILES: CCOc1ncc2ccccc2c1C(=O)O]

Step A: ethyl 3-hydroxyisoquinoline-4-carboxylate

To a suspension of ethyl 3-aminoisoquinoline-4-carboxylate (583 g, 2.70 mmol) in 6.8 mL of H$_2$SO$_4$ 5N cooled to 0° C. was added sodium nitrite (223 g, 3.24 mmol, dissolved in 1 mL of water). The reaction mixture was stirred at 0° C. for 2.5 h and then NaOH$_{(aq)}$ 1N was added until pH=7. The aqueous phase was extracted twice with DCM and the combined organic phases were dried over MgSO$_4$, filtered and evaporated to give the title compound of Step A which was used without further purification in the next step (583 g, 99%). MS (ESI) mass calcd. for C$_{12}$H$_{11}$NO$_3$, 217.1; m/z found 218.1 [M+H]$^+$.

Step B: ethyl 3-ethoxyisoquinoline-4-carboxylate

To the title compound of Step A (583 mg, 2.68 mmol) in THF (13 mL) was added triphenylphosphine (1.06 g, 4.03 mmol), ethanol (0.24 mL, 4.03 mmol) and DIAD (0.79 mL, 4.03 mmol). The reaction mixture was stirred at room temperature for 16 h and then the solvent was evaporated. The crude was purified via silica gel chromatography (0-30% EtOAc in hexanes) to afford the title compound of Step B (498 mg, 76%). MS (ESI) mass calcd. for C$_{14}$H$_{15}$NO$_3$, 245.1; m/z found 246.1 [M+H]$^+$. $^1$H NMR (500

MHz, Chloroform-d) δ 8.97 (s, 1H), 7.91-7.82 (m, 2H), 7.65-7.60 (m, 1H), 7.42-7.36 (m, 1H), 4.59-4.48 (m, 4H), 1.48-1.39 (m, 6H).

Step C: 3-ethoxyisoquinoline-4-carboxylic acid

The title compound of Step B (492 mg, 2 mmol) dissolved in MeOH (15 mL) was added NaOH$_{(aq)}$ 2M (2.5 mL). The reaction mixture was stirred at 60° C. for 16 h and then NaOH$_{(aq)}$ 4M (2 mL) was added and the mixture was stirred at 70° C. for 4 h. MeOH was evaporated and the aqueous phase was cooled to 0° C. and acidified with the addition of HCl$_{(aq)}$ 6N. The solid was filtered, washed with cold water and dried to afford the tilte compound (285 g, 65%). MS (ESI) mass calcd. for $C_{12}H_{11}O_3$, 217.1; m/z found 218.1 [M+H]$^+$. $^1$H NMR (400 MHz, DMSO-d6) δ 13.36 (s, 1H), 9.15 (s, 1H), 8.13-8.06 (m, 1H), 7.82-7.70 (m, 2H), 7.54-7.47 (m, 1H), 4.50 (q, J=7.0 Hz, 2H), 1.35 (t, J=7.0 Hz, 3H).

Intermediate A-23

4-(difluoromethoxy)-2-(2H-1,2,3-triazol-2-yl)benzoic acid

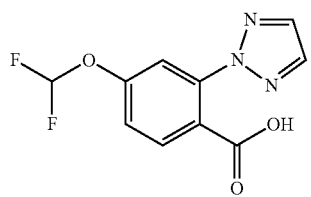 [SMILES: O=C(O)c1ccc(OC(F)F)cc1-n1nccn1]

Prepared analogous to Intermediate A-19 substituting 2-bromo-6-methyl-3-(2H-1,2,3-triazol-2-yl)pyridine with 4-(difluoromethoxy)-2-fluorobenzonitrile.

| Intermediate | Name | Structure | Reference |
|---|---|---|---|
| A-24 | 3-methyl-2-(2H-1,2,3-triazol-2-yl)benzoic acid | 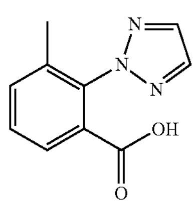 | Prepared according to WO 2011/050198 Intermediate 82 |
| A-25 | 4-fluoro-2-(pyrimidin-2-yl)benzoic acid | 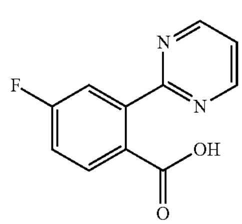 [SMILES: O=C(O)c1ccc(F)cc1-c1ncccn1] | Prepared according to WO 2011/050198 Intermediate 87 |

Intermediate A-26

3-methyl-2-(pyrimidin-2-yl)benzoic acid

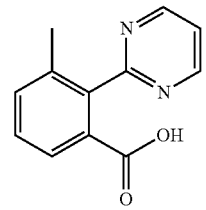 [SMILES: Cc1cccc(C(=O)O)c1-c1ncccn1]

Step A: methyl 3-methyl-2-(pyrimidin-2-yl)benzoate

In a microwave vial was dissolved methyl 3-methyl-2-(4,4,5,5-tetramethyl-1,3,2-dioxaborolan-2-yl)benzoate (619 g, 2.24 mmol) and 2-chloropyrimidine (314 g, 2.69 mmol) in 2-MeTHF (10 mL). Na$_2$CO$_3$ (713 mg, 6.73 mmol) was then added followed by water (3.4 mL) and the reaction mixture was degassed with N$_2$ for 45 minutes. Pd(dppf)Cl$_2$ (66 g, 0.09 mmol) and the reaction mixture was heated at 75° C. for 28 h. More Pd(dppf)Cl$_2$ (33 g, 0.045 mmol) was added and the reaction mixture was heated at 150° C. for 3.5 h. The mixture was filtered through a pad of celite and rinsed with EtOAc and water. The layers were separated and the aqueous was extracted once with EtOAc. The combined organic layers were dried over MgSO$_4$, filtered and evaporated. The crude was purified via silica gel chromatography (0-50% EtOAc in hexanes) to afford the title compound (116 g, 23%). MS (ESI) mass calcd. for $C_{13}H_{12}N_2O_2$, 228.1; m/z found 229.1 [M+H]$^+$. $^1$H NMR (500 MHz, CDCl3) 8.95-8.76 (m, 2H), 7.99-7.75 (m, 1H), 7.50-7.44 (m, 1H), 7.43-7.37 (m, 1H), 7.32-7.24 (m, 1H), 3.64 (s, 3H), 2.15 (s, 3H).

Step B: 3-methyl-2-(pyrimidin-2-yl)benzoic acid

Prepared analogous to intermediate A-31 step B to give title compound. MS (ESI) mass calcd. for $C_{12}H_{10}N_2O_2$, 214.1; m/z found 215.1 [M+H]$^+$.

| Intermediate | Name | Structure | Reference |
|---|---|---|---|
| A-27 | 3-(2H-1,2,3-triazol-2-yl)picolinic acid | 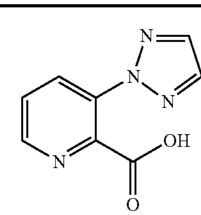 | Prepared according to WO 2011/050198 Intermediate 72 |

Intermediate A-28

2-methoxy-6-(pyrimidin-2-yl)benzoic acid

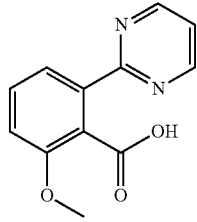 [SMILES: COc1cccc(-c2ncccn2)c1C(=O)O]

Step A: Methyl 2-methoxy-6-(pyrimidin-2-yl)benzoate

In a microwave vial was dissolved methyl 2-methoxy-6-(4,4,5,5-tetramethyl-1,3,2-dioxaborolan-2-yl)benzoate (500 mg, 1.71 mmol), commercially available from Combi-Blocks (CAS #1146214-77-8), and 2-bromopyrimidine (344 g, 2.05 mmol) in THF (8.5 mL). $Na_2CO_3$ (544 g, 5.14 mmol) was then added followed by water (4 mL) and the reaction mixture was degassed with $N_2$ for 10 minutes. $PdCl_2$(dtbpf) (45 g, 0.069 mmol) was then added and the reaction mixture was heated at 80° C. for 4 h. The mixture was cooled to room temperature and water and EtOAc added. The reaction mixture was extracted with EtOAc (3×). The combined organic layers were dried over $Na_2SO_4$, filtered, and concentrated. The crude was purified via silica gel chromatography (0-70% EtOAc in hexanes) to afford the title compound (265 g, 63%). MS (ESI) mass calcd. for $C_{13}H_{12}N_2O_3$, 244.1; m/z found 245.1 [M+H]$^+$. 1H NMR (400 MHz, Chloroform-d) 8.78 (d, J=4.9 Hz, 2H), 7.99 (dd, J=7.9, 0.9 Hz, 1H), 7.49 (t, J=8.1 Hz, 1H), 7.19 (t, J=4.8 Hz, 1H), 7.09 (dd, J=8.3, 0.9 Hz, 1H), 3.90 (s, 3H), 3.89 (s, 3H).

Step B: 2-methoxy-6-(pyrimidin-2-yl)benzoic acid

To a solution of the title compound of Step A (265 g, 1.09 mmol) in THF (4 mL) was added 2 N NaOH (2 mL). The mixture was heated at 50° C. for 72 h. The reaction mixture was concentrated in vacuo to a white solid which was used without further purification in subsequent steps. MS (ESI) mass calcd. for $C_{12}H_{10}N_2O_3$, 230.1; m/z found 231.1 [M+H]$^+$. 1H NMR (500 MHz, DMSO-$d_6$) 12.63 (s, 1H), 8.86 (d, J=4.9 Hz, 2H), 7.77 (dd, J=7.9, 1.0 Hz, 1H), 7.51 (t, J=8.1 Hz, 1H), 7.45 (t, J=4.9 Hz, 1H), 7.25 (dd, J=8.4, 1.0 Hz, 1H), 3.83 (s, 3H).

Intermediate A-29

7-ethoxyquinoline-8-carboxylic acid

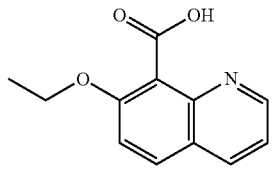 [SMILES: CCOc1ccc2cccnc2c1C(=O)O]

Step A: 7-methoxyquinoline-8-carboxylic acid

In 1 g separate batches a mixture of 2-amino-6methoxy-benzoic acid (1 g, 66 mmol) and acrolein (4.8 mL, 72 mmol) in 1,4-dioxane (66 mL) was heated in a microwave reactor for 20 min at 200° C. After combining the reactions, the mixture was concentrated and purified via silica gel chromatography (0-10% MeOH in DCM) to give the title compound (2.8 g, 20%). MS (ESI) mass calcd. for $C_{11}H_{19}NO_3$, 203.1; m/z found 204.0 [M+H]$^+$.

Step B: 7-hydroxyquinoline-8-carboxylic acid

The title compound of Step A (2.9 g, 14.1 mmol) in HBr (14 mL) was heated at 90° C. for 1 h. The mixture was then concentrated washed with PhCH3 and used without further purification in subsequent steps.

Step C: ethyl 7-ethoxyquinoline-8-carboxylate

To the title compound of Step B (800 mg, 3.9 mmol) and K2CO3 (1.4 g, 10.4 mmol) in DMF (15 mL) was added iodoethane (560 µL, 6.9 mmol). After stirring overnight at rt, the reaction was concentrated and purified via silica gel chromatography (0-30% EtOAc in hexanes) to give the title compound. MS (ESI) mass calcd. for $C_{14}H_{15}NO_3$, 245.1; m/z found 246.0 [M+H]$^+$.

Step D: 7-ethoxyquinoline-8-carboxylic acid

To the title compound of Step C (1.3 g, 5.4 mmol) in THF (22 mL) and $H_2O$ (11 mL) was added LiOH hydrate (675 g, 16.5 mmol) and MeOH. The mixture was heated at 67° C. for 12 h. Additional LiOH hydrate (675 mg, 16.5 mmol) was added and the heating was continued at 70° C. for 1 day. Additional LiOH hydrate (1.4 g, 33 mmol) was added and the heating was continued at 75° C. for 1 day. The reaction was allowed to cool to rt, acidified to pH=3 with 1N HCl (aq) and concentrated. Purification via prep HPLC gave the title compound (1 g, 84%). MS (ESI) mass calcd. for $C_{12}H_{11}NO_3$, 217.1; m/z found 218.0 [M+H]$^+$.

Intermediate A-30

2-(1,4-dimethyl-1H-pyrazol-5-yl)-6-methoxybenzoic acid

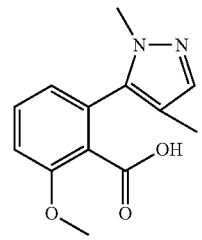 [SMILES: COc1cccc(-c2c(C)cnn2C)c1C(=O)O]

Step A: Ethyl 2-(1,4-dimethyl-1H-pyrazol-5-yl)-6-methoxybenzoate

In a microwave vial was dissolved ethyl 2-bromo-6-methoxybenzoate (500 g, 1.54 mmol) and 1,4-dimethyl-5-(4,4,5,5-tetramethyl-1,3,2-dioxaborolan-2-yl)-1H-pyrazole (377 g, 1.70 mmol) in DME (10 mL) and water (2 mL).

Na₂CO₃ (259 g, 3.09 mmol) was then added followed by Pd(PPh₃)₄ (89 mg, 0.077 mmol) and the reaction mixture was degassed with N₂ for 10 minutes. The reaction mixture was then heated at 100° C. for h in the microwave. The mixture was cooled to room temperature, filtered through Celite and washed with EtOAc and DCM. The crude solution was concentrated in vacuo and directly purified via silica gel chromatography (10-80% EtOAc in hexanes) to afford the title compound (402 g, 95%). MS (ESI) mass calcd. for C₁₅H₁₈N₂O₃, 274.1; m/z found 275.2 [M+H]⁺. 1H NMR (400 MHz, Chloroform-d) 7.45 (dd, J=8.4, 7.6 Hz, 1H), 7.29 (s, 1H), 7.04 (dd, J=8.5, 0.9 Hz, 1H), 6.84 (dd, J=7.6, 0.9 Hz, 1H), 4.07 (qd, J=7.2, 1.5 Hz, 2H), 3.90 (s, 3H), 3.61 (s, 3H), 1.86 (s, 3H), 1.01 (t, J=7.1 Hz, 3H).

Step B:
2-(1,4-dimethyl-1H-pyrazol-5-yl)-6-methoxybenzoic acid

Prepared analogous to intermediate A-28 step B to give title compound. MS (ESI) mass calcd. for C₁₃H₁₄N₂O₃, 246.1; m/z found 247.2 [M+H]⁺. ¹H NMR (500 MHz, DMSO-d₆) 7.50 (dd, J=8.5, 7.6 Hz, 1H), 7.25 (s, 1H), 7.21 (dd, J=8.5, 0.9 Hz, 1H), 6.85 (dd, J=7.6, 0.9 Hz, 1H), 3.84 (s, 3H), 3.49 (s, 3H), 1.79 (s, 3H).

Intermediate A-31

3-methyl-2-(oxazol-2-yl)benzoic acid

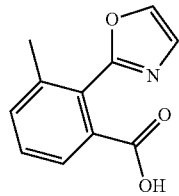

Step A: ethyl 3-methyl-2-(oxazol-2-yl)benzoate

In a microwave vial was dissolved ethyl 2-iodo-3-methylbenzoate (627 g, 2.16 mmol) and 2-(tributylstannyl)oxazole (0.54 mL, 0.07 mmol) in DME (2.59 mL). The solution was degassed with N₂ for 5 minutes then CuI (21 mg, 0.11 mmol) and Pd(PPh₃)₄ (125 g, 0.11 mmol) were added. The reaction was purged with N₂ and heated at 150° C. for 1 h. The reaction was cooled to rt, filtered through a pad of celite and purified via silica gel chromatography (0-40% EtOAc in hexanes) to give the title compound of step A (333 g, 67%). MS (ESI) mass calcd. for C₁₃H₁₃NO₃, 231.1; m/z found 232.1 [M+H]⁺. ¹H NMR (500 MHz, Chloroform-d) 7.89-7.82 (m, 1H), 7.79 (d, J=0.8 Hz, 1H), 7.48-7.43 (m, 2H), 7.30 (d, J=0.9 Hz, 1H), 4.17 (q, J=7.1 Hz, 2H), 2.27 (s, 3H), 1.18 (t, J=7.1 Hz, 3H).

Step B: 3-methyl-2-(oxazol-2-yl)benzoic acid

To the title compound of step A (166 mg, 0.72 mmol) was added MeOH (7.2 mL) and 1M NaOH(aq) (7.2 mL). MeOH was evaporated and then 1 M HCl(aq) was added. To the solution was added DCM and the aqueous was extracted with DCM (3×). The combined organic layers were dried over MgSO₄, filtered and evaporated to give the title compound (145 mg). MS (ESI) mass calcd. for C₁₁H₉NO₃, 203.1; m/z found 204.1 [M+H]⁺. ¹H NMR (400 MHz, DMSO-d₆) δ 8.20 (s, 1H), 7.79-7.68 (m, 1H), 7.65-7.49 (m, 2H), 7.35 (s, 1H), 4.34 (s, 1H), 2.20 (s, 3H).

Intermediate A-32

4-methyl-3-(2H-1,2,3-triazol-2-yl)picolinic acid

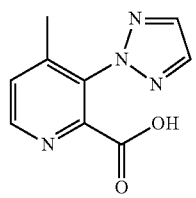

Step A:
4-methyl-3-(2H-1,2,3-triazol-2-yl)picolinonitrile

In a microwave vial was dissolved 2H-1,2,3-triazole (0.22 mL, 3.8 mmol) and CuI (26 mg) in DMF (4 mL). The reaction mixture was degassed with N₂ and 3-bromo-4-methylpicolinonitrile (300 g, 1.5 mmol) was added followed by trans-N,N'-dimethyl-1,2-cyclohexanediamine (41 μL, 0.3 mmol) and Cs₂CO₃ (844 g, 2.6 mmol). The reaction mixture was heated at 120° C. for 1 h in a microwave reactor. Then H2O was added and the mixture extracted with EtOAc. The combined organic layers were dried (MgSO₄). Purification via silica gel chromatography (0-50% EtOAc in heptane) gave the title compound (112 g, 27%). MS (ESI) mass calcd. for C₉H₇N₅, 185.2; m/z found 186 [M+H]⁺.

Step B: 4-methyl-3-(2H-1,2,3-triazol-2-yl)picolinic acid

Prepared analogous to Intermediate A-19 substituting 5-methyl-3-(2H-1,2,3-triazol-2-yl)picolinonitrile with the title compound of Step A. The reaction mixture was acidified to pH=4 before concentrating. MS (ESI) mass calcd. for C₁₁H₉NO₃, 203.1; m/z found 204.1 [M+H]⁺.

Intermediate A-33

3-(2H-1,2,3-triazol-2-yl)quinoline-2-carboxylic acid

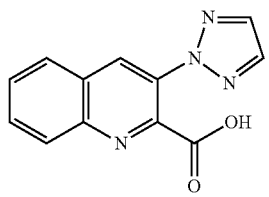 [SMILES: O=C(O)c1nc2ccccc2cc1-n1nccn1]

Step A: ethyl 3-(2H-1,2,3-triazol-2-yl)quinoline-2-carboxylate

Prepared analogous to Intermediate A-40 Step A substituting 2-bromo-4-methylbenzoic acid with ethyl 3-iodoquinoline-2-carboxylate (WO 2011093365) in <10% yield. MS (ESI) mass calcd. for $C_{14}H_{12}N_4O_2$, 268.3; m/z found 269.0 [M+H]$^+$.

Step B: 3-(2H-1,2,3-triazol-2-yl)quinoline-2-carboxylic acid

To the title compound of Step A (134 g, 0.5 mmol) in MeOH (1 mL) was added aqueous 2M NaOH (1 mL). After 1 h at rt, the reaction was heated to 50° C. for 1 h, cooled to rt, acidified with 1N HCl, concentrated and used in subsequent steps without further purification. MS (ESI) mass calcd. for $C_{12}H_8N_4O_2$, 240.2; m/z found 241.0 [M+H]$^+$.

| Intermediate | Name | Structure | Reference |
|---|---|---|---|
| A-34 | 5-methyl-2-(pyrimidin-2-yl)benzoic acid | 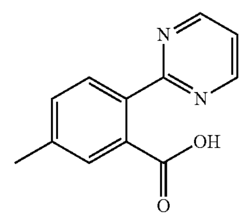 [SMILES: Cc1ccc(-c2ncccn2)c(C(=O)O)c1] | Prepared according to WO 2011/050198 Intermediate 50. |
| A-35 | 2-methyl-6-(pyrimidin-2-yl)benzoic acid | 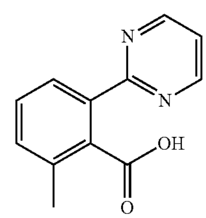 [SMILES: Cc1cccc(-c2ncccn2)c1C(=O)O] | Prepared according to intermediate A-34 or A-2 |
| A-36 | 4-methyl-2-(pyrimidin-2-yl)benzoic acid | 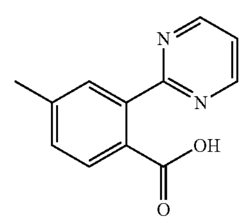 [SMILES: Cc1ccc(C(=O)O)c(-c2ncccn2)c1] | Prepared according to intermediate A-34 or A-2 |
| A-37 | 5-methyl-2-(2H-1,2,3-triazol-2-yl)benzoic acid | 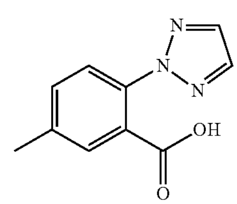 | Prepared according to WO 2011/050198 Intermediate 8. |
| A-38 | 5-chloro-2-(2H-1,2,3-triazol-2-yl)benzoic acid | 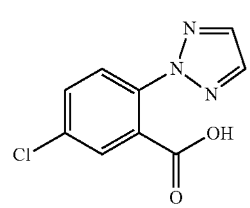 [SMILES: O=C(O)c1cc(Cl)ccc1-n1nccn1] | Prepared according to WO 2011/050198 Intermediate 9. |
| A-39 | 5-fluoro-2-(1H-pyrazol-5-yl)benzoic acid | 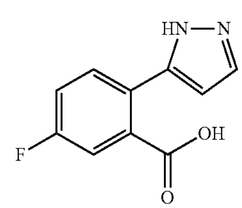 [SMILES: O=C(O)c1cc(F)ccc1-c1ccn[nH]1] | Prepared according to WO 2011/050198 Intermediate 51. |

Intermediate A-40

4-methyl-2-(2H-1,2,3-triazol-2-yl)benzoic acid

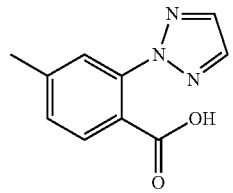

Step A: 4-methyl-2-(2H-1,2,3-triazol-2-yl)benzoic acid and 4-methyl-2-(1H-1,2,3-triazol-1-yl)benzoic acid In a microwave vial was dissolved 2H-1,2,3-triazole (0.34 mL, 5.81 mmol) and CuI (40 g, 0.21 mmol) in DMF (5 mL). The reaction mixture was degassed with $N_2$ for 10 minutes and 2-bromo-4-methylbenzoic acid (500 g, 2.33 mmol) was added followed by trans-N,N'-dimethyl-1,2-cyclohexanediamine (62 µL, 0.40 mmol) and $Cs_2CO_3$ (1.29 g, 3.95 mmol). The reaction mixture was stirred at 100° C. for 20 minutes using a microwave oven before being partitioned between water, $HCl_{(aq)}$ (pH=3) and EtOAc. The organic layer was dried over $MgSO_4$, filtered and evaporated to give the crude product mixture which was used in the next step without any further purification.

Step B: methyl 4-methyl-2-(2H-1,2,3-triazol-2-yl)benzoate

To the title compound of step A (945 g, 4.65 mmol) in DMF (28 mL) was added K2CO3 (1.3 g, 9.3 mmol) and iodomethane (0.3 mL, 4.7 mmol). The reaction mixture was stirred at room temperature for 16 h under N2. The solvent was evaporated and the residue was dissolved with a saturated solution of NaHCO3. The aqueous phase was extracted with DCM and the organic layer was dried over MgSO4, filtered and evaporated. The crude material was purified via silica gel chromatography (0% to 30% EtOAc/heptane) to afford the title compound (470 g, 47%).

Step C

Prepared analogous to Intermediate A-31 step B substituting ethyl 3-methyl-2-(oxazol-2-yl)benzoate with the title compound of Step B and used without further purification in subsequent steps.

| Intermediate | Name | Structure | Reference |
|---|---|---|---|
| A-41 | 2-(3-methyl-1,2,4-oxadiazol-5-yl)benzoic acid | 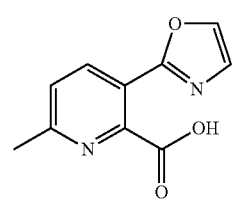 | Prepared analogous to intermediate A-17 |

Intermediate A-42

3,6'-dimethyl-[2,3'-bipyridine]-2'-carboxylic acid

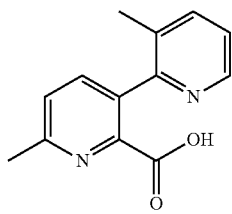 [SMILES: Cc1ccc(-c2ncccc2C)c(C(=O)O)n1]

Step A: 3-bromo-6-methylpicolinic acid

To 3-bromo-6-methylpicolinonitrile (4 g, 20.3 mmol) in EtOH (40 mL) in a sealed tube was added aqueous 4M NaOH (15 mL). The reaction was heated at 90° C. for 24 h. Additional aqueous 4M NaOH was added and heating continued at 90° C. for 24 h. The reaction was cooled to rt, acidified to pH=3 with 1N HCl (aq), concentrated and used without further purification in subsequent steps. MS (ESI) mass calcd. for $C_7H_6BrNO_2$, 216.0; m/z found 218 $[M+H]^+$.

Step B: Methyl 3-bromo-6-methylpicolinate

To the title compound of step A (10.3 g, 20 mmol) in MeOH (50 mL) was added thionyl chloride (4.4 mL, 60 mmol). The reaction was heated at reflux overnight, cooled to rt and concentrated. Purification via silica gel chromatography (0-15% EtOAc in heptane) gave the title compound (1.9 g, 40%). MS (ESI) mass calcd. for $C_8H_8BrNO_2$, 230.1; m/z found 232 $[M+H]^+$.

Step C: 3-methyl-2-(tributylstannyl)pyridine

To 2-bromo-3-methylpyridine (1.3 mL, 11.7 mmol) in THF (35 mL) at −78° C. was added n-BuLi (2.5 M in hexanes, 5.6 mL, 14 mmol). After 30 min, tri-n-butyltin chloride (3.8 mL, 14 mmol) was added. After 1 h at −78° C., the reaction was allowed to warm to rt. EtOAc was added and the reaction mixture was washed with 10% aq KF. The organic layer was dried (MgSO4). Purification via silica gel chromatography (0-15% EtOAc in heptane) gave the title compound (1.2 g, 27%). MS (ESI) mass calcd. for $C_{18}H_{33}NSn$, 382.2; m/z found 384.0 $[M+H]^+$.

Step D: methyl 3,6'-dimethyl-[2,3'-bipyridine]-2'-carboxylate

To the title compound of step B (509 g, 2.2 mmol) and the title compound of step C (1.1 g, 2.9 mmol) in PhCH3 (6.6 mL) was added Pd(PPh3)4 (225 g, 0.2 mmol). The reaction was degassed with $N_2$ and heated at 150° C. for 1.5 h using microwave reactor. The reaction was cooled to rt, diluted with H2O and extracted with EtOAc. The organic layer was dried (MgSO4). Purification via silica gel chromatography (0-100% EtOAc in heptane) gave the title compound (101 g, 18%). MS (ESI) mass calcd. for $C_{14}H_{14}N_2O_2$, 242.3; m/z found 243 $[M+H]^+$.

Step E: 3,6'-dimethyl-[2,3'-bipyridine]-2'-carboxylic acid

Prepared analogous to intermediate A-33 step B substituting ethyl 3-(2H-1,2,3-triazol-2-yl)quinoline-2-carboxylate with the title compound of step D. MS (ESI) mass calcd. for $C_{13}H_{12}N_2O_2$, 228.2; m/z found 229 $[M+H]^+$.

Intermediate A-43

6-methyl-3-(oxazol-2-yl)picolinic acid

Prepared analogous to Intermediate A-31 substituting ethyl 2-iodo-3-methylbenzoate with methyl 3-iodo-6-methylpicolinate. MS (ESI) mass calcd. for $C_{10}H_8N_2O_3$, 204.2; m/z found 161 $[M-CO2]^+$.

| Intermediate | Name | Structure | Reference |
|---|---|---|---|
| A-44 | 6-methyl-3-(3-methyl-1,2,4-oxadiazol-5-yl)picolinic acid | 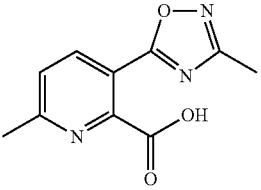 | WO 2010/063663 Description 64 |
| A-45 | 6-methyl-3-(3-methyl-1H-pyrazol-1-yl)picolinic acid | 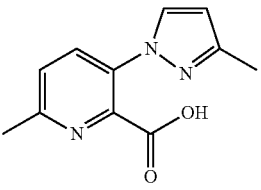 | WO 2010/063663 Description 71 |
| A-46 | 6-methyl-3-(4-methyl-1H-pyrazol-1-yl)picolinic acid | 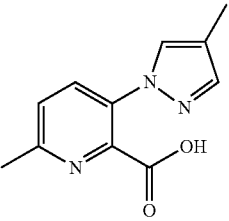 | WO 2010/063663 |
| A-47 | 6-methyl-3-(1H-pyrazol-1-yl)picolinic acid | 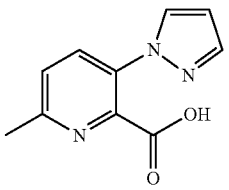 | WO 2010/063663 Description 73 |
| A-48 | 6-methyl-3-(3-methylisoxazol-5-yl)picolinic acid | 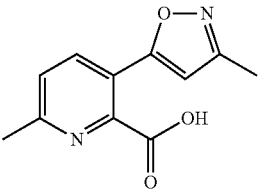 | WO 2010/063663 Description 117 |
| A-49 | 1-methyl-3-phenyl-1H-pyrazole-4-carboxylic acid | 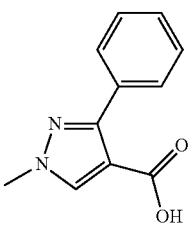 | Purchased |
| A-50 | 1-methyl-4-phenyl-1H-pyrazole-5-carboxylic acid | 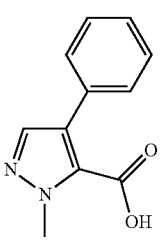 | Purchased |

-continued

| Intermediate | Name | Structure | Reference |
| --- | --- | --- | --- |
| A-51 | 1-methyl-5-phenyl-1H-pyrazole-4-carboxylic acid | 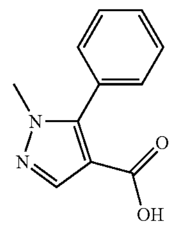 | Purchased |
| A-52 | 5-chloro-3-(2H-1,2,3-triazol-2-yl)picolinic acid | 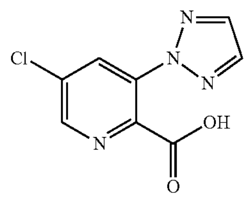 [SMILES: O=C(O)c1ncc(Cl)cc1-n1nccn1] | WO 2012/145581 Intermediate 105 |
| A-53 | 5-methoxy-3-(2H-1,2,3-triazol-2-yl)picolinic acid | 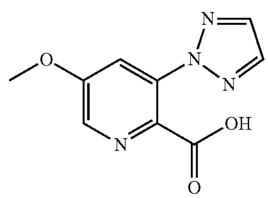 [SMILES: COc1cnc(C(=O)O)c(-n2nccn2)c1] | WO 2012/145581 Intermediate 105 |
| A-54 | 6-Methyl-3-(4-methyloxazol-2-yl)picolinic acid | 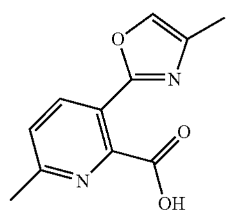 | |

Intermediate A-55

2-(5-fluoropyrimidin-2-yl)benzoic acid

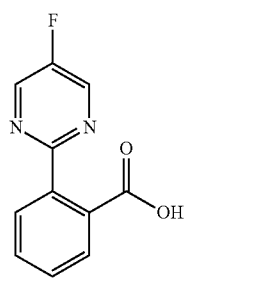 [SMILES: O=C(O)c1ccccc1-c1ncc(F)cn1]

Step A: 5-fluoro-2-iodopyrimidine

To a solution of 2-chloro-5-fluoropyrimidine (4 mL, 32 mmol) in propionitrile (33 mL) was added chlorotrimethylsilane (12 mL, 97 mmol) and sodium iodide (15 g, 97 mmol), and the reaction mixture was heated to 150° C. for 1 h. Upon completion of the reaction, the reaction mixture was cooled to room temperature and the solvent removed. The residue was taken up in EtOAc and a solution of saturated NaHCO₃. The organic layer was dried over MgSO₄, filtered and evaporated. Purification via silica gel chromatography (0-20% EtOAc in hexanes) gave the title compound (2.82 g, 39%).

Step B: 2-(5-fluoropyrimidin-2-yl)benzonitrile

In a microwave vial was dissolved cyanophenylboronic acid (500 g, 3.40 mmol) in THF (15 mL), and the reaction mixture was degassed with $N_2$. Then, the title compound of step A (915 g, 4.08 mmol), $Na_2CO_3$ (1.08 g, 10.2 mmol), water (5 mL), and PdCl₂(dtbpf) (CAS 95408-45-0) (89 g, 0.14 mmol) were added, and the reaction mixture was stirred at room temperature for 1 h and then heated via microwave heating to 75° C. for 2 h. The mixture was cooled to room temperature and water and EtOAc added. The reaction mixture was extracted with EtOAc. The combined organic layers were dried over MgSO₄, filtered and concentrated. The crude was purified via silica gel chromatography (0-30% EtOAc in hexanes) to afford the title compound (280 g, 41%). MS (ESI) mass calcd. for $C_{11}H_6FN_3$, 199.1; m/z found 200.0 [M+H]⁺.

Step C: 2-(5-fluoropyrimidin-2-yl)benzoic acid

A solution of the title compound of step B (1.24 g, 6.22 mmol) in $H_2SO_4$ (6 mL) and water (6 mL) was stirred at 80° C. for 1 h. Then, the reaction mixture was cooled to 0° C. and the aqueous phase extracted with DCM (2×). A solution of 20 M NaOH (11 mL) was added to the aqueous layer until pH ~3-4. The aqueous layer was extracted again with EtOAc and DCM. The combined organic layers were dried over MgSO₄, filtered and concentrated to afford the title compound (672 g, 50%). MS (ESI) mass calcd. for $C_{11}H_7FN_2O_2$, 218.1; m/z found 219.1 [M+H]⁺.

Intermediate A-56

2-(5-fluoropyrimidin-2-yl)-3-methylbenzoic acid

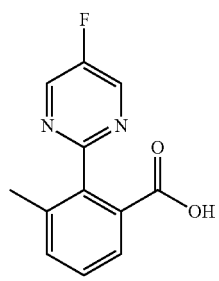 [SMILES: Cc1cccc(C(=O)O)c1-c1ncc(F)cn1]

Step A: Methyl 2-(5-fluoropyrimidin-2-yl)-3-methylbenzoate

A solution of methyl 3-methyl-2-(4,4,5,5-tetramethyl-1,3,2-dioxaborolan-2-yl)benzoate (CAS 887234-98-2) (3 g, 11 mmol) in THF (30 mL) was degassed with N₂. Then, 2-chloro-5-fluoropyrimidine (1.6 mL, 13.04 mmol), Na₂CO₃ (3.45 g, 32.6 mmol), water (10 mL), and Pd(dppf)Cl₂ (354 mg, 0.434 mmol) were added, and the reaction mixture was stirred at 100° C. overnight. The mixture was cooled to room temperature and water and EtOAc added. The reaction mixture was extracted with EtOAc. The combined organic layers were dried over MgSO₄, filtered and concentrated. The crude was purified via silica gel chromatography (0-40% EtOAc in hexanes) to afford the title compound (1.07 g, 40%).

Step B: 2-(5-fluoropyrimidin-2-yl)-3-methylbenzoic acid

To a solution of the title compound of Step A (1.46 g, 5.93 mmol) in MeOH (20 mL) was added 1 M NaOH (12 mL), and the reaction mixture was stirred at room temperature overnight. The solvent was removed and the crude was diluted with water until pH=10. The aqueous layer was extracted with EtOAc. The aqueous layer was further acidified with 12 M HCl$_{(aq)}$ until pH=2 and extracted with EtOAc. The combined organic layers were dried over MgSO₄, filtered and concentrated to afford the title compound (1.19 g, 83%). MS (ESI) mass calcd. for $C_{12}H_9FN_2O_2$, 232.1; m/z found 233.1 [M+H]⁺.

Intermediate A-57

3-fluoro-2-(5-fluoropyrimidin-2-yl)benzoic acid

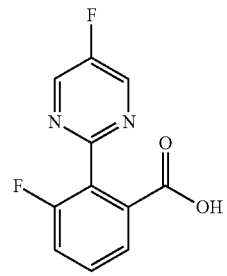

Prepared analogous to Intermediate A-55, substituting cyanophenylboronic acid with (2-cyano-6-fluorophenyl)boronic acid (CAS 656235-44-8). MS (ESI) mass calcd. for $C_{11}H_6F_2N_2O_2$, 236.0; m/z found 237.1 [M+H]⁺.

Intermediate A-58

Sodium 3-chloro-2-(pyrimidin-2-yl)benzoate

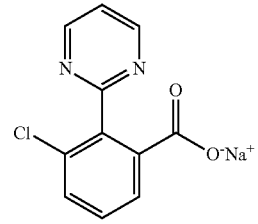

Step A: Methyl 2-(pyrimidin-2-yl)benzoate

Prepared analogous to Example 260 step B substituting 2-(tributylstannyl)oxazole with 2-(tributylstannyl)pyrimidine. MS (ESI) mass calcd. for $C_{12}H_{10}N_2O_2$, 214.1; m/z found 215.1 [M+H]⁺. ¹H NMR (500 MHz, CDCl₃) δ 8.84-8.78 (m, 2H), 8.06-7.99 (m, 1H), 7.76-7.71 (m, 1H), 7.60 (td, J=7.6, 1.4 Hz, 1H), 7.52 (td, J=7.5, 1.3 Hz, 1H), 7.24 (t, J=4.9 Hz, 1H), 3.75 (s, 3H).

Step B: Methyl 3-chloro-2-(pyrimidin-2-yl)benzoate

In a microwave vial was combined compound of step A (314 g, 1.47 mmol), Pd(OAc)₂ (49 g, 0.07 mmol), copper (II) trifluoroacetate (425 g, 1.47 mmol) and calcium chloride (651 g, 5.87 mmol). The vial was capped and acetic acid (21 mL) was added. The reaction mixture was stirred at 110° C. for 24 h and solvent was evaporated. The residue was taken up in EtOAc and a solution of saturated NaHCO₃. The aqueous phase was extracted 3 times with EtOAc and the combined organic layers were dried over MgSO₄, filtered and evaporated. Purification via silica gel chromatography (0-40% EtOAc in hexanes) gave the title compound (77 g, 21%). MS (ESI) mass calcd. for $C_{12}H_9ClN_2O_2$, 248.0; m/z found 249.1. ¹H NMR (500 MHz, CDCl₃) δ 8.86 (d, J=4.9 Hz, 2H), 8.00 (dd, J=7.9, 1.2 Hz, 1H), 7.68 (dd, J=8.1, 1.2 Hz, 1H), 7.46 (t, J=8.0 Hz, 1H), 7.33 (t, J=4.9 Hz, 1H), 3.65 (s, 3H).

Step C: Sodium 3-chloro-2-(pyrimidin-2-yl)benzoate

To a solution of compound of step B (103 g, 0.42 mmol) in THF (2 mL) was added 3.75M NaOH in water (0.44 mL, 1.66 mmol). The reaction mixture was stirred at 50° C. for 48 h and solvent was evaporated. The residue was taken up in water and lyophilized to give the title compound (106 g, 100%). MS (ESI) mass calcd. for $C_{11}H_7ClN_2O_2$, 234.0; m/z found 235.0. $^1$H NMR (500 MHz, CD3OD) δ 8.80 (d, J=5.0 Hz, 2H), 7.88 (dd, J=7.7, 1.2 Hz, 1H), 7.52 (dd, J=8.0, 1.2 Hz, 1H), 7.48-7.38 (m, 2H).

| Intermediate | Name | Structure | Reference |
|---|---|---|---|
| A-59 | 2-(pyrimidin-2-yl)benzoic acid | 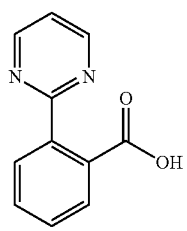 [SMILES: O=C(O)c1ccccc1-c1ncccn1] | Commercially available, CAS 400892-62-8 |
| A-60 | 5-methyl-2-(2H-1,2,3-triazol-2-yl)nicotinic acid | 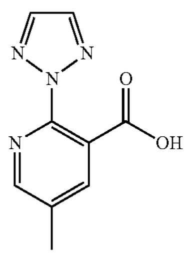 | Prepared analogous to WO 2011/050200 Intermediate 47, Example 160 |
| A-61 | 2-(2H-1,2,3-triazol-2-yl)nicotinic acid | 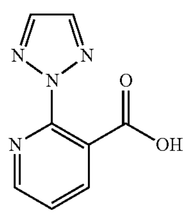 [SMILES: O=C(O)c1cccnc1-n1nccn1] | Commercially available, CAS 1369497-44-8 |
| A-62 | 6-methyl-3-(2H-1,2,3-triazol-2-yl)picolinic acid | 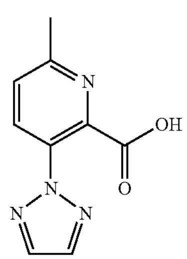 | 2012/089606 Intermediate D40. |
| A-63 | 6-methyl-3-(pyrimidin-2-yl)picolinic acid | 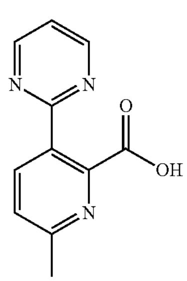 [SMILES: Cc1ccc(-c2ncccn2)c(C(=O)O)n1] | WO 2010/122151 Intermediate D28 |
| A-64 | 3-(pyrimidin-2-yl)picolinic acid | | WO 2010/122151 Intermediate D105 |
| A-65 | 2-chloro-6-methoxy-nicotinic acid | | Commercially available, CAS 1227515-71-0 |

Intermediate A-66

5-methyl-2-(pyrimidin-2-yl)nicotinic acid

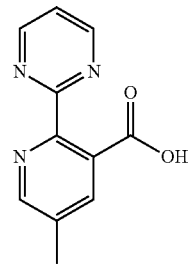 [SMILES: Cc1cnc(-c2ncccn2)c(C(=O)O)c1]

Step A: Methyl 5-methyl-2-(pyrimidin-2-yl)nicotinate

To a sealed tube containing methyl 2-chloro-5-methylnicotinate (CAS 65169-43-9) (745 g, 4.01 mmol), CuI (38 mg, 0.2 mmol), LiCl (169 g, 4.01 mmol), and Pd(PPh$_3$)$_4$ (231 g, 0.2 mmol) in toluene (15 mL) was added 2-(tributylstannyl)pyrimidine (1.5 mL, 4.4 mmol), and the reaction mixture was heated at 120° C. overnight. The reaction mixture was diluted with water and extracted with DCM. The combined organic layers were dried over MgSO$_4$, filtered and evaporated. Purification via silica gel chromatography (0-50% EtOAc in hexanes) gave the title compound (494 g, 52%). MS (ESI) mass calcd. for $C_{12}H_{11}N_3O_2$, 229.1; m/z found 229.99.

Step B: 5-methyl-2-(pyrimidin-2-yl)nicotinic acid

To a solution of the title compound of step A (466 g, 2.03 mmol) in MeOH (10 mL) was added 10 M NaOH (1 mL), and the reaction mixture was stirred at room temperature for 2 h. The solvent was removed and the crude residue was diluted with water and acidified with 6 M HCl$_{(aq)}$ until pH=3. The aqueous layer was saturated with solid NaCl and extracted with 20% iPrOH in CHCl$_3$ (3×). The combined organic layers were dried over MgSO$_4$, filtered and concentrated to afford the title compound (432 mg, 99%). MS (ESI)

mass calcd. for $C_{11}H_9N_3O_2$, 215.1; m/z found 216.1 [M+H]$^+$. $^1$H NMR (500 MHz, Methanol-d$_4$) δ 8.90 (br. s, 2H), 8.64 (br. s, 1H), 8.17 (s, 1H), 7.55 (br. s, 1H), 2.51 (s, 3H).

Intermediate A-67

Lithium 5-methyl-3-(pyrimidin-2-yl)picolinate

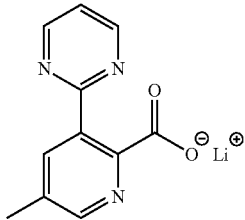

Step A: Methyl 5-methyl-3-(pyrimidin-2-yl)picolinate

Prepared analogous to intermediate A-66, step A substituting methyl 2-chloro-5-methylnicotinate with methyl 3-bromo-5-methylpicolinate. MS (ESI) mass calcd. for $C_{12}H_{11}N_3O_2$, 229.1; m/z found 230.0 [M+H]$^+$.

Step B: Lithium 5-methyl-3-(pyrimidin-2-yl)picolinate

To a solution of the title compound of step A (592 g, 2.58 mmol) in THF (5 mL) was added 4 M LiOH (0.8 mL) and water (1.5 mL), and the reaction mixture was stirred at room temperature for 2.5 h. The solvent was removed and the crude reaction mixture placed under vacuum overnight to give the title compound (591 mg), which was used in the next step without further purification. MS (ESI) mass calcd. for $C_{11}H_9N_3O_2$, 215.1; m/z found 216.1 [M+H]$^+$. $^1$H NMR (500 MHz, Methanol-d$_4$) δ 8.83 (d, J=4.9 Hz, 2H), 8.39 (br. s, 1H), 8.23-8.18 (m, 1H), 7.38 (t, J=4.9 Hz, 1H), 2.44 (s, 3H).

Intermediate A-68

3-fluoro-2-(oxazol-2-yl)benzoic acid

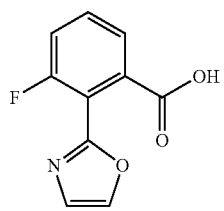 [SMILES: O=C(O)c1cccc(F)c1-c1ncco1]

Step A: 2-bromo-N-(2,2-dimethoxyethyl)-6-fluorobenzamide

To a solution of 2-bromo-6-fluorobenzoic acid (2 g, 9.1 mmol) in DMF (27 mL) was added HBTU (5.20 g, 13.7 mmol) and DIPEA (4.7 mL, 27 mmol), and the reaction mixture was stirred for 10 min. Then, 2,2-dimethoxyethylamine (1.3 mL, 11.9 mmol) was added and the reaction mixture stirred at room temperature for 12 h. The reaction mixture was diluted with EtOAc and washed with saturated aqueous NaHCO$_3$. The combined organic layers were dried over MgSO$_4$, filtered and concentrated. Purification via silica gel chromatography (0-25% EtOAc in hexanes) gave the title compound (2.3 g, 82%).

Step B: 2-(2-bromo-6-fluorophenyl)oxazole

To P$_2$O$_5$ (6.4 g, 22.6 mmol) was added methanesulfonic acid (52 mL, 801 mmol), and the reaction mixture was stirred at room temperature for 1 h. Then, the title compound of step A (2.3 g, 7.54 mmol) was added to the reaction mixture, and the mixture heated to 140° C. for 2 h. DCM was added and the mixture was slowly poured into a saturated solution of aqueous NaHCO$_3$ on ice. The mixture was extracted with DCM. The combined organic layers were dried over MgSO$_4$, filtered and concentrated. Purification via silica gel chromatography (0-10% EtOAc in hexanes) gave the title compound (1.5 g, 82%). MS (ESI) mass calcd. for $C_9H_5BrFNO$, 240.95; m/z found 242.0 [M+H]$^+$.

Step C: Methyl 3-fluoro-2-(oxazol-2-yl)benzoate

A solution of the title compound of step B (2.18 g, 8.99 mmol), Pd(OAc)$_2$ (40 g, 0.18 mmol), 1,1'-bis(diphenylphosphino)ferrocene (199 g, 0.36 mmol), and Et$_3$N (3.7 mL, 27 mmol) in 1:1 MeOH/1,4-dioxane (36 mL) was degassed with N$_2$ for 15 min. Then, the mixture was stirred at 95° C. under an atmosphere of carbon monoxide overnight. The reaction mixture was diluted with EtOAc and washed with a solution of NaHCO$_3$. The organic layer was separated, dried over MgSO$_4$, filtered, and concentrated. Purification via silica gel chromatography (0-12% EtOAc in hexanes) gave the title compound (1.7 g, 83%). MS (ESI) mass calcd. for $C_{11}H_8FNO_3$, 221.1; m/z found 222.0 [M+H]$^+$.

Step D: 3-fluoro-2-(oxazol-2-yl)benzoic acid

To a solution of the title compound of step C (1.65 g, 7.46 mmol) in MeOH (22 mL) was added 2 M NaOH (7.5 mL), and the reaction mixture was stirred at room temperature overnight. The reaction mixture was acidified with 1 M HCl$_{(aq)}$ and the solvents evaporated in vacuo. The mixture was diluted with water and extracted with DCM. The combined organic were dried over MgSO$_4$, filtered and concentrated to afford the title compound (905 g, 58%). MS (ESI) mass calcd. for $C_{10}H_6FNO_3$, 207.0; m/z found 208.0 [M+H]$^+$. MP=182° C.

Intermediate A-69

5-fluoro-2-(oxazol-2-yl)benzoic acid

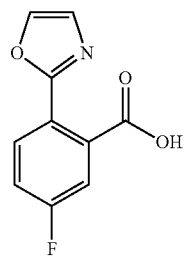 [SMILES: O=C(O)c1cc(F)ccc1-c1ncco1]

Step A: Methyl 5-fluoro-2-(oxazol-2-yl)benzoate

To a solution of methyl 2-bromo-5-fluorobenzoate (1.1 g, 4.8 mmol) and 2-(tri-n-butylstannyl)oxazole (1.3 mL, 6.2 mmol) in toluene (14 mL) was added Pd(PPh$_3$)$_4$ (550 g, 0.476 mmol), and the reaction mixture was heated via microwave heating to 150° C. for 30 min. The reaction mixture was diluted with water and extracted with EtOAc. The combined organic layers were dried over MgSO$_4$, filtered and concentrated. Purification via silica gel chromatography (0-40% EtOAc in hexanes, followed by a second column 0-10% EtOAc in hexanes) gave the title compound (553 g, 52%). MS (ESI) mass calcd. for C$_{11}$H$_6$FNO$_3$, 221.1; m/z found 222.1 [M+H]$^+$.

Step B: 5-fluoro-2-(oxazol-2-yl)benzoic acid

Prepared analogous to intermediate 68, step D, to give the title compound (858 g, 99%). MS (ESI) mass calcd. for C$_{10}$H$_6$FNO$_3$, 207.0; m/z found 208.1 [M+H]$^+$.

Intermediate A-70

2-fluoro-6-(oxazol-2-yl)benzoic acid

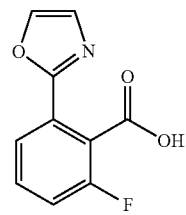

Prepared analogous to intermediate 68, substituting 2-bromo-6-fluorobenzoic acid with 2-bromo-3-fluorobenzoic acid. MS (ESI) mass calcd. for C$_{10}$H$_6$FNO$_3$, 207.0; m/z found 208.0 [M+H]$^+$.

Intermediate A-71

4-fluoro-2-(3-methyl-1,2,4-oxadiazol-5-yl)benzoic acid

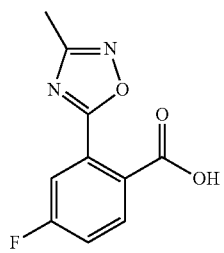 [SMILES: Cc1noc(-c2cc(F)ccc2C(=O)O)n1]

Step A: 5-(2-bromo-5-fluorophenyl)-3-methyl-1,2,4-oxadiazole

To a solution of 2-bromo-5-fluorobenzoyl chloride (2.17 g, 9.13 mmol) in THF (18 mL) was added DIPEA (1.7 mL, 10 mmol). Then, acetamide oxime (676 g, 9.13 mmol) was added portionwise, and the reaction mixture was stirred at 70° C. for 16 h. The reaction mixture was diluted with EtOAc and washed with a saturated solution of NaHCO$_3$. The combined organic layers were dried over MgSO$_4$, filtered and concentrated. Purification via silica gel chromatography (0-20% EtOAc in hexanes) gave the title compound (2.35 g, 57%). MS (ESI) mass calcd. for C$_9$H$_6$BrFN$_2$O, 255.96; m/z found 257.0 [M+H]$^+$.

Step B: 4-fluoro-2-(3-methyl-1,2,4-oxadiazol-5-yl)benzoic acid

Prepared analogous to intermediate 68, steps C and D, to give the title compound. MS (ESI) mass calcd. for C$_{10}$H$_7$FN$_2$O$_3$, 222.0; m/z found 223.0 [M+H]$^+$.

Intermediate B-1

(±)-7-(tert-butoxycarbonyl)-7-azabicyclo[2.2.1]heptane-2-carboxylic acid

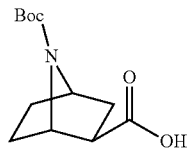 [SMILES: CC(C)(C)OC(=O)N1C2CCC1C(C(=O)O)C2]

Prepared as described in WO 2004/074 292 A1. $^1$H NMR (CDCl$_3$): 4.54 (d, J=4.6 Hz, 1H), 4.33-4.24 (m, 1H), 2.61-2.18 (m, 4H), 1.90-1.71 (m, 2H), 1.68-1.57 (m, 1H), 1.56-1.35 (m, 10H).

Intermediates (+)-B-2 and (−)-B-2

(1S,2R,4R)-2-benzyl 7-tert-butyl 7-azabicyclo[2.2.1]heptane-2,7-dicarboxylate

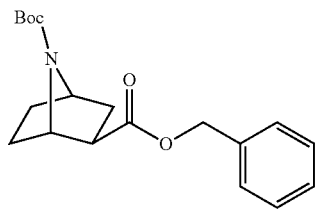 [SMILES: CC(C)(C)OC(=O)N1C2CCC1C(C(=O)OCc1ccccc1)C2]

And (1R,2S,4S)-2-benzyl 7-tert-butyl-7-azabicyclo[2.2.1]heptane-2,7-dicarboxylate

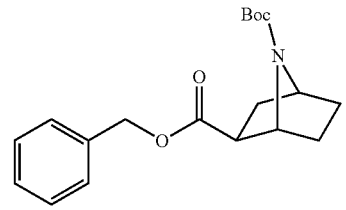 [SMILES: CC(C)(C)OC(=O)N1C2CCC1C(C(=O)OCc1ccccc1)C2]

The title compounds were obtained by chiral SFC (CHIRALPAK IC 5 μM 250×20 mm) resolution of Intermediate B-3 (17 g) using 80% CO₂/20% iPrOH as the mobile phase to give (−)-B-3 enantiomer A (7.5 g, 1st eluting enantiomer) and enantiomer (+)-B3 (7.3 g, 2$^{nd}$ eluting enantiomer).

Intermediate (−)-B-2

(−)-2-benzyl 7-tert-butyl-7-azabicyclo[2.2.1]heptane-2,7-dicarboxylate

Enantiomer A, $[\alpha]^D_{25}$ −25.2 (c 2.8, CHCl₃).

Intermediate (+)-B-2

(+)-2-benzyl 7-tert-butyl-7-azabicyclo[2.2.1]heptane-2,7-dicarboxylate

Enantiomer B, $[\alpha]^D_{25}$ +25.0 (c 2.8, CHCl₃). ¹H NMR (CDCl₃): 7.39-7.30 (m, 5H), 5.19-5.08 (m, 2H), 4.55 (s, 1H), 4.30 (s, 1H), 2.59 (dd, J=8.9, 5.0 Hz, 1H), 2.36-2.24 (m, 1H), 1.90-1.70 (m, 2H), 1.68-1.57 (m, 1H), 1.52-1.34 (m, 11H).

Intermediate B-3

(1S,2R,4R)-7-(tert-butoxycarbonyl)-7-azabicyclo[2.2.1]heptane-2-carboxylic

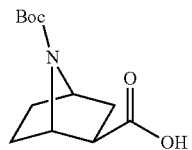 [SMILES: CC(C)(C)OC(=O)N1C2CCC1C(C(=O)O)C2]

To intermediate (+)-B-2 (3.5 g, 10.6 mmol) in EtOH (100 mL) was added 10 wt % Pd/C wet Degussa (750 mg). The reaction was purged with N₂ followed by H₂, then allowed to proceed under an atmosphere of H₂ (balloon). Upon completion, the reaction was filtered and concentrated to give the title compound (2.4 g, 94%) that was used without further purification. ¹H NMR (CDCl₃): 4.62-4.52 (m, 1H), 4.35-4.26 (m, 1H), 2.59 (ddd, J=8.9, 5.0, 1.5 Hz, 1H), 2.29-2.19 (m, 1H), 1.91-1.71 (m, 2H), 1.68-1.58 (m, 1H), 1.54-1.35 (m, 11H).

Intermediate B-4

(1S,2R,4R)-tert-butyl 2-(((benzyloxy)carbonyl)amino)-7-azabicyclo[2.2.1]heptane-7-carboxylate

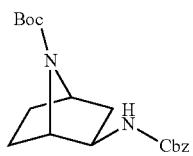 [SMILES: CC(C)(C)OC(=O)N1C2CCC1C(NC(=O)OCc1ccccc1)C2]

To intermediate B-3 (2.4 g, 9.9 mmol) in PhCH₃ (32 mL) was added TEA (1.5 mL, 10.9 mmol). After heating in an oil bath to 70° C., DPPA (2.4 mL, 10.9 mmol) in PhCH₃ (3 mL) was added. After 1 h, BnOH (1.0 g, 9.5 mmol) was added and the oil bath temperature increased to 90° C. After an additional 18 h. the reaction was cooled to rt, diluted with EtOAc and washed with saturated NaHCO₃ (aq). The aqueous layer was extracted with EtOAc (1×). The combined organics were washed with brine and dried (Na₂SO₄). Purification via silica gel chromatography (10-50% EtOAc in hexanes) gave the title compound (2.8 g, 78%). ¹H NMR (CDCl3): 7.39-7.28 (m, 5H), 5.20-4.84 (m, 3H), 4.30-4.06 (m, 3H), 3.86-3.68 (m, 1H), 1.93 (dd, J=13.4, 8.1 Hz, 1H), 1.85-1.63 (m, 2H), 1.54-1.29 (m, 11H).

Intermediate B-5

(+)-(1S,2R,4R)-tert-butyl 2-amino-7-azabicyclo[2.2.1]heptane-7-carboxylate

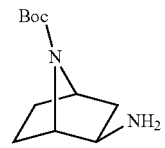 [SMILES: CC(C)(C)OC(=O)N1C2CCC1C(N)C2]

To intermediate B-4 (400 g, 1.2 mmol) in EtOH (5 mL) was added 10 wt % Pd/C wet Degussa (85 mg). The reaction was purged with N₂ followed by H₂, then allowed to proceed under an atmosphere of H₂ (balloon). Upon completion, the reaction was filtered and concentrated to give the title compound (244 g, 99%) that was used without further purification. MS (ESI) mass calcd. for C₁₁H₂₀N₂O₂, 212.1; m/z found 213.1 [M+H]⁺. $[\alpha]^D_{25}$ +9.8 (c 4.9, CHCl₃) ¹H NMR (CDCl3): 4.25-4.13 (m, 1H), 3.94-3.82 (m, 1H), 2.96 (dd, J=7.8, 3.0 Hz, 1H), 1.85-1.25 (m, 15H).

Intermediate B-6

(±)-tert-butyl 2-amino-7-azabicyclo[2.2.1]heptane-7-carboxylate

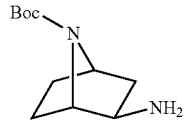

Prepared analogous to intermediate B-5 substituting intermediate B-4 with (±)-7-(tert-butoxycarbonyl)-7-azabicyclo[2.2.1]heptane-2-carboxylic acid (intermediate B-1).

Intermediate B-7

(±)-tert-butyl 2-amino-7-azabicyclo[2.2.1]heptane-7-carboxylate

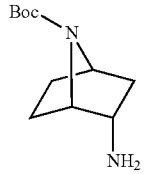

Intermediate B-8

(−)-(1R,2S,4S)-tert-butyl 2-amino-7-azabicyclo[2.2.1]heptane-7-carboxylate

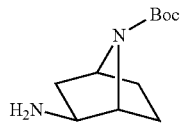

Prepared analogous to intermediate B-5 substituting enantiomer (1S,2R,4R)-2-benzyl 7-tert-butyl 7-azabicyclo[2.2.1]heptane-2,7-dicarboxylate (intermediate (+)-B-2) with enantiomer (1R,2S,4S)-2-benzyl 7-tert-butyl-7-azabicyclo[2.2.1]heptane-2,7-dicarboxylate (intermediate (−)-B-2).

Intermediate B-9

(1S,2R,4R)-tert-butyl 2-(hydroxymethyl)-7-azabicyclo[2.2.1]heptane-7-carboxylate

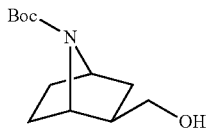

To intermediate (+)-B-2 (504 g, 1.5 mmol) in THF (12 mL) at 0° C. was added Dibal-H (1 M in THF, 4.6 mL). After 1 h, additional Dibal-H was added. The reaction allowed to warm to rt and quenched with Rochelle's Salt (20 wt %). EtOAc was added and the mixture allowed to stir until 2 clear layers had formed. The aqueous layer was extracted with EtOAc (2×). The combined organics were washed with brine and dried ($Na_2SO_4$). Purification via silica gel chromatography (10-50% EtOAc in hexanes) gave the title compound (171 g, 49%). MS (ESI) mass calcd. for $C_{12}H_{21}NO_3$, 227.2; m/z found 228.2 [M+H]$^+$, 172.2 [M−55]$^+$. $^1$H NMR (CDCl3): 4.26-4.12 (m, 2H), 3.45-3.32 (m, 2H), 3.00-2.04 (m, 1H), 1.95-1.90 (m, 1H), 1.83-1.73 (m, 2H), 1.53-1.37 (m, 12H), 1.32-1.28 (m, 1H).

Intermediate B-10

(±)-tert-butyl 2-(hydroxymethyl)-7-azabicyclo[2.2.1]heptane-7-carboxylate

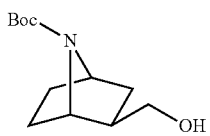

As in Org. Syn., 1997, 74, 212, Tet. Lett. 1997, 38, 6829 and Biorg. Med. Chem. Lett. 2006, 14, 8219. $^1$H NMR (CDCl$_3$): 4.25-4.13 (m, 2H), 3.47-3.32 (m, 2H), 1.98-1.68 (m, 4H), 1.56-1.26 (m, 13H).

Intermediate B-11

(±)-tert-Butyl 2-hydroxy-7-azabicyclo[2.2.1]heptane-7-carboxylate

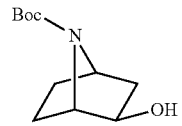 [SMILES: CC(C)(C)OC(=O)N1C2CCC1C(O)C2]

To a solution of (±)-tert-butyl 7-azabicyclo[2.2.1]hept-5-ene-7-carboxylate (3.4 g, 17.4 mmol; *Helvetica Chimica Acta*, 2004, 87, 2764) in THF (50 mL) was added borane THF complex (27 mL, 1M in THF). The solution was stirred at room temperature for ~2 h and then the excess borane was quenched by slow addition of water (7 mL, bubbling observed). 6M NaOH (25 mL) was then added followed by slow dropwise addition of $H_2O_2$ (15 mL, 30%). The resulting solution was stirred at room temperature overnight. The excess $H_2O_2$ was then quenched by slow addition of solid sodium meta-bisulfite. This mixture was diluted with water (200 mL) and extracted with DCM (3×75 mL). The combined organics were dried over $Na_2SO_4$, filtered and the solvent removed. Purification via silica gel chromatography (0-100% EtOAc in hexanes) gave the title compound (2.74 g) as a clear colorless oil that slowly solidified. MS (ESI): mass calcd. for $C_{11}H_{19}NO_3$, 213.2; m/z found, 158.1 [M+2H-tBu]$^+$. $^1$H NMR (400 MHz, CDCl$_3$) δ 4.28-4.20 (t, J=4.9 Hz, 1H), 4.16-4.06 (d, J=5.2 Hz, 1H), 3.91-3.80 (td, J=7.4, 6.4, 1.9 Hz, 1H), 2.00-1.88 (s, 1H), 1.88-1.80 (m, 1H), 1.78-1.69 (m, 1H), 1.69-1.55 (m, 2H), 1.50-1.40 (s, 9H), 1.31-1.20 (m, 2H).

Example 1

(5-fluoro-2-(pyrimidin-2-yl)phenyl)((1S,2R,4R)-2-((pyridin-2-yloxy)methyl)-7-azabicyclo[2.2.1]heptan-7-yl)methanone

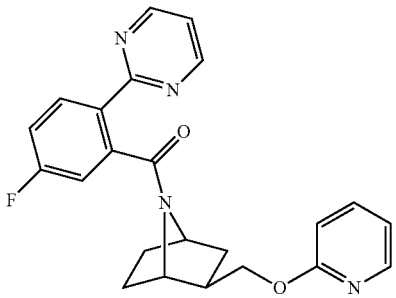 [SMILES: O=C(c1cc(F)ccc1-c1ncccn1)N1C2CCC1C(COc1ccccn1)C2]

Step A: (1S,2R,4R)-tert-butyl 2-((pyridin-2-yloxy)methyl)-7-azabicyclo[2.2.1]heptane-7-carboxylate To intermediate B-9 (170 g, 0.75 mmol) in DMF (3 mL) at 0° C. was added NaH (36 mg, 60 wt % in mineral oil, 0.9 mmol). After 30 min, 2-fluoropyridine (102 g, 1.0 mmol) in DMF (0.5 mL) was added dropwise and the 0° C. ice bath was removed. The flask was then heated to 90° C. in an oil bath. After 2 h, ½ saturated NH$_4$Cl was added and the reaction extracted with EtOAc (2×). The combined organics were washed with brine and dried (Na₂SO₄). Purification via silica gel chromatography (5-30% EtOAc in hexanes) gave the title compound (172 g, 76%) as a white solid. MS (ESI) mass calcd. for $C_{17}H_{24}N_2O_3$, 304.2; m/z found 305.1 [M+H]⁺. ¹H NMR (CDCl₃): 8.13 (dd, J=5.1, 2.0 Hz, 1H), 7.55 (ddd, J=8.7, 7.1, 2.0 Hz, 1H), 6.84 (dd, J=7.0, 5.0 Hz, 1H), 6.73 (d, J=8.3 Hz, 1H), 4.35-4.15 (m, 2H), 4.15-3.99 (m, 2H), 2.26-2.14 (m, 1H), 1.90-1.68 (m, 2H), 1.64-1.55 (m, 1H), 1.54-1.31 (m, 12H).

Step B: (1S,2R,4R)-tert-butyl-2-((pyridin-2-yloxy)methyl)-7-azabicyclo[2.2.1]heptane-7-carboxylate To the title compound from Step A (130 g, 0.4 mmol) in EtOAc was added 4M HCl in dioxane. After 3 h, the reaction was concentrated, neutralized with 5% Na₂CO₃ and extracted with DCM. The combined organics were dried (Na₂SO₄) to give the title compound from step B as a white solid that was used without further purification. MS (ESI) mass calcd. for $C_{12}H_{16}N_2O$, 204.1; m/z found 205.1 [M+H]⁺.

Step C: (5-fluoro-2-(pyrimidin-2-yl)phenyl)((1S,2R,4R)-2-((pyridin-2-yloxy)methyl)-7-azabicyclo[2.2.1]heptan-7-yl)methanone To the title compound of Step B (50 g, 0.18 mmol) in DMF (1.4 mL) was added DIPEA (0.078 mL, 0.45 mmol), intermediate A-7 (43 mg, 0.2 mmol) and HATU (75 g, 0.2 mmol). Upon completion of the reaction, purification was performed using Agilent prep method A to give the title compound. MS (ESI) mass calcd. for $C_{23}H_{21}FN_4O_2$, 404.2; m/z found 405.2 [M+H]⁺. ¹H NMR (CDCl₃): 8.78 (d, J=4.9 Hz, 1H), 8.71 (d, J=4.8 Hz, 1H), 8.26-8.21 (m, 2H), 7.60-7.50 (m, 1H), 7.23-7.00 (m, 3H), 6.90-6.82 (m, 1H), 6.78-6.71 (m, 0.5H), 6.59-6.51 (m, 0.5H), 4.88-4.78 (m, 1H), 4.26-4.09 (m, 1H), 4.09-3.95 (m, 1H), 3.92-3.79 (m, 1H), 2.39-2.18 (m, 1H), 2.04-1.86 (m, 1H), 1.81-1.31 (m, 5H).

Example 2

(±)-(6-methyl-3-(pyrimidin-2-yl)pyridin-2-yloxy)methyl)-7-azabicyclo[2.2.1]heptan-7-yl)methanone

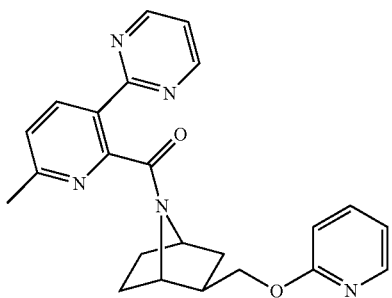 [SMILES: Cc1ccc(-c2ncccn2)c(C(=O)N2C3CCC2C(COc2ccccn2)C3)n1]

Prepared analogous to Example 1 substituting intermediate B-9 with intermediate B-10, 5-fluoro-2-(pyrimidin-2-yl) benzoic acid with intermediate A-9 and HATU with HBTU to give the title compound. MS (ESI) mass calcd. for $C_{23}H_{23}N_5O_2$, 401.2; m/z found 402.2 [M+H]⁺. ¹H NMR (DMSO-D₆): 8.92 (d, J=4.9 Hz, 1H), 8.84 (d, J=4.9 Hz, 1H), 8.32 (t, J=8.3 Hz, 1H), 8.24 (dd, J=5.0, 1.4 Hz, 0.5H), 8.15 (dd, J=5.0, 1.5 Hz, 0.5H), 7.76-7.69 (m, 0.5H), 7.69-7.62 (m, 0.5H), 7.52-7.42 (m, 1.5H), 7.34 (d, J=8.1 Hz, 0.5H), 7.05-6.92 (m, 1H), 6.87 (d, J=8.3 Hz, 0.5H), 6.68 (d, J=8.3 Hz, 0.5H), 4.60-4.56 (m, 1H), 4.19 (td, J=10.3, 3.7 Hz, 1H), 4.06 (dt, J=10.4, 5.3 Hz, 1H), 3.86 (t, J=4.0 Hz, 0.5H), 3.77 (d, J=4.1 Hz, 0.5H), 2.56 (s, 1.5H), 2.39-2.15 (m, 1H), 2.06 (s, 1.5H), 1.88-1.33 (m, 6H).

Example 3A (6-methyl-3-(pyrimidin-2-yl)pyridin-2-yl)((1S*,2R*,4R*)-2-((pyridin-2-yloxy)methyl)-7-azabicyclo[2.2.1]heptan-7-yl)methanone

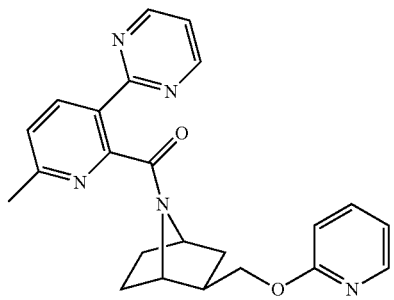 [SMILES: Cc1ccc(-c2ncccn2)c(C(=O)N2C3CCC2C(COc2ccccn2)C3)n1]

And Example 3B (6-methyl-3-(pyrimidin-2-yl)pyridin-2-yl)((1R*,2S*,4S*)-2-((pyridin-2-yloxy)methyl)-7-azabicyclo[2.2.1]heptan-7-yl)methanone

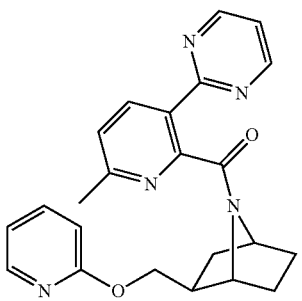 [SMILES: Cc1ccc(-c2ncccn2)c(C(=O)N2C3CCC2C(COc2ccccn2)C3)n1]

The title compounds were obtained by chiral SFC (CHIRALPAK AD-H 5 μM 250×20 mm) resolution of Example 2 (538 mg) using 70% CO₂/30% EtOH as the mobile phase to give enantiomer A (230 mg, 1st eluting enantiomer) and enantiomer B (226 mg, 2ⁿᵈ eluting enantiomer). The enantiomeric purity was confirmed by analytical SFC using a CHIRALPAK AD (250×4.6 mm) and a mobile phase of 70% CO₂, 30% EtOH containing 0.3% iPrNH₂ over 7 minutes. (Example 3A: >98% single enantiomer, 4.00 min retention time; Example 3B>98% single enantiomer, 5.12 min retention time). Example 3A: MS (ESI) mass calcd. for $C_{23}H_{23}N_5O_2$, 401.2; m/z found 402.1 [M+H]⁺. ¹H NMR (CDCl₃): 8.83 (d, J=4.8 Hz, 0.8H), 8.72 (d, J=4.8 Hz, 1.2H), 8.43-8.37 (m, 1H), 8.19-8.09 (m, 1H), 7.59-7.48 (m, 1H), 7.28 (d, J=8.0 Hz, 0.4H), 7.19-7.16 (m, 1.6H), 6.88-6.81 (m, 1H), 6.76 (dt, J=8.4, 1.0 Hz, 0.4H), 6.57 (dt, J=8.3, 0.9 Hz, 0.6H), 4.92-4.84 (m, 1H), 4.38-4.23 (m, 1H), 4.17 (ddd, J=15.4, 10.3, 5.7 Hz, 1H), 3.97-3.87 (m, 1H), 2.62 (s, 1H), 2.39-2.18 (m, 2.5H), 2.11-1.81 (m, 2H), 1.74 (dd, J=12.3, 8.6 Hz, 0.5H), 1.68-1.36 (m, 4H).

Example 3B

MS (ESI) mass calcd. for $C_{23}H_{23}N_5O_2$, 401.2; m/z found 402.1 [M+H]$^+$.

Example 4

(±)-(6-methyl-3-(2H-1,2,3-triazol-2-yl)pyridin-2-yl) (2-((pyridin-2-yloxy)methyl)-7-azabicyclo[2.2.1] heptan-7-yl)methanone

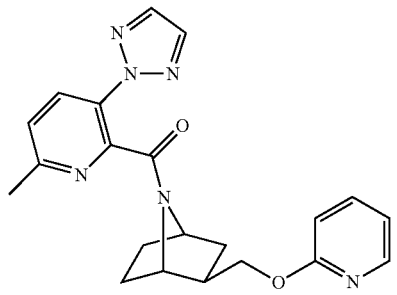

Prepared analogous to Example 1 substituting intermediate B-9 with intermediate B-10, intermediate A-7 with intermediate A-21 and HATU with HBTU to give the title compound. MS (ESI) mass calcd. for $C_{21}H_{22}N_6O_2$, 390.2; m/z found 391.2 [M+H]$^+$. $^1$H NMR (500 MHz, CDCl$_3$): 8.20-8.07 (m, 2H), 7.84-7.75 (m, 2H), 7.61-7.49 (m, 1H), 7.31 (d, J=8.4 Hz, 0.4H), 7.19 (d, J=8.4 Hz, 0.6H), 6.87-6.83 (m, 1H), 6.76 (dt, J=8.4, 0.9 Hz, 0.4H), 6.57 (dt, J=8.3, 0.9 Hz, 0.6H), 4.91-4.81 (m, 1H), 4.32-4.07 (m, 2H), 3.96-3.84 (m, 1H), 2.62 (s, 1.2H), 2.40-2.17 (m, 2.8H), 2.13-1.94 (m, 1H), 1.94-1.68 (m, 1.8H), 1.68-1.37 (m, 3.2H).

Example 5A (6-methyl-3-(2H-1,2,3-triazol-2-yl)pyridin-2-yl)((1S,2R,4R)-2-((pyridin-2-yloxy)methyl)-7-azabicyclo [2.2.1]heptan-7-yl)methanone

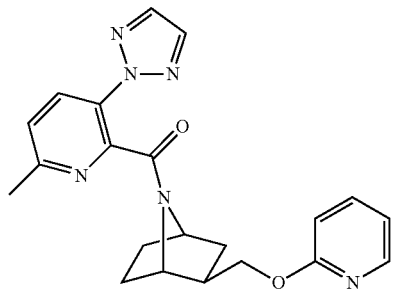 [SMILES: Cc1ccc(-n2nccn2)c(C(=O)N2C3CCC2C(COc2ccccn2)C3)n1]

And Example 5B (6-methyl-3-(2H-1,2,3-triazol-2-yl)pyridin-2-yl)(1R,2S,4S)-2-((pyridin-2-yloxy)methyl)-7-azabicyclo [2.2.1]heptan-7-yl)methanone

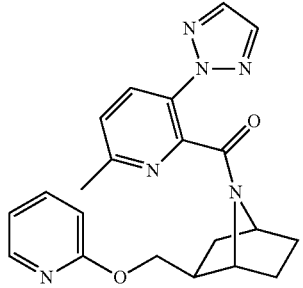 [SMILES: Cc1ccc(-n2nccn2)c(C(=O)N2C3CCC2C(COc2ccccn2)C3)n1]

The title compounds were obtained by chiral SFC (CHIRALPAK AD-H 5 μM 250×20 mm) resolution of Example 4 (555 mg) using 70% CO$_2$/30% EtOH as the mobile phase to give enantiomer A (264 mg, 1st eluting enantiomer) and enantiomer B (248 mg, 2$^{nd}$ eluting enantiomer). The enantiomeric purity was confirmed by analytical SFC using a CHIRALPAK AD (250×4.6 mm) and a mobile phase of 70% CO$_2$, 30% EtOH containing 0.3% iPrNH$_2$ over 7 minutes. (Example 5A: >98% single enantiomer, 2.80 min retention time; Example 5B>98% single enantiomer, 3.90 min retention time). Example 5A: MS (ESI) mass calcd. for $C_{21}H_{22}N_6O_2$, 390.2; m/z found 391.2 [M+H]$^+$. Example 5B: MS (ESI) mass calcd. for $C_{21}H_{22}N_6O_2$, 390.2; m/z found 391.2 [M+H]$^+$.

Example 6

(6-methyl-3-(2H-1,2,3-triazol-2-yl)pyridin-2-yl)((1S, 2R,4R)-2-((pyridin-2-yloxy)methyl)-7-azabicyclo [2.2.1]heptan-7-yl)methanone

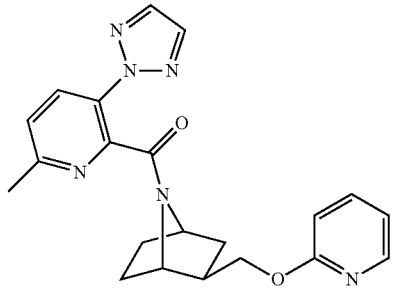 [SMILES: Cc1ccc(-n2nccn2)c(C(=O)N2C3CCC2C(COc2ccccn2)C3)n1]

Prepared analogous to Example 1 substituting intermediate A-7 with intermediate A-21. MS (ESI) mass calcd. for $C_{21}H_{22}N_6O_2$, 390.2; m/z found 391.2 [M+H]$^+$. [α]$_D^{20}$+ 11.4° (c 0.88, CHCl$_3$). $^1$H NMR (CDCl$_3$): 8.19-8.06 (m, 2H), 7.83-7.73 (m, 2H), 7.61-7.48 (m, 1H), 7.30 (d, J=8.4 Hz, 0.4H), 7.19 (d, J=8.4 Hz, 0.6H), 6.89-6.81 (m, 1H), 6.78-6.73 (m, 0.4H), 6.61-6.52 (m, 0.6H), 4.91-4.81 (m, 1H), 4.32-4.08 (m, 2H), 3.96-3.84 (m, 1H), 2.62 (s, 1.2H), 2.39-2.18 (m, 2.8H), 2.11-1.94 (m, 1.5H), 1.94-1.37 (m, 4.5H).

Example 7

(±)-(2-(((5-fluoropyridin-2-yl)oxy)methyl)-7-azabi-cyclo[2.2.1]heptan-7-yl)(6-methyl-3-(2H-1,2,3-tri-azol-2-yl)pyridin-2-yl)methanone

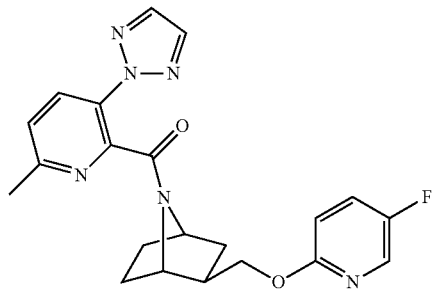 [SMILES: Cc1ccc(-n2nccn2)c(C(=O)N2C3CCC2C(COc2ccc(F)cn2)C3)n1]

Step A Method A: (±)-tert-butyl 2-(((5-fluoropyridin-2-yl)oxy)methyl)-7-azabicyclo[2.2.1]heptane-7-carboxylate Tri-n-butylphosphine (1.8 mL, 7.8 mmol) was added to intermediate B-10 (830 g, 3.7 mmol) and 5-fluoropyridin-2(1H)-one (500 g, 4.4 mmol) in THF (1 mL) under nitrogen bubbling at rt. After 5 min of stirring, DEAD (1.4 mL, 7.1 mmol) was added and the mixture was stirred at 50° C. for 18 hours. The mixture was concentrated and purified silica gel chromatography (0-15% EtOAc in Heptane) to give the title compound of step A (590 g, 45%) as a white solid.

Step A Method B: (±)-tert-butyl 2-(((5-fluoropyridin-2-yl)oxy)methyl)-7-azabicyclo[2.2.1]heptane-7-carboxylate Prepared analogous to Example B-6 substituting intermediate B-9 with (±)-B-9 and 2-fluoropyridine with 2,5-difluoropyridine. MS (ESI) mass calcd. for $C_{17}H_{23}FN_2O_3$, 322.2; m/z found 323.0 [M+H]$^+$. $^1$H NMR (CDCl$_3$): 8.02-7.87 (m, 1H), 7.41-7.27 (m, 1H), 6.70 (dd, J=9.1, 3.6 Hz, 1H), 4.39-4.10 (m, 2H), 4.09-3.89 (m, 2H), 2.25-2.09 (m, 1H), 1.91-1.26 (m, 15H).

Step B: (±)-2-(((5-fluoropyridin-2-yl)oxy)methyl)-7-azabicyclo[2.2.]heptane

Prepared analogous to Example 1 substituting (±)-tert-butyl-2-((pyridin-2-yloxy)methyl)-7-azabicyclo[2.2.1]heptane-7-carboxylate with the title compound from Step A. $^1$H NMR (CDCl$_3$): 7.96 (d, J=3.1 Hz, 1H), 7.33 (ddd, J=9.0, 7.6, 3.1 Hz, 1H), 6.70 (dd, J=9.0, 3.6 Hz, 1H), 4.09-3.98 (m, 2H), 3.72-3.56 (m, 2H), 2.22-1.99 (m, 3H), 1.72-1.53 (m, 3H), 1.49-1.34 (m, 1H).

Step C: (±)-2-(((5-fluoropyridin-2-yl)oxy)methyl)-7-azabicyclo[2.2.1]heptan-7-yl)(6-methyl-3-(2H-1,2,3-triazol-2-yl)pyridin-2-yl)methanone Prepared analogous to Example 1 substituting 5-fluoro-2-(pyrimidin-2-yl)benzoic acid with 6-methyl-3-(2H-1,2,3-triazol-2-yl)picolinic acid. MS (ESI) mass calcd. for $C_{21}H_{21}FN_6O_2$, 408.2; m/z found 409.2.

Example 8A ((1S,2R,4R)-2-(((5-fluoropyridin-2-yl)oxy)methyl)-7-azabicyclo[2.2.]heptan-7-yl)(6-methyl-3-(2H-1,2,3-triazol-2-yl)pyridin-2-yl)methanone

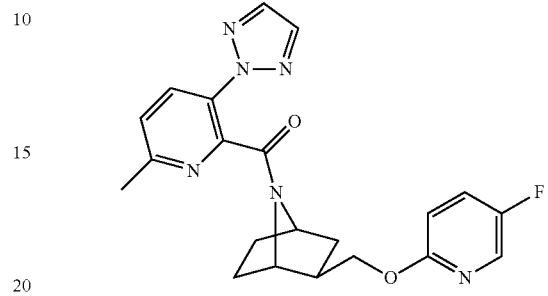

And Example 8B ((1R,2S,4S)-2-(((5-fluoropyridin-2-yl)oxy)methyl)-7-azabicyclo[2.2.1]heptan-7-yl)(6-methyl-3-(2H-1,2,3-triazol-2-yl)pyridin-2-yl)methanone

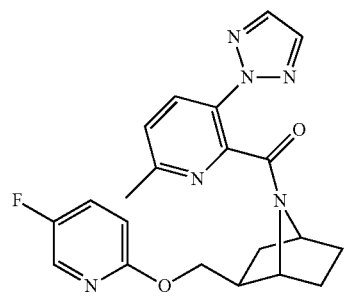

The title compounds were obtained by chiral SFC (CHI-RALPAK AD-H 5 µM 250×20 mm) resolution of Example 7 (259 mg) using 70% CO$_2$/30% mixture of EtOH/i-PrOH (50/50 v/v) as the mobile phase to give enantiomer A (72 mg, 1 st eluting enantiomer) and enantiomer B (84 mg, 2$^{nd}$ eluting enantiomer). The enantiomeric purity was confirmed by analytical SFC using a CHIRALPAK AD-H (250×4.6 mm) and a mobile phase of 70% CO$_2$, 15% EtOH, 15% iPrOH containing 0.3% iPrNH$_2$ over 7 minutes. (Example 8A: 100% single enantiomer, 3.10 min retention time; Example 8B 100% single enantiomer, 4.58 min retention time). Example 8A: MS (ESI) mass calcd. for $C_{21}H_{21}FN_6O_2$, 408.2; m/z found 409.2 [M+H]$^+$. Example 8B: MS (ESI) mass calcd. for $C_{21}H_{21}FN_6O_2$, 408.2; m/z found 409.2 [M+H]$^+$.

Example 9

(±)-(2-(((5-fluoropyridin-2-yl)oxy)methyl)-7-azabicyclo[2.2.1]heptan-7-yl)(5-methyl-2-(2H-1,2,3-triazol-2-yl)phenyl)methanone

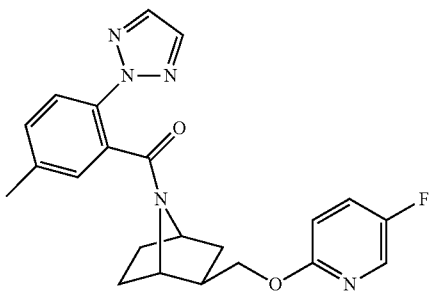

Prepared analogous to Example 7 substituting intermediate A-21 with intermediate A-37. MS (ESI) mass calcd. for $C_{22}H_{22}FN_5O_2$, 407.2; m/z found 408.3 [M+H]+. 1H NMR (CDCl3): 8.03-7.95 (m, 1H), 7.81-7.70 (m, 3H), 7.38-7.11 (m, 3H), 6.72 (dd, J=9.0, 3.6 Hz, 0.5H), 6.52 (dd, J=9.0, 3.5 Hz, 0.5H), 4.86-4.74 (m, 1H), 4.15-3.68 (m, 3H), 2.46-2.37 (s, 1.6H), 2.32-1.78 (m, 4.4H), 1.72-1.22 (m, 4H).

Example 10A ((1S,2R,4R)-2-(((5-fluoropyridin-2-yl)oxy)methyl)-7-azabicyclo[2.2.1]heptan-7-yl)(5-methyl-2-(2H-1,2,3-triazol-2-yl)phenyl)methanone

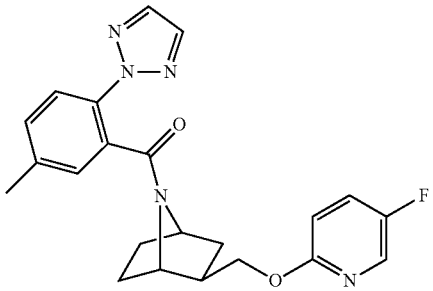 [SMILES: Cc1ccc(-n2nccn2)c(C(=O)N2C3CCC2C(COc2ccc(F)cn2)C3)c1]

And Example 10B ((1R,2S,4S)-2-(((5-fluoropyridin-2-yl)oxy)methyl)-7-azabicyclo[2.2.1]heptan-7-yl)(5-methyl-2-(2H-1,2,3-triazol-2-yl)phenyl)methanone

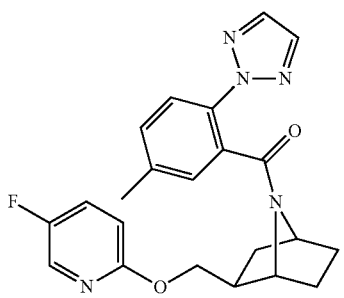 [SMILES: Cc1ccc(-n2nccn2)c(C(=O)N2C3CCC2C(COc2ccc(F)cn2)C3)c1]

The title compounds were obtained by chiral SFC (CHIRALPAK AD-H 5 μM 250×20 mm) resolution of Example 9 (290 mg) using 60% $CO_2$/40% i-PrOH as the mobile phase to give enantiomer A (140 mg, 1st eluting enantiomer) and enantiomer B (134 mg, 2nd eluting enantiomer). The enantiomeric purity was confirmed by analytical SFC using a CHIRALPAK AD-H (250×4.6 mm) and a mobile phase of 60% $CO_2$, 40% iPrOH containing 0.3% $iPrNH_2$ over 7 minutes. (Example 10A: >98% single enantiomer, 2.42 min retention time; Example 10B>98% single enantiomer, 3.20 min retention time).

Example 11

(±)-(2-(((5-fluoropyridin-2-yl)oxy)methyl)-7-azabicyclo[2.2.1]heptan-7-yl)(2-(thiophen-2-yl)phenyl)methanone

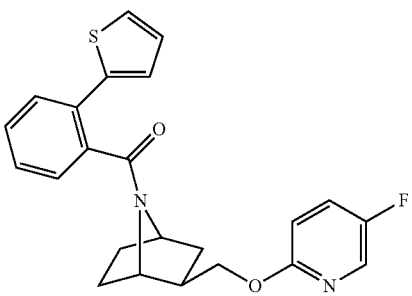 [SMILES: O=C(c1ccccc1-c1cccs1)N1C2CCC1C(COc1ccc(F)cn1)C2]

To (±)-2-(((5-fluoropyridin-2-yl)oxy)methyl)-7-azabicyclo[2.2.1]heptane (35 mg, 0.2 mmol) in DCM (2.5 mL) was added TEA (25 μL, 0.2 mmol)) followed by 2-(thiophen-2-yl)benzoyl chloride (40 g, 0.2 mmol) in DCM (2.5 mL). After 18 h, the reaction was diluted with DCM and washed with $H_2O$. The aqueous layer was extracted DCM (1×). The combined organics were dried ($Na_2SO_4$). Purification via silica gel chromatography (50-100% EtOAc in hexanes) gave the title compound (37 g, 57%). MS (ESI) mass calcd. for $C_{23}H_{21}FN_2O_2S$, 408.1; m/z found 409.1 [M+H]+.

Example 12A ((1 S*,2R*4R*)-2-(((5-fluoropyridin-2-yl)oxy)methyl)-7-azabicyclo[2.2.1]heptan-7-yl)(2-(thiophen-2-yl)phenyl)methanone

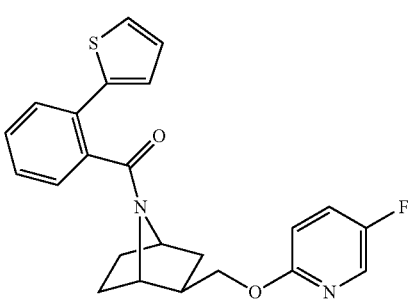 [SMILES: O=C(c1ccccc1-c1cccs1)N1C2CCC1C(COc1ccc(F)cn1)C2]

85

And Example 12B ((1R*2S*,4S*)-2-(((5-fluoropyridin-2-yl)oxy)methyl)-7-azabicyclo[2.2.1]heptan-7-yl)(2-(thiophen-2-yl)phenyl)methanone

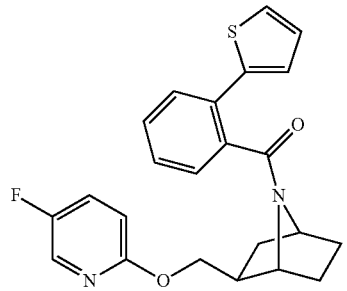 [SMILES: O=C(c1ccccc1-c1cccs1)N1C2CCC1C(COc1ccc(F)cn1)C2]

The title compounds were obtained by chiral SFC (CHIRALPAK AS-H 5 μM 250×20 mm at 40° C.) resolution of Example 11 using 4.2 mL/min MeOH with 0.2% TEA, 37 mL/min $CO_2$ as the mobile phase to give enantiomer A (1st eluting enantiomer) and enantiomer B ($2^{nd}$ eluting enantiomer).

Example 12A

MS (ESI) mass calcd. for $C_{23}H_{21}FN_2O_2S$, 408.2; m/z found 409.2 [M+H]+. $^1$H NMR ($CDCl_3$): 7.97 (dd, J=11.0, 3.0 Hz, 1H), 7.54-7.20 (m, 6.5H), 7.01 (dd, J=5.0, 3.7 Hz, 1.5H), 6.71 (dd, J=9.1, 3.5 Hz, 0.5H), 6.45 (dd, J=9.0, 3.6 Hz, 0.5H), 4.83-4.63 (m, 1H), 4.18-3.38 (m, 3H), 2.70-0.40 (m, 7H).

Example 12B

MS (ESI) mass calcd. for $C_{23}H_{21}FN_2O_2S$, 408.2; m/z found 409.2 [M+H]+. $^1$H NMR ($CDCl_3$): 7.97 (dd, J=11.0, 3.0 Hz, 1H), 7.54-7.20 (m, 6.5H), 7.01 (dd, J=5.0, 3.7 Hz, 1.5H), 6.71 (dd, J=9.1, 3.5 Hz, 0.5H), 6.45 (dd, J=9.0, 3.6 Hz, 0.5H), 4.83-4.63 (m, 1H), 4.18-3.38 (m, 3H), 2.70-0.40 (m, 7H).

Example 13

(±)-(5-methyl-2-(2H-1,2,3-triazol-2-yl)phenyl)(2-(((4-(trifluoromethyl)pyrimidin-2-yl)oxy)methyl)-7-azabicyclo[2.2.1]heptan-7-yl)methanone

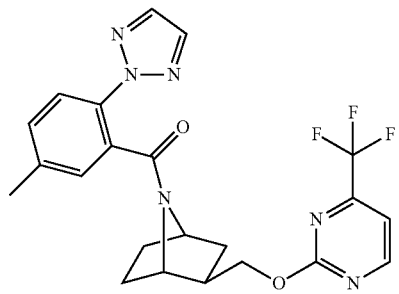 [SMILES: Cc1ccc(-n2nccn2)c(C(=O)N2C3CCC2C(COc2nccc(C(F)(F)F)n2)C3)c1]

86

Step A: (±)-7-azabicyclo[2.2.1]heptan-2-ylmethanol hydrochloride

To intermediate B-10 (1.1 g, 4.9 mmol) in MeOH (1 mL) was added 4M HCl in dioxane (3 mL). After 6 h. the reaction was concentrated to give the title compound that was used without further purification.

Step B: ((±)-2-(hydroxymethyl)-7-azabicyclo[2.2.1]heptan-7-yl)(5-methyl-2-(2H-1,2,3-triazol-2-yl)phenyl)methanone To the title compound of Step A in DMF was added TEA, 5-methyl-2-(2H-1,2,3-triazol-2-yl)benzoic acid and HATU. After 18 h, $H_2O$ was added and the mix extracted with EtOAc (2×). The combined organics were washed with brine and dried ($Na_2SO_4$). Silica gel chromatography (1-7% 2M $NH_3$/MeOH in DCM) gave the title compound (371 g, 46%). MS (ESI) mass calcd. for $C_{17}H_{20}N_4O_2$, 312.2; m/z found 313.2 [M+H]+.

Step C: (±)-(5-methyl-2-(2H-1,2,3-triazol-2-yl)phenyl)(2-(((4-(trifluoromethyl)pyrimidin-2-yl)oxy)methyl)-7-azabicyclo[2.2.]heptan-7-yl)methanone To the title compound of step B (33 g, 0.1 mmol) in THF (2 mL) was added NaOtBu (16 mg, 0.16 mmol). The reaction was then heated at reflux for 15 min and 2-chloro-4-trifluoromethylpyrimidine (19 g, 0.16 mmol) was added. The reaction was heated at reflux temperature for 1 h, cooled to rt, diluted with $H_2O$ and extracted with DCM (2×). The combined organics were dried ($Na_2SO_4$). Purification via silica gel chromatography (0.5-4% 2M $NH_3$/MeOH in DCM gave the title compound (28 g, 57%). MS (ESI) mass calcd. for $C_{22}H_{21}F_3N_6O_2$, 457.2; m/z found 458.2 [M+H]+. $^1$H NMR ($CDCl_3$): 8.82-8.72 (m, 1H), 7.86-7.69 (m, 3H), 7.36-7.10 (m, 3H), 4.85 (m, 1H), 4.47 (t, J=10.1 Hz, 0.5H), 4.20-3.98 (m, 1.5H), 3.90 (d, J=4.7 Hz, 0.5H), 3.78 (t, J=4.5 Hz, 0.5H), 2.51-2.20 (m, 3H), 2.14-1.82 (m, 2H), 1.78-1.17 (m, 5H).

Example 14

(±)-(5-methyl-2-(2H-1,2,3-triazol-2-yl)phenyl)(2-(((5-(trifluoromethyl)pyridin-2-yl)oxy)methyl)-7-azabicyclo[2.2.1]heptan-7-yl)methanone

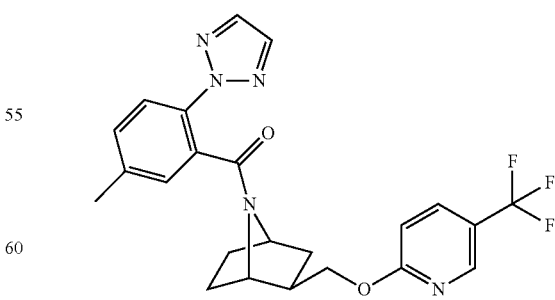

Prepared analogous to Example 13 substituting 2-chloro-4-(trifluoromethyl)pyrimidine with 2-chloro-5-(trifluoromethyl)pyridine. MS (ESI) mass calcd. for $C_{23}H_{22}F_3N_5O_2$, 457.2; m/z found 458.2 [M+H]+.

Example 15

(±)-(5-methyl-2-(2H-1,2,3-triazol-2-yl)phenyl)(2-(((3-(trifluoromethyl)pyridin-2-yl)oxy)methyl)-7-azabicyclo[2.2.1]heptan-7-yl)methanone

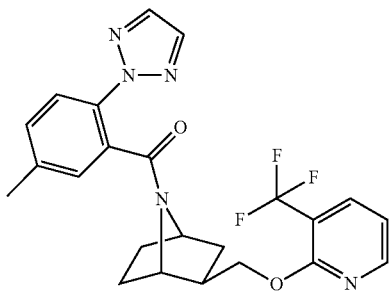 [SMILES: Cc1ccc(-n2nccn2)c(C(=O)N2C3CCC2C(COc2ncccc2C(F)(F)F)C3)c1]

Prepared analogous to Example 13 substituting 2-chloro-4-(trifluoromethyl)pyrimidine with 2-chloro-3-(trifluoromethyl)pyridine. MS (ESI) mass calcd. for $C_{23}H_{22}F_3N_5O_2$, 457.2; m/z found 458.2 [M+H]$^+$. $^1$H NMR (CDCl$_3$): 8.36-8.26 (m, 1H), 7.91-7.69 (m, 4H), 7.36-7.29 (m, 0.5H), 7.25-7.16 (m, 1H), 7.13-7.07 (m, 0.5H), 6.97 (dd, J=7.5, 5.1 Hz, 1H), 4.87-4.70 (m, 1H), 4.53-4.34 (m, 0.5H), 4.25-4.06 (m, 1H), 3.92 (t, J=10.9 Hz, 0.5H), 3.85-3.71 (m, 1H), 2.46-2.40 (m, 1.5H), 2.39-2.19 (m, 1.5H), 2.04-1.79 (m, 3H), 1.72-1.19 (m, 4H).

Example 16

(±)-(5-methyl-2-(2H-1,2,3-triazol-2-yl)phenyl)(2-(((6-(trifluoromethyl)pyridin-2-yl)oxy)methyl)-7-azabicyclo[2.2.1]heptan-7-yl)methanone

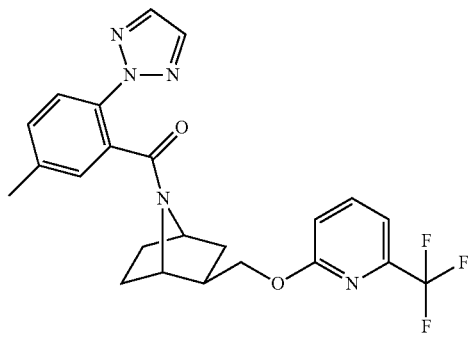 [SMILES: Cc1ccc(-n2nccn2)c(C(=O)N2C3CCC2C(COc2cccc(C(F)(F)F)n2)C3)c1]

Prepared analogous to Example 13 substituting 2-chloro-4-(trifluoromethyl)pyrimidine with 2-chloro-6-(trifluoromethyl)pyridine. MS (ESI) mass calcd. for $C_{23}H_{22}F_3N_5O_2$, 457.2; m/z found 458.2 [M+H]$^+$. $^1$H NMR (CDCl$_3$): 7.87-7.63 (m, 4H), 7.37-7.11 (m, 3H), 6.92 (d, J=8.4 Hz, 0.5H), 6.73 (d, J=8.4 Hz, 0.5H), 4.88-4.75 (m, 1H), 4.20-3.84 (m, 2H), 3.81-3.67 (m, 1H), 2.49-2.36 (s, 2H), 2.34-2.13 (m, 1H), 2.08-1.77 (m, 3H), 1.76-1.10 (m, 4H).

Example 17

(±)-(5-methyl-2-(2H-1,2,3-triazol-2-yl)phenyl)(2-(((4-methylpyridin-2-yl)oxy)methyl)-7-azabicyclo[2.2.1]heptan-7-yl)methanone

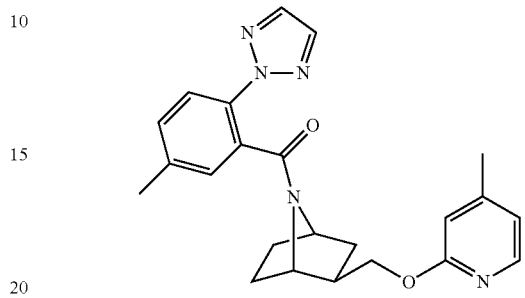

Prepared analogous to Example 13 substituting 2-chloro-4-(trifluoromethyl)pyrimidine with 2-chloro-4-(methyl)pyridine. MS (ESI) mass calcd. for $C_{23}H_{25}N_5O_2$, 403.2; m/z found 404.2 [M+H]$^+$. $^1$H NMR (CDCl$_3$): 8.10-7.91 (m, 1H), 7.87 (d, J=3.7 Hz, 2H), 7.82-7.70 (m, 1H), 7.50-7.42 (m, 1H), 7.34-7.24 (m, 0.5H), 7.16-7.08 (m, 0.5H), 6.90-6.80 (m, 1H), 6.77-6.66 (m, 0.4H), 6.59-6.45 (m, 0.6H), 4.68 (q, J=4.0, 3.3 Hz, 1H), 4.16-3.71 (m, 3H), 2.49-2.18 (m, 5H), 1.94-1.17 (m, 8H).

Example 18

(±)-(5-methyl-2-(2H-1,2,3-triazol-2-yl)phenyl)(2-(((6-methylpyridin-2-yl)oxy)methyl)-7-azabicyclo[2.2.1]heptan-7-yl)methanone

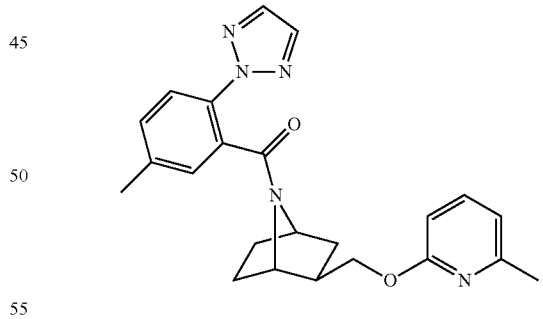

Prepared analogous to Example 13 substituting 2-chloro-4-(trifluoromethyl)pyrimidine with 2-chloro-6-(methyl)pyridine. MS (ESI) mass calcd. for $C_{23}H_{25}N_5O_2$, 403.2; m/z found 404.2 [M+H]$^+$. $^1$H NMR (CDCl$_3$): 7.89 (d, J=1.3 Hz, 2H), 7.82-7.66 (m, 1.5H), 7.61 (dd, J=8.3, 7.3 Hz, 0.5H), 7.43 (ddd, J=8.3, 1.9, 0.9 Hz, 0.5H), 7.35-7.26 (m, 1H), 7.16-7.09 (m, 0.5H), 6.88 (dd, J=16.1, 7.3 Hz, 1H), 6.76 (d, J=8.4 Hz, 0.5H), 6.53 (d, J=8.3 Hz, 0.5H), 4.74-4.64 (m, 1H), 4.24-4.04 (m, 1H), 4.02-3.76 (m, 2H), 2.55-2.21 (m, 5H), 2.05-1.23 (m, 8H).

Example 19

(±)-(5-methyl-2-(2H-1,2,3-triazol-2-yl)phenyl)(2-(((5-methylpyridin-2-yl)oxy)methyl)-7-azabicyclo[2.2.1]heptan-7-yl)methanone

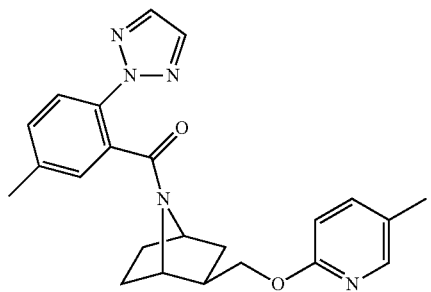

Prepared analogous to Example 13 substituting 2-chloro-4-(trifluoromethyl)pyrimidine with 2-chloro-5-(methyl)pyridine. MS (ESI) mass calcd. for $C_{23}H_{25}N_5O_2$, 403.2; m/z found 404.2 [M+H]$^+$. $^1$H NMR (CDCl$_3$): 8.10-7.58 (m, 4H), 7.43-7.29 (m, 1.5H), 7.26-7.11 (m, 1.5H), 6.66 (d, J=8.4 Hz, 0.5H), 6.45 (d, J=8.4 Hz, 0.5H), 4.86-4.71 (m, 1H), 4.17-3.66 (m, 3H), 2.46-2.38 (s, 1.2H), 2.31-2.14 (m, 3.8H), 2.01-1.79 (m, 2H), 1.71-1.18 (m, 6H).

Example 20

(±)-(2-(((3,6-dimethylpyrazin-2-yl)oxy)methyl)-7-azabicyclo[2.2.1]heptan-7-yl)(5-methyl-2-(2H-1,2,3-triazol-2-yl)phenyl)methanone

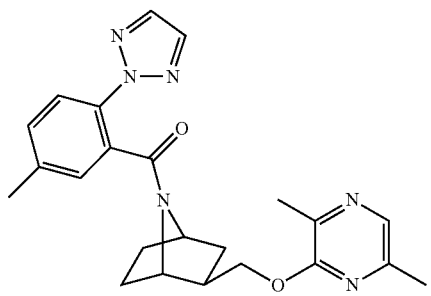

Prepared analogous to Example 13 substituting 2-chloro-4-(trifluoromethyl)pyrimidine with 3-chloro-2,5-dimethylpyrazine. MS (ESI) mass calcd. for $C_{23}H_{26}N_6O_2$, 418.2; m/z found 419.2 [M+H]$^+$. $^1$H NMR (400 MHz, CDCl$_3$) 7.88-7.84 (m, 1H), 7.81-7.72 (m, 2.5H), 7.36-7.12 (m, 2H), 7.11-7.06 (m, 0.5H), 4.86-4.75 (m, 1H), 4.26-4.15 (m, 0.5H), 4.08 (dd, J=11.0, 5.5 Hz, 1H), 3.86-3.71 (m, 1.5H), 2.48-2.34 (m, 6H), 2.34-2.13 (m, 3H), 1.96-1.25 (m, 7H).

Example 21

(±)-(5-methyl-2-(2H-1,2,3-triazol-2-yl)phenyl)(2-(((3-(trifluoromethyl)quinoxalin-2-yl)oxy)methyl)-7-azabicyclo[2.2.1]heptan-7-yl)methanone

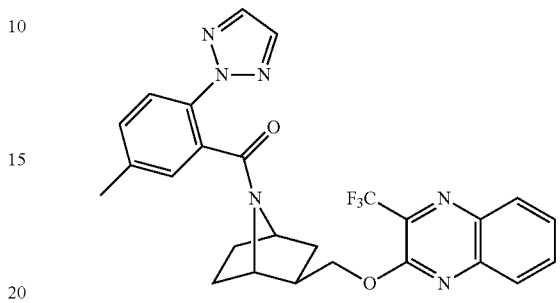

Prepared analogous to Example 13 substituting 2-chloro-4-(trifluoromethyl)pyrimidine with 2-chloro-3-(trifluoromethyl)quinoxaline. MS (ESI) mass calcd. for $C_{26}H_{23}F_3N_6O_2$, 508.2; m/z found 509.2 [M+H]$^+$. $^1$H NMR (CDCl$_3$): 8.16-8.09 (m, 1H), 7.97-7.62 (m, 6H), 7.37-7.23 (m, 1H), 7.19-7.06 (m, 1H), 4.87 (t, J=4.7 Hz, 0.5H), 4.80 (d, J=4.8 Hz, 0.5H), 4.71-4.56 (m, 0.5H), 4.38-4.22 (m, 1H), 4.16-4.01 (m, 0.5H), 3.87-3.73 (m, 1H), 2.49-2.23 (m, 4H), 2.05-1.24 (m, 6H).

Example 22

(±)-(2-(2H-1,2,3-triazol-2-yl)phenyl)(2-(((5-fluoropyridin-2-yl)oxy)methyl)-7-azabicyclo[2.2.1]heptan-7-yl)methanone

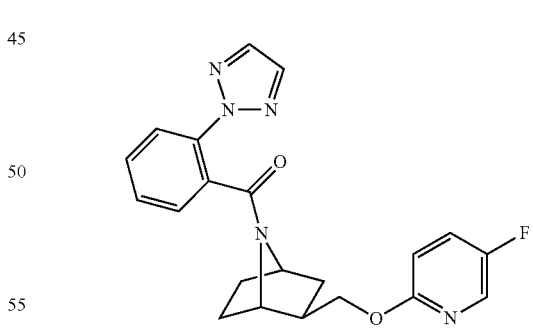

Prepared analogous to Example 7 substituting intermediate A-21 with intermediate A-1. MS (ESI) mass calcd. for $C_{21}H_{20}FN_5O_2$, 393.2; m/z found 394.2 [M+H]$^+$. $^1$H NMR (400 MHz, MeOD) 8.02-7.78 (m, 4H), 7.62-7.53 (m, 0.5H), 7.49-7.28 (m, 3H), 7.13-7.01 (m, 0.5H), 6.75 (dd, J=9.0, 3.6 Hz, 0.5H), 6.51 (dd, J=9.0, 3.6 Hz, 0.5H), 4.85-4.71 (m, 1H), 4.21-4.03 (m, 1H), 4.02-3.72 (m, 2H), 2.39-2.09 (m, 1H), 2.04-1.16 (m, 6H).

Example 23

(±)-2-(((5-fluoropyridin-2-yl)oxy)methyl)-7-azabicyclo[2.2.1]heptan-7-yl)(quinolin-8-yl)methanone

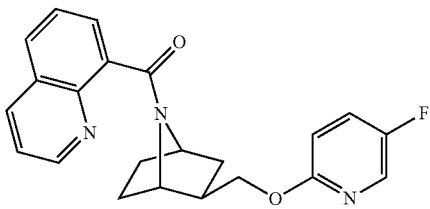 [SMILES: O=C(c1cccc2cccnc12)N1C2CCC1C(COc1ccc(F)cn1)C2]

Prepared analogous to Example 22 substituting intermediate A-1 with quinoline-8-carboxylic acid. MS (ESI) mass calcd. for $C_{22}H_{20}FN_3O_2$, 377.2; m/z found 378.2 $[M+H]^+$. $^1$H NMR (400 MHz, CDCl$_3$): 8.95-8.69 (m, 1H), 8.16 (dd, J=8.3, 1.8 Hz, 0.4H), 8.11-7.81 (m, 2H), 7.81-7.67 (m, 1H), 7.64-7.51 (m, 1H), 7.47-7.09 (m, 2.6H), 6.79 (dd, J=9.0, 3.6 Hz, 0.5H), 6.25 (s, 0.5H), 5.08-4.96 (m, 1H), 4.29 (s, 0.7H), 4.13-3.94 (m, 1.3H), 3.65-3.45 (m, 1H), 2.47-2.02 (m, 2H), 2.02-1.30 (m, 5H).

Example 24

(±)-2-(((5-fluoropyridin-2-yl)oxy)methyl)-7-azabicyclo[2.2.1]heptan-7-yl)(naphthalen-1-yl)methanone

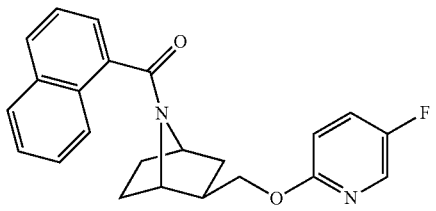

Prepared analogous to Example 22 substituting intermediate A-1 with 1-naphthoic acid. MS (ESI) mass calcd. for $C_{23}H_{21}FN_2O_2$, 376.2; m/z found 377.2 $[M+H]^+$. $^1$H NMR (400 MHz, CDCl$_3$): 8.10-7.95 (m, 1.5H), 7.92-7.83 (m, 1.5H), 7.81-7.71 (m, 1H), 7.58-7.31 (m, 4H), 7.25-7.13 (m, 1H), 6.77 (dd, J=9.0, 3.6 Hz, 0.5H), 6.36-6.24 (m, 0.5H), 5.04-4.92 (m, 1H), 4.30-4.13 (m, 1H), 4.07-3.84 (m, 1H), 3.81-3.64 (m, 1H), 2.44-2.30 (m, 0.5H), 2.27-2.00 (m, 1.5H), 1.89-1.37 (m, 5H).

Example 25

(±)-2-(((5-fluoropyridin-2-yl)oxy)methyl)-7-azabicyclo[2.2.1]heptan-7-yl)(2-methylnaphthalen-1-yl)methanone

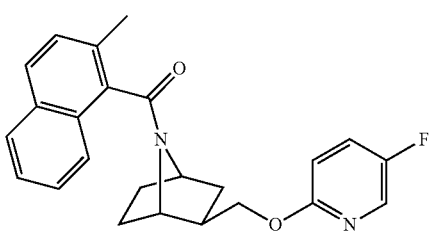 [SMILES: Cc1ccc2ccccc2c1C(=O)N1C2CCC1C(COc1ccc(F)cn1)C2]

Prepared analogous to Example 22 substituting intermediate A-1 with 2-methyl-1-naphthoic acid. $^1$H NMR (CDCl$_3$): 8.06-7.86 (m, 1H), 7.85-7.62 (m, 2.6H), 7.60-7.54 (m, 0.2H), 7.49-7.21 (m, 3.4H), 7.13 (m, 0.8H), 6.77 (ddd, J=12.7, 9.0, 3.6 Hz, 0.6H), 6.43 (dd, J=9.0, 3.6 Hz, 0.2H), 6.03 (dd, J=9.0, 3.6 Hz, 0.2H), 5.11-4.99 (m, 0.9H), 4.38-4.09 (m, 1.2H), 4.08-3.82 (m, 0.7H), 3.69-3.43 (m, 1.2H), 2.58-2.27 (m, 3.5H), 2.23-1.97 (m, 1.5H), 1.92-1.28 (m, 5H).

Example 26

(±)-2-(1H-pyrazol-1-yl)phenyl)(2-(((5-fluoropyridin-2-yl)oxy)methyl)-7-azabicyclo[2.2.1]heptan-7-yl)methanone

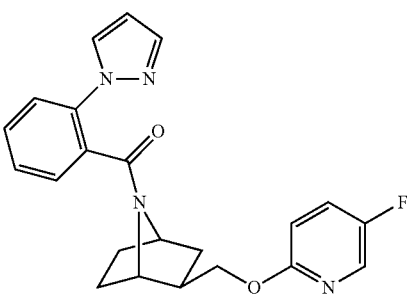 [SMILES: O=C(c1ccccc1-n1cccn1)N1C2CCC1C(COc1ccc(F)cn1)C2]

Prepared analogous to Example 22 substituting intermediate A-1 with 2-(1H-pyrazol-1-yl)benzoic acid. MS (ESI) mass calcd. for $C_{22}H_{21}FN_4O_2$, 392.2; m/z found 393.2 $[M+H]^+$. $^1$H NMR (CDCl$_3$): 7.98 (dd, J=8.3, 3.1 Hz, 1H), 7.91-7.83 (m, 1H), 7.69 (d, J=1.9 Hz, 1H), 7.64-7.23 (m, 4.5H), 6.99 (t, J=7.4 Hz, 0.5H), 6.71 (dd, J=9.0, 3.6 Hz, 0.5H), 6.47-6.34 (m, 1.5H), 4.79-4.63 (m, 1H), 4.03-3.65 (m, 2H), 3.66-3.54 (m, 1H), 2.27-2.03 (m, 1H), 1.86-0.74 (m, 6H).

Example 27

(±)-2-(((5-fluoropyridin-2-yl)oxy)methyl)-7-azabicyclo[2.2.1]heptan-7-yl)(3-phenylfuran-2-yl)methanone

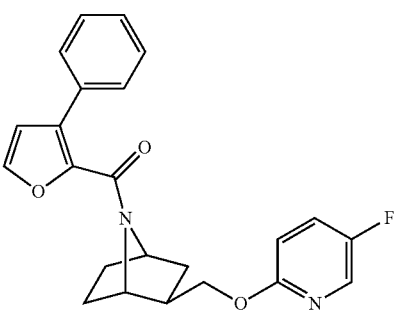 [SMILES: O=C(c1occc1-c1ccccc1)N1C2CCC1C(COc1ccc(F)cn1)C2]

Prepared analogous to Example 22 substituting intermediate A-1 with 3-phenylfuran-2-carboxylic acid. MS (ESI) mass calcd. for $C_{22}H_{21}FN_2O_3$, 392.2; m/z found 393.2 $[M+H]^+$. $^1$H NMR (CDCl$_3$): 8.05-7.82 (m, 1H), 7.59-7.44 (m, 7H), 6.77-6.40 (m, 2H), 4.85-4.61 (m, 1H), 4.45-4.29 (m, 0.5H), 4.24-4.08 (m, 0.5H), 4.06-3.76 (m, 2H), 2.32-2.11 (m, 1H), 2.01-0.83 (m, 6H).

Example 28

(±)-(2-ethoxynaphthalen-1-yl)(2-(((5-fluoropyridin-2-yl)oxy)methyl)-7-azabicyclo[2.2.1]heptan-7-yl)methanone

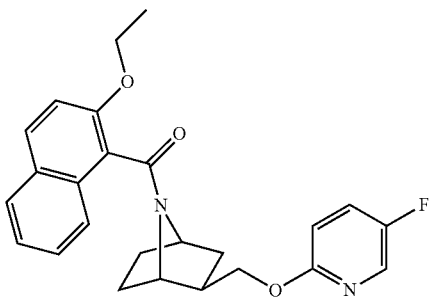 [SMILES: CCOc1ccc2ccccc2c1C(=O)N1C2CCC1C(COc1ccc(F)cn1)C2]

Prepared analogous to Example 22 substituting intermediate A-1 with 2-ethoxy-1-naphthoic acid. MS (ESI) mass calcd. for $C_{25}H_{25}FN_2O_3$, 420.2; m/z found 421.2 [M+H]$^+$. $^1$H NMR (CDCl$_3$): 8.03 (d, J=3.0 Hz, 0.2H), 7.95 (dd, J=8.1, 3.1 Hz, 0.5H), 7.86-7.70 (m, 2.6H), 7.69-7.63 (m, 0.3H), 7.60-7.55 (m, 0.3H), 7.50-7.00 (m, 4.2H), 6.76 (ddd, J=9.3, 6.1, 3.6 Hz, 0.5H), 6.44 (dd, J=9.0, 3.5 Hz, 0.2H), 6.03 (dd, J=9.0, 3.6 Hz, 0.2H), 5.08-4.97 (m, 1H), 4.35-3.92 (m, 3.3H), 3.91-3.76 (m, 0.5H), 3.68-3.52 (m, 1.2H), 2.44-2.27 (m, 0.8H), 2.20-1.93 (m, 2H), 1.85-1.18 (m, 7.2H).

Example 29

(±)-(5-(2-fluorophenyl)-2-methylthiazol-4-yl)(2-(((5-fluoropyridin-2-yl)oxy)methyl)-7-azabicyclo[2.2.1]heptan-7-yl)methanone

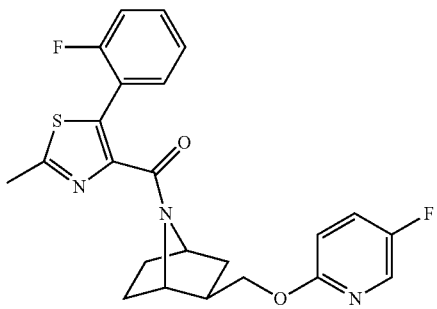 [SMILES: Cc1nc(C(=O)N2C3CCC2C(COc2ccc(F)cn2)C3)c(-c2ccccc2F)s1]

Prepared analogous to Example 22 substituting intermediate A-1 with 5-(2-fluorophenyl)-2-methylthiazole-4-carboxylic acid. MS (ESI) mass calcd. for $C_{23}H_{21}F_2N_3O_2S$, 441.2; m/z found 442.2 [M+H]$^+$. $^1$H NMR (CDCl$_3$): 7.99-7.93 (m, 1H), 7.53-7.44 (m, 1H), 7.36-7.09 (m, 3.5H), 7.04 (ddd, J=9.8, 8.5, 1.2 Hz, 0.5H), 6.66 (ddd, J=15.9, 9.0, 3.6 Hz, 1H), 4.79-4.68 (m, 1H), 4.27-4.21 (m, 0.5H), 4.07 (t, J=4.6 Hz, 0.5H), 3.96-3.73 (m, 2H), 2.74 (s, 1.5H), 2.42 (s, 1.5H), 2.23-2.11 (m, 1H), 1.89-1.57 (m, 2H), 1.54-1.24 (m, 3.5H), 0.92-0.81 (m, 0.5H).

Example 30

(±)-(5-fluoro-2-(2H-1,2,3-triazol-2-yl)phenyl)(2-(((5-fluoropyridin-2-yl)oxy)methyl)-7-azabicyclo[2.2.1]heptan-7-yl)methanone

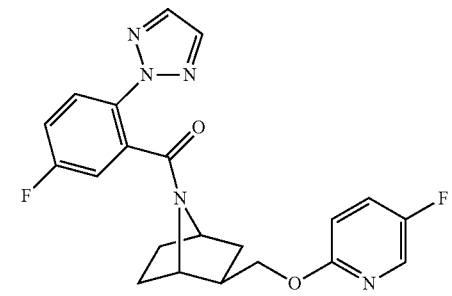 [SMILES: O=C(c1cc(F)ccc1-n1nccn1)N1C2CCC1C(COc1ccc(F)cn1)C2]

Prepared analogous to Example 22 substituting intermediate A-1 with intermediate A-10. MS (ESI) mass calcd. for $C_{21}H_{19}F_2N_5O_2$, 411.2; m/z found 412.2 [M+H]$^+$. $^1$H NMR (CDCl$_3$): 7.98 (dd, J=7.4, 3.0 Hz, 1H), 7.86 (ddd, J=21.7, 8.9, 4.7 Hz, 1H), 7.81-7.75 (m, 1.5H), 7.38-7.03 (m, 3.5H), 6.72 (dd, J=9.0, 3.6 Hz, 0.5H), 6.52 (dd, J=9.0, 3.6 Hz, 0.5H), 4.85-4.75 (m, 1H), 4.17-4.02 (m, 1H), 4.02-3.83 (m, 1H), 3.83-3.75 (m, 1H), 2.34-2.15 (m, 1H), 2.03-1.80 (m, 1H), 1.74-1.20 (m, 5H).

Example 31

(±)-(2-fluoro-6-(pyrimidin-2-yl)phenyl)(2-(((5-fluoropyridin-2-yl)oxy)methyl)-7-azabicyclo[2.2.1]heptan-7-yl)methanone

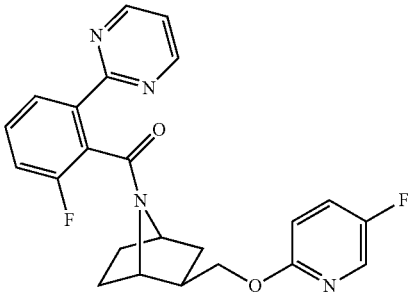

Prepared analogous to Example 22 substituting intermediate A-1 with intermediate A-6. MS (ESI) mass calcd. for $C_{23}H_{20}F_2N_4O_2$, 422.2; m/z found 423.2 [M+H]$^+$. $^1$H NMR (CDCl$_3$): 8.93-8.61 (m, 1.8H), 8.15-7.92 (m, 1.6H), 7.56-7.05 (m, 4.3H), 6.94 (t, J=8.6 Hz, 0.3H), 6.73 (ddd, J=8.9, 5.2, 3.5 Hz, 0.6H), 6.59-6.35 (m, 0.4H), 4.99-4.79 (m, 1H), 4.31 (t, J=9.9 Hz, 0.3H), 4.25-3.63 (m, 2.7H), 2.47-1.11 (m, 7H).

Example 32

(4)-(5-fluoro-2-(pyrimidin-2-yl)phenyl)(2-(((5-fluoropyridin-2-yl)oxy)methyl)-7-azabicyclo[2.2.1]heptan-7-yl)methanone

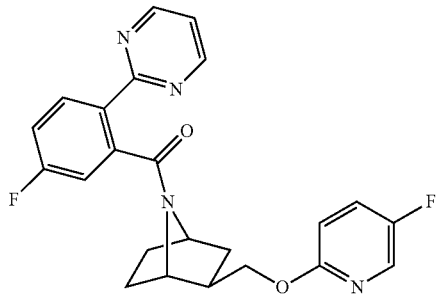 [SMILES: O=C(c1cc(F)ccc1-c1ncccn1)N1C2CCC1C(COc1ccc(F)cn1)C2]

Prepared analogous to Example 22 substituting intermediate A-1 with 5-fluoro-2-(pyrimidin-2-yl)benzoic acid. MS (ESI) mass calcd. for $C_{23}H_{20}F_2N_4O_2$, 422.2; m/z found 423.2 [M+H]$^+$. $^1$H NMR (500 MHz, CDCl$_3$) 8.78 (d, J=4.9 Hz, 1H), 8.72 (d, J=4.8 Hz, 1H), 8.22 (ddd, J=20.6, 8.7, 5.5 Hz, 1H), 8.01-7.93 (m, 1H), 7.37-7.27 (m, 1H), 7.23-7.13 (m, 1.5H), 7.13-6.99 (m, 1.5H), 6.72 (dd, J=9.0, 3.5 Hz, 0.5H), 6.52 (dd, J=9.0, 3.5 Hz, 0.5H), 4.90-4.75 (m, 1H), 4.25-3.91 (m, 2H), 3.91-3.78 (m, 1H), 2.39-2.15 (m, 1H), 2.08-1.13 (m, 6H).

Example 33

(±)-(2-(((5-fluoropyridin-2-yl)oxy)methyl)-7-azabicyclo[2.2.1]heptan-7-yl)(5-methyl-2-(pyrimidin-2-yl)phenyl)methanone

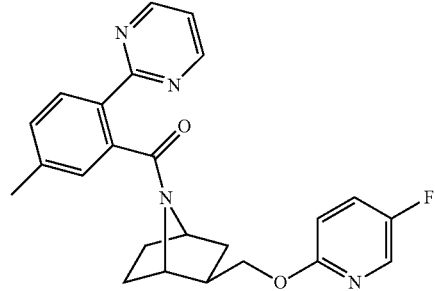 [SMILES: Cc1ccc(-c2ncccn2)c(C(=O)N2C3CCC2C(COc2ccc(F)cn2)C3)c1]

Prepared analogous to Example 22 substituting intermediate A-1 with 5-methyl-2-(pyrimidin-2-yl)benzoic acid. MS (ESI) mass calcd. for $C_{24}H_{23}FN_4O_2$, 418.2; m/z found 419.2 [M+H]$^+$. $^1$H NMR (CDCl$_3$): 8.81-8.68 (m, 2H), 8.09 (dd, J=9.9, 8.0 Hz, 1H), 7.98 (dd, J=8.6, 3.1 Hz, 1H), 7.41-7.24 (m, 1.5H), 7.22-7.16 (m, 1H), 7.16-7.09 (m, 1.5H), 6.73 (dd, J=9.1, 3.6 Hz, 0.5H), 6.52 (dd, J=9.0, 3.6 Hz, 0.5H), 4.88-4.77 (m, 1H), 4.21-4.01 (m, 1H), 4.01-3.89 (m, 1H), 3.88-3.76 (m, 1H), 2.42 (s, 1.6H), 2.35-2.10 (m, 1H), 2.07-1.81 (m, 2.4H), 1.81-1.16 (m, 5H).

Example 34

(±)-(2-(2H-1,2,3-triazol-2-yl)phenyl)(2-((quinoxalin-2-yloxy)methyl)-7-azabicyclo[2.2.1]heptan-7-yl)methanone

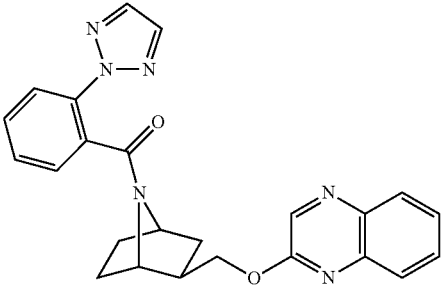 [SMILES: O=C(c1ccccc1-n1nccn1)N1C2CCC1C(COc1cnc3ccccc3n1)C2]

Step A: (±)-2-(-7-azabicyclo[2.2.1]heptan-2-ylmethoxy)quinoxaline

To intermediate B-10 (240 g, 1.1 mmol) in THF (4 mL) was added NaOtBu (130 g, 1.4 mmol). The reaction was heated at reflux for 15 min and 2-chloroquinoxaline (207 g, 1.3 mmol) was added. After min, the reaction was cooled to rt and ½ saturated NH$_4$Cl (aq) was added. The solution was made slightly basic with 5% Na2CO3 (aq) and extracted with DCM (3×). The combined organics were dried (Na$_2$SO$_4$). The resulting compound was treated with TFA in DCM. After the reaction was complete, the reaction was concentrated, neutralized with 5% Na$_2$CO$_3$ and extracted with DCM. The combined organics were dried (Na$_2$SO$_4$). Purification via silica gel chromatography (1-7% (2M NH$_3$ in MeOH)/DCM) gave the title compound (208 g, 78%). MS (ESI) mass calcd. for $C_{15}H_{17}N_3O$, 255.1; m/z found 256.2 [M+H]$^+$.

Step B: (±)-(2-(2H-1,2,3-triazol-2-yl)phenyl)(2-((quinoxalin-2-yloxy)methyl)-7-azabicyclo[2.2.1]heptan-7-yl)methanone Prepared analogous to Example 7 substituting 6-methyl-3-(2H-1,2,3-triazol-2-yl)picolinic acid with intermediate A-1 and (±)-2-(((5-fluoropyridin-2-yl)oxy)methyl)-7-azabicyclo[2.2.1]heptane with the title compound of Step A. MS (ESI) mass calcd. for $C_{24}H_{22}N_6O_2$, 426.2; m/z found 427.2 [M+H]$^+$. $^1$H NMR (CDCl$_3$): 8.49 (s, 0.5H), 8.31-8.21 (s, 0.5H), 8.08-7.98 (m, 1H), 7.95-7.75 (m, 3.4H), 7.75-7.66 (m, 1.1H), 7.65-7.50 (m, 1.7H), 7.50-7.39 (m, 1.1H), 7.36-7.28 (m, 1H), 7.24-7.13 (m, 0.7H), 4.92-4.80 (m, 1H), 4.47-4.28 (m, 1H), 4.22-4.07 (m, 1H), 3.87-3.77 (m, 1H), 2.46-2.23 (m, 1.7H), 2.07-1.83 (m, 1.3H), 1.82-1.29 (m, 4H).

Example 35

(±)-(2-fluoro-6-(2H-1,2,3-triazol-2-yl)phenyl)(2-((quinoxalin-2-yloxy)methyl)-7-azabicyclo[2.2.1]heptan-7-yl)methanone

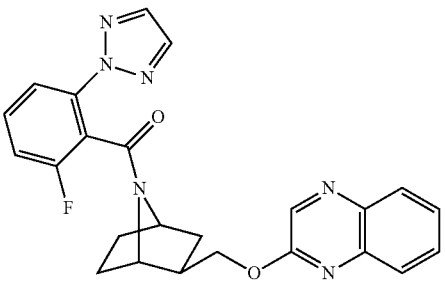 [SMILES: O=C(c1c(F)cccc1-n1nccn1)N1C2CCC1C(COc1cnc3ccccc3n1)C2]

Prepared analogous to Example 34 substituting intermediate A-1 with intermediate A-11. MS (ESI) mass calcd. for $C_{24}H_{21}FN_6O_2$, 444.2; m/z found 445.2 [M+H]$^+$. $^1$H NMR (CDCl$_3$): 8.52-8.47 (m, 0.5H), 8.27-8.21 (m, 0.4H), 8.07-7.95 (m, 1H), 7.91-7.09 (m, 7.8H), 6.72-6.63 (m, 0.3H), 4.98-4.87 (m, 1H), 4.63-4.54 (dd, J=10.7, 9.1 Hz, 0.5H), 4.46-4.29 (m, 1H), 4.20-4.04 (m, 0.5H), 3.96-3.76 (m, 1H), 2.51-2.23 (m, 1H), 2.17-1.88 (m, 1H), 1.84-1.19 (m, 5H).

Example 36

(±)-(5-methyl-2-(2H-1,2,3-triazol-2-yl)phenyl)(2-((quinoxalin-2-yloxy)methyl)-7-azabicyclo[2.2.1]heptan-7-yl)methanone

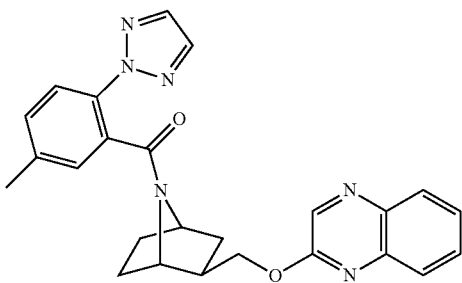 [SMILES: Cc1ccc(-n2nccn2)c(C(=O)N2C3CCC2C(COc2cnc4ccccc4n2)C3)c1]

Prepared analogous to Example 34 substituting intermediate A-1 with intermediate A-37. MS (ESI) mass calcd. for $C_{25}H_{24}N_6O_2$, 440.2; m/z found 441.2 [M+H]$^+$. $^1$H NMR (CDCl$_3$): 8.49 (s, 0.5H), 8.26 (s, 0.5H), 8.03 (ddd, J=8.3, 4.4, 1.4 Hz, 1H), 7.90-7.74 (m, 3H), 7.74-7.65 (m, 1H), 7.59 (dddd, J=8.3, 7.0, 4.8, 1.4 Hz, 1H), 7.33 (ddd, J=8.3, 1.9, 0.9 Hz, 0.6H), 7.29-7.22 (m, 1H), 7.21-7.10 (m, 1.4H), 4.90-4.79 (m, 1H), 4.46-3.98 (m, 2H), 3.91-3.72 (m, 1H), 2.47-2.20 (m, 4H), 2.05-1.22 (m, 6H).

Example 37

(±)-(5-fluoro-2-(2H-1,2,3-triazol-2-yl)phenyl)(2-((quinoxalin-2-yloxy)methyl)-7-azabicyclo[2.2.1]heptan-7-yl)methanone

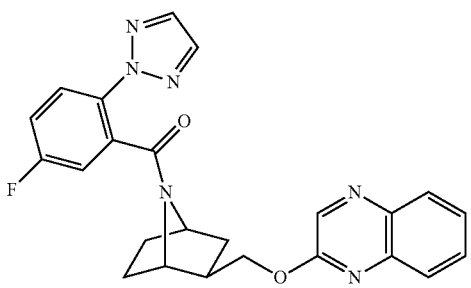 [SMILES: O=C(c1cc(F)ccc1-n1nccn1)N1C2CCC1C(COc1cnc3ccccc3n1)C2]

Prepared analogous to Example 34 substituting intermediate A-1 with intermediate A-10. MS (ESI) mass calcd. for $C_{24}H_{21}FN_6O_2$, 444.2; m/z found 445.2 [M+H]$^+$. $^1$H NMR (CDCl$_3$): 8.55-8.44 (m, 0.5H), 8.36-8.23 (m, 0.5H), 8.08-8.00 (m, 1H), 7.90-7.55 (m, 5H), 7.49-7.09 (m, 3H), 4.91-4.82 (m, 1H), 4.50-4.29 (m, 1H), 4.23-4.07 (m, 1H), 3.82 (dd, J=10.0, 5.0 Hz, 1H), 2.48-2.25 (m, 1H), 2.09-1.88 (m, 1H), 1.82-1.31 (m, 5H).

Example 38

(±)-(5-methyl-2-(pyrimidin-2-yl)phenyl)(2-((quinoxalin-2-yloxy)methyl)-7-azabicyclo[2.2.1]heptan-7-yl)methanone

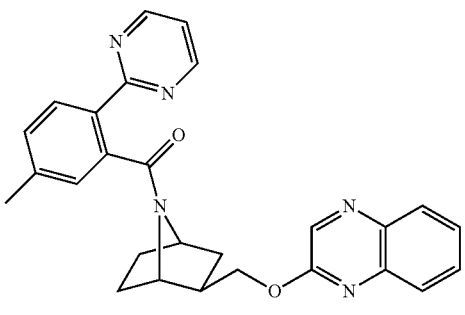 [SMILES: Cc1ccc(-c2ncccn2)c(C(=O)N2C3CCC2C(COc2cnc4ccccc4n2)C3)c1]

Prepared analogous to Example 34 substituting intermediate A-1 with intermediate A-34. MS (ESI) mass calcd. for $C_{27}H_{25}N_5O_2$, 451.2; m/z found 452.2 [M+H]$^+$. $^1$H NMR (CDCl$_3$): 8.87-8.79 (m, 1H), 8.75-8.68 (m, 1H), 8.49 (s, 0.5H), 8.27 (s, 0.5H), 8.14-7.98 (m, 2H), 7.85 (ddd, J=16.5, 8.3, 1.5 Hz, 1H), 7.74-7.66 (m, 1H), 7.64-7.54 (m, 1H), 7.35-7.29 (m, 0.5H), 7.24-7.19 (m, 0.5H), 7.18-7.07 (m, 2H), 4.94-4.83 (m, 1H), 4.52-4.07 (m, 2H), 3.93-3.82 (m, 1H), 2.51-2.20 (m, 2.6H), 2.08-1.83 (m, 1.4H), 1.81-1.12 (m, 6H).

Example 39

(±)-(2-(((4,6-dimethylpyrimidin-2-yl)oxy)methyl)-7-azabicyclo[2.2.1]heptan-7-yl)(5-methyl-2-(2H-1,2,3-triazol-2-yl)phenyl)methanone

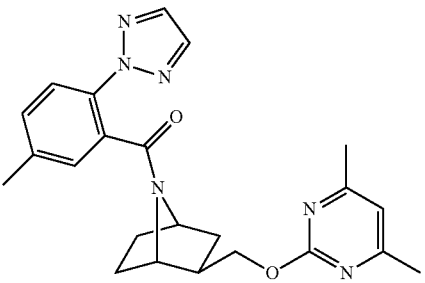

Step A: (±)-2-(((4,6-dimethylpyrimidin-2-yl)oxy)methyl)-7-azabicyclo[2.2.1]heptane Prepared analogous to Example 34 substituting 2-chloroquinoxaline with 2-chloro-4,6-dimethylpyrimidine. $^1$H NMR (CDCl$_3$): 6.65 (s, 1H), 4.21-3.99 (m, 2H), 3.74-3.56 (m, 2H), 2.39 (s, 6H), 2.14 (ddd, J=9.0, 5.1, 3.7 Hz, 1H), 1.86 (s, 2H), 1.67-1.49 (m, 2H), 1.47-1.30 (m, 2H).

Step B: (±)-(2-(((4,6-dimethylpyrimidin-2-yl)oxy)methyl)-7-azabicyclo[2.2.1]heptan-7-yl)(5-methyl-2-(2H-1,2,3-triazol-2-yl)phenyl)methanone Prepared analogous to Example 7 substituting 6-methyl-3-(2H-1,2,3-triazol-2-yl)picolinic acid with 5-methyl-2-

(2H-1,2,3-triazol-2-yl)benzoic acid and (±)-2-(((5-fluoropyridin-2-yl)oxy)methyl)-7-azabicyclo[2.2.1]heptane with the title compound of Step A. MS (ESI) mass calcd. for $C_{23}H_{26}N_6O_2$, 418.2; m/z found 419.2 [M+H]$^+$. $^1$H NMR (CDCl$_3$): 7.83-7.70 (m, 2.5H), 7.35-7.10 (m, 2.5H), 6.71-6.65 (m, 1H), 4.87-4.72 (m, 1H), 4.34 (dd, J=10.5, 8.8 Hz, 0.5H), 4.14-3.89 (m, 2H), 3.79-3.70 (m, 0.5H), 2.48-2.18 (m, 7.5H), 2.07-1.83 (m, 2.5H), 1.79-1.18 (m, 6H).

Example 40

(±)-2-(((4,6-dimethylpyrimidin-2-yl)oxy)methyl)-7-azabicyclo[2.2.1]heptan-7-yl)(3-methyl-5-phenylisoxazol-4-yl)methanone

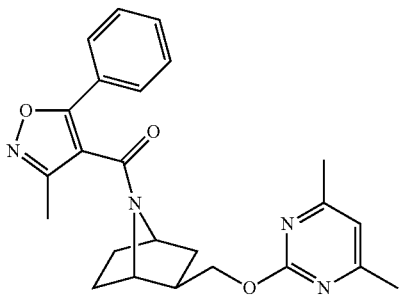 [SMILES: Cc1cc(C)nc(OCC2CC3CCC2N3C(=O)c2c(C)noc2-c2ccccc2)n1]

Prepared analogous to Example 39 substituting 5-methyl-2-(2H-1,2,3-triazol-2-yl)benzoic acid with 3-methyl-5-phenylisoxazole-4-carboxylic acid. MS (ESI) mass calcd. for $C_{24}H_{26}N_4O_3$, 418.2; m/z found 419.2 [M+H]$^+$. $^1$H NMR (CDCl$_3$): 7.67 (m, 2H), 7.50-7.31 (m, 3H), 6.69 (d, J=6.7 Hz, 1H), 4.74 (dd, J=10.8, 5.1 Hz, 1H), 4.17 (dd, J=10.8, 9.2 Hz, 0.5H), 3.85-3.78 (m, 1H), 3.70 (d, J=4.9 Hz, 0.5H), 3.64-3.42 (m, 1H), 2.55 (s, 1.4H), 2.49 (s, 1.6H), 2.43 (s, 3H), 2.39 (s, 3H), 2.29-2.07 (m, 1H), 1.90-1.55 (m, 2H), 1.53-1.06 (m, 3H), 0.76-0.53 (m, 1H).

Example 41

(±)-(2-(((4,6-dimethylpyrimidin-2-yl)oxy)methyl)-7-azabicyclo[2.2.1]heptan-7-yl)(2-ethoxynaphthalen-1-yl)methanone

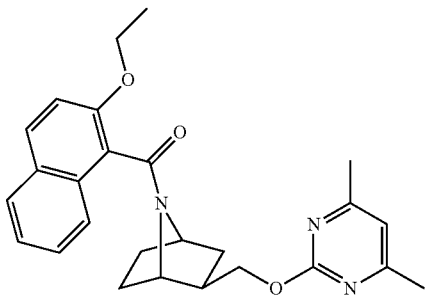 [SMILES: CCOc1ccc2ccccc2c1C(=O)N1C2CCC1C(COc1nc(C)cc(C)n1)C2]

Prepared analogous to Example 39 substituting 5-methyl-2-(2H-1,2,3-triazol-2-yl)benzoic acid with 2-ethoxy-1-naphthoic acid. $^1$H NMR (CDCl$_3$): 7.91-7.70 (m, 2.5H), 7.67-7.54 (m, 0.5H), 7.49-7.38 (m, 0.8H), 7.37-7.28 (m, 0.8H), 7.27-7.16 (m, 0.9H), 7.10-7.02 (m, 0.5H), 6.70 (s, 0.2H), 6.65 (s, 0.5H), 6.53 (s, 0.3H), 5.09-4.95 (m, 1H), 4.56-4.47 (m, 0.5H), 4.28-3.87 (m, 3.3H), 3.79-3.55 (m, 1.2H), 2.46-2.35 (m, 4.5H), 2.28 (s, 1.5H), 2.21-1.95 (m, 2H), 1.85-1.51 (m, 3.5H), 1.51-1.24 (m, 4.5H).

Example 42

(±)-(2-(((4,6-dimethylpyrimidin-2-yl)oxy)methyl)-7-azabicyclo[2.2.1]heptan-7-yl)(2-ethoxyphenyl)methanone)

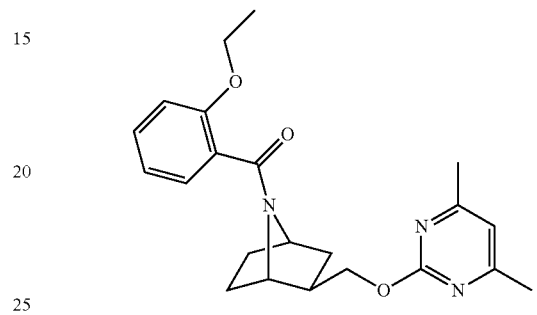

Prepared analogous to Example 39 substituting 5-methyl-2-(2H-1,2,3-triazol-2-yl)benzoic acid with 2-ethoxybenzoic acid. MS (ESI) mass calcd. for $C_{22}H_{27}N_3O_3$, 381.2; m/z found 382.2 [M+H]$^+$. $^1$H NMR (CDCl$_3$): 7.34-7.27 (m, 1H), 7.21-7.12 (m, 1H), 6.98-6.92 (m, 0.5H), 6.89 (d, J=8.2 Hz, 0.5H), 6.78 (d, J=8.3 Hz, 0.5H), 6.72-6.63 (m, 1.5H), 4.89-4.78 (m, 1H), 4.36 (dd, J=10.6, 8.7 Hz, 0.5H), 4.14-3.71 (m, 4.5H), 2.45-2.16 (m, 6.5H), 2.06-1.82 (m, 1.5H), 1.82-1.28 (m, 8H).

Example 43

(±)-(2-(((4,6-dimethylpyrimidin-2-yl)oxy)methyl)-7-azabicyclo[2.2.1]heptan-7-yl)(2-fluoro-6-(pyrimidin-2-yl)phenyl)methanone

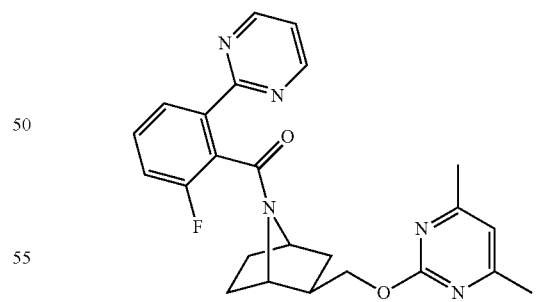

Prepared analogous to Example 39 substituting 5-methyl-2-(2H-1,2,3-triazol-2-yl)benzoic acid with 2-fluoro-6-(pyrimidin-2-yl)benzoic acid. MS (ESI) mass calcd. for $C_{24}H_{24}FN_5O_2$, 433.2; m/z found 434.2 [M+H]$^+$. $^1$H NMR (CDCl$_3$): 9.02-8.90 (m, 0.7H), 8.82-8.65 (m, 1.3H), 8.14-7.95 (m, 1H), 7.58-7.31 (m, 1H), 7.31-7.07 (m, 1.7H), 6.97-6.86 (m, 0.3H), 6.75-6.51 (m, 1H), 4.96-4.83 (m, 1H), 4.55 (dd, J=10.3, 9.0 Hz, 0.25H), 4.36 (dd, J=10.6, 8.9 Hz, 0.25H), 4.21-3.78 (m, 2.5H), 2.48-1.17 (m, 13H).

Example 44

(±)-(2-(((4,6-dimethylpyrimidin-2-yl)oxy)methyl)-7-azabicyclo[2.2.1]heptan-7-yl)(5-fluoro-2-(pyrimidin-2-yl)phenyl)methanone

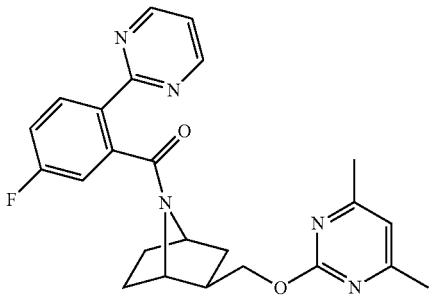 [SMILES: Cc1cc(C)nc(OCC2CC3CCC2N3C(=O)c2cc(F)ccc2-c2ncccn2)n1]

Prepared analogous to Example 39 substituting 5-methyl-2-(2H-1,2,3-triazol-2-yl)benzoic acid with 5-fluoro-2-(pyrimidin-2-yl)benzoic acid. MS (ESI) mass calcd. for $C_{24}H_{24}FN_5O_2$, 433.2; m/z found 434.2 [M+H]$^+$. $^1$H NMR (CDCl$_3$): 8.88-8.78 (m, 1H), 8.72 (d, J=4.8 Hz, 1H), 8.26 (dd, J=8.7, 5.5 Hz, 0.5H), 8.22-8.16 (m, 0.5H), 7.29-7.09 (m, 2H), 7.06-6.97 (m, 1H), 6.68 (s, 1H), 4.88-4.81 (m, 1H), 4.40 (t, J=9.7 Hz, 0.5H), 4.25 (t, J=10.8 Hz, 0.5H), 4.05 (dd, J=10.2, 6.2 Hz, 0.5H), 3.99-3.91 (m, 1H), 3.89-3.80 (m, 0.5H), 2.45-2.21 (m, 7H), 2.05-1.87 (m, 1H), 1.81-1.30 (m, 5H).

Example 45

(±)-(2-(((4,6-dimethylpyrimidin-2-yl)oxy)methyl)-7-azabicyclo[2.2.1]heptan-7-yl)(5-methyl-2-(pyrimidin-2-yl)phenyl)methanone

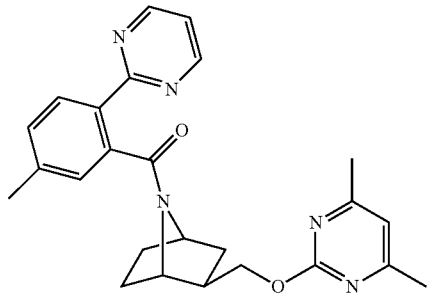

Prepared analogous to Example 39 substituting 5-methyl-2-(2H-1,2,3-triazol-2-yl)benzoic acid with 5-methyl-2-(pyrimidin-2-yl)benzoic acid. MS (ESI) mass calcd. for $C_{25}H_{27}N_5O_2$, 429.2; m/z found 430.2 [M+H]$^+$. $^1$H NMR (CDCl$_3$): 8.83 (d, J=5.0 Hz, 1H), 8.71 (d, J=4.8 Hz, 1H), 8.09 (dd, J=13.6, 8.0 Hz, 1H), 7.33-7.10 (m, 3H), 6.68 (d, J=1.4 Hz, 1H), 4.90-4.79 (m, 1H), 4.41 (dd, J=10.4, 8.8 Hz, 0.5H), 4.20 (t, J=10.6 Hz, 0.5H), 4.07-3.94 (m, 1.5H), 3.80 (t, J=4.7 Hz, 0.5H), 2.49-2.19 (m, 7H), 2.04-1.89 (m, 3H), 1.87-1.47 (m, 4.5H), 1.45-1.29 (m, 1.5H).

Example 46

(±)-(2-(((4,6-dimethylpyrimidin-2-yl)oxy)methyl)-7-azabicyclo[2.2.1]heptan-7-yl)(2-(thiophen-2-yl)phenyl)methanone

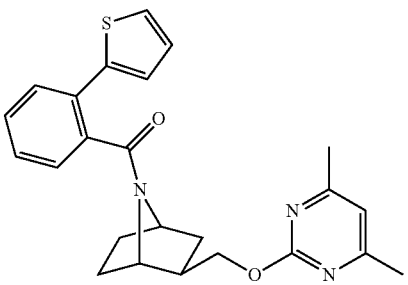 [SMILES: Cc1cc(C)nc(OCC2CC3CCC2N3C(=O)c2ccccc2-c2cccs2)n1]

Prepared analogous to Example 11 substituting (±)-2-(((5-fluoropyridin-2-yl)oxy)methyl)-7-azabicyclo[2.2.1]heptane with (±)-2-(((4,6-dimethylpyrimidin-2-yl)oxy)methyl)-7-azabicyclo[2.2.1]heptane. MS (ESI) mass calcd. for $C_{24}H_{25}N_3O_2S$, 419.2; m/z found 420.2 [M+H]$^+$. $^1$H NMR (400 MHz, CDCl$_3$): 7.55-6.83 (m, 7H), 6.75-6.62 (m, 1H), 4.87-4.62 (m, 1H), 4.09-3.38 (m, 3H), 2.54-2.32 (m, 6H), 2.32-2.03 (m, 1H), 1.97-0.87 (m, 6H).

Example 47

(±)-(6-methyl-3-(2H-1,2,3-triazol-2-yl)pyridin-2-yl)(2-(((5-(trifluoromethyl)pyridin-2-yl)oxy)methyl)-7-azabicyclo[2.2.1]heptan-7-yl)methanone Step A: (±)-2-(((5-(trifluoromethyl)pyridin-2-yl)oxy)methyl)-7-azabicyclo[2.2.1]heptane Prepared analogous to Example 49 substituting 5-bromo-2-fluoropyridine with 2-fluoro-5-(trifluoromethyl)pyridine. MS (ESI) mass calcd. for $C_{13}H_{15}F_3N_2O$, 272.1; m/z found 273.1, [M+H]$^+$.

Step B: (±)-(6-methyl-3-(2H-1,2,3-triazol-2-yl)pyridin-2-yl)(2-(((5-(trifluoromethyl)pyridin-2-yl)oxy)methyl)-7-azabicyclo[2.2.1]heptan-7-yl)methanone Prepared analogous to Example 1 substituting 5-fluoro-2-(pyrimidin-2-yl)benzoic acid with 6-methyl-3-(2H-1,2,3-triazol-2-yl)picolinic acid and (1S,2R,4R)-tert-butyl-2-((pyridin-2-yloxy)methyl)-7-azabicyclo[2.2.1]heptane-7-carboxylate with the title compound of Step A. MS (ESI)

mass calcd. for $C_{22}H_{21}F_3N_6O_2$, 458.2; m/z found 459.2 [M+H]$^+$. $^1$H NMR (CDCl$_3$): 8.47-8.37 (m, 1H), 8.12 (dd, J=13.2, 8.4 Hz, 1H), 7.85-7.69 (m, 3H), 7.32 (dd, J=8.4, 0.6 Hz, 0.5H), 7.22 (dd, J=8.4, 0.6 Hz, 0.5H), 6.88-6.82 (m, 0.5H), 6.69-6.59 (m, 0.5H), 4.93-4.81 (m, 1H), 4.39-4.18 (m, 2H), 3.94-3.87 (m, 1H), 2.65-2.60 (s, 1.2H), 2.39-2.22 (m, 2.8H), 2.11-1.33 (m, 6H).

Example 48

(±)-(3-ethoxy-6-methylpyridin-2-yl)(2-(((5-(trifluoromethyl)pyridin-2-yl)oxy)methyl)-7-azabicyclo[2.2.1]heptan-7-yl)methanone

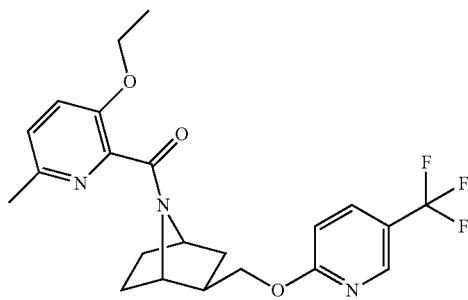 [SMILES: CCOc1ccc(C)nc1C(=O)N1C2CCC1C(COc1ccc(C(F)(F)F)cn1)C2]

Prepared analogous to Example 47 substituting 6-methyl-3-(2H-1,2,3-triazol-2-yl)picolinic acid with 3-ethoxy-6-methylpicolinic acid. MS (ESI) mass calcd. for $C_{22}H_{24}F_3N_3O_3$, 435.2; m/z found 436.2 [M+H]$^+$. $^1$H NMR (CDCl$_3$): 8.43-8.35 (m, 1H), 7.79-7.68 (m, 1H), 7.18-7.07 (m, 1H), 7.07-6.96 (m, 1H), 6.86 (d, J=8.7 Hz, 0.5H), 6.64 (d, J=8.7 Hz, 0.5H), 4.92-4.86 (m, 1H), 4.29-4.20 (m, 1H), 4.19-4.10 (m, 1H), 4.10-3.83 (m, 2H), 3.74 (t, J=3.9 Hz, 1H), 2.52-2.47 (s, 1.5H), 2.41-2.32 (m, 0.5H), 2.28-2.18 (m, 2H), 2.07-1.84 (m, 2H), 1.78-1.63 (m, 1H), 1.62-1.41 (m, 3H), 1.37 (dt, J=11.8, 7.0 Hz, 3H).

Example 49

(±)-(2-(((5-bromopyridin-2-yl)oxy)methyl)-7-azabicyclo[2.2.1]heptan-7-yl)(6-methyl-3-(2H-1,2,3-triazol-2-yl)pyridin-2-yl)methanone

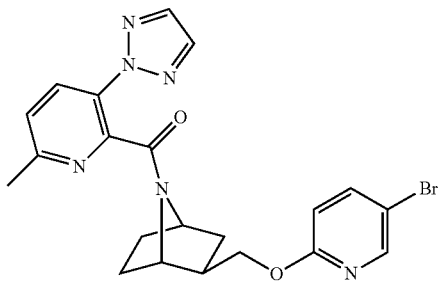 [SMILES: Cc1ccc(-n2nccn2)c(C(=O)N2C3CCC2C(COc2ccc(Br)cn2)C3)n1]

Step A: (±)-2-(((5-bromopyridin-2-yl)oxy)methyl)-7-azabicyclo[2.2.1]heptane

To intermediate B-10 (175 g, 0.8 mmol) in DMF (3.5 mL) at 0° C. was added NaH (60 wt % in mineral oil, 37 g, 0.9 mmol). After 30 min, 5-bromo-2-fluoropyridine (190 g, 1.1 mmol) in DMF (0.5 mL) was added dropwise and the 0° C. ice bath was removed. After 2 h, brine was added and the reaction extracted with EtOAc (2×). The combined organics were washed with brine and dried (Na$_2$SO$_4$) to give a clear oil which was treated with TFA and DCM (1:1, 10 mL). After 2 h. the reaction was concentrated, dissolved in DCM and neutralized with 5% Na2CO3 (aq). The combined organics were extracted with DCM (3×) and dried (Na$_2$SO$_4$) to give the title compound that was used in subsequent reactions without further purification. MS (ESI) mass calcd. for $C_{12}H_{11}BrN_2O$, 282.0; m/z found 283.1, 285.1 [M+H]$^+$. NMR (500 MHz, CDCl$_3$): 8.17 (d, J=2.5 Hz, 1H), 7.63 (dd, J=8.8, 2.5 Hz, 1H), 6.65 (d, J=8.8 Hz, 1H), 4.08-3.99 (m, 2H), 3.65 (t, J=4.5 Hz, 1H), 3.59 (d, J=4.1 Hz, 1H), 2.12-2.06 (m, 1H), 1.87 (s, 1H), 1.68-1.52 (m, 2H), 1.45-1.13 (m, 3H), 0.95-0.76 (m, 1H).

Step B

Prepared analogous to Example 1 substituting 5-fluoro-2-(pyrimidin-2-yl)benzoic acid with 6-methyl-3-(2H-1,2,3-triazol-2-yl)picolinic acid and (1S,2R,4R)-tert-butyl-2-((pyridin-2-yloxy)methyl)-7-azabicyclo[2.2.1]heptane-7-carboxylate with the title compound of Step A. MS (ESI) mass calcd. for $C_{21}H_{21}BrN_6O_2$, 468.1; m/z found 469.1, 471.1 [M+H]$^+$. $^1$H NMR (CDCl$_3$): 8.20 (d, J=2.6 Hz, 0.4H), 8.16 (d, J=2.6 Hz, 0.6H), 8.13 (d, J=8.3 Hz, 0.4H), 8.10 (d, J=8.4 Hz, 0.6H), 7.82-7.77 (m, 2H), 7.64 (dd, J=8.8, 2.6 Hz, 0.4H), 7.60 (dd, J=8.8, 2.6 Hz, 0.6H), 7.33-7.29 (m, 0.4H), 7.22 (d, J=8.4 Hz, 0.6H), 6.69 (d, J=8.8 Hz, 0.4H), 6.50 (d, J=8.8 Hz, 0.6H), 4.84 (dd, J=11.1, 5.2 Hz, 1H), 4.30-4.04 (m, 2H), 3.93-3.85 (m, 1H), 2.62 (s, 1.3H), 2.38-2.17 (m, 2.7H), 2.11-1.95 (m, 1H), 1.94-1.77 (m, 1H), 1.77-1.40 (m, 4H).

Example 50

(±)-(2-(((5-bromopyridin-2-yl)oxy)methyl)-7-azabicyclo[2.2.1]heptan-7-yl)(3-fluoro-2-methoxyphenyl)methanone

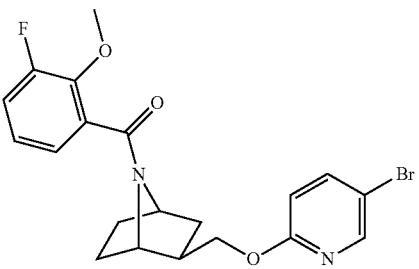 [SMILES: COc1c(F)cccc1C(=O)N1C2CCC1C(COc1ccc(Br)cn1)C2]

Prepared analogous to Example 49 substituting 6-methyl-3-(2H-1,2,3-triazol-2-yl)picolinic acid with 3-fluoro-2-methoxybenzoic acid. MS (ESI) mass calcd. for $C_{20}H_{20}BrFN_2O_3$, 434.1; m/z found 435.1, 437.1 [M+H]$^+$. $^1$H NMR (CDCl$_3$): 8.19-8.12 (m, 1H), 7.61 (ddd, J=26.6, 8.8, 2.5 Hz, 1H), 7.16-6.98 (m, 2H), 6.96 (dt, J=7.6, 1.3 Hz, 0.5H), 6.85-6.81 (m, 0.5H), 6.69 (dd, J=8.8, 0.8 Hz, 0.5H), 6.46 (d, J=8.7 Hz, 0.5H), 4.88-4.77 (m, 1H), 4.17-4.06 (m, 1H), 4.03-3.86 (m, 4H), 3.81-3.75 (m, 1H), 2.37-2.22 (m, 1H), 2.04-1.40 (m, 6H).

Example 51

(±)-(2-(((5-bromopyridin-2-yl)oxy)methyl)-7-azabi-cyclo[2.2.1]heptan-7-yl)(3-ethoxy-6-methylpyridin-2-yl)methanone

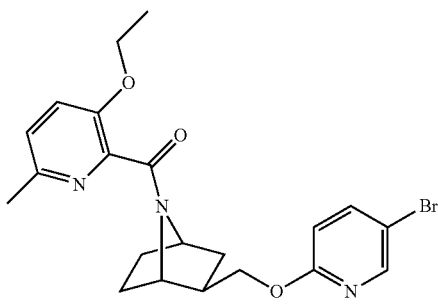 [SMILES: CCOc1ccc(C)nc1C(=O)N1C2CCC1C(COc1ccc(Br)cn1)C2]

Prepared analogous to Example 49 substituting 6-methyl-3-(2H-1,2,3-triazol-2-yl)picolinic acid with 3-ethoxy-6-methylpicolinic acid. MS (ESI) mass calcd. for $C_{21}H_{24}BrN_3O_3$, 445.1; m/z found 446.1, 448.1 [M+H]$^+$. $^1$H NMR (CDCl$_3$): 8.17-8.11 (m, 1H), 7.61 (ddd, J=19.5, 8.8, 2.6 Hz, 1H), 7.16-7.06 (m, 1H), 7.05-6.96 (m, 1H), 6.69 (dd, J=8.8, 0.7 Hz, 0.5H), 6.47 (dd, J=8.8, 0.7 Hz, 0.5H), 4.90-4.84 (m, 1H), 4.20-4.10 (m, 1H), 4.09-3.82 (m, 3H), 3.78-3.72 (m, 1H), 2.50 (s, 1.4H), 2.38-2.25 (m, 2.6H), 2.04-1.84 (m, 2H), 1.75-1.40 (m, 4H), 1.60-1.40 (m, 3H), 1.36 (dt, J=7.8, 7.0 Hz, 3H).

Example 52

(±)-(3-fluoro-2-(pyrimidin-2-yl)phenyl)(2-((pyridin-2-yloxy)methyl)-7-azabicyclo[2.2.1]heptan-7-yl)methanone

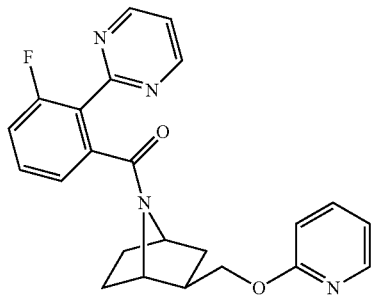 [SMILES: O=C(c1cccc(F)c1-c1ncccn1)N1C2CCC1C(COc1ccccn1)C2]

Prepared analogous to Example 1 substituting 5-fluoro-2-(pyrimidin-2-yl)benzoic acid with 3-fluoro-2-(pyrimidin-2-yl)benzoic acid and intermediate B-9 with intermediate B-10. MS (ESI) mass calcd. for $C_{23}H_{21}FN_4O_2$, 404.2; m/z found 405.2 [M+H]$^+$. $^1$H NMR (CDCl$_3$): 8.81 (dd, J=18.0, 4.9 Hz, 2H), 8.20-8.12 (m, 1H), 7.56 (ddd, J=8.3, 7.1, 2.0 Hz, 1H), 7.45 (td, J=8.0, 5.1 Hz, 0.5H), 7.28-7.22 (m, 1.5H), 7.21-7.08 (m, 1.5H), 7.05-6.96 (m, 0.5H), 6.88 (dddd, J=13.2, 7.1, 5.1, 1.0 Hz, 1H), 6.71 (dt, J=8.4, 0.9 Hz, 0.5H), 6.61 (dt, J=8.4, 0.9 Hz, 0.5H), 4.70-4.61 (m, 1H), 4.15-4.07 (m, 1H), 4.06-3.89 (m, 2H), 2.26 (ddt, J=15.3, 8.3, 4.5 Hz, 1H), 1.93-1.27 (m, 6H).

Example 53

(±)-(6-methyl-3-(2H-1,2,3-triazol-2-yl)pyridin-2-yl)(2-((pyridazin-3-yloxy)methyl)-7-azabicyclo[2.2.1]heptan-7-yl)methanone

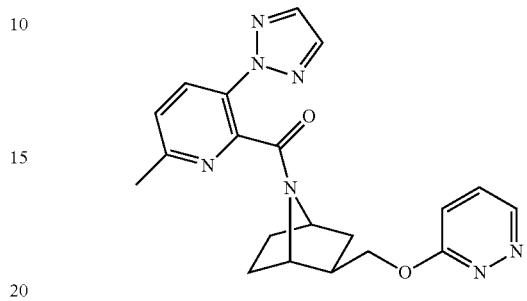

Step A: (±)-tert-butyl 2-((pyridazin-3-yloxy)methyl)-7-azabicyclo[2.2.1]heptane-7-carboxylate To intermediate B-10 (266 g, 1.2 mmol) in THF (4 mL) at 0° C. was added NaH (60 wt % in mineral oil, 70 g, 1.8 mmol). After 15 min, 3-chloropyridazine (160 g, 1.4 mmol) was added. The reaction allowed to warm to rt. After 18 h, H$_2$O was added and the mixture extracted with EtOAc. The organic layer was dried. Purification via silica gel chromatography (0-30% EtOAc in heptane) gave the title compound (300 g, 90%). MS (ESI) mass calcd. for $C_{16}H_{23}N_3O_3$, 305.2; m/z found 306.0 [M+H]$^+$.

Step B: (±)-2-((pyridazin-3-yloxy)methyl)-7-azabicyclo[2.2.1]heptane hydrochloride To the title compound from step A (300 g, 1 mmol) in 1,4-dioxane (3 mL) was added 6N HCl in iPrOH (1 mL). The reaction was heated to 70° C. for 3 h, cooled to rt and concentrated to give the title compound that was used without further purification. MS (ESI) mass calcd. for $C_{11}H_{15}N_3O$, 205.1; m/z found 206.0 [M+H]$^+$.

Step C: (±)-(6-methyl-3-(2H-1,2,3-triazol-2-yl)pyridin-2-yl)(2-((pyridazin-3-yloxy)methyl)-7-azabicyclo[2.2.1]heptan-7-yl)methanone To 6-methyl-3-(2H-1,2,3-triazol-2-yl)picolinic acid (270 g, 1.3 mmol) in DMF (3 mL) was added DIPEA (630 µL, 3.6 mmol). HBTU (590 g, 1.5 mmol) and the title compound from step B (250 g, 1 mmol). After stirring overnight, saturated NaHCO$_3$ (aq) was added and the mixture extracted with EtOAc (3×). The combined organics were dried (MgSO4). Purification by reverse phase chromatography gave material that was triturated with Et$_2$O/pentane to give the title compound (115 g, 28%) as a beige solid. MS (ESI) mass calcd. for $C_{20}H_{21}N_7O_2$, 391.2; m/z found 392.2 [M+H]$^+$. $^1$H NMR (DMSO-D$_6$): 8.91 (dd, J=8.5, 4.4 Hz, 1H), 8.23-8.04 (m, 3H), 7.69-7.52 (m, 1.5H), 7.41 (d, J=8.4 Hz, 0.5H), 7.28 (d, J=8.9 Hz, 0.5H), 7.10 (d, J=8.9 Hz, 0.5H), 4.60 (t, J=4.8 Hz, 1H), 4.40-4.19 (m, 2H), 3.87 (t, J=4.3 Hz, 0.5H), 3.79 (d, J=4.3 Hz, 0.5H), 2.58 (s, 1.5H), 2.46-2.24 (m, 1H), 2.06 (s, 1.5H), 1.81-1.34 (m, 6H).

Example 54

(±)-(6-methyl-3-(2H-1,2,3-triazol-2-yl)pyridin-2-yl) (2-(((2-methylpyridin-3-yl)oxy)methyl)-7-azabicyclo [2.2.1]heptan-7-yl)methanone

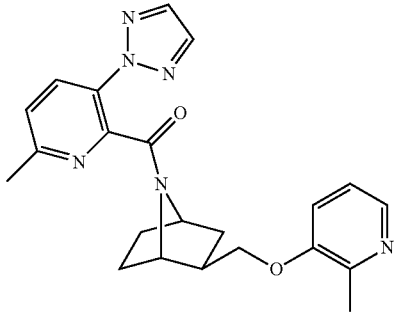 [SMILES: Cc1ccc(-n2nccn2)c(C(=O)N2C3CCC2C(COc2cccnc2C)C3)n1]

Step A: (±)-tert-butyl-2-(((methylsulfonyl)oxy) methyl)-7-azabicyclo[2.2.1]heptane-7-carboxylate To intermediate B-10 (545 g, 2.4 mmol) in DCM (12 mL) at 0° C. was added TEA (333 µL, 2.4 mmol) followed by MsCl (190 µL, 2.4 mmol). After 2 h, brine was added and the mixture was extracted with DCM (2×). The combined organics were dried (Na$_2$SO$_4$) to give the title compound (650 g, 89%) that was used without further purification. MS (ESI) mass calcd. for C$_{12}$H$_{23}$NO$_5$S, 305.1; m/z found 249.9 [M−55]$^+$.

Step B: (±)-tert-butyl 2-(((2-methylpyridin-3-yl) oxy)methyl)-7-azabicyclo[2.2.1]heptane-7-carboxylate To 2-methylpyridin-3-ol in DMF was added KOH. The solution was stirred for 30 min at rt, then the title compound from step A was added and the reaction was heated at 80° C. After 5 h, H$_2$O was added and the mixture extracted with EtOAc. The combined organic layers were dried (MgSO4). Purification via silica gel chromatography (0-7% MeOH in DCM) gave the title compound (201 g, 90%). MS (ESI) mass calcd. for C$_{18}$H$_{26}$N$_2$O$_3$, 318.2; m/z found 319.0 [M+1]$^+$.

Step C: (±)-2-(((2-methylpyridin-3-yl)oxy)methyl)-7-azabicyclo[2.2.1]heptane

Prepared analogous to example 53 step B substituting (±)-tert-butyl 2-((pyridazin-3-yloxy)methyl)-7-azabicyclo[2.2.1]heptane-7-carboxylate with (±)-tert-butyl 2-(((2-methylpyridin-3-yl)oxy)methyl)-7-azabicyclo[2.2.1]heptane-7-carboxylate. MS (ESI) mass calcd. for C$_{13}$H$_{18}$N$_2$O, 218.1; m/z found 219.1 [M+1]$^+$.

Step D: (±)-(6-methyl-3-(2H-1,2,3-triazol-2-yl)pyridin-2-yl)(2-(((2-methylpyridin-3-yl)oxy)methyl)-7-azabicyclo[2.2.1]heptan-7-yl)methanone Prepared analogous to example 53 step C substituting (±)-2-((pyridazin-3-yloxy)methyl)-7-azabicyclo[2.2.1]heptane hydrochloride with (±)-2-(((2-methylpyridin-3-yl)oxy) methyl)-7-azabicyclo[2.2.1]heptane. MS (ESI) mass calcd. for C$_{22}$H$_{24}$N$_6$O$_2$, 404.2; m/z found 405.2 [M+H]$^+$. $^1$H NMR (DMSO-D$_6$): 8.22-7.92 (m, 4H), 7.55 (d, J=8.4 Hz, 0.3H), 7.45-7.33 (m, 1H), 7.32-7.10 (m, 1.7H), 4, 60-4.57 (m, 1H), 3.92-3.67 (m, 3H), 2.57 (s, 0.9H), 2.42-2.18 (m, 1.9H), 2.08 (s, 2.1H), 1.95 (s, 2.1H), 1.80-1.31 (m, 6H).

Example 55

(±)-(6-methyl-3-(2H-1,2,3-triazol-2-yl)pyridin-2-yl) (2-(((3-methylpyridin-2-yl)oxy)methyl)-7-azabicyclo [2.2.1]heptan-7-yl)methanone

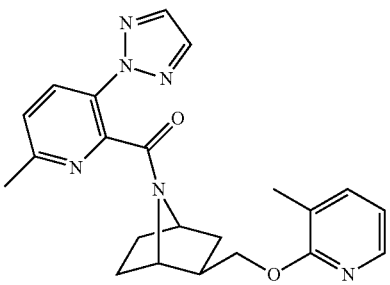 [SMILES: Cc1ccc(-n2nccn2)c(C(=O)N2C3CCC2C(COc2ncccc2C)C3)n1]

Step A: (±)-tert-butyl 2-(((2-methylpyridin-3-yl) oxy)methyl)-7-azabicyclo[2.2.1]heptane-7-carboxylate Prepared analogous to Example 7 Step A Method A substituting PBu3 with PPh3, DEAD with DIAD, 5-fluoropyridin-2(1H)-one with 3-methylpyridin-2-ol and performing the reaction at rt. MS (ESI) mass calcd. for C$_{18}$H$_{26}$N$_2$O$_3$, 318.2; m/z found 319.0 [M+H]$^+$.

Step B: (±)-2-(((2-methylpyridin-3-yl)oxy)methyl)-7-azabicyclo[2.2.1]heptane

Prepared analogous to Example 53 Step B substituting (±)-tert-butyl 2-((pyridazin-3-yloxy)methyl)-7-azabicyclo [2.2.1]heptane-7-carboxylate with (±)-tert-butyl 2-(((2-methylpyridin-3-yl)oxy)methyl)-7-azabicyclo[2.2.1]heptane-7-carboxylate. MS (ESI) mass calcd. for C$_{13}$H$_{18}$N$_2$O, 218.1; m/z found 219.0 [M+H]$^+$.

Step C: (±)-(6-methyl-3-(2H-1,2,3-triazol-2-yl)pyridin-2-yl)(2-(((3-methylpyridin-2-yl)oxy)methyl)-7-azabicyclo[2.2.]heptan-7-yl)methanone Prepared analogous to Example 53 Step C substituting (±)-2-((pyridazin-3-yloxy)methyl)-7-azabicyclo[2.2.1]heptane hydrochloride with (±)-2-(((2-methylpyridin-3-yl)oxy) methyl)-7-azabicyclo[2.2.1]heptane. MS (ESI) mass calcd. for C$_{22}$H$_{24}$N$_6$O$_2$, 404.2; m/z found 405.2 [M+H]$^+$.

Example 56

(±)-(2-(((1-methyl-1H-pyrazol-5-yl)oxy)methyl)-7-azabicyclo[2.2.1]heptan-7-yl)(6-methyl-3-(2H-1,2,3-triazol-2-yl)pyridin-2-yl)methanone

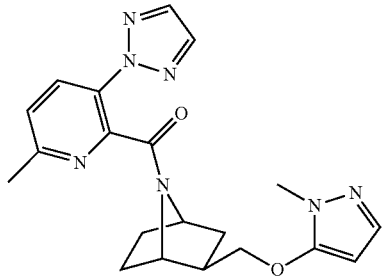 [SMILES: Cc1ccc(-n2nccn2)c(C(=O)N2C3CCC2C(COc2ccnn2C)C3)n1]

Step A: (±)-tert-butyl 2-(((1-methyl-1H-pyrazol-5-yl)oxy)methyl)-7-azabicyclo[2.2.1]heptane-7-carboxylate Prepared analogous to Example 7 Step A Method A substituting THF with PhCH$_3$ and 5-fluoropyridin-2(1H)-one with 1-methyl-1H-pyrazol-5-ol. MS (ESI) mass calcd. for C$_{16}$H$_{25}$N$_3$O$_3$, 307.2; m/z found 308.0 [M+H]$^+$.

Step B: (±)-2-(((1-methyl-1H-pyrazol-5-yl)oxy)methyl)-7-azabicyclo[2.2.1]heptane Prepared analogous to Example 53 Step B substituting (±)-tert-butyl 2-((pyridazin-3-yloxy)methyl)-7-azabicyclo[2.2.1]heptane-7-carboxylate the title compound of Step A. MS (ESI) mass calcd. for C$_{11}$H$_{17}$N$_3$O, 207.1; m/z found 208.0 [M+H]$^+$.

Step C: (±)-(2-(((1-methyl-1H-pyrazol-5-yl)oxy)methyl)-7-azabicyclo[2.2.1]heptan-7-yl)(6-methyl-3-(2H-1,2,3-triazol-2-yl)pyridin-2-yl)methanone Prepared analogous to Example 53 Step C substituting (±)-2-((pyridazin-3-yloxy)methyl)-7-azabicyclo[2.2.1]heptane hydrochloride with the title compound of Step B. MS (ESI) mass calcd. for C$_{20}$H$_{23}$N$_7$O$_2$, 393.2; m/z found 394.2 [M+H]$^+$. $^1$H NMR (DMSO-D$_6$): 8.18-8.05 (m, 3H), 7.56 (d, J=8.4 Hz, 0.4H), 7.49 (d, J=8.4 Hz, 0.6H), 7.23 (d, J=1.7 Hz, 0.4H), 7.19 (d, J=1.7 Hz, 0.6H), 5.70 (d, J=1.8 Hz, 0.4H), 5.59 (d, J=1.8 Hz, 0.6H), 4.59-4.56 (m, 1H), 3.96-3.76 (m, 3H), 3.57 (s, 1.2H), 3.34 (s, 1.8H), 2.58 (s, 1.2H), 2.39-2.17 (m, 2.8H), 1.87-1.27 (m, 6H).

Example 57

(±)-(6-methyl-3-(2H-1,2,3-triazol-2-yl)pyridin-2-yl)(2-((pyridin-4-yloxy)methyl)-7-azabicyclo[2.2.1]heptan-7-yl)methanone

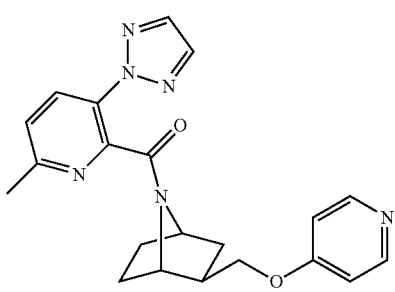 [SMILES: Cc1ccc(-n2nccn2)c(C(=O)N2C3CCC2C(COc2ccncc2)C3)n1]

Prepared analogous to Example 54 substituting 2-methylpyridin-3-ol with pyridin-4-ol. MS (ESI) mass calcd. for C$_{21}$H$_{22}$N$_6$O$_2$, 390.2; m/z found 391.2 [M+H]$^+$. $^1$H NMR (DMSO-D$_6$): 8.41 (d, J=5.5 Hz, 0.8H), 8.36 (d, J=5.5 Hz, 1.2H), 8.20-8.02 (m, 3H), 7.55 (d, J=8.4 Hz, 0.4H), 7.40 (d, J=8.4 Hz, 0.6H), 7.00 (d, J=6.2 Hz, 0.8H), 6.88 (d, J=6.2 Hz, 1.2H), 4.64-4.51 (m, 1H), 4.02-3.78 (m, 2.4H), 3.75 (d, J=4.4 Hz, 0.6H), 2.57 (s, 1.2H), 2.39-2.20 (m, 1H), 2.04 (s, 1.8H), 1.87-1.30 (m, 6H).

Example 58

(±)-(6-methyl-3-(2H-1,2,3-triazol-2-yl)pyridin-2-yl)(2-((pyridin-3-yloxy)methyl)-7-azabicyclo[2.2.1]heptan-7-yl)methanone

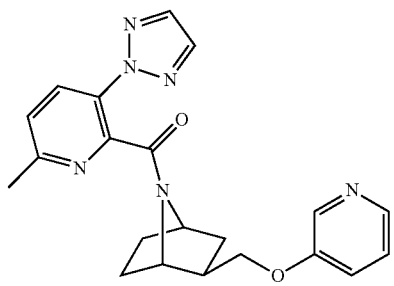 [SMILES: Cc1ccc(-n2nccn2)c(C(=O)N2C3CCC2C(COc2cccnc2)C3)n1]

Prepared analogous to Example 54 substituting 2-methylpyridin-3-ol with pyridin-3-ol. MS (ESI) mass calcd. for C$_{21}$H$_{22}$N$_6$O$_2$, 390.2; m/z found 391.2 [M+H]$^+$. $^1$H NMR (DMSO-D$_6$): 8.33 (d, J=2.7 Hz, 0.4H), 8.21-8.05 (m, 4.6H), 7.55 (d, J=8.4 Hz, 0.4H), 7.46-7.25 (m, 2.6H), 4.58 (t, J=4.8 Hz, 1H), 3.95-3.80 (m, 2.4H), 3.77 (d, J=4.4 Hz, 0.6H), 2.57 (s, 1.2H), 2.38-2.18 (m, 1H), 2.02 (s, 1.8H), 1.85-1.31 (m, 6H).

Example 59

(±)-(6-methyl-3-(2H-1,2,3-triazol-2-yl)pyridin-2-yl)(2-((pyrimidin-2-yloxy)methyl)-7-azabicyclo[2.2.1]heptan-7-yl)methanone

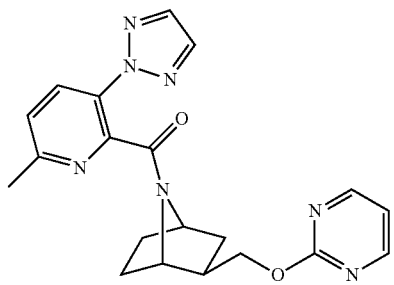 [SMILES: Cc1ccc(-n2nccn2)c(C(=O)N2C3CCC2C(COc2ncccn2)C3)n1]

Prepared analogous to Example 53 substituting 2-chloropyridazine with 2-chloropyrimidine. MS (ESI) mass calcd. for C$_{20}$H$_{21}$N$_7$O$_2$, 391.2; m/z found 392.2 [M+H]$^+$. $^1$H NMR (DMSO-D$_6$): 8.65 (d, J=4.8 Hz, 0.8H), 8.59 (d, J=4.8 Hz, 1.2H), 8.22-8.02 (m, 3H), 7.56 (d, J=8.4 Hz, 0.4H), 7.44 (d, J=8.4 Hz, 0.6H), 7.19-7.13 (m, 1H), 4.59 (t, J=4.5 Hz, 0.6H), 4.55 (d, J=4.4 Hz, 0.4H), 4.24-4.04 (m, 2H), 3.85 (t, J=4.3 Hz, 0.4H), 3.78 (d, J=4.0 Hz, 0.6H), 2.58 (s, 1.2H), 2.39-2.21 (m, 1H), 2.11 (s, 1.8H), 1.86-1.29 (m, 6H).

Example 60

(4)-(6-methyl-3-(2H-1,2,3-triazol-2-yl)pyridin-2-yl) (2-((pyrazin-2-yloxy)methyl)-7-azabicyclo[2.2.1]heptan-7-yl)methanone

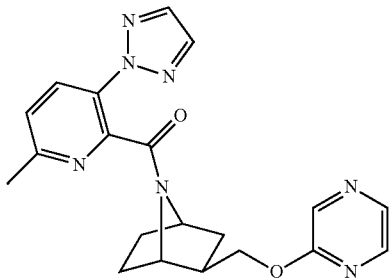 [SMILES: Cc1ccc(-n2nccn2)c(C(=O)N2C3CCC2C(COc2cnccn2)C3)n1]

Prepared analogous to Example 53 substituting 2-chloropyridazine with 2-pyrazine. MS (ESI) mass calcd. for $C_{20}H_{21}N_7O_2$, 391.2; m/z found 392.2 [M+H]$^+$.

Example 61

(±)-(6-methyl-3-(2H-1,2,3-triazol-2-yl)pyridin-2-yl) (2-((pyrimidin-4-yloxy)methyl)-7-azabicyclo[2.2.1]heptan-7-yl)methanone

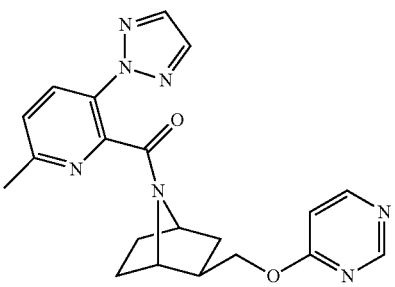 [SMILES: Cc1ccc(-n2nccn2)c(C(=O)N2C3CCC2C(COc2ccncn2)C3)n1]

Prepared analogous to Example 55 substituting 3-methylpyridin-2-ol with pyrimidin-4-ol. MS (ESI) mass calcd. for $C_{20}H_{21}N_7O_2$, 391.2; m/z found 392.2 [M+H]$^+$. The product is present as a mixture of conformers (ratio ca. 50:50) $^1$H NMR (300 MHz, DMSO) 8.84 (s, 0.5H), 8.77 (s, 0.5H), 8.53 (d, J=5.8 Hz, 0.5H), 8.49 (d, J=5.8 Hz, 0.5H), 8.22-8.01 (m, 3H), 7.55 (d, J=8.4 Hz, 0.5H), 7.43 (d, J=8.4 Hz, 0.5H), 7.00 (d, J=5.7 Hz, 0.5H), 6.85 (d, J=5.8 Hz, 0.5H), 4.58 (t, J=3.7 Hz, 0.5H), 4.53 (d, J=4.2 Hz, 0.5H), 4.25-4.04 (m, 2H), 3.85 (t, J=3.7 Hz, 0.5H), 3.75 (d, J=3.9 Hz, 0.5H), 2.57 (s, 1.5H), 2.40-2.16 (m, 1H), 2.12 (s, 1.5H), 1.85-1.31 (m, 6H).

Example 62

(±)-(6-methyl-3-(2H-1,2,3-triazol-2-yl)pyridin-2-yl) (2-(((6-methylpyridin-2-yl)oxy)methyl)-7-azabicyclo[2.2.1]heptan-7-yl)methanone

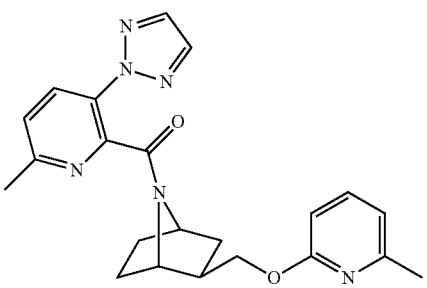

Prepared analogous to Example 55 substituting 3-methylpyridin-2-ol with 6-methylpyridin-2-ol. MS (ESI) mass calcd. for $C_{22}H_{24}N_6O_2$, 404.2; m/z found 405.2 [M+H]$^+$. $^1$H NMR (DMSO-D$_6$): 8.17 (d, J=8.4 Hz, 0.5H), 8.12 (d, J=8.4 Hz, 0.5H), 8.10 (s, 1H), 8.06 (s, 1H), 7.63-7.49 (m, 1.5H), 7.41 (d, J=8.4 Hz, 0.5H), 6.85 (d, J=7.2 Hz, 0.5H), 6.81 (d, J=7.2 Hz, 0.5H), 6.64 (d, J=8.2 Hz, 0.5H), 6.46 (d, J=8.2 Hz, 0.5H), 4.58 (t, J=4.4 Hz, 0.5H), 4.54 (d, J=4.5 Hz, 0.5H), 4.16-3.95 (m, 2H), 3.83 (t, J=4.4 Hz, 0.5H), 3.74 (d, J=4.4 Hz, 0.5H), 2.58 (s, 1.5H), 2.43 (s, 1.5H), 2.37 (s, 1.5H), 2.33-2.14 (m, 1H), 2.11 (s, 1.5H), 1.85-1.31 (m, 6H).

Example 63

(±)-(2-(((5-fluoropyridin-2-yl)oxy)methyl)-7-azabicyclo[2.2.1]heptan-7-yl)(6-methyl-3-(oxazol-2-yl)pyridin-2-yl)methanone

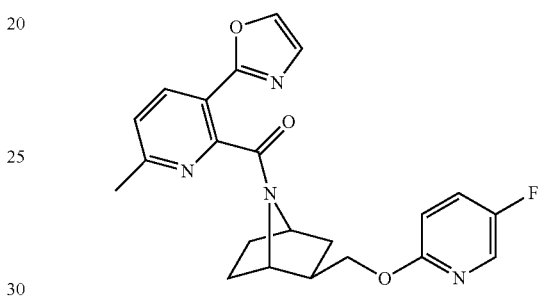

Prepared analogous to Example 7 substituting intermediate A-21 with intermediate A-43. MS (ESI) mass calcd. for $C_{22}H_{21}FN_4O_3$, 408.2; m/z found 409.2 [M+H]$^+$.

Example 64

(±)-(2-(((5-fluoropyridin-2-yl)oxy)methyl)-7-azabicyclo[2.2.1]heptan-7-yl)(6-methyl-3-(pyrimidin-2-yl)pyridin-2-yl)methanone

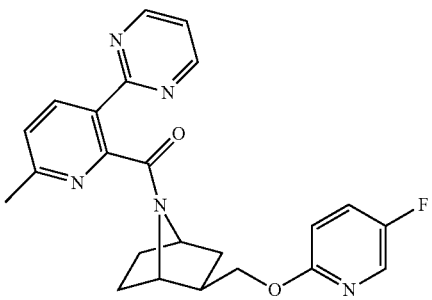 [SMILES: Cc1ccc(-c2ncccn2)c(C(=O)N2C3CCC2C(COc2ccc(F)cn2)C3)n1]

Prepared analogous to Example 7 substituting intermediate A-21 with 6-methyl-3-(pyrimidin-2-yl)picolinic acid. MS (ESI) mass calcd. for $C_{23}H_{22}FN_5O_2$, 419.2; m/z found 420.2 [M+H]$^+$. $^1$H NMR (DMSO-D$_6$): 8.91 (d, J=4.9 Hz, 0.8H), 8.84 (d, J=4.9 Hz, 1.2H), 8.33-8.29 (m, 1H), 8.22 (d, J=3.1 Hz, 0.4H), 8.13 (d, J=3.1 Hz, 0.6H), 7.76-7.59 (m, 1H), 7.53-7.41 (m, 1.4H), 7.35 (d, J=8.1 Hz, 0.6H), 6.94 (dd, J=9.1, 3.6 Hz, 0.4H), 6.75 (dd, J=9.1, 3.6 Hz, 0.6H), 4.59 (t, J=4.1 Hz, 0.6H), 4.56 (d, J=3.8 Hz, 0.4H), 4.16 (dd, J=14.6, 6.2 Hz, 1H), 4.08-3.97 (m, 1H), 3.87 (br s, 0.4H), 3.76 (d, J=3.9 Hz, 0.6H), 2.56 (s, 1.2H), 2.39-2.15 (m, 1H), 2.10 (s, 1.8H), 1.91-1.32 (m, 6H).

Example 65

(±)-(3,6'-dimethyl-[2,3'-bipyridin]-2'-yl)(2-(((5-fluoropyridin-2-yl)oxy)methyl)-7-azabicyclo[2.2.1]heptan-7-yl)methanone

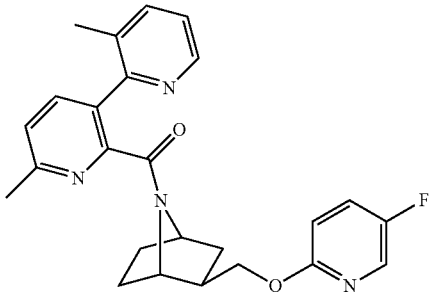

Prepared analogous to Example 7 substituting intermediate A-21 with 3,6'-dimethyl-[2,3'-bipyridine]-2'-carboxylic acid. MS (ESI) mass calcd. for $C_{25}H_{25}FN_4O_2$, 432.2; m/z found 433.2 [M+H]+. ¹H NMR (DMSO-D₆): 8.33 (t, J=5.1 Hz, 1H), 8.16 (s, 1H), 7.79-7.60 (m, 3H), 7.40 (d, J=7.9 Hz, 0.5H), 7.32-7.23 (m, 1H), 7.20 (dd, J=7.6, 4.8 Hz, 0.5H), 6.85 (dd, J=9.1, 3.6 Hz, 0.5H), 6.80 (dd, J=9.1, 3.6 Hz, 0.5H), 4.39 (brs, 0.5H), 4.35 (d, J=4.1 Hz, 0.5H), 4.19 (t, J=10.3 Hz, 0.5H), 4.04 (dd, J=10.4, 5.2 Hz, 0.5H), 3.90 (d, J=4.8 Hz, 0.5H), 3.85 (t, J=4.0 Hz, 0.5H), 3.75-3.53 (m, 1H), 2.56 (s, 1.5H), 2.22 2.17 (m, 3.5H), 2.11 (s, 1.5H), 1.90-1.81 (m, 0.5H), 1.79-1.17 (m, 6H).

Example 66

(±)-(2-(((5-fluoropyridin-2-yl)oxy)methyl)-7-azabicyclo[2.2.1]heptan-7-yl)(6-methyl-3-(3-methyl-1,2,4-oxadiazol-5-yl)pyridin-2-yl)methanone

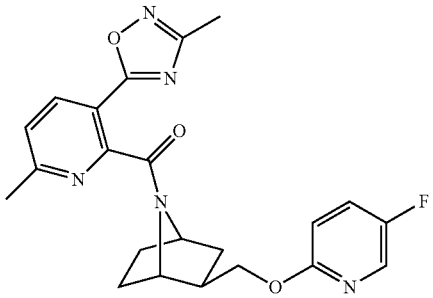

Prepared analogous to Example 7 substituting intermediate A-21 with 6-methyl-3-(3-methyl-1,2,4-oxadiazol-5-yl) picolinic acid. MS (ESI) mass calcd. for $C_{22}H_{22}FN_5O_3$, 423.2; m/z found 424.2 [M+H]+. ¹H NMR (DMSO-D₆): 8.33 (d, J=8.1 Hz, 0.4H), 8.28 (d, J=8.1 Hz, 0.6H), 8.14 (d, J=3.1 Hz, 0.4H), 8.10 (d, J=3.1 Hz, 0.6H), 7.76-7.60 (m, 1H), 7.58 (d, J=8.2 Hz, 0.4H), 7.47 (d, J=8.2 Hz, 0.6H), 6.95 (dd, J=3.6, 9.2 Hz, 0.4H), 6.72 (dd, J=3.6, 9.2 Hz, 0.6H), 4.67 (t, J=4.5 Hz, 0.6H), 4.62 (d, J=4.6 Hz, 0.4H), 4.16-3.92 (m, 2H), 3.81 (t, J=4.3 Hz, 0.4H), 3.73 (d, J=4.6 Hz, 0.6H), 2.60 (s, 1.2H), 2.41 (s, 1.2H), 2.38 (s, 1.8H), 2.37-2.19 (m, 1H), 2.18 (s, 1.8H), 1.90-1.30 (m, 6H).

Example 67

(±)-(2-(((5-fluoropyridin-2-yl)oxy)methyl)-7-azabicyclo[2.2.1]heptan-7-yl)(6-methyl-3-(3-methyl-1H-pyrazol-1-yl)pyridin-2-yl)methanone

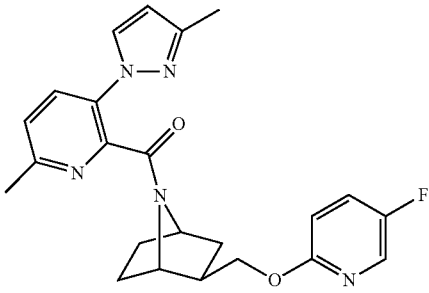 [SMILES: Cc1ccc(-n2ccc(C)n2)c(C(=O)N2C3CCC2C(COc2ccc(F)cn2)C3)n1]

Prepared analogous to Example 7 substituting intermediate A-21 with 6-methyl-3-(3-methyl-1H-pyrazol-1-yl)picolinic acid. MS (ESI) mass calcd. for $C_{23}H_{24}FN_5O_2$, 421.2; m/z found 422.2 [M+H]+. MP=123.2° C.

Example 68

(±)-(2-(((5-fluoropyridin-2-yl)oxy)methyl)-7-azabicyclo[2.2.1]heptan-7-yl)(6-methyl-3-(pyrrolidin-1-yl)pyridin-2-yl)methanone

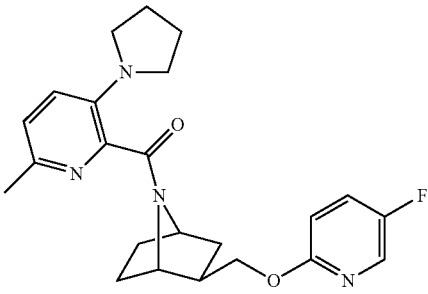 [SMILES: Cc1ccc(N2CCCC2)c(C(=O)N2C3CCC2C(COc2ccc(F)cn2)C3)n1]

Step A: 6-methyl-3-(pyrrolidin-1-yl)picolinonitrile

To 2-bromo-6-methyl-3-(2H-1,2,3-triazol-2-yl)pyridine (720 g, 3.7 mmol), pyrolidine (450 µL, 5.5 mmol), Pd(OAc)₂ (25 mg, 11 mol %), XPhos (122 mg, 25 mol %) and Cs₂CO₃ (2.4 g, 7.3 mmol) in a sealed tube was added PhCH3. The vessel was sealed and heated at 100° C. overnight. After cooling to rt, the reaction was diluted with EtOAc and H₂O. The organic layer was dried (MgSO4) and concentrated. Purification via silica gel chromatography (0-50% EtOAc in DCM) gave the title compound (186 mg, 27%).

Step B: 6-methyl-3-(pyrrolidin-1-yl)picolinic acid

To the title compound of Step A (162 mg, 0.9 mmol) in EtOH (2.6 mL) was added 4M KOH (650 µL, 2.6 mmol). The reaction was then heated at 90° C. for 18 h. Additional 4M KOH (1.5 mL, 6 mmol) was added and heating continued overnight. The reaction was then cooled to rt, acidified with 1N HCl (aq), concentrated and used without further purification in the next step.

Step C: (±)-(2-(((5-fluoropyridin-2-yl)oxy)methyl)-7-azabicyclo[2.2.1]heptan-7-yl)(6-methyl-3-(pyrrolidin-1-yl)pyridin-2-yl)methanone Prepared analogous to Example 7 substituting intermediate A-9 with the title compound from Step B. MS (ESI) mass calcd. for $C_{23}H_{27}FN_4O_2$, 410.2; m/z found 411.2 [M+H]$^+$. $^1$H NMR (DMSO-D$_6$): 8.14 (d, J=3.0 Hz, 0.5H), 8.10 (d, J=3.0 Hz, 0.5H), 7.68-7.38 (m, 2H), 6.92 (dd, J=9.1, 3.6 Hz, 0.5H), 6.71 (dd, J=9.1, 3.6 Hz, 0.5H), 4.66 (br s, 0.5H), 4.60 (br s, 0.5H), 4.08-3.01 (m, 7H), 2.45 (s, 1.5H), 2.40-2.01 (m, 2.5H), 1.94-1.30 (m, 10H).

Example 69

(±)-(2-(((5-fluoropyridin-2-yl)oxy)methyl)-7-azabicyclo[2.2.1]heptan-7-yl)(6-methyl-3-(3-methylisoxazol-5-yl)pyridin-2-yl)methanone

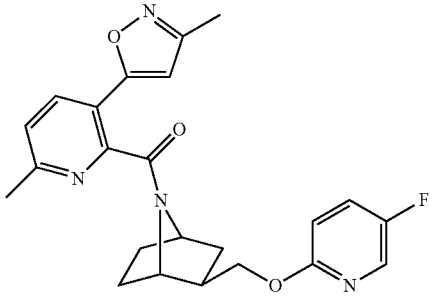

Prepared analogous to Example 7 substituting intermediate A-21 with 6-methyl-3-(3-methylisoxazol-5-yl)picolinic acid. MS (ESI) mass calcd. for $C_{23}H_{23}FN_4O_3$, 422.2; m/z found 423.2 [M+H]$^+$. $^1$H NMR (DMSO-D$_6$): 8.11 (dt, J=10.0, 5.4 Hz, 2H), 7.77-7.55 (m, 1H), 7.50 (d, J=8.2 Hz, 0.4H), 7.38 (d, J=8.2 Hz, 0.6H), 6.94 (dd, J=9.1, 3.6 Hz, 0.4H), 6.70 (dd, J=9.1, 3.6 Hz, 0.6H), 6.62 (d, J=1.6 Hz, 1H), 4.67 (t, J=4.6 Hz, 0.6H), 4.61 (d, J=4.7 Hz, 0.4H), 3.98-3.88 (m, 2H), 3.60 (t, J=4.5 Hz, 0.4H), 3.54 (d, J=3.8 Hz, 0.6H), 2.55 (s, 1.2H), 2.38-2.14 (m, 4H), 2.12 (s, 1.8H), 1.86-1.13 (m, 6H).

Example 70

(±)-(2-(((5-fluoropyridin-2-yl)oxy)methyl)-7-azabicyclo[2.2.1]heptan-7-yl)(6-methyl-3-(1H-pyrazol-1-yl)pyridin-2-yl)methanone

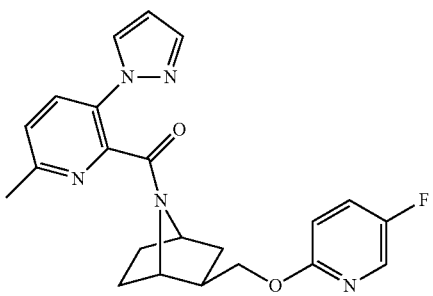 [SMILES: Cc1ccc(-n2cccn2)c(C(=O)N2C3CCC2C(COc2ccc(F)cn2)C3)n1]

Prepared analogous to Example 63 substituting 6-methyl-3-(oxazol-2-yl)picolinic acid with 6-methyl-3-(1H-pyrazol-1-yl)picolinic acid. MS (ESI) mass calcd. for $C_{22}H_{22}FN_5O_2$, 407.2; m/z found 408.2 [M+H]$^+$. $^1$H NMR (DMSO-D$_6$): 8.17 (d, J=3.1 Hz, 0.5H), 8.13 (d, J=3.1 Hz, 0.5H), 8.08 (t, J=2.4 Hz, 1H), 7.95 (t, J=8.5 Hz, 1H), 7.74-7.61 (m, 2H), 7.49 (d, J=8.3 Hz, 0.5H), 7.36 (d, J=8.4 Hz, 0.5H), 6.91 (dd, J=9.1, 3.6 Hz, 0.5H), 6.72 (dd, J=9.1, 3.6 Hz, 0.5H), 6.52-6.49 (m, 0.5H), 6.49-6.46 (m, 0.5H), 4.55 (t, J=4.5 Hz, 0.5H), 4.50 (d, J=4.7 Hz, 0.5H), 3.94 (d, J=7.6 Hz, 2H), 3.67 (t, J=4.2 Hz, 0.5H), 3.59 (d, J=4.5 Hz, 0.5H), 2.54 (s, 1.5H), 2.30-2.11 (m, 1H), 2.07 (s, 1.5H), 1.76-1.14 (m, 6H).

Example 71

(=)-(5-methyl-3-(2H-1,2,3-triazol-2-yl)pyridin-2-yl)(2-((pyridin-2-yloxy)methyl)-7-azabicyclo[2.2.1]heptan-7-yl)methanone

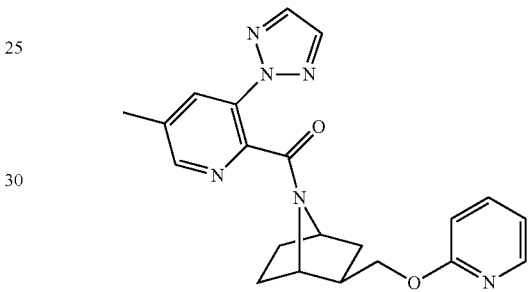

Prepared analogous to Example 2 substituting intermediate A-9 with 5-methyl-3-(2H-1,2,3-triazol-2-yl)picolinic acid. MS (ESI) mass calcd. for $C_{21}H_{22}N_6O_2$, 390.2; m/z found 391.0 [M+H]$^+$. MP=159.7° C.

Example 72

(±)-(4-methyl-3-(2H-1,2,3-triazol-2-yl)pyridin-2-yl)(2-((pyridin-2-yloxy)methyl)-7-azabicyclo[2.2.1]heptan-7-yl)methanone

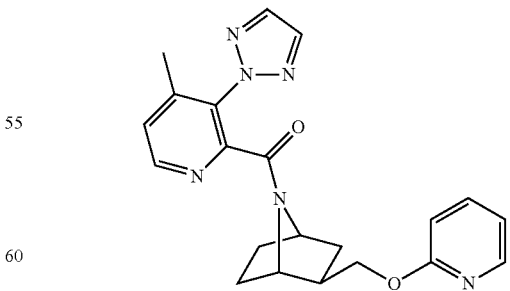

Prepared analogous to Example 2 substituting intermediate A-9 with 4-methyl-3-(2H-1,2,3-triazol-2-yl)picolinic acid. MS (ESI) mass calcd. for $C_{21}H_{22}N_6O_2$, 390.2; m/z found 391.0 [M+H]$^+$. MP=114.5° C.

Example 73

(±)-(3-(dimethylamino)-6-methylpyridin-2-yl)(2-((pyridin-2-yloxy)methyl)-7-azabicyclo[2.2.1]heptan-7-yl)methanone

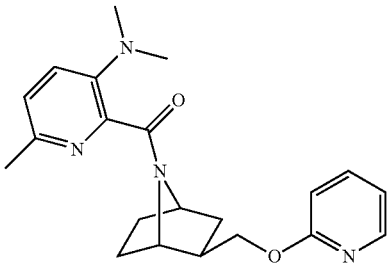 [SMILES: Cc1ccc(N(C)C)c(C(=O)N2C3CCC2C(COc2ccccn2)C3)n1]

Step A: 3-(dimethylamino)-6-methylpicolinamide

A mixture of 3-bromo-6-methylpicolinonitrile (1 g, 5 mmol) and dimethylamine (2 mL) were heated in a microwave reactor for 2 h at 140° C. The mixture was then concentrated and purified via silica gel chromatography (0-5% MeOH in DCM) to give the title compound (249 g, 27%). MS (ESI) mass calcd. for $C_9H_{13}N_3O$, 179.1; m/z found 180.0 $[M+H]^+$.

Step B: 3-(dimethylamino)-6-methylpicolinic acid

To the title compound of Step A (91 mg, 0.5 mmol) in EtOH (1 mL) was added 4M KOH (0.5 µL). The reaction was then heated at 90° C. for 18 h. The reaction was then cooled to rt, acidified with 1N HCl (aq) to pH=3, concentrated and used without further purification in the next step.

Step C

Prepared analogous to Example 2 substituting intermediate A-9 with the title compound of Step B. MS (ESI) mass calcd. for $C_{21}H_{26}N_4O_2$, 366.2; m/z found 367 $[M+H]^+$.

Example 74

(±)-(3-(2H-1,2,3-triazol-2-yl)quinolin-2-yl)(2-((pyridin-2-yloxy)methyl)-7-azabicyclo[2.2.1]heptan-7-yl)methanone

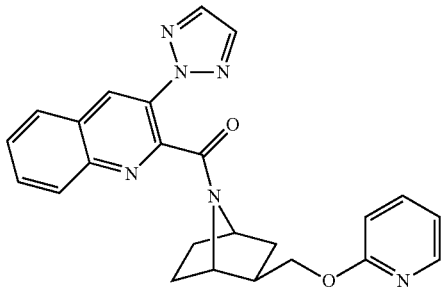 [SMILES: O=C(c1nc2ccccc2cc1-n1nccn1)N1C2CCC1C(COc1ccccn1)C2]

Prepared analogous to Example 2 substituting intermediate A-9 with 3-(2H-1,2,3-triazol-2-yl)quinoline-2-carboxylic acid. MS (ESI) mass calcd. for $C_{24}H_{22}N_6O_2$, 426.2; m/z found 427.2 $[M+H]^+$. $^1$H NMR (DMSO-$D_6$): 8.93 (s, 0.5H), 8.87 (s, 0.5H), 8.26-8.09 (m, 2H), 7.96-7.86 (m, 0.5H), 7.82-7.51 (m, 5H), 7.33 (d, J=8.4 Hz, 0.5H), 7.00 (t, J=6.0 Hz, 1H), 6.87 (d, J=8.3 Hz, 0.5H), 6.52 (d, J=8.3 Hz, 0.5H), 4.70-4.57 (m, 1H), 4.33 (t, J=10.5 Hz, 0.5H), 4.24-4.05 (m, 1.5H), 4.00 (br t, J=3.8 Hz, 0.5H), 3.93 (d, J=3.6 Hz, 0.5H), 2.44-2.20 (m, 1H), 2.01-1.35 (m, 6H).

Example 75

(±)-(7-ethoxyquinolin-8-yl)(2-((pyridin-2-yloxy)methyl)-7-azabicyclo[2.2.1]heptan-7-yl)methanone

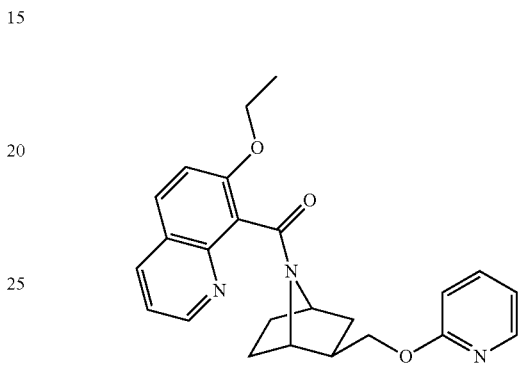

Prepared analogous to Example 2 substituting intermediate A-9 with intermediate A-29. MS (ESI) mass calcd. for $C_{24}H_{25}N_3O_3$, 403.2; m/z found 404.2 $[M+H]^+$. $^1$H NMR (DMSO-$D_6$): 9.02-8.54 (m, 1.6H), 8.42 (d, J=7.9 Hz, 0.8H), 8.31-7.83 (m, 2.2H), 7.83-6.75 (m, 3.8H), 6.64-6.46 (m, 0.2H), 6.24 (m, 0.4H), 4.86-4.62 (m, 1.2H), 4.46-4.01 (m, 3.6H), 3.61-3.23 (m, 1.2H), 2.44-2.06 (m, 1H), 2.06-1.15 (m, 9H).

Example 76

(±)-(3,6-dimethylimidazo[1,2-a]pyridin-5-yl)(2-((pyridin-2-yloxy)methyl)-7-azabicyclo[2.2.1]heptan-7-yl)methanone

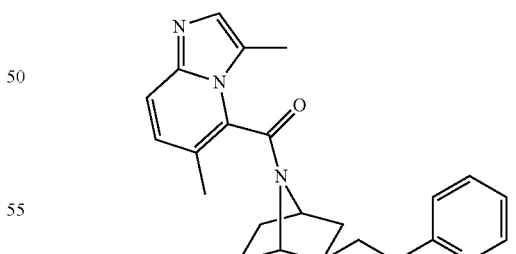

Step A: 3,6-dimethylimidazo[1,2-a]pyridine-5-carboxylic acid

Prepared analogous to Example 82 substituting chloroacetaldehyde with 2-bromopropanal. MS (ESI) mass calcd. for $C_{10}H_{10}N_2O_2$, 190.1; m/z found 191.0 $[M+H]^+$.

Step B: (±)-(3,6-dimethylimidazo[1,2-a]pyridin-5-yl)(2-((pyridin-2-yloxy)methyl)-7-azabicyclo[2.2.1]heptan-7-yl)methanone Prepared analogous to Example 2 substituting intermediate A-9 with the title compound of Step A. MS (ESI) mass calcd. for $C_{22}H_{24}N_4O_2$, 376.2; m/z found 377.2 [M+H]$^+$. The product is present as a mixture of conformers (ratio ca. 85:15). $^1$H NMR (300 MHz, DMSO) 8.18 (dd, J=4.5, 1.4 Hz, 0.85H), 7.91 (d, J=5.1 Hz, 0.15H), 7.74 (td, J=7.1, 1.8 Hz, 0.85H), 7.53 (d, J=9.1 Hz, 0.85H), 7.50-7.39 (m, 0.15H), 7.36 (s, 1H), 7.12 (dd, J=6.3 Hz, 1H), 7.06-6.95 (m, 0.85H), 6.88 (d, J=8.4 Hz, 0.85H), 6.72 (d, J=8.6 Hz, 0.15H), 6.62 (d, J=7.4 Hz, 0.15H), 6.46 (d, J=8.5 Hz, 0.15H), 4.77 (d, J=4.4 Hz, 0.85H), 4.72 (d, J=3.6 Hz, 0.15H), 4.25-4.10 (m, 1H), 4.10-3.98 (m, 1H), 3.78 (br s, 0.85H), 3.69 (br s, 0.15H), 2.48-2.38 (m, 1.85H), 2.36 (s, 2H), 2.30 (s, 2H), 2.25-2.21 (m, 0.85H), 2.20-2.16 (m, 0.3H), 1.98-1.32 (m, 6H).

Example 77

(±)-(1-methyl-4-phenyl-1H-pyrazol-3-yl)(2-((pyridin-2-yloxy)methyl)-7-azabicyclo[2.2.1]heptan-7-yl)methanone

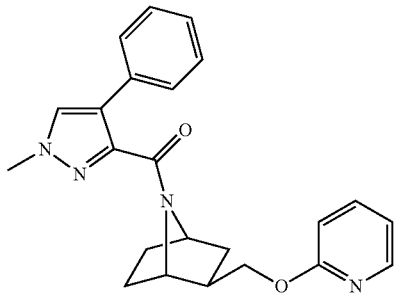 [SMILES: Cn1cc(-c2ccccc2)c(C(=O)N2C3CCC2C(COc2ccccn2)C3)n1]

Prepared analogous to Example 2 substituting intermediate A-9 with 1-methyl-4-phenyl-1H-pyrazole-3-carboxylic acid. MS (ESI) mass calcd. for $C_{23}H_{24}N_4O_2$, 388.2; m/z found 389.2 [M+H]$^+$. $^1$H NMR (DMSO-D$_6$): 8.18 (d, J=3.8 Hz, 0.5H), 8.08 (d, J=3.9 Hz, 0.5H), 8.03 (s, 0.5H), 7.92 (s, 0.5H), 7.76-7.62 (m, 1H), 7.46-7.16 (m, 5H), 7.04-6.90 (m, 1H), 6.84 (d, J=8.3 Hz, 0.5H), 6.71 (d, J=8.3 Hz, 0.5H), 4.60 (t, J=4.6 Hz, 0.5H), 4.56 (d, J=4.7 Hz, 0.5H), 4.15 (br s, 1H), 4.06 (br s, 1H), 3.98-3.83 (m, 2.5H), 3.55 (s, 1.5H), 2.29-2.15 (m, 1H), 1.79-1.22 (m, 6H).

Example 78

(±)-(1-methyl-3-phenyl-1H-pyrazol-4-yl)(2-((pyridin-2-yloxy)methyl)-7-azabicyclo[2.2.1]heptan-7-yl)methanone

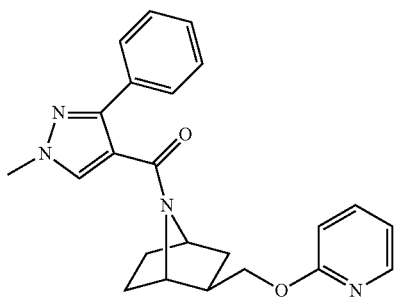 [SMILES: Cn1cc(C(=O)N2C3CCC2C(COc2ccccn2)C3)c(-c2ccccc2)n1]

Prepared analogous to Example 2 substituting intermediate A-9 with 1-methyl-3-phenyl-1H-pyrazole-4-carboxylic acid. MS (ESI) mass calcd. for $C_{23}H_{24}N_4O_2$, 388.2; m/z found 389.2 [M+H]$^+$. $^1$H NMR (DMSO-D$_6$): 8.16 (br s, 1H), 8.09-7.75 (m, 1H), 7.70 (t, J=7.2 Hz, 1H), 7.58 (d, J=7.0 Hz, 2H), 7.47-7.20 (m, 3H), 7.10-6.90 (m, 1H), 6.92-6.52 (br s, 1H), 4.48 (br s, 1H), 4.21-3.44 (m, 6H), 2.17 (br s, 1H), 1.86-1.05 (m, 6H).

Example 79

(±)-((3,7-dimethylimidazo[1,2-a]pyridin-8-yl)(2-((pyridin-2-yloxy)methyl)-7-azabicyclo[2.2.1]heptan-7-yl)methanone

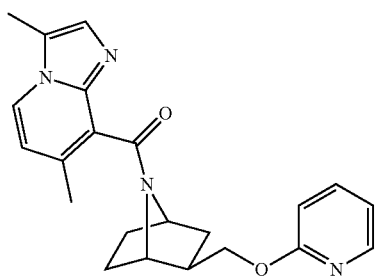 [SMILES: Cc1ccn2c(C)cnc2c1C(=O)N1C2CCC1C(COc1ccccn1)C2]

Step A

Prepared analogous to Example 76 substituting 6-amino-3-methylpicolinic acid with 2-amino-4-methylnicotinic acid.

Step B: (±)-((3,7-dimethylimidazo[1,2-a]pyridin-8-yl)(2-((pyridin-2-yloxy)methyl)-7-azabicyclo[2.2.1]heptan-7-yl)methanone Prepared analogous to Example 2 substituting intermediate A-9 with 3,7-dimethylimidazo[1,2-a]pyridine-8-carboxylic acid. MS (ESI) mass calcd. for $C_{22}H_{24}N_4O_2$, 376.2; m/z found 377.2 [M+H]$^+$. $^1$H NMR (DMSO-D$_6$): 8.24-8.03 (m, 2H), 7.80-7.68 (m, 0.5H), 7.61 (br s, 0.5H), 7.30 (s, 1H), 7.06-6.27 (m, 3H), 4.70 (t, J=4.3 Hz, 1H), 4.32-3.67 (m, 2H), 3.42 (m, 2H), 2.45 (s, 2H), 2.38-2.02 (m, 4H), 2.02-1.18 (m, 6H).

Example 80

(±)-(7-methylimidazo[1,2-a]pyridin-8-yl)(2-((pyridin-2-yloxy)methyl)-7-azabicyclo[2.2.1]heptan-7-yl)methanone

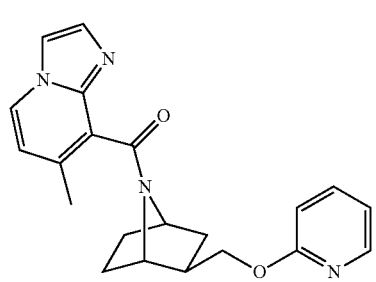 [SMILES: Cc1ccn2ccnc2c1C(=O)N1C2CCC1C(COc1ccccn1)C2]

Step A:
7-methylimidazo[1,2-a]pyridine-8-carboxylic acid

Prepared analogous to Example 82 substituting 6-amino-3-methylpicolinic acid with 2-amino-4-methylnicotinic acid.

Step B: (±)-(7-methylimidazo[1,2-a]pyridin-8-yl)(2-((pyridin-2-yloxy)methyl)-7-azabicyclo[2.2.1]heptan-7-yl)methanone Prepared analogous to Example 2 substituting intermediate A-9 with the title compound of Step A. MS (ESI) mass calcd. for $C_{21}H_{22}N_4O_2$, 362.2; m/z found 363.2 [M+H]$^+$. $^1$H NMR (DMSO-D$_6$): 8.46 (d, J=6.9 Hz, 0.5H), 8.38 (d, J=6.3 Hz, 0.5H), 8.17 (d, J=3.6 Hz, 0.5H), 8.12 (d, J=3.8 Hz, 0.5H), 7.91 (s, 1H), 7.79-7.39 (m, 2H), 7.14-6.70 (m, 2H), 6.70-6.33 (m, 1H), 4.71 (br s, 1H), 4.45-3.66 (m, 2H), 3.63-3.22 (m, 2H), 2.44-2.02 (m, 3H), 2.02-1.08 (m, 6H).

Example 81

(±)-(1-methyl-4-phenyl-1H-pyrazol-5-yl)(2-((pyridin-2-yloxy)methyl)-7-azabicyclo[2.2.1]heptan-7-yl)methanone

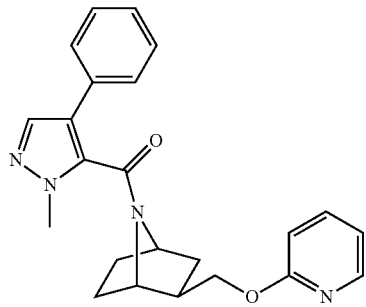 [SMILES: Cn1ncc(-c2ccccc2)c1C(=O)N1C2CCC1C(COc1ccccn1)C2]

Prepared analogous to Example 2 substituting intermediate A-9 with 1-methyl-4-phenyl-1H-pyrazole-5-carboxylic acid. MS (ESI) mass calcd. for $C_{23}H_{24}N_4O_2$, 388.2; m/z found 389.2 [M+H]$^+$. $^1$H NMR (DMSO-D$_6$): 8.19 (d, J=3.8 Hz, 0.6H), 8.09 (d, J=4.0 Hz, 0.4H), 7.79-7.57 (m, 2H), 7.43-7.19 (m, 5H), 7.05-6.91 (m, 1H), 6.84 (d, J=8.3 Hz, 0.6H), 6.62 (d, J=8.3 Hz, 0.4H), 4.62 (t, J=4.5 Hz, 0.4H), 4.57 (d, J=4.5 Hz, 0.6H), 3.96-3.87 (m, 2H), 3.85 (s, 1.8H), 3.79 (s, 1.2H), 3.58 (t, J=4.3 Hz, 0.6H), 3.52 (d, J=4.7 Hz, 0.4H), 2.28-2.02 (m, 1H), 1.76-1.07 (m, 6H).

Example 82

(±)-((6-methylimidazo[1,2-a]pyridin-5-yl)(2-((pyridin-2-yloxy)methyl)-7-azabicyclo[2.2.1]heptan-7-yl)methanone

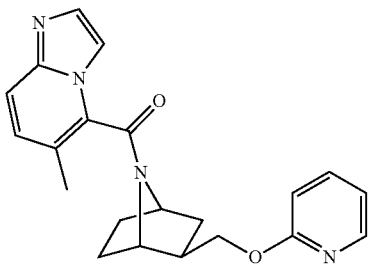 [SMILES: Cc1ccc2nccn2c1C(=O)N1C2CCC1C(COc1ccccn1)C2]

Step A: 6-amino-3-methylpicolinic acid

To methyl 6-amino-3-bromopicolinate (500 mg, 2.2 mmol), tetramethylstannane (900 µL, 6.5 mmol) and LiCl (354 g, 8.7 mmol) in DMF (6 mL) was added Pd(PPh$_3$)$_4$ (76 mg, 10 mol %). The reaction mixture was heated at 110° C. for 3 h. Additional tetramethylstannane, LiCl and Pd(PPh$_3$)$_4$ were added and heating continued for 6 h. Purification via silica gel chromatography (0-20% MeOH in DCM) gave the title compound.

Step B:
6-methylimidazo[1,2-a]pyridine-5-carboxylic acid

To the title compound of Step A (340 g, 2.2 mmol) in H$_2$O (7 mL) was added 1M aq. NaOH (2.2 mL, 2.2 mmol) and chloroacetaldehyde (210 µL, 3.4 mmol) and the reaction mixture heated in a microwave reactor at 150° C. for 2 h. Additional 1M aq. NaOH (2.2 mL, 2.2 mmol) and chloroacetaldehyde (210 µL, 3.4 mmol) were added and heating continued at 150° C. for 2 h. The reaction was purified via prep HPLC to give the title compound (282 g, 72%). MS (ESI) mass calcd. for $C_9H_8N_2O_2$, 176.1; m/z found 177.0 [M+H]$^+$.

Step C: (±)-((6-methylimidazo[1,2-a]pyridin-5-yl)(2-((pyridin-2-yloxy)methyl)-7-azabicyclo[2.2.1]heptan-7-yl)methanone Prepared analogous to Example 2 substituting intermediate A-9 with 6-methylimidazo[1,2-a]pyridine-5-carboxylic acid. The product is present as a mixture of conformers (ratio ca. 80:20)$^1$H NMR (300 MHz, DMSO) 8.44-8.13 (m, 1.6H), 8.13-7.86 (m, 3H), 7.86-7.41 (m, 1.2H), 6.97 (br d, J=33.5 Hz, 1.6H), 6.68 (br d, J=1.0 Hz, 0.2H), 6.39 (br d, J=1.0 Hz, 0.4H), 4.80 (d, J=16.5 Hz, 1.6H), 4.09-4.06 (m, 0.2H), 3.58 (s, 2H), 3.46-3.30 (m, 0.2H), 2.47-2.07 (m, 4H), 2.07-1.02 (m, 6H).

Example 83

(±)-(3-ethoxyisoquinolin-4-yl)(2-((pyridin-2-yloxy)methyl)-7-azabicyclo[2.2.1]heptan-7-yl)methanone

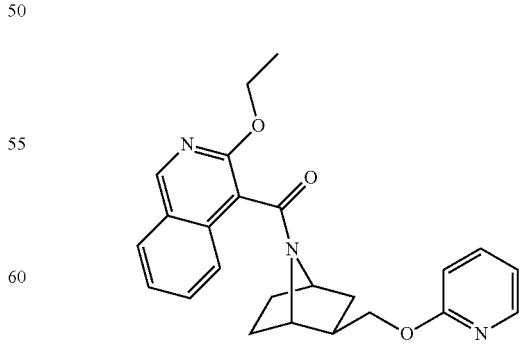

Prepared analogous to Example 164 substituting intermediate B-9 with intermediate B-10. MS (ESI) mass calcd. for $C_{24}H_{25}N_3O_3$, 403.2; m/z found 404.2 [M+H]$^+$.

Example 84

(±)-(1-methyl-5-phenyl-1H-pyrazol-4-yl)(-2-((pyridin-2-yloxy)methyl)-7-azabicyclo[2.2.1]heptan-7-yl)methanone

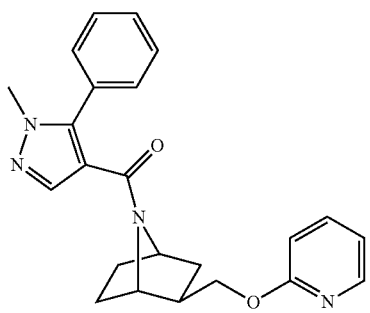 [SMILES: Cn1ncc(C(=O)N2C3CCC2C(COc2ccccn2)C3)c1-c1ccccc1]

Prepared analogous to Example 2 substituting intermediate A-9 with intermediate A-51. MS (ESI) mass calcd. for C?$_3$H$_{24}$N$_4$O$_2$, 388.2; m/z found 389.2 [M+H]$^+$.

Example 85

(±)-(6-methyl-3-(4-methylpiperazin-1-yl)pyridin-2-yl)(2-((pyridin-2-yloxy)methyl)-7-azabicyclo[2.2.1]heptan-7-yl)methanone

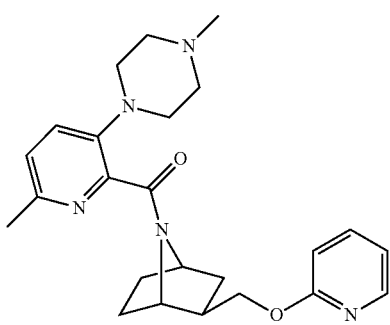 [SMILES: Cc1ccc(N2CCN(C)CC2)c(C(=O)N2C3CCC2C(COc2ccccn2)C3)n1]

Step A: 6-methyl-3-(4-methylpiperazin-1-yl)picolinonitrile

Prepared analogous to Example 68 substituting pyrolidine with 1-methylpiperazine. MS (ESI) mass calcd. for C$_{12}$H$_{16}$N$_4$, 216.1; m/z found 217.0 [M+H]$^+$.

Step B: 6-methyl-3-(4-methylpiperazin-1-yl)picolinic acid

Prepared analogous to Example 68 substituting 6-methyl-3-(pyrrolidin-1-yl)picolinonitrile with the title compound of Step A. MS (ESI) mass calcd. for C$_{12}$H$_{17}$N$_3$O$_2$, 235.1; m/z found 236.0 [M+H]$^+$.

Step C

Prepared analogous to Example 2 substituting intermediate A-9 with the title compound of Step B. MS (ESI) mass calcd. for C$_{24}$H$_{31}$N$_5$O$_2$, 421.2; m/z found 422.2 [M+H]$^+$. $^1$H NMR (DMSO-D$_6$): 8.19-8.14 (m, 0.5H), 8.12 (dd, J=5.0, 1.5 Hz, 0.5H), 7.78-7.68 (m, 0.5H), 7.68-7.59 (m, 0.5H), 7.52 (d, J=8.4 Hz, 0.5H), 7.37 (d, J=8.4 Hz, 0.5H), 7.23 (d, J=8.4 Hz, 0.5H), 7.07 (d, J=8.3 Hz, 0.5H), 6.97 (ddd, J=12.3, 6.7, 5.4 Hz, 1H), 6.87 (d, J=8.3 Hz, 0.5H), 6.59 (d, J=8.3 Hz, 0.5H), 4.63 (t, J=4.5 Hz, 0.5H), 4.59 (d, J=3.9 Hz, 0.5H), 4.19-3.81 (m, 2H), 3.46 (t, J=3.9 Hz, 0.5H), 3.39 (d, J=4.7 Hz, 0.5H), 3.07-2.92 (m, 2H), 2.92-2.78 (m, 2H), 2.46-2.27 (m, 6H), 2.22-2.05 (m, 3.5H), 1.97 (s, 1.5H), 1.94-1.27 (m, 6H).

Example 86

(±)-(6-methyl-3-(piperazin-1-yl)pyridin-2-yl)(2-((pyridin-2-yloxy)methyl)-7-azabicyclo[2.2.1]heptan-7-yl)methanone

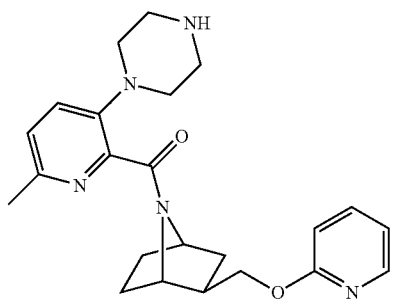 [SMILES: Cc1ccc(N2CCNCC2)c(C(=O)N2C3CCC2C(COc2ccccn2)C3)n1]

Step A: tert-butyl 4-(2-cyano-6-methylpyridin-3-yl)piperazine-1-carboxylate

Prepared analogous to Example 68 substituting pyrollidine with tert-butyl piperazine-1-carboxylate. MS (ESI) mass calcd. for C$_{16}$H$_{22}$N$_4$O$_2$, 302.2; m/z found 303.0 [M+H]$^+$.

Step B: 3-(4-(tert-butoxycarbonyl)piperazin-1-yl)-6-methylpicolinic acid

Prepared analogous to Example 68 substituting 6-methyl-3-(pyrrolidin-1-yl)picolinonitrile with the title compound of Step A. MS (ESI) mass calcd. for C$_{16}$H$_{23}$N$_3$O$_4$, 321.2; m/z found 322.0 [M+H]$^+$.

Step C: tert-butyl 4-(6-methyl-2-((±)-2-((pyridin-2-yloxy)methyl)-7-azabicyclo[2.2.1]heptane-7-carbonyl)pyridin-3-yl)piperazine-1-carboxylate Prepared analogous to example 2 substituting intermediate A-9 with the title compound of Step B.

Step D: (±)-(6-methyl-3-(piperazin-1-yl)pyridin-2-yl)(2-((pyridin-2-yloxy)methyl)-7-azabicyclo[2.2.1]heptan-7-yl)methanone To the title compound from step C (182 mg, 0.4 mmol) in 1,4-dioxane (1 mL) was added 6N HCl in iPrOH (400 SL). The reaction was heated to 70° C. for 3 h, cooled to rt, concentrated and purified via reverse phase chromatography. The mixture was dissolved with a saturated NaHCO3 (aq) and extracted with DCM (×3). The organic layers were dried over MgSO4 and concentrated. The crude product was triturated with diethyl ether and n-pentane to give the title compound (5 g, 3%). MS (ESI) mass calcd. for C$_{23}$H$_{29}$N$_5$O$_2$, 407.2; m/z found 408.2 [M+H]$^+$. $^1$H NMR (DMSO-D$_6$): 8.17 (d, J=4.0 Hz, 0.4H), 8.12 (d, J=3.8 Hz, 0.6H), 7.72 (t, J=7.6 Hz, 0.4H), 7.63 (t, J=6.9 Hz, 0.6H), 7.48 (d, J=8.3 Hz, 0.4H), 7.34 (d, J=8.3 Hz, 0.6H), 7.22 (d, J=8.3 Hz, 0.4H), 7.06 (d, J=8.3 Hz, 0.6H), 7.02-6.90 (m, 1H), 6.86 (d, J=8.1 Hz, 0.4H), 6.58 (d, J=8.3 Hz, 0.6H), 4.63-4.60 (m, 1H), 4.14-3.92 (m, 2H), 3.86 (t, J=10.4 Hz, 1H), 2.99-2.65 (m, 8H), 2.39 (s, 1H), 2.34-2.28 (m, 1H), 2.18-2.11 (m, 1H), 1.96-1.88 (m, 2H), 1.86-1.20 (m, 6H).

Example 87

(±)-(6-methyl-3-morpholinopyridin-2-yl)((1S,2R,4R)-2-((pyridin-2-yloxy)methyl)-7-azabicyclo[2.2.1]heptan-7-yl)methanone

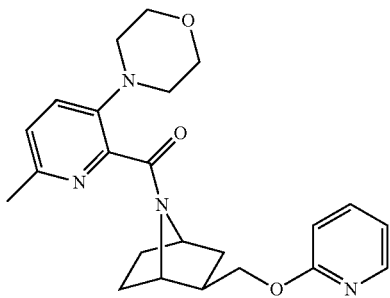 [SMILES: Cc1ccc(N2CCOCC2)c(C(=O)N2C3CCC2C(COc2ccccn2)C3)n1]

Step A: 6-methyl-3-morpholinopicolinonitrile

Prepared analogous to Example 68 substituting pyrolidine with morpholine. MS (ESI) mass calcd. for C$_{11}$H$_{13}$N$_3$O, 203.1; m/z found 204.0 [M+H]$^+$.

Step B: 6-methyl-3-morpholinopicolinic acid

Prepared analogous to Example 68 substituting 6-methyl-3-(pyrrolidin-1-yl)picolinonitrile with the title compound of Step A. MS (ESI) mass calcd. for C$_{11}$H$_{14}$N$_2$O$_3$, 222.1; m/z found 223.0 [M+H]$^+$.

Step C

Prepared analogous to Example 2 substituting intermediate A-9 with the title compound of Step B. MS (ESI) mass calcd. for C$_{23}$H$_{28}$N$_4$O$_3$, 408.2; m/z found 409.2 [M+H]$^+$.

Example 88

(±)-(7-methoxyquinolin-8-yl)(2-((pyridin-2-yloxy)methyl)-7-azabicyclo[2.2.1]heptan-7-yl)methanone

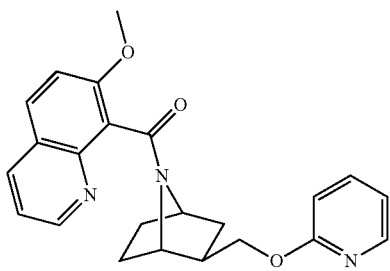 [SMILES: COc1ccc2cccnc2c1C(=O)N1C2CCC1C(COc1ccccn1)C2]

Step A: 7-methoxyquinoline-8-carboxylic acid

In 1 g separate batches a mixture of 2-amino-6-methoxybenzoic acid (1 g, 66 mmol) and acrolein (4.8 mL, 72 mmol) in 1,4-dioxane (66 mL) was heated in a microwave reactor for 20 min at 200° C. After combining the reactions, the mixture was concentrated and purified via silica gel chromatography (0-10% MeOH in DCM) to give the title compound (2.8 g, 20%). MS (ESI) mass calcd. for C$_{11}$H$_{19}$NO$_3$, 203.1; m/z found 204.0 [M+H]$^+$.

Step B

Prepared analogous to Example 2 substituting intermediate A-9 with the title compound of Step A. MS (ESI) mass calcd. for C$_{23}$H$_{23}$N$_3$O$_3$, 389.2; m/z found 390.2 [M+H]$^+$.

Example 89

(A)-(2-ethoxynaphthalen-1-yl)(2-((pyridin-2-yloxy)methyl)-7-azabicyclo[2.2.1]heptan-7-yl)methanone

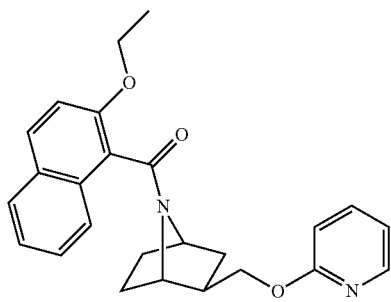

Prepared analogous to Example 2 substituting intermediate A-9 with 2-ethoxy-1-naphthoic acid. MS (ESI) mass calcd. for C$_{25}$H$_{26}$N$_2$O$_3$, 402.2; m/z found 403.2 [M+H]$^+$.

Example 90

(±)-(3,6'-dimethyl-[2,3'-bipyridin]-2'-yl)(2-((pyridin-2-yloxy)methyl)-7-azabicyclo[2.2.1]heptan-7-yl)methanone

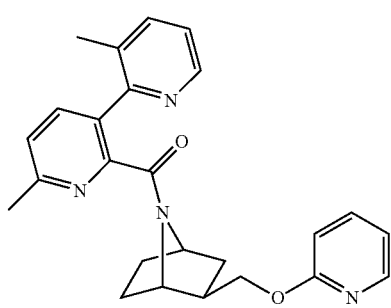 [SMILES: Cc1ccc(-c2ncccc2C)c(C(=O)N2C3CCC2C(COc2ccccn2)C3)n1]

Prepared analogous to Example 2 substituting intermediate A-9 with 3,6'-dimethyl-[2,3'-bipyridine]-2'-carboxylic acid. MS (ESI) mass calcd. for C$_{25}$H$_{26}$N$_4$O$_2$, 414.2; m/z found 415.2 [M+H]$^+$.

Example 91

(±)-(3-(2H-1,2,3-triazol-2-yl)pyridin-2-yl)(2-((pyridin-2-yloxy)methyl)-7-azabicyclo[2.2.1]heptan-7-yl)methanone

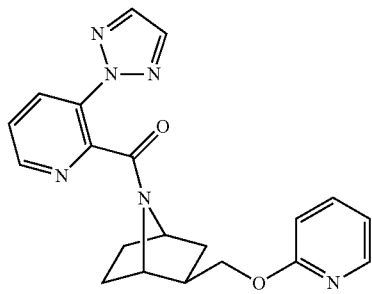 [SMILES: O=C(c1ncccc1-n1nccn1)N1C2CCC1C(COc1ccccn1)C2]

Prepared analogous to Example 2 substituting intermediate A-9 with 3-(2H-1,2,3-triazol-2-yl)picolinic acid. MS (ESI) mass calcd. for $C_{20}H_{20}N_6O_2$, 376.2; m/z found 377.2 [M+H]$^+$. $^1$H NMR (DMSO-D$_6$): 8.70 (d, J=3.6 Hz, 0.5H), 8.40-7.99 (m, 4.5H), 7.82-7.47 (m, 2H), 7.02-6.85 (m, 1H), 6.86 (d, J=8.2 Hz, 0.6H), 6.64 (d, J=8.1 Hz, 0.4H), 4.62-4.65 (m, 1H), 4.20-3.97 (m, 3H), 2.35-2.24 (m, 1H), 2.00-1.09 (m, 6H).

Example 92

(±)-(2-methyl-5-phenylthiazol-4-yl)(2-((pyridin-2-yloxy)methyl)-7-azabicyclo[2.2.1]heptan-7-yl)methanone

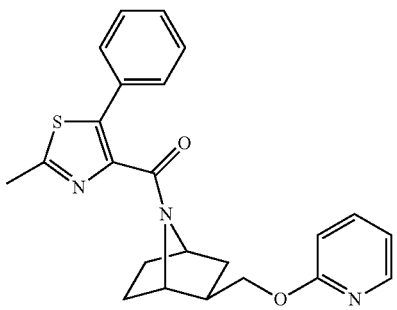 [SMILES: Cc1nc(C(=O)N2C3CCC2C(COc2ccccn2)C3)c(-c2ccccc2)s1]

Prepared analogous to Example 2 substituting intermediate A-9 with 2-methyl-5-phenylthiazole-4-carboxylic acid. MS (ESI) mass calcd. for $C_{23}H_{23}N_3O_2S$, 405.2; m/z found 406.2 [M+H]$^+$. $^1$H NMR (DMSO-D$_6$) 8.18 (dd, J=5.0, 1.4 Hz, 0.5H), 8.10 (dd, J=5.0, 1.4 Hz, 0.5H), 7.77-7.61 (m, 1H), 7.52-7.29 (m, 5H), 7.04-6.89 (m, 1H), 6.82 (d, J=8.3 Hz, 0.5H), 6.69 (d, J=8.3 Hz, 0.5H), 4.57 (t, J=4.5 Hz, 0.5H), 4.52 (d, J=4.7 Hz, 0.5H), 3.90-3.79 (m, 2.5H), 3.69 (t, J=10.6 Hz, 0.5H), 2.69 (s, 1.5H), 2.28 (s, 1.5H), 2.25-2.06 (m, 1H), 1.72-1.04 (m, 6H).

Example 93

(±)-(6-methyl-3-(oxazol-2-yl)pyridin-2-yl)(2-((pyridin-2-yloxy)methyl)-7-azabicyclo[2.2.1]heptan-7-yl)methanone

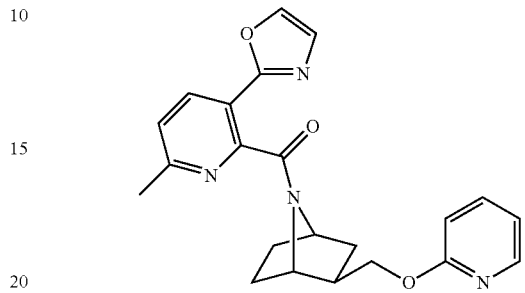

Prepared analogous to Example 2 substituting intermediate A-43. MS (ESI) mass calcd. for $C_{22}H_{22}N_4O_3$, 390.2; m/z found 391.2 [M+H]$^+$. $^1$H NMR (DMSO-D$_6$): 8.22 (dt, J=14.0, 7.8 Hz, 2.5H), 8.12 (dd, J=5.0, 1.4 Hz, 0.5H), 7.78-7.68 (m, 0.5H), 7.68-7.59 (m, 0.5H), 7.49 (d, J=8.2 Hz, 0.5H), 7.41-7.29 (m, 1.5H), 6.97 (ddd, J=14.7, 6.5, 5.2 Hz, 1H), 6.87 (d, J=8.4 Hz, 0.5H), 6.63 (d, J=8.3 Hz, 0.5H), 4.66 (t, J=4.6 Hz, 0.5H), 4.62 (d, J=4.8 Hz, 0.5H), 4.22-3.93 (m, 2H), 3.70 (t, J=4.4 Hz, 0.5H), 3.61 (d, J=4.0 Hz, 0.5H), 2.55 (s, 1.5H), 2.40-2.14 (m, 1H), 2.08 (s, 1.5H), 1.93-1.23 (m, 6H).

Example 94

(±)-(6-methyl-3-(3-methylisoxazol-5-yl)pyridin-2-yl)(2-((pyridin-2-yloxy)methyl)-7-azabicyclo[2.2.1]heptan-7-yl)methanone

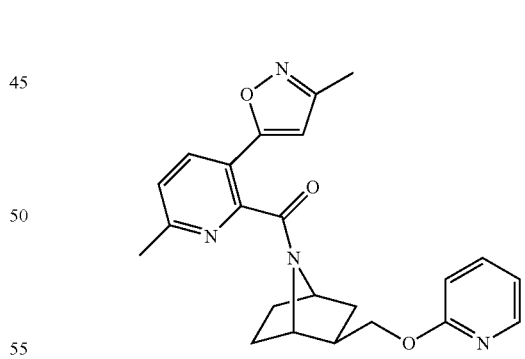

Prepared analogous to Example 2 substituting intermediate A-9 with 6-methyl-3-(3-methylisoxazol-5-yl)picolinic acid. MS (ESI) mass calcd. for $C_{23}H_{24}N_4O_3$, 404.2; m/z found 405.0 [M+H]$^+$. $^1$H NMR (DMSO-D$_6$): 8.20-8.02 (m, 2H), 7.73 (t, J=6.9 Hz, 0.4H), 7.65 (t, J=7.7 Hz, 0.6H), 7.50 (d, J=8.1 Hz, 0.4H), 7.37 (d, J=8.2 Hz, 0.6H), 7.03-6.91 (m, 1H), 6.87 (d, J=8.3 Hz, 0.4H), 6.68-6.58 (m, 1.6H), 4.68 (t, J=4.6 Hz, 0.6H), 4.62 (d, J=4.7 Hz, 0.4H), 4.01-3.93 (m, 2H), 3.60 (t, J=4.4 Hz, 0.4H), 3.55 (d, J=3.1 Hz, 0.6H), 2.55 (s, 1.2H), 2.36-2.14 (m, 4H), 2.09 (s, 1.8H), 1.88-1.07 (m, 6H).

Example 95

(±)-(6-methyl-3-(1H-pyrazol-1-yl)pyridin-2-yl)(2-((pyridin-2-yloxy)methyl)-7-azabicyclo[2.2.1]heptan-7-yl)methanone

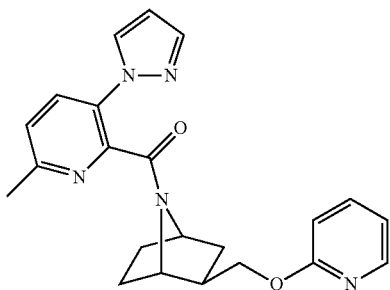 [SMILES: Cc1ccc(-n2cccn2)c(C(=O)N2C3CCC2C(COc2ccccn2)C3)n1]

Prepared analogous to Example 2 substituting intermediate A-9 with 6-methyl-3-(1H-pyrazol-1-yl)picolinic acid. $^1$H NMR (DMSO-D$_6$): 8.19 (dd, J=5.0, 1.4 Hz, 0.5H), 8.14 (dd, J=5.1, 1.5 Hz, 0.5H), 8.08 (t, J=2.9 Hz, 1H), 7.97 (d, J=8.3 Hz, 0.5H), 7.93 (d, J=8.3 Hz, 0.5H), 7.76-7.61 (m, 2H), 7.49 (d, J=8.4 Hz, 0.5H), 7.34 (d, J=8.4 Hz, 0.5H), 6.97 (td, J=7.3, 5.2 Hz, 1H), 6.84 (d, J=8.3 Hz, 0.5H), 6.65 (d, J=8.3 Hz, 0.5H), 6.53-6.48 (m, 0.5H), 6.48-6.43 (m, 0.5H), 4.55 (t, J=4.5 Hz, 0.5H), 4.51 (d, J=4.7 Hz, 0.5H), 4.02-3.93 (m, 2H), 3.67 (t, J=4.1 Hz, 0.5H), 3.60 (d, J=4.5 Hz, 0.5H), 2.54 (s, 1.5H), 2.31-2.11 (m, 1H), 2.04 (s, 1.5H), 1.75-1.16 (m, 6H).

Example 96

(±)-(6-methyl-3-(4-methyl-1H-pyrazol-1-yl)pyridin-2-yl))(2-((pyridin-2-yloxy)methyl)-7-azabicyclo[2.2.1]heptan-7-yl)methanone

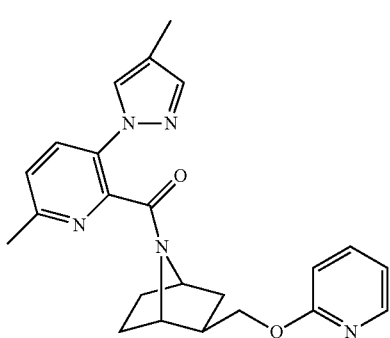 [SMILES: Cc1cnn(-c2ccc(C)nc2C(=O)N2C3CCC2C(COc2ccccn2)C3)c1]

Prepared analogous to Example 2 substituting intermediate A-9 with 6-methyl-3-(4-methyl-1H-pyrazol-1-yl)picolinic acid. MS (ESI) mass calcd. for C$_{23}$H$_{25}$N$_5$O$_2$, 403.2; m/z found 404.2 [M+H]$^+$.

Example 97

(±)-(6-methyl-3-(pyrrolidin-1-yl)pyridin-2-yl)(2-((pyridin-2-yloxy)methyl)-7-azabicyclo[2.2.1]heptan-7-yl)methanone

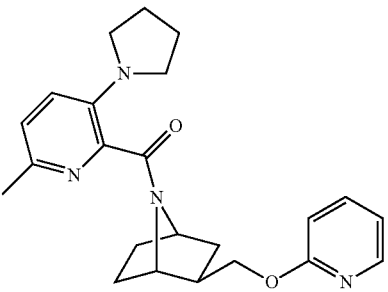 [SMILES: Cc1ccc(N2CCCC2)c(C(=O)N2C3CCC2C(COc2ccccn2)C3)n1]

Prepared analogous to Example 2 substituting intermediate A-9 with 6-methyl-3-(pyrrolidin-1-yl)picolinic acid (Example 68, Step B). MS (ESI) mass calcd. for C$_{23}$H$_{28}$N$_4$O$_2$, 392.2; m/z found 393.2 [M+H]$^+$. The product is present as a mixture of conformers (ratio ca. 50:50). $^1$H NMR (300 MHz, DMSO) 8.14 (dd, J=5.1, 1.4 Hz, 0.5H), 8.11 (dd, J=5.1, 1.4 Hz, 0.5H), 7.76-7.59 (m, 1H), 7.06 (q, J=8.6 Hz, 1H), 7.01-6.90 (m, 2H), 6.85 (d, J=8.3 Hz, 0.5H), 6.69 (d, J=8.3 Hz, 0.5H), 4.61 (t, J=4.6 Hz, 0.5H), 4.58 (d, J=4.7 Hz, 0.5H), 4.19-3.91 (m, 2.5H), 3.88 (d, J=4.6 Hz, 0.5H), 3.28-3.11 (m, 3H), 3.10-2.98 (m, 1H), 2.41-2.18 (m, 2.5H), 2.06 (s, 1.5H), 1.95-1.28 (m, 10H).

Example 98

(±)-(3,6'-dimethyl-[2,3'-bipyridin]-2'-yl)(2-(((5-fluoropyrimidin-2-yl)oxy)methyl)-7-azabicyclo[2.2.1]heptan-7-yl)methanone

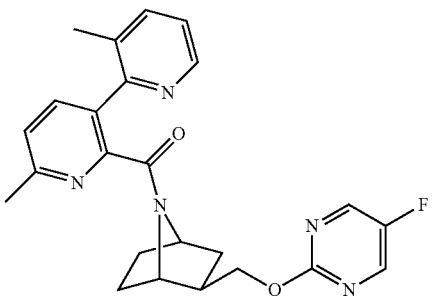 [SMILES: Cc1ccc(-c2ncccc2C)c(C(=O)N2C3CCC2C(COc2ncc(F)cn2)C3)n1]

Step A: (±)-tert-butyl 2-(((5-fluoropyrimidin-2-yl)oxy)methyl)-7-azabicyclo[2.2.1]heptane-7-carboxylate To intermediate B-10 (500 g, 2.2 mmol) in THF (11 mL) at 0° C. was added NaH (176 mg, 60 wt % in mineral oil, 4.4 mmol). After 15 min, 2-chloro-5-fluoropyrimidine (0.3 mL, 2.4 mmol) was added dropwise and the 0° C. ice bath was removed. After 12 h, H$_2$O was added and the reaction extracted with EtOAc. The combined organics dried (Na$_2$SO$_4$). Purification via silica gel chromatography (5-30% EtOAc in heptane) gave the title compound (490 g, 69%) as a white solid. MS (ESI) mass calcd. for $C_{16}H_{22}F_3N_3O_3$, 323.4; m/z found 224.1 [M−100]$^+$.

Step B: (±)-2-(((5-fluoropyrimidin-2-yl)oxy)methyl)-7-azabicyclo[2.2.1]heptane

To the title compound from step A (474 g, 1.5 mmol) in 1,4-dioxane (1.5 mL) was added 6N HCl in iPrOH (1.5 mL). The reaction was heated to 40° C. for 1.5 h and concentrated to give the title compound that was used without further purification in subsequent steps. MS (ESI) mass calcd. for $C_{11}H_{14}FN_3O$, 223.1; m/z found 224.0 [M+H]$^+$.

Step C: (±)-(3,6'-dimethyl-[2,3'-bipyridin]-2'-yl)(2-(((5-fluoropyrimidin-2-yl)oxy)methyl)-7-azabicyclo[2.2.1]heptan-7-yl)methanone Prepared analogous to example 2 substituting intermediate A-9 with 3,6'-dimethyl-[2,3'-bipyridine]-2'-carboxylic acid and intermediate B-10 with the title compound of Step B. MS (ESI) mass calcd. for $C_{24}H_{24}FN_5O_2$, 433.2; m/z found 434.2 [M+H]$^+$. $^1$H NMR (DMSO-D$_6$): 8.71 (s, 2H), 8.32 (t, J=4.5 Hz, 1H), 7.74 (d, J=7.9 Hz, 1H), 7.66 (t, J=7.3 Hz, 1H), 7.40 (d, J=7.9 Hz, 0.5H), 7.33-7.14 (m, 1.5H), 4.39 (br s, 0.5H), 4.34 (d, J=4.0 Hz, 0.5H), 4.27 (t, J=10.4 Hz, 0.5H), 4.10 (dd, J=5.2, 1.0 Hz, 0.5H), 3.90 (d, J=4.8 Hz, 0.5H), 3.85 (t, J=3.1 Hz, 0.5H), 3.69 (d, J=7.9 Hz, 1H), 2.55 (s, 1.5H), 2.31-2.20 (m, 0.5H), 2.18 (s, 1.5H), 2.16 (s, 1.5H), 2.12 (s, 1.5H), 2.01-1.82 (m, 0.5H), 1.81-1.14 (m, 6H).

Example 99

(±)-(2-(((5-fluoropyrimidin-2-yl)oxy)methyl)-7-azabicyclo[2.2.1]heptan-7-yl)(6-methyl-3-(3-methylisoxazol-5-yl)pyridin-2-yl)methanone

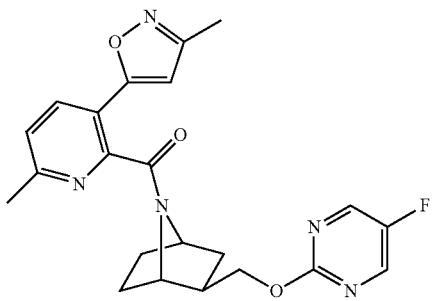

Prepared analogous to example 98 substituting 3,6'-dimethyl-[2,3'-bipyridine]-2'-carboxylic acid with 6-methyl-3-(3-methylisoxazol-5-yl)picolinic acid. MS (ESI) mass calcd. for $C_{22}H_{22}FN_5O_3$, 423.2; m/z found 424.2 [M+H]$^+$. $^1$H NMR (DMSO-D$_6$): 8.71 (s, 1H), 8.66 (s, 1H), 8.12 (d, J=8.1 Hz, 0.4H), 8.09 (d, J=8.2 Hz, 0.6H), 7.50 (d, J=8.2 Hz, 0.4H), 7.40 (d, J=8.2 Hz, 0.6H), 6.64-6.63 (m, 1H), 4.68 (t, J=4.6 Hz, 0.6H), 4.60 (d, J=4.7 Hz, 0.4H), 4.11-3.90 (m, 2H), 3.62 (t, J=4.2 Hz, 0.4H), 3.55 (d, J=4.1 Hz, 0.5H), 2.55 (s, 1.2H), 2.40-2.15 (m, 4H), 2.16 (s, 1.8H), 1.88-1.12 (m, 6H).

Example 100

(±)-(2-(((5-fluoropyrimidin-2-yl)oxy)methyl)-7-azabicyclo[2.2.1]heptan-7-yl)(6-methyl-3-(oxazol-2-yl)pyridin-2-yl)methanone

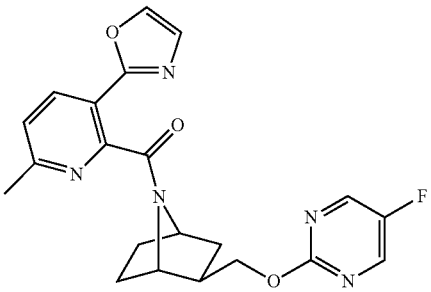 [SMILES: Cc1ccc(-c2ncco2)c(C(=O)N2C3CCC2C(COc2ncc(F)cn2)C3)n1]

Prepared analogous to example 98 substituting 3,6'-dimethyl-[2,3'-bipyridine]-2'-carboxylic acid with intermediate A-43. MS (ESI) mass calcd. for $C_{21}H_{20}FN_5O_3$, 409.2; m/z found 410.2 [M+H]$^+$. $^1$H NMR (DMSO-D$_6$): 8.74 (s, 0.8H), 8.66 (s, 1.2H), 8.31-8.16 (m, 2H), 7.50 (d, J=8.2 Hz, 0.4H), 7.38 (t, J=8.9 Hz, 1.6H), 4.67 (t, J=4.5 Hz, 0.6H), 4.62 (d, J=4.7 Hz, 0.4H), 4.23 (t, J=10.1 Hz, 0.4H), 4.07 (dt, J=10.0, 6.2 Hz, 1.6H), 3.72 (t, J=4.2 Hz, 0.4H), 3.62 (d, J=4.4 Hz, 0.6H), 2.56 (s, 1.2H), 2.43-2.19 (m, 1H), 2.16 (s, 1.8H), 1.93-1.23 (m, 6H).

Example 101

(±)-(2-(((5-fluoropyrimidin-2-yl)oxy)methyl)-7-azabicyclo[2.2.1]heptan-7-yl)(6-methyl-3-(pyrrolidin-1-yl)pyridin-2-yl)methanone

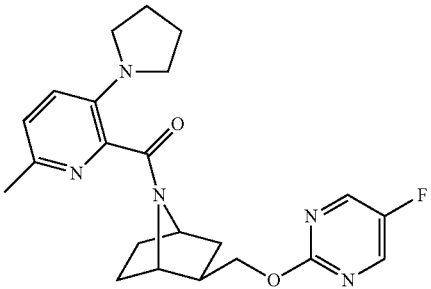 [SMILES: Cc1ccc(N2CCCC2)c(C(=O)N2C3CCC2C(COc2ncc(F)cn2)C3)n1]

Prepared analogous to example 98 substituting 3,6'-dimethyl-[2,3'-bipyridine]-2'-carboxylic acid with 6-methyl-3-(pyrrolidin-1-yl)picolinic acid (Example 68, Step B). MP=130° C.

Example 102

(±)-(2-(((5-fluoropyrimidin-2-yl)oxy)methyl)-7-azabicyclo[2.2.1]heptan-7-yl)(6-methyl-3-(pyrimidin-2-yl)pyridin-2-yl)methanone

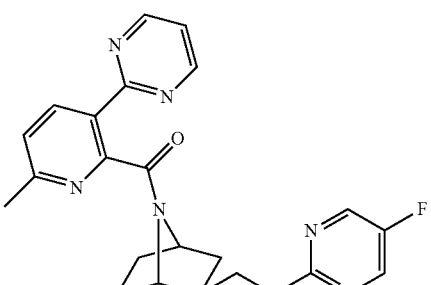

Prepared analogous to example 98 substituting 3,6'-dimethyl-[2,3'-bipyridine]-2'-carboxylic acid with intermediate A-9. MS (ESI) mass calcd. for $C_{22}H_{21}FN_6O_2$, 420.2; m/z found 421.2 [M+H]$^+$. $^1$H NMR (DMSO-D$_6$): 8.93 (d, J=4.9 Hz, 0.8H), 8.88 (d, J=4.9 Hz, 1.2H), 8.79 (s, 0.8H), 8.72 (s, 1.2H), 8.37-8.33 (m, 1H), 7.55-7.47 (m, 1.2H), 7.40 (d, J=8.1 Hz, 0.6H), 4.67-4.61 (br s, 0.6H), 4.59 (d, J=4.0 Hz, 0.4H), 4.33-4.22 (m, 1H), 4.18-4.07 (m, 1H), 3.91 (br s, 0.4H), 3.81 (d, J=3.4 Hz, 0.6H), 2.59 (s, 1.4H), 2.48-2.25 (m, 1H), 2.15 (s, 1.8H), 1.93-1.34 (m, 6H).

Example 103

(±)-(2-(((5-fluoropyrimidin-2-yl)oxy)methyl)-7-azabicyclo[2.2.1]heptan-7-yl)(6-methyl-3-(4-methyl-1H-pyrazol-1-yl)pyridin-2-yl)methanone

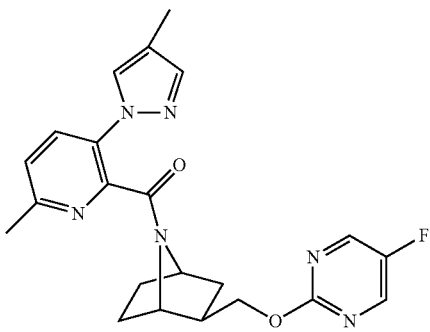 [SMILES: Cc1cnn(-c2ccc(C)nc2C(=O)N2C3CCC2C(COc2ncc(F)cn2)C3)c1]

Prepared analogous to example 98 substituting 3,6'-dimethyl-[2,3'-bipyridine]-2'-carboxylic acid with 6-methyl-3-(4-methyl-1H-pyrazol-1-yl)picolinic acid. MP=151.2° C. $^1$H NMR (DMSO-D$_6$): 8.73 (s, 1H), 8.69 (s, 1H), 7.92 (d, J=5.0 Hz, 0.5H), 7.90 (d, J=5.0 Hz, 0.5H), 7.85 (d, J=2.3 Hz, 1H), 7.51-7.54 (m, 1.5H), 7.35 (d, J=8.4 Hz, 0.5H), 4.57 (t, J=4.5 Hz, 0.5H), 4.51 (d, J=4.7 Hz, 0.5H), 4.08-3.90 (m, 2H), 3.66 (t, J=4.0 Hz, 0.5H), 3.60 (d, J=4.0 Hz, 0.5H), 2.53 (s, 1.5H), 2.35-2.14 (m, 1H), 2.10 (s, 1.5H), 2.07 (s, 1.5H), 2.04 (s, 1.5H), 1.77-1.14 (m, 6H).

Example 104

(±)-(2-(((5-fluoropyrimidin-2-yl)oxy)methyl)-7-azabicyclo[2.2.1]heptan-7-yl)(6-methyl-3-(1H-pyrazol-1-yl)pyridin-2-yl)methanone

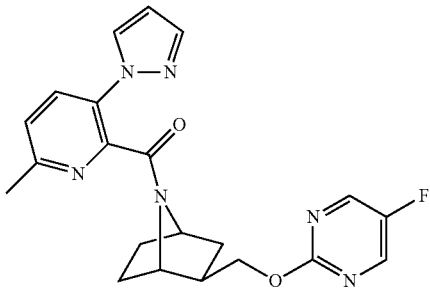 [SMILES: Cc1ccc(-n2cccn2)c(C(=O)N2C3CCC2C(COc2ncc(F)cn2)C3)n1]

Prepared analogous to example 98 substituting 3,6'-dimethyl-[2,3'-bipyridine]-2'-carboxylic acid with 6-methyl-3-(1H-pyrazol-1-yl)picolinic acid. MS (ESI) mass calcd. for $C_{21}H_{21}FN_6O_2$, 408.2; m/z found 409.2 [M+H]$^+$. MP-119.2° C.

Example 105

(±)-(2-(((5-fluoropyridin-2-yl)oxy)methyl)-7-azabicyclo[2.2.1]heptan-7-yl)(5-methyl-2-(2H-1,2,3-triazol-2-yl)phenyl)methanone

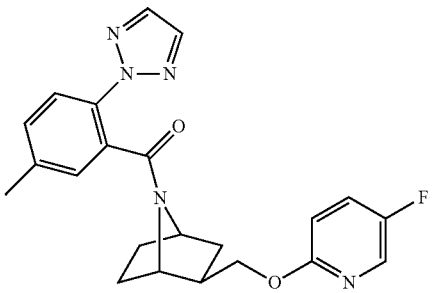 [SMILES: Cc1ccc(-n2nccn2)c(C(=O)N2C3CCC2C(COc2ccc(F)cn2)C3)c1]

Prepared analogous to Example 7 substituting 6-methyl-3-(2H-1,2,3-triazol-2-yl)picolinic acid with 5-methyl-2-(2H-1,2,3-triazol-2-yl)benzoic acid. (ESI) mass calcd. for $C_{22}H_{22}FN_5O_2$, 407.2; m/z found 408.2 [M+H]$^+$. $^1$H NMR (MeOD): 8.08-7.96 (m, 1H), 7.88 (s, 2H), 7.81-7.73 (m, 1H), 7.56-7.12 (m, 3H), 6.85-6.62 (m, 1H), 4.70-4.67 (m, 1H), 4.25-3.74 (m, 3H), 2.51-1.97 (m, 4H), 1.96-1.31 (m, 6H).

Example 106

(±)-(2,6-dimethoxyphenyl)(2-(((5-fluoropyridin-2-yl)oxy)methyl)-7-azabicyclo[2.2.1]heptan-7-yl)methanone

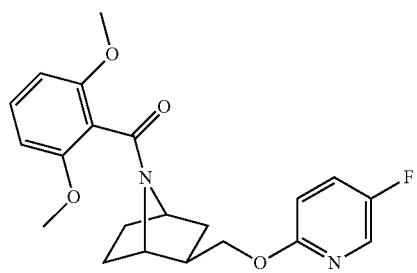 [SMILES: COc1cccc(OC)c1C(=O)N1C2CCC1C(COc1ccc(F)cn1)C2]

Prepared analogous to example 105 substituting 5-methyl-2-(2H-1,2,3-triazol-2-yl)benzoic acid with 2,6-dimethoxybenzoic acid. MS (ESI) mass calcd. for $C_{21}H_{23}FN_2O_4$, 386.2; m/z found 386.9 [M+H]$^+$. $^1$H NMR (MeOD): 8.02-7.93 (m, 1H), 7.57-7.40 (m, 1H), 7.39-7.21 (m, 1H), 6.87-6.63 (m, 2H), 6.62-6.38 (m, 1H), 4.83-4.65 (m, 1H), 4.49-4.07 (m, 1H), 4.07-3.52 (m, 8H), 2.48-2.09 (m, 1H), 2.06-1.07 (m, 6H).

Example 107

(±)-((3-fluoro-2-methoxyphenyl)(2-(((5-fluoropyridin-2-yl)oxy)methyl)-7-azabicyclo[2.2.1]heptan-7-yl)methanone

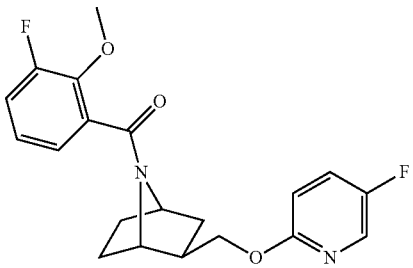 [SMILES: COc1c(F)cccc1C(=O)N1C2CCC1C(COc1ccc(F)cn1)C2]

Prepared analogous to example 105 substituting 5-methyl-2-(2H-1,2,3-triazol-2-yl)benzoic acid with 3-fluoro-2-methoxybenzoic acid. MS (ESI) mass calcd. for $C_{20}H_{20}F_2N_2O_3$, 374.1; m/z found 375.1 [M+H]$^+$. $^1$H NMR (MeOD): 8.01-7.90 (m, 1H), 7.56-7.38 (m, 1H), 7.28-7.06 (m, 2H), 7.02-6.53 (m, 2H), 4.82-4.66 (m, 1H), 4.50-3.73 (m, 6H), 2.85-2.22 (m, 1H), 2.21-1.10 (m, 6H).

Example 108

(±)-(2-(((5-fluoropyridin-2-yl)oxy)methyl)-7-azabicyclo[2.2.1]heptan-7-yl)(2-methoxy-6-(2H-1,2,3-triazol-2-yl)phenyl)methanone

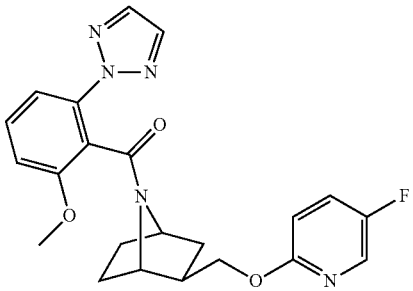 [SMILES: COc1cccc(-n2nccn2)c1C(=O)N1C2CCC1C(COc1ccc(F)cn1)C2]

Prepared analogous to example 105 substituting 5-methyl-2-(2H-1,2,3-triazol-2-yl)benzoic acid with 2-methoxy-6-(2H-1,2,3-triazol-2-yl)benzoic acid. MS (ESI) mass calcd. for $C_{22}H_{22}FN_5O_3$, 423.2; m/z found 424.2 [M+H]$^+$. $^1$H NMR (MeOD): 8.10-7.74 (m, 3H), 7.66-7.41 (m, 3H), 7.25-6.88 (m, 1H), 6.88-6.43 (m, 1H), 4.78-4.64 (m, 1H), 4.51-3.57 (m, 6H), 2.48-0.94 (m, 7H).

Example 109

(±)-(5-fluoro-2-(1H-pyrazol-5-yl)phenyl)(2-(((5-fluoropyridin-2-yl)oxy)methyl)-7-azabicyclo[2.2.1]heptan-7-yl)methanone

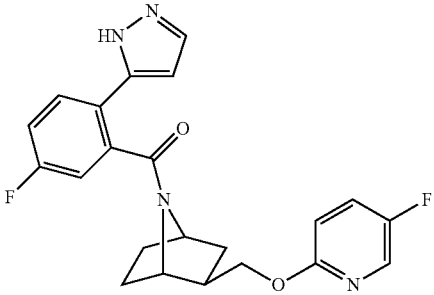 [SMILES: O=C(c1cc(F)ccc1-c1ccn[nH]1)N1C2CCC1C(COc1ccc(F)cn1)C2]

Prepared analogous to example 105 substituting 5-methyl-2-(2H-1,2,3-triazol-2-yl)benzoic acid with 5-fluoro-2-(1H-pyrazol-5-yl)benzoic acid. MS (ESI) mass calcd. for $C_{22}H_{20}F_2N_4O_2$, 410.2; m/z found 411.2 [M+H]$^+$. $^1$H NMR (MeOD): 8.11-7.90 (m, 1H), 7.80-7.59 (m, 2H), 7.58-7.40 (m, 1H), 7.36-6.94 (m, 2H), 6.88-6.47 (m, 2H), 4.78-4.58 (m, 1H), 4.41-3.47 (m, 3H), 2.69-0.60 (m, 8H).

Example 110

(±)-(2-(((5-fluoropyridin-2-yl)oxy)methyl)-7-azabicyclo[2.2.1]heptan-7-yl)(2-methyl-6-(2H-1,2,3-triazol-2-yl)phenyl)methanone

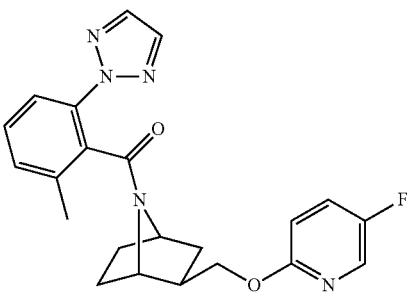 [SMILES: Cc1cccc(-n2nccn2)c1C(=O)N1C2CCC1C(COc1ccc(F)cn1)C2]

Prepared analogous to example 105 substituting 5-methyl-2-(2H-1,2,3-triazol-2-yl)benzoic acid with 2-methyl-6-(2H-1,2,3-triazol-2-yl)benzoic acid. MS (ESI) mass calcd. for $C_{22}H_{22}FN_5O_2$, 407.2; m/z found 408.2 [M+H]$^+$. $^1$H NMR (MeOD): 8.11-7.62 (m, 4H), 7.59-6.48 (m, 4H), 4.78-4.68 (m, 1H), 4.50-3.37 (m, 3H), 2.80-0.82 (m, 10H).

Example 111

(±)-(2-(((5-fluoropyridin-2-yl)oxy)methyl)-7-azabicyclo[2.2.1]heptan-7-yl)(6-methyl-3-(2H-1,2,3-triazol-2-yl)pyridin-2-yl)methanone

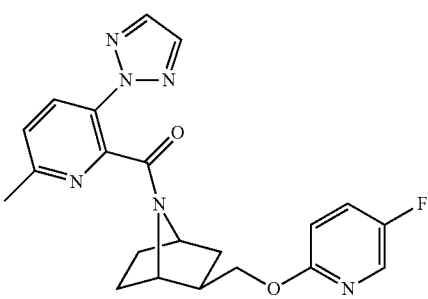

Prepared analogous to example 105 substituting 5-methyl-2-(2H-1,2,3-triazol-2-yl)benzoic acid with 6-methyl-3-(2H-1,2,3-triazol-2-yl)picolinic acid. MS (ESI) mass calcd. for $C_{21}H_{21}FN_6O_2$, 408.2; m/z found 409.2 [M+H]$^+$. $^1$H NMR (MeOD): 8.28-8.19 (m, 1H), 8.06-7.88 (m, 3H), 7.57-7.35 (m, 2H), 6.89-6.60 (m, 1H), 4.76-4.73 (m, 1H), 4.32-4.02 (m, 2H), 3.93-3.80 (m, 1H), 2.70-2.20 (m, 4H), 2.05-1.42 (m, 6H).

Example 112

(±)-(5-chloro-3-(2H-1,2,3-triazol-2-yl)pyridin-2-yl)
(2-(((5-fluoropyridin-2-yl)oxy)methyl)-7-azabicyclo
[2.2.1]heptan-7-yl)methanone

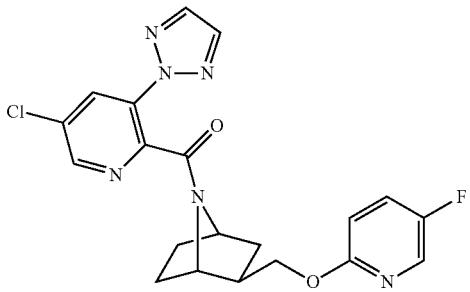 [SMILES: O=C(c1ncc(Cl)cc1-n1nccn1)N1C2CCC1C(COc1ccc(F)cn1)C2]

Prepared analogous to example 105 substituting 5-methyl-2-(2H-1,2,3-triazol-2-yl)benzoic acid with sodium 5-chloro-3-(2H-1,2,3-triazol-2-yl)picolinate. MS (ESI) mass calcd. for $C_{20}H_{18}ClFN_6O_2$, 428.1; m/z found 429.1 [M+H]$^+$. $^1$H NMR (MeOD): 8.74-8.17 (m, 4H), 8.13-7.96 (m, 2H), 7.59-7.46 (m, 1H), 4.90-4.18 (m, 3H), 3.99 (s, 1H), 2.98-2.39 (m, 1H), 2.10-1.19 (m, 6H).

Example 113

(±)-(2-(((5-fluoropyridin-2-yl)oxy)methyl)-7-azabi-
cyclo[2.2.1]heptan-7-yl)(5-methoxy-3-(2H-1,2,3-
triazol-2-yl)pyridin-2-yl)methanone

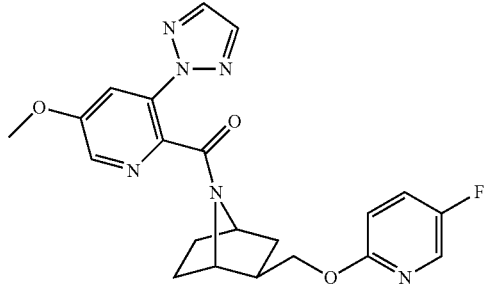

Prepared analogous to example 105 substituting 5-methyl-2-(2H-1,2,3-triazol-2-yl)benzoic acid with sodium 5-methoxy-3-(2H-1,2,3-triazol-2-yl)picolinate. MS (ESI) mass calcd. for $C_{21}H_{21}FN_6O_3$, 424.2; m/z found 425.1 [M+H]$^+$. $^1$H NMR (MeOD): 8.37-7.79 (m, 5H), 7.56-7.40 (m, 1H), 6.87-6.59 (m, 1H), 4.73 (s, 1H), 4.30-3.82 (m, 6H), 2.48-2.11 (m, 1H), 2.07-1.42 (m, 6H).

Example 114

(±)-(2-(((5-fluoropyridin-2-yl)oxy)methyl)-7-azabi-
cyclo[2.2.1]heptan-7-yl)(5-methoxy-2-(2H-1,2,3-
triazol-2-yl)phenyl)methanone

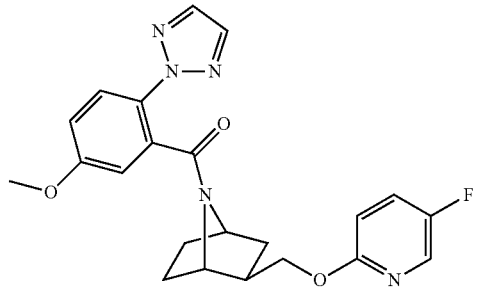 [SMILES: COc1ccc(-n2nccn2)c(C(=O)N2C3CCC2C(COc2ccc(F)cn2)C3)c1]

Prepared analogous to example 105 substituting 5-methyl-2-(2H-1,2,3-triazol-2-yl)benzoic acid with sodium 5-methoxy-2-(2H-1,2,3-triazol-2-yl)benzoate. MS (ESI) mass calcd. for $C_{22}H_{22}FN_5O_3$, 423.2; m/z found 424.2 [M+H]$^+$. $^1$H NMR (MeOD): 8.18-7.68 (m, 4H), 7.58-7.38 (m, 1H), 7.24-6.85 (m, 2H), 6.85-6.57 (m, 1H), 4.78-4.55 (m, 1H), 4.23-3.40 (m, 6H), 2.77-2.18 (m, 1H), 2.13-1.11 (m, 6H).

Example 115

(±)-(2-fluoro-6-(2H-1,2,3-triazol-2-yl)phenyl)(2-
(((5-fluoropyridin-2-yl)oxy)methyl)-7-azabicyclo
[2.2.1]heptan-7-yl)methanone

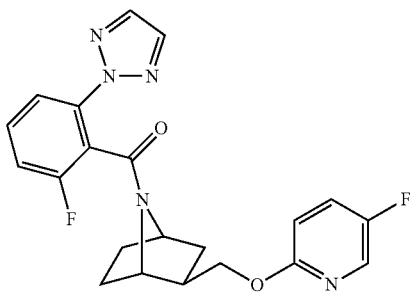

Prepared analogous to example 105 substituting 5-methyl-2-(2H-1,2,3-triazol-2-yl)benzoic acid with 2-fluoro-6-(2H-1,2,3-triazol-2-yl)benzoic acid. MS (ESI) mass calcd. for $C_{21}H_{19}F_2N_5O_2$, 411.2; m/z found 412.2 [M+H]$^+$. $^1$H NMR (MeOD): 8.11-7.71 (m, 4H), 7.69-7.24 (m, 3H), 6.98-6.43 (m, 1H), 4.83-4.67 (m, 1H), 4.53-3.34 (m, 3H), 2.50-0.96 (m, 7H).

Example 116

(±)-(4-fluoro-2-(2H-1,2,3-triazol-2-yl)phenyl)(2-
(((5-fluoropyridin-2-yl)oxy)methyl)-7-azabicyclo
[2.2.1]heptan-7-yl)methanone

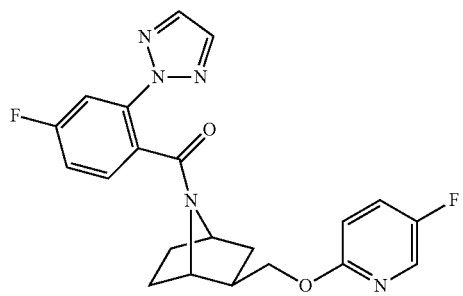 [SMILES: O=C(c1ccc(F)cc1-n1nccn1)N1C2CCC1C(COc1ccc(F)cn1)C2]

Prepared analogous to example 105 substituting 5-methyl-2-(2H-1,2,3-triazol-2-yl)benzoic acid with 4-fluoro-2-(2H-1,2,3-triazol-2-yl)benzoic acid. MS (ESI) mass calcd. for $C_{21}H_{19}F_2N_5O_2$, 411.2; m/z found 412.2 [M+H]$^+$. $^1$H NMR (MeOD): 8.11-7.71 (m, 4H), 7.69-7.24 (m, 3H), 6.98-6.43 (m, 1H), 4.83-4.67 (m, 1H), 4.53-3.34 (m, 3H), 2.50-0.96 (m, 7H).

Example 117

(±)-(3-fluoro-2-(2H-1,2,3-triazol-2-yl)phenyl)(2-(((5-fluoropyridin-2-yl)oxy)methyl)-7-azabicyclo[2.2.1]heptan-7-yl)methanone

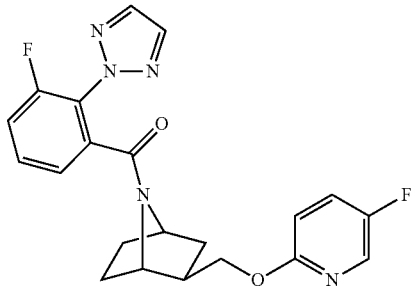

Prepared analogous to example 105 substituting 5-methyl-2-(2H-1,2,3-triazol-2-yl)benzoic acid with 3-fluoro-2-(2H-1,2,3-triazol-2-yl)benzoic acid. MS (ESI) mass calcd. for $C_{21}H_{19}F_2N_5O_2$, 411.2; m/z found 412.2 [M+H]$^+$. $^1$H NMR (MeOD): 8.14-7.85 (m, 3H), 7.70-7.18 (m, 4H), 6.81-6.65 (m, 1H), 4.67-4.32 (m, 1H), 4.24-3.79 (m, 3H), 2.42-2.24 (m, 1H), 1.97-1.32 (m, 6H).

Example 118

(±)-(3-ethoxy-6-methylpyridin-2-yl)(2-(((5-fluoropyridin-2-yl)oxy)methyl)-7-azabicyclo[2.2.1]heptan-7-yl)methanone

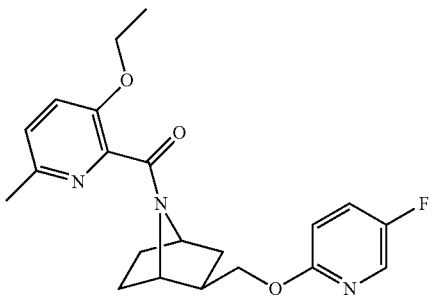 [SMILES: CCOc1ccc(C)nc1C(=O)N1C2CCC1C(COc1ccc(F)cn1)C2]

Prepared analogous to example 105 substituting 5-methyl-2-(2H-1,2,3-triazol-2-yl)benzoic acid with 3-ethoxy-6-methylpicolinic acid. MS (ESI) mass calcd. for $C_{21}H_{24}FN_3O_3$, 385.2; m/z found 385.9 [M+H]$^+$. $^1$H NMR (MeOD): 8.23-7.90 (m, 1H), 7.57-7.11 (m, 3H), 6.87-6.53 (m, 1H), 4.85-4.69 (m, 1H), 4.51-3.56 (m, 5H), 2.84-2.09 (m, 4H), 2.06-1.49 (m, 5H), 1.47-1.05 (m, 4H).

Example 119

(±)-(2-(((5-fluoropyridin-2-yl)oxy)methyl)-7-azabicyclo[2.2.1]heptan-7-yl)(4-methoxy-2-(2H-1,2,3-triazol-2-yl)phenyl)methanone

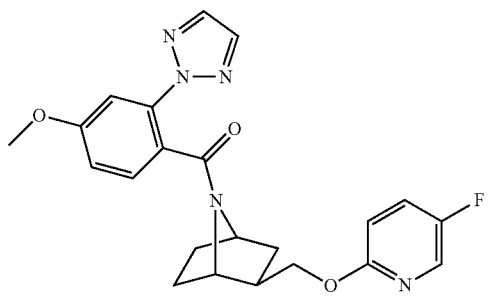

Prepared analogous to example 105 substituting 5-methyl-2-(2H-1,2,3-triazol-2-yl)benzoic acid with 4-methoxy-2-(2H-1,2,3-triazol-2-yl)benzoic acid. MS (ESI) mass calcd. for $C_{22}H_{22}FN_5O_3$, 423.2; m/z found 424.2 [M+H]$^+$. $^1$H NMR (MeOD): 8.12-7.81 (m, 3H), 7.58-7.22 (m, 3H), 7.15-6.57 (m, 2H), 4.75-4.58 (m, 1H), 4.48-3.74 (m, 6H), 2.83-2.08 (m, 1H), 2.02-0.98 (m, 6H).

Example 120

(±)-(5-chloro-2-(2H-1,2,3-triazol-2-yl)phenyl)(2-(((5-fluoropyridin-2-yl)oxy)methyl)-7-azabicyclo[2.2.1]heptan-7-yl)methanone

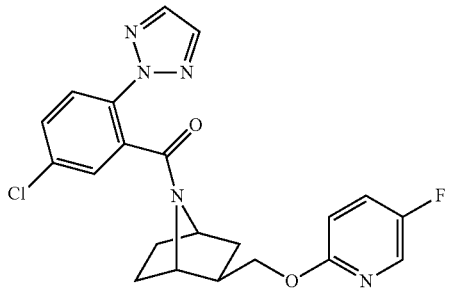 [SMILES: O=C(c1cc(Cl)ccc1-n1nccn1)N1C2CCC1C(COc1ccc(F)cn1)C2]

Prepared analogous to example 105 substituting 5-methyl-2-(2H-1,2,3-triazol-2-yl)benzoic acid with 5-chloro-2-(2H-1,2,3-triazol-2-yl)benzoic acid. MS (ESI) mass calcd. for $C_{21}H_{19}ClFN_5O_3$, 427.2; m/z found 428.2 [M+H]$^+$. $^1$H NMR (MeOD): 8.13-7.77 (m, 4H), 7.70-7.31 (m, 3H), 6.87-6.60 (m, 1H), 4.80-4.60 (m, 1H), 4.51-3.67 (m, 3H), 2.84-2.22 (m, 1H), 2.07-1.11 (m, 6H).

Example 121

(±)-(2-(((5-fluoropyridin-2-yl)oxy)methyl)-7-azabicyclo[2.2.1]heptan-7-yl)(4-methyl-2-(2H-1,2,3-triazol-2-yl)phenyl)methanone

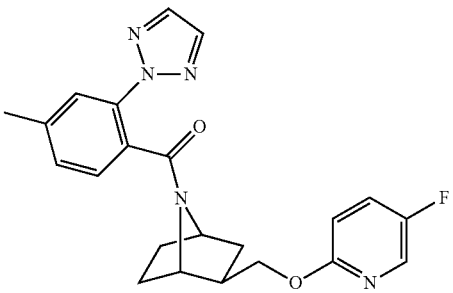 [SMILES: Cc1ccc(C(=O)N2C3CCC2C(COc2ccc(F)cn2)C3)c(-n2nccn2)c1]

Prepared analogous to example 105 substituting 5-methyl-2-(2H-1,2,3-triazol-2-yl)benzoic acid with 4-methyl-2-(2H-1,2,3-triazol-2-yl)benzoic acid. MS (ESI) mass calcd. for $C_{22}H_{22}FN_5O_2$, 407.2; m/z found 408.2 [M+H]$^+$. $^1$H NMR (MeOD): 8.10-7.84 (m, 3H), 7.76-7.69 (m, 1H), 7.56-6.87 (m, 3H), 6.87-6.53 (m, 1H), 4.75-4.59 (m, 1H), 4.49-3.65 (m, 3H), 2.80-2.09 (m, 4H), 2.01-1.00 (m, 6H).

Example 122

(±)-(2-(((5-fluoropyridin-2-yl)oxy)methyl)-7-azabi-cyclo[2.2.1]heptan-7-yl)(4-methyl-2-(pyrimidin-2-yl)phenyl)methanone

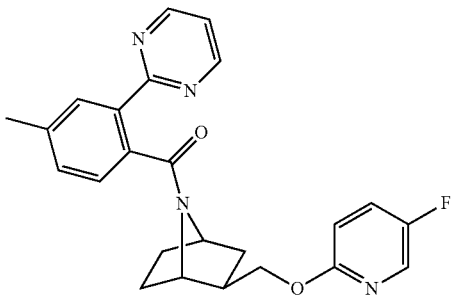 [SMILES: Cc1ccc(C(=O)N2C3CCC2C(COc2ccc(F)cn2)C3)c(-c2ncccn2)c1]

Prepared analogous to example 105 substituting 5-methyl-2-(2H-1,2,3-triazol-2-yl)benzoic acid with 4-methyl-2-(pyrimidin-2-yl)benzoic acid. MS (ESI) mass calcd. for $C_{24}H_{23}FN_4O_2$, 418.2; m/z found 419.2 [M+H]$^+$. $^1$H NMR (MeOD): 8.94-8.89 (m, 1H), 8.84-8.81 (m, 1H), 8.08-7.94 (m, 2H), 7.60-7.46 (m, 1H), 7.45-7.33 (m, 2H), 7.22-6.99 (m, 1H), 6.90-6.58 (m, 1H), 4.78-4.62 (m, 1H), 4.52-3.78 (m, 3H), 2.73-2.19 (m, 4H), 2.07-1.05 (m, 6H).

Example 123

(±)-(2-(((5-fluoropyridin-2-yl)oxy)methyl)-7-azabi-cyclo[2.2.1]heptan-7-yl)(2-methyl-6-(pyrimidin-2-yl)phenyl)methanone

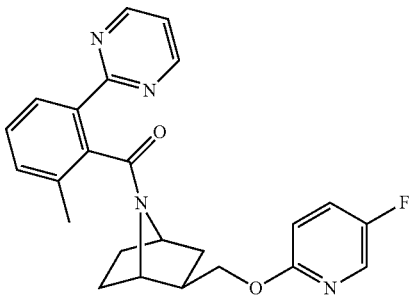 [SMILES: Cc1cccc(-c2ncccn2)c1C(=O)N1C2CCC1C(COc1ccc(F)cn1)C2]

Prepared analogous to example 105 substituting 5-methyl-2-(2H-1,2,3-triazol-2-yl)benzoic acid with 2-methyl-6-(pyrimidin-2-yl)benzoic acid. MS (ESI) mass calcd. for $C_{24}H_{23}FN_4O_2$, 418.2; m/z found 419.2 [M+H]$^+$. $^1$H NMR (MeOD): 8.99-8.63 (m, 2H), 8.14-7.70 (m, 2H), 7.61-7.27 (m, 4H), 7.15-6.45 (m, 1H), 4.86-4.65 (m, 1H), 4.55-3.44 (m, 3H), 2.53-2.35 (m, 3H), 2.34-0.78 (m, 7H).

Example 124

(±)-(3-fluoro-2-(pyrimidin-2-yl)phenyl)(-2-(((5-fluoropyridin-2-yl)oxy)methyl)-7-azabicyclo[2.2.1]heptan-7-yl)methanone

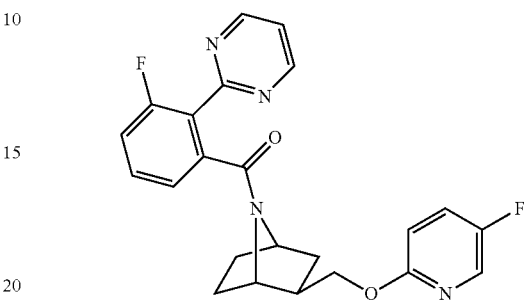

Prepared analogous to example 105 substituting 5-methyl-2-(2H-1,2,3-triazol-2-yl)benzoic acid with 3-fluoro-2-(pyrimidin-2-yl)benzoic acid. MS (ESI) mass calcd. for $C_{25}H_{20}F_2N_4O_2$, 422.2; m/z found 422.8 [M+H]$^+$. $^1$H NMR (MeOD): 9.03-8.62 (m, 2H), 8.19-7.82 (m, 1H), 7.67-7.11 (m, 5H), 6.85-6.62 (m, 1H), 4.54 (s, 1H), 4.26-3.76 (m, 3H), 2.33 (s, 1H), 2.01-1.32 (m, 6H).

Example 125

(±)-(2-(((5-fluoropyridin-2-yl)oxy)methyl)-7-azabi-cyclo[2.2.1]heptan-7-yl)(3-methyl-2-(2H-1,2,3-triazol-2-yl)phenyl)methanone

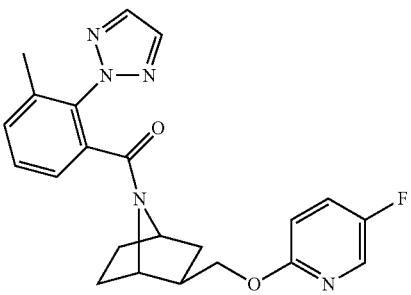

Prepared analogous to example 105 substituting 5-methyl-2-(2H-1,2,3-triazol-2-yl)benzoic acid with 3-methyl-2-(2H-1,2,3-triazol-2-yl)benzoic acid. MS (ESI) mass calcd. for $C_{22}H_{22}FN_5O_2$, 407.2; m/z found 408.2 [M+H]$^+$. $^1$H NMR (MeOD): 8.05-7.95 (m, 1H), 7.93-7.84 (m, 2H), 7.57-7.05 (m, 4H), 6.81-6.65 (m, 1H), 4.61-3.98 (m, 2H), 3.97-3.75 (m, 2H), 2.38-2.23 (m, 1H), 2.19-2.14 (m, 3H), 1.97-1.32 (m, 6H).

Example 126

(±)-(2-(((5-fluoropyridin-2-yl)oxy)methyl)-7-azabi-cyclo[2.2.1]heptan-7-yl)(5-(hydroxymethyl)-2-(2H-1,2,3-triazol-2-yl)phenyl)methanone

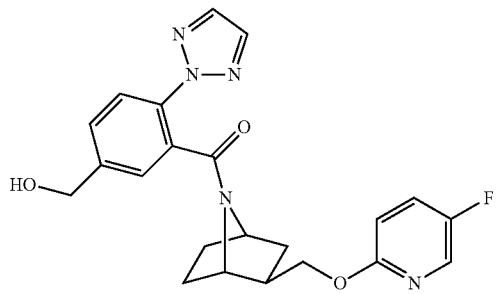 [SMILES: O=C(c1cc(CO)ccc1-n1nccn1)N1C2CCC1C(COc1ccc(F)cn1)C2]

Step A: (±)-(5-bromo-2-(2H-1,2,3-triazol-2-yl)phenyl)(-2-(((5-fluoropyridin-2-yl)oxy)methyl)-7-azabi-cyclo[2.2.1]heptan-7-yl)methanone Prepared analogous to example 105 substituting 5-methyl-2-(2H-1,2,3-triazol-2-yl)benzoic acid with 5-bromo-2-(2H-1,2,3-triazol-2-yl)benzoic acid.

Step B: (±)-methyl 3-(-2-(((5-fluoropyridin-2-yl)oxy)methyl)-7-azabicyclo[2.2.1]heptane-7-carbonyl)-4-(2H-1,2,3-triazol-2-yl)benzoate The title compound of step A (100 g, 0.2 mmol) and Pd(dppf)Cl$_2$ (35 mg) in MeOH (10 mL) was heated to 120° C. for 24 h in a sealed tube under an atmosphere of CO. The reaction was allowed to cool to rt and filtered. The filtrate was concentrated and purified via preparative TLC to give the title compound (20 g, 21%).

Step C: (±)-(2-(((5-fluoropyridin-2-yl)oxy)methyl)-7-azabicyclo[2.2.1]heptan-7-yl)(5-(hydroxymethyl)-2-(2H-1,2,3-triazol-2-yl)phenyl)methanone To the title compound of step B (40 g, 0.1 mmol)) in MeOH (0.2 mL) and THF (6 mL) at 0° C. was added NaBH$_4$ (4 mg, 0.1 mmol). After stirring overnight at rt, the reaction was concentrated and purified directly via silica gel chromatography (EtOAc in petroleum ethers) to give the title compound. MS (ESI) mass calcd. for C$_{21}$H$_{21}$FN$_6$O$_2$, 408.2; m/z found 409.2 [M+H]$^+$. $^1$H NMR (MeOD): 8.07-7.82 (m, 4H), 7.66-7.29 (m, 3H), 6.85-6.60 (m, 1H), 4.70 (d, J=8.7 Hz, 2H), 4.50-3.73 (m, 4H), 2.43-2.20 (m, 1H), 2.04-1.28 (m, 6H).

Example 127

(±)-(2-(3-methyl-1,2,4-oxadiazol-5-yl)phenyl)(2-((pyridin-2-yloxy)methyl)-7-azabicyclo[2.2.1]heptan-7-yl)methanone

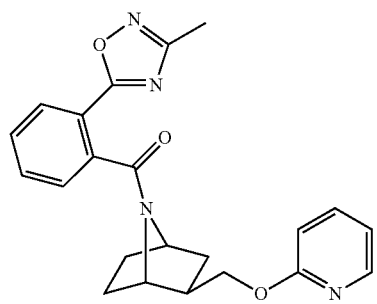 [SMILES: Cc1noc(-c2ccccc2C(=O)N2C3CCC2C(COc2ccccn2)C3)n1]

Prepared analogous to Example 2 substituting intermediate A-9 with 2-(3-methyl-1,2,4-oxadiazol-5-yl)benzoic acid. MS (ESI) mass calcd. for C$_{22}$H$_{22}$N$_4$O$_3$, 390.2; m/z found 391.1 [M+H]$^+$. $^1$H NMR (MeOD): 8.12-8.00 (m, 2H), 7.75-7.58 (m, 2H), 7.55-7.49 (m, 1H), 7.38-7.28 (m, 1H), 6.95-6.91 (m, 1H), 6.85-6.55 (m, 1H), 4.81-4.78 (m, 1H), 4.27-4.14 (m, 1H), 4.01-3.97 (m, 1H), 3.77-3.75 (m, 1H), 2.44-2.26 (m, 4H), 2.10-1.95 (m, 1H), 1.87-1.62 (m, 3H), 1.56-1.46 (m, 2H).

Example 128

(±)-(6-methyl-2-(2H-1,2,3-triazol-2-yl)pyridin-3-yl)(2-((pyridin-2-yloxy)methyl)-7-azabicyclo[2.2.1]heptan-7-yl)methanone

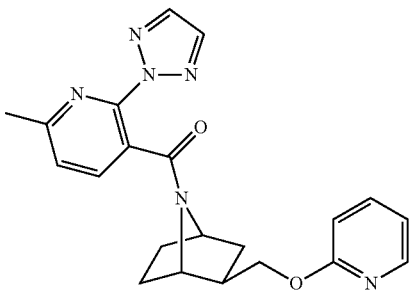 [SMILES: Cc1ccc(C(=O)N2C3CCC2C(COc2ccccn2)C3)c(-n2nccn2)n1]

Prepared analogous to Example 127 substituting 2-(3-methyl-1,2,4-oxadiazol-5-yl)benzoic acid with 6-methyl-2-(2H-1,2,3-triazol-2-yl)nicotinic acid. MS (ESI) mass calcd. for C$_{21}$H$_{22}$N$_6$O$_2$, 390.2; m/z found 391.2 [M+H]$^+$. $^1$H NMR (MeOD): 8.15-8.09 (m, 1H), 7.99 (s, 2H), 7.91-7.71 (m, 1H), 7.69-6.92 (m, 3H), 6.83-6.59 (m, 1H), 4.71-4.68 (m, 1H), 4.22-4.09 (m, 1H), 4.01-3.76 (m, 2H), 2.64-2.52 (m, 3H), 2.43-2.23 (m, 1H), 2.00-1.36 (m, 6H).

Example 129

(±)-(3-fluoro-2-(2H-1,2,3-triazol-2-yl)phenyl)(2-((pyridin-2-yloxy)methyl)-7-azabicyclo[2.2.1]heptan-7-yl)methanone

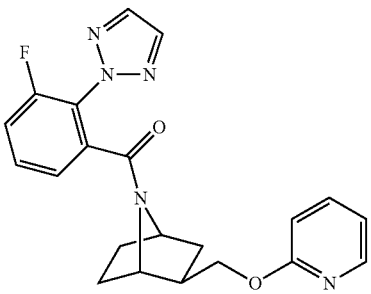 [SMILES: O=C(c1cccc(F)c1-n1nccn1)N1C2CCC1C(COc1ccccn1)C2]

Prepared analogous to Example 127 substituting 2-(3-methyl-1,2,4-oxadiazol-5-yl)benzoic acid with 3-fluoro-2-(2H-1,2,3-triazol-2-yl)benzoic acid. MS (ESI) mass calcd. for C$_{21}$H$_{20}$FN$_5$O$_2$, 393.2; m/z found 394.0 [M+H]$^+$. $^1$H NMR (MeOD): 8.14-8.12 (m, 1H), 7.95-7.93 (m, 2H), 7.69-7.46 (m, 2H), 7.40-7.31 (m, 1H), 7.22-7.12 (m, 1H), 6.99-6.91 (m, 1H), 6.80-6.66 (m, 1H), 4.57-4.56 (m, 1H), 4.04-3.88 (m, 3H), 2.38-2.27 (m, 1H), 1.85-1.43 (m, 6H).

Example 130

(±)-(6-methyl-2-(1H-1,2,3-triazol-1-yl)pyridin-3-yl)(2-((pyridin-2-yloxy)methyl)-7-azabicyclo[2.2.1]heptan-7-yl)methanone

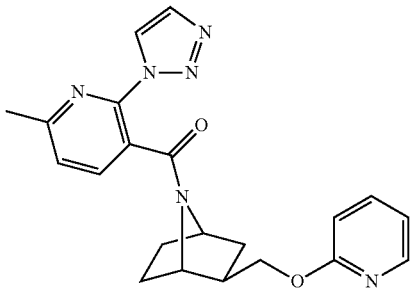 [SMILES: Cc1ccc(C(=O)N2C3CCC2C(COc2ccccn2)C3)c(-n2ccnn2)n1]

Prepared analogous to Example 127 substituting 2-(3-methyl-1,2,4-oxadiazol-5-yl)benzoic acid with 6-methyl-2-(1H-1,2,3-triazol-1-yl)nicotinic acid. MS (ESI) mass calcd. for $C_{21}H_{22}N_6O_2$, 390.2; m/z found 391.2 $[M+H]^+$. $^1$H NMR (MeOD): 8.62-8.61 (m, 1H), 8.12-8.09 (m, 1H), 7.99-7.73 (m, 2H), 7.71-7.62 (m, 1H), 7.50-6.91 (m, 2H), 6.87-6.61 (m, 1H), 4.74-4.71 (m, 1H), 4.17-3.79 (m, 3H), 2.64-2.53 (m, 3H), 2.46-2.26 (m, 1H), 2.06-1.90 (m, 1H), 1.83-1.38 (m, 5H).

Example 131

(±)-(6-methyl-2-(2H-1,2,3-triazol-2-yl)pyridin-3-yl)(2-(((4-(trifluoromethyl)pyrimidin-2-yl)oxy)methyl)-7-azabicyclo[2.2.1]heptan-7-yl)methanone

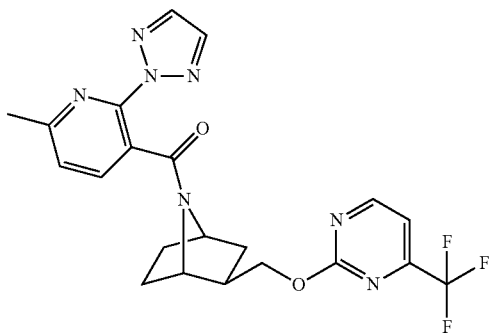

Step A: (±)-tert-butyl 2-(((4-(trifluoromethyl)pyrimidin-2-yl)oxy)methyl)-7-azabicyclo[2.2.1]heptane-7-carboxylate To intermediate B-10 (500 g, 2.2 mmol) in THF (5 mL) at 0° C. was added NaH (6.6 mmol). After 30 min at rt, 2-chloro-4-(trifluoromethyl)pyrimidine (1.8 g, 9.9 mmol). The flask was then heated to 50° C. in an oil bath. After 3 h, H$_2$O was added and the reaction extracted with EtOAc (2×). Purification via silica gel chromatography (20% EtOAc in petroleum ethers) gave the title compound (752 g, 92%).

Step B: (±)-2-(((4-(trifluoromethyl)pyrimidin-2-yl)oxy)methyl)-7-azabicyclo[2.2.1]heptane hydrochloride To the title compound of step A (752 g, 2 mmol) in MeOH (6 mL) was added HCl.

Step C: (±)-tert-butyl 2-(((4-(trifluoromethyl)pyrimidin-2-yl)oxy)methyl)-7-azabicyclo[2.2.1]heptane-7-carboxylate Prepared analogous to example 127 substituting 2-(3-methyl-1,2,4-oxadiazol-5-yl)benzoic acid with 6-methyl-2-(2H-1,2,3-triazol-2-yl)nicotinic acid with the title compound of step B. MS (ESI) mass calcd. for $C_{21}H_{20}F_3N_7O_2$, 459.2; m/z found 460.2 $[M+H]^+$. $^1$H NMR (MeOD): 8.89-8.82 (m, 1H), 8.02-7.82 (m, 3H), 7.48-7.14 (m, 2H), 4.75-4.71 (m, 1H), 4.44-4.07 (m, 2H), 3.91-3.84 (m, 1H), 2.64-2.56 (m, 3H), 2.48-2.30 (m, 1H), 2.02-1.43 (m, 6H).

Example 132

(±)-(6-methyl-2-(1H-1,2,3-triazol-1-yl)pyridin-3-yl)(2-(((4-(trifluoromethyl)pyrimidin-2-yl)oxy)methyl)-7-azabicyclo[2.2.1]heptan-7-yl)methanone

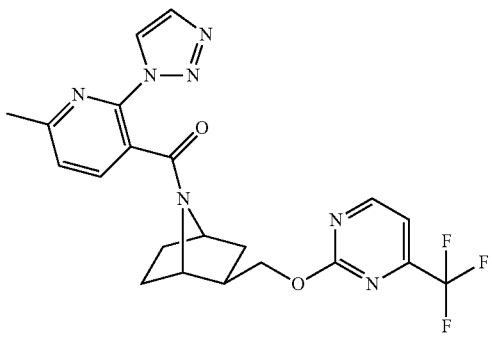

Prepared analogous to Example 131 substituting 6-methyl-2-(2H-1,2,3-triazol-2-yl)nicotinic acid with 6-methyl-2-(1H-1,2,3-triazol-1-yl)nicotinic acid. MS (ESI) mass calcd. for $C_{21}H_{20}F_3N_7O_2$, 459.2; m/z found 460.2 $[M+H]^+$. $^1$H NMR (MeOD): 8.86-8.83 (m, 1H), 8.63-8.61 (m, 1H), 8.03-7.84 (m, 2H), 7.49-7.15 (m, 2H), 4.76-4.72 (m, 1H), 4.41-4.31 (m, 1H), 4.27-4.04 (m, 1H), 3.90-3.84 (m, 1H), 2.63-2.54 (m, 3H), 2.47-2.30 (m, 1H), 2.03-1.43 (m, 6H).

Example 133

(±)-(2-(3-methyl-1,2,4-oxadiazol-5-yl)phenyl)(2-(((4-(trifluoromethyl)pyrimidin-2-yl)oxy)methyl)-7-azabicyclo[2.2.1]heptan-7-yl)methanone

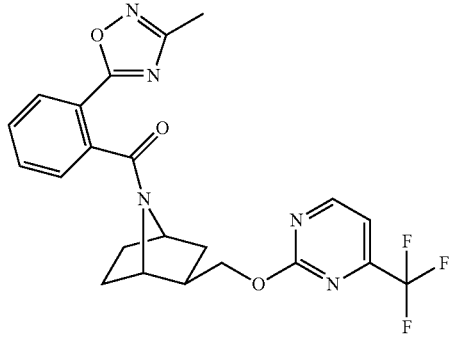 [SMILES: Cc1noc(-c2ccccc2C(=O)N2C3CCC2C(COc2nccc(C(F)(F)F)n2)C3)n1]

Prepared analogous to Example 131 substituting 6-methyl-2-(2H-1,2,3-triazol-2-yl)nicotinic acid with 2-(3-methyl-1,2,4-oxadiazol-5-yl)benzoic acid. MS (ESI) mass calcd. for $C_{22}H_{20}F_3N_5O_2$, 459.2; m/z found 460.2 [M+H]$^+$. $^1$H NMR (MeOD): 8.88-8.80 (m, 1H), 8.08-8.00 (m, 1H), 7.74-7.62 (m, 1H), 7.63-7.51 (m, 1H), 7.48-7.37 (m, 2H), 4.83-4.80 (m, 1H), 4.49-4.33 (m, 1H), 4.23-4.11 (m, 1H), 3.81-3.77 (m, 1H), 2.53-2.36 (m, 4H), 2.07-2.98 (m, 1H), 1.90-1.51 (m, 5H).

Example 134

(±)-(3-fluoro-2-(2H-1,2,3-triazol-2-yl)phenyl)(2-(((4-(trifluoromethyl)pyrimidin-2-yl)oxy)methyl)-7-azabicyclo[2.2.1]heptan-7-yl)methanone

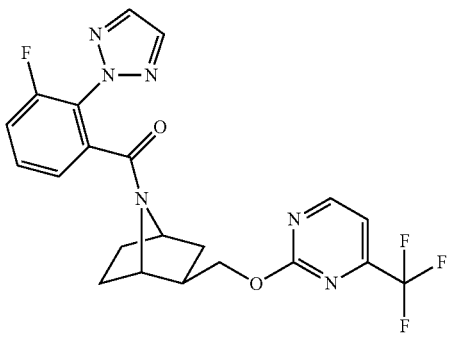 [SMILES: O=C(c1cccc(F)c1-n1nccn1)N1C2CCC1C(COc1nccc(C(F)(F)F)n1)C2]

Prepared analogous to Example 131 substituting 6-methyl-2-(2H-1,2,3-triazol-2-yl)nicotinic acid with 3-fluoro-2-(2H-1,2,3-triazol-2-yl)benzoic acid. MS (ESI) mass calcd. for $C_{21}H_{18}F_4N_6O_2$, 462.2; m/z found 463.2 [M+H]$^+$. $^1$H NMR (MeOD): 8.89-8.84 (m, 1H), 7.96-7.94 (m, 2H), 7.69-7.28 (m, 4H), 4.61-4.58 (m, 1H), 4.29-4.06 (m, 2H), 3.97-3.93 (m, 1H), 2.46-2.37 (m, 1H), 1.88-1.40 (m, 6H).

Example 135

(±)-(6-methyl-2-(2H-1,2,3-triazol-2-yl)pyridin-3-yl)(2-(((5-methylpyridin-2-yl)oxy)methyl)-7-azabicyclo[2.2.1]heptan-7-yl)methanone

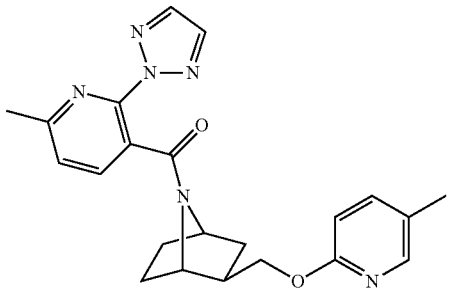

Prepared analogous to Example 131 substituting 2-chloro-4-(trifluoromethyl)pyrimidine with 2-chloro-5-methylpyridine. MS (ESI) mass calcd. for $C_{22}H_{24}N_6O_2$, 404.2; m/z found 405.2 [M+H]$^+$. $^1$H NMR (MeOD): 7.99-7.71 (m, 4H), 7.51-7.00 (m, 2H), 6.73-6.50 (m, 1H), 4.69 (d, J=3.6 Hz, 1H), 4.17-4.04 (m, 1H), 3.96-3.72 (m, 2H), 2.64-2.53 (m, 3H), 2.43-2.20 (m, 4H), 2.03-1.35 (m, 6H).

Example 136

(±)-(6-methyl-2-(1H-1,2,3-triazol-1-yl)pyridin-3-yl)(2-(((5-methylpyridin-2-yl)oxy)methyl)-7-azabicyclo[2.2.1]heptan-7-yl)methanone

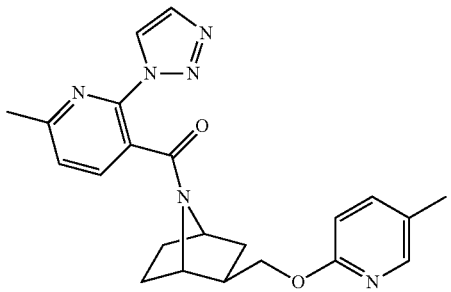

Prepared analogous to Example 135 substituting 6-methyl-2-(2H-1,2,3-triazol-2-yl)nicotinic acid with 6-methyl-2-(1H-1,2,3-triazol-1-yl)nicotinic acid. MS (ESI) mass calcd. for $C_{22}H_{24}N_6O_2$, 404.2; m/z found 405.2 [M+H]$^+$. $^1$H NMR (MeOD): 8.62-8.55 (m, 1H), 8.19-7.88 (m, 3H), 7.75-7.47 (m, 2H), 7.05-6.52 (m, 1H), 4.72-4.71 (m, 1H), 4.08-4.02 (m, 1H), 3.98-3.74 (m, 2H), 2.64-2.53 (m, 3H), 2.37-2.24 (m, 4H), 1.96 (brs, 1H), 1.82-1.35 (m, 5H).

Example 137

(±)-(2-(3-methyl-1,2,4-oxadiazol-5-yl)phenyl)(2-(((5-methylpyridin-2-yl)oxy)methyl)-7-azabicyclo[2.2.1]heptan-7-yl)methanone

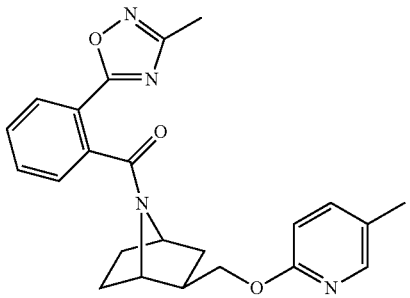 [SMILES: Cc1ccc(OCC2CC3CCC2N3C(=O)c2ccccc2-c2nc(C)no2)nc1]

Prepared analogous to Example 135 substituting 6-methyl-2-(2H-1,2,3-triazol-2-yl)nicotinic acid with 2-(3-methyl-1,2,4-oxadiazol-5-yl)benzoic acid. MS (ESI) mass calcd. for $C_{23}H_{24}N_4O$, 404.2; m/z found 405.2 [M+H]$^+$. $^1$H NMR (MeOD): 8.09-8.00 (m, 1H), 7.92-7.88 (m, 1H), 7.75-7.63 (m, 1H), 7.55-7.43 (m, 2H), 7.38-7.29 (m, 1H), 6.76-6.47 (m, 1H), 4.81-4.77 (m, 1H), 4.22-4.09 (m, 1H), 3.95 (d, J=8.1 Hz, 1H), 3.76-3.74 (m, 1H), 2.44-2.20 (m, 7H), 2.07-1.97 (m, 1H), 1.86-1.62 (m, 3H), 1.55-1.42 (m, 2H).

Example 138

(±)-(3-fluoro-2-(2H-1,2,3-triazol-2-yl)phenyl)(2-(((5-methylpyridin-2-yl)oxy)methyl)-7-azabicyclo[2.2.1]heptan-7-yl)methanone

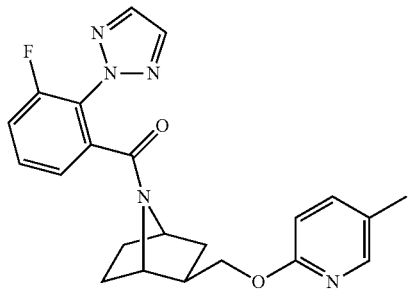 [SMILES: Cc1ccc(OCC2CC3CCC2N3C(=O)c2cccc(F)c2-n2nccn2)nc1]

Prepared analogous to Example 135 substituting 6-methyl-2-(2H-1,2,3-triazol-2-yl)nicotinic acid with 3-fluoro-2-(2H-1,2,3-triazol-2-yl)benzoic acid. MS (ESI) mass calcd. for $C_{22}H_{22}FN_5O_2$, 407.2; m/z found 408.2 [M+H]$^+$. $^1$H NMR (MeOD): 7.96-7.93 (m, 3H), 7.69-7.49 (m, 2H), 7.40-7.33 (m, 1H), 7.22-7.13 (m, 1H), 6.71-6.58 (m, 1H), 4.58-4.55 (m, 1H), 4.02-3.83 (m, 3H), 2.37-2.23 (m, 4H), 1.85-1.41 (m, 6H).

Example 139

(±)-(6-methyl-2-(2H-1,2,3-triazol-2-yl)pyridin-3-yl)(2-(((6-methylpyridin-2-yl)oxy)methyl)-7-azabicyclo[2.2.1]heptan-7-yl)methanone

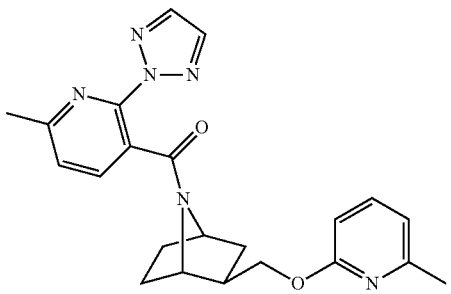

Prepared analogous to Example 135 substituting 2-chloro-4-(trifluoromethyl)pyrimidine with 2-chloro-6-methylpyridine. MS (ESI) mass calcd. for $C_{22}H_{24}N_6O_2$, 404.2; m/z found 405.2 [M+H]$^+$. $^1$H NMR (MeOD): 7.99 (s, 2H), 7.91-7.69 (m, 1H), 7.56-6.77 (m, 3H), 6.60-6.38 (m, 1H), 4.70-4.69 (m, 1H), 4.21-4.05 (m, 1H), 3.98-3.77 (m, 2H), 2.64-2.51 (m, 3H), 2.43-2.20 (m, 4H), 2.03-1.37 (m, 6H).

Example 140

(±)-(6-methyl-2-(1H-1,2,3-triazol-1-yl)pyridin-3-yl)(2-(((6-methylpyridin-2-yl)oxy)methyl)-7-azabicyclo[2.2.1]heptan-7-yl)methanone

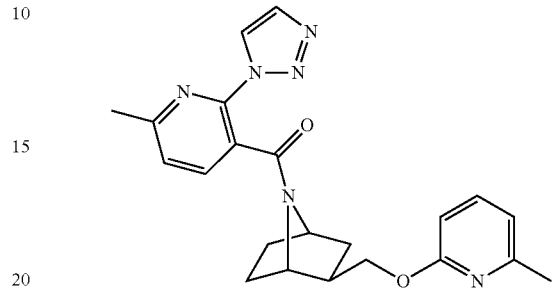

Prepared analogous to Example 139 substituting 6-methyl-2-(2H-1,2,3-triazol-2-yl)nicotinic acid with 6-methyl-2-(1H-1,2,3-triazol-1-yl)nicotinic acid. MS (ESI) mass calcd. for $C_{22}H_{24}N_6O_2$, 404.2; m/z found 405.2 [M+H]$^+$. $^1$H NMR (MeOD): 8.34 (d, J=7.1 Hz, 1H), 7.77-7.42 (m, 3H), 7.28-6.35 (m, 3H), 4.82-4.79 (m, 1H), 4.24-3.94 (m, 2H), 3.87-3.81 (m, 1H), 2.63-2.22 (m, 7H), 2.15-1.98 (m, 1H), 1.84-1.34 (m, 5H).

Example 141

(±)-(2-(3-methyl-1,2,4-oxadiazol-5-yl)phenyl)(2-(((6-methylpyridin-2-yl)oxy)methyl)-7-azabicyclo[2.2.1]heptan-7-yl)methanone

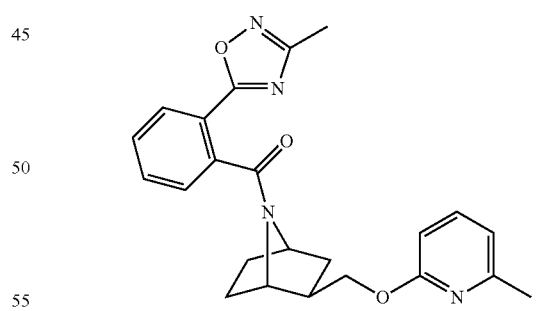

Prepared analogous to Example 139 substituting 6-methyl-2-(2H-1,2,3-triazol-2-yl)nicotinic acid with 2-(3-methyl-1,2,4-oxadiazol-5-yl)benzoic acid. MS (ESI) mass calcd. for $C_{23}H_{24}N_4O_3$, 404.2; m/z found 405.2 [M+H]$^+$. $^1$H NMR (MeOD): 8.10-8.00 (m, 1H), 7.75-7.63 (m, 1H), 7.57-7.47 (m, 2H), 7.37-7.26 (m, 1H), 6.79 (dd, J=7.2, 2.8 Hz, 1H), 6.64-6.35 (m, 1H), 4.81-4.78 (m, 1H), 4.25-4.11 (m, 1H), 3.98-3.95 (m, 1H), 3.79-3.74 (m, 1H), 2.42-2.25 (m, 7H), 2.08-1.95 (m, 1H), 1.86-1.63 (m, 3H), 1.58-1.44 (m, 2H).

Example 142

(±)-(3-fluoro-2-(2H-1,2,3-triazol-2-yl)phenyl)(2-(((6-methylpyridin-2-yl)oxy)methyl)-7-azabicyclo[2.2.1]heptan-7-yl)methanone

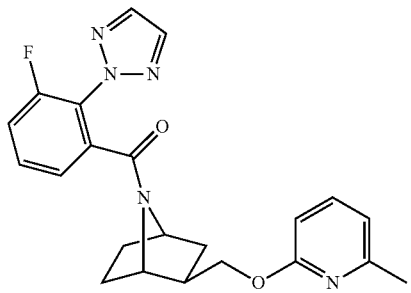 [SMILES: Cc1cccc(OCC2CC3CCC2N3C(=O)c2cccc(F)c2-n2nccn2)n1]

Prepared analogous to Example 139 substituting 6-methyl-2-(2H-1,2,3-triazol-2-yl)nicotinic acid with 3-fluoro-2-(2H-1,2,3-triazol-2-yl)benzoic acid. MS (ESI) mass calcd. for $C_{22}H_{22}FN_5O_2$, 407.2; m/z found 408.2 [M+H]$^+$. $^1$H NMR (MeOD): 7.95-7.93 (m, 2H), 7.68-7.47 (m, 2H), 7.40-7.31 (m, 1H), 7.21-7.09 (m, 1H), 6.80 (t, J=8.3 Hz, 1H), 6.58-6.46 (m, 1H), 4.56 (s, 1H), 4.01 (d, J=7.3 Hz, 1H), 3.91 (d, J=7.4 Hz, 2H), 2.43 (d, J=2.5 Hz, 3H), 2.38-2.28 (m, 1H), 1.83-1.45 (m, 6H).

Example 143

(±)-(6-methyl-2-(2H-1,2,3-triazol-2-yl)pyridin-3-yl)(2-(((6-(trifluoromethyl)pyridin-2-yl)oxy)methyl)-7-azabicyclo[2.2.1]heptan-7-yl)methanone

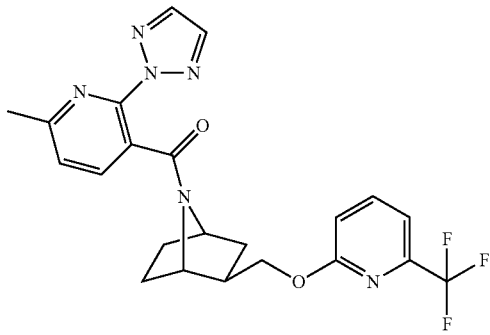

Prepared analogous to Example 131 substituting 2-chloro-4-(trifluoromethyl)pyrimidine with 2-chloro-6-(trifluoromethyl)pyridine. MS (ESI) mass calcd. for $C_{22}H_{21}F_3N_6O_2$, 458.2; m/z found 459.2 [M+H]$^+$. $^1$H NMR (MeOD): 7.91 (s, 1H), 7.84 (s, 1H), 7.73-7.65 (m, 2H), 7.29-7.25 (m, 2H), 6.93-6.69 (m, 1H), 4.85-4.82 (m, 1H), 4.25-4.16 (m, 1H), 3.98-3.96 (m, 1H), 3.79-3.69 (m, 1H), 2.69-2.56 (m, 3H), 2.38-2.16 (m, 1H), 2.05-1.24 (m, 6H).

Example 144

(±)-(6-methyl-2-(1H-1,2,3-triazol-1-yl)pyridin-3-yl)(2-(((6-(trifluoromethyl)pyridin-2-yl)oxy)methyl)-7-azabicyclo[2.2.1]heptan-7-yl)methanone

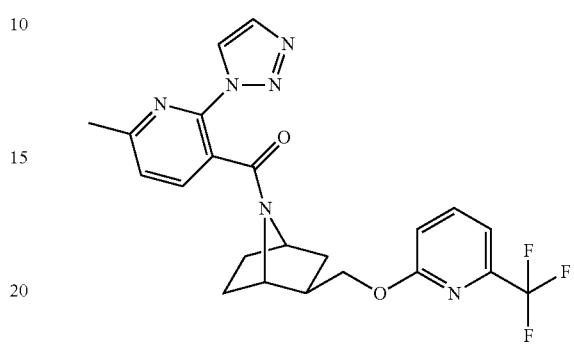

Prepared analogous to Example 143 substituting 6-methyl-2-(2H-1,2,3-triazol-2-yl)nicotinic acid with 6-methyl-2-(1H-1,2,3-triazol-1-yl)nicotinic acid. MS (ESI) mass calcd. for $C_{22}H_{21}F_3N_6O_2$, 458.2; m/z found 459.2 [M+H]$^+$. $^1$H NMR (MeOD): 8.61 (t, J=1.1 Hz, 1H), 8.00-7.72 (m, 3H), 7.49-6.83 (m, 3H), 4.75-4.71 (m, 1H), 4.31-4.10 (m, 1H), 4.08-3.95 (m, 1H), 3.89-3.77 (m, 1H), 2.64-2.52 (m, 3H), 2.43-2.27 (m, 1H), 2.06-1.89 (m, 1H), 1.82-1.37 (m, 5H).

Example 145

(±)-(2-(3-methyl-1,2,4-oxadiazol-5-yl)phenyl)(2-(((6-(trifluoromethyl)pyridin-2-yl)oxy)methyl)-7-azabicyclo[2.2.1]heptan-7-yl)methanone

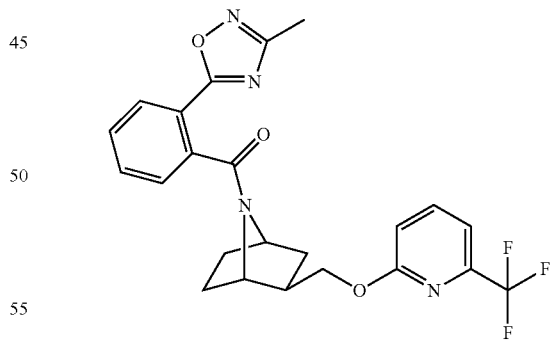

Prepared analogous to Example 143 substituting 6-methyl-2-(2H-1,2,3-triazol-2-yl)nicotinic acid with 2-(3-methyl-1,2,4-oxadiazol-5-yl)benzoic acid. MS (ESI) mass calcd. for $C_{23}H_{21}FN_4O_3$, 458.2; m/z found 459.2 [M+H]$^+$. $^1$H NMR (MeOD): 8.10-8.01 (m, 1H), 7.88-7.77 (m, 1H), 7.75-7.63 (m, 1H), 7.54-7.49 (m, 1H), 7.39-7.25 (m, 2H), 7.07-6.78 (m, 1H), 4.82-4.79 (m, 1H), 4.35-4.24 (m, 1H), 4.10-4.07 (m, 1H), 3.78-3.74 (m, 1H), 2.48-2.29 (m, 4H), 2.09-1.96 (m, 1H), 1.88-1.63 (m, 3H), 1.58-1.47 (m, 2H).

Example 146

(±)-(3-fluoro-2-(2H-1,2,3-triazol-2-yl)phenyl)(2-(((6-(trifluoromethyl)pyridin-2-yl)oxy)methyl)-7-azabicyclo[2.2.1]heptan-7-yl)methanone

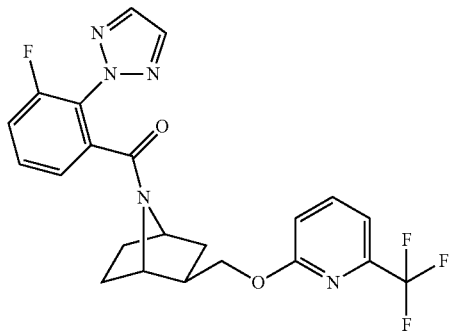 [SMILES: O=C(c1cccc(F)c1-n1nccn1)N1C2CCC1C(COc1cccc(C(F)(F)F)n1)C2]

Prepared analogous to Example 143 substituting 6-methyl-2-(2H-1,2,3-triazol-2-yl)nicotinic acid with 3-fluoro-2-(2H-1,2,3-triazol-2-yl)benzoic acid. MS (ESI) mass calcd. for $C_{22}H_{19}F_4N_5O_2$, 461.2; m/z found 462.0 [M+H]$^+$. $^1$H NMR (MeOD): 7.95-7.93 (m, 2H), 7.86-7.80 (m, 1H), 7.68-7.12 (m, 4H), 7.02-6.86 (m, 1H), 4.59-4.56 (m, 1H), 4.10-3.86 (m, 3H), 2.38-2.30 (m, 1H), 1.95-1.45 (m, 6H).

Example 147

(±)-(6-methyl-2-(2H-1,2,3-triazol-2-yl)pyridin-3-yl)(2-((quinoxalin-2-yloxy)methyl)-7-azabicyclo[2.2.1]heptan-7-yl)methanone

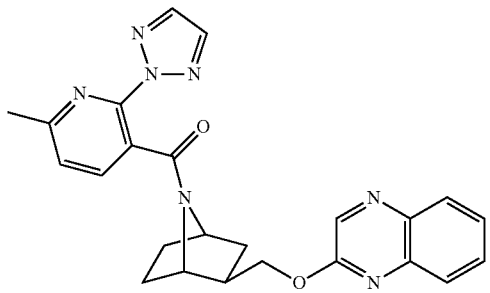 [SMILES: Cc1ccc(C(=O)N2C3CCC2C(COc2cnc4ccccc4n2)C3)c(-n2nccn2)n1]

Prepared analogous to Example 131 substituting 2-chloro-4-(trifluoromethyl)pyrimidine with 2-chloroquinoxaline. MS (ESI) mass calcd. for $C_{24}H_{23}N_7O_2$, 441.2; m/z found 442.2 [M+H]$^+$. $^1$H NMR (MeOD): 8.47-8.04 (m, 2H), 7.98-7.69 (m, 5H), 7.65-7.56 (m, 1H), 7.45-6.73 (m, 1H), 4.77-4.71 (m, 1H), 4.46-4.10 (m, 2H), 3.91-3.79 (m, 1H), 2.64-2.32 (m, 4H), 2.03-1.38 (m, 6H).

Example 148

(±)-(6-methyl-2-(1H-1,2,3-triazol-1-yl)pyridin-3-yl)(2-((quinoxalin-2-yloxy)methyl)-7-azabicyclo[2.2.1]heptan-7-yl)methanone

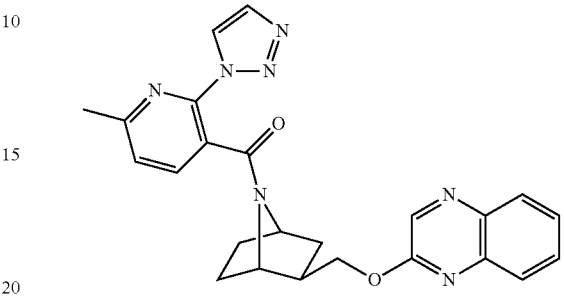

Prepared analogous to Example 147 substituting 6-methyl-2-(2H-1,2,3-triazol-2-yl)nicotinic acid with 6-methyl-2-(1H-1,2,3-triazol-1-yl)nicotinic acid. MS (ESI) mass calcd. for $C_{24}H_{23}N_7O_2$, 441.2; m/z found 441.2 [M+H]$^+$. $^1$H NMR (MeOD): 8.61-8.59 (m, 1H), 8.46-8.25 (m, 1H), 8.04-7.55 (m, 6H), 7.48-6.74 (m, 1H), 4.78-4.74 (m, 1H), 4.43-4.30 (m, 1H), 4.21-4.18 (m, 1H), 3.92-3.82 (m, 1H), 2.63-2.34 (m, 4H), 2.08-1.89 (m, 1H), 1.88-1.39 (m, 5H).

Example 149

(±)-(2-(3-methyl-1,2,4-oxadiazol-5-yl)phenyl)(2-((quinoxalin-2-yloxy)methyl)-7-azabicyclo[2.2.1]heptan-7-yl)methanone

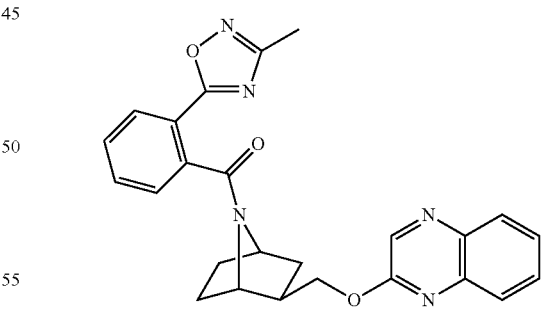

Prepared analogous to Example 147 substituting 6-methyl-2-(2H-1,2,3-triazol-2-yl)nicotinic acid with 2-(3-methyl-1,2,4-oxadiazol-5-yl)benzoic acid. MS (ESI) mass calcd. for $C_{25}H_{23}N_5O_3$, 441.2; m/z found 442.2 [M+H]$^+$. $^1$H NMR (MeOD): 8.48-8.20 (m, 1H), 8.08-7.91 (m, 2H), 7.83-7.12 (m, 6H), 4.86-4.81 (m, 1H), 4.50-4.36 (m, 1H), 4.26-4.18 (m, 1H), 3.80-3.77 (m, 1H), 2.55-2.34 (m, 4H), 2.09-1.97 (m, 1H), 1.91-1.64 (m, 3H), 1.61-1.50 (m, 2H).

Example 150

(±)-(3-fluoro-2-(2H-1,2,3-triazol-2-yl)phenyl)(2-(2-((quinoxalin-2-yloxy)methyl)-7-azabicyclo[2.2.1]heptan-7-yl)methanone

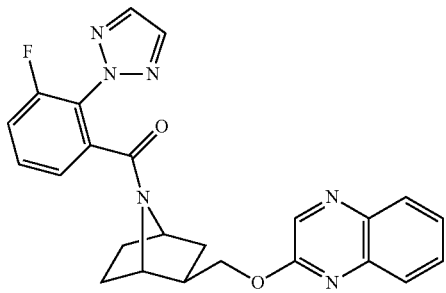 [SMILES: O=C(c1cccc(F)c1-n1nccn1)N1C2CCC1C(COc1cnc3ccccc3n1)C2]

Prepared analogous to Example 147 substituting 6-methyl-2-(2H-1,2,3-triazol-2-yl)nicotinic acid with 3-fluoro-2-(2H-1,2,3-triazol-2-yl)benzoic acid. MS (ESI) mass calcd. for $C_{24}H_{21}FN_6O_2$, 444.2; m/z found 445.1 [M+H]$^+$. $^1$H NMR (MeOD): 8.47-8.33 (m, 1H), 8.01-7.60 (m, 6H), 7.54-6.92 (m, 3H), 4.65-4.60 (m, 1H), 4.31-4.13 (m, 2H), 3.96-3.95 (m, 1H), 2.52-2.40 (m, 1H), 1.96-1.44 (m, 6H).

Example 151

(±)-(2-(((4,6-dimethylpyrimidin-2-yl)oxy)methyl)-7-azabicyclo[2.2.1]heptan-7-yl)(6-methyl-2-(2H-1,2,3-triazol-2-yl)pyridin-3-yl)methanone

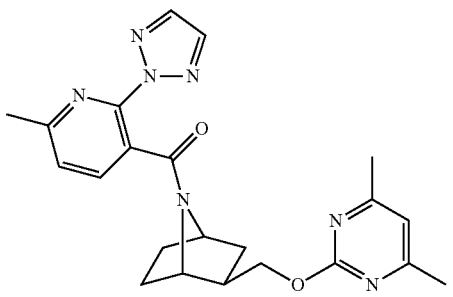

Prepared analogous to Example 131 substituting 2-chloro-4-(trifluoromethyl)pyrimidine with 2-chloro-4,6-dimethylpyrimidine. MS (ESI) mass calcd. for $C_{22}H_{25}N_7O_2$, 419.2; m/z found 420.2 [M+H]$^+$. $^1$H NMR (MeOD): 8.02-7.99 (m, 2H), 7.94-7.46 (m, 1H), 7.48-7.10 (m, 1H), 6.87 (s, 1H), 4.72-4.71 (m, 1H), 4.38-3.97 (m, 2H), 3.89-3.84 (m, 1H), 2.65-2.17 (m, 10H), 1.98-1.37 (m, 6H).

Example 152

(±)-(2-(((4,6-dimethylpyrimidin-2-yl)oxy)methyl)-7-azabicyclo[2.2.1]heptan-7-yl)(6-methyl-2-(1H-1,2,3-triazol-1-yl)pyridin-3-yl)methanone

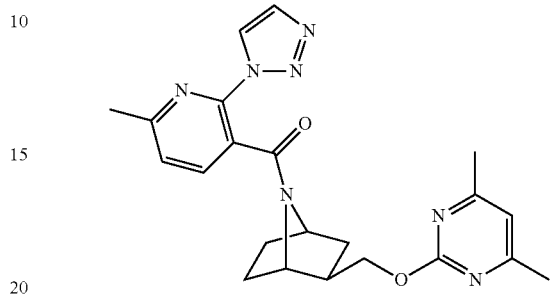

Prepared analogous to Example 151 substituting 6-methyl-2-(2H-1,2,3-triazol-2-yl)nicotinic acid with 6-methyl-2-(1H-1,2,3-triazol-1-yl)nicotinic acid. MS (ESI) mass calcd. for $C_{22}H_{25}N_7O_2$, 419.2; m/z found 420.2 [M+H]$^+$. $^1$H NMR (MeOD): 8.62-8.61 (m, 1H), 7.98-7.78 (m, 2H), 7.50-7.11 (m, 1H), 6.86 (d, J=9.7 Hz, 1H), 4.75-4.71 (m, 1H), 4.25-4.23 (m, 1H), 4.16-3.84 (m, 2H), 2.64-2.55 (m, 3H), 2.46-2.25 (m, 7H), 2.06-1.88 (m, 1H), 1.85-1.39 (m, 5H).

Example 153

(±)-(2-(((4,6-dimethylpyrimidin-2-yl)oxy)methyl)-7-azabicyclo[2.2.1]heptan-7-yl)(2-(3-methyl-1,2,4-oxadiazol-5-yl)phenyl)methanone

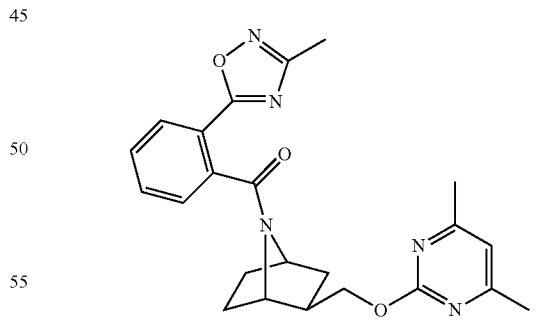

Prepared analogous to Example 151 substituting 6-methyl-2-(2H-1,2,3-triazol-2-yl)nicotinic acid with 2-(3-methyl-1,2,4-oxadiazol-5-yl)benzoic acid. MS (ESI) mass calcd. for $C_{23}H_{25}N_5O_3$, 419.2; m/z found 420.2 [M+H]$^+$. $^1$H NMR (MeOD): 8.10-8.01 (m, 1H), 7.76-7.64 (m, 1H), 7.58-7.51 (m, 1H), 7.42-7.36 (m, 1H), 6.86 (s, 1H), 4.83-4.80 (m, 1H), 4.42-4.22 (m, 1H), 4.13-4.00 (m, 1H), 3.83-3.76 (m, 1H), 2.49-2.28 (m, 10H), 2.08-1.98 (m, 1H), 1.89-1.65 (m, 3H), 1.58-1.48 (m, 2H).

Example 154

(±)-(2-(((4,6-dimethylpyrimidin-2-yl)oxy)methyl)-7-azabicyclo[2.2.1]heptan-7-yl)(3-fluoro-2-(2H-1,2,3-triazol-2-yl)phenyl)methanone

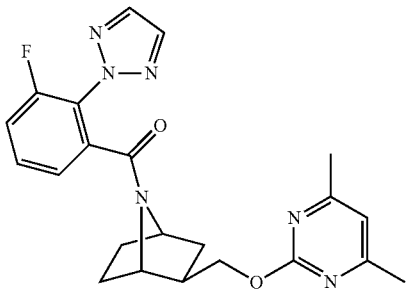 [SMILES: Cc1cc(C)nc(OCC2CC3CCC2N3C(=O)c2cccc(F)c2-n2nccn2)n1]

Prepared analogous to Example 151 substituting 6-methyl-2-(2H-1,2,3-triazol-2-yl)nicotinic acid with 3-fluoro-2-(2H-1,2,3-triazol-2-yl)benzoic acid. MS (ESI) mass calcd. for $C_{22}H_{23}FN_6O_2$, 422.2; m/z found 423.1 [M+H]$^+$. $^1$H NMR (MeOD): 7.96-7.95 (m, 2H), 7.69-7.22 (m, 3H), 6.87 (d, J=5.8 Hz, 1H), 4.58-4.56 (m, 1H), 4.19-3.89 (m, 3H), 2.42-2.34 (m, 7H), 1.90-1.37 (m, 6H).

Example 155

(±)-(2-ethoxy-4-methylpyridin-3-yl)(2-((pyridin-2-yloxy)methyl)-7-azabicyclo[2.2.1]heptan-7-yl)methanone

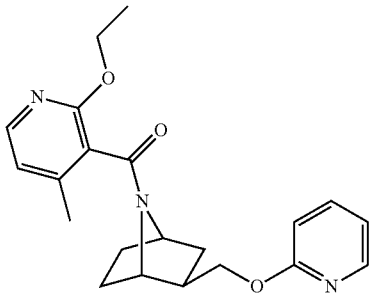

Prepared analogous to Example 1 substituting intermediate B-9 with B-10 and 5-fluoro-2-(pyrimidin-2-yl)benzoic acid with 2-ethoxy-4-methylnicotinic acid. MS (ESI) mass calcd. for $C_{21}H_{25}N_3O_3$, 367.2; m/z found 368.3 [M+H]$^+$. $^1$H NMR (CDCl$_3$): 8.13-8.05 (m, 1H), 7.99-7.87 (m, 1H), 7.58-7.46 (m, 1H), 6.87-6.79 (m, 1H), 6.76-6.67 (m, 1H), 6.55-6.49 (m, 1H), 4.92-4.84 (m, 1H), 4.43-3.64 (m, 5H), 2.43-1.22 (m, 13H).

Example 156

(±)-(6-methylimidazo[2,1-b]thiazol-5-yl)(2-((pyridin-2-yloxy)methyl)-7-azabicyclo[2.2.1]heptan-7-yl)methanone

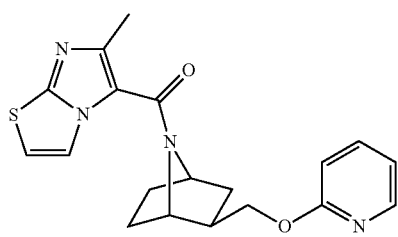 [SMILES: Cc1nc2sccn2c1C(=O)N1C2CCC1C(COc1ccccn1)C2]

Prepared analogous to Example 1 substituting intermediate B-9 with B-10 and 5-fluoro-2-(pyrimidin-2-yl)benzoic acid with 6-methylimidazo[2,1-b]thiazole-5-carboxylic acid. $^1$H NMR (CDCl$_3$): 8.05-7.98 (m, 1H), 7.79 (d, J=4.5 Hz, 1H), 7.54-7.47 (m, 1H), 6.84-6.78 (m, 1H), 6.76 (d, J=4.5 Hz, 1H), 6.62 (d, J=8.4 Hz, 1H), 4.54-4.35 (m, 2H), 4.11-4.03 (m, 1H), 4.02-3.88 (m, 1H), 2.46 (s, 3H), 2.39-2.28 (m, 1H), 2.07-1.97 (m, 1H), 1.80-1.70 (m, 2H), 1.65-1.52 (m, 3H).

Example 157

(±)-(5-bromo-2-ethoxypyridin-3-yl)(2-((pyridin-2-yloxy)methyl)-7-azabicyclo[2.2.1]heptan-7-yl)methanone

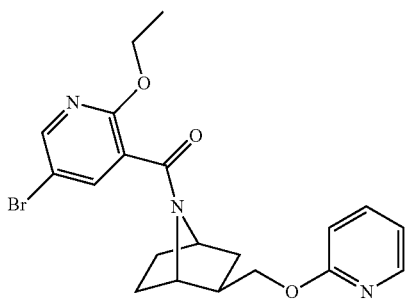 [SMILES: CCOc1ncc(Br)cc1C(=O)N1C2CCC1C(COc1ccccn1)C2]

Prepared analogous to Example 1 substituting intermediate B-9 with B-10 and 5-fluoro-2-(pyrimidin-2-yl)benzoic acid with 5-bromo-2-ethoxynicotinic acid. MS (ESI) mass calcd. for $C_{20}H_{22}BrN_3O_3$, 431.1; m/z found 432.2 [M+H]$^+$. $^1$H NMR (CDCl$_3$): 8.33-8.07 (m, 2H), 7.74 (d, J=2.5 Hz, 0.5H), 7.61 (d, J=2.5 Hz, 0.5H), 7.59-7.49 (m, 1H), 6.89-6.81 (m, 1H), 6.75 (d, J=8.3 Hz, 0.5H), 6.55 (d, J=8.4 Hz, 0.5H), 4.86-4.80 (m, 1H), 4.48-3.78 (m, 5H), 2.43-2.33 (m, 0.5H), 2.32-2.23 (m, 0.5H), 2.03-1.39 (m, 6H), 1.37-1.29 (m, 3H).

Example 158

(±)-(2-ethoxy-6-methylpyridin-3-yl)(2-((pyridin-2-yloxy)methyl)-7-azabicyclo[2.2.1]heptan-7-yl)methanone

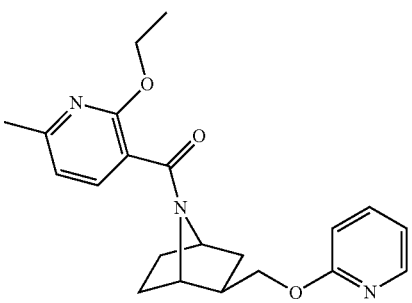 [SMILES: CCOc1nc(C)ccc1C(=O)N1C2CCC1C(COc1ccccn1)C2]

Prepared analogous to Example 1 substituting intermediate B-9 with intermediate B-10 and 5-fluoro-2-(pyrimidin-2-yl)benzoic acid with 2-ethoxy-6-methylnicotinic acid. MS (ESI) mass calcd. for $C_{21}H_{25}N_3O_3$, 367.2; m/z found 368.3 [M+H]$^+$. $^1$H NMR (CDCl$_3$): 8.14-8.08 (m, 1H), 7.57-7.47 (m, 1.5H), 7.38 (d, J=7.4 Hz, 0.5H), 6.86-6.82 (m, 1H), 6.74 (d, J=8.3 Hz, 0.5H), 6.72 (d, J=7.4 Hz, 0.5H), 6.51 (d, J=8.3 Hz, 0.5H), 6.46 (d, J=7.4 Hz, 0.5H), 4.84-4.79 (m, 1H), 4.44-4.34 (m, 1.5H), 4.27-4.09 (m, 1.5H), 4.06-4.01 (m, 0.5H), 3.92-3.80 (m, 1.5H), 2.43 (s, 1.5H), 2.38-2.32 (m, 2H), 2.26-2.20 (m, 0.5H), 2.01-1.40 (m, 6H), 1.36-1.28 (m, 3H).

Example 159

(±)-(7-hydroxyquinolin-8-yl)(2-((pyridin-2-yloxy)methyl)-7-azabicyclo[2.2.1]heptan-7-yl)methanone

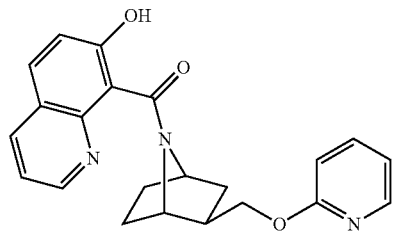 [SMILES: O=C(c1c(O)ccc2cccnc12)N1C2CCC1C(COc1ccccn1)C2]

Prepared analogous to Example 1 substituting intermediate B-9 with intermediate B-10 and 5-fluoro-2-(pyrimidin-2-yl)benzoic acid with 7-hydroxyquinoline-8-carboxylic acid (intermediate A-29 step B). MS (ESI) mass calcd. for $C_{22}H_{21}N_3O_3$, 375.2; m/z found 376.3 [M+H]$^+$. $^1$H NMR (CDCl$_3$): 8.88-8.66 (m, 1H), 8.19-7.93 (m, 2H), 7.80-7.41 (m, 2H), 7.26-6.25 (series of m, 4H), 5.10-4.87 (m, 1H), 4.34-3.60 (m, 3H), 2.51-1.00 (series of m, 7H).

Example 160

(±)-(2-ethoxy-5-phenylpyridin-3-yl)(2-((pyridin-2-yloxy)methyl)-7-azabicyclo[2.2.1]heptan-7-yl)methanone

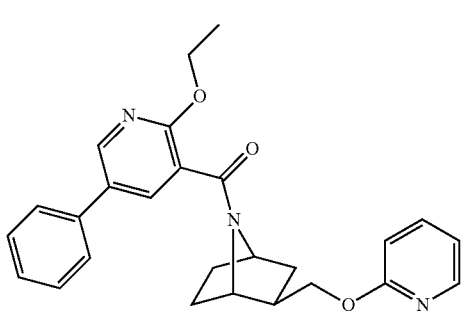 [SMILES: CCOc1ncc(-c2ccccc2)cc1C(=O)N1C2CCC1C(COc1ccccn1)C2]

Prepared analogous to Example 1 substituting intermediate B-9 with intermediate B-10 and 5-fluoro-2-(pyrimidin-2-yl)benzoic acid with 2-ethoxy-5-phenylnicotinic acid. MS (ESI) mass calcd. for $C_{26}H_{27}N_3O_3$, 429.2; m/z found 430.2 [M+H]$^+$. $^1$H NMR (CDCl$_3$): 8.40 and 8.30 (2d, J=2.5 Hz, 1H), 8.15-8.12 and 7.98-7.94 (2m, 1H), 7.87 and 7.74 (2d, J=2.5 Hz, 1H), 7.59-7.28 (m, 6H), 6.88-6.83 and 6.72-6.68 (2m, 1H), 6.76 and 6.47 (2d, J=8.3 Hz, 1H), 4.89-4.84 (m, 1H), 4.34-3.84 (series of m, 5H), 2.43-2.34 and 2.32-2.23 (m, 1H), 2.06-1.45 (series of m, 6H), 1.42-1.32 (m, 3H).

Example 161

(±)-(4-bromo-2-ethoxypyridin-3-yl)(2-((pyridin-2-yloxy)methyl)-7-azabicyclo[2.2.1]heptan-7-yl)methanone

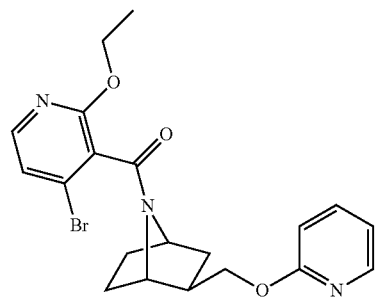 [SMILES: CCOc1nccc(Br)c1C(=O)N1C2CCC1C(COc1ccccn1)C2]

Prepared analogous to Example 1 substituting intermediate B-9 with intermediate B-10 and 5-fluoro-2-(pyrimidin-2-yl)benzoic acid with 4-bromo-2-ethoxynicotinic acid. MS (ESI) mass calcd. for $C_{20}H_{22}BrN_3O_3$, 431.1; m/z found 432.2 [M+H]$^+$. $^1$H NMR (CDCl$_3$): 8.15-8.08 (m, 1H), 7.96-7.87 (m, 1H), 7.60-7.49 (m, 1H), 7.11-6.92 (series of m, 1H), 6.88-6.82 (m, 1H), 6.78-6.52 (series of m, 1H), 4.94-4.87 (m, 1H), 4.47-3.67 (series of m, 5H), 2.45-1.41 (series of m, 7H), 1.38-1.27 (m, 3H).

Example 162

(±)-(2-chloro-4-ethoxypyridin-3-yl)(2-((pyridin-2-yloxy)methyl)-7-azabicyclo[2.2.1]heptan-7-yl)methanone

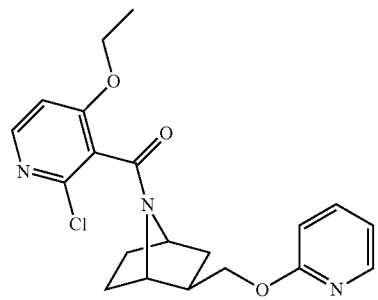 [SMILES: CCOc1ccnc(Cl)c1C(=O)N1C2CCC1C(COc1ccccn1)C2]

Prepared analogous to Example 1 substituting intermediate B-9 with intermediate B-10 and 5-fluoro-2-(pyrimidin-2-yl)benzoic acid with 2-chloro-4-ethoxynicotinic acid. MS (ESI) mass calcd. for $C_{20}H_{22}ClN_3O_3$, 387.1; m/z found 388.3 [M+H]$^+$. $^1$H NMR (CDCl$_3$): 8.27-8.17 (m, 1H), 8.15-8.07 (m, 1H), 7.60-7.48 (m, 1H), 6.88-6.82 (m, 1H), 6.80-6.73 (m, 1H), 6.58-6.49 (m, 1H), 4.93-4.87 (m, 1H), 4.27-4.02 (m, 3H), 3.92-3.58 (series of m, 2H), 2.44-1.35 (series of m, 10H).

Example 163

(±)-(2,4-diethoxypyridin-3-yl)(2-((pyridin-2-yloxy)methyl)-7-azabicyclo[2.2.1]heptan-7-yl)methanone

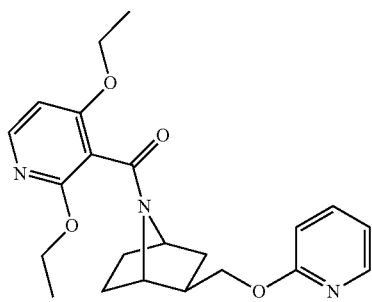 [SMILES: CCOc1ccnc(OCC)c1C(=O)N1C2CCC1C(COc1ccccn1)C2]

Prepared analogous to Example 1 substituting intermediate B-9 with intermediate B-10 and 5-fluoro-2-(pyrimidin-2-yl)benzoic acid with 2,4-diethoxynicotinic acid. MS (ESI) mass calcd. for $C_{22}H_{27}BrN_3O_4$, 397.2; m/z found 398.2 [M+H]$^+$. $^1$H NMR (CDCl$_3$): 8.15-8.07 (m, 1H), 8.03-7.94 (m, 1H), 7.60-7.46 (m, 1H), 6.87-6.80 (m, 1H), 6.77-6.73 (m, 0.5H), 6.56-6.45 (m, 1H), 6.30-6.27 (m, 0.5H) 4.88-4.83 (m, 1H), 4.50-3.51 (series of m, 7H), 2.40-1.15 (series of m, 13H).

Example 164

(3-ethoxyisoquinolin-4-yl)((1S,2R,4R)-2-((pyridin-2-yloxy)methyl)-7-azabicyclo[2.2.1]heptan-7-yl)methanone

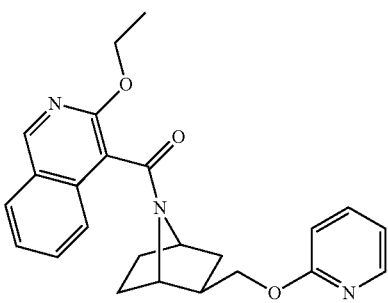 [SMILES: CCOc1ncc2ccccc2c1C(=O)N1C2CCC1C(COc1ccccn1)C2]

Prepared analogous to Example 1 substituting 5-fluoro-2-(pyrimidin-2-yl)benzoic acid with intermediate A-22. MS (ESI) mass calcd. for $C_{24}H_{25}N_3O_3$, 403.2; m/z found 404.2 [M+H]$^+$. $^1$H NMR (400 MHz, CDCl$_3$) 8.97-8.89 (m, 0.7H), 8.87-8.81 (m, 0.3H), 8.22-8.07 (m, 0.7H) 7.95-7.85 (m, 1H), 7.82 (dq, J=8.6, 0.9 Hz, 0.2H), 7.78-7.69 (m, 0.6H), 7.69-7.47 (m, 2H), 7.43-7.28 (m, 1.2H), 7.10 (ddd, J=8.0, 6.8, 1.0 Hz, 0.3H), 6.93-6.68 (m, 1.5H), 6.52-6.46 (m, 0.2H), 6.16-6.09 (m, 0.3H), 5.02 (td, J=9.5, 4.6 Hz, 1H), 4.65-3.99 (m, 3.5H), 3.92 (dd, J=10.5, 5.6 Hz, 0.25H), 3.74-3.58 (m, 1.25H), 2.52-2.29 (m, 0.5H), 2.27-1.93 (m, 2H), 1.86-0.78 (m, 7.5H).

Example 165

(±)-(2-ethoxyphenyl)(2-(((5-fluoropyridin-2-yl)oxy)methyl)-7-azabicyclo[2.2.1]heptan-7-yl)methanone

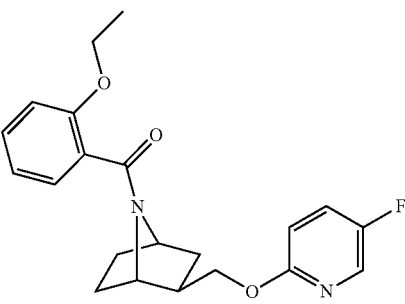 [SMILES: CCOc1ccccc1C(=O)N1C2CCC1C(COc1ccc(F)cn1)C2]

Prepared analogous to Example 7 substituting 6-methyl-3-(2H-1,2,3-triazol-2-yl)picolinic acid with 2-ethoxybenzoic acid. $^1$H NMR (400 MHz, CDCl$_3$): 7.95 (dd, J=7.3, 3.1 Hz, 1H), 7.37-7.18 (m, 2.5H), 7.14 (dd, J=7.4, 1.7 Hz, 0.5H), 6.95 (td, J=7.5, 0.9 Hz, 0.5H), 6.90 (dd, J=8.4, 1.0 Hz, 0.5H), 6.83-6.68 (m, 1.5H), 6.47 (dd, J=9.0, 3.6 Hz, 0.5H), 4.88-4.80 (m, 1H), 4.17-3.72 (m, 5H), 2.40-2.28 (m, 0.5H), 2.26-2.14 (m, 0.5H), 2.07-1.85 (m, 2H), 1.83-1.17 (m, 7H).

Example 166

(±)-(5-fluoro-2-(2H-1,2,3-triazol-2-yl)phenyl)(2-((quinoxalin-2-yloxy)methyl)-7-azabicyclo[2.2.1]heptan-7-yl)methanone

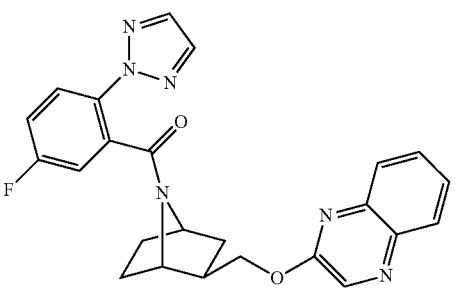 [SMILES: O=C(c1cc(F)ccc1-n1nccn1)N1C2CCC1C(COc1cnc3ccccc3n1)C2]

Prepared analogous to Example 2 substituting 6-methyl-3-(2H-1,2,3-triazol-2-yl)picolinic acid with intermediate A-10 and 2-fluoropyridine with 2-chloroquinoxaline. MS (ESI) mass calcd. for $C_{24}H_{21}FN_6O_2$, 444.2; m/z found 445.2 [M+H]$^+$. $^1$H NMR (400 MHz, CDCl$_3$): 8.49 (s, 0.4H), 8.30 (s, 0.4H), 8.04 (ddd, J=8.2, 6.9, 1.5 Hz, 1H), 7.90-7.76 (m, 2.5H), 7.75-7.66 (m, 1.5H), 7.65-7.55 (m, 1.5H), 7.44 (dd, J=8.5, 5.8 Hz, 0.5H), 7.32 (dd, J=8.5, 5.8 Hz, 0.5H), 7.29-7.22 (m, 0.2H), 7.21-7.10 (m, 1H), 6.49 (s, 0.5H), 4.93-4.84 (m, 1H), 4.52-4.30 (m, 1H), 4.23-4.07 (m, 1H), 3.87-3.78 (m, 1H), 2.48-2.25 (m, 1.8H), 2.10-1.88 (m, 1.2H), 1.83-1.31 (m, 4H).

Example 167

(±)-5-methyl-2-(2H-1,2,3-triazol-2-yl)phenyl)(2-(((5-methylpyridin-2-yl)oxy)methyl)-7-azabicyclo[2.2.1]heptan-7-yl)methanone

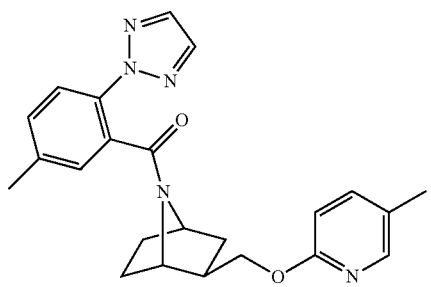

Prepared analogous to Example 13 substituting 2-chloro-4-trifluoromethylpyrimidine with 2-fluoro-5-methylpyridine. MS (ESI) mass calcd. for $C_{23}H_{25}N_5O_2$, 403.2; m/z found 404.2 [M+H]$^+$. $^1$H NMR (400 MHz, CDCl$_3$): 7.99-7.92 (m, 1H), 7.81-7.68 (m, 2.5H), 7.42-7.29 (m, 1.5H), 7.26-7.21 (m, 0.5H), 7.21-7.10 (m, 1H), 6.66 (d, J=8.4 Hz, 0.5H), 6.45 (d, J=8.4 Hz, 0.5H), 4.85-4.73 (m, 1H), 4.16-3.68 (m, 3H), 2.42 (s, 1.3H), 2.34-2.14 (m, 3.7H), 2.02-1.79 (m, 2.5H), 1.72-1.21 (m, 5.5H).

Example 168

(±)-(6-methyl-2-(2H-1,2,3-triazol-2-yl)pyridin-3-yl)(2-((quinoxalin-2-yloxy)methyl)-7-azabicyclo[2.2.1]heptan-7-yl)methanone

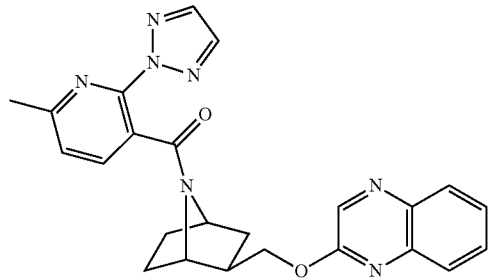 [SMILES: Cc1ccc(C(=O)N2C3CCC2C(COc2cnc4ccccc4n2)C3)c(-n2nccn2)n1]

Prepared analogous to Example 1 substituting intermediate B-9 with intermediate B-10, 2-fluoropyridine with 2-chloroquinoxaline and 5-fluoro-2-(pyrimidin-2-yl)benzoic acid with intermediate A-3 to give the title compound. MS (ESI) mass calcd. for $C_{24}H_{23}N_7O_2$, 441.2; m/z found 442.2 [M+H]$^+$. 1H NMR CD$_3$OD: 8.47-8.04 (m, 2H), 7.98-7.69 (m, 5H), 7.65-7.56 (m, 1H), 7.45-6.73 (m, 1H), 4.77-4.71 (m, 1H), 4.46-4.10 (m, 2H), 3.91-3.79 (m, 2H), 2.64-2.32 (m, 4H), 2.03-1.38 (m, 6H).

Example 169

(±)-(5-fluoro-2-(2H-1,2,3-triazol-2-yl)phenyl)(2-((pyridin-2-ylamino)methyl)-7-azabicyclo[2.2.1]heptan-7-yl)methanone

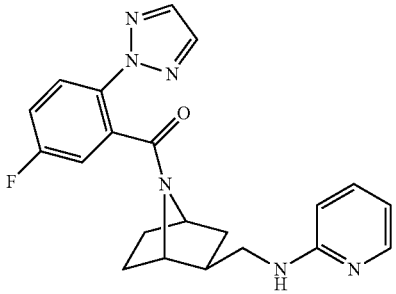 [SMILES: O=C(c1cc(F)ccc1-n1nccn1)N1C2CCC1C(CNc1ccccn1)C2]

Prepared analogous to example 170 substituting 2-chloro-4,6-dimethylpyrimidine with 2-fluoropyridine. MS (ESI) mass calcd. for $C_{21}H_{21}FN_6O$, 392.2; m/z found 393.1 [M+H]$^+$. 1H NMR (CD3OD): 8.02-7.83 (m, 4H), 7.47-7.23 (m, 3H), 6.59-6.38 (m, 2H), 4.73-4.55 (m, 1H), 3.87-3.70 (m, 1H), 3.24-2.80 (m, 2H), 2.27-2.03 (m, 1H), 1.97-1.34 (m, 6H).

Example 170

(±)-(2-(((4,6-dimethylpyrimidin-2-yl)amino)methyl)-7-azabicyclo[2.2.1]heptan-7-yl)(5-fluoro-2-(2H-1,2,3-triazol-2-yl)phenyl)methanone

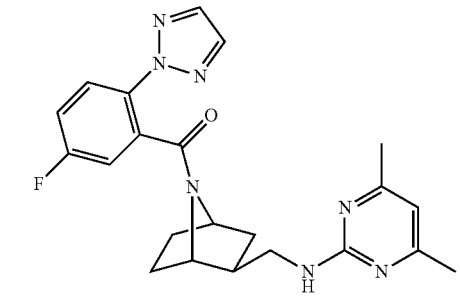 [SMILES: Cc1cc(C)nc(NCC2CC3CCC2N3C(=O)c2cc(F)ccc2-n2nccn2)n1]

Step A: (±)-tert-butyl 2-(((methylsulfonyl)oxy)methyl)-7-azabicyclo[2.2.1]heptane-7-carboxylate To intermediate B-10 (2.6 g, 11.5 mmol) and TEA (1.7 g, 17.2 mmol) in DCM (15 mL) at 0° C. was added MsCl (1.6 g, 13.7 mmol) dropwise over 10 minutes. This ice bath was removed and the reaction was allowed to stir at rt for 12 h and H$_2$O was added. The layers were separated and the organic layer was washed with brine and dried (Na$_2$SO$_4$). Purification via silica gel chromatography (15% EtOAc in petroleum ethers) gave the title compound (3.5 g).

Step B: (±)-tert-butyl 2-(azidomethyl)-7-azabicyclo[2.2.1]heptane-7-carboxylate

To the title compound of step A (3.4 g, 11.1 mmol) in DMF (15 mL) was added sodium azide (2.1 g, 33.4 mmol).

The mixture was heated at 100° C. overnight, cooled to rt, poured into H2O and extracted with DCM. The combined organics were washed with brine and dried (Na2SO4). Purification via silica gel chromatography (10% EtOAc in petroleum ethers) gave the title compound (2.6 g).

Step C: (±)-2-(azidomethyl)-7-azabicyclo[2.2.1]heptane

To the title compound of step B in DCM was added TFA. After 3 h at rt, the reaction mixture was concentrated to give the title compound (1.7 g) as the TFA salt.

Step D: (±)-2-(azidomethyl)-7-azabicyclo[2.2.1]heptan-7-yl)(5-fluoro-2-(2H-1,2,3-triazol-2-yl)phenyl)methanone Prepared analogous to example 22 substituting 2-(2H-1,2,3-triazol-2-yl)benzoic acid with 5-fluoro-2-(2H-1,2,3-triazol-2-yl)benzoic acid and using the title compound of step C.

Step E: 2-(aminomethyl)-7-azabicyclo[2.2.1]heptan-7-yl)(5-fluoro-2-(2H-1,2,3-triazol-2-yl)phenyl)methanone The title compound of step D in MeOH was placed under an atmosphere of hydrogen in the presence of 10 wt % Pd/C for 4 h. The catalyst was removed by filtration. Purification via silica gel chromatography (7% MeOH in DCM) gave the title compound.

Step F: (±)-(2-(((4,6-dimethylpyrimidin-2-yl)amino)methyl)-7-azabicyclo[2.2.1]heptan-7-yl)(5-fluoro-2-(2H-1,2,3-triazol-2-yl)phenyl)methanone To the title compound of step E (30 mg) in NMP (3 mL) was added 2-chloro-4,6-dimethylpyrimidine (16 mg) and Cs$_2$CO$_3$ (43 mg). The reaction was heated to 180° C. for 2 h. After cooling to rt, H2O was added and the mixture extracted with EtOAc. Purification via prep-HPLC gave the title compound. MS (ESI) mass calcd. for C$_{22}$H$_{24}$FN$_7$O, 421.2; m/z found 422.2 [M+H]$^+$. 1H NMR (CD3OD) 7.90-7.73 (m, 3H), 7.34-7.14 (m, 2H), 6.31-6.26 (m, 1H), 4.62-4.41 (m, 1H), 3.74-3.57 (m, 1H), 3.46-3.22 (m, 1H), 3.18-2.93 (m, 1H), 2.40-1.91 (m, 7H), 1.85-1.20 (m, 6H).

Example 171

(±)-(5-fluoro-2-(2H-1,2,3-triazol-2-yl)phenyl)(2-(((4-(trifluoromethyl)pyrimidin-2-yl)amino)methyl)-7-azabicyclo[2.2.1]heptan-7-yl)methanone

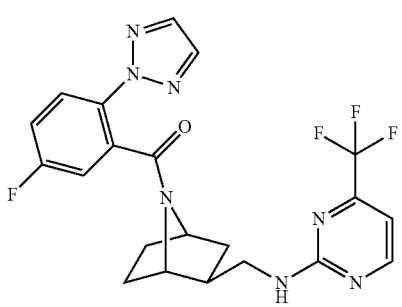 [SMILES: O=C(c1cc(F)ccc1-n1nccn1)N1C2CCC1C(CNc1nccc(C(F)(F)F)n1)C2]

Prepared analogous to example 170 substituting 2-chloro-4,6-dimethylpyrimidine with 2-chloro-4-(trifluoromethyl)pyrimidine. MS (ESI) mass calcd. for C$_{21}$H$_{19}$F$_4$N$_7$O, 461.2; m/z found 462.1 [M+H]$^+$. 1H NMR (CD3OD): 8.51 (s, 1H), 7.99-7.83 (m, 3H), 7.46-7.16 (m, 2H), 6.88 (d, J=4.9 Hz, 1H), 4.74-4.53 (m, 1H), 3.87-3.66 (m, 1H), 3.34 (s, 1H), 3.30-3.02 (m, 1H), 2.33-2.08 (m, 1H), 1.97-1.32 (m, 6H).

Example 172

(±)-(5-fluoro-2-(2H-1,2,3-triazol-2-yl)phenyl)(2-(((6-(trifluoromethyl)pyridin-2-yl)amino)methyl)-7-azabicyclo[2.2.1]heptan-7-yl)methanone

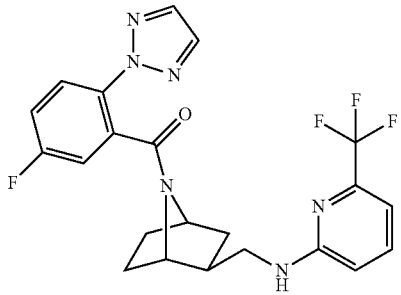

Prepared analogous to example 170 substituting 2-chloro-4,6-dimethylpyrimidine with 2-chloro-6-(trifluoromethyl)pyridine. MS (ESI) mass calcd. for C$_{22}$H$_{20}$F$_4$N$_6$O, 460.2; m/z found 461.2 [M+H]$^+$. 1H NMR (CD3OD): 8.07-7.84 (m, 3H), 7.60-7.22 (m, 3H), 6.90 (d, J=7.2 Hz, 1H), 6.74-6.58 (m, 1H), 4.77-4.58 (m, 1H), 3.90-3.72 (m, 1H), 3.30-3.05 (m, 2H), 2.37-2.12 (m, 1H), 1.99-1.37 (m, 6H).

Example 173

(±)-(3-fluoro-2-methoxyphenyl)(2-(((5-fluoropyridin-2-yl)oxy)methyl)-7-azabicyclo[2.2.1]heptan-7-yl)methanone

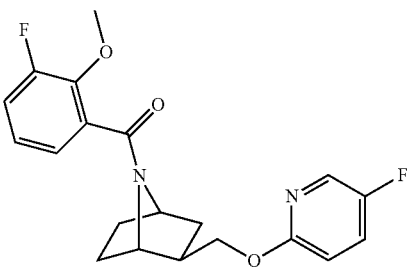 [SMILES: COc1c(F)cccc1C(=O)N1C2CCC1C(COc1ccc(F)cn1)C2]

Prepared analogous to Example 7 substituting 6-methyl-3-(2H-1,2,3-triazol-2-yl)picolinic acid with 3-fluoro-2-methoxybenzoic acid. MS (ESI) mass calcd. for C$_{22}$H$_{20}$F$_2$N$_2$O$_3$, 374.1; m/z found 375.1 [M+H]$^+$. 1H NMR (CD3OD): 8.01-7.90 (m, 1H), 7.56-7.38 (m, 1H), 7.28-7.06 (m, 2H), 7.02-6.53 (m, 2H), 4.82-4.66 (m, 1H), 4.50-3.73 (m, 6H), 2.85-2.22 (m, 1H), 2.21-1.10 (m, 6H).

Example 174

(±)-(5-fluoro-2-(2H-1,2,3-triazol-2-yl)phenyl)(2-((quinoxalin-2-ylamino)methyl)-7-azabicyclo[2.2.1]heptan-7-yl)methanone

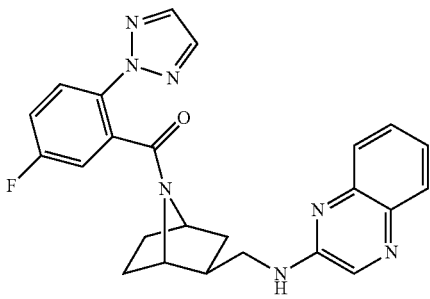 [SMILES: O=C(c1cc(F)ccc1-n1nccn1)N1C2CCC1C(CNc1cnc3ccccc3n1)C2]

Prepared analogous to example 170 substituting 2-chloro-4,6-dimethylpyrimidine with 2-chloroquinoxaline. MS (ESI) mass calcd. for $C_{24}H_{22}FN_7O$, 443.2; m/z found 444.2 [M+H]$^+$.

Example 175

(±)-(2-(((5-fluoropyrimidin-2-yl)oxy)methyl)-7-azabicyclo[2.2.1]heptan-7-yl)(6-methyl-3-(pyrimidin-2-yl)pyridin-2-yl)methanone

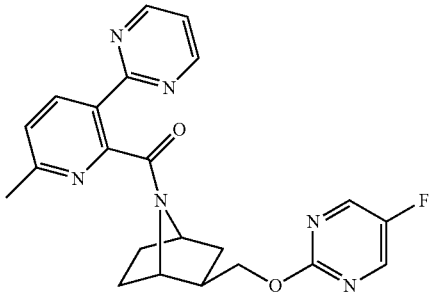 [SMILES: Cc1ccc(-c2ncccn2)c(C(=O)N2C3CCC2C(COc2ncc(F)cn2)C3)n1]

Prepared analogous to example 98 substituting 3,6'-dimethyl-[2,3'-bipyridine]-2'-carboxylic acid with intermediate A-9. MS (ESI) mass calcd. for $C_{22}H_{21}FN_6O_2$, 420.2; m/z found 421 [M+H]$^+$.

Example 176

(±)-(6-methyl-3-(2H-1,2,3-triazol-2-yl)pyridin-2-yl)(2-(((3-methylpyridin-2-yl)oxy)methyl)-7-azabicyclo[2.2.1]heptan-7-yl)methanone

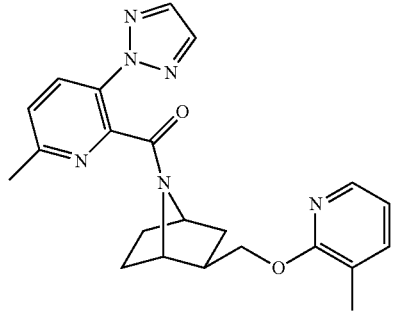 [SMILES: Cc1ccc(-n2nccn2)c(C(=O)N2C3CCC2C(COc2ncccc2C)C3)n1]

Prepared analogous to example 7 substituting 5-fluoropyridin-2(1H)-one with 3-methylpyridin-2-ol. MS (ESI) mass calcd. for $C_{22}H_{24}N_6O_2$, 404.2; m/z found 405 [M+H.

Example 177

(±)-(2-(((5-fluoropyridin-2-yl)oxy)methyl)-7-azabicyclo[2.2.1]heptan-7-yl)(6-methyl-3-(4-methyloxazol-2-yl)pyridin-2-yl)methanone

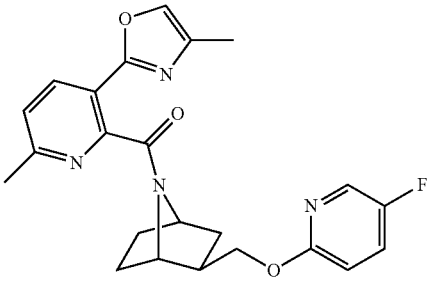 [SMILES: Cc1coc(-c2ccc(C)nc2C(=O)N2C3CCC2C(COc2ccc(F)cn2)C3)n1]

Prepared analogous to Example 7 substituting 6-methyl-3-(2H-1,2,3-triazol-2-yl)picolinic acid with intermediate A-54. MS (ESI) mass calcd. for $C_{23}H_{23}FN_4O_3$, 422.2; m/z found 423 [M+H]$^+$.

Example 178

(6-methyl-3-(4-methyloxazol-2-yl)pyridin-2-yl)((1S,2R,4R)-2-((pyridin-2-yloxy)methyl)-7-azabicyclo[2.2.1]heptan-7-yl)methanone

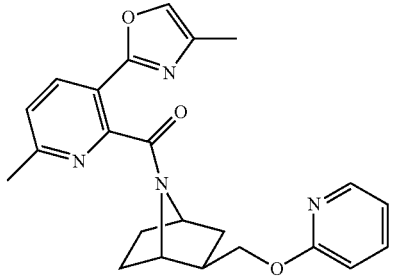 [SMILES: Cc1coc(-c2ccc(C)nc2C(=O)N2C3CCC2C(COc2ccccn2)C3)n1]

Prepared analogous to Example 1 substituting intermediate A-7 with intermediate A-54. MS (ESI) mass calcd. for $C_{23}H_{24}N_4O_3$, 404.2; m/z found 405 [M+H]$^+$.

Example 179

((1S,2R,4R)-2-(((5-fluoropyrimidin-2-yl)oxy)methyl)-7-azabicyclo[2.2.1]heptan-7-yl)(6-methyl-3-(4-methyloxazol-2-yl)pyridin-2-yl)methanone

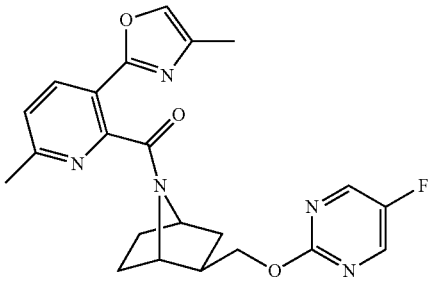 [SMILES: Cc1coc(-c2ccc(C)nc2C(=O)N2C3CCC2C(COc2ncc(F)cn2)C3)n1]

Prepared analogous to Example 98 substituting intermediate 3,6'-dimethyl-[2,3'-bipyridine]-2'-carboxylic acid with intermediate A-54. MS (ESI) mass calcd. for $C_{22}H_{22}FN_5O_3$, 423.2; m/z found 424 [M+H]$^+$.

Example 180

(±)-(5-methyl-2-(2H-1,2,3-triazol-2-yl)phenyl)(2-(((6-methyl-2-(trifluoromethyl)pyrimidin-4-yl)oxy)methyl)-7-azabicyclo[2.2.1]heptan-7-yl)methanone

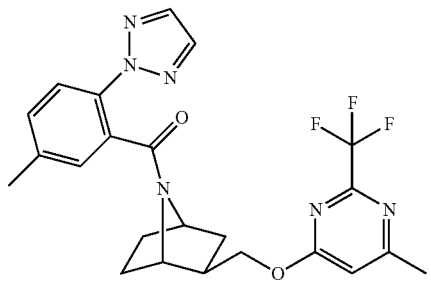

Prepared analogous to Example 13 substituting 2-chloro-4-(trifluoromethyl)pyrimidine with 4-chloro-6-methyl-2-(trifluoromethyl)pyrimidine. MS (ESI) mass calcd. for $C_{23}H_{23}F_3N_6O_2$, 472.2; m/z found 473.2 [M+H]$^+$. $^1$H NMR (CDCl$_3$): 7.88-7.72 (m, 3H), 7.38-7.12 (m, 2H), 6.74-6.70 (s, 0.6H), 6.55-6.50 (s, 0.4H), 4.89-4.75 (m, 1H), 4.30-3.87 (m, 2H), 3.85-3.46 (m, 1H), 2.56-2.49 (m, 3H), 2.46-2.39 (s, 2H), 2.32-1.80 (m, 3H), 1.74-1.11 (m, 5H).

Example 181

(2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone

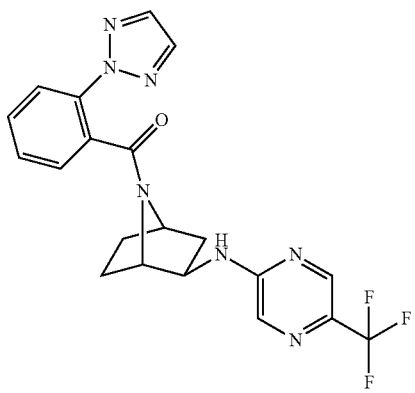

Step A: (1S,2R,4R)-tert-butyl 2-((5-(trifluoromethyl)pyrazin-2-yl)amino)-7-azabicyclo[2.2.1]heptane-7-carboxylate To intermediate B-5 (1.6 g, 7.3 mmol) and K$_2$CO$_3$ (1.5 g, 10 mmol) in DMF (11 mL) was added 2-chloro-5-(trifluoromethyl)pyrazine (1.1 mL, 8.8 mmol). After heating at 70° C. for 2 h. the mixture was cooled to rt, diluted with EtOAc and H$_2$O. The aqueous layer was extracted with EtOAc (3×). The combined organics were washed with 4% (aq) and dried (MgSO$_4$). Purification via silica gel chromatography (0-40% EtOAc in hexanes) gave the title compound (1.8 g, 67%). MS (ESI) mass calcd. for $C_{16}H_{21}F_3N_4O_2$, 358.2; m/z found 359.2 [M+H]$^+$. 1H NMR (CDCl3): 8.32 (s, 1H), 7.86-7.82 (m, 1H), 5.33 (s, 1H), 4.38-4.15 (m, 2H), 4.10-3.96 (m, 1H), 2.14-1.98 (m, 1H), 1.93-1.67 (m, 2H), 1.61-1.36 (m, 12H).

Step B: (1S,2R,4R)—N-(5-(trifluoromethyl)pyrazin-2-yl)-7-azabicyclo[2.2.1]heptan-2-amine To the title compound of step A (200 g, 0.6 mmol) in EtOAc (1 mL) was added 4M HCl in dioxane (3 mL). After 2 h, the reaction was concentrated, neutralized with 5% Na$_2$CO$_3$ (aq) and extracted with DCM (2×). The combined organics were dried (Na$_2$SO$_4$) to give the title compound of step B that was used without further purification. MS (ESI) mass calcd. for $C_{11}H_{13}F_3N_4$, 258.1; m/z found 259.1 [M+H]$^+$.

Step C: (2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone To the title compound of step B (140 mg, 0.5 mmol) and intermediate A-1 (113 g, 0.6 mmol) in DMF (4 mL) was added DIPEA (230 µL, 1.4 mmol) and HATU (155 g, 0.6 mmol). Upon completion of the reaction, purification was performed using Agilent prep method X to give the title compound (172 g, 74%). MS (ESI) mass calcd. for $C_{20}H_{18}F_3N_7O$, 429.2; m/z found 430 [M+H]$^+$. 1H NMR (CDCl3): 8.32 (s, 0.3H), 8.17 (s, 0.7H), 7.99-7.89 (m, 1.5H), 7.88-7.77 (m, 1.5H), 7.62-7.30 (m, 4H), 6.24-6.15 (m, 0.3H), 4.86 (s, 0.7H), 4.76 (d, J=5.4 Hz, 0.3H), 4.45-4.23 (m, 1H), 4.08-3.90 (m, 1H), 2.23-1.34 (m, 6H).

Example 182

(±)-((2-(2H-1,2,3-triazol-2-yl)phenyl)(2-((5-(trifluoromethyl)pyrazin-2-yl)amino)-7-azabicyclo[2.2.1]heptan-7-yl)methanone

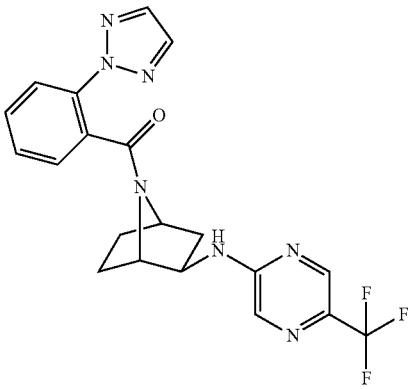 [SMILES: O=C(c1ccccc1-n1nccn1)N1C2CCC1C(Nc1cnc(C(F)(F)F)cn1)C2]

Step A: (±)-tert-butyl 2-((5-(trifluoromethyl)pyrazin-2-yl)amino)-7-azabicyclo[2.2.1]heptane-7-carboxylate Prepared analogous to Example 181 step A substituting intermediate B-5 with intermediate B-6.

Step B: (±)-N-(5-(trifluoromethyl)pyrazin-2-yl)-7-azabicyclo[2.2.1]heptan-2-amine Prepared analogous to Example 181 step B substituting (1S,2R,4R)-tert-butyl 2-((5-(trifluoromethyl)pyrazin-2-yl)

amino)-7-azabicyclo[2.2.1]heptane-7-carboxylate with (±)-tert-butyl 2-((5-(trifluoromethyl)pyrazin-2-yl)amino)-7-azabicyclo[2.2.1]heptane-7-carboxylate.

Step C: (±)-((2-(2H-1,2,3-triazol-2-yl)phenyl)(2-((5-(trifluoromethyl)pyrazin-2-yl)amino)-7-azabicyclo[2.2.1]heptan-7-yl)methanone To 2-(2H-1,2,3-triazol-2-yl)benzoic acid (125 g, 0.6 mmol) and DMF (4 mL) was added (i-Pr)$_2$NEt (0.23 mL, 1.3 mmol) and HBTU (155 g, 0.6 mmol). After 10 min, the title compound from step B (146 g, 0.4 mmol) was added. After stirring overnight at rt, saturated NaHCO$_3$ (aq.) was added and the mixture extracted with EtOAc (3×). The combined organics were dried (MgSO$_4$) and concentrated. Purification via preparative HPLC gave the title compound (89 mg, 47%) as a beige solid. MS (ESI) mass calcd. for $C_{20}H_{18}F_3N_7O$, 429.2; m/z found 430 [M+H]$^+$. 1H NMR (DMSO-D$_6$): 8.47 (s, 0.3H), 8.24 (s, 0.7H), 8.14-8.05 (m, 2.2H), 8.02 (s, 0.7H), 7.85 (d, J=7.2 Hz, 1.3H), 7.72-7.55 (m, 1.7H), 7.49-7.34 (m, 1.4H), 7.13 (t, J=7.4 Hz, 0.7H), 4.58 (t, J=4.3 Hz, 0.7H), 4.44 (d, J=4.7 Hz, 0.3H), 4.04-3.93 (m, 0.3H), 3.82 (t, J=4.1 Hz, 0.3H), 3.79-3.70 (m, 0.7H), 3.54 (d, J=4.8 Hz, 0.7H), 2.07-1.90 (m, 1H), 1.85-1.07 (m, 5H).

Example 183a (2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone

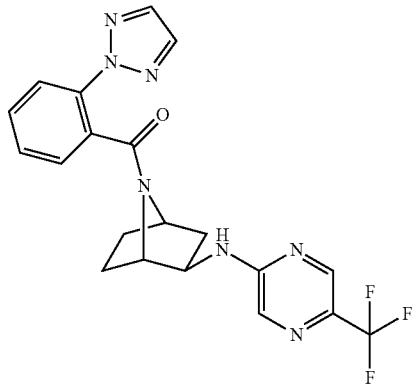 [SMILES: O=C(c1ccccc1-n1nccn1)N1C2CCC1C(Nc1cnc(C(F)(F)F)cn1)C2]

And Example 183 b (2-(2H-1,2,3-triazol-2-yl)phenyl)((1R,2S,4S)-2-((5-(trifluoromethyl)pyrazin-2-yl)amino)-7-azabicyclo[2.2.1]heptan-7-yl)methanone

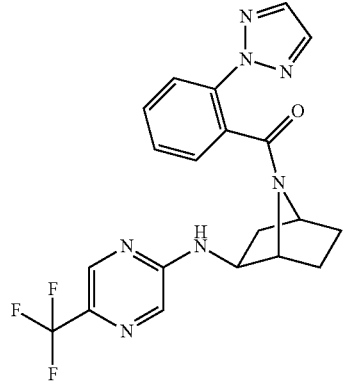 [SMILES: O=C(c1ccccc1-n1nccn1)N1C2CCC1C(Nc1cnc(C(F)(F)F)cn1)C2]

The title compounds were obtained by chiral SFC (CHIRALPAK OD-H 5 μM 250×20 mm) resolution of Example 182 (81 mg) using 70% CO$_2$/30% EtOH as the mobile phase to give enantiomer A (37 mg, 1st eluting enantiomer, example 183a) and enantiomer B (38 mg, 2$^{nd}$ eluting enantiomer, example 183b). Example 183a: >98% single enantiomer, 2.45 min retention time; Example 183b >98% single enantiomer, 3.33 min retention time.

Example 183a

Enantiomer A: MS (ESI) mass calcd. for $C_{20}H_{18}F_3N_7O$, 429.2; m/z found 430 [M+H]$^+$.

Example 183b

Enantiomer B: MS (ESI) mass calcd. for $C_{20}H_{18}F_3N_7O$, 429.2; m/z found 430 [M+H]$^+$.

Example 184

(±)-(5-methyl-3-(2H-1,2,3-triazol-2-yl)pyridin-2-yl)(2-((5-(trifluoromethyl)pyrazin-2-yl)amino)-7-azabicyclo[2.2.1]heptan-7-yl)methanone

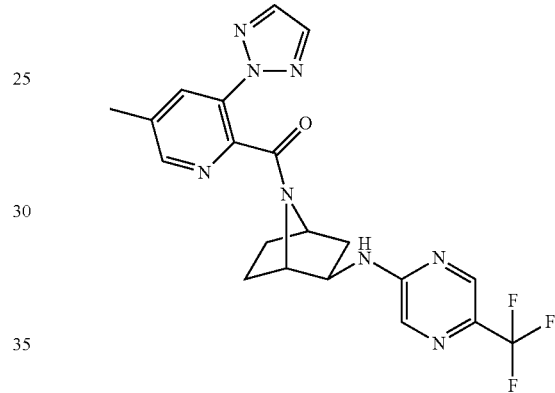

Prepared analogous to Example 182 substituting intermediate A-1 with intermediate A-19 and HBTU with HATU. MS (ESI) mass calcd. for $C_{20}H_{19}F_3N_8O$, 444.2; m/z found 445.1 [M+H]$^+$.

Example 185

(±)-(5-methyl-3-(1H-1,2,3-triazol-1-yl)pyridin-2-yl)(2-((5-(trifluoromethyl)pyrazin-2-yl)amino)-7-azabicyclo[2.2.1]heptan-7-yl)methanone

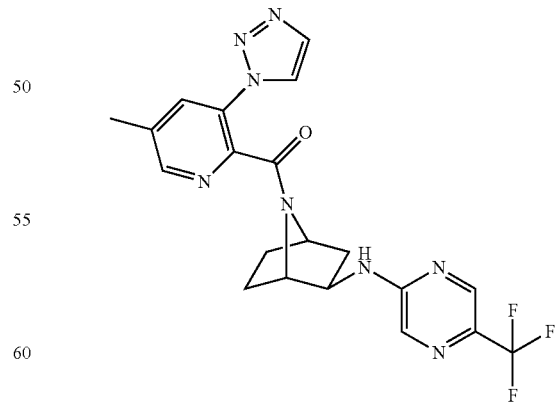

Prepared analogous to Example 184 substituting intermediate A-19 with intermediate A-20. MS (ESI) mass calcd. for $C_{20}H_{19}F_3N_8O$, 444.2; m/z found 445.1 [M+H]$^+$. HPLC R$_t$=1.13.

Example 186

(±)-(6-methyl-3-(2H-1,2,3-triazol-2-yl)pyridin-2-yl)(2-((5-(trifluoromethyl)pyrazin-2-yl)amino)-7-azabicyclo[2.2.1]heptan-7-yl)methanone

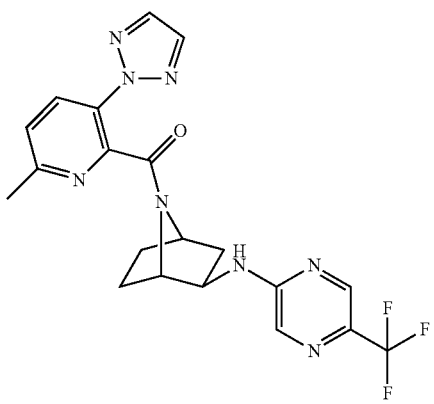

Prepared analogous to Example 184 substituting intermediate A-19 with intermediate A-21. MS (ESI) mass calcd. for $C_{20}H_{19}F_3N_8O$, 444.2; m/z found 445.1 [M+H]$^+$. $^1$H NMR (CDCl$_3$): 8.36-8.32 (s, 0.2H), 8.27-8.23 (s, 0.8H), 8.22-8.18 (d, J=8.4 Hz, 0.2H), 8.13-8.08 (d, J=8.3 Hz, 0.8H), 7.93-7.84 (m, 2H), 7.79-7.75 (m, 0.8H), 7.40-7.36 (d, J=8.4 Hz, 0.2H), 7.36-7.31 (d, J=8.4 Hz, 0.8H), 7.26-7.22 (m, 0.2H), 6.26-6.19 (d, J=8.5 Hz, 0.2H), 4.96-4.86 (t, J=4.8 Hz, 0.8H), 4.83-4.75 (d, J=5.4 Hz, 0.2H), 4.36-4.19 (m, 1H), 4.13-3.92 (d, J=5.0 Hz, 1H), 2.69-2.56 (m, 3H), 2.29-2.14 (dd, J=13.1, 7.5 Hz, 1H), 2.14-1.87 (m, 2H), 1.81-1.78 (m, 1H), 1.63-1.56 (m, 2H).

Example 187

(±)-(6-methyl-3-(2H-1,2,3-triazol-2-yl)pyridin-2-yl)(2-((5-(trifluoromethyl)pyridin-2-yl)amino)-7-azabicyclo[2.2.1]heptan-7-yl)methanone

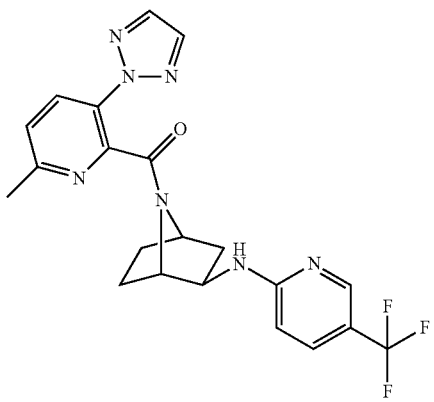

Step A: (±)-tert-butyl 2-((5-(trifluoromethyl)pyridin-2-yl)amino)-7-azabicyclo[2.2.1]heptane-7-carboxylate To intermediate B-6 (150 g, 0.7 mmol) in DMSO (10 mL) was added DIPEA (244 µL, 1.4 mmol) and 2-chloro-5-(trifluoromethyl)pyridine (170 µL, 1.4 mmol). After heating at 100° C. for 4 h, the mixture was cooled to rt and saturated NaHCO$_3$ (aq) was added. The mixture was extracted with DCM (3×). The combined organics were washed with brine and dried (MgSO$_4$). Purification via silica gel chromatography (0-13% EtOAc in heptanes) gave the title compound. MS (ESI) mass calcd. for $C_{17}H_{22}F_3N_7O_2$, 357.2; m/z found 358.0 [M+H]$^+$.

Step B: (±)-N-(5-(trifluoromethyl)pyridin-2-yl)-7-azabicyclo[2.2.1]heptan-2-amine hydrochloride To the title compound from step A (262 g, 0.7 mmol) in 1,4-dioxane (10 mL) was added 6N HCl in iPrOH (700 µL). The reaction was heated to 70° C. for 2 h, cooled to rt, concentrated and used without further purification in subsequent steps.

Step C: (±)-(6-methyl-3-(2H-1,2,3-triazol-2-yl)pyridin-2-yl)(2-((5-(trifluoromethyl)pyridin-2-yl)amino)-7-azabicyclo[2.2.1]heptan-7-yl)methanone Prepared analogous to Example 182 substituting intermediate A-1 with intermediate A-21 and (±)-N-(5-(trifluoromethyl)pyrazin-2-yl)-7-azabicyclo[2.2.1]heptan-2-amine with the title compound of step B. MP=193.9° C. $^1$H NMR (DMSO-D$_6$): 8.38 (s, 0.3H), 8.24-8.16 (m, 1H), 8.15-8.11 (m, 2H), 8.05 (d, J=8.3 Hz, 0.7H), 7.69 (dd, J=8.9, 2.3 Hz, 0.3H), 7.63 (dd, J=8.9, 2.4 Hz, 0.7H), 7.57 (d, J=8.4 Hz, 0.3H), 7.37 (d, J=8.4 Hz, 0.7H), 7.33 (d, J=5.8 Hz, 0.7H), 7.14 (d, J=4.5 Hz, 0.3H), 6.75 (d, J=8.9 Hz, 0.3H), 6.61 (d, J=8.9 Hz, 0.7H), 4.60 (t, J=4.5 Hz, 0.7H), 4.51 (d, J=4.8 Hz, 0.3H), 3.99-3.90 (m, 0.6H), 3.89-3.77 (m, 1.4H), 2.60 (s, 0.9H), 2.23 (s, 2.1H), 1.99 (dd, J=12.6, 7.6 Hz, 1H), 1.83-1.21 (m, 5H).

Example 188

(±)-(5-methyl-3-(2H-1,2,3-triazol-2-yl)pyridin-2-yl)(2-((5-(trifluoromethyl)pyridin-2-yl)amino)-7-azabicyclo[2.2.1]heptan-7-yl)methanone

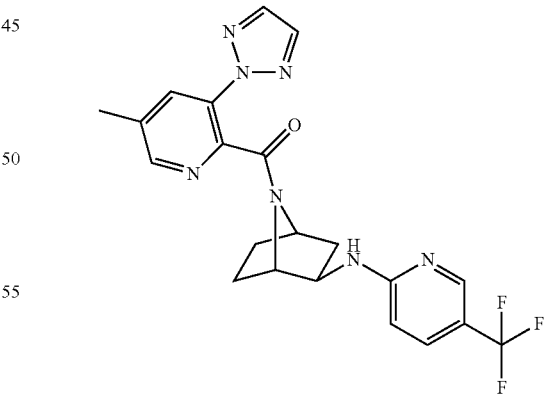

Prepared analogous to Example 187 substituting intermediate A-21 with intermediate A-19. MS (ESI) mass calcd. for $C_{21}H_{20}F_3N_7O$, 443.2; m/z found 444.1 [M+H]$^+$. $^1$H NMR (CDCl$_3$): 8.49-8.44 (dd, J=1.9, 0.9 Hz, 0.2H), 8.41-8.32 (m, 1H), 8.28-8.21 (m, 0.8H), 8.18-8.11 (m, 0.2H), 8.06-7.98 (m, 0.8H), 7.94-7.86 (m, 2H), 7.60-7.53 (dd, J=8.8, 2.4 Hz, 0.2H), 7.45-7.35 (dd, J=8.9, 2.4 Hz, 0.8H), 6.71-6.59 (d, J=8.7 Hz, 0.8H), 6.45-6.37 (d, J=8.8 Hz, 0.2H), 6.27-6.17 (d, J=8.8 Hz, 0.8H), 5.82-5.72 (m, 0.2H), 4.95-4.84 (t, J=4.6 Hz, 0.8H), 4.82-4.74 (d, J=5.2 Hz, 0.2H), 4.36-4.18 (m, 1H), 4.08-3.97 (m, 1H), 2.51-2.47 (s, 0.7H), 2.45-2.41 (m, 2.3H), 2.22-2.14 (dd, J=13.0, 7.7 Hz, 0.8H), 2.11-1.90 (m, 2.2H), 1.82-1.40 (m, 3H).

Example 189

(±)-(6-methyl-2-(2H-1,2,3-triazol-2-yl)pyridin-3-yl)(2-((5-(trifluoromethyl)pyridin-2-yl)amino)-7-azabicyclo[2.2.1]heptan-7-yl)methanone

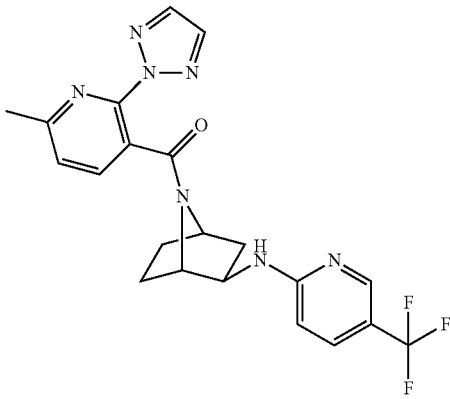

Prepared analogous to Example 187 substituting intermediate A-21 with intermediate A-3. MS (ESI) mass calcd. for $C_{21}H_{20}F_3N_7O$, 443.2; m/z found 444.1 [M+H]$^+$. $^1$H NMR (CDCl$_3$): 8.40-8.33 (s, 0.4H), 8.26-8.19 (d, J=2.0 Hz, 0.6H), 7.98-7.88 (m, 2H), 7.78-7.71 (d, J=7.7 Hz, 0.4H), 7.64-7.55 (m, 1H), 7.41-7.27 (m, 1.6H), 7.20-7.08 (m, 0.7H), 6.43-6.35 (d, J=8.8 Hz, 0.3H), 6.13-6.01 (d, J=8.7 Hz, 0.7H), 5.74-5.56 (m, 0.3H), 4.90-4.81 (m, 0.7H), 4.78-4.71 (d, J=5.3 Hz, 0.3H), 4.38-4.14 (m, 1H), 3.99-3.85 (m, 1H), 2.78-2.55 (m, 3H), 2.24-2.10 (dd, J=13.2, 7.9 Hz, 1H), 2.08-1.39 (m, 5H).

Example 190

(±)-(6-methyl-2-(1H-1,2,3-triazol-1-yl)pyridin-3-yl)(2-((5-(trifluoromethyl)pyridin-2-yl)amino)-7-azabicyclo[2.2.1]heptan-7-yl)methanone

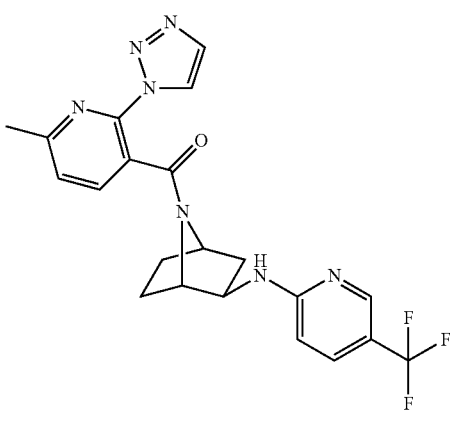 [SMILES: Cc1ccc(C(=O)N2C3CCC2C(Nc2ccc(C(F)(F)F)cn2)C3)c(-n2ccnn2)n1]

Prepared analogous to Example 187 substituting intermediate A-21 with intermediate A-4. MS (ESI) mass calcd. for $C_{21}H_{20}F_3N_7O$, 443.2; m/z found 444.1 [M+H]$^+$. $^1$H NMR (CDCl$_3$): 8.50-8.46 (m, 0.6H), 8.37-8.34 (d, J=1.2 Hz, 0.4H), 8.34-8.31 (s, 0.6H), 8.24-8.17 (s, 0.4H), 7.90-7.84 (m, 1H), 7.75-7.69 (d, J=7.7 Hz, 0.6H), 7.65-7.60 (d, J=7.8 Hz, 0.4H), 7.55-7.47 (dd, J=8.7, 2.4 Hz, 0.7H), 7.36-7.27 (m, 1.3H), 7.22-7.14 (m, 0.4H), 6.94-6.83 (d, J=8.7 Hz, 0.6H), 6.29-6.11 (d, J=8.9 Hz, 1H), 4.91-4.74 (d, J=5.3 Hz, 1H), 4.55-4.28 (m, 1H), 4.04-3.90 (m, 1H), 2.66-2.62 (s, 1.9H), 2.59-2.55 (s, 1.1H), 2.23-2.15 (dd, J=13.1, 8.1 Hz, 0.5H), 2.06-1.79 (m, 2.5H), 1.77-1.68 (m, 1H), 1.55-1.47 (m, 2H).

Example 191

(±)-(4-methoxy-2-(2H-1,2,3-triazol-2-yl)phenyl)(2-((5-(trifluoromethyl)pyridin-2-yl)amino)-7-azabicyclo[2.2.1]heptan-7-yl)methanone

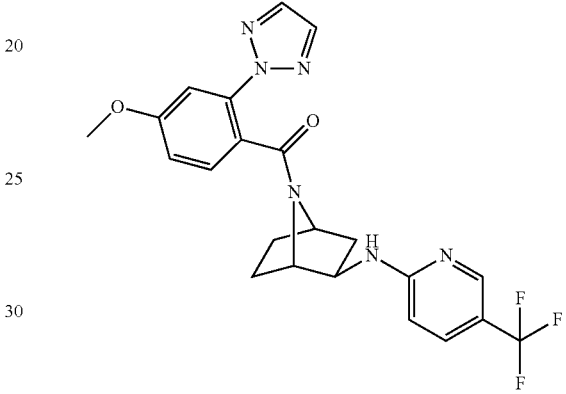

Prepared analogous to Example 187 substituting intermediate A-21 with intermediate A-5. MS (ESI) mass calcd. for $C_{22}H_{21}F_3N_6O_2$, 458.2; m/z found 459.1 [M+H]$^+$. $^1$H NMR (CDCl$_3$): 8.38-8.32 (s, 0.3H), 8.26-8.19 (s, 0.7H), 7.93-7.87 (s, 1.3H), 7.87-7.80 (s, 0.7H), 7.60-7.53 (m, 0.4H), 7.49-7.43 (d, J=2.5 Hz, 0.4H), 7.40-7.26 (m, 2.7H), 7.00-6.93 (dd, J=8.5, 2.5 Hz, 0.4H), 6.90-6.80 (d, J=8.4 Hz, 0.7H), 6.43-6.35 (d, J=8.7 Hz, 0.4H), 6.12-6.04 (d, J=8.8 Hz, 0.7H), 5.77-5.67 (m, 0.3H), 4.84-4.79 (m, 0.7H), 4.74-4.68 (m, 0.3H), 4.36-4.15 (m, 1H), 4.02-3.95 (m, 1H), 3.94-3.87 (s, 1H), 3.87-3.81 (s, 2H), 2.20-2.11 (dd, J=13.0, 8.0 Hz, 0.7H), 2.07-1.99 (dd, J=12.9, 7.6 Hz, 0.3H), 1.99-1.83 (s, 2H), 1.79-1.34 (m, 3H).

Example 192

(±)-(3-fluoro-2-(pyrimidin-2-yl)phenyl)(2-((5-(trifluoromethyl)pyridin-2-yl)amino)-7-azabicyclo[2.2.1]heptan-7-yl)methanone

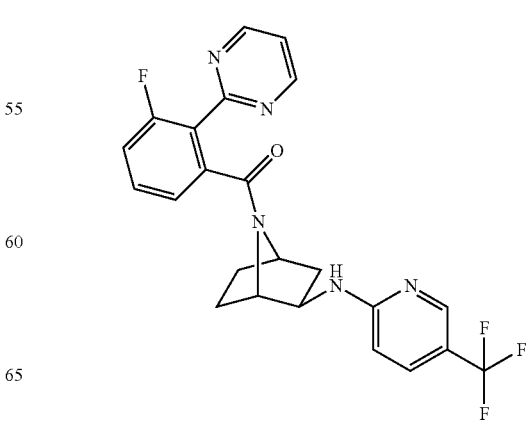

Prepared analogous to Example 187 substituting intermediate A-21 with intermediate A-6. MS (ESI) mass calcd. for $C_{23}H_{19}F_4N_5O$, 457.2; m/z found 458.1 [M+H]$^+$. $^1$H NMR (CDCl$_3$): 8.91-8.76 (m, 2H), 8.36-8.18 (m, 1H), 7.68-7.52 (m, 1H), 7.40-7.27 (m, 3H), 7.24-7.14 (m, 2H), 6.29-6.15 (m, 1H), 4.78-4.66 (t, J=4.9 Hz, 1H), 4.44-4.30 (m, 1H), 4.16-4.02 (d, J=5.0 Hz, 1H), 2.19-2.11 (dd, J=12.9, 8.2 Hz, 1H), 2.08-1.97 (m, 1H), 1.97-1.85 (m, 1H), 1.77-1.60 (m, 2H), 1.54-1.49 (m, 1H).

Example 193

(±)-((3-fluoro-2-methoxyphenyl)(2-((5-(trifluoromethyl)pyridin-2-yl)amino)-7-azabicyclo[2.2.1]heptan-7-yl)methanone

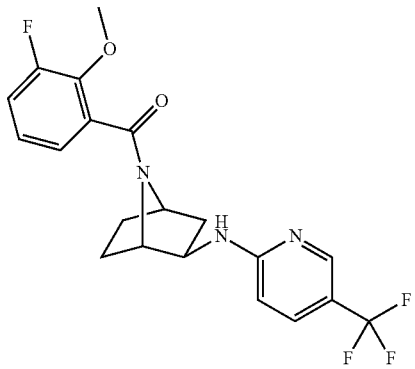 [SMILES: COc1c(F)cccc1C(=O)N1C2CCC1C(Nc1ccc(C(F)(F)F)cn1)C2]

Prepared analogous to Example 187 substituting intermediate A-21 with 3-fluoro-2-methoxybenzoic acid. MS (ESI) mass calcd. for $C_{20}H_{19}F_4N_3O_2$, 409.1; m/z found 410.4 [M+H]$^+$. $^1$H NMR (MeOD): 8.39 (s, 0.3H), 8.18 (s, 0.7H), 7.69 (dd, J=8.9, 2.3 Hz, 0.3H), 7.60 (dd, J=8.9, 2.4 Hz, 0.7H), 7.36 (ddd, J=11.7, 7.6, 2.1 Hz, 0.3H), 7.30-7.05 (m, 2.3H), 7.01 (d, J=7.6 Hz, 0.7H), 6.85-6.73 (m, 0.7H), 6.68 (d, J=8.8 Hz, 0.3H), 6.59 (d, J=8.9 Hz, 0.7H), 4.66 (br s, 0.7H), 4.54 (d, J=4.8 Hz, 0.3H), 4.00-3.90 (m, 0.3H), 3.89-3.77 (m, 3.7H), 3.75 (t, J=4.3 Hz, 0.3H), 3.64 (br s, 0.7H), 2.08-1.91 (m, 1H), 1.80-1.37 (m, 5H).

Example 194

(±)-(3-ethoxy-6-methylpyridin-2-yl)(2-((5-(trifluoromethyl)pyridin-2-yl)amino)-7-azabicyclo[2.2.1]heptan-7-yl)methanone

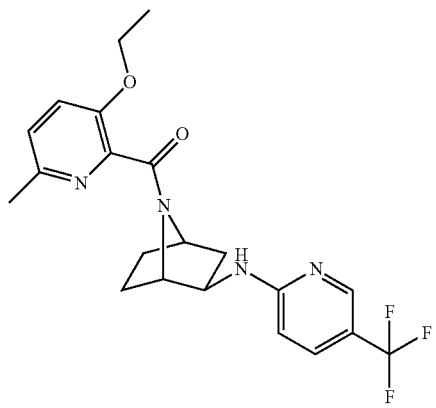

Prepared analogous to Example 187 substituting intermediate A-21 with intermediate A-8. MP=147° C. $^1$H NMR (DMSO-D$_6$): 8.38 (s, 0.3H), 8.16 (s, 0.7H), 7.68 (dd, J=8.9, 2.3 Hz, 0.3H), 7.59 (dd, J=8.9, 2.4 Hz, 0.7H), 7.46 (d, J=8.6 Hz, 0.3H), 7.36-7.18 (m, 2H), 7.05 (d, J=8.6 Hz, 0.7H), 6.71 (d, J=8.9 Hz, 0.3H), 6.57 (d, J=8.9 Hz, 0.7H), 4.65 (br s, 0.7H), 4.55 (d, J=2.8 Hz, 0.3H), 4.13-3.84 (m, 2.3H), 3.83-3.72 (m, 0.7H), 3.67 (d, J=3.5 Hz, 1H), 2.41 (s, 0.9H), 2.16 (s, 2.1H), 2.04-1.91 (m, 1H), 1.80-1.37 (m, 5H), 1.31-1.19 (m, 3H).

Example 195

(±)-(6-methyl-3-(pyrimidin-2-yl)pyridin-2-yl)(2-((5-(trifluoromethyl)pyridin-2-yl)amino)-7-azabicyclo[2.2.1]heptan-7-yl)methanone

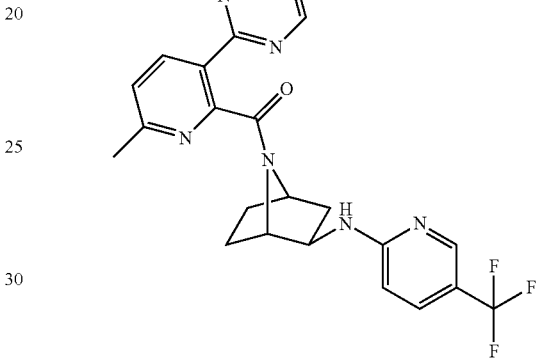

Prepared analogous to Example 187 substituting intermediate A-21 with intermediate A-9. MS (ESI) mass calcd. for $C_{23}H_{21}F_3N_6O$, 454.2; m/z found 455 [M+H]$^+$. $^1$H NMR (DMSO-D$_6$): 8.95-8.81 (m, 2H), 8.37 (s, 0.3H), 8.32 (d, J=8.0 Hz, 0.3H), 8.25-8.13 (m, 1.4H), 7.68 (dd, J=8.8, 2.1 Hz, 0.3H), 7.60 (dd, J=8.9, 2.2 Hz, 0.7H), 7.52-7.39 (m, 2H), 7.30 (d, J=8.1 Hz, 0.7H), 7.25 (d, J=3.7 Hz, 0.3H), 6.75 (d, J=8.8 Hz, 0.3H), 6.54 (d, J=8.9 Hz, 0.7H), 4.61 (t, J=4.2 Hz, 0.7H), 4.51 (d, J=4.2 Hz, 0.3H), 4.01-3.82 (m, 2H), 2.58 (s, 0.9H), 2.24 (s, 2.1H), 2.07-1.95 (m, 1H), 1.86-1.32 (m, 5H).

Example 196

(±)-(2-(2H-1,2,3-triazol-2-yl)phenyl)(2-((5-(trifluoromethyl)pyridin-2-yl)amino)-7-azabicyclo[2.2.1]heptan-7-yl)methanone

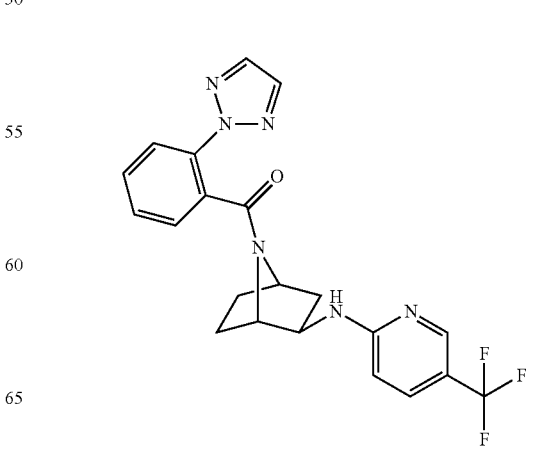

Prepared analogous to Example 187 substituting intermediate A-21 with intermediate A-1. MS (ESI) mass calcd. for C$_{21}$H$_{19}$F$_{3}$N$_{6}$O, 428.2; m/z found 409.2 [M+H]$^{+}$. $^{1}$H NMR (MeOD): 8.38 (s, 0.3H), 8.16 (s, 0.7H), 8.08 (s, 2H), 7.85 (d, J=7.2 Hz, 0.3H), 7.74-7.53 (m, 3H), 7.46-7.35 (m, 1.3H), 7.31 (d, J=6.1 Hz, 0.7H), 7.14 (t, J=7.5 Hz, 0.7H), 6.68 (d, J=8.9 Hz. 0.3H), 6.62 (d, J=8.9 Hz, 0.7H), 4.57 (t, J=4.5 Hz, 0.7H), 4.41 (d, J=4.8 Hz, 0.3H), 4.04-3.95 (m, 0.3H), 3.88-3.76 (m, 1H), 3.55 (br s, 0.7H), 1.97 (dd, J=12.7, 8.0 Hz, 1H), 1.79-1.23 (m, 5H).

Example 197

(±)-(2-((4,6-dimethylpyrimidin-2-yl)amino)-7-azabicyclo[2.2.1]heptan-7-yl)(5-fluoro-2-(2H-1,2,3-triazol-2-yl)phenyl)methanone

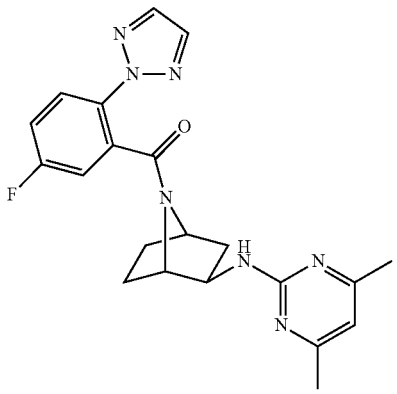 [SMILES: Cc1cc(C)nc(NC2CC3CCC2N3C(=O)c2cc(F)ccc2-n2nccn2)n1]

Step A: (±)-tert-butyl 2-((4,6-dimethylpyrimidin-2-yl)amino)-7-azabicyclo[2.2.1]heptane-7-carboxylate To a microwave vial was weighed intermediate B-6 (210 mg, 1 mmol), 2-chloro-4,6-dimethylpyrimidine (212 g, 1.5 mmol), sodium tert-butoxide (142 g, 1.5 mmol). Pd(dba)$_{2}$ (28 mg, 5 mol %), Ctc-Q-Phos (44 mg, 10 mol). The vial was capped, evacuated and refilled with N$_{2}$ (2×). Then PhCH3 (1 mL) was added and the reaction was heated at 125° C. for 4 h. The reaction allowed to cool to rt, applied directly purified via silica gel chromatography 1-7% 2M NH3/MeOH in DCM to give P1 (125 g, 40%). MS (ESI) mass calcd. for C$_{17}$H$_{26}$N$_{4}$O$_{2}$, 318.2; m/z found 319.3 [M+H]$^{+}$. $^{1}$H NMR (CDCl$_{3}$): 6.31 (s, 1H), 5.18-4.94 (min, 1H), 4.35-4.13 (m, 2H), 4.08 (td, J=7.9, 3.2 Hz, 1H), 2.27 (s, 6H), 1.97 (dd, J=12.9, 7.8 Hz, 1H), 1.82-1.62 (m, 2H), 1.62-1.30 (m, 12H).

Step B: (±)-N-(4,6-dimethylpyrimidin-2-yl)-7-azabicyclo[2.2.1]heptan-2-amine

To the title compound of step A (125 g, 0.4 mmol) in DCM (3 mL) was added TFA (3 mL). After starting material was consumed, the reaction was concentrated, neutralized with 5% Na$_{2}$CO$_{3}$ and extracted with DCM. The combined organics were dried (Na$_{2}$SO$_{4}$) to give the title compound that was used in subsequent reactions without further purification. MS (ESI) mass calcd. for C$_{12}$H$_{18}$N$_{4}$, 218.2; m/z found 219.2 [M+H]$^{+}$.

Step C: (±)-(2-((4,6-dimethylpyrimidin-2-yl)amino)-7-azabicyclo[2.2.1]heptan-7-yl)(5-fluoro-2-(2H-1,2,3-triazol-2-yl)phenyl)methanone Prepared analogous to Example 181 substituting intermediate A-1 with intermediate A-10 and (1S,2R,4R)—N-(5-(trifluoromethyl)pyrazin-2-yl)-7-azabicyclo[2.2.1]heptan-2-amine with the title compound of step B. MS (ESI) mass calcd. for C$_{21}$H$_{22}$FN$_{7}$O, 407.2; m/z found 408.2 [M+H]$^{+}$. $^{1}$H NMR (CDCl$_{3}$): 8.23-7.67 (m, 2.5H), 7.54-6.93 (m, 2.5H), 6.40-6.19 (m, 1H), 4.89-4.65 (m, 1H), 4.41-3.66 (m, 2H), 2.39-1.34 (m, 12H).

Example 198

(±)-(2-((4,6-dimethylpyrimidin-2-yl)amino)-7-azabicyclo[2.2.]heptan-7-yl)(2-fluoro-6-(2H-1,2,3-triazol-2-yl)phenyl)methanone

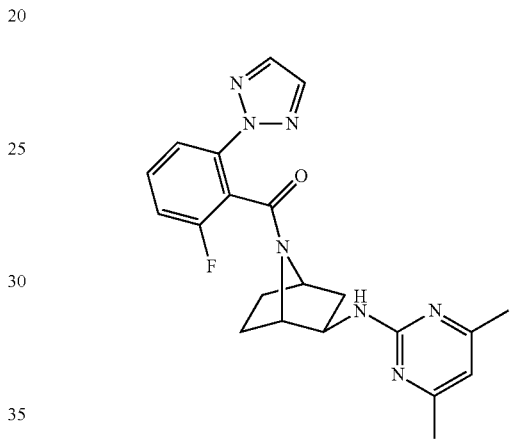

Prepared analogous to Example 197 substituting intermediate A-10 with intermediate A-11. MS (ESI) mass calcd. for C$_{21}$H$_{22}$FN$_{7}$O, 407.2; m/z found 408.2 [M+H]$^{+}$.

Example 199

(±)-(2-((4,6-dimethylpyrimidin-2-yl)amino)-7-azabicyclo[2.2.1]heptan-7-yl)(4-fluoro-2-(2H-1,2,3-triazol-2-yl)phenyl)methanone

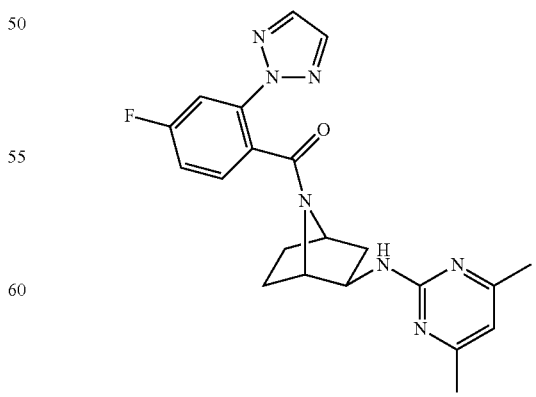

Prepared analogous to Example 197 substituting intermediate A-10 with intermediate A-12. MS (ESI) mass calcd. for C$_{21}$H$_{22}$FN$_7$O, 407.2; m/z found 408.2 [M+H]$^+$. $^1$H NMR (MeOD): 8.23-7.33 (m, 4H), 7.22-6.75 (m, 1H), 6.42-6.21 (m, 1H), 4.91-4.73 (m, 1H), 4.44-4.01 (m, 1H), 3.97-3.71 (m, 1H), 2.41-1.30 (m, 12H).

Example 200

(±)-(2-((4,6-dimethylpyrimidin-2-yl)amino)-7-azabicyclo[2.2.1]heptan-7-yl)(6-methyl-3-(pyrimidin-2-yl)pyridin-2-yl)methanone

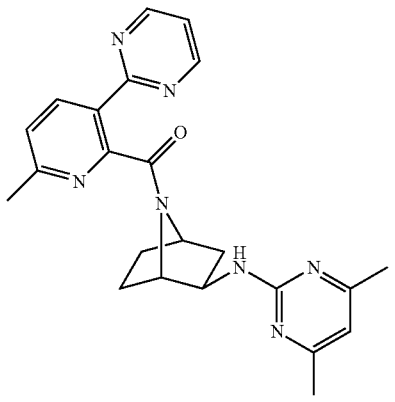

Prepared analogous to Example 187 substituting 2-chloro-5-(trifluoromethyl)pyridine with 2-chloro-4,6-dimethylpyrimidine and intermediate A-21 with intermediate A-9. MS (ESI) mass calcd. for C$_{23}$H$_{25}$N$_7$O, 415.2; m/z found 416 [M+H]$^+$. $^1$H NMR (DMSO-D$_6$): 9.05 (d, J=4.9 Hz, 0.6H), 8.90 (d, J=4.9 Hz, 1.4H), 8.37 (d, J=8.1 Hz, 0.3H), 8.28 (d, J=8.0 Hz, 0.7H), 7.57-7.45 (m, 1.3H), 7.41 (d, J=8.1 Hz, 0.7H), 7.09 (d, J=7.8 Hz, 0.7H), 6.46 (s, 0.3H), 6.43-6.29 (m, 1H), 4.62 (br s, 0.7H), 4.51 (d, J=4.4 Hz, 0.3H), 4.15-3.97 (m, 1H), 3.97-3.92 (m, 0.3H), 3.89 (d, J=3.7 Hz, 0.7H), 2.59 (s, 0.9H), 2.50 (s, 2.1H), 2.26 (s, 1.8H), 2.14 (s, 4.2H), 2.05 (dd, J=12.5, 7.6 Hz, 1H), 1.99-1.37 (m, 5H).

Example 201

(±)-(2-((4,6-dimethylpyrimidin-2-yl)amino)-7-azabicyclo[2.2.1]heptan-7-yl)(6-methyl-3-(2H-1,2,3-triazol-2-yl)pyridin-2-yl)methanone

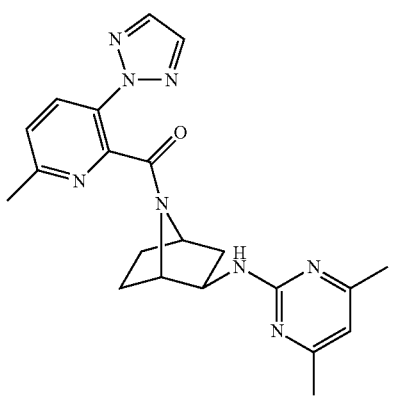

Prepared analogous to Example 200 substituting intermediate A-9 with intermediate A-21. MP=171.9° C. $^1$H NMR (DMSO-D$_6$): 8.28-8.17 (m, 1.2H), 8.17-8.09 (m, 1.8H), 7.57 (d, J=8.4 Hz, 0.4H), 7.46 (d, J=8.4 Hz, 0.6H), 6.89 (d, J=7.0 Hz, 0.6H), 6.46 (s, 0.4H), 6.42 (d, J=7.5 Hz, 0.4H), 6.35 (s, 0.6H), 4.59 (t, J=4.2 Hz, 0.6H), 4.50 (d, J=4.9 Hz, 0.4H), 4.08 (td, J=7.8, 3.0 Hz, 0.4H), 4.00-3.86 (m, 1.6H), 2.60 (s, 1.2H), 2.45 (s, 1.8H), 2.26 (s, 2.4H), 2.15 (s, 3.6H), 1.97 (ddd, J=16.3, 12.6, 7.9 Hz, 1H), 1.83-1.35 (m, 5H).

Example 202

(±)-(2-(2H-1,2,3-triazol-2-yl)phenyl)(2-((4,6-dimethylpyrimidin-2-yl)amino)-7-azabicyclo[2.2.1]heptan-7-yl)methanone

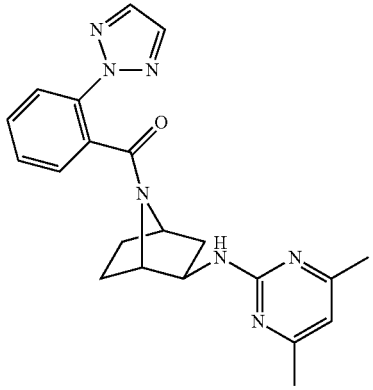 [SMILES: Cc1cc(C)nc(NC2CC3CCC2N3C(=O)c2ccccc2-n2nccn2)n1]

Prepared analogous to Example 200 substituting intermediate A-9 with intermediate A-1. MP=154.2° C. $^1$H NMR (DMSO-D$_6$): 8.12 (s, 1H), 8.07 (s, 1H), 7.85 (d, J=7.7 Hz, 0.5H), 7.77 (d, J=6.8 Hz, 0.5H), 7.72-7.61 (m, 1H), 7.58 (dd, J=10.7, 4.2 Hz, 0.5H), 7.49-7.39 (m, 1H), 7.15 (t, J=7.5 Hz, 0.5H), 6.99 (d, J=6.1 Hz, 0.5H), 6.87 (br s, 0.5H), 6.43 (s, 0.5H), 6.33 (s, 0.5H),), 4.51 (t, J=4.1 Hz, 0.5H), 4.37 (d, J=3.9 Hz, 0.5H), 4.12-3.97 (m, 0.5H), 3.88-3.72 (m, 1H), 3.68 (d, J=4.4 Hz, 0.5H), 2.24 (s, 3H), 2.15 (s, 3H), 1.97-1.21 (m, 6H).

Example 203

(±)-(2-((4,6-dimethylpyrimidin-2-yl)amino)-7-azabicyclo[2.2.1]heptan-7-yl)(3-ethoxy-6-methylpyridin-2-yl)methanone

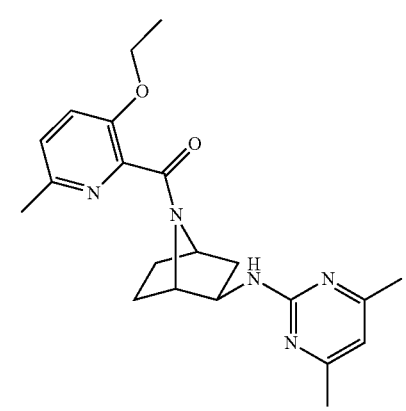

Prepared analogous to Example 200 substituting intermediate A-9 with intermediate A-8. MS (ESI) mass calcd. for $C_{21}H_{27}N_5O_2$, 381.2; m/z found 382.5 [M+H]$^+$. MP=137.8° C. $^1$H NMR (DMSO-D$_6$): 7.20-7.01 (m, 2H), 6.45 (d, J=8.5 Hz, 0.7H), 6.31 (s, 0.3H), 6.24 (s, 0.7H), 5.31 (d, J=8.6 Hz, 0.3H), 4.91 (t, J=4.5 Hz, 0.7H), 4.80 (d, J=5.1 Hz, 0.3H), 4.32-4.14 (m, 1.7H), 4.14-3.98 (m, 1.3H), 3.80 (t, J=4.7 Hz, 0.3H), 3.75 (d, J=4.6 Hz, 0.7H), 2.53 (s, 2.1H), 2.49 (s, 0.9H), 2.26 (s, 1.8H), 2.22 (s, 4.2H), 2.20-2.08 (m, 1H), 2.05-1.49 (m, 5H), 1.48-1.40 (m, 3H).

Example 204

(±)-(2-(2H-1,2,3-triazol-2-yl)phenyl)(2-(quinoxalin-2-ylamino)-7-azabicyclo[2.2.1]heptan-7-yl)methanone

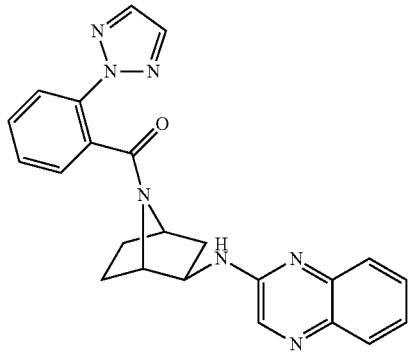 [SMILES: O=C(c1ccccc1-n1nccn1)N1C2CCC1C(Nc1cnc3ccccc3n1)C2]

Step A: (±)-tert-butyl 2-(quinoxalin-2-ylamino)-7-azabicyclo[2.2.1]heptane-7-carboxylate To intermediate B-6 (500 g, 2.4 mmol) in dry DMA (7 mL) was added K$_2$CO$_3$ (650 g, 4.7 mmol) and 2-chloroquinoxaline (580 g, 3.5 mmol). After heating at 80° C. for 48 h, the mixture was cooled to rt and saturated NaHCO$_3$ (aq) was added. The mixture was extracted with EtOAc (3×). The combined organics were washed with brine and dried (MgSO$_4$). Purification via silica gel chromatography (0-25% EtOAc in heptanes) gave the title compound. MS (ESI) mass calcd. for $C_{19}H_{24}N_4O_2$, 340.2; m/z found 341.0 [M+H]$^+$.

Step B: N-((±)-7-azabicyclo[2.2.1]heptan-2-yl)quinoxalin-2-amine hydrochloride

To the title compound from step A (343 g, 1 mmol) in 1,4-dioxane (10 mL) was added 6N HCl in iPrOH (1 mL). The reaction was heated to 70° C. for 2 h, cooled to rt, concentrated and used without further purification in subsequent steps.

Step C: (±)-(2-(2H-1,2,3-triazol-2-yl)phenyl)(2-(quinoxalin-2-ylamino)-7-azabicyclo[2.2.1]heptan-7-yl)methanone Prepared analogous to Example 187 substituting intermediate A-21 with intermediate A-1 and (±)-N-(5-(trifluoromethyl)pyridin-2-yl)-7-azabicyclo[2.2.1]heptan-2-amine hydrochloride with the title compound from step B. MS (ESI) mass calcd. for $C_{23}H_{21}N_7O$, 411.2; m/z found 412 [M+H]$^+$. $^1$H NMR (DMSO-D$_6$): 8.38 (s, 0.3H), 8.31 (s, 0.7H), 8.08 (s, 2H), 7.88-7.73 (m, 1.3H), 7.72-7.20 (m, 7H), 7.14-7.04 (m, 0.7H), 4.60 (t, J=4.4 Hz, 0.7H), 4.54 (d, J=4.7 Hz, 0.3H), 4.15-4.03 (m, 0.3H), 3.97-3.87 (m, 0.7H), 3.82 (t, J=3.9 Hz, 0.3H), 3.65 (d, J=3.2 Hz, 0.7H), 2.12-1.96 (m, 1H), 1.84-1.28 (m, 5H).

Example 205

(±)-(6-methyl-3-(2H-1,2,3-triazol-2-yl)pyridin-2-yl)(2-(quinoxalin-2-ylamino)-7-azabicyclo[2.2.1]heptan-7-yl)methanone

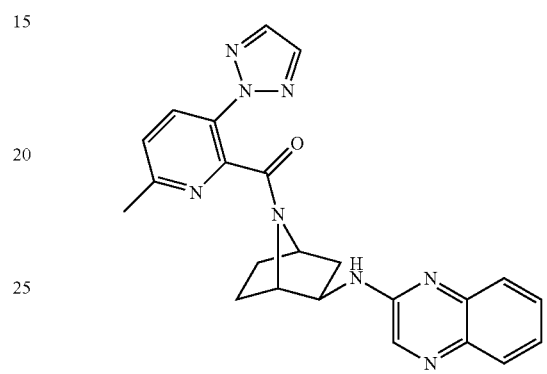

Prepared analogous to Example 204 substituting with intermediate A-1 with intermediate A-21. MP=260.8° C. $^1$H NMR (DMSO-D$_6$): 8.44 (s, 0.3H), 8.32 (s, 0.7H), 8.19 (d, J=8.4 Hz, 0.3H), 8.13 (s, 2H), 7.96 (d, J=8.3 Hz, 0.7H), 7.83-7.72 (m, 1H), 7.68-7.27 (m, 4.3H), 7.19 (d, J=8.4 Hz, 0.7H), 4.64 (br s, 1H), 4.06-3.86 (m, 2H), 2.61 (s, 0.9H), 2.09 (s, 2.1H), 2.06-1.99 (m, 1H), 1.88-1.62 (m, 2H), 1.62-1.38 (m, 3H).

Example 206

(±)-(3-fluoro-2-methoxyphenyl)(2-(quinoxalin-2-ylamino)-7-azabicyclo[2.2.1]heptan-7-yl)methanone

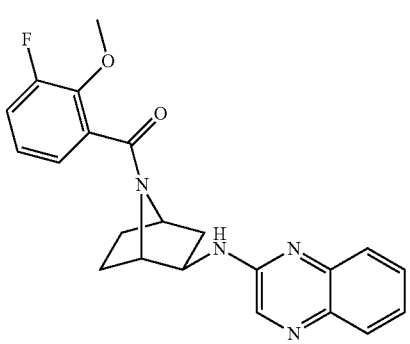 [SMILES: COc1c(F)cccc1C(=O)N1C2CCC1C(Nc1cnc3ccccc3n1)C2]

Prepared analogous to Example 204 substituting intermediate A-1 with 3-fluoro-2-methoxybenzoic acid. MP=179.2° C. $^1$H NMR (DMSO-D$_6$): 8.38 (s, 0.3H), 8.27 (s, 0.7H), 7.80 (d, J=8.0 Hz, 0.3H), 7.73 (d, J=8.0 Hz, 0.7H), 7.65-7.52 (m, 1.4H), 7.52-7.28 (m, 2.7H), 7.28-7.15 (m, 0.7H), 7.09 (d, J=7.6 Hz, 0.7H), 6.96 (ddd, J=11.7, 8.2, 1.4 Hz, 0.7H), 6.75 (td, J=7.9, 4.8 Hz, 0.7H), 4.75-4.63 (m, 1H), 4.11-4.01 (m, 0.4H), 3.99-3.90 (m, 0.7H), 3.86 (br s, 0.9H), 3.83-3.73 (m, 2.1H), 2.06 (dt, J=16.7, 8.4 Hz, 1H), 1.87-1.45 (m, 6H).

Example 207

(±)-(3-ethoxy-6-methylpyridin-2-yl)(2-(quinoxalin-2-ylamino)-7-azabicyclo[2.2.1]heptan-7-yl)methanone

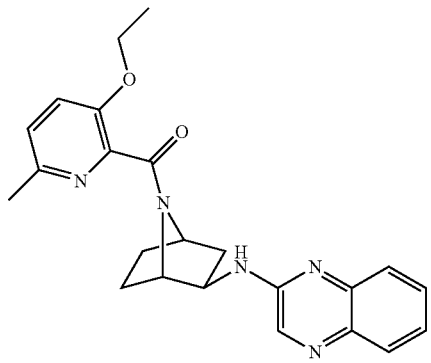 [SMILES: CCOc1ccc(C)nc1C(=O)N1C2CCC1C(Nc1cnc3ccccc3n1)C2]

Prepared analogous to Example 204 substituting with intermediate A-1 with intermediate A-8. MS (ESI) mass calcd. for $C_{23}H_{25}N_5O_2$, 403.2; m/z found 404 [M+H]$^+$. MP=184.9 C. $^1$H NMR (DMSO-D$_6$): 8.41 (s, 0.3H), 8.26 (s, 0.7H), 7.79 (d, J=8.1 Hz, 0.3H), 7.72 (d, J=8.0 Hz, 0.7H), 7.64-7.53 (m, 1.7H), 7.50-7.22 (m, 2.9H), 7.18 (d, J=8.6 Hz, 0.7H), 6.86 (d, J=8.6 Hz, 0.7H), 4.68 (br s, 1H), 4.12-3.83 (m, 3H), 3.79 (d, J=4.1 Hz, 0.7H), 3.71 (br s, 0.3H), 2.41 (s, 0.9H), 2.11-1.96 (m, 3.1H), 1.89-1.42 (m, 5H), 1.25 (t, J=6.9 Hz, 3H).

Example 208

(±)-(6-methyl-3-(pyrimidin-2-yl)pyridin-2-yl)(2-(quinoxalin-2-ylamino)-7-azabicyclo[2.2.1]heptan-7-yl)methanone

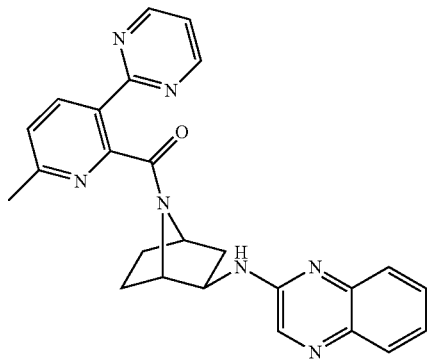 [SMILES: Cc1ccc(-c2ncccn2)c(C(=O)N2C3CCC2C(Nc2cnc4ccccc4n2)C3)n1]

Prepared analogous to Example 204 substituting with intermediate A-1 with intermediate A-9. MS (ESI) mass calcd. for $C_{25}H_{23}N_7O$, 437.2; m/z found 438 [M+H]$^+$. $^1$H NMR (DMSO-D$_6$): 8.93-8.82 (m, 2H), 8.46 (s, 0.3H), 8.33 (d, J=8.1 Hz, 0.3H), 8.27 (s, 0.7H), 8.14 (d, J=8.0 Hz, 0.7H), 7.81-7.26 (m, 6.3H), 7.17 (d, J=8.1 Hz, 0.7H), 4.66 (br s, 1H), 4.06-3.94 (m, 2H), 2.60 (s, 0.9H), 2.13-2.01 (m, 3.1H), 1.92-1.36 (m, 5H).

Example 209

(±)-(2-(2H-1,2,3-triazol-2-yl)phenyl)(2-((6-(trifluoromethyl)pyridin-2-yl)amino)-7-azabicyclo[2.2.1]heptan-7-yl)methanone

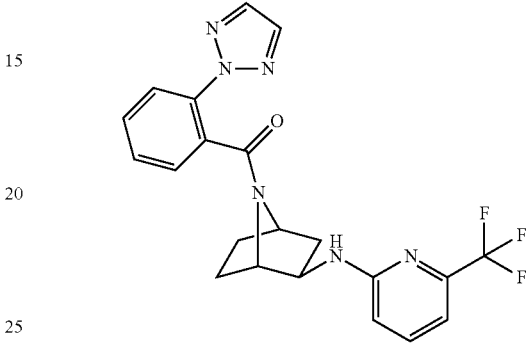

Step A: (±)-tert-butyl-2-((6-(trifluoromethyl)pyridin-2-yl)amino)-7-azabicyclo[2.2.1]heptane-7-carboxylate To 2-chloro-6-(trifluoromethyl)pyridine (113 mg, 0.6 mmol) in THF (3 mL) was added sodium tert-butoxide (120 g, 1.2 mmol), Xanphos (26 mg, 7 mol %) and Pd$_2$(dba)$_3$ (23 mg, 4 mol %) at rt while N$_2$ was bubbled through the solution. After 10 minutes, intermediate B-6 (132 g, 0.6 mmol) was added. The reaction mixture was heated at 90° C. for 3 h. After allowing to cool to rt, saturated NaHCO$_3$ (aq) the mixture extracted with EtOAc (2×). The combined organics were dried (MgSO$_4$). Purification via silica gel chromatography (0-7% EtOAc in heptane) gave the title compound. MS (ESI) mass calcd. for $C_{17}H_{22}F_3N_3O_2$, 357.2; m/z found 358.4 [M+H]$^+$.

Step B: (±)-N-(6-(trifluoromethyl)pyridin-2-yl)-7-azabicyclo[2.2.1]heptan-2-amine hydrochloride Prepared analogous to Example 204 substituting (±)-tert-butyl 2-(quinoxalin-2-ylamino)-7-azabicyclo[2.2.1]heptane-7-carboxylate with the title compound of step A.

Step C: (±)-tert-butyl-2-((6-(trifluoromethyl)pyridin-2-yl)amino)-7-azabicyclo[2.2.1]heptane-7-carboxylate Prepared analogous to Example 204 substituting N-((±)-7-azabicyclo[2.2.1]heptan-2-yl)quinoxalin-2-amine hydrochloride with the title compound of step B. MS (ESI) mass calcd. for $C_{21}H_{19}F_3N_6O$, 428.2; m/z found 429. [M+H]$^+$. MP=96.8° C. $^1$H NMR (DMSO-D$_6$): 8.07 (s, 2H), 7.85 (d, J=7.9 Hz, 0.3H), 7.74-7.51 (m, 2.7H), 7.46-7.36 (m, 1.3H), 7.17-6.94 (m, 2H), 0.6.86 (d, J=7.2 Hz, 0.7H), 6.82 (d, J=8.6 Hz, 0.3H), 6.74 (d, J=8.4 Hz, 0.7H), 4.55 (t, J=4.5 Hz, 0.7H), 4.41 (d, J=4.6 Hz, 0.3H), 3.94-3.84 (m, 0.3H), 3.84-3.71 (m, 1H), 3.61 (d, J=4.6 Hz, 0.7H), 1.96 (dd, J=12.6, 8.0 Hz, 1H), 1.80-1.21 (m, 5H).

Example 210

(±)-((2-(2H-1,2,3-triazol-2-yl)phenyl)(2-((4-(trifluoromethyl)pyridin-2-yl)amino)-7-azabicyclo[2.2.1]heptan-7-yl)methanone

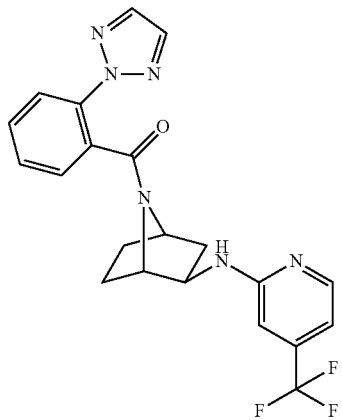 [SMILES: O=C(c1ccccc1-n1nccn1)N1C2CCC1C(Nc1cc(C(F)(F)F)ccn1)C2]

Prepared analogous to Example 209 substituting 2-chloro-6-(trifluoromethyl)pyridine with 2-chloro-4-(trifluoromethyl)pyridine. MP=153.5° C. MS (ESI) mass calcd. for $C_{21}H_{19}F_3N_6O$, 428.2; m/z found 429 [M+H]$^+$. $^1$H NMR (DMSO-D$_6$): 8.27 (d, J=5.3 Hz, 0.3H), 8.12-7.99 (m, 2.7H), 7.85 (d, J=7.9 Hz, 0.3H), 7.72-7.54 (m, 1.6H), 7.50-7.33 (m, 1.4H), 7.13-6.92 (m, 2H), 6.82 (d, J=12.6 Hz, 0.3H), 6.78 (s, 0.7H), 6.67 (d, J=5.3 Hz, 0.7H), 4.56 (t, J=4.5 Hz, 0.7H), 4.41 (d, J=4.6 Hz, 0.3H), 4.04-3.93 (m, 0.3H), 3.86-3.72 (m, 1H), 3.52 (br s, 0.7H), 1.96 (dd, J=12.6, 8.0 Hz, 1H), 1.78-1.17 (m, 5H).

Example 211

(±)-(2-(2H-1,2,3-triazol-2-yl)phenyl)(2-((5-chloropyridin-2-yl)amino)-7-azabicyclo[2.2.1]heptan-7-yl)methanone

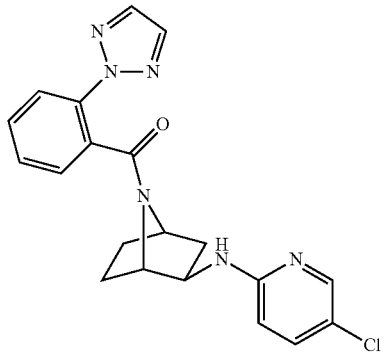 [SMILES: O=C(c1ccccc1-n1nccn1)N1C2CCC1C(Nc1ccc(Cl)cn1)C2]

Prepared analogous to Example 209 substituting 2-chloro-6-(trifluoromethyl)pyridine with 5-chloro-2-iodopyridine. MS (ESI) mass calcd. for $C_{20}H_{19}ClN_6O$, 394.1; m/z found 395 [M+H]$^+$. MP=157.0° C. $^1$H NMR (DMSO-D$_6$): 8.14-7.99 (m, 2.3H), 7.87-7.79 (m, 1H), 7.71-7.52 (m, 1.7H), 7.52-7.36 (m, 2.6H), 7.23-7.11 (m, 0.7H), 6.80 (d, J=6.4 Hz, 0.7H), 6.58 (d, J=9.0 Hz, 0.3H), 6.52 (d, J=8.9 Hz, 0.7H), 4.53 (t, J=4.6 Hz, 0.7H), 4.37 (d, J=4.6 Hz, 0.3H), 3.92-3.82 (m, 0.3H), 3.81-3.68 (m, 1H), 3.52 (d, J=4.3 Hz, 0.7H), 1.94 (dd, J=12.5, 8.1 Hz, 1H), 1.73-1.22 (m, 5H).

Example 212

(±)-(2-(2H-1,2,3-triazol-2-yl)phenyl)(2-((6-(trifluoromethyl)pyridazin-3-yl)amino)-7-azabicyclo[2.2.1]heptan-7-yl)methanone

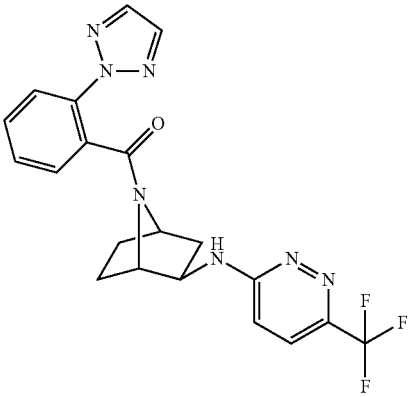

Prepared analogous to Example 209 substituting 2-chloro-6-(trifluoromethyl)pyridine with 3-chloro-6-(trifluoromethyl)pyridazine. MP=134.0° C. MS (ESI) mass calcd. for $C_{20}H_{18}F_3N_7O$, 429.2; m/z found 430 [M+H]$^+$. $^1$H NMR (DMSO-D$_6$): 8.08 (s, 1.4H), 8.07 (s, 0.6H), 7.85 (d, J=7.8 Hz, 0.3H), 7.77-7.46 (m, 3.6H), 7.44-7.31 (m, 1.4H), 7.20-7.09 (m, 0.7H), 7.06 (d, J=9.4 Hz, 0.3H), 6.98 (d, J=9.3 Hz, 0.7H), 4.59 (t, J=4.4 Hz, 0.7H), 4.48 (d, J=4.7 Hz, 0.3H), 3.97-3.87 (m, 0.7H), 3.81 (t, J=4.0 Hz, 0.3H), 3.58-3.56 (m, 1H), 2.01 (dd, J=12.9, 8.0 Hz, 1H), 1.82-1.18 (m, 5H).

Example 213

(±)-(2-(2H-1,2,3-triazol-2-yl)phenyl)(2-((5-methoxypyridin-2-yl)amino)-7-azabicyclo[2.2.1]heptan-7-yl)methanone

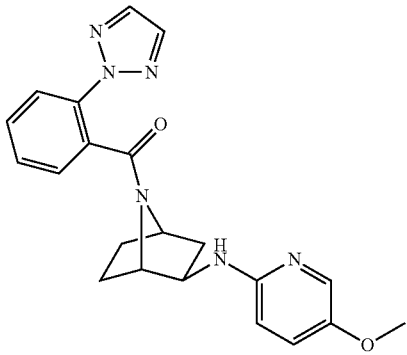 [SMILES: COc1ccc(NC2CC3CCC2N3C(=O)c2ccccc2-n2nccn2)nc1]

Prepared analogous to Example 209 substituting 2-chloro-6-(trifluoromethyl)pyridine with 2-chloro-5-methoxypyridine. MS (ESI) mass calcd. for $C_{21}H_{22}N_6O_2$, 390.2; m/z found 391 [M+H]$^+$. MP=174.0° C. $^1$H NMR (DMSO-D$_6$): 8.31 (s, 0.3H), 8.13-8.02 (m, 2H), 7.84 (d, J=8.0 Hz, 0.3H), 7.79 (d, J=3.0 Hz, 0.3H), 7.71-7.61 (m, 1.3H), 7.60-7.53 (m, 1H), 7.50-7.37 (m, 1.4H), 7.22-7.04 (m, 1.7H), 6.52 (d, J=9.0 Hz, 0.3H), 6.46 (d, J=9.0 Hz, 0.7H), 6.21 (d, J=6.9 Hz, 0.7H), 4.52 (t, J=4.5 Hz, 0.7H), 4.37 (d, J=4.5 Hz, 0.2H), 3.90-3.79 (m, 0.3H), 3.79-3.68 (m, 1.9H), 3.64 (s, 2.1H), 3.57 (d, J=4.0 Hz, 0.7H), 1.98-1.84 (m, 1H), 1.76-1.21 (m, 5H).

Example 214

(±)-(2-(2H-1,2,3-triazol-2-yl)phenyl)(2-((5-methylpyridin-2-yl)amino)-7-azabicyclo[2.2.1]heptan-7-yl)methanone

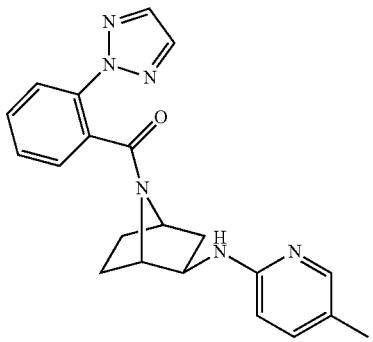 [SMILES: Cc1ccc(NC2CC3CCC2N3C(=O)c2ccccc2-n2nccn2)nc1]

Prepared analogous to Example 209 substituting 2-chloro-6-(trifluoromethyl)pyridine with 2-chloro-5-methylpyridine. MS (ESI) mass calcd. for $C_{21}H_{22}N_6O$, 374.2; m/z found 375.2 [M+H]$^+$. $^1$H NMR (DMSO-D$_6$): 8.32 (s, 0.7H), 8.09 (s, 0.6H), 8.07 (s, 1.4H), 7.89-7.80 (m, 0.6H), 7.72-7.53 (m, 2.1H), 7.52-7.37 (m, 1.3H), 7.27 (dd, J=8.5, 2.2 Hz, 0.3H), 7.23-7.11 (m, 1.3H), 6.47 (d, J=8.5 Hz, 0.3H), 6.41 (d, J=8.2 Hz, 0.7H), 6.35 (d, J=6.9 Hz, 0.7H), 4.53 (t, J=4.5 Hz, 0.7H), 4.37 (d, J=4.4 Hz, 0.3H), 3.95-3.84 (m, 0.3H), 3.84-3.70 (m, 1H), 3.56 (d, J=4.3 Hz, 0.7H), 2.12 (s, 0.9H), 2.04 (s, 2.1H), 1.99-1.86 (m, 1H), 1.78-1.24 (m, 5H).

Example 215

(±)-(2-(2H-1,2,3-triazol-2-yl)phenyl)(2-(pyridin-2-ylamino)-7-azabicyclo[2.2.1]heptan-7-yl)methanone

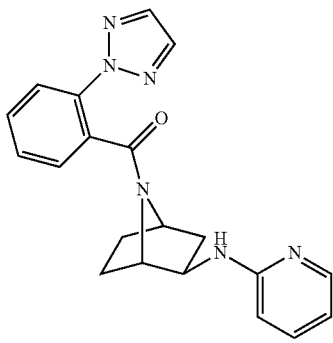 [SMILES: O=C(c1ccccc1-n1nccn1)N1C2CCC1C(Nc1ccccn1)C2]

Prepared analogous to Example 209 substituting 2-chloro-6-(trifluoromethyl)pyridine with 2-iodopyridine. MS (ESI) mass calcd. for $C_{20}H_{20}N_6O$, 360.2; m/z found 361 [M+H]$^+$. MP=167.9° C. $^1$H NMR (DMSO-D$_6$): 8.12-8.00 (m, 2.3H), 7.88-7.79 (m, 1H), 7.73-7.53 (m, 1.5H), 7.50-7.28 (m, 2.5H), 7.13 (t, J=7.4 Hz, 0.7H), 6.63-6.37 (m, 3H), 4.54 (t, J=4.5 Hz, 0.7H), 4.39 (d, J=4.4 Hz, 0.3H), 3.92 (td, J=7.5, 3.2 Hz, 0.3H), 3.86-3.73 (m, 1H), 3.58 (d, J=4.3 Hz, 0.7H), 2.02-1.86 (m, 1H), 1.78-1.23 (m, 5H).

Example 216

(±)-(2-(2H-1,2,3-triazol-2-yl)phenyl)(2-((5-chlorobenzo[d]oxazol-2-yl)amino)-7-azabicyclo[2.2.1]heptan-7-yl)methanone

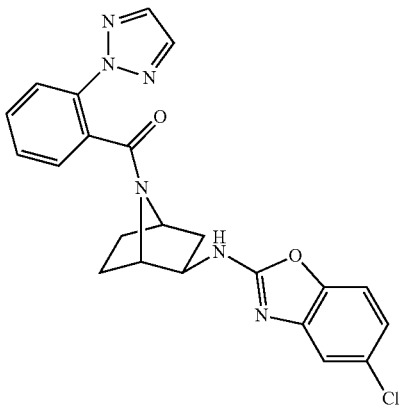 [SMILES: O=C(c1ccccc1-n1nccn1)N1C2CCC1C(Nc1nc3cc(Cl)ccc3o1)C2]

Step A: (±)-tert-butyl 2-((5-chlorobenzo[d]oxazol-2-yl)amino)-7-azabicyclo[2.2.1]heptane-7-carboxylate To intermediate B-6 (116 g, 0.6 mmol) in 1,4-dioxane (3 mL) was added DIPEA (190 µL, 1.1 mmol) and 5-chloro-2-(methylsulfinyl)benzo[d]oxazole (235 g, 1.1 mmol). After heating at 80° C. for 4 h, the mixture was cooled to rt and saturated NaHCO$_3$ (aq) was added. The aqueous layer was extracted with EtOAc (3×). The combined organics were dried (MgSO$_4$). Purification via silica gel chromatography (0-10% EtOAc in hexanes) gave the title compound (130 g, 66%). MS (ESI) mass calcd. for $C_{18}H_{22}ClN_3O_3$, 363.1; m/z found 364.0 [M+H]$^+$.

Step B: N-((±)-7-azabicyclo[2.2.1]heptan-2-yl)-5-chlorobenzo[d]oxazol-2-amine hydrochloride Prepared analogous to Example 209 substituting (±)-tert-butyl-2-((6-(trifluoromethyl)pyridin-2-yl)amino)-7-azabicyclo[2.2.1]heptane-7-carboxylate with the title compound of step A. MS (ESI) mass calcd. for $C_{13}H_{14}ClN_3O$, 263.1; m/z found 264.0 [M+H]$^+$.

Step C: (±)-(2-(2H-1,2,3-triazol-2-yl)phenyl)(2-((5-chlorobenzo[d]oxazol-2-yl)amino)-7-azabicyclo[2.2.1]heptan-7-yl)methanone Prepared analogous to Example 209 substituting (±)-N-(6-(trifluoromethyl)pyridin-2-yl)-7-azabicyclo[2.2.1]heptan-2-amine hydrochloride with the title compound of step B. MS (ESI) mass calcd. for $C_{22}H_{19}ClN_6O_2$, 434.1; m/z found 435 [M+H]$^+$. $^1$H NMR (DMSO-D$_6$): 8.20 (d, J=5.6 Hz, 1H), 8.13-8.05 (m, 2H), 7.85 (d, J=7.4 Hz, 0.3H), 7.76 (d, J=7.3 Hz, 0.3H), 7.72-7.55 (m, 1.3H), 7.53-7.44 (m, 0.7H), 7.44-7.29 (m, 2H), 7.24 (d, J=2.1 Hz, 0.7H), 7.16-

7.08 (m, 0.7H), 7.08-6.98 (m, 1H), 4.66-4.47 (m, 1H), 3.97-3.86 (m, 0.3H), 3.82 (t, J=3.9 Hz, 0.3H), 3.79-3.66 (m, 1.4H), 2.07-1.92 (m, 1H), 1.88-1.22 (m, 5H).

Example 217

(±)-(2-((5-bromopyridin-2-yl)amino)-7-azabicyclo[2.2.1]heptan-7-yl)(6-methyl-3-(pyrimidin-2-yl)pyridin-2-yl)methanone

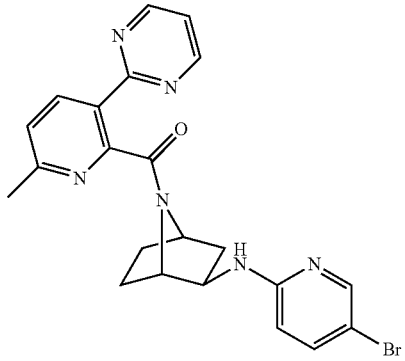 [SMILES: Cc1ccc(-c2ncccn2)c(C(=O)N2C3CCC2C(Nc2ccc(Br)cn2)C3)n1]

Prepared analogous to Example 209 substituting 2-chloro-6-(trifluoromethyl)pyridine with 5-bromo-2-iodopyridine and intermediate A-1 with intermediate A-9. MS (ESI) mass calcd. for $C_{22}H_{21}BrN_6O$, 464.1; m/z found 466 [M+H]$^+$. MP=221.8° C. $^1$H NMR (DMSO-D$_6$): 8.96-8.78 (m, 2H), 8.32 (d, J=8.0 Hz, 0.3H), 8.19 (d, J=8.0 Hz, 0.7H), 8.10 (d, J=2.4 Hz, 0.3H), 7.93 (d, J=2.4 Hz, 0.7H), 7.56 (dd, J=8.9, 2.5 Hz, 0.3H), 7.51-7.39 (m, 2H), 7.33 (d, J=8.1 Hz, 0.7H), 6.93 (d, J=7.1 Hz, 0.7H), 6.66 (d, J=5.6 Hz, 0.3H), 6.61 (d, J=9.0 Hz, 0.3H), 6.36 (d, J=8.9 Hz, 0.7H), 4.59 (t, J=4.1 Hz, 0.7H), 4.47 (d, J=4.3 Hz, 0.3H), 3.96-3.75 (m, 2H), 2.58 (s, 0.9H), 2.31 (s, 2.1H), 2.07-1.91 (m, 1H), 1.88-1.30 (m, 5H).

Example 218

(±)-(2-((5-bromopyridin-2-yl)amino)-7-azabicyclo[2.2.1]heptan-7-yl)(3-fluoro-2-methoxyphenyl)methanone

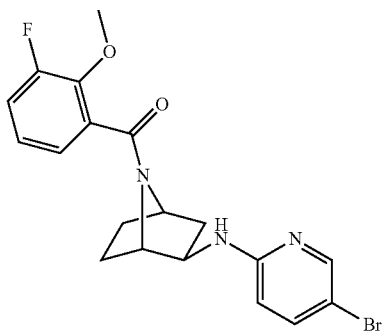 [SMILES: COc1c(F)cccc1C(=O)N1C2CCC1C(Nc1ccc(Br)cn1)C2]

Prepared analogous to Example 217 substituting intermediate A-9 with 3-fluoro-2-methoxybenzoic acid. MS (ESI) mass calcd. for $C_{19}H_{19}BrFN_3O_2$, 419.1; m/z found 420.1 [M+H]$^+$. MP=175.2° C. $^1$H NMR (DMSO-D$_6$): 8.10 (d, J=2.4 Hz, 0.3H), 7.90 (d, J=2.4 Hz, 0.7H), 7.56 (dd, J=8.9, 2.5 Hz, 0.3H), 7.47 (dd, J=8.9, 2.5 Hz, 0.7H), 7.34 (ddd, J=11.7, 7.5, 2.3 Hz, 0.3H), 7.24-7.08 (m, 1.3H), 7.02 (d, J=7.6 Hz, 0.7H), 6.87-6.66 (m, 1.7H), 6.54 (d, J=8.9 Hz, 0.3H), 6.46 (d, J=8.9 Hz, 0.7H), 4.63 (br s, 0.7H), 4.50 (d, J=4.8 Hz, 0.3H), 3.88-3.68 (m, 4.3H), 3.58 (d, J=2.9 Hz, 0.7H), 2.05-1.87 (m, 1H), 1.78-1.20 (m, 5H).

Example 219

(±)-(2-((5-bromopyridin-2-yl)amino)-7-azabicyclo[2.2.1]heptan-7-yl)(3-ethoxy-6-methylpyridin-2-yl)methanone

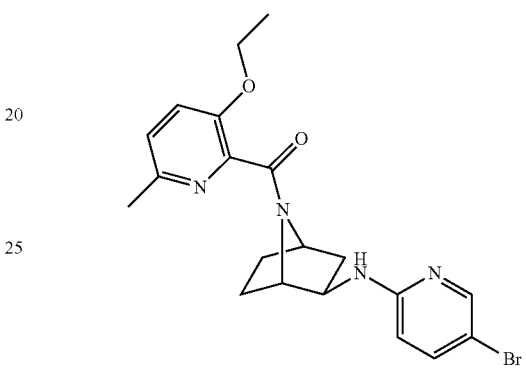

Prepared analogous to Example 217 substituting intermediate A-9 with intermediate A-8. MS (ESI) mass calcd. for $C_{20}H_{23}BrN_4O_2$, 430.1; m/z found 431.1 [M+H]$^+$. MP=134.5° C. $^1$H NMR (DMSO-D$_6$): 8.10 (d, J=2.4 Hz, 0.3H), 7.88 (d, J=2.4 Hz, 0.7H), 7.55 (dd, J=8.9, 2.5 Hz, 0.3H), 7.50-7.41 (m, 1H), 7.30 (d, J=8.6 Hz, 0.7H), 7.24 (d, J=8.6 Hz, 0.3H), 7.08 (d, J=8.6 Hz, 0.7H), 6.76 (d, J=5.7 Hz, 0.7H), 6.63 (d, J=5.3 Hz, 0.3H), 6.57 (d, J=8.9 Hz, 0.3H), 6.43 (d, J=8.9 Hz, 0.7H), 4.62 (brs, 0.7H), 4.51 (d, J=2.8 Hz, 0.3H), 4.13-3.88 (m, 2H), 3.83-3.73 (m, 0.3H), 3.72-3.61 (m, 1H), 3.59 (d, J=3.5 Hz, 0.7H), 2.39 (s, 0.9H), 2.21 (s, 2.1H), 2.02-1.85 (m, 1H), 1.75-1.33 (m, 5H), 1.25 (td, J=6.9, 3.6 Hz, 3H).

Example 220

(±)-(2-((5-bromopyridin-2-yl)amino)-7-azabicyclo[2.2.1]heptan-7-yl)(6-methyl-3-(2H-1,2,3-triazol-2-yl)pyridin-2-yl)methanone

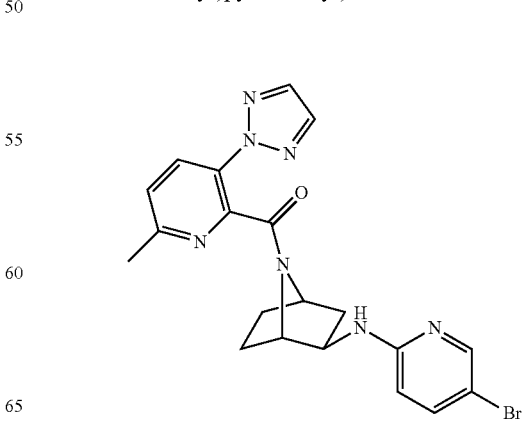

Prepared analogous to Example 217 substituting intermediate A-9 with intermediate A-21. MS (ESI) mass calcd. for $C_{20}H_{20}BrN_7O$, 453.1; m/z found 454.1 [M+H]+. MP=214.9° C. $^1$H NMR (DMSO-D$_6$): 8.18 (d, J=8.4 Hz, 0.3H), 8.14-8.09 (m, 2.3H), 8.05 (d, J=8.4 Hz, 0.7H), 7.93 (d, J=2.4 Hz, 0.7H), 7.62-7.53 (m, 0.6H), 7.50 (dd, J=8.9, 2.5 Hz, 0.7H), 7.40 (d, J=8.4 Hz, 0.7H), 6.76 (d, J=6.3 Hz, 0.7H), 6.61 (d, J=8.9 Hz, 0.3H), 6.52 (d, J=5.7 Hz, 0.3H), 6.45 (d, J=8.9 Hz, 0.7H), 4.58 (t, J=4.5 Hz, 0.7H), 4.47 (d, J=4.8 Hz, 0.3H), 3.91 (t, J=4.3 Hz, 0.3H), 3.88-3.68 (m, 1.7H), 2.60 (s, 0.9H), 2.31 (s, 2.1H), 2.03-1.90 (m, 1H), 1.81-1.29 (m, 5H).

Example 221

(±)-(2-(2H-1,2,3-triazol-2-yl)phenyl)(2-((5-(trifluoromethyl)pyrimidin-2-yl)amino)-7-azabicyclo[2.2.1]heptan-7-yl)methanone

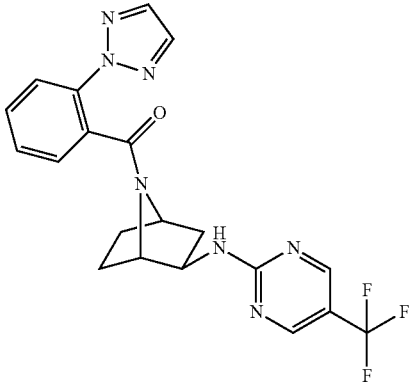

Prepared analogous to Example 220 substituting 5-bromo-2-iodopyridine with 2-chloro-5-(trifluoromethyl)pyrimidine and intermediate A-21 with intermediate A-1. MP=167.1° C. $^1$H NMR (DMSO-D$_6$): 8.75 (s, 0.4H), 8.70 (s, 0.4H), 8.66 (s, 0.6H), 8.53 (s, 0.6H), 8.12-8.03 (m, 2.6H), 7.86 (d, J=7.3 Hz, 0.4H), 7.80 (d, J=7.2 Hz, 0.4H), 7.72-7.54 (m, 1.6H), 7.48-7.34 (m, 1.4H), 7.16 (t, J=7.4 Hz, 0.6H), 4.56 (br s, 0.6H), 4.41 (d, J=4.3 Hz, 0.4H), 4.08 (dd, J=11.1, 6.8 Hz, 0.4H), 3.90-3.75 (m, 1H), 3.61 (d, J=4.3 Hz, 0.6H), 2.01-1.27 (m, 6H).

Example 222

(±)-(3-fluoro-2-methoxyphenyl)(2-((5-(trifluoromethyl)pyrimidin-2-yl)amino)-7-azabicyclo[2.2.1]heptan-7-yl)methanone

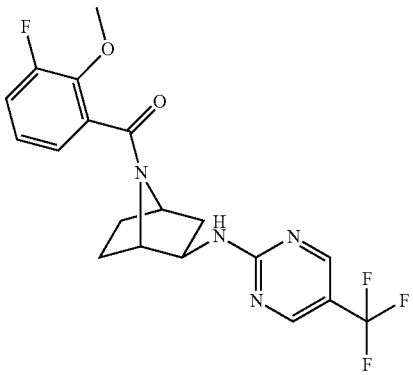 [SMILES: COc1c(F)cccc1C(=O)N1C2CCC1C(Nc1ncc(C(F)(F)F)cn1)C2]

Prepared analogous to Example 221 substituting intermediate A-1 with 3-fluoro-2-methoxybenzoic acid. $^1$H NMR (DMSO-D$_6$): 8.72 (br d, J=22.6 Hz, 0.8H), 8.58 (br d, J=24.1 Hz, 1.2H), 8.12 (br d, J=5.6 Hz, 0.4H), 7.99 (br d, J=5.0 Hz, 0.6H), 7.45-7.23 (m, 0.8H), 7.26-7.06 (m, 1.2H), 6.97 (d, J=7.5 Hz, 0.6H), 6.90-6.72 (m, 0.6H), 4.65 (br s, 0.6H), 4.53 (d, J=4.8 Hz, 0.4H), 3.97 (dd, J=11.4, 6.0 Hz, 0.4H), 3.84 (s, 1.2H), 3.93-3.71 (m, 1H), 3.78 (s, 1.8H), 3.69 (br d, J=2.9 Hz, 0.6H), 2.06-1.35 (m, 6H)

Example 223

(±)-(6-methyl-3-(2H-1,2,3-triazol-2-yl)pyridin-2-yl)(2-((5-(trifluoromethyl)pyrimidin-2-yl)amino)-7-azabicyclo[2.2.1]heptan-7-yl)methanone

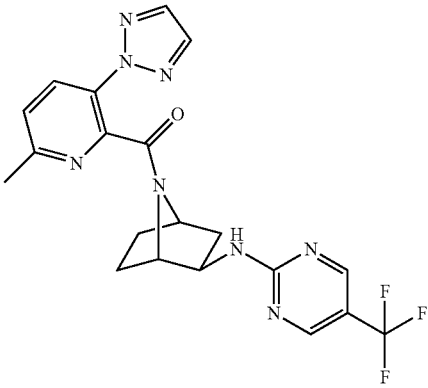 [SMILES: Cc1ccc(-n2nccn2)c(C(=O)N2C3CCC2C(Nc2ncc(C(F)(F)F)cn2)C3)n1]

Prepared analogous to Example 221 substituting intermediate A-1 with intermediate A-21. $^1$H NMR (DMSO-D$_6$): 8.74 (br d, J=12.1 Hz, 0.4H), 8.63 (br d, J=13.2 Hz, 1.2H), 8.26-8.01 (m, 3.4H), 7.61 (dd, J=21.8, 7.4 Hz, 0.4H), 7.43 (d, J=8.4 Hz, 0.6H), 4.61 (br s, 0.6H), 4.55 (d, J=5.0 Hz, 0.4H), 4.11-4.01 (m, 0.4H), 4.02-3.93 (m, 1H), 3.88 (dd, J=10.1, 6.1 Hz, 0.6H), 3.22-3.06 (m, 1H), 2.60 (s, 1H), 2.30 (s, 2H), 2.06-1.34 (m, 6H).

Example 224

(±)-(3-ethoxy-6-methylpyridin-2-yl)(2-((5-(trifluoromethyl)pyrimidin-2-yl)amino)-7-azabicyclo[2.2.1]heptan-7-yl)methanone

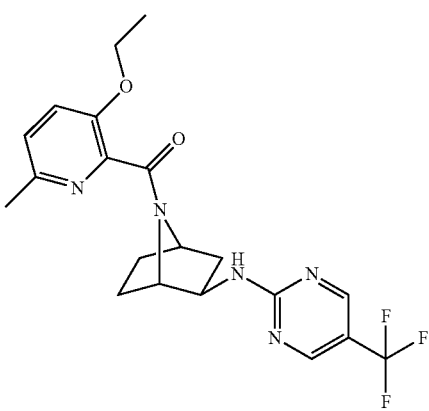 [SMILES: CCOc1ccc(C)nc1C(=O)N1C2CCC1C(Nc1ncc(C(F)(F)F)cn1)C2]

Prepared analogous to Example 221 substituting intermediate A-1 with intermediate A-8. ¹H NMR (DMSO-D₆): 8.79 (br d, J=22.9 Hz, 0.6H), 8.65 (br d, J=17.4 Hz, 1.4H), 8.21 (d, J=5.3 Hz, 0.7H), 7.92 (d, J=5.2 Hz, 0.3H), 7.52 (d, J=8.6 Hz, 0.3H), 7.42 (d, J=8.6 Hz, 0.7H), 7.32 (d, J=8.6 Hz, 0.3H), 7.18 (d, J=8.6 Hz, 0.7H), 4.71 (br s, 0.7H), 4.64 (br d, J=4.7 Hz, 0.3H), 4.23-3.93 (m, 2.5H), 3.93-3.78 (m, 1.4H), 3.78-3.55 (m, 1.7H), 3.31-3.07 (m, 1.4H), 2.47 (s, 1H), 2.31 (s, 2H), 2.06-1.40 (m, 6H).

Example 225

(±)-(6-methyl-3-(pyrimidin-2-yl)pyridin-2-yl)(2-((5-(trifluoromethyl)pyrimidin-2-yl)amino)-7-azabicyclo[2.2.1]heptan-7-yl)methanone

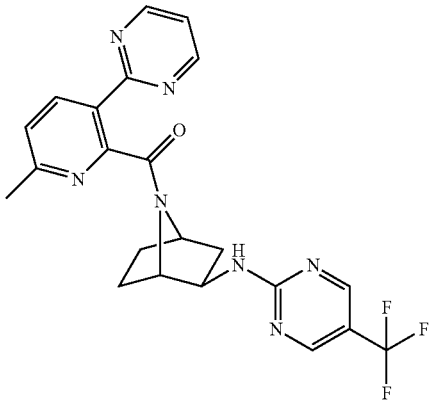 [SMILES: Cc1ccc(-c2ncccn2)c(C(=O)N2C3CCC2C(Nc2ncc(C(F)(F)F)cn2)C3)n1]

Prepared analogous to Example 221 substituting intermediate A-1 with intermediate A-9. MP=203° C. MS (ESI) mass calcd. for C₂₂H₂₀F₃N₇O, 455.2; m/z found 427.5 [M+H]⁺. ¹H NMR (DMSO-D₆): 8.94 (d, J=4.9 Hz, 0.4H), 8.89 (d, J=4.9 Hz, 1.6H), 8.77 (s, 0.2H), 8.71 (s, 0.2H), 8.61 (s, 1.4H), 8.36 (d, J=8.1 Hz, 0.2H), 8.24 (d, J=7.9 Hz, 1.8H), 7.72 (d, J=6.0 Hz, 0.2H), 7.54-7.44 (m, 1.2H), 7.38 (d, J=8.1 Hz, 0.8H), 4.64 (br s, 0.8H), 4.58 (d, J=4.6 Hz, 0.2H), 4.06-3.90 (m, 2H), 2.60 (s, 0.6H), 2.35 (s, 2.4H), 2.11-1.73 (m, 4H), 1.62-1.35 (m, 2H).

Example 226

(±)-(3-fluoro-2-methoxyphenyl)(2-((5-(trifluoromethyl)pyrimidin-2-yl)amino)-7-azabicyclo[2.2.1]heptan-7-yl)methanone

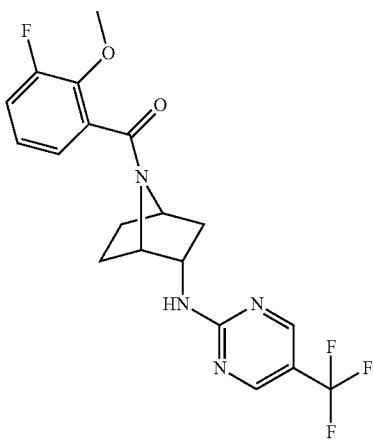 [SMILES: COc1c(F)cccc1C(=O)N1C2CCC1C(Nc1ncc(C(F)(F)F)cn1)C2]

Prepare analogous to Example 222 substituting intermediate B-6 with intermediate B-7. MS (ESI) mass calcd. for C₁₉H₁₈F₄N₄O₂, 410.2; m/z found 411.3 [M+H]⁺. ¹H NMR (DMSO-D₆): 8.75 (s, 0.5H), 8.68 (s, 0.5H), 8.61 (s, 0.5H), 8.57 (s, 0.5H), 8.52 (d, J=6.3 Hz, 0.5H), 8.44 (d, J=6.3 Hz, 0.5H), 7.44-7.29 (m, 1H), 7.23-7.08 (m, 2H), 4.82 (t, J=3.9 Hz, 0.5H), 4.58 (t, J=4.5 Hz, 0.5H), 4.34-4.12 (m, 1H), 3.94-3.81 (m, 3.5H), 3.68 (t, J=4.2 Hz, 0.5H), 2.31-2.11 (m, 1H), 1.93-1.40 (m, 5H).

Example 227

(±)-(3-ethoxy-6-methylpyridin-2-yl)(2-((5-(trifluoromethyl)pyrimidin-2-yl)amino)-7-azabicyclo[2.2.1]heptan-7-yl)methanone

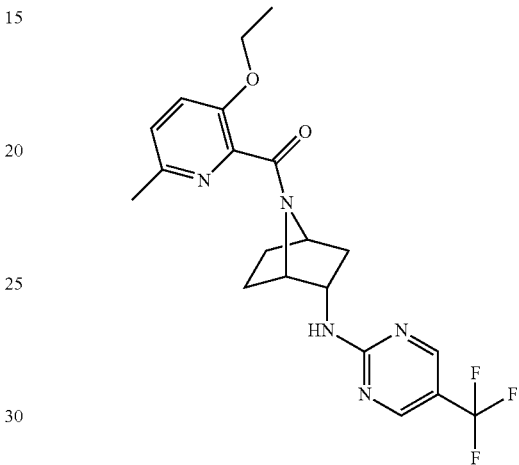

Prepare analogous to Example 224 substituting intermediate B-6 with intermediate B-7. MP=79.7° C. MS (ESI) mass calcd. for C₂₀H₂₂F₃N₅O₂, 421.2; m/z found 422.4 [M+H]⁺. ¹H NMR (DMSO-D₆): 8.76 (s, 0.5H), 8.68 (s, 0.5H), 8.61 (s, 0.5H), 8.56 (s, 0.5H), 8.52 (d, J=6.4 Hz, 0.5H), 8.44 (d, J=6.6 Hz, 0.5H), 7.48 (d, J=3.2 Hz, 0.5H), 7.45 (d, J=3.2 Hz, 0.5H), 7.28 (d, J=3.3 Hz, 0.5H), 7.25 (d, J=3.3 Hz, 0.5H), 4.83 (t, J=4.2 Hz, 0.5H), 4.59 (t, J=4.3 Hz, 0.5H), 4.40-4.29 (m, 0.5H), 4.28-4.19 (m, 0.5H), 4.16-4.01 (m, 2H), 3.79 (t, J=4.4 Hz, 0.5H), 3.61 (t, J=4.6 Hz, 0.5H), 2.41 (s, 1.5H), 2.40 (s, 1.5H), 2.30-2.09 (m, 1H), 1.93-1.41 (m, 5H), 1.34-1.23 (m, 3H).

Example 228

(±)-(6-methyl-3-(2H-1,2,3-triazol-2-yl)pyridin-2-yl)(2-((5-(trifluoromethyl)pyrimidin-2-yl)amino)-7-azabicyclo[2.2.1]heptan-7-yl)methanone

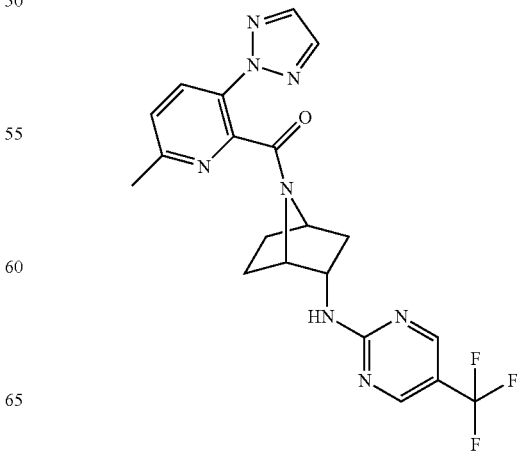

Prepare analogous to Example 223 substituting intermediate B-6 with intermediate B-7. MS (ESI) mass calcd. for $C_{20}H_{19}F_3N_8O$, 444.2; m/z found 445.4 [M+H]$^+$. MP=89.1° C. $^1$H NMR (DMSO-D$_6$): 8.77 (s, 0.6H), 8.68 (s, 0.6H), 8.61 (s, 0.4H), 8.55 (s, 0.4H), 8.51 (d, J=6.3 Hz, 0.6H), 8.44 (d, J=6.3 Hz, 0.4H), 8.24-8.16 (m, 1H), 8.13 (s, 1H), 8.12 (s, 1H), 7.63-7.52 (m, 1H), 4.81 (t, J=4.2 Hz, 0.6H), 4.55 (t, J=4.2 Hz, 0.4H), 4.40-4.21 (m, 1H), 4.06 (t, J=4.4 Hz, 0.4H), 3.79 (t, J=4.4 Hz, 0.6H), 2.61 (s, 1.2H), 2.58 (s, 1.8H), 2.34-2.20 (m, 0.6H), 2.19-2.03 (m, 0.6H), 1.94-1.50 (m, 4.2H), 1.44 (dd, J=12.3, 4.6 Hz, 0.6H).

Example 229

(±)-(3-ethoxy-6-methylpyridin-2-yl)(2-(quinoxalin-2-ylamino)-7-azabicyclo[2.2.1]heptan-7-yl)methanone

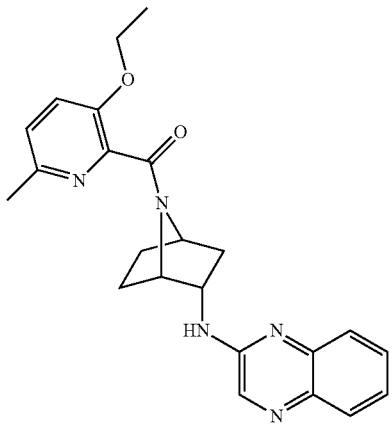 [SMILES: CCOc1ccc(C)nc1C(=O)N1C2CCC1C(Nc1cnc3ccccc3n1)C2]

Prepare analogous to Example 207 substituting intermediate B-6 with intermediate B-7. MS (ESI) mass calcd. for $C_{23}H_{25}N_5O_2$, 403.2; m/z found 404.5 [M+H]$^+$. MP=115.1° C. $^1$H NMR (DMSO-D$_6$): 8.37 (s, 0.5H), 8.30 (s, 0.5H), 7.97 (t, J=5.4 Hz, 1H), 7.80 (d, J=7.4 Hz, 0.5H), 7.75 (d, J=7.1 Hz, 0.5H), 7.69-7.44 (m, 2.5H), 7.43-7.23 (m, 2.5H), 4.99 (t, J=4.4 Hz, 0.5H), 4.63 (t, J=4.6 Hz, 0.5H), 4.48-4.27 (m, 1H), 4.26-4.13 (m, 2H), 3.96 (t, J=4.4 Hz, 0.5H), 3.64 (t, J=4.6 Hz, 0.5H), 2.44 (s, 1.5H), 2.41 (s, 1.5H), 2.39-2.26 (m, 1H), 1.98-1.37 (m, 5H), 1.36-1.28 (m, 3H).

Example 230

(±)-(6-methyl-3-(2H-1,2,3-triazol-2-yl)pyridin-2-yl)(2-(quinoxalin-2-ylamino)-7-azabicyclo[2.2.1]heptan-7-yl)methanone

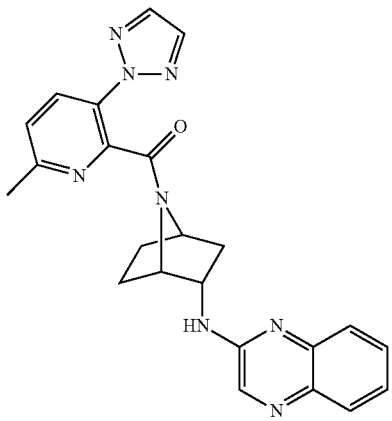

Prepare analogous to Example 205 substituting intermediate B-6 with intermediate B-7. MS (ESI) mass calcd. for $C_{23}H_{22}N_8O$, 426.2; m/z found 427.5 [M+H]$^+$. MP=152.3° C. $^1$H NMR (DMSO-D$_6$): 8.37 (s, 0.5H), 8.28-8.20 (m, 2H), 8.16-8.13 (m, 2H), 7.95 (dd, J=5.6, 3.6 Hz, 1H), 7.79 (d, J=8.1 Hz, 0.5H), 7.74 (d, J=8.1 Hz, 0.5H), 7.70-7.48 (m, 2.5H), 7.41-7.23 (m, 1.5H), 4.98 (t, J=4.2 Hz, 0.5H), 4.60 (t, J=4.6 Hz, 0.5H), 4.36-4.24 (m, 1H), 4.19 (t, J=4.5 Hz, 0.5H), 3.81 (t, J=4.6 Hz, 0.5H), 2.67 (s, 1.5H), 2.60 (s, 1.5H), 2.43-2.17 (m, 1H), 1.97-1.25 (m, 5H).

Example 231

(±)-(3-fluoro-2-methoxyphenyl)(2-(quinoxalin-2-ylamino)-7-azabicyclo[2.2.1]heptan-7-yl)methanone

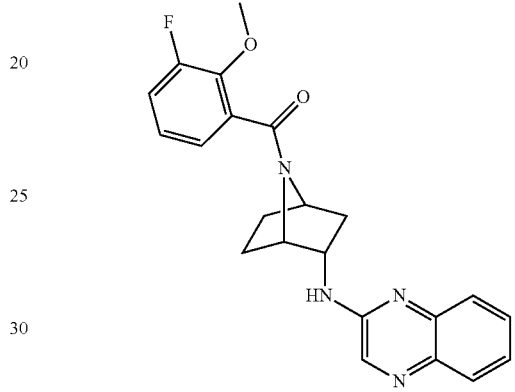

Prepare analogous to Example 206 substituting intermediate B-6 with intermediate B-7. $^1$H NMR (DMSO-D$_6$): 8.36 (s, 0.5H), 8.29 (s, 0.5H), 8.08-7.95 (m, 1H), 7.85-7.69 (m, 1H), 7.69-7.49 (m, 1.5H), 7.49-7.27 (m, 2H), 7.27-7.12 (m, 2.5H), 5.00 (t, J=4.2 Hz, 0.5H), 4.62 (t, J=4.2 Hz, 0.5H), 4.43-4.17 (m, 1H), 4.11 (t, J=4.3 Hz, 0.5H), 3.95 (s, 1.5H), 3.88 (s, 1.5H), 3.72 (t, J=4.5 Hz, 0.5H), 2.45-2.25 (m, 1H), 1.99-1.46 (m, 4H), 1.46-1.28 (m, 1H).

Example 232

(±)-(2-((5-bromopyridin-2-yl)amino)-7-azabicyclo[2.2.1]heptan-7-yl)(6-methyl-3-(2H-1,2,3-triazol-2-yl)pyridin-2-yl)methanone

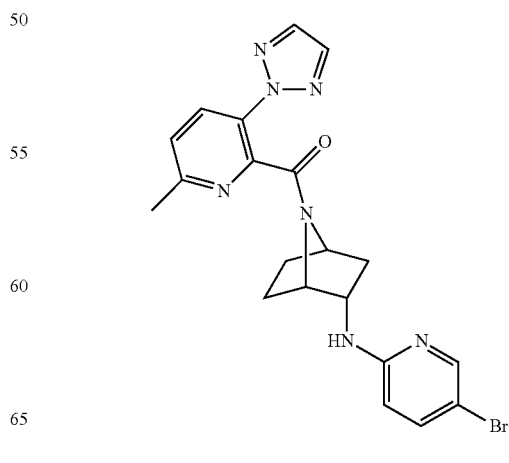

Prepare analogous to Example 220 substituting intermediate B-6 with intermediate B-7. MP=196.0° C. ¹H NMR (DMSO-D₆): 8.25-8.16 (m, 1H), 8.16-8.10 (m, 2.6H), 7.90 (d, J=2.4 Hz, 0.4H), 7.63-7.53 (m, 1.6H), 7.50 (dd, J=8.9, 2.5 Hz, 0.4H), 7.19 (d, J=6.0 Hz, 0.6H), 7.12 (d, J=6.1 Hz, 0.4H), 6.54 (d, J=8.9 Hz, 0.6H), 6.44 (d, J=8.9 Hz, 0.4H), 4.81 (t, J=4.2 Hz, 0.6H), 4.54 (t, J=4.2 Hz, 0.4H), 4.23-4.07 (m, 1H), 4.04 (t, J=4.5 Hz, 0.4H), 3.75 (t, J=4.5 Hz, 0.6H), 2.61 (s, 1.2H), 2.58 (s, 1.8H), 2.36-2.05 (m, 1H), 1.92-1.41 (m, 4H), 1.30 (dd, J=12.4, 4.4 Hz, 0.4H), 1.18 (dd, J=12.2, 4.6 Hz, 0.6H).

Example 233

(±)-2-((5-bromopyridin-2-yl)amino)-7-azabicyclo[2.2.1]heptan-7-yl)(3-ethoxy-6-methylpyridin-2-yl)methanone

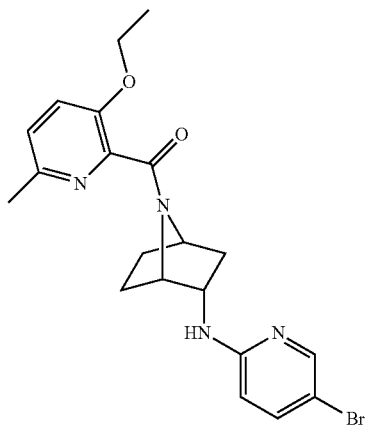 [SMILES: CCOc1ccc(C)nc1C(=O)N1C2CCC1C(Nc1ccc(Br)cn1)C2]

Prepare analogous to Example 219 substituting intermediate B-6 with intermediate B-7. MP=176.1° C. ¹H NMR (DMSO-D₆): 8.11 (d, J=2.4 Hz, 0.5H), 7.91 (d, J=2.4 Hz, 0.5H), 7.61-7.43 (m, 2H), 7.33-7.20 (m, 1.5H), 7.15 (d, J=6.1 Hz, 0.5H), 6.55 (d, J=8.9 Hz, 0.5H), 6.46 (d, J=8.9 Hz, 0.5H), 4.83 (t, J=4.3 Hz, 0.5H), 4.57 (t, J=4.6 Hz, 0.5H), 4.20 (d, J=5.5 Hz, 0.5H), 4.09 (dq, J=10.2, 6.9 Hz, 2.5H), 3.79 (t, J=4.3 Hz, 0.5H), 3.58 (t, J=4.6 Hz, 0.5H), 2.41 (s, 1.5H), 2.40 (s, 1.5H), 2.32-2.14 (m, 1H), 1.93-1.45 (m, 4H), 1.36-1.17 (m, 4H).

Example 234

(±)-(2-((5-bromopyridin-2-yl)amino)-7-azabicyclo[2.2.1]heptan-7-yl)(3-fluoro-2-methoxyphenyl)methanone

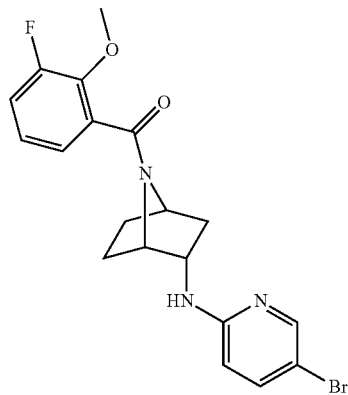 [SMILES: COc1c(F)cccc1C(=O)N1C2CCC1C(Nc1ccc(Br)cn1)C2]

Prepare analogous to Example 217 substituting intermediate B-6 with intermediate B-7. MP=144.5° C. ¹H NMR (DMSO-D₆): 8.11 (d, J=2.4 Hz, 0.6H), 7.91 (d, J=2.4 Hz, 0.4H), 7.56 (dd, J=8.9, 2.5 Hz, 0.6H), 7.50 (dd, J=8.9, 2.5 Hz, 0.4H), 7.43-7.30 (m, 1H), 7.27-7.05 (m, 3H), 6.54 (d, J=8.9 Hz, 0.6H), 6.46 (d, J=8.9 Hz, 0.4H), 4.83 (t, J=4.3 Hz, 0.6H), 4.57 (t, J=4.7 Hz, 0.4H), 4.21-3.99 (m, 1H), 3.95-3.81 (m, 3.4H), 3.66 (t, J=4.7 Hz, 0.6H), 2.36-2.14 (m, 1H), 1.94-1.43 (m, 4H), 1.36-1.14 (m, 1H).

Example 235

(±)-((2-(2H-1,2,3-triazol-2-yl)phenyl)(2-((4-(trifluoromethyl)pyridin-2-yl)amino)-7-azabicyclo[2.2.1]heptan-7-yl)methanone

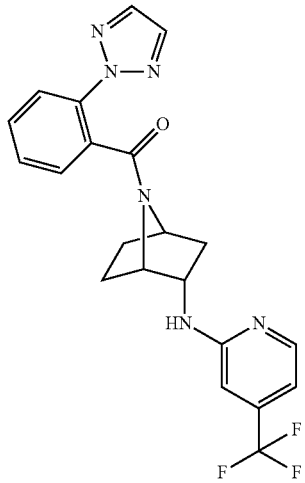 [SMILES: O=C(c1ccccc1-n1nccn1)N1C2CCC1C(Nc1cc(C(F)(F)F)ccn1)C2]

Prepare analogous to Example 210 substituting intermediate B-6 with intermediate B-7. MS (ESI) mass calcd. for C₂₁H₁₉F₃N₆O, 428.2; m/z found 429 [M+H]⁺. MP=274.2° C. ¹H NMR (DMSO-D₆): 8.27 (d, J=5.2 Hz, 0.5H), 8.13-8.01 (m, 2.5H), 7.89-7.80 (m, 1H), 7.73-7.61 (m, 1H), 7.61-7.51 (m, 2H), 7.44 (d, J=6.1 Hz, 0.5H), 7.38 (d, J=5.9 Hz, 0.5H), 6.83-6.75 (m, 1H), 6.73-6.63 (m, 1H), 4.78 (t, J=3.9 Hz, 0.5H), 4.50 (t, J=4.6 Hz, 0.5H), 4.27-4.04 (m, 1H), 3.96 (t, J=4.1 Hz, 0.5H), 3.64 (t, J=4.1 Hz, 0.5H), 2.40-2.21 (m, 0.5H), 2.17-1.99 (m, 0.5H), 1.88-1.32 (m, 4H), 1.27 (dd, J=12.3, 4.3 Hz, 0.5H), 1.12 (dd, J=12.2, 4.5 Hz, 0.5H).

Example 236

(±)-(2-((5-fluoropyridin-2-yl)amino)-7-azabicyclo[2.2.1]heptan-7-yl)(6-methyl-3-(2H-1,2,3-triazol-2-yl)pyridin-2-yl)methanone

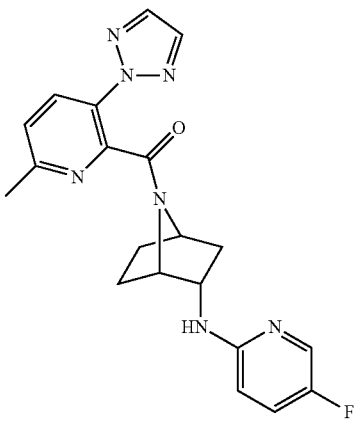 [SMILES: Cc1ccc(-n2nccn2)c(C(=O)N2C3CCC2C(Nc2ccc(F)cn2)C3)n1]

Prepared analogous to Example 209 substituting 2-chloro-6-(trifluoromethyl)pyridine with 5-fluoro-2-iodopyridine and intermediate A-1 with A-21. MP=100.1° C. MS (ESI) mass calcd. for $C_{20}H_{20}FN_7O$, 393.2; m/z found 394.2 [M+H]$^+$. $^1$H NMR (DMSO-D$_6$): 8.24-8.15 (m, 1H), 8.12 (s, 1.2H) 8.11 (s, 0.8H), 8.00 (d, J=2.9 Hz, 0.6H), 7.80 (d, J=2.8 Hz, 0.4H), 7.63-7.51 (m, 1H), 7.43-7.26 (m, 1H), 6.94 (d, J=5.9 Hz, 0.6H), 6.87 (d, J=6.0 Hz, 0.4H), 6.55 (dd, J=9.1, 3.6 Hz, 0.6H), 6.45 (dd, J=9.1, 3.7 Hz, 0.4H), 4.81 (t, J=4.2 Hz, 0.6H), 4.52 (t, J=4.6 Hz, 0.4H), 4.19-3.99 (m, 1.4H), 3.73 (t, J=4.6 Hz, 0.6H), 2.60 (s, 1.2H), 2.58 (s, 1.8H), 2.35-2.20 (m, 0.6H), 2.19-2.05 (m, 0.4H), 1.96-1.38 (m, 4H), 1.27 (dd, J=12.5, 4.2 Hz, 0.6H), 1.15 (dd, J=12.2, 4.8 Hz, 0.4H).

Example 237

(±)-(3-fluoro-2-methoxyphenyl)(2-((5-fluoropyridin-2-yl)amino)-7-azabicyclo[2.2.1]heptan-7-yl)methanone

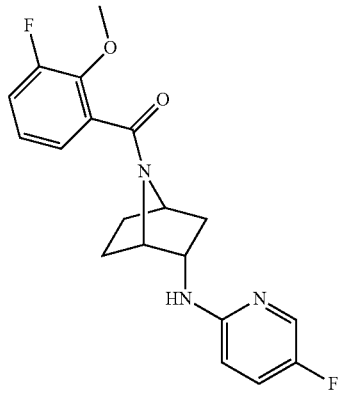 [SMILES: COc1c(F)cccc1C(=O)N1C2CCC1C(Nc1ccc(F)cn1)C2]

Prepared analogous to Example 209 substituting 2-chloro-6-(trifluoromethyl)pyridine with 5-fluoro-2-iodopyridine and intermediate A-1 with 3-fluoro-2-methoxybenzoic acid. MS (ESI) mass calcd. for $C_{19}H_{19}F_2N_3O_2$, 359.1; m/z found 360.2 [M+H]$^+$. MP=134.7° C. $^1$H NMR (DMSO-D$_6$): 8.00 (d, J=2.9 Hz, 0.5H), 7.80 (d, J=2.9 Hz, 0.5H), 7.45-7.26 (m, 2H), 7.24-7.06 (m, 2H), 6.96 (d, J=6.0 Hz, 0.5H), 6.89 (d, J=5.8 Hz, 0.5H), 6.56 (dd, J=9.1, 3.6 Hz, 0.5H), 6.48 (dd, J=9.2, 3.6 Hz, 0.5H), 4.83 (t, J=4.3 Hz, 0.5H), 4.56 (t, J=4.7 Hz, 0.5H), 4.18-3.98 (m, 1H), 3.95-3.81 (m, 3.5H), 3.64 (t, J=4.6 Hz, 0.5H), 2.35-2.14 (m, 1H), 1.96-1.43 (m, 4H), 1.30-1.13 (m, 1H).

Example 238

(3-fluoro-2-(pyrimidin-2-yl)phenyl)((1S,2R,4R)-2-((5-(trifluoromethyl)pyrazin-2-yl)amino)-7-azabicyclo[2.2.1]heptan-7-yl)methanone

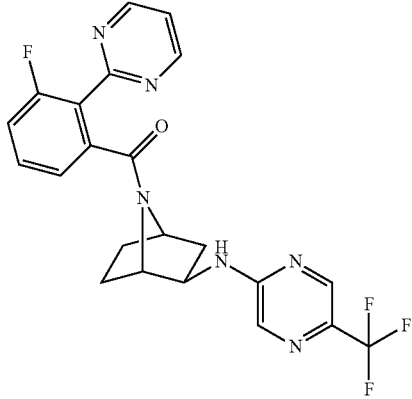

Step A: (1S,2R,4R)—N-(5-(trifluoromethyl)pyrazin-2-yl)-7-azabicyclo[2.2.1]heptan-2-amine hydrochloride To the intermediate of Example 181 Step A (100 g, 0.3 mmol) in DCM (3 mL) was added 4M HCl in dioxane (0.8 mL). The reaction was allowed to proceed overnight then concentrated neutralized with 5% Na$_2$CO$_3$ (aq) and extracted with DCM (2×). The combined organics were dried (Na$_2$SO$_4$) to give the title compound of step A that was used without further purification.

Step B: (3-fluoro-2-(pyrimidin-2-yl)phenyl)((1S,2R,4R)-2-((5-(trifluoromethyl)pyrazin-2-yl)amino)-7-azabicyclo[2.2.1]heptan-7-yl)methanone To the title compound of step A (1.44 g, 5.6 mmol) in DCM (56 mL) was added DIPEA (1.25 mL, 7.3 mmol) and intermediate A-2 (1.43 g, 6.1 mmol). Then T3P (50% solution in DMF, 10 mL, 17 mmol) was added dropwise and the reaction heated at 45° C. for 16 h. After allowing to cool to rt, DCM was added and the mixture washed with H$_2$O then saturated NaHCO$_3$ (aq). The combined aq layers were extracted with DCM. The combined organic layers were dried (Na$_2$SO$_4$). Purification via silica gel chromatography (10-100% EtOAc in hexanes) gave the title compound (2 g, 78%). MS (ESI) mass calcd. for $C_{22}H_{18}F_4N_6O$, 458.2; m/z found 459.1 [M+H]$^+$. $^1$H NMR (CDCl$_3$) 8.91-8.73 (m, 2H), 8.35-8.22 (m, 1H), 8.19 (s, 1H), 7.66 (s, 1H), 7.44-7.13 (m, 4H), 4.79-4.68 (m, 1H), 4.46-4.35 (m, 1H), 4.12-4.03 (m, 1H), 2.22-2.00 (m, 2H), 1.99-1.84 (m, 1H), 1.79-1.45 (m, 3H).

Example 238 was also prepared as follows:

Step A: 3-fluoro-2-(pyrimidin-2-yl)benzonitrile

To a 12-L 4-necked round-bottomed flask equipped with a thermocouple probe, mechanical stirrer, condenser and nitrogen inlet was charged 3-fluorobenzonitrile (140 g, 123.6 mmol), 2-isopropoxy-4,4,5,5-tetramethyl-1,3,2-dioxaborolane (353.7 mL, 1.699 mol), and THF (2.35 L). The mixture was cooled to −78° C. and lithium diisopropylamide (623 mL, 1.246 mol, 2 M) was added over 45 min maintaining a temperature of ←71° C. The mixture was stirred for 1 h at −76° C. then quenched with sodium bicarbonate$_{(aq)}$ (172 g in 1500 mL water). This mixture was warmed to room temperature to produce an off-white slurry. The slurry was treated with 2-bromopyrimidine (171.8 g, 1.059 mol) and then degassed with bubbling nitrogen. Dichloro[1,1'-bis(di-t-butylphosphino)ferrocene]palladium(II) (17 g, 25.8 mmol) was then added and the mixture was heated to 66° C. for 1 h. The mixture was cooled and ethyl acetate (5.6 L) was added. Solids were removed by filtration and washed with ethyl acetate (2×300 mL). The layers were cut and the aqueous layer was extracted with ethyl acetate (2 L). The combined organic layers were washed with brine (2×1.2 L) and then concentrated. Ethanol (600 mL) was added and the mixture was further concentrated to provide a dark brown liquid (382.0 g, 96% mass recovery, 75.5% desired, 19.1% regioisomer (3-fluoro-4-(pyrimidin-2-yl)benzonitrile). This liquid was warmed in ethanol (600 mL) at 66° C. until homogeneous and then gradually cooled to 20° C. The resulting solids were isolated by filtration and washed with cold 1/1 hexanes/ethanol (2×100 mL). After drying for 3 hours under air suction, the title compound was obtained as an off-white solid (118 g, 30%, 99.2% desired regioisomer). The mother liquor contained ~20% additional desired product that could be recovered through chromatography and crystallization. $^1$H NMR (400 MHz, CDCl$_3$) δ 8.97 (d, J=4.9 Hz, 2H), 7.69-7.61 (m, 1H), 7.61-7.52 (m, 1H), 7.51-7.43 (m, 1H), 7.41 (t, J=5.0 Hz, 1H).

Step B: 3-fluoro-2-(pyrimidin-2-yl)benzoic acid

To a 5-L, 4-necked round-bottomed flask equipped with a thermocouple, mechanical stirrer, condenser, and nitrogen inlet was charged the title compound of Step A (100 g, 502.0 mmol) in THF (500 mL) and methanol (500 mL). The mixture was stirred for 5 min at 20° C. and then sodium hydroxide$_{(aq)}$ (1.0 L, 3 N) was added. The resulting mixture was warmed to 60° C. for 24 h. The mixture was concentrated to 500 mL and the resulting thick aqueous layer was diluted with water (500 mL) and then transferred into a 5-L, 4-necked round-bottomed flask. The flask was cooled to 4° C. and the pH was adjusted from 14.0 to 2-3 with concentrated hydrogen chloride$_{(aq)}$ (260 mL, 37%). The resulting off-white slurry was stirred at 0° C. for 20 min, and then the solids were collected by filtration, washed with water (4×200 mL), dried under air suction for 20 h, and then placed in a vacuum oven at 60° C. for 20 h to provide the title compound as an off-white solid (106 g, 97%). $^1$H NMR (400 MHz, DMSO) δ 13.01 (s, 1H), 8.89 (d, J=5.0 Hz, 2H), 7.75 (dd, J=7.7, 1.2 Hz, 1H), 7.69-7.54 (m, 2H), 7.52 (t, 1H). HPLC retention time: 1.765 min.

Step C: (1S,2R,4R)-tert-butyl 2-(((benzyloxy)carbonyl)amino)-7-azabicyclo[2.2.1]-heptane-7-carboxylate A racemic mixture of tert-butyl 2-(((benzyloxy)carbonyl)amino)-7-azabicyclo[2.2.1]-heptane-7-carboxylate (578 g) was separated on a chiralcel OD column (1000 A, 20 um (Daicel), 110 mm diameter, 42 cm length) with a mobile phase of 90:10 heptane:ethanol over 126 injections with a run time of 15 min. Peak shaving was employed in conjunction with 1 recycling. The title compound was isolated through filtration after crystallization upon concentration (249.8 g, 86% of theory). $^1$H NMR (400 MHz, CDCl$_3$) δ 7.40-7.28 (m, 5H), 5.20-5.00 (m, 3H), 4.23 (s, 1H), 4.12 (d, J=4.9 Hz, 1H), 3.78 (td, J=8.0, 2.9 Hz, 1H), 1.93 (dd, J=13.1, 8.1 Hz, 1H), 1.83-1.62 (m, 2H), 1.54-1.29 (m, 3H), 1.43 (s, 9H). HPLC retention time: 3.461 min.

Step D: (1S,2R,4R)-tert-butyl 2-amino-7-azabicyclo[2.2.1]heptane-7-carboxylate To a 2.25 L Parr vessel were added (1S,2R,4R)-tert-butyl 2-(((benzyloxy)carbonyl)amino)-7-azabicyclo[2.2.1]heptane-7-carboxylate (91.2 g, 261.4 mmol) and 5% Pd/C (Johnson Matthey A102038-5, (9.6 g, 2.26 mmol). Ethanol (912 mL) was added and the vessel was agitated under a pressure of hydrogen gas (60 psi) for ~2.5 h. Mid-way through that time period the flask was evacuated and recharged with hydrogen gas (60 psi). The mixture was then filtered to remove residual heterogeneous catalyst. After washing the filter cake with ethanol (90 mL) the filtrate was concentrated under reduced pressure and concentrated again from acetonitrile to provide the title compound as a slightly yellow oil (57 g, quant. yield). $^1$H NMR (400 MHz, CDCl$_3$) δ 4.2 (bs, 1H), 3.88 (bs, 1H), 2.96 (dd, J=7.6, 3.1 Hz, 1H), 1.81 (dd, J=12.9, 7.8 Hz, 1H), 1.77-1.54 (m, 2H), 1.46 (s, 9H), 1.39-1.20 (m, 3H).

Step E: (1S,2R,4R)-tert-butyl 2-((5-(trifluoromethyl)pyrazin-2-yl)amino)-7-azabicyclo[2.2.1]heptane-7-carboxylate To a 3 L round-bottomed flask equipped with a mechanical stirring mechanism, temperature probe, reflux condenser, heating mantle, and nitrogen inlet was added (1S,2R,4R)-tert-butyl 2-amino-7-azabicyclo[2.2.1]heptane-7-carboxylate (56.92 g, 264.4 mmol) in acetonitrile (360 mL). Triethylamine (55.1 mL, 396.6 mmol) and 2-chloro-5-trifluoromethylpyrazine (57.91 g, 317.2 mmol) were added in rapid succession and the mixture was then heated to reflux for 16.5 h. The mixture was cooled to room temperature and concentrated under reduced pressure. The residue (189.57 g) was taken up in ammonium chloride$_{(aq)}$ (500 mL, 13 wt %) and ethyl acetate (500 mL). The layers were mixed and separated and the organic was washed with sodium carbonate$_{(aq)}$ (500 mL, ½ saturated). The organic layer was then dried over magnesium sulphate, filtered, and concentrated to a final mass of 94.73 g. This orange solid was taken up in heptane (500 mL) at 98° C. The homogeneous solution was allowed to cool slowly to room temperature, filtered, and washed with 100 mL of heptane to provide the title compound as a white solid (79.62 g, 84%). $^1$H NMR (400 MHz, CDCl$_3$) δ 8.31 (s, 1H), 7.86 (d, J=1.4 Hz, 1H), 5.45 (bs, 1H), 4.44-4.25 (m, 1H), 4.20 (d, J=5.2 Hz, 1H), 4.05 (td, J=7.6, 3.0 Hz, 1H), 2.06 (dd, J=13.1, 7.6 Hz, 1H), 1.92-1.70 (m, 2H), 1.61-1.38 (m, 3H), 1.44 (s, 9H). HPLC retention time: 3.424 min.

Step F: (1S,2R,4R)—N-(5-(trifluoromethyl)pyrazin-2-yl)-7-azabicyclo[2.2.1]heptan-2-amine In a 2-L round-bottomed flask, (1S,2R,4R)-tert-butyl 2-((5-(trifluoromethyl)pyrazin-2-yl)amino)-7-azabicyclo[2.2.1]heptane-7-carboxylate (79.52 g, 221.9 mmol) was taken up in IPA (584 mL). Hydrogen chloride (121.0 mL, 665.7 mmol, 5.5 M in IPA) was added and the reaction was warmed to 60° C. for 14 h. After cooling to room temperature, the mixture was poured over isopropyl acetate (1 L) and sodium carbonate$_{(aq)}$ (1 kg, 8.1 wt %). The layers were mixed and separated. The aqueous phase was washed with isopropyl acetate (500 mL), and the combined organics were washed with brine (700 mL), dried over MgSO$_4$, filtered, and concentrated to provide the title compound as a pinkish-white solid (57.11 g, 99%). $^1$H NMR (400 MHz, CDCl$_3$) δ 8.31 (s, 1H), 7.84 (d, J=1.4 Hz, 1H), 5.51 (d, J=7.7 Hz, 1H), 3.95 (td, J=7.8, 3.0 Hz, 1H), 3.76 (t, J=4.4 Hz, 1H), 3.60 (d, J=4.9 Hz, 1H), 1.95 (m, J=12.9, 7.8 Hz, 1H), 1.69-1.39 (m, 5H). HPLC retention time: 1.938 min.

Step G: (3-fluoro-2-(pyrimidin-2-yl)phenyl)((1S,2R,4R)-2-((5-(trifluoromethyl)pyrazin-2-yl)amino)-7-azabicyclo[2.2.1]heptan-7-yl)methanone A 3 L 3-necked round-bottom flask was fitted with mechanical stirring and a thermometer and charged with the amine from Step F (51.61 g, 200 mmol), acid from Step B (56.69 g, 260 mmol), and 2-MeTHF (1 L). The mixture was stirred at room temperature for several minutes until nearly all the solids had dissolved. Diisopropylethylamine (45.2 mL, 260 mmol) was added followed immediately by T3P (178 mL of a 50% solution in EtOAc, 300 mmol). Mild exotherm to 27° C. observed. The reaction was warmed to 40° C. and allowed to stir 9 h. A dark brown reaction mixture resulted. HPLC and MS analysis indicated complete conversion of the amine. The reaction was quenched by addition of 1:1 sat'd. NH$_4$Cl/water (1 L) and allowed to cool to room temperature. The layers were separated, and the aqueous layer was extracted once with 2-MeTHF (200 mL). The combined organic layers were washed with 3:1 sat'd. Na$_2$CO$_3$/water (1 L). The organic layer was washed with brine (1 L) causing an emulsion which was given several hours to clear. Layers were separated, and the organic layer was dried (MgSO$_4$) and concentrated to a viscous brown oil. This material was combined with material from two prior smaller scale reactions for product purification. Yield calculations are based upon the total combined amount of limiting amine for the three reactions, 221.3 mmol. The combined crude products were first flash chromatographed (1.5 kg silica gel cartridge, initial linear gradient elution of 50% EtOAc/hex to 100% EtOAc then elution with 20% THF/EtOAc and 40% THF/EtOAc, 400 mL/min, material loaded as a CH$_2$Cl$_2$ solution). Strong reddish purple colored band and several minor spots co-eluted with the initial fractions of product. The latter, less-colored three quarters of the product-containing fractions were combined and concentrated to a thick red-orange syrup (83 g). This material was treated with activated charcoal (17 g) in acetonitrile (1.1 L) at 46° C. for 30 min. The charcoal was removed by vacuum filtration through a pad of Celite, and the filter cake was washed with warm acetonitrile (500 mL) to provide a straw yellow solution. The solvents were removed in vacuo to give the impure crude product as an off-white foam (~70 g). To crystallize the material, the foam was dissolved in hot EtOAc (175 mL, 77° C.) with mechanical stirring. Heptane was added in portions at 76-80° C. At 300 mL of added heptane, solids were observed to slowly precipitate. Addition of heptane was continued until a total volume of 650 mL was added. Mixture was allowed to cool to room temperature over 5 h. The product was collected by vacuum filtration and washed with excess heptane and allowed to air dry. The product was dense off-white granular crystals (Form 1). HPLC analysis appeared to indicate a minor impurity (0.7% peak area, 2.23 min, 220 nm); therefore, a second crystallization was undertaken under identical conditions. During this crystallization, the product was observed to rapidly crystallize in fluffy white needles (Form 2) which "froze" the mixture preventing controlled stirring. Additional heptane was added, and a spatula was used to mechanically break up the mixture and restore stirring of a suspension of crystalline product. Due to continued observance of the minor peak, the product was crystallized twice more with similar crystallization behavior as observed in the second crystallization. It was noted that more EtOAc was necessary to initially dissolve the Form 2 crystals. The final product was dried in a vacuum oven (~10 torr) at 60° C. overnight and then 80° C. overnight to provide crystalline Form 2 (small fluffy white needles). Yield=54.46 g (54%). By $^1$H NMR, EtOAc content was 900 ppm, and heptane content was 660 ppm. The remaining product-containing chromatography fractions were concentrated and chromatographed a second time. Mixed fractions were chromatographed a third time. The product fractions were concentrated to give a light orange foam (28.6 g). The foam was decolorized with activated charcoal (5.6 g) in warm acetonitrile (46° C.). Charcoal was removed by vacuum filtration through a pad of Celite. The filter cake was washed with warm acetonitrile, and the filtrate was concentrated and crystallized from EtOAc/heptane as before. With this batch, crystalline Form 2 was generated upon the initial crystallization. Product was collected by vacuum filtration, washed with excess heptane, and dried in a vacuum oven (10 torr) at 50° C. overnight. Yield=23.69 g (23%). By 1H NMR, EtOAc content was 3500 ppm, and heptane content was 600 ppm. Total combined yield of two batches=78.15 g (77%). $^1$H NMR (400 MHz, CDCl$_3$) Major Rotamer (90%) δ 8.87 (d, J=4.9 Hz, 2H), 8.35 (m, 1H), 8.18 (s, 1H), 7.65 (d, J=1.3 Hz, 1H), 7.42-7.34 (m, 2H), 7.24-7.18 (m, 2H), 4.72 (t, J=4.8 Hz, 1H), 4.37 (td, J=8.8, 3.7 Hz, 1H), 4.07 (d, J=4.9 Hz, 1H), 2.15 (dd, J=12.8, 8.1 Hz, 1H), 2.09-1.98 (m, 1H), 1.97-1.84 (m, 1H), 1.76-1.58 (m, 1H), 1.56-1.44 (m, 2H). Minor Rotamer (10%) unique peaks only δ 8.76 (d, J=4.88 Hz, 2H), 7.70 (s, 1H), 7.50-7.44 (m, 1H), 7.33-7.27 (m, 2H), 6.21 (m, 1H), 4.59 (bd, J=4.1 Hz, 1H), 4.20-4.13 (m, 2H).

Example 239

(2-ethoxynaphthalen-1-yl)((1S,2R,4R)-2-((5-(trifluoromethyl)pyrazin-2-yl)amino)-7-azabicyclo[2.2.1]heptan-7-yl)methanone

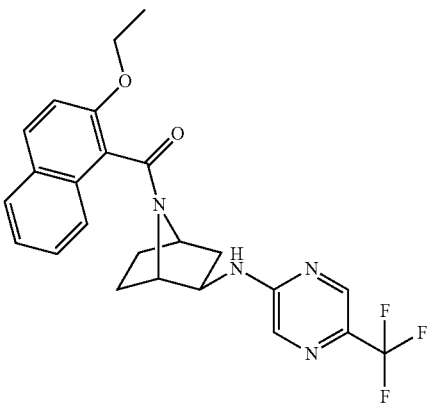 [SMILES: CCOc1ccc2ccccc2c1C(=O)N1C2CCC1C(Nc1cnc(C(F)(F)F)cn1)C2]

Prepared analogous to Example 181 substituting intermediate A-1 with 2-ethoxy-1-naphthoic acid. MS (ESI) mass calcd. for C$_{24}$H$_{23}$F$_3$N$_4$O$_2$, 456.2; m/z found 457.2 [M+H]$^+$. $^1$H NMR (CDCl$_3$): 8.39-8.31 (m, 0.3H), 8.18 (s, 0.5H), 8.08-7.98 (m, 0.3H), 7.96-7.67 (m, 3.6H), 7.57-7.32 (m, 2H), 7.31-7.16 (m, 1.3H), 7.10-7.04 (m, 0.2H), 6.34 (d, J=9.1 Hz, 0.5H), 5.90-5.75 (m, 0.3H), 5.17-4.95 (m, 1H), 4.70 (d, J=7.1 Hz, 0.2H), 4.49-4.07 (m, 2.7H), 3.90 (td, J=7.4, 2.9 Hz, 0.2H), 3.77-3.65 (m, 0.3H), 3.62-3.56 (m, 0.2H), 3.39 (d, J=5.1 Hz, 0.4H), 2.30-1.94 (m, 2H), 1.81-1.47 (m, 5H), 1.47-1.33 (m, 2H).

Example 240 isoquinolin-4-yl((1S,2R,4R)-2-((5-(trifluoromethyl)pyrazin-2-yl)amino)-7-azabicyclo[2.2.1]heptan-7-yl)methanone

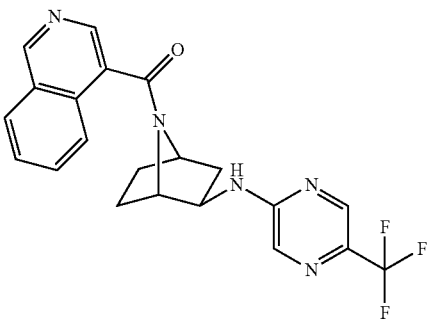 [SMILES: O=C(c1cncc2ccccc12)N1C2CCC1C(Nc1cnc(C(F)(F)F)cn1)C2]

Prepared analogous to Example 181 substituting intermediate A-1 with isoquinoline-4-carboxylic acid. MS (ESI) mass calcd. for C$_{21}$H$_{18}$F$_3$N$_5$O, 413.2; m/z found 414.2

[M+H]⁺. ¹H NMR (CDCl₃): 9.31 (s, 0.5H), 9.13 (s, 0.5H), 8.68-8.49 (m, 1H), 8.40-7.53 (m, 5.5H), 7.42 (s, 0.5H), 6.20 (s, 0.5H), 4.99 (s, 1.5H), 4.21 (s, 0.5H), 4.06-3.77 (m, 1.5H), 2.27-1.43 (m, 6H).

Example 241

(4-methoxy-2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone

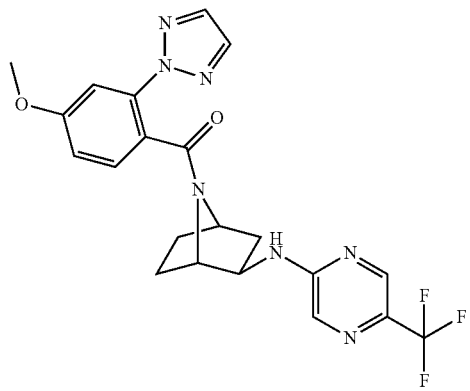 [SMILES: COc1ccc(C(=O)N2C3CCC2C(Nc2cnc(C(F)(F)F)cn2)C3)c(-n2nccn2)c1]

Prepared analogous to Example 181 substituting intermediate A-1 with intermediate A-5. MS (ESI) mass calcd. for C₂₁H₂₀F₃N₇O₂, 459.2; m/z found 460.3 [M+H]⁺. ¹H NMR (CDCl₃): 8.31 (s, 0.3H), 8.18 (s, 0.7H), 7.91 (s, 1.5H), 7.87-7.77 (m, 1H), 7.54 (s, 0.8H), 7.48-7.39 (m, 0.7H), 7.35-7.28 (m, 1.7H), 6.97 (dd, J=8.5, 2.5 Hz, 0.3H), 6.87 (d, J=8.3 Hz, 0.7H), 6.29 (s, 0.3H), 4.85-4.79 (m, 0.7H), 4.75-4.70 (m, 0.3H), 4.40-4.22 (m, 1H), 4.09-4.03 (m, 0.3H), 3.99 (s, 0.7H), 3.94-3.83 (m, 3H), 2.19-1.41 (m, 6H).

Example 242

(2-methoxy-6-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone

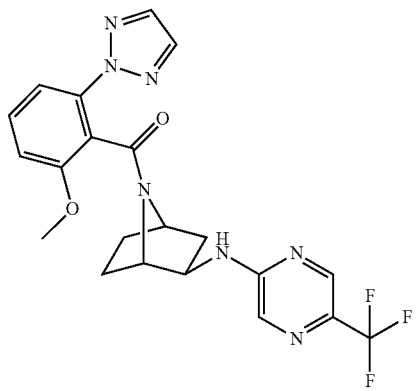 [SMILES: COc1cccc(-n2nccn2)c1C(=O)N1C2CCC1C(Nc1cnc(C(F)(F)F)cn1)C2]

Prepared analogous to Example 181 substituting intermediate A-1 with intermediate A-13. MS (ESI) mass calcd. for C₂₁H₂₀F₃N₇O₂, 459.2; m/z found 460.3 [M+H]⁺. ¹H NMR (CDCl₃): 8.37-8.30 (m, 0.3H), 8.25-8.17 (m, 0.7H), 7.97-7.85 (m, 1.5H), 7.84-7.74 (m, 0.8H), 7.65-7.56 (m, 0.4H), 7.55-7.37 (m, 2.7H), 7.05-6.94 (m, 1H), 6.17-5.98 (m, 0.2H), 5.90-5.66 (m, 0.4H), 5.02-4.86 (m, 0.7H), 4.86-4.71 (m, 0.3H), 4.45-4.18 (m, 0.8H), 4.05 (s, 0.7H), 3.97-3.75 (m, 3.3H), 3.62-3.57 (m, 0.2H), 2.25-1.29 (m, 6H).

Example 243

(5-fluoro-2-(pyrimidin-2-yl)phenyl)((1S,2R,4R)-2-((5-(trifluoromethyl)pyrazin-2-yl)amino)-7-azabicyclo[2.2.1]heptan-7-yl)methanone

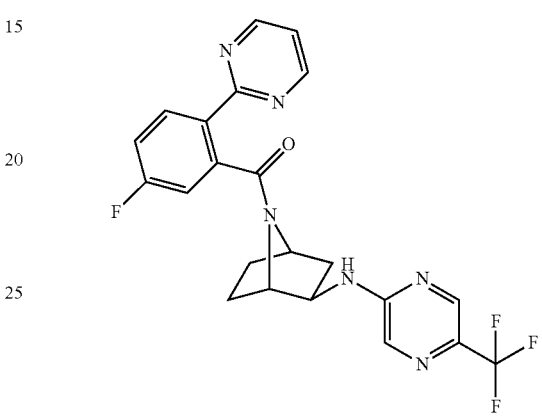

Prepared analogous to Example 181 substituting intermediate A-1 with intermediate A-7. MS (ESI) mass calcd. for C₂₂H₁₈F₄N₆O, 458.2; m/z found 459.3 [M+H]⁺. ¹H NMR (CDCl₃): 8.88-8.79 (m, 1.7H), 8.77-8.69 (m, 0.3H), 8.36-8.14 (m, 1.8H), 8.01 (dd, J=8.6, 5.4 Hz, 1H), 7.81 (s, 0.2H), 7.42-7.30-7.02 (m, 3.8H), 6.26 (d, J=7.8 Hz, 0.2H), 4.90-4.81 (m, 0.8H), 4.74 (d, J=5.2 Hz, 0.2H), 4.42 (s, 0.8H), 4.27 (s, 0.2H), 4.12-3.96 (m, 1H), 2.29-1.39 (m, 6H).

Example 244

(5-(4-fluorophenyl)-2-methylthiazol-4-yl)((1S,2R,4R)-2-((5-(trifluoromethyl)pyrazin-2-yl)amino)-7-azabicyclo[2.2.1]heptan-7-yl)methanone

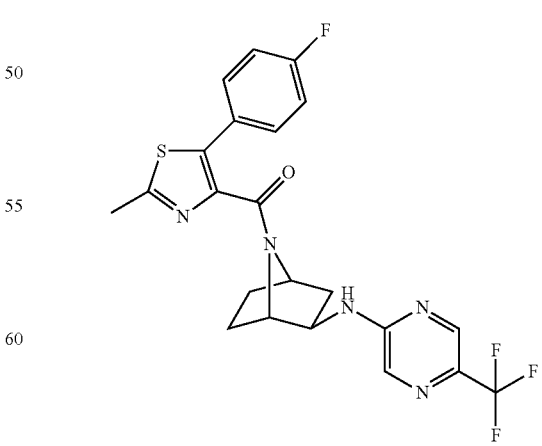

Prepared analogous to Example 181 substituting intermediate A-1 with 5-(4-fluorophenyl)-2-methylthiazole-4-carboxylic acid. MS (ESI) mass calcd. for $C_{22}H_{19}F_4N_5OS$, 477.2; m/z found 478.1 $[M+H]^+$. $^1H$ NMR (CDCl$_3$): 8.32-8.20 (m, 1H), 7.95-7.84 (m, 1H), 7.56-7.40 (m, 2H), 7.15-7.04 (m, 2H), 6.97-6.77 (m, 0.8H), 6.01-5.88 (m, 0.2H), 4.85 (t, J=4.5 Hz, 1H), 4.21-3.90 (m, 2H), 2.80-2.56 (m, 3H), 2.19-1.95 (m, 1.7H), 1.93-1.31 (m, 4.3H).

Example 245

(3-methyl-2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone

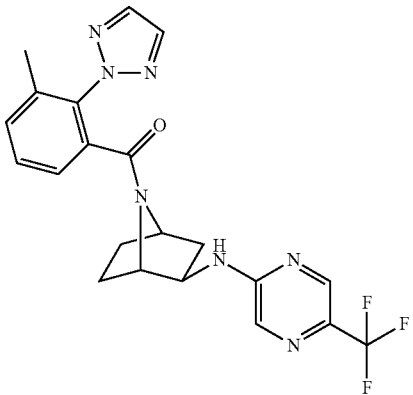 [SMILES: Cc1cccc(C(=O)N2C3CCC2C(Nc2cnc(C(F)(F)F)cn2)C3)c1-n1nccn1]

Prepared analogous to Example 181 substituting intermediate A-1 with intermediate A-24. MS (ESI) mass calcd. for $C_{21}H_{20}F_3N_7O$, 443.2; m/z found 444.3 $[M+H]^+$. $^1H$ NMR (CDCl$_3$): 8.29-8.23 (m, 0.2H), 8.21-8.15 (m, 0.8H), 7.95-7.88 (m, 1.6H), 7.84-7.74 (m, 1.3H), 7.62-7.39 (m, 1.2H), 7.37-7.19 (m, 2.7H), 5.81 (s, 0.2H), 4.79-4.65 (m, 0.8H), 4.61-4.51 (m, 0.2H), 4.38-3.90 (m, 2H), 2.19 (s, 3H), 2.14-1.42 (m, 6H).

Example 246

(3-ethoxyisoquinolin-4-yl)((1S,2R,4R)-2-((5-(trifluoromethyl)pyrazin-2-yl)amino)-7-azabicyclo[2.2.1]heptan-7-yl)methanone

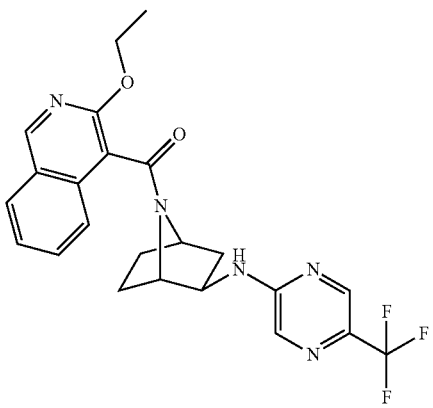

Prepared analogous to Example 181 substituting intermediate A-1 with intermediate A-22. MS (ESI) mass calcd. for $C_{23}H_{22}F_3N_5O_2$, 457.2; m/z found 458.3 $[M+H]^+$. $^1H$ NMR (CDCl$_3$): 9.01-8.92 (m, 0.8H), 8.82 (s, 0.2H), 8.35 (s, 0.5H), 8.22 (s, 0.3H), 8.05 (s, 0.1H), 8.00-7.85 (m, 1.6H), 7.84-7.71 (m, 1H), 7.71-7.54 (m, 1.2H), 7.50-7.39 (m, 0.8H), 7.39-7.31 (m, 0.4H), 7.18 (s, 0.3H), 6.11 (s, 0.1H), 5.95 (d, J=8.8 Hz, 0.3H), 5.83 (d, J=8.0 Hz, 0.4H), 5.15-5.06 (m, 0.3H), 5.06-4.94 (m, 0.7H), 4.92-4.72 (m, 0.5H), 4.68-4.41 (m, 1.5H), 4.40-4.30 (m, 0.3H), 4.24-4.07 (m, 0.4H), 3.89-3.81 (m, 0.2H), 3.81-3.67 (m, 0.7H), 3.51 (d, J=5.1 Hz, 0.3H), 2.30-1.95 (m, 2.5H), 1.91-1.21 (m, 6.5H).

Example 247

(6-methyl-2-(2H-1,2,3-triazol-2-yl)pyridin-3-yl)((1S,2R,4R)-2-((5-(trifluoromethyl)pyrazin-2-yl)amino)-7-azabicyclo[2.2.1]heptan-7-yl)methanone

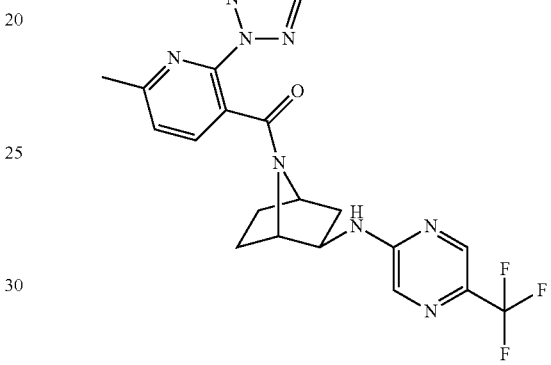

Prepared analogous to Example 181 substituting intermediate A-1 with intermediate A-3. MS (ESI) mass calcd. for $C_{20}H_{19}F_3N_8O$, 444.2; m/z found 445.2 $[M+H]^+$. $^1H$ NMR (CDCl$_3$): 8.32 (s, 0.4H), 8.18 (s, 0.6H), 7.96 (s, 1.3H), 7.88 (d, J=4.6 Hz, 1.1H), 7.79 (d, J=7.7 Hz, 0.5H), 7.73-7.52 (m, 1.5H), 7.35-7.27 (m, 0.5H), 7.18 (s, 0.7H), 6.28 (s, 0.4H), 4.89-4.70 (m, 1H), 4.42-4.19 (m, 1H), 4.03-3.81 (m, 1H), 2.76-2.56 (m, 3H), 2.26-1.40 (m, 6H).

Example 248

(6-methyl-2-(1H-1,2,3-triazol-1-yl)pyridin-3-yl)((1S,2R,4R)-2-((5-(trifluoromethyl)pyrazin-2-yl)amino)-7-azabicyclo[2.2.1]heptan-7-yl)methanone

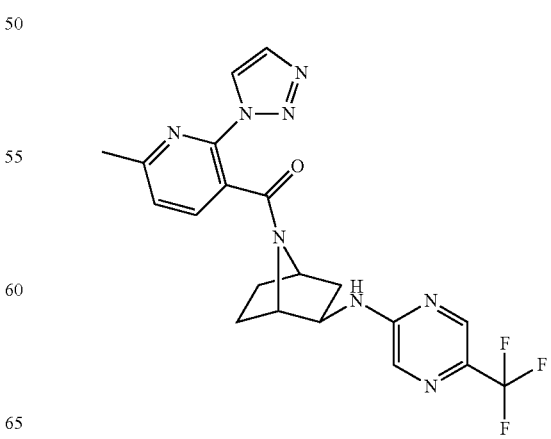

Prepared analogous to Example 181 substituting intermediate A-1 with intermediate A-4. MS (ESI) mass calcd. for $C_{20}H_{19}F_3N_8O$, 444.2; m/z found 445.2 [M+H]⁺. ¹H NMR (CDCl₃): 8.51-8.35 (m, 1.6H), 8.29 (s, 0.7H), 8.17 (s, 0.3H), 7.92-7.80 (m, 1H), 7.76-7.60 (m, 1.3H), 7.35-7.18 (m, 1.4H), 6.81-6.61 (m, 0.7H), 4.95-4.85 (m, 0.3H), 4.84-4.75 (m, 0.7H), 4.49-4.32 (m, 1H), 4.07 (t, J=4.4 Hz, 0.7H), 3.93 (s, 0.3H), 2.70-2.54 (m, 3H), 2.22 (dd, J=13.1, 8.0 Hz, 0.4H), 2.14-1.46 (m, 5.6H).

Example 249

(4-methoxy-2-(pyrimidin-2-yl)phenyl)((1S,2R,4R)-2-((5-(trifluoromethyl)pyrazin-2-yl)amino)-7-azabicyclo[2.2.1]heptan-7-yl)methanone

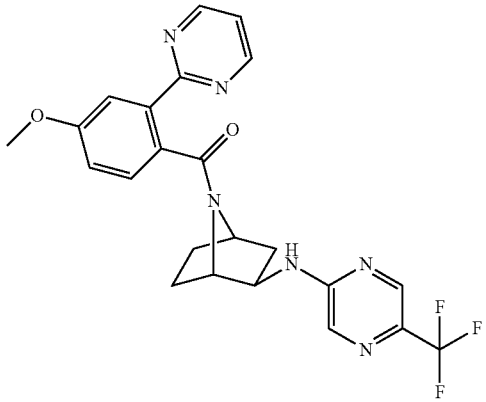 [SMILES: COc1ccc(C(=O)N2C3CCC2C(Nc2cnc(C(F)(F)F)cn2)C3)c(-c2ncccn2)c1]

Prepared analogous to Example 181 substituting intermediate A-1 with intermediate A-15. MS (ESI) mass calcd. for $C_{23}H_{21}F_3N_6O_2$, 470.2; m/z found 471.2 [M+H]⁺. ¹H NMR (CDCl₃): 8.89-8.69 (m, 2H), 8.38-8.12 (m, 2H), 7.81-7.74 (m, 0.1H), 7.70-7.62 (m, 0.1H), 7.49-7.28 (m, 3.8H), 6.91 (dd, J=8.4, 2.6 Hz, 0.9H), 6.48-6.39 (m, 0.1H), 4.85-4.77 (m, 0.9H), 4.73-4.67 (m, 0.1H), 4.48-4.34 (m, 0.9H), 4.24 (s, 0.1H), 4.09 (d, J=5.0 Hz, 1H), 3.94-3.79 (m, 3H), 2.18 (dd, J=13.0, 8.1 Hz, 1H), 2.13-1.37 (m, 5H).

Example 250

(1H-benzo[d]imidazol-2-yl)((1S,2R,4R)-2-((5-(trifluoromethyl)pyrazin-2-yl)amino)-7-azabicyclo[2.2.1]heptan-7-yl)methanone

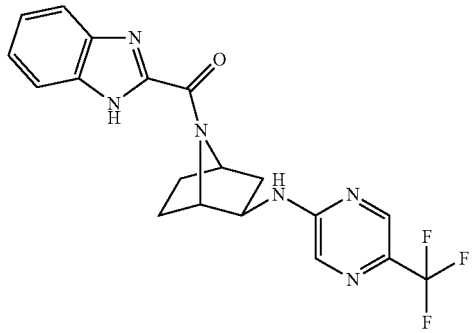

Prepared analogous to Example 181 substituting intermediate A-1 with 1H-benzo[d]imidazole-2-carboxylic acid. MS (ESI) mass calcd. for $C_{19}H_{17}F_3N_6O$, 402.1; m/z found 403.2 [M+H]⁺. ¹H NMR (CDCl₃): 8.35-7.61 (m, 3.5H), 7.40-7.13 (m, 3.5H), 6.26-5.75 (m, 1H), 5.06-4.63 (m, 1.5H), 4.27-3.95 (m, 1.5H), 2.86-2.47 (m, 1H), 2.33-1.45 (m, 5H).

Example 251

(1-methyl-1H-benzo[d]imidazol-2-yl)((1S,2R,4R)-2-((5-(trifluoromethyl)pyrazin-2-yl)amino)-7-azabicyclo[2.2.1]heptan-7-yl)methanone

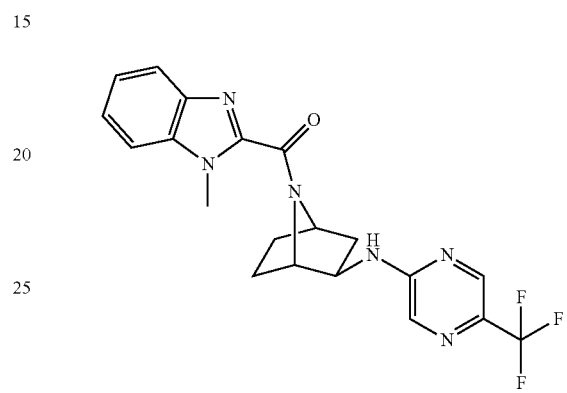

Prepared analogous to Example 181 substituting intermediate A-1 with 1-methyl-1H-benzo[d]imidazole-2-carboxylic acid. MS (ESI) mass calcd. for $C_{20}H_{19}F_3N_6O$, 416.2; m/z found 417.2 [M+H]⁺.

Example 252

(3-fluoro-2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone

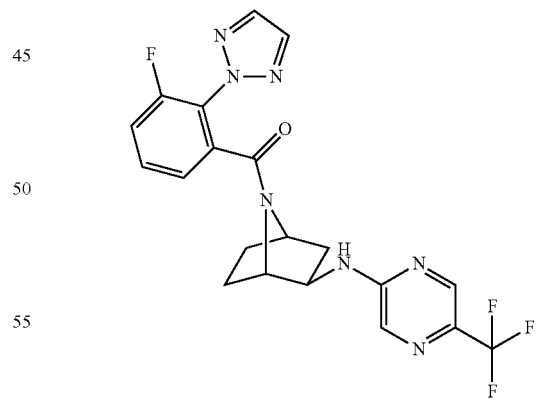

Prepared analogous to Example 181 substituting intermediate A-1 with intermediate A-16. MS (ESI) mass calcd. for $C_{20}H_{17}F_4N_7O$, 447.1; m/z found 448.3 [M+H]⁺. ¹H NMR (CDCl₃): 8.30 (s, 0.3H), 8.19 (s, 0.7H), 7.96-7.75 (m, 2.8H), 7.58-7.49 (m, 0.3H), 7.45-7.11 (m, 3.7H), 5.83 (s, 0.2H), 4.80-4.58 (m, 1H), 4.38-4.25 (m, 0.8H), 4.24-4.13 (m, 0.2H), 4.13-4.04 (m, 0.2H), 3.97 (d, J=4.9 Hz, 0.8H), 2.22-2.07 (m, 1H), 2.07-1.40 (m, 5H).

Example 253

(4-(difluoromethoxy)-2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone

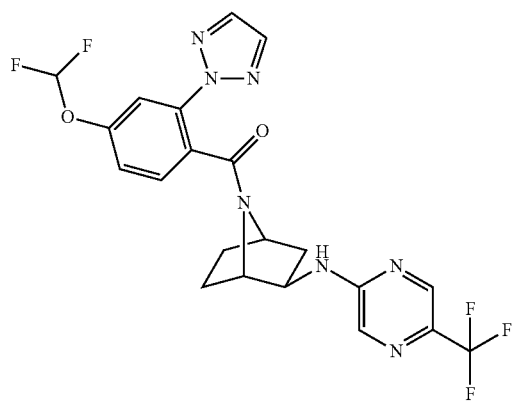 [SMILES: O=C(c1ccc(OC(F)F)cc1-n1nccn1)N1C2CCC1C(Nc1cnc(C(F)(F)F)cn1)C2]

Prepared analogous to Example 181 substituting intermediate A-1 with intermediate A-23. MS (ESI) mass calcd. for $C_{21}H_{18}F_5N_7O_2$, 495.1; m/z found 496.3 [M+H]$^+$. $^1$H NMR (CDCl$_3$): 8.32 (s, 0.3H), 8.19 (s, 0.7H), 7.98-7.81 (m, 2.4H), 7.77 (d, J=2.3 Hz, 0.4H), 7.61 (d, J=2.4 Hz, 0.7H), 7.58-7.45 (m, 1H), 7.39 (d, J=8.4 Hz, 0.7H), 7.21 (dd, J=8.4, 2.4 Hz, 0.5H), 7.18-7.00 (m, 0.9H), 6.59 (td, J=72.6, 31.4 Hz, 1H), 6.33-6.16 (m, 0.4H), 4.92-4.70 (m, 1H), 4.43-4.19 (m, 1H), 4.09-3.83 (m, 1H), 2.30-1.44 (m, 6H).

Example 254

(3-fluoro-2-(3-methyl-1,2,4-oxadiazol-5-yl)phenyl)((1S,2R,4R)-2-((5-(trifluoromethyl)pyrazin-2-yl)amino)-7-azabicyclo[2.2.1]heptan-7-yl)methanone

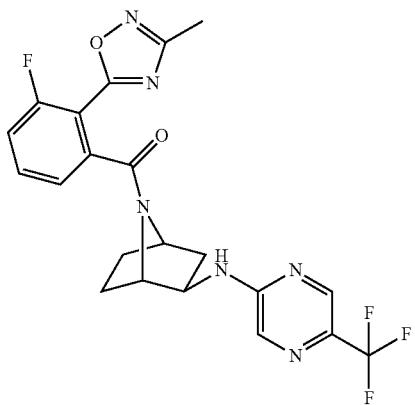 [SMILES: Cc1noc(-c2c(F)cccc2C(=O)N2C3CCC2C(Nc2cnc(C(F)(F)F)cn2)C3)n1]

Prepared analogous to Example 181 substituting intermediate A-1 with intermediate A-17. MS (ESI) mass calcd. for $C_{21}H_{18}F_4N_6O_2$, 462.1; m/z found 463.3 [M+H]$^+$. $^1$H NMR (CDCl$_3$): 8.31 (s, 0.3H), 8.18 (s, 0.7H), 8.09 (s, 0.3H), 7.75-7.68 (m, 0.7H), 7.63 (td, J=8.0, 5.0 Hz, 0.3H), 7.49 (td, J=7.9, 5.1 Hz, 0.7H), 7.44-7.13 (m, 2.6H), 5.79 (d, J=8.0 Hz, 0.4H), 4.88-4.67 (m, 1H), 4.40-4.22 (m, 1H), 4.10-3.88 (m, 1H), 2.52 (s, 3H), 2.28-1.54 (m, 6H).

Example 255

(5-methoxy-2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone

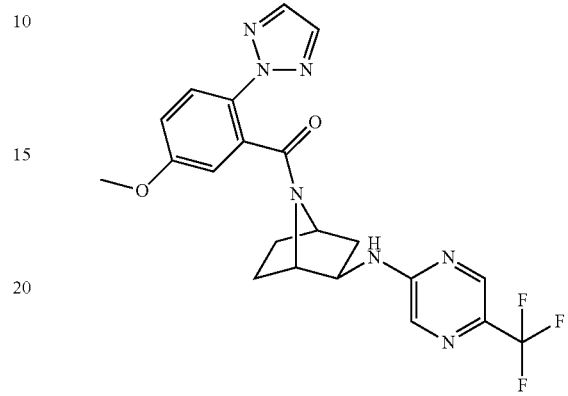

Prepared analogous to Example 181 substituting intermediate A-1 with intermediate A-18. MS (ESI) mass calcd. for $C_{21}H_{20}F_3N_7O_2$, 459.2; m/z found 460.3 [M+H]$^+$. $^1$H NMR (CDCl$_3$): 8.32 (s, 0.3H), 8.19 (s, 0.7H), 7.96-7.76 (m, 2.5H), 7.74-7.63 (m, 1H), 7.56 (s, 1H), 7.07 (dd, J=8.9, 2.9 Hz, 0.4H), 7.03-6.92 (m, 1H), 6.87 (d, J=2.9 Hz, 0.8H), 6.17-6.05 (m, 0.3H), 4.89-4.70 (m, 1H), 4.43-4.19 (m, 1H), 4.10-3.94 (m, 1H), 3.92-3.75 (m, 3H), 2.25-1.43 (m, 6H).

Example 256

(5-fluoro-2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone

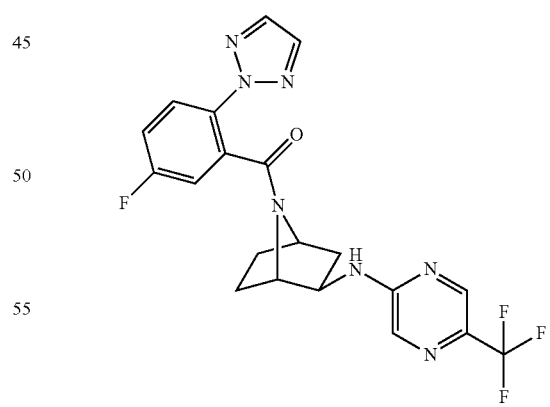

Prepared analogous to Example 181 substituting intermediate A-1 with intermediate A-10. MS (ESI) mass calcd. for $C_{20}H_{17}F_4N_7O$, 447.2; m/z found 448.3 [M+H]$^+$. $^1$H NMR (CDCl$_3$): 8.32 (s, 0.3H), 8.20 (s, 0.7H), 8.02-7.87 (m, 1.5H), 7.88-7.71 (m, 1.5H), 7.54 (s, 0.7H), 7.38-7.00 (m, 3H), 6.32-6.08 (m, 0.3H), 4.92-4.68 (m, 1H), 4.46-4.20 (m, 1H), 4.12-3.88 (m, 1H), 2.28-1.39 (m, 6H).

Example 257

(4-fluoro-2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone

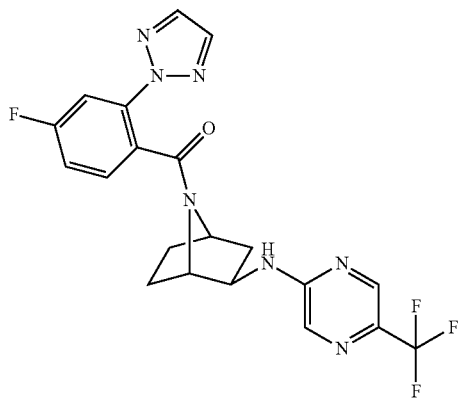 [SMILES: O=C(c1ccc(F)cc1-n1nccn1)N1C2CCC1C(Nc1cnc(C(F)(F)F)cn1)C2]

Prepared analogous to Example 181 substituting intermediate A-1 with intermediate A-12. MS (ESI) mass calcd. for $C_{20}H_{17}F_4N_7O$, 447.2; m/z found 448.3 [M+H]$^+$. $^1$H NMR (CDCl$_3$): 8.33 (s, 0.3H), 8.20 (s, 0.7H), 8.01-7.79 (m, 2.4H), 7.73 (dd, J=9.4, 2.6 Hz, 0.4H), 7.63-7.44 (m, 1.7H), 7.38 (dd, J=8.5, 5.7 Hz, 0.7H), 7.21-6.94 (m, 1.4H), 6.20 (d, J=8.5 Hz, 0.4H), 4.91-4.73 (m, 1H), 4.46-4.17 (m, 1H), 4.09-3.85 (m, 1H), 2.25-1.44 (m, 6H).

Example 258

(2-fluoro-6-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone

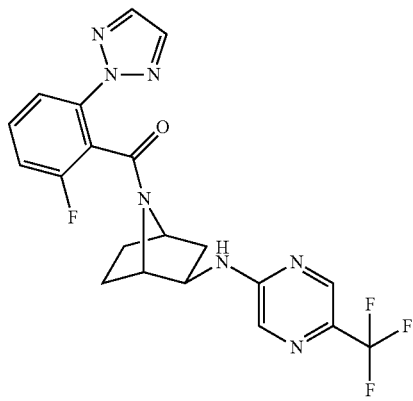 [SMILES: O=C(c1c(F)cccc1-n1nccn1)N1C2CCC1C(Nc1cnc(C(F)(F)F)cn1)C2]

Prepared analogous to Example 181 substituting intermediate A-1 with intermediate A-11. MS (ESI) mass calcd. for $C_{20}H_{17}F_4N_7O$, 447.2; m/z found 448.3 [M+H]$^+$. $^1$H NMR (CDCl$_3$): 8.41-8.29 (m, 0.3H), 8.20 (s, 0.7H), 8.01-7.60 (m, 3H), 7.60-7.11 (m, 3.2H), 7.03-6.89 (m, 0.2H), 6.20-6.06 (m, 0.2H), 5.45-5.34 (m, 0.2H), 5.16-5.04 (m, 0.2H), 4.99-4.75 (m, 1H), 4.49-4.16 (m, 1H), 4.13-4.00 (m, 0.3H), 3.88 (d, J=5.2 Hz, 0.5H), 3.69 (d, J=5.1 Hz, 0.2H), 2.33-1.36 (m, 6H).

Example 259

(6-methylimidazo[2,1-b]thiazol-5-yl)((1S,2R,4R)-2-((5-(trifluoromethyl)pyrazin-2-yl)amino)-7-azabicyclo[2.2.1]heptan-7-yl)methanone

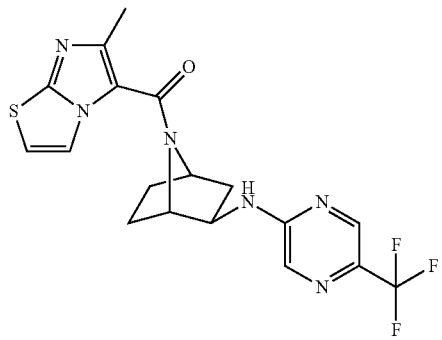 [SMILES: Cc1nc2sccn2c1C(=O)N1C2CCC1C(Nc1cnc(C(F)(F)F)cn1)C2]

Prepared analogous to Example 181 substituting intermediate A-1 with 6-methylimidazo[2,1-b]thiazole-5-carboxylic acid. MS (ESI) mass calcd. for $C_{18}H_{17}F_3N_6OS$, 422.2; m/z found 423.2 [M+H]$^+$. $^1$H NMR (CDCl$_3$): 8.26 (s, 1H), 7.91-7.75 (m, 2H), 6.96-6.80 (m, 1H), 5.91 (s, 1H), 4.58 (d, J=5.0 Hz, 1H), 4.42 (t, J=4.8 Hz, 1H), 4.21-4.05 (m, 1H), 2.49 (s, 3H), 2.25 (dd, J=13.2, 7.5 Hz, 1H), 2.10-1.88 (m, 2H), 1.73-1.54 (m, 3H).

Example 260

(3-fluoro-2-(oxazol-2-yl)phenyl)((1S,2R,4R)-2-((5-(trifluoromethyl)pyrazin-2-yl)amino)-7-azabicyclo[2.2.1]heptan-7-yl)methanone

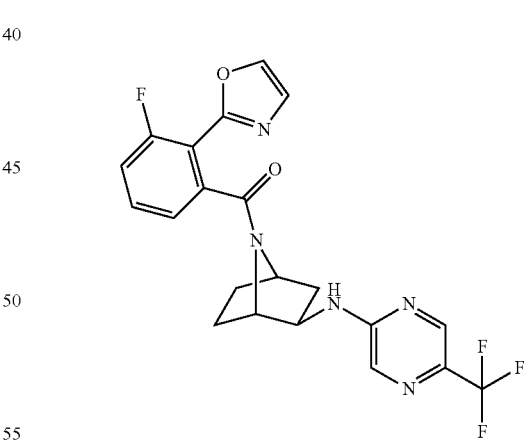

Step A: (3-fluoro-2-iodophenyl)((1S,2R,4R)-2-((5-(trifluoromethyl)pyrazin-2-yl)amino)-7-azabicyclo[2.2.1]heptan-7-yl)methanone Prepared analogous to Example 238 substituting intermediate A-2 with 3-fluoro-2-iodobenzoic acid. MS (ESI) mass calcd. for $C_{18}H_{15}F_4IN_4O$, 506.0; m/z found 507.2 [M+H]$^+$. $^1$H NMR (CDCl$_3$): 8.27-8.14 (m, 1H), 8.10-7.81 (m, 1H), 7.48-7.32 (m, 0.5H), 7.23-6.83 (m, 2.5H), 6.66-5.98 (m, 1H), 4.94-4.69 (m, 1H), 4.31-4.14 (m, 0.5H), 4.08-3.90 (m, 0.5H), 3.90-3.75 (m, 0.5H), 3.72-3.44 (m, 0.5H), 2.27-1.41 (m, 6H).

Step B: (3-fluoro-2-(oxazol-2-yl)phenyl)((1S,2R,4R)-2-((5-(trifluoromethyl)pyrazin-2-yl)amino)-7-azabicyclo[2.2.1]heptan-7-yl)methanone The title compound of step A (35 mg) and 2-(tributylstannyl)oxazole (17 µL) were dissolved in DME (I mL). The solution was degassed with $N_2$ as CuI (1 mg) and Pd(PPh$_3$)$_4$ (4 mg) was added. The reaction was heated at 120° C. for 3 h. Additional CuI and Pd(PPh$_3$)$_4$ and the reaction purged with $N_2$. Heating was continued overnight. The reaction was cooled to rt, filtered through a pad of celite and purified via prep HPLC to give the title compound (12 g, 39%). MS (ESI) mass calcd. for $C_{21}H_{17}F_4N_5O_2$, 447.1; m/z found 448.3 [M+H]$^+$. $^1$H NMR (CDCl$_3$): 8.34 (s, 1H), 8.16 (s, 1H), 7.98-7.78 (m, 1H), 7.69 (s, 0.8H), 7.60-7.06 (m, 4H), 6.80-6.61 (m, 0.2H), 4.92-4.66 (m, 1H), 4.46-4.23 (m, 1H), 4.06-3.80 (m, 1H), 2.36-1.51 (m, 6H).

Example 261

(2-((4,6-dimethylpyrimidin-2-yl)amino)-7-azabicyclo[2.2.1]heptan-7-yl)(3-fluoro-2-methoxyphenyl)methanone

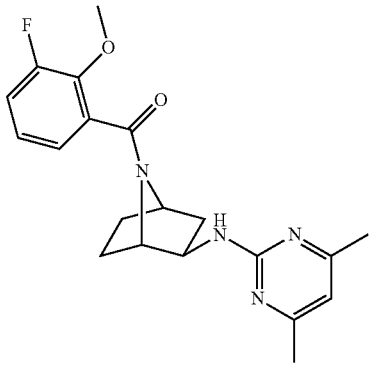 [SMILES: COc1c(F)cccc1C(=O)N1C2CCC1C(Nc1nc(C)cc(C)n1)C2]

Example 262

(3-fluoro-2-(pyridazin-3-yl)phenyl)((1S,2R,4R)-2-((5-(trifluoromethyl)pyrazin-2-yl)amino)-7-azabicyclo[2.2.1]heptan-7-yl)methanone

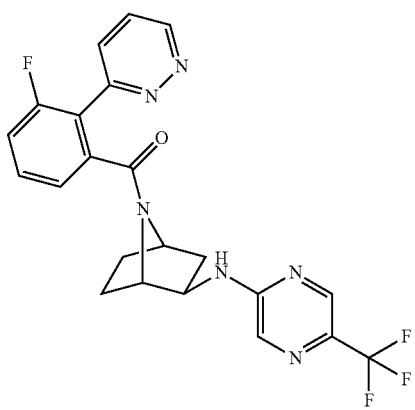 [SMILES: O=C(c1cccc(F)c1-c1cccnn1)N1C2CCC1C(Nc1cnc(C(F)(F)F)cn1)C2]

Prepared analogous to Example 260 substituting 2-(tributylstannyl)oxazole with 3-(tributylstannyl)pyridazine. MS (ESI) mass calcd. for $C_{22}H_{18}F_4N_6O$, 458.1; m/z found 459.1 [M+H]$^+$. $^1$H NMR (500 MHz, Chloroform-d) 9.25-9.14 (m, 1H), 8.50 (s, 0.5H), 8.28 (s, 0.8H), 8.17 (s, 0.5H), 7.97-7.80 (m, 1.5H), 7.72-7.59 (m, 1H), 7.55-7.41 (m, 1H), 7.34-7.18 (m, 2.2H), 6.96 (d, J=8.1 Hz, 0.5H), 4.79-4.72 (m, 0.55H), 4.71-4.64 (m, 0.45H), 4.53-4.43 (m, 0.6H), 4.38-4.28 (m, 0.45H), 4.18 (s, 0.4H), 4.13-4.05 (m, 0.55H), 2.30-1.47 (m, 6H).

Example 263

(3-methyl-2-(pyridazin-3-yl)phenyl)((1S,2R,4R)-2-((5-(trifluoromethyl)pyrazin-2-yl)amino)-7-azabicyclo[2.2.1]heptan-7-yl)methanone

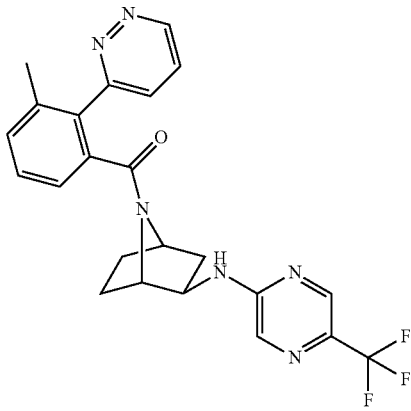 [SMILES: Cc1cccc(C(=O)N2C3CCC2C(Nc2cnc(C(F)(F)F)cn2)C3)c1-c1cccnn1]

Step A: (2-iodo-3-methylphenyl)((1S,2R,4R)-2-((5-(trifluoromethyl)pyrazin-2-yl)amino)-7-azabicyclo[2.2.1]heptan-7-yl)methanone Prepared analogous to Example 238 substituting intermediate A-2 with 2-iodo-3-methylbenzoic acid. MS (ESI) mass calcd. for $C_{19}H_{18}F_3IN_4O$, 502.0; m/z found 503.0 [M+H]$^+$. $^1$H NMR (400 MHz, Chloroform-d) 8.26-8.03 (m, 1.4H), 7.88-6.60 (m, 4.6H), 4.93-4.58 (m, 1H), 4.32-4.15 (m, 0.4H), 3.92 (s, 0.4H), 3.86-3.76 (m, 0.6H), 3.57 (s, 0.6H), 2.51 (s, 1.4H), 2.40 (s, 1.6H), 2.21-0.66 (m, 6H).

Step B: (3-methyl-2-(pyridazin-3-yl)phenyl)((1S,2R,4R)-2-((5-(trifluoromethyl)pyrazin-2-yl)amino)-7-azabicyclo[2.2.1]heptan-7-yl)methanone Prepared analogous to Example 260 Step B substituting 2-(tributylstannyl)oxazole with 3-(tributylstannyl)pyridazine. MS (ESI) mass calcd. for $C_{23}H_{21}F_3N_6O$, 454.2; m/z found 455.2 [M+H]$^+$. $^1$H NMR (400 MHz, Chloroform-d) 9.22 (dd, J=4.9, 1.7 Hz, 0.25H), 9.19 (dd, J=4.8, 1.8 Hz, 0.75H), 8.57 (s, 0.75H), 8.27 (s, 0.25H), 8.21 (s, 0.25H), 8.16 (s, 0.75H), 7.97 (s, 0.75H), 7.72-7.56 (m, 2H), 7.44-7.27 (m, 2.25H), 7.25-7.19 (m, 0.75H), 6.40 (d, J=8.0 Hz, 0.25H), 4.68-4.62 (m, 0.75H), 4.59-4.54 (m, 0.25H), 4.39 (ddd, J=9.3, 8.1, 3.9 Hz, 0.75H), 4.28-4.15 (m, 0.5H), 4.08-4.03 (m, 0.75H), 2.32 (s, 0.75H), 2.21 (s, 2.25H), 2.18-1.42 (m, 6H).

Example 264

(3-fluoro-2-(pyridazin-4-yl)phenyl)((1S,2R,4R)-2-((5-(trifluoromethyl)pyrazin-2-yl)amino)-7-azabicyclo[2.2.1]heptan-7-yl)methanone

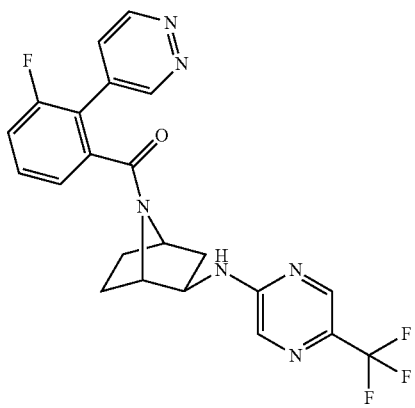

Prepared analogous to Example 260 substituting 2-(tributylstannyl)oxazole with 4-(tributylstannyl)pyridazine. MS (ESI) mass calcd. for $C_{22}H_{18}F_4N_6O$, 458.1; m/z found 459.2 [M+H]$^+$. $^1$H NMR (400 MHz, Chloroform-d) 9.38-9.20 (m, 2H), 8.28 (s, 0.6H), 8.19 (s, 0.4H), 8.00 (s, 0.6H), 7.94 (s, 0.4H), 7.71-7.63 (m, 0.6H), 7.62-7.50 (m, 1H), 7.40-7.29 (m, 1H), 7.24-7.08 (m, 1.4H), 5.24 (s, 0.4H), 4.80 (s, 0.6H), 4.67 (s, 0.4H), 4.61 (d, J=5.3 Hz, 0.6H), 4.02-3.92 (m, 0.6H), 3.85-3.75 (m, 0.4H), 3.70-3.59 (m, 1H), 1.90-2.07 (m, 1H), 1.84-0.79 (m, 5H).

Example 265

(3-fluoro-2-(pyrazin-2-yl)phenyl)((1S,2R,4R)-2-((5-(trifluoromethyl)pyrazin-2-yl)amino)-7-azabicyclo[2.2.1]heptan-7-yl)methanone

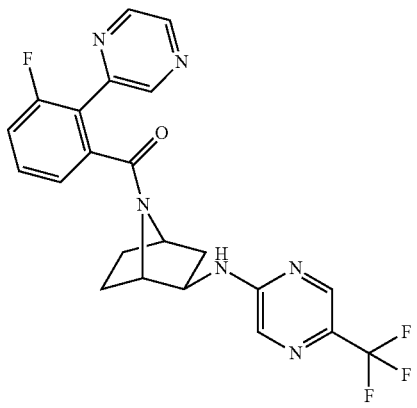 [SMILES: O=C(c1cccc(F)c1-c1cnccn1)N1C2CCC1C(Nc1cnc(C(F)(F)F)cn1)C2]

Prepared analogous to Example 260 substituting 2-(tributylstannyl)oxazole with 2-(tributylstannyl)pyrazine. MS (ESI) mass calcd. for $C_{22}H_{18}F_4N_6O$, 458.1; m/z found 459.2 [M+H]$^+$. $^1$H NMR (400 MHz, Chloroform-d) 8.99-8.94 (m, 1H), 8.69 (d, J=2.6 Hz, 1H), 8.58-8.51 (m, 1H), 8.19 (s, 1H), 8.03 (s, 1H), 7.57 (s, 1H), 7.44-7.37 (m, 1H), 7.25-7.20 (m, 2H), 4.80-4.74 (m, 1H), 4.40 (td, J=8.6, 3.6 Hz, 1H), 4.05 (d, J=5.1 Hz, 1H), 2.24-2.16 (m, 1H), 1.78-1.67 (m, 2H), 1.62-1.51 (m, 2H), 1.41-1.29 (m, 1H).

Example 266

(3-methyl-2-(oxazol-2-yl)phenyl)((1S,2R,4R)-2-((5-(trifluoromethyl)pyrazin-2-yl)amino)-7-azabicyclo[2.2.1]heptan-7-yl)methanone

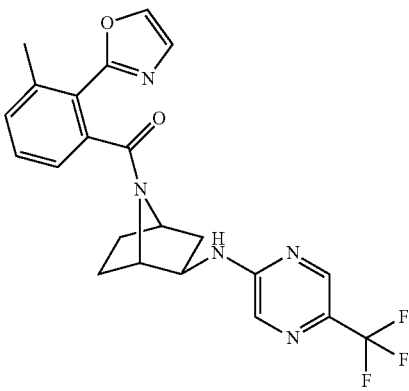

Prepared analogous to Example 263 substituting 3-(tributylstannyl)pyridazine with 2-(tributylstannyl)oxazole. MS (ESI) mass calcd. for $C_{22}H_{20}F_3N_5O_2$, 443.2 m/z found 444.2 [M+H]$^+$. $^1$H NMR (500 MHz, Chloroform-d) 8.57 (s, 1H), 8.14 (s, 1H), 7.88 (d, J=0.9 Hz, 1H), 7.79 (d, J=1.4 Hz, 1H), 7.33-7.23 (m, 3H), 7.20-7.14 (m, 1H), 4.82-4.75 (m, 1H), 4.29 (td, J=8.5, 3.7 Hz, 1H), 3.94 (d, J=4.9 Hz, 1H), 2.28 (s, 3H), 2.16-1.45 (m, 6H).

Example 267

(4-fluoro-2-(pyrimidin-2-yl)phenyl)((1S,2R,4R)-2-((5-(trifluoromethyl)pyrazin-2-yl)amino)-7-azabicyclo[2.2.1]heptan-7-yl)methanone

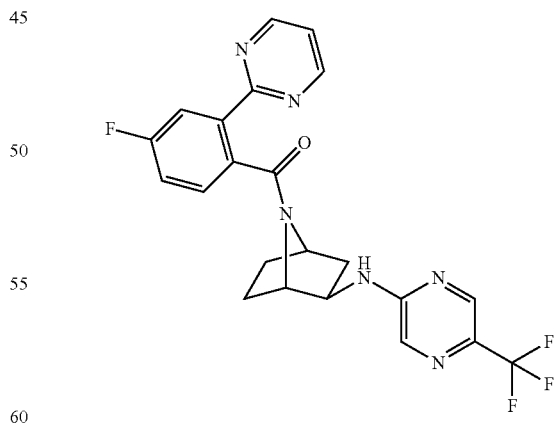

Prepared analogous to Example 238 substituting intermediate A-2 with intermediate A-25. MS (ESI) mass calcd. for: $C_{22}H_{18}F_4N_6O$, 458.1; m/z found 459.2 [M+H]$^+$. $^1$H NMR (500 MHz, Chloroform-d) 8.89-8.81 (m, 1.7H), 8.80-8.73 (m, 0.3H), 8.33-7.87 (m, 2H), 7.80 (s, 0.2H), 7.74-7.66 (m, 0.8H), 7.56-7.31 (m, 2.8H), 7.21-7.14 (m, 0.2H), 7.14-7.06

(m, 0.8H), 6.58 (s, 0.2H), 4.88-4.78 (m, 0.8H), 4.72 (d, J=5.2 Hz, 0.2H), 4.40 (s, 0.8H), 4.26 (s, 0.2H), 4.10-3.97 (m, 1H), 2.27-1.39 (m, 6H).

Example 268

(3-fluoro-2-(pyridin-4-yl)phenyl)((1S,2R,4R)-2-((5-(trifluoromethyl)pyrazin-2-yl)amino)-7-azabicyclo[2.2.1]heptan-7-yl)methanone

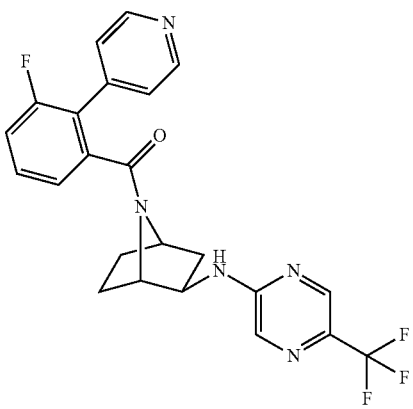 [SMILES: O=C(c1cccc(F)c1-c1ccncc1)N1C2CCC1C(Nc1cnc(C(F)(F)F)cn1)C2]

Prepared analogous to Example 260 substituting 2-(tributylstannyl)oxazole with 4-(tributylstannyl)pyridine. MS (ESI) mass calcd. for: $C_{23}H_{19}F_4N_5O$, 457.2; m/z found 458.2 [M+H]$^+$. $^1$H NMR (500 MHz, Chloroform-d) 8.78-8.61 (m, 2H), 8.28 (s, 0.6H), 8.15 (s, 0.4H), 7.87 (s, 1H), 7.72-7.28 (m, 4.2H), 7.23-7.02 (m, 1.4H), 5.49 (s, 0.4H), 4.67-4.60 (m, 0.4H), 4.56 (d, J=5.3 Hz, 0.6H), 3.99-3.89 (m, 0.6H), 3.82-3.72 (m, 0.4H), 3.65-3.58 (m, 0.6H), 3.56 (d, J=5.4 Hz, 0.4H), 2.00-0.80 (m, 6H).

Example 269

(3-fluoro-2-(2H-1,2,3-triazol-2-yl)phenyl)((1S,2R,4R)-2-((5-(trifluoromethyl)pyrimidin-2-yl)amino)-7-azabicyclo[2.2.1]heptan-7-yl)methanone

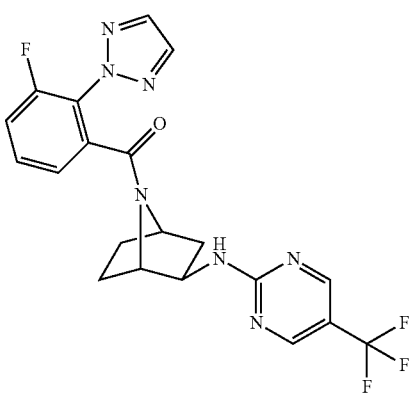

Step A: (1S,2R,4R)-tert-butyl 2-((5-(trifluoromethyl)pyrimidin-2-yl)amino)-7-azabicyclo[2.2.1]heptane-7-carboxylate To intermediate B-5 (250 g, 1.2 mmol) and K$_2$CO$_3$ (244 g, 1.8 mmol) in DMF (1.7 mL) was added 2-chloro-5-(trifluoromethyl)pyrimidine (258 mg, 1.4 mmol). After heating at 70° C. for 17 h, the mixture was cooled to rt, diluted with EtOAc and H$_2$O. The aqueous layer was extracted with EtOAc (3×). The combined organics were washed with 4% MgSO$_4$ (aq) and dried (MgSO$_4$). Purification via silica gel chromatography (0-30% EtOAc in hexanes) gave the title compound (356 g, 84%). MS (ESI) mass calcd. for $C_{16}H_{21}F_3N_4O_2$, 358.2; m/z found 359.2 [M+H]$^+$. $^1$H NMR (500 MHz, Chloroform-d) 8.58-8.37 (m, 2H), 5.70 (s, 1H), 4.30 (s, 1H), 1.78-1.68 (m, 1H), 4.25-4.17 (m, 1H), 1.89-1.79 (m, 1H), 4.12-4.03 (m, 1H), 2.03 (dd, J=13.1, 7.8 Hz, 1H), 1.63-1.37 (m, 12H).

Step B: (1S,2R,4R)—N-(5-(trifluoromethyl)pyrimidin-2-yl)-7-azabicyclo[2.2.1]heptan-2-amine To the title compound of step A (355 g, 1 mmol) in DCM (9.7 mL) was added 4M HCl in dioxane (1.2 mL). The reaction was allowed to proceed overnight then concentrated and neutralized with 5% Na$_2$CO$_3$ (aq) and extracted with DCM (2×). The combined organics were dried (Na$_2$SO$_4$) to give the title compound of step B that was used without further purification.

Step C: (3-fluoro-2-(2H-1,2,3-triazol-2-yl)phenyl)((1S,2R,4R)-2-((5-(trifluoromethyl)pyrimidin-2-yl)amino)-7-azabicyclo[2.2.1]heptan-7-yl)methanone To the title compound of step B (25 g, 0.1 mmol) in DCM (1 mL) was added DIPEA (22 μL, 0.13 mmol) and intermediate A-16 (22 g, 0.1 mmol). Then T3P (50% solution in DMF, 0.17 mL, 0.29 mmol) was added dropwise and the reaction heated at 45° C. for 12 h. After allowing to cool to rt, DCM was added and the mixture washed with H$_2$O then saturated NaHCO$_3$ (aq). The combined aq layers were extracted with DCM. The combined organic layers were dried (Na$_2$SO$_4$). Purification was performed using Agilent prep method X to give the title compound (35 mg, 80%). MS (ESI) mass calcd. for: $C_{20}H_{17}F_4N_7O$, 447.1; m/z found 448.2 [M+H]$^+$. $^1$H NMR (400 MHz, Chloroform-d) 8.50 (s, 0.9H), 8.41 (s, 1.1H), 8.09 (s, 0.9H), 7.95 (s, 1.1H), 7.56-7.47 (m, 0.5H), 7.44-7.32 (m, 1H), 7.33-7.23 (m, 1.5H), 7.20-7.14 (m, 0.5H), 6.18 (d, J=8.6 Hz, 0.5H), 4.83-4.74 (m, 0.5H), 4.67 (d, J=5.2 Hz, 0.5H), 4.34-4.19 (m, 1H), 4.11-4.04 (m, 0.5H), 3.99 (d, J=4.8 Hz, 0.5H), 2.21-1.44 (m, 6H).

Example 270

((1S,2R,4R)-2-((3-bromoimidazo[1,2-a]pyrazin-8-yl)amino)-7-azabicyclo[2.2.1]heptan-7-yl)(3-fluoro-2-(pyrimidin-2-yl)phenyl)methanone

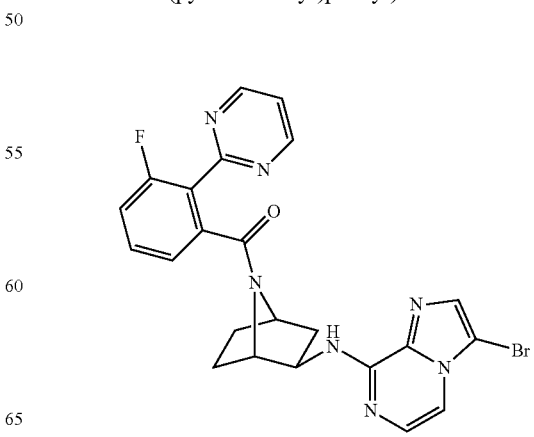

Step A: (1S,2R,4R)-tert-butyl 2-((3-bromoimidazo[1,2-a]pyrazin-8-yl)amino)-7-azabicyclo[2.2.1]heptane-7-carboxylate Prepared analogous to Example 269 step A substituting 2-chloro-5-(trifluoromethyl)pyrimidine with 3-bromo-8-chloroimidazo[1,2-a]pyrazine. MS (ESI) mass calcd. for: $C_{17}H_{22}BrN_5O_2$, 407.1; m/z found 408.1 [M+H]$^+$. $^1$H NMR (500 MHz, Chloroform-d) 7.45 (s, 1H), 7.43 (d, J=4.7 Hz, 1H), 7.40 (d, J=4.7 Hz, 1H), 6.15 (s, 1H), 4.37-4.27 (m, 2H), 4.27-4.21 (m, 1H), 2.08 (dd, J=13.0, 7.8 Hz, 1H), 1.90-1.33 (m, 14H).

Step B: N-((1S,2R,4R)-7-azabicyclo[2.2.1]heptan-2-yl)-3-bromoimidazo[1,2-a]pyrazin-8-amine Prepared analogous to Example 269 step B using title compound of step A.

Step C: ((1S,2R,4R)-2-((3-bromoimidazo[1,2-a]pyrazin-8-yl)amino)-7-azabicyclo[2.2.1]heptan-7-yl)(3-fluoro-2-(pyrimidin-2-yl)phenyl)methanone Prepared analogous to Example 269 step C substituting intermediate A-16 with intermediate A-2. MS (ESI) mass calcd. for: $C_{23}H_{19}BrFN_7O$, 507.1; m/z found 508.1 [M+H]$^+$. $^1$H NMR (400 MHz, Chloroform-d) 8.92 (d, J=4.9 Hz, 0.7H), 8.88 (d, J=4.9 Hz, 1.3H), 7.53-7.03 (m, 7.6H), 5.82 (d, J=7.6 Hz, 0.4H), 4.81-4.75 (m, 0.6H), 4.71 (d, J=5.1 Hz, 0.4H), 4.47-4.37 (m, 0.6H), 4.31-4.22 (m, 0.4H), 4.13-4.07 (m, 0.6H), 4.06-3.99 (m, 0.4H), 2.26-1.36 (m, 6H).

Example 271

(3-fluoro-2-(pyrimidin-2-yl)phenyl)((1S,2R,4R)-2-((5-(trifluoromethyl)pyrimidin-2-yl)amino)-7-azabicyclo[2.2.1]heptan-7-yl)methanone

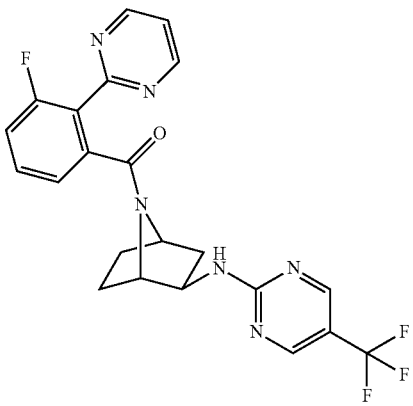

Prepared analogous to Example 269 substituting intermediate A-16 with intermediate A-2. MS (ESI) mass calcd. for: $C_{22}H_{18}F_4N_6O$, 458.1; m/z found 459.2 [M+H]$^+$. $^1$H NMR (400 MHz, Chloroform-d) 8.90 (d, J=5.0 Hz, 2H), 8.49 (s, 1H), 8.44-8.31 (m, 2H), 7.43-7.32 (m, 2H), 7.26-7.14 (m, 2H), 4.80-4.75 (m, 1H), 4.45-4.37 (m, 1H), 4.09 (d, J=5.0 Hz, 1H), 2.22 (dd, J=12.9, 8.0 Hz, 1H), 2.11-1.51 (m, 5H).

Example 272

(3-methyl-2-(2H-1,2,3-triazol-2-yl)phenyl)((1S,2R,4R)-2-((5-(trifluoromethyl)pyrimidin-2-yl)amino)-7-azabicyclo[2.2.1]heptan-7-yl)methanone

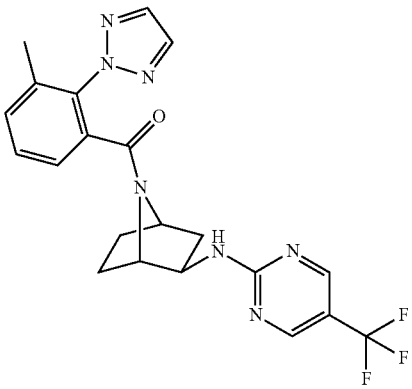

Prepared analogous to Example 269 substituting intermediate A-16 with intermediate A-24. MS (ESI) mass calcd. for: $C_{21}H_{20}F_3N_7O$, 443.2; m/z found 444.2 [M+H]$^+$. $^1$H NMR (400 MHz, Chloroform-d) 8.49 (s, 0.8H), 8.41 (s, 1.2H), 8.02 (s, 0.8H), 7.91 (s, 1.2H), 7.47-7.39 (m, 1H), 7.38-7.28 (m, 2H), 7.23-7.16 (m, 0.6H), 5.98 (d, J=8.4 Hz, 0.4H), 4.77-4.68 (m, 0.6H), 4.60 (d, J=5.1 Hz, 0.4H), 4.29-4.17 (m, 1H), 4.11-4.03 (m, 0.4H), 3.99 (d, J=5.0 Hz, 0.6H), 2.27 (s, 1.3H), 2.24 (s, 1.7H), 2.18-1.41 (m, 6H).

Example 273

(3-methyl-2-(pyrimidin-2-yl)phenyl)((1S,2R,4R)-2-((5-(trifluoromethyl)pyrazin-2-yl)amino)-7-azabicyclo[2.2.1]heptan-7-yl)methanone

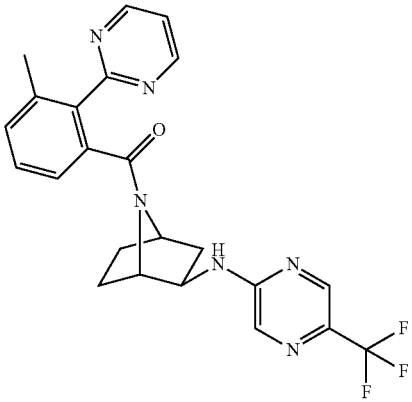

Prepared analogous to Example 238 substituting intermediate A-2 with intermediate A-26. MS (ESI) mass calcd. for: $C_{23}H_{21}F_3N_6O$, 454.2; m/z found 455.1 [M+H]$^+$. $^1$H NMR (400 MHz, Chloroform-d) 8.85 (d, J=5.0 Hz, 2H), 8.50 (d, J=9.2 Hz, 1H), 8.17 (s, 1H), 7.66 (d, J=1.3 Hz, 1H), 7.37 (t, J=5.0 Hz, 1H), 7.31-7.18 (m, 3H), 4.73-4.67 (m, 1H), 4.35 (td, J=8.7, 3.7 Hz, 1H), 4.14-4.09 (m, 1H), 2.29 (s, 3H), 2.19-1.45 (m, 6H).

Example 274

(3-fluoro-2-(pyrimidin-2-yl)phenyl)((1S,2R,4R)-2-((3-(trifluoromethyl)-[1,2,4]triazolo[4,3-a]pyrazin-8-yl)amino)-7-azabicyclo[2.2.1]heptan-7-yl)methanone

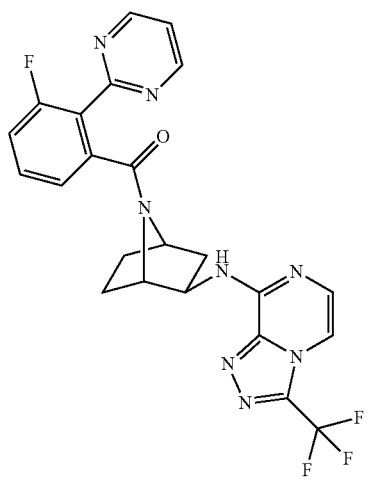 [SMILES: O=C(c1cccc(F)c1-c1ncccn1)N1C2CCC1C(Nc1nccn3c(C(F)(F)F)nnc13)C2]

Step A: (1S,2R,4R)-tert-butyl 2-((3-(trifluoromethyl)-[1,2,4]triazolo[4,3-a]pyrazin-8-yl)amino)-7-azabicyclo[2.2.1]heptane-7-carboxylate Prepared analogous to Example 269 step A substituting 2-chloro-5-(trifluoromethyl)pyrimidine with 8-chloro-3-(trifluoromethyl)-[1,2,4]triazolo[4,3-a]pyrazine. MS (ESI) mass calcd. for: $C_{17}H_{21}F_3N_6O_2$, 398.2; m/z found 399.2 [M+H]$^+$. $^1$H NMR (500 MHz, Chloroform-d) 7.51-7.48 (m, 1H), 7.48-7.45 (m, 1H), 6.58 (d, J=7.6 Hz, 1H), 4.41-4.25 (m, 3H), 1.94-1.83 (m, 1H), 2.12 (dd, J=13.1.7.8 Hz, 1H), 1.83-1.70 (m, 2H), 1.59-1.52 (m, 1H), 1.50-1.41 (m, 10H).

Step B: N-((1S,2R,4R)-7-azabicyclo[2.2.1]heptan-2-yl)-3-(trifluoromethyl)-[1,2,4]triazolo[4,3-a]pyrazin-8-amine Prepared analogous to Example 269 step B using title compound of step A.

Step C: (3-fluoro-2-(pyrimidin-2-yl)phenyl)((1S,2R,4R)-2-((3-(trifluoromethyl)-[1,2,4]triazolo[4,3-a]pyrazin-8-yl)amino)-7-azabicyclo[2.2.1]heptan-7-yl)methanone Prepared analogous to Example 269 step C substituting intermediate A-16 with intermediate A-2. MS (ESI) mass calcd. for: $C_{23}H_{18}F_4N_8O$, 498.2; m/z found 499.2 [M+H]$^+$. $^1$H NMR (400 MHz, Chloroform-d) 8.99 (d, J=4.9 Hz, 0.6H), 8.95 (d, J=5.0 Hz, 1.4H), 8.72 (s, 0.7H), 7.55-7.28 (m, 4.6H), 7.21-7.10 (m, 1.4H), 6.18 (d, J=7.5 Hz, 0.3H), 4.88-4.80 (m, 0.7H), 4.75 (d, J=5.1 Hz, 0.3H), 4.67 (s, 0.7H), 4.33 (s, 0.3H), 4.16-4.06 (m, 1H), 2.27 (dd, J=12.7, 8.2 Hz, 0.7H), 2.11 (dd, J=13.0, 8.1 Hz, 0.3H), 2.04-1.41 (m, 5H).

Example 275 methyl 5-(((1S,2R,4R)-7-(3-fluoro-2-(pyrimidin-2-yl)benzoyl)-7-azabicyclo[2.2.1]heptan-2-yl)amino)pyrazine-2-carboxylate

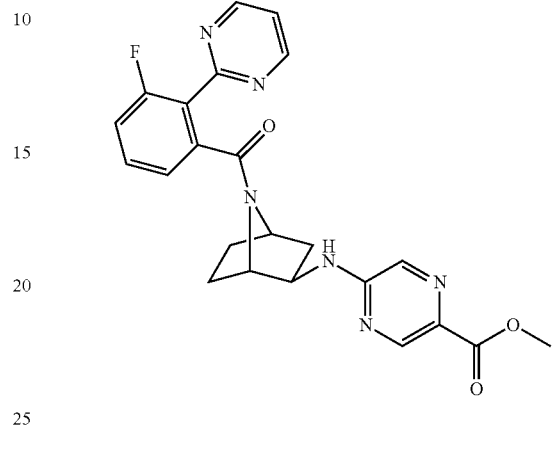

Step A: (1S,2R,4R)-tert-butyl 2-((5-(methoxycarbonyl)pyrazin-2-yl)amino)-7-azabicyclo[2.2.1]heptane-7-carboxylate Prepared analogous to Example 269 step A substituting 2-chloro-5-(trifluoromethyl)pyrimidine with methyl 5-chloropyrazine-2-carboxylate. MS (ESI) mass calcd. for: $C_{17}H_{24}N_4O_4$, 348.2; m/z found 349.2 [M+H]$^+$. $^1$H NMR (400 MHz, Chloroform-d) 8.77 (d, J=1.4 Hz, 1H), 7.88 (d, J=1.4 Hz, 1H), 5.55 (s, 1H), 4.34-4.27 (m, 1H), 4.25-4.18 (m, 1H), 4.12-4.06 (m, 1H), 3.95 (s, 3H), 2.12-2.05 (m, 1H), 1.92-1.72 (m, 2H), 1.63-1.38 (m, 12H).

Step B: methyl 5-((1S,2R,4R)-7-azabicyclo[2.2.1]heptan-2-ylamino)pyrazine-2-carboxylate Prepared analogous to Example 269 step B using title compound of step A.

Step C: methyl 5-(((1S,2R,4R)-7-(3-fluoro-2-(pyrimidin-2-yl)benzoyl)-7-azabicyclo[2.2.1]heptan-2-yl)amino)pyrazine-2-carboxylate Prepared analogous to Example 269 step C substituting intermediate A-16 with intermediate A-2. MS (ESI) mass calcd. for: $C_{23}H_{21}FN_6O_3$, 448.2; m/z found 449.2 [M+H]$^+$. $^1$H NMR (500 MHz, Chloroform-d) 8.87 (d, J=4.9 Hz, 2H), 8.65 (s, 1H), 8.37 (d, J=9.4 Hz, 1H), 7.67 (s, 1H), 7.42-7.34 (m, 2H), 7.24-7.17 (m, 2H), 4.77-4.70 (m, 1H), 4.48-4.39 (m, 1H), 4.07 (d, J=5.1 Hz, 1H), 3.90 (s, 3H), 2.18 (dd, J=13.0, 8.1 Hz, 1H), 2.11-2.00 (m, 1H), 1.97-1.62 (m, 3H), 1.58-1.48 (m, 1H).

Example 276

(2-iodo-3-methylphenyl)((1S,2R,4R)-2-((5-(trifluoromethyl)pyrimidin-2-yl)amino)-7-azabicyclo[2.2.1]heptan-7-yl)methanone

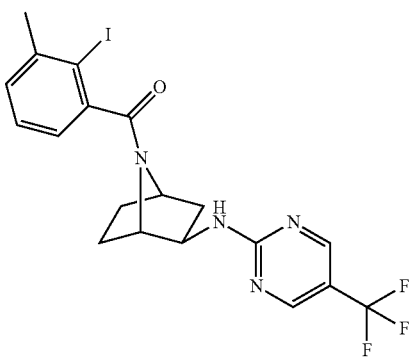 [SMILES: Cc1cccc(C(=O)N2C3CCC2C(Nc2ncc(C(F)(F)F)cn2)C3)c1I]

Prepared analogous to Example 269 substituting intermediate A-16 with 2-iodo-3-methylbenzoic acid. MS (ESI) mass calcd. for: $C_{19}H_{18}F_3IN_4O$, 502.0; m/z found 503.0 [M+H]$^+$. $^1$H NMR (400 MHz, Chloroform-d) 8.59-8.30 (m, 2H), 7.32-7.22 (m, 1.4H), 7.19-6.96 (m, 1H), 6.93-6.83 (m, 0.6H), 6.02 (s, 0.5H), 5.54 (s, 0.5H), 5.01-4.91 (m, 0.5H), 4.84 (d, J=5.1 Hz, 0.5H), 4.28 (s, 0.5H), 4.02 (s, 0.5H), 3.84-3.66 (m, 1H), 2.50 (s, 1.5H), 2.43 (s, 1.5H), 2.24-1.39 (m, 6H).

Example 277

(3-fluoro-2-iodophenyl)((1S,2R,4R)-2-((5-(trifluoromethyl)pyrimidin-2-yl)amino)-7-azabicyclo[2.2.1]heptan-7-yl)methanone

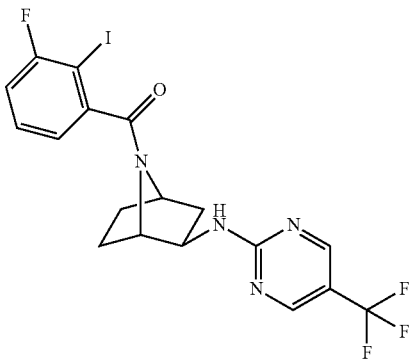 [SMILES: O=C(c1cccc(F)c1I)N1C2CCC1C(Nc1ncc(C(F)(F)F)cn1)C2]

Prepared analogous to Example 269 substituting intermediate A-16 with 3-fluoro-2-iodobenzoic acid. MS (ESI) mass calcd. for: $C_{18}H_{18}F_4IN_4O$, 506.0; m/z found 507.0 [M+H]$^+$. $^1$H NMR (400 MHz, Chloroform-d) 8.57-8.33 (m, 2H), 7.42-7.32 (m, 0.5H), 7.16-7.02 (m, 1.5H), 6.99-6.88 (m, 1H), 5.99 (d, J=7.6 Hz, 0.5H), 5.55 (s, 0.5H), 5.00-4.91 (m, 0.5H), 4.85 (d, J=5.3 Hz, 0.5H), 4.32-4.24 (m, 0.5H), 4.05-3.97 (m, 0.5H), 3.81-3.71 (m, 1H), 2.22-1.93 (m, 2H), 1.91-1.43 (m, 4H).

Example 278

(3-fluoro-2-(pyrimidin-2-yl)phenyl)((1S,2R,4R)-2-((5-methylpyrazin-2-yl)amino)-7-azabicyclo[2.2.1]heptan-7-yl)methanone

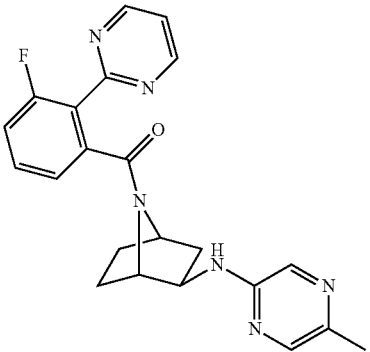 [SMILES: Cc1cnc(NC2CC3CCC2N3C(=O)c2cccc(F)c2-c2ncccn2)cn1]

Step A: (1S,2R,4R)-tert-butyl 2-((5-methylpyrazin-2-yl)amino)-7-azabicyclo[2.2.1]heptane-7-carboxylate Prepared analogous to Example 279 step A substituting 2-chloro-5-(trifluoromethyl)pyridine with 2-chloro-5-methylpyrazine. MS (ESI) mass calcd. for: $C_{16}H_{24}N_4O_2$, 304.2; m/z found 305.2 [M+H]$^+$. $^1$H NMR (400 MHz, Chloroform-d) 7.86 (s, 1H), 7.78 (d, J=1.5 Hz, 1H), 4.71 (s, 1H), 4.28 (s, 1H), 4.19 (d, J=4.9 Hz, 1H), 3.95-3.85 (m, 1H), 2.38 (s, 3H), 2.11-1.96 (m, 1H), 1.89-1.66 (m, 2H), 1.58-1.33 (m, 12H).

Step B: (1S,2R,4R)—N-(5-methylpyrazin-2-yl)-7-azabicyclo[2.2.1]heptan-2-amine

Prepared analogous to Example 279 step B using title compound of step A.

Step C: (3-fluoro-2-(pyrimidin-2-yl)phenyl)((1S,2R,4R)-2-((5-methylpyrazin-2-yl)amino)-7-azabicyclo[2.2.1]heptan-7-yl)methanone Prepared analogous to Example 279 step C. MS (ESI) mass calcd. for: $C_{22}H_{21}FN_6O$, 404.2; m/z found 405.2 [M+H]$^+$. $^1$H NMR (500 MHz, Chloroform-d) 8.87 (d, J=5.0 Hz, 2H), 7.74 (s, 1H), 7.60 (s, 1H), 7.41-7.30 (m, 3H), 7.23-7.12 (m, 2H), 4.76-4.68 (m, 1H), 4.30-4.17 (m, 1H), 4.08-4.01 (m, 1H), 2.30 (s, 3H), 2.15 (dd, J=12.9, 8.1 Hz, 1H), 2.07-1.95 (m, 1H), 1.95-1.84 (m, 1H), 1.74-1.46 (m, 3H).

Example 279

(3-fluoro-2-(pyrimidin-2-yl)phenyl)((1S,2R,4R)-2-((5-(trifluoromethyl)pyridin-2-yl)amino)-7-azabicyclo[2.2.1]heptan-7-yl)methanone

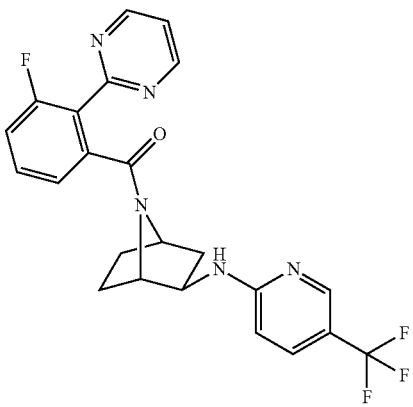

Step A: (1S,2R,4R)-tert-butyl 2-((5-(trifluoromethyl)pyridin-2-yl)amino)-7-azabicyclo[2.2.1]heptane-7-carboxylate In a microwave vial, toluene (8.3 mL) was degassed with $N_2$ for 10 minutes then Pd(OAc)$_2$ (22 g, 0.03 mmol) and racemic BINAP (21 mg, 0.03 mmol) were added and the solution was degassed with $N_2$ for 5 minutes. Then intermediate B-5, 2-chloro-5-(trifluoromethyl)pyridine (150 g, 0.83 mmol) and sodium tert-butoxide (115 mg, 1.16 mmol) were added and the reaction mixture was stirred at 70° C. After 15 h the reaction mixture was filtered through a pad of celite and solvent was evaporated. Purification via silica gel chromatography (0-40% EtOAc in hexanes) gave the title compound of step A (192 mg, 65%). MS (ESI) mass calcd. for: $C_{17}H_{22}F_3N_3O_2$, 357.2; m/z found 358.2 [M+H]$^+$. $^1$H NMR (500 MHz, Chloroform-d) 8.33 (s, 1H), 7.61-7.49 (m, 1H), 6.35 (d, J=8.8 Hz, 1H), 5.06 (s, 1H), 4.29 (s, 1H), 4.20 (s, 1H), 4.03-3.91 (m, 1H), 2.04 (dd, J=13.0, 7.6 Hz, 1H), 1.89-1.79 (m, 1H), 1.79-1.71 (m, 1H), 1.59-1.37 (m, 12H).

Step B: (1S,2R,4R)—N-(5-(trifluoromethyl)pyridin-2-yl)-7-azabicyclo[2.2.1]heptan-2-amine To the title compound of step A (319 g, 0.89 mmol) in DCM (8.7 mL) was added 4M HCl in dioxane (1.1 mL). The reaction was allowed to proceed overnight then concentrated and neutralized with 5% Na$_2$CO$_3$ (aq) and extracted with DCM (2×). The combined organics were dried (Na$_2$SO$_4$) to give the title compound of step B that was used without further purification.

Step C: (3-fluoro-2-(pyrimidin-2-yl)phenyl)((1S,2R,4R)-2-((5-(trifluoromethyl)pyridin-2-yl)amino)-7-azabicyclo[2.2.1]heptan-7-yl)methanone To the title compound of step B (100 mg, 0.39 mmol) in DCM (3.9 mL) was added DIPEA (87 µL, 0.51 mmol) and intermediate A-2 (100 mg, 0.43 mmol). Then T3P (50% solution in DMF, 0.7 mL, 1.16 mmol) was added dropwise and the reaction heated at 45° C. for 12 h. After allowing to cool to rt, DCM was added and the mixture washed with H$_2$O then saturated NaHCO$_3$ (aq). The combined aq layers were extracted with DCM. The combined organic layers were dried (Na$_2$SO$_4$). Purification was performed using Agilent prep method X to give the title compound (61 g, 34%). MS (ESI) mass calcd. for: $C_{23}H_{19}F_4N_5O$, 457.2; m/z found 458.2 [M+H]$^+$. $^1$H NMR (400 MHz, Chloroform-d) 8.88 (d, J=4.9 Hz, 2H), 8.22 (s, 1H), 7.67 (d, J=9.3 Hz, 1H), 7.43-7.28 (m, 3H), 7.24-7.12 (m, 2H), 6.19 (d, J=8.8 Hz, 1H), 4.76-4.68 (m, 1H), 4.43-4.32 (m, 1H), 4.08 (d, J=5.0 Hz, 1H), 2.16 (dd, J=12.9, 8.1 Hz, 1H), 2.08-1.83 (m, 2H), 1.77-1.38 (m, 3H).

Example 280

(4-fluoro-2-(pyrimidin-2-yl)phenyl)((1S,2R,4R)-2-((5-(trifluoromethyl)pyridin-2-yl)amino)-7-azabicyclo[2.2.1]heptan-7-yl)methanone

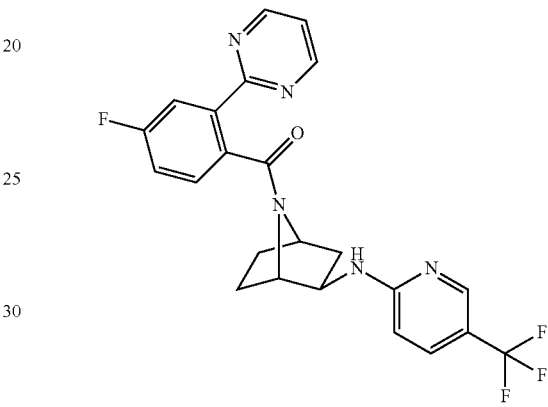

Prepared analogous to Example 279 substituting intermediate A-2 with intermediate A-25. MS (ESI) mass calcd. for: $C_{23}H_{19}F_4N_5O$, 457.2; m/z found 458.2 [M+H]$^+$. $^1$H NMR (400 MHz, Chloroform-d) 8.89-8.76 (m, 2H), 8.36 (s, 0.2H), 8.26-8.19 (m, 0.8H), 8.05-7.91 (m, 0.4H), 7.70 (dd, J=9.3, 2.7 Hz, 0.6H), 7.60-7.53 (m, 0.3H), 7.48-7.40 (m, 0.3H), 7.40-7.28 (m, 2.6H), 7.25-6.99 (m, 1.6H), 6.36 (d, J=8.7 Hz, 0.2H), 5.96 (d, J=8.8 Hz, 0.8H), 5.70 (s, 0.2H), 4.87-4.80 (m, 0.8H), 4.73 (d, J=5.3 Hz, 0.2H), 4.38 (s, 0.8H), 4.17 (s, 0.2H), 4.06-4.00 (m, 0.8H), 4.00-3.94 (m, 0.2H), 2.21 (dd, J=12.9, 8.0 Hz, 0.8H), 2.12-1.35 (m, 5.2H).

Example 281

(3-methyl-2-(pyrimidin-2-yl)phenyl)((1S,2R,4R)-2-((5-(trifluoromethyl)pyridin-2-yl)amino)-7-azabicyclo[2.2.1]heptan-7-yl)methanone

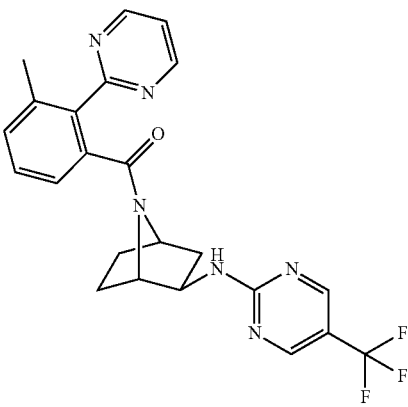

Prepared analogous to Example 269 substituting intermediate A-16 with intermediate A-26. MS (ESI) mass calcd. for: $C_{23}H_{21}F_3N_6O$, 454.2; m/z found 455.3 [M+H]$^+$. $^1$H NMR (500 MHz, Chloroform-d) 8.89-8.85 (m, 2H), 8.70 (s, 1H), 8.44-8.32 (m, 2H), 7.34-7.23 (m, 3H), 7.21-7.15 (m, 1H), 4.77-4.68 (m, 1H), 4.43-4.33 (m, 1H), 4.11 (d, J=5.1 Hz, 1H), 2.36 (s, 3H), 2.19 (dd, J=12.8, 7.9 Hz, 1H), 2.09-1.99 (m, 1H), 1.94-1.85 (m, 1H), 1.72-1.48 (m, 3H).

Example 282

(3-fluoro-2-(pyrimidin-2-yl)phenyl)((1S,2R,4R)-2-(methyl(5-(trifluoromethyl)pyrazin-2-yl)amino)-7-azabicyclo[2.2.1]heptan-7-yl)methanone

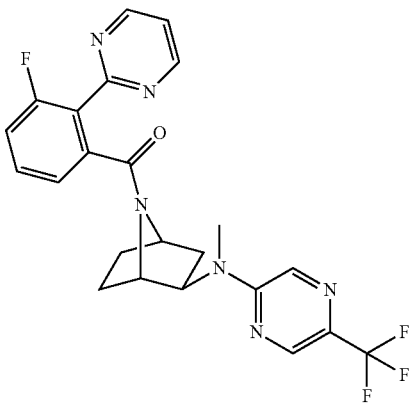 [SMILES: CN(c1cnc(C(F)(F)F)cn1)C1CC2CCC1N2C(=O)c1cccc(F)c1-c1ncccn1]

The title compound of Example 238 (63 g, 0.14 mmol) was dissolved in DMF (1.4 mL) and then sodium tert-butoxide (15 g, 0.15 mmol) followed by iodomethane (9 μL, 0.14 mmol) were added. After 15 h at room temperature the reaction mixture was diluted with EtOAc and water was added. The aqueous phase was extracted twice with EtOAc and the combined organic phases were dried over MgSO$_4$, filtered and evaporated. Purification was performed using Agilent prep method X to give the title compound (40 g, 62%). MS (ESI) mass calcd. for: $C_{23}H_{20}F_4N_6O$, 472.2; m/z found 473.2 [M+H]$^+$. $^1$H NMR (500 MHz, Chloroform-d) 8.81 (d, J=4.9 Hz, 2H), 8.35 (s, 1H), 8.02 (s, 1H), 7.55-7.46 (m, 1H), 7.34-7.20 (m, 3H), 4.81-4.73 (m, 1H), 4.67 (d, J=4.3 Hz, 1H), 4.17-4.08 (m, 1H), 3.05 (s, 3H), 2.12 (dd, J=12.8, 8.3 Hz, 1H), 1.98-1.44 (m, 5H).

Example 283

(3-methyl-2-(oxazol-2-yl)phenyl)((1S,2R,4R)-2-((5-(trifluoromethyl)pyrimidin-2-yl)amino)-7-azabicyclo[2.2.1]heptan-7-yl)methanone

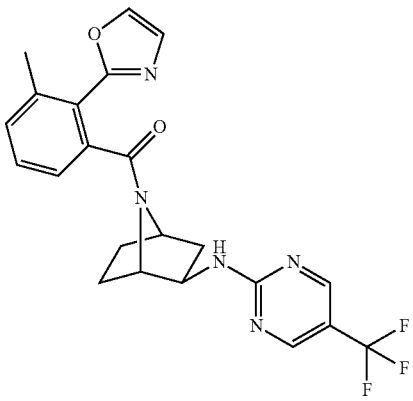

Prepared analogous to Example 269 substituting intermediate A-16 with intermediate A-31. MS (ESI) mass calcd. for: $C_{22}H_{20}F_3N_5O_2$, 443.2; m/z found 444.1 [M+H]$^+$. $^1$H NMR (400 MHz, Chloroform-d) 8.48 (s, 1H), 8.35 (s, 1H), 7.88-7.78 (m, 1H), 7.68 (s, 0.4H), 7.44-7.21 (m, 3.6H), 7.15 (dd, J=6.6, 2.2 Hz, 0.6H), 7.06-6.97 (m, 0.4H), 4.84-4.78 (m, 0.6H), 4.73-4.67 (m, 0.4H), 4.33 (td, J=8.4, 3.0 Hz, 0.4H), 4.24 (td, J=8.2, 3.7 Hz, 0.6H), 4.04-3.98 (m, 0.4H), 3.97-3.89 (m, 0.6H), 2.47 (s, 1.7H), 2.37 (s, 1.3H), 2.19-1.41 (m, 6H).

Example 284

(3-fluoro-2-(oxazol-2-yl)phenyl)((1S,2R,4R)-2-((5-(trifluoromethyl)pyrimidin-2-yl)amino)-7-azabicyclo[2.2.1]heptan-7-yl)methanone

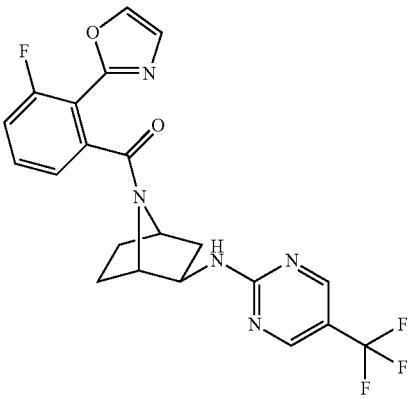

In a microwave vial was dissolved the title compound of Example 277 (30 mg, 0.06 mmol) and 2-(tributylstannyl)oxazole (15 μL, 0.07 mmol) in DME (1 mL). The solution was degassed with N$_2$ for 5 minutes then CuI (1 g, 0.0045 mmol) and Pd(PPh$_3$)$_4$ (5 mg, 0.0045 mmol) were added. The reaction was purged with N$_2$ and heated at 145° C. for 3 h. The reaction was cooled to rt, filtered through a pad of celite and purified via prep HPLC to give the title compound (19 g, 72%). MS (ESI) mass calcd. for: $C_{21}H_{17}F_4N_5O_2$, 447.1; m/z found 448.1 [M+H]$^+$. $^1$H NMR (500 MHz, Chloroform-d) 8.49 (s, 1H), 8.36 (s, 0.8H), 7.85 (s, 0.8H), 7.76 (s. 0.4H), 7.62-7.45 (m, 1H), 7.43-7.33 (m, 1H), 7.32-7.23 (m, 2H), 7.23-7.09 (m, 1H), 4.91-4.85 (m, 0.4H), 4.78 (d, J=5.4 Hz, 0.6H), 4.42 (td, J=8.6, 2.8 Hz, 0.6H), 4.28 (td, J=8.2, 3.6 Hz, 0.4H), 4.00-3.95 (m, 0.6H), 3.89 (d, J=4.4 Hz, 0.4H), 2.23-1.44 (m, 6H).

Example 285

(±)-(3-fluoro-2-(pyrimidin-2-yl)phenyl)(2-((5-(trifluoromethyl)pyrimidin-2-yl)oxy)-7-azabicyclo[2.2.1]heptan-7-yl)methanone

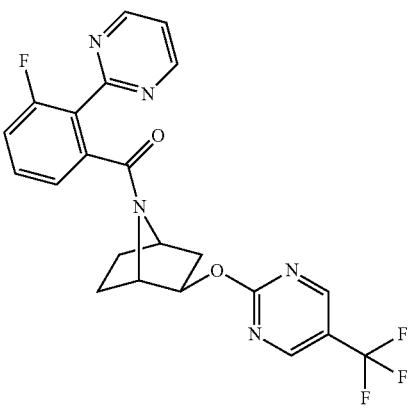

Step A: (±)-tert-butyl 2-((5-(trifluoromethyl)pyrimidin-2-yl)oxy)-7-azabicyclo[2.2.1]heptane-7-carboxylate To (±)-tert-butyl 2-hydroxy-7-azabicyclo[2.2.1]heptane-7-carboxylate (exo) (52 mg, 0.25 mol) in DMF (5 mL) was added 60 wt % NaH (20 g, 0.5 mmol) in one portion. The reaction was heated at 80° C. for 5 min, then 2-chloro-5-(trifluoromethyl)pyrimidine (89.7 g, 0.49 mmol) was added. After heating at 80° C. for 2 hours, water was added and the mixture extracted with DCM (3×). The combined organics were dried ($Na_2SO_4$) and concentrated. Purification via silica gel chromatography (0-50% EtOAc in hexanes) gave the title compound (20 g, 23%). MS (ESI) mass calcd. for: $C_{16}H_{20}F_3N_3O_3$, 359.4; m/z found 260.1 [M-Boc]$^+$.

Step B: (±)-(3-fluoro-2-(pyrimidin-2-yl)phenyl)(2-((5-(trifluoromethyl)pyrimidin-2-yl)oxy)-7-azabicyclo[2.2.1]heptan-7-yl)methanone To (±)-tert-butyl 2-((5-(trifluoromethyl)pyrimidin-2-yl)oxy)-7-azabicyclo[2.2.]heptane-7-carboxylate (20 mg, 0.06 mmol0 in DCM (2 mL) was added 2 mL (2M HCl in $Et_2O$) and stirred at rt for 3 h. The reaction mixture was concentrated and placed under high vacuum for 1 h. To the intermediate in DCM (2 mL) was added intermediate acid (A-2) (13.3 g, 0.06 mmol), HOBt (13.7 g, 0.101 mmol), EDCI (19.4 g, 0.101 mmol) and DIPEA (26 µL, 0.15 mmol). After stirring at rt for 2 h, saturated $NaHCO_3$ (aq.) was added and the mixture was extracted with DCM (3×). The combined organics were dried ($Na_2SO_4$), and concentrated. Purification via silica gel chromatography (0-100% EtOAc in hexanes) gave the title compound (9 g, 38%). MS (ESI) mass calcd. for: $C_{22}H_{17}F_4N_5O_2$, 459.1; m/z found 460.1 [M+H]$^+$. $^1$H NMR (500 MHz, Chloroform-d) 8.88 (d, J=4.9 Hz, 1H), 8.81 (d, J=4.9 Hz, 1H), 8.74 (d, J=12.6 Hz, 2H), 7.63-7.27 (m, 3H), 7.14 (t, J=8.9 Hz, 1H), 4.99 (dt, J=8.3, 4.8 Hz, 1H), 4.87-4.66 (m, 1H), 4.16-3.97 (m, 1H), 2.07 (d, J=4.3 Hz, 1H), 1.91 (d, J=32.9 Hz, 1H), 1.85-1.68 (m, 2H), 1.66-1.60 (m, 1H), 1.51 (dd, J=7.9, 4.8 Hz, 1H).

Example 286

(±)-(3-fluoro-2-(pyrimidin-2-yl)phenyl)(2-((5-(trifluoromethyl)pyrimidin-2-yl)oxy)-7-azabicyclo[2.2.1]heptan-7-yl)methanone

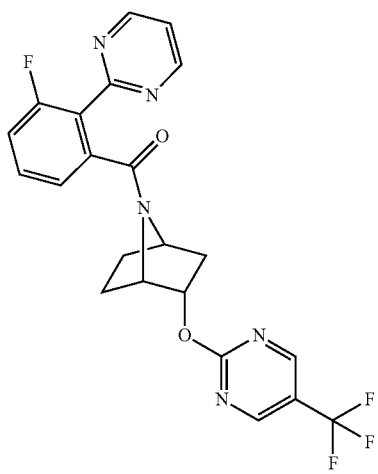 [SMILES: O=C(c1cccc(F)c1-c1ncccn1)N1C2CCC1C(Oc1ncc(C(F)(F)F)cn1)C2]

Step A: (±)-tert-butyl 2-((5-(trifluoromethyl)pyrimidin-2-yl)oxy)-7-azabicyclo[2.2.1]heptane-7-carboxylate To (±)-tert-butyl 2-hydroxy-7-azabicyclo[2.2.1]heptane-7-carboxylate (endo) (150 mg, 0.703 mmol) in DMF (8 mL) was added 60 wt % NaH (56.3 g, 1.41 mmol) in one portion. The reaction was heated at 80° C. for 5 min, then 2-chloro-5-(trifluoromethyl)pyrimidine (257 g, 1.4 mmol) was added. After heating at 80° C. for 2 hours, water was added and the mixture extracted with DCM (3×). The combined organics were dried ($Na_2SO_4$) and concentrated. Purification via silica gel chromatography (0-50% EtOAc in hexanes) gave the title compound (130 g, 51%). MS (ESI) mass calcd. for: $C_{16}H_{20}F_3N_3O_3$, 359.4; m/z found 260.1 [M-Boc]$^+$. 1H NMR (400 MHz, Chloroform-d) 8.82-8.71 (m, 2H), 5.28 (d, J=10.0 Hz, 1H), 4.59 (s, 1H), 4.25 (s, 1H), 2.43 (dddd, J=13.1, 10.1, 5.2, 2.8 Hz, 1H), 2.18-2.04 (m, 1H), 1.85 (dd, J=7.8, 3.8 Hz, 1H), 1.69 (s, 1H), 1.59 (s, 2H), 1.47 (s, 9H).

Step B: (3-fluoro-2-(pyrimidin-2-yl)phenyl)((1R,2S,4S)-2-((5-(trifluoromethyl)pyrimidin-2-yl)oxy)-7-azabicyclo[2.2.1]heptan-7-yl)methanone To (±)-tert-butyl 2-((5-(trifluoromethyl)pyrimidin-2-yl)oxy)-7-azabicyclo[2.2.1]heptane-7-carboxylate (143 mg, 0.398 mmol) in DCM (3 mL) was added 2M HCl in $Et_2O$ (3 mL). After 3 h at rt the reaction mixture was concentrated and placed under high vacuum for 1 h. To the intermediate in DCM (3 mL) was added carbocylic acid (A-2) (95.5 g, 0.438 mmol), HOBt (88.9 g, 0.658 mmol0, EDCI (126.1 g, 0.658 mmol) and DIPEA (170 µL, 0.987 mmol). After stirring at rt for 2 h, saturated $NaHCO_3$ (aq.) was added and the mixture was extracted with DCM (3×). The combined organics were dried ($Na_2SO_4$), and concentrated. Purification via silica gel chromatography (0-100% EtOAc in hexanes) gave the title compound (78.6 g, 47%). MS (ESI) mass calcd. for: $C_{22}H_{17}F_4N_5O_2$, 459.1; m/z found 460.1 [M+H]$^+$. 1H NMR (400 MHz, Chloroform-d) δ 8.85 (t, J=5.2 Hz, 2H), 8.76 (d, J=12.3 Hz, 2H), 7.47 (dd, J=8.5, 5.4 Hz, 1H), 7.29 (td, J=5.4, 4.9, 4.3 Hz, 3H), 5.58-5.40 (m, 1H), 5.30 (s, 1H), 5.09-4.92 (m, 1H), 4.67 (s, 1H), 4.34 (s, 1H), 4.02 (s, 1H), 2.61-2.39 (m, 1H), 2.32-2.08 (m, 1H), 1.90 (d, J=13.7 Hz, 1H).

Example 287

(3-ethoxy-6-methylpyridin-2-yl)((1S,2R,4R)-2-((5-(trifluoromethyl)pyrazin-2-yl)amino)-7-azabicyclo[2.2.1]heptan-7-yl)methanone

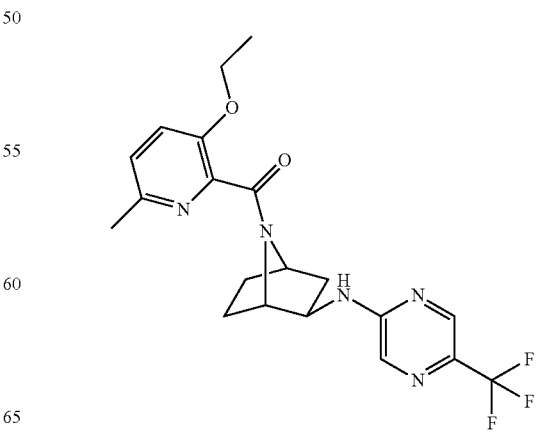

Prepared analogous to Example 238 substituting intermediate A-2 with intermediate A-8. MS (ESI) mass calcd. for: $C_{20}H_{22}F_3N_5O_2$, 421.2; m/z found 422.2 [M+H]+. 1H NMR (400 MHz, Chloroform-d) 8.31 (s, 0.2H), 8.24 (s, 0.8H), 8.01-7.81 (m, 1.8H), 7.25-7.09 (m, 2H), 6.15 (d, J=8.0 Hz, 0.2H), 5.01-4.93 (m, 0.8H), 4.87-4.80 (m, 0.2H), 4.32-4.24 (m, 0.2H), 4.18-4.02 (m, 2.8H), 3.95 (d, J=4.6 Hz, 0.8H), 3.88-3.82 (m, 0.2H), 2.55-2.46 (m, 3H), 2.26-1.23 (m, 9H).

Example 288

(3-(2H-1,2,3-triazol-2-yl)pyridin-2-yl)((1S,2R,4R)-2-((5-(trifluoromethyl)pyrazin-2-yl)amino)-7-azabicyclo[2.2.1]heptan-7-yl)methanone

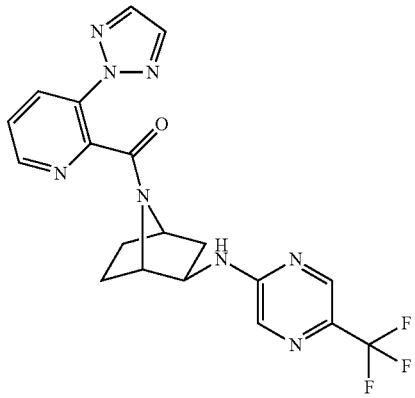 [SMILES: O=C(c1ncccc1-n1nccn1)N1C2CCC1C(Nc1cnc(C(F)(F)F)cn1)C2]

Prepared analogous to Example 238 substituting intermediate A-2 with intermediate A-27. MS (ESI) mass calcd. for: $C_{19}H_{17}F_3N_8O$, 430.1; m/z found 431.2 [M+H]+. 1H NMR (400 MHz, Chloroform-d) 8.65 (dd, J=4.7, 1.5 Hz, 0.2H), 8.55 (dd, J=4.8, 1.5 Hz, 0.8H), 8.39-8.32 (m, 0.4H), 8.29-8.18 (m, 1.6H), 7.97-7.86 (m, 2.2H), 7.70 (s, 0.8H), 7.56 (dd, J=8.3, 4.7 Hz, 0.2H), 7.50 (dd, J=8.3, 4.7 Hz, 0.8H), 7.15 (d, J=8.6 Hz, 0.8H), 6.12 (d, J=8.6 Hz, 0.2H), 4.97-4.89 (m, 0.8H), 4.82 (d, J=5.2 Hz, 0.2H), 4.29 (td, J=7.9, 2.8 Hz, 1H), 4.12-4.07 (m, 0.2H), 4.04 (d, J=5.0 Hz, 0.8H), 2.27-1.43 (m, 6H).

Example 289

(2-methoxy-6-(pyrimidin-2-yl)phenyl)((1S,2R,4R)-2-((5-(trifluoromethyl)pyrazin-2-yl)amino)-7-azabicyclo[2.2.1]heptan-7-yl)methanone

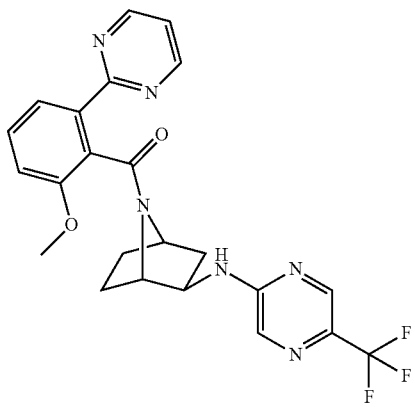 [SMILES: COc1cccc(-c2ncccn2)c1C(=O)N1C2CCC1C(Nc1cnc(C(F)(F)F)cn1)C2]

Prepared analogous to Example 238 substituting intermediate A-2 with intermediate A-28. MS (ESI) mass calcd. for: $C_{23}H_{21}F_3N_6O_2$, 470.2; m/z found 471.2[M+H]+. 1H NMR (400 MHz, Chloroform-d) 8.89-8.71 (m, 2H), 8.53-8.14 (m, 1.5H), 7.99-7.76 (m, 0.5H), 7.60-7.29 (m, 3.7H), 7.23-6.99 (m, 1H), 6.08 (d, J=8.9 Hz, 0.2H), 5.78 (d, J=8.5 Hz, 0.1H), 5.00-4.78 (m, 1H), 4.46-4.35 (m, 1H), 4.07 (s, 0.5H), 3.91-3.79 (m, 3.5H), 2.32-1.24 (m, 6H).

Example 290

(2-fluoro-6-(pyrimidin-2-yl)phenyl)((1S,2R,4R)-2-((5-(trifluoromethyl)pyrazin-2-yl)amino)-7-azabicyclo[2.2.1]heptan-7-yl)methanone

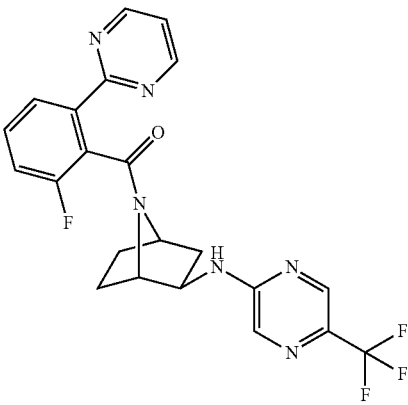 [SMILES: O=C(c1c(F)cccc1-c1ncccn1)N1C2CCC1C(Nc1cnc(C(F)(F)F)cn1)C2]

Prepared analogous to Example 238 substituting intermediate A-2 with intermediate A-6. MS (ESI) mass calcd. for: $C_{22}H_{18}F_4N_6O$, 458.1; m/z found 459.2 [M+H]+. 1H NMR (400 MHz, Chloroform-d) 8.89-8.72 (m, 2H), 8.38-8.16 (m, 2H), 7.78 (dd, J=7.8, 1.1 Hz, 1H), 7.55-7.44 (m, 1H), 7.43-7.35 (m, 1H), 7.34-7.14 (m, 2H), 4.93-4.85 (m, 1H), 4.50-4.39 (m, 1H), 3.98-3.88 (m, 1H), 2.31-1.11 (m, 6H).

Example 291

(7-ethoxyquinolin-8-yl)((1S,2R,4R)-2-((5-(trifluoromethyl)pyrazin-2-yl)amino)-7-azabicyclo[2.2.1]heptan-7-yl)methanone

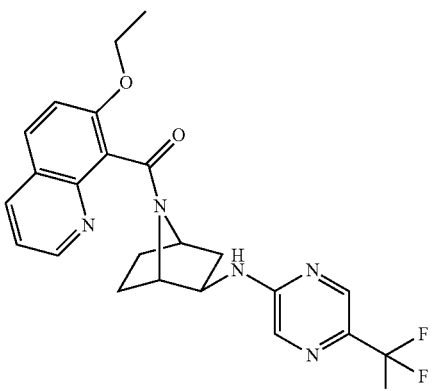

Prepared analogous to Example 238 substituting intermediate A-2 with intermediate A-29. MS (ESI) mass calcd. for: $C_{23}H_{22}F_3N_5O_2$, 457.2 m/z found 458.2 [M+H]+.

Example 292

(2-(1,4-dimethyl-1H-pyrazol-5-yl)-6-methoxyphenyl)((1S,2R,4R)-2-((5-(trifluoromethyl)pyrazin-2-yl)amino)-7-azabicyclo[2.2.1]heptan-7-yl)methanone

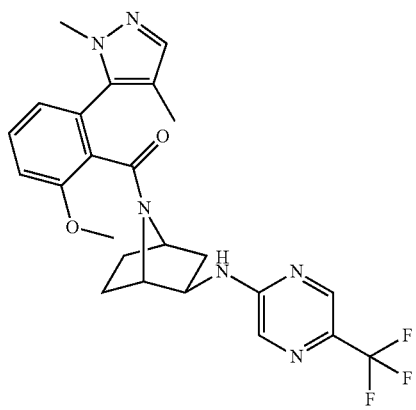 [SMILES: COc1cccc(-c2c(C)cnn2C)c1C(=O)N1C2CCC1C(Nc1cnc(C(F)(F)F)cn1)C2]

Prepared analogous to Example 238 substituting intermediate A-2 with intermediate A-30. MS (ESI) mass calcd. for: $C_{24}H_{25}F_3N_6O_2$, 486.2 m/z found 487.2 [M+H]$^+$.

Example 293

(3-methyl-2-(pyridin-2-yl)phenyl)((1S,2R,4R)-2-((5-(trifluoromethyl)pyrimidin-2-yl)amino)-7-azabicyclo[2.2.1]heptan-7-yl)methanone

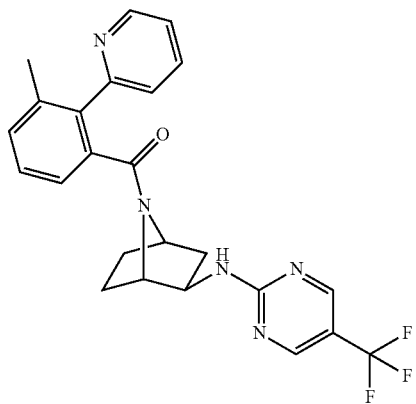

Prepared analogous to Example 284 substituting title compound of Example 277 with title compound of Example 276 and 2-(tributylstannyl)oxazole with 2-(tributylstannyl)pyridine. MS (ESI) mass calcd. for: $C_{24}H_{22}F_3N_5O$, 453.2 m/z found 454.2 [M+H]$^+$. $^1$H NMR (400 MHz, Chloroform-d) 8.72-8.66 (m, 1H), 8.45 (s, 0.5H), 8.39 (s, 1.5H), 7.86-7.75 (m, 1H), 7.52-7.44 (m, 1H), 7.38-7.20 (m, 4.2H), 7.18-7.12 (m, 0.8H), 4.72-4.65 (m, 0.8H), 4.49-4.45 (m, 0.2H), 4.32 (s, 0.8H), 4.03-3.95 (m, 1H), 3.88-3.83 (m, 0.2H), 2.26 (s, 2.2H), 2.23 (s, 0.8H), 2.16 (dd, J=12.8, 7.9 Hz, 0.8H), 1.98-1.08 (m, 5.2H).

Example 294

(3-fluoro-2-(2H-1,2,3-triazol-2-yl)phenyl)((1S,2R,4R)-2-((5-(trifluoromethyl)pyridin-2-yl)amino)-7-azabicyclo[2.2.1]heptan-7-yl)methanone

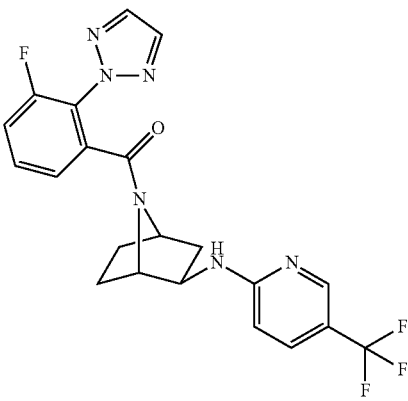 [SMILES: O=C(c1cccc(F)c1-n1nccn1)N1C2CCC1C(Nc1ccc(C(F)(F)F)cn1)C2]

Prepared analogous to Example 279 substituting intermediate A-2 with intermediate A-16. MS (ESI) mass calcd. for: $C_{21}H_{18}F_4N_6O$, 446.1 m/z found 447.2 [M+H]$^+$. $^1$H NMR (500 MHz, Chloroform-d) 8.33 (s, 0.2H), 8.23 (s, 0.8H), 7.96 (s, 1.55H), 7.91 (s, 0.45H), 7.57-7.48 (m, 0.4H), 7.44-7.29 (m, 2H), 7.30-7.21 (m, 1H), 7.21-7.13 (m, 0.8H), 6.72 (s, 0.6H), 6.36-6.25 (m, 1H), 5.34 (s, 0.2H), 4.78-4.69 (m, 0.8H), 4.61 (d, J=5.2 Hz, 0.2H), 4.28 (s, 0.8H), 4.12 (s, 0.2H), 4.05-3.95 (m, 1H), 2.17-1.41 (m, 6H).

Example 295

(3-methyl-2-(2H-1,2,3-triazol-2-yl)phenyl)((1S,2R,4R)-2-((5-(trifluoromethyl)pyridin-2-yl)amino)-7-azabicyclo[2.2.1]heptan-7-yl)methanone

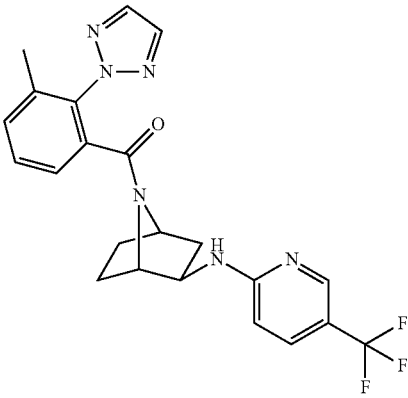 [SMILES: Cc1cccc(C(=O)N2C3CCC2C(Nc2ccc(C(F)(F)F)cn2)C3)c1-n1nccn1]

Prepared analogous to Example 279 substituting intermediate A-2 with intermediate A-24. MS (ESI) mass calcd. for: $C_{22}H_{21}F_3N_6O$, 442.1 m/z found 443.2 [M+H]$^+$. $^1$H NMR (500 MHz, Chloroform-d) 8.32 (s, 0.2H), 8.23 (s, 0.8H), 7.90 (s, 1.55H), 7.85 (s, 0.45H), 7.57-7.25 (m, 3.2H), 7.24-7.15 (m, 0.8H), 6.93 (s, 0.8H), 6.38-6.27 (m, 1H), 5.22

(s, 0.2H), 4.74-4.65 (m, 0.8H), 4.55 (d, J=4.7 Hz, 0.2H), 4.28 (s, 0.8H), 4.09 (s, 0.2H), 4.03-3.95 (m, 1H), 2.20 (s, 3H), 2.13-1.38 (m, 6H).

Example 296

(3-methyl-2-(oxazol-2-yl)phenyl)((1S,2R,4R)-2-((5-(trifluoromethyl)pyridin-2-yl)amino)-7-azabicyclo[2.2.1]heptan-7-yl)methanone

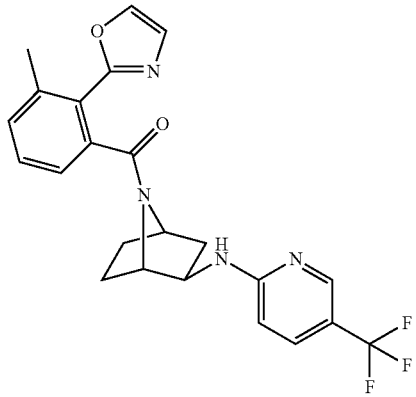 [SMILES: Cc1cccc(C(=O)N2C3CCC2C(Nc2ccc(C(F)(F)F)cn2)C3)c1-c1ncco1]

Prepared analogous to Example 279 substituting intermediate A-2 with intermediate A-31. MS (ESI) mass calcd. for: $C_{23}H_{21}F_3N_4O_2$, 442.2 m/z found 443.2 [M+H]$^+$. $^1$H NMR (500 MHz, Chloroform-d) 8.19 (s, 1H), 7.91-7.80 (m, 2H), 7.32-7.21 (m, 4H), 7.19-7.13 (m, 1H), 6.32 (d, J=8.8 Hz, 1H), 4.79-4.72 (m, 1H), 4.36-4.28 (m, 1H), 3.93 (d, J=4.6 Hz, 1H), 2.29 (s, 3H), 2.10 (dd, J=12.9, 8.1 Hz, 1H), 2.00-1.85 (m, 2H), 1.76-1.64 (m, 2H), 1.55-1.46 (m, 1H).

Example 297

(3-fluoro-2-(pyrimidin-2-yl)phenyl)((1R,2S,4S)-2-((5-(trifluoromethyl)pyrazin-2-yl)amino)-7-azabicyclo[2.2.1]heptan-7-yl)methanone

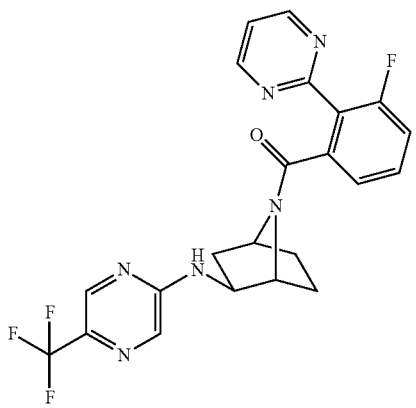 [SMILES: O=C(c1cccc(F)c1-c1ncccn1)N1C2CCC1C(Nc1cnc(C(F)(F)F)cn1)C2]

Prepared analogous to Example 238 substituting intermediate B-5 with intermediate B-8. MS (ESI) mass calcd. for $C_{22}H_{18}F_4N_6O$, 458.2; m/z found 459.1 [M+H]$^+$. $^1$H NMR (500 MHz, Chloroform-d) 8.91-8.84 (m, 2H), 8.27 (s, 1H), 8.19 (s, 1H), 7.65 (d, J=1.4 Hz, 1H), 7.44-7.34 (m, 2H), 7.24-7.16 (m, 2H), 4.77-4.68 (m, 1H), 4.43-4.33 (m, 1H), 4.07 (d, J=5.1 Hz, 1H), 2.16 (dd, J=13.0, 8.2 Hz, 1H), 2.10-1.99 (m, 1H), 1.98-1.86 (m, 1H), 1.78-1.65 (m, 2H), 1.58-1.48 (m, 1H).

Example 298

(3-fluoro-2-(oxazol-2-yl)phenyl)((1S,2R,4R)-2-((5-(trifluoromethyl)pyridin-2-yl)amino)-7-azabicyclo[2.2.1]heptan-7-yl)methanone

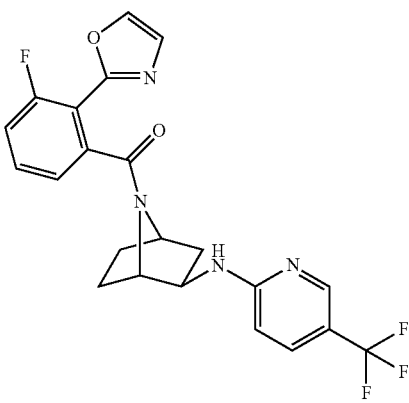 [SMILES: O=C(c1cccc(F)c1-c1ncco1)N1C2CCC1C(Nc1ccc(C(F)(F)F)cn1)C2]

Prepared analogous to Example 320 substituting 2-(tributylstannyl)pyridine with 2-(tributylstannyl)oxazole. MS (ESI) mass calcd. for $C_{22}H_{18}F_4N_4O_2$, 446.1; m/z found 447.1 [M+H]$^+$. $^1$H NMR (CDCl$_3$): 8.36 (s, 0.2H), 8.23-8.16 (m, 0.8H), 7.90 (s, 0.8H), 7.86 (s, 0.2H), 7.70-7.46 (m, 1.2H), 7.43-7.20 (m, 2.8H), 7.19-7.10 (m, 1.8H), 6.39 (d, J=8.8 Hz, 0.2H), 6.20 (d, J=8.8 Hz, 1H), 4.85-4.79 (m, 0.8H), 4.72 (d, J=5.3 Hz, 0.2H), 4.39-4.31 (m, 0.8H), 4.26 (s, 0.2H), 3.95-3.88 (m, 1H), 2.14 (dd, J=12.9, 8.2 Hz, 0.8H), 2.06-1.41 (m, 5.2H).

Example 299

(3-methyl-2-(pyrimidin-2-yl)phenyl)((1S,2R,4R)-2-((5-(trifluoromethyl)pyridin-2-yl)amino)-7-azabicyclo[2.2.1]heptan-7-yl)methanone

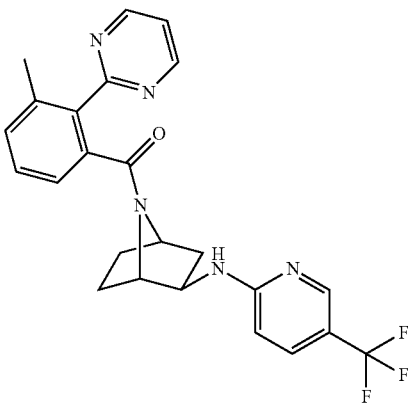 [SMILES: Cc1cccc(C(=O)N2C3CCC2C(Nc2ccc(C(F)(F)F)cn2)C3)c1-c1ncccn1]

Prepared analogous to Example 279 substituting intermediate A-2 with intermediate A-26. Analytical HPLC was obtained on a Agilent 1100 Series using an Inertsil ODS-3 column (3 μm, 50×3 mm), mobile phase of 5-99% ACN in 0.05% TFA over 1.6 min and then hold at 99% ACN for 0.4 min, at a flow rate of 2.2 mL/min (Temperature=50° C.). $R_t$=1.11 min (major rotamer) at 254 nm. $^1$H NMR (500 MHz, CDCl$_3$, Compound present as a mixture of rotamers (0.90:0.10), only major rotamer reported) δ 8.84 (d, J=4.9 Hz, 2H), 8.22 (s, 1H), 7.82 (d, J=9.3 Hz, 1H), 7.33 (t, J=5.0 Hz, 1H), 7.29-7.27 (m, 1H), 7.23 (t, J=7.5 Hz, 1H), 7.21-7.17 (m, 1H), 6.21 (d, J=8.7 Hz, 1H), 4.67 (t, J=4.8 Hz, 1H), 4.42-4.29 (m, 1H), 4.09 (d, J=5.0 Hz, 1H), 2.31 (s, 3H), 2.12 (dd, J=12.9, 8.1 Hz, 1H), 2.06-1.97 (m, 1H), 1.93-1.85 (m, 1H), 1.73-1.65 (m, 1H), 1.61-1.53 (m, 1H), 1.53-1.45 (m, 1H).

Example 300

(3-chloro-2-(pyrimidin-2-yl)phenyl)((1S,2R,4R)-2-((5-(trifluoromethyl)pyrazin-2-yl)amino)-7-azabicyclo[2.2.1]heptan-7-yl)methanone

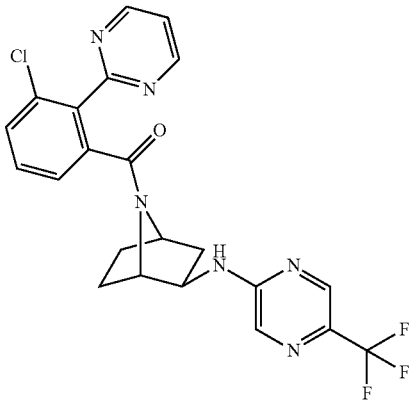

Prepared analogous to Example 238 substituting intermediate A-2 with intermediate A-58. Analytical HPLC was obtained on a Agilent 1100 Series using an Inertsil ODS-3 column (3 μm, 50×3 mm), mobile phase of 5-99% ACN in 0.05% TFA over 1.6 min and then hold at 99% ACN for 0.4 min, at a flow rate of 2.2 mL/min (Temperature=50° C.). $R_t$=1.26 min (major rotamer) at 254 nm. $^1$H NMR (500 MHz, CDCl$_3$, Compound present as a mixture of rotamers (0.92:0.08), only major rotamer reported) δ 8.88 (d, J=5.0 Hz, 2H), 8.26 (d, J=9.1 Hz, 1H), 8.18 (s, 1H), 7.74 (d, J=1.4 Hz, 1H), 7.49 (dd, J=7.2, 2.1 Hz, 1H), 7.41 (t, J=5.0 Hz, 1H), 7.31-7.29 (m, 1H), 4.71-4.65 (m, 1H), 4.34 (td, J=8.7, 3.8 Hz, 1H), 4.05 (d, J=5.1 Hz, 1H), 2.13 (dd, J=13.0, 8.1 Hz, 1H), 2.09-2.00 (m, 1H), 1.96-1.85 (m, 1H), 1.75-1.66 (m, 1H), 1.61-1.56 (m, 1H), 1.54-1.46 (m, 1H).

Example 301

((1S,2R,4R)-2-((5-bromopyridin-2-yl)amino)-7-azabicyclo[2.2.1]heptan-7-yl)(3-fluoro-2-(oxazol-2-yl)phenyl)methanone

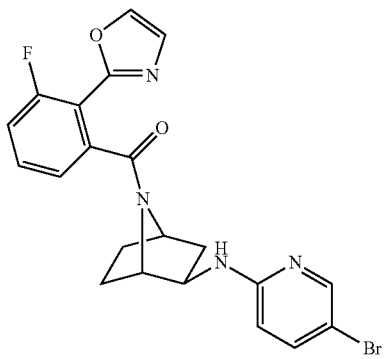 [SMILES: O=C(c1cccc(F)c1-c1ncco1)N1C2CCC1C(Nc1ccc(Br)cn1)C2]

Example 302

((1S,2R,4R)-2-((5-bromopyridin-2-yl)amino)-7-azabicyclo[2.2.1]heptan-7-yl)(3-methyl-2-(oxazol-2-yl)phenyl)methanone

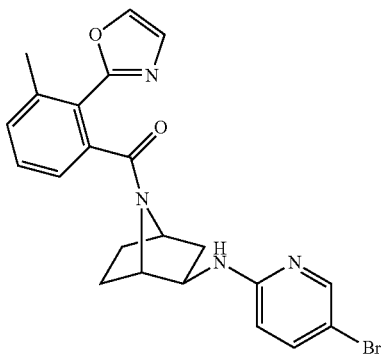 [SMILES: Cc1cccc(C(=O)N2C3CCC2C(Nc2ccc(Br)cn2)C3)c1-c1ncco1]

Prepared analogous to Example 305 substituting intermediate A-16 with intermediate A-31. MS (ESI): mass calcd. for C$_{22}$H$_{21}$BrN$_4$O$_2$, 452.1; m/z found, 452.9 [M+H]$^+$. $^1$H NMR (500 MHz, CDCl$_3$, Compound present as a mixture of rotamers) δ 7.96 (d, J=2.5 Hz, 1H), 7.85 (d, J=0.9 Hz, 1H), 7.28-7.26 (series m, 2H), 7.25-7.22 (m, 1H), 7.19 (dd, J=8.9, 2.5 Hz, 1H), 7.17-7.13 (m, 1H), 6.23 (d, J=9.0 Hz, 1H), 4.73 (t, J=4.5 Hz, 1H), 4.24-4.14 (m, 1H), 3.90 (d, J=4.6 Hz, 1H), 2.29 (s, 3H), 2.07 (dd, J=12.8, 8.1 Hz, 1H), 1.95-1.85 (series of m, 2H), 1.70-1.60 (series of m, 2H), 1.52-1.44 (m, 1H).

Example 303

((1S,2R,4R)-2-((5-bromopyridin-2-yl)amino)-7-azabicyclo[2.2.]heptan-7-yl)(3-fluoro-2-(pyrimidin-2-yl)phenyl)methanone

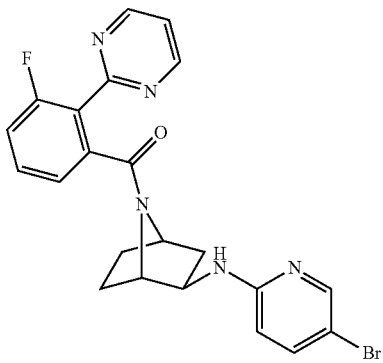

Prepared analogous to Example 305 substituting intermediate A-16 with intermediate A-2. MS (ESI): mass calcd. for C$_{22}$H$_{19}$BrFN$_5$O, 467.1; m/z found, 468.1 [M+H]$^+$. $^1$H NMR (500 MHz, CDCl$_3$, Compound present as a mixture of rotamers (0.87:0.13), only major rotamer reported) δ 8.87 (d, J=4.9 Hz, 2H), 8.00 (d, J=2.5 Hz, 1H), 7.40-7.31 (series of m, 2H), 7.24-7.20 (m, 1H), 7.19-7.14 (series of m, 2H), 6.10 (d, J=8.9 Hz, 1H), 4.70 (t, J=4.9 Hz, 1H), 4.28-4.19 (m, 1H), 4.06 (d, J=5.1 Hz, 1H), 2.13 (dd, J=12.9, 8.1 Hz, 1H), 2.06-1.83 (series of m, 2H), 1.73-1.46 (series of m, 2H). *1H buried under solvent peak.

Example 304

((1S,2R,4R)-2-((5-bromopyridin-2-yl)amino)-7-azabicyclo[2.2.1]heptan-7-yl)(3-methyl-2-(pyrimidin-2-yl)phenyl)methanone

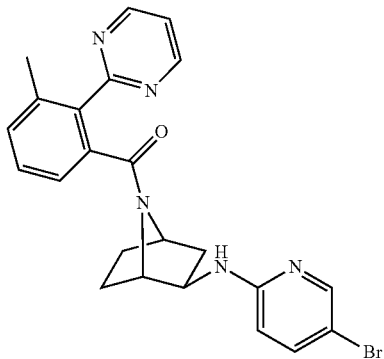

Prepared analogous to Example 305 substituting intermediate A-16 with intermediate A-26. MS (ESI): mass calcd. for $C_{23}H_{22}BrN_5O$, 463.1; m/z found, 464.1 [M+H]$^+$. $^1$H NMR (500 MHz, CDCl$_3$, Compound present as a mixture of rotamers (0.88:0.12), only major rotamer reported) δ 8.82 (d, J=4.9 Hz, 2H), 8.00 (d, J=2.5 Hz, 1H), 7.31 (t, J=4.9 Hz, 1H), 7.28-7.26 (m, 1H), 7.25-7.16 (m, 3H), 6.12 (d, J=8.8 Hz, 1H), 4.69-4.60 (m, 1H), 4.23-4.17 (m, 1H), 4.06 (d, J=5.1 Hz, 1H), 2.30 (s, 3H), 2.09 (dd, J=12.8, 8.1 Hz, 1H), 2.04-1.95 (m, 1H), 1.92-1.82 (m, 1H), 1.69-1.61 (m, 1H), 1.58-1.42 (m, 2H).

Example 305

((1S,2R,4R)-2-((5-bromopyridin-2-yl)amino)-7-azabicyclo[2.2.1]heptan-7-yl)(3-fluoro-2-(2H-1,2,3-triazol-2-yl)phenyl)methanone

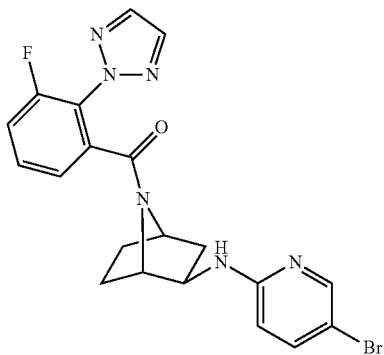

Step A: (1S,2R,4R)-tert-butyl 2-((5-bromopyridin-2-yl)amino)-7-azabicyclo[2.2.1]heptane-7-carboxylate In a microwave vial, 5-bromo-2-iodopyridine (133 mg, 0.47 mmol) was dissolved in THF (2.4 mL) and sodium tert-butoxide (91 g, 0.94 mmol) was added followed by Xantphos (20 g, 0.033 mmol) and Pd$_2$(dba)$_3$ (17 g, 0.019 mmol). The solution was degassed with N$_2$ for 10 minutes then intermediate B-5 (100 g, 0.47 mmol) was added. After 2 days at 90° C. the reaction mixture was filtered through a pad of celite and solvent was evaporated. Purification via silica gel chromatography (0-40% EtOAc in hexanes) gave the title compound of step A (87 g, 50%). MS (ESI): mass calcd. for $C_{16}H_{22}BrN_3O_2$, 367.1; m/z found, 368.1 [M+H]$^+$. $^1$H NMR (500 MHz, CDCl$_3$) 8.10 (d, J=2.4 Hz, 1H), 7.44 (dd, J=8.8, 2.5 Hz, 1H), 6.25 (d, J=8.8 Hz, 1H), 4.70 (s, 1H), 4.27 (s, 1H), 4.21-4.14 (m, 1H), 3.90-3.81 (m, 1H), 2.00 (dd, J=13.0, 7.6 Hz, 1H), 1.89-1.66 (m, 2H), 1.57-1.34 (m, 12H).

Step B: (1S,2R,4R)—N-(5-bromopyridin-2-yl)-7-azabicyclo[2.2.1]heptan-2-amine

Prepared analogous to Example 382 step B. MS (ESI): mass calcd. for $C_{11}H_{14}BrN_3$, 267.0; m/z found, 268.1 [M+H]$^+$.

Step C: ((1S,2R,4R)-2-((5-bromopyridin-2-yl)amino)-7-azabicyclo[2.2.1]heptan-7-yl)(3-fluoro-2-(2H-1,2,3-triazol-2-yl)phenyl)methanone Prepared analogous to Example 382 step C substituting intermediate A-2 with intermediate A-16. MS (ESI): mass calcd. for $C_{20}H_{18}BrFN_6O$, 456.1; m/z found, 457.1 [M+H]$^+$. $^1$H NMR (500 MHz, CDCl$_3$, Compound present as a mixture of rotamers (0.80:0.20), only major rotamer reported) δ 8.00 (d, J=2.5 Hz, 1H), 7.94 (s, 2H), 7.41-7.33 (m, 1H), 7.33-7.22 (m, 2H), 7.16 (dt, J=7.7, 1.1 Hz, 1H), 6.20 (d, J=8.7 Hz, 1H), 4.77-4.67 (m, 1H), 4.20-4.10 (m, 1H), 3.97 (d, J=4.9 Hz, 1H), 2.10 (dd, J=13.0, 8.1 Hz, 1H), 1.98-1.80 (m, 2H), 1.70-1.54 (m, 2H), 1.52-1.46 (m, 1H).

Example 306

((1S,2R,4R)-2-((5-bromopyridin-2-yl)amino)-7-azabicyclo[2.2.1]heptan-7-yl)(3-methyl-2-(2H-1,2,3-triazol-2-yl)phenyl)methanone

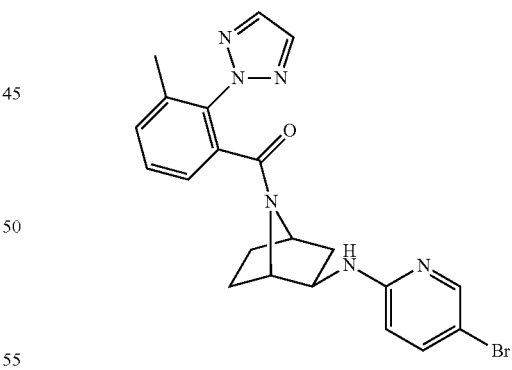

Prepared analogous to Example 305 substituting intermediate A-16 with intermediate A-24. MS (ESI): mass calcd. for $C_{21}H_{21}BrN_6O$, 452.1; m/z found, 452.9 [M+H]$^+$. $^1$H NMR (500 MHz, CDCl$_3$, Compound present as a mixture of rotamers) δ 8.00 (d, J=2.5 Hz, 1H), 7.89 (s, 2H), 7.42 (d, J=4.3 Hz, 1H), 7.36-7.31 (m, 1H), 7.28-7.24 (series of m, 2H), 7.22-7.16 (m, 1H), 6.24 (d, J=8.9 Hz, 1H), 4.67 (t, J=4.7 Hz, 1H), 4.21-4.06 (m, 1H), 3.95 (d, J=5.1 Hz, 1H), 2.20 (s, 3H), 2.07 (dd, J=12.9, 8.0 Hz, 1H), 1.98-1.90 (m, 1H), 1.87-1.78 (m, 1H), 1.66-1.60 (m, 1H), 1.57-1.50 (m, 1H), 1.50-1.43 (m, 1H).

Example 307

((1S,2R,4R)-2-((5-bromopyrazin-2-yl)amino)-7-azabicyclo[2.2.1]heptan-7-yl)(3-fluoro-2-(oxazol-2-yl)phenyl)methanone

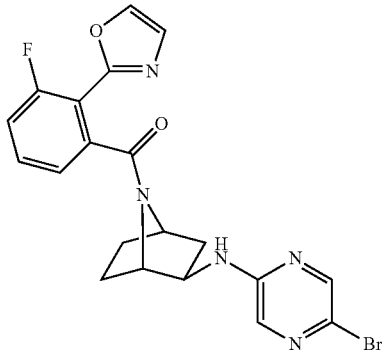

Example 308

((1S,2R,4R)-2-((5-bromopyrazin-2-yl)amino)-7-azabicyclo[2.2.1]heptan-7-yl)(3-methyl-2-(oxazol-2-yl)phenyl)methanone

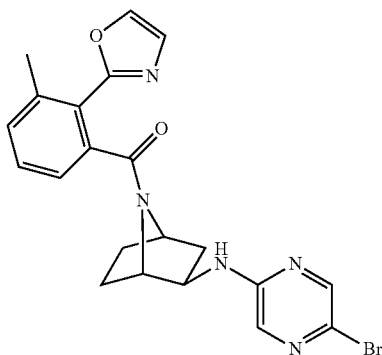 [SMILES: Cc1cccc(C(=O)N2C3CCC2C(Nc2cnc(Br)cn2)C3)c1-c1ncco1]

Prepared analogous to Example 311 substituting intermediate A-16 with intermediate A-31. MS (ESI): mass calcd. for $C_{21}H_{20}BrN_5O_2$, 453.1; m/z found, 453.9 [M+H]$^+$. $^1$H NMR (500 MHz, CDCl$_3$, Compound present as a mixture of rotamers) δ 8.04-7.93 (m, 1H), 7.88 (d, J=1.4 Hz, 1H), 7.86 (d, J=0.9 Hz, 1H), 7.54 (d, J=1.4 Hz, 1H), 7.29 (d, J=7.5 Hz, 1H), 7.29-7.22 (m, 1H), 7.18-7.14 (m, 1H), 4.75 (t, J=4.6 Hz, 1H), 4.17-4.09 (m, 1H), 3.90 (d, J=4.7 Hz, 1H), 2.28 (s, 3H), 2.08 (dd, J=12.9, 8.1 Hz, 1H), 1.99-1.85 (m, 2H), 1.73-1.63 (m, 2H), 1.53-1.45 (m, 1H).

Example 309

((1S,2R,4R)-2-((5-bromopyrazin-2-yl)amino)-7-azabicyclo[2.2.1]heptan-7-yl)(3-fluoro-2-(pyrimidin-2-yl)phenyl)methanone

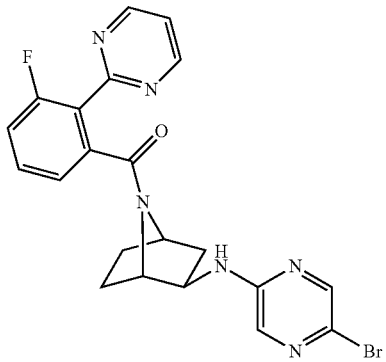 [SMILES: O=C(c1cccc(F)c1-c1ncccn1)N1C2CCC1C(Nc1cnc(Br)cn1)C2]

Prepared analogous Example 311 substituting intermediate A-16 with intermediate A-2. MS (ESI): mass calcd. for $C_{21}H_{18}BrFN_6O$, 468.1; m/z found, 469.9 [M+H]$^+$. $^1$H NMR (500 MHz, CDCl$_3$, Compound present as a mixture of rotamers) δ 8.86 (d, J=5.0 Hz, 2H), 7.94 (d, J=1.4 Hz, 1H), 7.42 (d, J=1.4 Hz, 1H), 7.40-7.35 (m, 2H), 7.25-7.20 (m, 1H), 7.19-7.15 (m, 1H), 4.76-4.66 (m, 1H), 4.27-4.16 (m, 1H), 4.04 (d, J=5.0 Hz, 1H), 2.14 (dd, J=12.9, 8.1 Hz, 1H), 2.07-1.99 (m, 1H), 1.95-1.86 (m, 1H), 1.73-1.62 (series of m, 2H), 1.54-1.47 (m, 1H).

Example 310

((1S,2R,4R)-2-((5-bromopyrazin-2-yl)amino)-7-azabicyclo[2.2.1]heptan-7-yl)(3-methyl-2-(pyrimidin-2-yl)phenyl)methanone

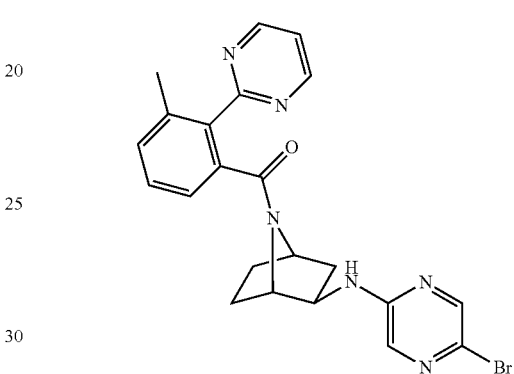

Prepared analogous Example 311 substituting intermediate A-16 with intermediate A-26. Analytical HPLC was obtained on a Agilent 1100 Series using an Inertsil ODS-3 column (3 μm, 50×3 mm), mobile phase of 5-99% ACN in 0.05% TFA over 1.6 min and then hold at 99% ACN for 0.4 min, at a flow rate of 2.2 mL/min (Temperature=50° C.). R$_t$=1.24 min (major rotamer) at 254 nm. $^1$H NMR (500 MHz, CDCl$_3$, Compound present as a mixture of rotamers) δ 8.83 (d, J=4.9 Hz, 2H), 7.92 (d, J=1.4 Hz, 1H), 7.41 (d, J=1.4 Hz, 1H), 7.34 (t, J=5.0 Hz, 1H), 7.30-7.27 (m, 1H), 7.24 (t, J=7.5 Hz, 1H), 7.21-7.17 (m, 1H), 4.71-4.61 (m, 1H), 4.21-4.12 (m, 1H), 4.06 (d, J=5.0 Hz, 1H), 2.28 (s, 3H), 2.09 (dd, J=12.9, 8.1 Hz, 1H), 2.06-1.97 (m, 1H), 1.93-1.84 (m, 1H), 1.66-1.62 (m, 1H), 1.61-1.54 (m, 1H), 1.51-1.43 (m, 1H).

Example 311

((1S,2R,4R)-2-((5-bromopyrazin-2-yl)amino)-7-azabicyclo[2.2.1]heptan-7-yl)(3-fluoro-2-(2H-1,2,3-triazol-2-yl)phenyl)methanone

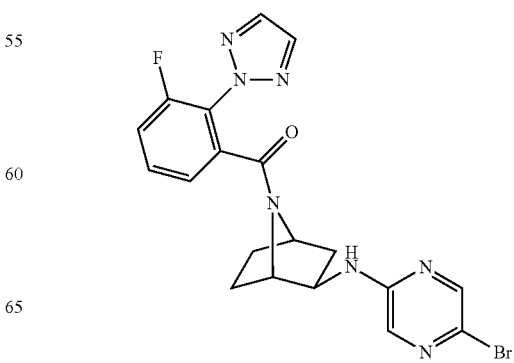

Step A: (1S,2R,4R)-tert-butyl 2-((5-bromopyrazin-2-yl)amino)-7-azabicyclo[2.2.1]heptane-7-carboxylate In a microwave vial was dissolved intermediate B-5 (830 g, 3.91 mmol) in DMSO (8 mL). K$_2$CO$_3$ (811 g, 5.87 mmol) was added followed by 2,5-dibromopyrazine (1.12 g, 4.70 mmol). The vial was capped and the reaction mixture was heated to 100° C. for 16 h. Then water and EtOAc were added and the aqueous phase was extracted twice with EtOAc. The combined organic phases were dried over MgSO$_4$, filtered and evaporated. Purification via silica gel chromatography (0-40% EtOAc in hexanes) gave the title compound (291 g, 20%). MS (ESI): mass calcd. for C$_{15}$H$_{21}$BrN$_4$O$_2$, 368.1; m/z found, 370.9 [M+H]$^+$. $^1$H NMR (500 MHz, CDCl$_3$) δ 8.07 (s, 1H), 7.62 (s, 1H), 4.95 (s, 1H), 4.28 (s, 1H), 4.18 (s, 1H), 3.95-3.81 (m, 1H), 2.05-1.99 (m, 1H), 1.89-1.70 (m, 2H), 1.57-1.37 (m, 12H).

Step B: (1S,2R,4R)—N-(5-bromopyrazin-2-yl)-7-azabicyclo[2.2.1]heptan-2-amine

Prepared analogous to Example 390 step B. MS (ESI): mass calcd. for C$_{10}$H$_{13}$BrN$_4$, 268.0; m/z found, 270.9 [M+H]$^+$.

Step C: ((1S,2R,4R)-2-((5-bromopyrazin-2-yl)amino)-7-azabicyclo[2.2.]heptan-7-yl)(3-fluoro-2-(2H-1,2,3-triazol-2-yl)phenyl)methanone Prepared analogous to Example 390 step C. MS (ESI): mass calcd. for C$_{19}$H$_{17}$BrFN$_7$O, 457.1; m/z found, 459.8 [M+H]$^+$. $^1$H NMR (500 MHz, CDCl$_3$, Compound present as a mixture of rotamers) δ 7.94 (s, 3H), 7.54 (d, J=1.4 Hz, 1H), 7.43-7.37 (m, 1H), 7.32-7.27 (m, 1H), 7.21-7.16 (m, 1H), 4.72 (t, J=4.8 Hz, 1H), 4.19-4.08 (m, 1H), 3.93 (d, J=5.0 Hz, 1H), 2.10 (dd, J=13.2, 8.2 Hz, 1H), 1.99-1.79 (series of m, 3H), 1.63-1.54 (m, 1H), 1.54-1.46 (m, 1H).

Example 312

((1S,2R,4R)-2-((5-bromopyrazin-2-yl)amino)-7-azabicyclo[2.2.1]heptan-7-yl)(3-methyl-2-(2H-1,2,3-triazol-2-yl)phenyl)methanone

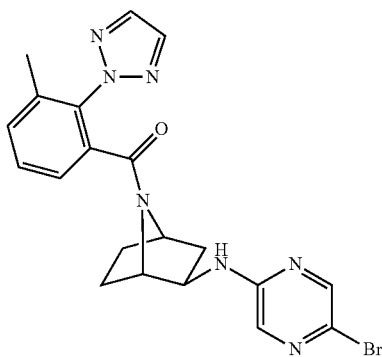 [SMILES: Cc1cccc(C(=O)N2C3CCC2C(Nc2cnc(Br)cn2)C3)c1-n1nccn1]

Prepared analogous to Example 311 substituting intermediate A-16 with intermediate A-24. MS (ESI): mass calcd. for C$_{20}$H$_{20}$BrN$_7$O, 453.1; m/z found, 453.9 [M+H]$^+$. $^1$H NMR (500 MHz, CDCl$_3$, Compound present as a mixture of rotamers) δ 7.93 (d, J=1.4 Hz, 1H), 7.90 (s, 2H), 7.56 (d, J=1.4 Hz, 1H), 7.36-7.32 (m, 1H), 7.30 (t, J=7.6 Hz, 1H), 7.23-7.18 (m, 1H), 4.68 (t, J=4.7 Hz, 1H), 4.14-4.07 (m, 1H), 3.94 (d, J=5.1 Hz, 1H), 2.19 (s, 3H), 2.10-2.04 (m, 1H), 2.00-1.92 (m, 1H), 1.90-1.80 (m, 1H), 1.64-1.42 (series of m, 3H).

Example 313

((1S,2R,4R)-2-((5-bromopyrimidin-2-yl)amino)-7-azabicyclo[2.2.1]heptan-7-yl)(3-fluoro-2-(oxazol-2-yl)phenyl)methanone

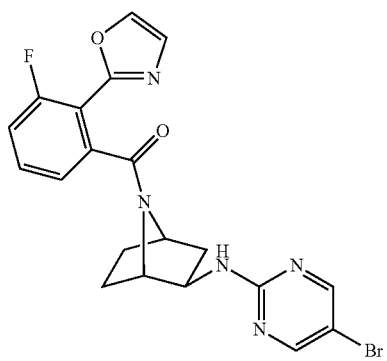 [SMILES: O=C(c1cccc(F)c1-c1ncco1)N1C2CCC1C(Nc1ncc(Br)cn1)C2]

Example 314

((1S,2R,4R)-2-((5-bromopyrimidin-2-yl)amino)-7-azabicyclo[2.2.1]heptan-7-yl)(3-methyl-2-(oxazol-2-yl)phenyl)methanone

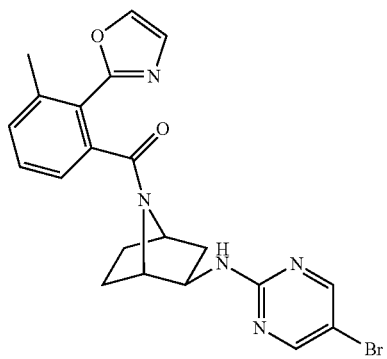 [SMILES: Cc1cccc(C(=O)N2C3CCC2C(Nc2ncc(Br)cn2)C3)c1-c1ncco1]

Prepared analogous to Example 317 substituting intermediate A-16 with intermediate A-31. MS (ESI): mass calcd. for C$_{21}$H$_{20}$BrN$_5$O$_2$, 453.1; m/z found, 453.9 [M+H]$^+$. $^1$H NMR (500 MHz, CDCl$_3$, Compound present as a mixture of rotamers (0.55:0.45), only major rotamer reported) δ 8.16 (s, 2H), 7.80 (s, 1H), 7.40-7.35 (m, 1H), 7.31 (s, 1H), 7.26-7.22 (series of m, 2H), 4.80-4.74 (m, 1H), 4.67 (d, J=5.3 Hz, 1H), 4.11-4.03 (m, 1H), 2.37 (s, 3H), 2.10 (dd, J=12.9, 8.0 Hz, 1H), 1.88-1.68 (series of m, 3H), 1.61-1.39 (series of m, 2H).

Example 315

((1S,2R,4R)-2-((5-bromopyrimidin-2-yl)amino)-7-azabicyclo[2.2.1]heptan-7-yl)(3-fluoro-2-(pyrimidin-2-yl)phenyl)methanone

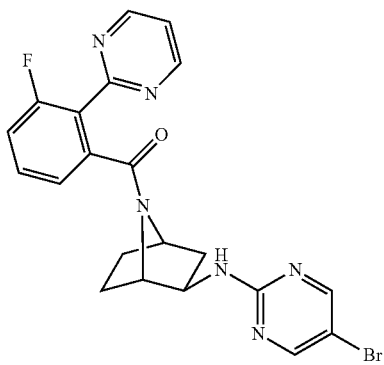

Prepared analogous to Example 317 substituting intermediate A-16 with intermediate A-2. MS (ESI): mass calcd. for $C_{21}H_{18}BrFN_6O$, 468.1; m/z found, 470.8 $[M+H]^+$. $^1$H NMR (500 MHz, CDCl$_3$, Compound present as a mixture of rotamers (0.80:0.20), only major rotamer reported) δ 8.88 (d, J=4.9 Hz, 2H), 8.18 (s, 2H), 7.41-7.35 (m, 1H), 7.32 (t, J=4.9 Hz, 1H), 7.25-7.19 (m, 1H), 7.16 (dd, J=7.6, 1.1 Hz, 1H), 4.77-4.71 (m, 1H), 4.28-4.18 (m, 1H), 4.06 (d, J=5.1 Hz, 1H), 2.18 (dd, J=12.9, 7.9 Hz, 1H), 2.02-1.79 (m, 2H), 1.56-1.49 (m, 1H). *2H buried under water peak.

Example 316

((1S,2R,4R)-2-((5-bromopyrimidin-2-yl)amino)-7-azabicyclo[2.2.1]heptan-7-yl)(3-methyl-2-(pyrimidin-2-yl)phenyl)methanone

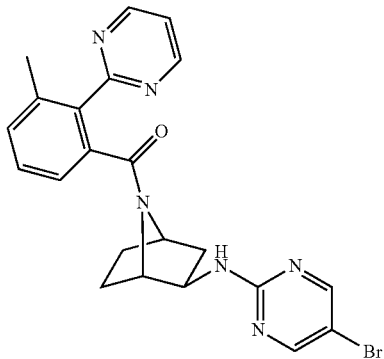

Prepared analogous to Example 317 substituting intermediate A-16 with intermediate A-26. Analytical HPLC was obtained on a Agilent 1100 Series using an Inertsil ODS-3 column (3 μm, 50×3 mm), mobile phase of 5-99% ACN in 0.05% TFA over 1.6 min and then hold at 99% ACN for 0.4 min, at a flow rate of 2.2 mL/min (Temperature=50° C.). $R_t$=0.82 min (major rotamer) at 254 nm. $^1$H NMR (500 MHz, CDCl$_3$, Compound present as a mixture of rotamers) δ 8.86 (d, J=4.9 Hz, 2H), 8.19 (s, 2H), 7.34-7.23 (series of m, 3H), 7.20-7.16 (m, 1H), 4.69 (t, J=4.6 Hz, 1H), 4.27-4.17 (m, 1H), 4.10-4.06 (m, 1H), 2.35 (s, 3H), 2.16 (dd, J=12.8, 7.9 Hz, 1H), 2.07-1.96 (m, 1H), 1.90-1.80 (m, 1H), 1.69-1.54 (series of m, 2H), 1.54-1.46 (m, 1H).

Example 317

((1S,2R,4R)-2-((5-bromopyrimidin-2-yl)amino)-7-azabicyclo[2.2.1]heptan-7-yl)(3-fluoro-2-(2H-1,2,3-triazol-2-yl)phenyl)methanone

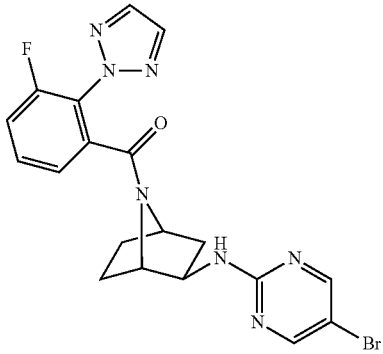

Step A: (1S,2R,4R)-tert-butyl 2-((5-bromopyrimidin-2-yl)amino)-7-azabicyclo[2.2.1]heptane-7-carboxylate To a solution of intermediate B-5 (520 g, 2.45 mmol) in DMA (8.2 mL) was added DIPEA (0.84 mL, 4.90 mmol) followed by 2,5-dibromopyrimidine (661 g, 2.69 mmol). The reaction mixture was heated at 120° C. for 30 minutes using microwave and was then diluted with water and EtOAc. The aqueous phase was extracted twice with EtOAc and the combined organic layers were washed with a saturated solution of NaCl, dried over MgSO$_4$, filtered and evaporated. Purification via silica gel chromatography (0-40% EtOAc in hexanes) gave the title compound (651 g, 72%). MS (ESI): mass calcd. for $C_{15}H_{21}BrN_4O_2$, 368.1; m/z found, 370.9 $[M+H]^+$. $^1$H NMR (500 MHz, CDCl$_3$) δ 8.28 (is, 2H), 5.56 (s, 1H), 4.29 (s, 1H), 4.23-4.15 (m, 1H), 3.99-3.91 (m, 1H), 2.03-1.93 (m, 1H), 1.87-1.63 (m, 2H), 1.62-1.32 (m, 12H).

Step B: (1S,2R,4R)—N-(5-bromopyrimidin-2-yl)-7-azabicyclo[2.2.1]heptan-2-amine

To the title compound of step A (812 g, 2.2 mmol) in DCM (11 mL) was added 4M HCl in dioxane (2.7 mL). After 16 h, the reaction was concentrated, neutralized with 5% Na$_2$CO$_3$ (aq) and extracted with DCM (2×). The combined organics were dried (Na$_2$SO$_4$) to give the title compound of step B that was used without further purification. MS (ESI): mass calcd. for $C_{10}H_{13}BrN_4$, 268.0; m/z found, 270.9 $[M+H]^+$.

Step C: ((1S,2R,4R)-2-((5-bromopyrimidin-2-yl)amino)-7-azabicyclo[2.2.1]heptan-7-yl)(3-fluoro-2-(2H-1,2,3-triazol-2-yl)phenyl)methanone To a solution of the title compound of step B (30 g, 0.11 mmol) and intermediate A-16 (25 g, 0.12 mmol) in DCM (1.1 mL) was added DIPEA (0.12 mL, 0.67 mmol) followed by HATU (51 g, 0.13 mmol). The reaction mixture was stirred at room temperature for 16 h. Solvent was evaporated and purification via prep HPLC gave the title compound (50 g, 98%). MS (ESI): mass calcd. for $C_{19}H_{17}BrFN_7O$, 457.1; m/z found, 459.8 [M+H]+. 1H NMR (500 MHz, CDCl3, Compound present as a mixture of rotamers (0.57:0.43), only major rotamer reported) δ 8.20 (s, 2H), 7.92 (s, 2H), 7.37-7.31 (m, 1H), 7.30-7.27 (m, 1H), 7.21-7.15 (m, 1H), 4.74 (t, J=4.8 Hz, 1H), 4.13 (td, J=8.3, 3.2 Hz, 1H), 3.95 (d, J=5.0 Hz, 1H), 2.11 (dd, J=13.0, 8.0 Hz, 1H), 1.88-1.73 (m, 2H), 1.65-1.59 (m, 1H), 1.52-1.42 (m, 2H).

Example 318

((1S,2R,4R)-2-((5-bromopyrimidin-2-yl)amino)-7-azabicyclo[2.2.1]heptan-7-yl)(3-methyl-2-(2H-1,2,3-triazol-2-yl)phenyl)methanone

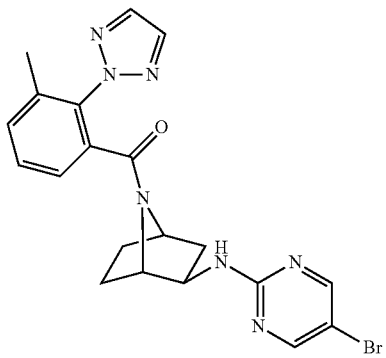 [SMILES: Cc1cccc(C(=O)N2C3CCC2C(Nc2ncc(Br)cn2)C3)c1-n1nccn1]

Prepared analogous to Example 317 substituting intermediate A-16 with intermediate A-24. MS (ESI): mass calcd. for $C_{20}H_{20}BrN_7O$, 453.1; m/z found, 453.9 [M+H]+. 1H NMR (500 MHz, CDCl3, Compound present as a mixture of rotamers (0.59:0.58), only major rotamer reported) δ 8.20 (s, 2H), 7.88 (s, 2H), 7.44-7.42 (m, 1H), 7.34-7.28 (m, 1H), 7.22-7.17 (m, 1H), 4.69 (t, J=4.9 Hz, 1H), 4.07 (dd, J=8.2, 3.4 Hz, 1H), 3.96 (d, J=5.1 Hz, 1H), 2.22 (s, 3H), 2.10 (dd, J=12.9, 8.0 Hz, 1H), 1.93-1.85 (m, 1H), 1.83-1.74 (m, 1H), 1.64-1.53 (m, 2H), 1.47-1.42 (m, 1H).

Example 319

(3-methyl-2-(pyridin-2-yl)phenyl)((1S,2R,4R)-2-((5-(trifluoromethyl)pyridin-2-yl)amino)-7-azabicyclo[2.2.1]heptan-7-yl)methanone

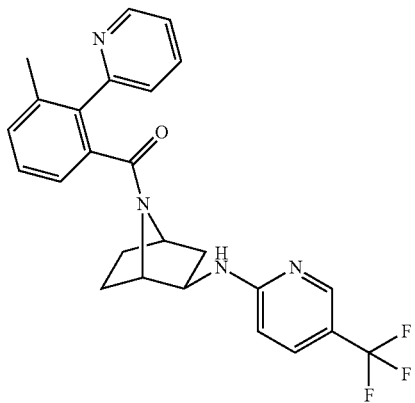

Example 320

(3-fluoro-2-(pyridin-2-yl)phenyl)((1S,2R,4R)-2-((5-(trifluoromethyl)pyridin-2-yl)amino)-7-azabicyclo[2.2.1]heptan-7-yl)methanone

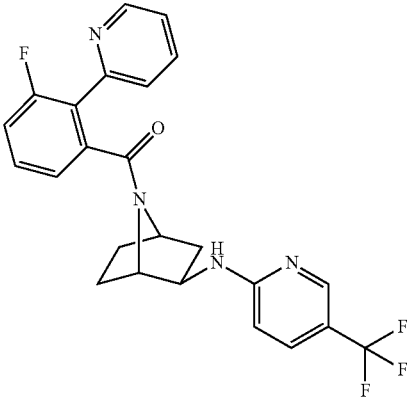

Step A: (3-fluoro-2-iodophenyl)((1S,2R,4R)-2-((5-(trifluoromethyl)pyridin-2-yl)amino)-7-azabicyclo[2.2.1]heptan-7-yl)methanone Prepared analogous to Example 279 substituting intermediate A-2 with 3-fluoro-2-iodobenzoic acid. MS (ESI): mass calcd. for $C_{19}H_{16}F_4IN_3O$, 505.0; m/z found 506.0 [M+H]+. 1H NMR (500 MHz, CDCl3) δ 8.35 (s, 0.5H), 8.24 (s, 0.5H), 7.60-7.50 (m, 1H), 7.40-7.33 (m, 0.6H), 7.14-7.02 (m, 1.4H), 6.98-6.92 (m, 0.5H), 6.90 (d, J=7.4 Hz, 0.5H), 6.47-6.37 (m, 1H), 5.36 (s, 0.5H), 4.95-4.90 (m, 0.5H), 4.82 (d, J=5.4 Hz, 0.5H), 4.76 (s, 0.5H), 4.28-4.20 (m, 0.5H), 3.99 (s, 0.5H), 3.80-3.75 (m, 0.5H), 3.73 (d, J=4.3 Hz, 0.5H), 2.21-2.11 (m, 1H), 2.08-1.44 (m, 5H).

Step B: (3-fluoro-2-(pyridin-2-yl)phenyl)((1S,2R,4R)-2-((5-(trifluoromethyl)pyridin-2-yl)amino)-7-azabicyclo[2.2.1]heptan-7-yl)methanone Prepared analogous to Example 260 Step B substituting 2-(tributylstannyl)oxazole with 2-(tributylstannyl)pyridine. MS (ESI): mass calcd. for $C_{24}H_{20}F_4N_4O$, 456.2; m/z found, 457.1 [M+H]+. Analytical HPLC was obtained on a Agilent 1100 Series using a XBridge C18 column (5 μm, 100×4.6 mm), mobile phase of 10-100% ACN in 20 mM NH4OH over 8 min and then hold at 100% ACN for 3 min, at a flow rate of 1 mL/min (Temperature=30° C.). $R_t$=7.26 min (major rotamer) at 254 nm.

Example 321

(3-fluoro-2-(pyridin-2-yl)phenyl)((1S,2R,4R)-2-((5-(trifluoromethyl)pyrimidin-2-yl)amino)-7-azabicyclo[2.2.1]heptan-7-yl)methanone

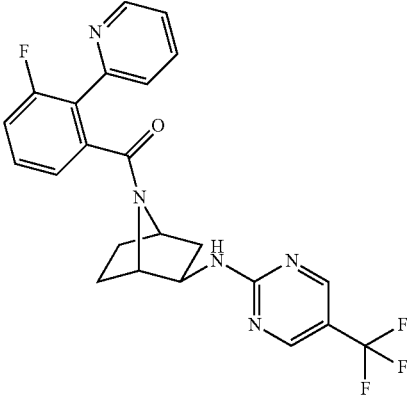

Example 322

(3-methyl-2-(pyridin-2-yl)phenyl)((1S,2R,4R)-2-((5-(trifluoromethyl)pyrazin-2-yl)amino)-7-azabicyclo[2.2.1]heptan-7-yl)methanone

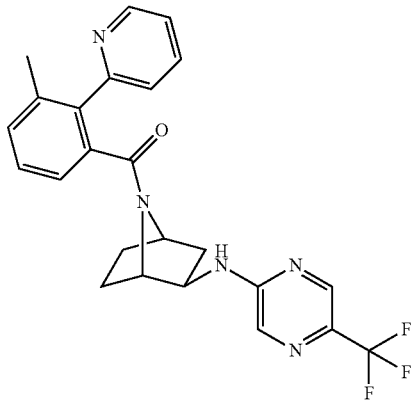

Example 323

(3-fluoro-2-(pyridin-2-yl)phenyl)((2S)-2-((5-(trifluoromethyl)pyrazin-2-yl)amino)-7-azabicyclo[2.2.1]heptan-7-yl)methanone

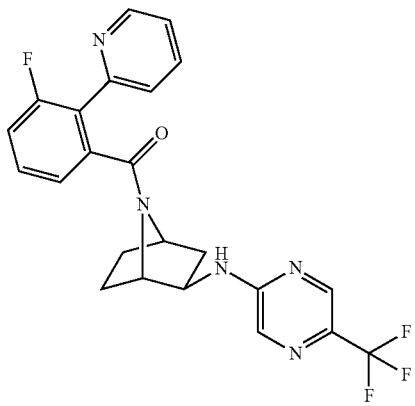

Example 324

(3-fluoro-2-(pyridin-2-yl)phenyl)((1S,2R,4R)-2-((5-(trifluoromethyl)pyrazin-2-yl)oxy)-7-azabicyclo[2.2.1]heptan-7-yl)methanone

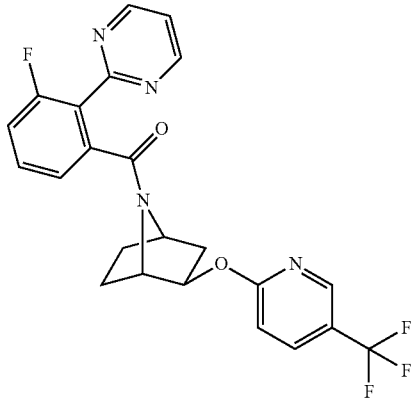

Example 325

(2-methoxy-6-(pyrimidin-2-yl)phenyl)((1S,2R,4R)-2-((5-(trifluoromethyl)pyridin-2-yl)oxy)-7-azabicyclo[2.2.1]heptan-7-yl)methanone

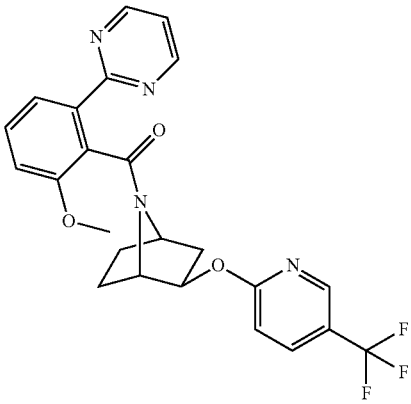

Example 326

(5-fluoro-2-(2H-1,2,3-triazol-2-yl)phenyl)((1S,2R,4R)-2-((5-(trifluoromethyl)pyridin-2-yl)oxy)-7-azabicyclo[2.2.1]heptan-7-yl)methanone

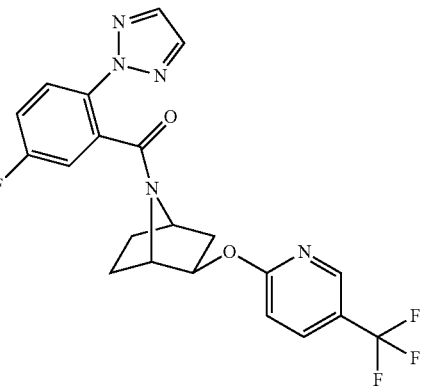

Example 327

(4-methyl-2-(2H-1,2,3-triazol-2-yl)phenyl)((1S,2R,4R)-2-((5-(trifluoromethyl)pyridin-2-yl)oxy)-7-azabicyclo[2.2.1]heptan-7-yl)methanone

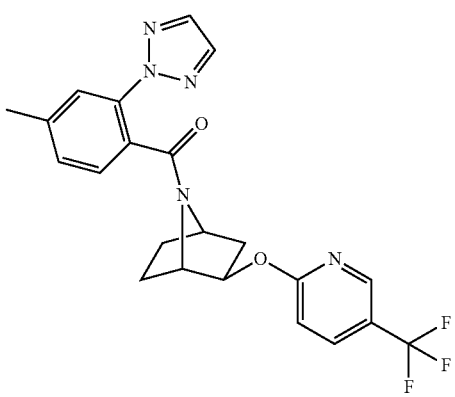 [SMILES: Cc1ccc(C(=O)N2C3CCC2C(Oc2ccc(C(F)(F)F)cn2)C3)c(-n2nccn2)c1]

Example 328

(3-methyl-2-(2H-1,2,3-triazol-2-yl)phenyl)((1S,2R,4R)-2-((5-(trifluoromethyl)pyridin-2-yl)oxy)-7-azabicyclo[2.2.1]heptan-7-yl)methanone

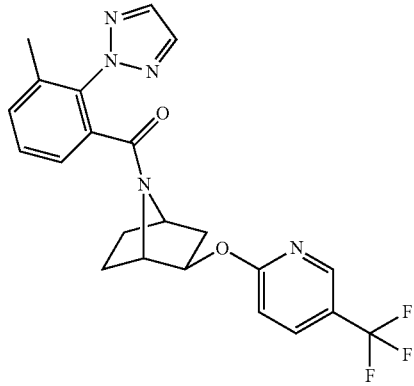 [SMILES: Cc1cccc(C(=O)N2C3CCC2C(Oc2ccc(C(F)(F)F)cn2)C3)c1-n1nccn1]

Example 329

(5-fluoro-2-(pyrimidin-2-yl)phenyl)((1S,2R,4R)-2-((5-(trifluoromethyl)pyridin-2-yl)oxy)-7-azabicyclo[2.2.1]heptan-7-yl)methanone

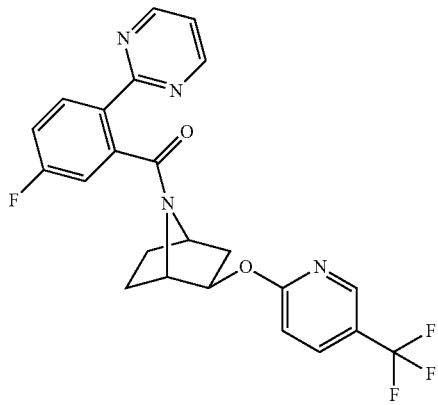

Example 330

(2-fluoro-6-(pyrimidin-2-yl)phenyl)((1S,2R,4R)-2-((5-(trifluoromethyl)pyridin-2-yl)oxy)-7-azabicyclo[2.2.1]heptan-7-yl)methanone

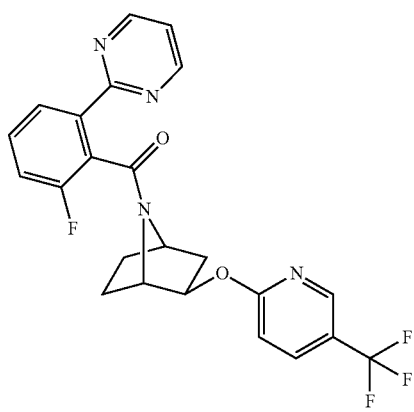 [SMILES: O=C(c1c(F)cccc1-c1ncccn1)N1C2CCC1C(Oc1ccc(C(F)(F)F)cn1)C2]

Example 331

(2-(2H-1,2,3-triazol-2-yl)phenyl)((1S,2R,4R)-2-((5-(trifluoromethyl)pyridin-2-yl)oxy)-7-azabicyclo[2.2.1]heptan-7-yl)methanone

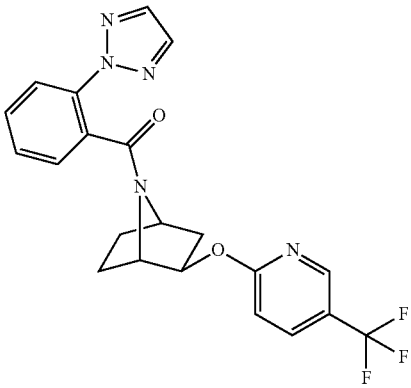 [SMILES: O=C(c1ccccc1-n1nccn1)N1C2CCC1C(Oc1ccc(C(F)(F)F)cn1)C2]

Example 332

(6-methyl-3-(2H-1,2,3-triazol-2-yl)pyridin-2-yl)((1S,2R,4R)-2-((5-(trifluoromethyl)pyridin-2-yl)oxy)-7-azabicyclo[2.2.1]heptan-7-yl)methanone

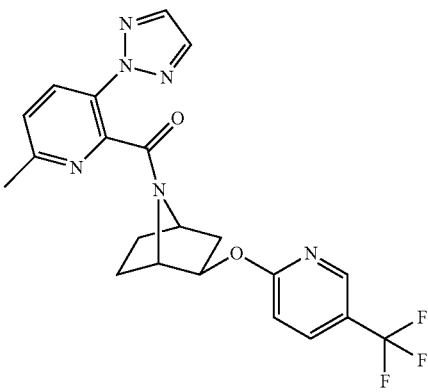 [SMILES: Cc1ccc(-n2nccn2)c(C(=O)N2C3CCC2C(Oc2ccc(C(F)(F)F)cn2)C3)n1]

Example 333

(3-methyl-2-(oxazol-2-yl)phenyl)((1S,2R,4R)-2-((5-(trifluoromethyl)pyridin-2-yl)oxy)-7-azabicyclo[2.2.1]heptan-7-yl)methanone

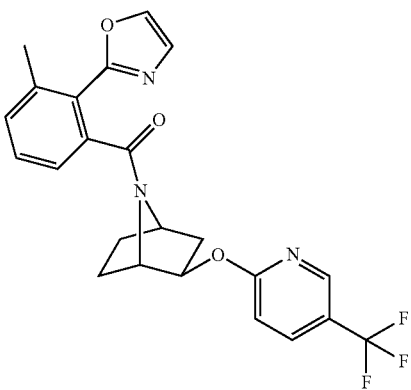 [SMILES: Cc1cccc(C(=O)N2C3CCC2C(Oc2ccc(C(F)(F)F)cn2)C3)c1-c1ncco1]

Example 334

(3-methyl-2-pyridin-2-yl)phenyl)((1S,2R,4R)-2-((5-(trifluoromethyl)pyridin-2-yl)oxy)-7-azabicyclo[2.2.1]heptan-7-yl)methanone

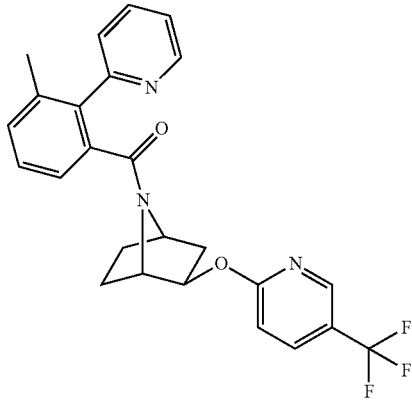

Example 335

(2-(5-fluoropyrimidin-2-yl)phenyl)((1S,2R,4R)-2-((5-(trifluoromethyl)pyridin-2-yl)oxy)-7-azabicyclo[2.2.1]heptan-7-yl)methanone

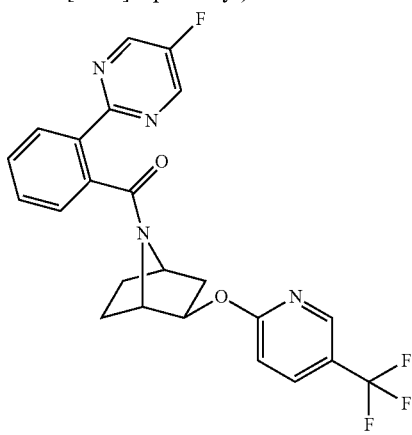

Example 336

(2-fluoro-6-(2H-1,2,3-triazol-2-yl)phenyl)((1S,2R,4R)-2-((5-(trifluoromethyl)pyridin-2-yl)oxy)-7-azabicyclo[2.2.1]heptan-7-yl)methanone

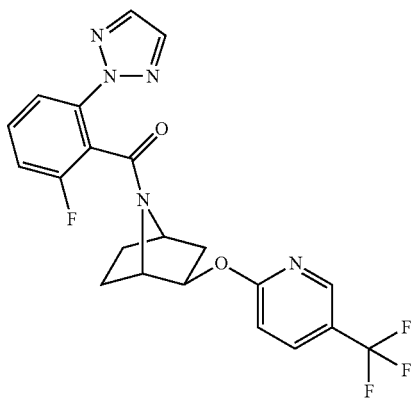

Example 337

(5-methyl-3-(2H-1,2,3-triazol-2-yl)pyridin-2-yl)((1S,2R,4R)-2-((5-(trifluoromethyl)pyridin-2-yl)oxy)-7-azabicyclo[2.2.1]heptan-7-yl)methanone

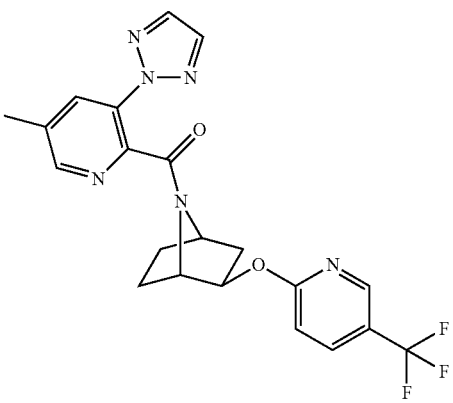 [SMILES: Cc1cnc(C(=O)N2C3CCC2C(Oc2ccc(C(F)(F)F)cn2)C3)c(-n2nccn2)c1]

Example 338

(2-bromo-3-fluorophenyl)((1S,2R,4R)-2-((5-(trifluoromethyl)pyridin-2-yl)oxy)-7-azabicyclo[2.2.1]heptan-7-yl)methanone

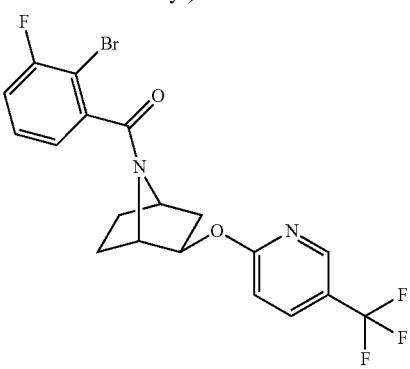

Example 339

(3-fluoro-2-(pyrimidin-2-yl)phenyl)((1S,2R,4R)-2-((5-(trifluoromethyl)pyrazin-2-yl)oxy)-7-azabicyclo[2.2.1]heptan-7-yl)methanone

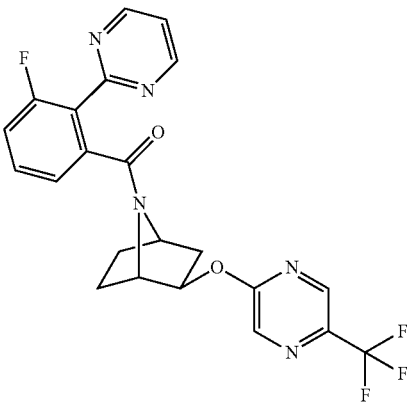

Example 340

(2-methoxy-6-(pyrimidin-2-yl)phenyl)((1S,2R,4R)-2-((5-(trifluoromethyl)pyrazin-2-yl)oxy)-7-azabicyclo[2.2.1]heptan-7-yl)methanone

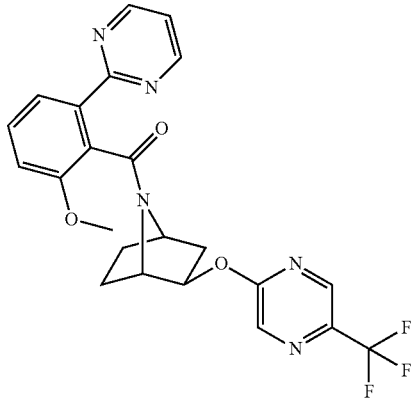

Example 341

(5-fluoro-2-(2H-1,2,3-triazol-2-yl)phenyl)((1S,2R,4R)-2-((5-(trifluoromethyl)pyrazin-2-yl)oxy)-7-azabicyclo[2.2.1]heptan-7-yl)methanone

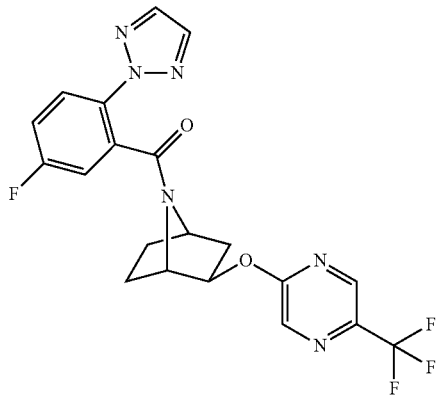

Example 342

(4-methyl-2-(2H-1,2,3-triazol-2-yl)phenyl)((1S,2R,4R)-2-((5-(trifluoromethyl)pyrazin-2-yl)oxy)-7-azabicyclo[2.2.1]heptan-7-yl)methanone

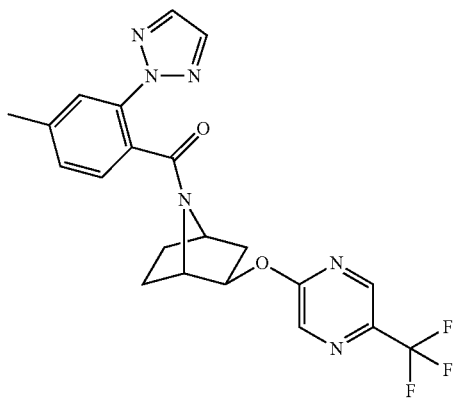

Example 343

(3-methyl-2-(2H-1,2,3-triazol-2-yl)phenyl)((1S,2R,4R)-2-((5-(trifluoromethyl)pyrazin-2-yl)oxy)-7-azabicyclo[2.2.1]heptan-7-yl)methanone

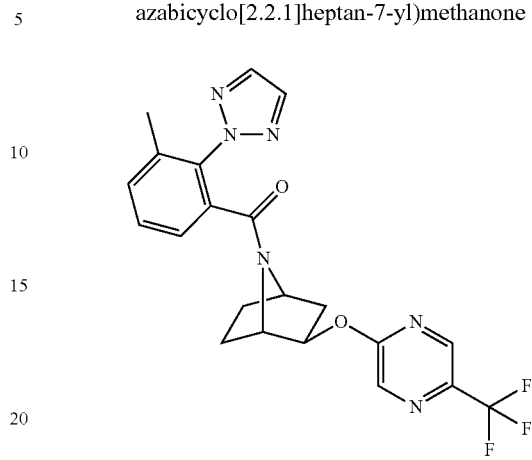

Example 344

(4-fluoro-2-(pyrimidin-2-yl)phenyl)((1S,2R,4R)-2-((5-(trifluoromethyl)pyrazin-2-yl)oxy)-7-azabicyclo[2.2.1]heptan-7-yl)methanone

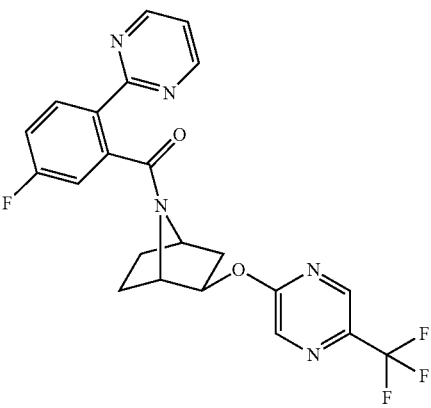

Example 345

(2-fluoro-6-(pyrimidin-2-yl)phenyl)((1S,2R,4R)-2-((5-(trifluoromethyl)pyrazin-2-yl)oxy)-7-azabicyclo[2.2.1]heptan-7-yl)methanone

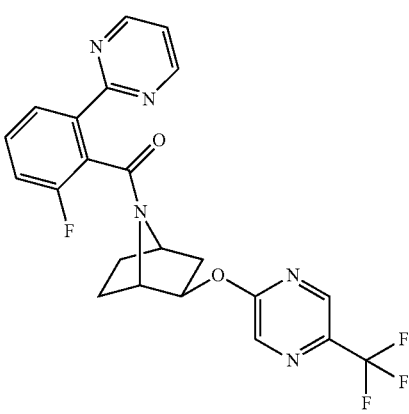 [SMILES: O=C(c1c(F)cccc1-c1ncccn1)N1C2CCC1C(Oc1cnc(C(F)(F)F)cn1)C2]

Example 346

(2-(2H-1,2,3-triazol-2-yl)phenyl)((1S,2R,4R)-2-((5-(trifluoromethyl)pyrazin-2-yl)oxy)-7-azabicyclo[2.2.1]heptan-7-yl)methanone

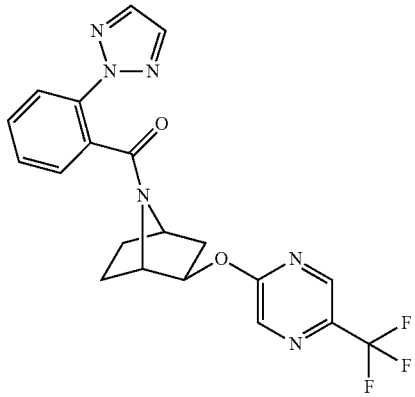

Example 347

(6-methyl-3-(2H-1,2,3-triazol-2-yl)pyridin-2-yl)((1S,2R,4R)-2-((5-(trifluoromethyl)pyrazin-2-yl)oxy)-7-azabicyclo[2.2.1]heptan-7-yl)methanone

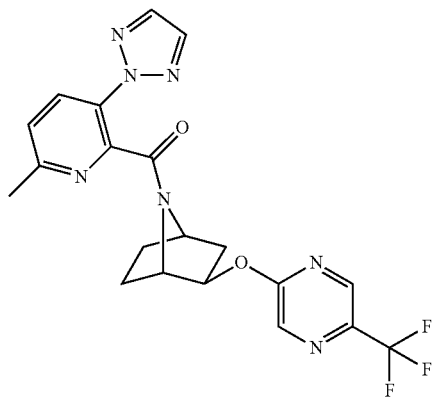 [SMILES: Cc1ccc(-n2nccn2)c(C(=O)N2C3CCC2C(Oc2cnc(C(F)(F)F)cn2)C3)n1]

Example 348

(3-methyl-2-(oxazol-2-yl)phenyl)((1S,2R,4R)-2-((5-(trifluoromethyl)pyrazin-2-yl)oxy)-7-azabicyclo[2.2.1]heptan-7-yl)methanone

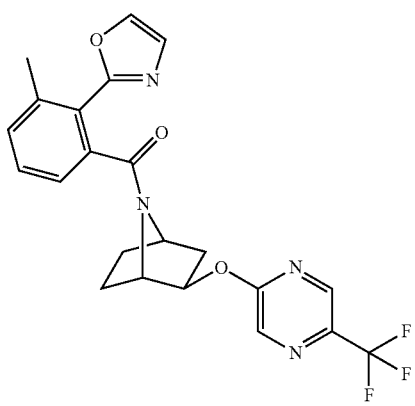

Example 349

(3-methyl-2-(oxazol-2-yl)phenyl)((1S,2R,4R)-2-((5-(trifluoromethyl)pyrazin-2-yl)oxy)-7-azabicyclo[2.2.1]heptan-7-yl)methanone

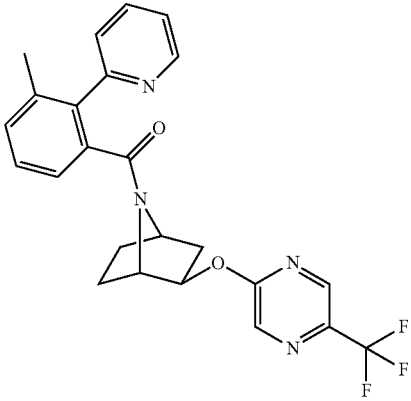 [SMILES: Cc1cccc(C(=O)N2C3CCC2C(Oc2cnc(C(F)(F)F)cn2)C3)c1-c1ccccn1]

Example 350

(2-(5-fluoropyrimidin-2-yl)phenyl)((1S,2R,4R)-2-((5-(trifluoromethyl)pyrazin-2-yl)oxy-7-azabicyclo[2.2.1]heptan-7-yl)methanone

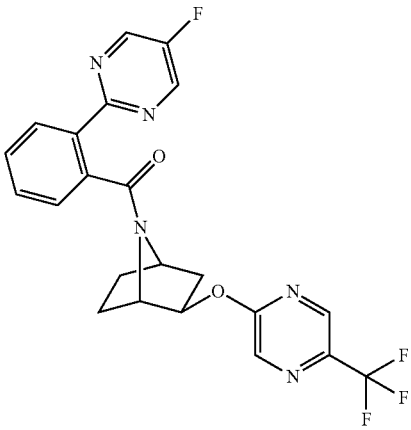 [SMILES: O=C(c1ccccc1-c1ncc(F)cn1)N1C2CCC1C(Oc1cnc(C(F)(F)F)cn1)C2]

Example 351

(2-fluoro-6-(2H-1,2,3-triazol-2-yl)phenyl)((1S,2R,4R)-2-((5-trifluoromethyl)pyrazin-2-yl)oxy)-7-azabicyclo[2.2.1]heptan-7-yl)methanone

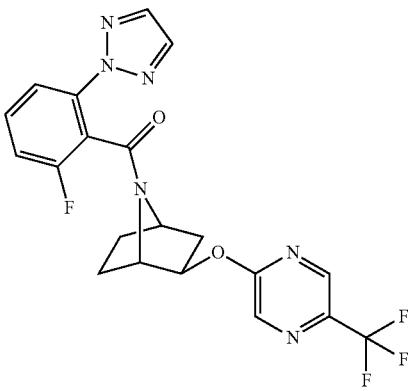 [SMILES: O=C(c1c(F)cccc1-n1nccn1)N1C2CCC1C(Oc1cnc(C(F)(F)F)cn1)C2]

Example 352

(5-methyl-3-(2H-1,2,3-triazol-2-yl)pyridin-2-yl)((1S,2R,4R)-2-((5-(trifluoromethyl)pyrazin-2-yl)oxy)-7-azabicyclo[2.2.1]heptan-7-yl)methanone

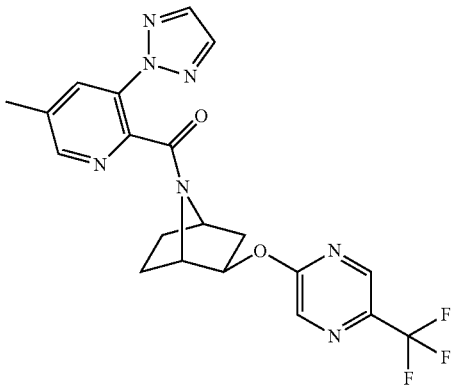 [SMILES: Cc1cnc(C(=O)N2C3CCC2C(Oc2cnc(C(F)(F)F)cn2)C3)c(-n2nccn2)c1]

Example 353

(2-bromo-3-fluorophenyl)((1S,2R,4R)-2-((5-(trifluoromethyl)pyrazin-2-yl)oxy)-7-azabicyclo[2.2.1]heptan-7-yl)methanone

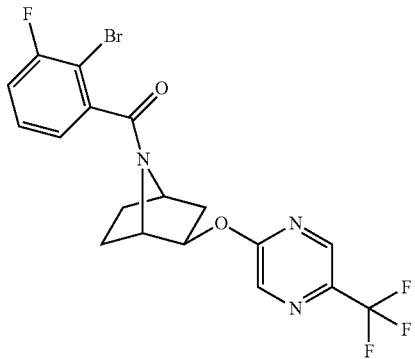 [SMILES: O=C(c1cccc(F)c1Br)N1C2CCC1C(Oc1cnc(C(F)(F)F)cn1)C2]

Example 354

(2-methoxy-6-(pyrimidin-2-yl)phenyl)((1S,2R,4R)-2-((5-(trifluoromethyl)pyrimidin-2-yl)oxy)-7-azabicyclo[2.2.1]heptan-7-yl)methanone

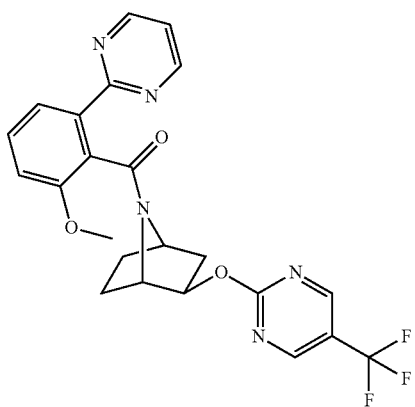 [SMILES: COc1cccc(-c2ncccn2)c1C(=O)N1C2CCC1C(Oc1ncc(C(F)(F)F)cn1)C2]

Example 355

(5-fluoro-2-(2H-1,2,3-triazol-2-yl)phenyl)((1S,2R,4R)-2-((5-(trifluoromethyl)pyrimidin-2-yl)oxy)-7-azabicyclo[2.2.1]heptan-7-yl)methanone

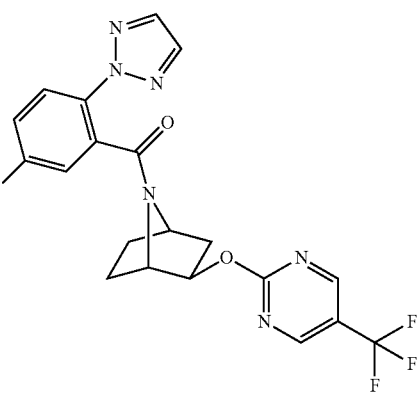

Example 356

(4-methyl-2-(2H-1,2,3-triazol-2-yl)phenyl(1S,2R,4R)-2-((5-(trifluoromethyl)pyrimidin-2-yl)oxy)-7-azabicyclo[2.2.1]heptan-7-yl)methanone

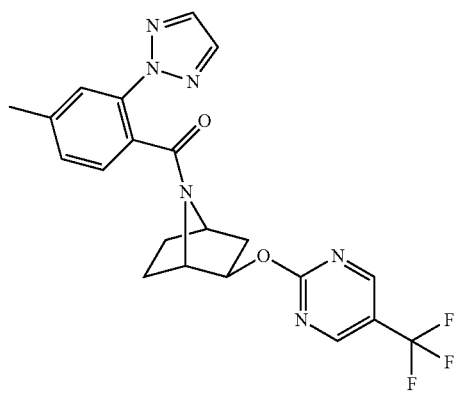

Example 357

(3-methyl-2-(2H-1,2,3-triazol-2-yl)phenyl)((1S,2R,4R)-2-((5-(trifluoromethyl)pyrimidin-2-yl)oxy)-7-azabicyclo[2.2.1]heptan-7-yl)methanone

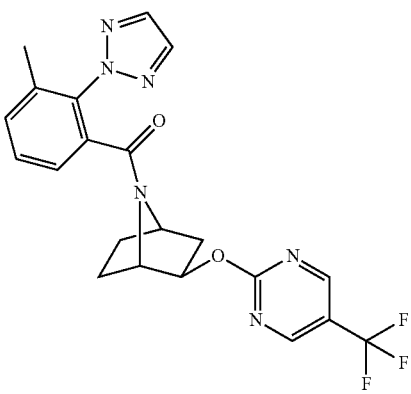 [SMILES: Cc1cccc(C(=O)N2C3CCC2C(Oc2ncc(C(F)(F)F)cn2)C3)c1-n1nccn1]

Example 358

(5-fluoro-2-(pyrimidin-2-yl)phenyl)((1S,2R,4R)-2-((5-(trifluoromethyl)pyrimidin-2-yl)oxy)-7-azabicyclo[2.2.1]heptan-7-yl)methanone

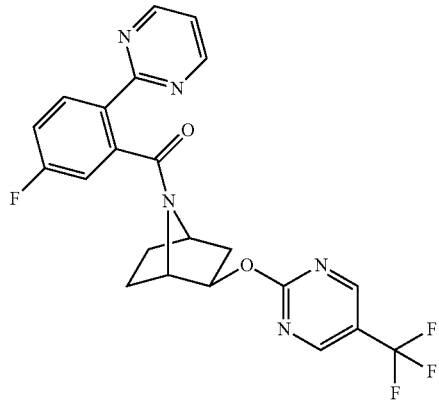 [SMILES: O=C(c1cc(F)ccc1-c1ncccn1)N1C2CCC1C(Oc1ncc(C(F)(F)F)cn1)C2]

Example 359

(2-fluoro-6-(pyrimidin-2-yl)phenyl)((1S,2R,4R)-2-((5-(trifluoromethyl)pyrimidin-2-yl)oxy)-7-azabicyclo[2.2.1]heptan-7-yl)methanone

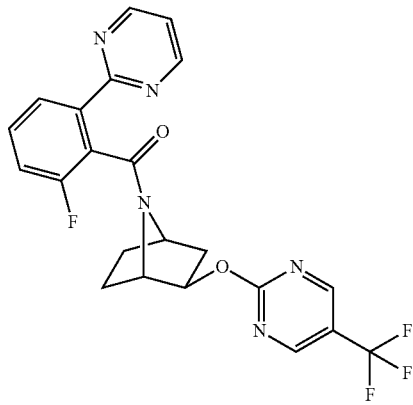

Example 360

(2-(2H-1,2,3-triazol-2-yl)phenyl)((1S,2R,4R)-2-((5-(trifluoromethyl)pyrimidin-2-yl)oxy)-7-azabicyclo[2.2.1]heptan-7-yl)methanone

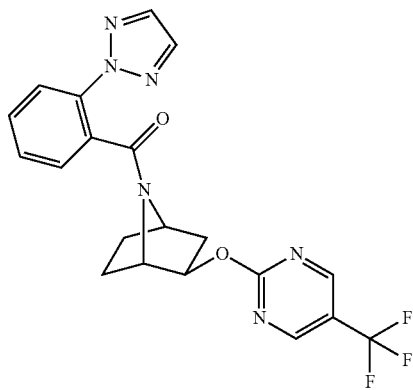 [SMILES: O=C(c1ccccc1-n1nccn1)N1C2CCC1C(Oc1ncc(C(F)(F)F)cn1)C2]

Example 361

(6-methyl-3-(2H-1,2,3-triazol-2-yl)pyridin-2-yl)((1S,2R,4R)-2-((5-(trifluoromethyl)pyrimidin-2-yl)oxy)-7-azabicyclo[2.2.1]heptan-7-yl)methanone

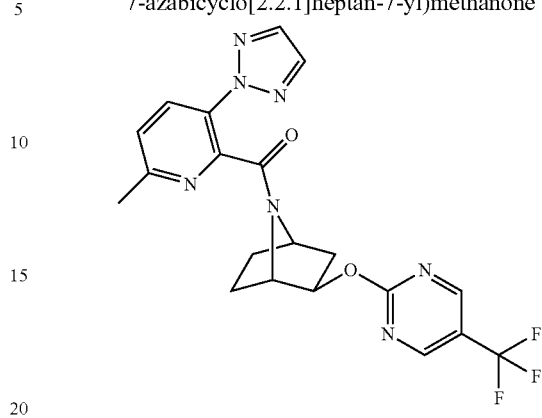

Example 362

(3-methyl-2-(oxazol-2-yl)phenyl)((1S,2R,4R)-2-((5-(trifluoromethyl)pyrimidin-2-yl)oxy)-7-azabicyclo[2.2.1]heptan-7-yl)methanone

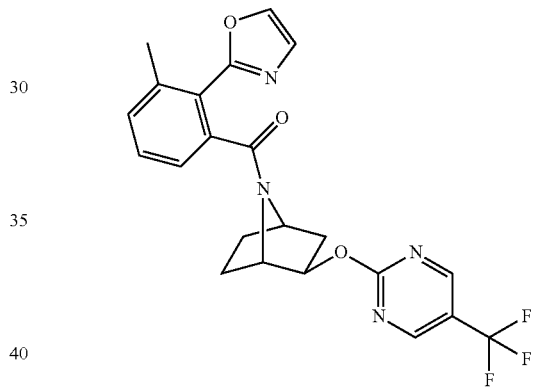

Example 363

(3-methyl-2-(pyridin-2-yl)phenyl)((1S,2R,4R)-2-((5-(trifluoromethyl)pyrimidin-2-yl)oxy)-7-azabicyclo[2.2.1]heptan-7-yl)methanone

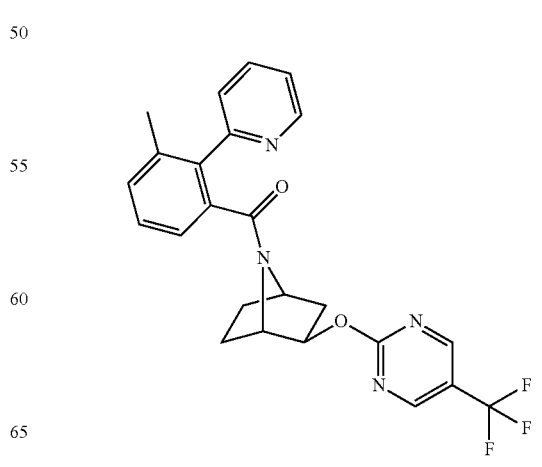

Example 364

(2-(5-fluoropyrimidin-2-yl)phenyl)((1S,2R,4R)-2-((5-(trifluoromethyl)pyrimidin-2-yl)oxy)-7-azabicyclo[2.2.1]heptan-7-yl)methanone

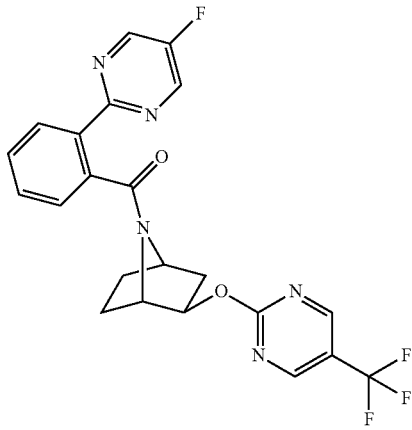

Example 365

(2-fluoro-6-(2H-1,2,3-triazol-2-yl)phenyl)((1S,2R,4R)-2-((5-(trifluoromethyl)pyrimidin-2-yl)oxy)-7-azabicyclo[2.2.1]heptan-7-yl)methanone

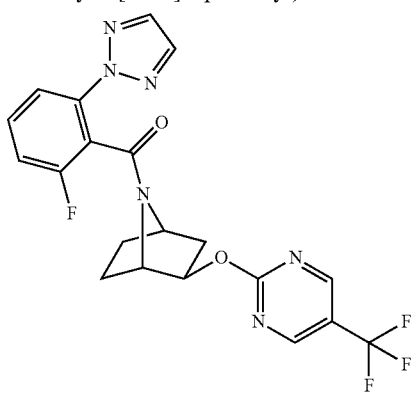

Example 366

(5-methyl-3-(2H-1,2,3-triazol-2-yl)pyridin-2-yl)((1S,2R,4R)-2-((5-(trifluoromethyl)pyrimidin-2-yl)oxy)-7-azabicyclo[2.2.1]heptan-7-yl)methanone

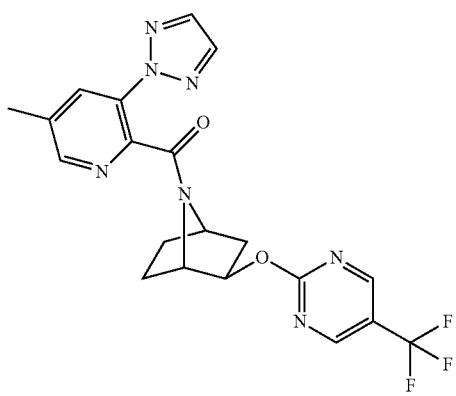 [SMILES: Cc1cnc(C(=O)N2C3CCC2C(Oc2ncc(C(F)(F)F)cn2)C3)c(-n2nccn2)c1]

Example 367

(2-bromo-3-fluorophenyl)((1S,2R,4R)-2-((5-(trifluoromethyl)pyrimidin-2-yl)oxy-7-azabicyclo[2.2.1]heptan-7-yl)methanone

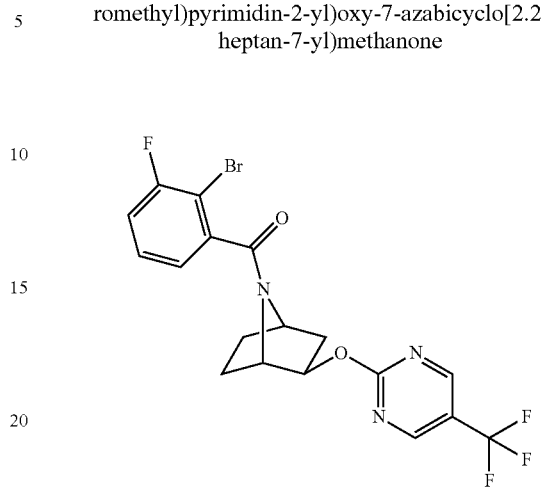

Example 368

(4-fluoro-2-(2H-1,2,3-triazol-2-yl)phenyl)((1S,2R,4R)-2-((5-(trifluoromethyl)pyridin-2-yl)amino)-7-azabicyclo[2.2.1]heptan-7-yl)methanone

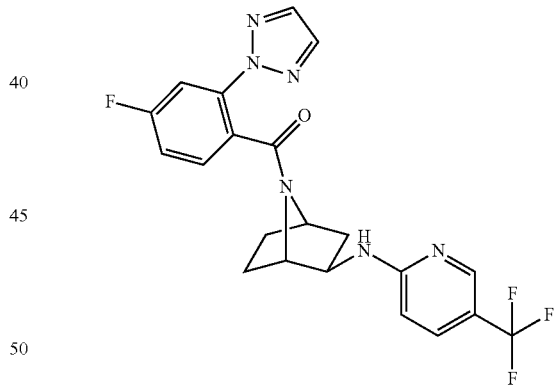

Prepared analogous to Example 279 substituting intermediate A-2 with intermediate A-12. MS (ESI): mass calcd. for $C_{21}H_{18}F_4N_6O$, 446.1; m/z found, 447.1 [M+H]$^+$. $^1$H NMR (500 MHz, CDCl$_3$, Compound present as a mixture of rotamers (0.64:0.36), only major rotamer reported) δ 8.22 (s, 1H), 7.91 (s, 2H), 7.57 (dd, J=9.1, 2.5 Hz, 1H), 7.40-7.33 (m, 2H), 6.38 (d, J=8.7 Hz, 1H), 6.05 (s, 1H), 4.83 (t, J=4.5 Hz, 1H), 4.24-4.16 (m, 1H), 3.93-3.88 (m, 1H), 2.22-2.10 (m, 1H), 2.09-1.86 (m, 2H), 1.68-1.61 (m, 2H), 1.57-1.50 (m, 1H).

Example 369

(5-fluoro-2-(2H-1,2,3-triazol-2-yl)phenyl)((1S,2R,4R)-2-((5-(trifluoromethyl)pyridin-2-yl)amino)-7-azabicyclo[2.2.1]heptan-7-yl)methanone

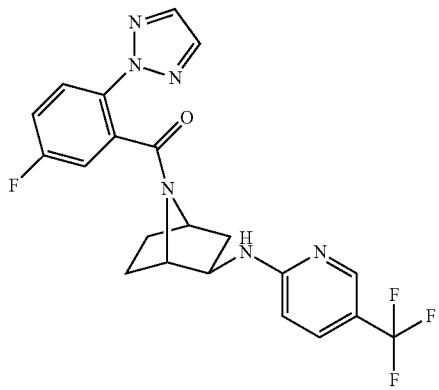 [SMILES: O=C(c1cc(F)ccc1-n1nccn1)N1C2CCC1C(Nc1ccc(C(F)(F)F)cn1)C2]

Prepared analogous to Example 279 substituting intermediate A-2 with intermediate A-10. MS (ESI): mass calcd. for $C_{21}H_{18}F_4N_6O$, 446.1; m/z found, 446.9 [M+H]$^+$. $^1$H NMR (400 MHz, CDCl$_3$, Compound present as a mixture of rotamers) δ 8.40-8.19 (m, 1H), 7.99-7.73 (series of m, 3H), 7.58-7.31 (m, 1H), 7.31-7.10 (series of m, 2H), 7.06 (dd, J=7.9, 2.9 Hz, 1H), 6.16-5.67 (series of m, 1H), 4.90-4.68 (series of m, 1H), 4.38-3.84 (series of m, 1H), 2.20-1.40 (series of m, 6H).

Example 370

(2-fluoro-6-(2H-1,2,3-triazol-2-yl)phenyl)((1S,2R,4R)-2-((5-(trifluoromethyl)pyridin-2-yl)amino)-7-azabicyclo[2.2.1]heptan-7-yl)methanone

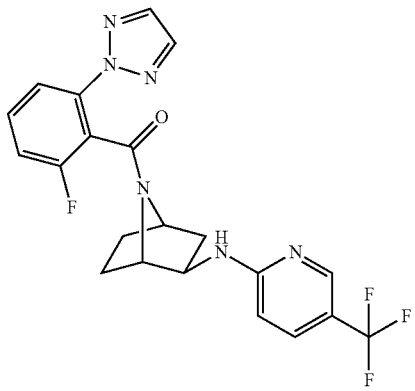

Prepared analogous to Example 279 substituting intermediate A-2 with intermediate A-11. MS (ESI): mass calcd. for $C_{21}H_{18}F_4N_6O$, 446.1; m/z found, 446.9 [M+H]$^+$. Analytical HPLC was obtained on a Agilent 1100 Series using an Inertsil ODS-3 column (3 μm, 50×3 mm), mobile phase of 5-99% ACN in 0.05% TFA over 1.6 min and then hold at 99% ACN for 0.4 min, at a flow rate of 2.2 mL/min (Temperature=50° C.). R$_t$=1.27 min (major rotamer) at 254 nm.

Example 371

(5-fluoro-2-(pyrimidin-2-yl)phenyl)((1S,2R,4R)-2-((5-(trifluoromethyl)pyridin-2-yl)amino)-7-azabicyclo[2.2.1]heptan-7-yl)methanone

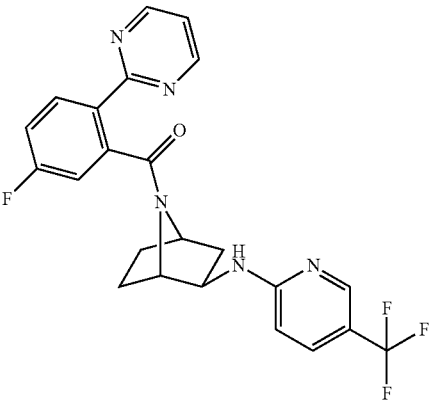

Prepared analogous to Example 279 substituting intermediate A-2 with intermediate A-7. MS (ESI): mass calcd. for $C_{23}H_{19}F_4N_5O$, 457.2; m/z found, 458.2 [M+H]$^+$. $^1$H NMR (500 MHz, CDCl$_3$, Compound present as a mixture of rotamers (0.80:0.20), only major rotamer reported) δ 8.82 (d, J=4.9 Hz, 2H), 8.22 (s, 1H), 8.02 (dd, J=8.6, 5.4 Hz, 1H), 7.34-7.27 (m, 2H), 7.15 (dd, J=8.3, 2.7 Hz, 1H), 7.04 (dd, J=8.4, 2.7 Hz, 1H), 6.01-5.88 (m, 1H), 4.84 (t, J=4.5 Hz, 1H), 4.37 (s, 1H), 4.07-4.01 (m, 1H), 2.20 (dd, J=13.0, 8.1 Hz, 1H), 2.00-1.89 (m, 2H), 1.80-1.51 (series of m, 3H).

Example 372

(2-fluoro-6-(pyrimidin-2-yl)phenyl)((1S,2R,4R)-2-((5-(trifluoromethyl)pyridin-2-yl)amino)-7-azabicyclo[2.2.1]heptan-7-yl)methanone

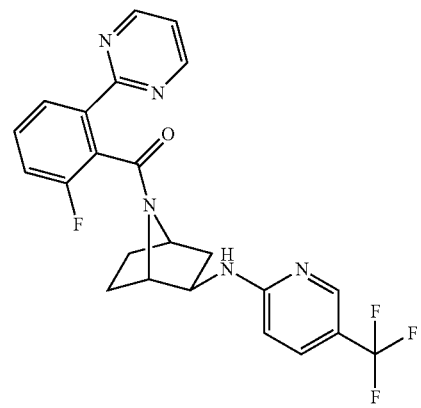

Prepared analogous to Example 279 substituting intermediate A-2 with intermediate A-6. MS (ESI): mass calcd. for $C_{23}H_{19}F_4N_5O$, 457.2; m/z found, 458.2 [M+H]$^+$. $^1$H NMR (500 MHz, CDCl$_3$, Compound present as mixture of rotamers) δ 8.85 (d, J=4.9 Hz, 2H), 8.22 (s, 1H), 7.78 (d, J=7.7 Hz, 1H), 7.66 (d, J=9.8 Hz, 1H), 7.48-7.43 (m, 1H), 7.37 (t, J=4.9 Hz, 1H), 7.18 (t, J=8.8 Hz, 1H), 5.88 (d, J=8.8 Hz, 1H), 4.88 (t, J=4.9 Hz, 1H), 4.49-4.36 (m, 1H), 3.93 (d, J=5.0 Hz, 1H), 2.25 (dd, J=12.9, 7.9 Hz, 1H), 2.18-2.08 (m, 1H), 2.03-1.93 (m, 1H), 1.81-1.67 (m, 2H). *1H buried under solvent peak.

Example 373

(2-(pyrimidin-2-yl)phenyl)((1S,2R,4R)-2-((5-(trifluoromethyl)pyridin-2-yl)amino)-7-azabicyclo[2.2.1]heptan-7-yl)methanone

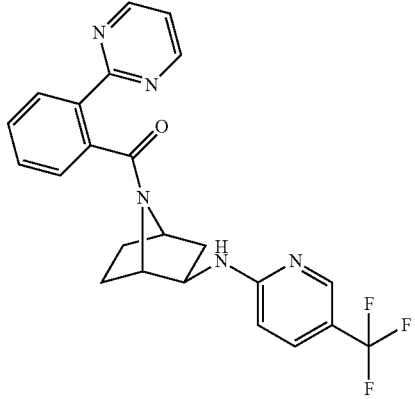

Prepared analogous to Example 279 substituting intermediate A-2 with intermediate A-59. MS (ESI): mass calcd. for $C_{23}H_{20}F_3N_5O$, 439.2; m/z found, 440.0 [M+H]$^+$. $^1$H NMR (500 MHz, CDCl$_3$, Compound present as a mixture of rotamers (0.82:0.18), only major rotamer reported) δ 8.83 (d, J=4.9 Hz, 2H), 8.23-8.20 (m, 1H), 7.97 (d, J=7.7 Hz, 1H), 7.50-7.45 (m, 1H), 7.41-7.35 (m, 2H), 7.32 (t, J=4.9 Hz, 1H), 5.94 (d, J=8.8 Hz, 1H), 4.84 (t, J=4.5 Hz, 1H), 4.46-4.30 (m, 1H), 4.06 (d, J=4.6 Hz, 1H), 2.20 (dd, J=12.9, 8.0 Hz, 1H), 1.99-1.91 (m, 2H), 1.82-1.59 (m, 2H), 1.59-1.50 (m, 1H). *1H buried under solvent peak.

Example 374

(2-(5-fluoropyrimidin-2-yl)phenyl)((1S,2R,4R)-2-((5-(trifluoromethyl)pyridin-2-yl)amino)-7-azabicyclo[2.2.1]heptan-7-yl)methanone

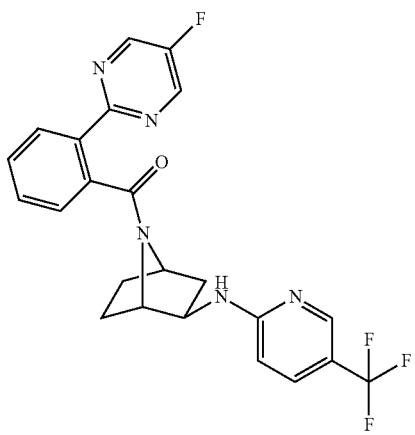

Prepared analogous to Example 279 substituting intermediate A-2 with intermediate A-55. MS (ESI): mass calcd. for $C_{23}H_{19}F_4N_5O$, 457.2; m/z found, 457.9 [M+H]$^+$. $^1$H NMR (500 MHz, CDCl$_3$) δ 8.68 (s, 2H), 8.21 (s, 1H), 7.93 (d, J=7.7 Hz, 1H), 7.48-7.42 (m, 1H), 7.38-7.30 (m, 3H), 6.00 (d, J=8.8 Hz, 1H), 4.83 (t, J=4.6 Hz, 1H), 4.29 (s, 1H), 4.05 (d, J=4.6 Hz, 1H), 2.18 (dd, J=13.0, 8.0 Hz, 1H), 2.05-1.92 (m, 2H), 1.71-1.64 (m, 2H), 1.59-1.54 (m, 1H).

Example 375

(3-fluoro-2-(5-fluoropyrimidin-2-yl)phenyl)((1S,2R,4R)-2-((5-(trifluoromethyl)pyridin-2-yl)amino)-7-azabicyclo[2.2.1]heptan-7-yl)methanone

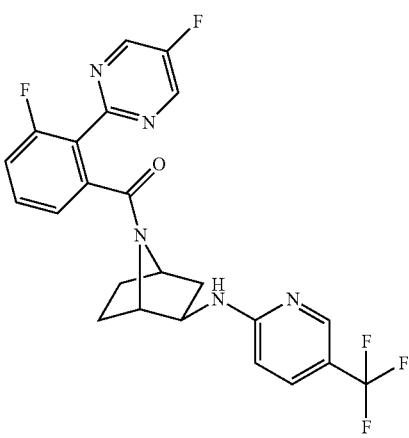

Prepared analogous to Example 279 substituting intermediate A-2 with intermediate A-57. MS (ESI): mass calcd. for $C_{23}H_{18}F_5N_5O$, 475.1; m/z found, 475.9 [M+H]$^+$. $^1$H NMR (400 MHz, CDCl$_3$) δ 8.73 (s, 2H), 8.28-8.13 (m, 1H), 7.38-7.31 (m, 2H), 7.18-7.14 (m, 2H), 6.19 (d, J=8.8 Hz, 1H), 4.72 (t, J=4.9 Hz, 1H), 4.38-4.26 (m, 1H), 4.09 (d, J=5.0 Hz, 1H), 2.16 (dd, J=12.9, 8.1 Hz, 1H), 2.07-1.98 (m, 1H), 1.95-1.86 (m, 1H), 1.75-1.66 (m, 1H), 1.66-1.57 (m, 1H), 1.57-1.48 (m, 1H).

Example 376

(3-chloro-2-(pyrimidin-2-yl)phenyl)((1S,2R,4R)-2-((5-(trifluoromethyl)pyridin-2-yl)amino)-7-azabicyclo[2.2.1]heptan-7-yl)methanone

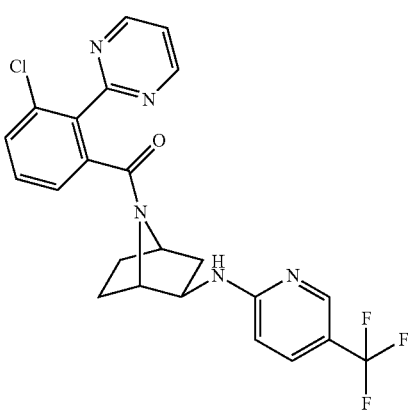

Prepared analogous to Example 279 substituting intermediate A-2 with intermediate A-58. MS (ESI): mass calcd. for C$_{23}$H$_{19}$ClF$_3$N$_5$O, 473.1; m/z found, 474.1 [M+H]$^+$. $^1$H NMR (500 MHz, CDCl$_3$, Compound present as a mixture of rotamers (0.92:0.08), only major rotamer reported) δ 8.88 (d, J=5.0 Hz, 2H), 8.24-8.19 (m, 1H), 7.67-7.60 (m, 1H), 7.45 (dd, J=5.9, 3.3 Hz, 1H), 7.39 (t, J=5.0 Hz, 1H), 7.32 (dd, J=8.8, 2.5 Hz, 1H), 7.27 (d, J=2.6 Hz, 1H), 6.29 (d, J=8.8 Hz, 1H), 4.66 (t, J=5.1 Hz, 1H), 4.32 (td, J=8.6, 3.7 Hz, 1H), 4.06 (d, J=4.9 Hz, 1H), 2.11 (dd, J=12.9, 8.2 Hz, 1H), 2.05-1.97 (m, 1H), 1.92-1.84 (m, 1H), 1.74-1.67 (m, 1H), 1.59-1.53 (m, 1H), 1.53-1.46 (m, 1H).

Example 377
(3-fluoro-2-(pyrimidin-2-yl)phenyl)((1S,2R,4R)-2-(methyl(5-(trifluoromethyl)pyridin-2-yl)amino)-7-azabicyclo[2.2.1]heptan-7-yl)methanone

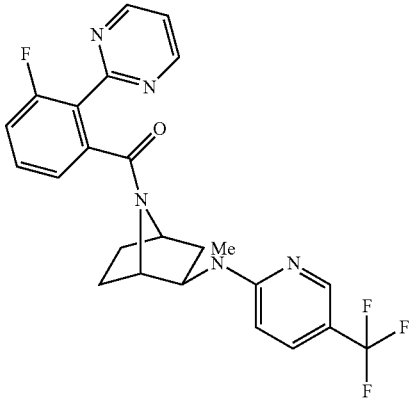

To a solution of compound of Example 279 (19 g, 0.042 mmol) in DMF (0.42 mL) was added sodium tert-butoxide (5 g, 0.05 mmol) followed by iodomethane (2.7 μL, 0.044 mmol). The reaction mixture was stirred at room temperature for 12 hours. Solvent was evaporated and purification via prep HPLC gave the title compound (16 g, 82%). MS (ESI): mass calcd. for C$_{24}$H$_{21}$F$_4$N$_5$O, 471.2; m/z found, 472.2 [M+H]$^+$. $^1$H NMR (500 MHz, CDCl$_3$, Compound present as a mixture of rotamers (0.82:0.18), only major rotamer reported) δ 8.80 (d, J=4.9 Hz, 2H), 8.37 (s, 1H), 7.62 (dd, J=9.1, 2.6 Hz, 1H), 7.51-7.44 (m, 1H), 7.32-7.22 (series of m, 3H), 6.50 (d, J=9.1 Hz, 1H), 4.93 (dd, J=8.3, 5.0 Hz, 1H), 4.63 (d, J=4.1 Hz, 1H), 4.08 (t, J=4.4 Hz, 1H), 2.93 (s, 3H), 2.09 (dd, J=12.7, 8.3 Hz, 1H), 1.92-1.81 (m, 2H), 1.70-1.60 (m, 2H), 1.54-1.45 (m, 1H).

Example 378
(5-methyl-2-(pyrimidin-2-yl)pyridin-3-yl)((1S,2R,4R)-2-((5-(trifluoromethyl)pyridin-2-yl)amino)-7-azabicyclo[2.2.1]heptan-7-yl)methanone

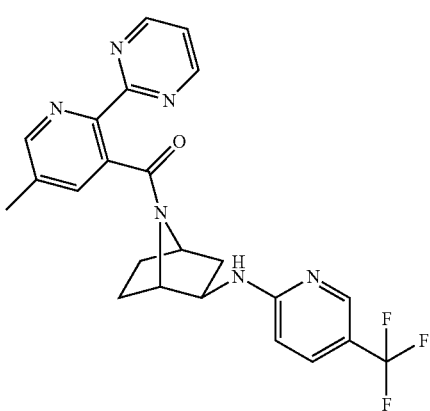

Prepared analogous to Example 279 substituting intermediate A-2 with intermediate A-66. MS (ESI): mass calcd. for C$_{23}$H$_{21}$F$_3$N$_6$O, 454.2; m/z found, 455.2 [M+H]$^+$. $^1$H NMR (400 MHz, CDCl$_3$, Compound present as a mixture of rotamers (0.81:0.19), only major rotamer reported) δ 8.89 (d, J=4.9 Hz, 2H), 8.56 (d, J=1.7 Hz, 1H), 8.26-8.20 (m, 1H), 7.48-7.41 (m, 1H), 7.39 (t, J=4.9 Hz, 1H), 7.35-7.28 (m, 1H), 6.01 (d, J=8.8 Hz, 1H), 4.84 (t, J=4.4 Hz, 1H), 4.33 (s, 1H), 3.98 (d, J=4.6 Hz, 1H), 2.31 (s, 3H), 2.20 (dd, J=13.0, 8.1 Hz, 1H), 2.00-1.88 (series of m, 2H), 1.79-1.50 (series of m, 3H).

Example 379
(6-methyl-3-(pyrimidin-2-yl)pyridin-2-yl)((1S,2R,4R)-2-((5-(trifluoromethyl)pyridin-2-yl)amino)-7-azabicyclo[2.2.1]heptan-7-yl)methanone

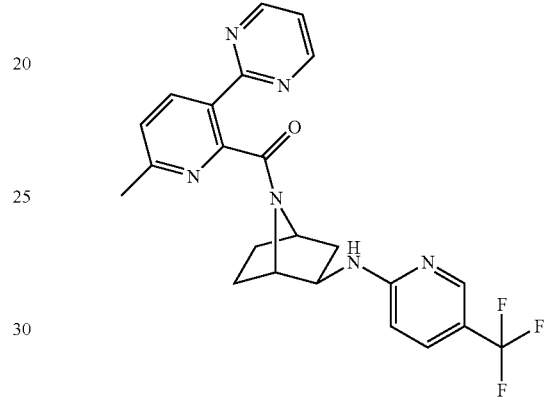

Prepared analogous to Example 279 substituting intermediate A-2 with intermediate A-63. MS (ESI): mass calcd. for C$_{23}$H$_{21}$F$_3$N$_6$O, 454.2; m/z found, [M+H]$^+$. $^1$H NMR (400 MHz, CDCl$_3$, Compound present as a mixture of rotamers (0.89:0.11), only major rotamer reported) δ 8.79 (d, J=4.9 Hz, 1H), 8.31 (d, J=8.1 Hz, 1H), 8.28-8.24 (m, 1H), 7.40 (dd, J=8.8, 2.5 Hz, 1H), 7.31-7.26 (series of m, 3H), 7.18 (d, J=8.8 Hz, 1H), 6.21 (d, J=8.8 Hz, 1H), 4.89 (t, J=4.7 Hz, 1H), 4.39-4.24 (m, 1H), 4.08 (d, J=5.1 Hz, 1H), 2.61 (s, 3H), 2.19 (dd, J=13.0, 7.5 Hz, 1H), 2.11-1.93 (series of m, 2H), 1.87-1.55 (series of m, 3H).

Example 380
(5-methyl-3-(pyrimidin-2-yl)pyridin-2-yl)((1S,2R,4R)-2-((5-(trifluoromethyl)pyridin-2-yl)amino)-7-azabicyclo[2.2.1]heptan-7-yl)methanone

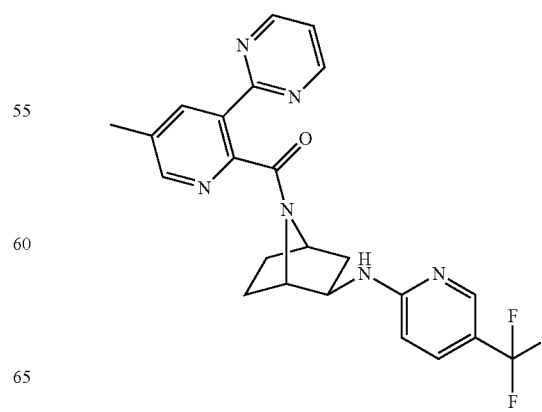

Prepared analogous to Example 279 substituting intermediate A-2 with intermediate A-67. MS (ESI): mass calcd. for $C_{23}H_{21}F_3N_6O$, 454.2; m/z found, 455.2 [M+H]$^+$. $^1$H NMR (400 MHz, CDCl$_3$, Compound present as a mixture of rotamers (0.88:0.12), only major rotamer reported) δ 8.83 (d, J=4.9 Hz, 2H), 8.40 (dd, J=2.1, 0.9 Hz, 1H), 8.26-8.22 (m, 1H), 8.16 (dd, J=2.0, 0.9 Hz, 1H), 7.36 (dd, J=8.8, 2.5 Hz, 1H), 7.32 (t, J=4.9 Hz, 1H), 7.28 (d, J=9.4 Hz, 1H), 6.14 (d, J=8.8 Hz, 1H), 4.86 (t, J=4.8 Hz, 1H), 4.34-4.25 (m, 1H), 4.13 (d, J=5.2 Hz, 1H), 2.41 (s, 3H), 2.19 (dd, J=12.9, 7.7 Hz, 1H), 2.12-2.05 (m, 1H), 2.03-1.93 (m, 1H), 1.81-1.73 (m, 1H), 1.65-1.52 (m, 2H).

Example 381

(3-(pyrimidin-2-yl)pyridin-2-yl)((1S,2R,4R)-2-((5-(trifluoromethyl)pyridin-2-yl)amino)-7-azabicyclo[2.2.1]heptan-7-yl)methanone

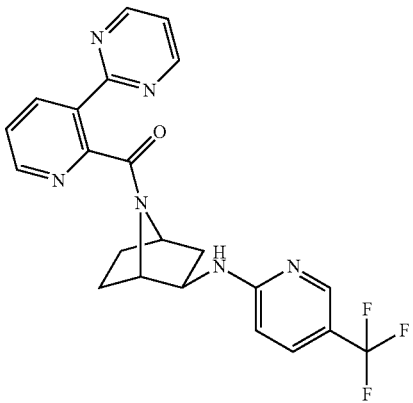

Prepared analogous to Example 279 substituting intermediate A-2 with intermediate A-64. MS (ESI): mass calcd. for $C_{22}H_{19}F_3N_6O$, 440.2; m/z found, 441.2 [M+H]$^+$. $^1$H NMR (400 MHz, CDCl$_3$, Compound present as a mixture of rotamers (0.87:0.13), only major rotamer reported) δ 8.83 (d, J=4.9 Hz, 2H), 8.59 (dd, J=4.8, 1.7 Hz, 1H), 8.39 (dd, J=7.9, 1.7 Hz, 1H), 8.26-8.22 (m, 1H), 7.43 (dd, J=7.9, 4.8 Hz, 1H), 7.37 (dd, J=8.9, 2.5 Hz, 1H), 7.33 (t, J=4.9 Hz, 1H), 7.23 (d, J=9.4 Hz, 1H), 6.15 (d, J=8.8 Hz, 1H), 4.88 (t, J=4.9 Hz, 1H), 4.35-4.26 (m, 1H), 4.11 (d, J=5.2 Hz, 1H), 2.20 (dd, J=13.0, 7.7 Hz, 1H), 2.14-2.07 (m, 1H), 2.04-1.91 (m, 1H), 1.84-1.74 (m, 1H), 1.66-1.53 (m, 2H).

Example 382

(3-fluoro-2-(pyrimidin-2-yl)phenyl)((1S,2R,4R)-2-((3-fluoro-5-(trifluoromethyl)pyridin-2-yl)amino)-7-azabicyclo[2.2.1]heptan-7-yl)methanone

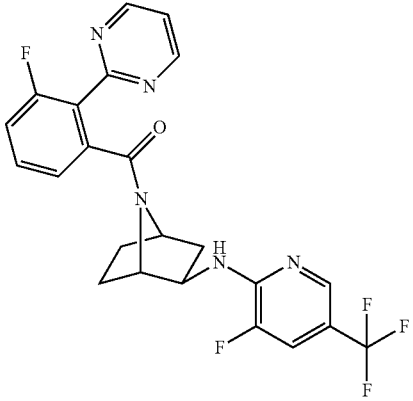

Step A: (1S,2R,4R)-tert-butyl 2-((3-fluoro-5-(trifluoromethyl)pyridin-2-yl)amino)-7-azabicyclo[2.2.1]heptane-7-carboxylate In a microwave vial was dissolved intermediate B-5 (1.6 g, 7.3 mmol) in ACN (11 mL). 2,3-difluoro-5-(trifluoromethyl)pyridine (0.74 mL, 5.82 mmol) was added followed by Et$_3$N (1 mL, 7.28 mmol). The microwave vial was capped and the reaction mixture was heated to reflux for 16 h. Solvent was evaporated and purification via silica gel chromatography (0-20% EtOAc in hexanes) gave the title compound (1.7 g, 94%). MS (ESI): mass calcd. for $C_{17}H_{21}F_4N_3O_2$, 375.2; m/z found, 376.2 [M+H]$^+$. $^1$H NMR (500 MHz, CDCl$_3$): δ 8.15 (s, 1H), 7.29 (dd, J=10.8, 2.0 Hz, 1H), 5.23 (s, 1H), 4.36-4.27 (m, 1H), 4.27-4.21 (m, 1H), 4.21-4.15 (m, 1H), 2.08 (dd, J=13.1, 7.7 Hz, 1H), 1.91-1.80 (m, 1H), 1.80-1.70 (m, 1H), 1.63-1.48 (m, 2H), 1.43 (s, 10H).

Step B: (1S,2R,4R)—N-(3-fluoro-5-(trifluoromethyl)pyridin-2-yl)-7-azabicyclo[2.2.1]heptan-2-amine To the title compound of step A (135 g, 0.36 mmol) in DCM (3.6 mL) was added 4M HCl in dioxane (0.9 mL). After 16 h, the reaction was concentrated, neutralized with 5% Na$_2$CO$_3$ (aq) and extracted with DCM (2×). The combined organics were dried (Na$_2$SO$_4$) to give the title compound of step B that was used without further purification. MS (ESI) mass calcd. for $C_{12}H_{13}F_4N_3$, 275.1; m/z found 276.0 [M+H]$^+$.

Step C: (3-fluoro-2-(pyrimidin-2-yl)phenyl)((1S,2R,4R)-2-((3-fluoro-5-(trifluoromethyl)pyridin-2-yl)amino)-7-azabicyclo[2.2.1]heptan-7-yl)methanone To the title compound of step B (98 g, 0.36 mmol) in DCM (3.6 mL) was added DIPEA (0.08 mL, 0.46 mmol) and intermediate A-2 (93 g, 0.43 mmol). Then T3P (50% solution in DMF, 0.64 mL, 1.07 mmol) was added dropwise and the reaction heated at 45° C. for 16 h. Solvent was evaporated and purification via prep HPLC gave the title compound (133 g, 79%). MS (ESI): mass calcd. for $C_{23}H_{18}F_5N_5O$, 475.1; m/z found, 476.1 [M+H]$^+$. $^1$H NMR (500 MHz, CDCl$_3$, Compound present as a mixture of rotamers (0.83:0.17), major rotamer reported) δ 8.84 (d, J=5.0 Hz, 2H), 8.05 (s, 1H), 7.59 (br s, 1H), 7.36-7.30 (m, 2H), 7.23-7.10 (m, 3H), 4.84-4.71 (m, 1H), 4.56-4.49 (m, 1H), 4.02 (d, J=4.8 Hz, 1H), 2.20 (dd, J=12.8, 8.3 Hz, 1H), 2.01-1.84 (m, 2H), 1.83-1.68 (m, 2H), 1.57-1.49 (m, 1H).

Example 383

((1S,2R,4R)-2-((3-chloro-5-(trifluoromethyl)pyridin-2-yl)amino)-7-azabicyclo[2.2.1]heptan-7-yl)(3-fluoro-2-(2H-1,2,3-triazol-2-yl)phenyl)methanone

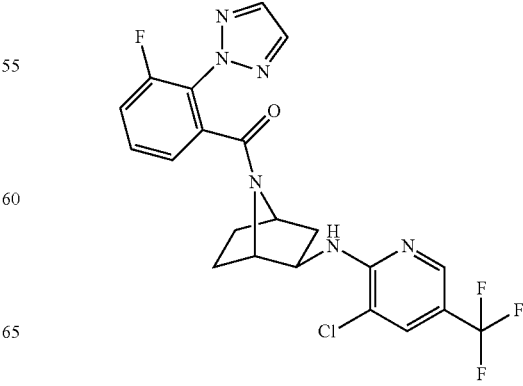

Step A: (1S,2R,4R)-tert-butyl 2-((3-chloro-5-(trifluoromethyl)pyridin-2-yl)amino)-7-azabicyclo[2.2.1]heptane-7-carboxylate Prepared analogous to Example 382 step A substituting 2,3-difluoro-5-(trifluoromethyl)pyridine with 3-chloro-2-fluoro-5-(trifluoromethyl(pyridine). MS (ESI): mass calcd. for $C_{17}H_{21}ClF_3N_3O_2$, 391.1; m/z found, 392.2 [M+H]$^+$. $^1$H NMR (500 MHz, CDCl$_3$) δ 8.26 (s, 1H), 7.62 (s, 1H), 5.65 (s, 1H), 4.39-4.22 (m, 2H), 4.22-4.13 (m, 1H), 2.09 (dd, J=13.1, 7.7 Hz, 1H), 1.90-1.81 (m, 1H), 1.81-1.71 (m, 1H), 1.62-1.49 (m, 2H), 1.44 (s, 10H).

Step B: (1S,2R,4R)—N-(3-chloro-5-(trifluoromethyl)pyridin-2-yl)-7-azabicyclo[2.2.1]heptan-2-amine Prepared analogous to Example 382 step B. MS (ESI): mass calcd. for $C_{12}H_{13}ClF_3N_3$, 291.1; m/z found, 292.1 [M+H]$^+$.

Step C: ((1S,2R,4R)-2-((3-chloro-5-(trifluoromethyl)pyridin-2-yl)amino)-7-azabicyclo[2.2.1]heptan-7-yl)(3-fluoro-2-(2H-1,2,3-triazol-2-yl)phenyl)methanone Prepared analogous to Example 382 step C substituting intermediate A-2 with intermediate A-16. MS (ESI): mass calcd. for $C_{21}H_{17}ClF_4N_6O$, 480.1; m/z found, 481.1 [M+H]$^+$. $^1$H NMR (400 MHz, CDCl$_3$, Compound present as a mixture of rotamers (0.64:0.36), only major rotamer reported) δ 8.16 (s, 1H), 7.88 (s, 2H), 7.60 (d, J=2.1 Hz, 1H), 7.43-7.30 (m, 1H), 7.25-7.21 (m, 1H), 7.18-7.12 (m, 1H), 4.77 (t, J=4.5 Hz, 1H), 4.29-4.19 (m, 1H), 3.92-3.89 (m, 1H), 2.13 (dd, J=13.1, 8.1 Hz, 1H), 1.80-1.36 (series of m, 5H).

Example 384

((1S,2R,4R)-2-((3-chloro-5-(trifluoromethyl)pyridin-2-yl)amino)-7-azabicyclo[2.2.1]heptan-7-yl)(3-fluoro-2-(pyrimidin-2-yl)phenyl)methanone

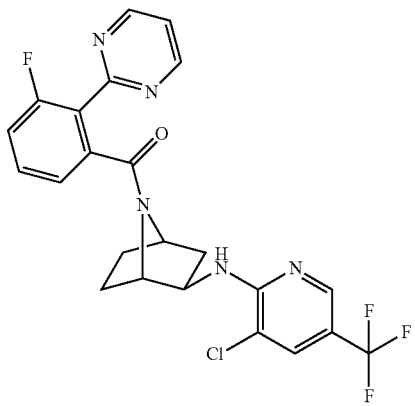

Prepared analogous to Example 383 substituting intermediate A-16 with A-2. MS (ESI): mass calcd. for $C_{23}H_{18}ClF_4N_5O$, 491.1; m/z found, 492.1 [M+H]$^+$. $^1$H NMR (400 MHz, CDCl$_3$, Compound present as a mixture of rotamers (0.74:0.26), only major rotamer reported) δ 8.84 (d, J=4.8 Hz, 2H), 8.17 (s, 1H), 7.55 (d, J=2.2 Hz, 1H), 7.32-7.26 (series of m, 2H), 7.19-7.12 (series of m, 2H), 4.77 (t, J=4.6 Hz, 1H), 4.46-4.31 (m, 1H), 3.98 (d, J=4.3 Hz, 1H), 2.25-2.13 (m, 1H), 1.93-1.63 (series of m, 4H), 1.59-1.35 (m, 1H).

Example 385

((1S,2R,4R)-2-((3-chloro-5-(trifluoromethyl)pyridin-2-yl)amino)-7-azabicyclo[2.2.1]heptan-7-yl)(2-(5-fluoropyrimidin-2-yl)phenyl)methanone

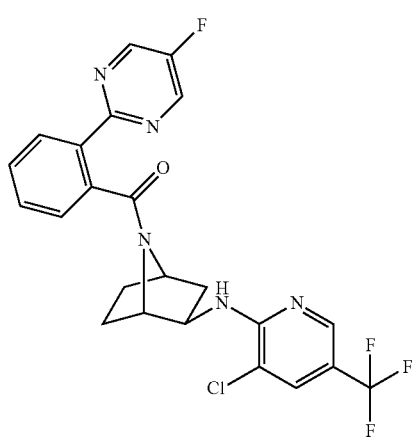

Prepared analogous to Example 383 substituting intermediate A-16 with A-55. MS (ESI): mass calcd. for $C_{23}H_{18}ClF_4N_5O$, 491.1; m/z found, 492.1 [M+H]$^+$. $^1$H NMR (400 MHz, CDCl$_3$, Compound present as a mixture of rotamers (0.72:0.28), only major rotamer reported) δ 8.63 (s, 2H), 8.17-8.12 (m, 1H), 8.08-8.02 (m, 1H), 7.56 (s, 1H), 7.57-7.37 (series of m, 2H), 7.37-7.29 (m, 1H), 4.93 (t, J=4.5 Hz, 1H), 4.36-4.24 (m, 1H), 3.90 (d, J=5.0 Hz, 1H), 2.21 (dd, J=13.0, 8.1 Hz, 1H), 2.00-1.51 (series of m, 5H).

Example 386

((1S,2R,4R)-2-((3-chloro-5-(trifluoromethyl)pyridin-2-yl)amino)-7-azabicyclo[2.2.1]heptan-7-yl)(2-(pyrimidin-2-yl)phenyl)methanone

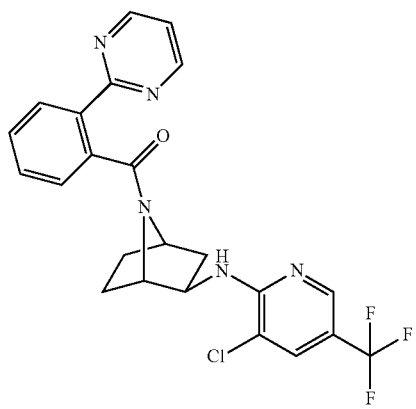

Prepared analogous to Example 383 substituting intermediate A-16 with A-59. MS (ESI): mass calcd. for $C_{23}H_{19}ClF_3N_5O$, 473.1; m/z found, 474.1 [M+H]$^+$. $^1$H NMR (400 MHz, CDCl$_3$, Compound present as a mixture of rotamers (0.74:0.26), only major rotamer reported) δ 8.79 (d, J=4.9 Hz, 2H), 8.15-8.10 (m, 2H), 7.54-7.52 (m, 1H), 7.46-7.39 (m, 1H), 7.37-7.29 (m, 2H), 7.22 (t, J=4.9 Hz, 1H), 4.93 (t, J=5.1 Hz, 1H), 4.42-4.24 (m, 1H), 3.89 (d, J=5.0 Hz, 1H), 2.20 (dd, J=12.9, 8.1 Hz, 1H), 1.99-1.47 (series of m, 5H).

Example 387

((1S,2R,4R)-2-((3-chloro-5-(trifluoromethyl)pyridin-2-yl)amino)-7-azabicyclo[2.2.1]heptan-7-yl)(3-(pyrimidin-2-yl)pyridin-2-yl)methanone

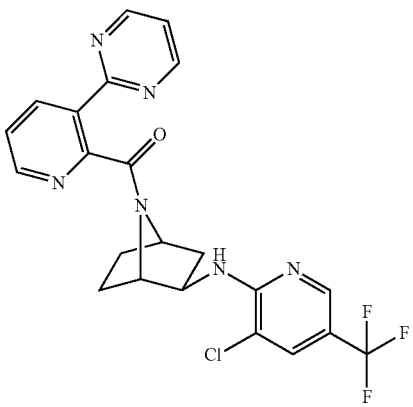

Prepared analogous to Example 383 substituting intermediate A-16 with A-64. MS (ESI): mass calcd. for $C_{22}H_{18}ClF_3N_6O$, 474.1; m/z found, 475.1 [M+H]$^+$. $^1$H NMR (400 MHz, CDCl$_3$, Compound present as a mixture of rotamers (0.89:0.11), only major rotamer reported) δ 8.79 (d, J=4.9 Hz, 2H), 8.64 (dd, J=4.8, 1.7 Hz, 1H), 8.50 (dd, J=7.9, 1.7 Hz, 1H), 8.23-8.19 (m, 1H), 7.60 (d, J=2.1 Hz, 1H), 7.47 (dd, J=7.9, 4.8 Hz, 1H), 7.38 (d, J=7.8 Hz, 1H), 7.25 (t, J=4.9 Hz, 1H), 4.94 (t, J=4.7 Hz, 1H), 4.38 (td, J=7.6, 2.9 Hz, 1H), 4.12 (d, J=4.8 Hz, 1H), 2.25 (dd, J=12.9, 7.4 Hz, 1H), 2.16-1.98 (series of m, 2H), 1.89-1.79 (m, 1H), 1.66-1.56 (series of m, 2H).

Example 388

((1S,2R,4R)-2-((5-(difluoromethyl)pyridin-2-yl)amino)-7-azabicyclo[2.2.1]heptan-7-yl)(3-fluoro-2-(2H-1,2,3-triazol-2-yl)phenyl)methanone

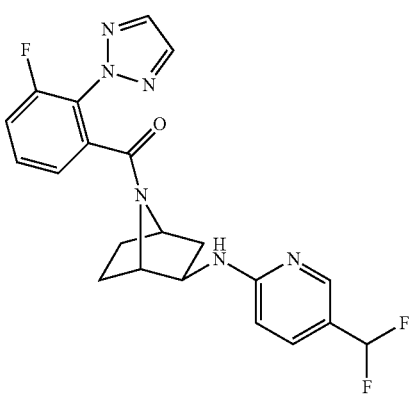 [SMILES: O=C(c1cccc(F)c1-n1nccn1)N1C2CCC1C(Nc1ccc(C(F)F)cn1)C2]

Step A: (1S,2R,4R)-tert-butyl 2-((5-(difluoromethyl)pyridin-2-yl)amino)-7-azabicyclo[2.2.1]heptane-7-carboxylate Prepared analogous to Example 279 step A substituting 2-chloro-5-(trifluoromethyl)pyridine with 2-chloro-5-(difluoromethyl)pyridine. MS (ESI): mass calcd. for $C_{17}H_{23}F_2N_3O_2$, 339.2; m/z found, 340.0 [M+H]$^+$. Analytical HPLC was obtained on a Agilent 1100 Series using an Inertsil ODS-3 column (3 μm, 50×3 mm), mobile phase of 5-99% ACN in 0.05% TFA over 1.6 min and then hold at 99% ACN for 0.4 min, at a flow rate of 2.2 ml/min (Temperature=50° C.). R$_t$=0.601 min at 254 nm.

Step B: (1S,2R,4R)—N-(5-(difluoromethyl)pyridin-2-yl)-7-azabicyclo[22.1]heptan-2-amine Prepared analogous to Example 279 step B. MS (ESI): mass calcd. for $C_{12}H_{15}F_2N_3$, 239.1; m/z found, 240.0 [M+H]$^+$.

Step C: ((1S,2R,4R)-2-((5-(difluoromethyl)pyridin-2-yl)amino)-7-azabicyclo[2.2.1]heptan-7-yl)(3-fluoro-2-(2H-1,2,3-triazol-2-yl)phenyl)methanone Prepared analogous to Example 181 step C substituting intermediate A-1 with intermediate A-16. MS (ESI): mass calcd. for $C_{21}H_{19}F_3N_6O$, 428.2; m/z found, 429.0 [M+H]$^+$. $^1$H NMR (500 MHz, CDCl$_3$, Compound present as a mixture of rotamers) δ 8.09-8.02 (m, 1H), 7.95 (s, 2H), 7.39-7.33 (m, 2H), 7.29-7.21 (m, 1H), 7.16 (dt, J=7.6, 1.2 Hz, 1H), 6.48 (t, J=56.3 Hz, 1H), 6.32 (d, J=8.8 Hz, 1H), 4.77-4.69 (m, 1H), 4.30-4.22 (m, 1H), 3.99 (d, J=4.9 Hz, 1H), 2.12 (dd, J=13.0, 8.1 Hz, 1H), 1.98-1.81 (m, 2H), 1.72-1.58 (m, 2H), 1.54-1.47 (m, 1H).

Example 389

((1S,2R,4R)-2-((5-(difluoromethyl)pyridin-2-yl)amino)-7-azabicyclo[2.2.1]heptan-7-yl)(3-fluoro-2-(pyrimidin-2-yl)phenyl)methanone

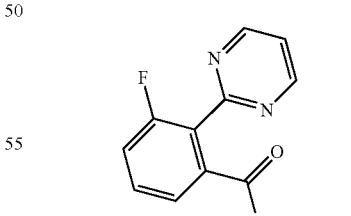

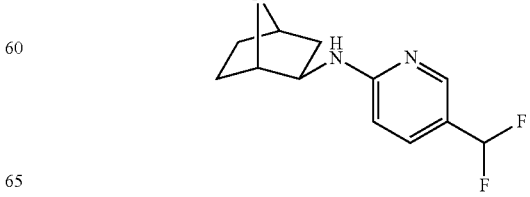

Prepared analogous to Example 388 substituting intermediate A-16 with intermediate A-2. MS (ESI): mass calcd. for $C_{23}H_{20}F_3N_5O$, 439.2; m/z found, 439.9 [M+H]$^+$. $^1$H NMR (500 MHz, CDCl$_3$, Compound present as a mixture of rotamers (0.89:0.11), only major rotamer reported) δ 8.87 (d, J=5.0 Hz, 2H), 8.09-8.02 (m, 1H), 7.51-7.43 (m, 1H), 7.37 (t, J=5.0 Hz, 1H), 7.34-7.28 (m, 1H), 7.21-7.12 (m, 2H), 6.47 (t, J=56.3 Hz, 1H), 6.22 (d, J=8.7 Hz, 1H), 4.78-4.65 (m, 1H), 4.35 (td, J=8.7, 3.7 Hz, 1H), 4.07 (d, J=4.9 Hz, 1H), 2.15 (dd, J=12.9, 8.1 Hz, 1H), 2.05-1.96 (m, 1H), 1.95-1.85 (m, 1H), 1.76-1.67 (m, 1H), 1.63-1.61 (m, 1H), 1.55-1.46 (m, 1H).

Example 390

6-(((1S,2R,4R)-7-(3-fluoro-2-(2H-1,2,3-triazol-2-yl)benzoyl)-7-azabicyclo[2.2.1]heptan-2-yl)amino)nicotinonitrile

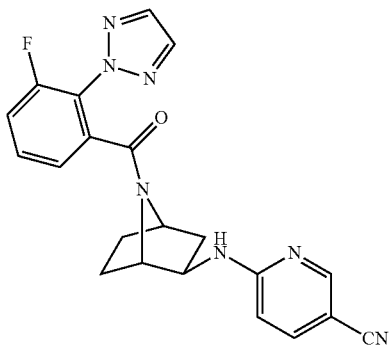

Step A: (1S,2R,4R)-tert-butyl 2-((5-cyanopyridin-2-yl)amino)-7-azabicyclo[2.2.1]heptane-7-carboxylate To a solution of intermediate B-5 (442 g, 2.08 mmol) in DMA (7 mL) was added DIPEA (0.72 mL, 4.16 mmol) followed by 2-chloro-5-cyanopyridine (324 g, 2.29 mmol). The reaction mixture was heated at 120° C. for 90 minutes using microwave and was then diluted with water and EtOAc. The aqueous phase was extracted twice with EtOAc and the combined organic layers were washed with a saturated solution of NaCl, dried over MgSO$_4$, filtered and evaporated. Purification via silica gel chromatography (0-40% EtOAc in hexanes) gave the title compound (416 g, 64%). MS (ESI): mass calcd. for $C_{17}H_{22}N_4O_2$, 314.2; m/z found, 315.1 [M+H]$^+$. $^1$H NMR (500 MHz, CDCl$_3$) δ 8.36 (d, J=2.2 Hz, 1H), 7.58-7.49 (m, 1H), 6.35 (d, J=8.7 Hz, 1H), 5.42 (s, 1H), 4.29 (s, 1H), 4.24-4.15 (m, 1H), 3.99 (s, 1H), 2.09-1.98 (m, 1H), 1.90-1.68 (m, 2H), 1.62-1.34 (m, 12H).

Step B: 6-((1S,2R,4R)-7-azabicyclo[2.2.1]heptan-2-ylamino)nicotinonitrile

To the title compound of step A (416 g, 1.32 mmol) in DCM (6.5 mL) was added 4M HCl in dioxane (1.7 mL). After 16 h, the reaction was concentrated, neutralized with 5% Na$_2$CO$_3$ (aq) and extracted with DCM (2×). The combined organics were dried (Na$_2$SO$_4$) to give the title compound of step B that was used without further purification. MS (ESI): mass calcd. for $C_{12}H_{14}N_4$, 214.1; m/z found, 215.0 [M+H]$^+$.

Step C: 6-(((1S,2R,4R)-7-(3-fluoro-2-(2H-1,2,3-triazol-2-yl)benzoyl)-7-azabicyclo[2.2.1]heptan-2-yl)amino)nicotinonitrile To a solution of the title compound of step B (30 g, 0.14 mmol) and intermediate A-16 (32 g, 0.15 mmol) in DCM (1.4 mL) was added DIPEA (0.15 mL, 0.84 mmol) followed by HATU (64 g, 0.17 mmol). The reaction mixture was stirred at room temperature for 16 h. Solvent was evaporated and purification via prep HPLC gave the title compound (44 g, 78%). MS (ESI): mass calcd. for $C_{21}H_{18}FN_7O$, 403.2; m/z found, 404.0 [M+H]$^+$. $^1$H NMR (500 MHz, CDCl$_3$, Compound present as a mixture of rotamers) δ 8.25 (d, J=2.1 Hz, 1H), 7.96 (s, 2H), 7.40-7.27 (series of m, 3H), 7.18 (dt, J=7.7, 1.1 Hz, 1H), 6.27 (d, J=8.9 Hz, 1H), 4.79-4.68 (m, 1H), 4.39-4.24 (m, 1H), 3.97 (d, J=5.0 Hz, 1H), 2.12 (dd, J=13.1, 8.2 Hz, 1H), 2.00-1.83 (m, 2H), 1.73-1.64 (m, 2H), 1.55-1.48 (m, 1H).

Example 391

6-(((1S,2R,4R)-7-(3-methyl-2-(2H-1,2,3-triazol-2-yl)benzoyl)-7-azabicyclo[2.2.1]heptan-2-yl)amino)nicotinonitrile

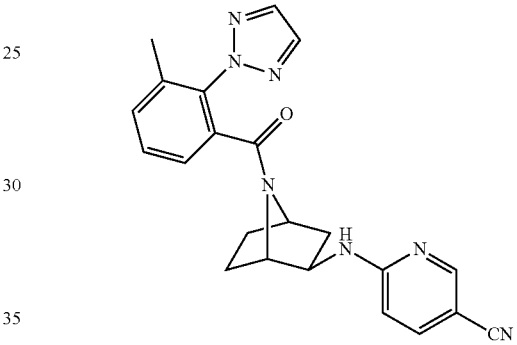

Prepared analogous to Example 390 substituting intermediate A-16 with A-24. MS (ESI): mass calcd. for $C_{22}H_{21}N_7O$, 399.2; m/z found, 400.0 [M+H]$^+$. $^1$H NMR (500 MHz, CDCl$_3$, Compound present as a mixture of rotamers (0.81:0.19), only major rotamer reported) δ 8.25 (d, J=2.3 Hz, 1H), 7.90 (s, 2H), 7.39-7.27 (series of m, 3H), 7.23-7.15 (m, 1H), 6.31 (d, J=9.0 Hz, 1H), 4.68 (t, J=4.8 Hz, 1H), 4.37-4.20 (m, 1H), 3.95 (d, J=5.1 Hz, 1H), 2.19 (s, 3H), 2.12-2.03 (m, 1H), 1.99-1.94 (m, 1H), 1.89-1.77 (m, 1H), 1.66-1.61 (m, 1H), 1.61-1.52 (m, 1H), 1.52-1.39 (m, 1H).

Example 392

6-(((1S,2R,4R)-7-(3-fluoro-2-(pyrimidin-2-yl)benzoyl)-7-azabicyclo[2.2.1]heptan-2-yl)amino)nicotinonitrile

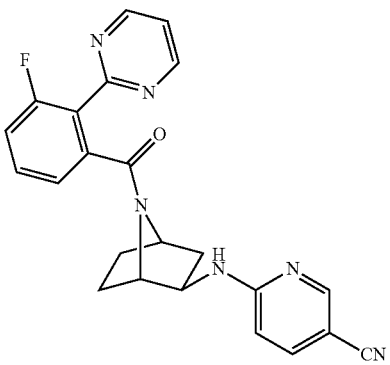

Prepared analogous to Example 390 substituting intermediate A-16 with A-2. MS (ESI): mass calcd. for $C_{23}H_{19}FN_6O$, 414.2; m/z found, 415.0 [M+H]+. 1H NMR (500 MHz, CDCl3, Compound present as a mixture of rotamers) δ 8.87 (d, J=5.0 Hz, 2H), 8.25 (d, J=2.2 Hz, 1H), 8.10-7.99 (m, 1H), 7.40 (t, J=4.9 Hz, 1H), 7.38-7.34 (m, 1H), 7.31-7.27 (m, 1H), 7.22-7.20 (m, 1H), 7.19-7.15 (m, 1H), 6.16 (d, J=8.8 Hz, 1H), 4.79-4.67 (m, 1H), 4.48-4.30 (m, 1H), 4.07 (d, J=5.0 Hz, 1H), 2.15 (dd, J=13.0, 8.2 Hz, 1H), 2.07-2.00 (m, 1H), 1.96-1.88 (m, 1H), 1.76-1.68 (m, 1H), 1.68-1.63 (m, 1H), 1.56-1.48 (m, 1H).

Example 393

6-(((1S,2R,4R)-7-(3-methyl-2-(pyrimidin-2-yl)benzoyl)-7-azabicyclo[2.2.1]heptan-2-yl)amino)nicotinonitrile

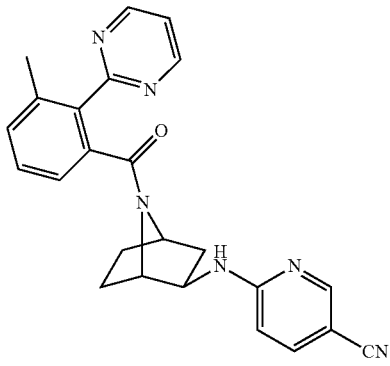

Prepared analogous to Example 390 substituting intermediate A-16 with A-26. MS (ESI): mass calcd. for $C_{24}H_{22}N_6O$, 410.2; m/z found, 411.0 [M+H]+. 1H NMR (500 MHz, CDCl3, Compound present as a mixture of rotamers) δ 8.83 (d, J=5.0 Hz, 2H), 8.25 (d, J=2.3 Hz, 1H), 7.35 (t, J=5.0 Hz, 1H), 7.32-7.21 (m, 3H), 7.21-7.18 (m, 1H), 6.17 (d, J=8.8 Hz, 1H), 4.72-4.62 (m, 1H), 4.42-4.31 (m, 1H), 4.07 (d, J=5.0 Hz, 1H), 2.30 (s, 3H), 2.11 (dd, J=12.9, 8.1 Hz, 1H), 2.07-1.98 (m, 1H), 1.95-1.84 (m, 1H), 1.72-1.65 (m, 1H), 1.61-1.54 (m, 1H), 1.52-1.45 (m, 1H).

Example 394

6-(((1S,2R,4R)-7-(3-methyl-2-(oxazol-2-yl)benzoyl)-7-azabicyclo[2.2.1]heptan-2-yl)amino)nicotinonitrile

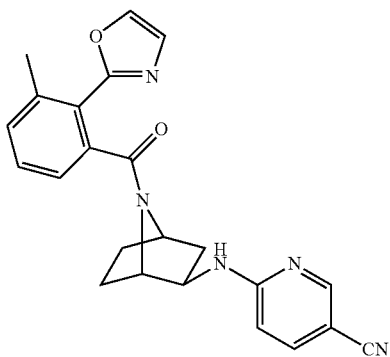 [SMILES: Cc1cccc(C(=O)N2C3CCC2C(Nc2ccc(C#N)cn2)C3)c1-c1ncco1]

Prepared analogous to Example 390 substituting intermediate A-16 with A-31. MS (ESI): mass calcd. for $C_{23}H_{21}N_5O_2$, 399.2; m/z found, 400.0 [M+H]+. 1H NMR (500 MHz, CDCl3, Compound present as a mixture of rotamers (0.89:0.11), only major rotamer reported) δ 8.22 (d, J=2.2 Hz, 1H), 7.88 (d, J=0.9 Hz, 1H), 7.32-7.22 (series of m, 4H), 7.20-7.13 (m, 1H), 6.29 (dd, J=9.0, 0.8 Hz, 1H), 4.79-4.70 (m, 1H), 4.39-4.27 (m, 1H), 3.91 (d, J=4.8 Hz, 1H), 2.28 (s, 3H), 2.09 (dd, J=12.9, 8.2 Hz, 1H), 2.00-1.87 (m, 2H), 1.73-1.64 (m, 2H), 1.54-1.46 (m, 1H).

Example 395

(3-fluoro-2-(pyrimidin-2-yl)phenyl)((1S,2R,4R)-(2-2H)-((5-(trifluoromethyl)pyrazin-2-yl)amino)-7-azabicyclo[2.2.1]heptan-7-yl)methanone

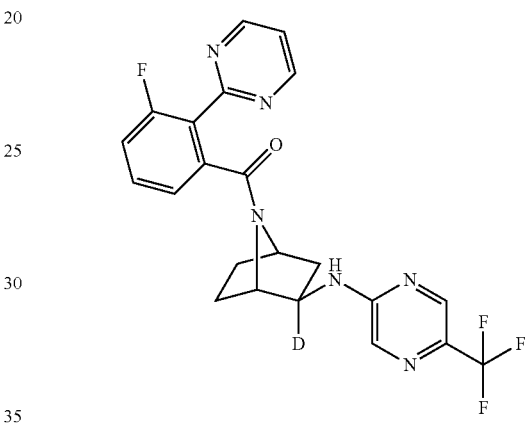

Step A: (1S,4R)-(2-2H)-tert-butyl 2-(((benzyloxy)carbonyl)amino)-7-azabicyclo[2.2.1]heptane-7-carboxylate To a solution of intermediate (+)-B-2 (640 mg, 1.9 mmol) in CD3OD (5.5 mL) was added 0.45M NaOCD3 in CD3OD (5.8 mL, 2.90 mmol). The reaction mixture was heated to reflux for 2 days and cooled to room temperature. 1N KHSO4 was added and the aqueous phase was extracted 3 times with DCM. The combined organic layers were dried over MgSO4, filtered and evaporated. The material was used in the next step without any further purification. To a solution of the residue in CD3OD (9.6 mL) cooled to 0° C. was added 2M NaOH in D2O (3.9 mL, 7.7 mmol). The reaction mixture was stirred for 2 h and was then acidified with 1N KHSO4 until pH 2-3. The aqueous phase was extracted 3 times with DCM and the combined organic layers were dried over MgSO4, filtered and evaporated. The material was used in the next step without any further purification. To the residue in PhCH3 (4.8 mL) was added TEA (0.3 mL, 2.1 mmol). After heating in an oil bath to 70° C., DPPA (0.46 mL, 2.1 mmol) in PhCH3 (1 mL) was added. After 2.5 h, BnOH (0.19 mL, 1.8 mmol) was added and the oil bath temperature increased to 90° C. After an additional 18 h, the reaction was cooled to rt, diluted with EtOAc and washed with saturated NaHCO3 (aq). The aqueous layer was extracted with EtOAc (1x). The combined organics were washed with brine and dried (MgSO4). Purification via prep HPLC gave the title compound (380 g, 57%) as a mixture of diastereoisomers (80/20). MS (ESI): mass calcd. for $C_{19}H_{25}DN_2O_4$, 347.2; m/z found, 348.2 [M+H]⁺. Reporting only the major diastereoisomer. ¹H NMR (500 MHz, CDCl₃) δ 7.40-7.28 (m, 5H), 5.22-4.91 (m, 3H), 4.22 (s, 1H), 4.14-4.06 (m, 1H), 1.92 (d, J=13.1 Hz, 1H), 1.85-1.59 (m, 2H), 1.44 (d, J=7.6 Hz, 12H).

Step B: (1S,2R,4R)-(2-²H)-tert-butyl 2-((5-(trifluoromethyl)pyrazin-2-yl)amino)-7-azabicyclo[2.2.1]heptane-7-carboxylate To intermediate of step A (380 g, 1.1 mmol) in EtOH (6.5 mL) was added 10 wt % Pd/C wet Degussa (79 mg). The reaction was purged with N₂ followed by H₂, then allowed to proceed under an atmosphere of H₂ (balloon). Upon completion, the reaction was filtered and concentrated to give the unprotected amine. MS (ESI): mass calcd. for $C_{11}H_{19}DN_2O_2$, 213.2; m/z found, 214.2 [M+H]⁺. In a microwave vial was dissolved the residue in ACN (3.7 mL). 5-chloro-2-trifluoromethylpyrazine (0.08 mL, 0.66 mmol) was added followed by Et₃N (0.11 mL, 0.82 mmol). The microwave vial was capped and the reaction mixture was heated to reflux for 16 h. Solvent was evaporated and purification via silica gel chromatography (0-30% EtOAc in hexanes) gave the title compound (119 g, 60%). Only the desired diastereoisomer was isolated. MS (ESI): mass calcd. for $C_{16}H_{20}DF_3N_4O_2$, 359.2; m/z found, 360.2 [M+H]⁺. ¹H NMR (400 MHz, CDCl₃) δ 8.32 (s, 1H), 7.85 (s, 1H), 5.38 (s, 1H), 4.30 (s, 1H), 4.21 (s, 1H), 2.06 (d, J=13.0 Hz, 1H), 1.95-1.68 (m, 2H), 1.66-1.35 (m, 12H).

Step C: (3-fluoro-2-(pyrimidin-2-yl)phenyl) ((1S,2R,4R)-(2-²H)-((5-(trifluoromethyl)pyrazin-2-yl)amino)-7-azabicyclo[2.2.1]heptan-7-yl)methanone To the title compound of step B (119 g, 0.33 mmol) in DCM (3.3 mL) was added 4M HCl in dioxane (0.4 mL). After 16 h, the reaction was concentrated, neutralized with 5% Na₂CO₃ (aq) and extracted with DCM (2×). The combined organics were dried (Na₂SO₄) to give the unprotected amine that was used without any further purification in the next step. MS (ESI): mass calcd. for $C_{11}H_{12}DF_3N_4$, 259.1; m/z found, 260.2 [M+H]⁺. To the residue in DCM (3.3 mL) was added DIPEA (0.07 mL, 0.43 mmol) and intermediate A-2 (86 g, 0.39 mmol). Then T3P (50% solution in DMF, 0.59 mL, 0.98 mmol) was added dropwise and the reaction heated at 45° C. for 16 h. Solvent was evaporated and purification via prep HPLC gave the title compound (107 mg, 71%). MS (ESI): mass calcd. for $C_{22}H_{17}DF_4N_6O$, 459.2; m/z found, 460.2 [M+H]⁺. ¹H NMR (500 MHz, CDCl₃, Compound present as a mixture of rotamers (0.93:0.07), only major rotamer reported) δ 8.88 (d, J=5.0 Hz, 2H), 8.27 (s, 1H), 8.19 (s, 1H), 7.65 (d, J=1.4 Hz, 1H), 7.42-7.36 (m, 2H), 7.25-7.17 (m, 2H), 4.77-4.72 (m, 1H), 4.07 (d, J=5.1 Hz, 1H), 2.17 (s, 1H), 2.09-2.02 (m, 1H), 1.98-1.89 (m, 1H), 1.75-1.71 (m, 1H), 1.69-1.64 (m, 1H), 1.55-1.49 (m, 1H).

Example 396

(4-methyl-3-(2H-1,2,3-triazol-2-yl)pyridin-2-yl)((1S,2R,4R)-2-((5-(trifluoromethyl)pyridin-2-yl)amino)-7-azabicyclo[2.2.1]heptan-7-yl)methanone

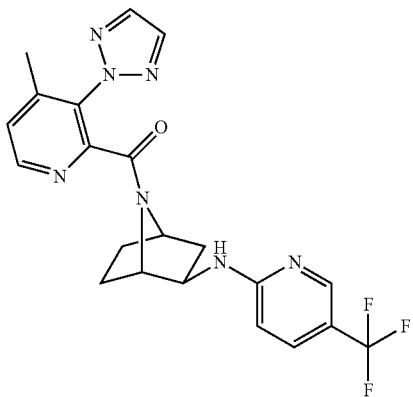

Example 397

(2-(5-fluoropyrimidin-2-yl)phenyl)((1S,2R,4R)-2-((5-(trifluoromethyl)pyrazin-2-yl)amino)-7-azabicyclo[2.2.1]heptan-7-yl)methanone

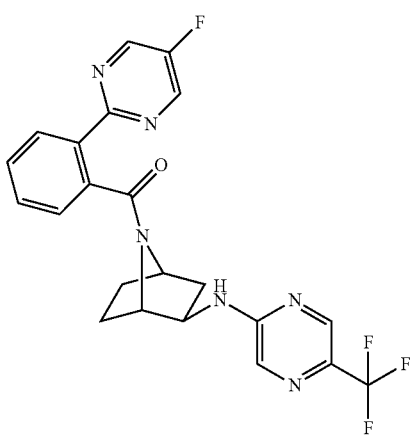

Prepared analogous to Example 238 substituting intermediate A-2 with intermediate A-55. MS (ESI): mass calcd. for $C_{22}H_{18}F_4N_6O$, 458.1; m/z found, 458.9 [M+H]⁺. ¹H NMR (500 MHz, CDCl₃) δ 8.69 (s, 2H), 8.15 (s, 1H), 7.91 (d, J=7.8 Hz, 1H), 7.48-7.31 (m, 4H), 4.86-4.77 (m, 1H), 4.29 (s, 1H), 4.09-3.90 (m, 1H), 2.19-1.50 (series of m, 6H).

Example 398

(3-fluoro-2-(5-fluoropyrimidin-2-yl)phenyl)((1S,2R,4R)-2-((5-(trifluoromethyl)pyrazin-2-yl)amino)-7-azabicyclo[2.2.1]heptan-7-yl)methanone

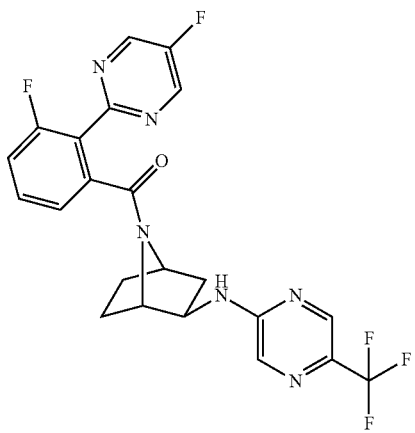

Prepared analogous to Example 238 substituting intermediate A-2 with intermediate A-57. MS (ESI): mass calcd. for $C_{22}H_{17}F_5N_6O$, 476.1; m/z found, 476.9 [M+H]$^+$. $^1$H NMR (400 MHz, CDCl$_3$) δ 8.73 (s, 2H), 8.19 (s, 1H), 7.69 (d, J=9.0 Hz, 1H), 7.64 (d, J=1.5 Hz, 1H), 7.40-7.32 (m, 1H), 7.20-7.17 (m, 1H), 4.72 (t, J=5.2 Hz, 1H), 4.33 (td, J=8.7, 3.6 Hz, 1H), 4.07 (d, J=5.0 Hz, 1H), 2.16 (dd, J=13.1, 8.1 Hz, 1H), 2.10-1.97 (m, 1H), 1.96-1.85 (m, 1H), 1.77-1.68 (m, 1H), 1.65-1.58 (m, 1H), 1.57-1.48 (m, 1H).

Example 399

(2-(5-fluoropyrimidin-2-yl)-3-methylphenyl)((1S,2R,4R)-2-((5-(trifluoromethyl)pyrazin-2-yl)amino)-7-azabicyclo[2.2.1]heptan-7-yl)methanone

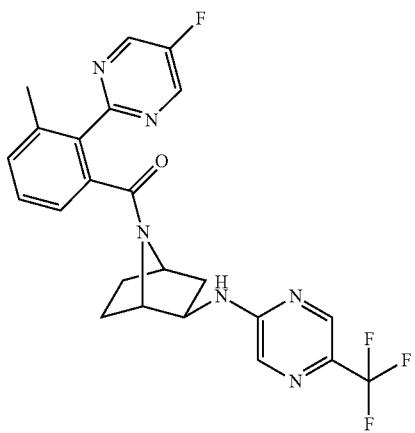

Prepared analogous to Example 238 substituting intermediate A-2 with intermediate A-56. Analytical HPLC was obtained on a Agilent 1100 Series using an Inertsil ODS-3 column (3 μm, 50×3 mm), mobile phase of 5-99% ACN in 0.05% TFA over 1.6 min and then hold at 99% ACN for 0.4 min, at a flow rate of 2.2 mL/min (Temperature=50° C.). R$_t$=1.38 min (major rotamer) at 254 nm. $^1$H NMR (500 MHz, CDCl$_3$) δ 8.70 (s, 2H), 8.17 (s, 1H), 7.88 (d, J=9.1 Hz, 1H), 7.63 (is, 1H), 7.26-7.18 (m, 2H), 4.73-4.65 (m, 1H), 4.36-4.26 (m, 1H), 4.11 (d, J=5.2 Hz, 1H), 2.26 (s, 3H), 2.13 (dd, J=13.0, 8.1 Hz, 1H), 2.10-2.01 (m, 1H), 1.95-1.86 (m, 1H), 1.70-1.64 (m, 1H), 1.60-1.55 (m, 1H), 1.54-1.45 (m, 1H).

Example 400

(2-(pyrimidin-2-yl)phenyl)((1S,2R,4R)-2-((5-(trifluoromethyl)pyrazin-2-yl)amino)-7-azabicyclo[2.2.1]heptan-7-yl)methanone

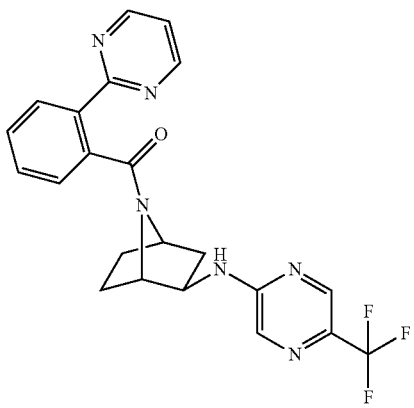

Prepared analogous to Example 238 substituting intermediate A-2 with intermediate A-59. MS (ESI): mass calcd. for $C_{22}H_{19}F_3N_6O$, 440.2; m/z found, 441.2 [M+H]$^+$. $^1$H NMR (500 MHz, CDCl$_3$, Compound present as a mixture of rotamers (0.88:0.12), only major rotamer reported) δ 8.84 (d, J=4.9 Hz, 2H), 8.16 (s, 1H), 7.99-7.92 (m, 1H), 7.53-7.47 (m, 1H), 7.45-7.32 (series of m, 4H), 4.85 (t, J=4.8 Hz, 1H), 4.46-4.33 (m, 1H), 4.07 (d, J=5.0 Hz, 1H), 2.20 (dd, J=13.0, 8.1 Hz, 1H), 2.06-1.91 (m, 2H), 1.86-1.66 (m, 2H), 1.59-1.52 (m, 1H).

Example 401

(5-methyl-2-(2H-1,2,3-triazol-2-yl)pyridin-3-yl)((1S,2R,4R)-2-((5-(trifluoromethyl)pyrazin-2-yl)amino)-7-azabicyclo[2.2.1]heptan-7-yl)methanone

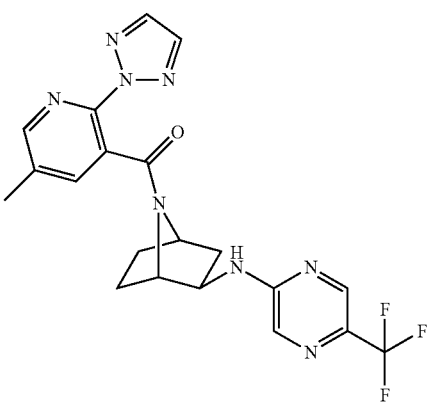 [SMILES: Cc1cnc(-n2nccn2)c(C(=O)N2C3CCC2C(Nc2cnc(C(F)(F)F)cn2)C3)c1]

Prepared analogous to Example 238 substituting intermediate A-2 with intermediate A-60. MS (ESI): mass calcd. for $C_{20}H_{19}F_3N_5O$, 444.2; m/z found, 445.2 [M+H]$^+$. Analytical HPLC was obtained on a Agilent 1100 Series using an Inertsil ODS-3 column (3 μm, 50×3 mm), mobile phase of 5-99% ACN in 0.05% TFA over 1.6 min and then hold at 99% ACN for 0.4 min, at a flow rate of 2.2 mL/min (Temperature=50° C.). $R_t$=1.13 min (major rotamer) at 254 nm.

Example 402

(2-(2H-1,2,3-triazol-2-yl)pyridin-3-yl)((1S,2R,4R)-2-((5-(trifluoromethyl)pyrazin-2-yl)amino)-7-azabicyclo[2.2.1]heptan-7-yl)methanone

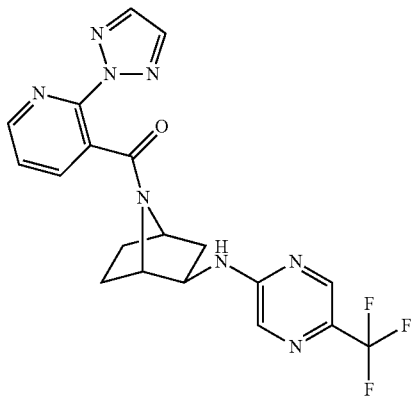

Prepared analogous to Example 238 substituting intermediate A-2 with intermediate A-61. MS (ESI): mass calcd. for $C_{19}H_{17}F_3N_5O$, 430.1; m/z found, 431.1 [M+H]$^+$. Analytical HPLC was obtained on a Agilent 1100 Series using an Inertsil ODS-3 column (3 μm, 50×3 mm), mobile phase of 5-99% ACN in 0.05% TFA over 1.6 min and then hold at 99% ACN for 0.4 min, at a flow rate of 2.2 mL/min (Temperature=50° C.). $R_t$=1.05 min (major rotamer) at 254 nm.

Example 403

(6-methyl-3-(pyrimidin-2-yl)pyridin-2-yl)((1S,2R,4R)-2-((5-(trifluoromethyl)pyrazin-2-yl)amino)-7-azabicyclo[2.2.1]heptan-7-yl)methanone

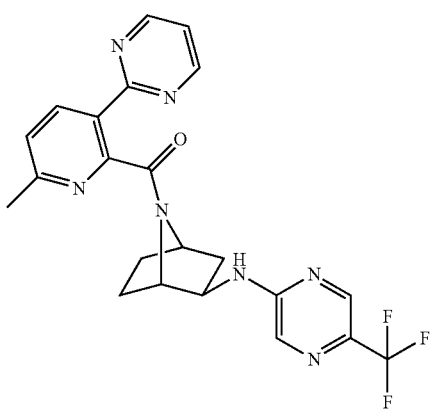

Prepared analogous to Example 238 substituting intermediate A-2 with intermediate A-63. MS (ESI): mass calcd. for $C_{22}H_{20}F_3N_7O$, 455.2; m/z found, 456.2 [M+H]$^+$. $^1$H NMR (500 MHz, CDCl$_3$, Compound present as a mixture of rotamers, major rotamer reported) δ 8.80 (d, J=4.9 Hz, 2H), 8.31 (d, J=8.0 Hz, 1H), 8.23 (s, 1H), 7.82 (d, J=8.5 Hz, 1H), 7.66 (d, J=1.4 Hz, 1H), 7.30 (d, J=1.2 Hz, 1H), 7.30-7.28 (m, 1H), 4.94-4.87 (m, 1H), 4.35-4.25 (m, 1H), 4.14 (d, J=5.3 Hz, 1H), 2.61 (s, 3H), 2.20 (dd, J=13.1, 7.6 Hz, 1H), 2.16-2.09 (m, 1H), 2.06-1.97 (m, 1H), 1.84-1.76 (m, 1H), 1.63-1.58 (m, 2H).

Example 404

(5-methyl-2-(pyrimidin-2-yl)pyridin-3-yl)((1S,2R,4R)-2-((5-(trifluoromethyl)pyrazin-2-yl)amino)-7-azabicyclo[2.2.1]heptan-7-yl)methanone

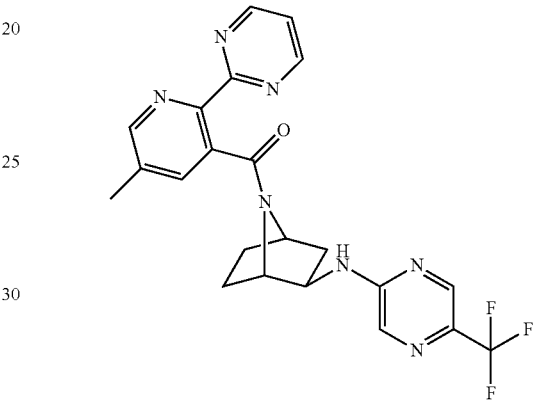

Prepared analogous to Example 238 substituting intermediate A-2 with intermediate A-66. MS (ESI): mass calcd. for $C_{22}H_{20}F_3N_7O$, 455.2; m/z found, 456.2 [M+H]$^+$. $^1$H NMR (400 MHz, CDCl$_3$, Compound present as a mixture of rotamers (0.79:0.21), only major rotamer reported) δ 8.89 (d, J=4.9 Hz, 2H), 8.61 (d, J=2.1 Hz, 1H), 8.18 (s, 1H), 7.54-7.46 (m, 2H), 7.41 (t, J=4.9 Hz, 1H), 4.85 (t, J=4.5 Hz, 1H), 4.39 (s, 1H), 3.97 (d, J=4.4 Hz, 1H), 2.37 (s, 3H), 2.22 (dd, J=13.0, 8.0 Hz, 1H), 2.07-1.90 (m, 2H), 1.85-1.65 (m, 2H), 1.61-1.52 (m, 1H).

Example 405

(5-methyl-3-(pyrimidin-2-yl)pyridin-2-yl)((1S,2R,4R)-2-((5-(trifluoromethyl)pyrazin-2-yl)amino)-7-azabicyclo[2.2.1]heptan-7-yl)methanone

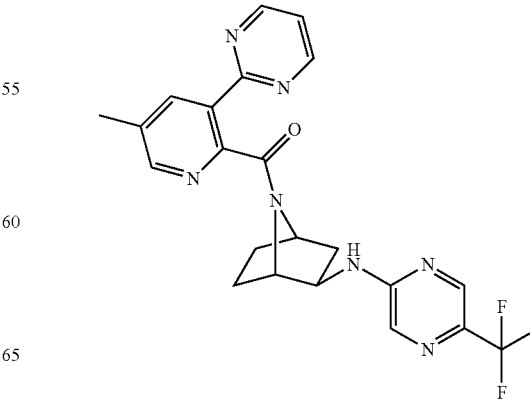

Prepared analogous to Example 238 substituting intermediate A-2 with intermediate A-67. MS (ESI): mass calcd. for $C_{22}H_{20}F_3N_7O$, 455.2; m/z found, 456.2 [M+H]$^+$. $^1$H NMR (500 MHz, CDCl$_3$, Compound present as a mixture of rotamers (0.90:0.10), only major rotamer reported) δ 8.83 (d, J=4.9 Hz, 2H), 8.43-8.37 (m, 1H), 8.21 (s, 1H), 8.18-8.13 (m, 1H), 7.93-7.85 (m, 1H), 7.56 (s, 1H), 7.34 (t, J=4.9 Hz, 1H), 4.93-4.84 (m, 1H), 4.31 (td, J=8.4, 3.0 Hz, 1H), 4.19 (d, J=5.3 Hz, 1H), 2.40 (s, 3H), 2.20 (dd, J=13.1, 7.8 Hz, 1H), 2.17-2.11 (m, 1H), 2.03-1.94 (m, 1H), 1.84-1.76 (m, 1H), 1.64-1.53 (series of m, 2H).

Example 406

(3-(pyrimidin-2-yl)pyridin-2-yl)((1S,2R,4R)-2-((5-(trifluoromethyl)pyrazin-2-yl)amino)-7-azabicyclo[2.2.1]heptan-7-yl)methanone

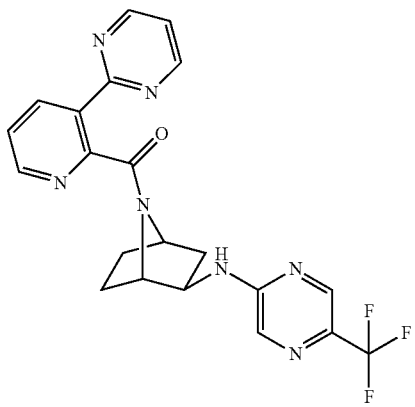

Prepared analogous to Example 238 substituting intermediate A-2 with intermediate A-64. MS (ESI): mass calcd. for $C_{21}H_{18}F_3N_7O$, 441.2; m/z found, 442.2 [M+H]$^+$. $^1$H NMR (500 MHz, CDCl$_3$, Compound present as a mixture of rotamers (0.91:0.09), only major rotamer reported) δ 8.84 (d, J=4.9 Hz, 2H), 8.58 (dd, J=4.8, 1.7 Hz, 1H), 8.38 (dd, J=7.9, 1.7 Hz, 1H), 8.21 (s, 1H), 7.83 (d, J=8.8 Hz, 1H), 7.58 (s, 1H), 7.44 (dd, J=7.9, 4.8 Hz, 1H), 7.34 (t, J=4.9 Hz, 1H), 4.90 (t, J=4.8 Hz, 1H), 4.40-4.26 (m, 1H), 4.16 (d, J=5.3 Hz, 1H), 2.21 (dd, J=13.1, 7.8 Hz, 1H), 2.18-2.11 (m, 1H), 2.05-1.94 (m, 1H), 1.87-1.78 (m, 1H), 1.68-1.55 (m, 2H).

Example 407

[1,1'-biphenyl]-2-yl((1S,2R,4R)-2-((5-(trifluoromethyl)pyrazin-2-yl)amino)-7-azabicyclo[2.2.1]heptan-7-yl)methanone

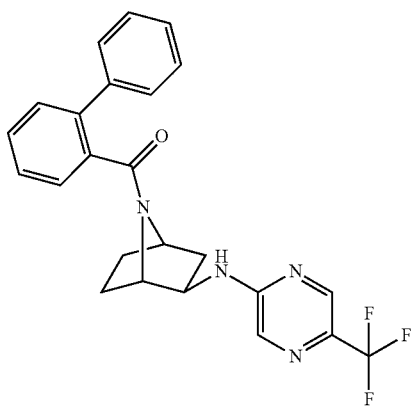

Prepared analogous to Example 238 substituting intermediate A-2 with 2-biphenylcarboxylic acid. MS (ESI): mass calcd. for $C_{24}H_{21}F_3N_4O$, 438.2; m/z found, 438.9 [M+H]$^+$. Analytical HPLC was obtained on a Agilent 1100 Series using an Inertsil ODS-3 column (31 μm, 50×3 mm), mobile phase of 5-99% ACN in 0.05% TFA over 1.6 min and then hold at 99% ACN for 0.4 min, at a flow rate of 2.2 mL/min (Temperature=50° C.). $R_t$=1.46 min (major rotamer) at 254 nm.

Example 408

(3-fluoro-2-(pyridin-2-yl)phenyl)((1S,2R,4R)-2-((5-(trifluoromethyl)pyrazin-2-yl)amino)-7-azabicyclo[2.2.1]heptan-7-yl)methanone

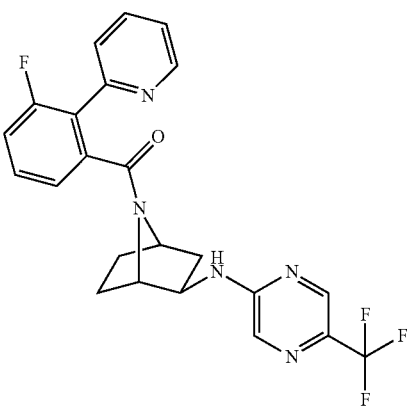

Prepared analogous to Example 260 substituting 2-(tributylstannyl)oxazole with 2-(tributylstannyl)pyridine. MS (ESI): mass calcd. for $C_{23}H_{19}F_4N_5O$, 457.2; m/z found, 458.2 [M+H]$^+$. $^1$H NMR (500 MHz, CDCl$_3$, Compound present as a mixture of rotamers, only major rotamer reported) δ 8.55 (d, J=5.4 Hz, 1H), 8.17 (s, 1H), 7.88 (td, J=7.8, 1.8 Hz, 1H), 7.68 (dd, J=8.0, 3.2 Hz, 1H), 7.59 (s, 1H), 7.43-7.38 (m, 1H), 7.37-7.31 (m, 1H), 7.20-7.14 (m, 2H), 4.78 (t, J=4.9 Hz, 1H), 4.53-4.42 (m, 1H), 4.02 (d, J=4.9 Hz, 1H), 2.19 (dd, J=12.9, 8.1 Hz, 1H), 2.11-1.86 (series of m, 2H), 1.81-1.68 (series of m, 2H), 1.58-1.49 (m, 1H).

Example 409

(3-methyl-2-(oxazol-2-yl)phenyl)((1S,2R,4R)-2-((5-(trifluoromethyl)pyrazin-2-yl)amino)-7-azabicyclo[2.2.1]heptan-7-yl)methanone

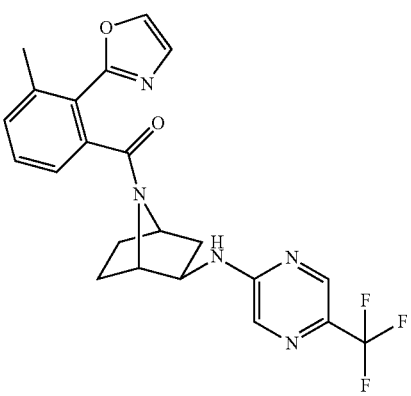 [SMILES: Cc1cccc(C(=O)N2C3CCC2C(Nc2cnc(C(F)(F)F)cn2)C3)c1-c1ncco1]

Prepared analogous to Example 263 substituting 3-(tributylstannyl)pyridazine with 2-(tributylstannyl)oxazole. MS (ESI): mass calcd. for $C_{22}H_{20}F_3N_5O_2$, 443.2; m/z found, 444.2 [M+H]+. 1H NMR (500 MHz, CDCl3, Compound present as a mixture of rotamers (0.91:0.09), only major rotamer reported) δ 8.14 (s, 1H), 7.88 (d, J=0.9 Hz, 1H), 7.79 (d, J=1.4 Hz, 1H), 7.31-7.27 (m, 2H), 7.26-7.23 (m, 1H), 7.20-7.13 (m, 1H), 4.78 (t, J=4.6 Hz, 1H), 4.33-4.26 (m, 1H), 3.94 (d, J=4.9 Hz, 1H), 2.28 (s, 3H), 2.12 (dd, J=13.0, 8.2 Hz, 1H), 2.06-1.88 (series of m, 2H), 1.77-1.64 (series of m, 2H), 1.56-1.48 (m, 1H).

Example 410

(5-fluoro-2-(oxazol-2-yl)phenyl)((1S,2R,4R)-2-((5-(trifluoromethyl)pyrazin-2-yl)amino)-7-azabicyclo[2.2.1]heptan-7-yl)methanone

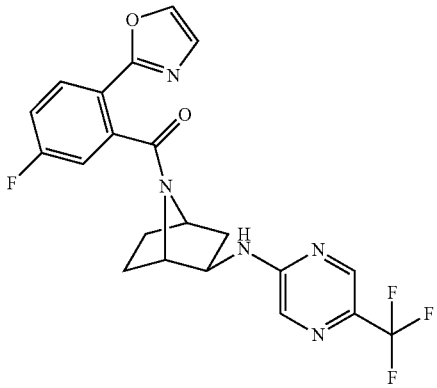 [SMILES: O=C(c1cc(F)ccc1-c1ncco1)N1C2CCC1C(Nc1cnc(C(F)(F)F)cn1)C2]

Prepared analogous to Example 238 substituting intermediate A-2 with intermediate A-69. MS (ESI): mass calcd. for $C_{21}H_{17}F_4N_5O_2$, 447.1; m/z found, 448.1 [M+H]+. 1H NMR (500 MHz, CDCl3, Compound present as a mixture of rotamers (0.65:0.35), only major rotamer reported) δ 8.16 (s, 1H), 7.86-7.79 (series of m, 2H), 7.37-7.30 (series of m, 2H), 7.19-7.09 (m, 1H), 7.04 (dd, J=8.2, 2.7 Hz, 1H), 4.93 (t, J=4.4 Hz, 1H), 4.37-4.30 (m, 1H), 3.87-3.81 (m, 1H), 2.19 (dd, J=13.1, 8.1 Hz, 1H), 2.05-1.68 (series of m, 4H), 1.62-1.43 (m, 1H).

Example 411

(2-fluoro-6-(oxazol-2-yl)phenyl)((1S,2R,4R)-2-((5-(trifluoromethyl)pyrazin-2-yl)amino)-7-azabicyclo[2.2.1]heptan-7-yl)methanone

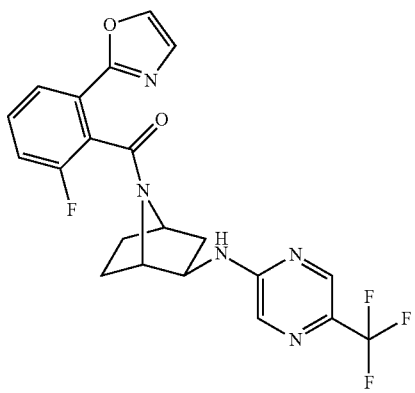 [SMILES: O=C(c1c(F)cccc1-c1ncco1)N1C2CCC1C(Nc1cnc(C(F)(F)F)cn1)C2]

Prepared analogous to Example 181 substituting intermediate A-1 with intermediate A-70. MS (ESI): mass calcd. for $C_{21}H_{17}F_4N_5O_2$, 447.1; m/z found, 448.1 [M+H]+. 1H NMR (500 MHz, CDCl3, Compound present as a mixture of rotamers) δ 8.16 (s, 1H), 7.87-7.83 (series of m, 2H), 7.63 (d, J=7.8 Hz, 1H), 7.47-7.40 (m, 1H), 7.36 (d, J=0.8 Hz, 1H), 7.19 (td, J=8.6, 1.1 Hz, 1H), 4.99 (t, J=5.0 Hz, 1H), 4.42-4.35 (m, 1H), 3.76 (d, J=5.0 Hz, 1H), 2.21 (dd, J=13.1, 8.0 Hz, 1H), 2.12-1.55 (series of m, 5H).

Example 412

(4-fluoro-2-(3-methyl-1,2,4-oxadiazol-5-yl)phenyl)((1S,2R,4R)-2-((5-(trifluoromethyl)pyrazin-2-yl)amino)-7-azabicyclo[2.2.1]heptan-7-yl)methanone

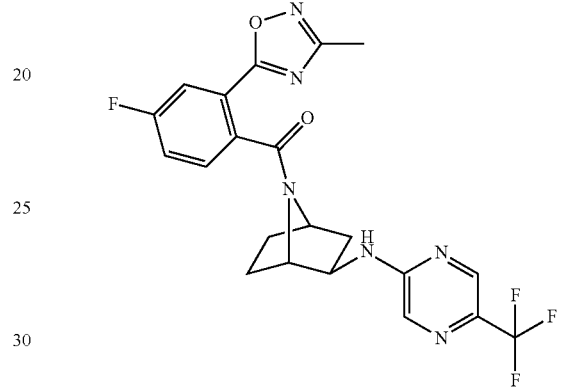

Prepared analogous to Example 238 substituting intermediate A-2 with intermediate A-71. MS (ESI): mass calcd. for $C_{21}H_{18}F_4N_6O_2$, 462.1; m/z found, 463.1 [M+H]+. 1H NMR (500 MHz, CDCl3, Compound present as a mixture of rotamers (0.50:0.50), both rotamers reported) δ 8.32 (s, 0.5H), 8.18 (s, 0.5H), 8.08 (d, J=1.4 Hz, 0.5H), 7.83 (dd, J=8.8, 2.7 Hz, 0.5H), 7.58 (dd, J=8.5, 2.6 Hz, 0.5H), 7.54 (s, 0.5H), 7.52-7.37 (m, 1H), 7.32 (td, J=8.1, 2.6 Hz, 0.5H), 7.18 (td, J=8.1, 2.6 Hz, 0.5H), 6.93 (s, 0.5H), 6.17 (d, J=8.3 Hz, 0.5H), 4.88 (t, J=4.5 Hz, 0.5H), 4.80 (d, J=5.3 Hz, 0.5H), 4.39-4.21 (m, 1H), 3.91 (t, J=4.7 Hz, 0.5H), 3.84 (d, J=4.4 Hz, 0.5H), 2.50 (two s, 3H), 2.23-2.06 (m, 1H), 2.07-1.67 (series of m, 4H), 1.64-1.46 (series of m, 1H).

Example 413

(2-chloro-6-methoxypyridin-3-yl)((1S,2R,4R)-2-((5-(trifluoromethyl)pyrazin-2-yl)amino)-7-azabicyclo[2.2.1]heptan-7-yl)methanone

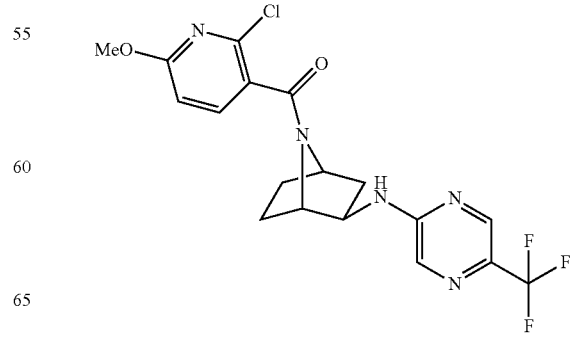

Prepared analogous to Example 181 substituting intermediate A-1 with intermediate A-65. MS (ESI): mass calcd. for $C_{18}H_{17}ClF_3N_5O_2$, 427.1; m/z found, 427.9 [M+H]$^+$. $^1$H NMR (500 MHz, CDCl$_3$, Compound present as a mixture of rotamers) δ 8.35-8.12 (m, 1H), 7.98-7.89 (m, 1H), 7.71-7.48 (m, 1H), 6.84-6.35 (m, 1H), 6.29-5.68 (m, 1H), 4.92-4.73 (m, 1H), 4.30-3.73 (series of m, 5H), 2.24-2.05 (m, 1H), 2.07-1.79 (m, 2H), 1.64-1.46 (m, 2H), 1.01 (d, J=6.6 Hz, 1H).

Example 414

(4-fluoro-2-(pyrimidin-2-yl)phenyl)((1S,2R,4R)-2-((5-(trifluoromethyl)pyrimidin-2-yl)amino)-7-azabicyclo[2.2.1]heptan-7-yl)methanone

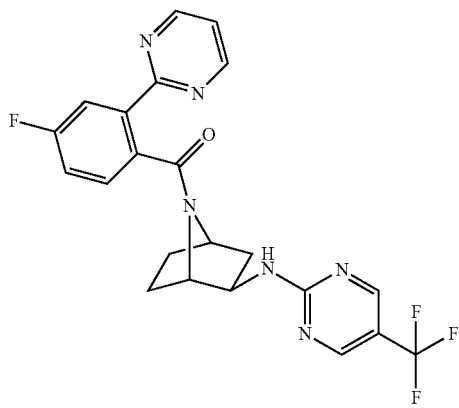 [SMILES: O=C(c1ccc(F)cc1-c1ncccn1)N1C2CCC1C(Nc1ncc(C(F)(F)F)cn1)C2]

Prepared analogous to Example 269 substituting intermediate A-16 with intermediate A-25. MS (ESI): mass calcd. for $C_{22}H_{18}F_4N_6O$, 458.1; m/z found, 459.2 [M+H]$^+$. $^1$H NMR (500 MHz, CDCl$_3$, Compound present as a mixture of rotamers (0.70:0.30), only major rotamer reported) δ 8.85 (d, J=4.9 Hz, 2H), 8.50 (d, J=2.6 Hz, 1H), 8.39 (s, 1H), 7.76 (dd, J=9.5, 2.7 Hz, 1H), 7.35 (dd, J=8.4, 5.4 Hz, 1H), 7.32 (t, J=4.9 Hz, 1H), 7.10 (td, J=8.2, 2.7 Hz, 1H), 4.87 (t, J=4.6 Hz, 1H), 4.48-4.35 (m, 1H), 4.04 (d, J=4.5 Hz, 1H), 2.24 (dd, J=12.9, 8.0 Hz, 1H), 1.99-1.93 (series of m, 2H), 1.83-1.76 (m, 1H), 1.72-1.65 (m, 1H), 1.61-1.54 (m, 1H).

Example 415

(5-fluoro-2-(pyrimidin-2-yl)phenyl)((1S,2R,4R)-2-((5-(trifluoromethyl)pyrimidin-2-yl)amino)-7-azabicyclo[2.2.1]heptan-7-yl)methanone

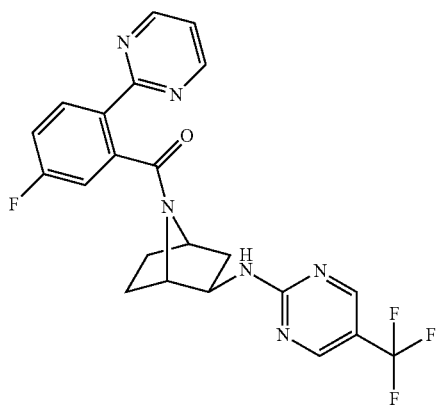

Prepared analogous to Example 269 substituting intermediate A-16 with intermediate A-7. MS (ESI): mass calcd. for $C_{22}H_{18}F_4N_6O$, 458.1; m/z found, 459.1 [M+H]$^+$. $^1$H NMR (500 MHz, CDCl$_3$, Compound present as a mixture of rotamers (0.70:0.30), only major rotamer reported) δ 8.82 (d, J=4.9 Hz, 2H), 8.50 (s, 1H), 8.38 (s, 1H), 8.06 (dd, J=8.6, 5.4 Hz, 1H), 7.28 (t, J=4.9 Hz, 1H), 7.21-7.15 (m, 1H), 7.04 (dd, J=8.4, 2.6 Hz, 1H), 4.95-4.84 (m, 1H), 4.48-4.28 (m, 1H), 4.11-4.05 (m, 1H), 2.24 (dd, J=12.9, 7.9 Hz, 1H), 2.10-1.89 (series of m, 2H), 1.82-1.63 (series of m, 2H), 1.63-1.54 (m, 1H).

Example 416

(2-fluoro-6-(pyrimidin-2-yl)phenyl)((1S,2R,4R)-2-((5-(trifluoromethyl)pyrimidin-2-yl)amino)-7-azabicyclo[2.2.1]heptan-7-yl)methanone

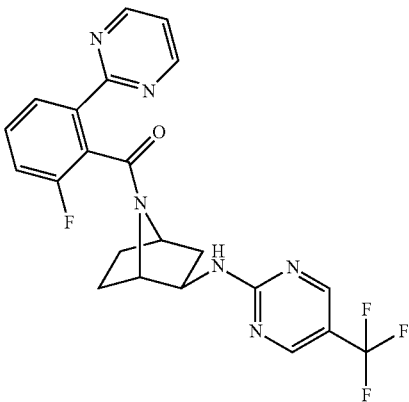 [SMILES: O=C(c1c(F)cccc1-c1ncccn1)N1C2CCC1C(Nc1ncc(C(F)(F)F)cn1)C2]

Prepared analogous to Example 269 substituting intermediate A-16 with intermediate A-6. MS (ESI): mass calcd. for $C_{22}H_{18}F_4N_6O$, 458.1; m/z found, 459.2 [M+H]$^+$. $^1$H NMR (500 MHz, CDCl$_3$, Compound present as a mixture of rotamers) δ 8.86 (d, J=4.9 Hz, 2H), 8.55 (d, J=9.7 Hz, 1H), 8.40 (s, 1H), 7.82 (d, J=7.9 Hz, 1H), 7.55-7.44 (m, 1H), 7.34 (t, J=4.9 Hz, 1H), 7.27-7.16 (m, 1H), 4.92 (t, J=4.8 Hz, 1H), 4.52-4.41 (m, 1H), 3.99 (d, J=5.2 Hz, 1H), 2.28 (dd, J=12.9, 7.8 Hz, 1H), 2.20-2.11 (m, 1H), 2.04-1.94 (m, 1H), 1.83-1.77 (m, 1H), 1.73-1.54 (series of m, 2H).

Example 417

(2-(pyrimidin-2-yl)phenyl)((1S,2R,4R)-2-((5-(trifluoromethyl)pyrimidin-2-yl)amino)-7-azabicyclo[2.2.1]heptan-7-yl)methanone

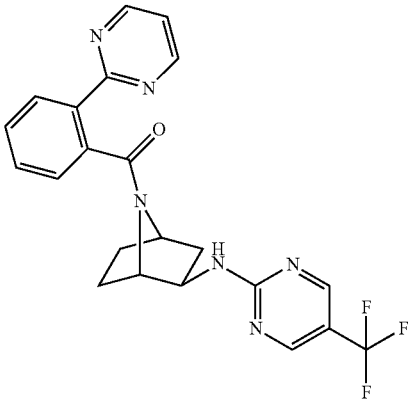

Prepared analogous to Example 269 substituting intermediate A-16 with intermediate A-59. MS (ESI): mass calcd. for $C_{22}H_{19}F_3N_6O$, 440.2; m/z found, 441.2 [M+H]$^+$. $^1$H NMR (500 MHz, CDCl$_3$, Compound present as a mixture of rotamers (0.74:0.26), only major rotamer reported) δ 8.84 (d, J=4.9 Hz, 2H), 8.50 (s, 1H), 8.38 (s, 1H), 8.03 (dd, J=7.7, 1.3 Hz, 1H), 7.53-7.47 (m, 1H), 7.45-7.39 (m, 1H), 7.36 (dd, J=7.4, 1.2 Hz, 1H), 7.29 (t, J=4.9 Hz, 1H), 4.88 (t, J=4.6 Hz, 1H), 4.44-4.38 (m, 1H), 4.07 (d, J=4.5 Hz, 1H), 2.24 (dd, J=12.9, 7.9 Hz, 1H), 1.99-1.96 (m, 1H), 1.84-1.76 (m, 1H), 1.73-1.65 (series of m, 2H), 1.60-1.52 (m, 1H).

Example 418

(3-fluoro-2-(pyrimidin-2-yl)phenyl)((1S,2R,4R)-2-((4-(trifluoromethyl)thiazol-2-yl)amino)-7-azabicyclo[2.2.1]heptan-7-yl)methanone

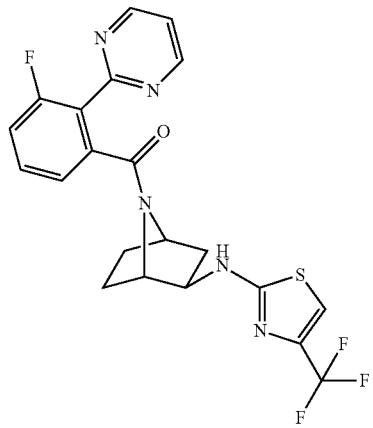 [SMILES: O=C(c1cccc(F)c1-c1ncccn1)N1C2CCC1C(Nc1nc(C(F)(F)F)cs1)C2]

Step A: (1S,2R,4R)-tert-butyl 2-((4-(trifluoromethyl)thiazol-2-yl)amino)-7-azabicyclo[2.2.1]heptane-7-carboxylate To a solution of intermediate B-5 (107 g, 0.50 mmol) in ACN (1.7 mL) was added DIPEA (0.22 mL, 1.26 mmol) followed by 2-chloro-4-(trifluoromethyl)thiazole (104 g, 0.55 mmol). The reaction mixture was heated at 170° C. for 2.5 h using microwave. Solvent was evaporated and purification via silica gel chromatography (0-40% EtOAc in hexanes) gave the title compound (37 g, 20%). MS (ESI): mass calcd. for $C_{15}H_{20}F_3N_3O_2S$, 363.1; m/z found, 364.0 [M+H]$^+$. $^1$H NMR (500 MHz, CDCl$_3$) δ 6.91 (s, 1H), 5.66 (s, 1H), 4.32-4.23 (m, 2H), 3.79-3.69 (m, 1H), 2.08-2.00 (m, 1H), 1.92-1.66 (m, 2H), 1.65-1.35 (m, 12H).

Step B: N-((1S,2R,4R)-7-azabicyclo[2.2.1]heptan-2-yl)-4-(trifluoromethyl)thiazol-2-amine To the title compound of step A (37 g, 0.10 mmol) in DCM (1 mL) was added 4M HCl in dioxane (0.26 mL). After 16 h, the reaction was concentrated, neutralized with 5% Na$_2$CO$_3$ (aq) and extracted with DCM (2×). The combined organics were dried (Na$_2$SO$_4$) to give the title compound of step B that was used without further purification. MS (ESI): mass calcd. for $C_{10}H_{12}F_3N_3S$, 263.1; m/z found, 264.0 [M+H]$^+$.

Step C: (3-fluoro-2-(pyrimidin-2-yl)phenyl)((1S,2R,4R)-2-((4-(trifluoromethyl)thiazol-2-yl)amino)-7-azabicyclo[2.2.1]heptan-7-yl)methanone To the title compound of step B (27 mg, 0.10 mmol) in DCM (1 mL) was added DIPEA (0.04 mL, 0.21 mmol) and intermediate A-2 (25 mg, 0.11 mmol). Then T3P (50% solution in DMF, 0.19 mL, 0.31 mmol) was added dropwise and the reaction heated at 45° C. for 16 h. Solvent was evaporated and purification via prep HPLC gave the title compound (16 g, 34%). MS (ESI): mass calcd. for $C_{21}H_{17}F_4N_5OS$, 463.1; m/z found, 463.9 [M+H]$^+$. $^1$H NMR (500 MHz, CDCl$_3$) δ 8.88 (d, J=4.9 Hz, 2H), 7.45-7.40 (m, 1H), 7.38 (t, J=4.9 Hz, 1H), 7.24-7.17 (m, 2H), 6.77-6.69 (m, 1H), 4.70 (t, J=4.9, 1.2 Hz, 1H), 4.22-4.16 (m, 2H), 2.16 (dd, J=13.1, 8.0 Hz, 1H), 2.10-2.01 (m, 1H), 1.96-1.86 (m, 1H), 1.76-1.57 (m, 2H), 1.55-1.44 (m, 1H).

Example 419

(3-fluoro-2-(pyrimidin-2-yl)phenyl)((1S,2R,4R)-2-((5-(trifluoromethyl)-1,3,4-thiadiazol-2-yl)amino)-7-azabicyclo[2.2.1]heptan-7-yl)methanone

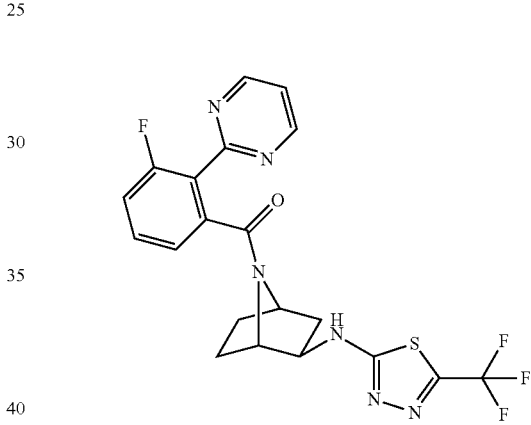

Step A: (1S,2R,4R)-tert-butyl 2-((5-(trifluoromethyl)-1,3,4-thiadiazol-2-yl)amino)-7-azabicyclo[2.2.1]heptane-7-carboxylate To a solution of intermediate B-5 (71 g, 0.33 mmol) in ACN (0.85 mL) was added DIPEA (0.14 mL, 0.84 mmol) followed by 2-chloro-5-(trifluoromethyl)-1,3,4-thiadiazole (73 g, 0.37 mmol). The reaction mixture was heated at 120° C. for 30 minutes using microwave. EtOAc was added and the organic phase was washed with a saturated solution of NaHCO$_3$ followed by a saturated solution of NaCl. The organic phase was dried over MgSO$_4$, filtered and evaporated. Purification via silica gel chromatography (0-40% EtOAc in hexanes) gave the title compound (85 g, 70%). $^1$H NMR (500 MHz, CDCl$_3$) δ 6.82 (s, 1H), 4.38-4.22 (m, 2H), 3.96-3.82 (m, 1H), 2.11-2.00 (m, 1H), 1.92-1.79 (m, 1H), 1.79-1.66 (m, 2H), 1.43 (s, 11H). MS (ESI): mass calcd. for $C_{14}H_{19}F_3N_4O_2S$, 364.1; m/z found, 365.0 [M+H]$^+$.

Step B: N-((1S,2R,4R)-7-azabicyclo[2.2.1]heptan-2-yl)-5-(trifluoromethyl)-1,3,4-thiadiazol-2-amine To the title compound of step A (85 g, 0.23 mmol) in DCM (2.3 mL) was added 4M HCl in dioxane (0.30 mL).

After 48 h, the reaction was concentrated, neutralized with 5% Na₂CO₃ (aq) and extracted with DCM (2×). The combined organics were dried (Na₂SO₄) to give the title compound of step B that was used without further purification. MS (ESI): mass calcd. for C₉H₁₁F₃N₄S, 264.1; m/z found, 265.0 [M+H]⁺.

Step C: (3-fluoro-2-(pyrimidin-2-yl)phenyl)((1S,2R,4R)-2-((5-(trifluoromethyl)-1,3,4-thiadiazol-2-yl)amino)-7-azabicyclo[2.2.1]heptan-7-yl)methanone To the title compound of step B (58 g, 0.10 mmol) in DCM (2.2 mL) was added DIPEA (0.1 mL, 0.55 mmol) and intermediate A-2 (53 g, 0.24 mmol). Then T3P (50% solution in DMF, 0.40 mL, 0.66 mmol) was added dropwise and the reaction heated at 45° C. for 16 h. Solvent was evaporated and purification via prep HPLC gave the title compound (63 g, 62%). MS (ESI): mass calcd. for C₂₀H₁₆F₄N₆OS, 464.1; m/z found, 464.9 [M+H]⁺. ¹H NMR (500 MHz, CDCl₃) 8.94 (d, J=9.3 Hz, 1H), 8.87 (d, J=5.0 Hz, 2H), 7.47-7.37 (m, 2H), 7.25-7.19 (m, 2H), 4.71 (td, J=4.8, 1.2 Hz, 1H), 4.33-4.18 (m, 2H), 2.17 (dd, J=13.3, 8.1 Hz, 1H), 2.13-2.03 (m, 1H), 1.98-1.85 (m, 1H), 1.74-1.62 (m, 2H), 1.57-1.45 (m, 1H).

Example 420

((1S,2R,4R)-2-((3-fluoro-5-(trifluoromethyl)pyridin-2-yl)amino)-7-azabicyclo[2.2.1]heptan-7-yl)(5-methyl-3-(2H-1,2,3-triazol-2-yl)pyridin-2-yl)methanone

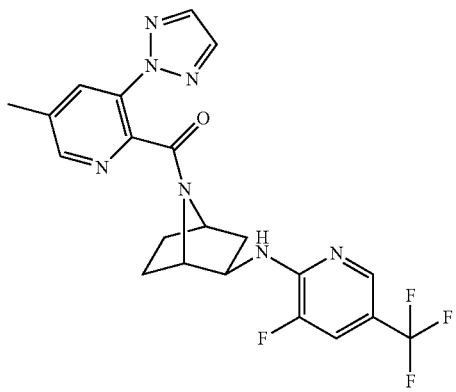 [SMILES: Cc1cnc(C(=O)N2C3CCC2C(Nc2ncc(C(F)(F)F)cc2F)C3)c(-n2nccn2)c1]

Prepared analogous to Example 382 substituting intermediate A-2 with intermediate A-19. MS (ESI): mass calcd. for C₂₁H₁₉F₄N₇O, 461.2; m/z found, 462.2 [M+H]⁺. ¹H NMR (500 MHz, CDCl₃) δ 8.39 (dd, J=1.9, 0.8 Hz, 1H), 8.12-8.08 (m, 2H), 7.86 (s, 2H), 7.26-7.22 (m, 1H), 5.77-5.70 (m, 1H), 4.97-4.91 (m, 1H), 4.38 (td, J=7.8, 3.0 Hz, 1H), 4.09-4.05 (m, 1H), 2.46 (s, 3H), 2.25 (dd, J=13.0, 7.5 Hz, 1H), 2.13-1.97 (m, 2H), 1.88-1.80 (m, 1H), 1.66-1.60 (m, 2H).

Example 421

(R/S)-(2-(2H-1,2,3-triazol-2-yl)phenyl)-2-((5-(trifluoromethyl)pyridin-2-yl)oxy)-7-azabicyclo[2.2.1]heptan-7-yl)methanone

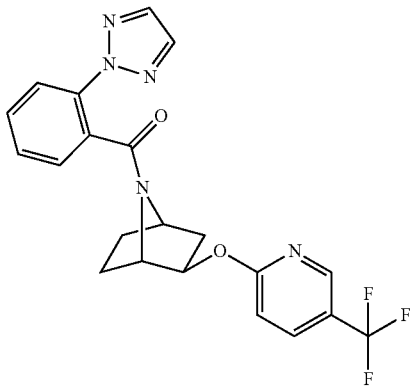

Prepared analogous to Example 433 substituting intermediate A-55 with intermediate A-1. MS (ESI): mass calcd. for C₂₁H₁₈F₃N₅O₂, 429.1; m/z found, 429.9 [M+H]⁺. ¹H NMR (400 MHz, CDCl₃) δ 8.32-8.25 (m, 1H), 7.82-7.74 (m, 4H), 7.49-7.39 (m, 2H), 7.20 (td, J=7.6, 1.2 Hz, 1H), 6.75 (d, J=8.7 Hz, 1H), 4.97 (dd, J=6.6, 2.5 Hz, 1H), 4.88 (t, J=5.0 Hz, 1H), 3.89 (d, J=5.3 Hz, 1H), 2.08-1.94 (m, 2H), 1.87-1.75 (m, 1H), 1.55-1.48 (m, 1H), 1.47-1.40 (m, 1H), 1.36-1.27 (m, 1H).

Example 422

(R/S)-(3-methyl-2-(2H-1,2,3-triazol-2-yl)phenyl)-2-((5-(trifluoromethyl)pyridin-2-yl)oxy)-7-azabicyclo[2.2.1]heptan-7-yl)methanone

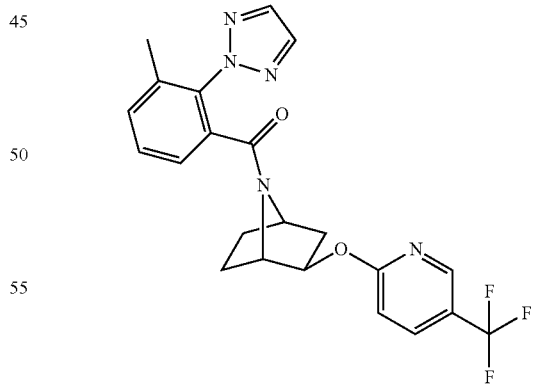

Prepared analogous to Example 433 substituting intermediate A-55 with intermediate A-24. MS (ESI): mass calcd. for C₂₂H₂₀F₃N₅O₂, 443.2; m/z found, 443.9 [M+H]⁺. ¹H NMR (500 MHz, CDCl₃, Compound present as a mixture of rotamers) δ 8.43-8.28 (m, 1H), 7.85-7.75 (series of m, 3H), 7.44-7.27 (series of m, 2H), 7.18 (t, J=7.6 Hz, 1H), 6.86-6.76 (m, 1H), 5.06-4.97 (m, 1H), 4.76-4.63 (m, 1H), 4.05-3.90

(m, 1H), 2.21-2.12 (m, 3H), 2.04-1.98 (m, 1H), 1.98-1.92 (m, 1H), 1.87-1.78 (m, 1H), 1.54-1.44 (m, 1H), 1.39-1.31 (m, 2H).

Example 423

(R/S)-(3-fluoro-2-(2H-1,2,3-triazol-2-yl)phenyl)-2-((5-(trifluoromethyl)pyridin-2-yl)oxy)-7-azabicyclo[2.2.1]heptan-7-yl)methanone

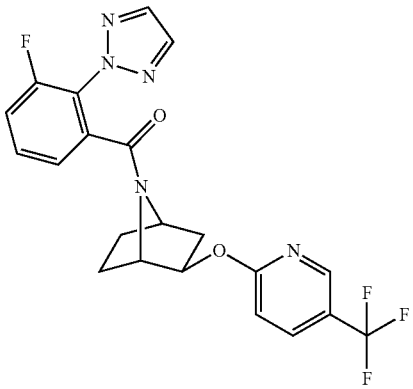

Prepared analogous to Example 433 substituting intermediate A-55 with intermediate A-16. MS (ESI): mass calcd. for $C_{21}H_{17}F_4N_5O_2$, 447.1; m/z found, 448.1 [M+H]$^+$. $^1$H NMR (400 MHz, CDCl$_3$) δ 8.42-8.29 (m, 1H), 7.91-7.82 (m, 2H), 7.79 (dd, J=8.7, 2.5 Hz, 1H), 7.41-7.19 (m, 3H), 6.84-6.75 (m, 1H), 5.07-4.96 (m, 1H), 4.82-4.68 (m, 1H), 4.03-3.86 (m, 1H), 2.08-1.91 (m, 2H), 1.77-1.47 (m, 2H), 1.44-1.31 (m, 2H).

Example 424

(R/S)-(3-fluoro-2-(1H-1,2,3-triazol-1-yl)phenyl)-2-((5-(trifluoromethyl)pyridin-2-yl)oxy)-7-azabicyclo[2.2.1]heptan-7-yl)methanone

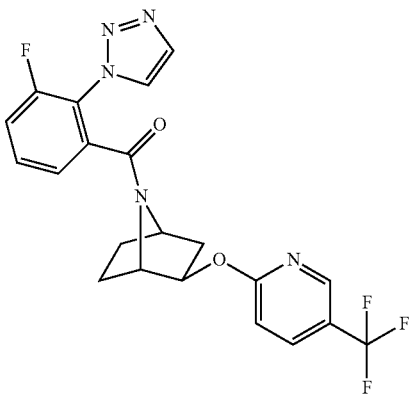 [SMILES: O=C(c1cccc(F)c1-n1ccnn1)N1C2CCC1C(Oc1ccc(C(F)(F)F)cn1)C2]

Prepared analogous to Example 433 substituting intermediate A-55 with 3-fluoro-2-(1H-1,2,3-triazol-1-yl)benzoic acid, obtained during the synthesis of intermediate A-16. MS (ESI): mass calcd. for $C_{21}H_{17}F_4N_5O_2$, 447.1; m/z found, 447.9 [M+H]$^+$. $^1$H NMR (400 MHz, CDCl$_3$) δ 8.36-8.32 (m, 1H), 7.93 (t, J=1.2 Hz, 1H), 7.84-7.79 (m, 2H), 7.41-7.27 (m, 3H), 6.88-6.84 (m, 1H), 5.04 (dd, J=6.9, 2.3 Hz, 1H), 4.69 (t, J=5.1 Hz, 1H), 4.06 (d, J=5.6 Hz, 1H), 2.12-2.01 (m, 1H), 1.99-1.90 (m, 1H), 1.87-1.78 (m, 1H), 1.71-1.59 (m, 1H), 1.41 (d, J=8.4 Hz, 2H).

Example 425

(R/S)-(2-fluoro-6-(2H-1,2,3-triazol-2-yl)phenyl)-2-((5-(trifluoromethyl)pyridin-2-yl)oxy)-7-azabicyclo[2.2.1]heptan-7-yl)methanone

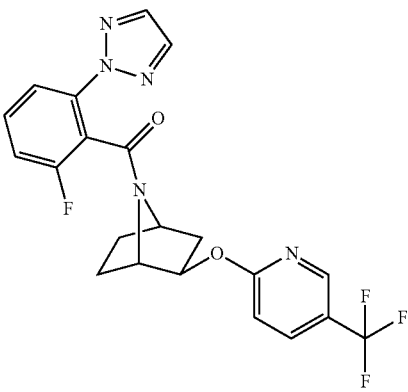 [SMILES: O=C(c1c(F)cccc1-n1nccn1)N1C2CCC1C(Oc1ccc(C(F)(F)F)cn1)C2]

Prepared analogous to Example 433 substituting intermediate A-55 with intermediate A-11. MS (ESI): mass calcd. for $C_{21}H_{17}F_4N_5O_2$, 447.1; m/z found, 447.9 [M+H]$^+$. 1H NMR (500 MHz, CDCl$_3$, Compound present as a mixture of rotamers) δ 8.47-8.24 (m, 1H), 7.86-7.66 (series of m, 4H), 7.53-7.34 (m, 1H), 7.20-6.94 (m, 1H), 6.92-6.79 (m, 1H), 5.19-4.90 (series of m, 2H), 3.95-3.77 (m, 1H), 2.12-1.97 (series of m, 2H), 1.96-1.56 (series of m, 2H), 1.48-1.26 (series of m, 2H).

Example 426

(R/S)-(2-(2H-1,2,3-triazol-2-yl)pyridin-3-yl)-2-((5-(trifluoromethyl)pyridin-2-yl)oxy)-7-azabicyclo[2.2.1]heptan-7-yl)methanone

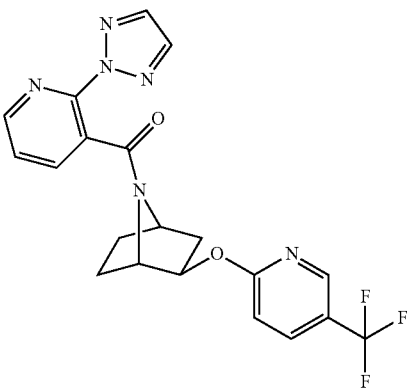

Prepared analogous to Example 433 substituting intermediate A-55 with intermediate A-61. MS (ESI): mass calcd. for $C_{20}H_{17}F_3N_6O_2$, 430.1; m/z found, 430.9 [M+H]$^+$. $^1$H NMR (400 MHz, CDCl$_3$) δ 8.55 (dd, J=4.8, 1.8 Hz, 1H), 8.34-8.25 (m, 1H), 7.89-7.84 (m, 3H), 7.78 (dd, J=8.8, 2.5 Hz, 1H), 7.21 (dd, J=7.6, 4.8 Hz, 1H), 6.73 (d, J=8.7 Hz, 1H), 4.99 (dd, J=6.8, 2.4 Hz, 1H), 4.91 (t, J=4.8 Hz, 1H), 3.88 (d, J=5.3 Hz, 1H), 2.08 (d, J=6.9 Hz, 1H), 2.04-2.00 (m, 1H), 1.93-1.83 (m, 1H), 1.57-1.44 (m, 2H), 1.39-1.31 (m, 1H).

Example 427

(R/S)-(6-methyl-2-(2H-1,2,3-triazol-2-yl)pyridin-3-yl)-2-((5-(trifluoromethyl)pyridin-2-yl)oxy)-7-azabicyclo[2.2.1]heptan-7-yl)methanone

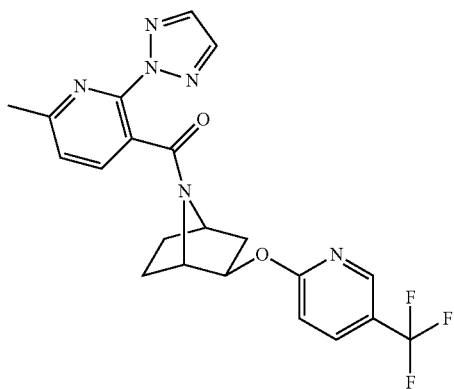

Prepared analogous to Example 433 substituting intermediate A-55 with intermediate A-3. MS (ESI): mass calcd. for $C_{21}H_{19}F_3N_6O_2$, 444.2; m/z found, 444.9 [M+H]$^+$. Analytical HPLC was obtained on a Agilent 1100 Series using an Inertsil ODS-3 column (3 μm, 50×3 mm), mobile phase of 5-99% ACN in 0.05% TFA over 1.6 min and then hold at 99% ACN for 0.4 min, at a flow rate of 2.2 mL/min (Temperature=50° C.). $R_t$=1.29 min (major rotamer) at 254 nm.

Example 428

(R/S)-(5-methyl-2-(2H-1,2,3-triazol-2-yl)pyridin-3-yl)-2-((5-(trifluoromethyl)pyridin-2-yl)oxy)-7-azabicyclo[2.2.1]heptan-7-yl)methanone

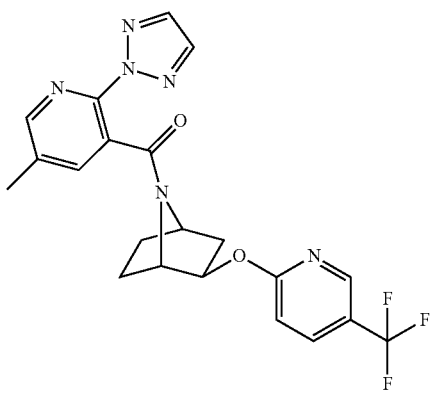 [SMILES: Cc1cnc(-n2nccn2)c(C(=O)N2C3CCC2C(Oc2ccc(C(F)(F)F)cn2)C3)c1]

Prepared analogous to Example 433 substituting intermediate A-55 with intermediate A-60. MS (ESI): mass calcd. for $C_{21}H_{19}F_3N_6O_2$, 444.2; m/z found, 444.9 [M+H]$^+$. $^1$H NMR (400 MHz, CDCl$_3$) δ 8.35-8.32 (m, 1H), 8.32-8.30 (m, 1H), 7.85 (s, 2H), 7.83-7.77 (m, 1H), 7.63-7.57 (m, 1H), 6.74 (d, J=8.6 Hz, 1H), 4.96 (dd, J=6.3, 3.0 Hz, 1H), 4.90 (t, J=4.5 Hz, 1H), 3.91 (d, J=5.3 Hz, 1H), 2.21 (s, 3H), 2.13-1.94 (m, 2H), 1.91-1.76 (m, 1H), 1.55-1.27 (m, 3H).

Example 429

(R/S)-(3-fluoro-2-(pyrimidin-2-yl)phenyl)-2-((5-(trifluoromethyl)pyridin-2-yl)oxy)-7-azabicyclo[2.2.1]heptan-7-yl)methanone

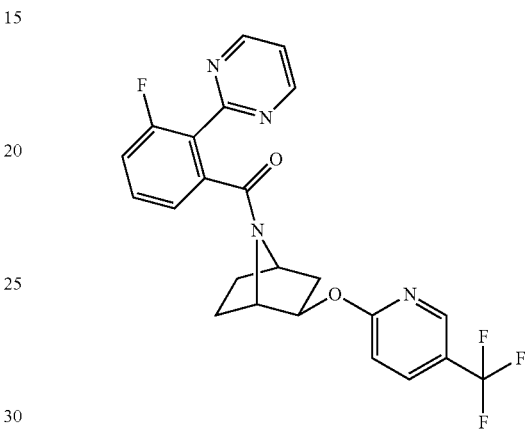

Prepared analogous to Example 433 substituting intermediate A-55 with intermediate A-2. MS (ESI): mass calcd. for $C_{23}H_{18}F_4N_4O_2$, 458.1; m/z found, 458.9 [M+H]$^+$. Analytical HPLC was obtained on a Agilent 1100 Series using an Inertsil ODS-3 column (3 μm, 50×3 mm), mobile phase of 5-99% ACN in 0.05% TFA over 1.6 min and then hold at 99% ACN for 0.4 min, at a flow rate of 2.2 mL/min (Temperature=50° C.). $R_t$=1.37 min (major rotamer) at 254 nm.

Example 430

(R/S)-(4-fluoro-2-(pyrimidin-2-yl)phenyl)-2-((5-(trifluoromethyl)pyridin-2-yl)oxy)-7-azabicyclo[2.2.1]heptan-7-yl)methanone

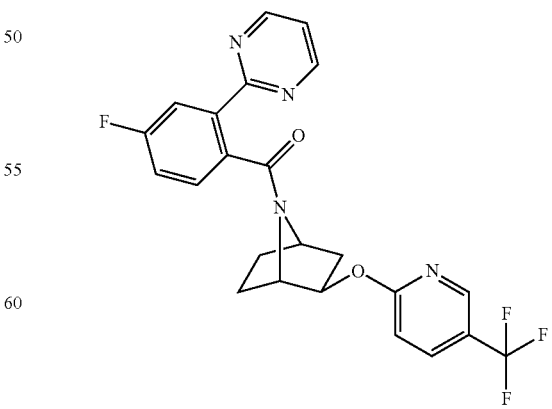

Prepared analogous to Example 433 substituting intermediate A-55 with intermediate A-25. MS (ESI): mass calcd.

for $C_{23}H_{18}F_4N_4O_2$, 458.1; m/z found, 458.9 [M+H]$^+$. $^1$H NMR (400 MHz, CDCl$_3$, Compound present as a mixture of rotamers, major rotamer reported) δ 8.76-8.74 (m, 2H), 8.34-8.28 (m, 1H), 7.85 (dd, J=9.8, 2.6 Hz, 1H), 7.80-7.75 (m, 1H), 7.44-7.40 (m, 1H), 7.21 (t, J=4.8 Hz, 1H), 6.95 (td, J=8.2, 2.7 Hz, 1H), 6.75 (d, J=8.7 Hz, 1H), 5.00 (dd, J=6.7, 2.4 Hz, 1H), 4.88 (t, J=4.8 Hz, 1H), 3.95 (d, J=5.5 Hz, 1H), 2.08-1.99 (m, 1H), 1.88-1.81 (m, 1H), 1.68-1.58 (m, 1H), 1.53-1.45 (m, 1H), 1.41-1.32 (m, 1H), 0.86-0.81 (m, 1H).

Example 431

(R/S)-(2-fluoro-6-(pyrimidin-2-yl)phenyl)-2-((5-(trifluoromethyl)pyridin-2-yl)oxy)-7-azabicyclo[2.2.1]heptan-7-yl)methanone

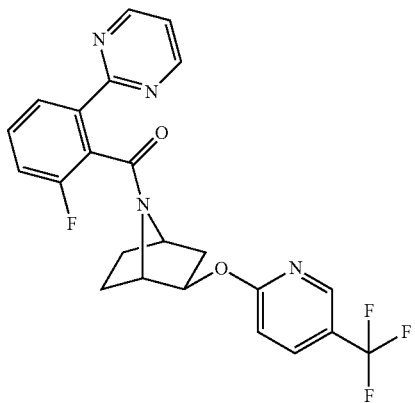 [SMILES: O=C(c1c(F)cccc1-c1ncccn1)N1C2CCC1C(Oc1ccc(C(F)(F)F)cn1)C2]

Prepared analogous to Example 433 substituting intermediate A-55 with intermediate A-6. MS (ESI): mass calcd. for $C_{23}H_{18}F_4N_4O_2$, 458.1; m/z found, 458.9 [M+H]$^+$. Analytical HPLC was obtained on a Agilent 1100 Series using an Inertsil ODS-3 column (3 μm, 50×3 mm), mobile phase of 5-99% ACN in 0.05% TFA over 1.6 min and then hold at 99% ACN for 0.4 min, at a flow rate of 2.2 mL/min (Temperature=50° C.). R$_t$=1.40 min (major rotamer) at 254 nm.

Example 432

(R/S)-(2-(pyrimidin-2-yl)phenyl)-2-((5-(trifluoromethyl)pyridin-2-yl)oxy)-7-azabicyclo[2.2.1]heptan-7-yl)methanone

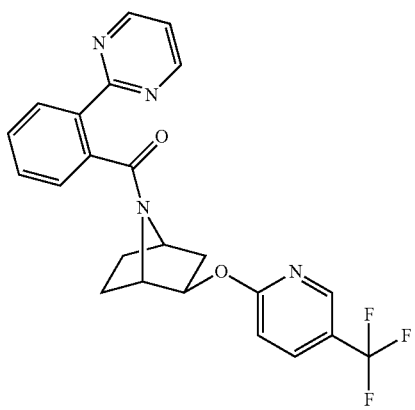 [SMILES: O=C(c1ccccc1-c1ncccn1)N1C2CCC1C(Oc1ccc(C(F)(F)F)cn1)C2]

Prepared analogous to Example 433 substituting intermediate A-55 with intermediate A-59. MS (ESI): mass calcd. for $C_{23}H_{19}F_3N_4O_2$, 440.1; m/z found, 441.1 [M+H]$^+$. $^1$H NMR (400 MHz, CDCl$_3$) δ 8.80-8.71 (m, 2H), 8.43-8.27 (m, 1H), 8.21-8.09 (m, 1H), 7.83-7.74 (m, 1H), 7.57-7.37 (m, 2H), 7.28-7.13 (m, 2H), 6.90-6.72 (m, 1H), 5.12-4.86 (m, 2H), 4.00-3.83 (m, 1H), 2.14-1.77 (m, 3H), 1.74-1.53 (m, 1H), 1.53-1.21 (m, 2H).

Example 433

(R/S)-(2-(5-fluoropyrimidin-2-yl)phenyl)-2-((5-(trifluoromethyl)pyridin-2-yl)oxy)-7-azabicyclo[2.2.1]heptan-7-yl)methanone

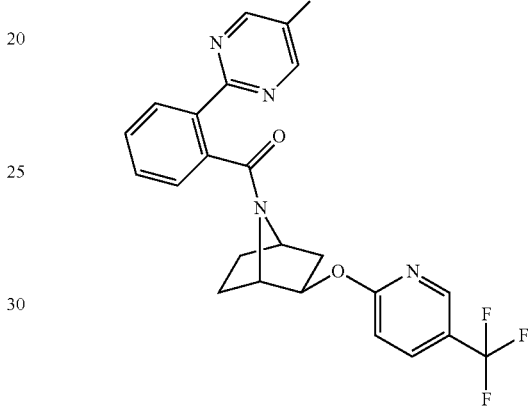

Step A. (R/S)-tert-Butyl 2-((5-(trifluoromethyl)pyridin-2-yl)oxy)-7-azabicyclo[2.2.1]heptane-7-carboxylate To a solution of intermediate B-11 (1.35 g, 6.33 mmol) and 2-chloro-5-(trifluoromethyl)pyridine (1.35 g, 7.44 mmol) in DMF (20 mL) at rt was added NaH (310 g, 7.75 mmol) and the mixture stirred at rt overnight. The reaction was diluted with water (200 mL) and extracted with EtOAc (3×50 mL). The combined organics were dried over Na$_2$SO$_4$, filtered and the solvent removed. Purification via silica gel chromatography (80 g redisep, 0-100% EtOAc in hexanes) provided 1.68 g of the title compound as a waxy solid. $^1$H NMR (400 MHz, CDCl$_3$) 8.42 (s, 1H), 7.76 (dd, J=8.8, 2.6 Hz, 1H), 6.77 (d, J=8.7 Hz, 1H), 5.03 (dd, J=6.9, 2.6 Hz, 1H), 4.45-4.24 (m, 2H), 2.02-1.95 (m, 1H), 1.95-1.67 (m, 3H), 1.50-1.31 (m, 11H).

Step B. (R/S)-2-((5-(trifluoromethyl)pyridin-2-yl)oxy)-7-azabicyclo[2.2.1]heptane To a solution of (R/S)-tert-Butyl 2-((5-(trifluoromethyl)pyridin-2-yl)oxy)-7-azabicyclo[2.2.1]heptane-7-carboxylate from step A (1.35 g, 3.77 mmol) in DCM (20 mL) was added TFA (5 mL). This solution was stirred at rt for ~4 h. The solvent was the removed and the residue was then partitioned between 2M Na$_2$CO$_3$ (20 mL) and DCM (20 mL). The layers were separated and the aqueous layer was extracted with DCM (2×20 mL). The combined organics were dried over Na$_2$SO$_4$, filtered and the solvent removed to reveal 0.98 g of the title compound. The material was utilized as is. $^1$H NMR (400 MHz, CDCl$_3$) δ 8.42 (dt, J=2.0, 1.1 Hz, 1H), 7.75 (dd, J=8.7, 2.5 Hz, 1H), 6.78 (d, J=8.7 Hz, 1H), 5.05 (dd, J=6.7, 2.1 Hz, 1H), 3.73 (q, J=4.9 Hz, 2H), 2.01 (dd, J=13.3, 6.7 Hz, 1H), 1.96-1.88 (m, 1H), 1.74-1.55 (m, 3H), 1.40-1.22 (m, 2H).

Step C. (R/S)-(2-(5-fluoropyrimidin-2-yl)phenyl)-2-((5-(trifluoromethyl)pyridin-2-yl)oxy)-7-azabicyclo[2.2.1]heptan-7-yl)methanone To a 20 mL screw cap vial were added intermediate A-55 (60 g, 0.27 mmol), (R/S)-2-((5-(trifluoromethyl)pyridin-2-yl)oxy)-7-azabicyclo[2.2.1]heptane from step B (56 g, 0.217 mmol), HOBt (40 g, 0.29 mmol), and EDCI (75 g, 0.39 mmol). DMF (2 mL) and TEA (50 μL) were then added and vial capped and stirred at rt. overnight. The resulting reddish mixture was diluted with water (25 mL) and extracted with EtOAc (3×10 mL) and the organic layers combined and the solvent removed. Purification via silica gel chromatography (0-100% EtOAc in hexanes) provided 80.4 mg of the title compound. $^1$H NMR exhibits a mixture of rotamers. MS (ESI): mass calcd. for C$_{23}$H$_{18}$F$_4$N$_4$O$_2$, 458.1; m/z found, 459.2 [M+H]$^+$. $^1$H NMR (500 MHz, CDCl$_3$) δ 8.65-8.56 (m, 2H), 8.45-8.28 (m, 1H), 8.15-8.03 (m, 1H), 7.85-7.75 (m, 1H), 7.56-7.37 (m, 2.5H), 7.25-7.22 (m, 0.5H), 6.89-6.75 (m, 1H), 5.13-4.99 (m, 1H), 4.97-4.85 (m, 1H), 4.03-3.84 (m, 1H), 2.15-1.93 (m, 2H), 1.92-1.66 (m, 2H), 1.55-1.21 (m, 2H).

Example 434

(R/S)-(3-fluoro-2-(5-fluoropyrimidin-2-yl)phenyl)-2-((5-(trifluoromethyl)pyridin-2-yl)oxy)-7-azabicyclo[2.2.1]heptan-7-yl)methanone

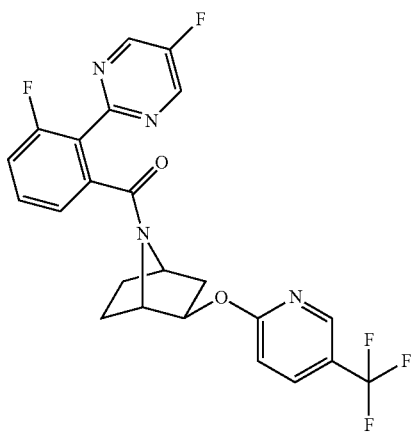

Prepared analogous to Example 433 substituting intermediate A-55 with intermediate A-57. MS (ESI): mass calcd. for C$_{23}$H$_{17}$F$_5$N$_4$O$_2$, 476.1; m/z found, 476.9 [M+H]$^+$. $^1$H NMR (400 MHz, CDCl$_3$, Compound present as a mixture of rotamers, major rotamer reported) δ 8.66 (s, 2H), 8.38-8.32 (m, 1H), 7.80 (dt, J=8.8, 2.6 Hz, 1H), 7.33-7.27 (m, 1H), 7.25-7.19 (m, 1H), 7.18-7.11 (m, 1H), 6.84 (d, J=8.7 Hz, 1H), 5.09-4.98 (m, 1H), 4.76 (d, J=5.4 Hz, 1H), 4.72 (t, J=4.4 Hz, 1H), 4.12 (d, J=5.5 Hz, 1H), 3.97 (t, J=4.7 Hz, 1H), 2.11-1.32 (m, 4H).

Example 435

(R/S)-(3-methyl-2-(oxazol-2-yl)phenyl)-2-((5-(trifluoromethyl)pyridin-2-yl)oxy)-7-azabicyclo[2.2.1]heptan-7-yl)methanone

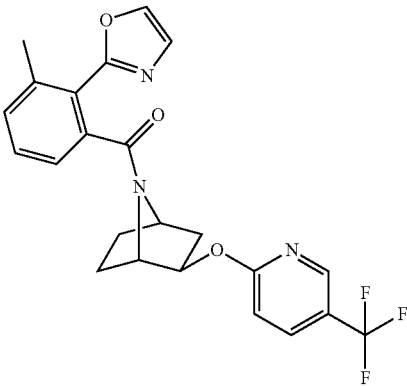 [SMILES: Cc1cccc(C(=O)N2C3CCC2C(Oc2ccc(C(F)(F)F)cn2)C3)c1-c1ncco1]

Prepared analogous to Example 433 substituting intermediate A-55 with intermediate A-31. MS (ESI): mass calcd. for C$_{23}$H$_{20}$F$_3$N$_3$O$_3$, 443.1; m/z found, 443.9 [M+H]$^+$. $^1$H NMR (400 MHz, CDCl$_3$, Compound present as a mixture of rotamers, major rotamer reported) δ 8.32-8.26 (m, 1H), 7.78-7.73 (m, 2H), 7.39-7.19 (m, 3H), 7.18 (d, J=7.6 Hz, 1H), 6.76 (d, J=8.7 Hz, 1H), 4.98 (dd, J=6.6, 2.6 Hz, 1H), 4.76 (t, J=4.5 Hz, 1H), 3.93 (d, J=5.0 Hz, 1H), 2.39 (s, 3H), 2.07-1.28 (m, 6H).

Example 436

(R/S)-(3-fluoro-2-(oxazol-2-yl)phenyl)-2-((5-(trifluoromethyl)pyridin-2-yl)oxy)-7-azabicyclo[2.2.1]heptan-7-yl)methanone

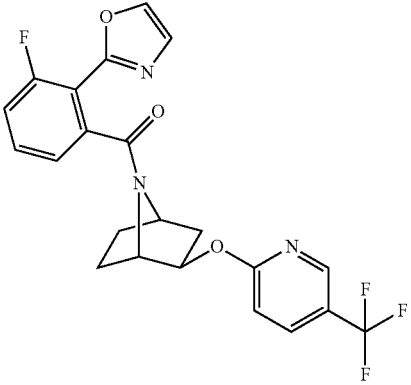

Prepared analogous to Example 433 substituting intermediate A-55 with intermediate A-68. MS (ESI): mass calcd. for C$_{22}$H$_{17}$F$_4$N$_3$O$_3$, 447.1; m/z found, 448.9 [M+H]$^+$. $^1$H NMR (400 MHz, CDCl$_3$, Compound present as a mixture of rotamers (0.69:0.31), major rotamer reported) δ 8.34-8.27 (m, 1H), 7.78-7.74 (m, 2H), 7.30-7.22 (m, 3H), 7.18-7.09 (m, 1H), 6.73 (d, J=8.6 Hz, 1H), 4.98 (dd, J=6.8, 2.5 Hz, 1H), 4.85 (t, J=4.7 Hz, 1H), 3.89 (d, J=5.6 Hz, 1H), 2.11-1.20 (m, 6H).

Example 437

(R/S)-(3-methyl-2-(2H-1,2,3-triazol-2-yl)phenyl)-2-((6-(trifluoromethyl)pyridin-3-yl)oxy)-7-azabicyclo[2.2.1]heptan-7-yl)methanone

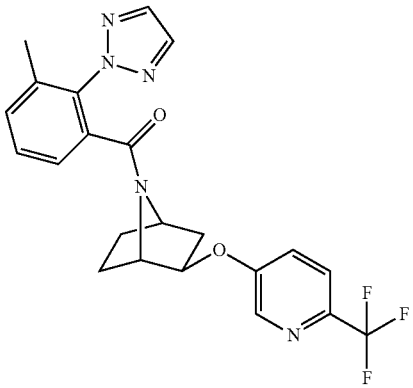

Prepared analogous to Example 433 substituting 2-chloro-5-(trifluoromethyl)pyridine with 5-fluoro-2-(trifluoromethyl)pyridine and intermediate A-55 with intermediate A-24. MS (ESI): mass calcd. for $C_{22}H_{20}F_3N_5O_2$, 443.2; m/z found, 444.9 [M+H]$^+$. $^1$H NMR (500 MHz, CDCl$_3$, Compound present as a mixture of rotamers) δ 8.33-8.25 (m, 1H), 7.85-7.72 (m, 2H), 7.64-7.54 (m, 1H), 7.44-7.27 (series of m, 3H), 7.23-7.12 (m, 1H), 4.82-4.66 (m, 1H), 4.44-4.35 (m, 1H), 4.06-3.95 (m, 1H), 2.16 (s, 3H), 2.06-1.92 (series of m, 2H), 1.91-1.75 (m, 1H), 1.56-1.22 (series of m, 3H).

Example 438

(R/S)-(3-fluoro-2-(2H-1,2,3-triazol-2-yl)phenyl)-2-((6-(trifluoromethyl)pyridin-3-yl)oxy)-7-azabicyclo[2.2.1]heptan-7-yl)methanone

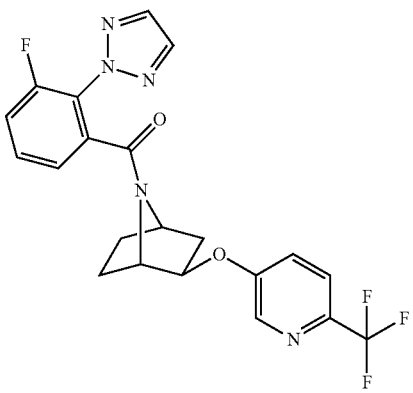

Prepared analogous to Example 437 substituting intermediate A-24 with intermediate A-16. MS (ESI): mass calcd. for $C_{21}H_{17}F_4N_5O_2$, 447.1; m/z found, 447.9 [M+H]$^+$. $^1$H NMR (500 MHz, CDCl$_3$, Compound present as a mixture of rotamers) δ 8.33-8.23 (m, 1H), 7.89-7.78 (m, 2H), 7.66-7.55 (m, 1H), 7.42-7.27 (series of m, 3H), 7.25-7.09 (m, 1H), 4.84-4.71 (m, 1H), 4.46-4.37 (m, 1H), 3.98 (d, J=5.5 Hz, 1H), 2.09-1.56 (series of m, 4H), 1.48-1.26 (series of m, 2H).

Example 439

(R/S)-(2-fluoro-6-(2H-1,2,3-triazol-2-yl)phenyl)-2-((6-(trifluoromethyl)pyridin-3-yl)oxy)-7-azabicyclo[2.2.1]heptan-7-yl)methanone

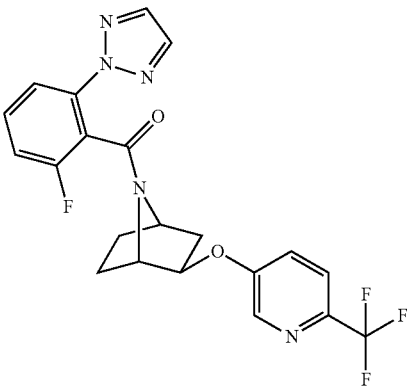

Prepared analogous to Example 437 substituting intermediate A-24 with intermediate A-11. MS (ESI): mass calcd. for $C_{21}H_{17}F_4N_5O_2$, 447.1; m/z found, 448.9 [M+H]$^+$. Analytical HPLC was obtained on a Agilent 1100 Series using a XBridge C18 column (5 μm, 100×4.6 mm), mobile phase of 10-100% ACN in 20 mM NH$_4$OH over 8 min and then hold at 100% ACN for 3 min, at a flow rate of 1 mL/min (Temperature=30° C.). R$_t$=1.29 min (major rotamer) at 254 nm.

Example 440

(R/S)-2-((5-bromopyridin-2-yl)oxy)-7-azabicyclo[2.2.1]heptan-7-yl)(3-fluoro-2-(2H-1,2,3-triazol-2-yl)phenyl)methanone

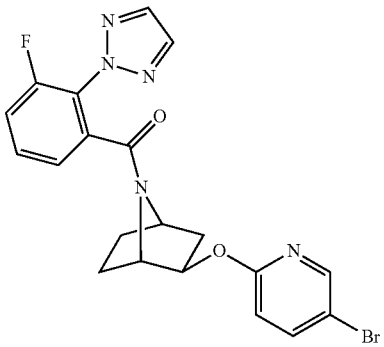 [SMILES: O=C(c1cccc(F)c1-n1nccn1)N1C2CCC1C(Oc1ccc(Br)cn1)C2]

Step A: (R/S)-Benzyl 7-azabicyclo[2.2.1]hept-5-ene-7-carboxylate

To a solution of (R/S)-benzyl 2-bromo-7-azabicyclo[2.2.1]heptane-7-carboxylate (2.96 g, 9.5 mmol; *J. Org. Chem.* 2007, 72, 8656) in THF (65 mL) under N$_2$ was added 16.5 mL of tBuOK 1M solution in THF. This mixture was stirred at rt, and slowly a suspension forms (~2 h) and reaction monitored by LC/MS. Upon completion the mixture was diluted with saturated NH₄Cl (20 mL) solution and water then extracted with EtOAc (3×50 mL). The combined organics were washed with brine and dried over Na₂SO₄ then solvent concentrated to give 1.34 g the title compound that was utilized without purification. MS (ESI) mass calcd. for: $C_{14}H_{15}NO_2$, 229.1; m/z found 230.1 [M+H]+.

Step B: (R/S)-Benzyl 2-hydroxy-7-azabicyclo[2.2.1]heptane-7-carboxylate

To a solution of (R/S)-Benzyl 7-azabicyclo[2.2.1]hept-5-ene-7-carboxylate (1 g, 4.36 mmol) from step A in THF (25 mL), cooled to 0° C., was added 1M BH₃ in THF (9.6 mL) drop-wise and the solution was allowed to warm to rt. After 3 h the reaction mixture was cooled in an ice bath and the excess borane quenched with water (2.38 mL), followed by addition of 4M NaOH (2.38 mL), and the drop-wise addition of H₂O₂ (50% by weight, 2.38 mL). The reaction was then removed from the ice bath and warmed to 40° C. for 2 h. The mixture was then cooled to rt. and solid K₂CO₃ (1.0 g) added. THF was removed under vacuum and the reaction diluted with water (100 mL) and extracted with DCM (3×). The combined organics were washed with water, dried with Na₂SO₄, filtered and concentrated. Purification via silica gel chromatography (0-3% 2M NH₃ in MeOH/DCM) provided 0.9 g of the title compound. MS (ESI) mass calcd. for: $C_{14}H_{17}NO_3$, 247.1; m/z found 248.1 [M+H]⁺ ¹H NMR (400 MHz, CDCl₃) δ 7.46-7.18 (m, 5H), 5.09 (s, 2H), 4.31 (t, J=4.7 Hz, 1H), 4.19 (d, J=5.1 Hz, 1H), 3.86 (ddd, J=6.7, 4.6, 1.8 Hz, 1H), 1.78 (dd, J=13.1, 6.8 Hz, 1H), 1.72-1.54 (m, 3H), 1.22 (dt, J=10.2, 2.4 Hz, 2H).

Step C: (R/S)-7-azabicyclo[2.2.1]heptan-2-ol

A solution of (R/S)-benzyl 2-hydroxy-7-azabicyclo[2.2.1] heptane-7-carboxylate (504 g, 2.038 mmol) from step B in MeOH (20 mL) was charged with 10% Pd/C (217 g, 0.204 mmol) and then stirred at rt under an atmosphere of hydrogen. Upon completion the reaction was filtered through a bed of celite and concentrated to give 180 mg of the title compound that was utilized without purification. MS (ESI) mass calcd. for: $C_6H_{11}NO$, 113; m/z found 114.10 [M+H]⁺.

Step D. (3-fluoro-2-(2H-1,2,3-triazol-2-yl)phenyl) ((R/S)-2-hydroxy-7-azabicyclo[2.2.1]heptan-7-yl) methanone To a 20 mL screw cap vial was added intermediate A-16 (400 g, 1.9 mmol), (R/S)-7-azabicyclo[2.2.1]heptan-2-ol from step C (198 g, 1.75 mmol), HOBt (425 g, 3.14 mmol), and EDCI (600 g, 3.13 mmol). DMF (10 mL) and TEA (0.7 mL) were then added and the vial was capped and stirred at rt overnight. The resulting mixture was diluted with water (100 mL) and extracted with EtOAc (3×20 mL) and the organic layers combined and the solvent removed. Purification via silica gel chromatography (40 g redisep, 0-100% EtOAc in hexanes) provided 160 mg of the title compound as a white solid. MS (ESI) mass calcd. for: $C_{15}H_{15}FN_4O_2$, 302.3; m/z found 303.1 [M+H]⁺.

Step E. (R/S)-2-((5-bromopyridin-2-yl)oxy)-7-azabicyclo[2.2.1]heptan-7-yl)(3-fluoro-2-(2H-1,2,3-triazol-2-yl)phenyl)methanone To a solution of (3-fluoro-2-(2H-1,2,3-triazol-2-yl)phenyl)((R/S)-2-hydroxy-7-azabicyclo[2.2.1]heptan-7-yl) methanone from step D (26.7 mg, 0.08 mmol) and 5-bromo-2-fluoropyridine in DMF (2 mL) at rt was added NaH (8 mg, 0.2 mmol) in a single portion. The mixture was stirred overnight then diluted with water (20 mL) and extracted with EtOAc (3×10 mL). The organic layers were combined and the solvent removed. Purification via silica gel chromatography (0-100% EtOAc in hexanes) provided 35.7 mg of the title compound as a light tan solid. MS (ESI): mass calcd. for $C_{20}H_{17}BrFN_5O_2$, 457.1; m/z found, 458.0 [M+H]⁺. ¹H NMR (400 MHz, CDCl₃) d 8.17-8.05 (m, 1H), 7.89-7.78 (m, 2H), 7.65 (dd, J=8.7, 2.6 Hz, 1H), 7.39-7.20 (m, 3H), 6.66-6.58 (m, 1H), 4.95-4.86 (m, 1H), 4.79-4.66 (m, 1H), 3.98-3.85 (m, 1H), 2.03-1.89 (m, 2H), 1.73-1.45 (m, 2H), 1.41-1.29 (m, 2H).

Example 441

(R/S)-2-((5-bromopyrimidin-2-yl)oxy)-7-azabicyclo [2.2.1]heptan-7-yl)(3-fluoro-2-(2H-1,2,3-triazol-2-yl)phenyl)methanone

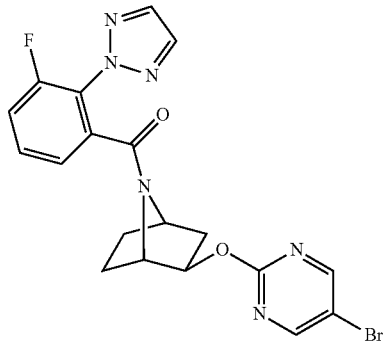 [SMILES: O=C(c1cccc(F)c1-n1nccn1)N1C2CCC1C(Oc1ncc(Br)cn1)C2]

Prepared analogous to Example 440 substituting 5-bromo-2-fluoropyridine with 5-bromo-2-chloropyrimidine. MS (ESI): mass calcd. for $C_{19}H_{16}BrFN_6O_2$, 458.1; m/z found, 459.0 [M+H]⁺. ¹H NMR (500 MHz, CDCl₃) δ 8.54-8.47 (m, 2H), 7.91-7.83 (m, 2H), 7.49-7.45 (m, 1H), 7.39-7.31 (m, 1H), 7.26-7.20 (m, 1H), 4.89-4.81 (m, 1H), 4.74-4.70 (m, 1H), 4.01-3.89 (m, 1H), 2.05-2.00 (m, 1H), 2.00-1.69 (m, 3H), 1.46-1.28 (m, 2H).

Example 442

(R/S)-(3-fluoro-2-(2H-1,2,3-triazol-2-yl)phenyl)-2-(quinoxalin-2-yloxy)-7-azabicyclo[2.2.1]heptan-7-yl)methanone

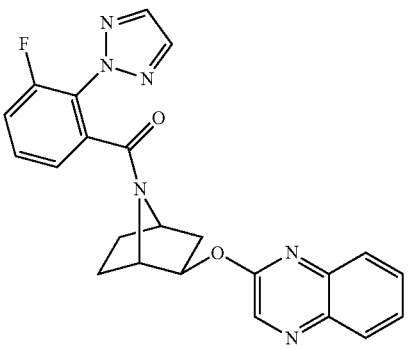 [SMILES: O=C(c1cccc(F)c1-n1nccn1)N1C2CCC1C(Oc1cnc3ccccc3n1)C2]

Prepared analogous to Example 440 substituting 5-bromo-2-fluoropyridine with 2-chloroquinoxaline. MS (ESI): mass calcd. for $C_{23}H_{19}FN_6O_2$, 430.2; m/z found, 431.1 [M+H]$^+$. $^1$H NMR (500 MHz, CDCl$_3$) δ 8.47-8.40 (m, 1H), 8.07-7.99 (m, 1H), 7.91-7.82 (m, 2H), 7.81-7.72 (m, 1H), 7.70-7.63 (m, 1H), 7.61-7.55 (m, 1H), 7.42-7.33 (m, 1H), 7.33-7.27 (m, 1H), 7.19-7.11 (m, 1H), 5.21-5.12 (m, 1H), 4.94-4.73 (m, 1H), 4.08-3.93 (m, 1H), 2.15-2.01 (m, 2H), 1.78-1.53 (m, 2H), 1.49-1.35 (m, 2H).

Example 443

(R/S)-2-((5-bromo-2-chloropyridin-3-yl)oxy)-7-azabicyclo[2.2.1]heptan-7-yl)(3-fluoro-2-(2H-1,2,3-triazol-2-yl)phenyl)methanone

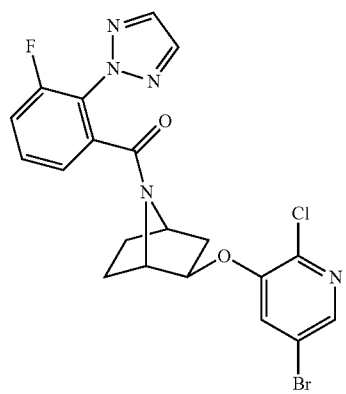 [SMILES: O=C(c1cccc(F)c1-n1nccn1)N1C2CCC1C(Oc1cc(Br)cnc1Cl)C2]

Prepared analogous to Example 440 substituting 5-bromo-2-fluoropyridine with 5-bromo-2-chloro-3-fluoro-pyridine. MS (ESI): mass calcd. for $C_{20}H_{16}BrClFN_5O_2$, 491.0; m/z found, 491.8 [M+H]$^+$. 1H NMR (400 MHz, CDCl$_3$, Compound present as a mixture of rotamers) δ 8.10 (d, J=2.0 Hz, 1H), 7.86 (s, 2H), 7.67 (dt, J=7.7, 1.2 Hz, 1H), 7.48-7.39 (m, 1H), 7.39-7.28 (m, 1H), 7.10 (d, J=2.0 Hz, 1H), 4.84-4.76 (m, 1H), 4.41-4.31 (m, 1H), 4.17-4.08 (m, 1H), 2.14-2.07 (m, 1H), 2.04-1.79 (m, 2H), 1.77-1.61 (m, 1H), 1.48-1.29 (m, 2H).

Example 444

(R/S)-(3-methyl-2-(2H-1,2,3-triazol-2-yl)phenyl)-2-((5-(trifluoromethyl)pyrazin-2-yl)oxy)-7-azabicyclo[2.2.1]heptan-7-yl)methanone

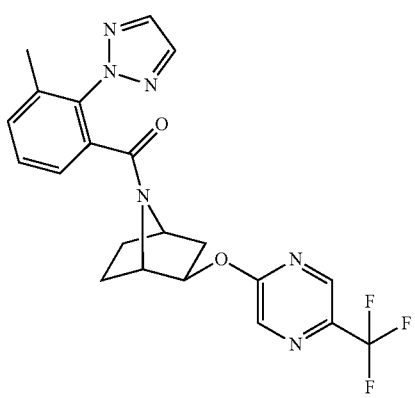

Example 445

(R/S)-(3-fluoro-2-(2H-1,2,3-triazol-2-yl)phenyl)(2-((5-(trifluoromethyl)pyrazin-2-yl)oxy)-7-azabicyclo[2.2.1]heptan-7-yl)methanone

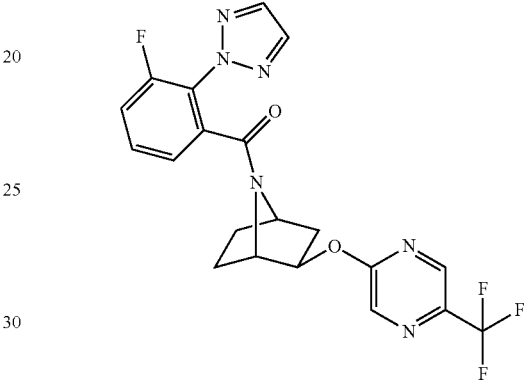

Prepared analogous to Example 445 substituting intermediate A-16 with intermediate A-24. MS (ESI): mass calcd. for $C_{21}H_{19}F_3N_6O_2$, 444.2; m/z found, 444.9 [M+H]$^+$. $^1$H NMR (400 MHz, CDCl$_3$, Compound present as a mixture of rotamers) δ 8.45-8.32 (m, 1H), 8.30-8.19 (m, 1H), 7.86-7.76 (m, 2H), 7.47-7.17 (series of m, 3H), 5.04-4.94 (series of m, 1H), 4.79-4.67 (series of m, 1H), 4.04-3.93 (m, 1H), 2.16 (two s, 3H), 2.07-1.96 (series of m, 1H), 1.90-1.76 (series of m, 2H), 1.55-1.30 (series of m, 3H).

Step A: (R/S)-tert-butyl 2-((5-(trifluoromethyl)pyrazin-2-yl)oxy)-7-azabicyclo[2.2.1]heptane-7-carboxylate To intermediate B-11 (43 mg, 0.203 mol) in DMF (5 mL) was added NaH (11 g, 0.26 mmol, 60% dispersion in mineral oil) in one portion, and the reaction mixture was heated at 80° C. for 5 minutes. Then, 2-chloro-5-(trifluoromethyl)pyrazine (59 g, 0.325 mmol) was added. After heating at 80° C. overnight, water was added and the mixture extracted with DCM (3×). The combined organics were dried (Na$_2$SO$_4$) and concentrated. Purification via silica gel chromatography (0-50% EtOAc in hexanes) gave the title compound (30 g, 41%). MS (ESI) mass calcd. for $C_{16}H_{20}F_3N_3O_3$, 359.2; m/z found 304.1 [M+2H-tBu]$^+$.

Step B: (R/S)-2-((5-(trifluoromethyl)pyrazin-2-yl)oxy)-7-azabicyclo[2.2.1]heptane To the title compound of step A (30 g, 0.106 mmol) in DCM (2 mL) was added 2M HCl in Et$_2$O (2 mL), and the reaction mixture was stirred at room temperature for 3 h. The reaction mixture was concentrated and placed under high vacuum for 1 h to give the title compound of step B. MS (ESI) mass calcd. for $C_{11}H_{12}F_3N_3O$, 259.1; m/z found 260.1 [M+H]$^+$.

Step C: (R/S)-(3-fluoro-2-(2H-1,2,3-triazol-2-yl)phenyl)(-2-((5-(trifluoromethyl)pyrazin-2-yl)oxy)-7-azabicyclo[2.2.1]heptan-7-yl)methanone To the title compound of step B (30 mg, 0.101 mmol) in DCM (5 mL) was added intermediate A-16 (23 g, 0.112 mmol), HOBt (23 mg, 0.168 mmol), EDCI (32 g, 0.168 mmol) and DIPEA (43 µL, 0.252 mmol). After stirring at room temperature for 2 h, saturated NaHCO$_3$ (aq.) was added and the mixture was extracted with DCM (3×). The combined organics were dried (Na$_2$SO$_4$), filtered and concentrated. Purification via silica gel chromatography (0-100% EtOAc in hexanes) gave the title compound (29 mg, 64%). MS (ESI): mass calcd. for C$_{20}$H$_{16}$F$_4$N$_6$O$_2$, 448.1; m/z found, 448.9 [M+H]$^+$. $^1$H NMR (400 MHz, CDCl$_3$, Compound present as a mixture of rotamers) δ 8.48-8.21 (series of m, 2H), 7.95-7.78 (m, 2H), 7.59-7.18 (series of m, 3H), 5.09-4.95 (m, 1H), 4.85-4.71 (m, 1H), 3.96 (d, J=5.2 Hz, 1H), 2.11-1.94 (series of m, 2H), 1.90-1.61 (series of m, 1H), 1.56-1.47 (series of m, 1H), 1.43-1.29 (series of m, 2H).

Example 446

(R/S)-(6-methyl-2-(2H-1,2,3-triazol-2-yl)pyridin-3-yl)(2-((5-(trifluoromethyl)pyrazin-2-yl)oxy)-7-azabicyclo[2.2.1]heptan-7-yl)methanone

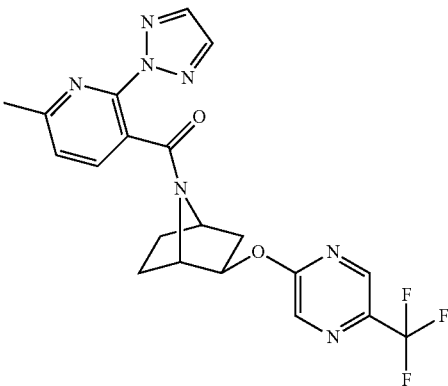

Prepared analogous to Example 445 substituting intermediate A-16 with intermediate A-3. MS (ESI): mass calcd. for C$_{20}$H$_{18}$F$_3$N$_7$O$_2$, 445.1; m/z found, 445.9 [M+H]$^+$. $^1$H NMR (400 MHz, CDCl$_3$, Compound present as a mixture of rotamers) δ 8.31 (series of three s, 2H), 7.93-7.83 (m, 2H), 7.83-7.70 (m, 1H), 7.36-7.04 (m, 1H), 5.10-4.86 (series of m, 2H), 3.91-3.78 (m, 1H), 2.65 (two s, 3H), 2.14-1.65 (series of m, 3H), 1.54-1.27 (series of m, 3H).

Example 447

(R/S)-(3-fluoro-2-(pyrimidin-2-yl)phenyl)(2-((5-(trifluoromethyl)pyrazin-2-yl)oxy)-7-azabicyclo[2.2.1]heptan-7-yl)methanone

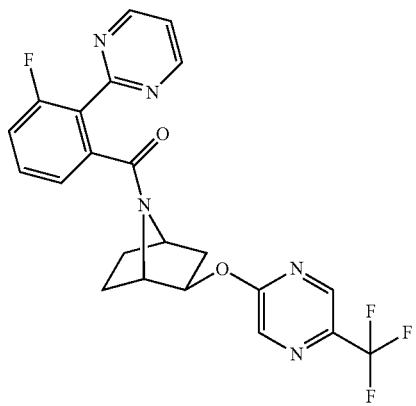

Prepared analogous to Example 445 substituting intermediate A-16 with intermediate A-2. MS (ESI): mass calcd. for C$_{22}$H$_{17}$F$_4$N$_5$O$_2$, 459.1; m/z found, 459.9 [M+H]$^+$. $^1$H NMR (400 MHz, CDCl$_3$, Compound present as a mixture of rotamers) δ 8.85-8.79 (m, 2H), 8.49-8.31 (m, 1H), 8.30-8.17 (m, 1H), 7.53-7.27 (series of m, 3H), 7.26-7.11 (m, 1H), 5.06-4.97 (m, 1H), 4.83-4.69 (m, 1H), 4.10-4.01 (m, 1H), 2.06-2.00 (m, 1H), 1.94-1.71 (m, 1H), 1.69-1.31 (series of m, 4H).

Example 448

(2-(2H-1,2,3-triazol-2-yl)phenyl)((1S,2R,4R)-2-((3-fluoro-5-(trifluoromethyl)pyridin-2-yl)amino)-7-azabicyclo[2.2.1]heptan-7-yl)methanone

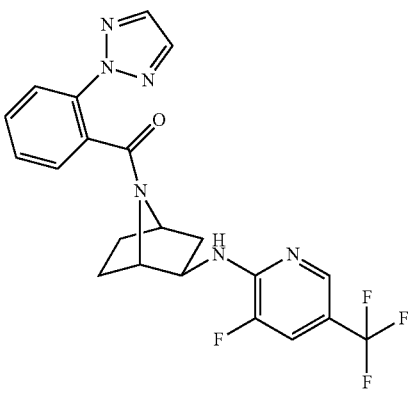 [SMILES: O=C(c1ccccc1-n1nccn1)N1C2CCC1C(Nc1ncc(C(F)(F)F)cc1F)C2]

Prepared analogous to Example 382 substituting intermediate A-2 with intermediate A-1. MS (ESI): mass calcd. for C$_{21}$H$_{18}$F$_4$N$_6$O, 446.1; m/z found, 447.2 [M+H]$^+$. Agilent 1100 Series using an Inertsil ODS-3 column (3 µm, 50×3 mm), mobile phase of 5-99% ACN in 0.05% TFA over 1.6 min and then hold at 99% ACN for 0.4 min, at a flow rate of 2.2 mL/min (Temperature=50° C.). R$_t$=1.39 min at 254 nm.

Example 449

(3-fluoro-2-(2H-1,2,3-triazol-2-yl)phenyl)((1S,2R,4R)-2-((3-fluoro-5-(trifluoromethyl)pyridin-2-yl)amino)-7-azabicyclo[2.2.1]heptan-7-yl)methanone

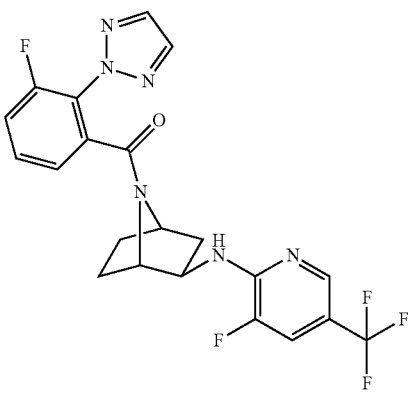

Prepared analogous to Example 382 substituting intermediate A-2 with intermediate A-16. MS (ESI): mass calcd. for C$_{21}$H$_{17}$F$_5$N$_6$O, 464.1; m/z found, 465.2 [M+H]$^+$. $^1$H NMR (500 MHz, CDCl$_3$) δ 8.15 (s, 0.4H), 8.06 (s, 0.6H), 7.91 (s, 2H), 7.57-7.48 (m, 0.4H), 7.43-7.12 (m, 3.6H), 6.48 (s, 0.6H), 5.12-5.04 (m, 0.4H), 4.78 (t, J=4.5 Hz, 0.6H), 4.62 (d, J=5.2 Hz, 0.4H), 4.40 (is, 0.6H), 4.31 (td, J=8.0, 3.3 Hz, 0.4H), 4.01-3.91 (m, 1H), 2.21-2.13 (m, 0.6H), 2.09-2.01 (m, 0.4H), 1.96-1.41 (m, 5H).

Example 450

((1S,2R,4R)-2-((3-fluoro-5-(trifluoromethyl)pyridin-2-yl)amino)-7-azabicyclo[2.2.1]heptan-7-yl)(3-methyl-2-(2H-1,2,3-triazol-2-yl)phenyl)methanone

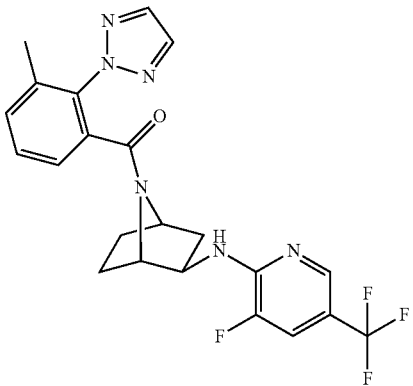 [SMILES: Cc1cccc(C(=O)N2C3CCC2C(Nc2ncc(C(F)(F)F)cc2F)C3)c1-n1nccn1]

Prepared analogous to Example 382 substituting intermediate A-2 with intermediate A-24. MS (ESI): mass calcd. for C$_{22}$H$_{20}$F$_4$N$_6$O, 460.2; m/z found, 461.2 [M+H]$^+$. $^1$H NMR (500 MHz, CDCl$_3$) δ 8.14 (s, 0.3H), 8.06 (s, 0.7H), 7.89-7.82 (m, 2H), 7.46-7.41 (m, 0.7H), 7.36-7.24 (m, 2H), 7.23-7.16 (m, 1.3H), 6.84 (s, 0.7H), 5.00-4.93 (m, 0.3H), 4.76-4.70 (m, 0.7H), 4.55 (d, J=5.2 Hz, 0.3H), 4.40 (s, 0.7H), 4.30-4.22 (m, 0.3H), 3.99-3.92 (m, 1H), 2.22 (s, 2H), 2.19 (s, 1H), 2.15 (dd, J=12.9, 8.2 Hz, 0.7H), 2.03 (dd, J=13.1, 8.0 Hz, 0.3H), 1.97-1.55 (m, 4H), 1.53-1.46 (m, 0.7H), 1.46-1.39 (m, 0.3H).

Example 451

((1S,2R,4R)-2-((3-fluoro-5-(trifluoromethyl)pyridin-2-yl)amino)-7-azabicyclo[2.2.1]heptan-7-yl)(6-methyl-3-(2H-1,2,3-triazol-2-yl)pyridin-2-yl)methanone

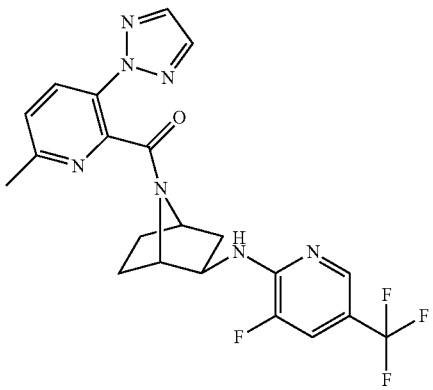

Prepared analogous to Example 382 substituting intermediate A-2 with intermediate A-21. MS (ESI): mass calcd. for C$_{21}$H$_{19}$F$_4$N$_7$O, 461.2; m/z found, 462.2 [M+H]$^+$. $^1$H NMR (500 MHz, CDCl$_3$) δ 8.23-8.17 (m, 0.4H), 8.14-8.08 (m, 1.6H), 7.87 (s, 0.4H), 7.84 (s, 1.6H), 7.39-7.30 (m, 1.2H), 7.24 (dd, J=10.9, 2.0 Hz, 0.8H), 6.69 (d, J=8.0 Hz, 0.8H), 5.78 (d, J=8.8 Hz, 0.2H), 4.94-4.90 (m, 0.8H), 4.79 (d, J=5.3 Hz, 0.2H), 4.48 (td, J=8.3, 3.2 Hz, 0.2H), 4.39 (td, J=7.9, 2.9 Hz, 0.8H), 4.08-4.03 (m, 0.8H), 4.02-3.98 (m, 0.2H), 2.64 (s, 0.6H), 2.59 (s, 2.4H), 2.27-2.19 (m, 0.8H), 2.12-1.92 (m, 2.2H), 1.86-1.56 (m, 2.8H), 1.50-1.42 (m, 0.2H).

Example 452

((1S,2R,4R)-2-((3-fluoro-5-(trifluoromethyl)pyridin-2-yl)amino)-7-azabicyclo[2.2.1]heptan-7-yl)(6-methyl-2-(2H-1,2,3-triazol-2-yl)pyridin-3-yl)methanone

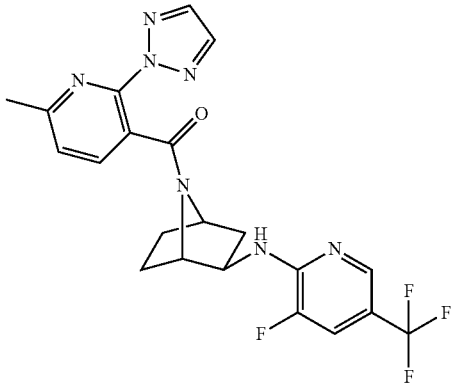

Prepared analogous to Example 382 substituting intermediate A-2 with intermediate A-3. MS (ESI): mass calcd. for C$_{21}$H$_{19}$F$_4$N$_7$O, 461.2; m/z found, 462.2 [M+H]$^+$. Analytical HPLC was obtained on a Agilent 1100 Series using a XBridge C18 column (5 μm, 100×4.6 mm), mobile phase of 10-100% ACN in 20 mM NH$_4$OH over 8 min and then hold at 100% ACN for 3 min, at a flow rate of 1 mL/min (Temperature=30° C.). R$_t$=6.59 min at 254 nm.

Example 453

((1S,2R,4R)-2-((3-fluoro-5-(trifluoromethyl)pyridin-2-yl)amino)-7-azabicyclo[2.2.1]heptan-7-yl)(5-methyl-2-(2H-1,2,3-triazol-2-yl)pyridin-3-yl)methanone

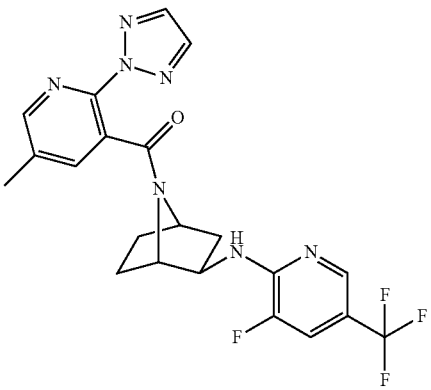

Prepared analogous to Example 382 substituting intermediate A-2 with intermediate A-60. MS (ESI): mass calcd. for C₂₁H₁₉F₄N₇O, 461.2; m/z found, 462.2 [M+H]⁺. Analytical HPLC was obtained on a Agilent 1100 Series using a XBridge C18 column (5 μm, 100×4.6 mm), mobile phase of 10-100% ACN in 20 mM NH₄OH over 8 min and then hold at 100% ACN for 3 min, at a flow rate of 1 mL/min (Temperature=30° C.). R$_t$=6.60 min at 254 nm.

Example 454

(3-fluoro-2-(oxazol-2-yl)phenyl)((1S,2R,4R)-2-((3-fluoro-5-(trifluoromethyl)pyridin-2-yl)amino)-7-azabicyclo[2.2.1]heptan-7-yl)methanone

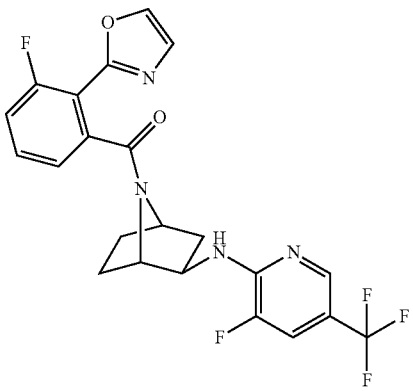 [SMILES: O=C(c1cccc(F)c1-c1ncco1)N1C2CCC1C(Nc1ncc(C(F)(F)F)cc1F)C2]

Prepared analogous to Example 382 substituting intermediate A-2 with intermediate A-68. MS (ESI): mass calcd. for C₂₂H₁₇F₅N₄O₂, 464.1; m/z found, 465.2 [M+H]⁺. ¹H NMR (500 MHz, CDCl₃) δ 8.18 (s, 0.4H), 8.03 (s, 0.6H), 7.85-7.81 (m, 1H), 7.53-7.46 (m, 0.4H), 7.41-7.27 (m, 2.6H), 7.23-7.09 (m, 2.4H), 6.05 (d, J=8.6 Hz, 0.6H), 4.91-4.87 (m, 0.6H), 4.73 (d, J=5.3 Hz, 0.4H), 4.49-4.43 (m, 1H), 3.91-3.87 (m, 0.4H), 3.85 (d, J=4.8 Hz, 0.6H), 2.23-2.16 (m, 0.6H), 2.06-2.00 (m, 0.4H), 1.99-1.82 (m, 2.6H), 1.81-1.65 (m, 1.4H), 1.59-1.52 (m, 0.6H), 1.49-1.42 (m, 0.4H).

Example 455

((1S,2R,4R)-2-((3-fluoro-5-(trifluoromethyl)pyridin-2-yl)amino)-7-azabicyclo[2.2.1]heptan-7-yl)(5-methyl-2-(pyrimidin-2-yl)pyridin-3-yl)methanone

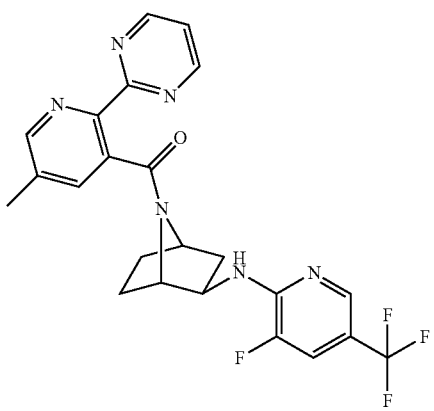 [SMILES: Cc1cnc(-c2ncccn2)c(C(=O)N2C3CCC2C(Nc2ncc(C(F)(F)F)cc2F)C3)c1]

Prepared analogous to Example 382 substituting intermediate A-2 with intermediate A-66. MS (ESI): mass calcd. for C₂₃H₂₀F₄N₆O, 472.2; m/z found, 473.2 [M+H]⁺. Analytical HPLC was obtained on a Agilent 1100 Series using a XBridge C18 column (5 μm, 100×4.6 mm), mobile phase of 10-100% ACN in 20 mM NH₄OH over 8 min and then hold at 100% ACN for 3 min, at a flow rate of 1 mL/min (Temperature=30° C.). R$_t$=6.08 min at 254 nm.

Example 456

((1S,2R,4R)-2-((3-fluoro-5-(trifluoromethyl)pyridin-2-yl)amino)-7-azabicyclo[2.2.1]heptan-7-yl)(6-methyl-3-(pyrimidin-2-yl)pyridin-2-yl)methanone

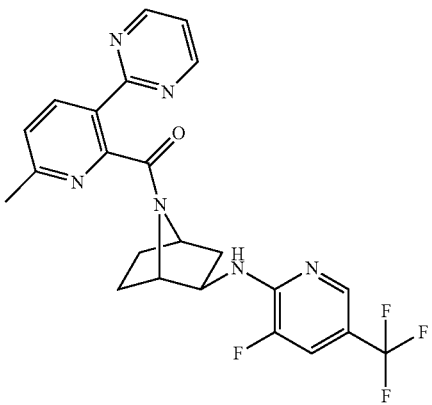 [SMILES: Cc1ccc(-c2ncccn2)c(C(=O)N2C3CCC2C(Nc2ncc(C(F)(F)F)cc2F)C3)n1]

Prepared analogous to Example 382 substituting intermediate A-2 with intermediate A-63. MS (ESI): mass calcd. for C₂₃H₂₀F₄N₆O, 472.2; m/z found, 473.2 [M+H]⁺. ¹H NMR (500 MHz, CDCl₃) δ 8.77 (d, J=4.9 Hz, 2H), 8.36 (d, J=8.0 Hz, 1H), 8.09 (s, 1H), 7.31-7.22 (m, 2H), 7.19 (dd, J=11.0, 2.0 Hz, 1H), 7.07 (d, J=8.4 Hz, 1H), 4.95-4.90 (m, 1H), 4.46-4.40 (m, 1H), 4.08 (d, J=5.1 Hz, 1H), 2.59 (s, 3H), 2.24 (dd, J=13.0, 7.6 Hz, 1H), 2.14-2.01 (m, 2H), 1.88-1.81 (m, 1H), 1.66-1.57 (m, 2H).

Example 457

((1S,2R,4R)-2-((3-fluoro-5-(trifluoromethyl)pyridin-2-yl)amino)-7-azabicyclo[2.2.1]heptan-7-yl)(5-methyl-3-(pyrimidin-2-yl)pyridin-2-yl)methanone

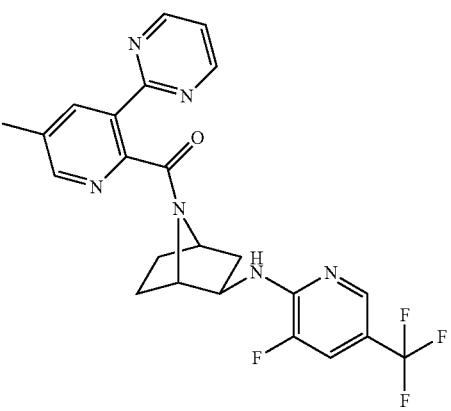 [SMILES: Cc1cnc(C(=O)N2C3CCC2C(Nc2ncc(C(F)(F)F)cc2F)C3)c(-c2ncccn2)c1]

Prepared analogous to Example 382 substituting intermediate A-2 with intermediate A-67. MS (ESI): mass calcd. for $C_{23}H_{20}F_4N_6O$, 472.2; m/z found, 473.2 [M+H]$^+$. $^1$H NMR (500 MHz, CDCl$_3$) δ 8.79 (d, J=4.9 Hz, 2H), 8.44 (dd, J=2.0, 0.9 Hz, 1H), 8.26 (dd, J=2.1, 0.9 Hz, 1H), 8.09 (s, 1H), 7.72 (d, J=8.2 Hz, 1H), 7.30-7.24 (m, 1H), 7.19 (dd, J=11.0, 2.0 Hz, 1H), 4.95-4.90 (m, 1H), 4.46-4.39 (m, 1H), 4.12 (d, J=5.3 Hz, 1H), 2.44 (s, 3H), 2.29-2.22 (m, 1H), 2.16-2.06 (m, 1H), 2.04-1.96 (m, 1H), 1.90-1.82 (m, 1H), 1.68-1.55 (m, 2H).

Example 458

((1S,2R,4R)-2-((3-fluoro-5-(trifluoromethyl)pyridin-2-yl)amino)-7-azabicyclo[2.2.1]heptan-7-yl)(3-(pyrimidin-2-yl)pyridin-2-yl)methanone

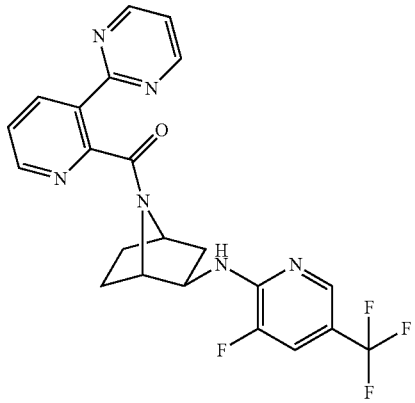

Prepared analogous to Example 382 substituting intermediate A-2 with intermediate A-64. MS (ESI): mass calcd. for $C_{22}H_{18}F_4N_6O$, 458.1; m/z found, 459.2 [M+H]$^+$. $^1$H NMR (500 MHz, CDCl$_3$) δ 8.80 (d, J=4.9 Hz, 2H), 8.62 (dd, J=4.8, 1.6 Hz, 1H), 8.48 (dd, J=7.9, 1.7 Hz, 1H), 8.08 (s, 1H), 7.66 (d, J=8.4 Hz, 1H), 7.46 (dd, J=8.0, 4.8 Hz, 1H), 7.28 (t, J=4.9 Hz, 1H), 7.19 (dd, J=11.0, 2.0 Hz, 1H), 4.96-4.91 (m, 1H), 4.47-4.41 (m, 1H), 4.11 (d, J=5.2 Hz, 1H), 2.27 (dd, J=12.9, 7.5 Hz, 1H), 2.12 (ddd, J=14.0, 8.7, 4.3 Hz, 1H), 2.06-1.97 (m, 1H), 1.91-1.83 (m, 1H), 1.68-1.59 (m, 2H).

Example 459

((1S,2R,4R)-2-((3-fluoro-5-(trifluoromethyl)pyridin-2-yl)amino)-7-azabicyclo[2.2.1]heptan-7-yl)(2-fluoro-6-(pyrimidin-2-yl)phenyl)methanone

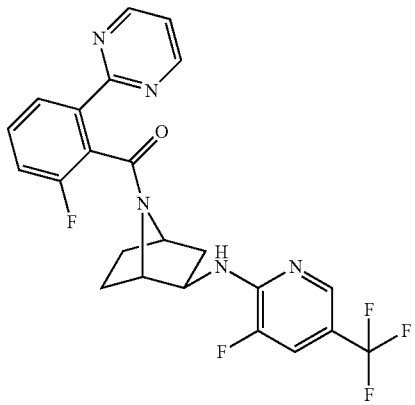

Prepared analogous to Example 382 substituting intermediate A-2 with intermediate A-6. MS (ESI): mass calcd. for $C_{23}H_{18}F_5N_5O$, 475.1; m/z found, 476.2 [M+H]$^+$. Agilent 1100 Series using an Inertsil ODS-3 column (3 μm, 50×3 mm), mobile phase of 5-99% ACN in 0.05% TFA over 1.6 min and then hold at 99% ACN for 0.4 min, at a flow rate of 2.2 mL/min (Temperature=50° C.). R$_t$=1.41 min at 254 nm.

Example 460

((1S,2R,4R)-2-((3-fluoro-5-(trifluoromethyl)pyridin-2-yl)amino)-7-azabicyclo[2.2.1]heptan-7-yl)(2-(5-fluoropyrimidin-2-yl)phenyl)methanone

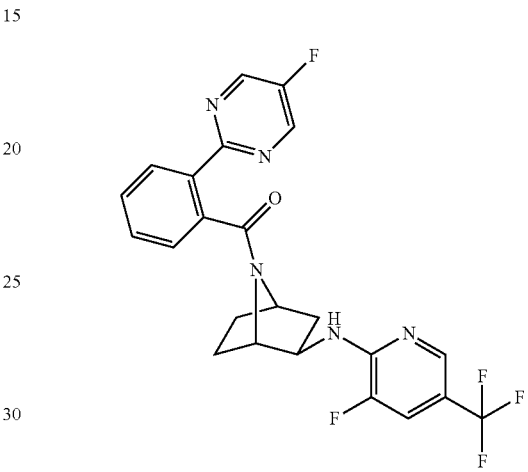

Prepared analogous to Example 382 substituting intermediate A-2 with intermediate A-55. MS (ESI): mass calcd. for $C_{23}H_{18}F_5N_5O$, 475.1; m/z found, 476.2 [M+H]$^+$. $^1$H NMR (500 MHz, CDCl$_3$) δ 8.65 (s, 1.6H), 8.60 (s, 0.4H), 8.18 (s, 0.2H), 8.11 (dd, J=7.6, 1.4 Hz, 0.2H), 8.06-7.99 (m, 1.6H), 7.58-7.42 (m, 1.8H), 7.41-7.30 (m, 2.2H), 7.11 (d, J=10.9 Hz, 0.8H), 5.49 (d, J=7.9 Hz, 0.2H), 4.93-4.87 (m, 0.8H), 4.75 (d, J=5.3 Hz, 0.2H), 4.50 (s, 0.8H), 4.42-4.36 (m, 0.2H), 4.03-3.97 (m, 1H), 2.25 (dd, J=12.9, 8.2 Hz, 0.8H), 2.11 (dd, J=12.8, 7.7 Hz, 0.2H), 2.00-1.89 (m, 1.6H), 1.88-1.78 (m, 0.4H), 1.74-1.53 (m, 2.8H), 1.48-1.40 (m, 0.2H).

Example 461

((1S,2R,4R)-2-((3-fluoro-5-(trifluoromethyl)pyridin-2-yl)amino)-7-azabicyclo[2.2.1]heptan-7-yl)(2-(pyrimidin-2-yl)phenyl)methanone

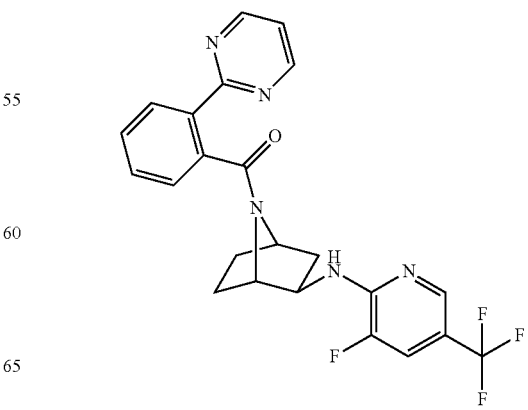

Prepared analogous to Example 382 substituting intermediate A-2 with intermediate A-59. MS (ESI): mass calcd. for $C_{23}H_{19}F_4N_5O$, 457.2; m/z found, 458.2 [M+H]$^+$. Agilent 1100 Series using an Inertsil ODS-3 column (3 μm, 50×3 mm), mobile phase of 5-99% ACN in 0.05% TFA over 1.6 min and then hold at 99% ACN for 0.4 min, at a flow rate of 2.2 mL/min (Temperature=50° C.). $R_t$=1.38 min at 254 nm.

Example 462

((1S,2R,4R)-2-((3-fluoro-5-(trifluoromethyl)pyridin-2-yl)amino)-7-azabicyclo[2.2.1]heptan-7-yl)(3-methyl-2-(pyrimidin-2-yl)phenyl)methanone

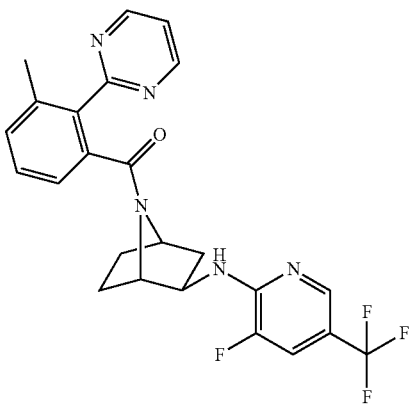

Prepared analogous to Example 382 substituting intermediate A-2 with intermediate A-26. $^1$H NMR (500 MHz, CDCl$_3$) δ 8.80 (d, J=4.9 Hz, 2H), 8.05 (s, 1H), 7.97 (s, 1H), 7.32-7.15 (m, 4H), 7.10 (dd, J=11.1, 2.0 Hz, 1H), 4.76-4.70 (m, 1H), 4.57-4.49 (m, 1H), 4.03 (d, J=4.9 Hz, 1H), 2.33 (s, 3H), 2.17 (dd, J=12.7, 8.3 Hz, 1H), 2.04-1.94 (m, 1H), 1.94-1.82 (m, 1H), 1.77-1.68 (m, 2H), 1.54-1.46 (m, 1H). Agilent 1100 Series using an Inertsil ODS-3 column (3 m, 50×3 mm), mobile phase of 5-99% ACN in 0.05% TFA over 1.6 min and then hold at 99% ACN for 0.4 min, at a flow rate of 2.2 mL/min (Temperature=50° C.). $R_t$=1.42 min at 254 nm.

Example 463

(3-fluoro-2-(5-fluoropyrimidin-2-yl)phenyl)((1S,2R,4R)-2-((3-fluoro-5-(trifluoromethyl)pyridin-2-yl)amino)-7-azabicyclo[2.2.1]heptan-7-yl)methanone

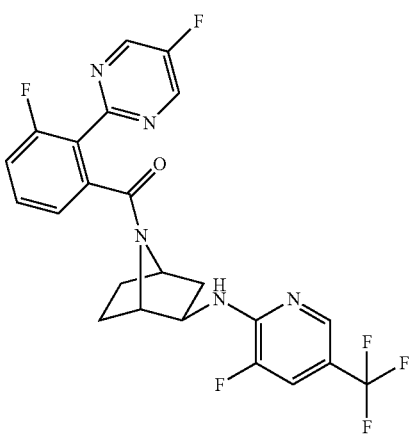 [SMILES: O=C(c1cccc(F)c1-c1ncc(F)cn1)N1C2CCC1C(Nc1ncc(C(F)(F)F)cc1F)C2]

Prepared analogous to Example 382 substituting intermediate A-2 with intermediate A-57. MS (ESI): mass calcd. for $C_{23}H_{17}F_6N_5O$, 493.1; m/z found, 494.1 [M+H]$^+$. $^1$H NMR (500 MHz, CDCl$_3$) δ 8.69 (s, 2H), 8.06 (s, 1H), 7.39-7.32 (m, 1H), 7.24-7.07 (m, 4H), 4.80-4.75 (m, 1H), 4.56-4.48 (m, 1H), 4.04 (d, J=4.9 Hz, 1H), 2.21 (dd, J=12.9, 8.2 Hz, 1H), 2.01-1.94 (m, 1H), 1.94-1.86 (m, 1H), 1.79-1.69 (m, 2H), 1.58-1.50 (m, 1H).

Example 464

((1S,2R,4R)-2-((3-chloro-5-(trifluoromethyl)pyridin-2-yl)amino)-7-azabicyclo[2.2.1]heptan-7-yl)(3-methyl-2-(pyrimidin-2-yl)phenyl)methanone

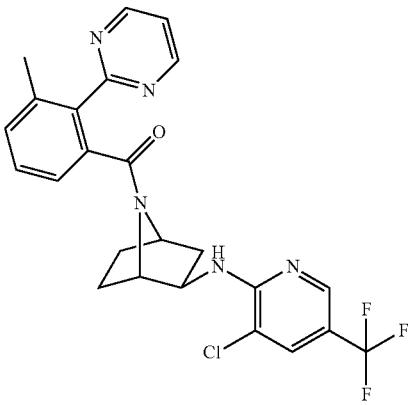

Example 465

((1S,2R,4R)-2-((3-chloro-5-(trifluoromethyl)pyridin-2-yl)amino)-7-azabicyclo[2.2.1]heptan-7-yl)(3-fluoro-2-(5-fluoropyrimidin-2-yl)phenyl)methanone

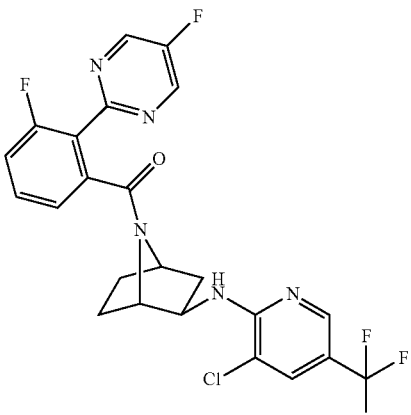

Example 466

((1S,2R,4R)-2-((3-chloro-5-(trifluoromethyl)pyridin-2-yl)amino)-7-azabicyclo[2.2.1]heptan-7-yl)(2-fluoro-6-(pyrimidin-2-yl)phenyl)methanone

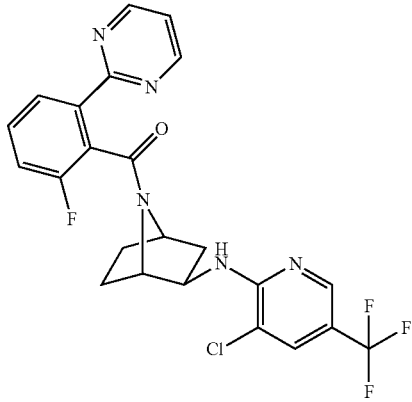

Example 467

((1S,2R,4R)-2-((3-chloro-5-(trifluoromethyl)pyridin-2-yl)amino)-7-azabicyclo[2.2.1]heptan-7-yl)(5-methyl-2-(pyrimidin-2-yl)pyridin-3-yl)methanone

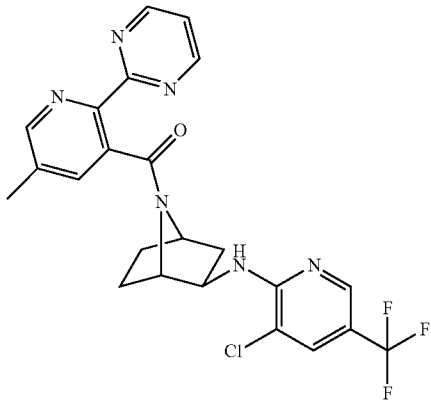 [SMILES: Cc1cnc(-c2ncccn2)c(C(=O)N2C3CCC2C(Nc2ncc(C(F)(F)F)cc2Cl)C3)c1]

Example 468

((1S,2R,4R)-2-((3-chloro-5-(trifluoromethyl)pyridin-2-yl)amino)-7-azabicyclo[2.2.1]heptan-7-yl)(6-methyl-3-(pyrimidin-2-yl)pyridin-2-yl)methanone

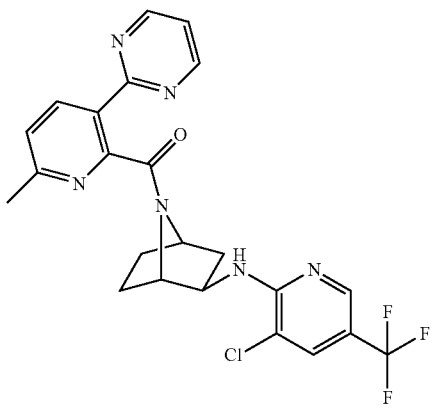 [SMILES: Cc1ccc(-c2ncccn2)c(C(=O)N2C3CCC2C(Nc2ncc(C(F)(F)F)cc2Cl)C3)n1]

Example 469

((1S,2R,4R)-2-((3-chloro-5-(trifluoromethyl)pyridin-2-yl)amino)-7-azabicyclo[2.2.1]heptan-7-yl)(5-methyl-3-(pyrimidin-2-yl)pyridin-2-yl)methanone

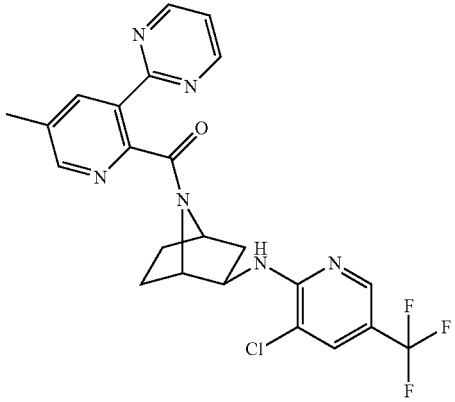

Example 470

(2-(2H-1,2,3-triazol-2-yl)phenyl)((1S,2R,4R)-2-((3-chloro-5-(trifluoromethyl)pyridin-2-yl)amino)-7-azabicyclo[2.2.1]heptan-7-yl)methanone

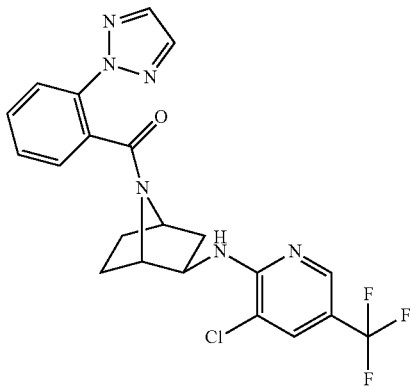

Example 471

((1S,2R,4R)-2-((3-chloro-5-(trifluoromethyl)pyridin-2-yl)amino)-7-azabicyclo[2.2.1]heptan-7-yl)(3-methyl-2-(2H-1,2,3-triazol-2-yl)phenyl)methanone

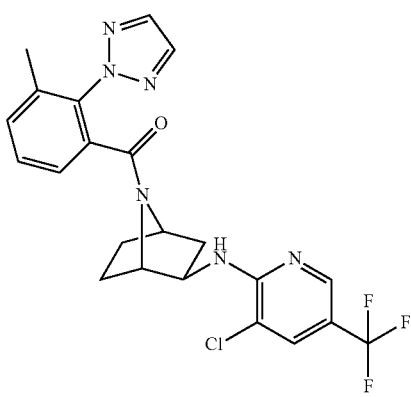

Example 472

((1S,2R,4R)-2-((3-chloro-5-(trifluoromethyl)pyridin-2-yl)amino)-7-azabicyclo[2.2.1]heptan-7-yl)(6-methyl-3-(2H-1,2,3-triazol-2-yl)pyridin-2-yl)methanone

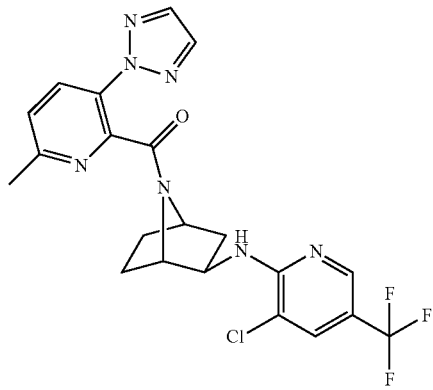 [SMILES: Cc1ccc(-n2nccn2)c(C(=O)N2C3CCC2C(Nc2ncc(C(F)(F)F)cc2Cl)C3)n1]

Example 473

((1S,2R,4R)-2-((3-chloro-5-(trifluoromethyl)pyridin-2-yl)amino)-7-azabicyclo[2.2.1]heptan-7-yl)(6-methyl-2-(2H-1,2,3-triazol-2-yl)pyridin-3-yl)methanone

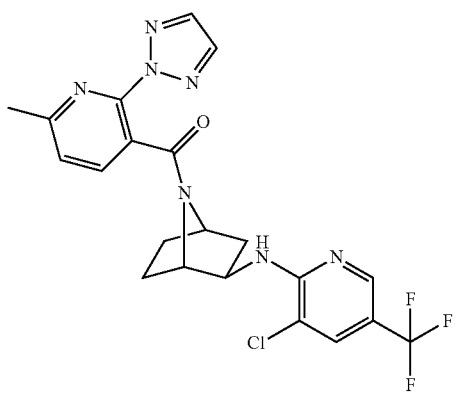

Example 474

((1S,2R,4R)-2-((3-chloro-5-(trifluoromethyl)pyridin-2-yl)amino)-7-azabicyclo[2.2.1]heptan-7-yl)(5-methyl-2-(2H-1,2,3-triazol-2-yl)pyridin-3-yl)methanone

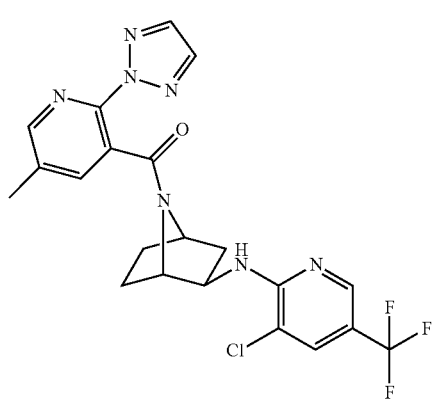 [SMILES: Cc1cnc(-n2nccn2)c(C(=O)N2C3CCC2C(Nc2ncc(C(F)(F)F)cc2Cl)C3)c1]

Example 475

((1S,2R,4R)-2-((3-chloro-5-(trifluoromethyl)pyridin-2-yl)amino)-7-azabicyclo[2.2.1]heptan-7-yl)(3-fluoro-2-(oxazol-2-yl)phenyl)methanone

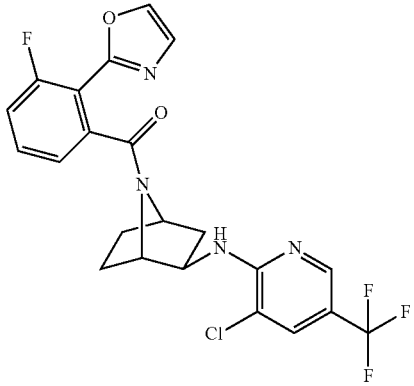

Example 476

(3-fluoro-2-(pyrimidin-2-yl)phenyl)((1S,2R,4R)-2-((5-(trifluoromethyl)pyrazin-2-yl)amino)-7-azabicyclo[2.2.1]-(3-$^2$H,$^2$H)-heptan-7-yl)methanone

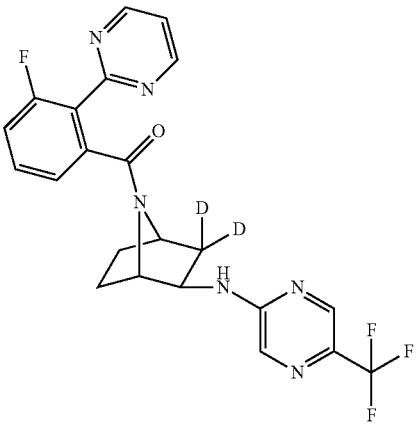 [SMILES: [2H]C1([2H])C(Nc2cnc(C(F)(F)F)cn2)C2CCC1N2C(=O)c1cccc(F)c1-c1ncccn1]

Example 477

(3-fluoro-2-(pyrimidin-2-yl)phenyl)((1S,2R,4R)-(2-$^2$H)-((5-(trifluoromethyl)pyrazin-2-yl)amino)-7-azabicyclo[2.2.1]-(3-$^2$H,$^2$H)-heptan-7-yl)methanone

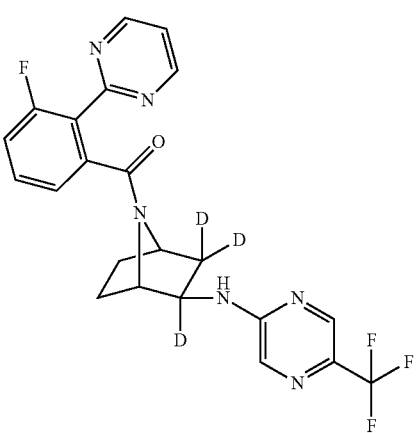 [SMILES: [2H]C1([2H])C2CCC(N2C(=O)c2cccc(F)c2-c2ncccn2)C1([2H])Nc1cnc(C(F)(F)F)cn1]

Example 478

((1S,2R,4R)-2-((3-fluoro-5-(trifluoromethyl)pyridin-2-yl)amino)-7-azabicyclo[2.2.1]heptan-7-yl)(4-methyl-3-(pyrimidin-2-yl)pyridin-2-yl)methanone

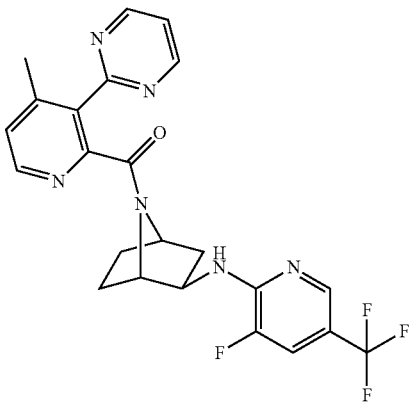

Example 479

(4-methyl-3-(pyrimidin-2-yl)pyridin-2-yl)((1S,2R,4R)-2-((5-(trifluoromethyl)pyridin-2-yl)amino)-7-azabicyclo[2.2.1]heptan-7-yl)methanone

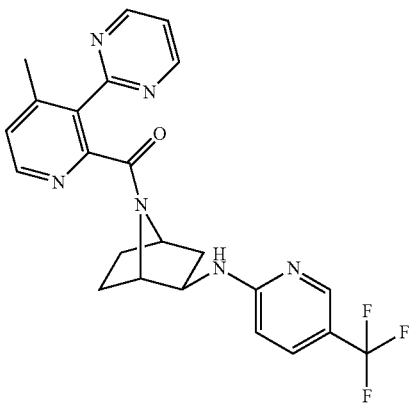

Example 480

(4-methyl-3-(pyrimidin-2-yl)pyridin-2-yl)((1S,2R,4R)-2-((5-(trifluoromethyl)pyrazin-2-yl)amino)-7-azabicyclo[2.2.1]heptan-7-yl)methanone

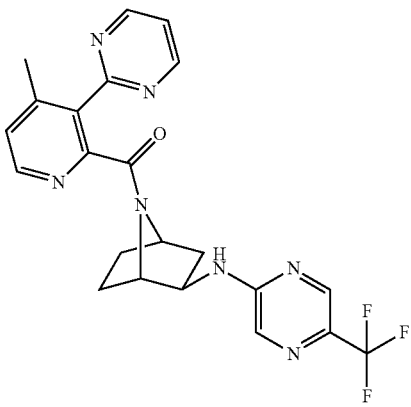

Example 481

(4-methyl-3-(pyrimidin-2-yl)pyridin-2-yl)((1S,2R,4R)-2-((5-(trifluoromethyl)pyrimidin-2-yl)amino)-7-azabicyclo[2.2.1]heptan-7-yl)methanone

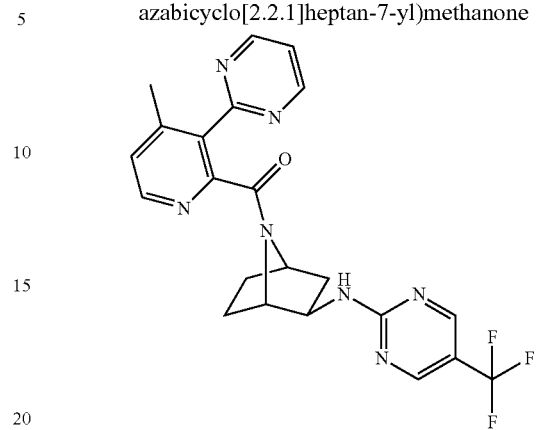

Example 482

(4-methyl-3-(2H-1,2,3-triazol-2-yl)pyridin-2-yl)((1S,2R,4R)-2-((5-(trifluoromethyl)pyrazin-2-yl)amino)-7-azabicyclo[2.2.1]heptan-7-yl)methanone

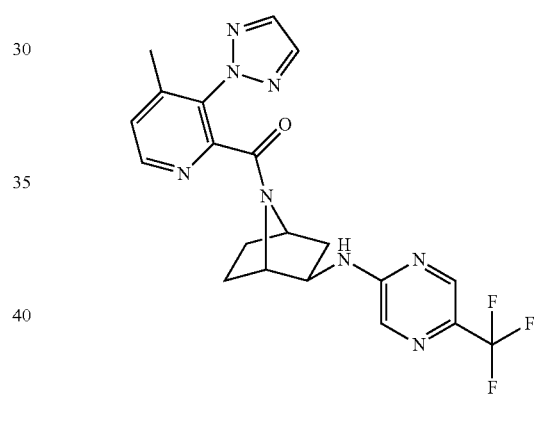

Example 483

(3-fluoro-4-methyl-2-(2H-1,2,3-triazol-2-yl)phenyl)((1S,2R,4R)-2-((3-fluoro-5-(trifluoromethyl)pyridin-2-yl)amino)-7-azabicyclo[2.2.1]heptan-7-yl)methanone

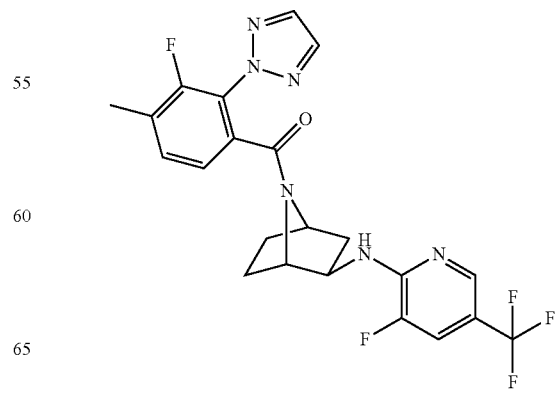

Example 484

(4,5-dimethyl-3-(pyrimidin-2-yl)pyridin-2-yl)((1S,2R,4R)-2-((3-fluoro-5-(trifluoromethyl)pyridin-2-yl)amino)-7-azabicyclo[2.2.1]heptan-7-yl)methanone

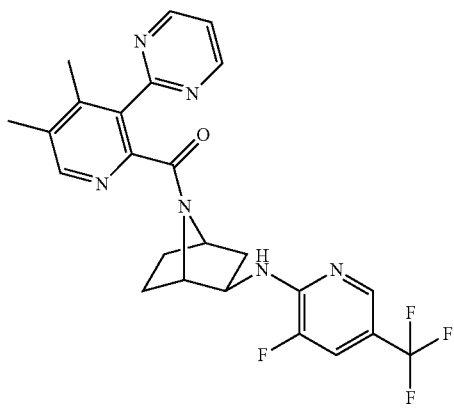 [SMILES: Cc1cnc(C(=O)N2C3CCC2C(Nc2ncc(C(F)(F)F)cc2F)C3)c(-c2ncccn2)c1C]

Example 485

((1S,2R,4R)-2-((3-fluoro-5-(trifluoromethyl)pyridin-2-yl)amino)-7-azabicyclo[2.2.1]heptan-7-yl)(3-fluoro-6-methyl-2-(pyrimidin-2-yl)phenyl)methanone

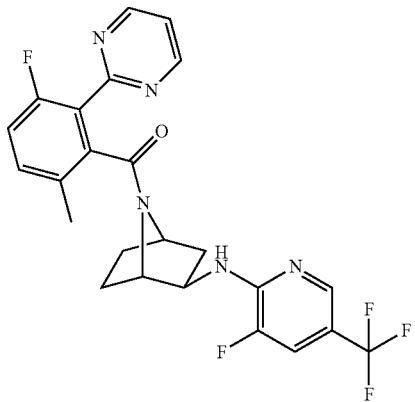 [SMILES: Cc1ccc(F)c(-c2ncccn2)c1C(=O)N1C2CCC1C(Nc1ncc(C(F)(F)F)cc1F)C2]

Example 486

(3-fluoro-4-methyl-2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone

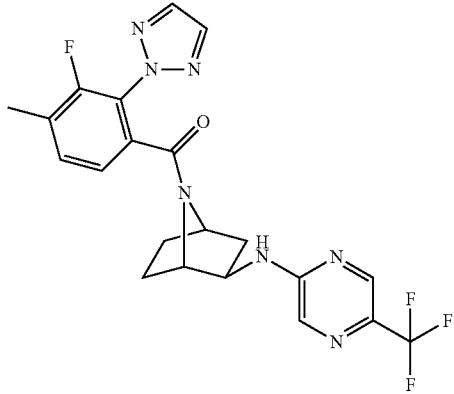 [SMILES: Cc1ccc(C(=O)N2C3CCC2C(Nc2cnc(C(F)(F)F)cn2)C3)c(-n2nccn2)c1F]

Example 487

(4,5-dimethyl-3-(pyrimidin-2-yl)pyridin-2-yl)((1S,2R,4R)-2-((5-(trifluoromethyl)pyrazin-2-yl)amino)-7-azabicyclo[2.2.1]heptan-7-yl)methanone

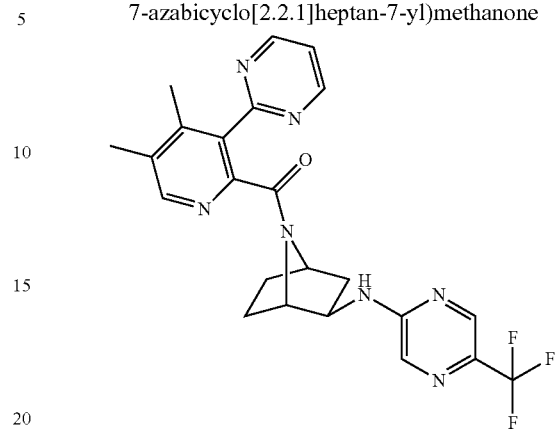

Example 488

(3-fluoro-6-methyl-2-(pyrimidin-2-yl)phenyl)((1S,2R,4R)-2-((5-(trifluoromethyl)pyrazin-2-yl)amino)-7-azabicyclo[2.2.1]heptan-7-yl)methanone

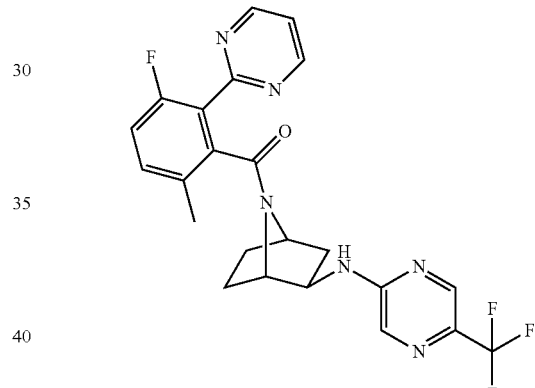

Example 489

(3-fluoro-4-methyl-2-(2H-1,2,3-triazol-2-yl)phenyl)((1S,2R,4R)-2-((5-(trifluoromethyl)pyridin-2-yl)amino)-7-azabicyclo[2.2.1]heptan-7-yl)methanone

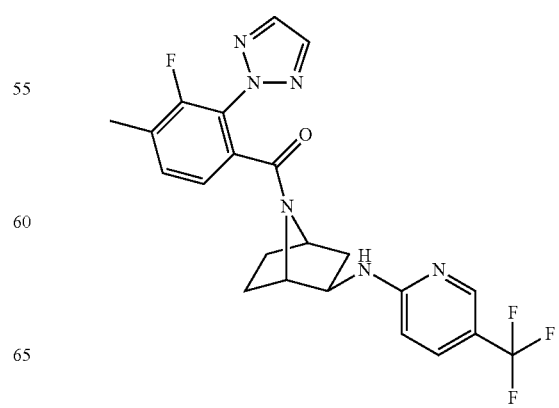

Example 490

(4,5-dimethyl-3-(pyrimidin-2-yl)pyridin-2-yl)((S,2R, 4R)-2-((5-(trifluoromethyl)pyridin-2-yl)amino)-7-azabicyclo[2.2.1]heptan-7-yl)methanone

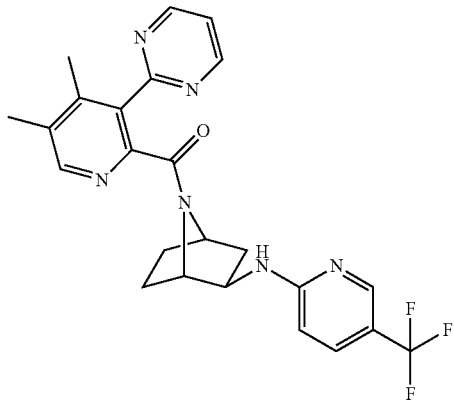 [SMILES: Cc1cnc(C(=O)N2C3CCC2C(Nc2ccc(C(F)(F)F)cn2)C3)c(-c2ncccn2)c1C]

Example 491

(3-fluoro-6-methyl-2-(pyrimidin-2-yl)phenyl)((1S, 2R,4R)-2-((5-(trifluoromethyl)pyridin-2-yl)amino)-7-azabicyclo[2.2.1]heptan-7-yl)methanone

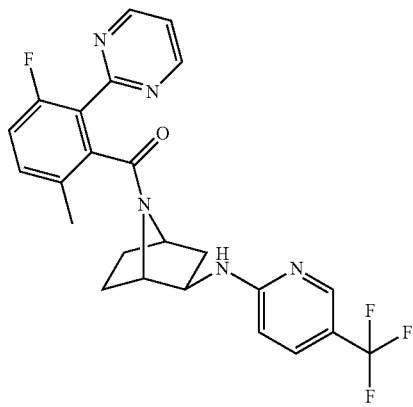 [SMILES: Cc1ccc(F)c(-c2ncccn2)c1C(=O)N1C2CCC1C(Nc1ccc(C(F)(F)F)cn1)C2]

Example 492

(3-fluoro-4-methyl-2-(pyrimidin-2-yl)phenyl)((1S, 2R,4R)-2-((5-(trifluoromethyl)pyrazin-2-yl)amino)-7-azabicyclo[2.2.1]heptan-7-yl)methanone

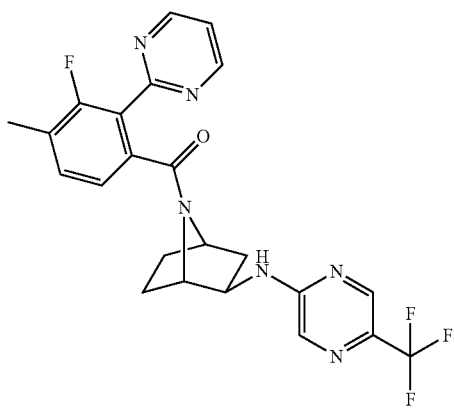 [SMILES: Cc1ccc(C(=O)N2C3CCC2C(Nc2cnc(C(F)(F)F)cn2)C3)c(-c2ncccn2)c1F]

Example 493

(3-fluoro-4-methyl-2-(pyrimidin-2-yl)phenyl)((1S, 2R,4R)-2-((5-(trifluoromethyl)pyridin-2-yl)amino)-7-azabicyclo[2.2.1]heptan-7-yl)methanone

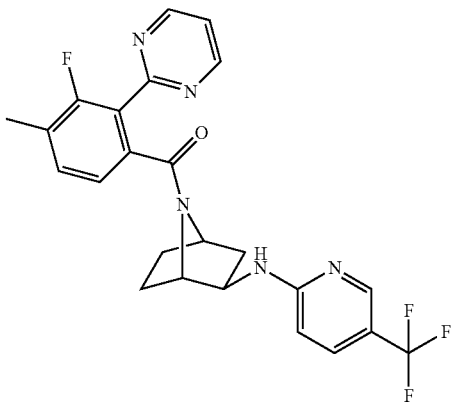 [SMILES: Cc1ccc(C(=O)N2C3CCC2C(Nc2ccc(C(F)(F)F)cn2)C3)c(-c2ncccn2)c1F]

Example 494

(3-fluoro-4-methyl-2-(pyrimidin-2-yl)phenyl)((1S, 2R,4R)-2-((5-(trifluoromethyl)pyridin-2-yl)amino)-7-azabicyclo[2.2.1]heptan-7-yl)methanone

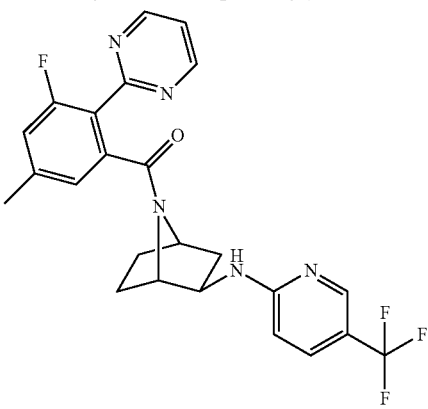 [SMILES: Cc1cc(F)c(-c2ncccn2)c(C(=O)N2C3CCC2C(Nc2ccc(C(F)(F)F)cn2)C3)c1]

Example 495

(3-fluoro-5-methyl-2-(pyrimidin-2-yl)phenyl)((1S, 2R,4R)-2-((5-(trifluoromethyl)pyridin-2-yl)amino)-7-azabicyclo[2.2.1]heptan-7-yl)methanone

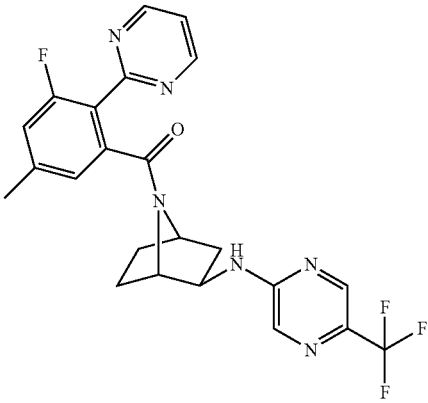 [SMILES: Cc1cc(F)c(-c2ncccn2)c(C(=O)N2C3CCC2C(Nc2cnc(C(F)(F)F)cn2)C3)c1]

Assays:

The in vitro affinity of the compounds of the invention for the rat/human orexin 1 and human orexin 2 receptors was determined by competitive radioligand binding using [3H](1-(5-(2-fluoro-phenyl)-2-methyl-thiazol-4-yl)-1-((S)-2-(5-phenyl-(1,3,4)oxadiazol-2-ylmethyl)-pyrrolidin-1-yl)-methanone) (Langmead et al., 2004) and [3H]EMPA (n-ethyl-2[96-methoxypyridin-3-yl)-(toluene-2-sulfonyl)-amino]-N-pyridin-3-ylmethyl acetamide), respectively (Langmead et al., 2004, British Journal of Pharmacology 141:340-346; Malherbe et al., 2004, British Journal of Pharmacology 156:1326-41).

The in vitro functional antagonism of the compounds on the human orexin 1 and orexin 2 receptors was determined using fluorometric imaging plate reader (FLIPR) based calcium assays.

Data are analyzed using pc-Sandy macro and graphed on Graphpad Prism 5. For analysis, each concentration point is averaged from triplicate values and the averaged values are plotted on Graphpad Prism. The IC50 is determined by applying the following equation (GraphPad Prism 5.0, SanDiego) for one site competition where X=log (concentration) and Y=specific binding. Top denotes the total [$^3$H]-(1-(5-(2-fluoro-phenyl)-2-methyl-thiazol-4-yl)-1-((S)-2-(5-phenyl-(1,3,4)oxadiazol-2-ylmethyl)-pyrrolidin-1-yl)-methanone) binding, bottom denotes the nonspecific [$^3$H]-(1-(5-(2-fluoro-phenyl)-2-methyl-thiazol-4-yl)-1-((S)-2-(5-phenyl-(1,3,4)oxadiazol-2-ylmethyl)-pyrrolidin-1-yl)-methanone) binding. Graphpad Prism calculates Ki value from IC50 and the pre-determined Kd values for [$^3$H]-(1-(5-(2-fluoro-phenyl)-2-methyl-thiazol-4-yl)-1-((S)-2-(5-phenyl-(1,3,4)oxadiazol-2-ylmethyl)-pyrrolidin-1-yl)-methanone) and [3H]-EMPA. The Ki for each compound is then uploaded into 3DX. Each run comprises individual compounds in triplicate. The data in Table 1 and Table 2 represent averages from between 2-20 runs.

Rat and Human Orexin 1 Receptor Radioligand Binding Studies

Human Embryonic Kidney 293 cells (HEK293) stably expressing rat orexin 1 receptor (Genebank accession number NM_001525) or Chinese ovary cells (CHO) stably expressing human orexin 1 receptor (Genebank accession number NM_001526) were grown to confluency in DMEM (Hyclone, cat #SH30022), 10% FBS, 1× sodium pyruvate, 10 mM HEPES, 600 μg/mL G418 and DMEM/F12 (Gibco, Cat #11039), 10% FBS, 1× Pen/Strep, 600 μg/mL G418 media, respectively on 150 cm2 tissue culture plates, washed with 5 mM EDTA in PBS (HyClone Dulbecco's Phosphate Buffered Saline 1× with Calcium and Magnesium, Cat #SH30264.01, hereafter referred to simply as PBS) and scraped into 50 ml tubes. After centrifugation (2K×G, 5 min at 4° C.), the supernatant was aspirated and the pellets frozen and stored at −800 C. Cells were resuspended in PBS in the presence of 1 tablet of protease inhibitor cocktail (Roche, Cat. #11836145001) per 50 mL. Each cell pellet from a 15 cm plate was resuspended in 10 mL, stored on ice, and homogenized for 45 sec prior to addition to the reactions. Competition binding experiments in 96 well polypropylene plates were performed using [3H]-(1-(5-(2-fluoro-phenyl)-2-methyl-thiazol-4-yl)-1-((S)-2-(5-phenyl-(1,3,4)oxadiazol-2-ylmethyl)-pyrrolidin-1-yl)-methanone) (Moraveck Corporation, specific activity=35.3 Ci/mmol), diluted to a 10 nM concentration in PBS (4 nM final). Compounds were solubilized in 100% DMSO (Acros Organics, Cat. #61042-1000) and tested over a range of 7 concentrations (from 0.1 nM to 10 μM). The final concentration of DMSO in the reactions is equal to or less than 0.1%. Total and nonspecific binding was determined in the absence and presence of 10 μM almorexant. The total volume of each reaction is 200 μL (20 μL of diluted compounds, 80 μL of [3H]-(1-(5-(2-fluoro-phenyl)-2-methyl-thiazol-4-yl)-1-((S)-2-(5-phenyl-(1,3,4)oxadiazol-2-ylmethyl)-pyrrolidin-1-yl)-methanone) diluted in PBS and 100 μL of the cell suspension). Reactions were run for 60 min at room temperature and terminated by filtration through GF/C filter plates (PerkinElmer, Cat. #6005174) presoaked in 0.3% polyethylenimine using the cell harvester (PerkinElmer Filtermate). The plates were washed 3 times by aspirating 30 ml PBS through the plates. Plates were dried in 55° C. oven for 60 min, scintillation fluid was added, and the radioactivity was counted on a Topcount (Packard).

$IC_{50}$ values (i.e. concentration of unlabelled compound required to compete for 50% of specific binding to the radioligand) was calculated using the GraphPad Prism software (GraphPad Prism Software Inc., San Diego, Calif.) with a fit to a sigmoidal dose-response curve. Apparent Ki values were calculated as $Ki=IC_{50}/(1+C/Kd)$, where C is concentration of radioligand and Kd=4 nM for rat orexin 1 receptor and 6 nM for human orexin 1 receptor.

Human Orexin 2 Receptor Radioligand Binding Studies

HEK293 stably expressing human orexin 2 receptor (Genebank accession number NM_001526) were grown to confluency in DMEM (Hyclone, cat #SH30022), 10% FBS, 1× Pen/Strep, 1× NaPyruvate, 10 mM HEPES, 600 ug/ml G418 media on 150 cm$^2$ tissue culture plates, washed with 5 mM EDTA in PBS (HyClone Dulbecco's Phosphate Buffered Saline 1× with Calcium and Magnesium, Cat #SH30264.01, hereafter referred to simply as PBS) and scraped into 50 ml tubes. After centrifugation (2K×G, 5 min at 40° C.), the supernatant was aspirated and the pellets frozen and stored at −800° C. Cells were resuspended in PBS in the presence of 1 tablet of protease inhibitor cocktail (Roche, Cat. #11836145001) per 50 mL. Each cell pellet from a 15 cm plate was resuspended in 10 mL, stored on ice, and homogenized for 45 sec just prior to addition to the reactions. Competition binding experiments in 96 well polypropylene plates were performed using [3H]-EMPA (Moraveck Corporation, specific activity=29.6 Ci/mmol), diluted to a 5 nM concentration in PBS (2 nM final concentration). Compounds were solubilized in 100% DMSO (Acros Organics, Cat. #61042-1000) and tested over a range of 7 concentration (from 0.1 nM to 10 μM). The final concentration of DMSO in the reactions is equal to or less than 0.1%. Total and nonspecific binding was determined in the absence and presence of 10 μM almorexant. The total volume of each reaction is 200 μL (20 μL of diluted compounds, 80 μL of [3H]-EMPA diluted in PBS and 100 μL of the cell suspension). Reactions were run for 60 min at room temperature and terminated by filtration through GF/C filter plates (PerkinElmer, Cat. #6005174) presoaked in 0.3% polyethylenimine using the cell harvester (PerkinElmer Filtermate). The plates were washed 3 times by aspirating 30 ml PBS through the plates. Plates were dried in 55° C. oven for 60 min, scintillation fluid was added, and the radioactivity was counted on a Topcount (Packard).

$IC_{50}$ values (i.e. concentration of unlabelled compound required to compete for 50% of specific binding to the radioligand) was calculated using the GraphPad Prism software (GraphPad Prism Software Inc., San Diego, Calif.) with a fit to a sigmoidal dose-response curve. Apparent Ki values were calculated as $Ki=IC_{50}/(1+C/Kd)$, where C is concentration of radioligand and Kd=2 nM.

Human Orexin 1 Receptor Ca2+ Mobilization Assay

CHO cells stably transfected with the human orexin 1 receptor (Genebank accession number NM_001526) were grown to confluency in DMEM/F12, 10% FBS, 1× pen-strep, 400 µg/ml G418. Cells were seeded on to 384-well Packard viewplates at a density of 10,000 cells/well and incubated overnight at 370 C, 5% $CO_2$. The cells were dye-loaded with BD Calcium Assay kit (BD, cat #640178) in HBSS (Gibco, cat #14025-092) with 2.5 mM probenecid and incubated at 37° C., 5% CO2 for 45 min. Cells were pre-incubated with compounds (diluted in DMEM/F-12) for 15-30 minutes before agonist (orexin A, 10 nM) stimulation. Ligand-induced $Ca^{2+}$ release was measured using a Fluorometric Imaging Plate Reader (FLIPR, Molecular Devices, Sunnyvale, Calif.). Functional responses were measured as peak fluorescence intensity minus basal. The concentration of agonist that produced a half-maximal response is represented by the $EC_{50}$ value. Antagonistic potency values were converted to apparent pKB values using a modified Cheng-Prusoff correction. Apparent pKB=−log $IC_{50}$/1+[conc agonist/$EC_{50}$].

Human Orexin 2 Receptor Ca2+ Mobilization Assay

PFSK-1 cells endogenously expressing the human orexin 2 receptor were grown to confluency in RPMI1640 (Hyclone, cat #30027.02), 10% FBS, 1× pen-strep. Cells were seeded on to 384-well Packard viewplates at a density of 5,000 cells/well and incubated overnight at 370 C, 5% $CO_2$. The cells were dye-loaded with BD Calcium Assay kit (BD, cat #640178) in HBSS (Gibco, cat #14025-092) with 2.5 mM probenecid and incubated at 37° C., 5% CO2 for 45 min. Cells were pre-incubated with compounds (diluted in DMEM/F-12) for 15-30 minutes before agonist (orexin B, 100 nM) stimulation. Ligand-induced $Ca^{2+}$ release was measured using a Fluorometric Imaging Plate Reader (FLIPR, Molecular Devices, Sunnyvale, Calif.). Functional responses were measured as peak fluorescence intensity minus basal. The concentration of agonist that produced a half-maximal response is represented by the $EC_{50}$ value. Antagonistic potency values were converted to apparent pKB values using a modified Cheng-Prusoff correction. Apparent pKB=−log $IC_{50}$/1+[conc agonist/EC50].

Preferred compounds of the invention are set forth in Table 1 below. Orexin receptor activity of certain compounds of the invention is also set forth in Table 1 below

TABLE 1

| Ex. No. | Compound | rOX1 Ki (nM) | hOX1 Ki (nM) | hOX2 Ki (nM) | Compound Name |
|---|---|---|---|---|---|
| 1 | | 25 | 41 | 276 | (5-fluoro-2-(pyrimidin-2-yl)phenyl)((1S,2R,4R)-2-((pyridin-2-yloxy)methyl)-7-azabicyclo[2.2.1]heptan-7-yl)methanone |
| 2 | | 31 | 23 | 500 | (±)-(6-methyl-3-(pyrimidin-2-yl)pyridin-2-yl)(2-((pyridin-2-yloxy)methyl)-7-azabicyclo[2.2.1]heptan-7-yl)methanone |
| 3A | | 24 | 19 | 268 | (6-methyl-3-(pyrimidin-2-yl)pyridin-2-yl)((1S*,2R*,4R*)-2-((pyridin-2-yloxy)methyl)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 3B | | >10000 | | >10000 | (6-methyl-3-(pyrimidin-2-yl)pyridin-2-yl)((1R*,2S*,4S*)-2-((pyridin-2-yloxy)methyl)-7-azabicyclo[2.2.1]heptan-7-yl)methanone |
| 4 | | 36 | 41 | 927 | (±)-(6-methyl-3-(2H-1,2,3-triazol-2-yl)pyridin-2-yl)(2-((pyridin-2-yloxy)methyl)-7-azabicyclo[2.2.1]heptan-7-yl)methanone |
| 5A | | 14 | 15 | 428 | (6-methyl-3-(2H-1,2,3-triazol-2-yl)pyridin-2-yl)((1S,2R,4R)-2-((pyridin-2-yloxy)methyl)-7-azabicyclo[2.2.1]heptan-7-yl)methanone |
| 5B | | >10000 | | >10000 | (6-methyl-3-(2H-1,2,3-triazol-2-yl)pyridin-2-yl)((1R,2S,4S)-2-((pyridin-2-yloxy)methyl)-7-azabicyclo[2.2.1]heptan-7-yl)methanone |
| 6 | | 14 | 15 | 428 | (6-methyl-3-(2H-1,2,3-triazol-2-yl)pyridine-2-yl)((1S,2R,4R)-2-((pyridin-2-yloxy)methyl)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 7 | | | 19 | 19 | 198 | (±)-(2-(((5-fluoropyridin-2-yl)oxy)methyl)-7-azabicyclo[2.2.1]heptan-7-yl)(6-methyl-3-(2H-1,2,3-triazol-2-yl)pyridin-2-yl)methanone |
| 8A | | | 9 | 14 | 94 | ((1S,2R,4R)-2-(((5-fluoropyridin-2-yl)oxy)methyl)-7-azabicylo[2.2.1]heptan-7-yl)(6-methyl-3-(2H-1,2,3-triazol-2-yl)pyridin-2-yl)methanone |
| 8B | | | >10000 | | >10000 | ((1R,2S,4S)-2-(((5-fluoropyridin-2-yl)oxy)methyl)-7-azabicyclo[2.2.1]heptan-7-yl)(6-methyl-3-(2H-1,2,3-triazol-2-yl)pyridin-2-yl)methanone |
| 9 | | | | 9 | 57 | (±)-(2-(((5-fluoropyridin-2-yl)oxy)methyl)-7-azabicyclo[2.2.1]heptan-7-yl)(5-methyl-2-(2H-1,2,3-triazol-2-yl)phenyl)methanone |
| 10A | | | 4 | 3 | 32 | ((1S,2R,4R)-2-(((5-fluoropyridin-2-yl)oxy)methyl)-7-azabicyclo[2.2.1]heptan-7-yl)(5-methyl-2-(2H-1,2,3-triazol-2-yl)phenyl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 10B | | 3937 | 3200 | 5148 | ((1R,2S,4S)-4-(((5-fluoropyridin-2-yl)oxy)methyl)-7-azabicyclo[2.2.1]heptan-7-yl)(5-methyl-2-(2H-1,2,3-triazol-2-yl)phenyl)methanone |
| 11 | | | 10 | 12 | (±)-(2-(((5-fluoropyridin-2-yl)oxy)methyl)-7-azabicyclo[2.2.1]heptan-7-yl)(2-(thiophen-2-yl)phenyl)methanone |
| 12A | | | 177 | 339 | ((1S*,2R*,4R*)-2-(((5-fluoropyridin-2-yl)oxy)methyl)-7-azabicyclo[2.2.1]heptan-7-yl)(2-(thiophen-2-yl)phenyl)methanone |
| 12B | | | 3 | 5 | ((1R*,2S*,4S*)-2-(((5-fluoropyridin-2-yl)oxy)methyl)-7-azabicyclo[2.2.1]heptan-7-yl)(2-(thiophen-2-yl)phenyl)methanone |
| 13 | | | 118 | 109 | (±)-(5-methyl-2-(2H-1,2,3-triazol-2-yl)phenyl)(2-(((4-(trifluoromethyl)pyrimidin-2-yl)oxy)methyl)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 14 | | | 50 | 71 | (±)-(5-methyl-2-(2H-1,2,3-triazol-2-yl)phenyl)(2-(((5-(trifluoromethyl)pyridin-2-yl)oxy)methyl)-7-azabicyclo[2.2.1]heptan-7-yl)methanone |
| 15 | | | 56 | 120 | (±)-(5-methyl-2-(2H-1,2,3-triazol-2-yl)phenyl)(2-(((3-(trifluoromethyl)pyridin-2-yl)oxy)methyl)-7-azabicyclo[2.2.1]heptan-7-yl)methanone |
| 16 | | | 20 | 42 | (±)-(5-methyl-2-(2H-1,2,3-triazol-2-yl)phenyl)(2-(((6-(trifluoromethyl)pyridin-2-yl)oxy)methyl)-7-azabicyclo[2.2.1]heptan-7-yl)methanone |
| 17 | | | 41 | 69 | (±)-(5-methyl-2-(2H-1,2,3-triazol-2-yl)phenyl)(2-(((4-methylpyridin-2-yl)oxy)methyl)-7-azabicyclo[2.2.1]heptan-7-yl)methanone |
| 18 | | | 12 | 44 | (±)-(5-methyl-2-(2H-1,2,3-triazol-2-yl)phenyl)(2-(((6-methylpyridin-2-yl)oxy)methyl)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 19 | | | 12 | 44 | (±)-(5-methyl-2-(2H-1,2,3-triazol-2-yl)phenyl)(2-(((5-methylpyridin-2-yl)oxy)methyl)-7-azabicyclo[2.2.1]heptan-7-yl)methanone |
| 20 | | | 270 | 364 | (±)-(2-(((3,6-dimethylpyrazin-2-yl)oxy)methyl)-7-azabicyclo[2.2.1]heptan-7-yl)(5-methyl-2-(2H-1,2,3-triazol-2-yl)phenyl)methanone |
| 21 | | | 300 | 487 | (±)-(5-methyl-2-(2H-1,2,3-triazol-2-yl)phenyl)(2-(((3-(trifluoromethyl)quinoxalin-2-yl)oxy)methyl)-7-azabicyclo[2.2.1]heptan-7-yl)methanone |
| 22 | | | 47 | 50 | (±)-(2-(2H-1,2,3-triazol-2-yl)phenyl)(2-(((5-fluoropyridin-2-yl)oxy)methyl)-7-azabicyclo[2.2.1]heptan-7-yl)methanone |
| 23 | | | 322 | 1500 | (±)-2-(((5-fluoropyridin-2-yl)oxy)methyl)-7-azabicyclo[2.2.1]heptan-7-yl)(quinolin-8-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 24 | | | 122 | 164 | (±)-2-(((5-fluoropyridin-2-yl)oxy)methyl)-7-azabicyclo[2.2.1]heptan-7-yl)(naphthalen-1-yl)methanone |
| 25 | | | 74 | 160 | (±)-2-(((5-fluoropyridin-2-yl)oxy)methyl)-7-azabicyclo[2.2.1]heptan-7-yl)(2-methylnaphthalen-1-yl)methanone |
| 26 | | | 117 | 394 | (±)-2-(1H-pyrazol-1-yl)phenyl)(2-(((5-fluoropyridin-2-yl)oxy)methyl)-7-azabicyclo[2.2.1]heptan-7-yl)methanone |
| 27 | | | 677 | 380 | (±)-2-(((5-fluoropyridin-2-yl)oxy)methyl)-7-yl)(3-phenylfuran-2-yl)methanone |
| 28 | | | 14 | 11 | (±)-(2-ethoxynaphthalen-1-yl)(2-(((5-fluoropyridin-2-yl)oxy)methyl)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 29 | | | 11 | 60 | (±)-(5-(2-fluorophenyl)-2-methylthiazol-4-yl)(2-(((5-fluoropyridin-2-yl)oxy)methyl)-7-azabicyclo[2.2.1]heptan-7-yl)methanone |
| 30 | | | 47 | 149 | (±)-(5-fluoro-2-(2H-1,2,3-triazol-2-yl)phenyl)(2-(((5-fluoropyridin-2-yl)oxy)methyl)-7-azabicyclo[2.2.1]heptan-7-yl)methanone |
| 31 | | | 33 | 122 | (±)-(2-fluoro-6-(pyrimidin-2-yl)phenyl)(2-(((5-fluoropyridin-2-yl)oxy)methyl)-7-azabicyclo[2.2.1]heptan-7-yl)methanone |
| 32 | | | 21 | 123 | (±)-(5-fluoro-2-(pyrimidin-2-yl)phenyl(2-(((5-fluoropyridin-2-yl)oxy)methyl)-7-azabicyclo[2.2.1]heptan-7-yl)methanone |
| 33 | | 15 | 9 | 39 | (±)-(2-(((5-fluoropyridin-2-yl)oxy)methyl)-7-azabicyclo[2.2.1]heptan-7-yl)(5-methyl-2-(pyrimidin-2-yl)phenyl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 34 | | | 60 | 467 | (±)-(2-(2H-1,2,3-triazol-2-yl)phenyl)(2-((quinoxalin-2-yloxy)methyl)-7-azabicyclo[2.2.1]heptan-7-yl)methanone |
| 35 | | 69 | 58 | 693 | (±)-(2-fluoro-6-(2H-1,2,3-triazol-2-yl)phenyl)(2-((quinoxalin-2-yloxy)methyl)-7-azabicyclo[2.2.1]heptan-7-yl)methanone |
| 36 | | | 70 | 107 | (±)-(5-methyl-2-(2H-1,2,3-trazol-2-yl)phenyl)(2-((quinoxalin-2-yloxy)methyl)-7-azabicyclo[2.2.1]heptan-7-yl)methanone |
| 37 | | | 300 | 487 | (±)-(5-fluoro-2-(2H-1,2,3-triazol-2-yl)phenyl)(2-((quinoxalin-2-yloxy)methyl)-7-azabicyclo[2.2.1]heptan-7-yl)methanone |
| 38 | | | 120 | 383 | (±)-(5-methyl-2-(pyrimidin-2-yl)phenyl)(2-((quinoxalin-2-yloxy)methyl)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 39 | | | 29 | 27 | (±)-(2-(((4,6-dimethylpyrimidin-2-yl)oxy)methyl)-7-azabicyclo[2.2.1]heptan-7-yl)(5-methyl-2-(2H-1,2,3-triazol-2-yl)phenyl)methanone |
| 40 | | | 5000 | 1203 | (±)-2-(((4,6-dimethylpyrimidin-2-yl)oxy)methyl)-7-azabicyclo[2.2.1]heptan-7-yl)(3-methyl-5-phenylisoxazol-4-yl)methanone |
| 41 | | | 35 | 22 | (±)-(2-(((4,6-dimethylpyrimidin-2-yl)oxy)methyl)-7-azabicyclo[2.2.1]heptan-7-yl)(2-ethoxynaphthalen-1-yl)methanone |
| 42 | | | 1277 | 253 | (±)-(2-(((4,6-dimethylpyrimidin-2-yloxy)methyl)-7-azabicyclo[2.2.1]heptan-7-yl)(2-ethoxyphenyl)methanone) |
| 43 | | | 222 | 92 | (±)-(2-(((4,6-dimethylpyrimidin-2-yl)oxy)methyl)-7-azabicyclo[2.2.1]heptan-7-yl)(2-fluoro-6-(pyrimidin-2-yl)phenyl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 44 | | | 400 | 104 | (±)-(2-(((4,6-dimethylpyrimidin-2-yl)oxy)methyl)-7-azabicyclo[2.2.1]heptan-7-yl)(5-fluoro-2-(pyrimidin-2-yl)phenyl)methanone |
| 45 | | | 79 | 59 | (±)-(2-(((4,6-dimethylpyrimidin-2-yl)oxy)methyl)-7-azabicyclo[2.2.1]heptan-7-yl)(5-methyl-2-(pyrimidin-2-yl)phenyl)methanone |
| 46 | | | 82 | 10 | (±)-(2-(((4,6-dimethylpyrimidin-2-yl)oxy)methyl)-7-azabicyclo[2.2.1]heptan-7-yl)(2-(thiophen-2-yl)phenyl)methanone |
| 47 | | | 460 | 418 | (±)-(6-methyl-3-(2H-1,2,3-triazol-2-yl)pyridin-2-yl)(2-(((5-(trifluoromethyl)pyridin-2-yl)oxy)methyl)-7-azabicyclo[2.2.1]heptan-7-yl)methanone |
| 48 | | | 3900 | 4700 | (±)-(3-ethoxy-6-methylpyridin-2-yl)(2-(((5-(trifluoromethyl)pyridin-2-yl)oxy)methyl)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 49 | | | 81 | 69 | 192 | (±)-(2-(((5-bromopyridin-2-yl)oxy)methyl)-7-azabicyclo[2.2.1]heptan-7-yl)(6-methyl-3-(2H-1,2,3-triazol-2-yl)pyridin-2-yl)methanone |
| 50 | | 460 | | 4399 | (±)-(2-(((5-bromopyridin-2-yl)oxy)methyl)-7-azabicyclo[2.2.1]heptan-7-yl)(3-fluoro-2-methoxyphenyl)methanone |
| 51 | | 974 | | 1800 | (±)-(2-(((5-bromopyridin-2-yl)oxy)methyl)-7-azabicyclo[2.2.1]heptan-7-yl)(3-ethoxy-6-methylpyridin-2-yl)methanone |
| 52 | | 350 | | 2300 | (±)-(3-fluoro-2-(pyrimidin-2-yl)phenyl)(2-((pyridin-2-yloxy)methyl)-7-azabicyclo[2.2.1]heptan-7-yl)methanone |
| 53 | | 2200 | | >10000 | (±)-(6-methyl-3-(2H-1,2,3-triazol-2-yl)pyridin-2-yl)(2-((pyridazin-3-yloxy)methyl)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 54 | | 3500 | | 2200 | (±)-(6-methyl-3-(2H-1,2,3-triazol-2-yl)pyridin-2-yl)(2-(((2-methylpyridin-3-yl)oxy)methyl)-7-azabicyclo[2.2.1]heptan-7-yl)methanone |
| 55 | | 119 | 150 | 202 | (±)-(6-methy-3-(2H-1,2,3-triazol-2-yl)pyridin-2-yl)(2-(((3-methylpyridin-2-yl)oxy)methyl)-7-azabicyclo[2.2.1]heptan-7-yl)methanone |
| 56 | | >10000 | | >10000 | (±)-(2-(((1-methyl-1H-pyrazol-5-yl)oxy)methyl)-7-azabicyclo[2.2.1]heptan-7-yl)(6-methyl-3-(2H-1,2,3-triazol-2-yl)pyridin-2-yl)methanone |
| 57 | | 1000 | | 7300 | (±)-(6-methyl-3-(2H-1,2,3-triazol-2-yl)pyridin-2-yl)(2-((pyridin-4-yloxy)methyl)-7-azabicyclo[2.2.1]heptan-7-yl)methanone |
| 58 | | 88 | 117 | 2400 | (±)-(6-methyl-3-(2H-1,2,3-triazol-2-yl)pyridin-2-yl)(2-((pyridin-3-yloxy)methyl)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 59 | | | 2600 | | 4900 | (±)-(6-methyl-3-(2H-1,2,3-triazol-2-yl)pyridin-2-yl)(2-((pyrimidin-2-yloxy)methyl)-7-azabicyclo[2.2.1]heptan-7-yl)methanone |
| 60 | | | 7800 | | >10000 | (±)-(6-methyl-3-(2H-1,2,3-triazol-2-yl)pyridin-2-yl)(2-((pyrazin-2-yloxy)methyl)-7-azabicyclo[2.2.1]heptan-7-yl)methanone |
| 61 | | | 2800 | | >10000 | (±)-(6-methyl-3-(2H-1,2,3-triazol-2-yl)pyridin-2-yl)(2-((pyrimidin-4-yloxy)methyl)-7-azabicyclo[2.2.1]heptan-7-yl)methanone |
| 62 | | 74 | 46 | 188 | (±)-(6-methyl-3-(2H-1,2,3-triazol-2-yl)pyridin-2-yl)(2-(((6-methylpyridin-2-yl)oxy)methyl)-7-azabicyclo[2.2.1]heptan-7-yl)methanone |
| 63 | | 25 | 25 | 339 | (±)-(2-(((5-fluoropyridin-2-yl)oxy)methyl)-7-azabicyclo[2.2.1]heptan-7-yl)(6-methyl-3-(oxazol-2-yl)pyridin-2-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 64 | | 18 | 24 | 81 | (±)-(2-(((5-fluoropyridin-2-yl)oxy)methyl)-7-azabicyclo[2.2.1]heptan-7-yl)(6-methyl-3-(pyrimidin-2-yl)pyridin-2-yl)methanone |
| 65 | | 1440 | | 6200 | (±)-(3,6'-dimethyl-[2,3'-bipyridin]-2'-yl)(2-(((5-fluoropyridin-2-yl)oxy)methyl)-7-azabicyclo[2.2.1]heptan-7-yl)methanone |
| 66 | | 197 | 293 | 620 | (±)-(2-(((5-fluoropyridin-2-yl)oxy)methyl)-7-azabicyclo[2.2.1]heptan-7-yl)(6-methyl-3-(3-methyl-1,2,4-oxadiazol-5-yl)pyridin-2-yl)methanone |
| 67 | | 48 | 69 | 258 | (±)-(2-(((5-fluoropyridin-2-yl)oxy)methyl)-7-azabicyclo[2.2.1]heptan-7-yl)(6-methyl-3-(3-methyl-1H-pyrazol-1-yl)pyridin-2-yl)methanone |
| 68 | | 27 | 22 | 576 | (±)-(2-(((5-fluoropyridin-2-yl)oxy)methyl)-7-azabicyclo[2.2.1]heptan-7-yl)(6-methyl-2-(pyrrolidin-1-yl)pyridin-2-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 69 | 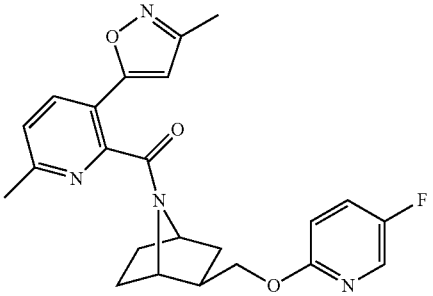 [SMILES: Cc1cc(-c2ccc(C)nc2C(=O)N2C3CCC2C(COc2ccc(F)cn2)C3)on1] | 40 | 64 | 174 | (±)-(2-(((5-fluoropyridin-2-yl)oxy)methyl)-7-azabicyclo[2.2.1]heptan-7-yl)(6-methyl-3-(3-methylisoxazol-5-yl)pyridin-2-yl)methanone |
| 70 | 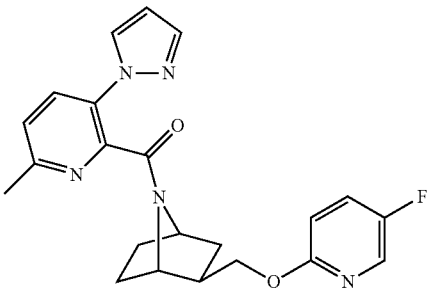 [SMILES: Cc1ccc(-n2cccn2)c(C(=O)N2C3CCC2C(COc2ccc(F)cn2)C3)n1] | 88 | 62 | 624 | (±)-(2-(((5-fluoropyridin-2-yl)oxy)methyl)-7-azabicyclo[2.2.1]heptan-7-yl)(6-methyl-3-(1H-pyrazol-1-yl)pyridin-2-yl)methanone |
| 71 | 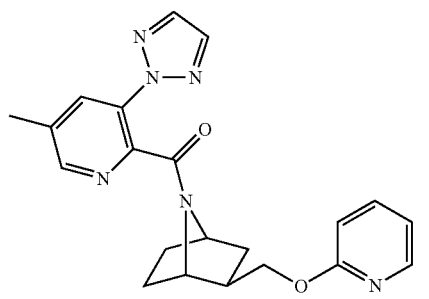 | 1200 | | 3700 | (±)-(5-methyl-3-(2H-1,2,3-triazol-2-yl)pyridin-2-yl)(2-((pyridin-2-yloxy)methyl)-7-azabicyclo[2.2.1]heptan-7-yl)methanone |
| 72 | 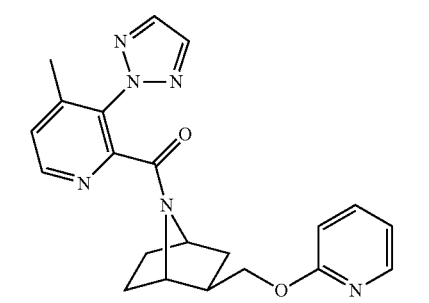 [SMILES: Cc1ccnc(C(=O)N2C3CCC2C(COc2ccccn2)C3)c1-n1nccn1] | 137 | 162 | 2400 | (±)-(4-methyl-3-(2H-1,2,3-triazol-2-yl)pyridin-2-yl)(2-((pyridin-2-yloxy)methyl)-7-azabicyclo[2.2.1]heptan-7-yl)methanone |
| 73 | 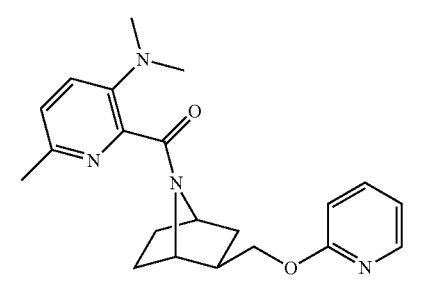 [SMILES: Cc1ccc(N(C)C)c(C(=O)N2C3CCC2C(COc2ccccn2)C3)n1] | 278 | | 7900 | (±)-(3-(dimethylamino)-6-methylpyridin-2-yl)(2-((pyridin-2-yloxy)methyl)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 74 | | | 359 | 1700 | (±)-(3-(2H-1,2,3-triazol-2-yl)quinolin-2-yl)(2-((pyridin-2-yloxy)methyl)-7-azabicyclo[2.2.1]heptan-7-yl)methanone |
| 75 | | 18 | 7 | 220 | (±)-(7-ethoxyquinolin-8-yl)(2-((pyridin-2-yloxy)methyl)-7-azabicyclo[2.2.1]heptan-7-yl)methanone |
| 76 | | >10000 | | >10000 | (±)-(3,6-dimethylimidazo[1,2-a]pyridin-5-yl)(2-((pyridin-2-yloxy)methyl)-7-azabicyclo[2.2.1]heptan-7-yl)methanone |
| 77 | | 103 | 66 | 867 | (±)-(1-methyl-4-phenyl-1H-pyrazol-3-yl)((1S,2R,4R)-2-((pyridin-2-yloxy)methyl)-7-azabicyclo[2.2.1]heptan-7-yl)methanone |
| 78 | | | 418 | 3100 | (±)-(1-methyl-3-phenyl-1H-pyrazol-4-yl)((1S,2R,4R)-2-((pyridin-2-yloxy)methyl)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 79 | | | 2400 | 8500 | (±)-((3,7-dimethylimidazo[1,2-a]pyridin-8-yl)(2-((pyridin-2-yloxy)methyl)-7-azabicyclo[2.2.1]heptan-7-yl)methanone |
| 80 | | | 1100 | >10000 | (±)-(7-methylimidazo[1,2-a]pyridin-8-yl)(2-((pyridin-2-yloxy)methyl)-7-azabicyclo[2.2.1]heptan-7-yl)methanone |
| 81 | | | 916 | 2900 | (±)-(1-methyl-4-phenyl-1H-pyrazol-5-yl)(2-((pyridin-2-yloxy)methyl)-7-azabicyclo[2.2.1]heptan-7-yl)methanone |
| 82 | | | >10000 | >10000 | (±)-((6-methylimidazo[1,2-a]pyridin-5-yl)(2-((pyridin-2-yloxy)methyl)-7-azabicyclo[2.2.1]heptan-7-yl)methanone |
| 83 | | 17 | 12 | 271 | (±)-(3-ethoxyisoquinolin-4-yl)(2-((pyridin-2-yloxy)methyl)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 84 | | 2600 | | 9701 | (±)-(1-methyl-5-phenyl-1H-pyrazol-4-yl)(-2-((pyridin-2-yloxy)methyl)-7-azabicyclo[2.2.1]heptan-7-yl)methanone |
| 85 | | >10000 | | >10000 | (±)-(6-methyl-3-(4-methylpiperazin-1-yl)pyridin-2-yl)(2-((pyridin-2-yloxy)methyl)-7-azabicyclo[2.2.1]heptan-7-yl)methanone |
| 86 | | >10000 | | >10000 | (±)-(6-methyl-3-(piperazin-1-yl)pyridin-2-yl)(2-((pyridin-2-yloxy)methyl)-7-azabicyclo[2.2.1]heptan-7-yl)methanone |
| 87 | | 4200 | | >10000 | (±)-(6-methyl-3-morpholinopyridin-2-yl)((1S,2R,4R)-2-((pyridin-2-yloxy)methyl)-7-azabicyclo[2.2.1]heptan-7-yl)methanone |
| 88 | | 47 | 49 | 690 | (±)-(7-methoxyquinolin-8-yl)(2-((pyridin-2-yloxy)methyl)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 89 | | | 11 | 10 | 38 | (±)-(2-ethoxynaphthalen-1-yl)(2-((pyridin-2-yloxy)methyl)-7-azabicyclo[2.2.1]heptan-7-yl)methanone |
| 90 | | | 3000 | | >10000 | (±)-(3,6'-dimethyl-[2,3'-bipyridin]-2'-yl)(2-((pyridin-2-yloxy)methyl)-7-azabicyclo[2.2.1]heptan-7-yl)methanone |
| 91 | | | 624 | | 3300 | (±)-(3-(2H-1,2,3-trizol-2-yl)pyridin-2-yl)(2-((pyridin-2-yloxy)methyl)-7-azabicyclo[2.2.1]heptan-7-yl)methanone |
| 92 | | | 20 | 11 | 218 | (±)-(2-methyl-5-phenylthiazol-4-yl)(2-((pyridin-2-yloxy)methyl)-7-azabicyclo[2.2.1]heptan-7-yl)methanone |
| 93 | | | 40 | 73 | 836 | (±)-(6-methyl-3-(oxazol-2-yl)pyridin-2-yl)(2-((pyridin-2-yloxy)methyl)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 94 | | | 170 | 200 | 2100 | (±)-(6-methyl-3-(3-methylisoxazol-5-yl)pyridin-2-yl)(2-((pyridin-2-yloxy)methyl)-7-azabicyclo[2.2.1]heptan-7-yl)methanone |
| 95 | | | 247 | | 3700 | (±)-(6-methyl-3-(1H-pyrazol-1-yl)pyridin-2-yl)(2-((pyridin-2-yloxy)methyl)-7-azabicyclo[2.2.1]heptan-7-yl)methanone |
| 96 | | | 70 | 76 | 950 | (±)-(6-methyl-3-(4-methyl-1H-pyrazol-1-yl)pyridin-2-yl)(2-((pyridin-2-yloxy)methyl)-7-azabicyclo[2.2.1]heptan-7-yl)methanone |
| 97 | | | 35 | 32 | 840 | (±)-(6-methyl-3-(pyrrolidin-1-yl)pyridin-2-yl)(2-((pyridin-2-yloxy)methyl)-7-azabicyclo[2.2.1]heptan-7-yl)methanone |
| 98 | | | >10000 | | >10000 | (±)-(3,6'-dimethyl-[2,3'-bipyridin]-2'-yl)(2-(((5-fluoropyrimidin-2-yl)oxy)methyl)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 99 | 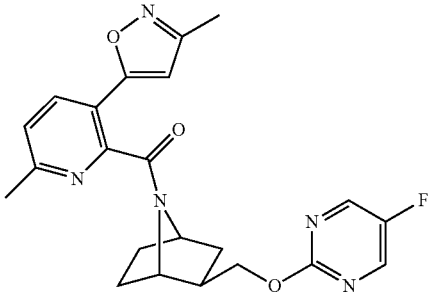 | | 1500 | 2900 | (±)-(2-(((5-fluoropyrimidin-2-yl)oxy)methyl)-7-azabicyclo[2.2.1]heptan-7-yl)(6-methyl-3-(3-methylisoxazol-5-yl)pyridin-2-yl)methanone |
| 100 | 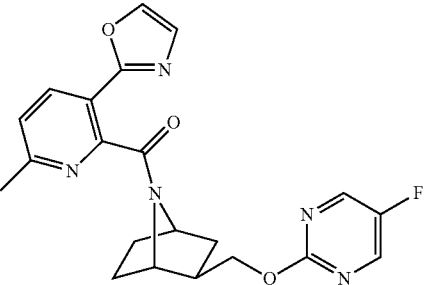 | | 950 | 1800 | (±)-(2-(((5-fluoropyrimidin-2-yl)oxy)methyl)-7-azabicyclo[2.2.1]heptan-7-yl)(6-methyl-3-(oxazol-2-yl)pyridin-2-yl)methanone |
| 101 | 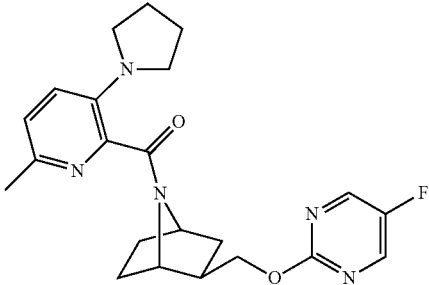 | | 650 | 1200 | (±)-(2-(((5-fluoropyrimidin-2-yl)oxy)methyl)-7-azabicyclo[2.2.1]heptan-7-yl)(6-methyl-3-(pyrrolidin-1-yl)pyridin-2-yl)methanone |
| 102 | 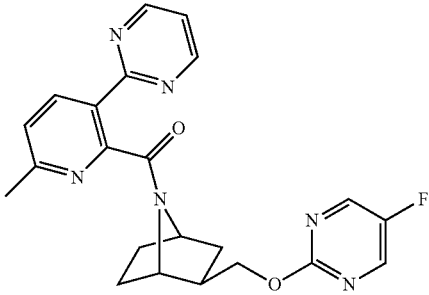 [SMILES: Cc1ccc(-c2ncccn2)c(C(=O)N2C3CCC2C(COc2ncc(F)cn2)C3)n1] | | | | (±)-(2-(((5-fluoropyrimidin-2-yl)oxy)methyl)-7-azabicyclo[2.2.1]heptan-7-yl)(6-methyl-3-(pyrimidin-2-yl)pyridin-2-yl)methanone |
| 103 | 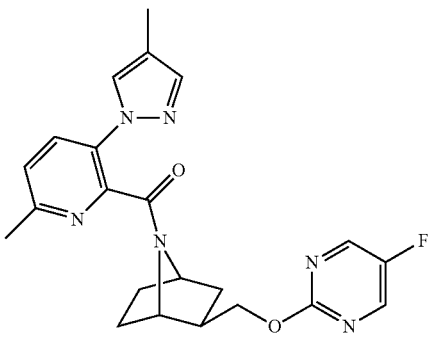 [SMILES: Cc1cnn(-c2ccc(C)nc2C(=O)N2C3CCC2C(COc2ncc(F)cn2)C3)c1] | | 1700 | 3600 | (±)-(2-(((5-fluoropyrimidin-2-yl)oxy)methyl)-7-azabicyclo[2.2.1]heptan-7-yl)(6-methyl-3-(4-methyl-1H-pyrazol-1-yl)pyridin-2-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 104 | | | 1100 | 4600 | (±)-(2-(((5-fluoropyrimidin-2-yl)oxy)methyl)-7-azabicyclo[2.2.1]heptan-7-yl)(6-methyl-3-(1H-pyrazol-1-yl)pyridin-2-yl)methanone |
| 105 | | | | | (±)-(2-(((5-fluoropyridin-2-yl)oxy)methyl)-7-azabicyclo[2.2.1]heptan-7-yl)(5-methyl-2-(2H-1,2,3-triazol-2-yl)phenyl)methanone |
| 106 | | | 300 | 154 | (±)-(2,6-dimethoxyphenyl)(2-(((5-fluoropyridin-2-yl)oxy)methyl)-7-azabicyclo[2.2.1]heptan-7-yl)methanone |
| 107 | | | 440 | 2200 | (±)-((3-fluoro-2-methoxyphenyl)(2-(((5-fluoropyridin-2-yl)oxy)methyl)-7-azabicyclo[2.2.1]heptan-7-yl)methanone |
| 108 | | 10 | 12 | 12 | (±)-(2-(((5-fluoropyridin-2-yl)oxy)methyl)-7-azabicyclo[2.2.1]heptan-7-yl)(2-methoxy-6-(2H-1,2,3-triazol-2-yl)phenyl)methanone |

| Ex. No. | Compound | rOX1 Ki (nM) | hOX1 Ki (nM) | hOX2 Ki (nM) | Compound Name |
|---|---|---|---|---|---|
| 109 | | 29 | 20 | 99 | (±)-(5-fluoro-2-(1H-pyrazol-5-yl)phenyl)(2-(((5-fluoropyridin-2-yl)oxy)methyl)-7-azabicyclo[2.2.1]heptan-7-yl)methanone |
| 110 | | 54 | 67 | 94 | (±)-(2-(((5-fluoropyridin-2-yl)oxy)methyl)-7-azabicyclo[2.2.1]heptan-7-yl)(2-methyl-6-(2H-1,2,3-triazol-2-yl)phenyl)methanone |
| 111 | | 19 | 19 | 198 | (±)-(2-(((5-fluoropyridin-2-yl)oxy)methyl)-7-azabicyclo[2.2.1]heptan-7-yl)(6-methyl-3-(2H-1,2,3-triazol-2-yl)pyridin-2-yl)methanone |
| 112 | | | 480 | 1000 | (±)-(5-chloro-3-(2H-1,2,3-triazol-2-yl)pyridin-2-yl)(2-(((5-fluoropyridin-2-yl)oxy)methyl)-7-azabicyclo[2.2.1]heptan-7-yl)methanone |
| 113 | | | 3400 | 4800 | (±)-(2-(((5-fluoropyridin-2-yl)oxy)methyl)-7-azabicyclo[2.2.1]heptan-7-yl)(5-methoxy-3-(2H-1,2,3-triazol-2-yl)pyridin-2-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 114 | | 20 | 48 | 73 | (±)-(2-(((5-fluoropyridin-2-yl)oxy)methyl)-7-azabicyclo[2.2.1]heptan-7-yl)(5-methoxy-2-(2H-1,2,3-triazol-2-yl)phenyl)methanone |
| 115 | | 57 | 78 | 108 | (±)-(2-fluoro-6-(2H-1,2,3-triazol-2-yl)phenyl)(2-(((5-fluoropyridin-2-yl)oxy)methyl)-7-azabicyclo[2.2.1]heptan-7-yl)methanone |
| 116 | | 142 | 250 | 315 | (±)-(4-fluoro-2-(2H-1,2,3-triazol-2-yl)phenyl)(2-(((5-fluoropyridin-2-yl)oxy)methyl)-7-azabicyclo[2.2.1]heptan-7-yl)methanone |
| 117 | | 62 | 82 | 245 | (±)-(3-fluoro-2-(2H-1,2,3-triazol-2-yl)phenyl)(2-(((5-fluoropyridin-2-yl)oxy)methyl)-7-azabicyclo[2.2.1]heptan-7-yl)methanone |
| 118 | | 440 | | 2200 | (±)-(3-ethoxy-6-methylpyridin-2-yl)(2-(((5-fluoropyridin-2-yl)oxy)methyl)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 119 | | 500 | | 1300 | (±)-(2-(((5-fluoropyridin-2-yl)oxy)methyl)-7-azabicyclo[2.2.1]heptan-7-yl)(4-methoxy-2-(2H-1,2,3-triazol-2-yl)phenyl)methanone |
| 120 | | 15 | 14 | 124 | (±)-(5-chloro-2-(2H-1,2,3-triazol-2-yl)phenyl)(2-(((5-fluoropyridin-2-yl)oxy)methyl)-7-azabicyclo[2.2.1]heptan-7-yl)methanone |
| 121 | | 78 | 68 | 340 | (±)-(2-(((5-fluoropyridin-2-yl)oxy)methyl)-7-azabicyclo[2.2.1]heptan-7-yl)(4-methyl-2-(2H-1,2,3-triazol-2-yl)phenyl)methanone |
| 122 | | 118 | 154 | 1000 | (±)-(2-(((5-fluoropyridin-2-yl)oxy)methyl)-7-azabicyclo[2.2.1]heptan-7-yl)(4-methyl-2-(pyrimidin-2-yl)phenyl)methanone |
| 123 | | 400 | | 286 | (±)-(2-(((5-fluoropyridin-2-yl)oxy)methyl)-7-azabicyclo[2.2.1]heptan-7-yl)(2-methyl-6-(pyrimidin-2-yl)phenyl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 124 | | 83 | 52 | 355 | (±)-(3-fluoro-2-(pyrimidin-2-yl)phenyl)(-2-(((5-fluoropyridin-2-yl)oxy)methyl)-7-azabicyclo[2.2.1]heptan-7-yl)methanone |
| 125 | | 47 | 29 | 132 | (±)-(2-(((5-fluoropyridin-2-yl)oxy)methyl)-7-azabicyclo[2.2.1]heptan-7-yl)(3-methyl-2-(2H-1,2,3-triazol-2-yl)phenyl)methanone |
| 126 | | 23 | 27 | 231 | (±)-(2-(((5-fluoropyridin-2-yl)oxy)methyl)-7-azabicyclo[2.2.1]heptan-7-yl)(5-(hydroxymethyl)-2-(2H-1,2,3-triazol-2-yl)phenyl)methanone |
| 127 | | | 190 | 1100 | (±)-(2-(3-methyl-1,2,4-oxadiazol-5-yl)phenyl)(2-((pyridin-2-yloxy)methyl)-7-azabicyclo[2.2.1]heptan-7-yl)methanone |
| 128 | | | 5700 | 10000 | (±)-(6-methyl-2-(2H-1,2,3-triazol-2-yl)pyridin-3-yl)(2-((pyridin-2-yloxy)methyl-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 129 | | | 190 | 1000 | (±)-(3-fluoro-2-(2H-1,2,3-triazol-2-yl)phenyl)(2-((pyridin-2-yloxy)methyl)-7-azabicyclo[2.2.1]heptan-7-yl)methanone |
| 130 | | | 3700 | 7199 | (±)-(6-methyl-2-(1H-1,2,3-triazol-1-yl)pyridin-3-yl)(2-((pyridin-2-yl)oxy)methyl)-7-azabicyclo[2.2.1]heptan-7-yl)methanone |
| 131 | | | 10000 | 10000 | (±)-(6-methyl-2-(2H-1,2,3-triazol-2-yl)pyridin-3-yl)(2-(((4-(trifluoromethyl)pyrimidin-2-yl)oxy)methyl)-7-azabicyclo[2.2.1]heptan-7-yl)methanone |
| 132 | | | 10000 | 7399 | (±)-(6-methyl-2-(1H-1,2,3-triazol-1-yl)pyridin-3-yl)(2-(((4-(trifluoromethyl)pyrimidin-2-yl)oxy)methyl)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 133 | | | 1400 | 950 | (±)-(2-(3-methyl-1,2,4-oxadiazol-5-yl)phenyl)(2-(((4-(trifluoromethyl)pyrimidin-2-yl)oxy)methyl)-7-azabicyclo[2.2.1]heptan-7-yl)methanone |
| 134 | | | 1500 | 690 | (±)-(3-fluoro-2-(2H-1,2,3-triazol-2-yl)phenyl)(2-(((4-(trifluoromethyl)pyrimidin-2-yl)oxy)methyl)-7-azabicyclo[2.2.1]heptan-7-yl)methanone |
| 135 | | | 5400 | 3900 | (±)-(6-methyl-2-(2H-1,2,3-triazol-2-yl)pyridin-3-yl)(2-(((5-methylpyridin-2-yl)oxy)methyl)-7-azabicyclo[2.2.1]heptan-7-yl)methanone |
| 136 | | | 6800 | 1200 | (±)-(6-methyl-2-(1H-1,2,3-triazol-1-yl)pyridin-3-yl)(2-(((5-methylpyridin-2-yl)oxy)methyl)-7-azabicyclo[2.2.1]heptan-7-yl)methanone |
| 137 | | | 950 | 425 | (±)-(2-(3-methyl-1,2,4-oxadiazol-5-yl)phenyl)(2-(((5-methylpyridin-2-yl)oxy)methyl)-7-azabicyclo[2.2.1]heptan-7-yl)methanone |

| Ex. No. | Compound | rOX1 Ki (nM) | hOX1 Ki (nM) | hOX2 Ki (nM) | Compound Name |
|---|---|---|---|---|---|
| 138 | | | 606 | 250 | (±)-(3-fluoro-2-(2H-1,2,3-triazol-2-yl)phenyl)(2-(((5-methylpyridin-2-yl)oxy)methyl)-7-azabicyclo[2.2.1]heptan-7-yl)methanone |
| 139 | | | 4399 | 6500 | (±)-(6-methyl-2-(2H-1,2,3-triazol-2-yl)pyridin-3-yl)(2-(((6-methylpyridin-2-yl)oxy)methyl)-7-azabicyclo[2.2.1]heptan-7-yl)methanone |
| 140 | | | 3100 | 2300 | (±)-(6-methyl-2-(1H-1,2,3-triazol-1-yl)pyridin-3-yl)(2-(((6-methylpyridin-2-yl)oxy)methyl)-7-azabicyclo[2.2.1]heptan-7-yl)methanone |
| 141 | | | 280 | 300 | (±)-(2-(3-methyl-1,2,4-oxadiazol-5-yl)phenyl)(2-(((6-methylpyridin-2-yl)oxy)methyl)-7-azabicyclo[2.2.1]heptan-7-yl)methanone |
| 142 | | | 207 | 300 | (±)-(3-fluoro-2-(2H-1,2,3-triazol-2-yl)phenyl)(2-(((6-methylpyridin-2-yl)oxy)methyl)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 143 | | | 3900 | 4600 | (±)-(6-methyl-2-(2H-1,2,3-triazol-2-yl)pyridin-3-yl)(2-(((6-(trifluoromethyl)pyridin-2-yl)oxy)methyl)-7-azabicyclo[2.2.1]heptan-7-yl)methanone |
| 144 | | | 3600 | 3200 | (±)-(6-methyl-2-(1H-1,2,3-triazol-1-yl)pyridin-3-yl)(2-(((6-(trifluoromethyl)pyridin-2-yl)oxy)methyl)-7-azabicyclo[2.2.1]heptan-7-yl)methanone |
| 145 | | | 340 | 330 | (±)-(2-(3-methyl-1,2,4-oxadiazol-5-yl)phenyl)(2-(((6-(trifluoromethyl)pyridin-2-yl)oxy)methyl)-7-azabicyclo[2.2.1]heptan-7-yl)methanone |
| 146 | | | 180 | 196 | (±)-(3-fluoro-2-(2H-1,2,3-triazol-2-yl)phenyl)(2-(((6-(trifluoromethyl)pyridin-2-yl)oxy)methyl)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 147 | | | | | (±)-(6-methyl-2-(2H-1,2,3-triazol-2-yl)pyridin-3-yl)(2-((quinoxalin-2-yloxy)methyl)-7-azabicyclo[2.2.1]heptan-7-yl)methanone |
| 148 | | | 6299 | 3200 | (±)-(6-methyl-2-(1H-1,2,3-triazol-1-yl)pyridin-3-yl)(2-((quinoxalin-2-yloxy)methyl)-7-azabicyclo[2.2.1]heptan-7-yl)methanone |
| 149 | | | 220 | 2000 | (±)-(2-(3-methyl-1,2,4-oxadiazol-5-yl)phenyl)(2-((quinoxalin-2-yloxy)methyl)-7-azabicyclo[2.2.1]heptan-7-yl)methanone |
| 150 | | | 180 | 990 | (±)-(3-fluoro-2-(2H-1,2,3-triazol-2-yl)phenyl)(2-((quinoxalin-2-yloxy)methyl)-7-azabicyclo[2.2.1]heptan-7-yl)methanone |
| 151 | | | 10000 | 10000 | (±)-(2-(((4,6-dimethylpyrimidin-2-yl)oxy)methyl)-7-azabicyclo[2.2.1]heptan-7-yl)(6-methyl-2-(2H-1,2,3-triazol-2-yl)pyridin-3-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 152 | 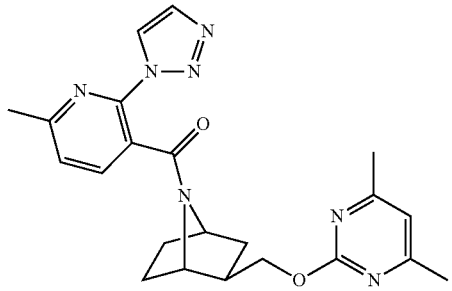 | | 10000 | 5899 | (±)-(2-(((4,6-dimethylpyrimidin-2-yl)oxy)methyl)-7-azabicyclo[2.2.1]heptan-7-yl)(6-methyl-2-(1H-1,2,3-triazol-1-yl)pyridin-3-yl)methanone |
| 153 | 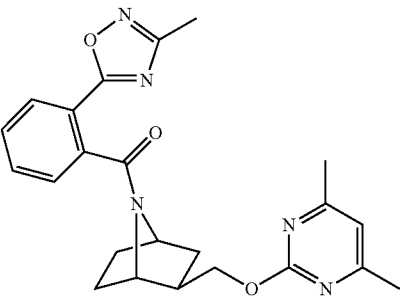 [SMILES: Cc1cc(C)nc(OCC2CC3CCC2N3C(=O)c2ccccc2-c2nc(C)no2)n1] | | 1100 | 440 | (±)-(2-(((4,6-dimethylpyrimidin-2-yl)oxy)methyl)-7-azabicyclo[2.2.1]heptan-7-yl)(2-(3-methyl-1,2,4-oxadiazol-5-yl)phenyl)methanone |
| 154 | 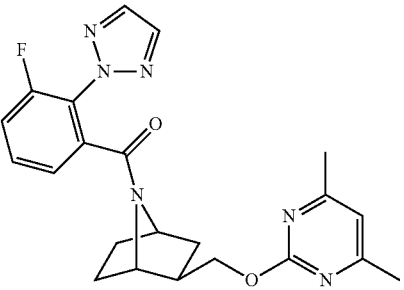 [SMILES: Cc1cc(C)nc(OCC2CC3CCC2N3C(=O)c2cccc(F)c2-n2nccn2)n1] | | 690 | 300 | (±)-(2-(((4,6-dimethylpyrimidin-2-yl)oxy)methyl)-7-azabicyclo[2.2.1]heptan-7-yl)(3-fluoro-2-(1H-1,2,3-triazol-2-yl)phenyl)methaone |
| 155 | 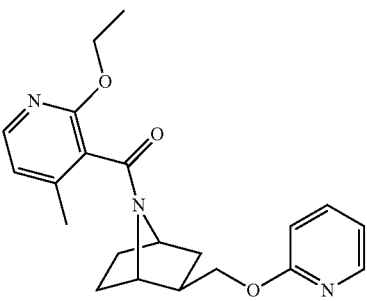 [SMILES: CCOc1nccc(C)c1C(=O)N1C2CCC1C(COc1ccccn1)C2] | 1570 | | 3600 | (±)-(2-ethoxy-4-methylpyridin-3-yl)(2-((pyridin-2-yloxy)methyl)-7-azabicyclo[2.2.1]heptan-7-yl)methanone |
| 156 | 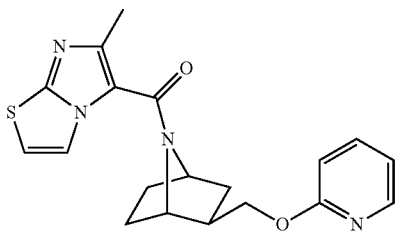 | | >10000 | >10000 | (±)-(6-methylimidazo[2,1-b]thiazol-5-yl)(2-(pyridin-2-yloxy)methyl)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 157 | | | 94 | 134 | 537 | (±)-(5-bromo-2-ethoxypyridin-3-yl)(2-((pyridin-2-yloxy)methyl)-7-azabicyclo[2.2.1]heptan-7-yl)methanone |
| 158 | | | 2930 | | 1780 | (±)-(2-ethoxy-6-methylpyridin-3-yl)(2-((pyridin-2-yloxy)methyl)-7-azabicyclo[2.2.1]heptan-7-yl)methanone |
| 159 | | | 262 | | 786 | (±)-(7-hydroxyquinolin-8-yl)(2-((pyridin-2-yloxy)methyl)-7-azabicyclo[2.2.1]heptan-7-yl)methanone |
| 160 | | | 8700 | | >10000 | (±)-(2-ethoxy-5-phenylpyridin-3-yl)(2-((pyridin-2-yloxy)methyl)-7-azabicyclo[2.2.1]heptan-7-yl)methanone |
| 161 | | | 478 | | 1450 | (±)-(4-bromo-2-ethoxypyridin-3-yl)(2-((pyridin-2-yloxy)methyl)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 162 | | 8500 | | >10000 | (±)-(2-chloro-4-ethoxypyridin-3-yl)(2-((pyridin-2-yloxy)methyl)-7-azabicyclo[2.2.1]heptan-7-yl)methanone |
| 163 | | 150 | 153 | 150 | (±)-(2,4-diethoxypyridin-3-yl)(2-((pyridin-2-yloxy)methyl)-7-azabicyclo[2.2.1]heptan-7-yl)methanone |
| 164 | | 9 | 7 | 195 | (3-ethoxyisoquinolin-4-yl)((1S,2R,4R)-2-((pyridin-2-yloxy)methyl)-7-azabicyclo[2.2.1]heptan-7-yl)methanone |
| 165 | | | 409 | 550 | (±)-(2-ethoxyphenyl)(2-(((5-fluoropyridin-2-yl)oxy)methyl)-7-azabicyclo[2.2.1]heptan-7-yl)methanone |
| 166 | | | 106 | 1141 | (±)-(5-fluoro-2-(2H-1,2,3-triazol-2-yl)phenyl)(2-((quinoxalin-2-yloxy)methyl)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 167 | | | 9 | 14 | (±)-5-methyl-2-(2H-1,2,3-triazol-2-yl)phenyl)(2-(((5-methylpyridin-2-yl)oxy)methyl)-7-azabicyclo[2.2.1]heptan-7-yl)methanone |
| 168 | | | 2300 | 7300 | (±)-(6-methyl-2-(2H-1,2,3-triazol-2-yl)pyridin-3-yl)(2-((quinoxalin-2-yloxy)methyl)-7-azabicyclo[2.2.1]heptan-7-yl)methanone |
| 169 | | | 8999 | 2526 | (±)-(5-fluoro-2-(2H-1,2,3-triazol-2-yl)phenyl)(2-((pyridin-2-ylamino)methyl)-7-azabicyclo[2.2.1]heptan-7-yl)methanone |
| 170 | | | 1965 | 512 | (±)-(2-(((4,6-dimethylpyrimidin-2-yl)amino)methyl)-7-azabicyclo[2.2.1]heptan-7-yl)(5-fluoro-2-(2H-1,2,3-triazol-2-yl)phenyl)methanone |
| 171 | | | 1935 | | (±)-(5-fluoro-2-(2H-1,2,3-triazol-2-yl)phenyl)(2-(((4-(trifluoromethyl)pyrimidin-2-yl)amino)methyl)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 172 | | | | 686 | (±)-(5-fluoro-2-(2H-1,2,3-triazol-2-yl)phenyl)(2-(((6-(trifluoromethyl)pyridin-2-yl)amino)methyl)-7-azabicyclo[2.2.1]heptan-7-yl)methanone |
| 173 | | | 1260 | 3000 | (±)-(3-fluoro-2-methoxyphenyl)(2-(((5-fluoropyridin-2-yl)oxy)methyl)-7-azabicyclo[2.2.1]heptan-7-yl)methanone |
| 174 | | | 373 | 1000 | (±)-(5-fluoro-2-(2H-1,2,3-triazol-2-yl)phenyl)(2-((quinoxalin-2-ylamino)methyl)-7-azabicyclo[2.2.1]heptan-7-yl)methanone |
| 175 | | | 2500 | 4000 | (±)-(2-(((5-fluoropyrimidin-2-yl)oxy)methyl)-7-azabicyclo[2.2.1]heptan-7-yl)(6-methyl-3-(pyrimidin-2-yl)pyridin-2-yl)methanone |
| 176 | | 119 | 150 | 202 | (±)-(6-methyl-3-(2H-1,2,3-triazol-2-yl)pyridin-2-yl)(2-(((3-methylpyridin-2-yl)oxy)methyl)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 177 | | | 535 | 4000 | (±)-(2-(((5-fluoropyridin-2-yl)oxy)methyl)-7-azabicyclo[2.2.1]heptan-7-yl)(6-methyl-3-(4-methyloxazol-2-yl)pyridin-2-yl)methanone |
| 178 | | | 964 | >10000 | (6-methyl-3-(4-methyloxazol-2-yl)pyridin-2-yl)((1S,2R,4R)-2-((pyridin-2-yloxy)methyl)-7-azabicyclo[2.2.1]heptan-7-yl)methanone |
| 179 | | | | | ((1S,2R,4R)-2-(((5-fluoropyrimidin-2-yl)oxy)methyl)-7-azabicyclo[2.2.1]heptan-7-yl)(6-methyl-3-(4-methyloxazol-2-yl)pyridin-2-yl)methanone |
| 180 | | | 33 | 32 | (±)-(5-methyl-2-(2H-1,2,3-triazol-2-yl)phenyl)(2-(((6-methyl-2-(trifluoromethyl)pyrimidin-4-yl)oxy)methyl)-7-azabicyclo[2.2.1]heptan-7-yl)methanone |
| 181 | | 34 | 28 | 700 | (2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 182 | | 47 | 38 | 1100 | (±)-((2-(2H-1,2,3-triazol-2-yl)phenyl)(2-((5-(trifluoromethyl)pyrazin-2-yl)amino)-7-azabicyclo[2.2.1]heptan-7-yl)methanone |
| 183a | | >10000 | | >10000 | (2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone |
| 183b | | 34 | 28 | 700 | (2-(2H-1,2,3-triazol-2-yl)phenyl)((1R,2S,4S)-2-((5-(trifluoromethyl)pyrazin-2-yl)amino)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 184 | | | 189 | 349 | 4100 | (±)-(5-methyl-3-(2H-1,2,3-triazol-2-yl)pyridin-2-yl)(2-((5-(trifluoromethyl)pyriazin-2-yl)amino)-7-azabicyclo[2.2.1]heptan-7-yl)methanone |
| 185 | | | 1500 | | 2700 | (±)-(5-methyl-3-(1H-1,2,3-triazol-1-yl)pyridin-2-yl)(2-((5-(trifluoromethyl)pyrazin-2-yl)amino)-7-azabicyclo[2.2.1]heptan-7-yl)methanone |
| 186 | | | 134 | 164 | 1200 | (±)-(6-methyl-3-(2H-1,2,3-triazol-2-yl)pyridin-2-yl)(2-((5-(trifluoromethyl)pyrazin-2-yl)amino)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 187 | | 81 | 48 | 620 | (±)-(6-methyl-3-(2H-1,2,3-triazol-2-yl)pyridin-2-yl)(2-((5-(trifluoromethyl)pyridin-2-yl)amino)-7-azabicyclo[2.2.1]heptan-7-yl)methanone |
| 188 | | 295 | | 1500 | (±)-(5-methyl-3-(2H-1,2,3-triazol-2-yl)pyridin-2-yl)(2-((5-(trifluoromethyl)pyridin-2-yl)amino)-7-azabicyclo[2.2.1]heptan-7-yl)methanone |
| 189 | | 766 | | 1500 | (±)-(6-methyl-2-(2H-1,2,3-triazol-2-yl)pyridin-3-yl)(2-((5-(trifluoromethyl)pyridin-2-yl)amino)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 190 | 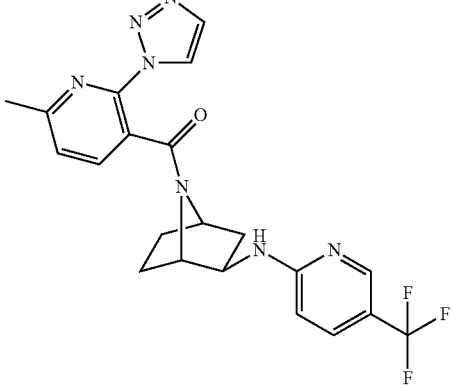 | | 589 | 1200 | (±)-(6-methyl-2-(1H-1,2,3-triazol-1-yl)pyridin-3-yl)(2-((5-(trifluoromethyl)pyridin-2-yl)amino)-7-azabicyclo[2.2.1]heptan-7-yl)methanone |
| 191 | 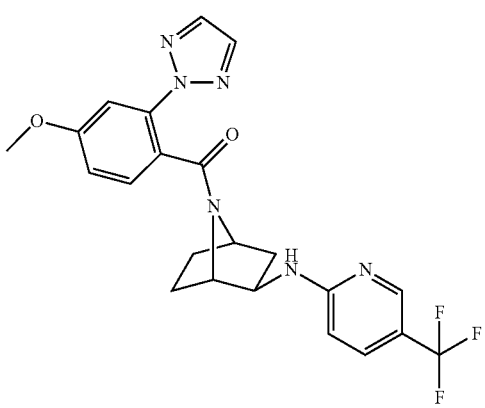 [SMILES: COc1ccc(C(=O)N2C3CCC2C(Nc2ccc(C(F)(F)F)cn2)C3)c(-n2nccn2)c1] | | 257 | 8800 | (±)-(4-methoxy-2-(2H-1,2,3-triazol-2-yl)phenyl)(2-((5-(trifluoromethyl)pyridin-2-yl)amino)-7-azabicyclo[2.2.1]heptan-7-yl)methanone |
| 192 | 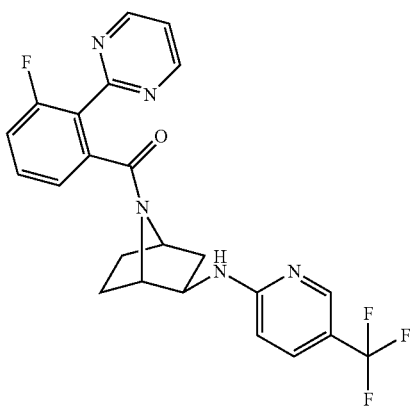 [SMILES: O=C(c1cccc(F)c1-c1ncccn1)N1C2CCC1C(Nc1ccc(C(F)(F)F)cn1)C2] | 60 | 52 | 1500 | (±)-(3-fluoro-2-(pyrimidin-2-yl)phenyl)(2-((5-(trifluoromethyl)pyridin-2-yl)amino)-7-azabicyclo[2.2.1]heptan-7-yl)methanone |
| 193 | 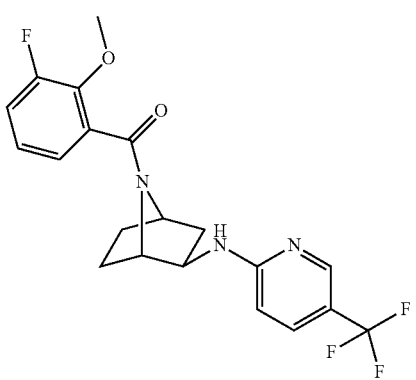 [SMILES: COc1c(F)cccc1C(=O)N1C2CCC1C(Nc1ccc(C(F)(F)F)cn1)C2] | | 2900 | >10000 | (±)-((3-fluoro-2-methoxyphenyl)(2-((5-(trifluoromethyl)pyridin-2-yl)amino)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 194 | | | 450 | 800 | (±)-(3-ethoxy-6-methylpyridin-2-yl)(2-((5-(trifluoromethyl)pyridin-2-yl)amino)-7-azabicyclo[2.2.1]heptan-7-yl)methanone |
| 195 | | 57 | 37 | 325 | (±)-(6-methyl-3-(pyrimidin-2-yl)pyridin-2-yl)(2-((5-(trifluoromethyl)pyridin-2-yl)amino)-7-azabicyclo[2.2.1]heptan-7-yl)methanone |
| 196 | | 59 | 61 | 1500 | (±)-(2-(2H-1,2,3-triazol-2-yl)phenyl)(2-((5-(trifluoromethyl)pyridin-2-yl)amino)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 197 | | | 8999 | 862 | (±)-(2-((4,6-dimethylpyrimidin-2-yl)amino)-7-azabicyclo[2.2.1]heptan-7-yl)(5-fluoro-2-(2H-1,2,3-triazol-2-yl)phenyl)methanone |
| 198 | | | 1411 | 704 | (±)-(2-((4,6-dimethylpyrimidin-2-yl)amino)-7-azabicyclo[2.2.1]heptan-7-yl)(2-fluoro-6-(2H-1,2,3-triazol-2-yl)phenyl)methanone |
| 199 | | | 1634 | 553 | (±)-(2-((4,6-dimethylpyrimidin-2-yl)amino)-7-azabicyclo[2.2.1]heptan-7-yl)(4-fluoro-2-(2H-1,2,3-triazol-2-yl)phenyl)methanone |
| 200 | | | 1100 | 552 | (±)-(2-((4,6-dimethylpyrimidin-2-yl)amino)-7-azabicyclo[2.2.1]heptan-7-yl)(6-methyl-3-(pyrimidin-2-yl)pyridin-2-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 201 | | | 3700 | 1100 | (±)-(2-((4,6-dimethylpyrimidin-2-yl)amino)-7-azabicyclo[2.2.1]heptan-7-yl)(6-methyl-3-(2H-1,2,3-triazol-2-yl)pyridin-2-yl)methanone |
| 202 | | | 760 | 444 | (±)-(2-(2H-1,2,3-triazol-2-yl)phenyl)(2-((4,6-dimethylpyrimidin-2-yl)amino)-7-azabicyclo[2.2.1]heptan-7-yl)methanone |
| 203 | | | >10000 | 490 | (±)-(2-((4,6-dimethylpyrimidin-2-yl)amino)-7-azabicyclo[2.2.1]heptan-7-yl)(3-ethoxy-6-methylpyridin-2-yl)methanone |
| 204 | | 33 | 25 | 220 | (±)-(2-(2H-1,2,3-triazol-2-yl)phenyl)(2-(quinoxalin-2-ylamino)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 205 | | | 79 | 50 | 168 | (±)-(6-methyl-3-(2H-1,2,3-triazol-2-yl)pyridin-2-yl)(2-(quinoxalin-2-ylamino)-7-azabicyclo[2.2.1]heptan-7-yl)methanone |
| 206 | | | 1200 | | 1500 | (±)-(3-fluoro-2-methoxyphenyl)(2-(quinoxalin-2-ylamino)-7-azabicyclo[2.2.1]heptan-7-yl)methanone |
| 207 | | | 120 | 95 | 64 | (±)-(3-ethoxy-6-methylpyridin-2-yl)(2-(quinoxalin-2-ylamino)-7-azabicyclo[2.2.1]heptan-7-yl)methanone |
| 208 | | | 26 | 30 | 90 | (±)-(6-methyl-3-(pyrimidin-2-yl)pyridin-2-yl)(2-(quinoxalin-2-ylamino)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 209 | | | 1100 | 736 | (±)-(2-(2H-1,2,3-triazol-2-yl)phenyl)(2-((6-(trifluoromethyl)pyridin-2-yl)amino)-7-azabicyclo[2.2.1]heptan-7-yl)methanone |
| 210 | | | 211 | 128 | (±)-((2-(2H-1,2,3-triazol-2-yl)phenyl)(2-((4-(trifluoromethyl)pyridin-2-yl)amino)-7-azabicyclo[2.2.1]heptan-7-yl)methanone |
| 211 | | 110 | 55 | 1800 | (±)-(2-(2H-1,2,3-triazol-2-yl)phenyl)(2-((5-chloropyridin-2-yl)amino)-7-azabicyclo[2.2.1]heptan-7-yl)methanone |
| 212 | | | 734 | 4900 | (±)-(2-(2H-1,2,3-triazol-2-yl)phenyl)(2-((6-(trifluoromethyl)pyridazin-3-yl)amino)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 213 | | | 2800 | 7501 | (±)-(2-(2H-1,2,3-trizaol-2-yl)phenyl)(2-((5-methoxypyridin-2-yl)amino)-7-azabicyclo[2.2.1]heptan-7-yl)methanone |
| 214 | | | 500 | 3100 | (±)-(2-(2H-1,2,3-triazol-2-yl)phenyl)(2-((5-methylpyridin-2-yl)amino)-7-azabicyclo[2.2.1]heptan-7-yl)methanone |
| 215 | | | 1700 | 8999 | (±)-(2-(2H-1,2,3-triazol-2-yl)phenyl)(2-(pyridin-2-ylamino)-7-azabicyclo[2.2.1]heptan-7-yl)methanone |
| 216 | | 99 | 71 | 475 | (±)-(2-(2H-1,2,3-triazol-2-yl)phenyl)(2-((5-chlorobenzo[d]oxazol-2-yl)amino)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 217 | | 59 | 40 | 770 | (±)-(2-((5-bromopyridin-2-yl)amino)-7-azabicyclo[2.2.1]heptan-7-yl)(6-methyl-3-(pyrimidin-2-yl)pyridin-2-yl)methanone |
| 218 | | 2700 | | 6700 | (±)-(2-((5-bromopyridin-2-yl)amino)-7-azabicyclo[2.2.1]heptan-7-yl)(3-fluoro-2-methoxyphenyl)methanone |
| 219 | | 257 | | 1700 | (±)-(2-((5-bromopyridin-2-yl)amino)-7-azabicyclo[2.2.1]heptan-7-yl)(3-ethoxy-6-methylpyridin-2-yl)methanone |
| 220 | | 38 | 26 | 1100 | (±)-(2-((5-bromopyridin-2-yl)amino)-7-azabicyclo[2.2.1]heptan-7-yl)(6-methyl-3-(2H-1,2,3-triazol-2-yl)pyridin-2-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 221 | | | 172 | 200 | 3300 | (±)-(2-(2H-1,2,3-triazol-2-yl)phenyl)(2-((5-(trifluoromethyl)pyrimidin-2-yl)amino)-7-azabicyclo[2.2.1]heptan-7-yl)methanone |
| 222 | | | 4800 | | >10000 | (±)-(3-fluoro-2-methoxyphenyl)(2-((5-(trifluoromethyl)pyrimidin-2-yl)amino)-7-azabicyclo[2.2.1]heptan-7-yl)methanone |
| 223 | | | 550 | | 4000 | (±)-(6-methyl-3-(2H-1,2,3-triazol-2-yl)pyridin-2-yl)(2-((5-(trifluoromethyl)pyrimidin-2-yl)amino)-7-azabicyclo[2.2.1]heptan-7-yl)methanone |
| 224 | | | 2500 | | 7399 | (±)-(3-ethoxy-6-methylpyridin-2-yl)(2-((5-(trifluoromethyl)pyrimidin-2-yl)amino)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 225 | | | 530 | 3300 | (±)-(6-methyl-3-(pyrimidin-2-yl)pyridin-2-yl)(2-((5-(trifluoromethyl)pyrimidin-2-yl)amino)-7-azabicyclo[2.2.1]heptan-7-yl)methanone |
| 226 | | | >10000 | >10000 | (±)-(3-fluoro-2-methoxyphenyl)(2-((5-(trifluoromethyl)pyrimidin-2-yl)amino)-7-azabicyclo[2.2.1]heptan-7-yl)methanone |
| 227 | | | >10000 | >10000 | (±)-(3-ethoxy-6-methylpyridin-2-yl)(2-((5-(trifluoromethyl)pyrimidin-2-yl)amino)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 228 | | | >10000 | >10000 | (±)-(6-methyl-3-(2H-1,2,3-triazol-2-yl)pyridin-2-yl)(2-((5-(trifluoromethyl)pyrimidin-2-yl)amino)-7-azabicyclo[2.2.1]heptan-7-yl)methanone |
| 229 | | | >10000 | >10000 | (±)-(3-ethoxy-6-methylpyridin-2-yl)(2-(quinoxalin-2-ylamino)-7-azabicyclo[2.2.1]heptan-7-yl)methanone |
| 230 | | | >10000 | >10000 | (±)-(6-methyl-3-(2H-1,2,3-triazol-2-yl)pyridin-2-yl)(2-(quinoxalin-2-ylamino)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 231 | | | >10000 | >10000 | (±)-(3-fluoro-2-methoxyphenyl)(2-(quinoxalin-2-ylamino)-7-azabicyclo[2.2.1]heptan-7-yl)methanone |
| 232 | | | | | (±)-(2-((5-bromopyridin-2-yl)amino)-7-azabicyclo[2.2.1]heptan-7-yl)(6-methyl-3-(2H-1,2,3-triazol-2-yl)pyridin-2-yl)methanone |
| 233 | | | | | (±)-(2-((5-bromopyridin-2-yl)amino)-7-azabicyclo[2.2.1]heptan-7-yl)(3-ethoxy-6-methylpyridin-2-yl)methanone |

| Ex. No. | Compound | rOX1 Ki (nM) | hOX1 Ki (nM) | hOX2 Ki (nM) | Compound Name |
|---|---|---|---|---|---|
| 234 | 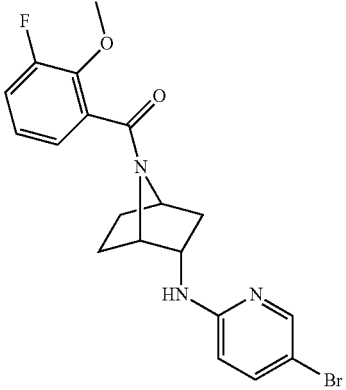 [SMILES: COc1c(F)cccc1C(=O)N1C2CCC1C(Nc1ccc(Br)cn1)C2] | | | | (±)-(2-((5-bromopyridin-2-yl)amino)-7-azabicyclo[2.2.1]heptan-7-yl)(3-fluoro-2-methoxyphenyl)methanone |
| 235 | 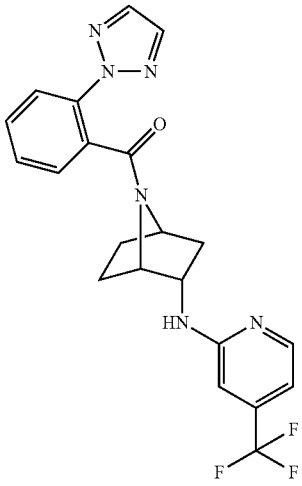 [SMILES: O=C(c1ccccc1-n1nccn1)N1C2CCC1C(Nc1cc(C(F)(F)F)ccn1)C2] | | >10000 | >10000 | (±)-((2-(2H-1,2,3-triazol-2-yl)phenyl)(2-((4-(trifluoromethyl)pyridin-2-yl)amino)-7-azabicyclo[2.2.1]heptan-7-yl)methanone |
| 236 | 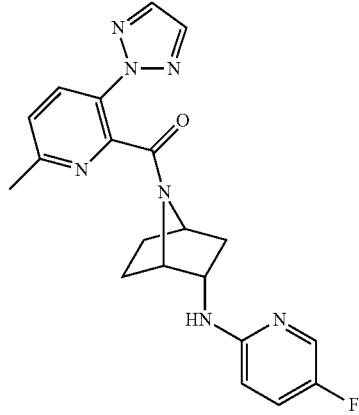 [SMILES: Cc1ccc(-n2nccn2)c(C(=O)N2C3CCC2C(Nc2ccc(F)cn2)C3)n1] | | >10000 | >10000 | (±)-(2-((5-fluoropyridin-2-yl)amino)-7-azabicyclo[2.2.1]heptan-7-yl)(6-methyl-3-(2H-1,2,3-triazol-2-yl)pyridin-2-yl)methanone |

TABLE 1-continued

| Ex. No. | Compound | rOX1 Ki (nM) | hOX1 Ki (nM) | hOX2 Ki (nM) | Compound Name |
| --- | --- | --- | --- | --- | --- |
| 237 | | | >10000 | >10000 | (±)-(3-fluoro-2-methoxyphenyl)(2-((5-fluoropyridin-2-yl)amino)-7-azabicyclo[2.2.1]heptan-7-yl)methanone |
| 238 | | | 16 | 16 | 955 | (3-fluoro-2-(pyrimidin-2-yl)phenyl)((1S,2R,4R)-2-((5-(trifluoromethyl)pyrazin-2-yl)amino)-7-azabicyclo[2.2.1]heptan-7-yl)methanone |
| 239 | | | 22 | 19 | 490 | (2-ethoxynaphthalen-1-yl)((1S,2R,4R)-2-((5-(trifluoromethyl)pyrazin-2-yl)amino)-7-azabicyclo[2.2.1]heptan-7-yl)methanone |
| 240 | | | 400 | | 2100 | isoquinolin-4-yl((1S,2R,4R)-2-((5-(trifluoromethyl)pyrazin-2-yl)amino)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 241 | | 134 | 159 | 5064 | (4-methoxy-2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone |
| 242 | | 31 | 41 | 239 | (2-methoxy-6-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone |
| 243 | | 34 | 45 | 723 | (5-fluoro-2-(pyrimidin-2-yl)phenyl)((1S,2R,4R)-2-((5-(trifluoromethyl)pyrazin-2-yl)amino)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 244 | | 74 | 46 | 235 | (5-(4-fluorophenyl)-2-methylthiazol-4-yl)((1S,2R,4R)-2-((5-(trifluoromethyl)pyrazin-2-yl)amino)-7-azabicyclo[2.2.1]heptan-7-yl)methanone |
| 245 | | 10 | 7 | 288 | (3-methyl-2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone |
| 246 | | 29 | 17 | 1022 | (3-ethoxyisoquinolin-4-yl)((1S,2R,4R)-2-((5-(trifluoromethyl)pyrazin-2-yl)amino)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 247 | | | 420 | 1130 | (6-methyl-2-(2H-1,2,3-triazol-2-yl)pyridin-3-yl)((1S,2R,4R)-2-((5-(trifluoromethyl)pyrazin-2-yl)amino)-7-azabicyclo[2.2.1]heptan-7-yl)methanone |
| 248 | | 153 | 119 | >10000 | (6-methyl-2-(1H-1,2,3-triazol-1-yl)pyridin-3-yl)((1S,2R,4R)-2-((5-(trifluoromethyl)pyrazin-2-yl)amino)-7-azabicyclo[2.2.1]heptan-7-yl)methanone |
| 249 | | 57 | 54 | 5600 | (4-methoxy-2-(pyrimidin-2-yl)phenyl)((1S,2R,4R)-2-((5-(trifluoromethyl)pyrazin-2-yl)amino)-7-azabicyclo[2.2.1]heptan-7-yl)methanone |
| 250 | | 5649 | | >10000 | (1H-benzo[d]imidazol-2-yl)((1S,2R,4R)-2-((5-(trifluoromethyl)pyrazin-2-yl)amino)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 251 | | | 520 | 5300 | (1-methyl-1H-benzo[d]imidazol-2-yl)((1S,2R,4R)-2-((5-(trifluoromethyl)pyrazin-2-yl)amino)-7-azabicyclo[2.2.1]heptan-7-yl)methanone |
| 252 | | 45 | 27 | 1230 | (3-fluoro-2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone |
| 253 | | 155 | 152 | 9601 | (4-(difluoromethoxy)-2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone |
| 254 | | 23 | 20 | 377 | (3-fluoro-2-(3-methyl-1,2,4-oxadiazol-5-yl)phenyl)((1S,2R,4R)-2-((5-(trifluoromethyl)pyrazin-2-yl)amino)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 255 | 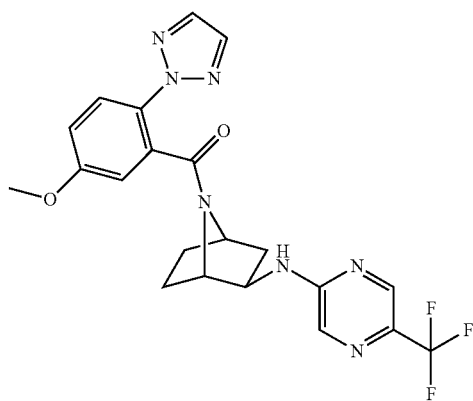 [SMILES: COc1ccc(-n2nccn2)c(C(=O)N2C3CCC2C(Nc2cnc(C(F)(F)F)cn2)C3)c1] | 32 | 29 | 265 | (5-methoxy-2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone |
| 256 | 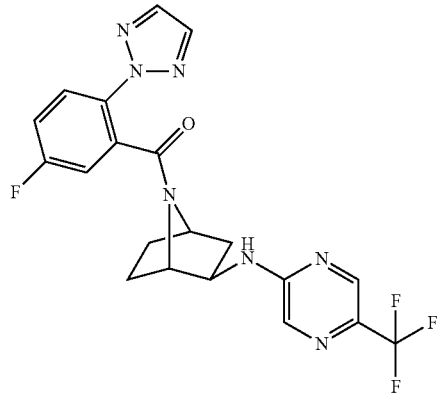 [SMILES: O=C(c1cc(F)ccc1-n1nccn1)N1C2CCC1C(Nc1cnc(C(F)(F)F)cn1)C2] | 84 | 60 | 1100 | (5-fluoro-2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone |
| 257 | 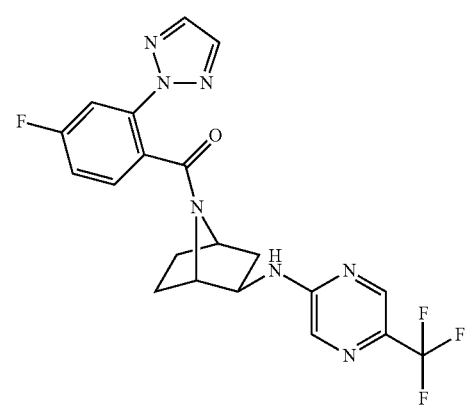 [SMILES: O=C(c1ccc(F)cc1-n1nccn1)N1C2CCC1C(Nc1cnc(C(F)(F)F)cn1)C2] | 85 | 102 | 3200 | (4-fluoro-2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 258 | 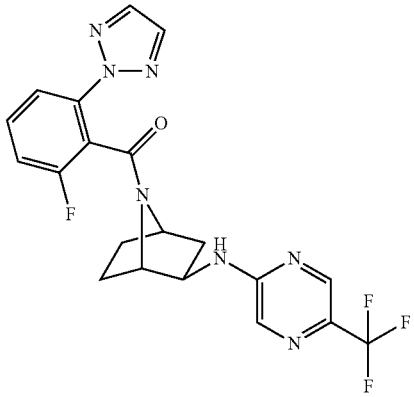 [SMILES: O=C(c1c(F)cccc1-n1nccn1)N1C2CCC1C(Nc1cnc(C(F)(F)F)cn1)C2] | 42 | 48 | 690 | (2-fluoro-6-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone |
| 259 | 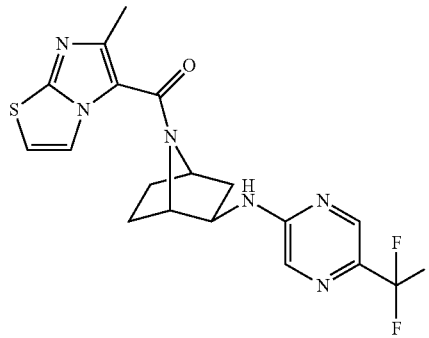 | >10000 | | >10000 | (6-methylimidazo[2,1-b]thiazol-5-yl)((1S,2R,4R)-2-((5-(trifluoromethyl)pyrazin-2-yl)amino)-7-azabicyclo[2.2.1]heptan-7-yl)methanone |
| 260 | 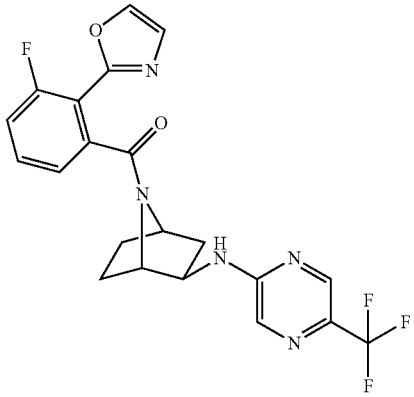 [SMILES: O=C(c1cccc(F)c1-c1ncco1)N1C2CCC1C(Nc1cnc(C(F)(F)F)cn1)C2] | 14 | 10 | 519 | (3-fluoro-2-(oxazol-2-yl)phenyl)((1S,2R,4R)-2-((5-(trifluoromethyl)pyrazin-2-yl)amino)-7-azabicyclo[2.2.1]heptan-7-yl)methanone |
| 261 | 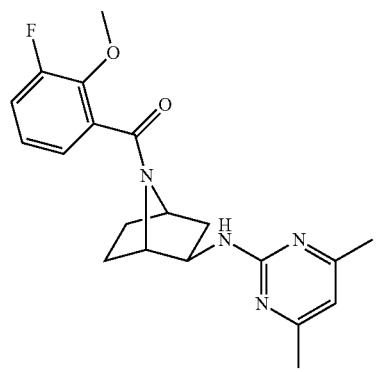 [SMILES: COc1c(F)cccc1C(=O)N1C2CCC1C(Nc1nc(C)cc(C)n1)C2] | >10000 | | 5000 | (2-((4,6-dimethylpyrimidin-2-yl)amino)-7-azabicyclo[2.2.1]heptan-7-yl)(3-fluoro-2-methoxyphenyl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 262 | | | 106 | 175 | 4200 | (3-fluoro-2-(pyridazin-3-yl)phenyl)((1S,2R,4R)-2-((5-(trifluoromethyl)pyrazin-2-yl)amino)-7-azabicyclo[2.2.1]heptan-7-yl)methanone |
| 263 | | 44 | 41 | 1100 | (3-methyl-2-(pyridazin-3-yl)phenyl)((1S,2R,4R)-2-((5-(trifluoromethyl)pyrazin-2-yl)amino)-7-azabicyclo[2.2.1]heptan-7-yl)methanone |
| 264 | | | 1400 | >10000 | (3-fluoro-2-(pyridazin-4-yl)phenyl)((1S,2R,4R)-2-((5-(trifluoromethyl)pyrazin-2-yl)amino)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 265 | | 20 | 23 | 188 | (3-fluoro-2-(pyrazin-2-yl)phenyl)((1S,2R,4R)-2-((5-(trifluoromethyl)pyrazin-2-yl)amino)-7-azabicyclo[2.2.1]heptan-7-yl)methanone |
| 266 | | 5 | 7 | 121 | (3-methyl-2-(oxazol-2-yl)phenyl)((1S,2R,4R)-2-((5-(trifluoromethyl)pyrazin-2-yl)amino)-7-azabicyclo[2.2.1]heptan-7-yl)methanone |
| 267 | | 33 | 61 | 1700 | (4-fluoro-2-(pyrimidin-2-yl)phenyl)((1S,2R,4R)-2-((5-(trifluoromethyl)pyrazin-2-yl)amino)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 268 | | | 450 | 3700 | (3-fluoro-2-(pyridin-4-yl)phenyl)((1S,2R,4R)-2-((5-(trifluoromethyl)pyrazin-2-yl)amino)-7-azabicyclo[2.2.1]heptan-7-yl)methanone |
| 269 | | 48 | 111 | 1700 | (3-fluoro-2-(2H-1,2,3-triazol-2-yl)phenyl)((1S,2R,4R)-2-((5-(trifluoromethyl)pyrimidin-2-yl)amino)-7-azabicyclo[2.2.1]heptan-7-yl)methanone |
| 270 | | 325 | | 145 | ((1S,2R,4R)-2-((3-bromoimidazo[1,2-a]pyrazin-8-yl)amino)-7-azabicyclo[2.2.1]heptan-7-yl)(3-fluoro-2-(pyrimidin-2-yl)phenyl)methanone |
| 271 | | 41 | 42 | 2300 | (3-fluoro-2-(pyrimidin-2-yl)phenyl)((1S,2R,4R)-2-((5-(trifluoromethyl)pyrimidin-2-yl)amino)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 272 | | | 21 | 26 | 742 | (3-methyl-2-(2H-1,2,3-triazol-2-yl)phenyl)((1S,2R,4R)-2-((5-(trifluoromethyl)pyrimidin-2-yl)amino)-7-azabicyclo[2.2.1]heptan-7-yl)methanone |
| 273 | | | 17 | 12 | 328 | (3-methyl-2-(pyrimidin-2-yl)phenyl)((1S,2R,4R)-2-((5-(trifluoromethyl)pyrazin-2-yl)amino)-7-azabicyclo[2.2.1]heptan-7-yl)methanone |
| 274 | | | >10000 | | 2560 | (3-fluoro-2-(pyrimidin-2-yl)phenyl)((1S,2R,4R)-2-((3-(trifluoromethyl)-[1,2,4]triazolo[4,3-a]pyrazin-8-yl)amino)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 275 | | >10000 | | >10000 | methyl 5-(((1S,2R,4R)-7-(3-fluoro-2-(pyrimidin-2-yl)benzoyl)-7-azabicyclo[2.2.1]heptan-2-yl)amino)pyrazine-2-carboxylate |
| 276 | | 133 | 97 | 2500 | (2-iodo-3-methylphenyl)((1S,2R,4R)-2-((5-(trifluoromethyl)pyrimidin-2-yl)amino)-7-azabicyclo[2.2.1]heptan-7-yl)methanone |
| 277 | | 457 | | 7399 | (3-fluoro-2-iodophenyl)((1S,2R,4R)-2-((5-(trifluoromethyl)pyrimidin-2-yl)amino)-7-azabicyclo[2.2.1]heptan-7-yl)methanone |
| 278 | | 87 | 77 | 934 | (3-fluoro-2-(pyrimidin-2-yl)phenyl)((1S,2R,4R)-2-((5-methylpyrazin-2-yl)amino)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 279 | | | 15 | 8 | 1100 | (3-fluoro-2-(pyrimidin-2-yl)phenyl)((1S,2R,4R)-2-((5-(trifluoromethyl)pyridin-2-yl)amino)-7-azabicyclo[2.2.1]heptan-7-yl)methanone |
| 280 | | 39 | 37 | 1300 | (4-fluoro-2-(pyrimidin-2-yl)phenyl)((1S,2R,4R)-2-((5-(trifluoromethyl)pyridin-2-yl)amino)-7-azabicyclo[2.2.1]heptan-7-yl)methanone |
| 281 | | 21 | 17 | 1200 | (3-methyl-2-(pyrimidin-2-yl)phenyl)((1S,2R,4R)-2-((5-(trifluoromethyl)pyrimidin-2-yl)amino)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 282 | | | 486 | >10000 | (3-fluoro-2-(pyrimidin-2-yl)phenyl)((1S,2R,4R)-2-(methyl(5-(trifluoromethyl)pyrazin-2-yl)amino)-7-azabicyclo[2.2.1]heptan-7-yl)methanone |
| 283 | | 14 | 9 | 417 | (3-methyl-2-(oxazol-2-yl)phenyl)((1S,2R,4R)-2-((5-(trifluoromethyl)pyrimidin-2-yl)amino)-7-azabicyclo[2.2.1]heptan-7-yl)methanone |
| 284 | | 29 | 27 | 1700 | (3-fluoro-2-(oxazol-2-yl)phenyl)((1S,2R,4R)-2-((5-(trifluoromethyl)pyrimidin-2-yl)amino)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 285 | | | 720 | >10000 | (±)-(3-fluoro-2-(pyrimidin-2-yl)phenyl)(2-((5-(trifluoromethyl)pyrimidin-2-yl)oxy)-7-azabicyclo[2.2.1]heptan-7-yl)methanone |
| 286 | | | >10000 | >10000 | (±)-(3-fluoro-2-(pyrimidin-2-yl)phenyl)(2-((5-(trifluoromethyl)pyrimidin-2-yl)oxy)-7-azabicyclo[2.2.1]heptan-7-yl)methanone |
| 287 | | | 472 | 767 | (3-ethoxy-6-methylpyridin-2-yl)((1S,2R,4R)-2-((5-(trifluoromethyl)pyrazin-2-yl)amino)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 288 | | 94 | 128 | 1900 | (3-(2H-1,2,3-triazol-2-yl)pyridin-2-yl)((1S,2R,4R)-2-((5-(trifluoromethyl)pyrazin-2-yl)amino)-7-azabicyclo[2.2.1]heptan-7-yl)methanone |
| 289 | | 13 | 32 | 173 | (2-methoxy-6-(pyrimidin-2-yl)phenyl)((1S,2R,4R)-2-((5-(trifluoromethyl)pyrazin-2-yl)amino)-7-azabicyclo[2.2.1]heptan-7-yl)methanone |
| 290 | | 21 | 19 | 558 | (2-fluoro-6-(pyrimidin-2-yl)phenyl)((1S,2R,4R)-2-((5-(trifluoromethyl)pyrazin-2-yl)amino)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 291 | | 15 | 35 | 425 | (7-ethoxyquinolin-8-yl)((1S,2R,4R)-2-((5-(trifluoromethyl)pyrazin-2-yl)amino)-7-azabicyclo[2.2.1]heptan-7-yl)methanone |
| 292 | | >10000 | | >10000 | (2-(1,4-dimethyl-1H-pyrazol-5-yl)-6-methoxyphenyl)((1S,2R,4R)-2-((5-(trifluoromethyl)pyrazin-2-yl)amino)-7-azabicyclo[2.2.1]heptan-7-yl)methanone |
| 293 | | 23 | 37 | 1100 | (3-methyl-2-(pyridin-2-yl)phenyl)((1S,2R,4R)-2-((5-(trifluoromethyl)pyrimidin-2-yl)amino)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 294 | | 21 | 15 | 1200 | (3-fluoro-2-(2H-1,2,3-triazol-2-yl)phenyl)((1S,2R,4R)-2-((5-(trifluoromethyl)pyridin-2-yl)amino)-7-azabicyclo[2.2.1]heptan-7-yl)methanone |
| 295 | | 9 | 8 | 257 | (3-methyl-2-(2H-1,2,3-triazol-2-yl)phenyl)((1S,2R,4R)-2-((5-(trifluoromethyl)pyridin-2-yl)amino)-7-azabicyclo[2.2.1]heptan-7-yl)methanone |
| 296 | | 5 | 6 | 114 | (3-methyl-2-(oxazol-2-yl)phenyl)((1S,2R,4R)-2-((5-(trifluoromethyl)pyridin-2-yl)amino)-7-azabicyclo[2.2.1]heptan-7-yl)methanone |

| Ex. No. | Compound | rOX1 Ki (nM) | hOX1 Ki (nM) | hOX2 Ki (nM) | Compound Name |
|---|---|---|---|---|---|
| 297 | | | >10000 | >10000 | (3-fluoro-2-(pyrimidin-2-yl)phenyl)((1R,2S,4S)-2-((5-(trifluoromethyl)pyrazin-2-yl)amino)-7-azabicyclo[2.2.1]heptan-7-yl)methanone |
| 298 | | | | | (3-fluoro-2-(oxazol-2-yl)phenyl)((1S,2R,4R)-2-((5-(trifluoromethyl)pyridin-2-yl)amino)-7-azabicyclo[2.2.1]heptan-7-yl)methanone |
| 299 | | | | | (3-methyl-2-(pyrimidin-2-yl)phenyl)((1S,2R,4R)-2-((5-(trifluoromethyl)pyridin-2-yl)amino)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 300 | | | | | (3-chloro-2-(pyrimidin-2-yl)phenyl)((1S,2R,4R)-2-((5-(trifluoromethyl) pyrazin-2-yl)amino)-7-azabicyclo[2.2.1]heptan-7-yl)methanone |
| 301 | | | | | ((1S,2R,4R)-2-((5-bromopyridin-2-yl)amino)-7-azabicyclo[2.2.1]heptan-7-yl)(3-fluoro-2-(oxazol-2-yl)phenyl)methanone |
| 302 | | | | | ((1S,2R,4R)-2-((5-bromopyridin-2-yl)amino)-7-azabicyclo[2.2.1]heptan-7-yl)(3-methyl-2-(oxazol-2-yl)phenyl)methanone |
| 303 | | | | | ((1S,2R,4R)-2-((5-bromopyridin-2-yl)amino)-7-azabicyclo[2.2.1]heptan-7-yl)(3-fluoro-2-(pyrimidin-2-yl)phenyl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 304 | | | | | ((1S,2R,4R)-2-((5-bromopyridin-2-yl)amino)-7-azabicyclo[2.2.1]heptan-7-yl)(3-methyl-2-(pyrimidin-2-yl)phenyl)methanone |
| 305 | | | | | ((1S,2R,4R)-2-((5-bromopyridin-2-yl)amino)-7-azabicyclo[2.2.1]heptan-7-yl)(3-fluoro-2-(2H-1,2,3-triazol-2-yl)phenyl)methanone |
| 306 | | | | | ((1S,2R,4R)-2-((5-bromopyridin-2-yl)amino)-7-azabicyclo[2.2.1]heptan-7-yl)(3-fluoro-2-(2H-1,2,3-triazol-2-yl)phenyl)methanone |
| 307 | | | | | ((1S,2R,4R)-2-((5-bromopyridin-2-yl)amino)-7-azabicyclo[2.2.1]heptan-7-yl)(3-fluoro-2-(oxazol-2-yl)phenyl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 308 | | | | | ((1S,2R,4R)-2-((5-bromopyrazin-2-yl)amino)-7-azabicyclo[2.2.1]heptan-7-yl)(3-fluoro-2-(oxazol-2-yl)phenyl)methanone |
| 309 | | | | | ((1S,2R,4R)-2-((5-bromopyrazin-2-yl)amino)-7-azabicyclo[2.2.1]heptan-7-yl)(3-fluoro-2-(pyrimidin-2-yl)phenyl)methanone |
| 310 | | | | | ((1S,2R,4R)-2-((5-bromopyridin-2-yl)amino)-7-azabicyclo[2.2.1]heptan-7-yl)(3-methyl-2-(pyrimidin-2-yl)phenyl)methanone |
| 311 | | | | | ((1S,2R,4R)-2-((5-bromopyrazin-2-yl)amino)-7-azabicyclo[2.2.1]heptan-7-yl)(3-fluoro-2-(2H-1,2,3-triazol-2-yl)phenyl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 312 | | | | | ((1S,2R,4R)-2-((5-bromopyrazin-2-yl)amino)-7-azabicyclo[2.2.1]heptan-7-yl)(3-fluoro-2-(2H-1,2,3-triazol-2-yl)phenyl)methanone |
| 313 | | | | | ((1S,2R,4R)-2-((5-bromopyrimidin-2-yl)amino)-7-azabicyclo[2.2.1]heptan-7-yl)(3-fluoro-2-(oxazol-2-yl)phenyl)methanone |
| 314 | | | | | ((1S,2R,4R)-2-((5-bromopyrimidin-2-yl)amino)-7-azabicyclo[2.2.1]heptan-7-yl)(3-methyl-2-(oxazol-2-yl)phenyl)methanone |
| 315 | | | | | ((1S,2R,4R)-2-((5-bromopyrimidin-2-yl)amino)-7-azabicyclo[2.2.1]heptan-7-yl)(3-fluoro-2-(pyrimidin-2-yl)phenyl)methanone |

| Ex. No. | Compound | rOX1 Ki (nM) | hOX1 Ki (nM) | hOX2 Ki (nM) | Compound Name |
|---|---|---|---|---|---|
| 316 | | | | | ((1S,2R,4R)-2-((5-bromopyrimidin-2-yl)amino)-7-azabicyclo[2.2.1]heptan-7-yl)(3-methyl-2-(pyrimidin-2-yl)phenyl)methanone |
| 317 | | | | | ((1S,2R,4R)-2-((5-bromopyrimidin-2-yl)amino)-7-azabicyclo[2.2.1]heptan-7-yl)(3-fluoro-2-(2H-1,2,3-triazol-2-yl)phenyl)methanone |
| 318 | | | | | ((1S,2R,4R)-2-((5-bromopyrimidin-2-yl)amino)-7-azabicyclo[2.2.1]heptan-7-yl)(3-methyl-2-(2H-1,2,3-triazol-2-yl)phenyl)methanone |
| 319 | | | | | (3-methyl-2-(pyridin-2-yl)phenyl)((1S,2R,4R)-2-((5-(trifluoromethyl)pyridin-2-yl)amino)-7-azabicyclo[2.2.1]heptan-7-yl)methanone |

| Ex. No. | Compound | rOX1 Ki (nM) | hOX1 Ki (nM) | hOX2 Ki (nM) | Compound Name |
|---|---|---|---|---|---|
| 320 | | | | | (3-fluoro-2-(pyridin-2-yl)phenyl)((1S,2R,4R)-2-((5-(trifluoromethyl)pyridin-2-yl)amino)-7-azabicyclo[2.2.1]heptan-7-yl)methanone |
| 321 | | | | | (3-fluoro-2-(pyridin-2-yl)phenyl)((1S,2R,4R)-2-((5-(trifluoromethyl)pyrimidin-2-yl)amino)-7-azabicyclo[2.2.1]heptan-7-yl)methanone |
| 322 | | | | | (3-methyl-2-(pyridin-2-yl)phenyl)((1S,2R,4R)-2-((5-(trifluoromethyl)pyridin-2-yl)amino)-7-azabicyclo[2.2.1]heptan-7-yl)methanone |

TABLE 1-continued
| Ex. No. | Compound | rOX1 Ki (nM) | hOX1 Ki (nM) | hOX2 Ki (nM) | Compound Name |
|---|---|---|---|---|---|
| 323 | 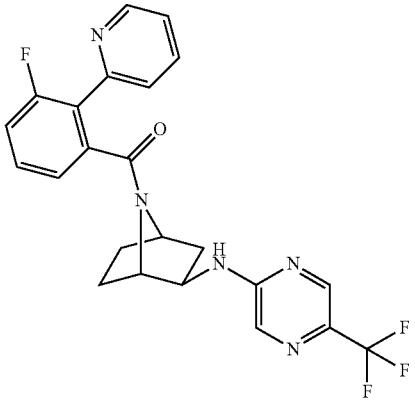 | | | | (3-fluoro-2-(pyridin-2-yl)phenyl)((2S)-2-((5-(trifluoromethyl)pyridin-2-yl)amino)-7-azabicyclo[2.2.1]heptan-7-yl)methanone |
| 324 | 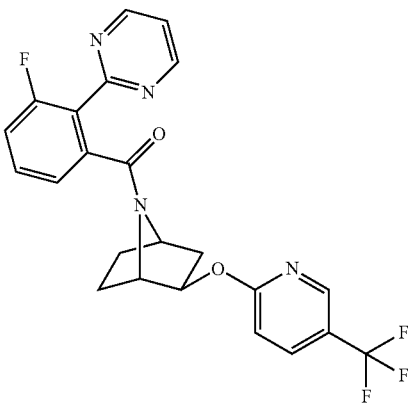 [SMILES: O=C(c1cccc(F)c1-c1ncccn1)N1C2CCC1C(Oc1ccc(C(F)(F)F)cn1)C2] | | | | (3-fluoro-2-(pyrimidin-2-yl)phenyl)((1S,2R,4R)-2-((5-(trifluoromethyl)pyridin-2-yl)oxy)-7-azabicyclo[2.2.1]heptan-7-yl)methanone |
| 325 | 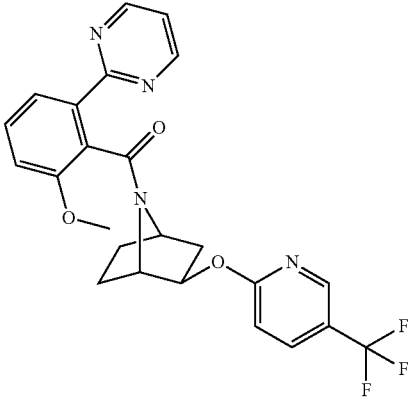 [SMILES: COc1cccc(-c2ncccn2)c1C(=O)N1C2CCC1C(Oc1ccc(C(F)(F)F)cn1)C2] | | | | (2-methoxy-6-(pyrimidin-2-yl)phenyl)((1S,2R,4R)-2-((5-(trifluoromethyl)pyridin-2-yl)oxy)-7-azabicyclo[2.2.1]heptan-7-yl)methanone |

TABLE 1-continued
| Ex. No. | Compound | rOX1 Ki (nM) | hOX1 Ki (nM) | hOX2 Ki (nM) | Compound Name |
|---|---|---|---|---|---|
| 326 | 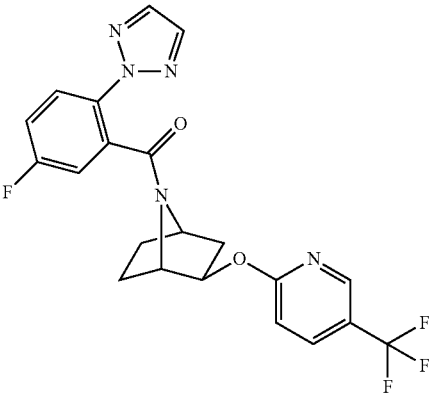 [SMILES: O=C(c1cc(F)ccc1-n1nccn1)N1C2CCC1C(Oc1ccc(C(F)(F)F)cn1)C2] | | | | (5-fluoro-2-(2H-1,2,3-triazol-2-yl)phenyl)((1S,2R,4R)-2-((5-(trifluoromethyl)pyridin-2-yl)oxy)-7-azabicyclo[2.2.1]heptan-7-yl)methanone |
| 327 | 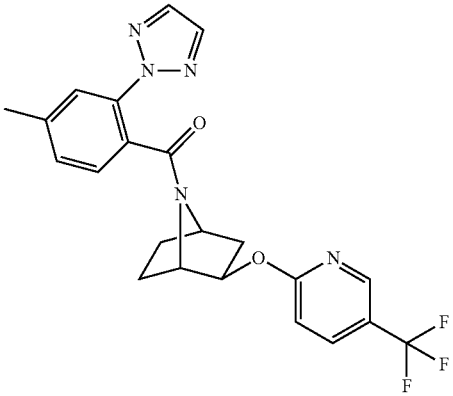 [SMILES: Cc1ccc(C(=O)N2C3CCC2C(Oc2ccc(C(F)(F)F)cn2)C3)c(-n2nccn2)c1] | | | | (4-methyl-2-(2H-1,2,3-triazol-2-yl)phenyl)((1S,2R,4R)-2-((5-(trifluoromethyl)pyridin-2-yl)oxy)-7-azabicyclo[2.2.1]heptan-7-yl)methanone |
| 328 | 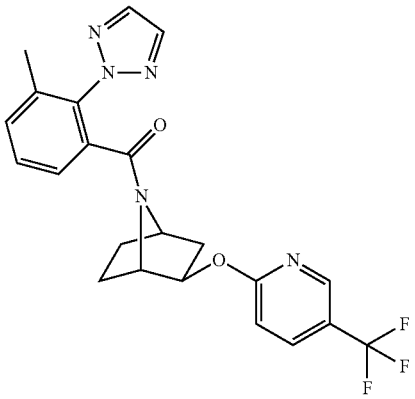 [SMILES: Cc1cccc(C(=O)N2C3CCC2C(Oc2ccc(C(F)(F)F)cn2)C3)c1-n1nccn1] | | | | (3-methyl-2-(2H-1,2,3-triazol-2-yl)phenyl)((1S,2R,4R)-2-((5-(trifluoromethyl)pyridin-2-yl)oxy)-7-azabicyclo[2.2.1]heptan-7-yl)methanone |

| Ex. No. | Compound | rOX1 Ki (nM) | hOX1 Ki (nM) | hOX2 Ki (nM) | Compound Name |
|---------|----------|--------------|--------------|--------------|---------------|
| 329 | | | | | (5-fluoro-2-(pyrimidin-2-yl)phenyl)((1S,2R,4R)-2-((5-(trifluoromethyl)pyridin-2-yl)oxy)-7-azabicyclo[2.2.1]heptan-7-yl)methanone |
| 330 | | | | | (2-fluoro-6-(pyrimidin-2-yl)phenyl)((1S,2R,4R)-2-((5-(trifluoromethyl)pyridin-2-yl)oxy)-7-azabicyclo[2.2.1]heptan-7-yl)methanone |
| 331 | | | | | (2-(2H-1,2,3-triazol-2-yl)phenyl)((1S,2R,4R)-2-((5-(trifluoromethyl)pyridin-2-yl)oxy)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 332 | | | | | (6-methyl-3-(2H-1,2,3-triazol-2-yl)pyridin-2-yl)((1S,2R,4R)-2-((5-(trifluoromethyl)pyridin-2-yl)oxy)-7-azabicyclo[2.2.1]heptan-7-yl)methanone |
| 333 | | | | | (3-methyl-2-(oxazol-2-yl)phenyl)((1S,2R,4R)-2-((5-(trifluoromethyl)pyridin-2-yl)oxy)-7-azabicyclo[2.2.1]heptan-7-yl)methanone |
| 334 | | | | | (3-methyl-2-(pyridin-2-yl)phenyl)((1S,2R,4R)-2-((5-(trifluoromethyl)pyridin-2-yl)oxy)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 335 | | | | | (2-(5-fluoropyrimidin-2-yl)phenyl)((1S,2R,4R)-2-((5-(trifluoromethyl)pyridin-2-yl)oxy)-7-azabicyclo[2.2.1]heptan-7-yl)methanone |
| 336 | | | | | (2-fluoro-6-(2H-1,2,3-triazol-2-yl)phenyl)((1S,2R,4R)-2-((5-(trifluoromethyl)pyridin-2-yl)oxy)-7-azabicyclo[2.2.1]heptan-7-yl)methanone |
| 337 | | | | | (5-methyl-3-(2H-1,2,3-triazol-2-yl)pyridin-2-yl)((1S,2R,4R)-2-((5-(trifluoromethyl)pyridin-2-yl)oxy)-7-azabicyclo[2.2.1]heptan-7-yl)methanone |
| 338 | | | | | (2-bromo-3-fluorophenyl)((1S,2R,4R)-2-((5-(trifluoromethyl)pyridin-2-yl)oxy)-7-azabicyclo[2.2.1]heptan-7-yl)methanone |

| Ex. No. | Compound | rOX1 Ki (nM) | hOX1 Ki (nM) | hOX2 Ki (nM) | Compound Name |
|---|---|---|---|---|---|
| 339 | 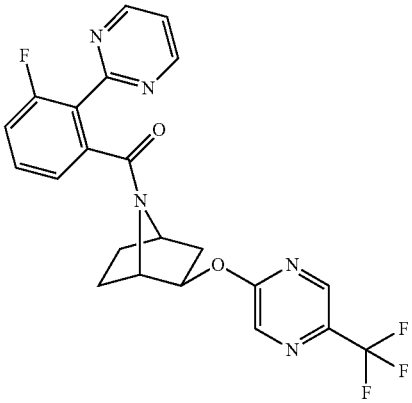 [SMILES: O=C(c1cccc(F)c1-c1ncccn1)N1C2CCC1C(Oc1cnc(C(F)(F)F)cn1)C2] | | | | (3-fluoro-2-(pyrimidin-2-yl)phenyl)((1S,2R,4R)-2-((5-(trifluoromethyl)pyrazin-2-yl)oxy)-7-azabicyclo[2.2.1]heptan-7-yl)methanone |
| 340 | 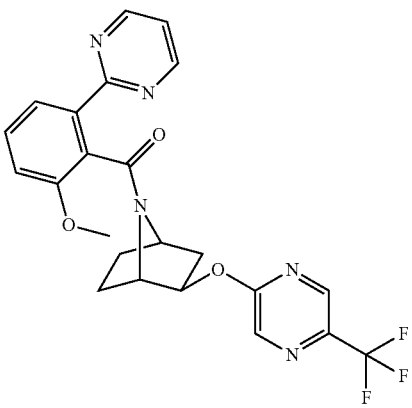 [SMILES: COc1cccc(-c2ncccn2)c1C(=O)N1C2CCC1C(Oc1cnc(C(F)(F)F)cn1)C2] | | | | (2-methoxy-6-(pyrimidin-2-yl)phenyl)((1S,2R,4R)-2-((5-(trifluoromethyl)pyridin-2-yl)oxy)-7-azabicyclo[2.2.1]heptan-7-yl)methanone |
| 341 | 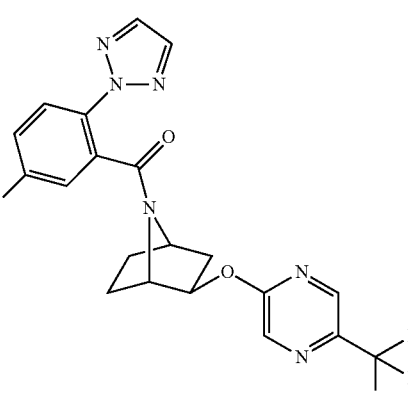 | | | | (5-fluoro-2-(2H-1,2,3-triazol-2-yl)phenyl)((1S,2R,4R)-2-((5-(trifluoromethyl)pyrazin-2-yl)oxy)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 342 | | | | | (4-methyl-2-(2H-1,2,3-triazol-2-yl)phenyl)((1S,2R,4R)-2-((5-(trifluoromethyl)pyrazin-2-yl)oxy)-7-azabicyclo[2.2.1]heptan-7-yl)methanone |
| 343 | | | | | (3-methyl-2-(2H-1,2,3-triazol-2-yl)phenyl)((1S,2R,4R)-2-((5-(trifluoromethyl)pyrazin-2-yl)oxy)-7-azabicyclo[2.2.1]heptan-7-yl)methanone |
| 344 | | | | | (5-fluoro-2-(pyrimidin-2-yl)phenyl)((1S,2R,4R)-2-((5-(trifluoromethyl)pyrazin-2-yl)oxy)-7-azabicyclo[2.2.1]heptan-7-yl)methanone |

| Ex. No. | Compound | rOX1 Ki (nM) | hOX1 Ki (nM) | hOX2 Ki (nM) | Compound Name |
|---|---|---|---|---|---|
| 345 | 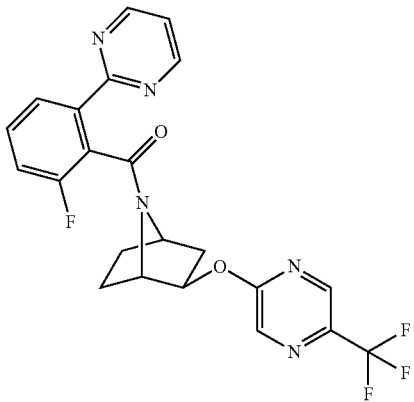 [SMILES: O=C(c1c(F)cccc1-c1ncccn1)N1C2CCC1C(Oc1cnc(C(F)(F)F)cn1)C2] | | | | (2-fluoro-6-(pyrimidin-2-yl)phenyl)((1S,2R,4R)-2-((5-(trifluoromethyl)pyrazin-2-yl)oxy)-7-azabicyclo[2.2.1]heptan-7-yl)methanone |
| 346 | 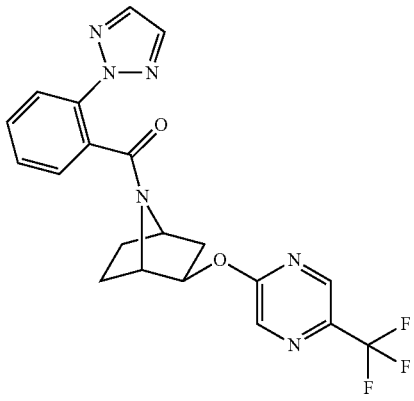 [SMILES: O=C(c1ccccc1-n1nccn1)N1C2CCC1C(Oc1cnc(C(F)(F)F)cn1)C2] | | | | (2-(2H-1,2,3-triazol-2-yl)phenyl)((1S,2R,4R)-2-((5-(trifluoromethyl)pyrazin-2-yl)oxy)-7-azabicyclo[2.2.1]heptan-7-yl)methanone |
| 347 | 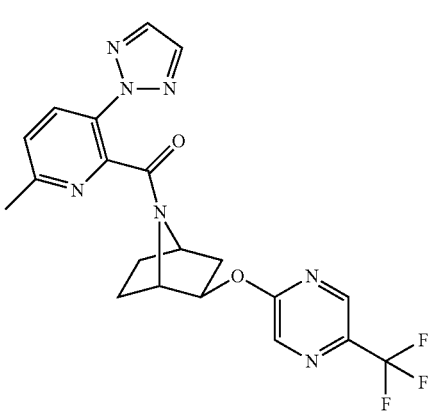 [SMILES: Cc1ccc(-n2nccn2)c(C(=O)N2C3CCC2C(Oc2cnc(C(F)(F)F)cn2)C3)n1] | | | | (6-methyl-3-(2H-1,2,3-triazol-2-yl)pyridin-2-yl)((1S,2R,4R)-2-((5-(trifluoromethyl)pyrazin-2-yl)oxy)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 348 | | | | | (3-methyl-2-(oxazol-2-yl)phenyl)((1S,2R,4R)-2-((5-(trifluoromethyl)pyrazin-2-yl)oxy)-7-azabicyclo[2.2.1]heptan-7-yl)methanone |
| 349 | | | | | (3-methyl-2-(pyridin-2-yl)phenyl)((1S,2R,4R)-2-((5-(trifluoromethyl)pyrazin-2-yl)oxy)-7-azabicyclo[2.2.1]heptan-7-yl)methanone |
| 350 | | | | | (2-(5-fluoropyrimidin-2-yl)phenyl)((1S,2R,4R)-2-((5-(trifluoromethyl)pyrazin-2-yl)oxy)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 351 | | | | | (2-fluoro-6-(2H-1,2,3-triazol-2-yl)phenyl)((1S,2R,4R)-2-((5-(trifluoromethyl)pyrazin-2-yl)oxy)-7-azabicyclo[2.2.1]heptan-7-yl)methanone |
| 352 | | | | | (5-methyl-3-(2H-1,2,3-triazol-2-yl)pyridin-2-yl)((1S,2R,4R)-2-((5-(trifluoromethyl)pyrazin-2-yl)oxy)-7-azabicyclo[2.2.1]heptan-7-yl)methanone |
| 353 | | | | | (2-bromo-3-fluorophenyl)((1S,2R,4R)-2-((5-(trifluoromethyl)pyrazin-2-yl)oxy)-7-azabicyclo[2.2.1]heptan-7-yl)methanone |
| 354 | | | | | (2-methoxy-6-(pyrimidin-2-yl)phenyl)((1S,2R,4R)-2-((5-(trifluoromethyl)pyrimidin-2-yl)oxy)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 355 | | | | | (5-fluoro-2-(2H-1,2,3-triazol-2-yl)phenyl)((1S,2R,4R)-2-((5-(trifluoromethyl)pyrimidin-2-yl)oxy)-7-azabicyclo[2.2.1]heptan-7-yl)methanone |
| 356 | | | | | (4-methyl-2-(2H-1,2,3-triazol-2-yl)phenyl)((1S,2R,4R)-2-((5-(trifluoromethyl)pyrimidin-2-yl)oxy)-7-azabicyclo[2.2.1]heptan-7-yl)methanone |
| 357 | | | | | (3-methyl-2-(2H-1,2,3-triazol-2-yl)phenyl)((1S,2R,4R)-2-((5-(trifluoromethyl)pyrimidin-2-yl)oxy)-7-azabicyclo[2.2.1]heptan-7-yl)methanone |

TABLE 1-continued
| Ex. No. | Compound | rOX1 Ki (nM) | hOX1 Ki (nM) | hOX2 Ki (nM) | Compound Name |
|---|---|---|---|---|---|
| 358 | 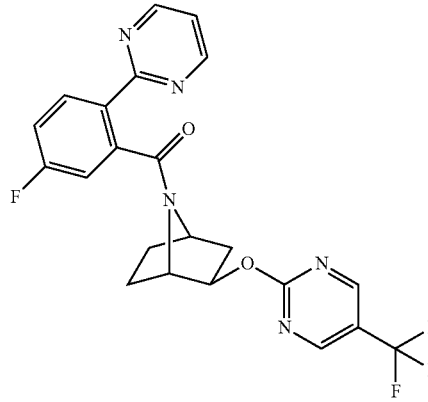 | | | | (5-fluoro-2-(pyrimidin-2-yl)phenyl)((1S,2R,4R)-2-((5-(trifluoromethyl)pyrimidin-2-yl)oxy)-7-azabicyclo[2.2.1]heptan-7-yl)methanone |
| 359 | 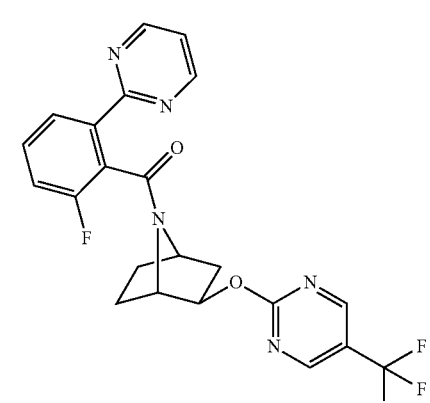 | | | | (2-fluoro-6-(pyrimidin-2-yl)phenyl)((1S,2R,4R)-2-((5-(trifluoromethyl)pyrimidin-2-yl)oxy)-7-azabicyclo[2.2.1]heptan-7-yl)methanone |
| 360 | 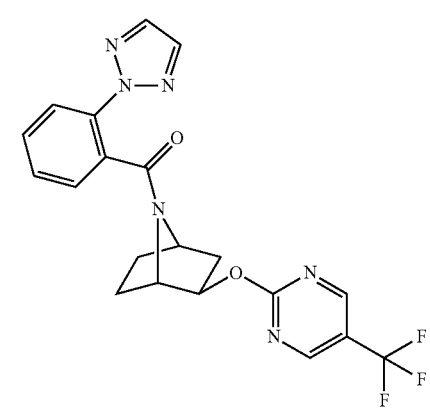 [SMILES: O=C(c1ccccc1-n1nccn1)N1C2CCC1C(Oc1ncc(C(F)(F)F)cn1)C2] | | | | (2-(2H-1,2,3-triazol-2-yl)phenyl)((1S,2R,4R)-2-((5-(trifluoromethyl)pyrimidin-2-yl)oxy)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 361 | | | | | (6-methyl-3-(2H-1,2,3-triazol-2-yl)pyridin-2-yl)((1S,2R,4R)-2-((5-(trifluoromethyl)pyrimidin-2-yl)oxy)-7-azabicyclo[2.2.1]heptan-7-yl)methanone |
| 362 | | | | | (3-methyl-2-(oxazol-2-yl)phenyl)((1S,2R,4R)-2-((5-(trifluoromethyl)pyrimidin-2-yl)oxy)-7-azabicyclo[2.2.1]heptan-7-yl)methanone |
| 363 | | | | | (3-methyl-2-(pyridin-2-yl)phenyl)((1S,2R,4R)-2-((5-(trifluoromethyl)pyrimidin-2-yl)oxy)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 364 | 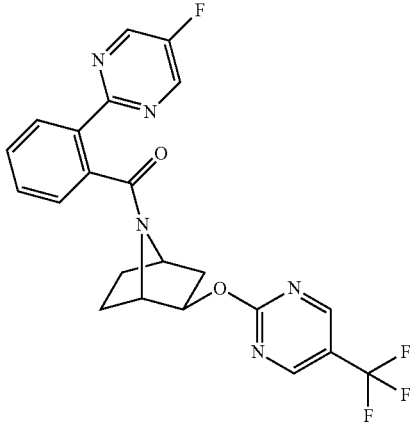 | | | | (2-(5-fluoropyrimidin-2-yl)phenyl)((1S,2R,4R)-2-((5-(trifluoromethyl)pyrimidin-2-yl)oxy)-7-azabicyclo[2.2.1]heptan-7-yl)methanone |
| 365 | 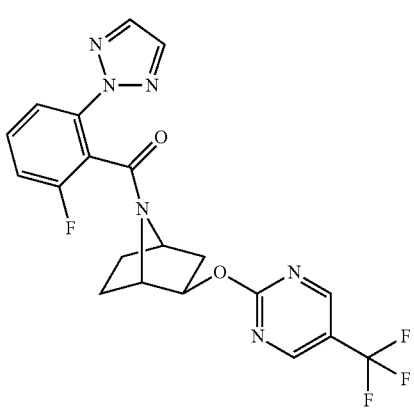 [SMILES: O=C(c1c(F)cccc1-n1nccn1)N1C2CCC1C(Oc1ncc(C(F)(F)F)cn1)C2] | | | | (2-fluoro-6-(2H-1,2,3-triazol-2-yl)phenyl)((1S,2R,4R)-2-((5-(trifluoromethyl)pyrimidin-2-yl)oxy)-7-azabicyclo[2.2.1]heptan-7-yl)methanone |
| 366 | 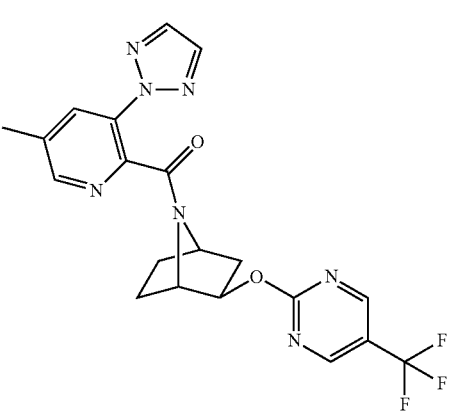 | | | | (5-methyl-3-(2H-1,2,3-triazol-2-yl)pyridin-2-yl)((1S,2R,4R)-2-((5-(trifluoromethyl)pyrimidin-2-yl)oxy)-7-azabicyclo[2.2.1]heptan-7-yl)methanone |

TABLE 1-continued

| Ex. No. | Compound | rOX1 Ki (nM) | hOX1 Ki (nM) | hOX2 Ki (nM) | Compound Name |
|---|---|---|---|---|---|
| 367 | 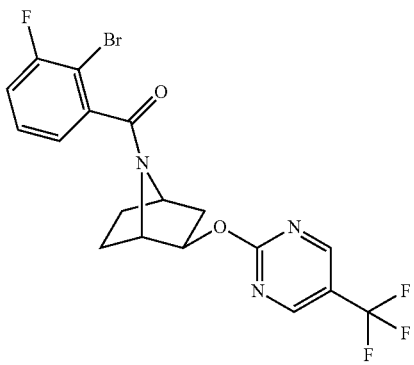 [SMILES: O=C(c1cccc(F)c1Br)N1C2CCC1C(Oc1ncc(C(F)(F)F)cn1)C2] | | | | (2-bromo-3-fluorophenyl)((1S,2R,4R)-2-((5-(trifluoromethyl)pyrimidin-2-yl)oxy)-7-azabicyclo[2.2.1]heptan-7-yl)methanone |

In another embodiment, preferred compounds of the invention are set forth in Table 2 below. Orexin receptor activity from further testing of certain compounds of the invention is set forth in Table 2 below.

TABLE 2

| Ex. No. | Compound | rOX1 K$_i$ (nM) | hOX1 K$_i$ (nM) | hOX2 K$_i$ (nM) | Compound Name |
|---|---|---|---|---|---|
| 1 | 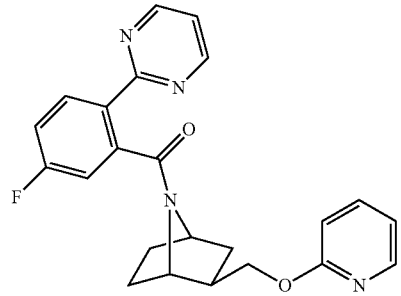 | 25 | 41 | 276 | (5-fluoro-2-(pyrimidin-2-yl)phenyl)((1S,2R,4R)-2-((pyridin-2-yloxy)methyl)-7-azabicyclo[2.2.1]heptan-7-yl)methanone |
| 2 | 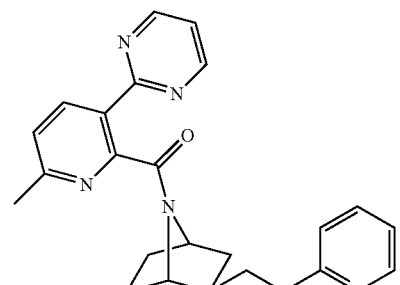 | 31 | 23 | 500 | (±)-(6-methyl-3-(pyrimidin-2-yl)pyridin-2-yl)(2-((pyridin-2-yloxy)methyl)-7-azabicyclo[2.2.1]heptan-7-yl)methanone |
| 3A | 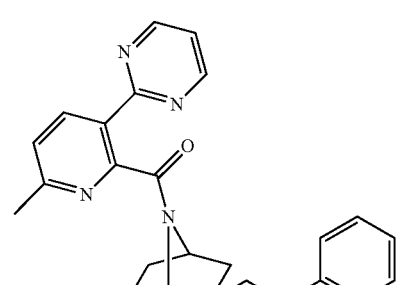 | 24 | 19 | 271 | (6-methyl-3-(pyrimidin-2-yl)pyridin-2-yl)((1S*,2R*,4R*)-2-((pyridin-2-yloxy)methyl)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 3B | | | >10000 | >10000 | (6-methyl-3-(pyrimidin-2-yl)pyridin-2-yl)((1R*,2S*,4S*)-2-((pyridin-2-yloxy)methyl)-7-azabicyclo[2.2.1]heptan-7-yl)methanone |
| 4 | | 36 | 41 | 927 | (±)-(6-methyl-3-(2H-1,2,3-triazol-2-yl)pyridin-2-yl)(2-((pyridin-2-yloxy)methyl)-7-azabicyclo[2.2.1]heptan-7-yl)methanone |
| 5A | | 15 | 15 | 428 | (6-methyl-3-(2H-1,2,3-triazol-2-yl)pyridin-2-yl)((1S,2R,4R)-2-((pyridin-2-yloxy)methyl)-7-azabicyclo[2.2.1]heptan-7-yl)methanone |
| 5B | | | >10000 | >10000 | (6-methyl-3-(2H-1,2,3-triazol-2-yl)pyridin-2-yl)((1R,2S,4S)-2-((pyridin-2-yloxy)methyl)-7-azabicyclo[2.2.1]heptan-7-yl)methanone |
| 6 | | 15 | 15 | 428 | (6-methyl-3-(2H-1,2,3-triazol-2-yl)-pyridin-2-yl)((1S,2R,4R)-2-((pyridin-2-yloxy)methyl)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 7 | | 19 | 19 | 198 | (±)-(2-(((5-fluoropyridin-2-yl)oxy)methyl)-7-azabicyclo[2.2.1]heptan-7-yl)(6-methyl-3-(2H-1,2,3-triazol-2-yl)pyridin-2-yl)methanone |
| 8A | | 9 | 14 | 94 | ((1S,2R,4R)-2-(((5-fluoropyridin-2-yl)oxy)methyl)-7-azabicyclo[2.2.1]heptan-7-yl)(6-methyl-3-(2H-1,2,3-triazol-2-yl)pyridin-2-yl)methanone |
| 8B | | >10000 | | >10000 | ((1R,2S,4S)-2-(((5-fluoropyridin-2-yl)oxy)methyl)-7-azabicyclo[2.2.1]heptan-7-yl)(6-methyl-3-(2H-1,2,3-triazol-2-yl)pyridin-2-yl)methanone |
| 9 | | | 9 | 60 | (±)-(2-(((5-fluoropyridin-2-yl)oxy)methyl)-7-azabicyclo[2.2.1]heptan-7-yl)(5-methyl-2-(2H-1,2,3-triazol-2-yl)phenyl)methanone |
| 10A | | 4 | 3 | 32 | ((1S,2R,4R)-2-(((5-fluoropyridin-2-yl)oxy)methyl)-7-azabicyclo[2.2.1]heptan-7-yl)(5-methyl-2-(2H-1,2,3-triazol-2-yl)phenyl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 10B | | 4050 | 3200 | 5150 | ((1R,2S,4S)-2-(((5-fluoropyridin-2-yl)oxy)methyl)-7-azabicyclo[2.2.1]heptan-7-yl)(5-methyl-2-(2H-1,2,3-triazol-2-phenyl)methanone |
| 11 | | | 10 | 13 | (±)-(2-(((5-fluoropyridin-2-yl)oxy)methyl)-7-azabicyclo[2.2.1]heptan-7-yl)(2-(thiophen-2-yl)phenyl)methanone |
| 12A | | | 177 | 339 | ((1S*,2R*,4R*)-2-(((5-fluoropyridin-2-yl)oxy)methyl)-7-azabicyclo[2.2.1]heptan-7-yl)(2-(thiophen-2-yl)phenyl)methanone |
| 12B | | | 3 | 5 | ((1R*,2S*,4S*)-2-(((5-fluoropyridin-2-yl)oxy)methyl)-7-azabicyclo[2.2.1]heptan-7-yl)(2-(thiophen-2-yl)phenyl)methanone |
| 13 | | | 118 | 109 | (±)-(5-methyl-2-(2H-1,2,3-triazol-2-yl)phenyl)(2-(((4-(trifluoromethyl)pyrimidin-2-yl)oxy)methyl)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 14 | | | 50 | 71 | (±)-(5-methyl-2-(2H-1,2,3-triazol-2-yl)phenyl)(2-(((5-(trifluoromethyl)pyridin-2-yl)oxy)methyl)-7-azabicyclo[2.2.1]heptan-7-yl)methanone |
| 15 | | | 56 | 120 | (±)-(5-methyl-2-(2H-1,2,3-triazol-2-yl)phenyl)(2-(((3-(trifluoromethyl)pyridin-2-yl)oxy)methyl)-7-azabicyclo[2.2.1]heptan-7-yl)methanone |
| 16 | | | 20 | 43 | (±)-(5-methyl-2-(2H-1,2,3-triazol-2-yl)phenyl)(2-(((6-(trifluoromethyl)pyridin-2-yl)oxy)methyl)-7-azabicyclo[2.2.1]heptan-7-yl)methanone |
| 17 | | | 42 | 69 | (±)-(5-methyl-2-(2H-1,2,3-triazol-2-yl)phenyl)(2-(((4-methylpyridin-2-yl)oxy)methyl)-7-azabicyclo[2.2.1]heptan-7-yl)methanone |
| 18 | | | 12 | 45 | (±)-(5-methyl-2-(2H-1,2,3-triazol-2-yl)phenyl)(2-(((6-methylpyridin-2-yl)oxy)methyl)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 19 | | | 12 | 45 | (±)-(5-methyl-2-(2H-1,2,3-triazol-2-yl)phenyl)(2-(((5-methylpyridin-2-yl)oxy)methyl)-7-azabicyclo[2.2.1]heptan-7-yl)methanone |
| 20 | | | 270 | 364 | (±)-(2-(((3,6-dimethylpyrazin-2-yl)oxy)methyl)-7-azabicyclo[2.2.1]heptan-7-yl)(5-methyl-2-(2H-1,2,3-triazol-2-yl)phenyl)methanone |
| 21 | | | 300 | 487 | (±)-(5-methyl-2-(2H-1,2,3-triazol-2-yl)phenyl)(2-(((3-(trifluoromethyl)quinoxalin-2-yl)oxy)methyl)-7-azabicyclo[2.2.1]heptan-7-yl)methanone |
| 22 | | | 47 | 50 | (±)-(2-(2H-1,2,3-triazol-2-yl)phenyl)(2-(((5-fluoropyridin-2-yl)oxy)methyl)-7-azabicyclo[2.2.1]heptan-7-yl)methanone |
| 23 | | | 322 | 1500 | (±)-2-(((5-fluoropyridin-2-yl)oxy)methyl)-7-azabicyclo[2.2.1]heptan-7-yl)(quinolin-8-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 24 | | | 122 | 164 | (±)-2-(((5-fluoropyridin-2-yl)oxy)methyl)-7-azabicyclo[2.2.1]heptan-7-yl)(naphthalen-1-yl)methanone |
| 25 | | | 74 | 160 | (±)-2-(((5-fluoropyridin-2-yl)oxy)methyl)-7-azabicyclo[2.2.1]heptan-7-yl)(2-methylnaphthalen-1-yl)methanone |
| 26 | | | 134 | 394 | (±)-2-(1H-pyrazol-1-yl)phenyl)(2-(((5-fluoropyridin-2-yl)oxy)methyl)-7-azabicyclo[2.2.1]heptan-7-yl)methanone |
| 27 | | | 677 | 380 | (±)-2-(((5-fluoropyridin-2-yl)oxy)methyl-7-azabicyclo[2.2.1]heptan-7-yl)(3-phenylfuran-2-yl)methanone |
| 28 | | | 14 | 11 | (±)-(2-ethoxynaphthalen-1-yl)(2-(((5-fluoropyridin-2-yl)oxy)methyl)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 29 | | | 11 | 60 | (±)-(5-(2-fluorophenyl)-2-methylthiazol-4-yl)(2-(((5-fluoropyridin-2-yl)oxy)methyl)-7-azabicyclo[2.2.1]heptan-7-yl)methanone |
| 30 | | | 60 | 160 | (±)-(5-fluoro-2-(2H-1,2,3-triazol-2-yl)phenyl)(2-(((5-fluoropyridin-2-yl)oxy)methyl)-7-azabicyclo[2.2.1]heptan-7-yl)methanone |
| 31 | | | 43 | 125 | (±)-(2-fluoro-6-(pyrimidin-2-yl)phenyl)(2-(((5-fluoropyridin-2-yl)oxy)methyl)-7-azabicyclo[2.2.1]heptan-7-yl)methanone |
| 32 | | | 21 | 130 | (±)-(5-fluoro-2-(pyrimidin-2-yl)phenyl)(2-(((5-fluoropyridin-2-yl)oxy)methyl-7-azabicyclo[2.2.1]heptan-7-yl)methanone |
| 33 | | 15 | 9 | 40 | (±)-(2-(((5-fluoropyridin-2-yl)oxy)methyl)-7-azabicyclo[2.2.1]heptan-7-yl)(5-methyl-2-(pyrimidin-2-yl)phenyl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 34 | | | 60 | 467 | (±)-(2-(2H-1,2,3-triazol-2-yl)phenyl)(2-((quinoxalin-2-yloxy)methyl)-7-azabicyclo[2.2.1]heptan-7-yl)methanone |
| 35 | | 69 | 60 | 708 | (±)-(2-fluoro-6-(2H-1,2,3-triazol-2-yl)phenyl)(2-((quinoxalin-2-yloxy)methyl)-7-azabicyclo[2.2.1]heptan-7-yl)methanone |
| 36 | | | 70 | 108 | (±)-(5-methyl-2-(2H-1,2,3-triazol-2-yl)phenyl)(2-((quinoxalin-2-yloxy)methyl)-7-azabicyclo[2.2.1]heptan-7-yl)methanone |
| 37 | | | 300 | 487 | (±)-(5-fluoro-2-(2H-1,2,3-triazol-2-yl)phenyl)(2-((quinoxalin-2-yloxy)methyl)-7-azabicyclo[2.2.1]heptan-7-yl)methanone |
| 38 | | | 120 | 383 | (±)-(5-methyl-2-(pyrimidin-2-yl)phenyl)(2-((quinoxalin-2-yl)oxy)methyl)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 39 | | | 30 | 28 | (±)-(2-(((4,6-dimethylpyrimidin-2-yl)oxy)methyl)-7-azabicyclo[2.2.1]heptan-7-yl)(5-methyl-2-(2H-1,2,3-triazol-2-yl)phenyl)methanone |
| 40 | | | 5000 | 1203 | (±)-2-(((4,6-dimethylpyrimidin-2-yl)oxy)methyl)-7-azabicyclo[2.2.1]heptan-7-yl)(3-methyl-5-phenylisoxazol-4-yl)methanone |
| 41 | | | 35 | 23 | (±)-(2-(((4,6-dimethylpyrimidin-2-yl)oxy)methyl)-7-azabicyclo[2.2.1]heptan-7-yl)(2-ethoxynaphthalen-1-yl)methanone |
| 42 | | | 1277 | 253 | (±)-2-(((4,6-dimethylpyrimidin-2-yl)oxy)methyl)-7-azabicyclo[2.2.1]heptan-7-yl)(2-ethoxyphenyl)methanone) |
| 43 | | | 222 | 92 | (±)-(2-(((4,6-dimethylpyrimidin-2-yl)oxy)methyl)-7-azabicyclo[2.2.1]heptan-7-yl)(2-fuoro-6-(pyrimidin-2-yl)phenyl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 44 | | | 400 | 104 | (±)-(2-(((4,6-dimethylpyrimidin-2-yl)oxy)methyl)-7-azabicyclo[2.2.1]heptan-7-yl)(5-fluoro-2-(pyrimidin-2-yl)phenyl)methanone |
| 45 | | | 79 | 59 | (±)-(2-(((4,6-dimethylpyrimidin-2-yl)oxy)methyl)-7-azabicyclo[2.2.1]heptan-7-yl)(5-methyl-2-(pyrimidin-2-yl)phenyl)methanone |
| 46 | | | 111 | 10 | (±)-(2-(((4,6-dimethylpyrimidin-2-yl)oxy)methyl)-7-azabicyclo[2.2.1]heptan-7-yl)(2-(thiophen-2-yl)phenyl)methanone |
| 47 | | | 460 | 418 | (±)-(6-methyl-3-(2H-1,2,3-triazol-2-yl)pyridin-2-yl)(2-(((5-(trifluoromethyl)pyridin-2-yl)oxy)methyl)-7-azabicyclo[2.2.1]heptan-7-yl)methanone |
| 48 | | | 3900 | 4700 | (±)-(3-ethoxy-6-methylpyridin-2-yl)(2-(((5-(trifluoromethyl)pyridin-2-yl)oxy)methyl)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 49 | | 81 | 69 | 192 | (±)-(2-(((5-bromopyridin-2-yl)oxy)methyl)-7-azabicyclo[2.2.1]heptan-7-yl)(6-methyl-3-(2H-1,2,3-triazol-2-yl)pyridin-2-yl)methanone |
| 50 | | 460 | | 4400 | (±)-(2-(((5-bromopyridin-2-yl)oxy)methyl)-7-azabicyclo[2.2.1]heptan-7-yl)(3-fluoro-2-methoxyphenyl)methanone |
| 51 | | 974 | | 1800 | (±)-(2-(((5-bromopyridin-2-yl)oxy)methyl)-7-azabicyclo[2.2.1]heptan-7-yl)(3-ethoxy-6-methylpyridin-2-yl)methanone |
| 52 | | 350 | | 2300 | (±)-(3-fluoro-2-(pyrimidin-2-yl)phenyl)(2-((pyridin-2-yloxy)methyl)-7-azabicyclo[2.2.1]heptan-7-yl)methanone |
| 53 | | 2200 | | >10000 | (±)-(6-methyl-3-(2H-1,2,3-triazol-2-yl)pyridin-2-yl)(2-((pyridazin-3-yloxy)methyl)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 54 | | | 3500 | 2200 | (±)-(6-methyl-3-(2H-1,2,3-triazol-2-yl)pyridin-2-yl)(2-(((2-methylpyridin-3-yl)oxy)methyl)-7-azabicyclo[2.2.1]heptan-7-yl)methanone |
| 55 | | 119 | 150 | 202 | (±)-(6-methyl-3-(2H-1,2,3-triazol-2-yl)pyridin-2-yl)(2-(((3-methylpyridin-2-yl)oxy)methyl)-7-azabicyclo[2.2.1]heptan-7-yl)methanone |
| 56 | | >10000 | | >10000 | (+)-(2-(((1-methyl-1H-pyrazol-5-yl)oxy)methyl)-7-azabicyclo[2.2.1]heptan-7-yl)(6-methyl-3-(2H-1,2,3-triazol-2-yl)pyridin-2-yl)methanone |
| 57 | | | 1000 | 7300 | (±)-(6-methyl-3-(2H-1,2,3-triazol-2-yl)pyridin-2-yl)(2-((pyridin-4-yloxy)methyl)-7-azabicyclo[2.2.1]heptan-7-yl)methanone |
| 58 | | 88 | 117 | 2400 | (±)-(6-methyl-3-(2H-1,2,3-triazol-2-yl)pyridin-2-yl)(2-((pyridin-3-yloxy)methyl)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 59 | 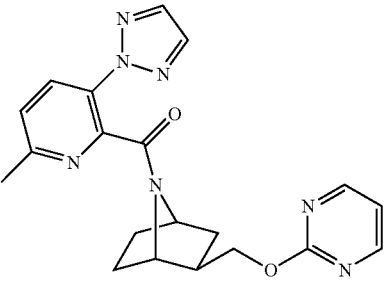 |  | 2600 | 4900 | (±)-(6-methyl-3-(2H-1,2,3-triazol-2-yl)pyridin-2-yl)(2-((pyrimidin-2-yloxy)methyl)-7-azabicyclo[2.2.1]heptan-7-yl)methanone |
| 60 | 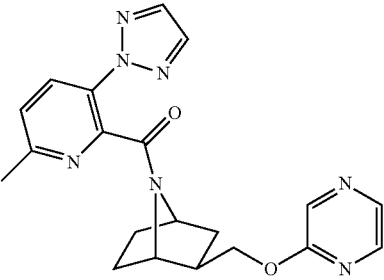 |  | 7800 | >10000 | (±)-(6-methyl-3-(2H-1,2,3-triazol-2-yl)pyridin-2-yl)(2-((pyrazin-2-yloxy)methyl)-7-azabicyclo[2.2.1]heptan-7-yl)methanone |
| 61 | 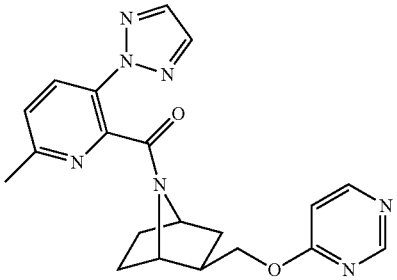 |  | 2800 | >10000 | (±)-(6-methyl-3-(2H-1,2,3-triazol-2-yl)pyridin-2-yl)(2-((pyrimidin-4-yloxy)methyl)-7-azabicyclo[2.2.1]heptan-7-yl)methanone |
| 62 | 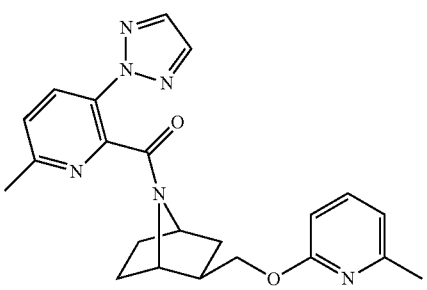 | 74 | 46 | 188 | (±)-(6-methyl-3-(2H-1,2,3-triazol-2-yl)pyridin-2-yl)(2-(((6-methylpyridin-2-yl)oxy)methyl)-7-azabicyclo[2.2.1]heptan-7-yl)methanone |
| 63 | 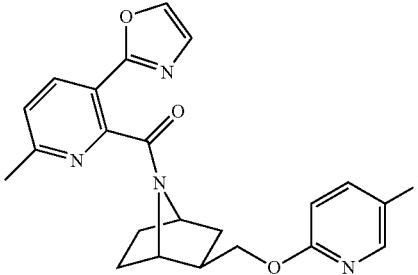 | 25 | 25 | 339 | (±)-(2-(((5-fluoropyridin-2-yl)oxy)methyl)-7-azabicyclo[2.2.1]heptan-7-yl)(6-methyl-3-(oxazol-2-yl)pyridin-2-yl)methanone |

TABLE 2-continued

| Ex. No. | Compound | rOX1 K_i (nM) | hOX1 K_i (nM) | hOX2 K_i (nM) | Compound Name |
|---|---|---|---|---|---|
| 64 | | | 18 | 24 | 81 | (±)-(2-(((5-fluoropyridin-2-yl)oxy)methyl)-7-azabicyclo[2.2.1]heptan-7-yl)(6-methyl-3-(pyrimidin-2-yl)pyridin-2-yl)methanone |
| 65 | | 1440 | | 6200 | (±)-(3,6'-dimethyl-[2,3'-bipyridin]-2'-yl)(2-(((5-fluoropyridin-2-yl)oxy)methyl)-7-azabicyclo[2.2.1]heptan-7-yl)methanone |
| 66 | | 197 | 293 | 620 | (±)-(2-(((5-fluoropyridin-2-yl)oxy)methyl)-7-azabicyclo[2.2.1]heptan-7-yl)(6-methyl-3-(3-methyl-1,2,4-oxadiazol-5-yl)pyridin-2-yl)methanone |
| 67 | | 48 | 69 | 258 | (±)-(2-(((5-fluoropyridin-2-yl)oxy)methyl)-7-azabicyclo[2.2.1]heptan-7-yl)(6-methyl-3-(3-methyl-1H-pyrazol-1-yl)pyridin-2-yl)methanone |
| 68 | | 27 | 22 | 576 | (±)-(2-(((5-fluoropyridin-2-yl)oxy)methyl)-7-azabicyclo[2.2.1]heptan-7-yl)(6-methyl-3-(pyrrolidin-1-yl)pyridin-2-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 69 | 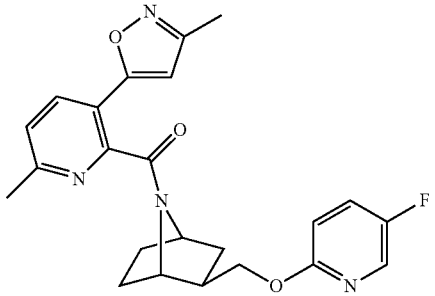 | 40 | 64 | 174 | (±)-(2-(((5-fluoropyridin-2-yl)oxy)methyl)-7-azabicyclo[2.2.1]heptan-7-yl)(6-methyl-3-(3-methylisoxazol-5-yl)pyridin-2-yl)methanone |
| 70 | 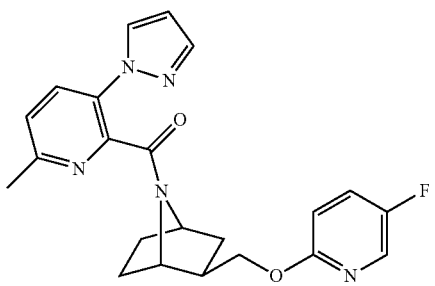 | 88 | 62 | 624 | (±)-(2-(((5-fluoropyridin-2-yl)oxy)methyl)-7-azabicyclo[2.2.1]heptan-7-yl)(6-methyl-3-(1H-pyrazol-1-yl)pyridin-2-yl)methanone |
| 71 | 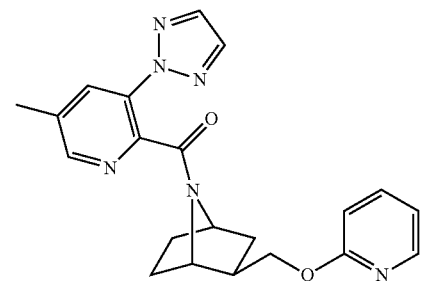 | 1200 | | 3700 | (±)-(5-methyl-3-(2H-1,2,3-triazol-2-yl)pyridin-2-yl)(2-((pyridin-2-yl)oxy)methyl)-7-azabicyclo[2.2.1]heptan-7-yl)methanone |
| 72 | 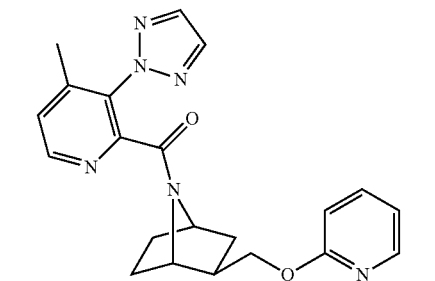 | 137 | 162 | 2400 | (±)-(4-methyl-3-(2H-1,2,3-triazol-2-yl)pyridin-2-yl)(2-((pyridin-2-yloxy)methyl)-7-azabicyclo[2.2.1]heptan-7-yl)methanone |
| 73 | 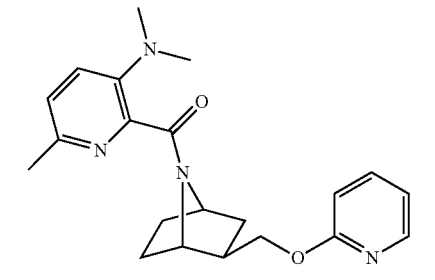 | 278 | | 7900 | (±)-(3-(dimethylamino)-6-methylpyridin-2-yl)(2-((pyridin-2-yloxy)methyl)-7-azabicyclo[2.2.1]heptan-7-yl)methanone |

TABLE 2-continued

| Ex. No. | Compound | rOX1 K<sub>i</sub> (nM) | hOX1 K<sub>i</sub> (nM) | hOX2 K<sub>i</sub> (nM) | Compound Name |
|---|---|---|---|---|---|
| 74 | | | 359 | 1700 | (±)-(3-(2H-1,2,3-triazol-2-yl)quinolin-2-yl)(2-((pyridin-2-yloxy)methyl)-7-azabicyclo[2.2.1]heptan-7-yl)methanone |
| 75 | | 18 | 7 | 220 | (±)-(7-ethoxyquinolin-8-yl)(2-((pyridin-2-yloxy)methyl)-7-azabicyclo[2.2.1]heptan-7-yl)methanone |
| 76 | | | >10000 | >10000 | (±)-(3,6-dimethylimidazo[1,2-a]pyridin-5-yl)(2-((pyridin-2-yloxy)methyl)-7-azabicyclo[2.2.1]heptan-7-yl)methanone |
| 77 | | 103 | 66 | 867 | (±)-(1-methyl-4-phenyl-1H-pyrazol-3-yl)((1S,2R,4R)-2-((pyridin-2-yloxy)methyl)-7-azabicyclo[2.2.1]heptan-7-yl)methanone |
| 78 | | | 418 | 3100 | (±)-(1-methyl-3-phenyl-1H-pyrazol-4-yl)((1S,2R,4R)-2-((pyridin-2-yloxy)methyl)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 79 | | | 2400 | 8500 | (±)-((3,7-dimethylimidazo[1,2-a]pyridin-8-yl)(2-((pyridin-2-yloxy)methyl)-7-azabicyclo[2.2.1]heptan-7-yl)methanone |
| 80 | | | 1100 | >10000 | (±)-(7-methylimidazo[1,2-a]pyridin-8-yl)(2-((pyridin-2-yloxy)-methyl)-7-azabicyclo[2.2.1]heptan-7-yl)methanone |
| 81 | | | 916 | 2900 | (±)-(1-methyl-4-phenyl-1H-pyrazol-5-yl)(2-((pyridin-2-yloxy)methyl)-7-azabicyclo[2.2.1]heptan-7-yl)methanone |
| 82 | | | >10000 | >10000 | (±)-((6-methylimidazo[1,2-a]pyridin-5-yl)(2-((pyridin 2-yloxy)methyl)-7-azabicyclo[2.2.1]heptan-7-yl)methanone |
| 83 | | 17 | 13 | 277 | (±)-(3-ethoxyisoquinolin-4-yl)(2-((pyridin-2-yloxy)methyl)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 84 | | | 2600 | 9700 | (±)-(1-methyl-5-phenyl-1H-pyrazol-4-yl)(-2-((pyridin-2-yloxy)methyl)-7-azabicyclo[2.2.1]heptan-7-yl)methanone |
| 85 | | | >10000 | >10000 | (±)-(6-methyl-3-(4-methylpiperazin-1-yl)pyridin-2-yl)(2-((pyridin-2-yloxy)methyl)-7-azabicyclo[2.2.1]heptan-7-yl)methanone |
| 86 | | | >10000 | >10000 | (±)-(6-methyl-3-(piperazin-1-yl)pyridin-2-yl)(2-(pyridin-2-yloxy)methyl)-7-azabicyclo[2.2.1]heptan-7-yl)methanone |
| 87 | | | 4200 | >10000 | (±)-(6-methyl-3-morpholinopyridin-2-yl)((1S,2R,4R)-2-((pyridin-2-yloxy)methyl)-7-azabicyclo[2.2.1]heptan-7-yl)methanone |
| 88 | | 47 | 49 | 690 | (±)-(7-methoxyquinolin-8-yl)(2-((pyridin-2-yloxy)methyl)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 89 | | | 11 | 10 | 38 | (±)-(2-ethoxynaphthalen-1-yl)(2-((pyridin-2-yloxy)methyl)-7-azabicyclo[2.2.1]heptan-7-yl)methanone |
| 90 | | | | 3000 | >10000 | (±)-(3,6'-dimethyl-[2,3'-bipyridin]-2'-yl)(2-((pyridin-2-yloxy)methyl)-7-azabicyclo[2.2.1]heptan-7-yl)methanone |
| 91 | | | | 624 | 3300 | (±)-(3-(2H-1,2,3-triazol-2-yl)pyridin-2-yl)(2-((pyridin-2-yloxy)methyl)-7-azabicyclo[2.2.1]heptan-7-yl)methanone |
| 92 | | | 20 | 11 | 218 | (±)-(2-methyl-5-phenylthiazol-4-yl)(2-((pyridin-2-yloxy)methyl)-7-azabicyclo[2.2.1]heptan-7-yl)methanone |
| 93 | | | 40 | 73 | 836 | (±)-(6-methyl-3-(oxazol-2-yl)pyridin-2-yl)(2-((pyridin-2-yloxy)methyl)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 94 | | | 170 | 200 | 2100 | (±)-(6-methyl-3-(3-methylisoxazol-5-yl)pyridin-2-yl)(2-((pyridin-2-yloxy)methyl)-7-azabicyclo[2.2.1]heptan-7-yl)methanone |
| 95 | | | 247 | | 3700 | (±)-(6-methyl-3-(1H-pyrazol-1-yl)pyridin-2-yl)(2-((pyridin-2-yloxy)methyl)-7-azabicyclo[2.2.1]heptan-7-yl)methanone |
| 96 | | | 70 | 76 | 950 | (±)-(6-methyl-3-(4-methyl-1H-pyrazol-1-yl)pyridin-2-yl)(2-((pyridin-2-yloxy)methyl)-7-azabicyclo[2.2.1]heptan-7-yl)methanone |
| 97 | | | 35 | 32 | 840 | (±)-(6-methyl-3-(pyrrolidin-1-yl)pyridin-2-yl)(2-((pyridin-2-yloxy)methyl)-7-azabicyclo[2.2.1]heptan-7-yl)methanone |
| 98 | | | >10000 | | >10000 | (±)-(3,6'-dimethyl-[2,3'-bipyridin]-2'-yl)(2-(((5-fluoropyrimidin-2-yl)oxy)methyl)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 99 | | | 1500 | 2900 | (±)-(2-(((5-fluoropyrimidin-2-yl)oxy)methyl)-7-azabicyclo[2.2.1]heptan-7-yl)(6-methyl-3-(3-methylisoxazol-5-yl)pyridin-2-yl)methanone |
| 100 | | | 950 | 1800 | (±)-(2-(((5-fluoropyrimidin-2-yl)oxy)methyl)-7-azabicyclo[2.2.1]heptan-7-yl)(6-methyl-3-(oxazol-2-yl)pyridin-2-yl)methanone |
| 101 | | | 650 | 1200 | (±)-(2-(((5-fluoropyrimidin-2-yl)oxy)methyl)-7-azabicyclo[2.2.1]heptan-7-yl)(6-methyl-3-(pyrrolidin-1-yl)pyridin-2-yl)methanone |
| 102 | | | | | (±)-(2-(((5-fluoropyrimidin-2-yl)oxy)methyl)-7-azabicyclo[2.2.1]heptan-7-yl)(6-methyl-3-(pyrimidin-2-yl)pyridin-2-yl)methanone |
| 103 | | | 1700 | 3600 | (±)-(2-(((5-fluoropyrimidin-2-yl)oxy)methyl)-7-azabicyclo[2.2.1]heptan-7-yl)(6-methyl-3-(4-methyl-1H-pyrazol-1-yl)pyridin-2-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 104 | 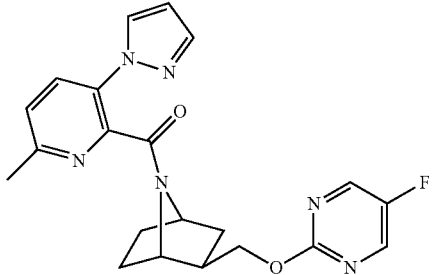 | | 1100 | 4600 | (±)-(2-(((5-fluoropyrimidin-2-yl)oxy)methyl)-7-azabicyclo[2.2.1]heptan-7-yl)(6-methyl-3-(1H-pyrazol-1-yl)pyridin-2-yl)methanone |
| 105 | 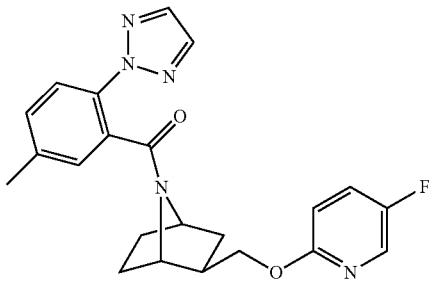 | | | | (±)-(2-(((5-fluoropyridin-2-yl)oxy)methyl)-7-azabicyclo[2.2.1]heptan-7-yl)(5-methyl-2-(2H-1,2,3-triazol-2-yl)phenyl)methanone |
| 106 | 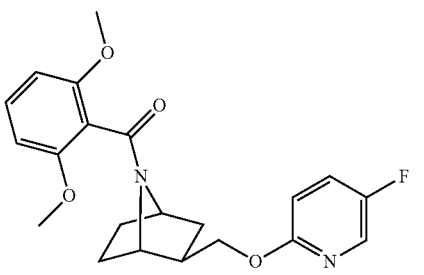 | | 300 | 154 | (±)-(2,6-dimethoxyphenyl)(2-(((5-fluoropyridin-2-yl)oxy)methyl)-7-azabicyclo[2.2.1]heptan-7-yl)methanone |
| 107 | 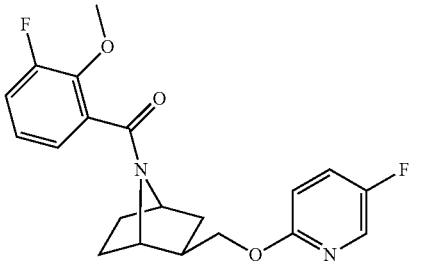 | | 440 | 2200 | (±)-((3-fluoro-2-methoxyphenyl)(2-(((5-fluoropyridin-2-yl)oxy)methyl)-7-azabicyclo[2.2.1]heptan-7-yl)methanone |
| 108 | 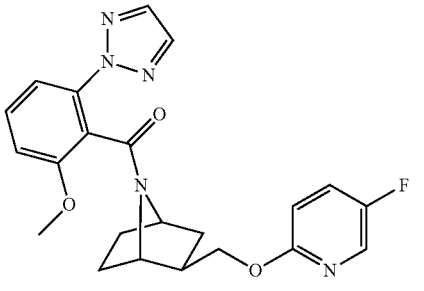 | 10 | 12 | 12 | (±)-(2-(((5-fluoropyridin-2-yl)oxy)methyl)-7-azabicyclo[2.2.1]heptan-7-yl)(2-methoxy-6-(2H-1,2,3-triazol-2-yl)phenyl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 109 | | 29 | 20 | 99 | (±)-(5-fluoro-2-(1H-pyrazol-5-yl)phenyl)(2-(((5-fluoropyridin-2-yl)oxy)methyl)-7-azabicyclo[2.2.1]heptan-7-yl)methanone |
| 110 | | 54 | 67 | 94 | (±)-(2-(((5-fluoropyridin-2-yl)oxy)methyl)-7-azabicyclo[2.2.1]heptan-7-yl)(2-methyl-6-(2H-1,2,3-triazol-2-yl)phenyl)methanone |
| 111 | | 19 | 19 | 198 | (±)-(2-(((5-fluoropyridin-2-yl)oxy)methyl)-7-azabicyclo[2.2.1]heptan-7-yl)(6-methyl-3-(2H-1,2,3-triazol-2-yl)pyridin-2-yl)methanone |
| 112 | | 480 | | 1000 | (±)-(5-chloro-3-(2H-1,2,3-triazol-2-yl)pyridin-2-yl)(2-(((5-fluoropyridin-2-yl)oxy)methyl)-7-azabicyclo[2.2.1]heptan-7-yl)methanone |
| 113 | | 3400 | | 4800 | (±)-(2-(((5-fluoropyridin-2-yl)oxy)-methyl)-7-azabicyclo[2.2.1]heptan-7-yl)(5-methoxy-3-(2H-1,2,3-triazol-2-yl)pyridin-2-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 114 | | 20 | 48 | 73 | (±)-(2-(((5-fluoropyridin-2-yl)oxy)methyl)-7-azabicyclo[2.2.1]heptan-7-yl)(5-methoxy-2-(2H-1,2,3-triazol-2-yl)phenyl)methanone |
| 115 | | 57 | 78 | 108 | (±)-(2-fluoro-6-(2H-1,2,3-triazol-2-yl)phenyl)(2-(((5-fluoropyridin-2-yl)oxy)methyl)-7-azabicyclo[2.2.1]heptan-7-yl)methanone |
| 116 | | 142 | 250 | 315 | (±)-(4-fluoro-2-(2H-1,2,3-triazol-2-yl)phenyl)(2-(((5-fluoropyridin-2-yl)oxy)methyl)-7-azabicyclo[2.2.1]heptan-7-yl)methanone |
| 117 | | 62 | 82 | 245 | (±)-(3-fluoro-2-(2H-1,2,3-triazol-2-yl)phenyl)(2-(((5-fluoropyridin-2-yl)oxy)methyl)-7-azabicyclo[2.2.1]heptan-7-yl)methanone |
| 118 | | 440 | | 2200 | (±)-(3-ethoxy-6-methylpyridin-2-yl)(2-(((5-fluoropyridin-2-yl)oxy)methyl)-7-azabicyclo[2.2.1]heptan-7-yl)methanone |

TABLE 2-continued

| Ex. No. | Compound | rOX1 K_i (nM) | hOX1 K_i (nM) | hOX2 K_i (nM) | Compound Name |
|---|---|---|---|---|---|
| 119 | | | 500 | 1300 | (±)-(2-(((5-fluoropyridin-2-yl)oxy)methyl)-7-azabicyclo[2.2.1]heptan-7-yl)(4-methoxy-2-(2H-1,2,3-triazol-2-yl)phenyl)methanone |
| 120 | | 15 | 14 | 124 | (±)-(5-chloro-2-(2H-1,2,3-triazol-2-yl)phenyl)(2-(((5-fluoropyridin-2-yl)oxy)methyl)-7-azabicyclo[2.2.1]heptan-7-yl)methanone |
| 121 | | 78 | 68 | 340 | (±)-(2-(((5-fluoropyridin-2-yl)oxy)methyl)-7-azabicyclo[2.2.1]heptan-7-yl)(4-methyl-2-(2H-1,2,3-triazol-2-yl)phenyl)methanone |
| 122 | | 118 | 154 | 1000 | (±)-(2-(((5-fluoropyridin-2-yl)oxy)methyl-7-azabicyclo[2.2.1]heptan-7-yl)(4-methyl-2-(pyrimidin-2-yl)phenyl)methanone |
| 123 | | | 400 | 286 | (±)-(2-(((5-fluoropyridin-2-yl)oxy)methyl)-7-azabicyclo[2.2.1]heptan-7-yl)(2-methyl-6-(pyrimidin-2-yl)phenyl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 124 | | 83 | 75 | 355 | (±)-(3-fluoro-2-(pyrimidin-2-yl)phenyl)(-2-(((5-fluoropyridin-2-yl)oxy)methyl)-7-azabicyclo[2.2.1]heptan-7-yl)methanone |
| 125 | | 47 | 29 | 132 | (±)-(2-(((5-fluoropyridin-2-yl)oxy)methyl)-7-azabicyclo[2.2.1]heptan-7-yl)(3-methyl-2-(2H-1,2,3-triazol-2-yl)phenyl)methanone |
| 126 | | 23 | 27 | 231 | (±)-(2-(((5-fluoropyridin-2-yl)oxy)methyl)-7-azabicyclo[2.2.1]heptan-7-yl)(5-(hydroxymethyl)-2-(2H-1,2,3-triazol-2-yl)phenyl)methanone |
| 127 | | | 190 | 1100 | (±)-(2-(3-methyl-1,2,4-oxadiazol-5-yl)phenyl)(2-((pyridin-2-yloxy)methyl)-7-azabicyclo[2.2.1]heptan-7-yl)methanone |
| 128 | | | 5700 | 10000 | (±)-(6-methyl-2-(2H-1,2,3-triazol-2-yl)pyridin-3-yl)(2-((pyridin-2-yloxy)methyl)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 129 | | | 190 | 1000 | (±)-(3-fluoro-2-(2H-1,2,3-triazol-2-yl)phenyl)(2-((pyridin-2-yloxy)methyl)-7-azabicyclo[2.2.1]heptan-7-yl)methanone |
| 130 | | | 3700 | 7200 | (±)-(6-methyl-2-(1H-1,2,3-triazol-1-yl)pyridin-3-yl)(2-((pyridin-2-yloxy)methyl)-7-azabicyclo[2.2.1]heptan-7-yl)methanone |
| 131 | | | 10000 | 10000 | (±)-(6-methyl-2-(2H-1,2,3-triazol-2-yl)pyridin-3-yl)(2-(((4-(trifluoromethyl)pyrimidin-2-yl)oxy)methyl)-7-azabicyclo[2.2.1]heptan-7-yl)methanone |
| 132 | | | 10000 | 7400 | (±)-(6-methyl-2-(1H-1,2,3-triazol-1-yl)pyridin-3-yl)(2-(((4-(trifluoromethyl)pyrimidin-2-yl)oxy)methyl)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 133 | | | 1400 | 950 | (±)-(2-(3-methyl-1,2,4-oxadiazol-5-yl)phenyl)(2-(((4-(trifluoromethyl)pyrimidin-2-yl)oxy)methyl)-7-azabicyclo[2.2.1]heptan-7-yl)methanone |
| 134 | | | 1500 | 690 | (±)-(3-fluoro-2-(2H-1,2,3-triazol-2-yl)phenyl)(2-(((4-(trifluoromethyl)pyrimidin-2-yl)oxy)methyl)-7-azabicyclo[2.2.1]heptan-7-yl)methanone |
| 135 | | | 5400 | 3900 | (±)-(6-methyl-2-(2H-1,2,3-triazol-2-yl)pyridin-3-yl)(2-(((5-methylpyridin-2-yl)oxy)methyl)-7-azabicyclo[2.2.1]heptan-7-yl)methanone |
| 136 | | | 6800 | 1200 | (±)-(6-methyl-2-(1H-1,2,3-triazol-1-yl)pyridin-3-yl)(2-(((5-methylpyridin-2-yl)oxy)methyl)-7-azabicyclo[2.2.1]heptan-7-yl)methanone |
| 137 | | | 950 | 425 | (±)-(2-(3-methyl-1,2,4-oxadiazol-5-yl)phenyl)(2-(((5-methylpyridin-2-yl)oxy)methyl)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 138 | | | 606 | 250 | (±)-(3-fluoro-2-(2H-1,2,3-triazol-2-yl)phenyl)(2-(((5-methylpyridin-2-yl)oxy)methyl)-7-azabicyclo[2.2.1]heptan-7-yl)methanone |
| 139 | | | 4400 | 6500 | (±)-(6-methyl-2-(2H-1,2,3-triazol-2-yl)pyridin-3-yl)(2-(((6-methylpyridin-2-yl)oxy)methyl)-7-azabicyclo[2.2.1]heptan-7-yl)methanone |
| 140 | | | 3100 | 2300 | (±)-(6-methyl-2-(1H-1,2,3-triazol-1-yl)pyridin-3-yl)(2-(((6-methylpyridin-2-yl)oxy)methyl)-7-azabicyclo[2.2.1]heptan-7-yl)methanone |
| 141 | | | 280 | 300 | (±)-(2-(3-methyl-1,2,4-oxadiazol-5-yl)phenyl)(2-(((6-methylpyridin-2-yl)oxy)methyl)-7-azabicyclo[2.2.1]heptan-7-yl)methanone |
| 142 | | | 207 | 300 | (±)-(3-fluoro-2-(2H-1,2,3-triazol-2-yl)phenyl)(2-(((6-methylpyridin-2-yl)oxy)methyl)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 143 | | | 3900 | 4600 | (±)-(6-methyl-2-(2H-1,2,3-triazol-2-yl)pyridin-3-yl)(2-(((6-(trifluoromethyl)pyridin-2-yl)oxy)methyl)-7-azabicyclo[2.2.1]heptan-7-yl)methanone |
| 144 | | | 3600 | 3200 | (±)-(6-methyl-2-(1H-1,2,3-triazol-1-yl)pyridin-3-yl)(2-(((6-(trifluoromethyl)pyridin-2-yl)oxy)methyl)-7-azabicyclo[2.2.1]heptan-7-yl)methanone |
| 145 | | | 340 | 330 | (±)-(2-(3-methyl-1,2,4-oxadiazol-5-yl)phenyl)(2-(((6-(trifluoromethyl)pyridin-2-yl)oxy)methyl)-7-azabicyclo[2.2.1]heptan-7-yl)methanone |
| 146 | | | 180 | 196 | (±)-(3-fluoro-2-(2H-1,2,3-triazol-2-yl)phenyl)(2-(((6-(trifluoromethyl)pyridin-2-yl)oxy)methyl)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 147 | 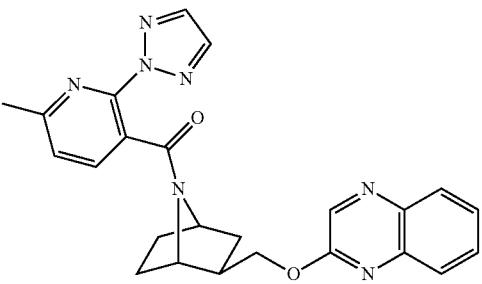 | | | | (±)-(6-methyl-2-(2H-1,2,3-triazol-2-yl)pyridin-3-yl)(2-((quinoxalin-2-yloxy)methyl)-7-azabicyclo[2.2.1]heptan-7-yl)methanone |
| 148 | 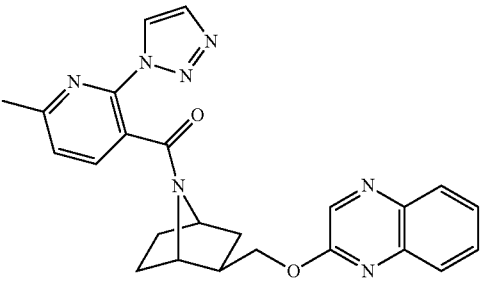 | | 6300 | 3200 | (±)-(6-methyl-2-(1H-1,2,3-triazol-1-yl)pyridin-3-yl)(2-((quinoxalin-2-yloxy)methyl)-7-azabicyclo[2.2.1]heptan-7-yl)methanone |
| 149 | 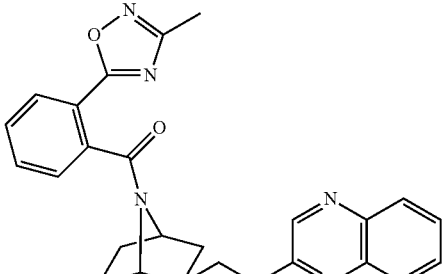 | | 220 | 2000 | (±)-(2-(3-methyl-1,2,4-oxadiazol-5-yl)phenyl)(2-((quinoxalin-2-yloxy)methyl)-7-azabicyclo[2.2.1]heptan-7-yl)methanone |
| 150 | 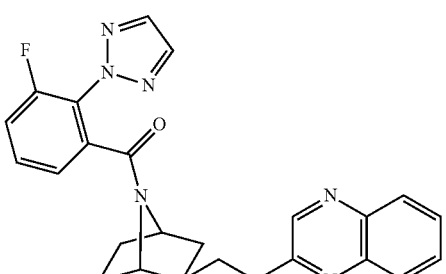 | | 180 | 990 | (±)-(3-fluoro-2-(2H-1,2,3-triazol-2-yl)phenyl)(2-((quinoxalin-2-yloxy)methyl)-7-azabicyclo[2.2.1]heptan-7-yl)methanone |
| 151 | 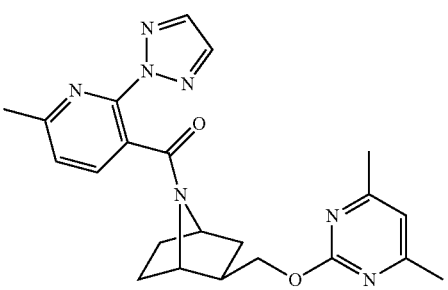 | | 10000 | 10000 | (±)-(2-(((4,6-dimethylpyrimidin-2-yl)oxy)methyl)-7-azabicyclo[2.2.1]heptan-7-yl)(6-methyl-2-(2H-1,2,3-triazol-2-yl)pyridin-3-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 152 | | | 10000 | 5900 | (±)-(2-(((4,6-dimethylpyrimidin-2-yl)oxy)methyl)-7-azabicyclo[2.2.1]heptan-7-yl)(6-methyl-2-(1H-1,2,3-triazol-1-yl)pyridin-3-yl)methanone |
| 153 | | | 1100 | 440 | (±)-(2-(((4,6-dimethylpyrimidin-2-yl)oxy)methyl)-7-azabicyclo[2.2.1]heptan-7-yl)(2-(3-methyl-1,2,4-oxadiazol-5-yl)phenyl)methanone |
| 154 | | | 690 | 300 | (±)-(2-(((4,6-dimethylpyrimidin-2-yl)oxy)methyl)-7-azabicyclo[2.2.1]heptan-7-yl)(3-fluoro-2-(2H-1,2,3-triazol-2-yl)phenyl)methanone |
| 155 | | | 1570 | 3600 | (±)-(2-ethoxy-4-methylpyridin-3-yl)(2-((pyridin-2-yloxy)methyl)-7-azobicyclo[2.2.1]heptan-7-yl)methanone |
| 156 | | | >10000 | >10000 | (±)-(6-methylimidazo[2,1-b]thiazol-5-yl)(2-((pyridin-2-yloxy)methyl)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 157 | | | 94 | 134 | 537 | (±)-(5-bromo-2-ethoxypyridin-3-yl)(2-((pyridin-2-yloxy)methyl)-7-azabicyclo[2.2.1]heptan-7-yl)methanone |
| 158 | | | | 2930 | 1780 | (±)-(2-ethoxy-6-methylpyridin-3-yl)(2-((pyridin-2-yloxy)methyl)-7-azabicyclo[2.2.1]heptan-7-yl)methanone |
| 159 | | | | 262 | 786 | (±)-(7-hydroxyquinolin-8-yl)(2-((pyridin-2-yloxy)methyl)-7-azabicyclo[2.2.1]heptan-7-yl)methanone |
| 160 | | | | 8700 | >10000 | (±)-(2-ethoxy-5-phenylpyridin-3-yl)(2-((pyridin-2-yloxy)methyl)-7-azabicyclo[2.2.1]heptan-7-yl)methanone |
| 161 | | | | 478 | 1450 | (±)-(4-bromo-2-ethoxypyridin-3-yl)(2-((pyridin-2-yloxy)methyl)-7-azabicyclo[2.2.1]heptan-7-yl)methanone |

TABLE 2-continued

| Ex. No. | Compound | rOX1 K_i (nM) | hOX1 K_i (nM) | hOX2 K_i (nM) | Compound Name |
|---|---|---|---|---|---|
| 162 | | | 8500 | >10000 | (±)-(2-chloro-4-ethoxypyridin-3-yl)(2-((pyridin-2-yloxy)methyl)-7-azabicyclo[2.2.1]heptan-7-yl)methanone |
| 163 | | | 150 | 153 | 150 | (±)-(2,4-diethoxypyridin-3-yl)(2-((pyridin-2-yloxy)methyl)-7-azabicyclo[2.2.1]heptan-7-yl)methanone |
| 164 | | 9 | 7 | 195 | (3-ethoxyisoquinolin-4-yl)((1S,2R,4R)-2-((pyridin-2-yloxy)methyl)-7-azabicyclo[2.2.1]heptan-7-yl)methanone |
| 165 | | | 409 | 550 | (±)-(2-ethoxyphenyl)(2-(((5-fluoropyridin-2-yl)oxy)methyl)-7-azabicyclo[2.2.1]heptan-7-yl)methanone |
| 166 | | | 107 | 1177 | (±)-(5-fluoro-2-(2H-1,2,3-triazol-2-yl)phenyl)(2-((quinoxalin-2-yloxy)methyl)-7-azabicyclo[2.2.1]heptan-7-yl)methanone |

TABLE 2-continued

| Ex. No. | Compound | rOX1 K_i (nM) | hOX1 K_i (nM) | hOX2 K_i (nM) | Compound Name |
|---|---|---|---|---|---|
| 167 | | | 9 | 14 | (±)-5-methyl-2-(2H-1,2,3-triazol-2-yl)phenyl)(2-(((5-methylpyridin-2-yl)oxy)methyl)-7-azabicyclo[2.2.1]heptan-7-yl)methanone |
| 168 | | | 2300 | 7300 | (±)-(6-methyl-2-(2H-1,2,3-triazol-2-yl)pyridin-3-yl)(2-((quinoxalin-2-yloxy)methyl)-7-azabicyclo[2.2.1]heptan-7-yl)methanone |
| 169 | | | 9000 | 2526 | (±)-(5-fluoro-2-(2H-1,2,3-triazol-2-yl)phenyl)(2-((pyridin-2-ylamino)methyl)-7-azabicyclo[2.2.1]heptan-7-yl)methanone |
| 170 | | | 1965 | 512 | (±)-(2-(((4,6-dimethylpyrimidin-2-yl)amino)methyl)-7-azabicyclo[2.2.1]heptan-7-yl)(5-fluoro-2-(2H-1,2,3-triazol-2-yl)phenyl)methanone |
| 171 | | | 1935 | | (±)-(5-fluoro-2-(2H-1,2,3-triazol-2-yl)phenyl)(2-(((4-(trifluoromethyl)pyrimidin-2-yl)amino)methyl)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 172 | | | 686 | | (±)-(5-fluoro-2-(2H-1,2,3-triazol-2-yl)phenyl)(2-(((6-(trifluoromethyl)pyridin-2-yl)amino)methyl)-7-azabicyclo[2.2.1]heptan-7-yl)methanone |
| 173 | | | 1260 | 3000 | (±)-(3-fluoro-2-methoxyphenyl)(2-(((5-fluoropyridin-2-yl)oxy)methyl)-7-azabicyclo[2.2.1]heptan-7-yl)methanone |
| 174 | | | 373 | 1000 | (±)-(5-fluoro-2-(2H-1,2,3-triazol-2-yl)phenyl)(2-((quinoxalin-2-ylamino)methyl)-7-azabicyclo[2.2.1]heptan-7-yl)methanone |
| 175 | | | 2500 | 4000 | (±)-(2-(((5-fluoropyrimidin-2-yl)oxy)methyl)-7-azabicyclo[2.2.1]heptan-7-yl)(6-methyl-3-(pyrimidin-2-yl)pyridin-2-yl)methanone |
| 176 | | 119 | 150 | 202 | (±)-(6-methyl-3-(2H-1,2,3-triazol-2-yl)pyridin-2-yl)(2-(((3-methylpyridin-2-yl)oxy)methyl)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 177 | 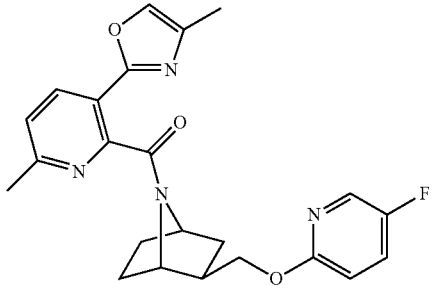 | | 535 | 4000 | (±)-(2-(((5-fluoropyridin-2-yl)oxy)methyl)-7-azabicyclo[2.2.1]heptan-7-yl)(6-methyl-3-(4-methyloxazol-2-yl)pyridin-2-yl)methanone |
| 178 | 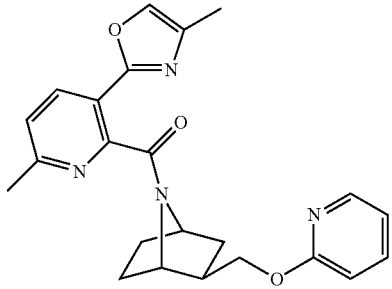 | | 964 | >10000 | (6-methyl-3-(4-methyloxazol-2-yl)pyridin-2-yl)((1S,2R,4R)-2-((pyridin-2-yloxy)methyl)-7-azabicyclo[2.2.1]heptan-7-yl)methanone |
| 179 | 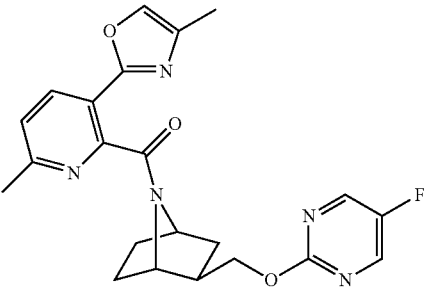 | | 2400 | 5400 | ((1S,2R,4R)-2-(((5-fluoropyrimidin-2-yl)oxy)methyl)-7-azabicyclo[2.2.1]heptan-7-yl)(6-methyl-3-(4-methyloxazol-2-yl)pyridin-2-yl)methanone |
| 180 | 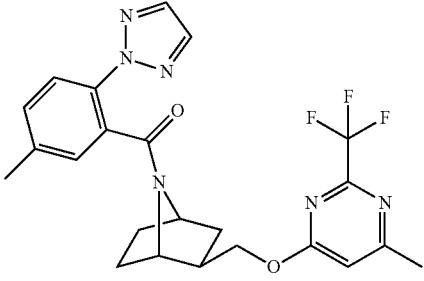 | | 33 | 32 | (±)-(5-methyl-2-(2H-1,2,3-triazol-2-yl)phenyl)(2-(((6-methyl-2-(trifluoromethyl)pyrimidin-4-yl)oxy)methyl)-7-azabicyclo[2.2.1]heptan-7-yl)methanone |
| 181 | 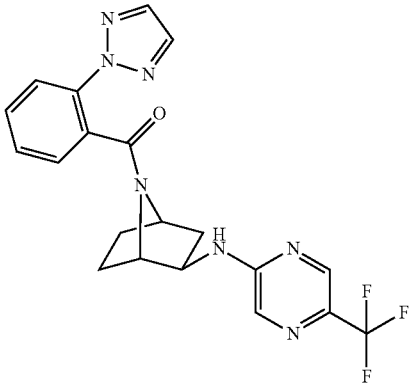 | | 35 | 28 728 | (2-(2H-1,2,3-triazol-2-yl)phenyl)(1S,2R,4R)-2-((5-(trifluoromethyl)pyrazin-2-yl)amino)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 182 | | 47 | 38 | 1100 | (±)-((2-(2H-1,2,3-triazol-2-yl)phenyl)(2-((5-(trifluoromethyl)pyrazin-2-yl)amino)-7-azabicyclo[2.2.1]heptan-7-yl)methanone |
| 183A | | >10000 | >10000 | | (2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone |
| 183B | | 35 | 28 | 728 | (2-(2H-1,2,3-triazol-2-yl)phenyl)((1R,2S,4S)-2-((5-(trifluoromethyl)pyrazin-2-yl)amino)-7-azabicyclo[2.2.1]heptan-7-yl)methanone |
| 184 | | 189 | 349 | 4100 | (±)-(5-methyl-3-(2H-1,2,3-triazol-2-yl)pyridin-2-yl)(2-((5-(trifluoromethyl)pyrazin-2-yl)amino)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 185 | | | 1500 | 2700 | (±)-(5-methyl-3-(1H-1,2,3-triazol-1-yl)pyridin-2-yl)(2-((5-(trifluoromethyl)pyrazin-2-yl)amino)-7-azabicyclo[2.2.1]heptan-7-yl)methanone |
| 186 | | | 134 | 164 | 1200 | (±)-(6-methyl-3-(2H-1,2,3-triazol-2-yl)pyridin-2-yl)(2-((5-(trifluoromethyl)pyrazin-2-yl)amino)-7-azabicyclo[2.2.1]heptan-7-yl)methanone |
| 187 | | | 81 | 48 | 620 | (±)-(6-methyl-3-(2H-1,2,3-triazol-2-yl)pyridin-2-yl)(2-((5-(trifluoromethyl)pyridin-2-yl)amino)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 188 | 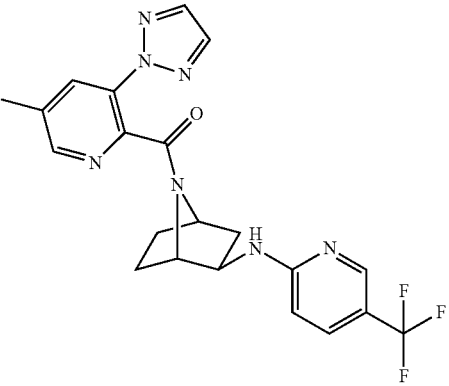 | | 295 | 1500 | (±)-(5-methyl-3-(2H-1,2,3-triazol-2-yl)pyridin-2-yl)(2-((5-(trifluoromethyl)pyridin-2-yl)amino)-7-azabicyclo[2.2.1]heptan-7-yl)methanone |
| 189 | 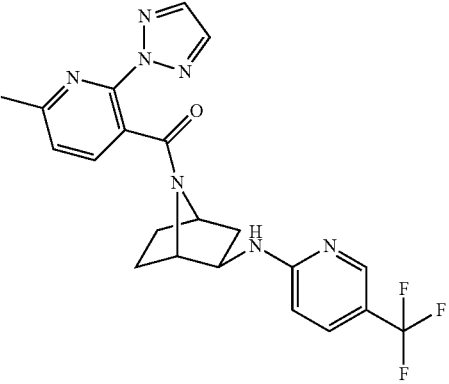 | | 766 | 1500 | (±)-(6-methyl-2-(2H-1,2,3-triazol-2-yl)pyridin-3-yl)(2-((5-(trifluoromethyl)pyridin-2-yl)amino)-7-azabicyclo[2.2.1]heptan-7-yl)methanone |
| 190 | 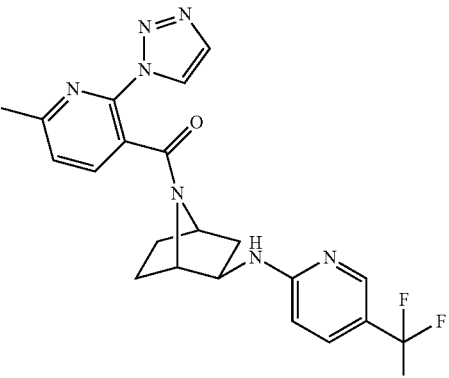 | | 589 | 1200 | (±)-(6-methyl-2-(1H-1,2,3-triazol-1-yl)pyridin-3-yl)(2-((5-(trifluoromethyl)pyridin-2-yl)amino)-7-azabicyclo[2.2.1]heptan-7-yl)methanone |
| 191 | 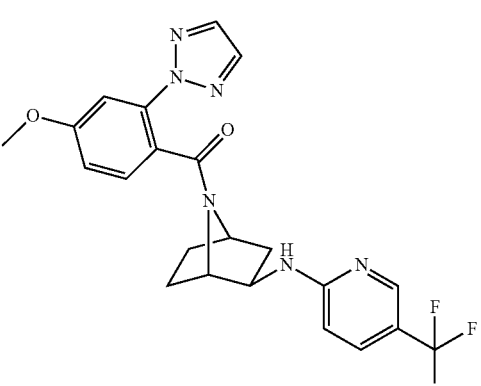 | | 257 | 8800 | (±)-(4-methoxy-2-(2H-1,2,3-triazol-2-yl)phenyl)(2-((5-(trifluoromethyl)pyridin-2-yl)amino)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 192 | | | 60 | 52 | 1500 | (±)-(3-fluoro-2-(pyrimidin-2-yl)phenyl)(2-((5-(trifluoromethyl)pyridin-2-yl)amino)-7-azabicyclo[2.2.1]heptan-7-yl)methanone |
| 193 | | | | 2900 | >10000 | (±)-((3-fluoro-2-methoxyphenyl)(2-((5-(trifluoromethyl)pyridin-2-yl)amino)-7-azabicyclo[2.2.1]heptan-7-yl)methanone |
| 194 | | | | 450 | 800 | (±)-(3-ethoxy-6-methylpyridin-2-yl)(2-((5-(trifluoromethyl)pyridin-2-yl)amino)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 195 | 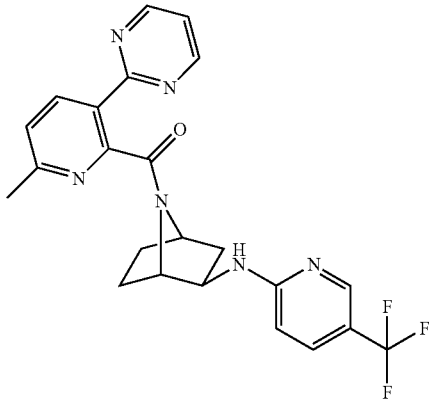 | | 57 | 37 | 325 | (±)-(6-methyl-3-(pyrimidin-2-yl)pyridin-2-yl)(2-((5-(trifluoromethyl)pyridin-2-yl)amino)-7-azabicyclo[2.2.1]heptan-7-yl)methanone |
| 196 | 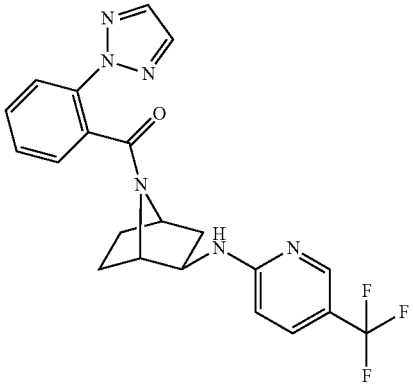 | | 59 | 61 | 1500 | (±)-(2-(2H-1,2,3-triazol-2-yl)phenyl)(2-((5-(trifluoromethyl)pyridin-2-yl)amino)-7-azabicyclo[2.2.1]heptan-7-yl)methanone |
| 197 | 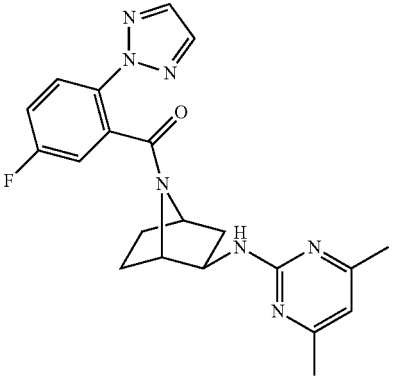 | | | 9000 | 862 | (±)-(2-((4,6-dimethylpyrimidin-2-yl)amino)-7-azabicyclo[2.2.1]heptan-7-yl)(5-fluoro-2-(2H-1,2,3-triazol-2-yl)phenyl)methanone |
| 198 | 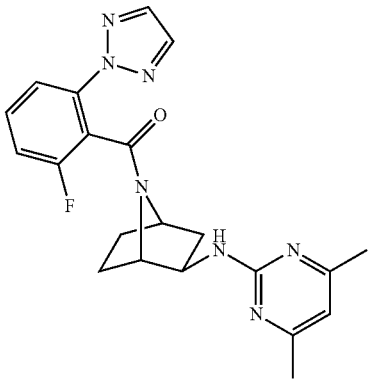 | | | 1411 | 704 | (±)-(2-((4,6-dimethylpyrimidin-2-yl)amino)-7-azabicyclo[2.2.1]heptan-7-yl)(2-fluoro-6-(2H-1,2,3-triazol-2-yl)phenyl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 199 | | | 1634 | 553 | (±)-(2-((4,6-dimethylpyrimidin-2-yl)amino)-7-azabicyclo[2.2.1]heptan-7-yl)(4-fluoro-2-(2H-1,2,3-triazol-2-yl)phenyl)methanone |
| 200 | | | 1100 | 552 | (±)-(2-((4,6-dimethylpyrimidin-2-yl)amino)-7-azabicyclo[2.2.1]heptan-7-yl)(6-methyl-3-(pyrimidin-2-yl)pyridin-2-yl)methanone |
| 201 | | | 3700 | 1100 | (±)-(2-((4,6-dimethylpyrimidin-2-yl)amino)-7-azabicyclo[2.2.1]heptan-7-yl)(6-methyl-3-(2H-1,2,3-triazol-2-yl)pyridin-2-yl)methanone |
| 202 | | | 760 | 444 | (±)-(2-(2H-1,2,3-triazol-2-yl)phenyl)(2-((4,6-dimethylpyrimidin-2-yl)amino)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 203 | | | >10000 | 490 | (±)-(2-((4,6-dimethylpyrimidin-2-yl)amino)-7-azabicyclo[2.2.1]heptan-7-yl)(3-ethoxy-6-methylpyridin-2-yl)methanone |
| 204 | | 33 | 25 | 220 | (±)-(2-(2H-1,2,3-triazol-2-yl)pheny)(2-(quinoxalin-2-ylamino)-7-azabicyclo[2.2.1]heptan-7-yl)methanone |
| 205 | | 79 | 50 | 168 | (±)-(6-methyl-3-(2H-1,2,3-triazol-2-yl)pyridin-2-yl)(2-(quinoxalin-2-yl)amino)-7-azabicyclo[2.2.1]heptan-7-yl)methanone |
| 206 | | | 1200 | 1500 | (±)-(3-fluoro-2-methoxyphenyl)(2-(quinoxalin-2-ylamino)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 207 | | | 120 | 95 | 64 | (±)-(3-ethoxy-6-methylpyridin-2-yl)(2-(quinoxalin-2-ylamino)-7-azabicyclo[2.2.1]heptan-7-yl)methanone |
| 208 | | | 26 | 30 | 90 | (±)-(6-methyl-3-(pyrimidin-2-yl)pyridin-2-yl)(2-(quinoxalin-2-ylamino)-7-azabicyclo[2.2.1]heptan-7-yl)methanone |
| 209 | | | | 1100 | 736 | (±)-(2-(2H-1,2,3-triazol-2-yl)phenyl)(2-((6-(trifluoromethyl)pyridin-2-yl)amino)-7-azabicyclo[2.2.1]heptan-7-yl)methanone |
| 210 | | | | 211 | 128 | (±)-((2-(2H-1,2,3-triazol-2-yl)phenyl)(2-((4-(trifluoromethyl)pyridin-2-yl)amino)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 211 | | | 110 | 55 | 1800 | (±)-(2-(2H-1,2,3-triazol-2-yl)phenyl)(2-((5-chloropyridin-2-yl)amino)-7-azabicyclo[2.2.1]heptan-7-yl)methanone |
| 212 | | | 734 | | 4900 | (±)-(2-(2H-1,2,3-triazol-2-yl)phenyl)(2-((6-(trifluoromethyl)pyridazin-3-yl)amino)-7-azabicyclo[2.2.1]heptan-7-yl)methanone |
| 213 | | | 2800 | | 7500 | (±)-(2-(2H-1,2,3-triazol-2-yl)phenyl)(2((5-methoxypyridin-2-yl)amino)-7-azabicyclo[2.2.1]heptan-7-yl)methanone |
| 214 | | | 500 | | 3100 | (±)-(2-(2H-1,2,3-triazol-2-yl)phenyl)(2-((5-methylpyridin-2-yl)amino)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 215 | | | 1700 | 9000 | (±)-(2-(2H-1,2,3-triazol-2-yl)phenyl)(2-(pyridin-2-ylamino)-7-azabicyclo[2.2.1]heptan-7-yl)methanone |
| 216 | | | 99 | 71 | 475 | (±)-(2-(2H-1,2,3-triazol-2-yl)phenyl)(2-((5-chlorobenzo[d]oxazol-2-yl)amino)-7-azabicyclo[2.2.1]heptan-7-yl)methanone |
| 217 | | | 59 | 40 | 770 | (±)-(2-((5-bromopyridin-2-yl)amino)-7-azabicyclo[2.2.1]heptan-7-yl)(6-methyl-3-(pyrimidin-2-yl)pyridin-2-yl)methanone |
| 218 | | | 2700 | | 6700 | (±)-(2-((5-bromopyridin-2-yl)amino)-7-azabicyclo[2.2.1]heptan-7-yl)(3-fluoro-2-methoxyphenyl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 219 | | 257 | | 1700 | (±)-(2-((5-bromopyridin-2-yl)amino)-7-azabicyclo[2.2.1]heptan-7-yl)(3-ethoxy-6-methylpyridin-2-yl)methanone |
| 220 | | 38 | 26 | 1100 | (±)-(2-((5-bromopyridin-2-yl)amino)-7-azabicyclo[2.2.1]heptan-7-yl)(6-methyl-3-(2H-1,2,3-triazol-2-yl)pyridin-2-yl)methanone |
| 221 | | 172 | 200 | 3300 | (±)-(2-(2H-1,2,3-triazol-2-yl)phenyl)(2-((5-(trifluoromethyl)pyrimidin-2-yl)amino)-7-azabicyclo[2.2.1]heptan-7-yl)methanone |
| 222 | | 4800 | | >10000 | (±)-(3-fluoro-2-methoxyphenyl)(2-((5-(trifluoromethyl)pyrimidin-2-yl)amino)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 223 | 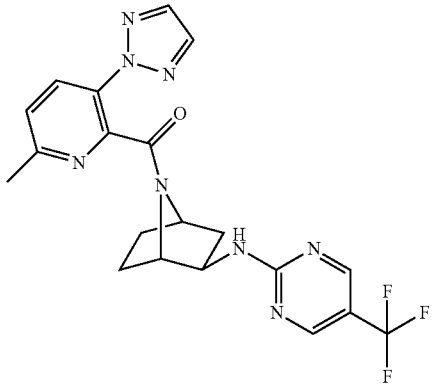 | | 550 | 4000 | (±)-(6-methyl-3-(2H-1,2,3-triazol-2-yl)pyridin-2-yl)(2-((5-(trifluoromethyl)pyrimidin-2-yl)amino)-7-azabicyclo[2.2.1]heptan-7-yl)methanone |
| 224 | 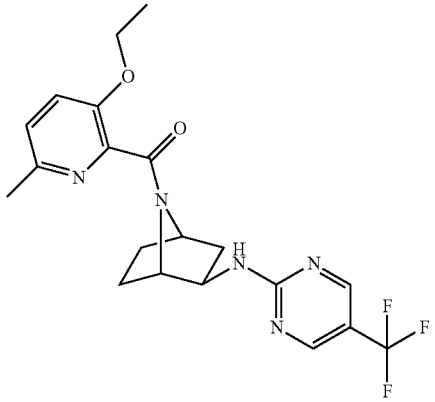 | | 2500 | 7400 | (±)-(3-ethoxy-6-methylpyridin-2-yl)(2-((5-(trifluoromethyl)pyrimidin-2-yl)amino)-7-azabicyclo[2.2.1]heptan-7-yl)methanone |
| 225 | 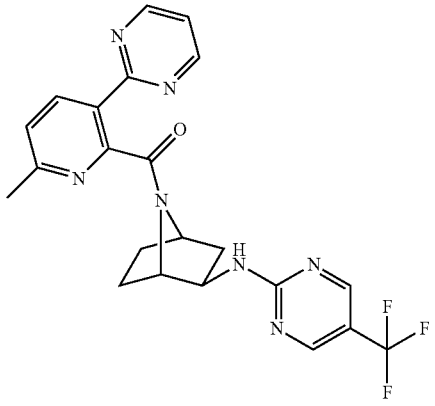 | | 530 | 3300 | (±)-(6-methyl-3-(pyrimidin-2-yl)pyridin-2-yl)(2-((5-(trifluoromethyl)pyrimidin-2-yl)amino)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 226 | | | >10000 | >10000 | (±)-(3-fluoro-2-methoxyphenyl)(2-((5-(trifluoromethyl)pyrimidin-2-yl)amino)-7-azabicyclo[2.2.1]heptan-7-yl)methanone |
| 227 | | | >10000 | >10000 | (±)-(3-ethoxy-6-methylpyridin-2-yl)(2-((5-(trifluoromethyl)pyrimidin-2-yl)amino)-7-azabicyclo[2.2.1]heptan-7-yl)methanone |
| 228 | | | >10000 | >10000 | (±)-(6-methyl-3-(2H-1,2,3-triazol-2-yl)pyridin-2-yl)(2-((5-(trifluoromethyl)pyrimidin-2-yl)amino)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 229 | | | >10000 | >10000 | (±)-(3-ethoxy-6-methylpyridin-2-yl)(2-(quinoxalin-2-ylamino)-7-azabicyclo[2.2.1]heptan-7-yl)methanone |
| 230 | | | >10000 | >10000 | (±)-(6-methyl-3-(2H-1,2,3-triazol-2-yl)pyridin-2-yl)(2-(quinoxalin-2-ylamino)-7-azabicyclo[2.2.1]heptan-7-yl)methanone |
| 231 | | | >10000 | >10000 | (±)-(3-fluoro-2-methoxyphenyl)(2-(quinoxalin-2-ylamino)-7-azabicyclo[2.2.1]heptan-7-yl)methanone |

TABLE 2-continued
| Ex. No. | Compound | rOX1 K$_i$ (nM) | hOX1 K$_i$ (nM) | hOX2 K$_i$ (nM) | Compound Name |
|---|---|---|---|---|---|
| 232 | 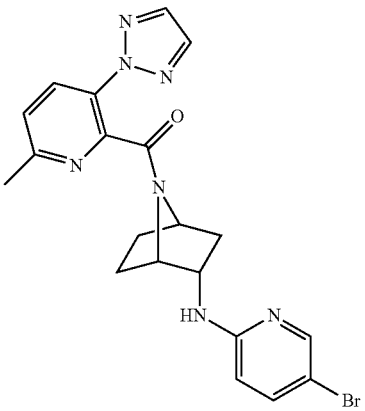 | | | | (±)-(2-((5-bromopyridin-2-yl)amino)-7-azabicyclo[2.2.1]heptan-7-yl)(6-methyl-3-(2H-1,2,3-triazol-2-yl)pyridin-2-yl)methanone |
| 233 | 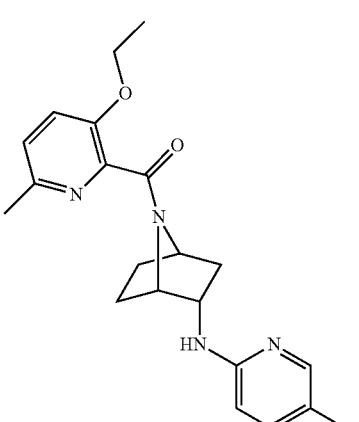 | | | | (±)-(2-((5-bromopyridin-2-yl)amino)-7-azabicyclo[2.2.1]heptan-7-yl)(3-ethoxy-6-methylpyridin-2-yl)methanone |
| 234 | 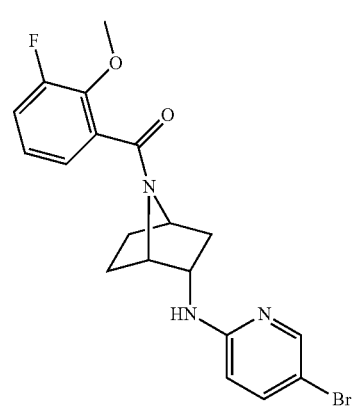 | | | | (±)-(2-((5-bromopyridin-2-yl)amino)-7-azabicyclo[2.2.1]heptan-7-yl)(3-fluoro-2-methoxyphenyl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 235 | | | >10000 | >10000 | (±)-((2-(2H-1,2,3-triazol-2-yl)phenyl)(2-((4-(trifluoromethyl)pyridin-2-yl)amino)-7-azabicyclo[2.2.1]heptan-7-yl)methanone |
| 236 | | | >10000 | >10000 | (±)-(2-((5-fluoropyridin-2-yl)amino)-7-azabicyclo[2.2.1]heptan-7-yl)(6-methyl-3-(2H-1,2,3-triazol-2-yl)pyridin-2-yl)methanone |
| 237 | | | >1000 | >10000 | (±)-(3-fluoro-2-methoxyphenyl)(2-((5-fluoropyridin-2-yl)amino)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 238 | | 15 | 15 | 763 | (3-fluoro-2-(pyrimidin-2-yl)phenyl)((1S,2R,4R)-2-((5-(trifluoromethyl)pyrazin-2-yl)amino)-7-azabicyclo[2.2.1]heptan-7-yl)methanone |
| 239 | | 22 | 19 | 490 | (2-ethoxynaphthalen-1-yl)((1S,2R,4R)-2-((5-(trifluoromethyl)pyrazin-2-yl)amino)-7-azabicyclo[2.2.1]heptan-7-yl)methanone |
| 240 | | | 400 | 2100 | isoquinolin-4-yl((1S,2R,4R)-2-((5-(trifluoromethyl)pyrazin-2-yl)amino)-7-azabicyclo[2.2.1]heptan-7-yl)methanone |
| 241 | | 135 | 159 | 5100 | (4-methoxy-2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 242 | 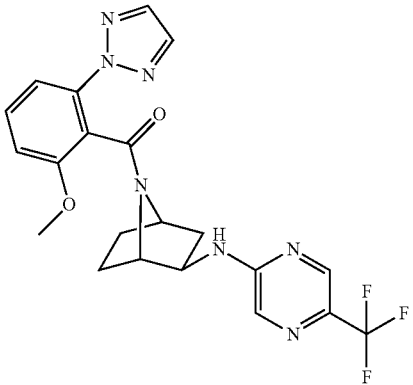 | 31 | 41 | 239 | (2-methoxy-6-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone |
| 243 | 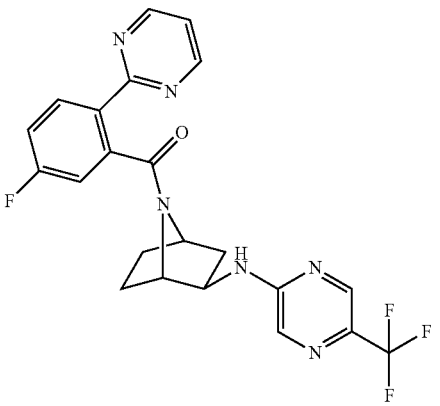 | 35 | 45 | 725 | (5-fluoro-2-(pyrimidin-2-yl)phenyl)((1S,2R,4R)-2-((5-(trifluoromethyl)pyrazin-2-yl)amino)-7-azabicyclo[2.2.1]heptan-7-yl)methanone |
| 244 | 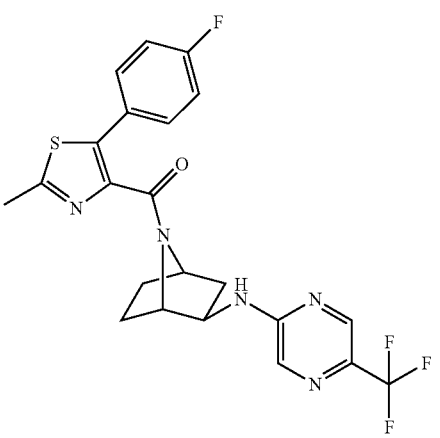 | 74 | 46 | 235 | (5-(4-fluorophenyl)-2-methylthiazol-4-yl)((1S,2R,4R)-2-((5-(trifluoromethyl)pyrazin-2-yl)amino)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 245 | 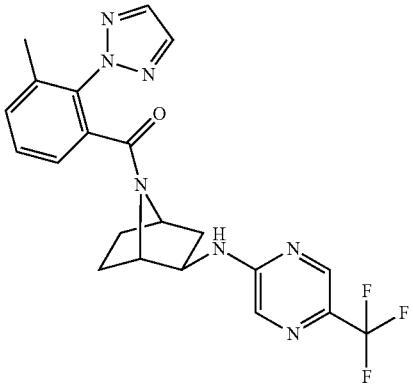 | 10 | 7 | 288 | (3-methyl-2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone |
| 246 | 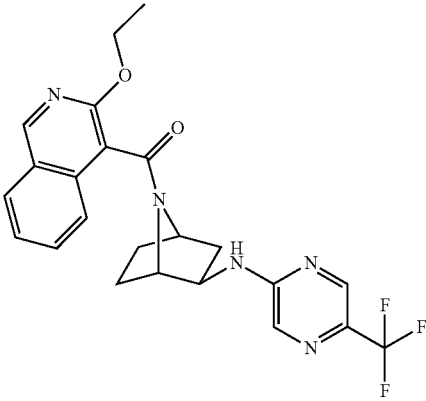 | 30 | 17 | 1027 | (3-ethoxyisoquinolin-4-yl)((1S,2R,4R)-2-((5-(trifluoromethyl)pyrazin-2-yl)amino)-7-azabicyclo[2.2.1]heptan-7-yl)methanone |
| 247 | 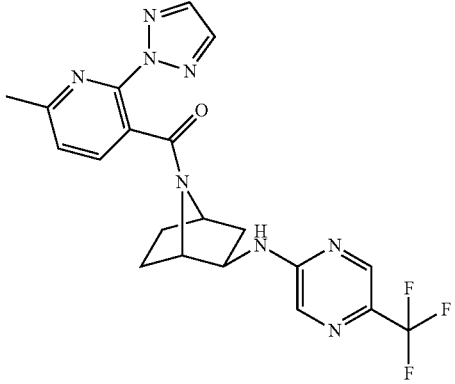 | 420 | | 1130 | (6-methyl-2-(2H-1,2,3-triazol-2-yl)pyridin-3-yl)((1S,2R,4R)-2-((5-(trifluoromethyl)pyrazin-2-yl)amino)-7-azabicyclo[2.2.1]heptan-7-yl)methanone |
| 248 | 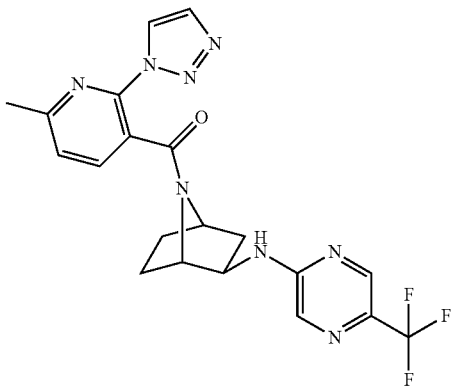 | 153 | 119 | >10000 | (6-methyl-2-(1H-1,2,3-triazol-1-yl)pyridin-3-yl)((1S,2R,4R)-2-((5-(trifluoromethyl)pyrazin-2-yl)amino-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 249 | | | 57 | 54 | 5600 | (4-methoxy-2-(pyrimidin-2-yl)phenyl)((1S,2R,4R)-2-((5-(trifluoromethyl)pyrazin-2-yl)amino)-7-azabicyclo[2.2.1]heptan-7-yl)methanone |
| 250 | | | 5650 | | >10000 | (1H-benzo[d]imidazol-2-yl)((1S,2R,4R)-2-((5-(trifluoromethyl)pyrazin-2-yl)amino)-7-azabicyclo[2.2.1]heptan-7-yl)methanone |
| 251 | | | 520 | | 5300 | (1-methyl-1H-benzo[d]imidazol-2-yl)((1S,2R,4R)-2-((5-(trifluoromethyl)pyrazin-2-yl)amino)-7-azabicyclo[2.2.1]heptan-7-yl)methanone |
| 252 | | | 45 | 27 | 1230 | (3-fluoro-2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 253 | | 155 | 152 | 9600 | (4-difluoromethoxy)-2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone |
| 254 | | 23 | 20 | 377 | (3-fluoro-2-(3-methyl-1,2,4-oxadiazol-5-yl)phenyl)((1S,2R,4R)-2-((5-(trifluoromethyl)pyrazin-2-yl)amino)-7-azabicyclo[2.2.1]heptan-7-yl)methanone |
| 255 | | 32 | 29 | 265 | (5-methoxy-2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 256 | 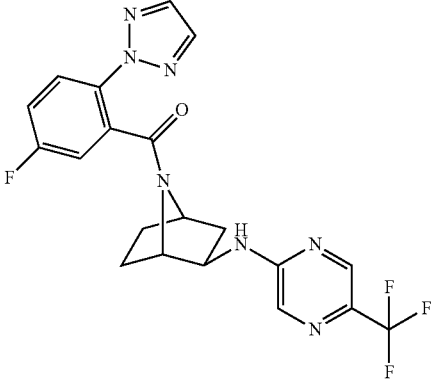 | 84 | 60 | 1100 | (5-fluoro-2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone |
| 257 | 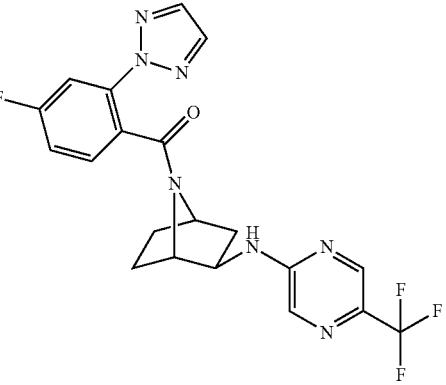 | 85 | 102 | 3200 | (4-fluoro-2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone |
| 258 | 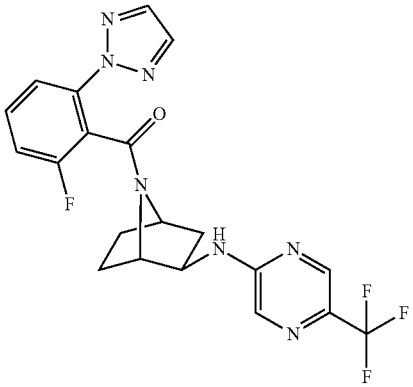 | 42 | 48 | 690 | (2-fluoro-6-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone |
| 259 | 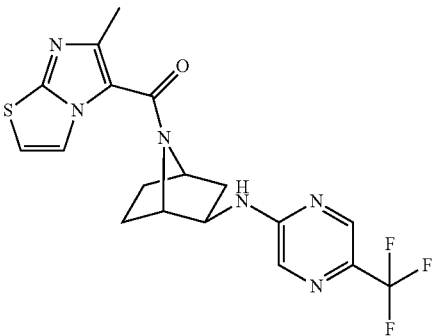 | >10000 | | >10000 | (6-methylimidazo[2,1-b]thiazol-5-yl)((1S,2R,4R)-2-((5-(trifluoromethyl)pyrazin-2-yl)amino)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
| --- | --- | --- | --- | --- | --- |
| 260 | | | 14 | 10 | 519 | (3-fluoro-2-(oxazol-2-yl)phenyl)((1S,2R,4R)-2-((5-(trifluoromethyl)pyrazin-2-yl)amino)-7-azabicyclo[2.2.1]heptan-7-yl)methanone |
| 261 | | >10000 | | 5000 | (2-((4,6-dimethylpyrimidin-2-yl)amino)-7-azabicyclo[2.2.1]heptan-7-yl)(3-fluoro-2-methoxyphenyl)methanone |
| 262 | | 106 | 175 | 4200 | (3-fluoro-2-(pyridazin-3-yl)phenyl)((1S,2R,4R)-2-((5-(trifluoromethyl)pyrazin-2-yl)amino)-7-azabicyclo[2.2.1]heptan-7-yl)methanone |
| 263 | | 44 | 41 | 1100 | (3-methyl-2-(pyridazin-3-yl)phenyl)((1S,2R,4R)-2-((5-(trifluoromethyl)pyrazin-2-yl)amino)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 264 | | | 1400 | >10000 | (3-fluoro-2-(pyridazin-4-yl)phenyl)((1S,2R,4R)-2-((5-(trifluoromethyl)pyrazin-2-yl)amino)-7-azabicyclo[2.2.1]heptan-7-yl)methanone |
| 265 | | 20 | 23 | 188 | (3-fluoro-2-(pyrazin-2-yl)phenyl)((1S,2R,4R)-2-((5-(trifluoromethyl)pyrazin-2-yl)amino)-7-azabicyclo[2.2.1]heptan-7-yl)methanone |
| 266 | | 6 | 7 | 121 | (3-methyl-2-(oxazol-2-yl)phenyl)((1S,2R,4R)-2-((5-(trifluoromethyl)pyrazin-2-yl)amino)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 267 | | | 33 | 61 | 1700 | (4-fluoro-2-(pyrimidin-2-yl)phenyl)((1S,2R,4R)-2-((5-(trifluoromethyl)pyrazin-2-yl)amino-7-azabicyclo[2.2.1]heptan-7-yl)methanone |
| 268 | | | | 450 | 3700 | (3-fluoro-2-(pyridin-4-yl)phenyl)((1S,2R,4R)-2-((5-(trifluoromethyl)pyrazin-2-yl)amino)-7-azabicyclo[2.2.1]heptan-7-yl)methanone |
| 269 | | | 48 | 111 | 1700 | (3-fluoro-2-(2H-1,2,3-triazol-2-yl)phenyl)((1S,2R,4R)-2-((5-(trifluoromethyl)pyrimidin-2-2-yl)amino)-7-azabicyclo[2.21]heptan-7-yl)methanone |
| 270 | | | | 325 | 145 | ((1S,2R,4R)-2-((3-bromoimidazo[1,2-a]pyrazin-8-yl)amino)-7-azabicyclo[2.2.1]heptan-7-yl)(3-fluoro-2-(pyrimidin-2-yl)phenyl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 271 | | 41 | 42 | 2300 | (3-fluoro-2-(pyrimidin-2-yl)phenyl)((1S,2R,4R)-2-((5-(trifluoromethyl)pyrimidin-2-yl)amino)-7-azabicyclo[2.2.1]heptan-7-yl)methanone |
| 272 | | 21 | 26 | 742 | (3-methyl-2-(2H-1,2,3-triazol-2-yl)phenyl)((1S,2R,4R)-2-((5-(trifluoromethyl)pyrimidin-2-yl)amino)-7-azabicyclo[2.2.1]heptan-7-yl)methanone |
| 273 | | 17 | 12 | 328 | (3-methyl-2-(pyrimidin-2-yl)phenyl)((1S,2R,4R)-2-((5-(trifluoromethyl)pyrazin-2-yl)amino)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 274 | | | >10000 | 2560 | (3-fluoro-2-(pyrimidin-2-yl)phenyl)((1S,2R,4R)-2-((3-(trifluoromethyl)-[1,2,4]triazolo[4,3-a]pyrazin-8-yl)amino)-7-azabicyclo[2.2.1]heptan-7-yl)methanone |
| 275 | | | >10000 | >10000 | methyl 5-(((1S,2R,4R)-7-(3-fluoro-2-(pyrimidin-2-yl)benzoyl)-7-azabicyclo[2.2.1]heptan-2-yl)amino)pyrazine-2-carboxylate |
| 276 | | 133 | 97 | 2500 | (2-iodo-3-methylphenyl)((1S,2R,4R)-2-((5-(trifluoromethyl)pyrimidin-2-yl)amino)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 277 | | | 457 | 7400 | (3-fluoro-2-iodophenyl)((1S,2R,4R)-2-((5-(trifluoromethyl)pyrimidin-2-yl)amino)-7-azabicyclo[2.2.1]heptan-7-yl)methanone |
| 278 | | 87 | 77 | 934 | (3-fluoro-2-(pyrimidin-2-yl)phenyl)((1S,2R,4R)-2-((5-methylpyrazin-2-yl)amino)-7-azabicyclo[2.2.1]heptan-7-yl)methanone |
| 279 | | 18 | 9 | 990 | (3-fluoro-2-(pyrimidin-2-yl)phenyl)((1S,2R,4R)-2-((5-(trifluoromethyl)pyridin-2-yl)amino)-7-azabicyclo[2.2.1]heptan-7-yl)methanone |
| 280 | | 39 | 37 | 1300 | (4-fluoro-2-(pyrimidin-2-yl)phenyl)((1S,2R,4R)-2-((5-(trifluoromethyl)pyridin-2-yl)amino)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 281 | | | 21 | 17 | 1200 | (3-methyl-2-(pyrimidin-2-yl)phehyl)((1S,2R,4R)-2-((5-(trifluoromethyl)pyrimidin-2-yl)amino)-7-azabicyclo[2.2.1]heptan-7-yl)methanone |
| 282 | | | 486 | | >10000 | (3-fluoro-2-(pyrimidin-2-yl)phenyl)((1S,2R,4R)-2-(methyl(5-(trifluoromethyl)pyrazin-2-yl)amino)-7-azabicyclo[2.2.1]heptan-7-yl)methanone |
| 283 | | | 14 | 9 | 417 | (3-methyl-2-(oxazol-2-yl)phenyl)((1S,2R,4R)-2-((5-(trifluoromethyl)pyrimidin-2-yl)amino)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 284 | | 29 | 27 | 1700 | (3-fluoro-2-(oxazol-2-yl)phenyl)((1S,2R,4R)-2-((5-(trifluoromethyl)pyrimidin-2-yl)amino)-7-azabicyclo[2.2.1]heptan-7-yl)methanone |
| 285 | | 720 | | >10000 | (±)-(3-fluoro-2-(pyrimidin-2-yl)phenyl)(2-((5-(trifluoromethyl)pyrimidin-2-yl)oxy)-7-azabicyclo[2.2.1]heptan-7-yl)methanone |
| 286 | | >10000 | | >10000 | (±)-(3-fluoro-2-(pyrimidin-2-yl)phenyl)(2-((5-(trifluoromethyl)pyrimidin-2-yl)oxy)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 287 | | | 472 | 767 | (3-ethoxy-6-methylpyridin-2-yl)((1S,2R,4R)-2-((5-(trifluoromethyl)pyrazin-2-yl)amino)-7-azabicyclo[2.2.1]heptan-7-yl)methanone |
| 288 | | 94 | 128 | 1900 | (3-(2H-1,2,3-triazol-2-yl)pyridin-2-yl)((1S,2R,4R)-2-((5-(trifluoromethyl)pyrazin-2-yl)amino)-7-azabicyclo[2.2.1]heptan-7-yl)methanone |
| 289 | | 13 | 32 | 173 | (2-methoxy-6-(pyrimidin-2-yl)phenyl)((1S,2R,4R)-2-((5-(trifluoromethyl)pyrazin-2-yl)amino)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 290 | | | 21 | 19 | 558 | (2-fluoro-6-(pyrimidin-2-yl)phenyl)((1S,2R,4R)-2-((5-(trifluoromethyl)pyrazin-2-yl)amino)-7-azabicyclo[2.2.1]heptan-7-yl)methanone |
| 291 | | | 15 | 15 | 425 | (7-ethoxyquinolin-8-yl)((1S,2R,4R)-2-((5-(trifluoromethyl)pyrazin-2-yl)amino)-7-azabicyclo[2.2.1]heptan-7-yl)methanone |
| 292 | | | | >10000 | >10000 | (2-(1,4-dimethyl-1H-pyrazol-5-yl)-6-methoxyphenyl)((1S,2R,4R)-2-((5-(trifluoromethyl)pyrazin-2-yl)amino)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 293 | | 23 | 37 | 1100 | (3-methyl-2-(pyridin-2-yl)phenyl)((1S,2R,4R)-2-((5-(trifluoromethyl)pyrinlidin-2-yl)amino)-7-azabicyclo[2.2.1]heptan-7-yl)methanone |
| 294 | | 21 | 15 | 1200 | (3-fluoro-2-(2H-1,2,3-triazol-2-yl)phenyl)((1S,2R,4R)-2-((5-(trifluoromethyl)pyridin-2-yl)amino)-7-azabicyclo[2.2.1]heptan-7-yl)methanone |
| 295 | | 9 | 8 | 257 | (3-methyl-2-(2H-1,2,3-triazol-2-yl)phenyl)((1S,2R,4R)-2-((5-(trifluoromethyl)pyridin-2-yl)amino)-7-azabicyclo[2.2.1]heptan-7-yl)methanone |
| 296 | | 5 | 6 | 114 | (3-methyl-2-(oxazol-2-yl)phenyl)((1S,2R,4R)-2-((5-(trifluoromethyl)pyridin-2-yl)amino)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
| --- | --- | --- | --- | --- | --- |
| 297 | | 402 | >10000 | >10000 | (3-fluoro-2-(pyrimidin-2-yl)phenyl)((1R,2S,4S)-2-((5-(trifluoromethyl)pyrazin-2-yl)amino)-7-azabicyclo[2.2.1]heptan-7-yl)methanone |
| 298 | | 18 | 18 | 500 | (3-fluoro-2-(oxazol-2-yl)phenyl)((1S,2R,4R)-2-((5-(trifluoromethyl)pyridin-2-yl)amino)-7-azabicyclo[2.2.1]heptan-7-yl)methanone |
| 299 | | 16 | 7 | 234 | (3-methyl-2-(pyrimidin-2-yl)phenyl)((1S,2R,4R)-2-((5-(trifluoromethyl)pyridin-2-yl)amino)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 300 | | 9 | 9 | 93 | (3-chloro-2-(pyrimidin-2-yl)phenyl)((1S,2R,4R)-2-((5-(trifluoromethyl)pyrazin-2-yl)amino-7-azabicyclo[2.2.1]heptan-7-yl)methanone |
| 302 | | 5 | 5 | 188 | ((1S,2R,4R)-2-((5-bromopyridin-2-yl)amino)-7-azabicyclo[2.2.1]heptan-7-yl)(3-methyl-2-(oxazol-2-yl)phenyl)methanone |
| 303 | | 22 | 16 | 1300 | ((1S,2R,4R)-2-((5-bromopyridin-2-yl)amino)-7-azabicyclo[2.2.1]heptan-7-yl)(3-fluoro-2-(pyrimidin-2-yl)phenyl)methanone |
| 304 | | 12 | 16 | 455 | ((1S,2R,4R)-2-((5-bromopyridin-2-yl)amino)-7-azabicyclo[2.2.1]heptan-7-yl)(3-methyl-2-(pyrimidin-2-yl)phenyl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 305 | | 24 | 12 | 980 | ((1S,2R,4R)-2-((5-bromopyridin-2-yl)amino)-7-azabicyclo[2.2.1]heptan-7-yl)(3-fluoro-2-(2H-1,2,3-triazol-2-yl)phenyl)methanone |
| 306 | | 11 | 4 | 396 | ((1S,2R,4R)-2-((5-bromopyridin-2-yl)amino)-7-azabicyclo[2.2.1]heptan-7-yl)(3-methyl-2-(2H-1,2,3-triazol-2-yl)phenyl)methanone |
| 308 | | 6 | 4 | 173 | ((1S,2R,4R)-2-((5-bromopyrazin-2-yl)amino)-7-azabicyclo[2.2.1]heptan-7-yl)(3-methyl-2-(oxazol-2-yl)phenyl)methanone |
| 309 | | 19 | 22 | 1100 | ((1S,2R,4R)-2-((5-bromopyrazin-2-yl)amino)-7-azabicyclo[2.2.1]heptan-7-yl)(3-fluoro-2-(pyrimidin-2-yl)phenyl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 310 | | 9 | 7 | 381 | ((1S,2R,4R)-2-((5-bromopyrazin-2-yl)amino)-7-azabicyclo[2.2.1]heptan-7-yl)(3-methyl-2-(pyrimidin-2-yl)phenyl)methanone |
| 311 | | 17 | 21 | 1000 | ((1S,2R,4R)-2-((5-bromopyrazin-2-yl)amino)-7-azabicyclo[2.2.1]heptan-7-yl)(3-fluoro-2-(2H-1,2,3-triazol-2-yl)phenyl)methanone |
| 312 | | 6 | 9 | 360 | ((1S,2R,4R)-2-((5-bromopyrazin-2-yl)amino)-7-azabicyclo[2.2.1]heptan-7-yl)(3-methyl-2-(2H-1,2,3-triazol-2-yl)phenyl)methanone |
| 314 | | 6 | 14 | 349 | ((1S,2R,4R)-2-((5-bromopyrimidin-2-yl)amino)-7-azabicyclo[2.2.1]heptan-7-yl)(3-methyl-2-(oxazol-2-yl)phenyl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 315 | | 30 | 52 | 1850 | ((1S,2R,4R)-2-((5-bromopyrimidin-2-yl)amino)-7-azabicyclo[2.2.1]heptan-7-yl)(3-fluoro-2-(pyrimidin-2-yl)phenyl)methanone |
| 316 | | 20 | 59 | 796 | ((1S,2R,4R)-2-((5-bromopyrimidin-2-yl)amino)-7-azabicyclo[2.2.1]heptan-7-yl)(3-methyl-2-(pyrimidin-2-yl)phenyl)methanone |
| 317 | | 31 | 70 | 1600 | ((1S,2R,4R)2-((5-bromopyrimidin-2-yl)amino)-7-azabicyclo[2.2.1]heptan-7-yl)(3-fluoro-2-(2H-1,2,3-triazol-2-yl)phenyl)methanone |
| 318 | | 9 | 13 | 768 | ((1S,2R,4R)-2-((5-bromopyrimidin-2-yl)amino)-7-azabicyclo[2.2.1]heptan-7-yl)(3-methyl-2-(2H-1,2,3-triazol-2-yl)phenyl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 320 | 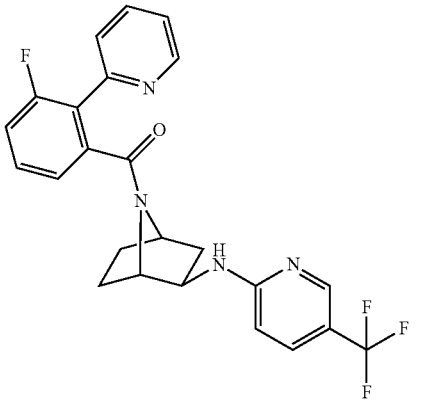 | | 37 | 14 | 260 | (3-fluoro-2-(pyridin-2-yl)phenyl)((1S,2R,4R)-2-((5-(trifluoromethyl)pyridin-2-yl)amino)-7-azabicyclo[2.2.1]heptan-7-yl)methanone |
| 368 | 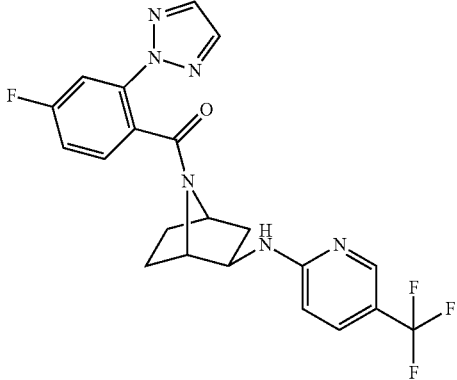 | | 78 | 71 | 2600 | (4-fluoro-2-(2H-1,2,3-triazol-2-yl)phenyl)((1S,2R,4R)-2-((5-(trifluoromethyl)pyridin-2-yl)amino)-7-azabicyclo[2.2.1]heptan-7-yl)methanone |
| 369 | 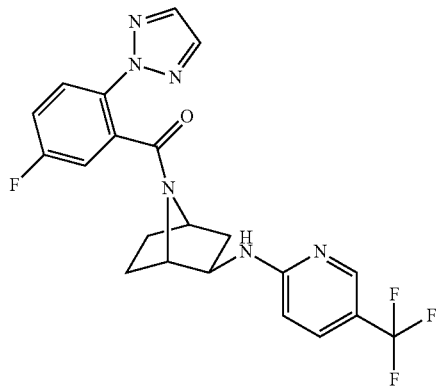 | | 67 | 45 | 629 | (5-fluoro-2-(2H-1,2,3-triazol-2-yl)phenyl)((1S,2R,4R)-2-((5-(trifluoromethyl)pyridin-2-yl)amino)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 370 | 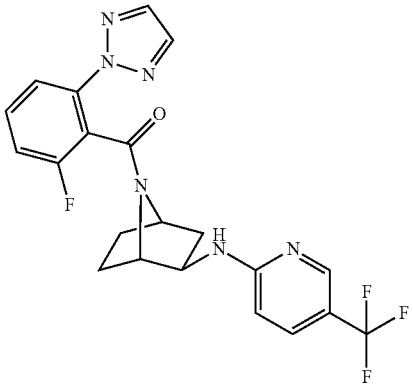 | 104 | 142 | 508 | (2-fluoro-6-(2H-1,2,3-triazol-2-yl)phenyl)((1S,2R,4R)-2-((5-(trifluoromethyl)pyridin-2-yl)amino)-7-azabicyclo[2.2.1]heptan-7-yl)methanone |
| 371 | 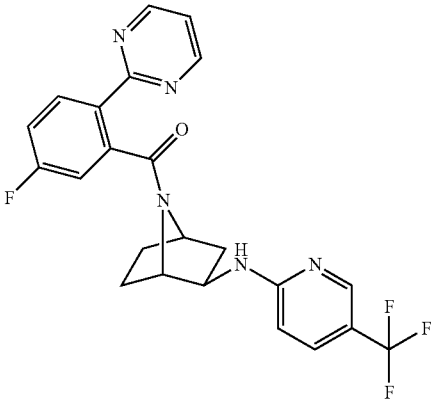 | 42 | 27 | 615 | (5-fluoro-2-(pyrimidin-2-yl)phenyl)((1S,2R,4R)-2-((5-(trifluoromethyl)pyridin-2-yl)amino)-7-azabicyclo[2.2.1]heptan-7-yl)methanone |
| 372 | 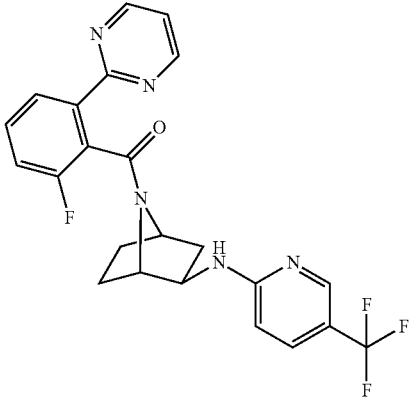 | 19 | 13 | 420 | (2-fluoro-6-(pyrimidin-2-yl)phenyl)((1S,2R,4R)-2-((5-(trifluoromethyl)pyridin-2-yl)amino)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 373 | | | 34 | 36 | 679 | (2-(pyrimidin-2-yl)phenyl)((1S,2R,4R)-2-((5-(trifluoromethyl)pyridin-2-yl)amino)-7-azabicyclo[2.2.1]heptan-7-yl)methanone |
| 374 | | 41 | 31 | 921 | (2-(5-fluoropyrimidin-2-yl)phenyl)((1S,2R,4R)-2-((5-(trifluoromethyl)pyridin-2-yl)amino)-7-azabicyclo[2.2.1]heptan-7-yl)methanone |
| 375 | | 49 | 89 | 2200 | (3-fluoro-2-(5-fluoropyrimidin-2-yl)phenyl)((1S,2R,4R)-2-((5-(trifluoromethyl)pyridin-2-yl)amino)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 376 | 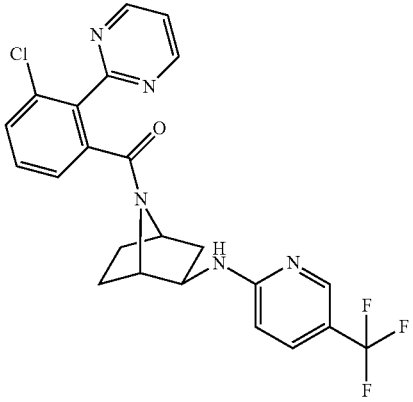 | 10 | 4 | 110 | (3-chloro-2-(pyrimidin-2-yl)phenyl)((1S,2R,4R)-2-((5-(trifluoromethyl)pyridin-2-yl)amino)-7-azabicyclo[2.2.1]heptan-7-yl)methanone |
| 377 | 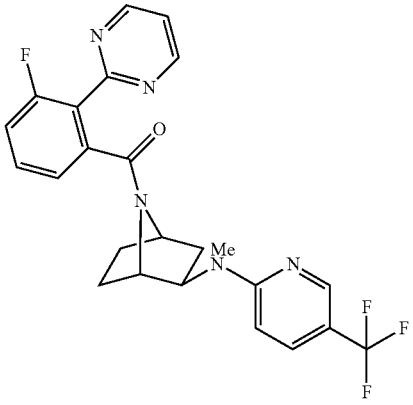 | 224 | 141 | 9000 | (3-fluoro)-2-(pyrimidin-2-yl)phenyl)((1S,2R,4R)-2-(methyl(5-(trifluoromethyl)pyridin-2-yl)amino)-7-azabicyclo[2.2.1]heptan-7-yl)methanone |
| 378 | 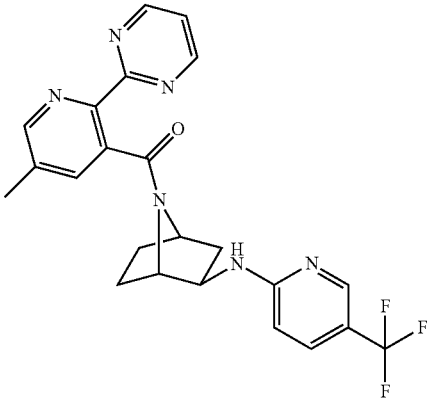 |  | 310 | >10000 | (5-methyl-2-(pyrimidin-2-yl)pyridin-3-yl)((1S,2R,4R)-2-((5-(trifluoromethyl)pyridin-2-yl)amino)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 379 | | 25 | 24 | 336 | (6-methyl-3-(pyrimidin-2-yl)pyridin-2-yl)((1S,2R,4R)-2-((5-(trifluoromethyl)pyridin-2-yl)amino)-7-azabicyclo[2.2.1]heptan-7-yl)methanone |
| 380 | | 28 | 48 | 8500 | (5-methyl-3-(pyrimidin-2-yl)pyridin-2-yl)((1S,2R,4R)-2-((5-(trifluoromethyl)pyridin-2-yl)amino)-7-azabicyclo[2.2.1]heptan-7-yl)methanone |
| 381 | | 25 | 25 | 790 | (3-(pyrimidin-2-yl)pyridin-2-yl)((1S,2R,4R)-2-((5-(trifluoromethyl)pyridin-2-yl)amino)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 382 | | 18 | 15 | 1100 | (3-fluoro-2-(pyrimidin-2-yl)phenyl)((1S,2R,4R)-2-((3-fluoro-5-(trifluoromethyl)pyridin-2-yl)amino)-7-azabicyclo[2.2.1]heptan-7-yl)methanone |
| 383 | | 33 | 16 | 767 | ((1S,2R,4R)-2-((3-chloro-5-(trifluoromethyl)pyridin-2-yl)amino)-7-azabicyclo[2.2.1]heptan-7-yl)(3-fluoro-2-(2H-1,2,3-triazol-2-yl)phenyl)methanone |
| 384 | | 15 | 12 | 612 | ((1S,2R,4R)-2-((3-chloro-5-(trifluoromethyl)pyridin-2-yl)amino)-7-azabicyclo[2.2.1]heptan-7-yl)(3-fluoro-2-(pyrimidin-2-yl)phenyl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 385 | 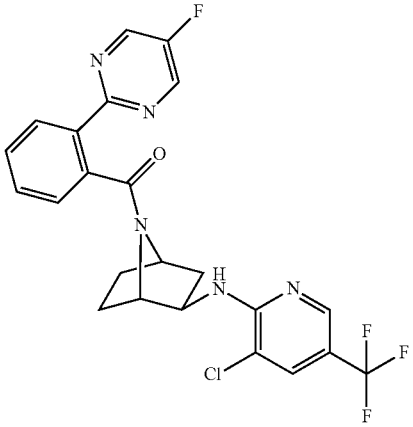 | 37 | 44 | 696 | ((1S,2R,4R)-2-((3-chloro-5-(trifluoromethyl)pyridin-2-yl)amino)-7-azabicyclo[2.2.1]heptan-7-yl)(2-(5-fluoropyrimidin-2-yl)phenyl)methanone |
| 386 | 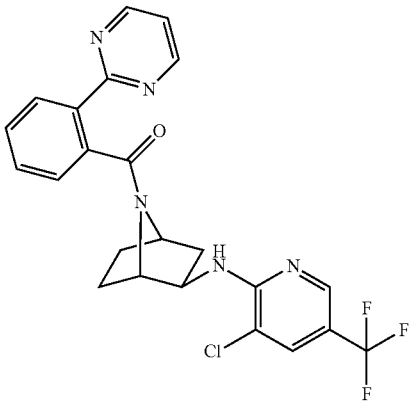 | 20 | 29 | 499 | ((1S,2R,4R)-2-((3-chloro-5-(trifluoromethyl)pyridin-2-yl)amino)-7-azabicyclo[2.2.1]heptan-7-yl)(2-(pyrimidin-2-yl)phenyl)methanone |
| 387 | 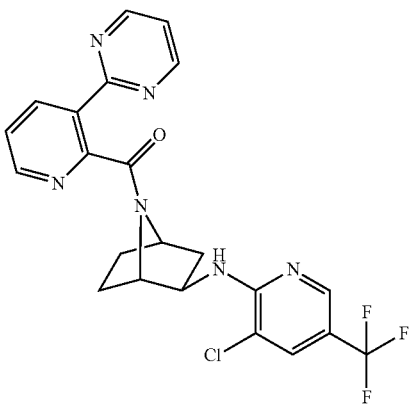 | 40 | 33 | 1100 | ((1S,2R,4R)-2-((3-chloro-5-(trifluoromethyl)pyridin-2-yl)amino)-7-azabicyclo[2.2.1]heptan-7-yl)(3-(pyrimidin-2-yl)pyridin-2-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 388 | 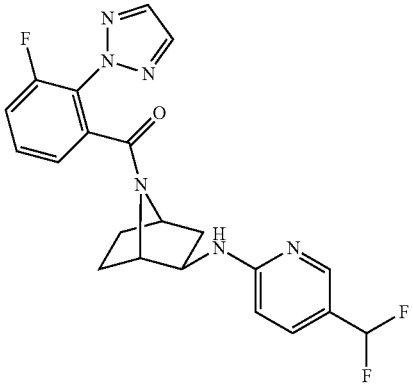 | 130 | 118 | 1100 | ((1S,2R,4R)-2-((5-(difluoromethyl)pyridin-2-yl)amino)-7-azabicyclo[2.2.1]heptan-7-yl)(3-fluoro-2-(2H-1,2,3-triazol-2-yl)phenyl)methanone |
| 389 | 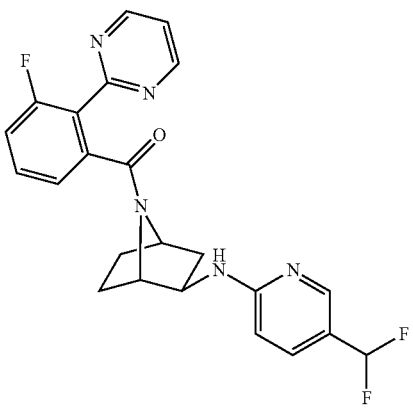 | 123 | 168 | 741 | ((1S,2R,4R)-2-((5-(difluoromethyl)pyridin-2-yl)amino)-7-azabicyclo[2.2.1]heptan-7-yl)(3-fluoro-2-(pyrimidin-2-yl)phenyl)methanone |
| 390 | 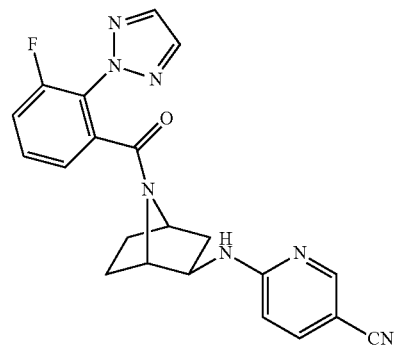 | 1500 | 1400 | >10000 | 6-(((1S,2R,4R)-7-(3-fluoro-2-(2H-1,2,3-triazol-2-yl)benzoyl)-7-azabicyclo[2.2.1]heptan-2-yl)amino)nicotinonitrile |
| 391 | 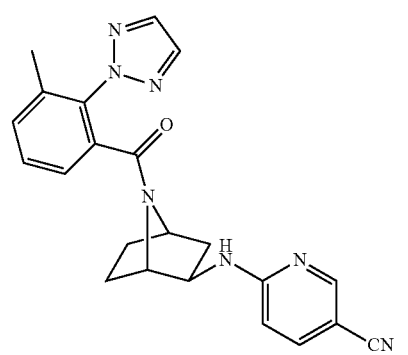 | 220 | 315 | 4400 | 6-(((1S,2R,4R)-7-(3-methyl-2-(2H-1,2,3-triazol-2-yl)benzoyl)-7-azabicyclo[2.2.1]heptan-2-yl)amino)nicotinonitrile |

TABLE 2-continued

| Ex. No. | Compound | rOX1 K<sub>i</sub> (nM) | hOX1 K<sub>i</sub> (nM) | hOX2 K<sub>i</sub> (nM) | Compound Name |
|---|---|---|---|---|---|
| 392 | | 1000 | 1400 | >10000 | 6-(((1S,2R,4R)-7-(3-fluoro-2-(pyrimidin-2-yl)benzoyl)-7-azabicyclo[2.2.1]heptan-2-yl)amino)nicotinonitrile |
| 393 | | 500 | 323 | 8300 | 6-(((1S,2R,4R)-7-(3-methyl-2-(pyrimidin-2-yl)benzoyl)-7-azabicyclo[2.2.1]heptan-2-yl)amino)nicotinonitrile |
| 394 | | 187 | 250 | 2100 | 6-(((1S,2R,4R)-7-(3-methyl-2-(oxazol-2-yl)benzoyl)-7-azabicyclo[2.2.1]heptan-2-yl)amino)nicotinonitrile |
| 395 | | 17 | 14 | 899 | (3-fluoro-2-(pyrimidin-2-yl)phenyl)((1S,2R,4R)-(2-$^2$H)-((5-(trifluoromethyl)pyrazin-2-yl)amino-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 397 | | 50 | 24 | 985 | (2-(5-fluoropyrimidin-2-yl)phenyl)((1S,2R,4R)-2-((5-(trifluoromethyl)pyrazin-2-yl)amino-7-azabicyclo[2.2.1]heptan-7-yl)methanone |
| 398 | | 61 | 81 | 2100 | (3-fluoro-2-(5-fluoropyrimidin-2-yl)phenyl)((1S,2R,4R)-2-((5-(trifluoromethyl)pyrazin-2-yl)amino)-7-azabicyclo[2.2.1]heptan-7-yl)methanone |
| 399 | | 10 | 9 | 300 | (2-(5-fluoropyrimidin-2-yl)-3-methylphenyl)((1S,2R,4R)-2-((5-(trifluoromethyl)pyrazin-2-yl)amino)-7-azabicyclo[2.2.1]heptan-7-yl)methanone |

TABLE 2-continued

| Ex. No. | Compound | rOX1 $K_i$ (nM) | hOX1 $K_i$ (nM) | hOX2 $K_i$ (nM) | Compound Name |
|---|---|---|---|---|---|
| 400 | 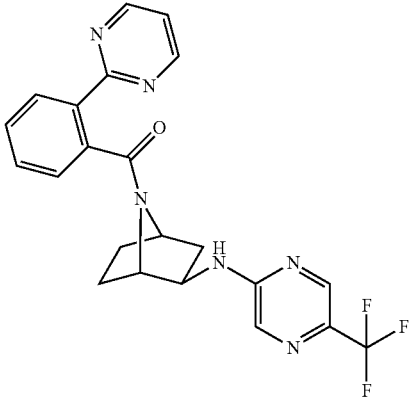 | 27 | 19 | 571 | (2-(pyrimidin-2-yl)phenyl)((1S,2R,4R)-2-((5-(trifluoromethyl)pyrazin-2-yl)amino)-7-azabicyclo[2.2.1]heptan-7-yl)methanone |
| 401 | 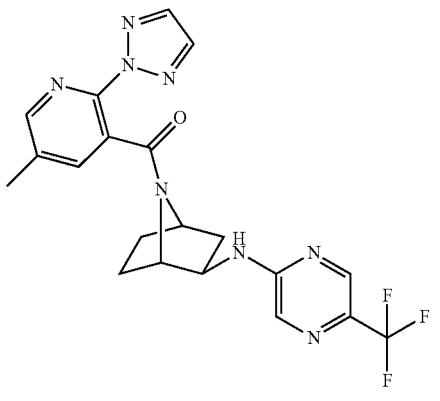 | 196 | 394 | >10000 | (5-methyl-2-(2H-1,2,3-triazol-2-yl)pyridin-3-yl)((1S,2R,4R)-2-((5-(trifluoromethyl)pyrazin-2-yl)amino)-7-azabicyclo[2.2.1]heptan-7-yl)methanone |
| 402 | 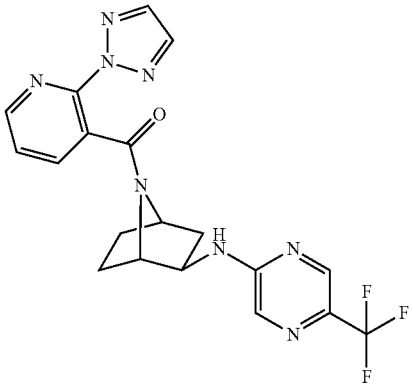 | | 575 | >10000 | (2-(2H-1,2,3-triazol-2-yl)pyridin-3-yl)((1S,2R,4R)-2-((5-(trifluoromethyl)pyrazin-2-yl)amino)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 403 | 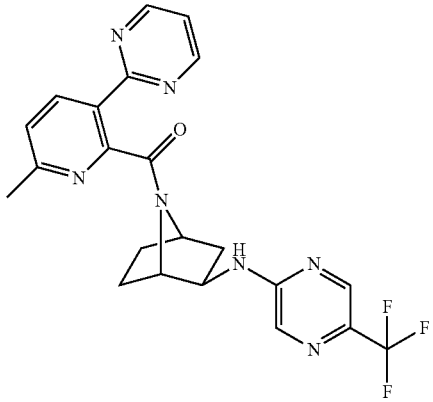 | | 88 | 67 | 431 | (6-methyl-3-(pyrimidin-2-yl)pyridin-2-yl)((1S,2R,4R)-2-((5-(trifluoromethyl)pyrazin-2-yl)amino)-7-azabicyclo[2.2.1]heptan-7-yl)methanone |
| 404 | 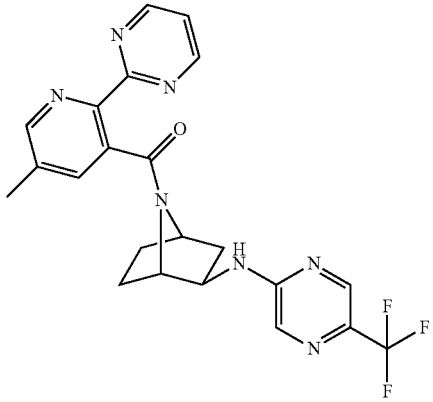 | | 419 | | >10000 | (5-methyl-2-(pyrimidin-2-yl)pyridin-3-yl)((1S,2R,4R)-2-((5-(trifluoromethyl)pyrazin-2-yl)amino)-7-azabicyclo[2.2.1]heptan-7-yl)methanone |
| 405 | 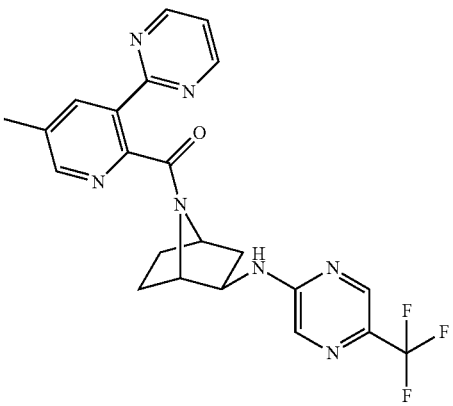 | 53 | 59 | >10000 | (5-methyl-3-(pyrimidin-2-yl)pyridin-2-yl)((1S,2R,4R)-2-((5-(trifluoromethyl)pyrazin-2-yl)amino)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 406 | | 59 | 44 | 972 | (3-(pyrimidin-2-yl)pyridin-2-yl)((1S,2R,4R)-2-((5-(trifluoromethyl)pyrazin-2-yl)amino)-7-azabicyclo[2.2.1]heptan-7-yl)methanone |
| 407 | | 18 | 17 | 104 | [1,1'-biphenyl]-2-yl((1S,2R,4R)-2-((5-(trifluoromethyl)pyrazin-2-yl)amino)-7-azabicyclo[2.2.1]heptan-7-yl)methanone |
| 408 | | 12 | 19 | 150 | (3-fluoro-2-(pyridin-2-yl)phenyl)((1S,2R,4R)-2-((5-(trifluoromethyl)pyrazin-2-yl)amino)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 409 | | 6 | 7 | 121 | (3-methyl-2-(oxazol-2-yl)phenyl)((1S,2R,4R)-2-((5-(trifluoromethyl)pyrazin-2-yl)amino)-7-azabicyclo[2.2.1]heptan-7-yl)methanone |
| 410 | | 67 | 90 | 1000 | (5-fluoro-2-(oxazol-2-yl)phenyl)((1S,2R,4R)-2-((5-(trifluoromethyl)pyrazin-2-yl)amino)-7-azabicyclo[2.2.1]heptan-7-yl)methanone |
| 411 | | 53 | 31 | 622 | (2-fluoro-6-(oxazol-2-yl)phenyl)((1S,2R,4R)-2-((5-(trifluoromethyl)pyrazin-2-yl)amino)-7-azabicyclo[2.2.1]heptan-7-yl)methanone |
| 412 | | 126 | 329 | 4800 | (4-fluoro-2-(3-methyl-1,2,4-oxadiazol-5-yl)phenyl)((1S,2R,4R)-2-((5-(trifluoromethyl)pyrazin-2-yl)amino)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 413 | | | >10000 | >10000 | (2-chloro-6-methoxy-pyridin-3-yl)((1S,2R,4R)-2-((5-(trifluoromethyl)pyrazin-2-yl)amino)-7-azabicyclo[2.2.1]heptan-7-yl)methanone |
| 414 | | 160 | 81 | 5800 | (4-fluoro-2-(pyrimidin-2-yl)phenyl)((1S,2R,4R)-2-((5-(trifluoromethyl)pyrimidin-2-yl)amino)-7-azabicyclo[2.2.1]heptan-7-yl)methanone |
| 415 | | 102 | 70 | 2100 | (5-fluoro-2-(pyrimidin-2-yl)phenyl)((1S,2R,4R)-2-((5-(trifluoromethyl)pyrimidin-2-yl)amino)-7-azabicyclo[2.2.1]heptan-7-yl)methanone |

TABLE 2-continued

| Ex. No. | Compound | rOX1 K<sub>i</sub> (nM) | hOX1 K<sub>i</sub> (nM) | hOX2 K<sub>i</sub> (nM) | Compound Name |
|---|---|---|---|---|---|
| 416 | | 138 | 85 | 2100 | (2-fluoro-6-(pyrimidin-2-yl)phenyl)((1S,2R,4R)-2-((5-(trifluoromethyl)pyrimidin-2-yl)amino)-7-azabicyclo[2.2.1]heptan-7-yl)methanone |
| 417 | | 52 | 41 | 1900 | (2-(pyrimidin-2-yl)phenyl)((1S,2R,4R)-2-((5-(trifluoromethyl)pyrimidin-2-yl)amino)-7-azabicyclo[2.2.1]heptan-7-yl)methanone |
| 418 | | | 459 | 2500 | (3-fluoro-2-(pyrimidin-2-yl)phenyl)((1S,2R,4R)-2-((4-(trifluoromethyl)thiazol-2-yl)amino)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 419 | 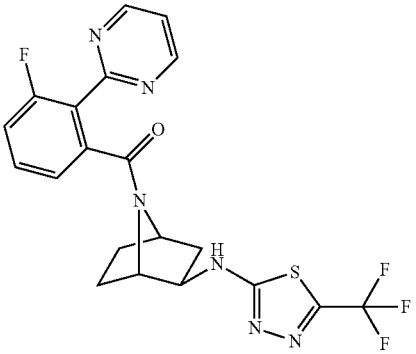 | 853 | | 7400 | (3-fluoro-2-(pyrimidin-2-yl)phenyl)((1S,2R,4R)-2-((5-(trifluoromethyl)-1,3,4-thiadiazol-2-yl)amino)-7-azabicyclo[2.2.1]heptan-7-yl)methanone |
| 420 | 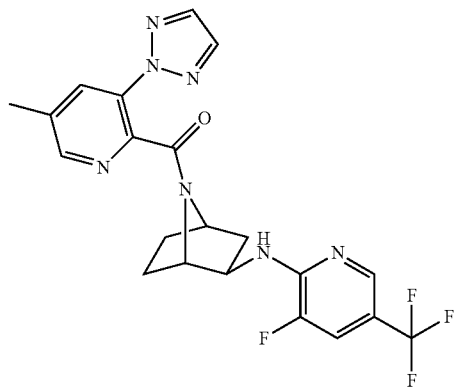 | 100 | 114 | 884 | ((1S,2R,4R)-2-((3-fluoro-5-(trifluoromethyl)pyridin-2-yl)amino)-7-azabicyclo[2.2.1]heptan-7-yl)(5-methyl-3-(2H-1,2,3-triazol-2-yl)pyridin-2-yl)methanone |
| 421 | 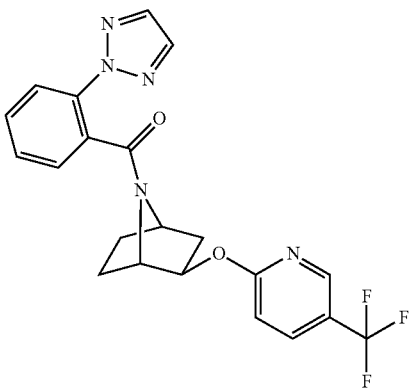 | 205 | 154 | 4200 | (R/S)-(2-(2H-1,2,3-triazol-2-yl)phenyl)-2-((5-(trifluoromethyl)pyridin-2-yl)oxy)-7-azabicyclo[2.2.1]heptan-7-yl)methanone |
| 422 | 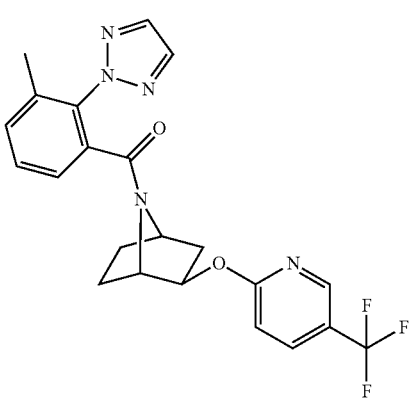 | 91 | 57 | 2150 | (R/S)-(3-melhyl-2-(2H-1,2,3-triazol-2-yl)phenyl)-2-((5-(trifluoromethyl)pyridin-2-yl)oxy)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 423 | | | 202 | 174 | 4867 | (R/S)-(3-fluoro-2-(2H-1,2,3-triazol-2-yl)phenyl)-2-((5-(trifluoromethyl)pyridin-2-yl)oxy)-7-azabicyclo[2.2.1]heptan-7-yl)methanone |
| 424 | | | | 2700 | >10000 | (R/S)-(3-fluoro-2-(1H-1,2,3-triazol-1-yl)phenyl)-2-((5-(trifluoromethyl)pyridin-2-azabicyclo[2.2.1]heptan-7-yl)methanone |
| 425 | | | | 587 | 5100 | (R/S)-(2-fluoro-6-(2H-1,2,3-triazol-2-yl)phenyl)-2-((5-(trifluoromethyl)pyridin-2-yl)oxy)-7-azabicyclo[2.2.1]heptan-7-yl)methanone |
| 426 | | | | 5400 | >10000 | (R/S)-(2-(2H-1,2,3-triazol-2-yl)pyridin-3-yl)-2-((5-(trifluoromethyl)pyridin-2-yl)oxy)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 427 | | | 560 | >10000 | (R/S)-(6-methyl-2-(2H-1,2,3-triazol-2-yl)pyridin-3-yl)-2-((5-(trifluoromethyl)pyridin-2-yl)oxy)-7-azabicyclo[2.2.1]heptan-7-yl)methanone |
| 428 | | | 1100 | >10000 | (R/S)-(5-methyl-2-(2H-1,2,3-triazol-2-yl)pyridin-3-yl)-2-((5-(trifluoromethyl)pyridin-2-yl)oxy)-7-azabicyclo[2.2.1]heptan-7-yl)methanone |
| 429 | | 77 | 120 | 6300 | (R/S)-(3-fluoro-2-(pyrimidin-2-yl)phenyl)-2-((5-(trifluoromethyl)pyridin-2-yl)oxy)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 430 | | 245 | 300 | >10000 | (R/S)-(4-fluoro-2-(pyrimidin-2-yl)phenyl)-2-((5-(trifluoromethyl)pyridin-2-yl)oxy)-7-azabicyclo[2.2.1]heptan-7-yl)methanone |
| 431 | | 143 | 180 | 5100 | (R/S)-(2-fluoro-6-(pyrimidin-2-yl)phenyl)-2-((5-(trifluoromethyl)pyridin-2-yl)oxy)-7-azabicyclo[2.2.1]heptan-7-yl)methanone |
| 432 | | 147 | 307 | 6000 | (R/S)-(2-(pyrimidin-2-yl)phenyl)-2-((5-(trifluoromethyl)pyridin-2-yl)oxy)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 433 | | 107 | 73 | 2500 | (R/S)-(2-(5-fluoropyrimidin-2-yl)phenyl)-2-((5-(trifluoromethyl)pyridin-2-yl)oxy)-7-azabicyclo[2.2.1]heptan-7-yl)methanone |
| 434 | | 134 | 172 | >10000 | (R/S)-(3-fluoro-2-(5-fluoropyrimidin-2-yl)phenyl)-2-((5-(trifluoromethyl)pyridin-2-yl)oxy)-7-azabicyclo[2.2.1]heptan-7-yl)methanone |
| 435 | | 50 | 29 | 520 | (R/S)-(3-methyl-2-(oxazol-2-yl)phenyl)-2-((5-(trifluoromethyl)pyridin-2-yl)oxy)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 436 | | | 143 | 116 | 3500 | (R/S)-(3-fluoro-2-(oxazol-2-yl)phenyl)-2-((5-(trifluoromethyl)pyridin-2-yl)oxy)-7-azabicyclo[2.2.1]heptan-7-yl)methanone |
| 437 | | | >10000 | | >10000 | (R/S)-(3-methyl-2-(2H-1,2,3-triazol-2-yl)phenyl)-2-((6-(trifluoromethyl)pyridin-3-yl)oxy)-7-azabicyclo[2.2.1]heptan-7-yl)methanone |
| 438 | | | >10000 | | >10000 | (R/S)-(3-fluoro-2-(2H-1,2,3-triazol-2-yl)phenyl)-2-((6-(trifluoromethyl)pyridin-3-yl)oxy)-7-azabicyclo[2.2.1]heptan-7-yl)methanone |
| 439 | | | >10000 | | >10000 | (R/S)-(2-fluoro-6-(2H-1,2,3-triazol-2-yl)phenyl)-2-((6-(trifluoromethyl)pyridin-3-yl)oxy)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 440 | | | 118 | 100 | 6000 | (R/S)-2-((5-bromopyridin-2-yl)oxy)-7-azabicyclo[2.2.1]heptan-7-yl)(3-fluoro-2-(2H-1,2,3-triazol-2-yl)phenyl)methanone |
| 441 | | | 1500 | >10000 | | (R/S)-2-((5-bromopyrimidin-2-yl)oxy)-7-azabicyclo[2.2.1]heptan-7-yl)(3-fluoro-2-(2H-1,2,3-triazol-2-yl)phenyl)methanone |
| 442 | | | 349 | 1900 | | (R/S)-(3-fluoro-2-(2H-1,2,3-triazol-2-yl)phenyl)-2-(quinoxalin-2-oxy)-7-azabicyclo[2.2.1]heptan-7-yl)methanone |
| 443 | | | >10000 | >10000 | | (R/S)-2-((5-bromo-2-chloropyridin-3-yl)oxy)-7-azabicyclo[2.2.1]heptan-7-yl)(3-fluoro-2-(2H-1,2,3-triazol-2-yl)phenyl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 444 | | | 165 | 237 | 4200 | (R/S)-(3-methyl-2-(2H-1,2,3-triazol-2-yl)phenyl)-2-((5-(trifluoromethyl)pyrazin-2-yl)oxy)-7-azabicyclo[2.2.1]heptan-7-yl)methanone |
| 445 | | | | 460 | >10000 | (R/S)-(3-fluoro-2-(2H-1,2,3-triazol-2-yl)phenyl)(2-((5-(trifluoromethyl)pyrazin-2-yl)oxy)-7-azabicyclo[2.2.1]heptan-7-yl)methanone |
| 446 | | | | 4700 | >10000 | (R/S)-(6-methyl-2-(2H-1,2,3-triazol-2-yl)pyridin-3-yl)(2-((5-(trifluoromethyl)pyrazin-2-yl)oxy)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 447 | 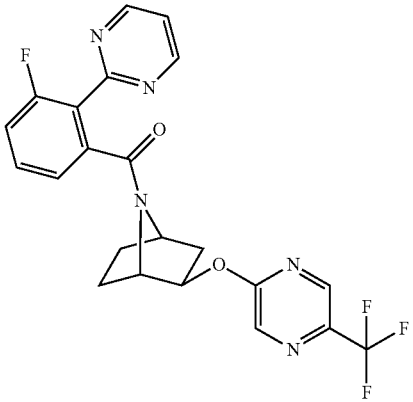 | | 293 | >10000 | (R/S)-(3-fluoro-2-(pyrimidin-2-yl)phenyl)(2-((5-(trifluoromethyl)pyrazin-2-yl)oxy)-7-azabicyclo[2.2.1]heptan-7-yl)methanone |
| 448 | 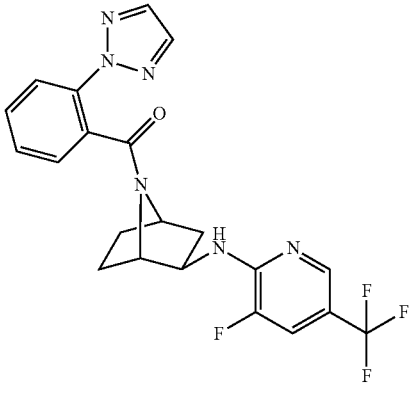 | 41 | 33 | 666 | (2-(2H-1,2,3-triazol-2-yl)phenyl)((1S,2R,4R)-2-((3-fluoro-5-(trifluoromethyl)pyridin-2-yl)amino)-7-azabicyclo[2.2.1]heptan-7-yl)methanone |
| 449 | 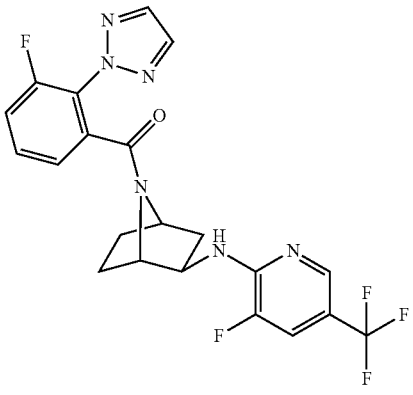 | 34 | 41 | 873 | (3-fluoro-2-(2H-1,2,3-triazol-2-yl)phenyl)((1S,2R,4R)-2-((3-fluoro-5-(trifluoromethyl)pyridin-2-yl)amino)-7-azabicyclo[2.2.1]heptan-7-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 450 | | 14 | 32 | 340 | ((1S,2R,4R)-2-((3-fluoro-5-(trifluoromethyl)pyridin-2-yl)amino)-7-azabicyclo[2.2.1]heptan-7-yl)(3-methyl-2-(2H-1,2,3-triazol-2-yl)phenyl)methanone |
| 451 | | 82 | 84 | 517 | ((1S,2R,4R)-2-((3-fluoro-5-(trifluoromethyl)pyridin-2-yl)amino)-7-azabicyclo[2.2.1]heptan-7-yl)(6-methyl-3-(2H-1,2,3-triazol-2-yl)pyridin-2-yl)methanone |
| 452 | | 176 | 223 | 437 | ((1S,2R,4R)-2-(3-fluoro-5-(trifluoromethyl)pyridin-2-yl)amino)-7-azabicyclo[2.2.1]heptan-7-yl)(6-methyl-2-(2H-1,2,3-triazol-2-yl)pyridin-3-yl)methanone |
| 453 | | 210 | 305 | >10000 | ((1S,2R,4R)-2-((3-fluoro-5-(trifluoromethyl)pyridin-2-yl)amino)-7-azabicyclo[2.2.1]heptan-7-yl)(5-methyl-2-(2H-1,2,3-triazol-2-yl)pyridin-3-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 454 | | | 18 | 23 | 590 | (3-fluoro-(oxazol-2-yl)phenyl)((1S,2R,4R)-2-((3-fluoro-5-(trifluoromethyl)pyridin-2-yl)amino)-7-azabicyclo[2.2.1]heptan-7-yl)methanone |
| 455 | | | 464 | >10000 | | ((1S,2R,4R)-2-((3-fluoro-5-(trifluoromethyl)pyridin-2-yl)amino)-7-azabicyclo[2.2.1]heptan-7-yl)(5-methyl-2-(pyrimidin-2-yl)pyridin-3-yl)methanone |
| 456 | | | 68 | 48 | 454 | ((1S,2R,4R)-2-((3-fluoro-5-(trifluoromethyl)pyridin-2-yl)amino)-7-azabicyclo[2.2.1]heptan-7-yl)(6-methyl-3-(pyrimidin-2-yl)pyridin-2-yl)methanone |

TABLE 2-continued

| Ex. No. | Compound | rOX1 K$_i$ (nM) | hOX1 K$_i$ (nM) | hOX2 K$_i$ (nM) | Compound Name |
|---|---|---|---|---|---|
| 457 | 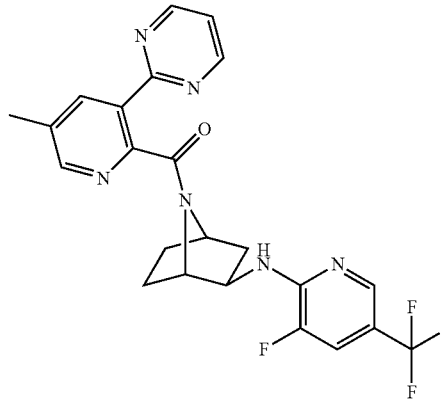 | 55 | 98 | 9100 | ((1S,2R,4R)-2-((3-fluoro-5-(trifluoromethyl)pyridin-2-yl)amino)-7-azabicyclo[2.2.1]heptan-7-yl)(5-methyl-3-(pyrimidin-2-yl)pyridin-2-yl)methanone |
| 458 | 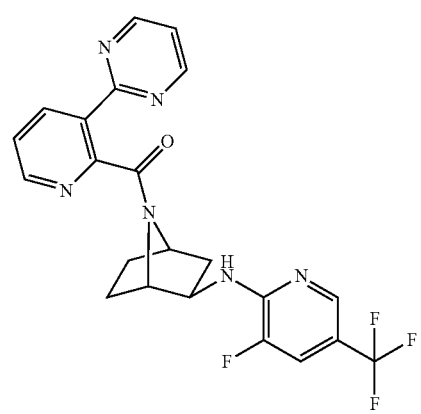 | 46 | 45 | 932 | ((1S,2R,4R)-2-((3-fluoro-5-((trifluoromethyl)pyridin-2-yl)amino)-7-azabicyclo[2.2.1]heptan-7-yl)(3-(pyrimidin-2-yl)pyridin-2-yl)methanone |
| 459 | 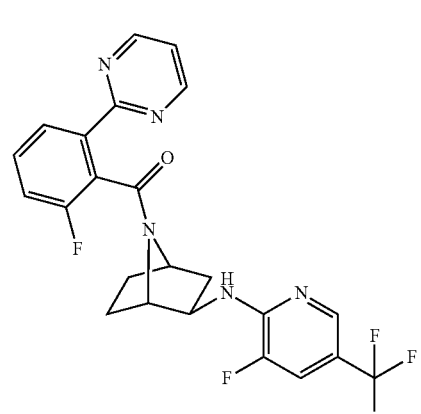 | 26 | 71 | 530 | ((1S,2R,4R)-2-((3-fluoro-5-(trifluoromethyl)pyridin-2-yl)amino)-7-azabicyclo[2.2.1]heptan-7-yl)(2-fluoro-6-(pyrimidin-2-yl)phenyl)methanone |

TABLE 2-continued

| Ex. No. | Compound | rOX1 K_i (nM) | hOX1 K_i (nM) | hOX2 K_i (nM) | Compound Name |
|---|---|---|---|---|---|
| 460 | | 57 | 41 | 1300 | ((1S,2R,4R)-2-((3-fluoro-5-(trifluoromethyl)pyridin-2-yl)amino)-7-azabicyclo[2.2.1]heptan-7-yl)(2-(5-fluoropyrimidin-2-yl)phenyl)methanone |
| 461 | | 30 | 24 | 760 | ((1S,2R,4R)-2-((3-fluoro-5-(trifluoromethyl)pyridin-2-yl)amino)-7-azabicyclo[2.2.1]heptan-7-yl)(2-(pyrimidin-2-yl)phenyl)methanone |
| 462 | | 18 | 31 | 339 | ((1S,2R,4R)-2-((3-fluoro-5-(trifluoromethyl)pyridin-2-yl)amino-7-azabicyclo[2.2.1]heptan-7-yl)(3-methyl-2-(pyrimidin-2-yl)phenyl)methanone |

TABLE 2-continued

| Ex. No. | Compound | rOX1 $K_i$ (nM) | hOX1 $K_i$ (nM) | hOX2 $K_i$ (nM) | Compound Name |
|---|---|---|---|---|---|
| 463 | 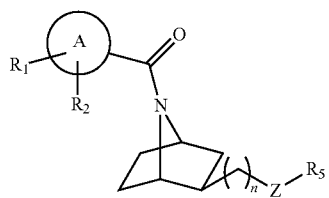 | 53 | 50 | 1900 | (3-fluoro-2-(5-fluoropyrimidin-2-yl)phenyl)((1S,2R,4R)-2-((3-fluoro-5-(trifluoromethyl)pyridin-2-yl)amino)-7-azabicyclo[2.2.1]heptan-7-yl)methanone |

What is claimed is:

1. A compound of formula I:

I or an enantiomer diastereomer, tautomer, or isotopic variant thereof;
or a pharmaceutically acceptable salt or solvate thereof;
wherein
ring A is phenyl, naphthalenyl, pyridyl, quinolinyl, isoquinolinyl, imidazopyridyl, furanyl, thiazolyl, isoxazolyl, pyrazolyl, imidazothiazolyl, benzimidazolyl, or indazolyl;
$R_1$ is H, alkyl, alkoxy, hydroxyalkylene, OH, halo, phenyl, triazolyl, oxazolyl, isoxazolyl, pyridyl, pyrimidinyl, pyrazinyl, pyridazinyl, piperazinyl, pyrazolyl, oxadiazolyl, pyrrolidinyl, thiophenyl, morpholinyl, or dialkylamino, wherein phenyl, triazolyl, oxazolyl, isoxazolyl, pyridyl, pyrimidinyl, pyrazinyl, pyridazinyl, piperazinyl, pyrazolyl, oxadiazolyl, pyrrolidinyl, thiophenyl, or morpholinyl is optionally substituted with up to two substituents selected from halo or alkyl;
$R_2$ is H, alkyl, alkoxy, hydroxyalkylene, or halo;
Z is NH, N-alkyl, or O;
$R_5$ is pyridyl, pyrimidinyl, pyrazinyl, pyridazinyl, quinazolinyl, quinoxalinyl, pyrazolyl, thiazolyl, thiadiazolyl, benzoxazolyl, imidazopyrazinyl, or triazolopyrazinyl, optionally substituted with one or two substituents independently selected from the group consisting of alkyl, cyano, alkyl carboxylate, alkoxy, and halo; and
n is 0 or 1.

2. The compound of claim 1, wherein Z is NH.
3. The compound of claim 1, wherein Z is N-alkyl.
4. The compound of claim 3, wherein Z is N—CH$_3$.
5. The compound of claim 1, wherein Z is O.
6. The compound of claim 1, wherein ring A is furanyl, thiazolyl, isoxazolyl, pyrazolyl, or imidazothiazolyl.
7. The compound of claim 1, wherein ring A is phenyl or naphthalenyl.
8. The compound of claim 1, wherein ring A is pyridyl, quinolinyl, isoquinolinyl, imidazopyridyl, benzimidazolyl, or indazolyl.
9. The compound of claim 1, wherein $R_1$ is alkyl.
10. The compound of claim 1, wherein $R_1$ is alkoxy.
11. The compound of claim 10, wherein alkoxy is haloalkoxy.
12. The compound of claim 1, wherein $R_1$ is hydroxyalkylene or OH.
13. The compound of claim 1, wherein $R_1$ is halo.
14. The compound of claim 1, wherein $R_1$ is phenyl.
15. The compound of claim 14, wherein phenyl is halophenyl.
16. The compound of claim 1, wherein $R_1$ is triazolyl, oxazolyl, or isoxazolyl.
17. The compound of claim 16, wherein oxazolyl is methyl-oxazolyl.
18. The compound of claim 16, wherein isoxazolyl is methyl-isoxazolyl.
19. The compound of claim 1, wherein $R_1$ is pyridyl.
20. The compound of claim 19, wherein pyridyl is methyl-pyridyl.
21. The compound of claim 1, wherein $R_1$ is pyrimidinyl, pyrazinyl, or pyridazinyl.
22. The compound of claim 1, wherein $R_1$ is piperazinyl, morpholinyl, pyrrolidinyl, or dialkylamino.
23. The compound of claim 1, wherein $R_1$ is pyrazolyl, oxadiazolyl, or thiophenyl.
24. The compound of claim 23, wherein pyrazolyl is methyl-pyrazolyl or dimethyl-pyrazolyl.
25. The compound of claim 23, wherein oxadiazolyl is methyl-oxadiazolyl.
26. The compound of claim 1, wherein $R_2$ is H.
27. The compound of claim 1, wherein $R_2$ is alkyl.
28. The compound of claim 1, wherein $R_2$ is alkoxy.
29. The compound of claim 1, wherein $R_2$ is hydroxyalkylene.

30. The compound of claim 1, wherein R$_2$ is halo.

31. The compound of claim 1, wherein R$_5$ is pyridyl, pyrimidinyl, pyrazinyl, or pyridazinyl optionally substituted with a one or two substituents independently selected from the group consisting of alkyl, alkoxy, and halo.

32. The compound of claim 31, wherein alkyl is trihaloalkyl.

33. The compound of claim 32, wherein R$_5$ is pyridyl substituted with trifluoromethyl.

34. The compound of claim 32, wherein R$_5$ is pyrimidinyl substituted with trifluoromethyl.

35. The compound of claim 32, wherein R$_5$ is pyrazinyl substituted with trifluoromethyl.

36. The compound of claim 32, wherein R$_5$ is pyridazinyl substituted with trifluoromethyl.

37. The compound of claim 1, wherein R$_5$ is quinazolinyl or quinoxalinyl, optionally substituted with one or two substituents independently selected from the group consisting of alkyl, alkoxy, and halo.

38. The compound of claim 37, wherein alkyl is trihaloalkyl.

39. The compound of claim 38, wherein R$_5$ is quinazolinyl substituted with trifluoromethyl.

40. The compound of claim 38, wherein R$_5$ is quinoxalinyl substituted with trifluoromethyl.

41. The compound of claim 1, wherein R$_5$ is pyrazolyl, benzoxazolyl, imidazopyrazinyl, or triazolopyrazinyl optionally substituted with a one or two substituents independently selected from the group consisting of alkyl, alkoxy, and halo.

42. The compound of claim 41, wherein pyrazolyl is methyl-pyrazolyl.

43. The compound of claim 41, wherein alkyl is trihaloalkyl.

44. The compound of claim 43, wherein R$_5$ is pyrazolyl substituted with trifluoromethyl.

45. The compound of claim 43, wherein R$_5$ is benzoxazolyl substituted with trifluoromethyl.

46. The compound of claim 43 wherein R$_5$ is imidazopyrazinyl substituted with trifluoromethyl.

47. The compound of claim 43, wherein R$_5$ is triazolopyrazinyl substituted with trifluoromethyl.

48. The compound of claim 1, wherein n is 0.

49. The compound of claim 1, wherein n is 1.

50. A compound selected from the group consisting of

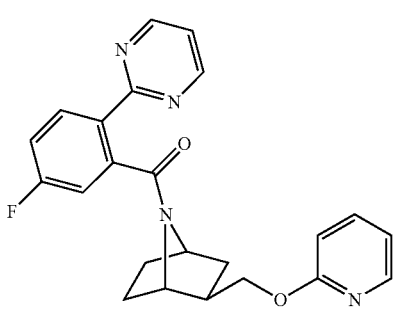 [SMILES: O=C(c1cc(F)ccc1-c1ncccn1)N1C2CCC1C(COc1ccccn1)C2]

(5-fluoro-2-(pyrimidin-2-yl)phenyl)((1S,2R,4R)-2-((pyridin-2-yloxy)methyl)-7-azabicyclo[2.2.1]heptan-7-yl)methanone,

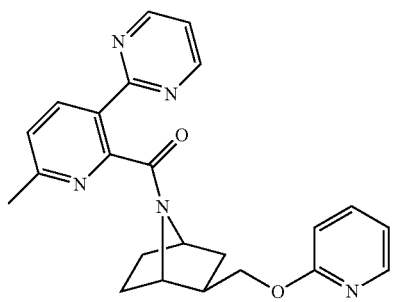 [SMILES: Cc1ccc(-c2ncccn2)c(C(=O)N2C3CCC2C(COc2ccccn2)C3)n1]

(±)-(6-methyl-3-(pyrimidin-2-yl)pyridin-2-yl)(2-((pyridin-2-yloxy)methyl)-7-azabicyclo[2.2.1]heptan-7-yl)methanone,

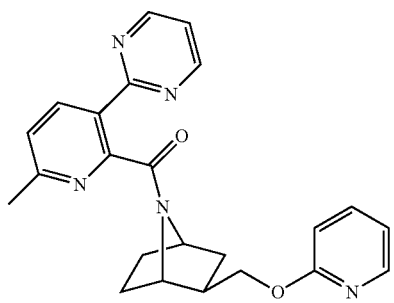 [SMILES: Cc1ccc(-c2ncccn2)c(C(=O)N2C3CCC2C(COc2ccccn2)C3)n1]

(6-methyl-3-(pyrimidin-2-yl)pyridin-2-yl)((1S*,2R*,4R*)-2-((pyridin-2-yloxy)methyl)-7-azabicyclo[2.2.1]heptan-7-yl)methanone,

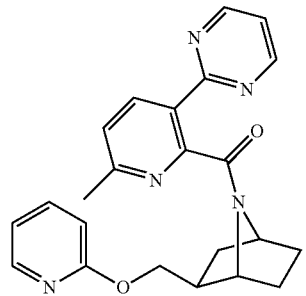 [SMILES: Cc1ccc(-c2ncccn2)c(C(=O)N2C3CCC2C(COc2ccccn2)C3)n1]

(6-methyl-3-(pyrimidin-2-yl)pyridin-2-yl)((1R*,2S*,4S*)-2-((pyridin-2-yloxy)methyl)-7-azabicyclo[2.2.1]heptan-7-yl)methanone,

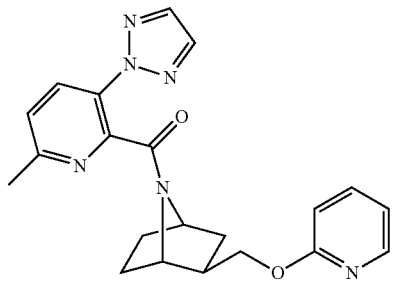 [SMILES: Cc1ccc(-n2nccn2)c(C(=O)N2C3CCC2C(COc2ccccn2)C3)n1]

(±)-(6-methyl-3-(2H-1,2,3-triazol-2-yl)pyridin-2-yl)(2-((pyridin-2-yloxy)methyl)-7-azabicyclo[2.2.1]heptan-7-yl)methanone, -continued

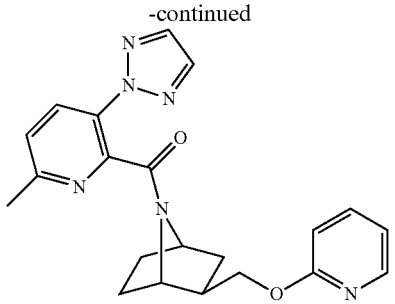

(6-methyl-3-(2H-1,2,3-triazol-2-yl)pyridin-2-yl)((1S,2R,4R)-2-((pyridin-2-yloxy)methyl)-7-azabicyclo[2.2.1]heptan-7-yl)methanone,

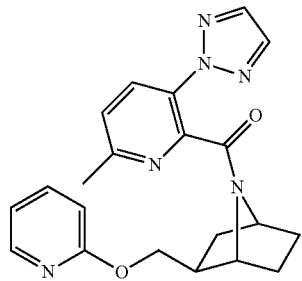 [SMILES: Cc1ccc(-n2nccn2)c(C(=O)N2C3CCC2C(COc2ccccn2)C3)n1]

(6-methyl-3-(2H-1,2,3-triazol-2-yl)pyridin-2-yl)((1R,2S,4S)-2-((pyridin-2-yloxy)methyl)-7-azabicyclo[2.2.1]heptan-7-yl)methanone,

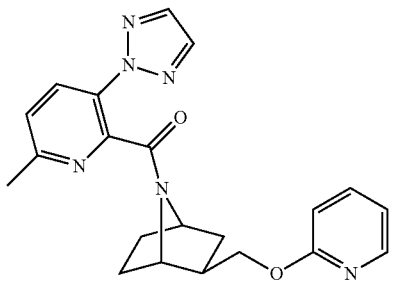 [SMILES: Cc1ccc(-n2nccn2)c(C(=O)N2C3CCC2C(COc2ccccn2)C3)n1]

(6-methyl-3-(2H-1,2,3-triazol-2-yl)pyridin-2-yl)((1S,2R,4R)-2-((pyridin-2-yloxy)methyl)-7-azabicyclo[2.2.1]heptan-7-yl)methanone,

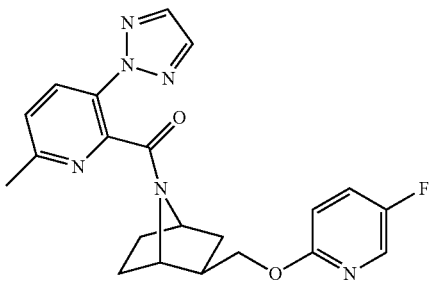 [SMILES: Cc1ccc(-n2nccn2)c(C(=O)N2C3CCC2C(COc2ccc(F)cn2)C3)n1]

(±)-(2-(((5-fluoropyridin-2-yl)oxy)methyl)-7-azabicyclo[2.2.1]heptan-7-yl)(6-methyl-3-(2H-1,2,3-triazol-2-yl)pyridin-2-yl)methanone, -continued

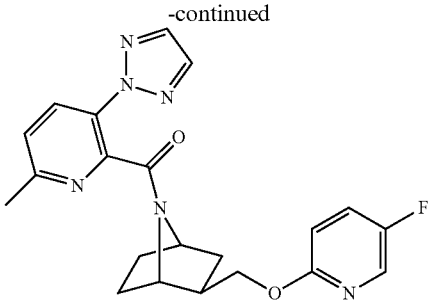

((1S,2R,4R)-2-(((5-fluoropyridin-2-yl)oxy)methyl)-7-azabicyclo[2.2.1]heptan-7-yl)(6-methyl-3-(2H-1,2,3-triazol-2-yl)pyridin-2-yl)methanone,

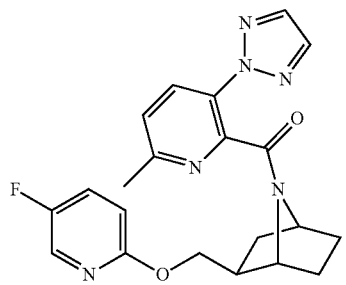 [SMILES: Cc1ccc(-n2nccn2)c(C(=O)N2C3CCC2C(COc2ccc(F)cn2)C3)n1]

((1R,2S,4S)-2-(((5-fluoropyridin-2-yl)oxy)methyl)-7-azabicyclo[2.2.1]heptan-7-yl)(6-methyl-3-(2H-1,2,3-triazol-2-yl)pyridin-2-yl)methanone,

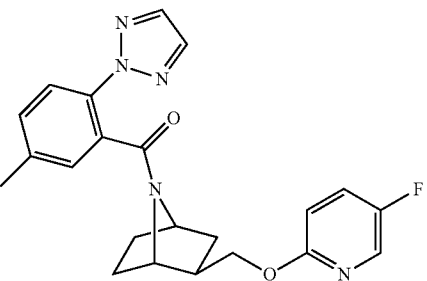 [SMILES: Cc1ccc(-n2nccn2)c(C(=O)N2C3CCC2C(COc2ccc(F)cn2)C3)c1]

(±)-(2-(((5-fluoropyridin-2-yl)oxy)methyl)-7-azabicyclo[2.2.1]heptan-7-yl)(5-methyl-2-(2H-1,2,3-triazol-2-yl)phenyl)methanone,

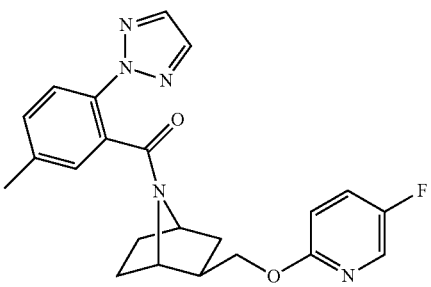

((1S,2R,4R)-2-(((5-fluoropyridin-2-yl)oxy)methyl)-7-azabicyclo[2.2.1]heptan-7-yl)(5-methyl-2-(2H-1,2,3-triazol-2-yl)phenyl)methanone,

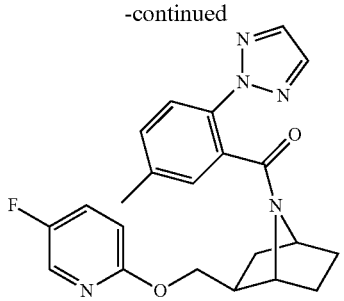

((1R,2S,4S)-2-(((5-fluoropyridin-2-
yl)oxy)methyl)-7-
azabicyclo[2.2.1]heptan-7-yl)(5-methyl-
2-(2H-1,2,3-triazol-2-
yl)phenyl)methanone,

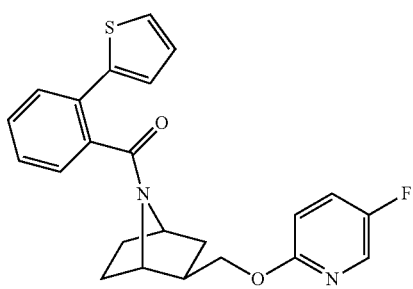 [SMILES: O=C(c1ccccc1-c1cccs1)N1C2CCC1C(COc1ccc(F)cn1)C2]

(±)-2-(((5-fluoropyridin-2-
yl)oxy)methyl)-7-
azabicyclo[2.2.1]heptan-7-yl)(2-
(thiophen-2-yl)phenyl)methanone,

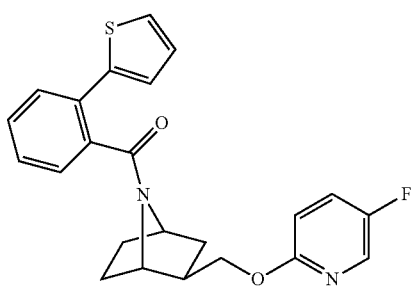 [SMILES: O=C(c1ccccc1-c1cccs1)N1C2CCC1C(COc1ccc(F)cn1)C2]

((1S*,2R*,4R*)-2-(((5-fluoropyridin-2-
yl)oxy)methyl)-7-
azabicyclo[2.2.1]heptan-7-yl)(2-
(thiophen-2-yl)phenyl)methanone,

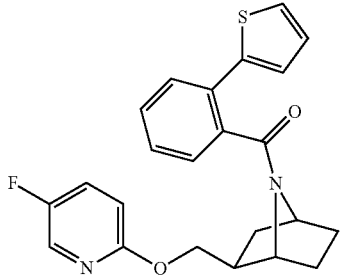 [SMILES: O=C(c1ccccc1-c1cccs1)N1C2CCC1C(COc1ccc(F)cn1)C2]

((1R*,2S*,4S*)-2-(((5-fluoropyridin-2-
yl)oxy)methyl)-7-
azabicyclo[2.2.1]heptan-7-yl)(2-
(thiophen-2-yl)phenyl)methanone,

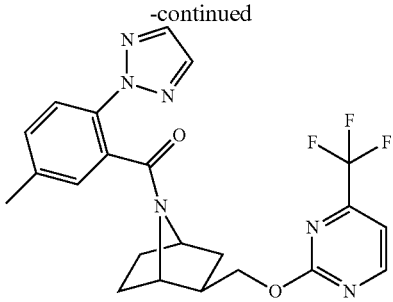

(±)-(5-methyl-2-(2H-1,2,3-triazol-2-
yl)phenyl)(2-(((4-
(trifluoromethyl)pyrimidin-2-
yl)oxy)methyl)-7-
azabicyclo[2.2.1]heptan-7-
yl)methanone,

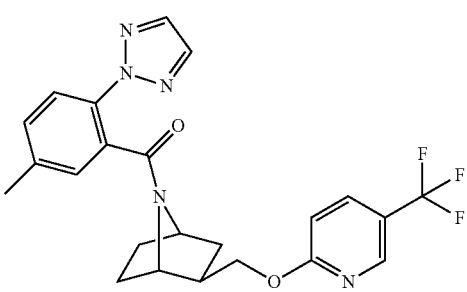 [SMILES: Cc1ccc(-n2nccn2)c(C(=O)N2C3CCC2C(COc2ccc(C(F)(F)F)cn2)C3)c1]

(±)-(5-methyl-2-(2H-1,2,3-triazol-2-
yl)phenyl)(2-(((5-
(trifluoromethyl)pyridin-2-
yl)oxy)methyl)-7-
azabicyclo[2.2.1]heptan-7-
yl)methanone,

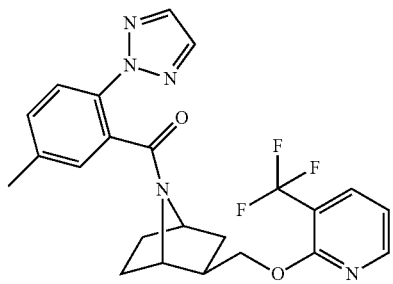 [SMILES: Cc1ccc(-n2nccn2)c(C(=O)N2C3CCC2C(COc2ncccc2C(F)(F)F)C3)c1]

(±)-(5-methyl-2-(2H-1,2,3-triazol-2-
yl)phenyl)(2-(((3-
(trifluoromethyl)pyridin-2-
yl)oxy)methyl)-7-
azabicyclo[2.2.1]heptan-7-
yl)methanone, -continued

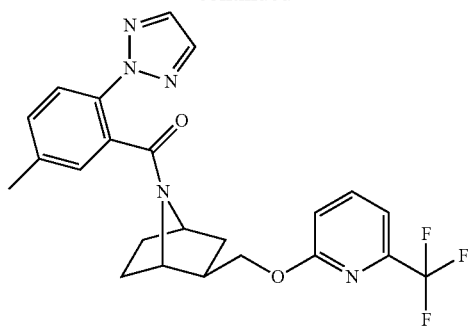 [SMILES: Cc1ccc(-n2nccn2)c(C(=O)N2C3CCC2C(COc2cccc(C(F)(F)F)n2)C3)c1]

(±)-(5-methyl-2-(2H-1,2,3-triazol-2-yl)phenyl)(2-(((6-(trifluoromethyl)pyridin-2-yl)oxy)methyl)-7-azabicyclo[2.2.1]heptan-7-yl)methanone,

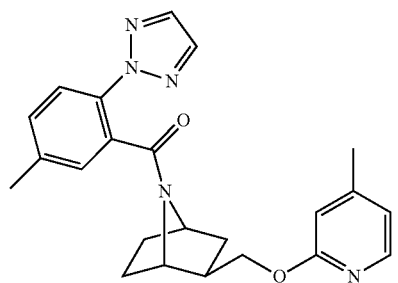 [SMILES: Cc1ccnc(OCC2CC3CCC2N3C(=O)c2cc(C)ccc2-n2nccn2)c1]

(±)-(5-methyl-2-(2H-1,2,3-triazol-2-yl)phenyl)(2-(((4-methylpyridin-2-yl)oxy)methyl)-7-azabicyclo[2.2.1]heptan-7-yl)methanone,

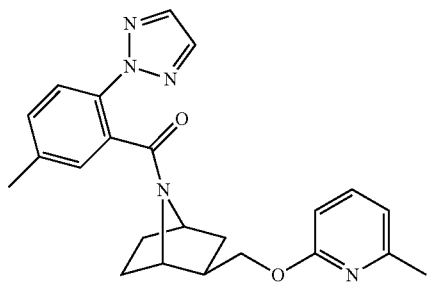

(±)-(5-methyl-2-(2H-1,2,3-triazol-2-yl)phenyl)(2-(((6-methylpyridin-2-yl)oxy)methyl)-7-azabicyclo[2.2.1]heptan-7-yl)methanone,

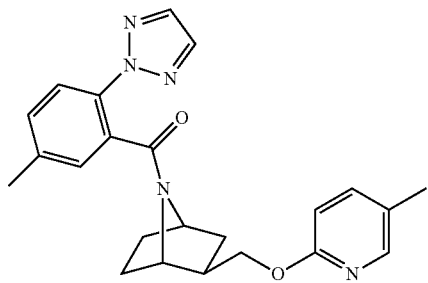

(±)-(5-methyl-2-(2H-1,2,3-triazol-2-yl)phenyl)(2-(((5-methylpyridin-2-yl)oxy)methyl)-7-azabicyclo[2.2.1]heptan-7-yl)methanone, -continued

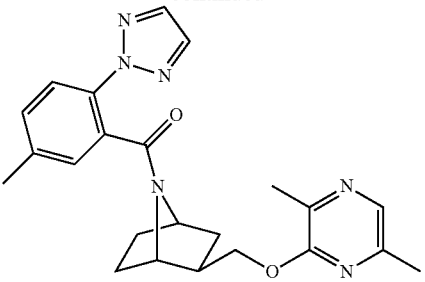

(±)-(2-(((3,6-dimethylpyrazin-2-yl)oxy)methyl)-7-azabicyclo[2.2.1]heptan-7-yl)(5-methyl-2-(2H-1,2,3-triazol-2-yl)phenyl)methanone,

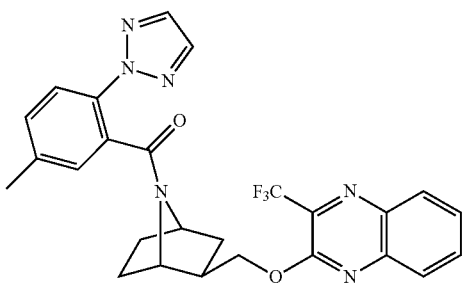 [SMILES: Cc1ccc(-n2nccn2)c(C(=O)N2C3CCC2C(COc2nc4ccccc4nc2C(F)(F)F)C3)c1]

(±)-(5-methyl-2-(2H-1,2,3-triazol-2-yl)phenyl)(2-(((3-(trifluoromethyl)quinoxalin-2-yl)oxy)methyl)-7-azabicyclo[2.2.1]heptan-7-yl)methanone,

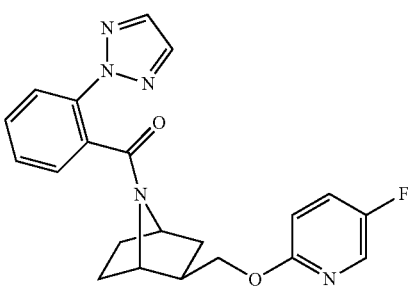 [SMILES: O=C(c1ccccc1-n1nccn1)N1C2CCC1C(COc1ccc(F)cn1)C2]

(±)-(2-(2H-1,2,3-triazol-2-yl)phenyl)(2-(((5-fluoropyridin-2-yl)oxy)methyl)-7-azabicyclo[2.2.1]heptan-7-yl)methanone,

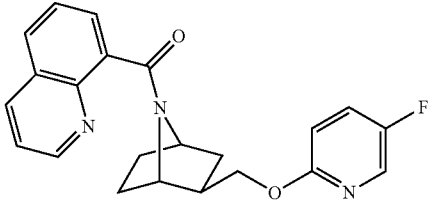 [SMILES: O=C(c1cccc2cccnc12)N1C2CCC1C(COc1ccc(F)cn1)C2]

(±)-2-(((5-fluoropyridin-2-yl)oxy)methyl)-7-azabicyclo[2.2.1]heptan-7-yl)(quinolin-8-yl)methanone, 743
-continued

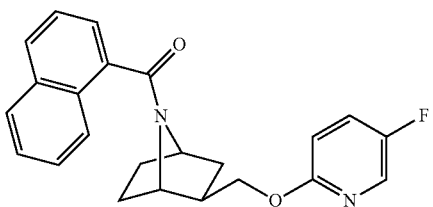 [SMILES: O=C(c1cccc2ccccc12)N1C2CCC1C(COc1ccc(F)cn1)C2]

(±)-2-(((5-fluoropyridin-2-
yl)oxy)methyl)-7-
azabicyclo[2.2.1]heptan-7-
yl)(naphthalen-1-yl)methanone,

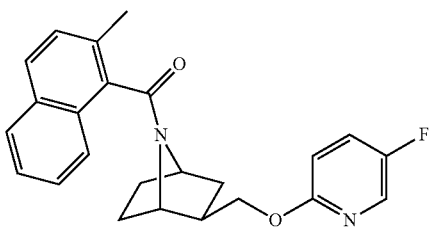 [SMILES: Cc1ccc2ccccc2c1C(=O)N1C2CCC1C(COc1ccc(F)cn1)C2]

(±)-2-(((5-fluoropyridin-2-
yl)oxy)methyl)-7-
azabicyclo[2.2.1]heptan-7-yl)(2-
methylnaphthalen-1-yl)methanone,

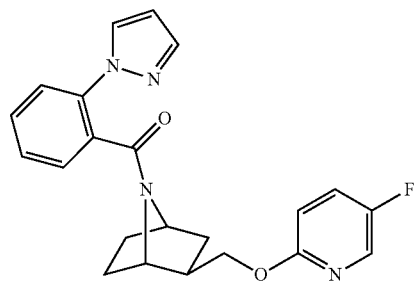 [SMILES: O=C(c1ccccc1-n1cccn1)N1C2CCC1C(COc1ccc(F)cn1)C2]

(±)-2-(1H-pyrazol-1-yl)phenyl)(2-(((5-
fluoropyridin-2-yl)oxy)methyl)-7-
azabicyclo[2.2.1]heptan-7-
yl)methanone,

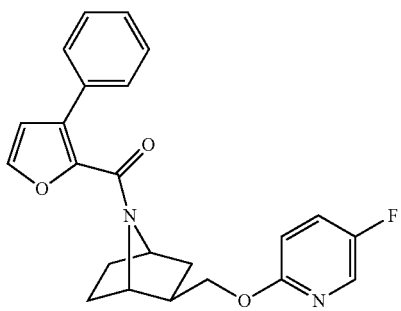

(±)-2-(((5-fluoropyridin-2-
yl)oxy)methyl)-7-
azabicyclo[2.2.1]heptan-7-yl)(3-
phenylfuran-2-yl)methanone, 744
-continued

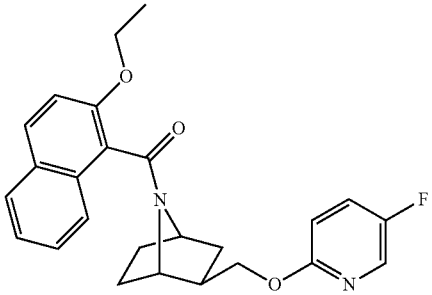 [SMILES: CCOc1ccc2ccccc2c1C(=O)N1C2CCC1C(COc1ccc(F)cn1)C2]

(±)-(2-ethoxynaphthalen-1-yl)(2-(((5-
fluoropyridin-2-yl)oxy)methyl)-7-
azabicyclo[2.2.1]heptan-7-
yl)methanone,

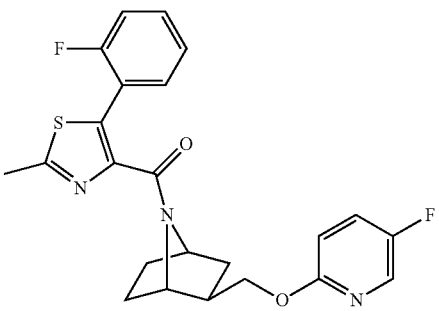

(±)-(5-(2-fluorophenyl)-2-
methylthiazol-4-yl)(2-(((5-
fluoropyridin-2-yl)oxy)methyl)-7-
azabicyclo[2.2.1]heptan-7-
yl)methanone,

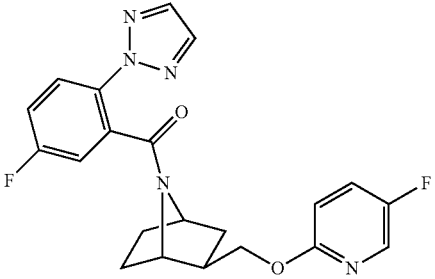 [SMILES: O=C(c1cc(F)ccc1-n1nccn1)N1C2CCC1C(COc1ccc(F)cn1)C2]

(±)-(5-fluoro-2-(2H-1,2,3-triazol-2-
yl)phenyl)(2-(((5-fluoropyridin-2-
yl)oxy)methyl)-7-
azabicyclo[2.2.1]heptan-7-
yl)methanone,

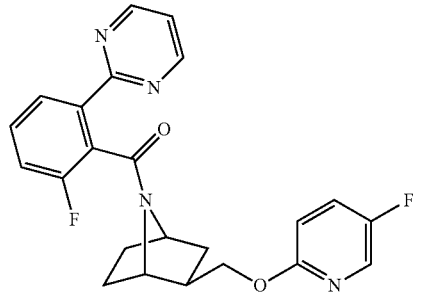

(±)-(2-fluoro-6-(pyrimidin-2-
yl)phenyl)(2-(((5-fluoropyridin-2-
yl)oxy)methyl)-7-
azabicyclo[2.2.1]heptan-7-
yl)methanone, -continued

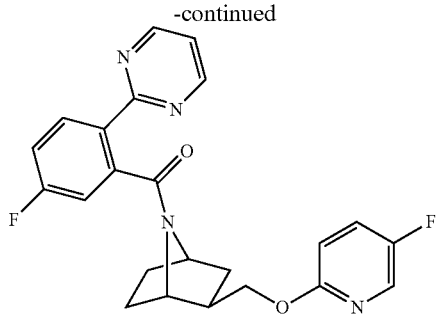

(±)-(5-fluoro-2-(pyrimidin-2-yl)phenyl)(2-(((5-fluoropyridin-2-yl)oxy)methyl)-7-azabicyclo[2.2.1]heptan-7-yl)methanone,

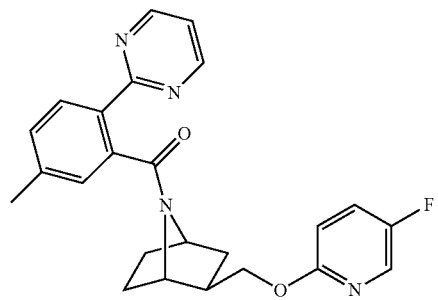

(±)-(2-(((5-fluoropyridin-2-yl)oxy)methyl)-7-azabicyclo[2.2.1]heptan-7-yl)(5-methyl-2-(pyrimidin-2-yl)phenyl)methanone,

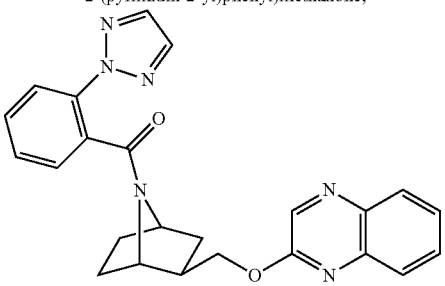

(±)-(2-(2H-1,2,3-triazol-2-yl)phenyl)(2-((quinoxalin-2-yloxy)methyl)-7-azabicyclo[2.2.1]heptan-7-yl)methanone,

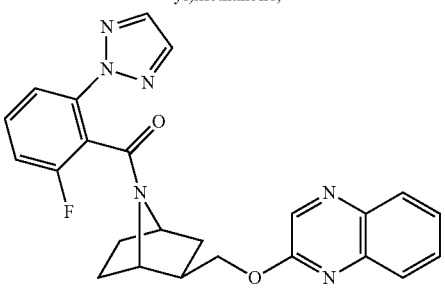

(±)-(2-fluoro-6-(2H-1,2,3-triazol-2-yl)phenyl)(2-((quinoxalin-2-yloxy)methyl)-7-azabicyclo[2.2.1]heptan-7-yl)methanone, -continued

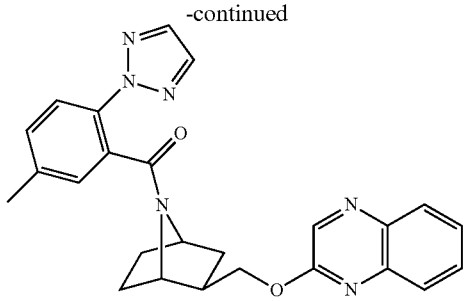

(±)-(5-methyl-2-(2H-1,2,3-triazol-2-yl)phenyl)(2-((quinoxalin-2-yloxy)methyl)-7-azabicyclo[2.2.1]heptan-7-yl)methanone,

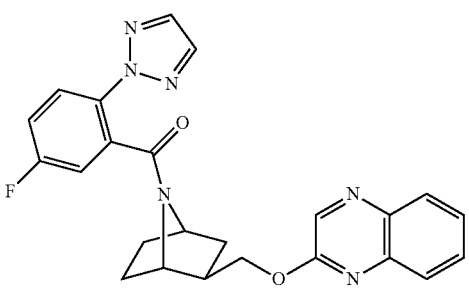 [SMILES: O=C(c1cc(F)ccc1-n1nccn1)N1C2CCC1C(COc1cnc3ccccc3n1)C2]

(±)-(5-fluoro-2-(2H-1,2,3-triazol-2-yl)phenyl)(2-((quinoxalin-2-yloxy)methyl)-7-azabicyclo[2.2.1]heptan-7-yl)methanone,

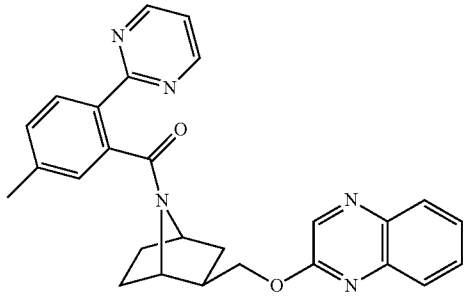 [SMILES: Cc1ccc(-c2ncccn2)c(C(=O)N2C3CCC2C(COc2cnc4ccccc4n2)C3)c1]

(±)-(5-methyl-2-(pyrimidin-2-yl)phenyl)(2-((quinoxalin-2-yloxy)methyl)-7-azabicyclo[2.2.1]heptan-7-yl)methanone,

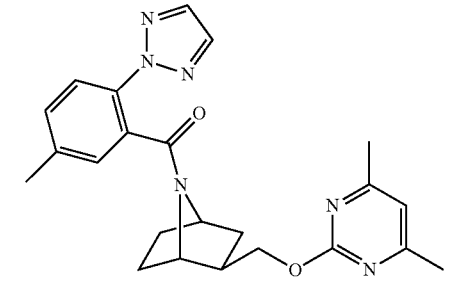

(±)-(2-(((4,6-dimethylpyrimidin-2-yl)oxy)methyl)-7-azabicyclo[2.2.1]heptan-7-yl)(5-methyl-2-(2H-1,2,3-triazol-2-yl)phenyl)methanone,

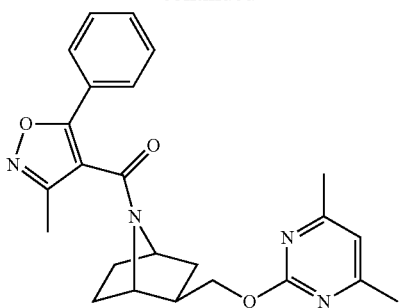

(±)-2-(((4,6-dimethylpyrimidin-2-yl)oxy)methyl)-7-azabicyclo[2.2.1]heptan-7-yl)(3-methyl-5-phenylisoxazol-4-yl)methanone

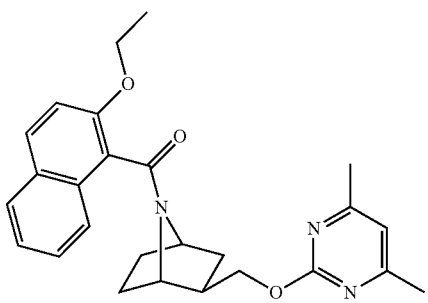 [SMILES: CCOc1ccc2ccccc2c1C(=O)N1C2CCC1C(COc1nc(C)cc(C)n1)C2]

(±)-(2-(((4,6-dimethylpyrimidin-2-yl)oxy)methyl)-7-azabicyclo[2.2.1]heptan-7-yl)(2-ethoxynaphthalen-1-yl)methanone,

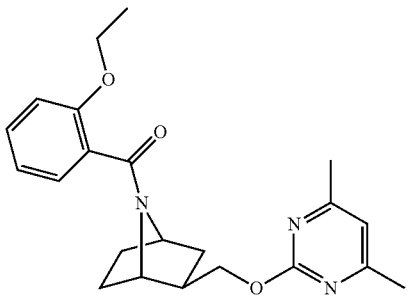 [SMILES: CCOc1ccccc1C(=O)N1C2CCC1C(COc1nc(C)cc(C)n1)C2]

(±)-(2-(((4,6-dimethylpyrimidin-2-yl)oxy)methyl)-7-azabicyclo[2.2.1]heptan-7-yl)(2-ethoxyphenyl)methanone),

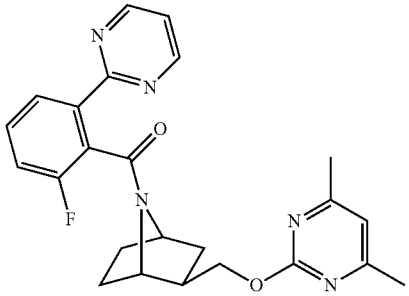 [SMILES: Cc1cc(C)nc(OCC2CC3CCC2N3C(=O)c2c(F)cccc2-c2ncccn2)n1]

(±)-(2-(((4,6-dimethylpyrimidin-2-yl)oxy)methyl)-7-azabicyclo[2.2.1]heptan-7-yl)(2-fluoro-6-(pyrimidin-2-yl)phenyl)methanone,

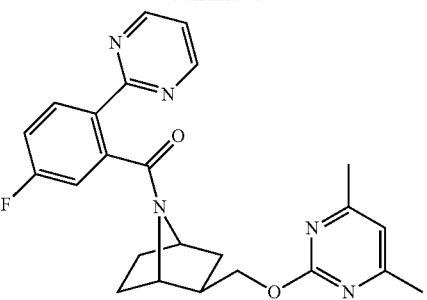 [SMILES: Cc1cc(C)nc(OCC2CC3CCC2N3C(=O)c2cc(F)ccc2-c2ncccn2)n1]

(±)-(2-(((4,6-dimethylpyrimidin-2-yl)oxy)methyl)-7-azabicyclo[2.2.1]heptan-7-yl)(5-fluoro-2-(pyrimidin-2-yl)phenyl)methanone,

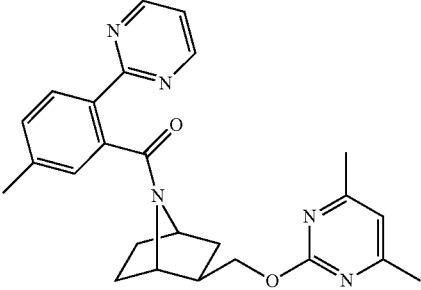

(±)-(2-(((4,6-dimethylpyrimidin-2-yl)oxy)methyl)-7-azabicyclo[2.2.1]heptan-7-yl)(5-methyl-2-(pyrimidin-2-yl)phenyl)methanone,

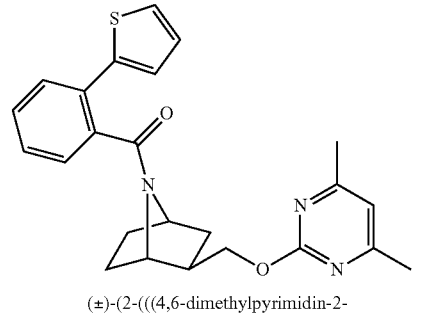

(±)-(2-(((4,6-dimethylpyrimidin-2-yl)oxy)methyl)-7-azabicyclo[2.2.1]heptan-7-yl)(2-(thiophen-2-yl)phenyl)methanone,

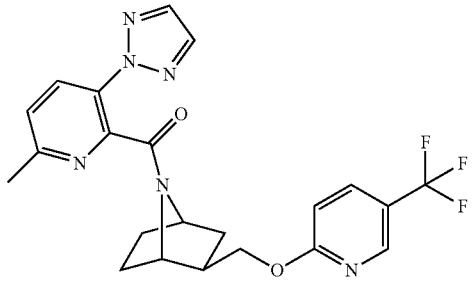

(±)-(6-methyl-3-(2H-1,2,3-triazol-2-yl)pyridin-2-yl)(2-(((5-(trifluoromethyl)pyridin-2-yl)oxy)methyl)-7-azabicyclo[2.2.1]heptan-7-yl)methanone,

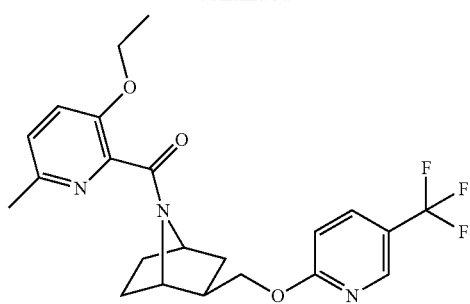 [SMILES: CCOc1ccc(C)nc1C(=O)N1C2CCC1C(COc1ccc(C(F)(F)F)cn1)C2]

(±)-(3-ethoxy-6-methylpyridin-2-yl)(2-(((5-(trifluoromethyl)pyridin-2-yl)oxy)methyl)-7-azabicyclo[2.2.1]heptan-7-yl)methanone,

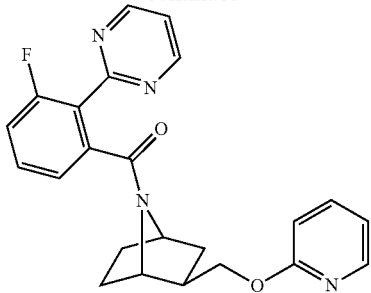

(±)-(3-fluoro-2-(pyrimidin-2-yl)phenyl)(2-((pyridin-2-yloxy)methyl)-7-azabicyclo[2.2.1]heptan-7-yl)methanone,

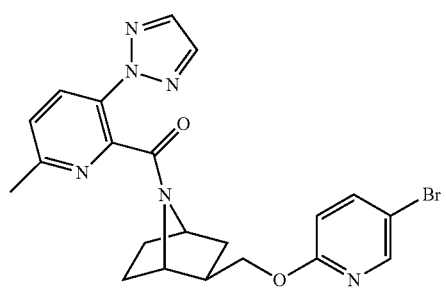 [SMILES: Cc1ccc(-n2nccn2)c(C(=O)N2C3CCC2C(COc2ccc(Br)cn2)C3)n1]

(±)-(2-(((5-bromopyridin-2-yl)oxy)methyl)-7-azabicyclo[2.2.1]heptan-7-yl)(6-methyl-3-(2H-1,2,3-triazol-2-yl)pyridin-2-yl)methanone,

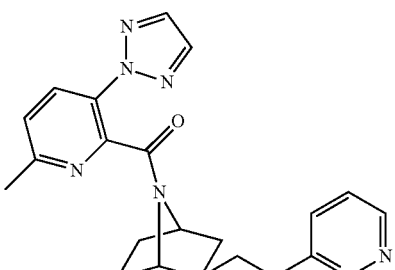

(±)-(6-methyl-3-(2H-1,2,3-triazol-2-yl)pyridin-2-yl)(2-((pyridazin-3-yloxy)methyl)-7-azabicyclo[2.2.1]heptan-7-yl)methanone,

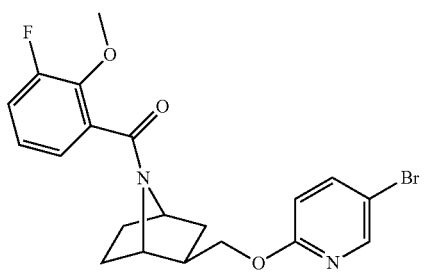 [SMILES: COc1c(F)cccc1C(=O)N1C2CCC1C(COc1ccc(Br)cn1)C2]

(±)-(2-(((5-bromopyridin-2-yl)oxy)methyl)-7-azabicyclo[2.2.1]heptan-7-yl)(3-fluoro-2-methoxyphenyl)methanone,

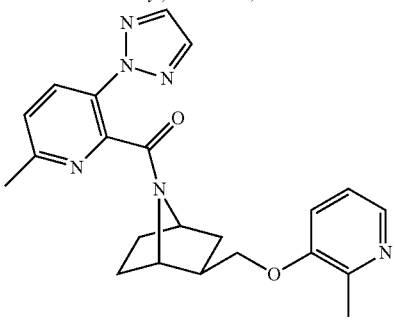

(±)-(6-methyl-3-(2H-1,2,3-triazol-2-yl)pyridin-2-yl)(2-(((2-methylpyridin-3-yl)oxy)methyl)-7-azabicyclo[2.2.1]heptan-7-yl)methanone,

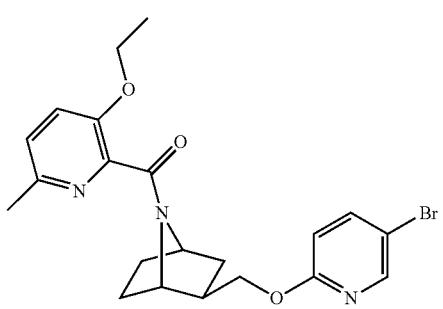 [SMILES: CCOc1ccc(C)nc1C(=O)N1C2CCC1C(COc1ccc(Br)cn1)C2]

(±)-(2-(((5-bromopyridin-2-yl)oxy)methyl)-7-azabicyclo[2.2.1]heptan-7-yl)(3-ethoxy-6-methylpyridin-2-yl)methanone,

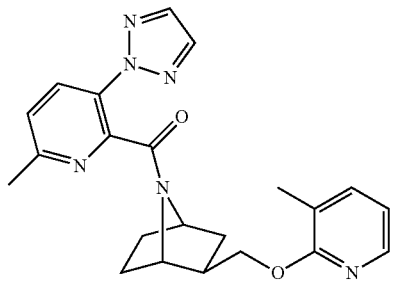 [SMILES: Cc1ccc(-n2nccn2)c(C(=O)N2C3CCC2C(COc2ncccc2C)C3)n1]

(±)-(6-methyl-3-(2H-1,2,3-triazol-2-yl)pyridin-2-yl)(2-(((3-methylpyridin-2-yl)oxy)methyl)-7-azabicyclo[2.2.1]heptan-7-yl)methanone,

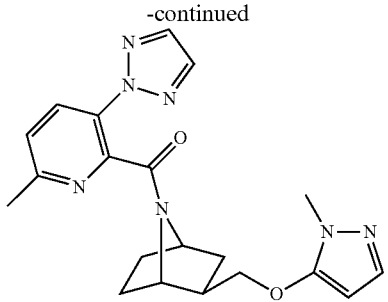

(±)-(2-(((1-methyl-1H-pyrazol-5-yl)oxy)methyl)-7-azabicyclo[2.2.1]heptan-7-yl)(6-methyl-3-(2H-1,2,3-triazol-2-yl)pyridin-2-yl)methanone,

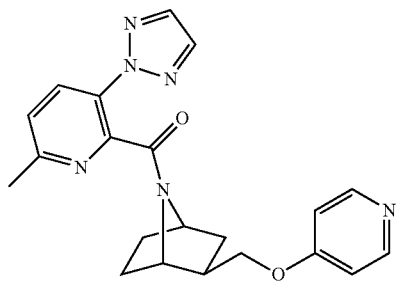 [SMILES: Cc1ccc(-n2nccn2)c(C(=O)N2C3CCC2C(COc2ccncc2)C3)n1]

(±)-(6-methyl-3-(2H-1,2,3-triazol-2-yl)pyridin-2-yl)(2-((pyridin-4-yloxy)methyl)-7-azabicyclo[2.2.1]heptan-7-yl)methanone,

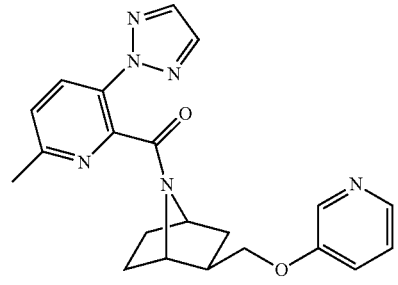 [SMILES: Cc1ccc(-n2nccn2)c(C(=O)N2C3CCC2C(COc2cccnc2)C3)n1]

(±)-(6-methyl-3-(2H-1,2,3-triazol-2-yl)pyridin-2-yl)(2-((pyridin-3-yloxy)methyl)-7-azabicyclo[2.2.1]heptan-7-yl)methanone,

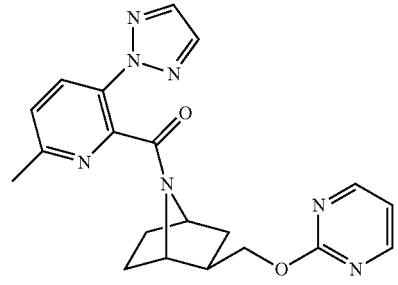 [SMILES: Cc1ccc(-n2nccn2)c(C(=O)N2C3CCC2C(COc2ncccn2)C3)n1]

(±)-(6-methyl-3-(2H-1,2,3-triazol-2-yl)pyridin-2-yl)(2-((pyrimidin-2-yloxy)methyl)-7-azabicyclo[2.2.1]heptan-7-yl)methanone,

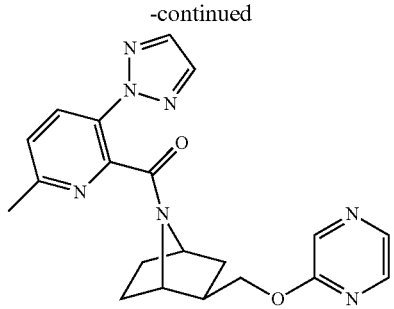

(±)-(6-methyl-3-(2H-1,2,3-triazol-2-yl)pyridin-2-yl)(2-((pyrazin-2-yloxy)methyl)-7-azabicyclo[2.2.1]heptan-7-yl)methanone,

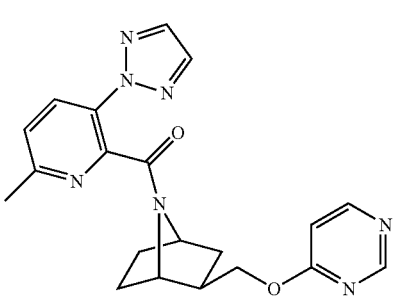 [SMILES: Cc1ccc(-n2nccn2)c(C(=O)N2C3CCC2C(COc2ccncn2)C3)n1]

(±)-(6-methyl-3-(2H-1,2,3-triazol-2-yl)pyridin-2-yl)(2-[[ ]]((pyrimidin-4-yloxy)methyl)-7-azabicyclo[2.2.1]heptan-7-yl)methanone,

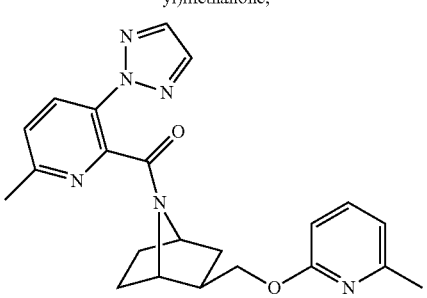

(±)-(6-methyl-3-(2H-1,2,3-triazol-2-yl)pyridin-2-yl)(2-(((6-methylpyridin-2-yl)oxy)methyl)-7-azabicyclo[2.2.1]heptan-7-yl)methanone,

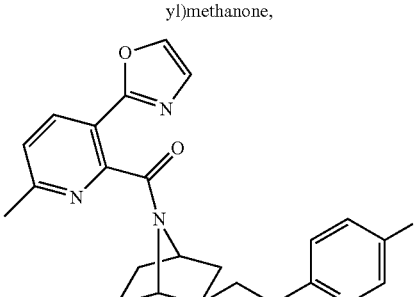

(±)-(2-(((5-fluoropyridin-2-yl)oxy)methyl)-7-azabicyclo[2.2.1]heptan-7-yl)(6-methyl-3-(oxazol-2-yl)pyridin-2-yl)methanone, -continued

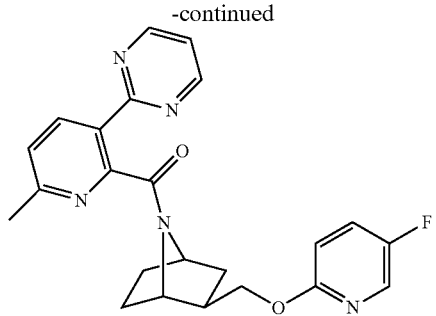

(±)-(2-(((5-fluoropyridin-2-yl)oxy)methyl)-7-azabicyclo[2.2.1]heptan-7-yl)(6-methyl-3-(pyrimidin-2-yl)pyridin-2-yl)methanone,

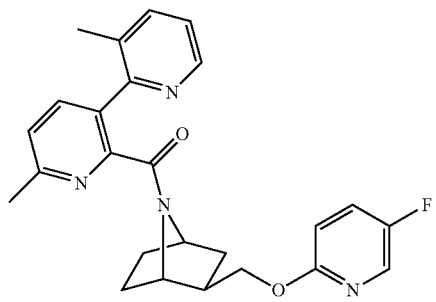

(±)-(3,6'-dimethyl-[2,3'-bipyridin]-2'-yl)(2-(((5-fluoropyridin-2-yl)oxy)methyl)-7-azabicyclo[2.2.1]heptan-7-yl)methanone,

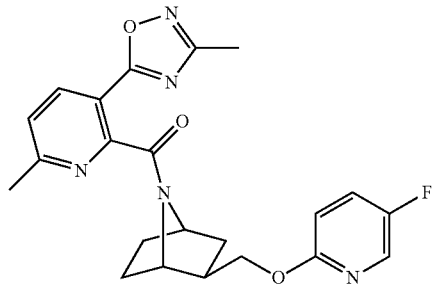

(±)-(2-(((5-fluoropyridin-2-yl)oxy)methyl)-7-azabicyclo[2.2.1]heptan-7-yl)(6-methyl-3-(3-methyl-1,2,4-oxadiazol-5-yl)pyridin-2-yl)methanone,

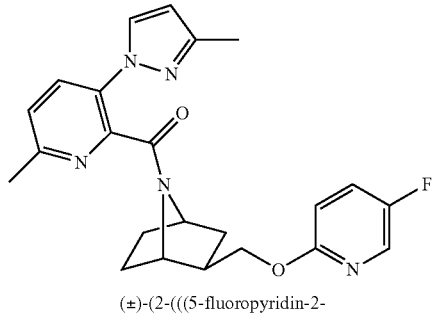

(±)-(2-(((5-fluoropyridin-2-yl)oxy)methyl)-7-azabicyclo[2.2.1]heptan-7-yl)(6-methyl-3-(3-methyl-1H-pyrazol-1-yl)pyridin-2-yl)methanone, -continued

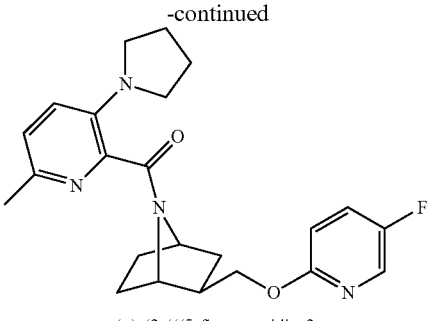

(±)-(2-(((5-fluoropyridin-2-yl)oxy)methyl)-7-azabicyclo[2.2.1]heptan-7-yl)(6-methyl-3-(pyrrolidin-1-yl)pyridin-2-yl)methanone,

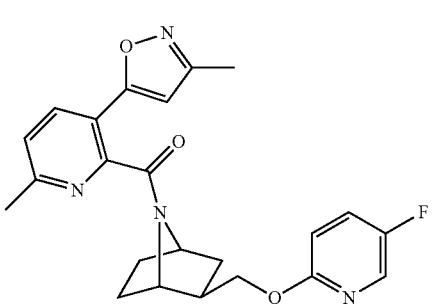

(±)-(2-(((5-fluoropyridin-2-yl)oxy)methyl)-7-azabicyclo[2.2.1]heptan-7-yl)(6-methyl-3-(3-methylisoxazol-5-yl)pyridin-2-yl)methanone,

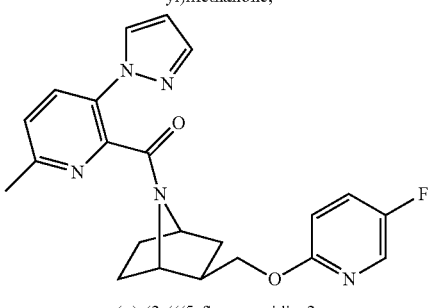

(±)-(2-(((5-fluoropyridin-2-yl)oxy)methyl)-7-azabicyclo[2.2.1]heptan-7-yl)(6-methyl-3-(1H-pyrazol-1-yl)pyridin-2-yl)methanone,

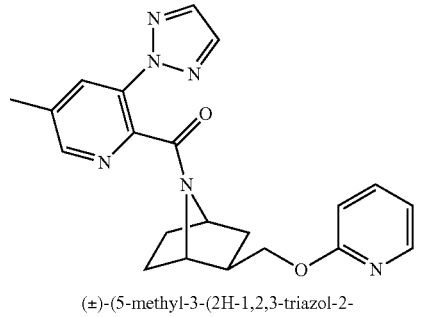

(±)-(5-methyl-3-(2H-1,2,3-triazol-2-yl)pyridin-2-yl)(2-((pyridin-2-yloxy)methyl)-7-azabicyclo[2.2.1]heptan-7-yl)methanone,

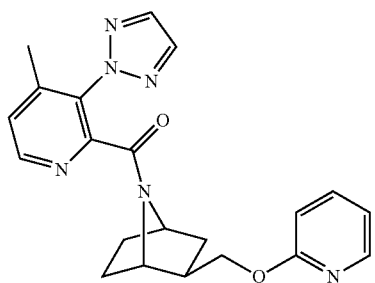 [SMILES: Cc1ccnc(C(=O)N2C3CCC2C(COc2ccccn2)C3)c1-n1nccn1]

(±)-(4-methyl-3-(2H-1,2,3-triazol-2-yl)pyridin-2-yl)(2-((pyridin-2-yloxy)methyl)-7-azabicyclo[2.2.1]heptan-7-yl)methanone,

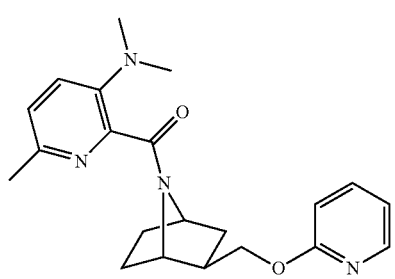 [SMILES: Cc1ccc(N(C)C)c(C(=O)N2C3CCC2C(COc2ccccn2)C3)n1]

(±)-(3-(dimethylamino)-6-methylpyridin-2-yl)(2-((pyridin-2-yloxy)methyl)-7-azabicyclo[2.2.1]heptan-7-yl)methanone,

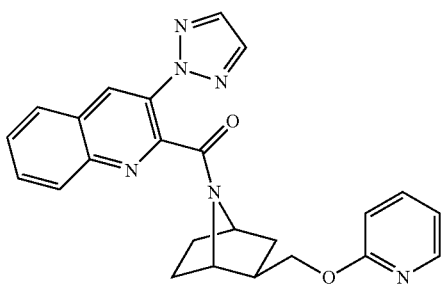 [SMILES: O=C(c1nc2ccccc2cc1-n1nccn1)N1C2CCC1C(COc1ccccn1)C2]

(±)-(3-(2H-1,2,3-triazol-2-yl)quinolin-2-yl)(2-((pyridin-2-yloxy)methyl)-7-azabicyclo[2.2.1]heptan-7-yl)methanone,

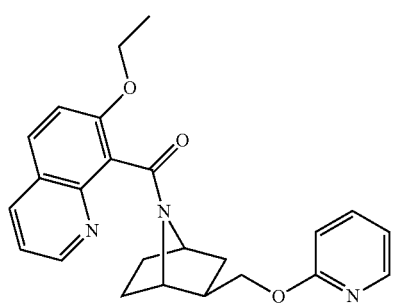

(±)-(7-ethoxyquinolin-8-yl)(2-((pyridin-2-yloxy)methyl)-7-azabicyclo[2.2.1]heptan-7-yl)methanone,

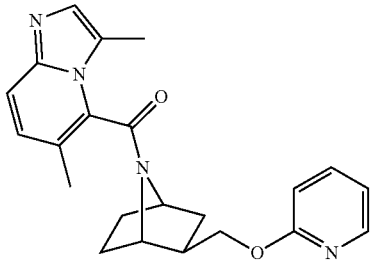

(±)-(3,6-dimethylimidazo[1,2-a]pyridin-5-yl)(2-((pyridin-2-yloxy)methyl)-7-azabicyclo[2.2.1]heptan-7-yl)methanone,

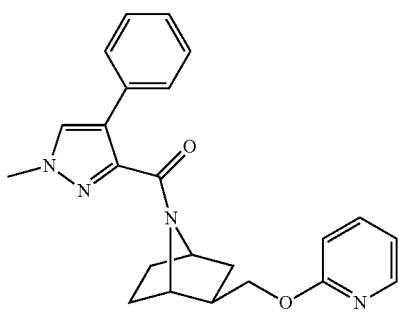

(±)-(1-methyl-4-phenyl-1H-pyrazol-3-yl)((1S,2R,4R)-2-((pyridin-2-yloxy)methyl)-7-azabicyclo[2.2.1]heptan-7-yl)methanone,

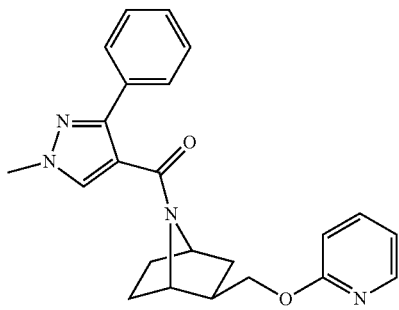

(±)-(1-methyl-3-phenyl-1H-pyrazol-4-yl)((1S,2R,4R)-2-((pyridin-2-yloxy)methyl)-7-azabicyclo[2.2.1]heptan-7-yl)methanone,

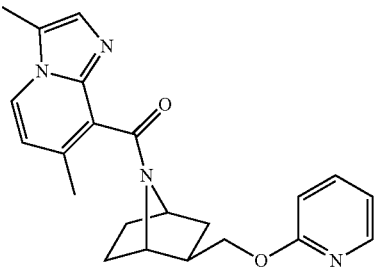

(±)-((3,7-dimethylimidazo[1,2-a]pyridin-8-yl)(2-((pyridin-2-yloxy)methyl)-7-azabicyclo[2.2.1]heptan-7-yl)methanone, -continued

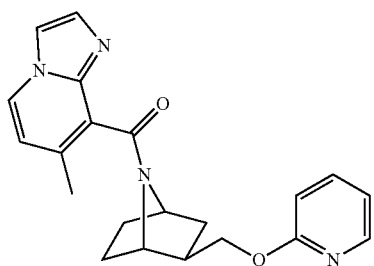

(±)-(7-methylimidazo[1,2-a]pyridin-8-yl)(2-((pyridin-2-yloxy)methyl)-7-azabicyclo[2.2.1]heptan-7-yl)methanone,

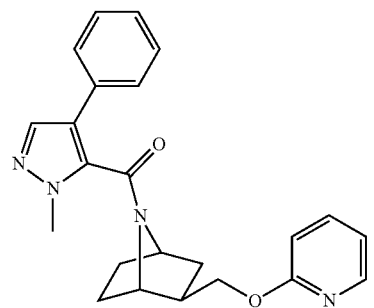

(±)-(1-methyl-4-phenyl-1H-pyrazol-5-yl)(2-((pyridin-2-yloxy)methyl)-7-azabicyclo[2.2.1]heptan-7-yl)methanone,

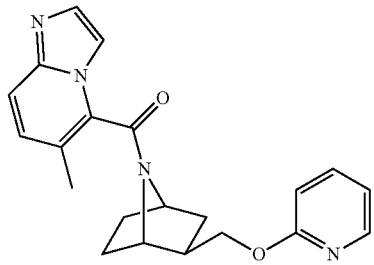

(±)-((6-methylimidazo[1,2-a]pyridin-5-yl)(2-((pyridin-2-yloxy)methyl)-7-azabicyclo[2.2.1]heptan-7-yl)methanone,

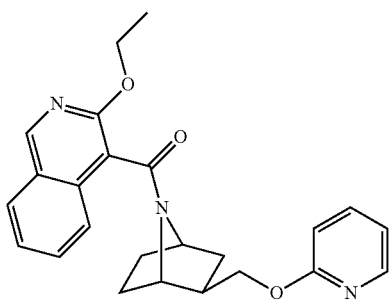

(±)-(3-ethoxyisoquinolin-4-yl)(2-((pyridin-2-yloxy)methyl)-7-azabicyclo[2.2.1]heptan-7-yl)methanone, -continued

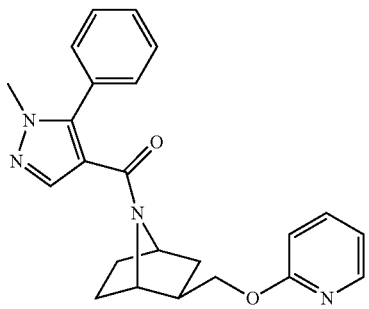

(±)-(1-methyl-5-phenyl-1H-pyrazol-4-yl)(-2-((pyridin-2-yloxy)methyl)-7-azabicyclo[2.2.1]heptan-7-yl)methanone,

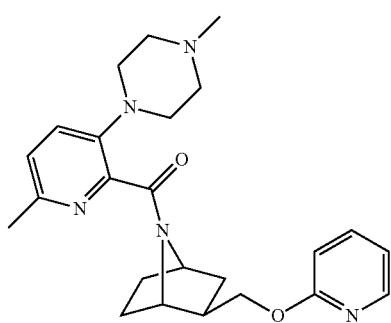

(±)-(6-methyl-3-(4-methylpiperazin-1-yl)pyridin-2-yl)(2-((pyridin-2-yloxy)methyl)-7-azabicyclo[2.2.1]heptan-7-yl)methanone,

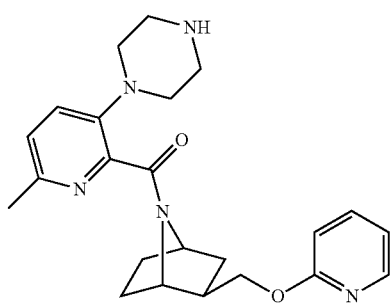

(±)-(6-methyl-3-(piperazin-1-yl)pyridin-2-yl)(2-((pyridin-2-yloxy)methyl)-7-azabicyclo[2.2.1]heptan-7-yl)methanone,

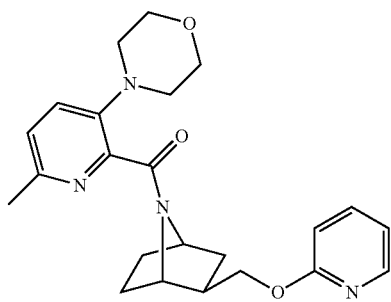

(±)-(6-methyl-3-morpholinopyridin-2-yl)((1S,2R,4R)-2-((pyridin-2-yloxy)methyl)-7-azabicyclo[2.2.1]heptan-7-yl)methanone, -continued

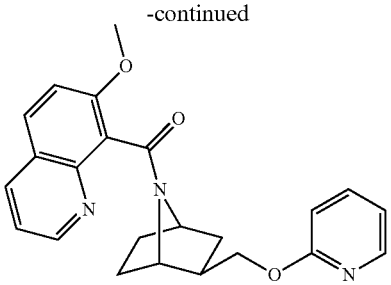

(±)-(7-methoxyquinolin-8-yl)(2-
((pyridin-2-yloxy)methyl)-7-
azabicyclo[2.2.1]heptan-7-
yl)methanone,

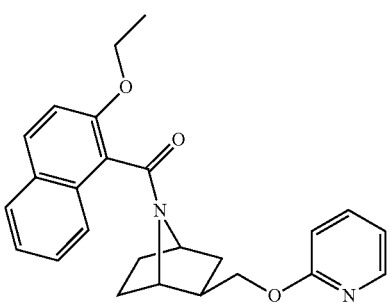

(±)-(2-ethoxynaphthalen-1-yl)(2-
((pyridin-2-yloxy)methyl)-7-
azabicyclo[2.2.1]heptan-7-
yl)methanone,

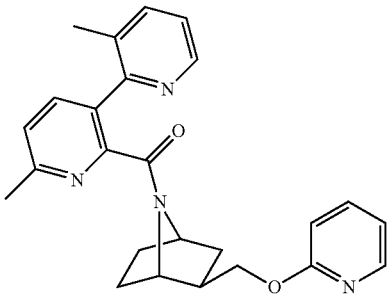 [SMILES: Cc1ccc(-c2ncccc2C)c(C(=O)N2C3CCC2C(COc2ccccn2)C3)n1]

(±)-(3,6'-dimethyl-[2,3'-bipyridin]-2'-
yl)(2-((pyridin-2-yloxy)methyl)-7-
azabicyclo[2.2.1]heptan-7-
yl)methanone,

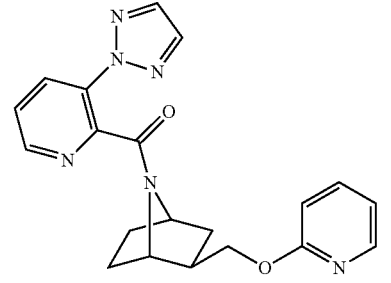 [SMILES: O=C(c1ncccc1-n1nccn1)N1C2CCC1C(COc1ccccn1)C2]

(±)-(3-(2H-1,2,3-triazol-2-yl)pyridin-2-
yl)(2-((pyridin-2-yloxy)methyl)-7-
azabicyclo[2.2.1]heptan-7-
yl)methanone, -continued

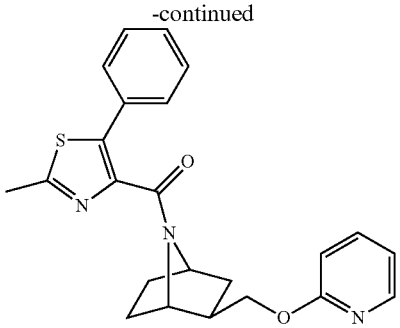

(±)-(2-methyl-5-phenylthiazol-4-yl)(2-
((pyridin-2-yloxy)methyl)-7-
azabicyclo[2.2.1]heptan-7-
yl)methanone,

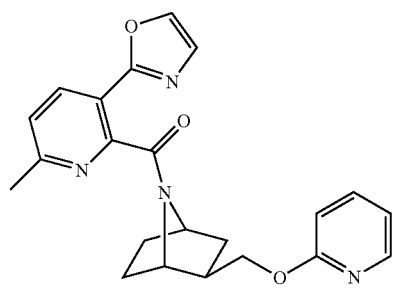 [SMILES: Cc1ccc(-c2ncco2)c(C(=O)N2C3CCC2C(COc2ccccn2)C3)n1]

(±)-(6-methyl-3-(oxazol-2-yl)pyridin-2-
yl)(2-((pyridin-2-yloxy)methyl)-7-
azabicyclo[2.2.1]heptan-7-
yl)methanone,

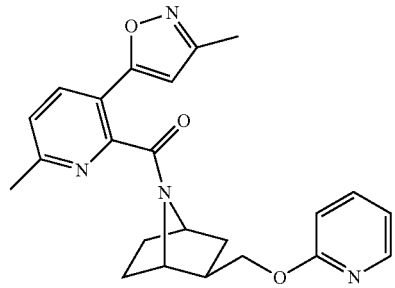

(±)-(6-methyl-3-(3-methylisoxazol-5-
yl)pyridin-2-yl)(2-((pyridin-2-
yloxy)methyl)-7-
azabicyclo[2.2.1]heptan-7-
yl)methanone,

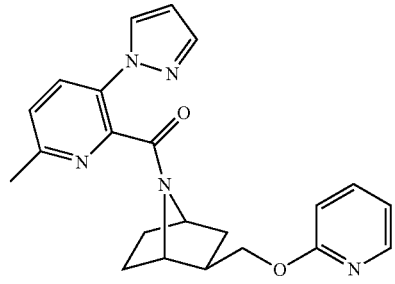 [SMILES: Cc1ccc(-n2cccn2)c(C(=O)N2C3CCC2C(COc2ccccn2)C3)n1]

(±)-(6-methyl-3-(1H-pyrazol-1-
yl)pyridin-2-yl)(2-((pyridin-2-
yloxy)methyl)-7-
azabicyclo[2.2.1]heptan-7-
yl)methanone,

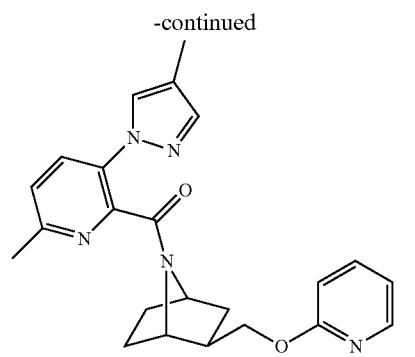

(±)-(6-methyl-3-(4-methyl-1H-pyrazol-1-yl)pyridin-2-yl)(2-((pyridin-2-yloxy)methyl)-7-azabicyclo[2.2.1]heptan-7-yl)methanone,

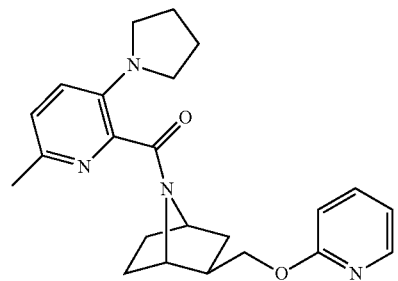 [SMILES: Cc1ccc(N2CCCC2)c(C(=O)N2C3CCC2C(COc2ccccn2)C3)n1]

(±)-(6-methyl-3-(pyrrolidin-1-yl)pyridin-2-yl)(2-((pyridin-2-yloxy)methyl)-7-azabicyclo[2.2.1]heptan-7-yl)methanone,

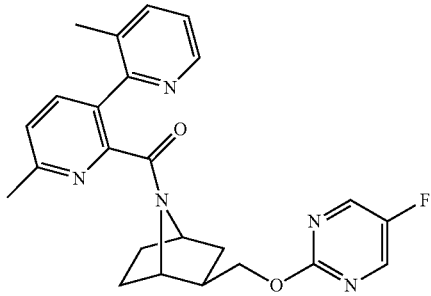

(±)-(3,6'-dimethyl-[2,3'-bipyridin]-2'-yl)(2-(((5-fluoropyrimidin-2-yl)oxy)methyl)-7-azabicyclo[2.2.1]heptan-7-yl)methanone,

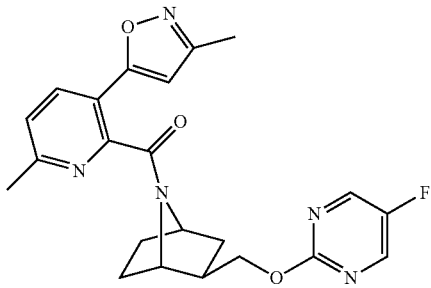

(±)-(2-(((5-fluoropyrimidin-2-yl)oxy)methyl)-7-azabicyclo[2.2.1]heptan-7-yl)(6-methyl-3-(3-methylisoxazol-5-yl)pyridin-2-yl)methanone,

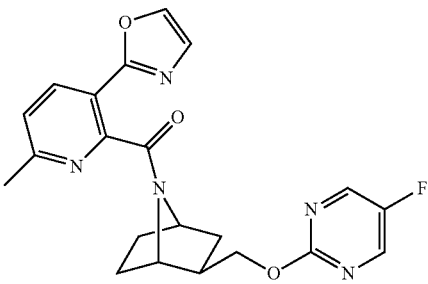 [SMILES: Cc1ccc(-c2ncco2)c(C(=O)N2C3CCC2C(COc2ncc(F)cn2)C3)n1]

(±)-(2-(((5-fluoropyrimidin-2-yl)oxy)methyl)-7-azabicyclo[2.2.1]heptan-7-yl)(6-methyl-3-(oxazol-2-yl)pyridin-2-yl)methanone,

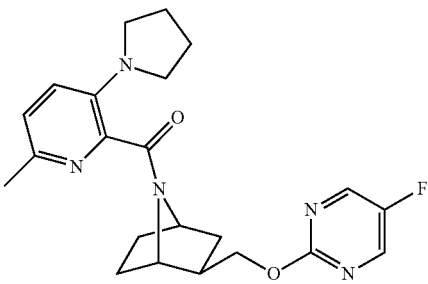 [SMILES: Cc1ccc(N2CCCC2)c(C(=O)N2C3CCC2C(COc2ncc(F)cn2)C3)n1]

(±)-(2-(((5-fluoropyrimidin-2-yl)oxy)methyl)-7-azabicyclo[2.2.1]heptan-7-yl)(6-methyl-3-(pyrrolidin-1-yl)pyridin-2-yl)methanone,

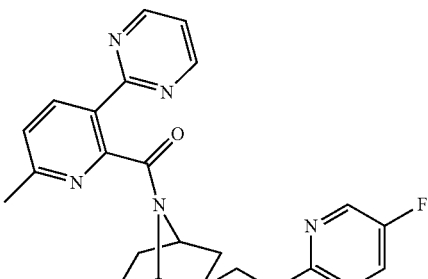

(±)-(2-(((5-fluoropyrimidin-2-yl)oxy)methyl)-7-azabicyclo[2.2.1]heptan-7-yl)(6-methyl-3-(pyrimidin-2-yl)pyridin-2-yl)methanone,

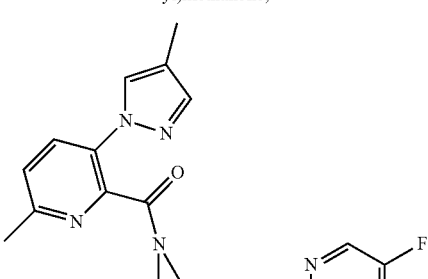

(±)-(2-(((5-fluoropyrimidin-2-yl)oxy)methyl)-7-azabicyclo[2.2.1]heptan-7-yl)(6-methyl-3-(4-methyl-1H-pyrazol-1-yl)pyridin-2-yl)methanone, -continued

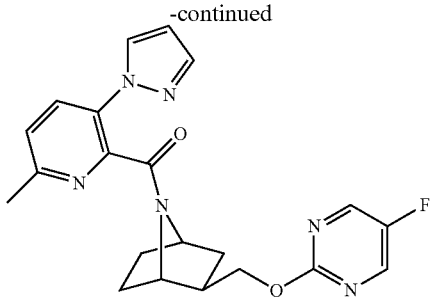

(±)-(2-(((5-fluoropyrimidin-2-
yl)oxy)methyl)-7-
azabicyclo[2.2.1]heptan-7-yl)(6-methyl-
3-(1H-pyrazol-1-yl)pyridin-2-
yl)methanone,

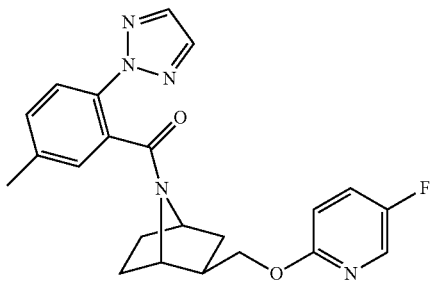 [SMILES: Cc1ccc(-n2nccn2)c(C(=O)N2C3CCC2C(COc2ccc(F)cn2)C3)c1]

(±)-(2-(((5-fluoropyridin-2-
yl)oxy)methyl)-7-
azabicyclo[2.2.1]heptan-7-yl)(5-methyl-
2-(2H-1,2,3-triazol-2-
yl)phenyl)methanone,

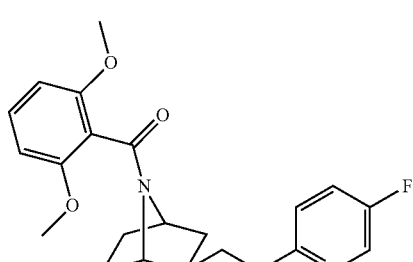

(±)-(2,6-dimethoxyphenyl)(2-(((5-
fluoropyridin-2-yl)oxy)methyl)-7-
azabicyclo[2.2.1]heptan-7-
yl)methanone,

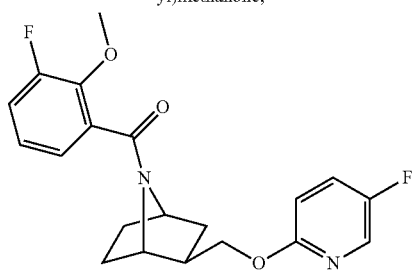

(±)-((3-fluoro-2-methoxyphenyl)(2-(((5-
fluoropyridin-2-yl)oxy)methyl)-7-
azabicyclo[2.2.1]heptan-7-
yl)methanone, -continued

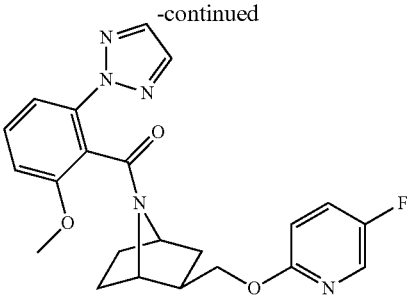

(±)-(2-(((5-fluoropyridin-2-
yl)oxy)methyl)-7-
azabicyclo[2.2.1]heptan-7-yl)(2-
methoxy-6-(2H-1,2,3-triazol-2-
yl)phenyl)methanone,

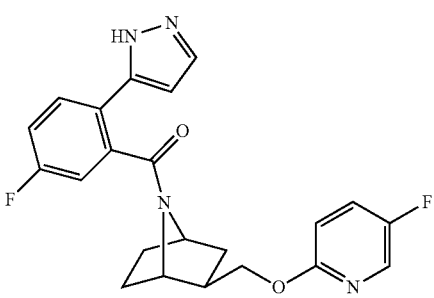 [SMILES: O=C(c1cc(F)ccc1-c1ccn[nH]1)N1C2CCC1C(COc1ccc(F)cn1)C2]

(±)-(5-fluoro-2-(1H-pyrazol-5-
yl)phenyl)(2-(((5-fluoropyridin-2-
yl)oxy)methyl)-7-
azabicyclo[2.2.1]heptan-7-
yl)methanone,

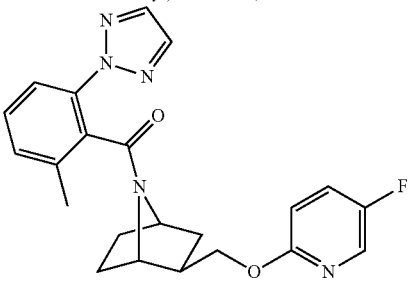

(±)-(2-(((5-fluoropyridin-2-
yl)oxy)methyl)-7-
azabicyclo[2.2.1]heptan-7-yl)(2-methyl-
6-(2H-1,2,3-triazol-2-
yl)phenyl)methanone,

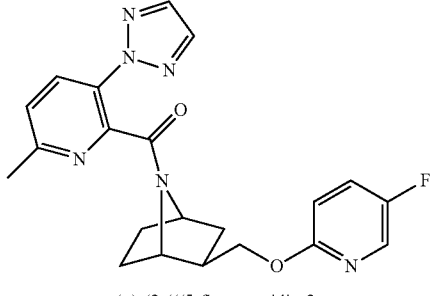

(±)-(2-(((5-fluoropyridin-2-
yl)oxy)methyl)-7-
azabicyclo[2.2.1]heptan-7-yl)(6-methyl-
3-(2H-1,2,3-triazol-2-yl)pyridin-2-
yl)methanone,

765

-continued

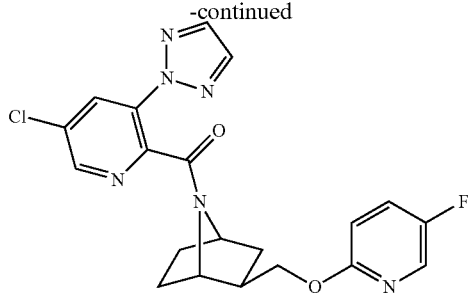

(±)-(5-chloro-3-(2H-1,2,3-triazol-2-yl)pyridin-2-yl)(2-(((5-fluoropyridin-2-yl)oxy)methyl)-7-azabicyclo[2.2.1]heptan-7-yl)methanone,

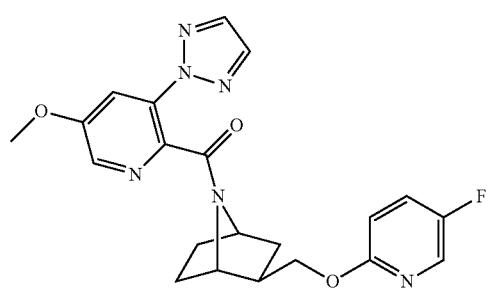 [SMILES: COc1cnc(C(=O)N2C3CCC2C(COc2ccc(F)cn2)C3)c(-n2nccn2)c1]

(±)-(2-(((5-fluoropyridin-2-yl)oxy)methyl)-7-azabicyclo[2.2.1]heptan-7-yl)(5-methoxy-3-(2H-1,2,3-triazol-2-yl)pyridin-2-yl)methanone,

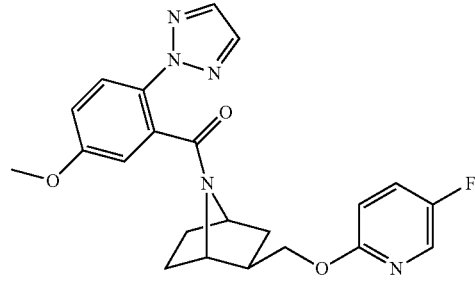 [SMILES: COc1ccc(-n2nccn2)c(C(=O)N2C3CCC2C(COc2ccc(F)cn2)C3)c1]

(±)-(2-(((5-fluoropyridin-2-yl)oxy)methyl)-7-azabicyclo[2.2.1]heptan-7-yl)(5-methoxy-2-(2H-1,2,3-triazol-2-yl)phenyl)methanone,

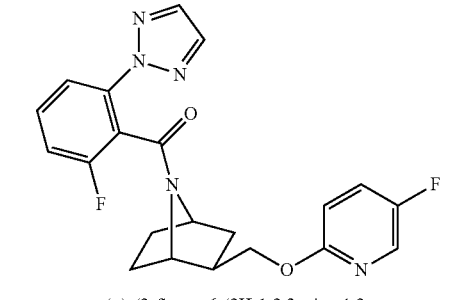

(±)-(2-fluoro-6-(2H-1,2,3-triazol-2-yl)phenyl)(2-(((5-fluoropyridin-2-yl)oxy)methyl)-7-azabicyclo[2.2.1]heptan-7-yl)methanone,

766

-continued

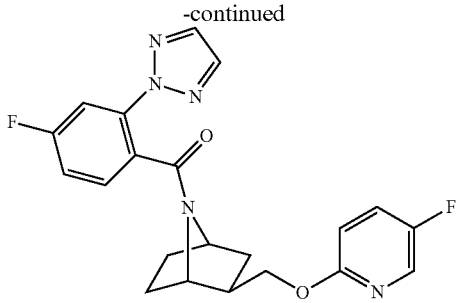

(±)-(4-fluoro-2-(2H-1,2,3-triazol-2-yl)phenyl)(2-(((5-fluoropyridin-2-yl)oxy)methyl)-7-azabicyclo[2.2.1]heptan-7-yl)methanone,

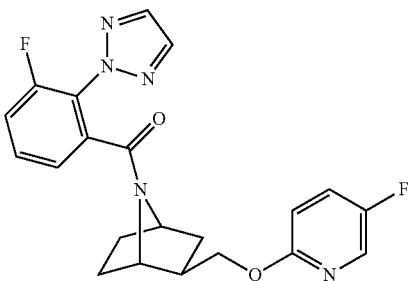

(±)-(3-fluoro-2-(2H-1,2,3-triazol-2-yl)phenyl)(2-(((5-fluoropyridin-2-yl)oxy)methyl)-7-azabicyclo[2.2.1]heptan-7-yl)methanone,

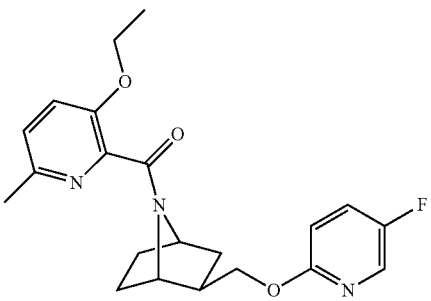 [SMILES: CCOc1ccc(C)nc1C(=O)N1C2CCC1C(COc1ccc(F)cn1)C2]

(±)-(3-ethoxy-6-methylpyridin-2-yl)(2-(((5-fluoropyridin-2-yl)oxy)methyl)-7-azabicyclo[2.2.1]heptan-7-yl)methanone,

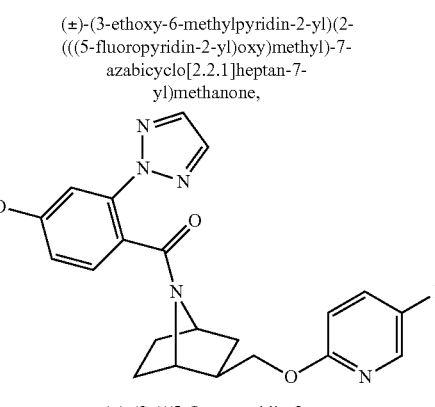

(±)-(2-(((5-fluoropyridin-2-yl)oxy)methyl)-7-azabicyclo[2.2.1]heptan-7-yl)(4-methoxy-2-(2H-1,2,3-triazol-2-yl)phenyl)methanone,

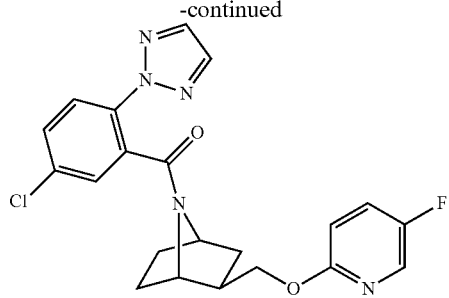

(±)-(5-chloro-2-(2H-1,2,3-triazol-2-yl)phenyl)(2-(((5-fluoropyridin-2-yl)oxy)methyl)-7-azabicyclo[2.2.1]heptan-7-yl)methanone,

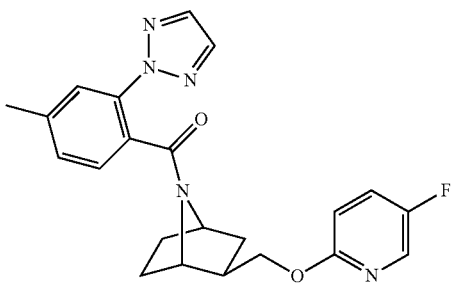 [SMILES: Cc1ccc(C(=O)N2C3CCC2C(COc2ccc(F)cn2)C3)c(-n2nccn2)c1]

(±)-(2-(((5-fluoropyridin-2-yl)oxy)methyl)-7-azabicyclo[2.2.1]heptan-7-yl)(4-methyl-2-(2H-1,2,3-triazol-2-yl)phenyl)methanone,

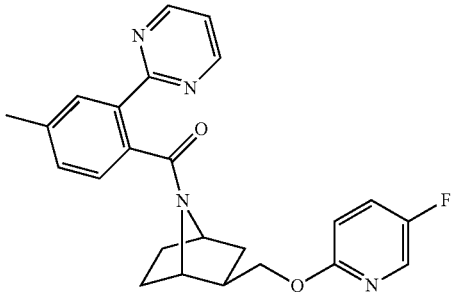 [SMILES: Cc1ccc(C(=O)N2C3CCC2C(COc2ccc(F)cn2)C3)c(-c2ncccn2)c1]

(±)-(2-(((5-fluoropyridin-2-yl)oxy)methyl)-7-azabicyclo[2.2.1]heptan-7-yl)(4-methyl-2-(pyrimidin-2-yl)phenyl)methanone,

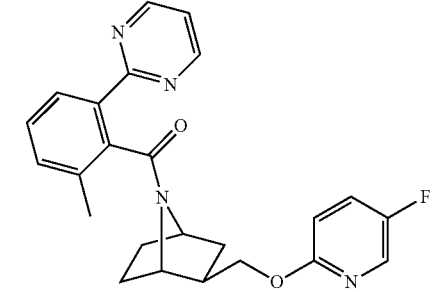 [SMILES: Cc1cccc(-c2ncccn2)c1C(=O)N1C2CCC1C(COc1ccc(F)cn1)C2]

(±)-(2-(((5-fluoropyridin-2-yl)oxy)methyl)-7-azabicyclo[2.2.1]heptan-7-yl)(2-methyl-6-(pyrimidin-2-yl)phenyl)methanone,

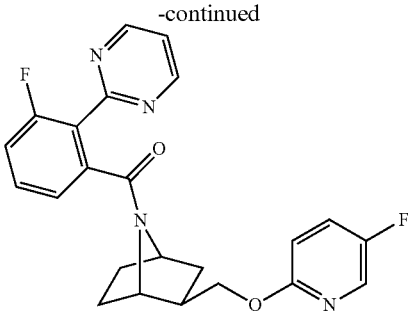

(±)-(3-fluoro-2-(pyrimidin-2-yl)phenyl)(-2-(((5-fluoropyridin-2-yl)oxy)methyl)-7-azabicyclo[2.2.1]heptan-7-yl)methanone,

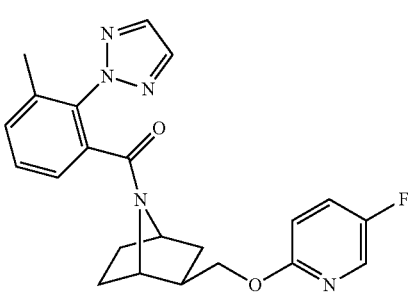 [SMILES: Cc1cccc(C(=O)N2C3CCC2C(COc2ccc(F)cn2)C3)c1-n1nccn1]

(±)-(2-(((5-fluoropyridin-2-yl)oxy)methyl)-7-azabicyclo[2.2.1]heptan-7-yl)(3-methyl-2-(2H-1,2,3-triazol-2-yl)phenyl)methanone,

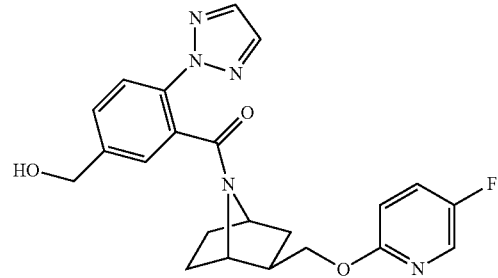 [SMILES: O=C(c1cc(CO)ccc1-n1nccn1)N1C2CCC1C(COc1ccc(F)cn1)C2]

(±)-(2-(((5-fluoropyridin-2-yl)oxy)methyl)-7-azabicyclo[2.2.1]heptan-7-yl)(5-(hydroxymethyl)-2-(2H-1,2,3-triazol-2-yl)phenyl)methanone,

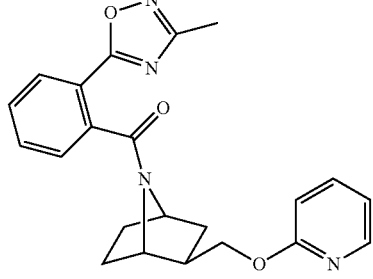

(±)-(2-(3-methyl-1,2,4-oxadiazol-5-yl)phenyl)(2-((pyridin-2-yloxy)methyl)-7-azabicyclo[2.2.1]heptan-7-yl)methanone, -continued

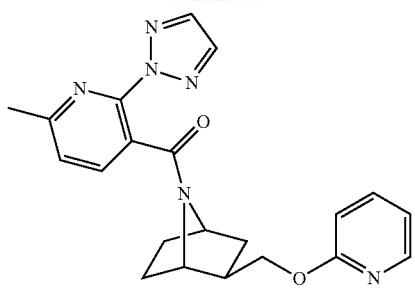 [SMILES: Cc1ccc(C(=O)N2C3CCC2C(COc2ccccn2)C3)c(-n2nccn2)n1]

(±)-(6-methyl-2-(2H-1,2,3-triazol-2-yl)pyridin-3-yl)(2-((pyridin-2-yloxy)methyl)-7-azabicyclo[2.2.1]heptan-7-yl)methanone,

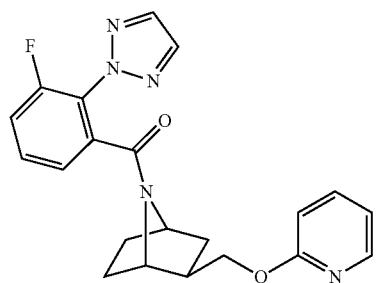 [SMILES: O=C(c1cccc(F)c1-n1nccn1)N1C2CCC1C(COc1ccccn1)C2]

(±)-(3-fluoro-2-(2H-1,2,3-triazol-2-yl)phenyl)(2-((pyridin-2-yloxy)methyl)-7-azabicyclo[2.2.1]heptan-7-yl)methanone,

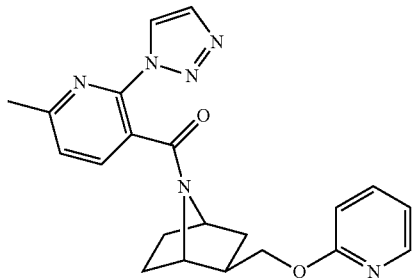 [SMILES: Cc1ccc(C(=O)N2C3CCC2C(COc2ccccn2)C3)c(-n2ccnn2)n1]

(±)-(6-methyl-2-(1H-1,2,3-triazol-1-yl)pyridin-3-yl)(2-((pyridin-2-yloxy)methyl)-7-azabicyclo[2.2.1]heptan-7-yl)methanone,

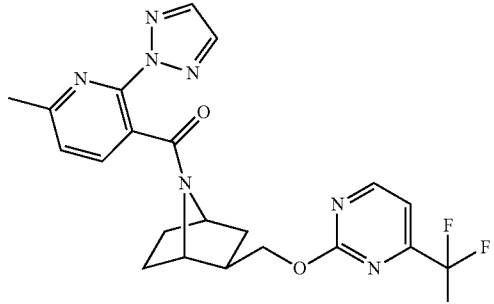

(±)-(6-methyl-2-(2H-1,2,3-triazol-2-yl)pyridin-3-yl)(2-(((4-(trifluoromethyl)pyrimidin-2-yl)oxy)methyl)-7-azabicyclo[2.2.1]heptan-7-yl)methanone, -continued

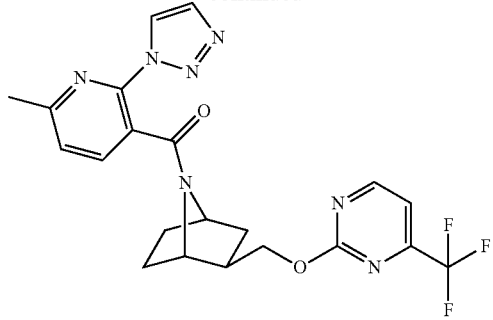 [SMILES: Cc1ccc(C(=O)N2C3CCC2C(COc2nccc(C(F)(F)F)n2)C3)c(-n2ccnn2)n1]

(±)-(6-methyl-2-(1H-1,2,3-triazol-1-yl)pyridin-3-yl)(2-(((4-(trifluoromethyl)pyrimidin-2-yl)oxy)methyl)-7-azabicyclo[2.2.1]heptan-7-yl)methanone,

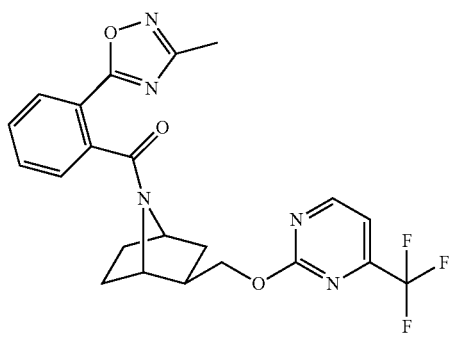

(±)-(2-(3-methyl-1,2,4-oxadiazol-5-yl)phenyl)(2-(((4-(trifluoromethyl)pyrimidin-2-yl)oxy)methyl)-7-azabicyclo[2.2.1]heptan-7-yl)methanone,

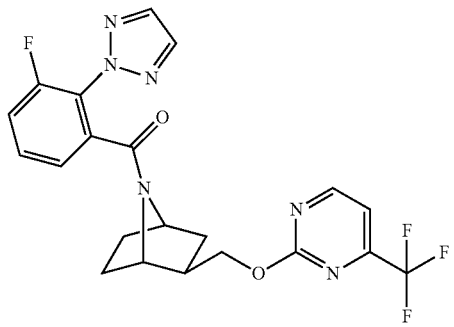 [SMILES: O=C(c1cccc(F)c1-n1nccn1)N1C2CCC1C(COc1nccc(C(F)(F)F)n1)C2]

(±)-(3-fluoro-2-(2H-1,2,3-triazol-2-yl)phenyl)(2-(((4-(trifluoromethyl)pyrimidin-2-yl)oxy)methyl)-7-azabicyclo[2.2.1]heptan-7-yl)methanone,

771

-continued

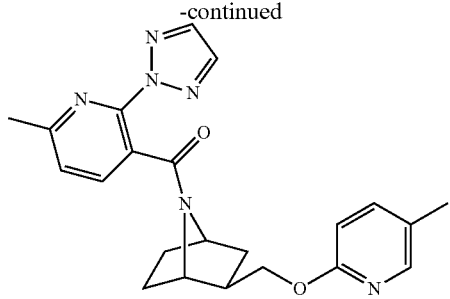

(±)-(6-methyl-2-(2H-1,2,3-triazol-2-
yl)pyridin-3-yl)(2-(((5-methylpyridin-2-
yl)oxy)methyl)-7-
azabicyclo[2.2.1]heptan-7-
yl)methanone,

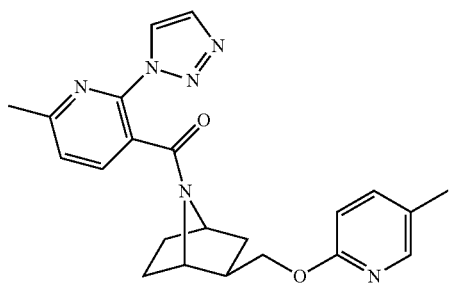

(±)-(6-methyl-2-(1H-1,2,3-triazol-1-
yl)pyridin-3-yl)(2-(((5-methylpyridin-2-
yl)oxy)methyl)-7-
azabicyclo[2.2.1]heptan-7-
yl)methanone,

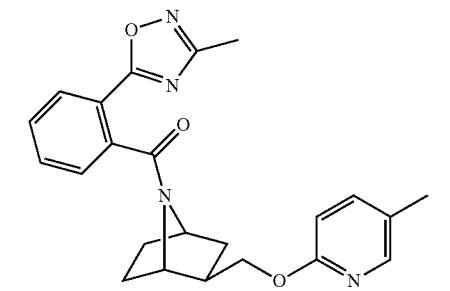

(±)-(2-(3-methyl-1,2,4-oxadiazol-5-
yl)phenyl)(2-(((5-methylpyridin-2-
yl)oxy)methyl)-7-
azabicyclo[2.2.1]heptan-7-
yl)methanone,

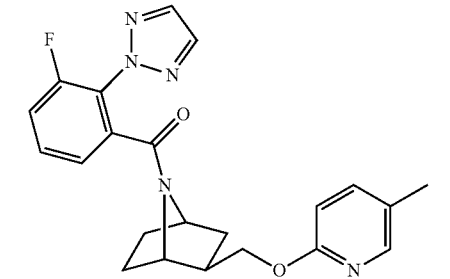 [SMILES: Cc1ccc(OCC2CC3CCC2N3C(=O)c2cccc(F)c2-n2nccn2)nc1]

(±)-(3-fluoro-2-(2H-1,2,3-triazol-2-
yl)phenyl)(2-(((5-methylpyridin-2-
yl)oxy)methyl)-7-
azabicyclo[2.2.1]heptan-7-
yl)methanone,

772

-continued

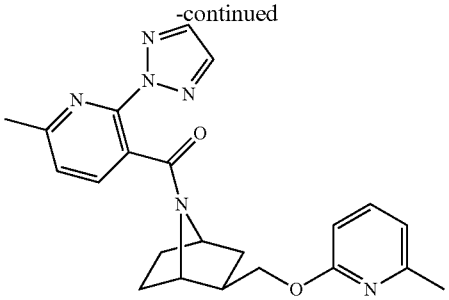

(±)-(6-methyl-2-(2H-1,2,3-triazol-2-
yl)pyridin-3-yl)(2-(((6-methylpyridin-2-
yl)oxy)methyl)-7-
azabicyclo[2.2.1]heptan-7-
yl)methanone,

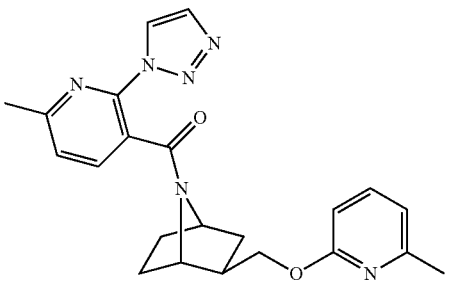

(±)-(6-methyl-2-(1H-1,2,3-triazol-1-
yl)pyridin-3-yl)(2-(((6-methylpyridin-2-
yl)oxy)methyl)-7-
azabicyclo[2.2.1]heptan-7-
yl)methanone,

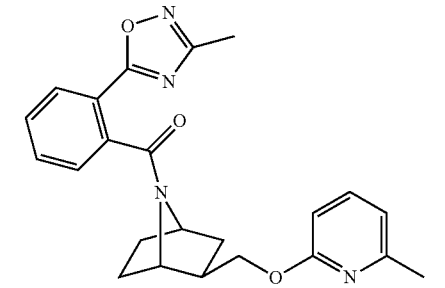

(±)-(2-(3-methyl-1,2,4-oxadiazol-5-
yl)phenyl)(2-(((6-methylpyridin-2-
yl)oxy)methyl)-7-
azabicyclo[2.2.1]heptan-7-
yl)methanone,

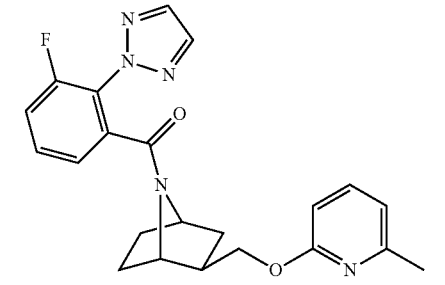 [SMILES: Cc1cccc(OCC2CC3CCC2N3C(=O)c2cccc(F)c2-n2nccn2)n1]

(±)-(3-fluoro-2-(2H-1,2,3-triazol-2-
yl)phenyl)(2-(((6-methylpyridin-2-
yl)oxy)methyl)-7-
azabicyclo[2.2.1]heptan-7-
yl)methanone,

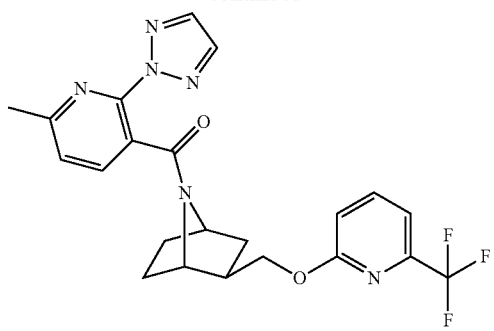 [SMILES: Cc1ccc(C(=O)N2C3CCC2C(COc2cccc(C(F)(F)F)n2)C3)c(-n2nccn2)n1]

(±)-(6-methyl-2-(2H-1,2,3-triazol-2-
yl)pyridin-3-yl)(2-(((6-
(trifluoromethyl)pyridin-2-
yl)oxy)methyl)-7-
azabicyclo[2.2.1]heptan-7-
yl)methanone,

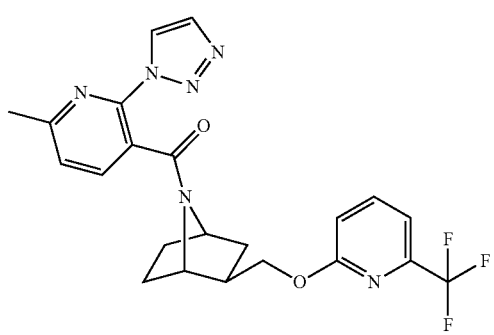

(±)-(6-methyl-2-(1H-1,2,3-triazol-1-
yl)pyridin-3-yl)(2-(((6-
(trifluoromethyl)pyridin-2-
yl)oxy)methyl)-7-
azabicyclo[2.2.1]heptan-7-
yl)methanone,

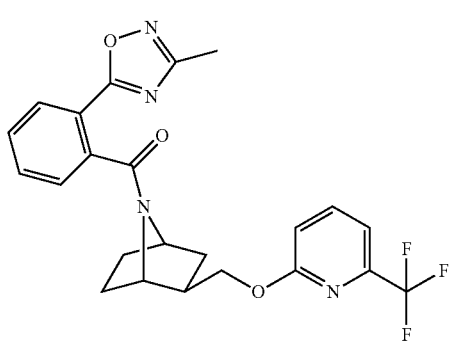

(±)-(2-(3-methyl-1,2,4-oxadiazol-5-
yl)phenyl)(2-(((6-
(trifluoromethyl)pyridin-2-
yl)oxy)methyl)-7-
azabicyclo[2.2.1]heptan-7-
yl)methanone,

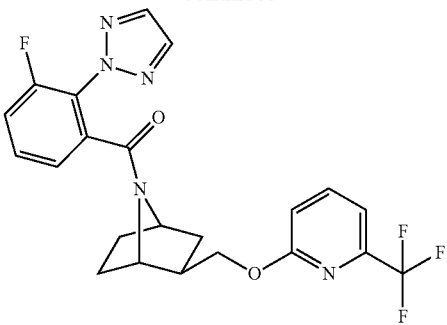 [SMILES: O=C(c1cccc(F)c1-n1nccn1)N1C2CCC1C(COc1cccc(C(F)(F)F)n1)C2]

(±)-(3-fluoro-2-(2H-1,2,3-triazol-2-
yl)phenyl)(2-(((6-
(trifluoromethyl)pyridin-2-
yl)oxy)methyl)-7-
azabicyclo[2.2.1]heptan-7-
yl)methanone,

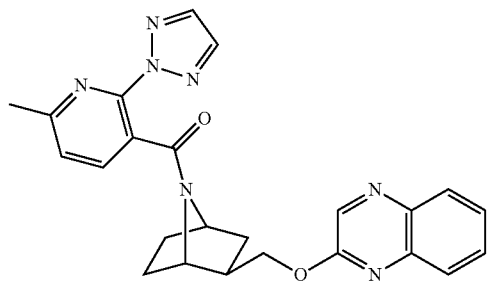 [SMILES: Cc1ccc(C(=O)N2C3CCC2C(COc2cnc4ccccc4n2)C3)c(-n2nccn2)n1]

(±)-(6-methyl-2-(2H-1,2,3-triazol-2-
yl)pyridin-3-yl)(2-((quinoxalin-2-
yloxy)methyl)-7-
azabicyclo[2.2.1]heptan-7-
yl)methanone,

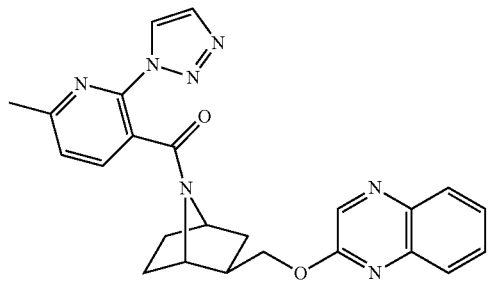 [SMILES: Cc1ccc(C(=O)N2C3CCC2C(COc2cnc4ccccc4n2)C3)c(-n2ccnn2)n1]

(±)-(6-methyl-2-(1H-1,2,3-triazol-1-
yl)pyridin-3-yl)(2-((quinoxalin-2-
yloxy)methyl)-7-
azabicyclo[2.2.1]heptan-7-
yl)methanone,

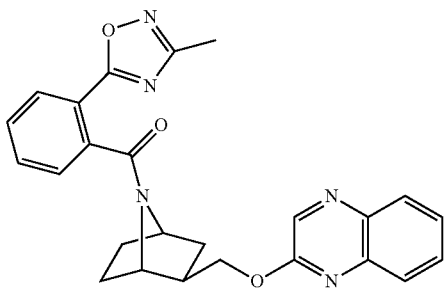

(±)-(2-(3-methyl-1,2,4-oxadiazol-5-
yl)phenyl)(2-((quinoxalin-2-
yloxy)methyl)-7-
azabicyclo[2.2.1]heptan-7-
yl)methanone, -continued

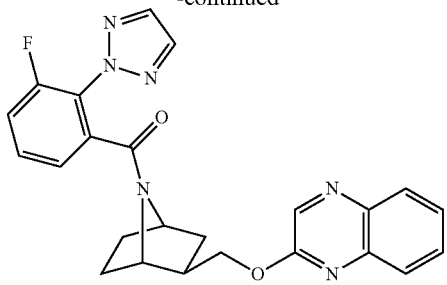

(±)-(3-fluoro-2-(2H-1,2,3-triazol-2-yl)phenyl)(2-((quinoxalin-2-yloxy)methyl)-7-azabicyclo[2.2.1]heptan-7-yl)methanone,

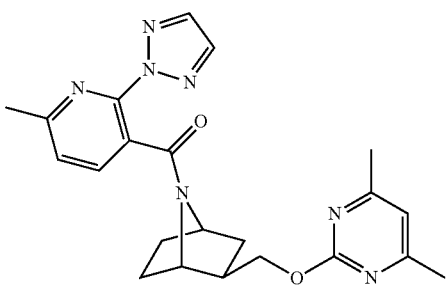

(±)-(2-(((4,6-dimethylpyrimidin-2-yl)oxy)methyl)-7-azabicyclo[2.2.1]heptan-7-yl)(6-methyl-2-(2H-1,2,3-triazol-2-yl)pyridin-3-yl)methanone,

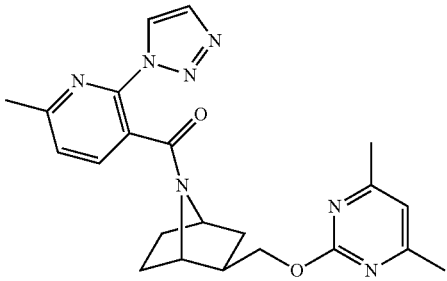

(±)-(2-(((4,6-dimethylpyrimidin-2-yl)oxy)methyl)-7-azabicyclo[2.2.1]heptan-7-yl)(6-methyl-2-(1H-1,2,3-triazol-1-yl)pyridin-3-yl)methanone,

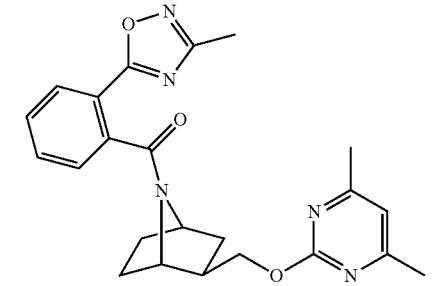

(±)-(2-(((4,6-dimethylpyrimidin-2-yl)oxy)methyl)-7-azabicyclo[2.2.1]heptan-7-yl)(2-(3-methyl-1,2,4-oxadiazol-5-yl)phenyl)methanone, -continued

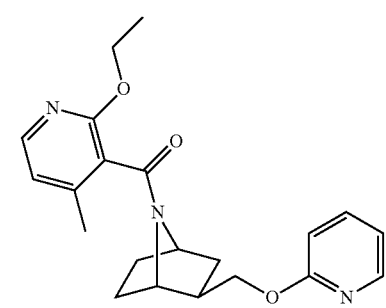 [SMILES: CCOc1nccc(C)c1C(=O)N1C2CCC1C(COc1ccccn1)C2]

(±)-(2-(((4,6-dimethylpyrimidin-2-yl)oxy)methyl)-7-azabicyclo[2.2.1]heptan-7-yl)(3-fluoro-2-(2H-1,2,3-triazol-2-yl)phenyl)methanone,

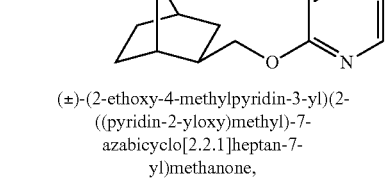

(±)-(2-ethoxy-4-methylpyridin-3-yl)(2-((pyridin-2-yloxy)methyl)-7-azabicyclo[2.2.1]heptan-7-yl)methanone,

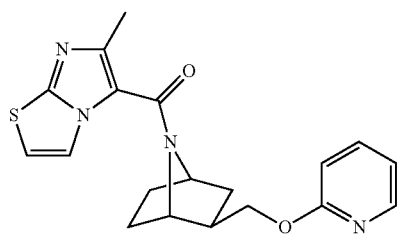 [SMILES: Cc1nc2sccn2c1C(=O)N1C2CCC1C(COc1ccccn1)C2]

(±)-(6-methylimidazo[2,1-b]thiazol-5-yl)(2-((pyridin-2-yloxy)methyl)-7-azabicyclo[2.2.1]heptan-7-yl)methanone,

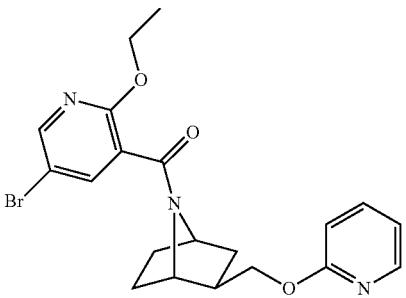 [SMILES: CCOc1ncc(Br)cc1C(=O)N1C2CCC1C(COc1ccccn1)C2]

(±)-(5-bromo-2-ethoxypyridin-3-yl)(2-((pyridin-2-yloxy)methyl)-7-azabicyclo[2.2.1]heptan-7-yl)methanone, -continued

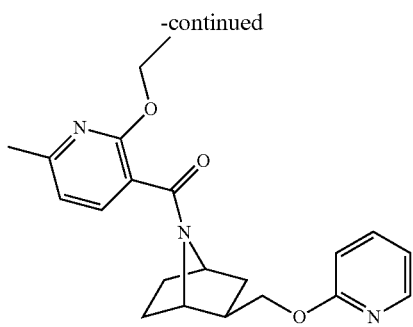

(±)-(2-ethoxy-6-methylpyridin-3-yl)(2-
((pyridin-2-yloxy)methyl)-7-
azabicyclo[2.2.1]heptan-7-
yl)methanone,

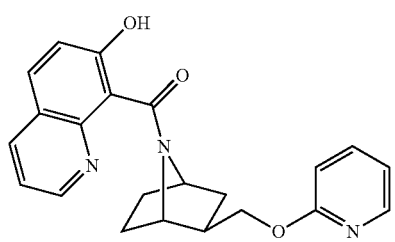 [SMILES: O=C(c1c(O)ccc2cccnc12)N1C2CCC1C(COc1ccccn1)C2]

(±)-(7-hydroxyquinolin-8-yl)(2-
((pyridin-2-yloxy)methyl)-7-
azabicyclo[2.2.1]heptan-7-
yl)methanone,

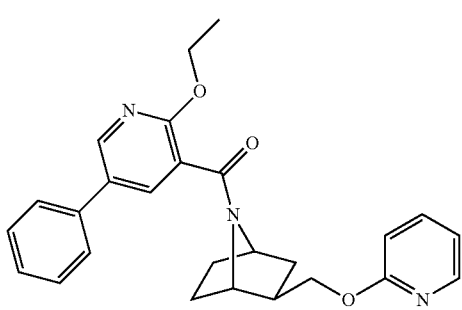 [SMILES: CCOc1ncc(-c2ccccc2)cc1C(=O)N1C2CCC1C(COc1ccccn1)C2]

(±)-(2-ethoxy-5-phenylpyridin-3-yl)(2-
((pyridin-2-yloxy)methyl)-7-
azabicyclo[2.2.1]heptan-7-
yl)methanone,

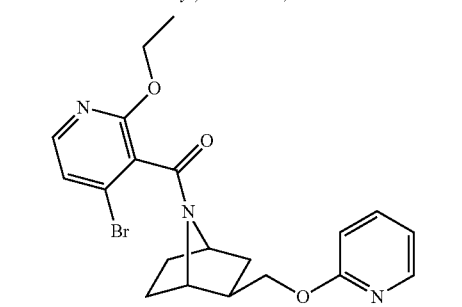

(±)-(4-bromo-2-ethoxypyridin-3-yl)(2-
((pyridin-2-yloxy)methyl)-7-
azabicyclo[2.2.1]heptan-7-
yl)methanone, -continued

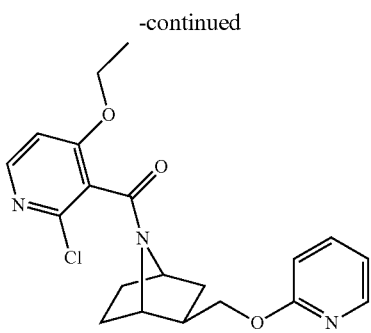

(±)-(2-chloro-4-ethoxypyridin-3-yl)(2-
((pyridin-2-yloxy)methyl)-7-
azabicyclo[2.2.1]heptan-7-
yl)methanone,

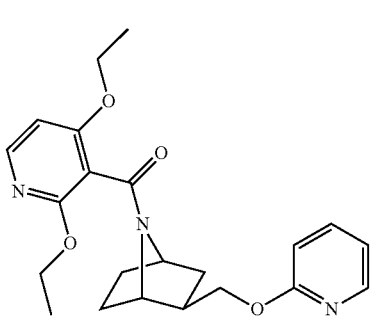 [SMILES: CCOc1ccnc(OCC)c1C(=O)N1C2CCC1C(COc1ccccn1)C2]

(±)-(2,4-diethoxypyridin-3-yl)(2-
((pyridin-2-yloxy)methyl)-7-
azabicyclo[2.2.1]heptan-7-
yl)methanone,

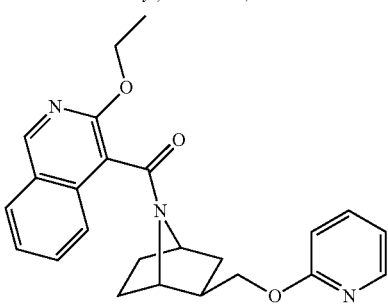

(3-ethoxyisoquinolin-4-yl)((1S,2R,4R)-
2-((pyridin-2-yloxy)methyl)-7-
azabicyclo[2.2.1]heptan-7-
yl)methanone,

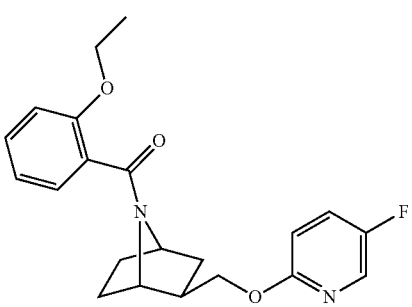 [SMILES: CCOc1ccccc1C(=O)N1C2CCC1C(COc1ccc(F)cn1)C2]

(±)-(2-ethoxyphenyl)(2-(((5-
fluoropyridin-2-yl)oxy)methyl)-7-
azabicyclo[2.2.1]heptan-7-
yl)methanone,

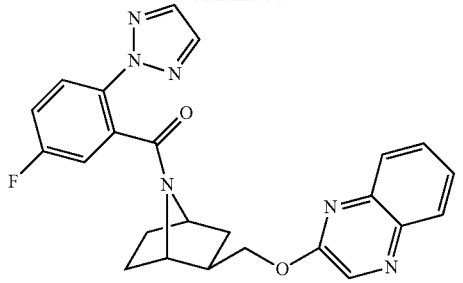 [SMILES: O=C(c1cc(F)ccc1-n1nccn1)N1C2CCC1C(COc1cnc3ccccc3n1)C2]

(±)-(5-fluoro-2-(2H-1,2,3-triazol-2-yl)phenyl)(2-((quinoxalin-2-yloxy)methyl)-7-azabicyclo[2.2.1]heptan-7-yl)methanone,

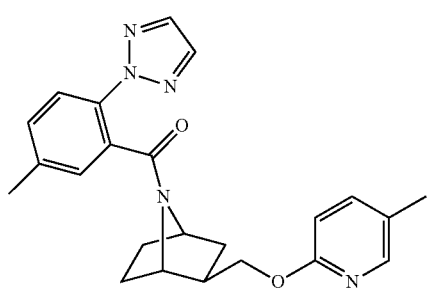

(±)-5-methyl-2-(2H-1,2,3-triazol-2-yl)phenyl)(2-(((5-methylpyridin-2-yl)oxy)methyl)-7-azabicyclo[2.2.1]heptan-7-yl)methanone,

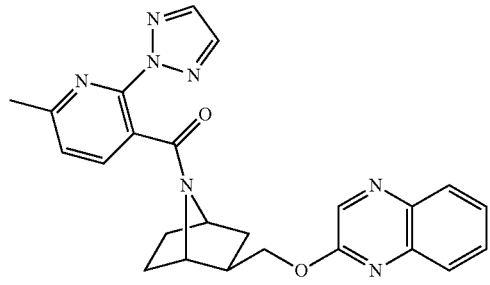 [SMILES: Cc1ccc(C(=O)N2C3CCC2C(COc2cnc4ccccc4n2)C3)c(-n2nccn2)n1]

(±)-(6-methyl-2-(2H-1,2,3-triazol-2-yl)pyridin-3-yl)(2-((quinoxalin-2-yloxy)methyl)-7-azabicyclo[2.2.1]heptan-7-yl)methanone,

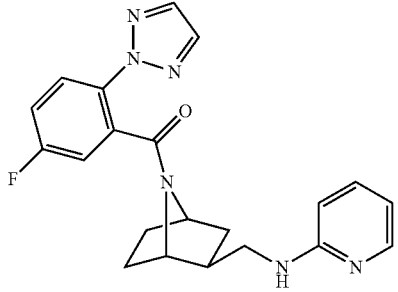 [SMILES: O=C(c1cc(F)ccc1-n1nccn1)N1C2CCC1C(CNc1ccccn1)C2]

(±)-(5-fluoro-2-(2H-1,2,3-triazol-2-yl)phenyl)(2-((pyridin-2-ylamino)methyl)-7-azabicyclo[2.2.1]heptan-7-yl)methanone,

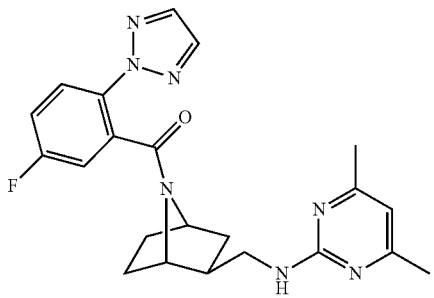 [SMILES: Cc1cc(C)nc(NCC2CC3CCC2N3C(=O)c2cc(F)ccc2-n2nccn2)n1]

(±)-(2-(((4,6-dimethylpyrimidin-2-yl)amino)methyl)-7-azabicyclo[2.2.1]heptan-7-yl)(5-fluoro-2-(2H-1,2,3-triazol-2-yl)phenyl)methanone,

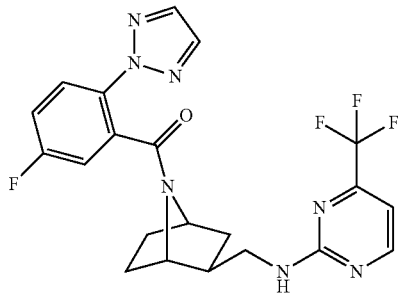

(±)-(5-fluoro-2-(2H-1,2,3-triazol-2-yl)phenyl)(2-(((4-(trifluoromethyl)pyrimidin-2-yl)amino)methyl)-7-azabicyclo[2.2.1]heptan-7-yl)methanone,

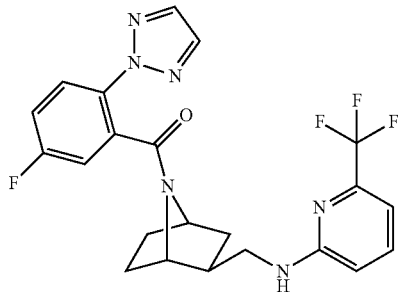 [SMILES: O=C(c1cc(F)ccc1-n1nccn1)N1C2CCC1C(CNc1cccc(C(F)(F)F)n1)C2]

(±)-(5-fluoro-2-(2H-1,2,3-triazol-2-yl)phenyl)(2-(((6-(trifluoromethyl)pyridin-2-yl)amino)methyl)-7-azabicyclo[2.2.1]heptan-7-yl)methanone,

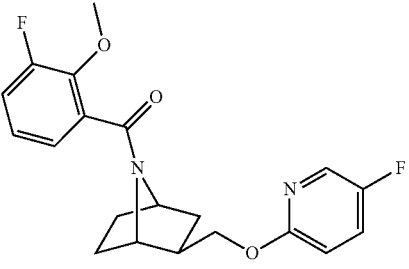 [SMILES: COc1c(F)cccc1C(=O)N1C2CCC1C(COc1ccc(F)cn1)C2]

(±)-(3-fluoro-2-methoxyphenyl)(2-(((5-fluoropyridin-2-yl)oxy)methyl)-7-azabicyclo[2.2.1]heptan-7-yl)methanone,

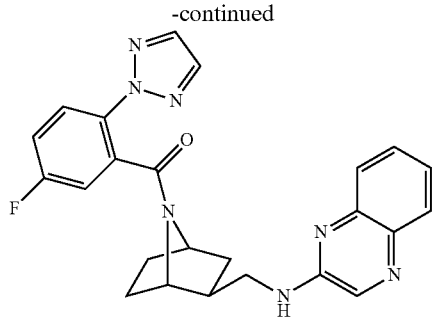

(±)-(5-fluoro-2-(2H-1,2,3-triazol-2-
yl)phenyl)(2-((quinoxalin-2-
ylamino)methyl)-7-
azabicyclo[2.2.1]heptan-7-
yl)methanone,

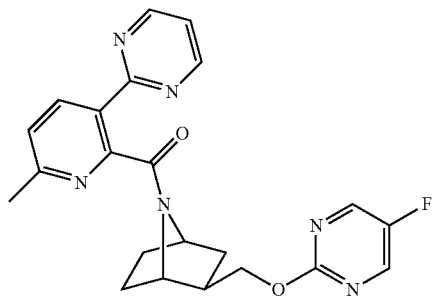 [SMILES: Cc1ccc(-c2ncccn2)c(C(=O)N2C3CCC2C(COc2ncc(F)cn2)C3)n1]

(±)-(2-(((5-fluoropyrimidin-2-
yl)oxy)methyl)-7-
azabicyclo[2.2.1]heptan-7-yl)(6-methyl-
3-(pyrimidin-2-yl)pyridin-2-
yl)methanone,

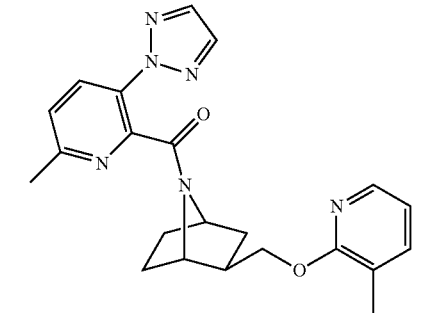 [SMILES: Cc1ccc(-n2nccn2)c(C(=O)N2C3CCC2C(COc2ncccc2C)C3)n1]

(±)-(6-methyl-3-(2H-1,2,3-triazol-2-
yl)pyridin-2-yl)(2-(((3-methylpyridin-2-
yl)oxy)methyl)-7-
azabicyclo[2.2.1]heptan-7-
yl)methanone,

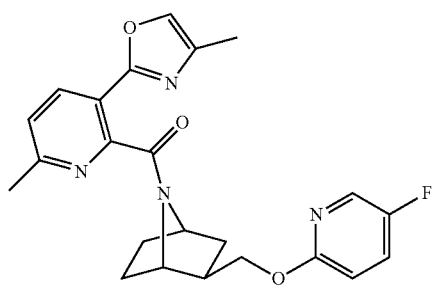

(±)-(2-(((5-fluoropyridin-2-
yl)oxy)methyl)-7-
azabicyclo[2.2.1]heptan-7-yl)(6-methyl-
3-(4-methyloxazol-2-yl)pyridin-2-
yl)methanone,

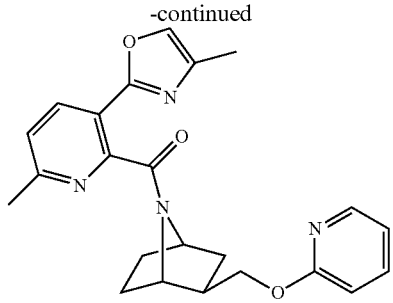

(6-methyl-3-(4-methyloxazol-2-
yl)pyridin-2-yl)((1S,2R,4R)-2-((pyridin-
2-yloxy)methyl)-7-
azabicyclo[2.2.1]heptan-7-
yl)methanone,

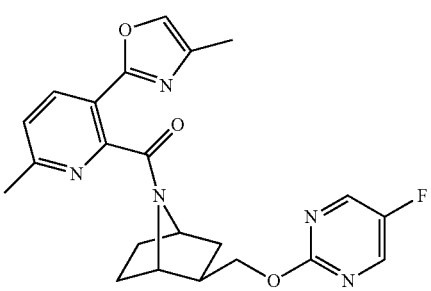

((1S,2R,4R)-2-(((5-fluoropyrimidin-2-
yl)oxy)methyl)-7-
azabicyclo[2.2.1]heptan-7-yl)(6-methyl-
3-(4-methyloxazol-2-yl)pyridin-2-
yl)methanone,

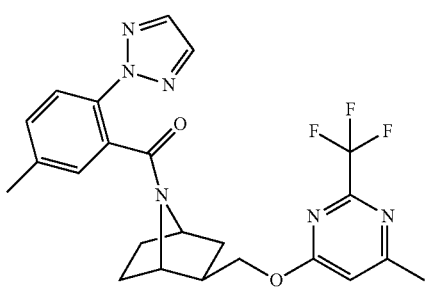

(±)-(5-methyl-2-(2H-1,2,3-triazol-2-
yl)phenyl)(2-(((6-methyl-2-
(trifluoromethyl)pyrimidin-4-
yl)oxy)methyl)-7-
azabicyclo[2.2.1]heptan-7-
yl)methanone,

783

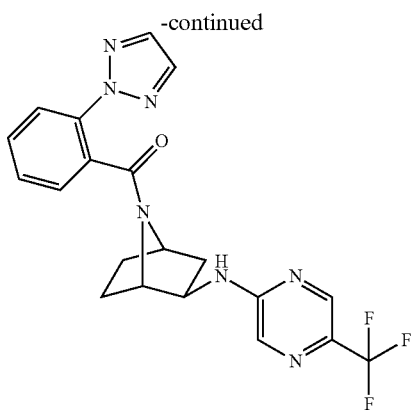

(2-(2H-1,2,3-triazol-2-
yl)phenyl)(1S,2R,4R)-2-((5-
(trifluoromethyl)pyrazin-2-yl)amino)-7-
azabicyclo[2.2.1]heptan-7-
yl)methanone,

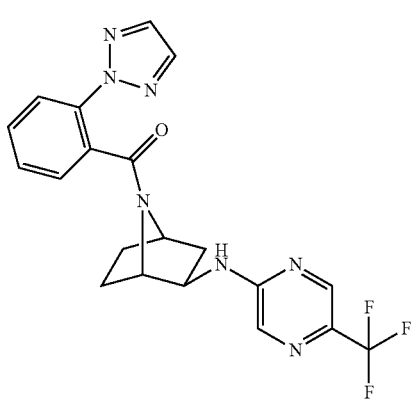 [SMILES: O=C(c1ccccc1-n1nccn1)N1C2CCC1C(Nc1cnc(C(F)(F)F)cn1)C2]

(±)-((2-(2H-1,2,3-triazol-2-
yl)phenyl)(2-((5-
(trifluoromethyl)pyrazin-2-yl)amino)-7-
azabicyclo[2.2.1]heptan-7-
yl)methanone,

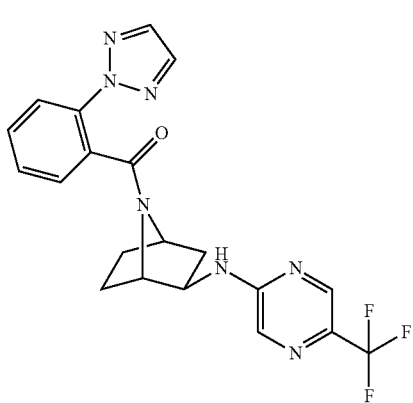 [SMILES: O=C(c1ccccc1-n1nccn1)N1C2CCC1C(Nc1cnc(C(F)(F)F)cn1)C2]

(2-(2H-1,2,3-triazol-2-
yl)phenyl)((1S,2R,4R)-2-((5-
(trifluoromethyl)pyrazin-2-yl)amino)-7-
azabicyclo[2.2.1]heptan-7-
yl)methanone,

784

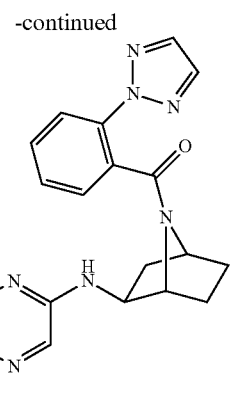

(2-(2H-1,2,3-triazol-2-
yl)phenyl)((1R,2S,4S)-2-((5-
(trifluoromethyl)pyrazin-2-yl)amino)-7-
azabicyclo[2.2.1]heptan-7-
yl)methanone,

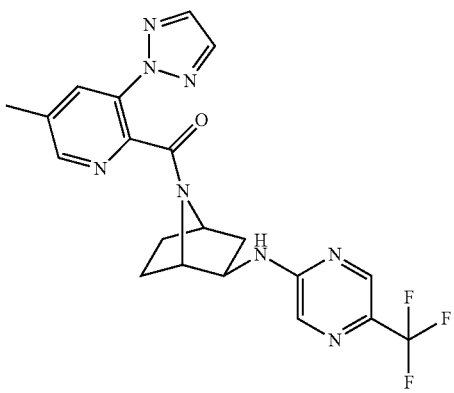 [SMILES: Cc1cnc(C(=O)N2C3CCC2C(Nc2cnc(C(F)(F)F)cn2)C3)c(-n2nccn2)c1]

(±)-(5-methyl-3-(2H-1,2,3-triazol-2-
yl)pyridin-2-yl)(2-((5-
(trifluoromethyl)pyrazin-2-yl)amino)-7-
azabicyclo[2.2.1]heptan-7-
yl)methanone,

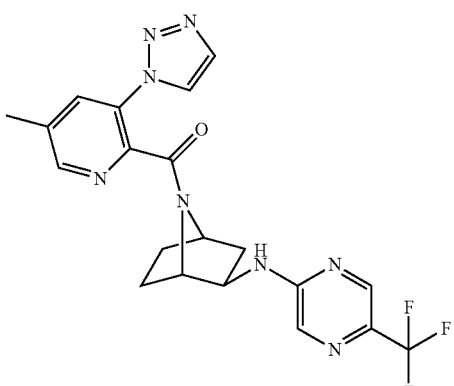

(±)-(5-methyl-3-(1H-1,2,3-triazol-1-
yl)pyridin-2-yl)(2-((5-
(trifluoromethyl)pyrazin-2-yl)amino)-7-
azabicyclo[2.2.1]heptan-7-
yl)methanone, -continued

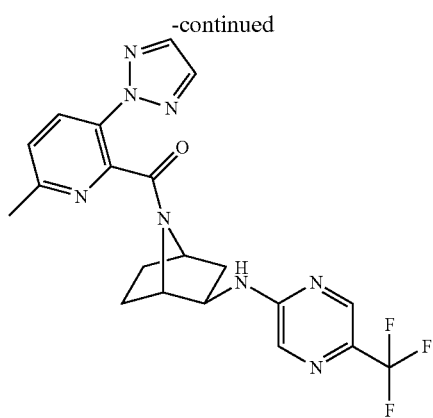

(±)-(6-methyl-3-(2H-1,2,3-triazol-2-
yl)pyridin-2-yl)(2-((5-
(trifluoromethyl)pyrazin-2-yl)amino)-7-
azabicyclo[2.2.1]heptan-7-
yl)methanone,

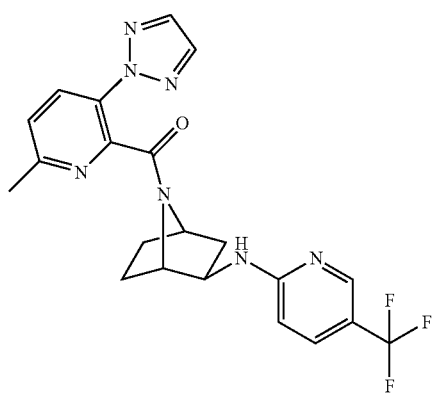 [SMILES: Cc1ccc(-n2nccn2)c(C(=O)N2C3CCC2C(Nc2ccc(C(F)(F)F)cn2)C3)n1]

(±)-(6-methyl-3-(2H-1,2,3-triazol-2-
yl)pyridin-2-yl)(2-((5-
(trifluoromethyl)pyridin-2-yl)amino)-7-
azabicyclo[2.2.1]heptan-7-
yl)methanone,

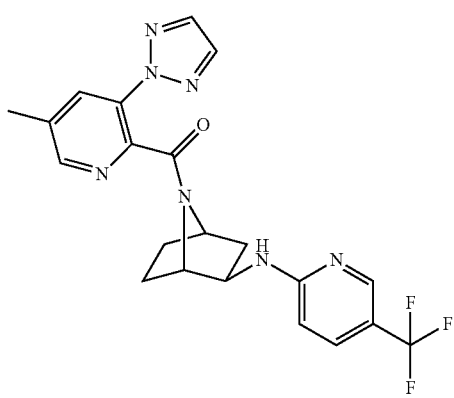 [SMILES: Cc1cnc(C(=O)N2C3CCC2C(Nc2ccc(C(F)(F)F)cn2)C3)c(-n2nccn2)c1]

(±)-(5-methyl-3-(2H-1,2,3-triazol-2-
yl)pyridin-2-yl)(2-((5-
(trifluoromethyl)pyridin-2-yl)amino)-7-
azabicyclo[2.2.1]heptan-7-
yl)methanone, -continued

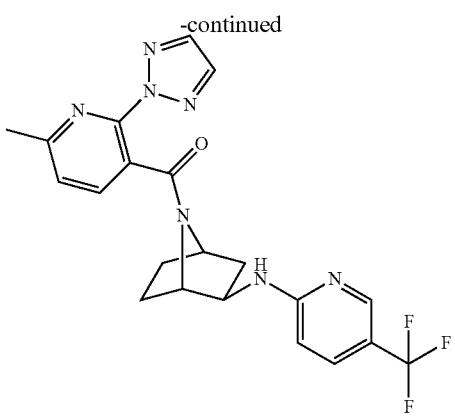

(±)-(6-methyl-2-(2H-1,2,3-triazol-2-
yl)pyridin-3-yl)(2-((5-
(trifluoromethyl)pyridin-2-yl)amino)-7-
azabicyclo[2.2.1]heptan-7-
yl)methanone,

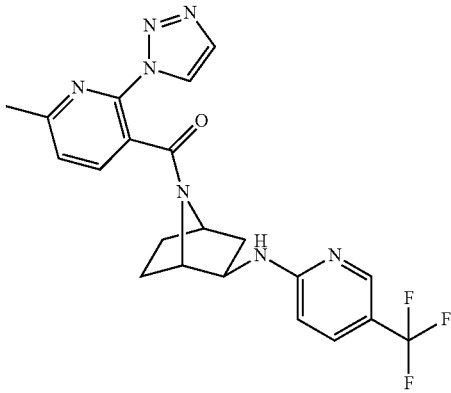 [SMILES: Cc1ccc(C(=O)N2C3CCC2C(Nc2ccc(C(F)(F)F)cn2)C3)c(-n2ccnn2)n1]

(±)-(6-methyl-2-(1H-1,2,3-triazol-1-
yl)pyridin-3-yl)(2-((5-
(trifluoromethyl)pyridin-2-yl)amino)-7-
azabicyclo[2.2.1]heptan-7-
yl)methanone,

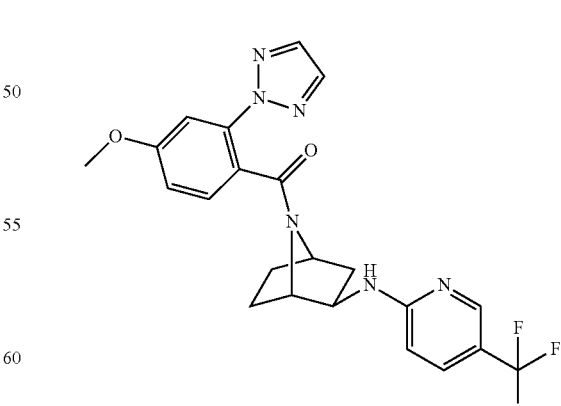

(±)-(4-methoxy-2-(2H-1,2,3-triazol-2-
yl)phenyl)(2-((5-
(trifluoromethyl)pyridin-2-yl)amino)-7-
azabicyclo[2.2.1]heptan-7-
yl)methanone,

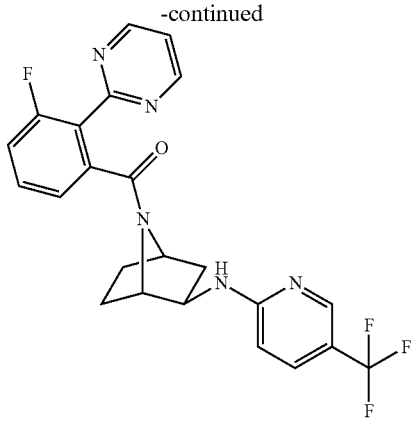

(±)-(3-fluoro-2-(pyrimidin-2-yl)phenyl)(2-((5-(trifluoromethyl)pyridin-2-yl)amino)-7-azabicyclo[2.2.1]heptan-7-yl)methanone,

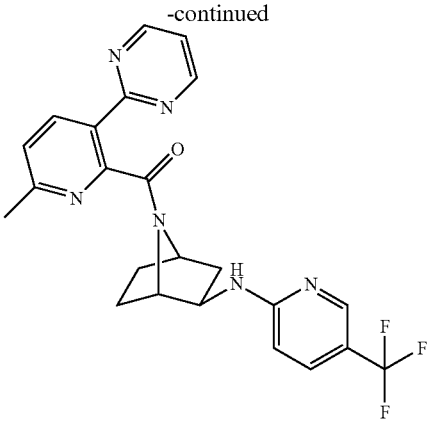

(±)-(6-methyl-3-(pyrimidin-2-yl)pyridin-2-yl)(2-((5-(trifluoromethyl)pyridin-2-yl)amino)-7-azabicyclo[2.2.1]heptan-7-yl)methanone, (±)-((3-fluoro-2-methoxyphenyl)(2-((5-(trifluoromethyl)pyridin-2-yl)amino)-7-azabicyclo[2.2.1]heptan-7-yl)methanone,

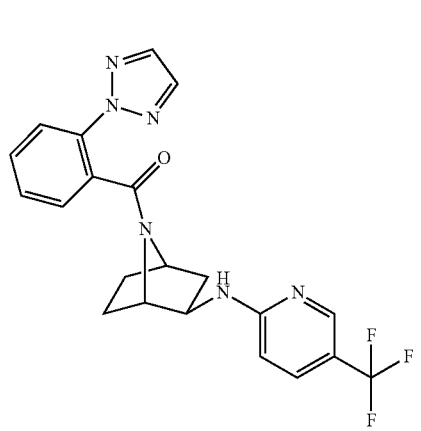

(±)-(2-(2H-1,2,3-triazol-2-yl)phenyl)(2-((5-(trifluoromethyl)pyridin-2-yl)amino)-7-azabicyclo[2.2.1]heptan-7-yl)methanone,

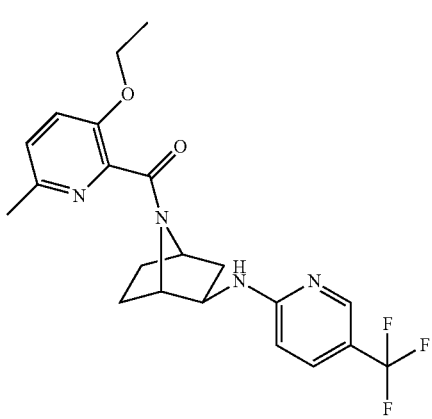 [SMILES: CCOc1ccc(C)nc1C(=O)N1C2CCC1C(Nc1ccc(C(F)(F)F)cn1)C2]

(±)-(3-ethoxy-6-methylpyridin-2-yl)(2-((5-(trifluoromethyl)pyridin-2-yl)amino)-7-azabicyclo[2.2.1]heptan-7-yl)methanone,

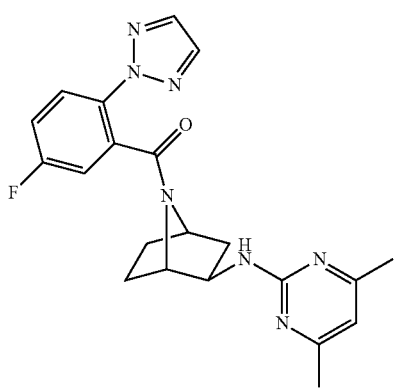 [SMILES: Cc1cc(C)nc(NC2CC3CCC2N3C(=O)c2cc(F)ccc2-n2nccn2)n1]

(±)-(2-((4,6-dimethylpyrimidin-2-yl)amino)-7-azabicyclo[2.2.1]heptan-7-yl)(5-fluoro-2-(2H-1,2,3-triazol-2-yl)phenyl)methanone, -continued

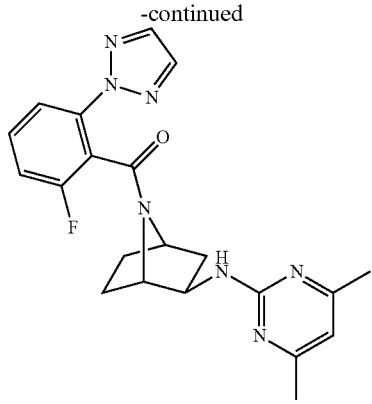

(±)-(2-((4,6-dimethylpyrimidin-2-yl)amino)-7-azabicyclo[2.2.1]heptan-7-yl)(2-fluoro-6-(2H-1,2,3-triazol-2-yl)phenyl)methanone,

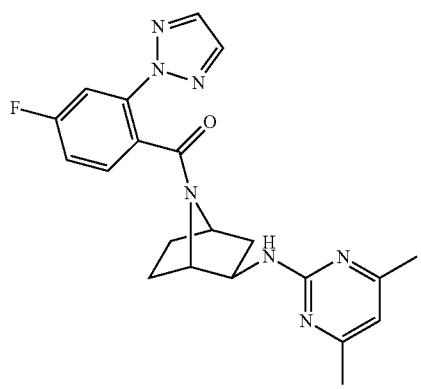 [SMILES: Cc1cc(C)nc(NC2CC3CCC2N3C(=O)c2ccc(F)cc2-n2nccn2)n1]

(±)-(2-((4,6-dimethylpyrimidin-2-yl)amino)-7-azabicyclo[2.2.1]heptan-7-yl)(4-fluoro-2-(2H-1,2,3-triazol-2-yl)phenyl)methanone,

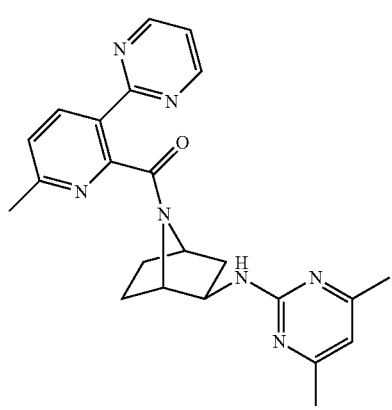

(±)-(2-((4,6-dimethylpyrimidin-2-yl)amino)-7-azabicyclo[2.2.1]heptan-7-yl)(6-methyl-3-(pyrimidin-2-yl)pyridin-2-yl)methanone, -continued

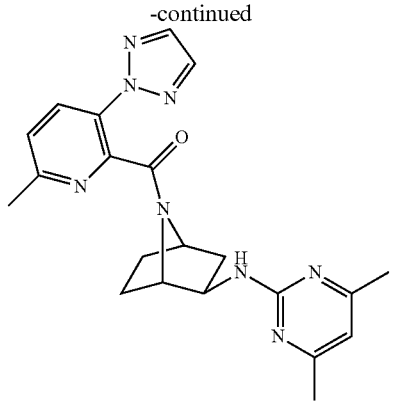

(±)-(2-((4,6-dimethylpyrimidin-2-yl)amino)-7-azabicyclo[2.2.1]heptan-7-yl)(6-methyl-3-(2H-1,2,3-triazol-2-yl)pyridin-2-yl)methanone,

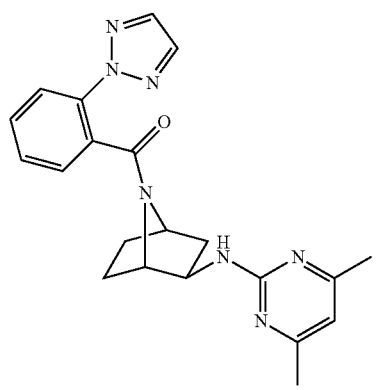 [SMILES: Cc1cc(C)nc(NC2CC3CCC2N3C(=O)c2ccccc2-n2nccn2)n1]

(±)-(2-(2H-1,2,3-triazol-2-yl)phenyl)(2-((4,6-dimethylpyrimidin-2-yl)amino)-7-azabicyclo[2.2.1]heptan-7-yl)methanone,

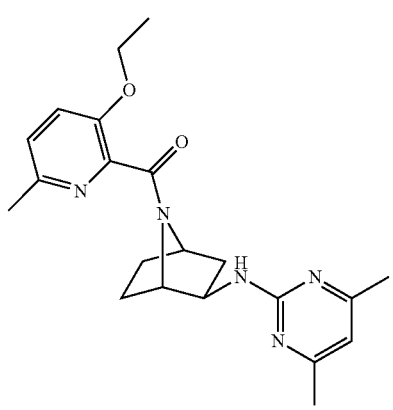

(±)-(2-((4,6-dimethylpyrimidin-2-yl)amino)-7-azabicyclo[2.2.1]heptan-7-yl)(3-ethoxy-6-methylpyridin-2-yl)methanone, 791
-continued

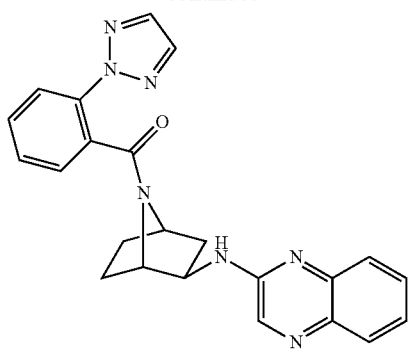 [SMILES: O=C(c1ccccc1-n1nccn1)N1C2CCC1C(Nc1cnc3ccccc3n1)C2]

(±)-(2-(2H-1,2,3-triazol-2-yl)phenyl)(2-
(quinoxalin-2-ylamino)-7-
azabicyclo[2.2.1]heptan-7-
yl)methanone,

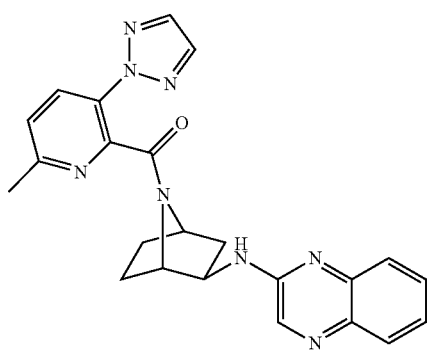 [SMILES: Cc1ccc(-n2nccn2)c(C(=O)N2C3CCC2C(Nc2cnc4ccccc4n2)C3)n1]

(±)-(6-methyl-3-(2H-1,2,3-triazol-2-
yl)pyridin-2-yl)(2-(quinoxalin-2-
ylamino)-7-azabicyclo[2.2.1]heptan-7-
yl)methanone,

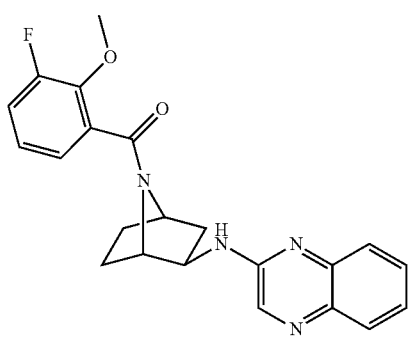 [SMILES: COc1c(F)cccc1C(=O)N1C2CCC1C(Nc1cnc3ccccc3n1)C2]

(±)-(3-fluoro-2-methoxyphenyl)(2-
(quinoxalin-2-ylamino)-7-
azabicyclo[2.2.1]heptan-7-
yl)methanone, 792
-continued

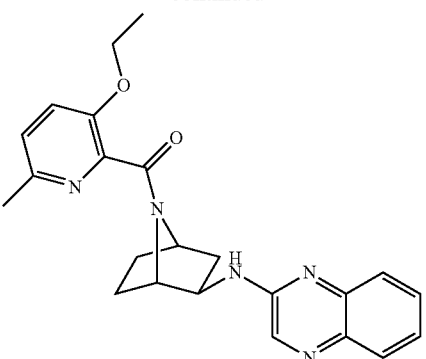

(±)-(3-ethoxy-6-methylpyridin-2-yl)(2-
(quinoxalin-2-ylamino)-7-
azabicyclo[2.2.1]heptan-7-
yl)methanone,

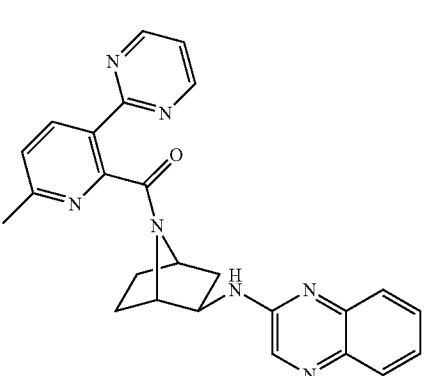

(±)-(6-methyl-3-(pyrimidin-2-
yl)pyridin-2-yl)(2-(quinoxalin-2-
ylamino)-7-azabicyclo[2.2.1]heptan-7-
yl)methanone,

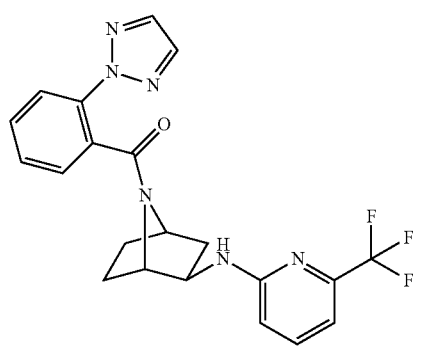 [SMILES: O=C(c1ccccc1-n1nccn1)N1C2CCC1C(Nc1cccc(C(F)(F)F)n1)C2]

(±)-(2-(2H-1,2,3-triazol-2-yl)phenyl)(2-
((6-(trifluoromethyl)pyridin-2-
yl)amino)-7-azabicyclo[2.2.1]heptan-7-
yl)methanone, -continued

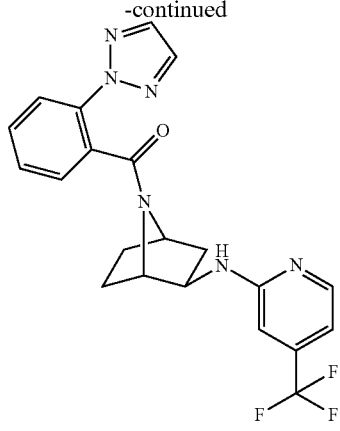

(±)-((2-(2H-1,2,3-triazol-2-yl)phenyl)(2-((4-(trifluoromethyl)pyridin-2-yl)amino)-7-azabicyclo[2.2.1]heptan-7-yl)methanone,

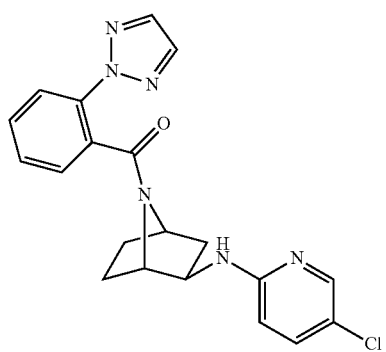 [SMILES: O=C(c1ccccc1-n1nccn1)N1C2CCC1C(Nc1ccc(Cl)cn1)C2]

(±)-(2-(2H-1,2,3-triazol-2-yl)phenyl)(2-((5-chloropyridin-2-yl)amino)-7-azabicyclo[2.2.1]heptan-7-yl)methanone,

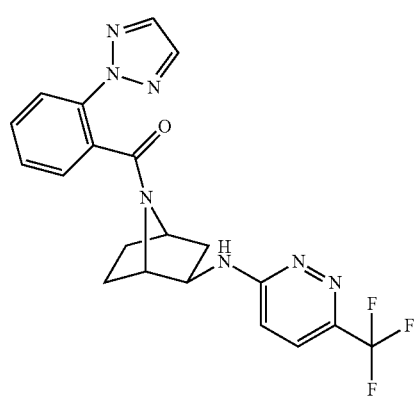

(±)-(2-(2H-1,2,3-triazol-2-yl)phenyl)(2-((6-(trifluoromethyl)pyridazin-3-yl)amino)-7-azabicyclo[2.2.1]heptan-7-yl)methanone,

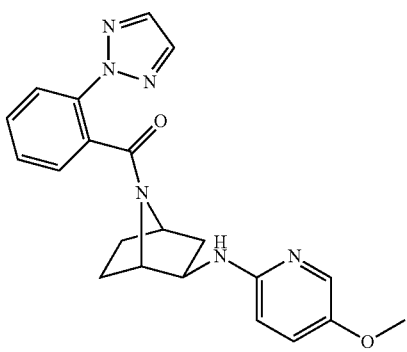 [SMILES: COc1ccc(NC2CC3CCC2N3C(=O)c2ccccc2-n2nccn2)nc1]

(±)-(2-(2H-1,2,3-triazol-2-yl)phenyl)(2-((5-methoxypyridin-2-yl)amino)-7-azabicyclo[2.2.1]heptan-7-yl)methanone,

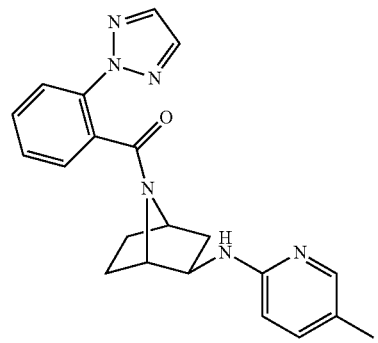 [SMILES: Cc1ccc(NC2CC3CCC2N3C(=O)c2ccccc2-n2nccn2)nc1]

(±)-(2-(2H-1,2,3-triazol-2-yl)phenyl)(2-((5-methylpyridin-2-yl)amino)-7-azabicyclo[2.2.1]heptan-7-yl)methanone,

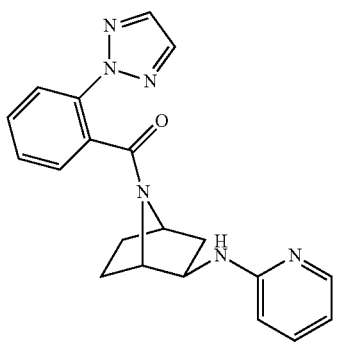 [SMILES: O=C(c1ccccc1-n1nccn1)N1C2CCC1C(Nc1ccccn1)C2]

(±)-(2-(2H-1,2,3-triazol-2-yl)phenyl)(2-(pyridin-2-ylamino)-7-azabicyclo[2.2.1]heptan-7-yl)methanone,

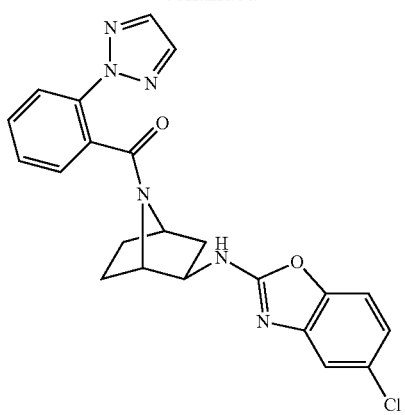 [SMILES: O=C(c1ccccc1-n1nccn1)N1C2CCC1C(Nc1nc3cc(Cl)ccc3o1)C2]

(±)-(2-(2H-1,2,3-triazol-2-yl)phenyl)(2-
((5-chlorobenzo[d]oxazol-2-yl)amino)-
7-azabicyclo[2.2.1]heptan-7-
yl)methanone,

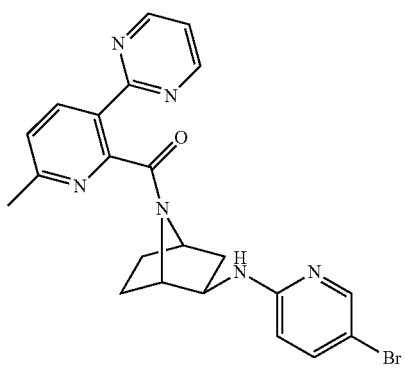 [SMILES: Cc1ccc(-c2ncccn2)c(C(=O)N2C3CCC2C(Nc2ccc(Br)cn2)C3)n1]

(±)-(2-((5-bromopyridin-2-yl)amino)-7-
azabicyclo[2.2.1]heptan-7-yl)(6-methyl-
3-(pyrimidin-2-yl)pyridin-2-
yl)methanone,

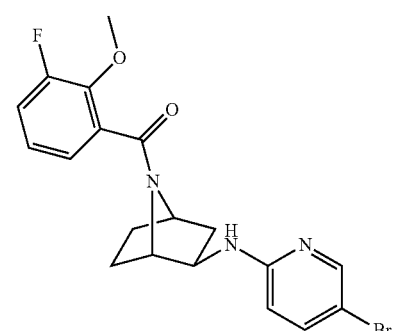

(±)-(2-((5-bromopyridin-2-yl)amino)-7-
azabicyclo[2.2.1]heptan-7-yl)(3-fluoro-
2-methoxyphenyl)methanone

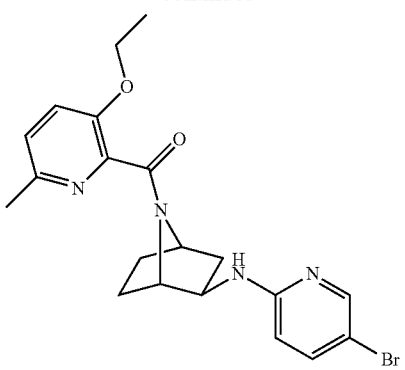 [SMILES: CCOc1ccc(C)nc1C(=O)N1C2CCC1C(Nc1ccc(Br)cn1)C2]

(±)-(2-((5-bromopyridin-2-yl)amino)-7-
azabicyclo[2.2.1]heptan-7-yl)(3-ethoxy-
6-methylpyridin-2-yl)methanone,

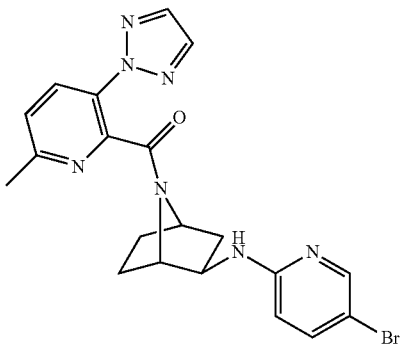 [SMILES: Cc1ccc(-n2nccn2)c(C(=O)N2C3CCC2C(Nc2ccc(Br)cn2)C3)n1]

(±)-(2-((5-bromopyridin-2-yl)amino)-7-
azabicyclo[2.2.1]heptan-7-yl)(6-methyl-
3-(2H-1,2,3-triazol-2-yl)pyridin-2-
yl)methanone,

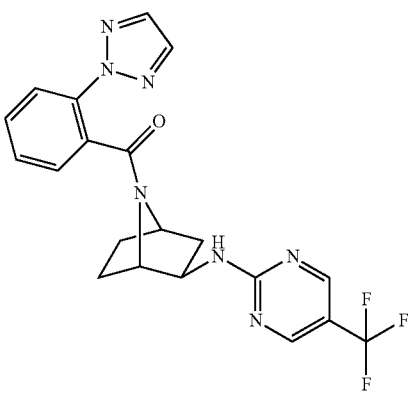

(±)-(2-(2H-1,2,3-triazol-2-yl)phenyl)(2-
((5-(trifluoromethyl)pyrimidin-2-
yl)amino)-7-azabicyclo[2.2.1]heptan-7-
yl)methanone,

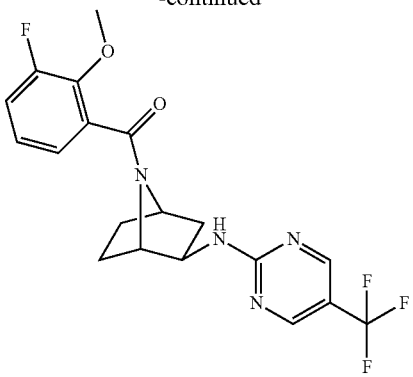

(±)-(3-fluoro-2-methoxyphenyl)(2-((5-(trifluoromethyl)pyrimidin-2-yl)amino)-7-azabicyclo[2.2.1]heptan-7-yl)methanone,

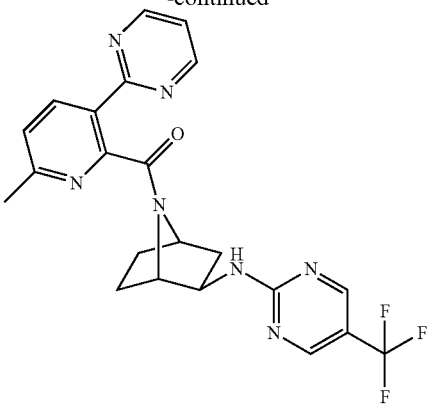

(±)-(6-methyl-3-(pyrimidin-2-yl)pyridin-2-yl)(2-((5-(trifluoromethyl)pyrimidin-2-yl)amino)-7-azabicyclo[2.2.1]heptan-7-yl)methanone,

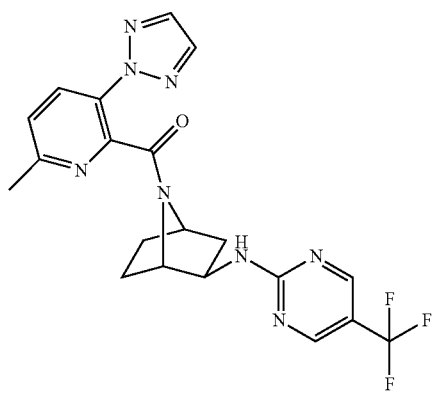 [SMILES: Cc1ccc(-n2nccn2)c(C(=O)N2C3CCC2C(Nc2ncc(C(F)(F)F)cn2)C3)n1]

(±)-(6-methyl-3-(2H-1,2,3-triazol-2-yl)pyridin-2-yl)(2-((5-(trifluoromethyl)pyrimidin-2-yl)amino)-7-azabicyclo[2.2.1]heptan-7-yl)methanone,

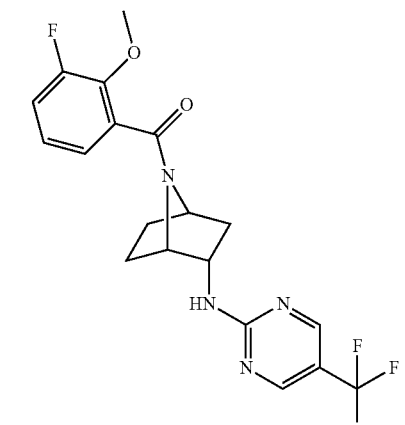

(±)-(3-fluoro-2-methoxyphenyl)(2-((5-(trifluoromethyl)pyrimidin-2-yl)amino)-7-azabicyclo[2.2.1]heptan-7-yl)methanone,

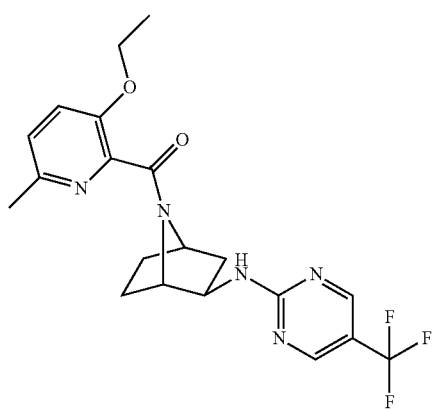 [SMILES: CCOc1ccc(C)nc1C(=O)N1C2CCC1C(Nc1ncc(C(F)(F)F)cn1)C2]

(±)-(3-ethoxy-6-methylpyridin-2-yl)(2-((5-(trifluoromethyl)pyrimidin-2-yl)amino)-7-azabicyclo[2.2.1]heptan-7-yl)methanone,

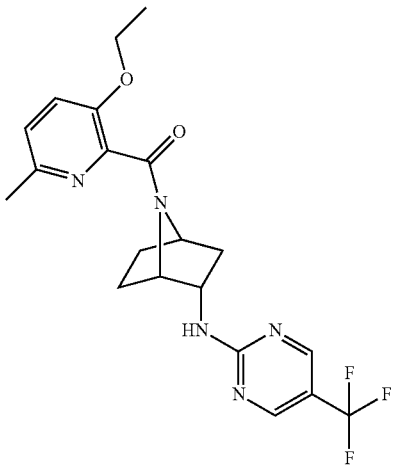 [SMILES: CCOc1ccc(C)nc1C(=O)N1C2CCC1C(Nc1ncc(C(F)(F)F)cn1)C2]

(±)-(3-ethoxy-6-methylpyridin-2-yl)(2-((5-(trifluoromethyl)pyrimidin-2-yl)amino)-7-azabicyclo[2.2.1]heptan-7-yl)methanone,

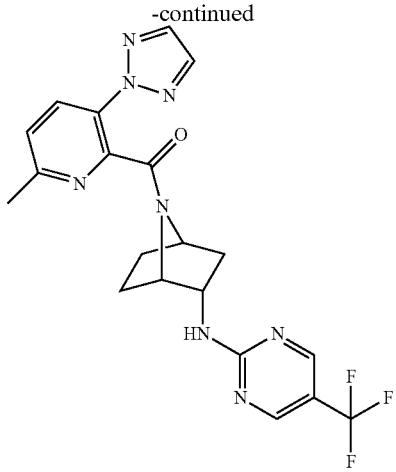

(±)-(6-methyl-3-(2H-1,2,3-triazol-2-yl)pyridin-2-yl)(2-((5-(trifluoromethyl)pyrimidin-2-yl)amino)-7-azabicyclo[2.2.1]heptan-7-yl)methanone,

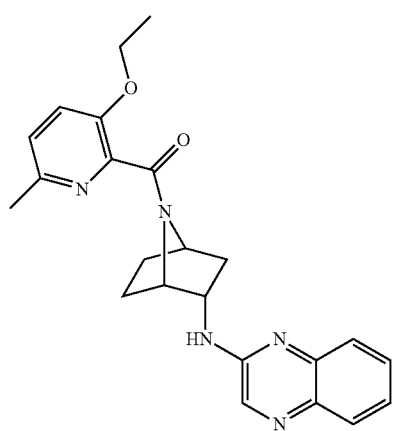 [SMILES: CCOc1ccc(C)nc1C(=O)N1C2CCC1C(Nc1cnc3ccccc3n1)C2]

(±)-(3-ethoxy-6-methylpyridin-2-yl)(2-(quinoxalin-2-ylamino)-7-azabicyclo[2.2.1]heptan-7-yl)methanone,

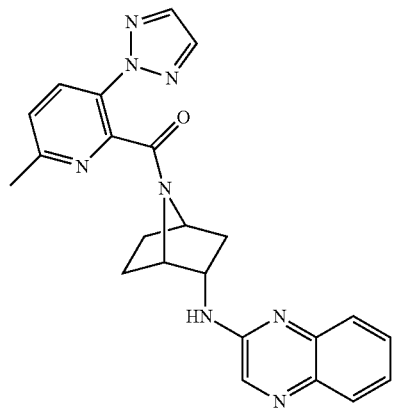 [SMILES: Cc1ccc(-n2nccn2)c(C(=O)N2C3CCC2C(Nc2cnc4ccccc4n2)C3)n1]

(±)-(6-methyl-3-(2H-1,2,3-triazol-2-yl)pyridin-2-yl)(2-(quinoxalin-2-ylamino)-7-azabicyclo[2.2.1]heptan-7-yl)methanone,

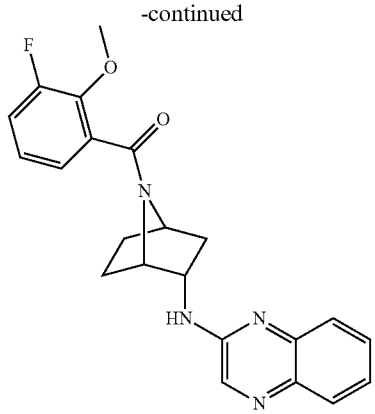

(±)-(3-fluoro-2-methoxyphenyl)(2-(quinoxalin-2-ylamino)-7-azabicyclo[2.2.1]heptan-7-yl)methanone,

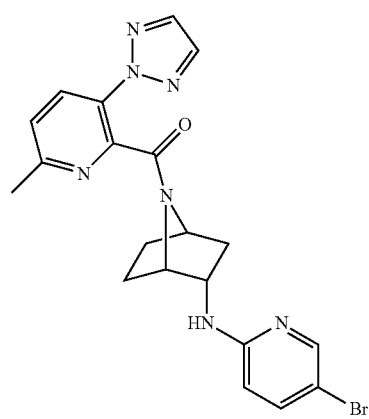 [SMILES: Cc1ccc(-n2nccn2)c(C(=O)N2C3CCC2C(Nc2ccc(Br)cn2)C3)n1]

(±)-(2-((5-bromopyridin-2-yl)amino)-7-azabicyclo[2.2.1]heptan-7-yl)(6-methyl-3-(2H-1,2,3-triazol-2-yl)pyridin-2-yl)methanone,

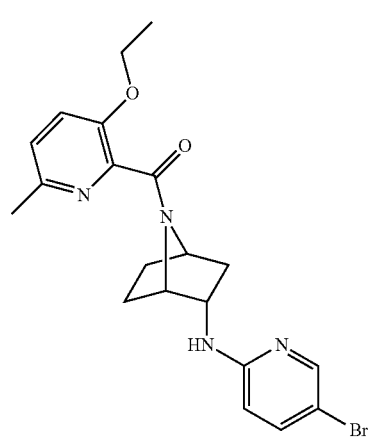 [SMILES: CCOc1ccc(C)nc1C(=O)N1C2CCC1C(Nc1ccc(Br)cn1)C2]

(±)-(2-((5-bromopyridin-2-yl)amino)-7-azabicyclo[2.2.1]heptan-7-yl)(3-ethoxy-6-methylpyridin-2-yl)methanone,

801
-continued

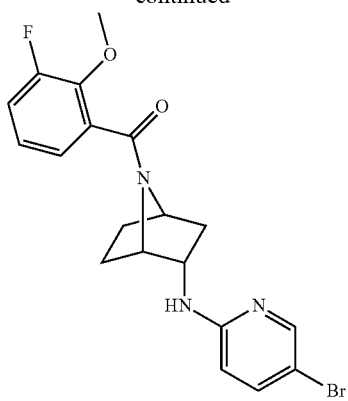

(±)-(2-((5-bromopyridin-2-yl)amino)-7-
azabicyclo[2.2.1]heptan-7-yl)(3-fluoro-
2-methoxyphenyl)methanone,

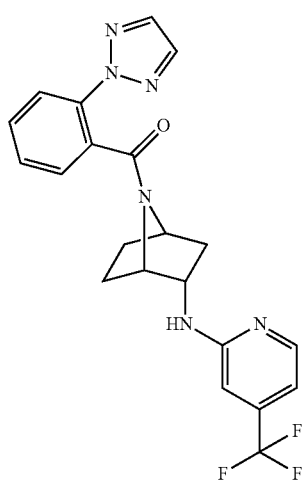 [SMILES: O=C(c1ccccc1-n1nccn1)N1C2CCC1C(Nc1cc(C(F)(F)F)ccn1)C2]

(±)-((2-(2H-1,2,3-triazol-2-
yl)phenyl)(2-((4-
(trifluoromethyl)pyridin-2-yl)amino)-7-
azabicyclo[2.2.1]heptan-7-
yl)methanone,

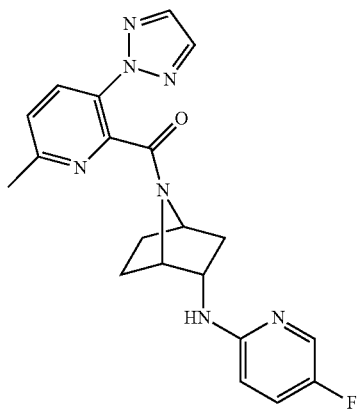 [SMILES: Cc1ccc(-n2nccn2)c(C(=O)N2C3CCC2C(Nc2ccc(F)cn2)C3)n1]

(±)-(2-((5-fluoropyridin-2-yl)amino)-7-
azabicyclo[2.2.1]heptan-7-yl)(6-methyl-
3-(2H-1,2,3-triazol-2-yl)pyridin-2-
yl)methanone,

802
-continued

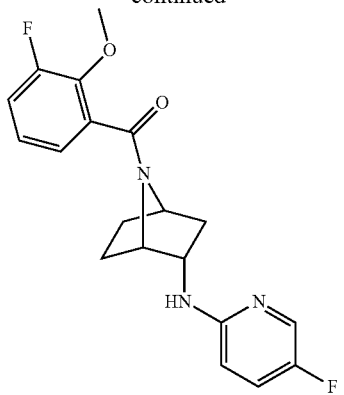

(±)-(3-fluoro-2-methoxyphenyl)(2-((5-
fluoropyridin-2-yl)amino)-7-
azabicyclo[2.2.1]heptan-7-
yl)methanone,

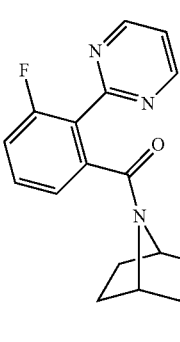

(3-fluoro-2-(pyrimidin-2-
yl)phenyl)((1S,2R,4R)-2-((5-
(trifluoromethyl)pyrazin-2-yl)amino)-7-
azabicyclo[2.2.1]heptan-7-
yl)methanone,

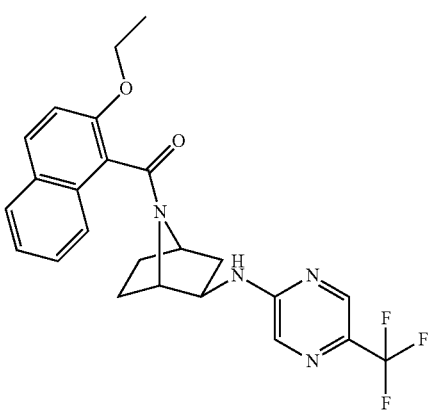

(2-ethoxynaphthalen-1-yl)((1S,2R,4R)-
2-((5-(trifluoromethyl)pyrazin-2-
yl)amino)-7-azabicyclo[2.2.1]heptan-7-
yl)methanone, -continued

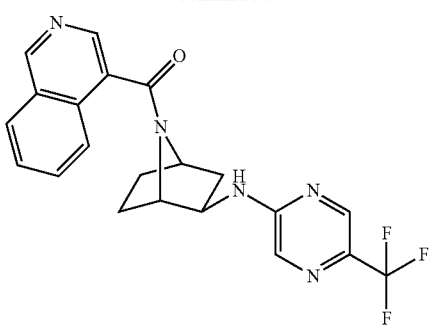 [SMILES: O=C(c1cncc2ccccc12)N1C2CCC1C(Nc1cnc(C(F)(F)F)cn1)C2]

isoquinolin-4-yl((1S,2R,4R)-2-((5-(trifluoromethyl)pyrazin-2-yl)amino)-7-azabicyclo[2.2.1]heptan-7-yl)methanone,

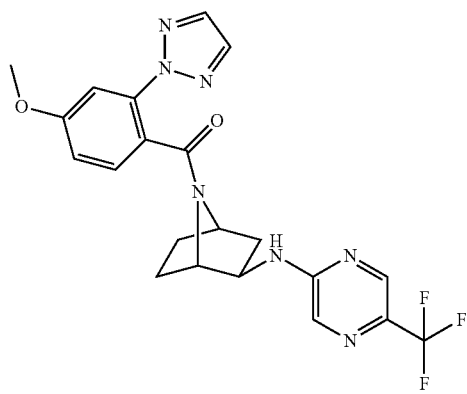 [SMILES: COc1ccc(C(=O)N2C3CCC2C(Nc2cnc(C(F)(F)F)cn2)C3)c(-n2nccn2)c1]

(4-methoxy-2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone,

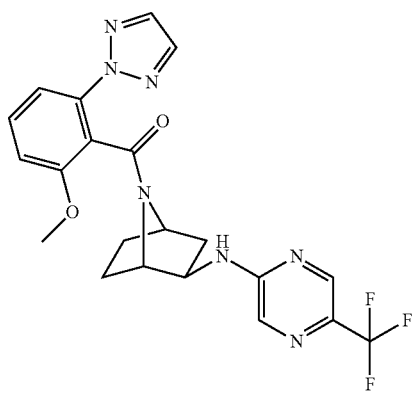 [SMILES: COc1cccc(-n2nccn2)c1C(=O)N1C2CCC1C(Nc1cnc(C(F)(F)F)cn1)C2]

(2-methoxy-6-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone, -continued

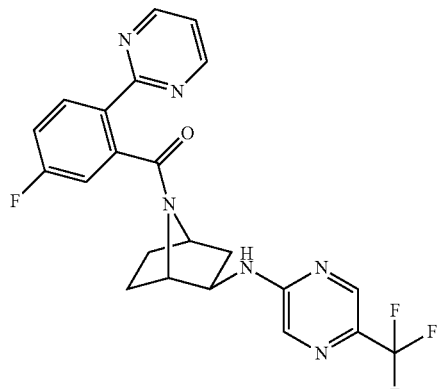

(5-fluoro-2-(pyrimidin-2-yl)phenyl)((1S,2R,4R)-2-((5-(trifluoromethyl)pyrazin-2-yl)amino)-7-azabicyclo[2.2.1]heptan-7-yl)methanone,

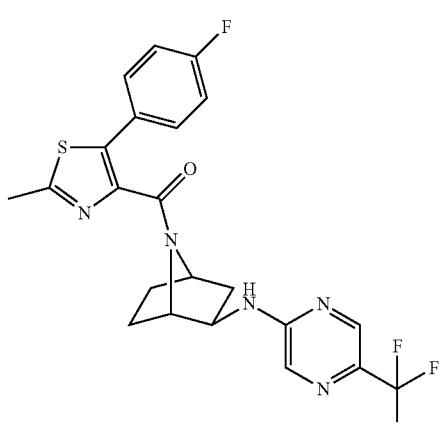

(5-(4-fluorophenyl)-2-methylthiazol-4-yl)((1S,2R,4R)-2-((5-(trifluoromethyl)pyrazin-2-yl)amino)-7-azabicyclo[2.2.1]heptan-7-yl)methanone,

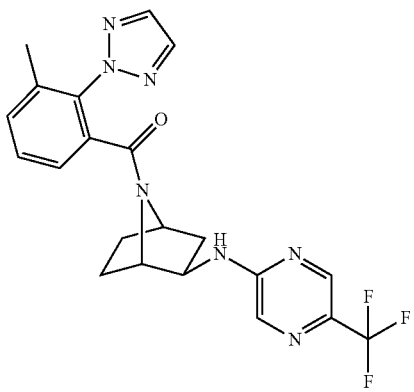 [SMILES: Cc1cccc(C(=O)N2C3CCC2C(Nc2cnc(C(F)(F)F)cn2)C3)c1-n1nccn1]

(3-methyl-2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone, 805
-continued

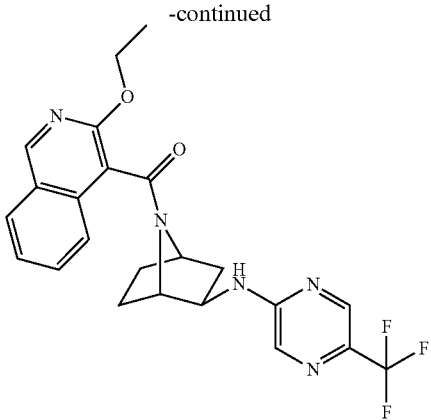

(3-ethoxyisoquinolin-4-yl)((1S,2R,4R)-
2-((5-(trifluoromethyl)pyrazin-2-
yl)amino)-7-azabicyclo[2.2.1]heptan-7-
yl)methanone,

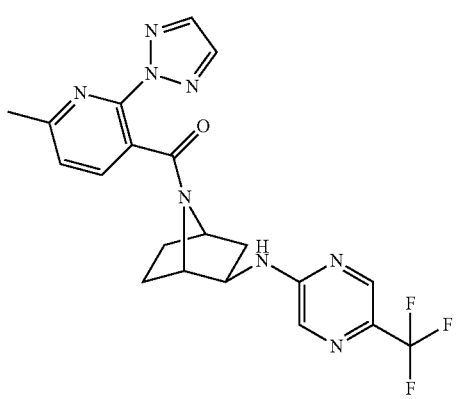 [SMILES: Cc1ccc(C(=O)N2C3CCC2C(Nc2cnc(C(F)(F)F)cn2)C3)c(-n2nccn2)n1]

(6-methyl-2-(2H-1,2,3-triazol-2-
yl)pyridin-3-yl)((1S,2R,4R)-2-((5-
(trifluoromethyl)pyrazin-2-yl)amino)-7-
azabicyclo[2.2.1]heptan-7-
yl)methanone,

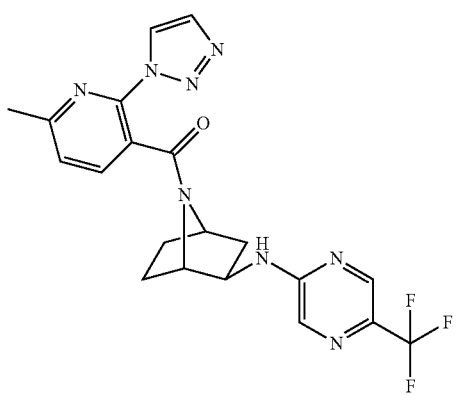 [SMILES: Cc1ccc(C(=O)N2C3CCC2C(Nc2cnc(C(F)(F)F)cn2)C3)c(-n2ccnn2)n1]

(6-methyl-2-(1H-1,2,3-triazol-1-
yl)pyridin-3-yl)((1S,2R,4R)-2-((5-
(trifluoromethyl)pyrazin-2-yl)amino)-7-
azabicyclo[2.2.1]heptan-7-
yl)methanone, 806
-continued

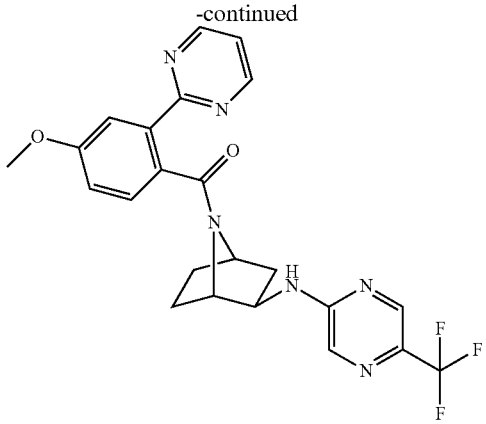

(4-methoxy-2-(pyrimidin-2-
yl)phenyl)((1S,2R,4R)-2-((5-
(trifluoromethyl)pyrazin-2-yl)amino)-7-
azabicyclo[2.2.1]heptan-7-
yl)methanone,

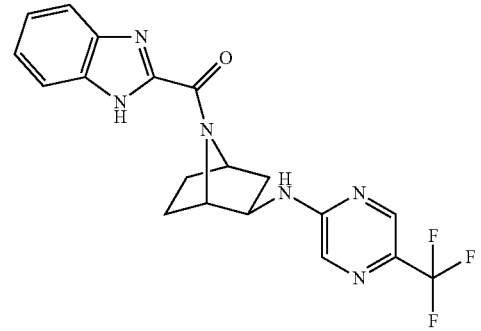

(1H-benzo[d]imidazol-2-
yl)((1S,2R,4R)-2-((5-
(trifluoromethyl)pyrazin-2-yl)amino)-7-
azabicyclo[2.2.1]heptan-7-
yl)methanone,

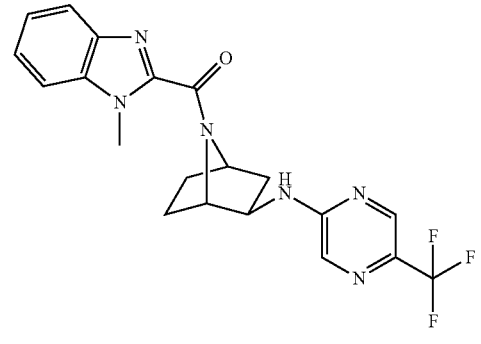

(1-methyl-1H-benzo[d]imidazol-2-
yl)((1S,2R,4R)-2-((5-
(trifluoromethyl)pyrazin-2-yl)amino)-7-
azabicyclo[2.2.1]heptan-7-
yl)methanone, 807
-continued

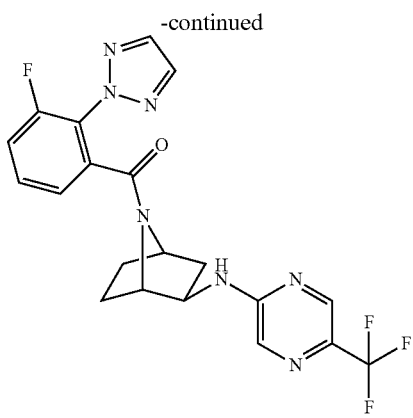

(3-fluoro-2-(2H-1,2,3-triazol-2-
yl)phenyl)((1S,2R,4R)-2-((5-
(trifluoromethyl)pyrazin-2-yl)amino)-7-
azabicyclo[2.2.1]heptan-7-
yl)methanone,

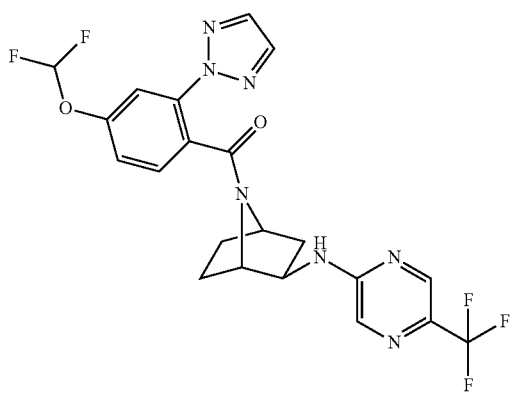 [SMILES: O=C(c1ccc(OC(F)F)cc1-n1nccn1)N1C2CCC1C(Nc1cnc(C(F)(F)F)cn1)C2]

(4-(difluoromethoxy)-2-(2H-1,2,3-
triazol-2-yl)phenyl)((1S,2R,4R)-2-((5-
(trifluoromethyl)pyrazin-2-yl)amino)-7-
azabicyclo[2.2.1]heptan-7-
yl)methanone,

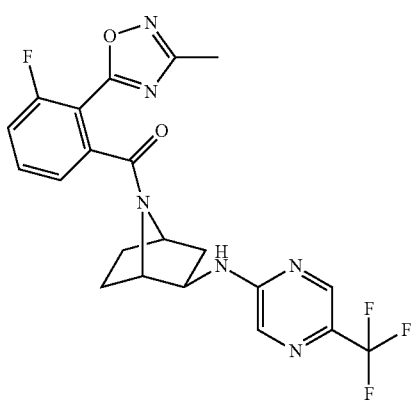

(3-fluoro-2-(3-methyl-1,2,4-oxadiazol-
5-yl)phenyl)((1S,2R,4R)-2-((5-
(trifluoromethyl)pyrazin-2-yl)amino)-7-
azabicyclo[2.2.1]heptan-7-
yl)methanone, 808
-continued

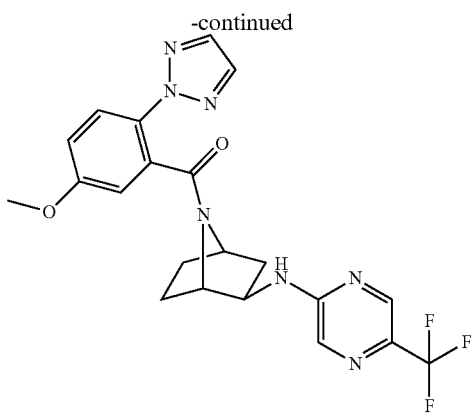

(5-methoxy-2-(2H-1,2,3-triazol-2-
yl)phenyl)((1S,2R,4R)-2-((5-
(trifluoromethyl)pyrazin-2-yl)amino)-7-
azabicyclo[2.2.1]heptan-7-
yl)methanone,

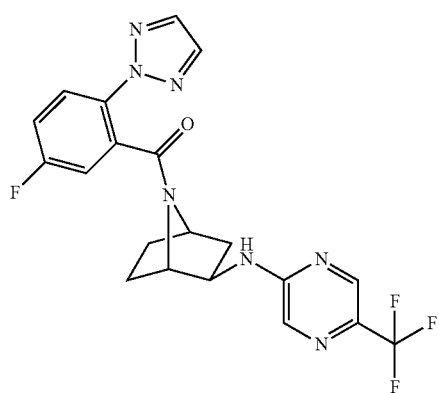 [SMILES: O=C(c1cc(F)ccc1-n1nccn1)N1C2CCC1C(Nc1cnc(C(F)(F)F)cn1)C2]

(5-fluoro-2-(2H-1,2,3-triazol-2-
yl)phenyl)((1S,2R,4R)-2-((5-
(trifluoromethyl)pyrazin-2-yl)amino)-7-
azabicyclo[2.2.1]heptan-7-
yl)methanone,

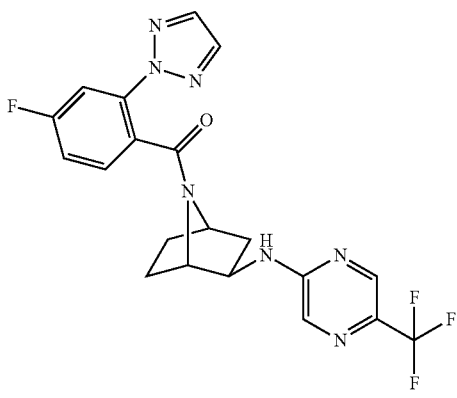 [SMILES: O=C(c1ccc(F)cc1-n1nccn1)N1C2CCC1C(Nc1cnc(C(F)(F)F)cn1)C2]

(4-fluoro-2-(2H-1,2,3-triazol-2-
yl)phenyl)((1S,2R,4R)-2-((5-
(trifluoromethyl)pyrazin-2-yl)amino)-7-
azabicyclo[2.2.1]heptan-7-
yl)methanone, -continued

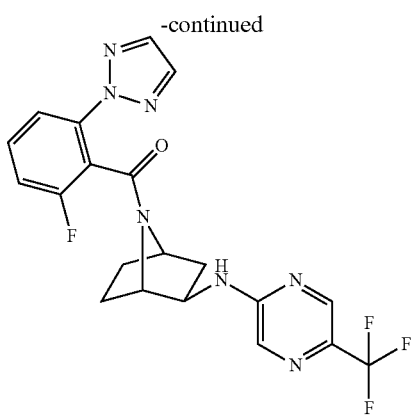

(2-fluoro-6-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone,

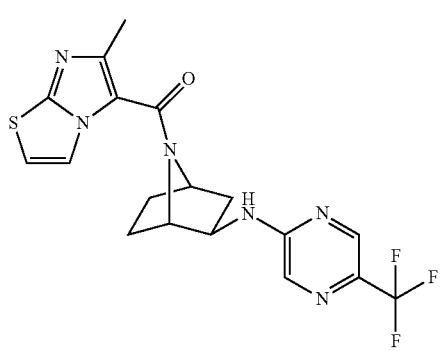 [SMILES: Cc1nc2sccn2c1C(=O)N1C2CCC1C(Nc1cnc(C(F)(F)F)cn1)C2]

(6-methylimidazo[2,1-b]thiazol-5-yl)((1S,2R,4R)-2-((5-(trifluoromethyl)pyrazin-2-yl)amino)-7-azabicyclo[2.2.1]heptan-7-yl)methanone,

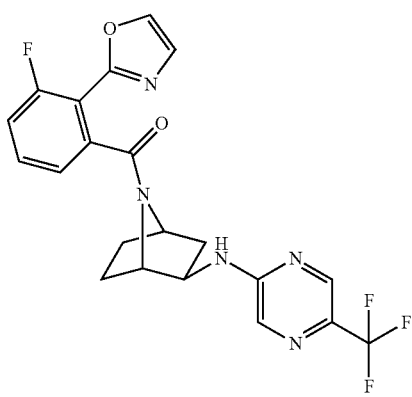 [SMILES: O=C(c1cccc(F)c1-c1ncco1)N1C2CCC1C(Nc1cnc(C(F)(F)F)cn1)C2]

(3-fluoro-2-(oxazol-2-yl)phenyl)((1S,2R,4R)-2-((5-(trifluoromethyl)pyrazin-2-yl)amino)-7-azabicyclo[2.2.1]heptan-7-yl)methanone, -continued

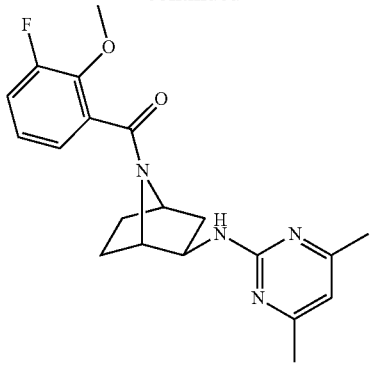 [SMILES: COc1c(F)cccc1C(=O)N1C2CCC1C(Nc1nc(C)cc(C)n1)C2]

(2-((4,6-dimethylpyrimidin-2-yl)amino)-7-azabicyclo[2.2.1]heptan-7-yl)(3-fluoro-2-methoxyphenyl)methanone,

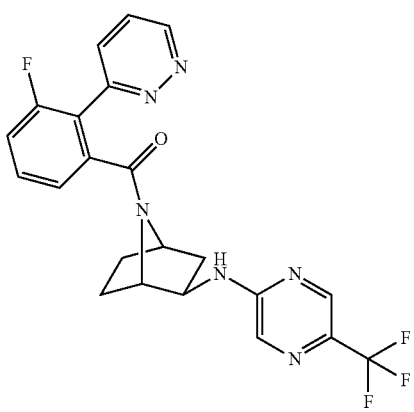 [SMILES: O=C(c1cccc(F)c1-c1cccnn1)N1C2CCC1C(Nc1cnc(C(F)(F)F)cn1)C2]

(3-fluoro-2-(pyridazin-3-yl)phenyl)((1S,2R,4R)-2-((5-(trifluoromethyl)pyrazin-2-yl)amino)-7-azabicyclo[2.2.1]heptan-7-yl)methanone,

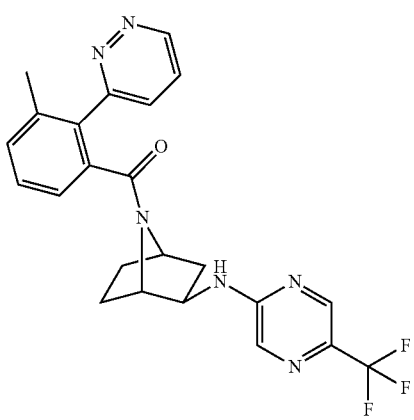 [SMILES: Cc1cccc(C(=O)N2C3CCC2C(Nc2cnc(C(F)(F)F)cn2)C3)c1-c1cccnn1]

(3-methyl-2-(pyridazin-3-yl)phenyl)((1S,2R,4R)-2-((5-(trifluoromethyl)pyrazin-2-yl)amino)-7-azabicyclo[2.2.1]heptan-7-yl)methanone, 811
-continued

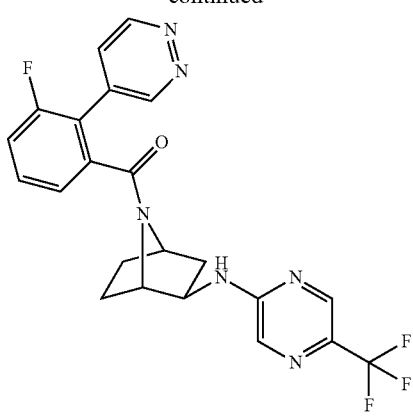

(3-fluoro-2-(pyridazin-4-yl)phenyl)((1S,2R,4R)-2-((5-(trifluoromethyl)pyrazin-2-yl)amino)-7-azabicyclo[2.2.1]heptan-7-yl)methanone,

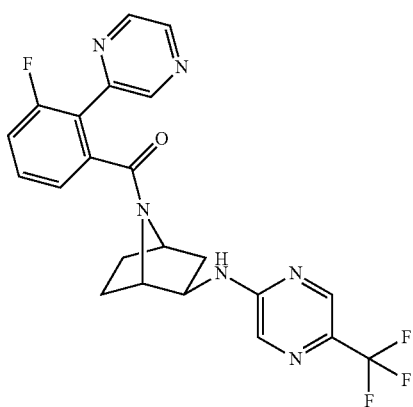 [SMILES: O=C(c1cccc(F)c1-c1cnccn1)N1C2CCC1C(Nc1cnc(C(F)(F)F)cn1)C2]

(3-fluoro-2-(pyrazin-2-yl)phenyl)((1S,2R,4R)-2-((5-(trifluoromethyl)pyrazin-2-yl)amino)-7-azabicyclo[2.2.1]heptan-7-yl)methanone,

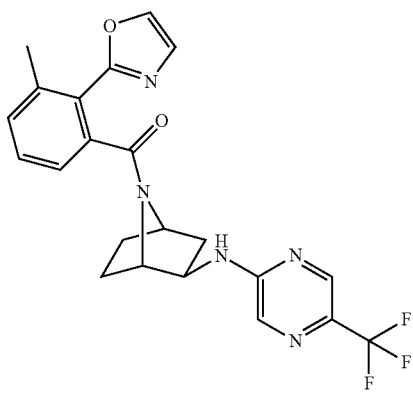 [SMILES: Cc1cccc(C(=O)N2C3CCC2C(Nc2cnc(C(F)(F)F)cn2)C3)c1-c1ncco1]

(3-methyl-2-(oxazol-2-yl)phenyl)((1S,2R,4R)-2-((5-(trifluoromethyl)pyrazin-2-yl)amino)-7-azabicyclo[2.2.1]heptan-7-yl)methanone, 812
-continued

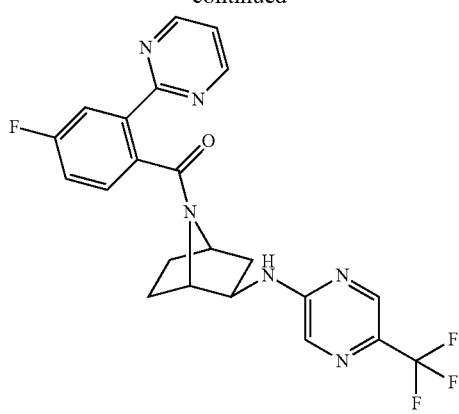

(4-fluoro-2-(pyrimidin-2-yl)phenyl)((1S,2R,4R)-2-((5-(trifluoromethyl)pyrazin-2-yl)amino)-7-azabicyclo[2.2.1]heptan-7-yl)methanone,

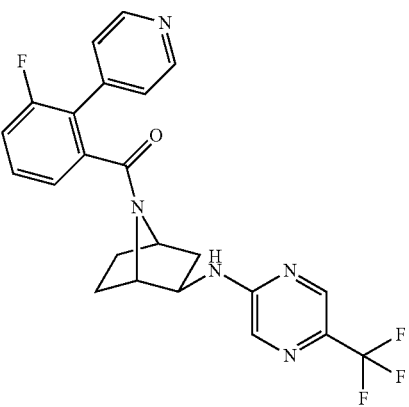 [SMILES: O=C(c1cccc(F)c1-c1ccncc1)N1C2CCC1C(Nc1cnc(C(F)(F)F)cn1)C2]

(3-fluoro-2-(pyridin-4-yl)phenyl)((1S,2R,4R)-2-((5-(trifluoromethyl)pyrazin-2-yl)amino)-7-azabicyclo[2.2.1]heptan-7-yl)methanone,

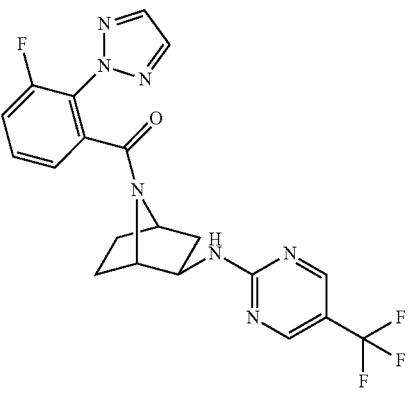 [SMILES: O=C(c1cccc(F)c1-n1nccn1)N1C2CCC1C(Nc1ncc(C(F)(F)F)cn1)C2]

(3-fluoro-2-(2H-1,2,3-triazol-2-yl)phenyl)((1S,2R,4R)-2-((5-(trifluoromethyl)pyrimidin-2-yl)amino)-7-azabicyclo[2.2.1]heptan-7-yl)methanone,

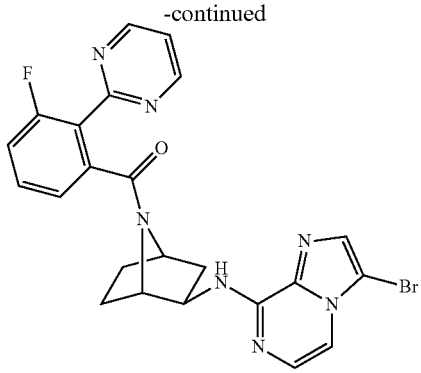

(((1S,2R,4R)-2-((3-bromoimidazo[1,2-a]pyrazin-8-yl)amino)-7-azabicyclo[2.2.1]heptan-7-yl)(3-fluoro-2-(pyrimidin-2-yl)phenyl)methanone,

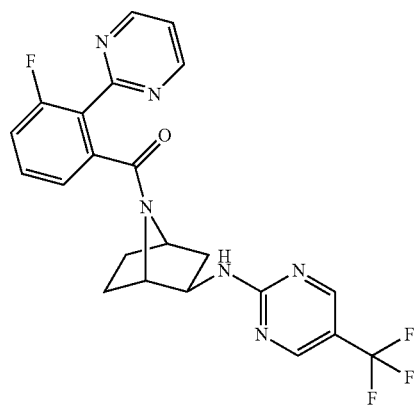

(3-fluoro-2-(pyrimidin-2-yl)phenyl)((1S,2R,4R)-2-((5-(trifluoromethyl)pyrimidin-2-yl)amino)-7-azabicyclo[2.2.1]heptan-7-yl)methanone,

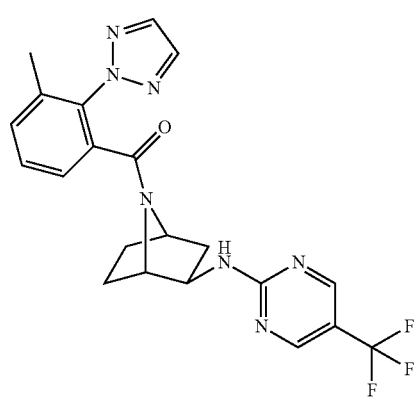 [SMILES: Cc1cccc(C(=O)N2C3CCC2C(Nc2ncc(C(F)(F)F)cn2)C3)c1-n1nccn1]

(3-methyl-2-(2H-1,2,3-triazol-2-yl)phenyl)((1S,2R,4R)-2-((5-(trifluoromethyl)pyrimidin-2-yl)amino)-7-azabicyclo[2.2.1]heptan-7-yl)methanone,

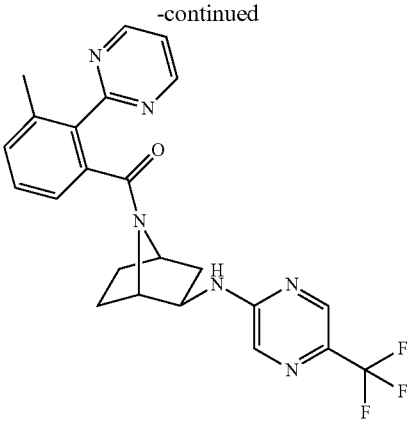

(3-methyl-2-(pyrimidin-2-yl)phenyl)((1S,2R,4R)-2-((5-(trifluoromethyl)pyrazin-2-yl)amino)-7-azabicyclo[2.2.1]heptan-7-yl)methanone,

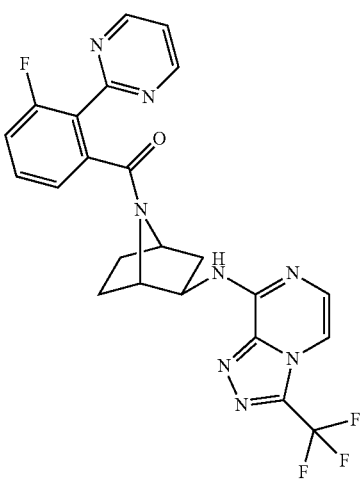 [SMILES: O=C(c1cccc(F)c1-c1ncccn1)N1C2CCC1C(Nc1nccn3c(C(F)(F)F)nnc13)C2]

(3-fluoro-2-(pyrimidin-2-yl)phenyl)((1S,2R,4R)-2-((3-(trifluoromethyl)-[1,2,4]triazolo[4,3-a]pyrazin-8-yl)amino)-7-azabicyclo[2.2.1]heptan-7-yl)methanone,

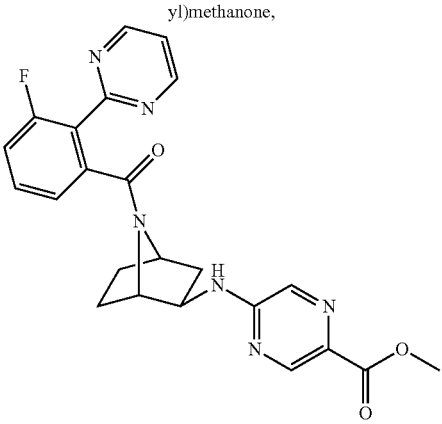

methyl 5-(((1S,2R,4R)-7-(3-fluoro-2-(pyrimidin-2-yl)benzoyl)-7-azabicyclo[2.2.1]heptan-2-yl)amino)pyrazine-2-carboxylate, 815
-continued

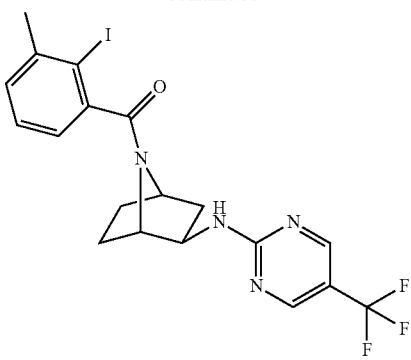 [SMILES: Cc1cccc(C(=O)N2C3CCC2C(Nc2ncc(C(F)(F)F)cn2)C3)c1I]

(2-iodo-3-methylphenyl)((1S,2R,4R)-2-
((5-(trifluoromethyl)pyrimidin-2-
yl)amino)-7-azabicyclo[2.2.1]heptan-7-
yl)methanone,

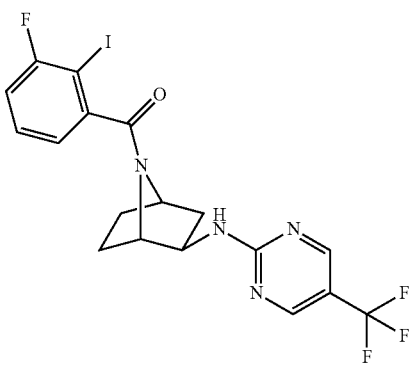 [SMILES: O=C(c1cccc(F)c1I)N1C2CCC1C(Nc1ncc(C(F)(F)F)cn1)C2]

(3-fluoro-2-iodophenyl)((1S,2R,4R)-2-
((5-(trifluoromethyl)pyrimidin-2-
yl)amino)-7-azabicyclo[2.2.1]heptan-7-
yl)methanone,

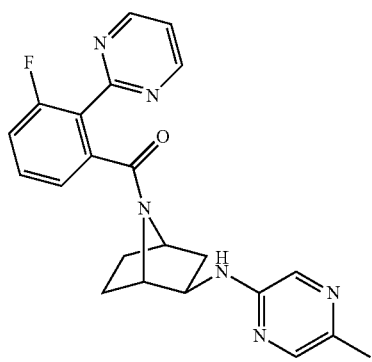 [SMILES: Cc1cnc(NC2CC3CCC2N3C(=O)c2cccc(F)c2-c2ncccn2)cn1]

(3-fluoro-2-(pyrimidin-2-
yl)phenyl)((1S,2R,4R)-2-((5-
methylpyrazin-2-yl)amino)-7-
azabicyclo[2.2.1]heptan-7-
yl)methanone, 816
-continued

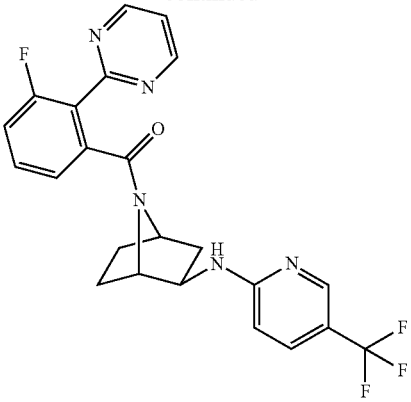 [SMILES: O=C(c1cccc(F)c1-c1ncccn1)N1C2CCC1C(Nc1ccc(C(F)(F)F)cn1)C2]

(3-fluoro-2-(pyrimidin-2-
yl)phenyl)((1S,2R,4R)-2-((5-
(trifluoromethyl)pyridin-2-yl)amino)-7-
azabicyclo[2.2.1]heptan-7-
yl)methanone,

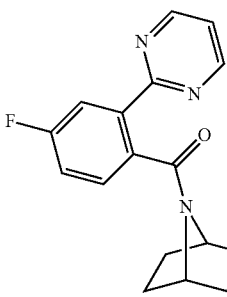

(4-fluoro-2-(pyrimidin-2-
yl)phenyl)((1S,2R,4R)-2-((5-
(trifluoromethyl)pyridin-2-yl)amino)-7-
azabicyclo[2.2.1]heptan-7-
yl)methanone,

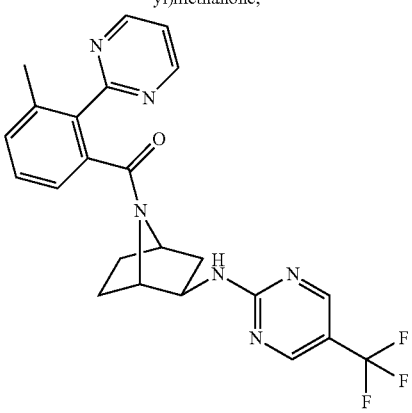

(3-methyl-2-(pyrimidin-2-
yl)phenyl)((1S,2R,4R)-2-((5-
(trifluoromethyl)pyrimidin-2-yl)amino)-
7-azabicyclo[2.2.1]heptan-7-
yl)methanone, 817
-continued

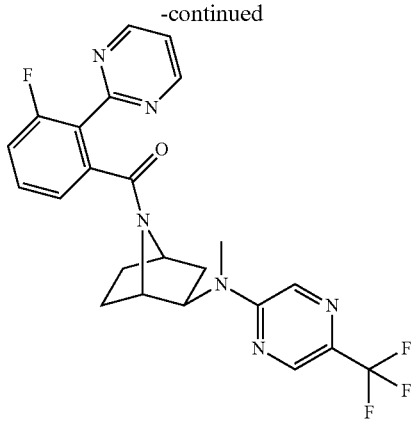

(3-fluoro-2-(pyrimidin-2-yl)phenyl)((1S,2R,4R)-2-(methyl(5-(trifluoromethyl)pyrazin-2-yl)amino)-7-azabicyclo[2.2.1]heptan-7-yl)methanone,

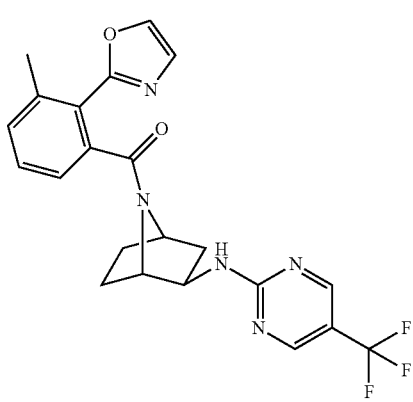

(3-methyl-2-(oxazol-2-yl)phenyl)((1S,2R,4R)-2-((5-(trifluoromethyl)pyrimidin-2-yl)amino)-7-azabicyclo[2.2.1]heptan-7-yl)methanone,

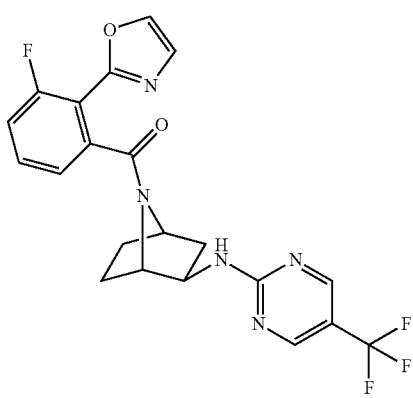 [SMILES: O=C(c1cccc(F)c1-c1ncco1)N1C2CCC1C(Nc1ncc(C(F)(F)F)cn1)C2]

(3-fluoro-2-(oxazol-2-yl)phenyl)((1S,2R,4R)-2-((5-(trifluoromethyl)pyrimidin-2-yl)amino)-7-azabicyclo[2.2.1]heptan-7-yl)methanone, 818
-continued

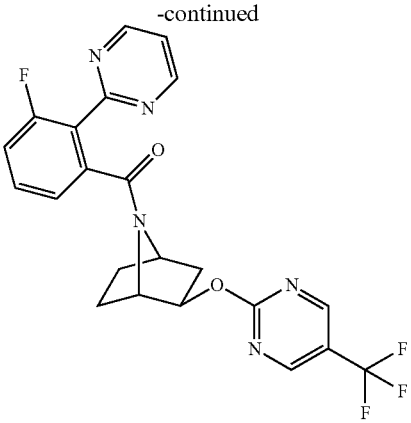

(±)-(3-fluoro-2-(pyrimidin-2-yl)phenyl)(2-((5-(trifluoromethyl)pyrimidin-2-yl)oxy)-7-azabicyclo[2.2.1]heptan-7-yl)methanone,

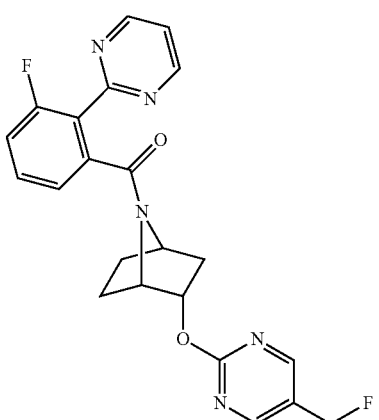

(±)-(3-fluoro-2-(pyrimidin-2-yl)phenyl)(2-((5-(trifluoromethyl)pyrimidin-2-yl)oxy)-7-azabicyclo[2.2.1]heptan-7-yl)methanone,

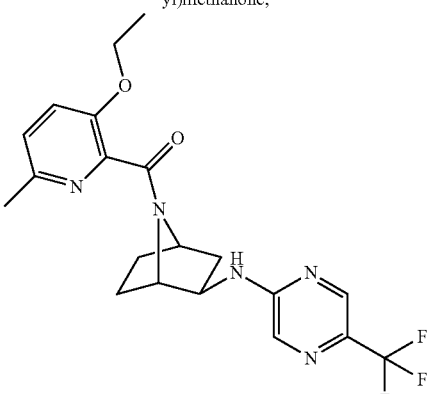

(3-ethoxy-6-methylpyridin-2-yl)((1S,2R,4R)-2-((5-(trifluoromethyl)pyrazin-2-yl)amino)-7-azabicyclo[2.2.1]heptan-7-yl)methanone, -continued

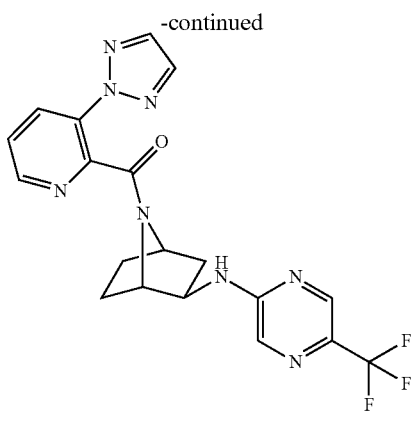

(3-(2H-1,2,3-triazol-2-yl)pyridin-2-
yl)((1S,2R,4R)-2-((5-
(trifluoromethyl)pyrazin-2-yl)amino)-7-
azabicyclo[2.2.1]heptan-7-
yl)methanone,

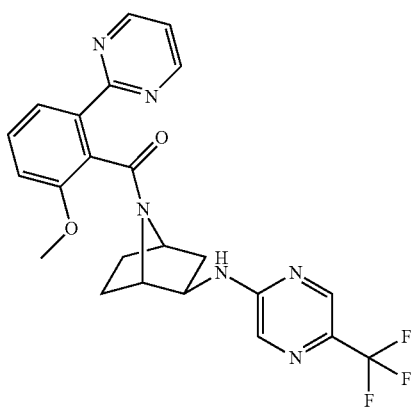 [SMILES: COc1cccc(-c2ncccn2)c1C(=O)N1C2CCC1C(Nc1cnc(C(F)(F)F)cn1)C2]

(2-methoxy-6-(pyrimidin-2-
yl)phenyl)((1S,2R,4R)-2-((5-
(trifluoromethyl)pyrazin-2-yl)amino)-7-
azabicyclo[2.2.1]heptan-7-
yl)methanone,

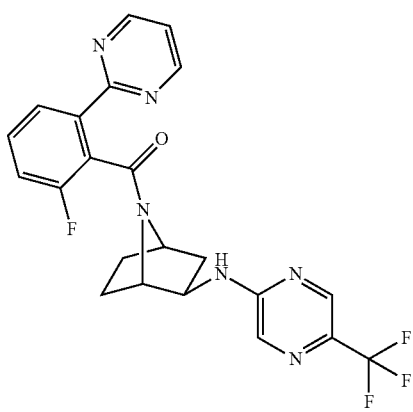 [SMILES: O=C(c1c(F)cccc1-c1ncccn1)N1C2CCC1C(Nc1cnc(C(F)(F)F)cn1)C2]

(2-fluoro-6-(pyrimidin-2-
yl)phenyl)((1S,2R,4R)-2-((5-
(trifluoromethyl)pyrazin-2-yl)amino)-7-
azabicyclo[2.2.1]heptan-7-
yl)methanone, -continued

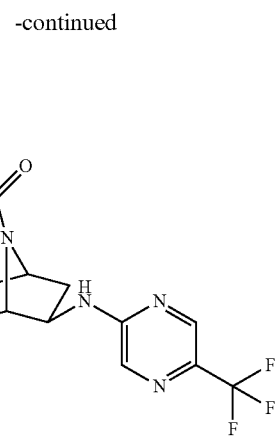

(7-ethoxyquinolin-8-yl)((1S,2R,4R)-2-
((5-(trifluoromethyl)pyrazin-2-
yl)amino)-7-azabicyclo[2.2.1]heptan-7-
yl)methanone,

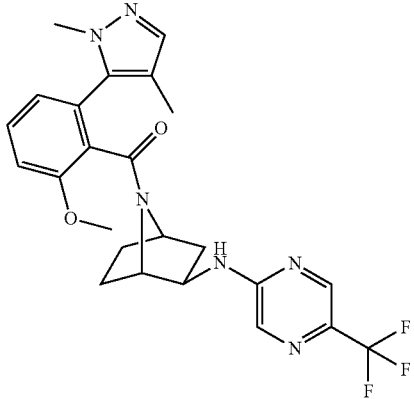 [SMILES: COc1cccc(-c2c(C)cnn2C)c1C(=O)N1C2CCC1C(Nc1cnc(C(F)(F)F)cn1)C2]

(2-(1,4-dimethyl-1H-pyrazol-5-yl)-6-
methoxyphenyl)((1S,2R,4R)-2-((5-
(trifluoromethyl)pyrazin-2-yl)amino)-7-
azabicyclo[2.2.1]heptan-7-
yl)methanone,

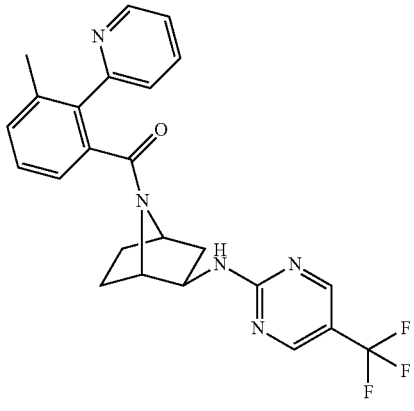 [SMILES: Cc1cccc(C(=O)N2C3CCC2C(Nc2ncc(C(F)(F)F)cn2)C3)c1-c1ccccn1]

(3-methyl-2-(pyridin-2-
yl)phenyl)((1S,2R,4R)-2-((5-
(trifluoromethyl)pyrimidin-2-yl)amino)-
7-azabicyclo[2.2.1]heptan-7-
yl)methanone, -continued

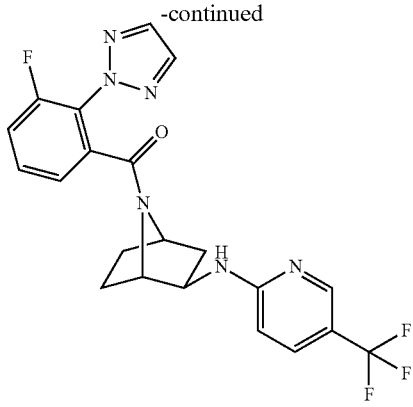

(3-fluoro-2-(2H-1,2,3-triazol-2-
yl)phenyl)((1S,2R,4R)-2-((5-
(trifluoromethyl)pyridin-2-yl)amino)-7-
azabicyclo[2.2.1]heptan-7-
yl)methanone,

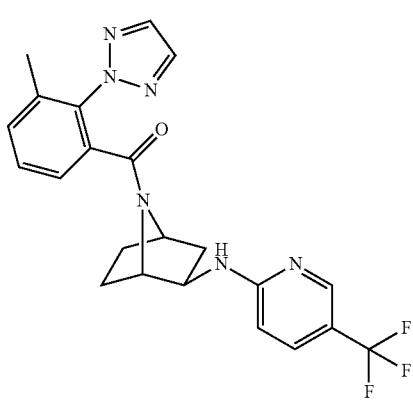 [SMILES: Cc1cccc(C(=O)N2C3CCC2C(Nc2ccc(C(F)(F)F)cn2)C3)c1-n1nccn1]

(3-methyl-2-(2H-1,2,3-triazol-2-
yl)phenyl)((1S,2R,4R)-2-((5-
(trifluoromethyl)pyridin-2-yl)amino)-7-
azabicyclo[2.2.1]heptan-7-
yl)methanone,

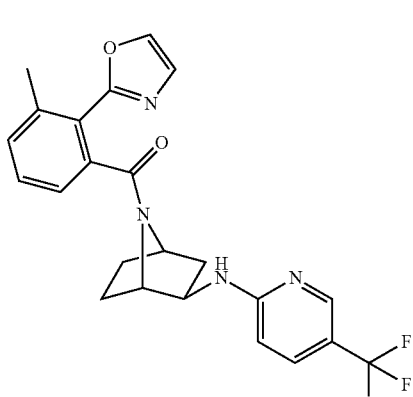

(3-methyl-2-(oxazol-2-
yl)phenyl)((1S,2R,4R)-2-((5-
(trifluoromethyl)pyridin-2-yl)amino)-7-
azabicyclo[2.2.1]heptan-7-
yl)methanone, -continued

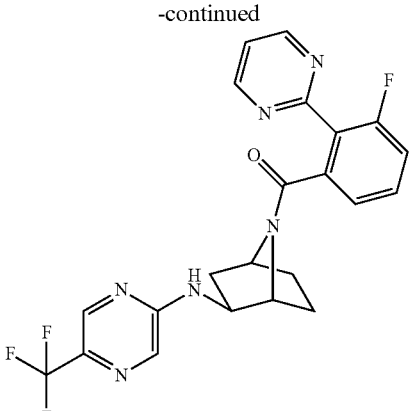

(3-fluoro-2-(pyrimidin-2-
yl)phenyl)((1R,2S,4S)-2-((5-
(trifluoromethyl)pyrazin-2-yl)amino)-7-
azabicyclo[2.2.1]heptan-7-
yl)methanone,

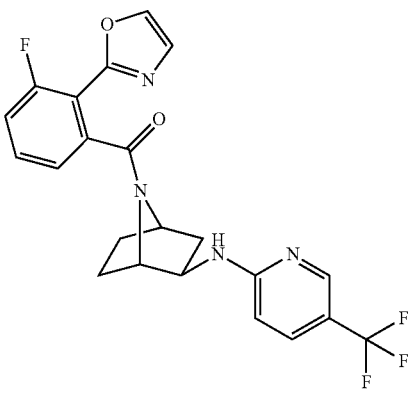

(3-fluoro-2-(oxazol-2-
yl)phenyl)((1S,2R,4R)-2-((5-
(trifluoromethyl)pyridin-2-yl)amino)-7-
azabicyclo[2.2.1]heptan-7-
yl)methanone,

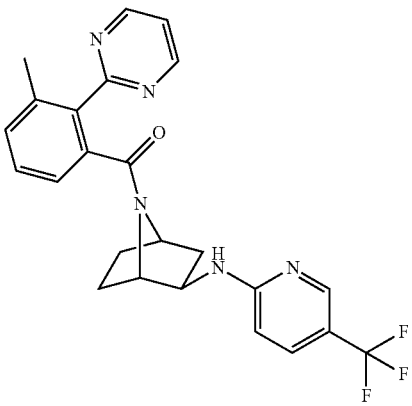

(3-methyl-2-(pyrimidin-2-
yl)phenyl)((1S,2R,4R)-2-((5-
(trifluoromethyl)pyridin-2-yl)amino)-7-
azabicyclo[2.2.1]heptan-7-
yl)methanone,

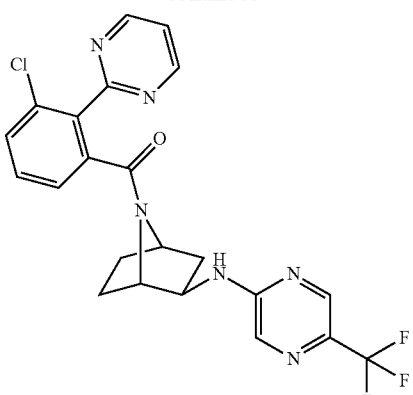

(3-chloro-2-(pyrimidin-2-
yl)phenyl)((1S,2R,4R)-2-((5-
(trifluoromethyl)pyrazin-2-yl)amino)-7-
azabicyclo[2.2.1]heptan-7-
yl)methanone,

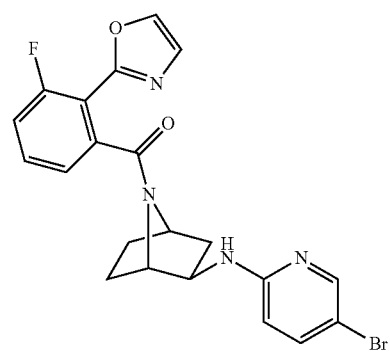

((1S,2R,4R)-2-((5-bromopyridin-2-
yl)amino)-7-azabicyclo[2.2.1]heptan-7-
yl)(3-fluoro-2-(oxazol-2-
yl)phenyl)methanone,

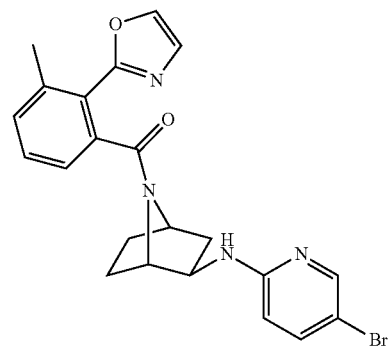 [SMILES: Cc1cccc(C(=O)N2C3CCC2C(Nc2ccc(Br)cn2)C3)c1-c1ncco1]

((1S,2R,4R)-2-((5-bromopyridin-2-
yl)amino)-7-azabicyclo[2.2.1]heptan-7-
yl)(3-methyl-2-(oxazol-2-
yl)phenyl)methanone,

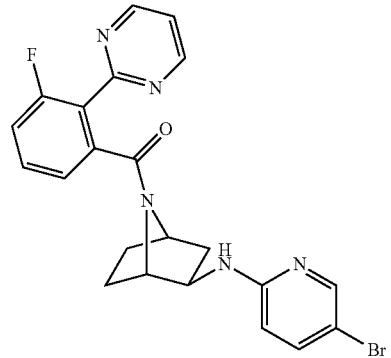 [SMILES: O=C(c1cccc(F)c1-c1ncccn1)N1C2CCC1C(Nc1ccc(Br)cn1)C2]

((1S,2R,4R)-2-((5-bromopyridin-2-
yl)amino)-7-azabicyclo[2.2.1]heptan-7-
yl)(3-fluoro-2-(pyrimidin-2-
yl)phenyl)methanone,

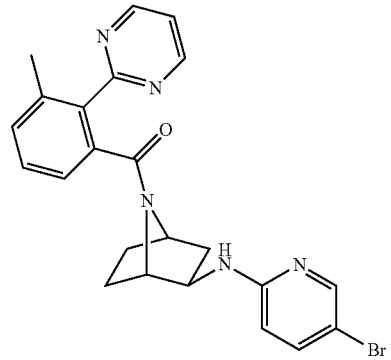 [SMILES: Cc1cccc(C(=O)N2C3CCC2C(Nc2ccc(Br)cn2)C3)c1-c1ncccn1]

((1S,2R,4R)-2-((5-bromopyridin-2-
yl)amino)-7-azabicyclo[2.2.1]heptan-7-
yl)(3-methyl-2-(pyrimidin-2-
yl)phenyl)methanone,

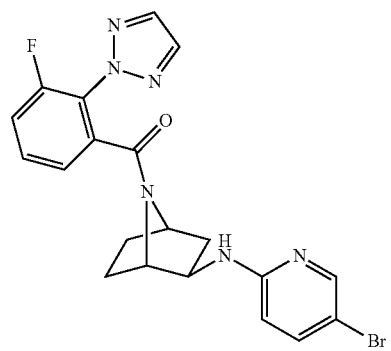

((1S,2R,4R)-2-((5-bromopyridin-2-
yl)amino)-7-azabicyclo[2.2.1]heptan-7-
yl)(3-fluoro-2-(2H-1,2,3-triazol-2-
yl)phenyl)methanone, 825
-continued

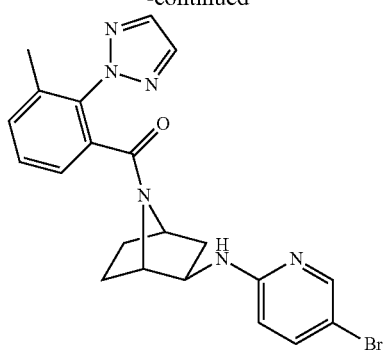

((1S,2R,4R)-2-((5-bromopyridin-2-yl)amino)-7-azabicyclo[2.2.1]heptan-7-yl)(3-methyl-2-(2H-1,2,3-triazol-2-yl)phenyl)methanone,

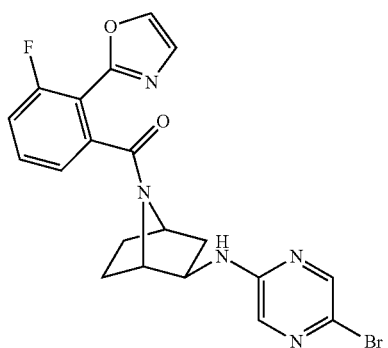 [SMILES: Cc1cccc(C(=O)N2C3CCC2C(Nc2cnc(Br)cn2)C3)c1-c1ncco1]

((1S,2R,4R)-2-((5-bromopyrazin-2-yl)amino)-7-azabicyclo[2.2.1]heptan-7-yl)(3-fluoro-2-(oxazol-2-yl)phenyl)methanone,

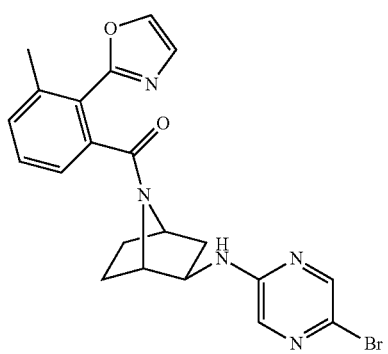

((1S,2R,4R)-2-((5-bromopyrazin-2-yl)amino)-7-azabicyclo[2.2.1]heptan-7-yl)(3-methyl-2-(oxazol-2-yl)phenyl)methanone, 826
-continued

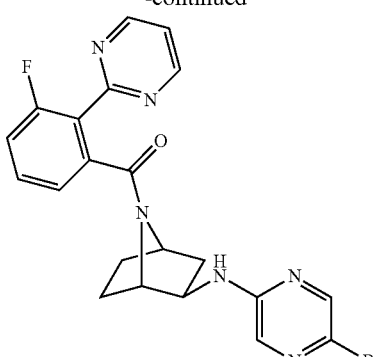

((1S,2R,4R)-2-((5-bromopyrazin-2-yl)amino)-7-azabicyclo[2.2.1]heptan-7-yl)(3-fluoro-2-(pyrimidin-2-yl)phenyl)methanone,

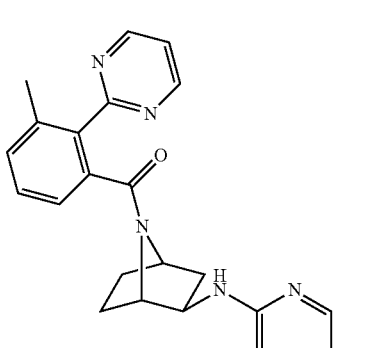

((1S,2R,4R)-2-((5-bromopyrazin-2-yl)amino)-7-azabicyclo[2.2.1]heptan-7-yl)(3-methyl-2-(pyrimidin-2-yl)phenyl)methanone,

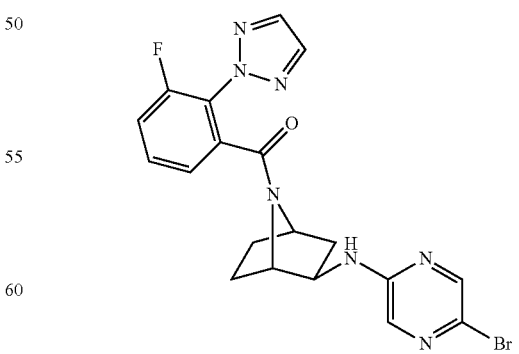

((1S,2R,4R)-2-((5-bromopyrazin-2-yl)amino)-7-azabicyclo[2.2.1]heptan-7-yl)(3-fluoro-2-(2H-1,2,3-triazol-2-yl)phenyl)methanone,

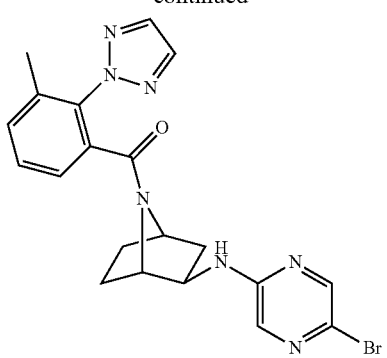

((1S,2R,4R)-2-((5-bromopyrazin-2-yl)amino)-7-azabicyclo[2.2.1]heptan-7-yl)(3-methyl-2-(2H-1,2,3-triazol-2-yl)phenyl)methanone,

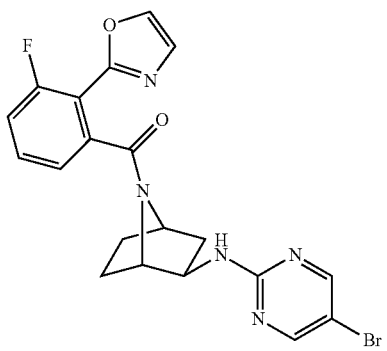

((1S,2R,4R)-2-((5-bromopyrimidin-2-yl)amino)-7-azabicyclo[2.2.1]heptan-7-yl)(3-fluoro-2-(oxazol-2-yl)phenyl)methanone,

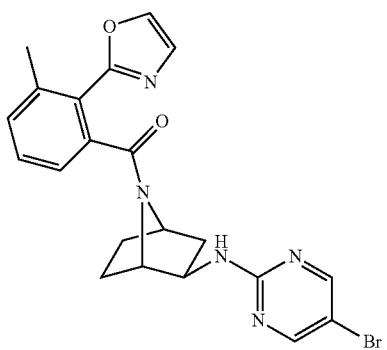 [SMILES: Cc1cccc(C(=O)N2C3CCC2C(Nc2ncc(Br)cn2)C3)c1-c1ncco1]

((1S,2R,4R)-2-((5-bromopyrimidin-2-yl)amino)-7-azabicyclo[2.2.1]heptan-7-yl)(3-methyl-2-(oxazol-2-yl)phenyl)methanone,

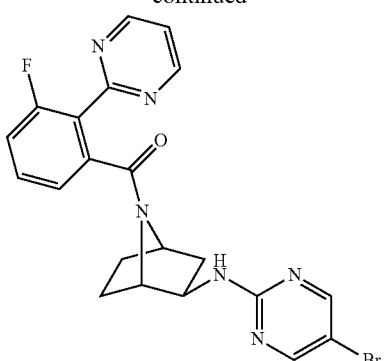

((1S,2R,4R)-2-((5-bromopyrimidin-2-yl)amino)-7-azabicyclo[2.2.1]heptan-7-yl)(3-fluoro-2-(pyrimidin-2-yl)phenyl)methanone,

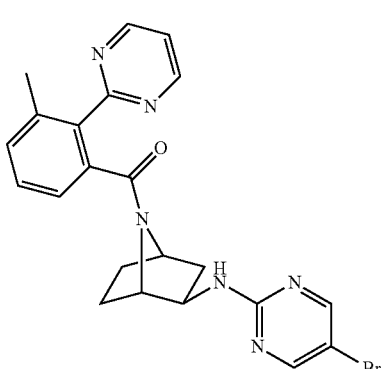

((1S,2R,4R)-2-((5-bromopyrimidin-2-yl)amino)-7-azabicyclo[2.2.1]heptan-7-yl)(3-methyl-2-(pyrimidin-2-yl)phenyl)methanone,

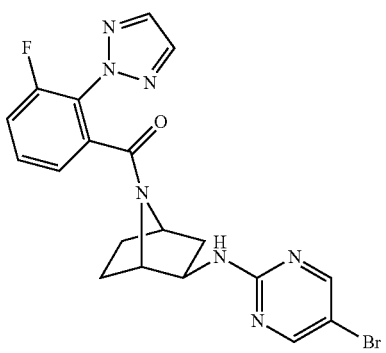 [SMILES: Cc1cccc(C(=O)N2C3CCC2C(Nc2ncc(Br)cn2)C3)c1-n1nccn1]

((1S,2R,4R)-2-((5-bromopyrimidin-2-yl)amino)-7-azabicyclo[2.2.1]heptan-7-yl)(3-fluoro-2-(2H-1,2,3-triazol-2-yl)phenyl)methanone, -continued

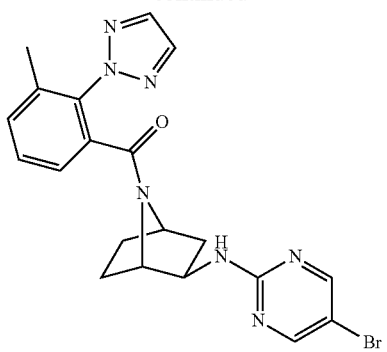

((1S,2R,4R)-2-((5-bromopyrimidin-2-yl)amino)-7-azabicyclo[2.2.1]heptan-7-yl)(3-methyl-2-(2H-1,2,3-triazol-2-yl)phenyl)methanone,

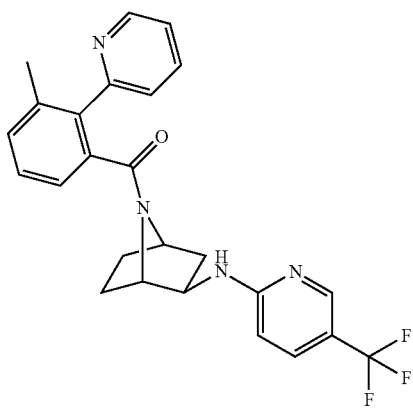

(3-methyl-2-(pyridin-2-yl)phenyl)((1S,2R,4R)-2-((5-(trifluoromethyl)pyridin-2-yl)amino)-7-azabicyclo[2.2.1]heptan-7-yl)methanone,

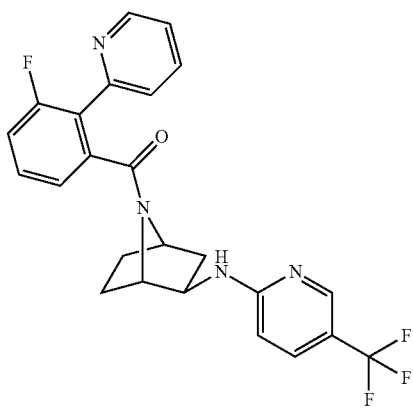

(3-fluoro-2-(pyridin-2-yl)phenyl)((1S,2R,4R)-2-((5-(trifluoromethyl)pyridin-2-yl)amino)-7-azabicyclo[2.2.1]heptan-7-yl)methanone, -continued

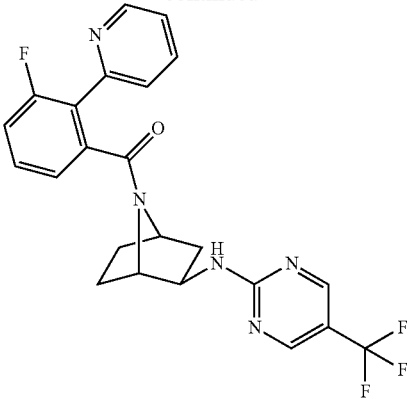

(3-fluoro-2-(pyridin-2-yl)phenyl)((1S,2R,4R)-2-((5-(trifluoromethyl)pyrimidin-2-yl)amino)-7-azabicyclo[2.2.1]heptan-7-yl)methanone,

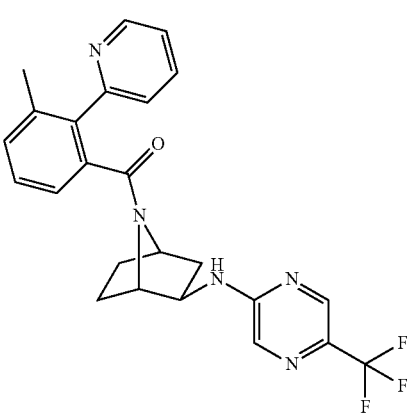

(3-methyl-2-(pyridin-2-yl)phenyl)((1S,2R,4R)-2-((5-(trifluoromethyl)pyrazin-2-yl)amino)-7-azabicyclo[2.2.1]heptan-7-yl)methanone,

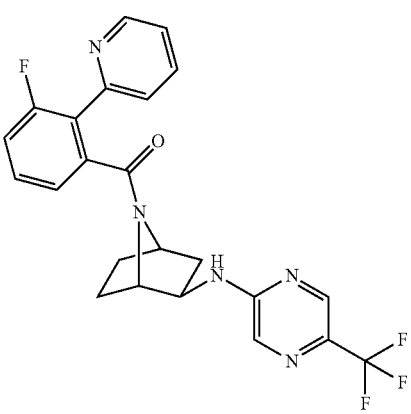

(3-fluoro-2-(pyridin-2-yl)phenyl)((2S)-2-((5-(trifluoromethyl)pyrazin-2-yl)amino)-7-azabicyclo[2.2.1]heptan-7-yl)methanone,

831
-continued

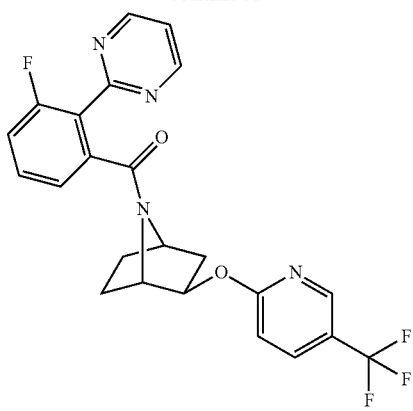

(3-fluoro-2-(pyrimidin-2-yl)phenyl)((1S,2R,4R)-2-((5-(trifluoromethyl)pyridin-2-yl)oxy)-7-azabicyclo[2.2.1]heptan-7-yl)methanone,

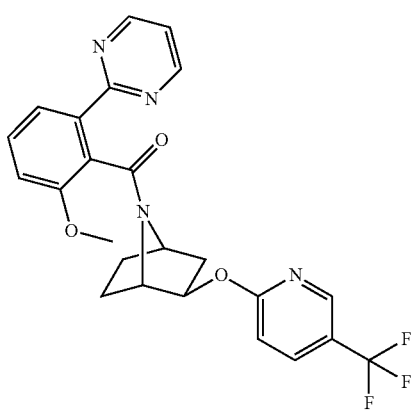

(2-methoxy-6-(pyrimidin-2-yl)phenyl)((1S,2R,4R)-2-((5-(trifluoromethyl)pyridin-2-yl)oxy)-7-azabicyclo[2.2.1]heptan-7-yl)methanone,

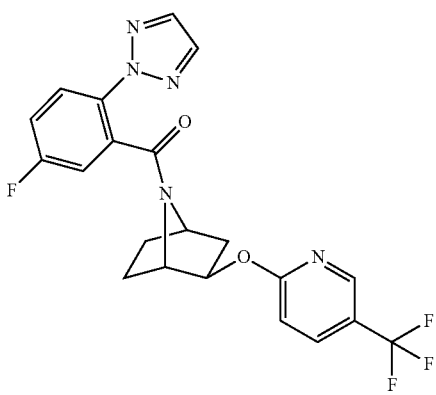

(5-fluoro-2-(2H-1,2,3-triazol-2-yl)phenyl)((1S,2R,4R)-2-((5-(trifluoromethyl)pyridin-2-yl)oxy)-7-azabicyclo[2.2.1]heptan-7-yl)methanone,

832
-continued

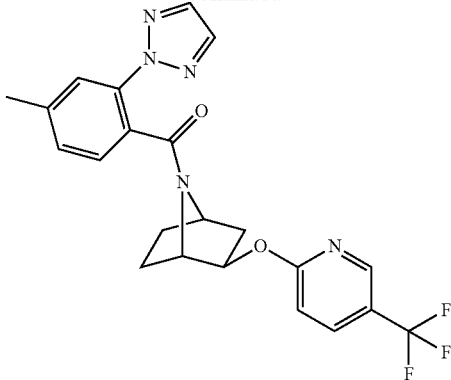

(4-methyl-2-(2H-1,2,3-triazol-2-yl)phenyl)((1S,2R,4R)-2-((5-(trifluoromethyl)pyridin-2-yl)oxy)-7-azabicyclo[2.2.1]heptan-7-yl)methanone,

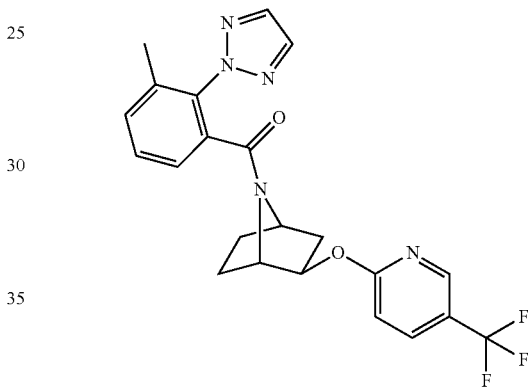

(3-methyl-2-(2H-1,2,3-triazol-2-yl)phenyl)((1S,2R,4R)-2-((5-(trifluoromethyl)pyridin-2-yl)oxy)-7-azabicyclo[2.2.1]heptan-7-yl)methanone,

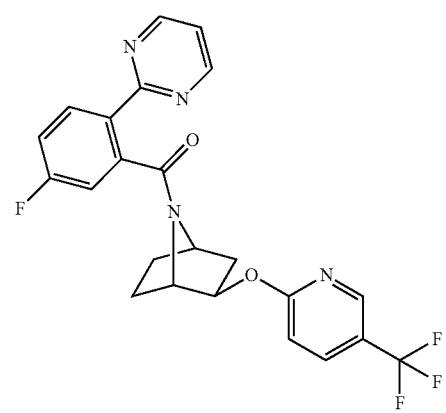

(5-fluoro-2-(pyrimidin-2-yl)phenyl)((1S,2R,4R)-2-((5-(trifluoromethyl)pyridin-2-yl)oxy)-7-azabicyclo[2.2.1]heptan-7-yl)methanone,

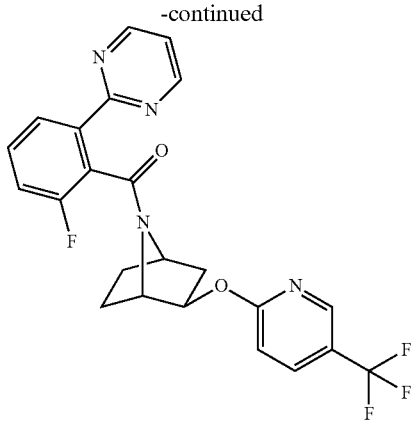

(2-fluoro-6-(pyrimidin-2-yl)phenyl)((1S,2R,4R)-2-((5-(trifluoromethyl)pyridin-2-yl)oxy)-7-azabicyclo[2.2.1]heptan-7-yl)methanone,

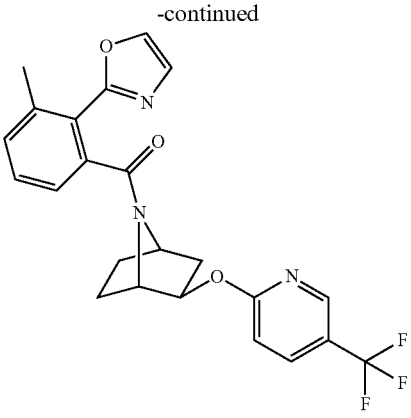

(3-methyl-2-(oxazol-2-yl)phenyl)((1S,2R,4R)-2-((5-(trifluoromethyl)pyridin-2-yl)oxy)-7-azabicyclo[2.2.1]heptan-7-yl)methanone,

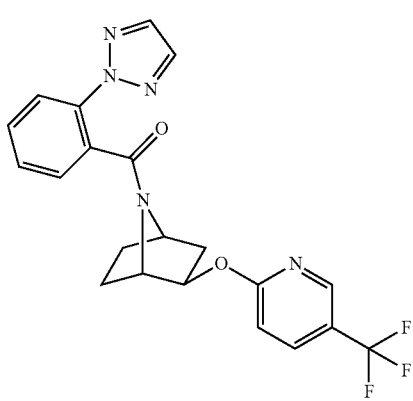

(2-(2H-1,2,3-triazol-2-yl)phenyl)((1S,2R,4R)-2-((5-(trifluoromethyl)pyridin-2-yl)oxy)-7-azabicyclo[2.2.1]heptan-7-yl)methanone,

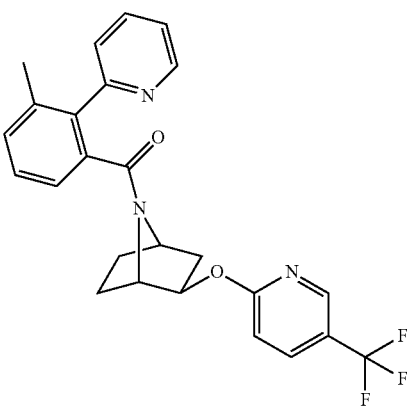

(3-methyl-2-(pyridin-2-yl)phenyl)((1S,2R,4R)-2-((5-(trifluoromethyl)pyridin-2-yl)oxy)-7-azabicyclo[2.2.1]heptan-7-yl)methanone,

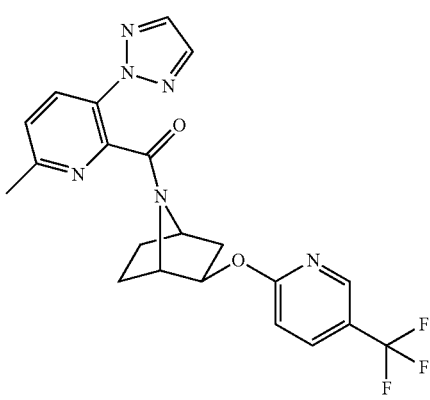

(6-methyl-3-(2H-1,2,3-triazol-2-yl)pyridin-2-yl)((1S,2R,4R)-2-((5-(trifluoromethyl)pyridin-2-yl)oxy)-7-azabicyclo[2.2.1]heptan-7-yl)methanone,

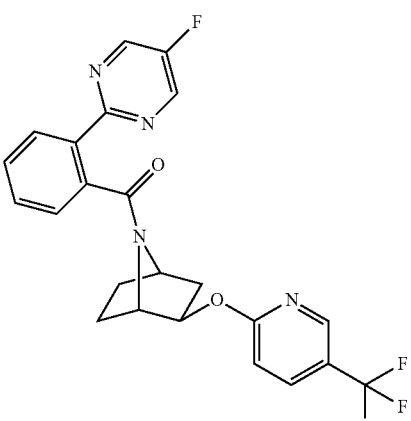

(2-(5-fluoropyrimidin-2-yl)phenyl)((1S,2R,4R)-2-((5-(trifluoromethyl)pyridin-2-yl)oxy)-7-azabicyclo[2.2.1]heptan-7-yl)methanone, 835
-continued

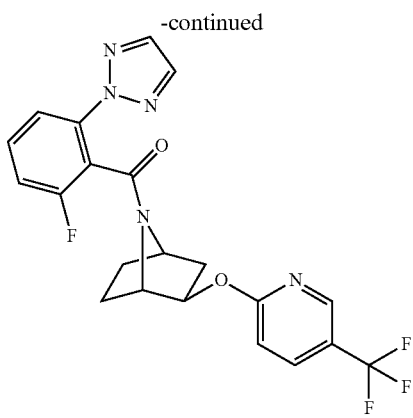

(2-fluoro-6-(2H-1,2,3-triazol-2-
yl)phenyl)((1S,2R,4R)-2-((5-
(trifluoromethyl)pyridin-2-yl)oxy)-7-
azabicyclo[2.2.1]heptan-7-
yl)methanone,

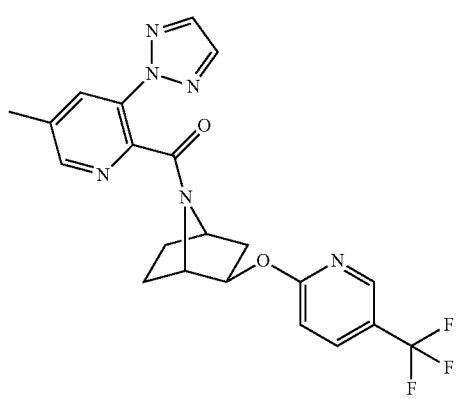

(5-methyl-3-(2H-1,2,3-triazol-2-
yl)pyridin-2-yl)((1S,2R,4R)-2-((5-
(trifluoromethyl)pyridin-2-yl)oxy)-7-
azabicyclo[2.2.1]heptan-7-
yl)methanone,

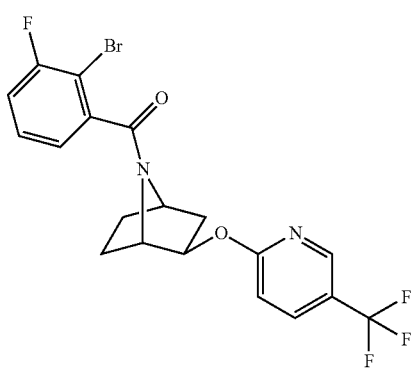

(2-bromo-3-fluorophenyl)((1S,2R,4R)-
2-((5-(trifluoromethyl)pyridin-2-
yl)oxy)-7-azabicyclo[2.2.1]heptan-7-
yl)methanone, 836
-continued

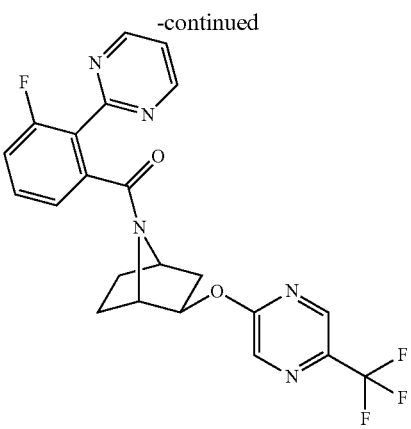

(3-fluoro-2-(pyrimidin-2-
yl)phenyl)((1S,2R,4R)-2-((5-
(trifluoromethyl)pyrazin-2-yl)oxy)-7-
azabicyclo[2.2.1]heptan-7-
yl)methanone,

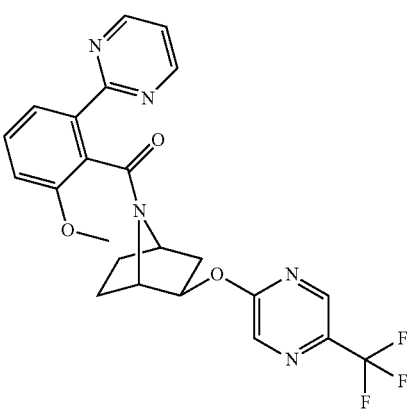

(2-methoxy-6-(pyrimidin-2-
yl)phenyl)((1S,2R,4R)-2-((5-
(trifluoromethyl)pyrazin-2-yl)oxy)-7-
azabicyclo[2.2.1]heptan-7-
yl)methanone,

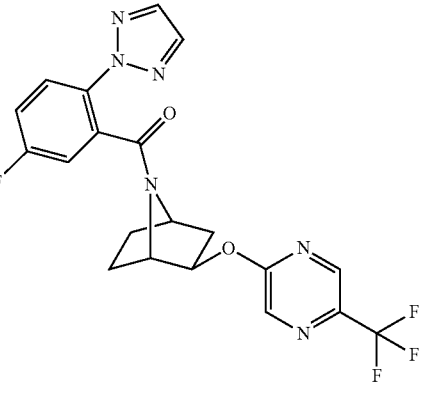

(5-fluoro-2-(2H-1,2,3-triazol-2-
yl)phenyl)((1S,2R,4R)-2-((5-
(trifluoromethyl)pyrazin-2-yl)oxy)-7-
azabicyclo[2.2.1]heptan-7-
yl)methanone,

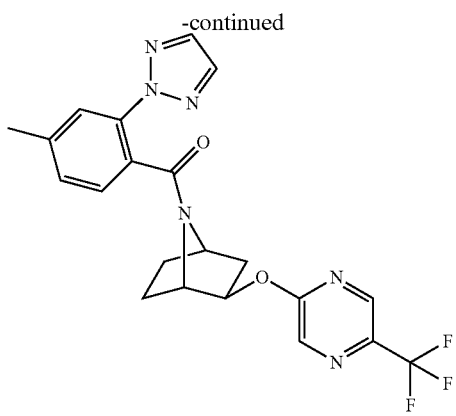

(4-methyl-2-(2H-1,2,3-triazol-2-yl)phenyl)((1S,2R,4R)-2-((5-(trifluoromethyl)pyrazin-2-yl)oxy)-7-azabicyclo[2.2.1]heptan-7-yl)methanone,

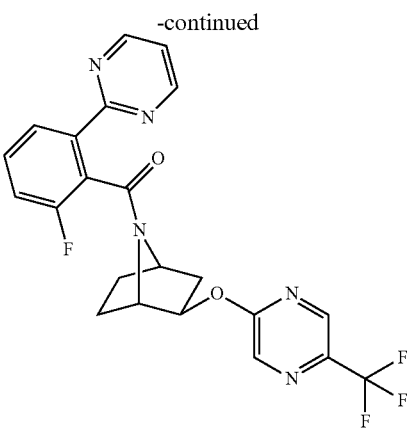

(2-fluoro-6-(pyrimidin-2-yl)phenyl)((1S,2R,4R)-2-((5-(trifluoromethyl)pyrazin-2-yl)oxy)-7-azabicyclo[2.2.1]heptan-7-yl)methanone,

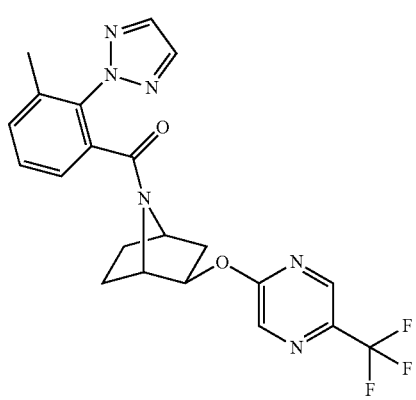

(3-methyl-2-(2H-1,2,3-triazol-2-yl)phenyl)((1S,2R,4R)-2-((5-(trifluoromethyl)pyrazin-2-yl)oxy)-7-azabicyclo[2.2.1]heptan-7-yl)methanone,

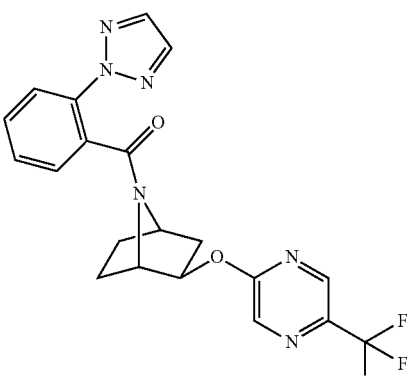

(2-(2H-1,2,3-triazol-2-yl)phenyl)((1S,2R,4R)-2-((5-(trifluoromethyl)pyrazin-2-yl)oxy)-7-azabicyclo[2.2.1]heptan-7-yl)methanone,

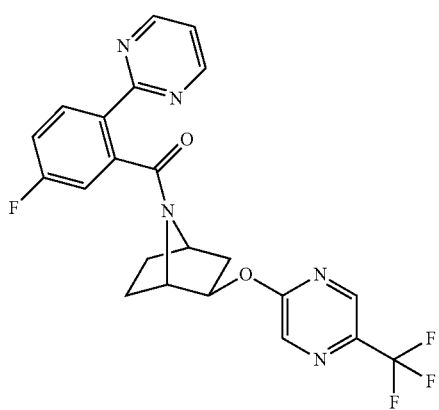

(5-fluoro-2-(pyrimidin-2-yl)phenyl)((1S,2R,4R)-2-((5-(trifluoromethyl)pyrazin-2-yl)oxy)-7-azabicyclo[2.2.1]heptan-7-yl)methanone,

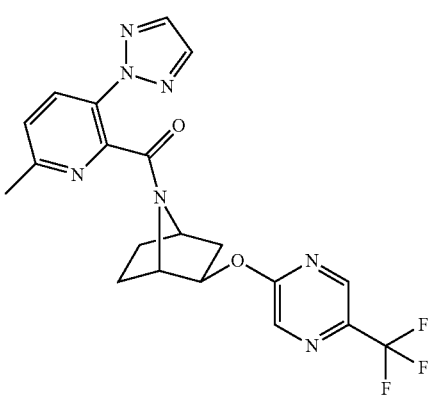

(6-methyl-3-(2H-1,2,3-triazol-2-yl)pyridin-2-yl)((1S,2R,4R)-2-((5-(trifluoromethyl)pyrazin-2-yl)oxy)-7-azabicyclo[2.2.1]heptan-7-yl)methanone, -continued

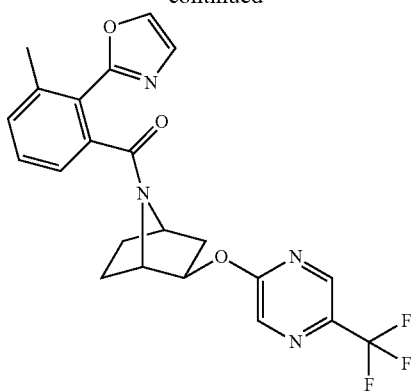

(3-methyl-2-(oxazol-2-yl)phenyl)((1S,2R,4R)-2-((5-(trifluoromethyl)pyrazin-2-yl)oxy)-7-azabicyclo[2.2.1]heptan-7-yl)methanone,

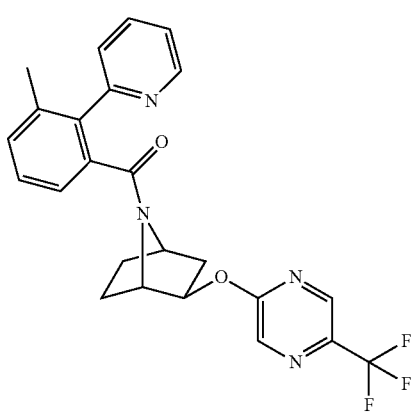

(3-methyl-2-(pyridin-2-yl)phenyl)((1S,2R,4R)-2-((5-(trifluoromethyl)pyrazin-2-yl)oxy)-7-azabicyclo[2.2.1]heptan-7-yl)methanone,

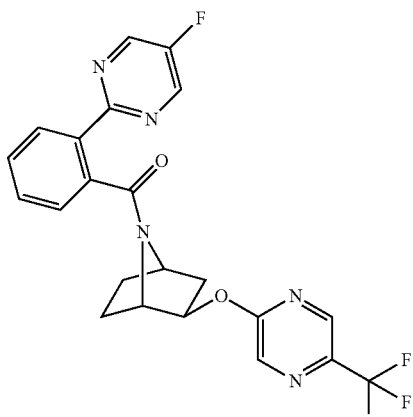

(2-(5-fluoropyrimidin-2-yl)phenyl)((1S,2R,4R)-2-((5-(trifluoromethyl)pyrazin-2-yl)oxy)-7-azabicyclo[2.2.1]heptan-7-yl)methanone, -continued

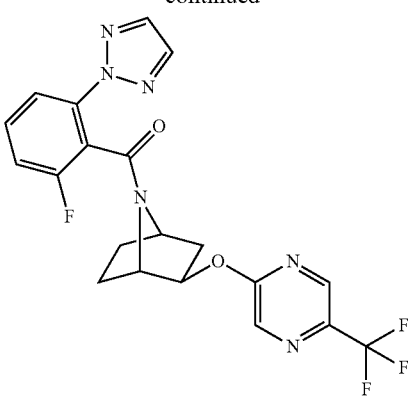

(2-fluoro-6-(2H-1,2,3-triazol-2-yl)phenyl)((1S,2R,4R)-2-((5-(trifluoromethyl)pyrazin-2-yl)oxy)-7-azabicyclo[2.2.1]heptan-7-yl)methanone,

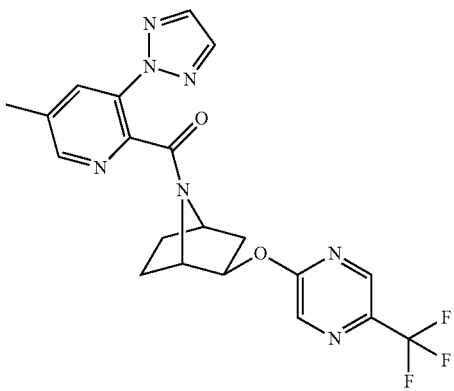

(5-methyl-3-(2H-1,2,3-triazol-2-yl)pyridin-2-yl)((1S,2R,4R)-2-((5-(trifluoromethyl)pyrazin-2-yl)oxy)-7-azabicyclo[2.2.1]heptan-7-yl)methanone,

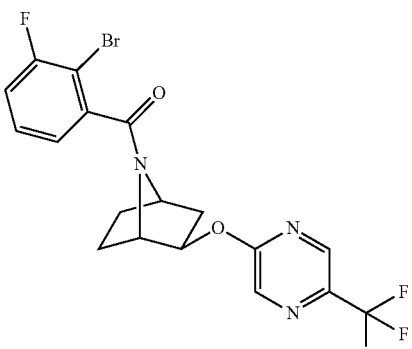

(2-bromo-3-fluorophenyl)((1S,2R,4R)-2-((5-(trifluoromethyl)pyrazin-2-yl)oxy)-7-azabicyclo[2.2.1]heptan-7-yl)methanone,

841

-continued

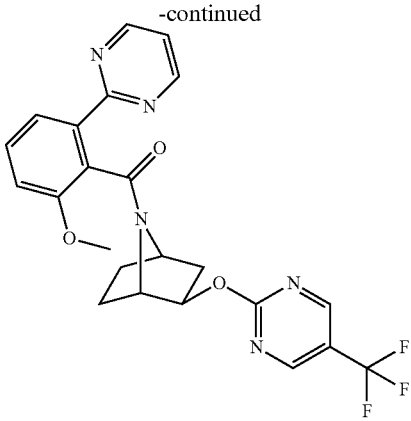

(2-methoxy-6-(pyrimidin-2-
yl)phenyl)((1S,2R,4R)-2-((5-
(trifluoromethyl)pyrimidin-2-yl)oxy)-7-
azabicyclo[2.2.1]heptan-7-
yl)methanone,

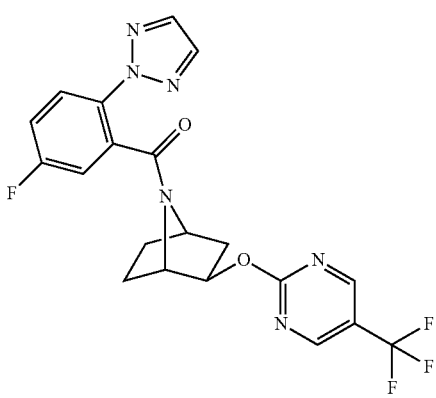

(5-fluoro-2-(2H-1,2,3-triazol-2-
yl)phenyl)((1S,2R,4R)-2-((5-
(trifluoromethyl)pyrimidin-2-yl)oxy)-7-
azabicyclo[2.2.1]heptan-7-
yl)methanone,

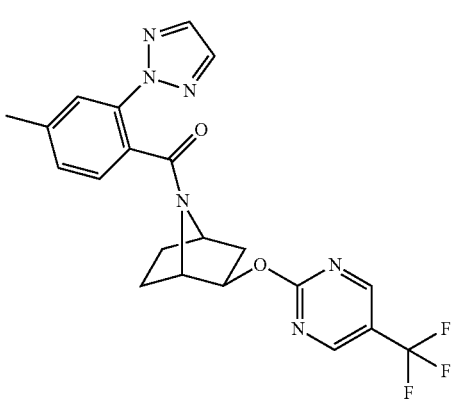

(4-methyl-2-(2H-1,2,3-triazol-2-
yl)phenyl)((1S,2R,4R)-2-((5-
(trifluoromethyl)pyrimidin-2-yl)oxy)-7-
azabicyclo[2.2.1]heptan-7-
yl)methanone,

842

-continued

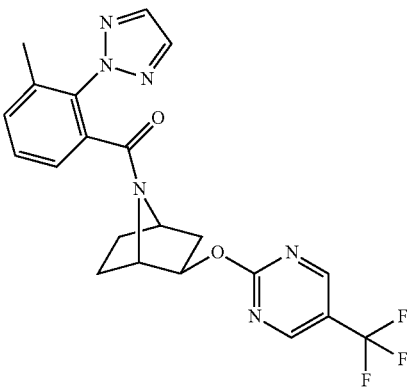

(3-methyl-2-(2H-1,2,3-triazol-2-
yl)phenyl)((1S,2R,4R)-2-((5-
(trifluoromethyl)pyrimidin-2-yl)oxy)-7-
azabicyclo[2.2.1]heptan-7-
yl)methanone,

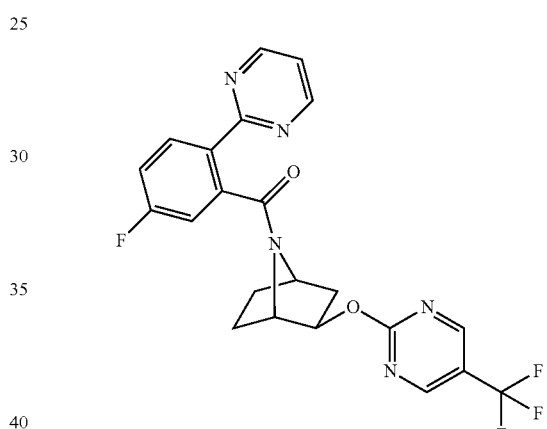

(5-fluoro-2-(pyrimidin-2-
yl)phenyl)((1S,2R,4R)-2-((5-
(trifluoromethyl)pyrimidin-2-yl)oxy)-7-
azabicyclo[2.2.1]heptan-7-
yl)methanone,

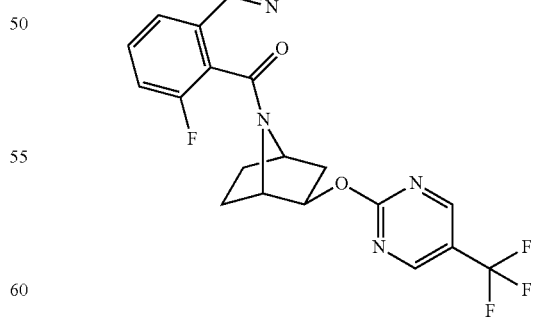

(2-fluoro-6-(pyrimidin-2-
yl)phenyl)((1S,2R,4R)-2-((5-
(trifluoromethyl)pyrimidin-2-yl)oxy)-7-
azabicyclo[2.2.1]heptan-7-
yl)methanone,

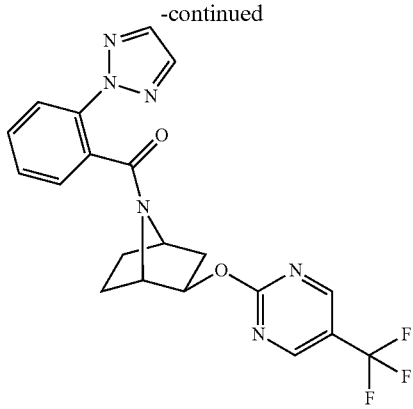

(2-(2H-1,2,3-triazol-2-
yl)phenyl)((1S,2R,4R)-2-((5-
(trifluoromethyl)pyrimidin-2-yl)oxy)-7-
azabicyclo[2.2.1]heptan-7-
yl)methanone,

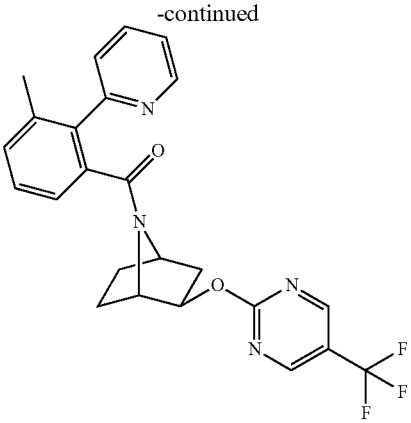

(3-methyl-2-(pyridin-2-
yl)phenyl)((1S,2R,4R)-2-((5-
(trifluoromethyl)pyrimidin-2-yl)oxy)-7-
azabicyclo[2.2.1]heptan-7-
yl)methanone,

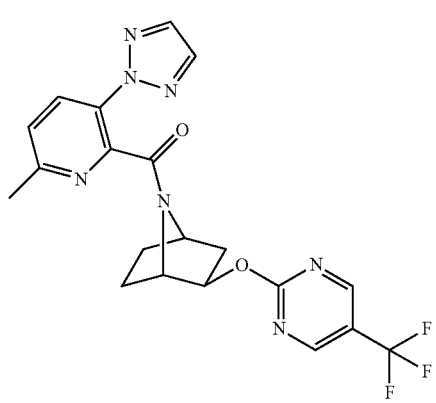

(6-methyl-3-(2H-1,2,3-triazol-2-
yl)pyridin-2-yl)((1S,2R,4R)-2-((5-
(trifluoromethyl)pyrimidin-2-yl)oxy)-7-
azabicyclo[2.2.1]heptan-7-
yl)methanone,

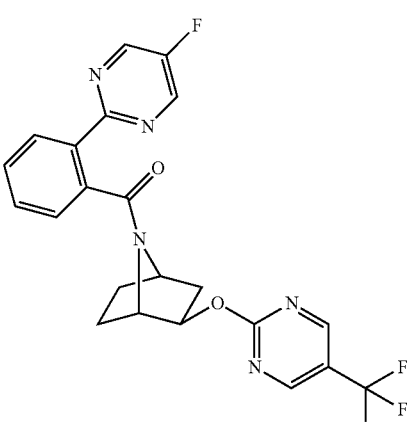

(2-(5-fluoropyrimidin-2-
yl)phenyl)((1S,2R,4R)-2-((5-
(trifluoromethyl)pyrimidin-2-yl)oxy)-7-
azabicyclo[2.2.1]heptan-7-
yl)methanone,

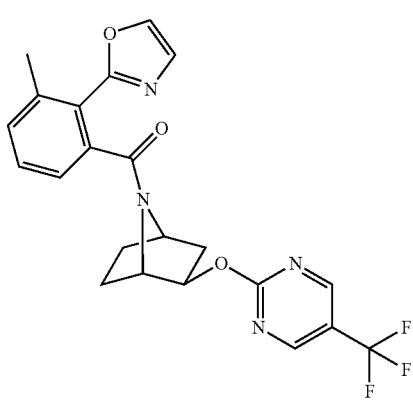

(3-methyl-2-(oxazol-2-
yl)phenyl)((1S,2R,4R)-2-((5-
(trifluoromethyl)pyrimidin-2-yl)oxy)-7-
azabicyclo[2.2.1]heptan-7-
yl)methanone,

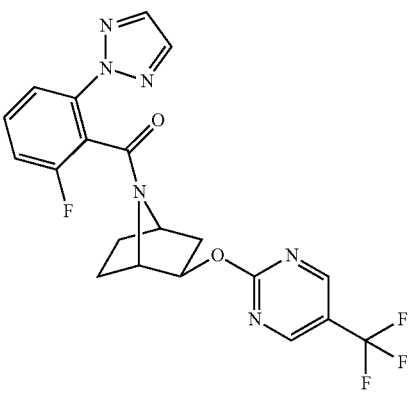

(2-fluoro-6-(2H-1,2,3-triazol-2-
yl)phenyl)((1S,2R,4R)-2-((5-
(trifluoromethyl)pyrimidin-2-yl)oxy)-7-
azabicyclo[2.2.1]heptan-7-
yl)methanone,

845

-continued

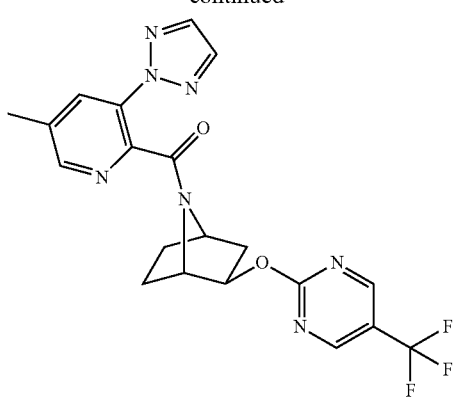

(5-methyl-3-(2H-1,2,3-triazol-2-
yl)pyridin-2-yl)((1S,2R,4R)-2-((5-
(trifluoromethyl)pyrimidin-2-yl)oxy)-7-
azabicyclo[2.2.1]heptan-7-
yl)methanone,

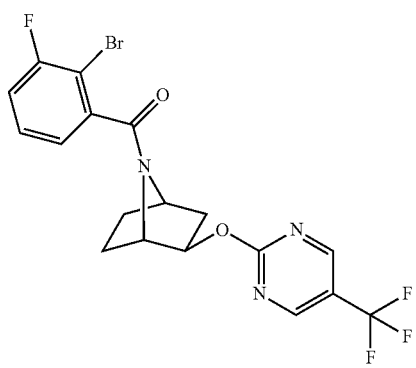

(2-bromo-3-fluorophenyl)((1S,2R,4R)-
2-((5-(trifluoromethyl)pyrimidin-2-
yl)oxy)-7-azabicyclo[2.2.1]heptan-7-
yl)methanone,

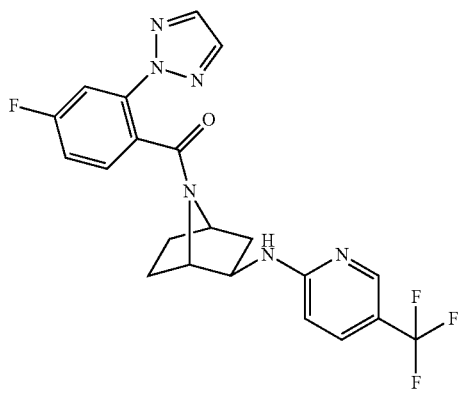 [SMILES: O=C(c1ccc(F)cc1-n1nccn1)N1C2CCC1C(Nc1ccc(C(F)(F)F)cn1)C2]

(4-fluoro-2-(2H-1,2,3-triazol-2-
yl)phenyl)((1S,2R,4R)-2-((5-
(trifluoromethyl)pyridin-2-yl)amino)-7-
azabicyclo[2.2.1]heptan-7-
yl)methanone,

846

-continued

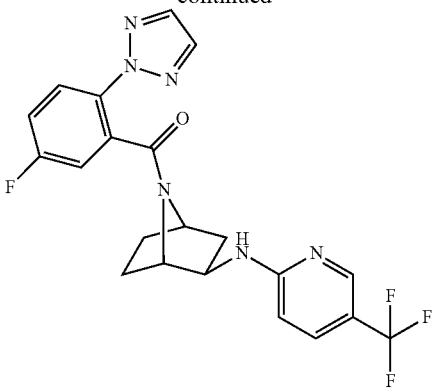

(5-fluoro-2-(2H-1,2,3-triazol-2-
yl)phenyl)((1S,2R,4R)-2-((5-
(trifluoromethyl)pyridin-2-yl)amino)-7-
azabicyclo[2.2.1]heptan-7-
yl)methanone,

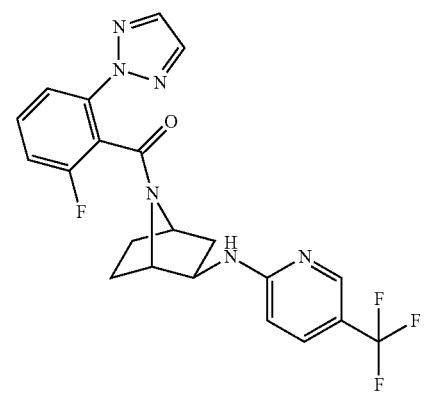 [SMILES: O=C(c1c(F)cccc1-n1nccn1)N1C2CCC1C(Nc1ccc(C(F)(F)F)cn1)C2]

(2-fluoro-6-(2H-1,2,3-triazol-2-
yl)phenyl)((1S,2R,4R)-2-((5-
(trifluoromethyl)pyridin-2-yl)amino)-7-
azabicyclo[2.2.1]heptan-7-
yl)methanone,

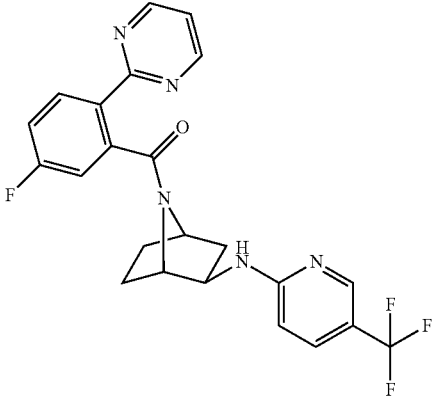 [SMILES: O=C(c1cc(F)ccc1-c1ncccn1)N1C2CCC1C(Nc1ccc(C(F)(F)F)cn1)C2]

(5-fluoro-2-(pyrimidin-2-
yl)phenyl)((1S,2R,4R)-2-((5-
(trifluoromethyl)pyridin-2-yl)amino)-7-
azabicyclo[2.2.1]heptan-7-
yl)methanone, 847
-continued

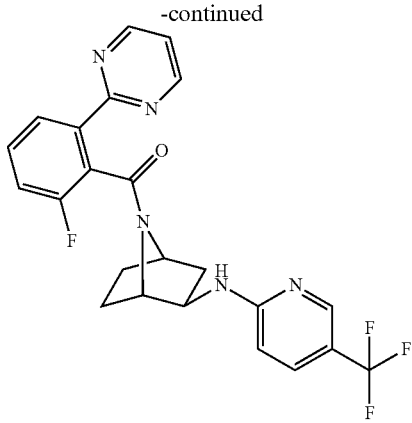

(2-fluoro-6-(pyrimidin-2-
yl)phenyl)((1S,2R,4R)-2-((5-
(trifluoromethyl)pyridin-2-yl)amino)-7-
azabicyclo[2.2.1]heptan-7-
yl)methanone,

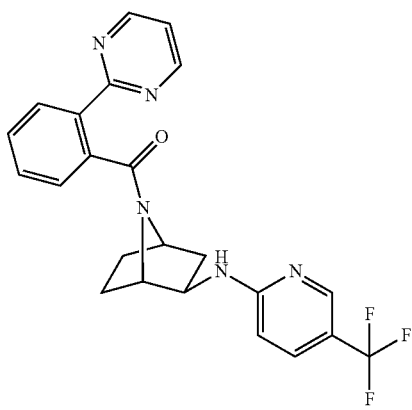 [SMILES: O=C(c1ccccc1-c1ncccn1)N1C2CCC1C(Nc1ccc(C(F)(F)F)cn1)C2]

(2-(pyrimidin-2-yl)phenyl)((1S,2R,4R)-
2-((5-(trifluoromethyl)pyridin-2-
yl)amino)-7-azabicyclo[2.2.1]heptan-7-
yl)methanone,

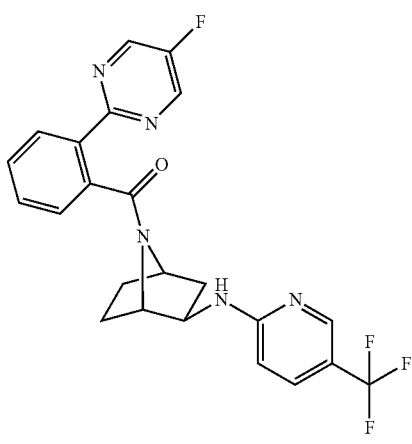 [SMILES: O=C(c1ccccc1-c1ncc(F)cn1)N1C2CCC1C(Nc1ccc(C(F)(F)F)cn1)C2]

(2-(5-fluoropyrimidin-2-
yl)phenyl)((1S,2R,4R)-2-((5-
(trifluoromethyl)pyridin-2-yl)amino)-7-
azabicyclo[2.2.1]heptan-7-
yl)methanone, 848
-continued

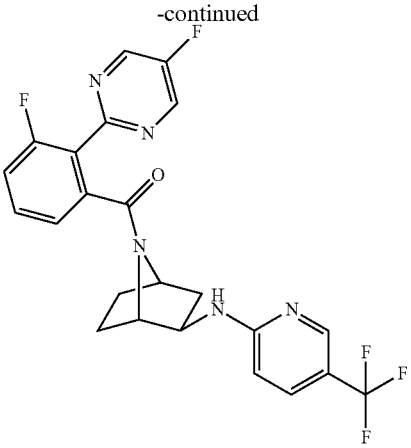

(3-fluoro-2-(5-fluoropyrimidin-2-
yl)phenyl)((1S,2R,4R)-2-((5-
(trifluoromethyl)pyridin-2-yl)amino)-7-
azabicyclo[2.2.1]heptan-7-
yl)methanone,

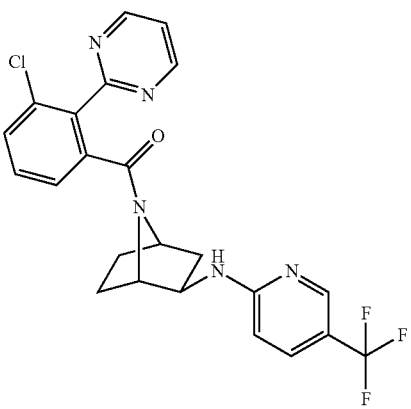 [SMILES: O=C(c1cccc(Cl)c1-c1ncccn1)N1C2CCC1C(Nc1ccc(C(F)(F)F)cn1)C2]

(3-chloro-2-(pyrimidin-2-
yl)phenyl)((1S,2R,4R)-2-((5-
(trifluoromethyl)pyridin-2-yl)amino)-7-
azabicyclo[2.2.1]heptan-7-
yl)methanone,

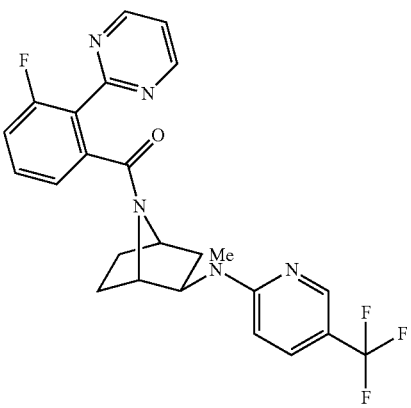 [SMILES: CN(c1ccc(C(F)(F)F)cn1)C1CC2CCC1N2C(=O)c1cccc(F)c1-c1ncccn1]

(3-fluoro-2-(pyrimidin-2-
yl)phenyl)((1S,2R,4R)-2-(methyl(5-
(trifluoromethyl)pyridin-2-yl)amino)-7-
azabicyclo[2.2.1]heptan-7-
yl)methanone,

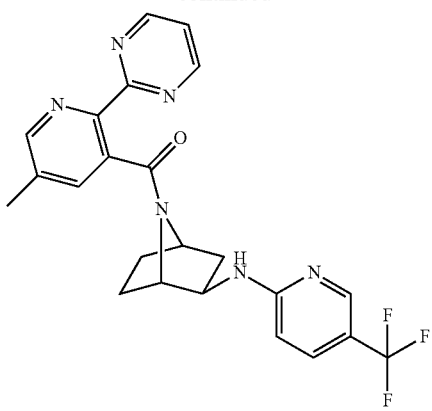 [SMILES: Cc1cnc(-c2ncccn2)c(C(=O)N2C3CCC2C(Nc2ccc(C(F)(F)F)cn2)C3)c1]

(5-methyl-2-(pyrimidin-2-yl)pyridin-3-
yl)((1S,2R,4R)-2-((5-
(trifluoromethyl)pyridin-2-yl)amino)-7-
azabicyclo[2.2.1]heptan-7-
yl)methanone,

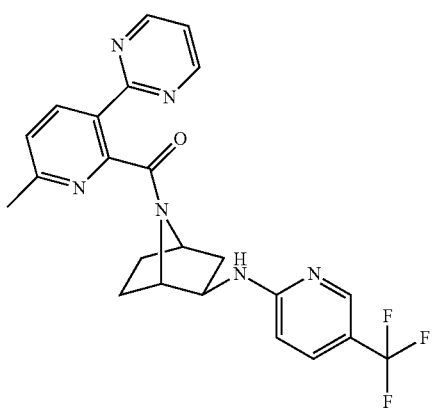

(6-methyl-3-(pyrimidin-2-yl)pyridin-2-
yl)((1S,2R,4R)-2-((5-
(trifluoromethyl)pyridin-2-yl)amino)-7-
azabicyclo[2.2.1]heptan-7-
yl)methanone,

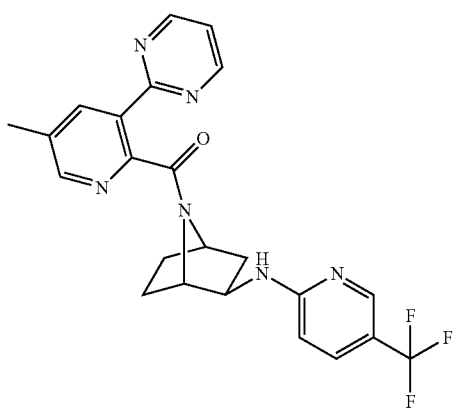 [SMILES: Cc1cnc(C(=O)N2C3CCC2C(Nc2ccc(C(F)(F)F)cn2)C3)c(-c2ncccn2)c1]

(5-methyl-3-(pyrimidin-2-yl)pyridin-2-
yl)((1S,2R,4R)-2-((5-
(trifluoromethyl)pyridin-2-yl)amino)-7-
azabicyclo[2.2.1]heptan-7-
yl)methanone,

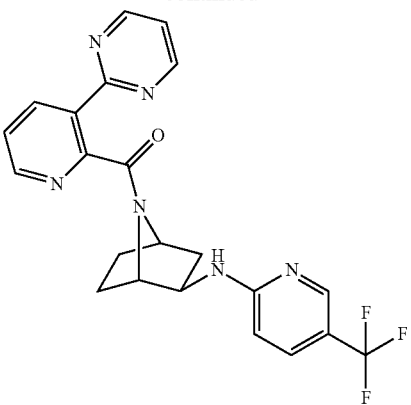 [SMILES: O=C(c1ncccc1-c1ncccn1)N1C2CCC1C(Nc1ccc(C(F)(F)F)cn1)C2]

(3-(pyrimidin-2-yl)pyridin-2-
yl)((1S,2R,4R)-2-((5-
(trifluoromethyl)pyridin-2-yl)amino)-7-
azabicyclo[2.2.1]heptan-7-
yl)methanone,

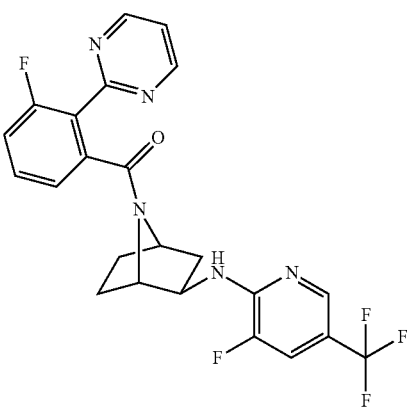 [SMILES: O=C(c1cccc(F)c1-c1ncccn1)N1C2CCC1C(Nc1ncc(C(F)(F)F)cc1F)C2]

(3-fluoro-2-(pyrimidin-2-
yl)phenyl)((1S,2R,4R)-2-((3-fluoro-5-
(trifluoromethyl)pyridin-2-yl)amino)-7-
azabicyclo[2.2.1]heptan-7-
yl)methanone,

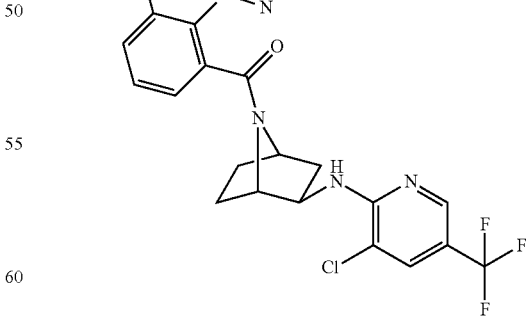

((1S,2R,4R)-2-((3-chloro-5-
(trifluoromethyl)pyridin-2-yl)amino)-7-
azabicyclo[2.2.1]heptan-7-yl)(3-fluoro-
2-(2H-1,2,3-triazol-2-
yl)phenyl)methanone, 851
-continued

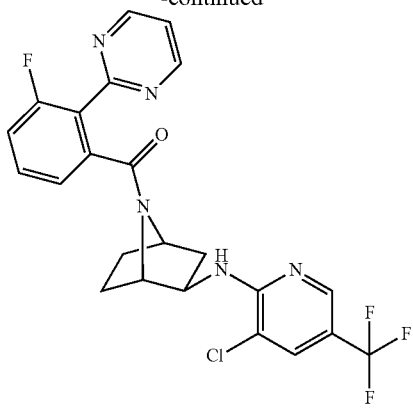

((1S,2R,4R)-2-((3-chloro-5-
(trifluoromethyl)pyridin-2-yl)amino)-7-
azabicyclo[2.2.1]heptan-7-yl)(3-fluoro-
2-(pyrimidin-2-yl)phenyl)methanone,

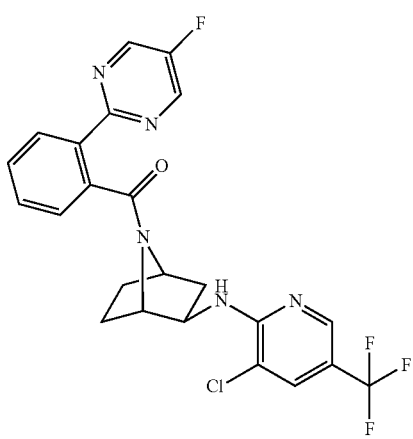 [SMILES: O=C(c1ccccc1-c1ncc(F)cn1)N1C2CCC1C(Nc1ncc(C(F)(F)F)cc1Cl)C2]

((1S,2R,4R)-2-((3-chloro-5-
(trifluoromethyl)pyridin-2-yl)amino)-7-
azabicyclo[2.2.1]heptan-7-yl)(2-(5-
fluoropyrimidin-2-
yl)phenyl)methanone,

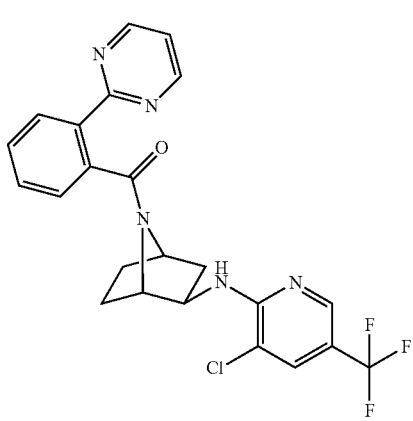 [SMILES: O=C(c1ccccc1-c1ncccn1)N1C2CCC1C(Nc1ncc(C(F)(F)F)cc1Cl)C2]

((1S,2R,4R)-2-((3-chloro-5-
(trifluoromethyl)pyridin-2-yl)amino)-7-
azabicyclo[2.2.1]heptan-7-yl)(2-
(pyrimidin-2-yl)phenyl)methanone, 852
-continued

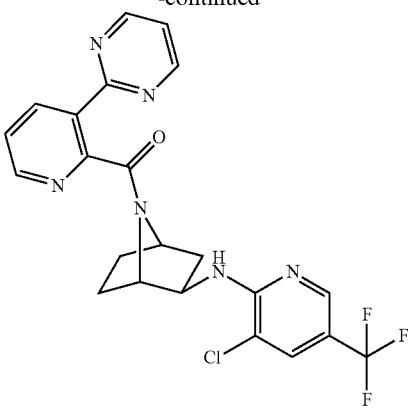

((1S,2R,4R)-2-((3-chloro-5-
(trifluoromethyl)pyridin-2-yl)amino)-7-
azabicyclo[2.2.1]heptan-7-yl)(3-
(pyrimidin-2-yl)pyridin-2-
yl)methanone,

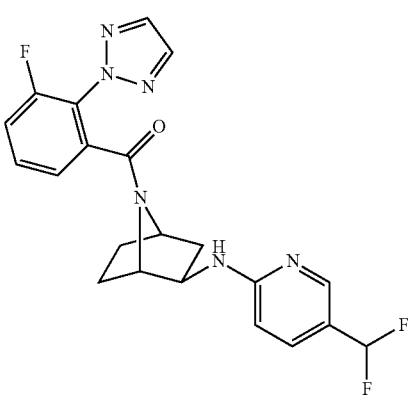 [SMILES: O=C(c1cccc(F)c1-n1nccn1)N1C2CCC1C(Nc1ccc(C(F)F)cn1)C2]

((1S,2R,4R)-2-((5-
(difluoromethyl)pyridin-2-yl)amino)-7-
azabicyclo[2.2.1]heptan-7-yl)(3-fluoro-
2-(2H-1,2,3-triazol-2-
yl)phenyl)methanone,

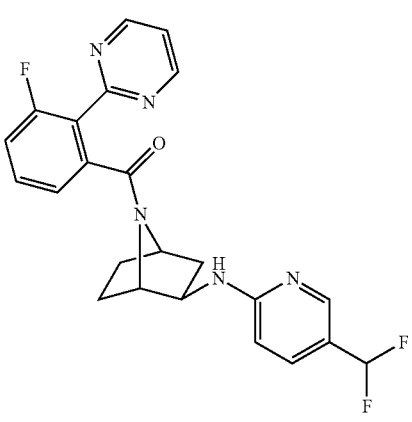 [SMILES: O=C(c1cccc(F)c1-c1ncccn1)N1C2CCC1C(Nc1ccc(C(F)F)cn1)C2]

((1S,2R,4R)-2-((5-
(difluoromethyl)pyridin-2-yl)amino)-7-
azabicyclo[2.2.1]heptan-7-yl)(3-fluoro-
2-(pyrimidin-2-yl)phenyl)methanone,

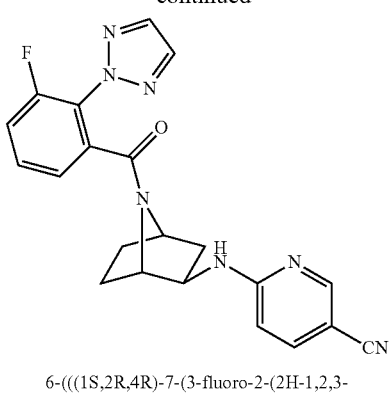

6-(((1S,2R,4R)-7-(3-fluoro-2-(2H-1,2,3-triazol-2-yl)benzoyl)-7-azabicyclo[2.2.1]heptan-2-yl)amino)nicotinonitrile,

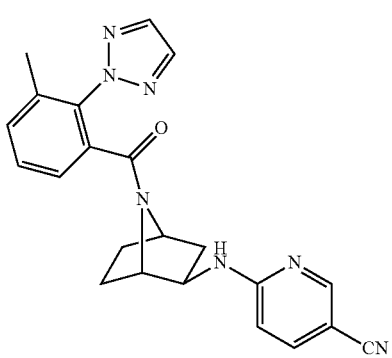 [SMILES: Cc1cccc(C(=O)N2C3CCC2C(Nc2ccc(C#N)cn2)C3)c1-n1nccn1]

6-(((1S,2R,4R)-7-(3-methyl-2-(2H-1,2,3-triazol-2-yl)benzoyl)-7-azabicyclo[2.2.1]heptan-2-yl)amino)nicotinonitrile,

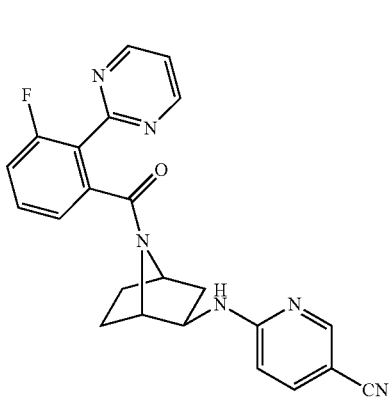 [SMILES: N#Cc1ccc(NC2CC3CCC2N3C(=O)c2cccc(F)c2-c2ncccn2)nc1]

6-(((1S,2R,4R)-7-(3-fluoro-2-(pyrimidin-2-yl)benzoyl)-7-azabicyclo[2.2.1]heptan-2-yl)amino)nicotinonitrile,

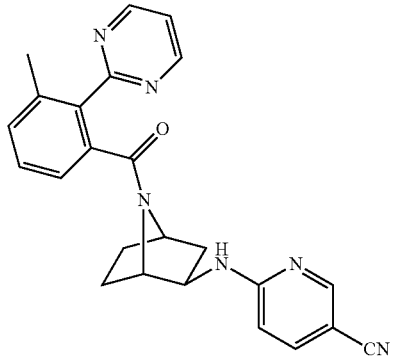 [SMILES: Cc1cccc(C(=O)N2C3CCC2C(Nc2ccc(C#N)cn2)C3)c1-c1ncccn1]

6-(((1S,2R,4R)-7-(3-methyl-2-(pyrimidin-2-yl)benzoyl)-7-azabicyclo[2.2.1]heptan-2-yl)amino)nicotinonitrile,

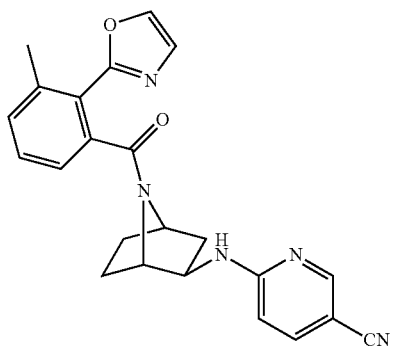 [SMILES: Cc1cccc(C(=O)N2C3CCC2C(Nc2ccc(C#N)cn2)C3)c1-c1ncco1]

6-(((1S,2R,4R)-7-(3-methyl-2-(oxazol-2-yl)benzoyl)-7-azabicyclo[2.2.1]heptan-2-yl)amino)nicotinonitrile,

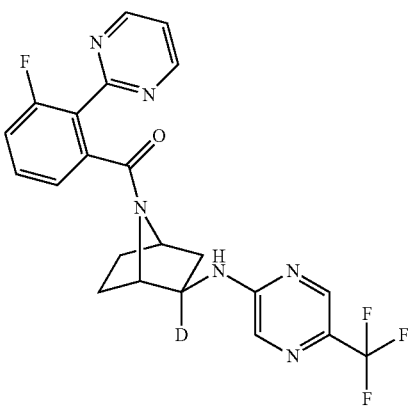 [SMILES: [2H]C1(Nc2cnc(C(F)(F)F)cn2)CC2CCC1N2C(=O)c1cccc(F)c1-c1ncccn1]

(3-fluoro-2-(pyrimidin-2-yl)phenyl)((1S,2R,4R)-(2-$^2$H)-((5-(trifluoromethyl)pyrazin-2-yl)amino)-7-azabicyclo[2.2.1]heptan-7-yl)methanone,

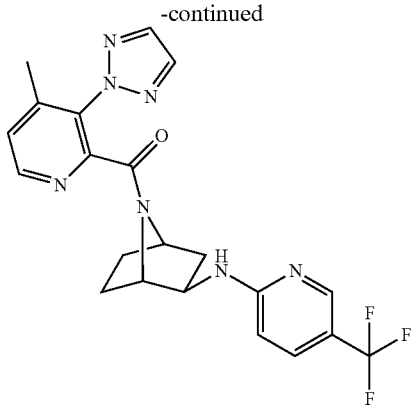

(4-methyl-3-(2H-1,2,3-triazol-2-yl)pyridin-2-yl)((1S,2R,4R)-2-((5-(trifluoromethyl)pyridin-2-yl)amino)-7-azabicyclo[2.2.1]heptan-7-yl)methanone,

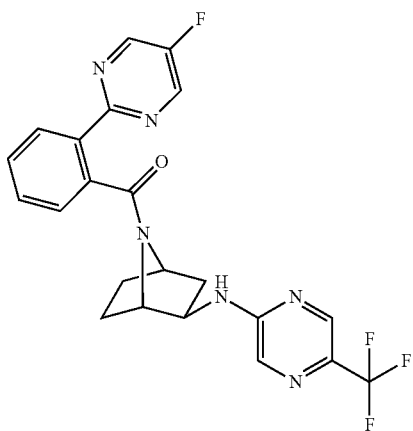 [SMILES: O=C(c1ccccc1-c1ncc(F)cn1)N1C2CCC1C(Nc1cnc(C(F)(F)F)cn1)C2]

(2-(5-fluoropyrimidin-2-yl)phenyl)((1S,2R,4R)-2-((5-(trifluoromethyl)pyrazin-2-yl)amino)-7-azabicyclo[2.2.1]heptan-7-yl)methanone,

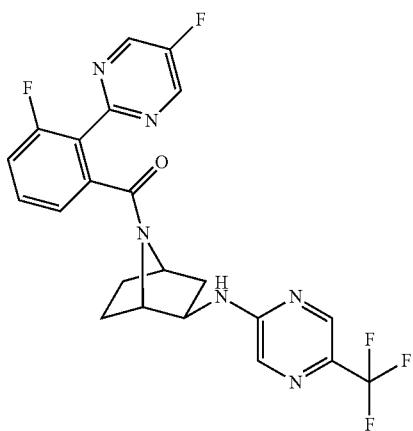 [SMILES: Cc1cccc(C(=O)N2C3CCC2C(Nc2cnc(C(F)(F)F)cn2)C3)c1-c1ncc(F)cn1]

(3-fluoro-2-(5-fluoropyrimidin-2-yl)phenyl)((1S,2R,4R)-2-((5-(trifluoromethyl)pyrazin-2-yl)amino)-7-azabicyclo[2.2.1]heptan-7-yl)methanone,

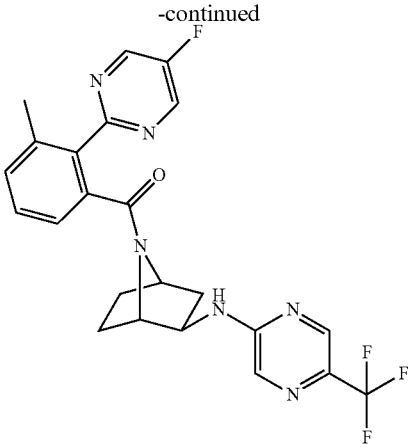

(2-(5-fluoropyrimidin-2-yl)-3-methylphenyl)((1S,2R,4R)-2-((5-(trifluoromethyl)pyrazin-2-yl)amino)-7-azabicyclo[2.2.1]heptan-7-yl)methanone,

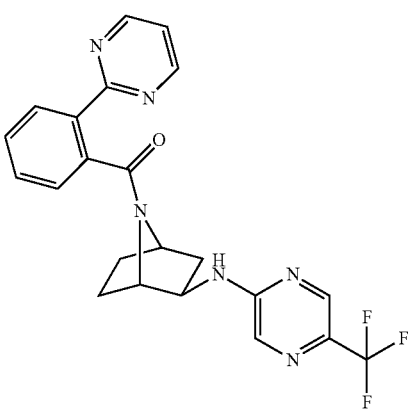 [SMILES: O=C(c1ccccc1-c1ncccn1)N1C2CCC1C(Nc1cnc(C(F)(F)F)cn1)C2]

(2-(pyrimidin-2-yl)phenyl)((1S,2R,4R)-2-((5-(trifluoromethyl)pyrazin-2-yl)amino)-7-azabicyclo[2.2.1]heptan-7-yl)methanone,

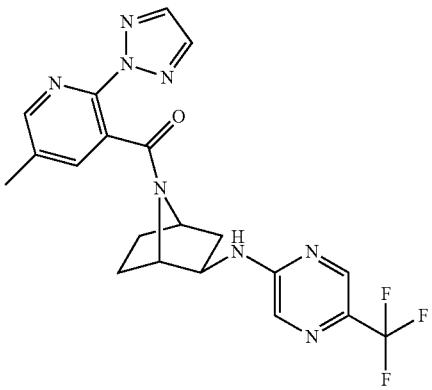 [SMILES: Cc1cnc(-n2nccn2)c(C(=O)N2C3CCC2C(Nc2cnc(C(F)(F)F)cn2)C3)c1]

(5-methyl-2-(2H-1,2,3-triazol-2-yl)pyridin-3-yl)((1S,2R,4R)-2-((5-(trifluoromethyl)pyrazin-2-yl)amino)-7-azabicyclo[2.2.1]heptan-7-yl)methanone, -continued

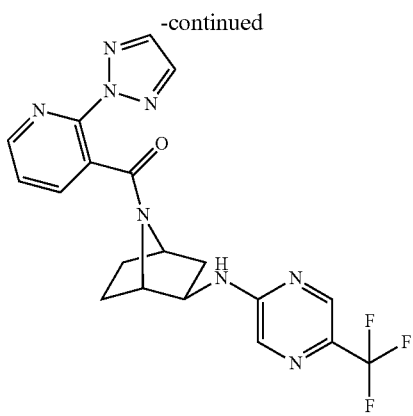

(2-(2H-1,2,3-triazol-2-yl)pyridin-3-yl)((1S,2R,4R)-2-((5-(trifluoromethyl)pyrazin-2-yl)amino)-7-azabicyclo[2.2.1]heptan-7-yl)methanone,

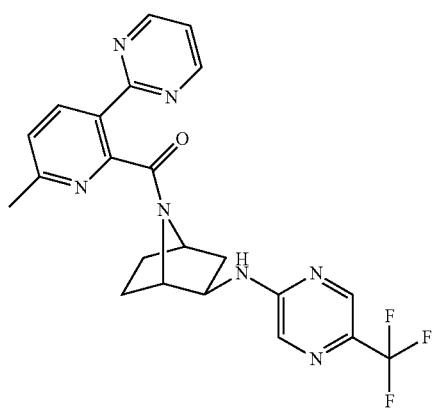

(6-methyl-3-(pyrimidin-2-yl)pyridin-2-yl)((1S,2R,4R)-2-((5-(trifluoromethyl)pyrazin-2-yl)amino)-7-azabicyclo[2.2.1]heptan-7-yl)methanone,

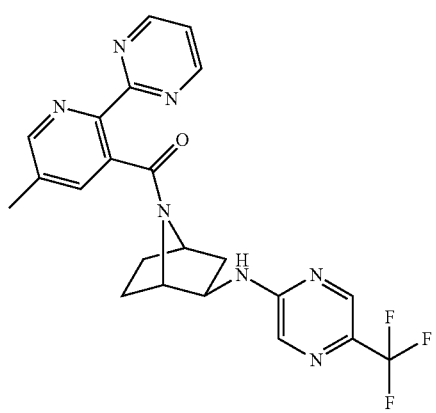 [SMILES: Cc1cnc(-c2ncccn2)c(C(=O)N2C3CCC2C(Nc2cnc(C(F)(F)F)cn2)C3)c1]

(5-methyl-2-(pyrimidin-2-yl)pyridin-3-yl)((1S,2R,4R)-2-((5-(trifluoromethyl)pyrazin-2-yl)amino)-7-azabicyclo[2.2.1]heptan-7-yl)methanone, -continued

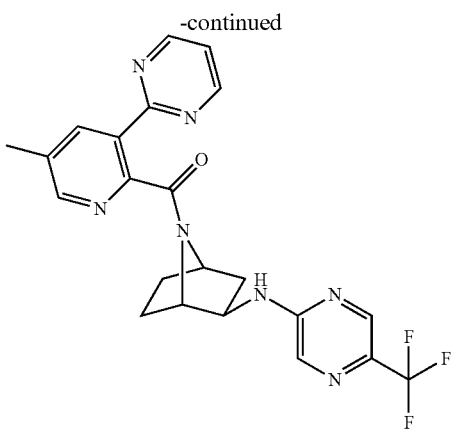

(5-methyl-3-(pyrimidin-2-yl)pyridin-2-yl)((1S,2R,4R)-2-((5-(trifluoromethyl)pyrazin-2-yl)amino)-7-azabicyclo[2.2.1]heptan-7-yl)methanone,

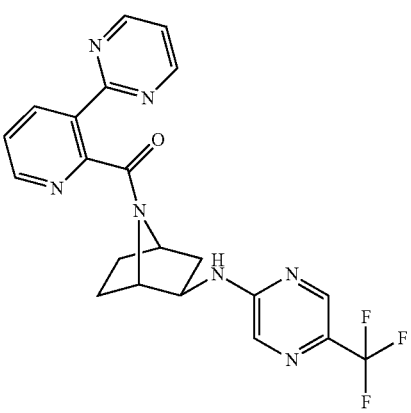 [SMILES: O=C(c1ncccc1-c1ncccn1)N1C2CCC1C(Nc1cnc(C(F)(F)F)cn1)C2]

(3-(pyrimidin-2-yl)pyridin-2-yl)((1S,2R,4R)-2-((5-(trifluoromethyl)pyrazin-2-yl)amino)-7-azabicyclo[2.2.1]heptan-7-yl)methanone,

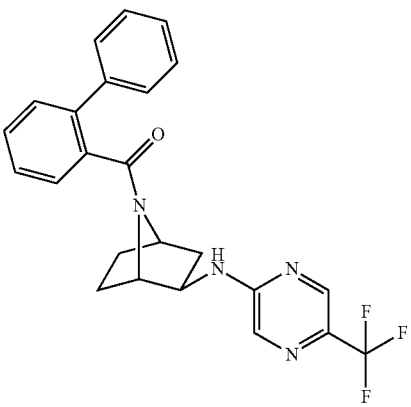 [SMILES: O=C(c1ccccc1-c1ccccc1)N1C2CCC1C(Nc1cnc(C(F)(F)F)cn1)C2]

[1,1'-biphenyl]-2-yl((1S,2R,4R)-2-((5-(trifluoromethyl)pyrazin-2-yl)amino)-7-azabicyclo[2.2.1]heptan-7-yl)methanone, -continued

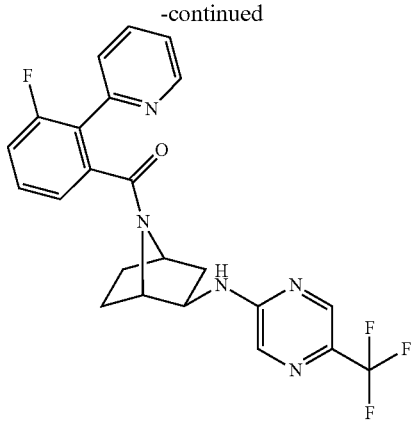

(3-fluoro-2-(pyridin-2-yl)phenyl)((1S,2R,4R)-2-((5-(trifluoromethyl)pyrazin-2-yl)amino)-7-azabicyclo[2.2.1]heptan-7-yl)methanone,

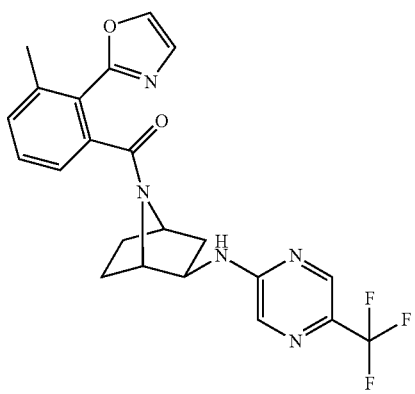 [SMILES: Cc1cccc(C(=O)N2C3CCC2C(Nc2cnc(C(F)(F)F)cn2)C3)c1-c1ncco1]

(3-methyl-2-(oxazol-2-yl)phenyl)((1S,2R,4R)-2-((5-(trifluoromethyl)pyrazin-2-yl)amino)-7-azabicyclo[2.2.1]heptan-7-yl)methanone,

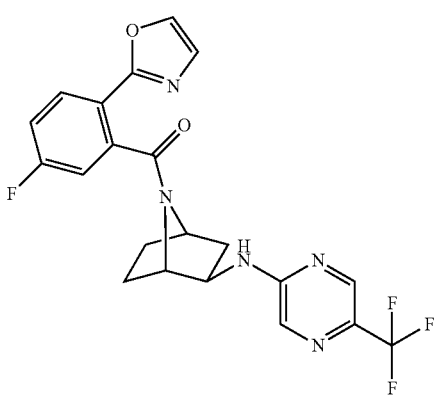 [SMILES: O=C(c1cc(F)ccc1-c1ncco1)N1C2CCC1C(Nc1cnc(C(F)(F)F)cn1)C2]

(5-fluoro-2-(oxazol-2-yl)phenyl)((1S,2R,4R)-2-((5-(trifluoromethyl)pyrazin-2-yl)amino)-7-azabicyclo[2.2.1]heptan-7-yl)methanone, -continued

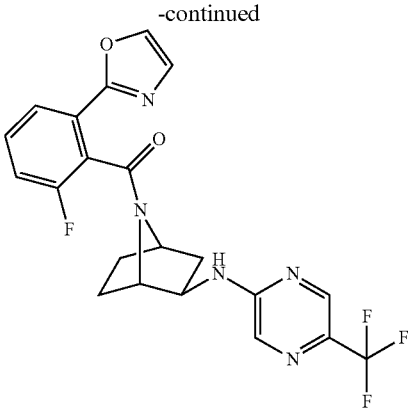

(2-fluoro-6-(oxazol-2-yl)phenyl)((1S,2R,4R)-2-((5-(trifluoromethyl)pyrazin-2-yl)amino)-7-azabicyclo[2.2.1]heptan-7-yl)methanone,

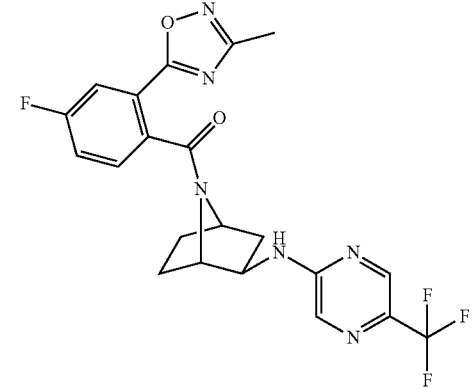

(4-fluoro-2-(3-methyl-1,2,4-oxadiazol-5-yl)phenyl)((1S,2R,4R)-2-((5-(trifluoromethyl)pyrazin-2-yl)amino)-7-azabicyclo[2.2.1]heptan-7-yl)methanone,

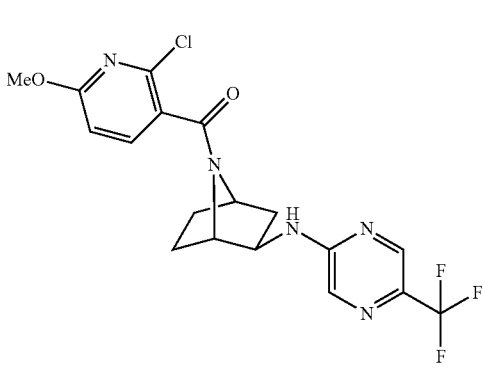 [SMILES: COc1ccc(C(=O)N2C3CCC2C(Nc2cnc(C(F)(F)F)cn2)C3)c(Cl)n1]

(2-chloro-6-methoxypyridin-3-yl)((1S,2R,4R)-2-((5-(trifluoromethyl)pyrazin-2-yl)amino)-7-azabicyclo[2.2.1]heptan-7-yl)methanone,

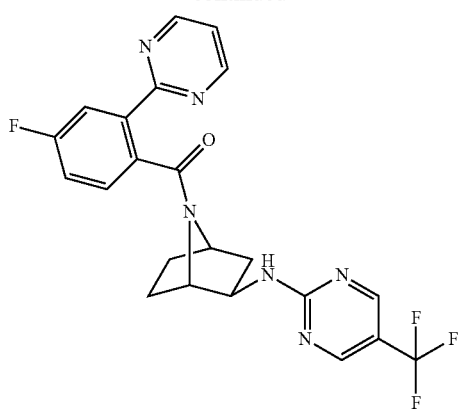 [SMILES: O=C(c1ccc(F)cc1-c1ncccn1)N1C2CCC1C(Nc1ncc(C(F)(F)F)cn1)C2]

(4-fluoro-2-(pyrimidin-2-
yl)phenyl)((1S,2R,4R)-2-((5-
(trifluoromethyl)pyrimidin-2-yl)amino)-
7-azabicyclo[2.2.1]heptan-7-
yl)methanone,

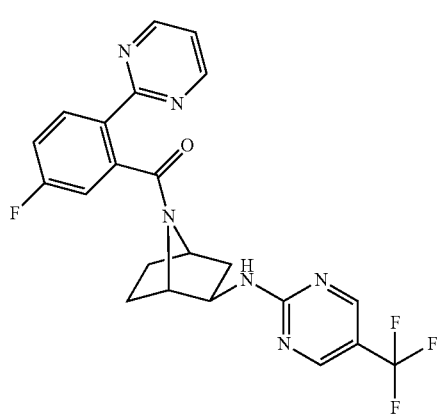 [SMILES: O=C(c1cc(F)ccc1-c1ncccn1)N1C2CCC1C(Nc1ncc(C(F)(F)F)cn1)C2]

(5-fluoro-2-(pyrimidin-2-
yl)phenyl)((1S,2R,4R)-2-((5-
(trifluoromethyl)pyrimidin-2-yl)amino)-
7-azabicyclo[2.2.1]heptan-7-
yl)methanone,

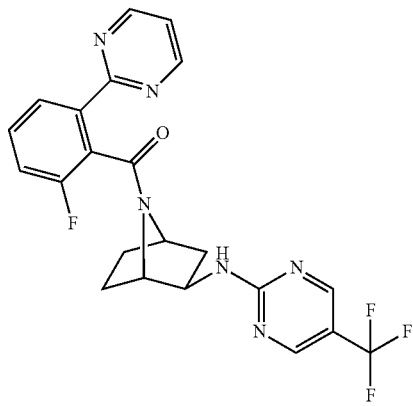 [SMILES: O=C(c1c(F)cccc1-c1ncccn1)N1C2CCC1C(Nc1ncc(C(F)(F)F)cn1)C2]

(2-fluoro-6-(pyrimidin-2-
yl)phenyl)((1S,2R,4R)-2-((5-
(trifluoromethyl)pyrimidin-2-yl)amino)-
7-azabicyclo[2.2.1]heptan-7-
yl)methanone,

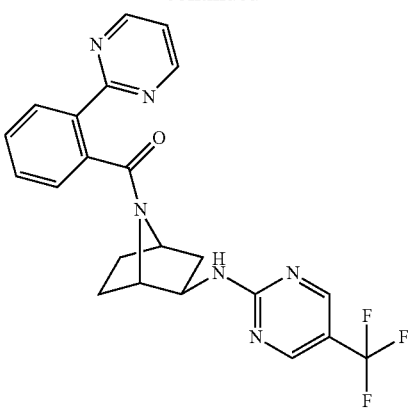 [SMILES: O=C(c1ccccc1-c1ncccn1)N1C2CCC1C(Nc1ncc(C(F)(F)F)cn1)C2]

(2-(pyrimidin-2-yl)phenyl)((1S,2R,4R)-
2-((5-(trifluoromethyl)pyrimidin-2-
yl)amino)-7-azabicyclo[2.2.1]heptan-7-
yl)methanone,

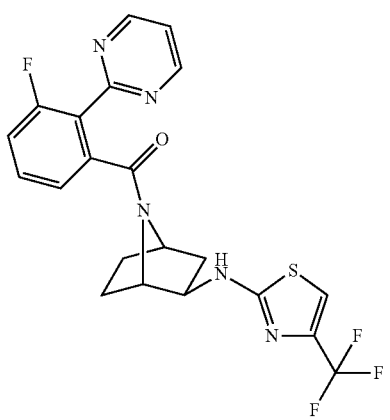

(3-fluoro-2-(pyrimidin-2-
yl)phenyl)((1S,2R,4R)-2-((4-
(trifluoromethyl)thiazol-2-yl)amino)-7-
azabicyclo[2.2.1]heptan-7-
yl)methanone,

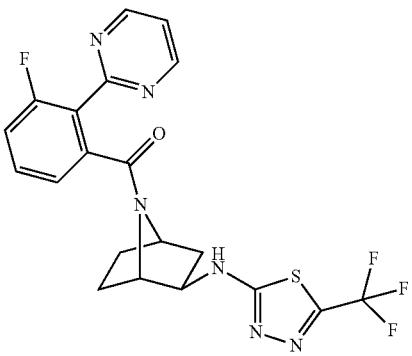

(3-fluoro-2-(pyrimidin-2-
yl)phenyl)((1S,2R,4R)-2-((5-
(trifluoromethyl)-1,3,4-thiadiazol-2-
yl)amino)-7-azabicyclo[2.2.1]heptan-7-
yl)methanone, 863
-continued

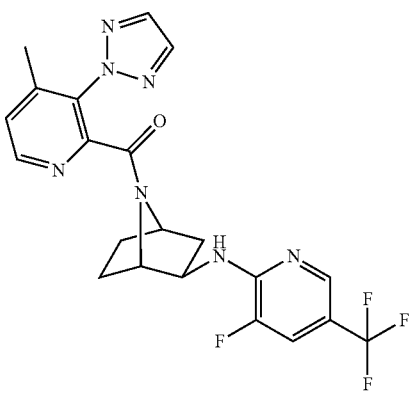

((1S,2R,4R)-2-((3-fluoro-5-
(trifluoromethyl)pyridin-2-yl)amino)-7-
azabicyclo[2.2.1]heptan-7-yl)(4-methyl-
3-(2H-1,2,3-triazol-2-yl)pyridin-2-
yl)methanone,

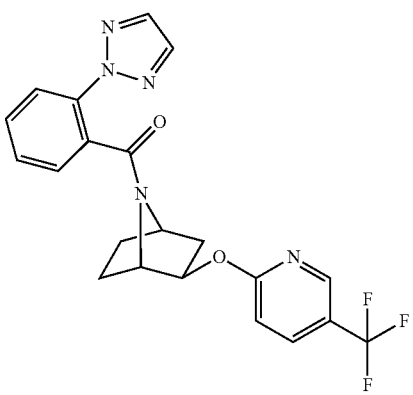 [SMILES: O=C(c1ccccc1-n1nccn1)N1C2CCC1C(Oc1ccc(C(F)(F)F)cn1)C2]

(R/S)-(2-(2H-1,2,3-triazol-2-yl)phenyl)-
2-((5-(trifluoromethyl)pyridin-2-
yl)oxy)-7-azabicyclo[2.2.1]heptan-7-
yl)methanone,

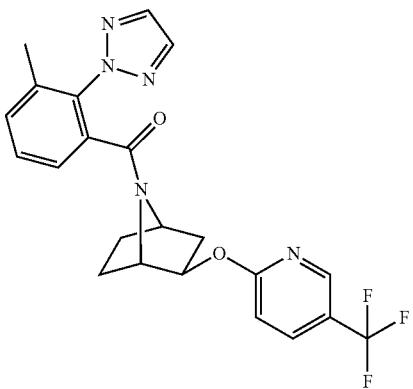 [SMILES: Cc1cccc(C(=O)N2C3CCC2C(Oc2ccc(C(F)(F)F)cn2)C3)c1-n1nccn1]

(R/S)-(3-methyl-2-(2H-1,2,3-triazol-2-
yl)phenyl)-2-((5-
(trifluoromethyl)pyridin-2-yl)oxy)-7-
azabicyclo[2.2.1]heptan-7-
yl)methanone, 864
-continued

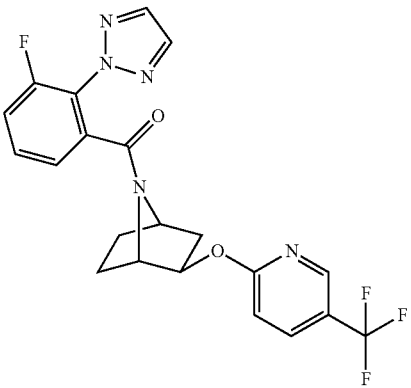 [SMILES: O=C(c1cccc(F)c1-n1nccn1)N1C2CCC1C(Oc1ccc(C(F)(F)F)cn1)C2]

(R/S)-(3-fluoro-2-(2H-1,2,3-triazol-2-
yl)phenyl)-2-((5-
(trifluoromethyl)pyridin-2-yl)oxy)-7-
azabicyclo[2.2.1]heptan-7-
yl)methanone,

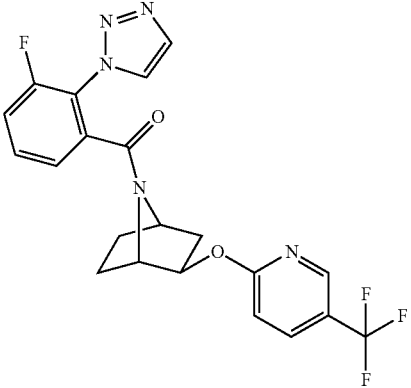 [SMILES: O=C(c1cccc(F)c1-n1ccnn1)N1C2CCC1C(Oc1ccc(C(F)(F)F)cn1)C2]

(R/S)-(3-fluoro-2-(1H-1,2,3-triazol-1-
yl)phenyl)-2-((5-
(trifluoromethyl)pyridin-2-yl)oxy)-7-
azabicyclo[2.2.1]heptan-7-
yl)methanone,

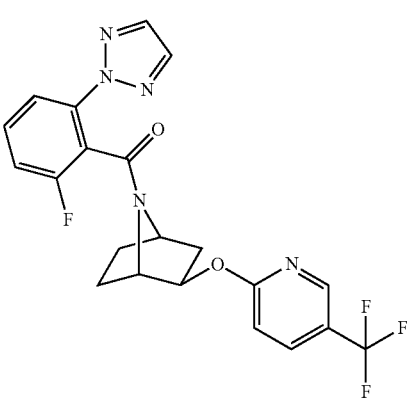 [SMILES: O=C(c1c(F)cccc1-n1nccn1)N1C2CCC1C(Oc1ccc(C(F)(F)F)cn1)C2]

(R/S)-(2-fluoro-6-(2H-1,2,3-triazol-2-
yl)phenyl)-2-((5-
(trifluoromethyl)pyridin-2-yl)oxy)-7-
azabicyclo[2.2.1]heptan-7-
yl)methanone,

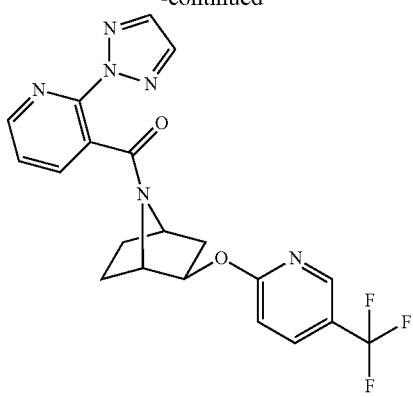

(R/S)-(2-(2H-1,2,3-triazol-2-yl)pyridin-3-yl)-2-((5-(trifluoromethyl)pyridin-2-yl)oxy)-7-azabicyclo[2.2.1]heptan-7-yl)methanone,

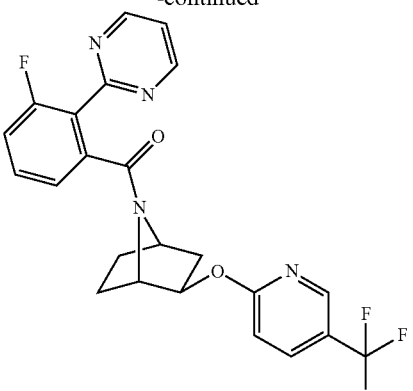

(R/S)-(3-fluoro-2-(pyrimidin-2-yl)phenyl)-2-((5-(trifluoromethyl)pyridin-2-yl)oxy)-7-azabicyclo[2.2.1]heptan-7-yl)methanone,

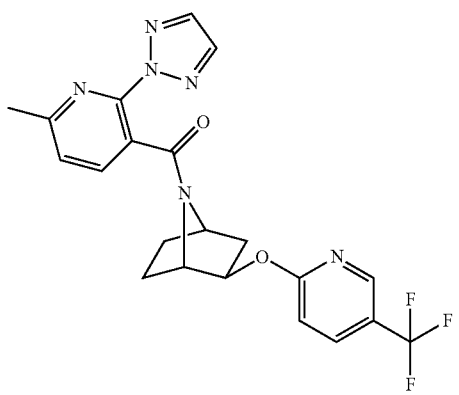 [SMILES: Cc1ccc(C(=O)N2C3CCC2C(Oc2ccc(C(F)(F)F)cn2)C3)c(-n2nccn2)n1]

(R/S)-(6-methyl-2-(2H-1,2,3-triazol-2-yl)pyridin-3-yl)-2-((5-(trifluoromethyl)pyridin-2-yl)oxy)-7-azabicyclo[2.2.1]heptan-7-yl)methanone,

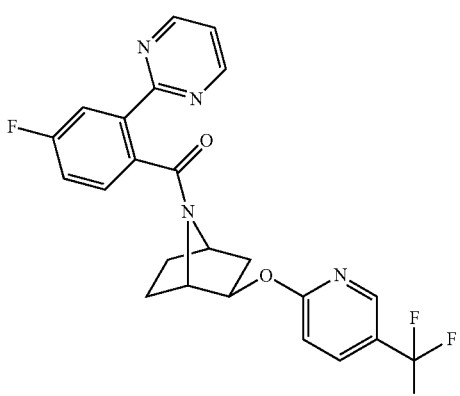

(R/S)-(4-fluoro-2-(pyrimidin-2-yl)phenyl)-2-((5-(trifluoromethyl)pyridin-2-yl)oxy)-7-azabicyclo[2.2.1]heptan-7-yl)methanone,

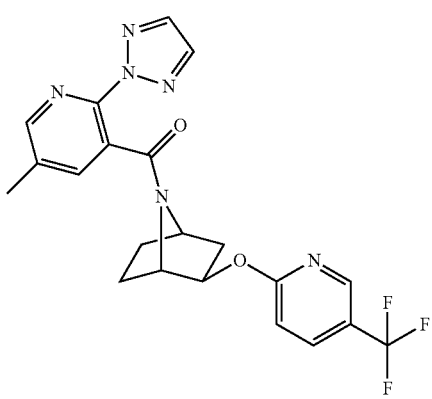 [SMILES: Cc1cnc(-n2nccn2)c(C(=O)N2C3CCC2C(Oc2ccc(C(F)(F)F)cn2)C3)c1]

(R/S)-(5-methyl-2-(2H-1,2,3-triazol-2-yl)pyridin-3-yl)-2-((5-(trifluoromethyl)pyridin-2-yl)oxy)-7-azabicyclo[2.2.1]heptan-7-yl)methanone,

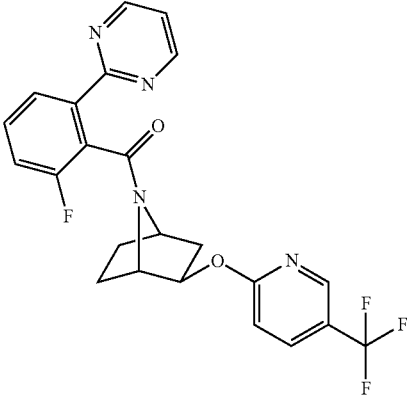 [SMILES: O=C(c1c(F)cccc1-c1ncccn1)N1C2CCC1C(Oc1ccc(C(F)(F)F)cn1)C2]

(R/S)-(2-fluoro-6-(pyrimidin-2-yl)phenyl)-2-((5-(trifluoromethyl)pyridin-2-yl)oxy)-7-azabicyclo[2.2.1]heptan-7-yl)methanone, 867
-continued

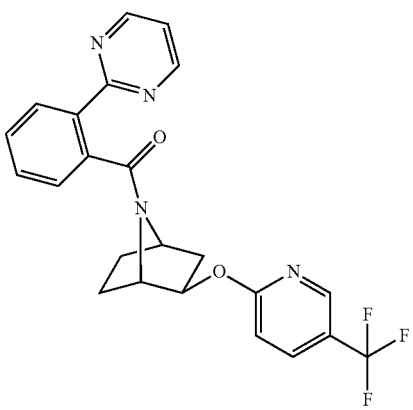 [SMILES: O=C(c1ccccc1-c1ncccn1)N1C2CCC1C(Oc1ccc(C(F)(F)F)cn1)C2]

(R/S)-(2-(pyrimidin-2-yl)phenyl)-2-((5-(trifluoromethyl)pyridin-2-yl)oxy)-7-azabicyclo[2.2.1]heptan-7-yl)methanone,

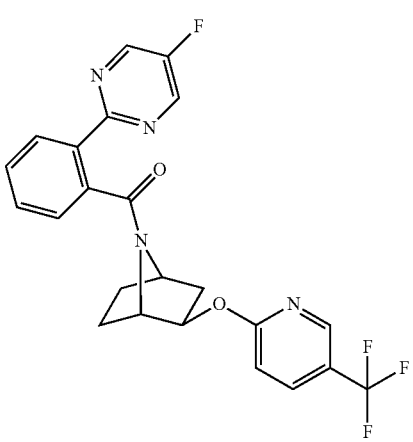 [SMILES: O=C(c1ccccc1-c1ncc(F)cn1)N1C2CCC1C(Oc1ccc(C(F)(F)F)cn1)C2]

(R/S)-(2-(5-fluoropyrimidin-2-yl)phenyl)-2-((5-(trifluoromethyl)pyridin-2-yl)oxy)-7-azabicyclo[2.2.1]heptan-7-yl)methanone,

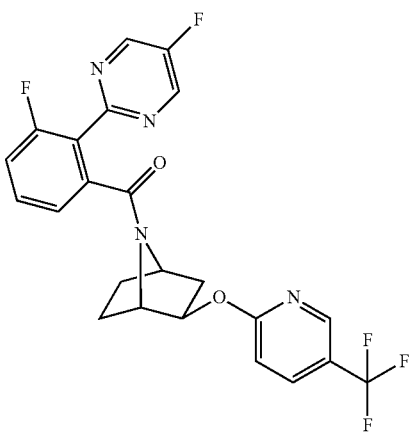 [SMILES: O=C(c1cccc(F)c1-c1ncc(F)cn1)N1C2CCC1C(Oc1ccc(C(F)(F)F)cn1)C2]

(R/S)-(3-fluoro-2-(5-fluoropyrimidin-2-yl)phenyl)-2-((5-(trifluoromethyl)pyridin-2-yl)oxy)-7-azabicyclo[2.2.1]heptan-7-yl)methanone, 868
-continued

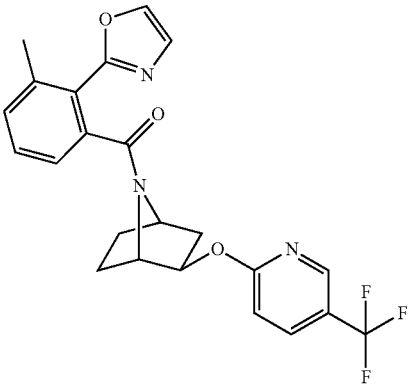 [SMILES: Cc1cccc(C(=O)N2C3CCC2C(Oc2ccc(C(F)(F)F)cn2)C3)c1-c1ncco1]

(R/S)-(3-methyl-2-(oxazol-2-yl)phenyl)-2-((5-(trifluoromethyl)pyridin-2-yl)oxy)-7-azabicyclo[2.2.1]heptan-7-yl)methanone,

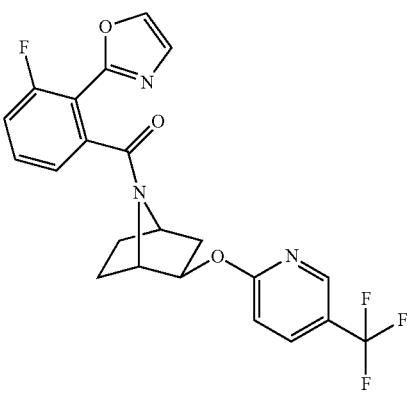 [SMILES: O=C(c1cccc(F)c1-c1ncco1)N1C2CCC1C(Oc1ccc(C(F)(F)F)cn1)C2]

(R/S)-(3-fluoro-2-(oxazol-2-yl)phenyl)-2-((5-(trifluoromethyl)pyridin-2-yl)oxy)-7-azabicyclo[2.2.1]heptan-7-yl)methanone,

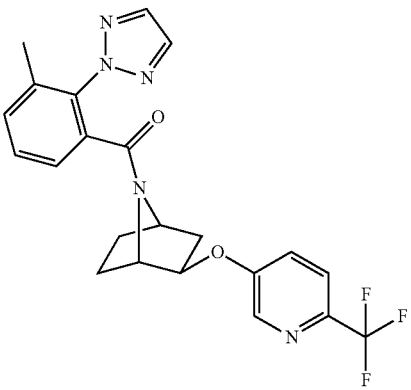 [SMILES: Cc1cccc(C(=O)N2C3CCC2C(Oc2ccc(C(F)(F)F)nc2)C3)c1-n1nccn1]

(R/S)-(3-methyl-2-(2H-1,2,3-triazol-2-yl)phenyl)-2-((6-(trifluoromethyl)pyridin-3-yl)oxy)-7-azabicyclo[2.2.1]heptan-7-yl)methanone, -continued

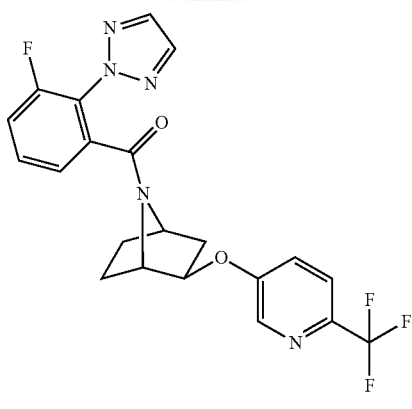 [SMILES: O=C(c1cccc(F)c1-n1nccn1)N1C2CCC1C(Oc1ccc(C(F)(F)F)nc1)C2]

(R/S)-(3-fluoro-2-(2H-1,2,3-triazol-2-yl)phenyl)-2-((6-(trifluoromethyl)pyridin-3-yl)oxy)-7-azabicyclo[2.2.1]heptan-7-yl)methanone,

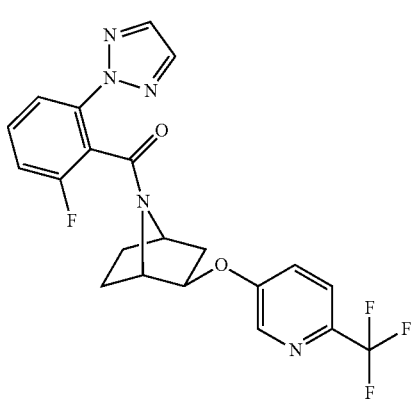 [SMILES: O=C(c1c(F)cccc1-n1nccn1)N1C2CCC1C(Oc1ccc(C(F)(F)F)nc1)C2]

(R/S)-(2-fluoro-6-(2H-1,2,3-triazol-2-yl)phenyl)-2-((6-(trifluoromethyl)pyridin-3-yl)oxy)-7-azabicyclo[2.2.1]heptan-7-yl)methanone,

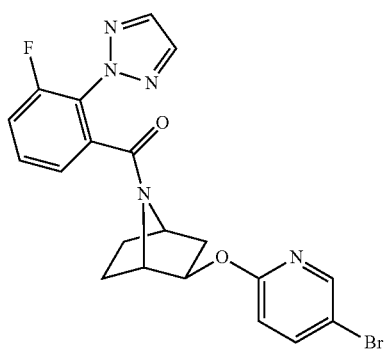 [SMILES: O=C(c1cccc(F)c1-n1nccn1)N1C2CCC1C(Oc1ncc(Br)cn1)C2]

(R/S)-2-((5-bromopyridin-2-yl)oxy)-7-azabicyclo[2.2.1]heptan-7-yl)(3-fluoro-2-(2H-1,2,3-triazol-2-yl)phenyl)methanone, -continued

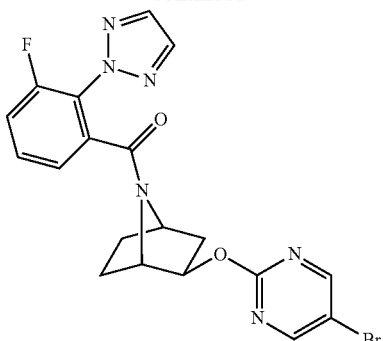

(R/S)-2-((5-bromopyridin-2-yl)oxy)-7-azabicyclo[2.2.1]heptan-7-yl)(3-fluoro-2-(2H-1,2,3-triazol-2-yl)phenyl)methanone,

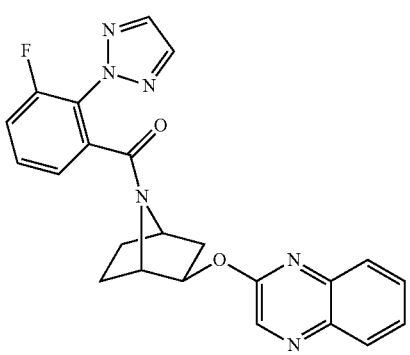 [SMILES: O=C(c1cccc(F)c1-n1nccn1)N1C2CCC1C(Oc1cnc3ccccc3n1)C2]

(R/S)-(3-fluoro-2-(2H-1,2,3-triazol-2-yl)phenyl)-2-(quinoxalin-2-yloxy)-7-azabicyclo[2.2.1]heptan-7-yl)methanone,

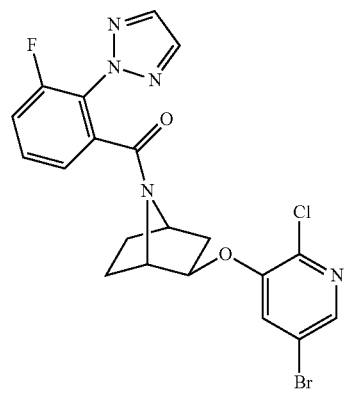 [SMILES: O=C(c1cccc(F)c1-n1nccn1)N1C2CCC1C(Oc1cc(Br)cnc1Cl)C2]

(R/S)-2-((5-bromo-2-chloropyridin-3-yl)oxy)-7-azabicyclo[2.2.1]heptan-7-yl)(3-fluoro-2-(2H-1,2,3-triazol-2-yl)phenyl)methanone, -continued

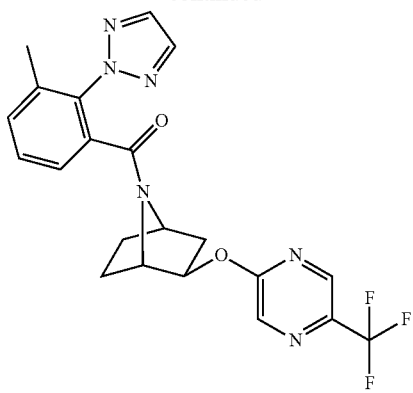 [SMILES: Cc1cccc(C(=O)N2C3CCC2C(Oc2cnc(C(F)(F)F)cn2)C3)c1-n1nccn1]

(R/S)-(3-methyl-2-(2H-1,2,3-triazol-2-yl)phenyl)-2-((5-(trifluoromethyl)pyrazin-2-yl)oxy)-7-azabicyclo[2.2.1]heptan-7-yl)methanone,

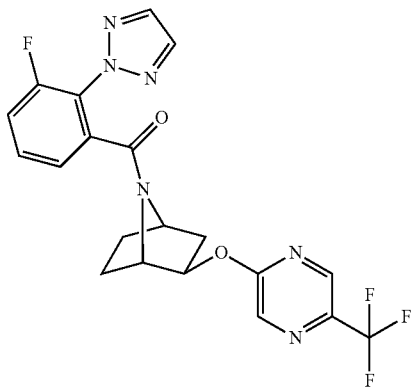 [SMILES: O=C(c1cccc(F)c1-n1nccn1)N1C2CCC1C(Oc1cnc(C(F)(F)F)cn1)C2]

(R/S)-(3-fluoro-2-(2H-1,2,3-triazol-2-yl)phenyl)(2-((5-(trifluoromethyl)pyrazin-2-yl)oxy)-7-azabicyclo[2.2.1]heptan-7-yl)methanone,

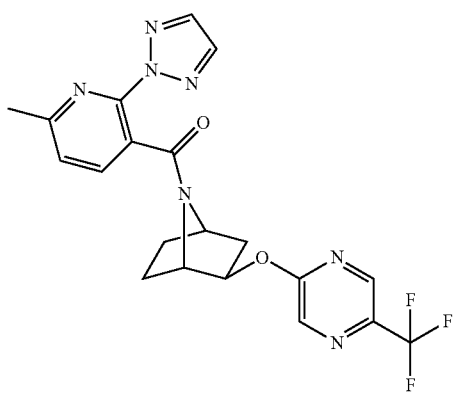 [SMILES: Cc1ccc(C(=O)N2C3CCC2C(Oc2cnc(C(F)(F)F)cn2)C3)c(-n2nccn2)n1]

(R/S)-(6-methyl-2-(2H-1,2,3-triazol-2-yl)pyridin-3-yl)(2-((5-(trifluoromethyl)pyrazin-2-yl)oxy)-7-azabicyclo[2.2.1]heptan-7-yl)methanone, -continued

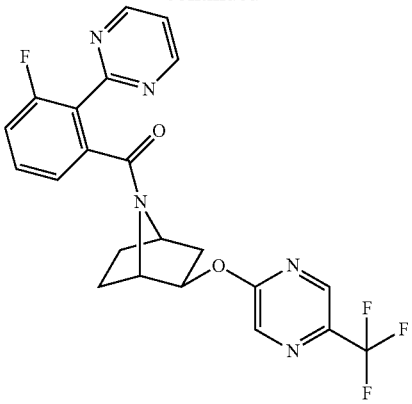

(R/S)-(3-fluoro-2-(pyrimidin-2-yl)phenyl)(2-((5-(trifluoromethyl)pyrazin-2-yl)oxy)-7-azabicyclo[2.2.1]heptan-7-yl)methanone,

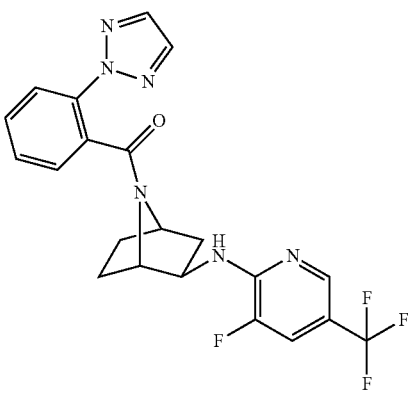 [SMILES: O=C(c1ccccc1-n1nccn1)N1C2CCC1C(Nc1ncc(C(F)(F)F)cc1F)C2]

(2-(2H-1,2,3-triazol-2-yl)phenyl)((1S,2R,4R)-2-((3-fluoro-5-(trifluoromethyl)pyridin-2-yl)amino)-7-azabicyclo[2.2.1]heptan-7-yl)methanone,

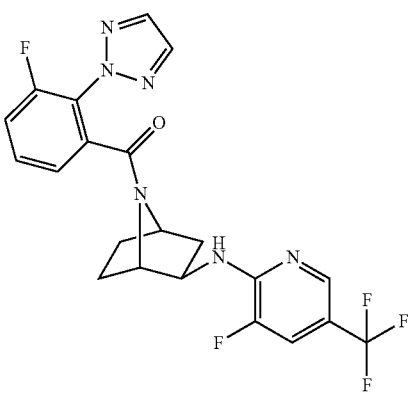 [SMILES: O=C(c1cccc(F)c1-n1nccn1)N1C2CCC1C(Nc1ncc(C(F)(F)F)cc1F)C2]

(3-fluoro-2-(2H-1,2,3-triazol-2-yl)phenyl)((1S,2R,4R)-2-((3-fluoro-5-(trifluoromethyl)pyridin-2-yl)amino)-7-azabicyclo[2.2.1]heptan-7-yl)methanone,

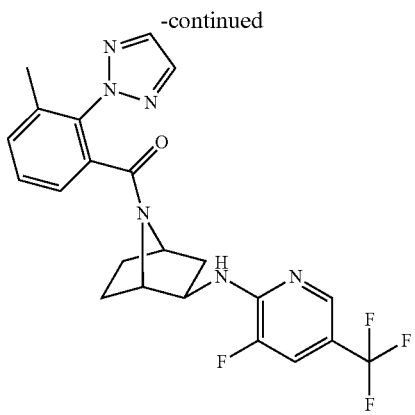

((1S,2R,4R)-2-((3-fluoro-5-(trifluoromethyl)pyridin-2-yl)amino)-7-azabicyclo[2.2.1]heptan-7-yl)(3-methyl-2-(2H-1,2,3-triazol-2-yl)phenyl)methanone,

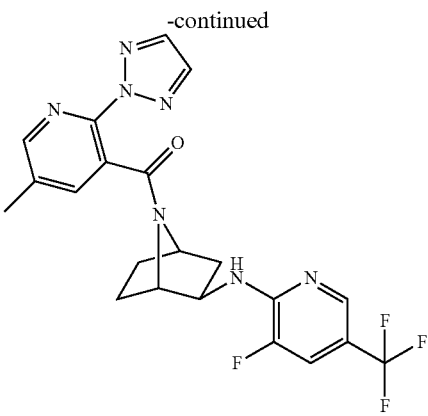

((1S,2R,4R)-2-((3-fluoro-5-(trifluoromethyl)pyridin-2-yl)amino)-7-azabicyclo[2.2.1]heptan-7-yl)(5-methyl-2-(2H-1,2,3-triazol-2-yl)pyridin-3-yl)methanone,

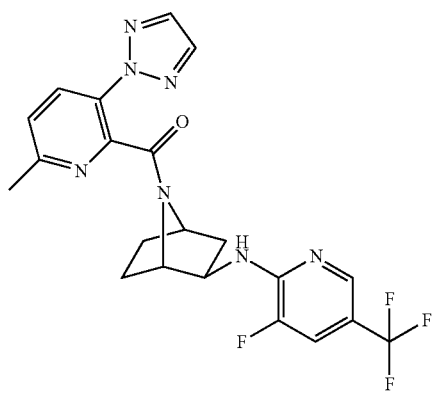 [SMILES: Cc1ccc(-n2nccn2)c(C(=O)N2C3CCC2C(Nc2ncc(C(F)(F)F)cc2F)C3)n1]

((1S,2R,4R)-2-((3-fluoro-5-(trifluoromethyl)pyridin-2-yl)amino)-7-azabicyclo[2.2.1]heptan-7-yl)(6-methyl-3-(2H-1,2,3-triazol-2-yl)pyridin-2-yl)methanone,

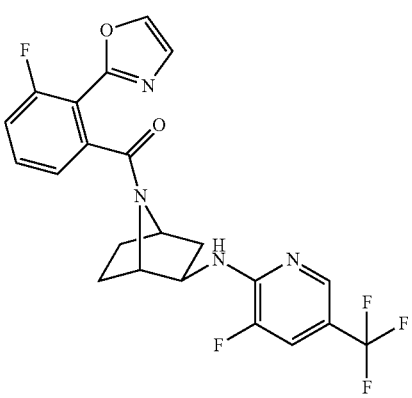 [SMILES: O=C(c1cccc(F)c1-c1ncco1)N1C2CCC1C(Nc1ncc(C(F)(F)F)cc1F)C2]

(3-fluoro-2-(oxazol-2-yl)phenyl)((1S,2R,4R)-2-((3-fluoro-5-(trifluoromethyl)pyridin-2-yl)amino)-7-azabicyclo[2.2.1]heptan-7-yl)methanone,

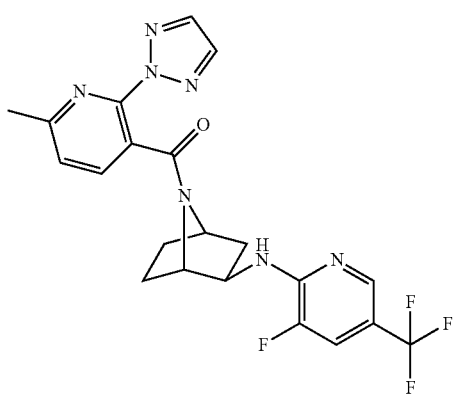

((1S,2R,4R)-2-((3-fluoro-5-(trifluoromethyl)pyridin-2-yl)amino)-7-azabicyclo[2.2.1]heptan-7-yl)(6-methyl-2-(2H-1,2,3-triazol-2-yl)pyridin-3-yl)methanone,

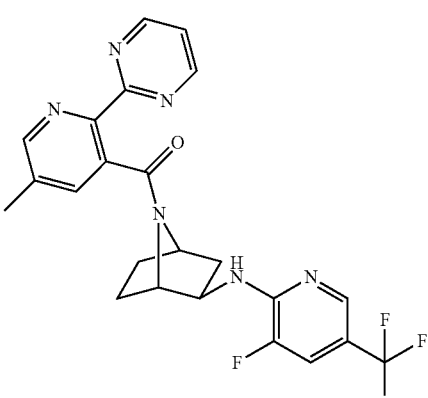

((1S,2R,4R)-2-((3-fluoro-5-(trifluoromethyl)pyridin-2-yl)amino)-7-azabicyclo[2.2.1]heptan-7-yl)(5-methyl-2-(pyrimidin-2-yl)pyridin-3-yl)methanone,

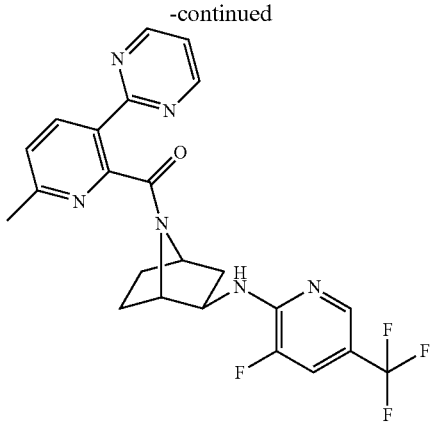

((1S,2R,4R)-2-((3-fluoro-5-
(trifluoromethyl)pyridin-2-yl)amino)-7-
azabicyclo[2.2.1]heptan-7-yl)(6-methyl-
3-(pyrimidin-2-yl)pyridin-2-
yl)methanone,

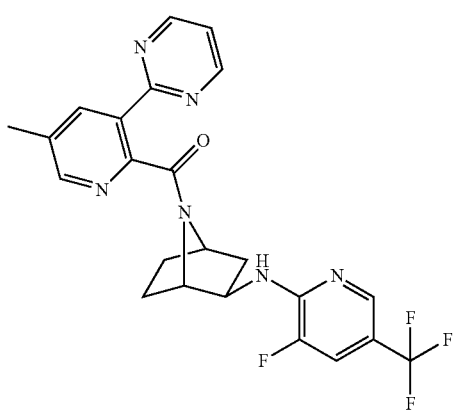 [SMILES: Cc1cnc(C(=O)N2C3CCC2C(Nc2ncc(C(F)(F)F)cc2F)C3)c(-c2ncccn2)c1]

((1S,2R,4R)-2-((3-fluoro-5-
(trifluoromethyl)pyridin-2-yl)amino)-7-
azabicyclo[2.2.1]heptan-7-yl)(5-methyl-
3-(pyrimidin-2-yl)pyridin-2-
yl)methanone,

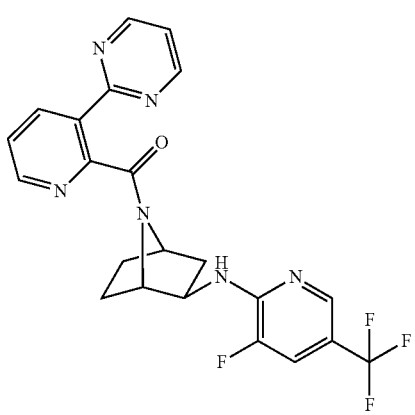

((1S,2R,4R)-2-((3-fluoro-5-
(trifluoromethyl)pyridin-2-yl)amino)-7-
azabicyclo[2.2.1]heptan-7-yl)(3-
(pyrimidin-2-yl)pyridin-2-
yl)methanone,

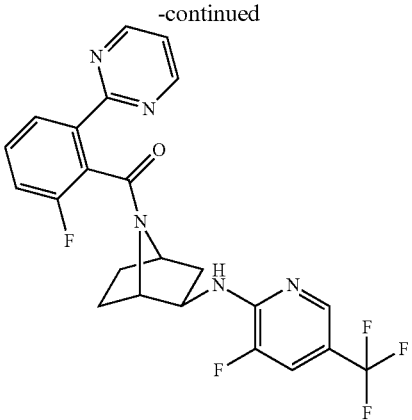

((1S,2R,4R)-2-((3-fluoro-5-
(trifluoromethyl)pyridin-2-yl)amino)-7-
azabicyclo[2.2.1]heptan-7-yl)(2-fluoro-
6-(pyrimidin-2-yl)phenyl)methanone,

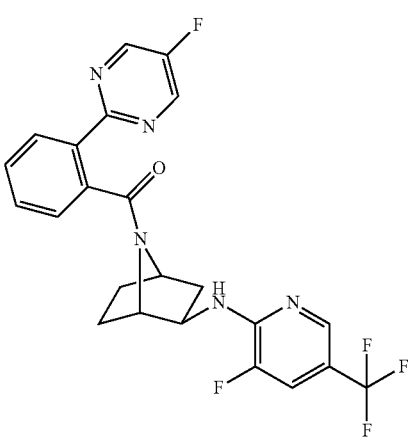 [SMILES: O=C(c1ccccc1-c1ncc(F)cn1)N1C2CCC1C(Nc1ncc(C(F)(F)F)cc1F)C2]

((1S,2R,4R)-2-((3-fluoro-5-
(trifluoromethyl)pyridin-2-yl)amino)-7-
azabicyclo[2.2.1]heptan-7-yl)(2-(5-
fluoropyrimidin-2-
yl)phenyl)methanone,

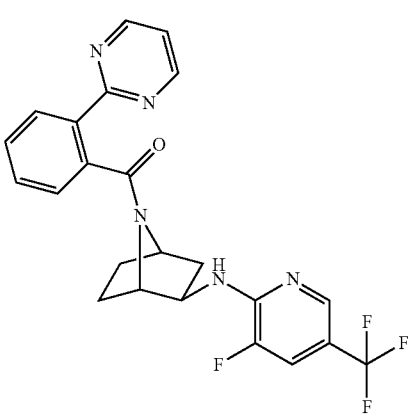 [SMILES: O=C(c1ccccc1-c1ncccn1)N1C2CCC1C(Nc1ncc(C(F)(F)F)cc1F)C2]

((1S,2R,4R)-2-((3-fluoro-5-
(trifluoromethyl)pyridin-2-yl)amino)-7-
azabicyclo[2.2.1]heptan-7-yl)(2-
(pyrimidin-2-yl)phenyl)methanone, 877
-continued

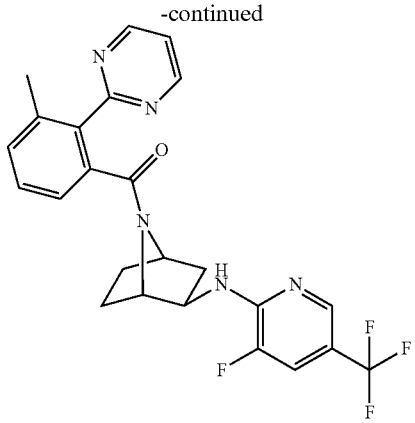

((1S,2R,4R)-2-((3-fluoro-5-
(trifluoromethyl)pyridin-2-yl)amino)-7-
azabicyclo[2.2.1]heptan-7-yl)(3-methyl-
2-(pyrimidin-2-yl)phenyl)methanone,

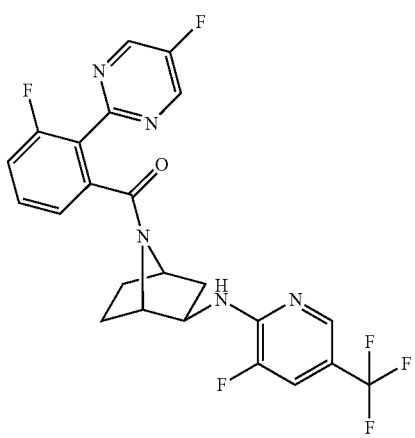

(3-fluoro-2-(5-fluoropyrimidin-2-
yl)phenyl)((1S,2R,4R)-2-((3-fluoro-5-
(trifluoromethyl)pyridin-2-yl)amino)-7-
azabicyclo[2.2.1]heptan-7-
yl)methanone,

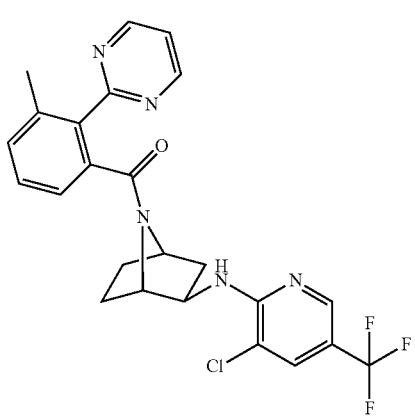

((1S,2R,4R)-2-((3-chloro-5-
(trifluoromethyl)pyridin-2-yl)amino)-7-
azabicyclo[2.2.1]heptan-7-yl)(3-methyl-
2-(pyrimidin-2-yl)phenyl)methanone, 878
-continued

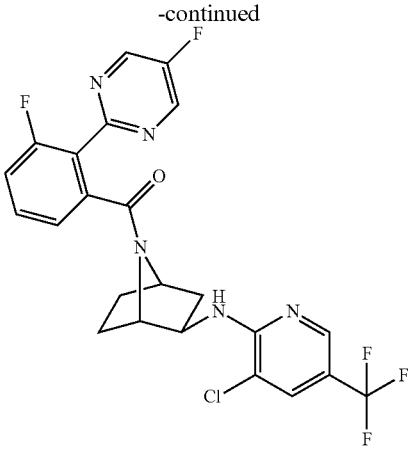

((1S,2R,4R)-2-((3-chloro-5-
(trifluoromethyl)pyridin-2-yl)amino)-7-
azabicyclo[2.2.1]heptan-7-yl)(3-fluoro-
2-(5-fluoropyrimidin-2-
yl)phenyl)methanone,

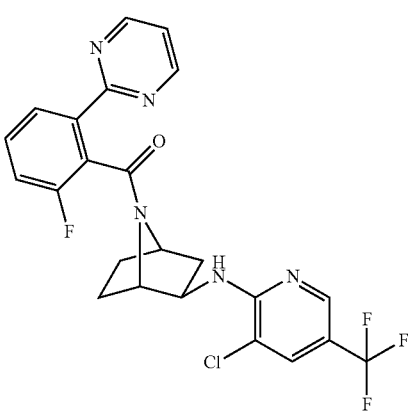

((1S,2R,4R)-2-((3-chloro-5-
(trifluoromethyl)pyridin-2-yl)amino)-7-
azabicyclo[2.2.1]heptan-7-yl)(2-fluoro-
6-(pyrimidin-2-yl)phenyl)methanone,

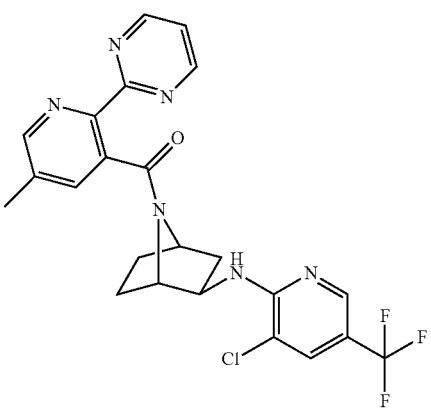

((1S,2R,4R)-2-((3-chloro-5-
(trifluoromethyl)pyridin-2-yl)amino)-7-
azabicyclo[2.2.1]heptan-7-yl)(5-methyl-
2-(pyrimidin-2-yl)pyridin-3-
yl)methanone,

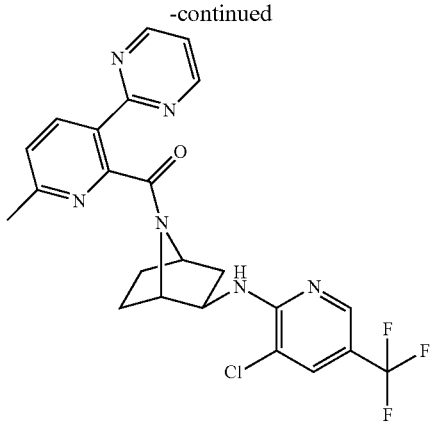

((1S,2R,4R)-2-((3-chloro-5-
(trifluoromethyl)pyridin-2-yl)amino)-7-
azabicyclo[2.2.1]heptan-7-yl)(6-methyl-
3-(pyrimidin-2-yl)pyridin-2-
yl)methanone,

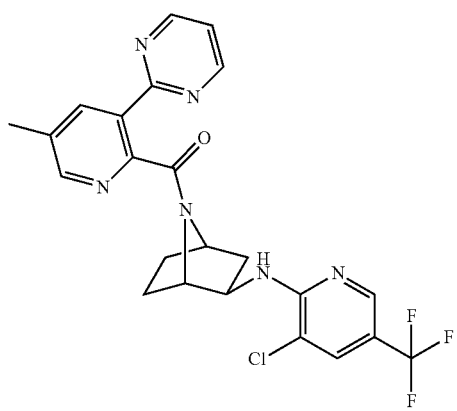

((1S,2R,4R)-2-((3-chloro-5-
(trifluoromethyl)pyridin-2-yl)amino)-7-
azabicyclo[2.2.1]heptan-7-yl)(5-methyl-
3-(pyrimidin-2-yl)pyridin-2-
yl)methanone,

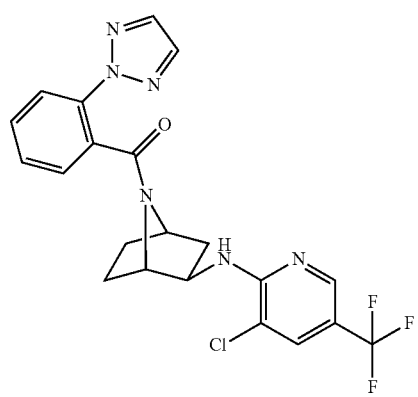

(2-(2H-1,2,3-triazol-2-
yl)phenyl)((1S,2R,4R)-2-((3-chloro-5-
(trifluoromethyl)pyridin-2-yl)amino)-7-
azabicyclo[2.2.1]heptan-7-
yl)methanone,

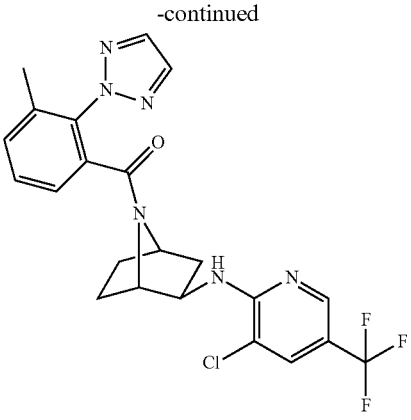

((1S,2R,4R)-2-((3-chloro-5-
(trifluoromethyl)pyridin-2-yl)amino)-7-
azabicyclo[2.2.1]heptan-7-yl)(3-methyl-
2-(2H-1,2,3-triazol-2-
yl)phenyl)methanone,

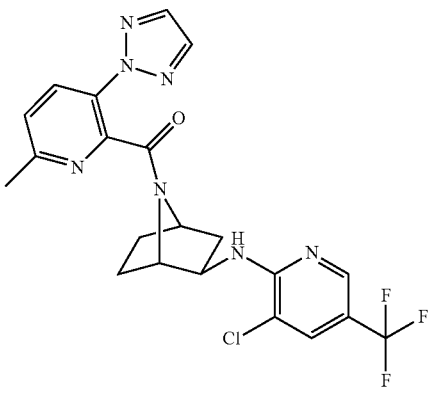

((1S,2R,4R)-2-((3-chloro-5-
(trifluoromethyl)pyridin-2-yl)amino)-7-
azabicyclo[2.2.1]heptan-7-yl)(6-methyl-
3-(2H-1,2,3-triazol-2-yl)pyridin-2-
yl)methanone,

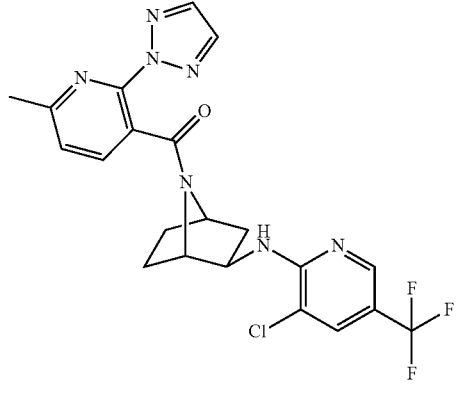

((1S,2R,4R)-2-((3-chloro-5-
(trifluoromethyl)pyridin-2-yl)amino)-7-
azabicyclo[2.2.1]heptan-7-yl)(6-methyl-
2-(2H-1,2,3-triazol-2-yl)pyridin-3-
yl)methanone,

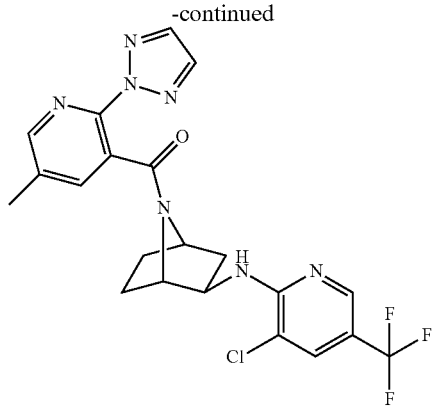

((1S,2R,4R)-2-((3-chloro-5-
(trifluoromethyl)pyridin-2-yl)amino)-7-
azabicyclo[2.2.1]heptan-7-yl)(5-methyl-
2-(2H-1,2,3-triazol-2-yl)pyridin-3-
yl)methanone,

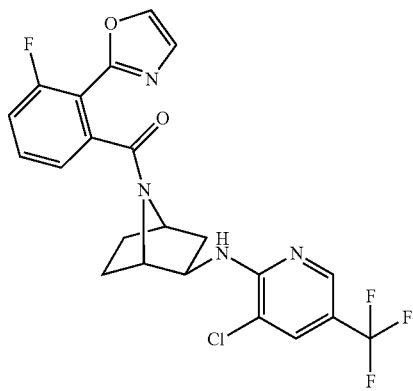

((1S,2R,4R)-2-((3-chloro-5-
(trifluoromethyl)pyridin-2-yl)amino)-7-
azabicyclo[2.2.1]heptan-7-yl)(3-fluoro-
2-(oxazol-2-yl)phenyl)methanone,

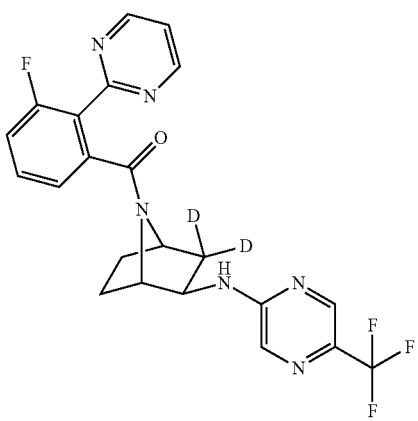

(3-fluoro-2-(pyrimidin-2-
yl)phenyl)((1S,2R,4R)-2-((5-
(trifluoromethyl)pyrazin-2-yl)amino)-7-
azabicyclo[2.2.1]-(3-$^2$H,$^2$H)-heptan-7-
yl)methanone,

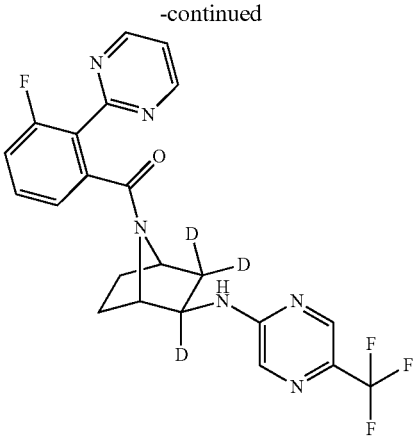

(3-fluoro-2-(pyrimidin-2-
yl)phenyl)((1S,2R,4R)-(2-$^2$H)-((5-
(trifluoromethyl)pyrazin-2-yl)amino)-7-
azabicyclo[2.2.1]-3-$^2$H,$^2$H)-heptan-7-
yl)methanone,

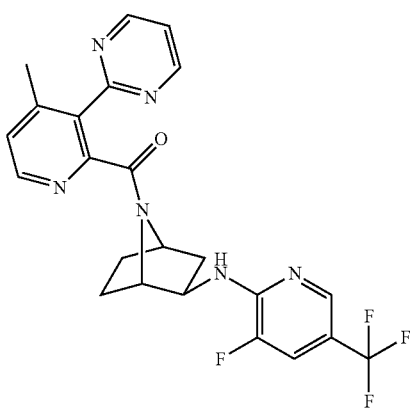 [SMILES: Cc1cccc(C(=O)N2C3CCC2C(Nc2ncc(C(F)(F)F)cc2F)C3)c1-c1ncccn1]

((1S,2R,4R)-2-((3-fluoro-5-
(trifluoromethyl)pyridin-2-yl)amino)-7-
azabicyclo[2.2.1]heptan-7-yl)(4-methyl-
3-(pyrimidin-2-yl)pyridin-2-
yl)methanone,

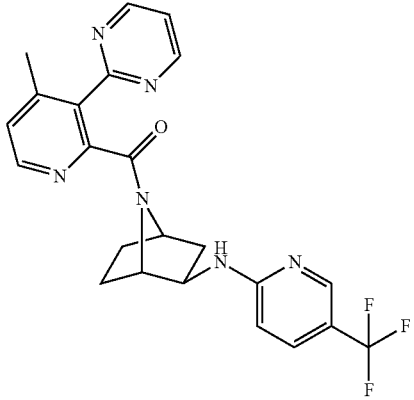

(4-methyl-3-(pyrimidin-2-yl)pyridin-2-
yl)((1S,2R,4R)-2-((5-
(trifluoromethyl)pyridin-2-yl)amino)-7-
azabicyclo[2.2.1]heptan-7-
yl)methanone,

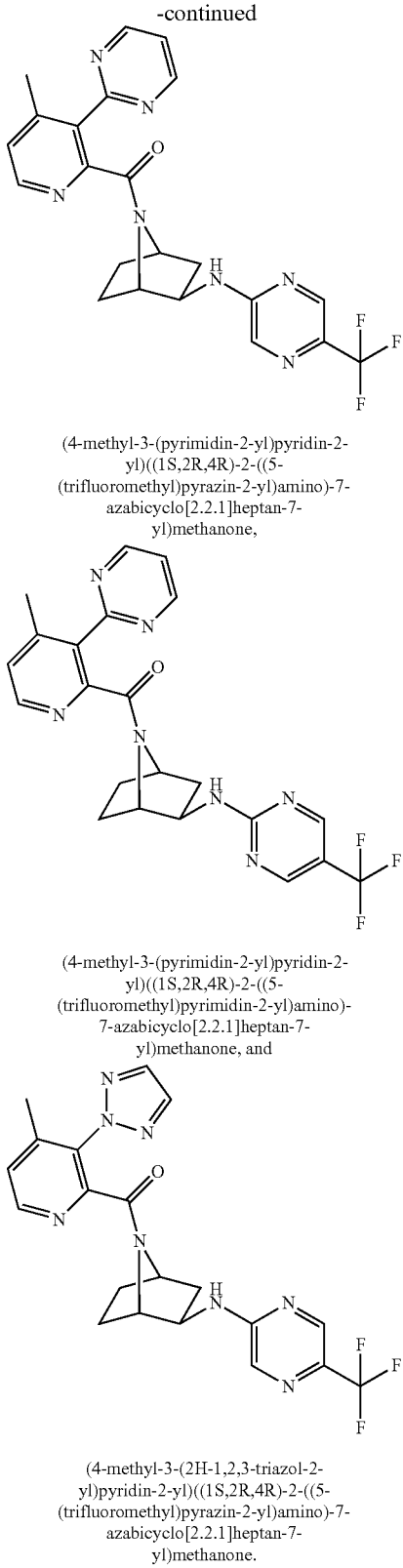

(4-methyl-3-(pyrimidin-2-yl)pyridin-2-yl)((1S,2R,4R)-2-((5-(trifluoromethyl)pyrazin-2-yl)amino)-7-azabicyclo[2.2.1]heptan-7-yl)methanone, (4-methyl-3-(pyrimidin-2-yl)pyridin-2-yl)((1S,2R,4R)-2-((5-(trifluoromethyl)pyrimidin-2-yl)amino)-7-azabicyclo[2.2.1]heptan-7-yl)methanone, and (4-methyl-3-(2H-1,2,3-triazol-2-yl)pyridin-2-yl)((1S,2R,4R)-2-((5-(trifluoromethyl)pyrazin-2-yl)amino)-7-azabicyclo[2.2.1]heptan-7-yl)methanone.

51. A pharmaceutical composition comprising a therapeutically effective amount of a compound according to claim 1 and at least one pharmaceutically acceptable excipient.

52. A method of treating a subject suffering from or diagnosed with a disease, disorder, or medical condition mediated by orexin receptor activity, comprising administering to the subject an effective amount of a compound of claim 1; wherein said disease, disorder or medical condition is a sleep disorder, a metabolic disorder, a neurological disorder, arrhythmia, acute heart failure, ulcer, irritable bowel syndrome, diarrhea, gastroesophageal reflux, mood disorder, post-traumatic stress disorder, panic disorder, attention deficit disorder, cognitive deficiency, or substance abuse.

53. The method of claim 52, wherein the sleep disorder is a sleep-wake transition disorder, insomnia, restless legs syndrome, jet-lag, disturbed sleep, or a sleep disorder secondary to a neurological disorder.

54. The method of claim 52 wherein the disease, disorder, or medical condition is mood disorder, post-traumatic stress disorder, panic disorder, attention deficit disorder, cognitive deficiency, or substance abuse.

55. A compound of Formula IA:

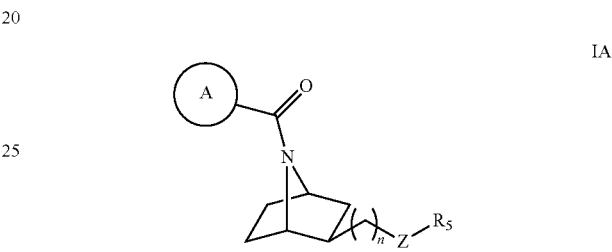

IA or an enantiomer, diastereomer, tautomer, or isotopic variant thereof;
or a pharmaceutically acceptable salt or solvate thereof;
wherein ring A is

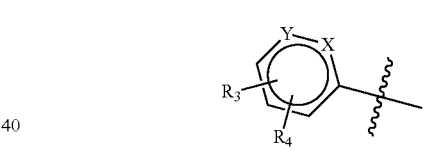

wherein
X is $CR_6$, N, or $NR_6$;
Y is $CR_7$, N, or $NR_7$;
$R_6$ is H, alkyl, alkoxy, OH, halo, triazolyl, oxazolyl, oxadiazolyl, pyridyl, pyrimidinyl, pyrazinyl, pyridazinyl, pyrazolyl, or thiophenyl, wherein triazolyl, oxazolyl, oxadiazolyl, pyridyl, pyrimidinyl, pyrazinyl, pyridazinyl, pyrazolyl, or thiophenyl is optionally substituted with up to two substituents selected from halo or alkyl;
$R_7$ is H, alkyl, alkoxy, or halo;
$R_3$ is H, alkyl, alkoxy, hydroxyalkylene, OH, halo, phenyl, triazolyl, oxazolyl, isoxazolyl, pyridyl, pyrimidinyl, pyrazinyl, pyridazinyl, piperazinyl, pyrazolyl, oxadiazolyl, pyrrolidinyl, thiophenyl, morpholinyl, or dialkylamino, wherein phenyl, triazolyl, oxazolyl, isoxazolyl, pyridyl, pyrimidinyl, pyrazinyl, pyridazinyl, piperazinyl, pyrazolyl, oxadiazolyl, pyrrolidinyl, thiophenyl, or morpholinyl is optionally substituted with up to two substituents selected from halo or alkyl;
$R_4$ is H, alkyl, alkoxy, or halo;
or
$R_6$ and $R_7$, together with the atoms to which they are attached, form a 5- or 6-membered heteroaryl ring optionally substituted with alkyl; or R₃ and R₄, together with the atoms to which they are attached, form a 6-membered aryl or 6-membered heteroaryl ring; or R₇ and R₄, together with the atoms to which they are attached, form a 6-membered aryl or 6-membered heteroaryl ring;

Z is NH, N-alkyl, or O;

R₅ is pyridyl, pyrimidinyl, pyrazinyl, pyridazinyl, quinazolinyl, quinoxalinyl, pyrazolyl, thiazolyl, thiadiazolyl, benzoxazolyl, imidazopyrazinyl, or triazolopyrazinyl, optionally substituted with one or two substituents independently selected from the group consisting of alkyl, cyano, alkyl carboxylate, alkoxy, and halo; and n is 0 or 1.

56. The compound of claim 55, wherein X is CR₆ and Y is CR₇.

57. The compound of claim 55, wherein X is CR₆ and Y is N.

58. The compound of claim 55, wherein X is N and Y is CR₇.

59. The compound of claim 55, wherein R₆ is H.

60. The compound of claim 55, wherein R₆ is alkyl, alkoxy, OH, or halo.

61. The compound of claim 55, wherein R₆ is triazolyl, oxazolyl, oxadiazolyl, pyrazolyl, or thiophenyl.

62. The compound of claim 61, wherein oxazolyl is methyl-oxazolyl.

63. The compound of claim 61, wherein pyrazolyl is methyl-pyrazolyl or dimethyl-pyrazolyl.

64. The compound of claim 61, wherein oxadiazolyl is methyl-oxadiazolyl.

65. The compound of claim 54, wherein R₆ is pyridyl.

66. The compound of claim 65, wherein pyridyl is methyl-pyridyl.

67. The compound of claim 55, wherein R₆ is pyrimidinyl, pyrazinyl, or pyridazinyl.

68. The compound of claim 55, wherein R₇ is H.

69. The compound of claim 55, wherein R₇ is alkyl, alkoxy, or halo.

70. The compound of claim 69, wherein alkoxy is haloalkoxy.

71. The compound of claim 55, wherein X is NR₆ and Y is CR₇.

72. The compound of claim 55, wherein X is CR₆ and Y is NR₇.

73. The compound of claim 55, wherein R₆ and R₇, together with the atoms to which they are attached, form a 5-membered heteroaryl ring optionally substituted with alkyl.

74. The compound of claim 55, wherein R₆ and R₇, together with the atoms to which they are attached, form a 6-membered heteroaryl ring optionally substituted with alkyl.

75. The compound of claim 55, wherein R₇ and R₄, together with the atoms to which they are attached, form a 6-membered aryl ring.

76. The compound of claim 55, wherein R₇ and R₄, together with the atoms to which they are attached, form a 6-membered heteroaryl ring.

77. The compound according to claim 55, wherein R₃ is H.

78. The compound according to claim 55, wherein R₃ is alkyl, alkoxy, hydroxyalkylene, OH, halo, or phenyl.

79. The compound of claim 78, wherein alkoxy is haloalkoxy.

80. The compound according to claim 55, wherein R₃ is triazolyl, oxazolyl, isoxazolyl, oxadiazolyl, pyridyl, or pyrazolyl.

81. The compound of claim 80, wherein oxazolyl is methyl-oxazolyl.

82. The compound of claim 80, wherein isoxazolyl is methyl-isoxazolyl.

83. The compound of claim 80, wherein pyridyl is methyl-pyridyl.

84. The compound of claim 80, wherein pyrazolyl is methyl-pyrazolyl or dimethyl-pyrazolyl.

85. The compound of claim 80, wherein oxadiazolyl is methyl-oxadiazolyl.

86. The compound according to claim 55, wherein R₃ is pyrimidinyl, pyrazinyl, or pyridazinyl.

87. The compound according to claim 55, wherein R₃ is piperazinyl, pyrazolyl, pyrrolidinyl, thiophenyl, morpholinyl, or dialkylamino.

88. The compound of claim 55, wherein R₄ is H.

89. The compound of claim 55, wherein R₄ is alkyl, alkoxy, or halo.

90. The compound of claim 55, wherein R₃ and R₄, together with the atoms to which they are attached, form a 6-membered aryl ring.

91. The compound according to claim 55, wherein R₃ and R₄, together with the atoms to which they are attached, form a 6-membered heteroaryl ring.

92. The compound of claim 55 selected from the following

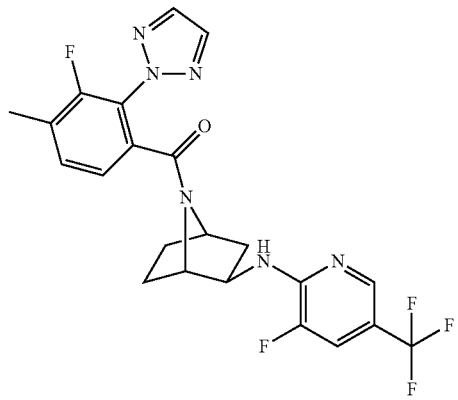

(3-fluoro-4-methyl-2-(2H-1,2,3-triazol-2-yl)phenyl)((1S,2R,4R)-2-((3-fluoro-5-(trifluoromethyl)pyridin-2-yl)amino)-7-azabicyclo[2.2.1]heptan-7-yl)methanone,

887
-continued

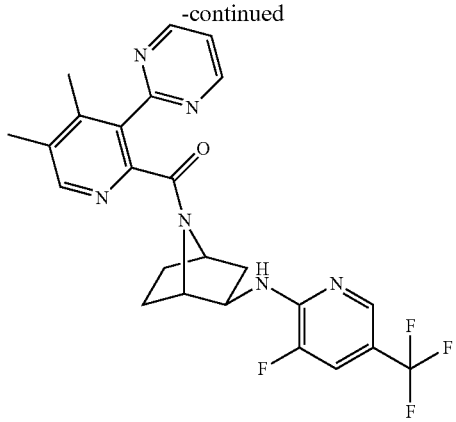

(4,5-dimethyl-3-(pyrimidin-2-yl)pyridin-2-yl)((1S,2R,4R)-2-((3-fluoro-5-(trifluoromethyl)pyridin-2-yl)amino)-7-azabicyclo[2.2.1]heptan-7-yl)methanone,

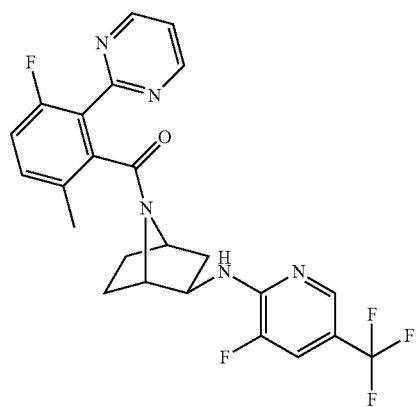

((1S,2R,4R)-2-((3-fluoro-5-(trifluoromethyl)pyridin-2-yl)amino)-7-azabicyclo[2.2.1]heptan-7-yl)(3-fluoro-6-methyl-2-(pyrimidin-2-yl)phenyl)methanone,

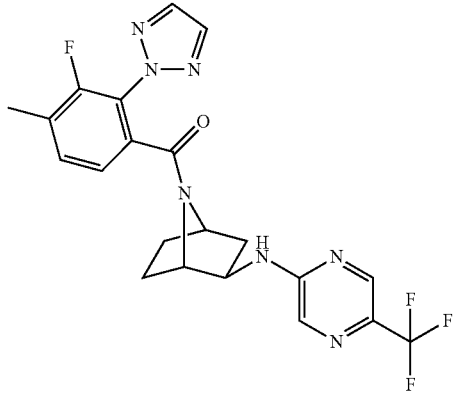

(3-fluoro-4-methyl-2-(2H-1,2,3-triazol-2-yl)phenyl)((1S,2R,4R)-2-((5-(trifluoromethyl)pyrazin-2-yl)amino)-7-azabicyclo[2.2.1]heptan-7-yl)methanone,

888
-continued

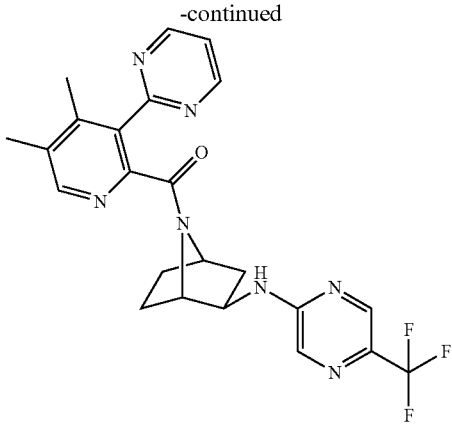

(4,5-dimethyl-3-(pyrimidin-2-yl)pyridin-2-yl)((1S,2R,4R)-2-((5-(trifluoromethyl)pyrazin-2-yl)amino)-7-azabicyclo[2.2.1]heptan-7-yl)methanone,

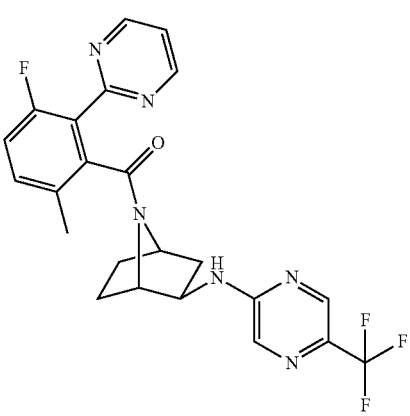

(3-fluoro-6-methyl-2-(pyrimidin-2-yl)phenyl)((1S,2R,4R)-2-((5-(trifluoromethyl)pyrazin-2-yl)amino)-7-azabicyclo[2.2.1]heptan-7-yl)methanone,

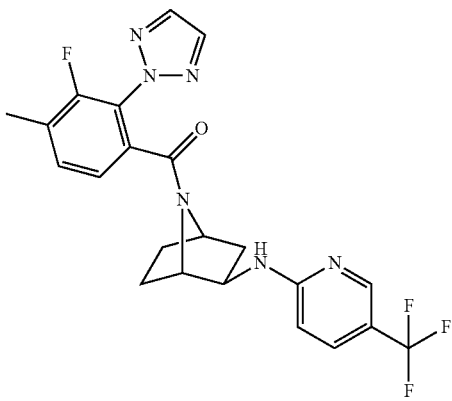

(3-fluoro-4-methyl-2-(2H-1,2,3-triazol-2-yl)phenyl)((1S,2R,4R)-2-((5-(trifluoromethyl)pyridin-2-yl)amino)-7-azabicyclo[2.2.1]heptan-7-yl)methanone, 889
-continued

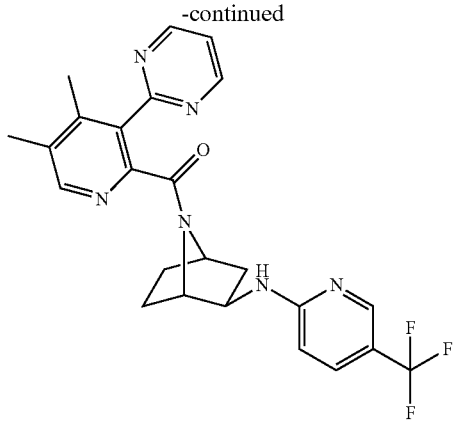

(4,5-dimethyl-3-(pyrimidin-2-yl)pyridin-2-yl)((1S,2R,4R)-2-((5-(trifluoromethyl)pyridin-2-yl)amino)-7-azabicyclo[2.2.1]heptan-7-yl)methanone,

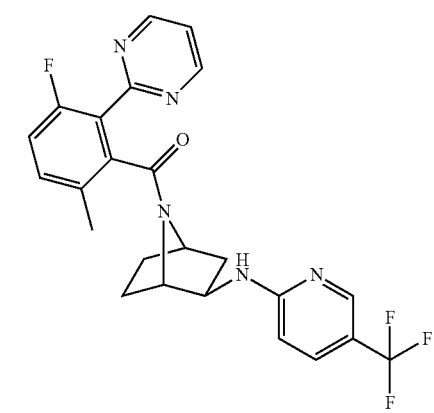

(3-fluoro-6-methyl-2-(pyrimidin-2-yl)phenyl)((1S,2R,4R)-2-((5-(trifluoromethyl)pyridin-2-yl)amino)-7-azabicyclo[2.2.1]heptan-7-yl)methanone,

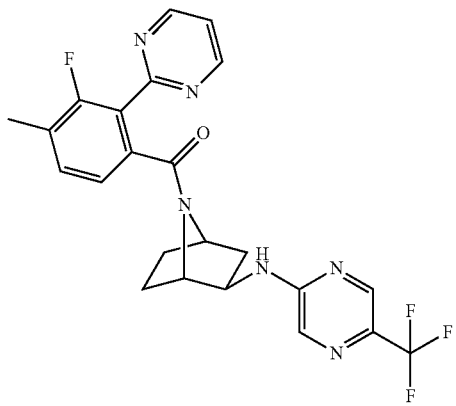

(3-fluoro-4-methyl-2-(pyrimidin-2-yl)phenyl)((1S,2R,4R)-2-((5-(trifluoromethyl)pyrazin-2-yl)amino)-7-azabicyclo[2.2.1]heptan-7-yl)methanone, 890
-continued

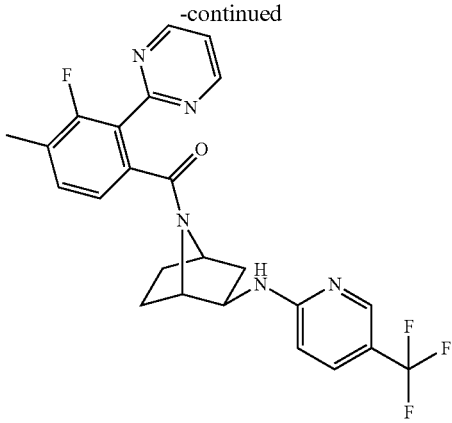

(3-fluoro-4-methyl-2-(pyrimidin-2-yl)phenyl)((1S,2R,4R)-2-((5-(trifluoromethyl)pyridin-2-yl)amino)-7-azabicyclo[2.2.1]heptan-7-yl)methanone,

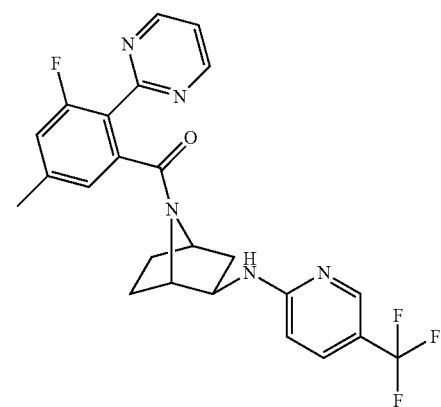

(3-fluoro-5-methyl-2-(pyrimidin-2-yl)phenyl)((1S,2R,4R)-2-((5-(trifluoromethyl)pyridin-2-yl)amino)-7-azabicyclo[2.2.1]heptan-7-yl)methanone, or

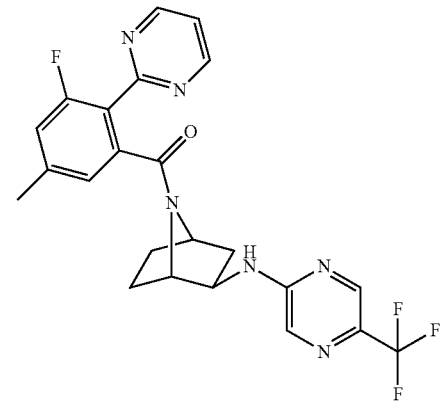

(3-fluoro-5-methyl-2-(pyrimidin-2-yl)phenyl)((1S,2R,4R)-2-((5-(trifluoromethyl)pyrazin-2-yl)amino)-7-azabicyclo[2.2.1]heptan-7-yl)methanone.

93. A pharmaceutical composition comprising a therapeutically effective amount of a compound according to claim 55 and at least one pharmaceutically acceptable excipient.

94. A method of treating a subject suffering from or diagnosed with a disease, disorder, or medical condition mediated by orexin receptor activity, comprising administering to the subject an effective amount of a compound according to claim 55;
wherein the disease, disorder, or medical condition is a sleep disorder, a metabolic disorder, a neurological disorder, arrhythmia, acute heart failure, ulcer, irritable bowel syndrome, diarrhea, gastroesophageal reflux, mood disorder, post-traumatic stress disorder, panic disorder, attention deficit disorder, cognitive deficiency, or substance abuse.

95. The method of claim 94, wherein the sleep disorder is a sleep-wake transition disorder, insomnia, restless legs syndrome, jet-lag, disturbed sleep, or a sleep disorder secondary to a neurological disorder.

96. The method of claim 94 wherein the disease, disorder, or medical condition is mood disorder, post-traumatic stress disorder, panic disorder, attention deficit disorder, cognitive deficiency, or substance abuse.

97. The compound of claim 1 which is

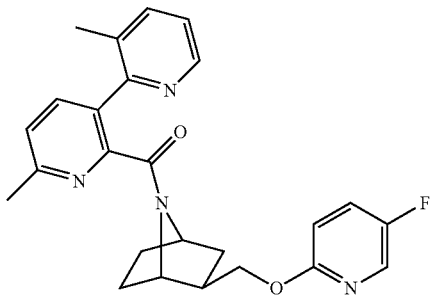

(±)-(3,6'-dimethyl-[2,3'-bipyridin]-2'-yl)(2-(((5-fluoropyridin-2-yl)oxy)methyl)-7-azabicyclo[2.2.1]heptan-7-yl)methanone or an enantiomer, diastereomer, tautomer, isotopic variant, pharmaceutically acceptable salt, or solvate thereof.

98. The compound of claim 97 which is

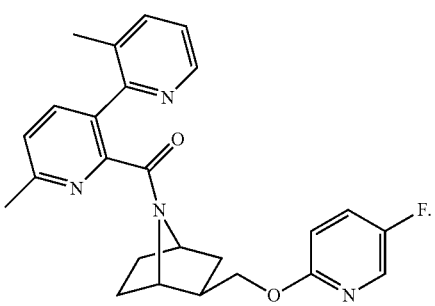

(±)-(3,6'-dimethyl-[2,3'-bipyridin]-2'-yl)(2-(((5-fluoropyridin-2-yl)oxy)methyl)-7-azabicyclo[2.2.1]heptan-7-yl)methanone 99. The compound of claim 1 which is

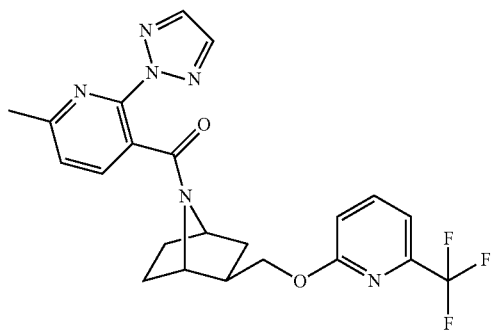

(±)-(6-methyl-2-(2H-1,2,3-triazol-2-yl)pyridin-3-yl)(2-(((6-(trifluoromethyl)pyridin-2-yl)oxy)methyl)-7-azabicyclo[2.2.1]heptan-7-yl)methanone or an enantiomer, diastereomer, tautomer, isotopic variant, pharmaceutically acceptable salt, or solvate thereof.

100. The compound of claim 99 which is

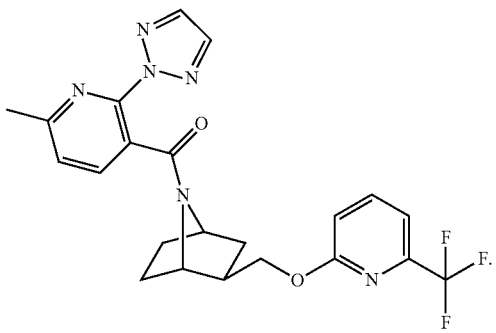

(±)-(6-methyl-2-(2H-1,2,3-triazol-2-yl)pyridin-3-yl)(2-(((6-(trifluoromethyl)pyridin-2-yl)oxy)methyl)-7-azabicyclo[2.2.1]heptan-7-yl)methanone 101. The compound of claim 1 which is

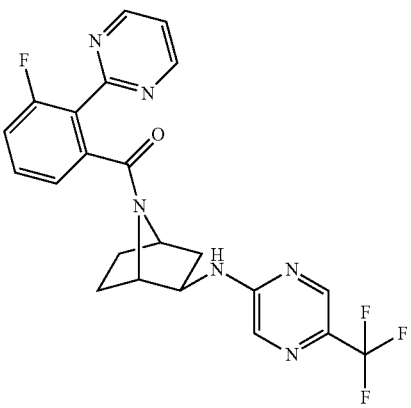

(3-fluoro-2-(pyrimidin-2-yl)phenyl)((1S,2R,4R)-2-((5-(trifluoromethyl)pyrazin-2-yl)amino)-7-azabicyclo[2.2.1]heptan-7-yl)methanone or an enantiomer, diastereomer, tautomer, isotopic variant, pharmaceutically acceptable salt, or solvate thereof.

102. The compound of claim 101 which is

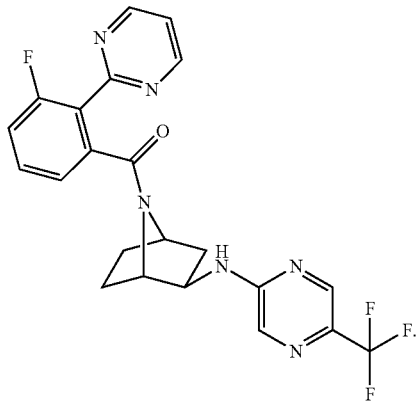

(3-fluoro-2-(pyrimidin-2-yl)phenyl)((1S,2R,4R)-2-((5-(trifluoromethyl)pyrazin-2-yl)amino)-7-azabicyclo[2.2.1]heptan-7-yl)methanone

103. The compound of claim 1 which is

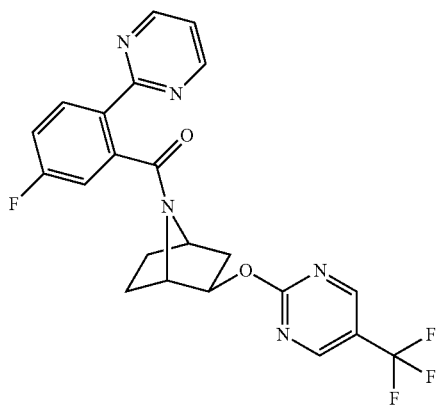

(5-fluoro-2-(pyrimidin-2-yl)phenyl)((1S,2R,4R)-2-((5-(trifluoromethyl)pyrimidin-2-yl)oxy)-7-azabicyclo[2.2.1]heptan-7-yl)methanone or an enantiomer, diastereomer, tautomer, isotopic variant, pharmaceutically acceptable salt, or solvate thereof.

104. The compound of claim 103 which is

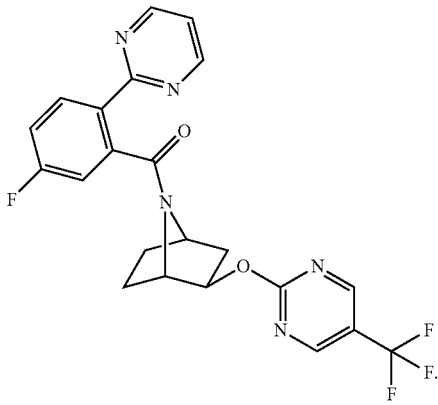

(5-fluoro-2-(pyrimidin-2-yl)phenyl)((1S,2R,4R)-2-((5-(trifluoromethyl)pyrimidin-2-yl)oxy)-7-azabicyclo[2.2.1]heptan-7-yl)methanone

105. The compound of claim 1 which is

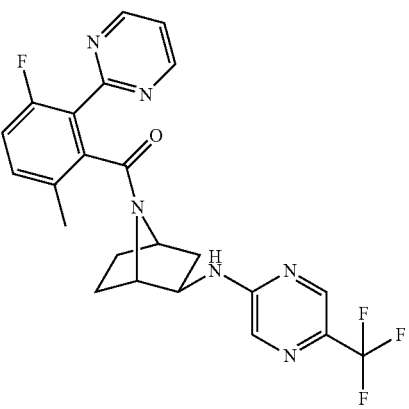

(3-fluoro-6-methyl-2-(pyrimidin-2-yl)phenyl)((1S,2R,4R)-2-((5-(trifluoromethyl)pyrazin-2-yl)amino)-7-azabicyclo[2.2.1]heptan-7-yl)methanone or an enantiomer, diastereomer, tautomer, isotopic variant, pharmaceutically acceptable salt, or solvate thereof.

106. The compound of claim 105 which is

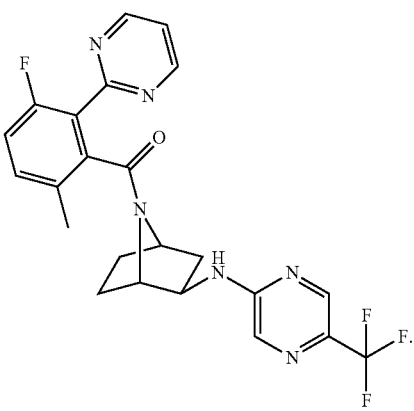

(3-fluoro-6-methyl-2-(pyrimidin-2-yl)phenyl)((1S,2R,4R)-2-((5-(trifluoromethyl)pyrazin-2-yl)amino)-7-azabicyclo[2.2.1]heptan-7-yl)methanone 107. The method of claim 52, wherein the metabolic disorder is overweight, obesity, insulin resistance, type II diabetes, hyperlipidemia, gallstones, angina, hypertension, breathlessness, tachycardia, infertility, sleep apnea, back and joint pain, varicose veins, or osteoarthritis.

108. The method of claim 52, wherein the neurological disorder is Parkinson's disease, Alzheimer's disease, Tourette's syndrome, catatonia, anxiety, delirium, or dementias.

109. The method of claim 94, wherein the metabolic disorder is overweight, obesity, insulin resistance, type II diabetes, hyperlipidemia, gallstones, angina, hypertension, breathlessness, tachycardia, infertility, sleep apnea, back and joint pain, varicose veins, or osteoarthritis.

110. The method of claim 94, wherein the neurological disorder is Parkinson's disease, Alzheimer's disease, Tourette's syndrome, catatonia, anxiety, delirium, or dementias.

* * * * *